US011866431B2

(12) United States Patent
Konradi et al.

(10) Patent No.: US 11,866,431 B2
(45) Date of Patent: Jan. 9, 2024

(54) BICYCLIC COMPOUNDS

(71) Applicant: Vivace Therapeutics, Inc., San Mateo, CA (US)

(72) Inventors: Andrei W. Konradi, Burlingame, CA (US); Tracy Tzu-Ling Tang Lin, Redwood City, CA (US)

(73) Assignee: VIVACE THERAPEUTICS, INC., San Mateo, CA (US)

( * ) Notice: Subject to any disclaimer, the term of this patent is extended or adjusted under 35 U.S.C. 154(b) by 146 days.

(21) Appl. No.: 17/291,765

(22) PCT Filed: Nov. 7, 2019

(86) PCT No.: PCT/US2019/060350
§ 371 (c)(1),
(2) Date: May 6, 2021

(87) PCT Pub. No.: WO2020/097389
PCT Pub. Date: May 14, 2020

(65) Prior Publication Data
US 2023/0061429 A1 Mar. 2, 2023

Related U.S. Application Data

(60) Provisional application No. 62/916,739, filed on Oct. 17, 2019, provisional application No. 62/758,364, filed on Nov. 9, 2018.

(51) Int. Cl.
| | | |
|---|---|---|
| *C07D 471/04* | (2006.01) | |
| *C07C 233/65* | (2006.01) | |
| *C07C 233/69* | (2006.01) | |
| *C07C 235/66* | (2006.01) | |
| *C07C 237/48* | (2006.01) | |
| *C07C 271/16* | (2006.01) | |
| *C07C 307/06* | (2006.01) | |
| *C07C 311/16* | (2006.01) | |
| *C07C 311/51* | (2006.01) | |
| *C07C 317/32* | (2006.01) | |
| *C07D 205/04* | (2006.01) | |
| *C07D 213/40* | (2006.01) | |

(Continued)

(52) U.S. Cl.
CPC .......... *C07D 471/04* (2013.01); *C07C 233/65* (2013.01); *C07C 233/69* (2013.01); *C07C 235/66* (2013.01); *C07C 237/48* (2013.01); *C07C 271/16* (2013.01); *C07C 307/06* (2013.01); *C07C 311/16* (2013.01); *C07C 311/51* (2013.01); *C07C 317/32* (2013.01); *C07D 205/04* (2013.01); *C07D 213/40* (2013.01); *C07D 213/61* (2013.01); *C07D 213/73* (2013.01); *C07D 213/74* (2013.01); *C07D 213/84* (2013.01); *C07D 215/48* (2013.01); *C07D 215/54* (2013.01); *C07D 217/18* (2013.01); *C07D 231/56* (2013.01); *C07D 233/64* (2013.01); *C07D 235/06* (2013.01); *C07D 239/26* (2013.01); *C07D 239/28* (2013.01); *C07D 241/12* (2013.01); *C07D 241/44* (2013.01); *C07D 257/04* (2013.01); *C07D 261/12* (2013.01); *C07D 263/56* (2013.01); *C07D 271/12* (2013.01); *C07D 277/82* (2013.01); *C07D 285/08* (2013.01); *C07D 295/13* (2013.01); *C07D 305/06* (2013.01); *C07D 307/22* (2013.01); *C07D 333/58* (2013.01); *C07D 401/12* (2013.01); *C07D 413/12* (2013.01)

(58) Field of Classification Search
CPC .. C07D 413/12; C07D 401/12; C07D 333/58; C07D 307/22; C07D 305/06; C07D 295/13; C07D 285/08; C07D 277/82; C07D 271/12; C07D 263/56; C07D 261/12; C07D 241/44; C07D 241/12; C07D 239/28; C07D 239/26; C07D 235/06; C07D 233/64; C07D 231/56; C07D 217/18; C07D 215/54; C07D 215/48; C07D 213/84; C07D 213/74; C07D 213/73; C07D 213/61; C07D 213/40; C07D 205/04; C07D 471/04; C07C 317/32; C07C 311/51; C07C 311/16; C07C 307/06; C07C 271/16; C07C 237/48; C07C 235/66; C07C 233/69; C07C 233/65
See application file for complete search history.

(56) References Cited

U.S. PATENT DOCUMENTS 7,718,703 B2  5/2010  Harada et al.
7,960,409 B2  6/2011  Grimm et al.
(Continued)

FOREIGN PATENT DOCUMENTS

CN   101679357 A   3/2010
CN   107438598 A   12/2017
(Continued)

OTHER PUBLICATIONS

Registry No. 1310490-70-0, File REGISTRY on STN, entered STN Jun. 27, 2011.*
Cancer and Metastasis Reviews (1998), 17(1), 91-106.*
Ence (1999), vol. 286, 531-537.*
El-Feky et al. Design, Synthesis, and Anti-inflammatory Activity of Novel Quinazolines. Oriental Journal Of Chemistry 33(2):707-716 (2017).
(Continued)

*Primary Examiner* — Rebecca L Anderson
(74) *Attorney, Agent, or Firm* — WILSON SONSINI GOODRICH & ROSATI

(57) ABSTRACT

Provided herein are compounds and pharmaceutical compositions comprising said compounds that are useful for treating cancers. Specific cancers include those that are mediated by YAP/TAZ or those that are modulated by the interaction between YAP/TAZ and TEAD.

12 Claims, 2 Drawing Sheets

(51) Int. Cl.

| | | |
|---|---|---|
| C07D 213/61 | (2006.01) |
| C07D 213/73 | (2006.01) |
| C07D 213/74 | (2006.01) |
| C07D 213/84 | (2006.01) |
| C07D 215/48 | (2006.01) |
| C07D 215/54 | (2006.01) |
| C07D 217/18 | (2006.01) |
| C07D 231/56 | (2006.01) |
| C07D 233/64 | (2006.01) |
| C07D 235/06 | (2006.01) |
| C07D 239/26 | (2006.01) |
| C07D 239/28 | (2006.01) |
| C07D 241/12 | (2006.01) |
| C07D 241/44 | (2006.01) |
| C07D 257/04 | (2006.01) |
| C07D 261/12 | (2006.01) |
| C07D 263/56 | (2006.01) |
| C07D 271/12 | (2006.01) |
| C07D 277/82 | (2006.01) |
| C07D 285/08 | (2006.01) |
| C07D 295/13 | (2006.01) |
| C07D 305/06 | (2006.01) |
| C07D 307/22 | (2006.01) |
| C07D 333/58 | (2006.01) |
| C07D 401/12 | (2006.01) |
| C07D 413/12 | (2006.01) |

(56) References Cited

U.S. PATENT DOCUMENTS

| | | |
|---|---|---|
| 8,362,000 B2 | 1/2013 | Bian et al. |
| 8,426,401 B2 | 4/2013 | Bian et al. |
| 8,748,417 B2 | 6/2014 | Zhang et al. |
| 9,012,443 B2 | 4/2015 | Boezio et al. |
| 9,452,986 B2 | 9/2016 | Bogdan et al. |
| 9,776,995 B2 | 10/2017 | Weiss et al. |
| 2002/0042426 A1 | 4/2002 | Makovec et al. |
| 2005/0059705 A1 | 3/2005 | Mjalli et al. |
| 2012/0040936 A1 | 2/2012 | Kanno et al. |
| 2012/0302752 A1 | 11/2012 | Zhao et al. |
| 2014/0336182 A1 | 11/2014 | Cee et al. |
| 2015/0157584 A1 | 6/2015 | Guan et al. |
| 2015/0166500 A1 | 6/2015 | Zhao et al. |
| 2016/0194285 A1 | 7/2016 | Thompson et al. |
| 2020/0347009 A1 | 11/2020 | Konradi et al. |
| 2022/0298102 A1 | 9/2022 | Konradi et al. |

FOREIGN PATENT DOCUMENTS

| | | |
|---|---|---|
| EP | 0765871 A1 | 4/1997 |
| EP | 0765871 B1 | 3/2004 |
| EP | 1042295 B1 | 9/2005 |
| WO | WO-9835967 A2 | 8/1998 |
| WO | WO-9932450 A1 | 7/1999 |
| WO | WO-0075145 A1 | 12/2000 |
| WO | WO-0200622 A2 | 1/2002 |
| WO | WO-0244166 A1 | 6/2002 |
| WO | WO-03010146 A1 | 2/2003 |
| WO | WO-2005014533 A2 | 2/2005 |
| WO | WO-2005082865 A1 | 9/2005 |
| WO | WO-2007090068 A2 | 8/2007 |
| WO | WO-2007097929 A1 | 8/2007 |
| WO | WO-2007099326 A1 | 9/2007 |
| WO | WO-2008023157 A1 | 2/2008 |
| WO | WO-2009018609 A1 | 2/2009 |
| WO | WO-2009073153 A2 | 6/2009 |
| WO | WO-2009075826 A1 | 6/2009 |
| WO | WO-2010124082 A1 | 10/2010 |
| WO | WO-2012003498 A1 | 1/2012 |
| WO | WO-2012054721 A1 | 4/2012 |
| WO | WO-2013066736 A1 | 5/2013 |
| WO | WO-2013188138 A1 | 12/2013 |
| WO | WO-2014177596 A1 | 11/2014 |
| WO | WO-2015144001 A1 | 10/2015 |
| WO | WO-2016118565 A1 | 7/2016 |
| WO | WO-2017064277 A1 | 4/2017 |
| WO | WO-2017087608 A1 | 5/2017 |
| WO | WO-2018028591 A1 | 2/2018 |
| WO | WO-2019040389 A1 | 2/2019 |
| WO | WO-2019148044 A1 | 8/2019 |
| WO | WO-2019152440 A1 | 8/2019 |
| WO | WO-2020097389 A1 | 5/2020 |
| WO | WO-2020214734 A1 | 10/2020 |
| WO | WO-2022087008 A1 | 4/2022 |

OTHER PUBLICATIONS

PCT/US2021/055668 International Search Report and Written Opinion dated Feb. 10, 2022.
Berge et al. Pharmaceutical Salts. Journal of Pharmaceutical Sciences 66(1):1-19 (Jan. 1977).
Bundgaard et al. Design of Prodrugs pp. 7-9, 21-24 (1985).
Dimauro et al. Application of a Parallel Synthetic Strategy in the Discovery of Biaryl Acyl Sulfonamides as Efficient and Selective NaV1.7 Inhibitors. J Med Chem 59(17):7818-39 (2016).
Fleisher et al. Improved oral drug delivery: solubility limitations overcome by the use of prodrugs. Advanced Drug Delivery Reviews 19:115-130 (1996).
Goodell et al. Acridine-based agents with topoisomerase II activity inhibit pancreatic cancer cell proliferation and induce apoptosis. J Med Chem 51(2):179-182 (2008).
Harvey, et al. The Hippo pathway and human cancer. Nat Rev Cancer. 13(4):246-57 (2013).
La et al. The discovery of benzoxazine sulfonamide inhibitors of Na V 1.7: Tools that bridge efficacy and target engagement. Bioorg Med Chem Lett. 27(15):3477-3485 (2017).
Ma et al. The Hippo Pathway: Biology and Pathophysiology. Annu Rev Biochem 88:577-604 (2019).
Marx et al. Sulfonamides as Selective Na V 1.7 Inhibitors: Optimizing Potency and Pharmacokinetics to Enable in Vivo Target Engagement. ACS Med Chem Lett 7(12):1062-1067 (2016).
Nara et al. Discovery of Novel, Highly Potent, and Selective Quinazoline-2-carboxamide-Based Matrix Metalloproteinase (MMP)-13 Inhibitors without a Zinc Binding Group Using a Structure-Based Design Approach. J Med Chem 57(21):8886-8902 (2014).
PCT/US2019/060350 International Search Report and Written Opinion dated Apr. 9, 2020.
PCT/US2019/060350 Invitation to Pay Additional Fees dated Feb. 4, 2020.
PCT/US2020/028363 International Search Report and Written Opinion dated Aug. 27, 2020.
PCT/US2020/028363 Invitation to Pay Additional Fees dated Jun. 25, 2020.
PubChem-CID-59944252, Create Date: Aug. 20, 2012 (Aug. 20, 2012).
PubChem-CID-68784747, Create Date: Nov. 30, 2012 (Nov. 30, 2012).
PubChem-CID-70167127, Create Date: Dec. 1, 2012 (Dec. 1, 2012).
Roecker et al. Discovery of selective, orallybioavailable, N-linked arylsulfonamide Na v 1.7 inhibitors with pain efficacyin mice. Bioorg Med Chem Lett. 27(10):2087-2093(2017).
Science IP Report dated May 22, 2018 (141 pgs).
Weiss et al. Sulfonamides as Selective Na V 1.7 Inhibitors: Optimizing Potency and Pharmacokinetics While Mitigating Metabolic Liabilities. J Med Chem 60(14):5969-5989 (2017).
Yu et al. Hippo Pathway in Organ Size Control, Tissue Homeostasis, and Cancer. Cell 163(4):811-28 (2015).

* cited by examiner

BICYCLIC COMPOUNDS

CROSS-REFERENCE

This application is a U.S. National Stage of International Application No. PCT/US2019/060350, filed Nov. 7, 2019, which claims the benefit of U.S. Provisional Patent Application No. 62/758,364 filed on Nov. 9, 2018 and U.S. Provisional Patent Application No. 62/916,739 filed on Oct. 17, 2019, each of which is incorporated by reference herein in its entirety.

BACKGROUND OF THE DISCLOSURE

YAP and TAZ are transcriptional co-activators of the Hippo pathway network and regulate cell proliferation, migration, and apoptosis. Inhibition of the Hippo pathway promotes YAP/TAZ translocation to the nucleus, wherein YAP/TAZ interact with transcriptional enhancer associate domain (TEAD) transcription factors and coactivate the expression of target genes and promote cell proliferation. Hyperactivation of YAP and TAZ and/or mutations in one or more members of the Hippo pathway network have been implicated in numerous cancers. Described herein are inhibitors associated with one or more members of the Hippo pathway network, such as inhibitors of YAP/TAZ or inhibitors that modulate the interaction between YAP/TAZ and TEAD.

SUMMARY OF THE DISCLOSURE

Provided herein are bicyclic compounds and pharmaceutical compositions comprising said compounds. In some embodiments, the subject compounds are useful for the treatment of cancer.

In one aspect, the present disclosure provides a compound of Formula (I) or a pharmaceutically acceptable salt or a pharmaceutically acceptable solvate thereof:

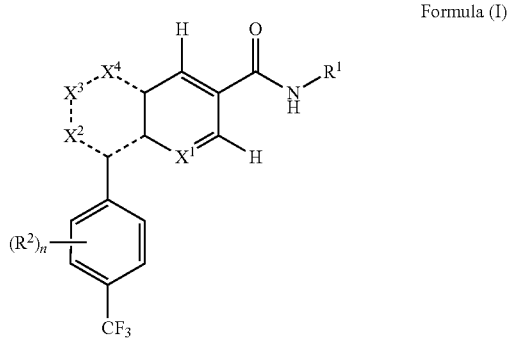

Formula (I)

wherein,
each $X^1$ and $X^2$ is independently N, $NR^X$, C(=O), or $CR^X$;
each $X^3$ and $X^4$ is independently N, $NR^X$, C(=O), or $CR^X$; or if both $X^3$ and $X^4$ are each independently $NR^X$ or $CR^X$, then the two $R^X$ are taken together with the intervening atoms to which they are attached to form a 5-membered heterocyclic ring;
each $R^X$ is independently hydrogen, halogen, nitro, oxo, thioxo, imino, oximo, $-OR^3$, $-SR^3$, $-CN$, $-C(=O)R^2$, $-S(=O)R^3$, $-S(=O)_2R^3$, $-N(R^3)_2$, $-NR^3S(=O)_2R^3$, $-NR^3C(=O)R^3$, $-NR^3C(=O)OR^3$, substituted or unsubstituted $C_1$-$C_6$ alkyl, substituted or unsubstituted $C_1$-$C_6$haloalkyl, substituted or unsubstituted $C_2$-$C_4$alkenyl, substituted or unsubstituted $C_2$-$C_4$alkynyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;
$R^1$ is substituted or unsubstituted $C_1$-$C_6$alkyl, substituted or unsubstituted $C_1$-$C_6$haloalkyl, substituted or unsubstituted $C_2$-$C_4$alkenyl, substituted or unsubstituted $C_2$-$C_4$alkynyl, substituted or unsubstituted $C_3$-$C_{10}$cycloalkyl, substituted or unsubstituted $C_2$-$C_{10}$heterocycloalkyl, substituted or unsubstituted $C_1$-$C_6$heteroalkyl, or $-S(=O)_2R^4$;
each $R^2$ is independently $-N_3$, $-CN$, $-OR^3$, $-SR^3$, $-S(=O)_2R^3$, $-N(R^3)_2$, $-C(=O)OR^3$, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;
each $R^3$ is independently hydrogen, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;
$R^4$ is substituted or unsubstituted $C_1$-$C_6$alkyl, substituted or unsubstituted $C_1$-$C_6$haloalkyl, substituted or unsubstituted $C_3$-$C_{10}$cycloalkyl, or $-NH_2$;
each -- is independently a single or double bond; and
n is 0, 1, 2, 3, or 4.

In another aspect, the present disclosure provides a compound of Formula (Ia) or a pharmaceutically acceptable salt or a pharmaceutically acceptable solvate thereof:

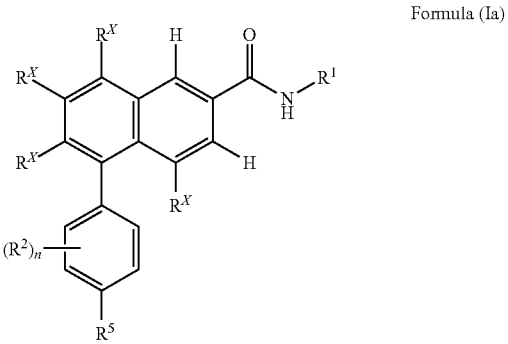

Formula (Ia)

wherein,
each $R^X$ is independently hydrogen, halogen, $-OH$, $-NH_2$, $-CH_3$, $-CH_2CH_3$, cyclopropyl, $-CF_3$, $-OCH_3$, $-OCH_2CH_3$, cyclopropyloxy, or $-OCF_3$;
$R^1$ is substituted or unsubstituted $C_1$-$C_6$alkyl, wherein if $C_1$-$C_6$alkyl is substituted, then it is substituted with 1 or 2 substituents each independently selected from $-OH$, $-NH_2$, azetidinyl, pyridyl, and aminopyridyl;

R² is F;
R⁵ is —CF₃; and
n is 0 or 1.

In another aspect, the present disclosure provides a compound of Formula (II) or a pharmaceutically acceptable salt or a pharmaceutically acceptable solvate thereof:

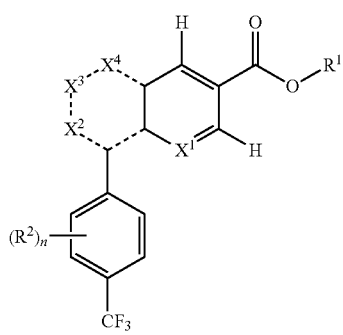

Formula (II)

wherein,
each $X^1$ and $X^2$ is independently N, $NR^X$, C(=O), or $CR^X$;
each $X^3$ and $X^4$ is independently N, $NR^X$, C(=O), or $CR^X$; or if both $X^3$ and $X^4$ are each independently $NR^X$ or $CR^X$, then the two $R^X$ are taken together with the intervening atoms to which they are attached to form a 5-membered heterocyclic ring;
each $R^X$ is independently hydrogen, halogen, nitro, oxo, thioxo, imino, oximo, —OR³, —SR³, —CN, —C(=O)R², —S(=O)R³, —S(=O)₂R³, —N(R³)₂, —NR³S(=O)₂R³, —NR³C(=O)R³, —NR³C(=O)OR³, substituted or unsubstituted C₁-C₆ alkyl, substituted or unsubstituted C₁-C₆haloalkyl, substituted or unsubstituted C₂-C₄alkenyl, substituted or unsubstituted C₂-C₄alkynyl, substituted or unsubstituted C₁-C₆heteroalkyl, substituted or unsubstituted C₃-C₁₀cycloalkyl, substituted or unsubstituted C₂-C₁₀heterocycloalkyl, substituted or unsubstituted aralkyl, substituted or unsubstituted aryl, or substituted or unsubstituted heteroaryl;
$R^1$ is substituted or unsubstituted C₁-C₆alkyl, substituted or unsubstituted C₁-C₆haloalkyl, substituted or unsubstituted C₁-C₆heteroalkyl, substituted or unsubstituted C₃-C₁₀cycloalkyl, substituted or unsubstituted C₂-C₁₀heterocycloalkyl, substituted or unsubstituted aralkyl, substituted or unsubstituted aryl, or substituted or unsubstituted heteroaryl;
each $R^2$ is independently —N₃, —CN, —OR³, —SR³, —S(=O)₂R³, —N(R³)₂, —C(=O)OR³, substituted or unsubstituted C₁-C₆alkyl, substituted or unsubstituted C₁-C₆haloalkyl, substituted or unsubstituted C₁-C₆heteroalkyl, substituted or unsubstituted C₃-C₁₀cycloalkyl, substituted or unsubstituted C₂-C₁₀heterocycloalkyl, substituted or unsubstituted aralkyl, substituted or unsubstituted aryl, or substituted or unsubstituted heteroaryl;
each $R^3$ is independently hydrogen, substituted or unsubstituted C₁-C₆alkyl, substituted or unsubstituted C₁-C₆haloalkyl, substituted or unsubstituted C₁-C₆heteroalkyl, substituted or unsubstituted C₃-C₁₀cycloalkyl, substituted or unsubstituted C₂-C₁₀heterocycloalkyl, substituted or unsubstituted aralkyl, substituted or unsubstituted aryl, or substituted or unsubstituted heteroaryl;
each -- is independently a single or double bond; and
n is 0, 1, 2, 3, or 4.

In another aspect, the present disclosure provides a compound of Formula (III) or a pharmaceutically acceptable salt or a pharmaceutically acceptable solvate thereof:

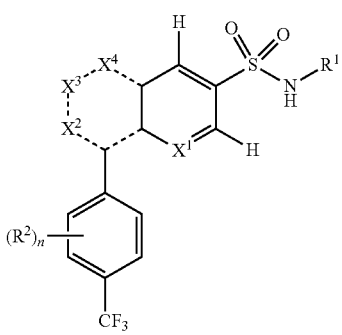

Formula (III)

wherein,
each $X^1$ and $X^2$ is independently N, $NR^X$, C(=O), or $CR^X$;
each $X^3$ and $X^4$ is independently N, $NR^X$, C(=O), or $CR^X$; or if both $X^3$ and $X^4$ are each independently $NR^X$ or $CR^X$, then the two $R^X$ are taken together with the intervening atoms to which they are attached to form a 5-membered heterocyclic ring;
each $R^X$ is independently hydrogen, halogen, nitro, oxo, thioxo, imino, oximo, —OR³, —SR³, —CN, —C(=O)R², —S(=O)R³, —S(=O)₂R³, —N(R³)₂, —NR³S(=O)₂R³, —NR³C(=O)R³, —NR³C(=O)OR³, substituted or unsubstituted C₁-C₆ alkyl, substituted or unsubstituted C₁-C₆haloalkyl, substituted or unsubstituted C₂-C₄alkenyl, substituted or unsubstituted C₂-C₄alkynyl, substituted or unsubstituted C₁-C₆heteroalkyl, substituted or unsubstituted C₃-C₁₀cycloalkyl, substituted or unsubstituted C₂-C₁₀heterocycloalkyl, substituted or unsubstituted aralkyl, substituted or unsubstituted aryl, or substituted or unsubstituted heteroaryl;
$R^1$ is substituted or unsubstituted C₁-C₆alkyl, substituted or unsubstituted C₁-C₆haloalkyl, substituted or unsubstituted C₁-C₆heteroalkyl, substituted or unsubstituted C₃-C₁₀cycloalkyl, or substituted or unsubstituted C₂-C₁₀heterocycloalkyl;
each $R^2$ is independently —N₃, —CN, —OR³, —SR³, —S(=O)₂R³, —N(R³)₂, —C(=O)OR³, substituted or unsubstituted C₁-C₆alkyl, substituted or unsubstituted C₁-C₆haloalkyl, substituted or unsubstituted C₁-C₆heteroalkyl, substituted or unsubstituted C₃-C₁₀cycloalkyl, substituted or unsubstituted C₂-C₁₀heterocycloalkyl, substituted or unsubstituted aralkyl, substituted or unsubstituted aryl, or substituted or unsubstituted heteroaryl;
each $R^3$ is independently hydrogen, substituted or unsubstituted C₁-C₆alkyl, substituted or unsubstituted C₁-C₆haloalkyl, substituted or unsubstituted C₁-C₆heteroalkyl, substituted or unsubstituted C₃-C₁₀cycloalkyl, substituted or unsubstituted C₂-C₁₀heterocycloalkyl, substituted or unsubstituted aralkyl, substituted or unsubstituted aryl, or substituted or unsubstituted heteroaryl;

$R^4$ is substituted or unsubstituted $C_1$-$C_6$alkyl, substituted or unsubstituted $C_3$-$C_{10}$cycloalkyl, or —$NH_2$;

each -- is independently a single or double bond; and n is 0, 1, 2, 3, or 4.

In another aspect, the present disclosure provides a compound of Formula (IV), or a pharmaceutically acceptable salt or a pharmaceutically acceptable solvate thereof:

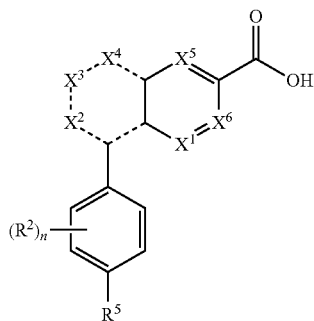

Formula (IV)

wherein, each $X^1$, $X^2$, $X^5$, and $X^6$, is independently N, $NR^X$, C(=O), or $CR^X$;

each $X^3$ and $X^4$ is independently N, $NR^X$, C(=O), or $CR^X$; or if both $X^3$ and $X^4$ are each independently $NR^X$ or $CR^X$, then the two $R^X$ are taken together with the intervening atoms to which they are attached to form a 5-membered heterocyclic ring;

each $R^X$ is independently hydrogen, halogen, nitro, oxo, thioxo, imino, oximo, —$OR^3$, —$SR^3$, —CN, —C(=O)$R^2$, —S(=O)$R^3$, —S(=O)$_2R^3$, —N(R^3)_2$, —$NR^3$S(=O)$_2R^3$, —$NR^3$C(=O)$R^3$, —$NR^3$C(=O)$OR^3$, substituted or unsubstituted $C_1$-$C_6$ alkyl, substituted or unsubstituted $C_1$-$C_6$haloalkyl, substituted or unsubstituted $C_2$-$C_4$alkenyl, substituted or unsubstituted $C_2$-$C_4$alkynyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;

each $R^2$ is independently —CN, —$OR^3$, —$SR^3$, —S(=O)$_2R^3$, —N(R^3)_2$, —C(=O)$OR^3$, —$N_3$, F, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;

each $R^3$ is independently hydrogen, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or unsubstituted heteroaryl;

$R^5$ is F, —$SF_5$, substituted $C_1$-$C_6$alkyl, substituted or unsubstituted $C_1$-$C_6$haloalkyl, substituted $C_1$-$C_6$alkyloxy, or substituted $C_1$-$C_6$alkylthio;

each -- is independently a single or double bond; and n is 0, 1, 2, 3, or 4.

In another aspect, the present disclosure provides a compound of Formula (V), or a pharmaceutically acceptable salt or a pharmaceutically acceptable solvate thereof:

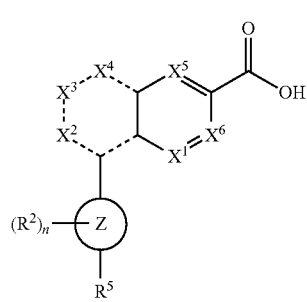

Formula (V)

wherein, each $X^1$, $X^2$, $X^5$, and $X^6$, is independently N, $NR^X$, C(=O), or $CR^X$;

each $X^3$ and $X^4$ is independently N, $NR^X$, C(=O), or $CR^X$; or if both $X^3$ and $X^4$ are each independently $NR^X$ or $CR^X$, then the two $R^X$ are taken together with the intervening atoms to which they are attached to form a 5-membered heterocyclic ring;

each $R^X$ is independently hydrogen, halogen, nitro, oxo, thioxo, imino, oximo, —$OR^3$, —$SR^3$, —CN, —C(=O)$R^2$, —S(=O)$R^3$, —S(=O)$_2R^3$, —N(R^3)_2$, —$NR^3$S(=O)$_2R^3$, —$NR^3$C(=O)$R^3$, —$NR^3$C(=O)$OR^3$, substituted or unsubstituted $C_1$-$C_6$ alkyl, substituted or unsubstituted $C_1$-$C_6$haloalkyl, substituted or unsubstituted $C_2$-$C_4$alkenyl, substituted or unsubstituted $C_2$-$C_4$alkynyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;

Ring Z is a substituted monocyclic 5-membered heterocyclic ring containing at least one N, O, or S atom or a substituted monocyclic 6-membered heterocyclic ring containing at least one N atom;

each $R^2$ is independently —CN, —$OR^3$, —$SR^3$, —S(=O)$_2R^3$, —N(R^3)_2$, —C(=O)$OR^3$, —$N_3$, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;

each $R^3$ is independently hydrogen, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;

$R^5$ is F, —$SF_5$, substituted $C_1$-$C_6$alkyl, substituted or unsubstituted $C_1$-$C_6$haloalkyl, substituted $C_1$-$C_6$alkyloxy, or substituted $C_1$-$C_6$alkylthio;

each -- is independently a single or double bond; and n is 0, 1, 2, 3, or 4.

Any combination of the groups described above for the various variables is contemplated herein. Throughout the specification, groups and substituents thereof are chosen by one skilled in the relevant field to provide stable moieties and compounds.

In another aspect, the present disclosure provides a compound or a pharmaceutically acceptable salt or a pharmaceutically acceptable solvate thereof, wherein the compound is a compound from Table 1, or a pharmaceutically acceptable salt or a pharmaceutically acceptable solvate thereof.

In another aspect, the present disclosure provides a compound or a pharmaceutically acceptable salt or a pharmaceutically acceptable solvate thereof, wherein the compound is a compound from Table 2, or a pharmaceutically acceptable salt or a pharmaceutically acceptable solvate thereof.

In another aspect, the present disclosure provides a compound or a pharmaceutically acceptable salt or a pharmaceutically acceptable solvate thereof, wherein the compound is a compound from Table 3, or a pharmaceutically acceptable salt or a pharmaceutically acceptable solvate thereof.

In some embodiments, a compound disclosed herein exhibits an $IC_{50}$ of no more than 3 µM.

In some embodiments, a compound disclosed herein exhibits an $IC_{50}$ of no more than 1 µM.

In another aspect, the present disclosure provides a pharmaceutical composition comprising a pharmaceutically acceptable excipient and a compound disclosed herein or a pharmaceutically acceptable salt or a pharmaceutically acceptable solvate thereof.

In another aspect, the present disclosure provides a method for treating a cancer in a subject in need thereof comprising administering a therapeutically effective amount of a compound disclosed herein or a pharmaceutically acceptable salt or a pharmaceutically acceptable solvate thereof.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

Various aspects of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION OF THE DISCLOSURE

Certain Terminology

Figure 1:
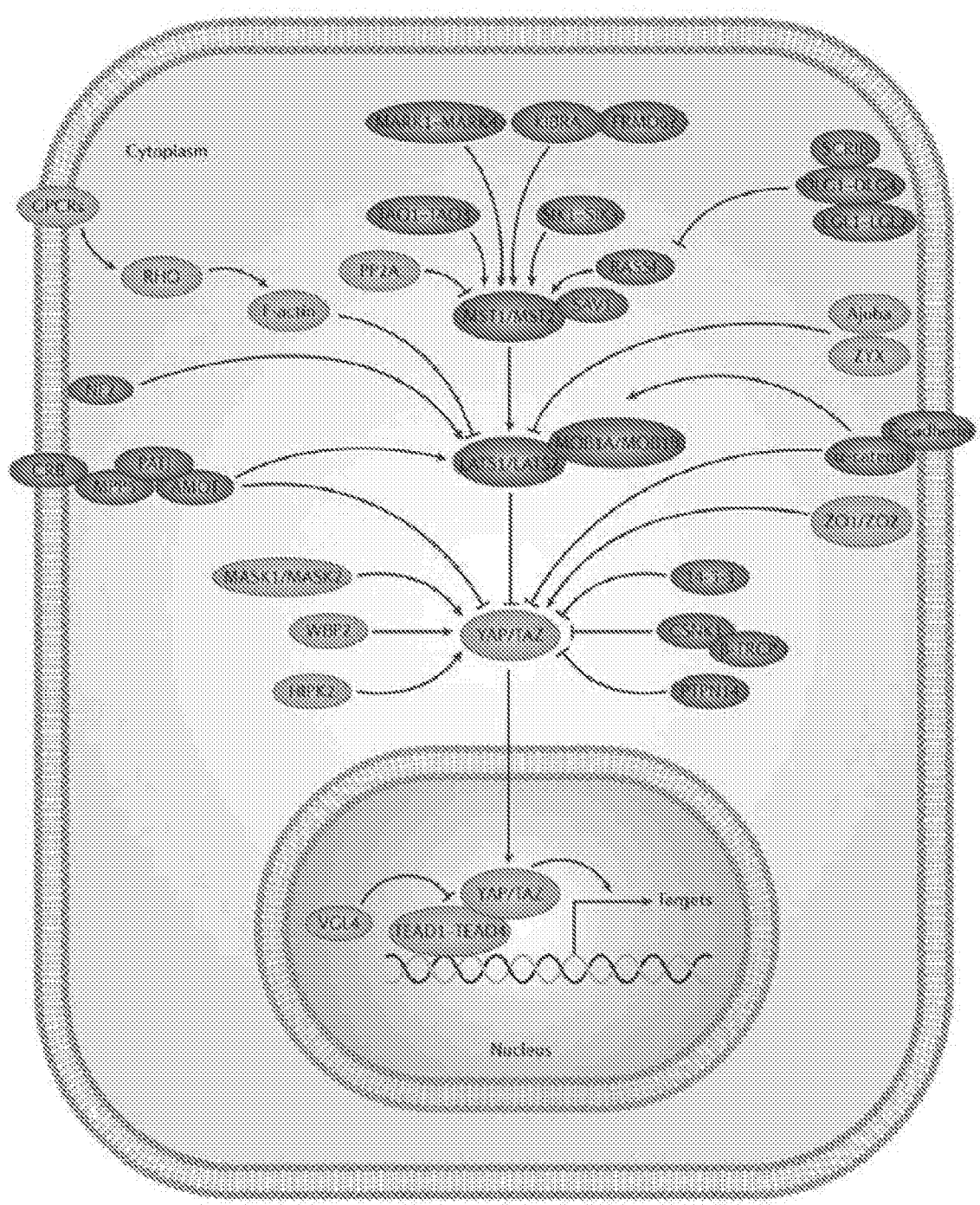
FIG. 1 illustrates a schematic representation of the Hippo signaling network. Hippo pathway components shaded in dark gray indicate components that inhibit YAP/TAZ activity. Hippo pathway components shaded in light gray indicate components that promote YAP/TAZ activity. Pointed and blunt arrowheads indicate activating and inhibitory interactions, respectively. Abbreviations: α-CAT (α-Catenin), AJUB (Ajuba), AMOT (Angiomotin), β-TRCP (β-transducing repeat containing protein), CK1 (Casein Kinase 1), CRB (Crumbs), E-CAD (E-cadherin), EX (Expanded), GPCR (G-protein coupled receptor), HIPK (Homeodomain interacting protein kinase), KIBRA (Kidney brain), LATS (Large tumor suppressor), LGL (Lethal giant larvae), MASK (Multiple ankyrin single KH), MER (Merlin), MOB (Mps one binder), MST (Mammalian sterile 20 like), PALS (Protein Associated with Lin-7), PATJ (Pals1-associated tight junction protein), PP2A (Protein phosphatase 2A), PTPN14 (Protein tyrosine phosphatase non-receptor type 14), RASSF (Ras associated factor), SAV (Salvador), SCRIB (Scribble), SIK (Salt inducible kinase), TAO (Thousand and one amino acid protein), TAZ (transcriptional coactivator with PDZ-binding motif), TEAD (TEA domain protein), VGL4 (Vestigial-like 4), WBP2 (WW domain binding protein 2), YAP (Yes associated protein), ZO (Zonula occludens), ZYX (Zyxin).

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

As used herein, in some embodiments, ranges and amounts are expressed as "about" particular value or range. About also includes the exact amount. Hence "about 5 µL" means "about 5 µL" and also "5 µL." Generally, the term "about" includes an amount that is expected to be within experimental error.

The section headings used herein are for organizational purposes only and are not to be construed as limiting the subject matter described.

As used herein, the terms "individual(s)", "subject(s)" and "patient(s)" mean any mammal. In some embodiments, the mammal is a human. In some embodiments, the mammal is a non-human. None of the terms require or are limited to situations characterized by the supervision (e.g. constant or intermittent) of a health care worker (e.g. a doctor, a registered nurse, a nurse practitioner, a physician's assistant, an orderly, or a hospice worker).

As used in the specification and appended claims, unless specified to the contrary, the following terms have the meaning indicated below.

"Amino" refers to the —$NH_2$ radical.
"Cyano" refers to the —CN radical.
"Nitro" refers to the —$NO_2$ radical.
"Oxa" refers to the —O— radical.
"Oxo" refers to the =O radical.
"Thioxo" refers to the =S radical.
"Imino" refers to the =N—H radical.
"Oximo" refers to the =N—OH radical.
"Alkyl" refers to a straight or branched hydrocarbon chain radical consisting solely of carbon and hydrogen atoms, containing no unsaturation, having from one to fifteen carbon atoms (e.g., $C_1$-$C_{15}$ alkyl). In certain embodiments, an alkyl comprises one to thirteen carbon atoms (e.g., $C_1$-$C_{13}$ alkyl). In certain embodiments, an alkyl comprises one to eight carbon atoms (e.g., $C_1$-$C_8$ alkyl). In other embodiments, an alkyl comprises one to five carbon atoms (e.g., $C_1$-$C_5$ alkyl). In other embodiments, an alkyl comprises one to four carbon atoms (e.g., $C_1$-$C_4$ alkyl). In other embodiments, an alkyl comprises one to three carbon atoms (e.g., $C_1$-$C_3$ alkyl). In other embodiments, an alkyl comprises one to two carbon atoms (e.g., $C_1$-$C_2$ alkyl). In other embodiments, an alkyl comprises one carbon atom (e.g., $C_1$ alkyl). In other embodiments, an alkyl comprises five to fifteen carbon atoms (e.g., $C_5$-$C_{15}$ alkyl). In other embodiments, an alkyl comprises five to eight carbon atoms (e.g., $C_5$-$C_8$ alkyl). In other embodiments, an alkyl comprises two to five carbon atoms (e.g., $C_2$-$C_5$ alkyl). In other embodiments, an alkyl comprises three to five carbon atoms (e.g., $C_3$-$C_5$ alkyl). In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). The alkyl is attached to the rest of the molecule by a single bond. Unless stated otherwise specifically in the specification, an alkyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)O$R^a$, —C(O)N($R^a$)$_2$, —N($R^a$)C(O)O$R^f$, —OC(O)—N$R^a R^f$, —N($R^a$)C(O)$R^f$, —N($R^a$)S(O)$_t R^f$ (where t is 1 or 2), —S(O)$_t$O$R^a$ (where t is 1 or 2), —S(O)$_t R^f$ (where t is 1 or 2), and —S(O)$_t$N($R^a$)$_2$ (where t is 1 or 2), where each $R^a$ is independently hydrogen, alkyl, fluoroalkyl, carbocyclyl, carbocyclylalkyl, aryl, aralkyl, heterocyclyl, heterocyclylalkyl, heteroaryl, or heteroarylalkyl, and each $R^f$ is independently alkyl, fluoroalkyl, carbocyclyl, carbocyclylalkyl, aryl, aralkyl, heterocyclyl, heterocyclylalkyl, heteroaryl, or heteroarylalkyl.

"Alkoxy" refers to a radical bonded through an oxygen atom of the formula —O-alkyl, where alkyl is an alkyl chain as defined above.

"Alkenyl" refers to a straight or branched hydrocarbon chain radical group consisting solely of carbon and hydrogen atoms, containing at least one carbon-carbon double bond, and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise specifically in the specification, an alkenyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)O$R^a$, —C(O)N($R^a$)$_2$, —N($R^a$)C(O)O$R^f$, —OC(O)—N$R^a R^f$, —N($R^a$)C(O)$R^f$, —N($R^a$)S(O)$_t R^f$ (where t is 1 or 2), —S(O)$_t$O$R^a$ (where t is 1 or 2), —S(O)$_t R^f$ (where t is 1 or 2), and —S(O)$_t$N($R^a$)$_2$ (where t is 1 or 2), where each $R^a$ is independently hydrogen, alkyl, fluoroalkyl, carbocyclyl, carbocyclylalkyl, aryl, aralkyl, heterocyclyl, heterocyclylalkyl, heteroaryl, or heteroarylalkyl, and each $R^f$ is independently alkyl, fluoroalkyl, carbocyclyl, carbocyclylalkyl, aryl, aralkyl, heterocyclyl, heterocyclylalkyl, heteroaryl, or heteroarylalkyl.

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise specifically in the specification, an alkynyl group is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)O$R^a$, —C(O)N($R^a$)$_2$, —N($R^a$)C(O)O$R^f$, —OC(O)—N$R^a R^f$, —N($R^a$)C(O)$R^f$, —N($R^a$)S(O)$_t R^f$ (where t is 1 or 2), —S(O)$_t$O$R^a$ (where t is 1 or 2), —S(O)$_t R^f$ (where t is 1 or 2), and —S(O)$_t$N($R^a$)$_2$ (where t is 1 or 2), where each $R^a$ is independently hydrogen, alkyl, fluoroalkyl, carbocyclyl, carbocyclylalkyl, aryl, aralkyl, heterocyclyl, heterocyclylalkyl, heteroaryl, or heteroarylalkyl, and each $R^f$ is independently alkyl, fluoroalkyl, carbocyclyl, carbocyclylalkyl, aryl, aralkyl, heterocyclyl, heterocyclylalkyl, heteroaryl, or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. In some embodiments, the points of attachment of the alkylene chain to the rest of the molecule and to the radical group are through one carbon in the alkylene chain or through any two carbons within the chain. In certain embodiments, an alkylene comprises one to eight carbon atoms (e.g., $C_1$-$C_8$ alkylene). In other embodiments, an alkylene comprises one to five carbon atoms (e.g., $C_1$-$C_5$ alkylene). In other embodiments, an alkylene comprises one to four carbon atoms (e.g., $C_1$-$C_4$ alkylene). In other embodiments, an alkylene comprises one to three carbon atoms (e.g., $C_1$-$C_3$ alkylene). In other embodiments, an alkylene comprises one to two carbon atoms (e.g., $C_1$-$C_2$ alkylene). In other embodiments, an alkylene comprises one carbon atom (e.g., $C_1$ alkylene). In other embodiments, an alkylene comprises five to eight carbon atoms (e.g., $C_5$-$C_8$ alkylene). In other embodiments, an alkylene comprises two to five carbon atoms (e.g., $C_2$-$C_5$ alkylene). In other embodiments, an alkylene comprises three to five carbon atoms (e.g., $C_3$-$C_5$ alkylene). Unless stated otherwise specifically in the specification, an alkylene chain is optionally substituted by one or more of the following substituents: halo, cyano, nitro, oxo, thioxo, imino, oximo, trimethylsilanyl, —$OR^a$, —$SR^a$, —OC(O)—$R^a$, —$N(R^a)_2$, —C(O)$R^a$, —C(O)O$R^a$, —C(O)N($R^a$)$_2$, —N($R^a$)C(O)O$R^f$, —OC(O)—N$R^a R^f$, —N($R^a$)C(O)$R^f$, —N($R^a$)S(O)$_t R^f$ (where t is 1 or 2), —S(O)$_t$O$R^a$ (where t is 1 or 2), —S(O)$_t R^f$ (where t is 1 or 2), and —S(O)$_t$N($R^a$)$_2$ (where t is 1 or 2), where each $R^a$ is independently hydrogen, alkyl, fluoroalkyl, carbocyclyl, carbocyclylalkyl, aryl, aralkyl, heterocyclyl, heterocyclylalkyl, heteroaryl, or heteroarylalkyl, and each $R^f$ is independently alkyl, fluoroalkyl, carbocyclyl, carbocyclylalkyl, aryl, aralkyl, heterocyclyl, heterocyclylalkyl, heteroaryl, or heteroarylalkyl.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon from five to eighteen carbon atoms, where at least one of the rings in the ring system is fully unsaturated, i.e., it contains a cyclic, delocalized (4n+2) π-electron system in accordance with the Hückel theory. The ring system from which aryl groups are derived include, but are not limited to, groups such as benzene, fluorene, indane, indene, tetralin, and naphthalene. Unless stated otherwise specifically in the specification, the term "aryl" or the prefix "ar-" (such as in "aralkyl") is meant to include aryl radicals optionally substituted by one or more substituents independently selected from alkyl, alkenyl, alkynyl, halo, fluoroalkyl, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—CN, —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—$C(O)R^a$, —$R^b$—C(O)$OR^a$, —$R^b$—C(O)$N(R^a)_2$, —$R^b$—O—$R^c$—C(O)$N(R^a)_2$, —$R^b$—$N(R^a)C(O)OR^a$, —$R^b$—$N(R^a)$ $C(O)R^a$, —$R^b$—N$(R^a)S(O)_tR^a$ (where t is 1 or 2), —$R^b$—$S(O)_tOR^a$ (where t is 1 or 2), —$R^b$—$S(O)_tR^a$ (where t is 1 or 2), and —$R^b$—S$(O)_tN(R^a)_2$ (where t is 1 or 2), where each $R^a$ is independently hydrogen, alkyl, fluoroalkyl, cycloalkyl, cycloalkylalkyl, aryl (optionally substituted with one or more halo groups), aralkyl, heterocyclyl, heterocyclylalkyl, heteroaryl, or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Aryloxy" refers to a radical bonded through an oxygen atom of the formula —O-aryl, where aryl is as defined above.

"Aralkyl" refers to a radical of the formula —$R^c$-aryl where $R^c$ is an alkylene chain as defined above, for example, methylene, ethylene, and the like. The alkylene chain part of the aralkyl radical is optionally substituted as described above for an alkylene chain. The aryl part of the aralkyl radical is optionally substituted as described above for an aryl group.

"Aralkenyl" refers to a radical of the formula —$R^d$-aryl where $R^d$ is an alkenylene chain as defined above. The aryl part of the aralkenyl radical is optionally substituted as described above for an aryl group. The alkenylene chain part of the aralkenyl radical is optionally substituted as defined above for an alkenylene group.

"Aralkynyl" refers to a radical of the formula —$R^e$-aryl, where $R^e$ is an alkynylene chain as defined above. The aryl part of the aralkynyl radical is optionally substituted as described above for an aryl group. The alkynylene chain part of the aralkynyl radical is optionally substituted as defined above for an alkynylene chain.

"Carbocyclyl" refers to a stable non-aromatic monocyclic or polycyclic hydrocarbon radical consisting solely of carbon and hydrogen atoms, and in some embodiments, include fused or bridged ring systems, having from three to fifteen carbon atoms. In certain embodiments, a carbocyclyl comprises three to ten carbon atoms. In other embodiments, a carbocyclyl comprises five to seven carbon atoms. The carbocyclyl is attached to the rest of the molecule by a single bond. In some embodiments, the carbocyclyl is saturated, (i.e., containing single C—C bonds only) or unsaturated (i.e., containing one or more double bonds or triple bonds.) A fully saturated carbocyclyl radical is also referred to as "cycloalkyl." Examples of monocyclic cycloalkyls include, e.g., cyclopropyl, cyclobutyl, cyclopentyl, cyclohexyl, cycloheptyl, and cyclooctyl. In certain embodiments, a cycloalkyl comprises three to eight carbon atoms (e.g., $C_3$-$C_8$ cycloalkyl). In other embodiments, a cycloalkyl comprises three to seven carbon atoms (e.g., $C_3$-$C_7$ cycloalkyl). In other embodiments, a cycloalkyl comprises three to six carbon atoms (e.g., $C_3$-$C_6$ cycloalkyl). In other embodiments, a cycloalkyl comprises three to five carbon atoms (e.g., $C_3$-$C_5$ cycloalkyl). In other embodiments, a cycloalkyl comprises three to four carbon atoms (e.g., $C_3$-$C_4$ cycloalkyl). An unsaturated carbocyclyl is also referred to as "cycloalkenyl." Examples of monocyclic cycloalkenyls include, e.g., cyclopentenyl, cyclohexenyl, cycloheptenyl, and cyclooctenyl. Polycyclic carbocyclyl radicals include, for example, adamantyl, norbornyl (i.e., bicyclo[2.2.1]heptanyl), norbornenyl, decalinyl, 7,7-dimethyl-bicyclo[2.2.1] heptanyl, and the like. Unless otherwise stated specifically in the specification, the term "carbocyclyl" is meant to include carbocyclyl radicals that are optionally substituted by one or more substituents independently selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —CN, —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—$C(O)R^a$, —$R^b$—C(O)$OR^a$, —$R^b$—C(O)$N(R^a)_2$, —$R^b$—O—$R^c$—C(O)$N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tOR^a$ (where t is 1 or 2), —$R^b$—$S(O)_tR^a$ (where t is 1 or 2), and —$R^b$—$S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl, or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Carbocyclylalkyl" refers to a radical of the formula —$R^c$-carbocyclyl where $R^c$ is an alkylene chain as defined above. The alkylene chain and the carbocyclyl radical are optionally substituted as defined above.

"Halo" or "halogen" refers to bromo, chloro, fluoro, or iodo substituents.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like. In some embodiments, the alkyl part of the fluoroalkyl radical is optionally substituted as defined above for an alkyl group.

"Heterocyclyl" or "heterocycle" refers to a stable 3- to 18-membered non-aromatic ring radical that comprises two to twelve carbon atoms and from one to six heteroatoms selected from nitrogen, oxygen, and sulfur. Unless stated otherwise specifically in the specification, the heterocyclyl radical is a monocyclic, bicyclic, tricyclic, or tetracyclic ring system, which include fused or bridged ring systems in some embodiments. The heteroatoms in the heterocyclyl radical are optionally oxidized. One or more nitrogen atoms, if present, are optionally quaternized. The heterocyclyl radical is partially or fully saturated. In some embodiments, the heterocyclyl is attached to the rest of the molecule through any atom of the ring(s). In some embodiments, the heterocyclyl is saturated, (i.e., containing single bonds only) or unsaturated (i.e., containing one or more double bonds or triple bonds.) A fully saturated heterocyclyl radical is also referred to as "heterocycloalkyl." Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "heterocyclyl" is meant to include heterocyclyl radicals as defined above that are optionally substituted by one or more substituents selected from alkyl, alkenyl, alkynyl, halo, fluoroalkyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —CN, —$R^b$—CN, —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—$C(O)R^a$, —$R^b$—C(O)O $R^a$, —$R^b$—C(O)N$(R^a)_2$, —$R^b$—O—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tOR^a$ (where t is 1 or 2), —$R^b$—$S(O)_tR^a$ (where t is 1 or 2), and —$R^b$—$S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl, or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"Heteroalkyl" refers to an alkyl group in which one or more skeletal atoms of the alkyl are selected from an atom other than carbon, e.g., oxygen, nitrogen (e.g. —NH—, —N(alkyl)-, sulfur, or combinations thereof. A heteroalkyl is attached to the rest of the molecule at a carbon atom of the heteroalkyl. In one aspect, a heteroalkyl is a $C_1$-$C_6$heteroalkyl. In some embodiments, the alkyl part of the heteroalkyl radical is optionally substituted as defined for an alkyl group.

"Heterocyclylalkyl" refers to a radical of the formula —$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkyl radical is optionally substituted as defined above for an alkylene chain. The heterocyclyl part of the heterocyclylalkyl radical is optionally substituted as defined above for a heterocyclyl group.

"Heterocyclylalkoxy" refers to a radical bonded through an oxygen atom of the formula —O—$R^c$-heterocyclyl where $R^c$ is an alkylene chain as defined above. If the heterocyclyl is a nitrogen-containing heterocyclyl, the heterocyclyl is optionally attached to the alkyl radical at the nitrogen atom. The alkylene chain of the heterocyclylalkoxy radical is optionally substituted as defined above for an alkylene chain. The heterocyclyl part of the heterocyclylalkoxy radical is optionally substituted as defined above for a heterocyclyl group.

"Heteroaryl" refers to a radical derived from a 3- to 18-membered aromatic ring radical that comprises two to seventeen carbon atoms and from one to six heteroatoms selected from nitrogen, oxygen, and sulfur. As used herein, in some embodiments, the heteroaryl radical is a monocyclic, bicyclic, tricyclic, or tetracyclic ring system, wherein at least one of the rings in the ring system is fully unsaturated, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzooxazolyl, benzo[d]thiazolyl, benzothiadiazolyl, benzo[6][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a, 7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, triazolyl, tetrazolyl, triazinyl, thieno[2,3-d]pyrimidinyl, thieno[3,2-d]pyrimidinyl, thieno[2,3-c]pyridinyl, and thiophenyl (i.e. thienyl). Unless stated otherwise specifically in the specification, the term "heteroaryl" is meant to include heteroaryl radicals as defined above which are optionally substituted by one or more substituents selected from alkyl, alkenyl, alkynyl, halo, fluoroalkyl, haloalkenyl, haloalkynyl, oxo, thioxo, cyano, nitro, optionally substituted aryl, optionally substituted aralkyl, optionally substituted aralkenyl, optionally substituted aralkynyl, optionally substituted carbocyclyl, optionally substituted carbocyclylalkyl, optionally substituted heterocyclyl, optionally substituted heterocyclylalkyl, optionally substituted heteroaryl, optionally substituted heteroarylalkyl, —$R^b$—$OR^a$, —$R^b$—OC(O)—$R^a$, —$R^b$—OC(O)—$OR^a$, —$R^b$—OC(O)—$N(R^a)_2$, —$R^b$—$N(R^a)_2$, —$R^b$—$C(O)R^a$, —$R^b$—$C(O)OR^a$, —$R^b$—C(O)N$(R^a)_2$, —$R^b$—O—$R^c$—$C(O)N(R^a)_2$, —$R^b$—$N(R^a)C(O)OR^a$, —$R^b$—$N(R^a)C(O)R^a$, —$R^b$—$N(R^a)S(O)_tR^a$ (where t is 1 or 2), —$R^b$—$S(O)_tOR^a$ (where t is 1 or 2), —$R^b$—$S(O)_tR^a$ (where t is 1 or 2), and —$R^b$—$S(O)_tN(R^a)_2$ (where t is 1 or 2), where each $R^a$ is independently hydrogen, alkyl, fluoroalkyl, cycloalkyl, cycloalkylalkyl, aryl, aralkyl, heterocyclyl, heterocyclylalkyl, heteroaryl, or heteroarylalkyl, each $R^b$ is independently a direct bond or a straight or branched alkylene or alkenylene chain, and $R^c$ is a straight or branched alkylene or alkenylene chain, and where each of the above substituents is unsubstituted unless otherwise indicated.

"N-heteroaryl" refers to a heteroaryl radical as defined above containing at least one nitrogen and where the point of attachment of the heteroaryl radical to the rest of the molecule is through a nitrogen atom in the heteroaryl radical. An A-heteroaryl radical is optionally substituted as described above for heteroaryl radicals.

"C-heteroaryl" refers to a heteroaryl radical as defined above and where the point of attachment of the heteroaryl radical to the rest of the molecule is through a carbon atom in the heteroaryl radical. A C-heteroaryl radical is optionally substituted as described above for heteroaryl radicals.

"Heteroaryloxy" refers to radical bonded through an oxygen atom of the formula —O-heteroaryl, where heteroaryl is as defined above.

"Heteroarylalkyl" refers to a radical of the formula —$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkyl radical is optionally substituted as defined above for an alkylene chain. The heteroaryl part of the heteroarylalkyl radical is optionally substituted as defined above for a heteroaryl group.

"Heteroarylalkoxy" refers to a radical bonded through an oxygen atom of the formula —O—$R^c$-heteroaryl, where $R^c$ is an alkylene chain as defined above. If the heteroaryl is a nitrogen-containing heteroaryl, the heteroaryl is optionally attached to the alkyl radical at the nitrogen atom. The alkylene chain of the heteroarylalkoxy radical is optionally substituted as defined above for an alkylene chain. The heteroaryl part of the heteroarylalkoxy radical is optionally substituted as defined above for a heteroaryl group.

In some embodiments, the compounds disclosed herein contain one or more asymmetric centers and thus give rise to enantiomers, diastereomers, and other stereoisomeric forms that are defined, in terms of absolute stereochemistry, as (R)- or (S)—. Unless stated otherwise, it is intended that all stereoisomeric forms of the compounds disclosed herein are contemplated by this disclosure. When the compounds described herein contain alkene double bonds, and unless specified otherwise, it is intended that this disclosure includes both E and Z geometric isomers (e.g., cis or trans). Likewise, all possible isomers, as well as their racemic and optically pure forms, and all tautomeric forms are also intended to be included. The term "geometric isomer" refers to E or Z geometric isomers (e.g., cis or trans) of an alkene double bond. The term "positional isomer" refers to structural isomers around a central ring, such as ortho-, meta-, and para-isomers around a benzene ring.

A "tautomer" refers to a molecule wherein a proton shift from one atom of a molecule to another atom of the same molecule is possible. The compounds presented herein, in certain embodiments, exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

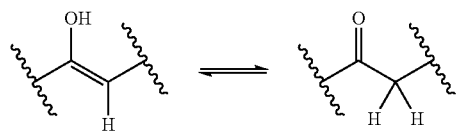

-continued

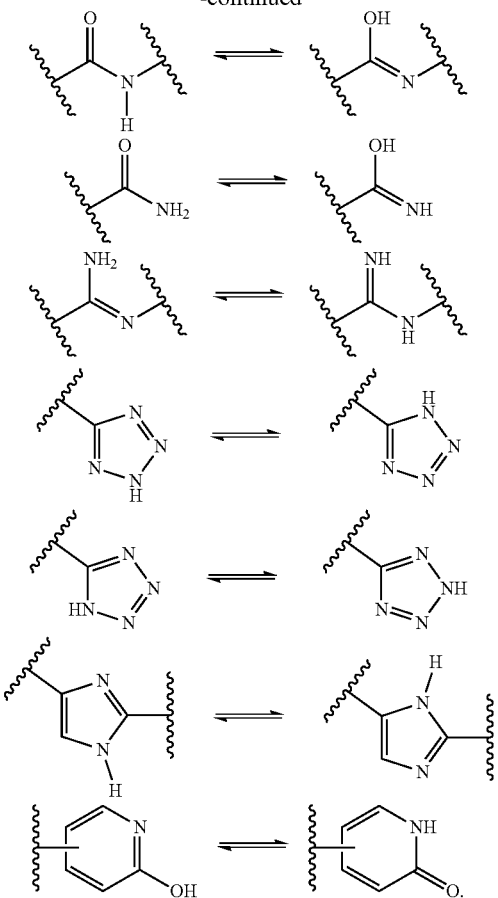

"Optional" or "optionally" means that a subsequently described event or circumstance may or may not occur and that the description includes instances when the event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts. A pharmaceutically acceptable salt of any one of the compounds described herein is intended to encompass any and all pharmaceutically suitable salt forms. Pharmaceutically acceptable salts of the compounds described herein are optionally pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66: 1-19 (1997), which is hereby incorporated by reference in its entirety). In some embodiments, acid addition salts of basic compounds are prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. In some embodiments, pharmaceutically acceptable base addition salts are formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts, and the like. Salts derived from organic bases include, but are not limited to, salts of primary, secondary, and tertiary amines, substituted amines including naturally occurring substituted amines, cyclic amines, and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins, and the like. See Berge et al., supra.

As used herein, "treatment" or "treating" or "palliating" or "ameliorating" are used interchangeably herein. These terms refer to an approach for obtaining beneficial or desired results including, but not limited to, therapeutic benefit and/or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient is afflicted with the underlying disorder in some embodiments. For prophylactic benefit, in some embodiments, the compositions are administered to a patient at risk of developing a particular disease, or to a patient reporting one or more of the physiological symptoms of a disease, even though a diagnosis of this disease has not been made.

"Prodrug" is meant to indicate a compound that is converted under physiological conditions or by solvolysis to a biologically active compound described herein. Thus, the term "prodrug" refers to a precursor of a biologically active compound that is pharmaceutically acceptable. In some embodiments, a prodrug is inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers, which release the active compound in vivo when such prodrug is administered to a mammalian subject. In some embodiments, prodrugs of an active compound, as described herein, are prepared by modifying functional groups present in the active compound in such a way that the modifications are cleaved, either in routine manipulation or in vivo, to the parent active compound. Prodrugs include compounds wherein a hydroxy, amino, or mercapto group is bonded to any group that, when the prodrug of the active compound is administered to a mammalian subject, cleaves to form a free hydroxy, free amino, or free mercapto group, respectively. Examples of prodrugs include, but are not limited to, acetate, formate, and benzoate derivatives of alcohol or amine functional groups in the active compounds and the like.

Compounds

In some embodiments, the compounds disclosed herein are bicyclic compounds.

In one aspect, the present disclosure provides a compound of Formula (I), or a pharmaceutically acceptable salt or a pharmaceutically acceptable solvate thereof:

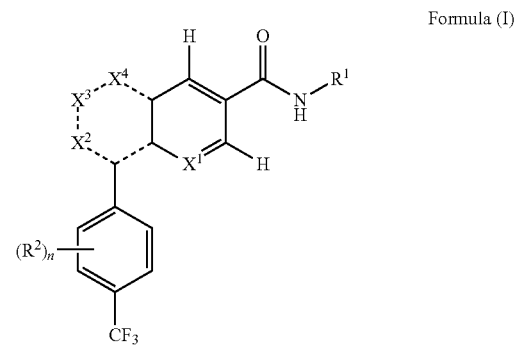

Formula (I)

wherein, each $X^1$ and $X^2$ is independently N, $NR^X$, C(=O), or $CR^X$;

each $X^3$ and $X^4$ is independently N, $NR^X$, C(=O), or $CR^X$; or if both $X^3$ and $X^4$ are each independently $NR^X$ or $CR^X$, then the two $R^X$ are taken together with the intervening atoms to which they are attached to form a 5-membered heterocyclic ring;

each $R^X$ is independently hydrogen, halogen, nitro, oxo, thioxo, imino, oximo, —$OR^3$, —$SR^3$, —CN, —C(=O)$R^2$, —S(=O)$R^3$, —S(=O)$_2R^3$, —N($R^3$)$_2$, —$NR^3$S(=O)$_2R^3$, —$NR^3$C(=O)$R^3$, —$NR^3$C(=O)$OR^3$, substituted or unsubstituted $C_1$-$C_6$ alkyl, substituted or unsubstituted $C_1$-$C_6$haloalkyl, substituted or unsubstituted $C_2$-$C_4$alkenyl, substituted or unsubstituted C₂-C₄alkynyl, substituted or unsubstituted C₁-C₆heteroalkyl, substituted or unsubstituted C₃-C₁₀cycloalkyl, substituted or unsubstituted C₂-C₁₀heterocycloalkyl, substituted or unsubstituted aralkyl, substituted or unsubstituted aryl, or substituted or unsubstituted heteroaryl;

R¹ is substituted or unsubstituted C₁-C₆alkyl, substituted or unsubstituted C₁-C₆haloalkyl, substituted or unsubstituted C₂-C₄alkenyl, substituted or unsubstituted C₂-C₄alkynyl, substituted or unsubstituted C₃-C₁₀cycloalkyl, substituted or unsubstituted C₂-C₁₀heterocycloalkyl, substituted or unsubstituted C₁-C₆heteroalkyl, or —S(=O)₂R⁴;

each R² is independently —N₃, —CN, —OR³, —SR³, —S(=O)₂R³, —N(R³)₂, —C(=O)OR³, substituted or unsubstituted C₁-C₆alkyl, substituted or unsubstituted C₁-C₆haloalkyl, substituted or unsubstituted C₁-C₆heteroalkyl, substituted or unsubstituted C₃-C₁₀cycloalkyl, substituted or unsubstituted C₂-C₁₀heterocycloalkyl, substituted or unsubstituted aralkyl, substituted or unsubstituted aryl, or substituted or unsubstituted heteroaryl;

each R³ is independently hydrogen, substituted or unsubstituted C₁-C₆alkyl, substituted or unsubstituted C₁-C₆haloalkyl, substituted or unsubstituted C₁-C₆heteroalkyl, substituted or unsubstituted C₃-C₁₀cycloalkyl, substituted or unsubstituted C₂-C₁₀heterocycloalkyl, substituted or unsubstituted aralkyl, substituted or unsubstituted aryl, or substituted or unsubstituted heteroaryl;

R⁴ is substituted or unsubstituted C₁-C₆alkyl, substituted or unsubstituted C₁-C₆haloalkyl, substituted or unsubstituted C₃-C₁₀cycloalkyl, or —NH₂;

each -- is independently a single or double bond; and
n is 0, 1, 2, 3, or 4.

In some embodiments of a compound of Formula (I), each X¹ and X² is CR$^X$. In some embodiments of a compound of Formula (I), X¹ is N and X² is CR$^X$. In some embodiments of a compound of Formula (I), X¹ is CR$^X$ and X² is N. In some embodiments of a compound of Formula (I), each X¹ and X² is N.

In some embodiments of a compound of Formula (I), each X³ and X⁴ is CR$^X$. In some embodiments of a compound of Formula (I), X³ is N and X⁴ is CR$^X$. In some embodiments of a compound of Formula (I), X³ is CR$^X$ and X⁴ is N. In some embodiments of a compound of Formula (I), each X³ and X⁴ is N.

In some embodiments of a compound of Formula (I), each R$^X$ is independently hydrogen, halogen, —OR³, —SR³, —CN, —S(=O)R³, —S(=O)₂R³, —N(R³)₂, —NR³S(=O)₂R³, —NR³C(=O)R³, substituted or unsubstituted C₁-C₆alkyl, substituted or unsubstituted C₁-C₆haloalkyl, substituted or unsubstituted C₂-C₄alkenyl, substituted or unsubstituted C₂-C₄alkynyl, or substituted or unsubstituted C₁-C₆heteroalkyl; and each R³ is independently hydrogen, substituted or unsubstituted C₁-C₆alkyl, substituted or unsubstituted C₁-C₆haloalkyl, substituted or unsubstituted C₁-C₆heteroalkyl, substituted or unsubstituted C₃-C₁₀cycloalkyl, or substituted or unsubstituted C₂-C₁₀heterocycloalkyl. In some embodiments of a compound of Formula (I), each R$^X$ is independently hydrogen, halogen, —OR³, —SR³, —S(=O)R³, —S(=O)₂R³, —N(R³)₂, —NR³S(=O)₂R³, —NR³C(=O)R³, substituted or unsubstituted C₁-C₆alkyl, substituted or unsubstituted C₁-C₆haloalkyl, or substituted or unsubstituted C₂-C₄alkynyl; and each R³ is independently hydrogen, substituted or unsubstituted C₁-C₆haloalkyl, or substituted or unsubstituted C₃-C₁₀cycloalkyl. In some embodiments of a compound of Formula (I), each R$^X$ is independently hydrogen, F, Cl, Br, I, —CH₃, —CH₂CH₃, —CH₂OH, —CH₂CH₂OH, —CH₂CN, —CH₂CO₂H, —CH₂CO₂CH₃, —CH₂CO₂CH₂CH₃, —CH₂C(=O)NH₂, —CH₂C(=O)NHCH₃, —CH₂C(=O)N(CH₃)₂, —CH₂NH₂, —CH₂NHCH₃, —CH₂N(CH₃)₂, —CH₂F, —CHF₂, —CF₃, —CH=CH₂, —C≡CH, cyclopropyloxy, cyclobutyloxy, cyclopentyloxy, oxetanyloxy, tetrahydrofuranyloxy, tetrahydropyranyloxy, azetidinyl, pyrrolidinyl, tetrazolyl, —CN, —OH, —OCH₃, —OCH₂CH₃, —OCH₂CH₂OH, —OCH₂CN, —OCF₃, —CO₂H, —CO₂CH₃, —CO₂CH₂CH₃, —C(=O)NH₂, —C(=O)NHCH₃, —C(=O)N(CH₃)₂, —NH₂, —NHCH₃, —N(CH₃)₂, —NHC(=O)CH₃, —N(CH₃)C(=O)CH₃, —NHC(=O)OCH₃, —N(CH₃)C(=O)OCH₃, —S(=O)CH₃, —S(=O)₂CH₃, —NHS(=O)₂CH₃, or —N(CH₃)S(=O)₂CH₃. In some embodiments of a compound of Formula (I), each R$^X$ is independently hydrogen, F, Cl, Br, I, —CH₃, —CH₂CH₃, cyclopropyl, —C≡CH, —OH, —OCH₃, —OCH₂CH₃, —OCF₃, —SCH₃, cyclopropyl oxy, —NH₂, —NHC(=O)CH₃, —N(CH₃)C(=O)CH₃, —NHS(=O)₂CH₃, —N(CH₃)S(=O)₂CH₃, —S(=O)CH₃, or —S(=O)₂CH₃. In some embodiments of a compound of Formula (I), each R$^X$ is independently hydrogen, halogen, —OCH₃, —OCH₂CH₃, cyclopropyl oxy, or —OCF₃. In some embodiments of a compound of Formula (I), each R$^X$ is independently hydrogen or halogen. In some embodiments of a compound of Formula (I), each R$^X$ is independently hydrogen, F, or Cl. In some embodiments of a compound of Formula (I), each R$^X$ is hydrogen.

In some embodiments of a compound of Formula (I), each X³ and X⁴ is independently NR$^X$ or CR$^X$, wherein the two R$^X$ are taken together with the intervening atoms to which they are attached to form a 5-membered heterocyclic ring. In some embodiments of a compound of Formula (I), when the two R$^X$ are taken together with the intervening atoms to which they are attached to form a 5-membered heterocyclic ring, the 5-membered heterocyclic ring is selected from:

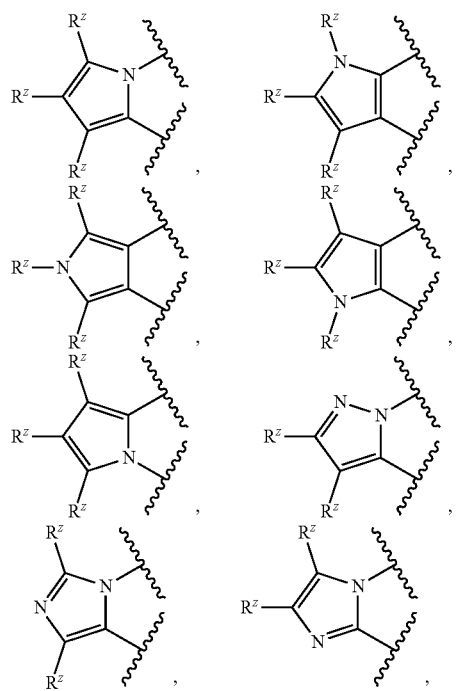

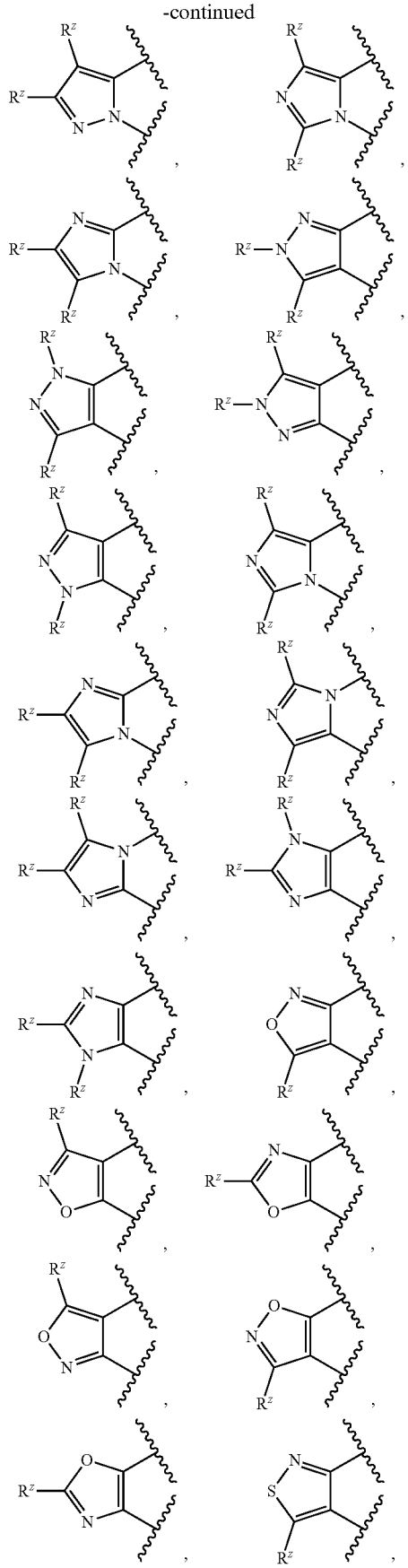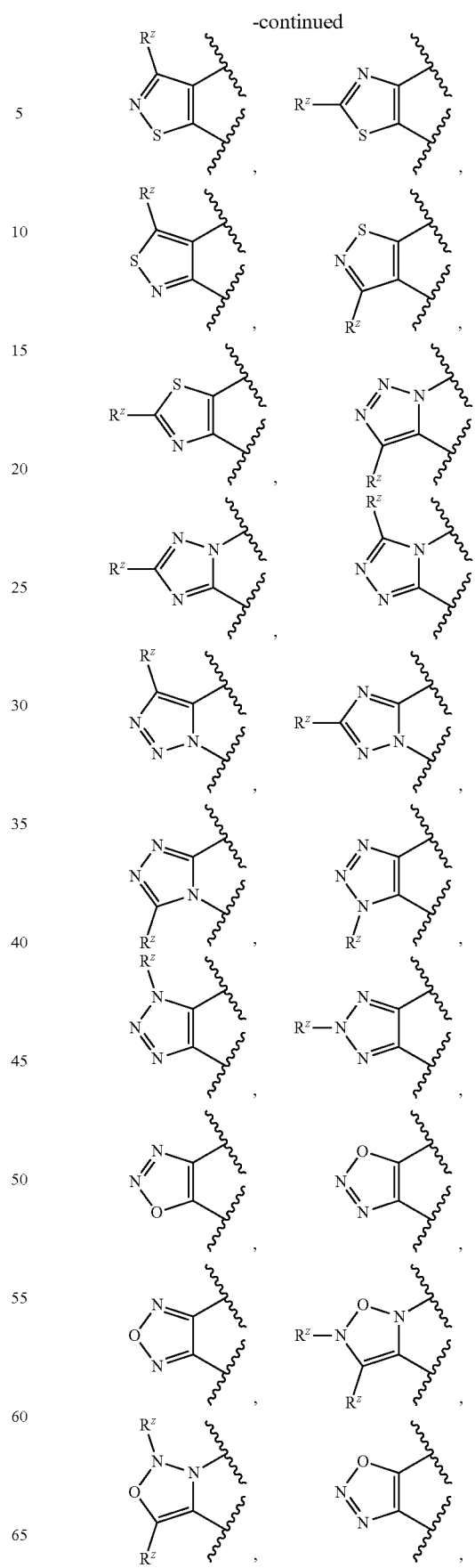

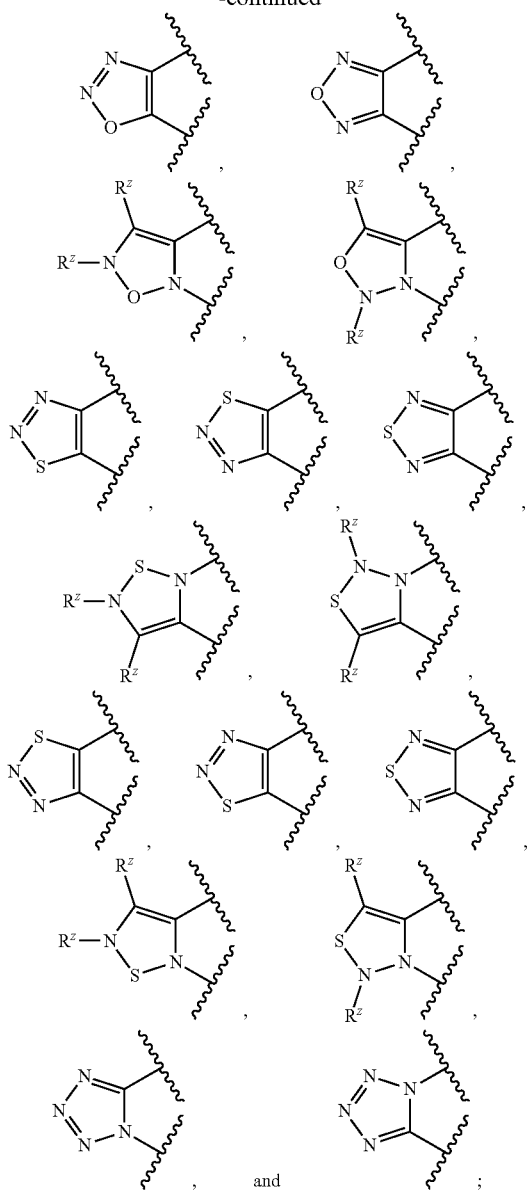

wherein each $R^z$ is independently hydrogen, halogen, —CN, —OR³, —SR³, —S(=O)₂R³, —N(R³)₂, —C(=O)OR³, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl; and each $R^3$ is independently hydrogen, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, or substituted or unsubstituted $C_2$-$C_{10}$heterocycloalkyl.

In some embodiments of a compound of Formula (I), when the two $R^X$ are taken together with the intervening atoms to which they are attached to form a 5-membered heterocyclic ring, the 5-membered heterocyclic ring is selected from:

wherein
each $R^z$ is independently hydrogen, halogen, —CN, —OR³, —SR³, —S(=O)₂R³, —N(R³)₂, —C(=O)OR³, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl; and
each $R^3$ is independently hydrogen, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, or substituted or unsubstituted $C_2$-$C_{10}$heterocycloalkyl.

In some embodiments of a compound of Formula (I), when the two $R^X$ are taken together with the intervening atoms to which they are attached to form a 5-membered heterocyclic ring, the 5-membered heterocyclic ring is selected from:

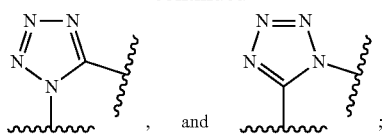

wherein each $R^z$ is independently hydrogen, F, Cl, —CN, or —NH$_2$.

In some embodiments of a compound of Formula (I), when the two $R^X$ are taken together with the intervening atoms to which they are attached to form a 5-membered heterocyclic ring, the 5-membered heterocyclic ring is selected from:

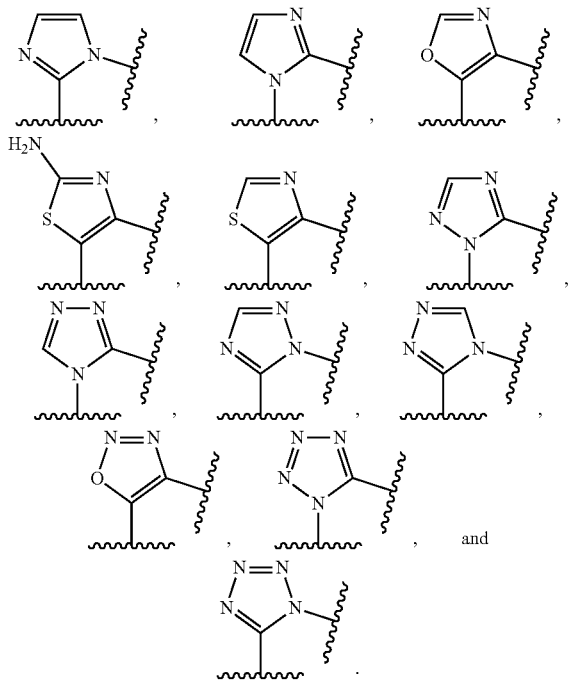

In some embodiments of a compound of Formula (I), $R^1$ is substituted or unsubstituted $C_1$-$C_6$alkyl. In some embodiments of a compound of Formula (I), $R^1$ is $C_1$-$C_6$alkyl substituted with substituted or unsubstituted $C_3$-$C_{10}$cycloalkyl or substituted or unsubstituted $C_2$-$C_{10}$heterocycloalkyl. In some embodiments of a compound of Formula (I), $R^1$ is $C_1$-$C_6$alkyl substituted with 5-membered heterocyclic ring containing at least one N atom. In some embodiments of a compound of Formula (I), $R^1$ is $C_1$-$C_6$alkyl substituted with 5-membered heterocyclic ring selected from substituted or unsubstituted pyrrolyl, substituted or unsubstituted imidazolyl, substituted or unsubstituted pyrazolyl, substituted or unsubstituted oxazolyl, substituted or unsubstituted isoxazolyl, substituted or unsubstituted thiazolyl, substituted or unsubstituted isothiazolyl, substituted or unsubstituted triazolyl, substituted or unsubstituted tetrazolyl, substituted or unsubstituted oxadiazolyl, substituted or unsubstituted thiadiazolyl, and substituted or unsubstituted dithiazolyl. In some embodiments of a compound of Formula (I), $R^1$ is $C_1$-$C_6$alkyl substituted with 5-membered heterocyclic ring selected from:

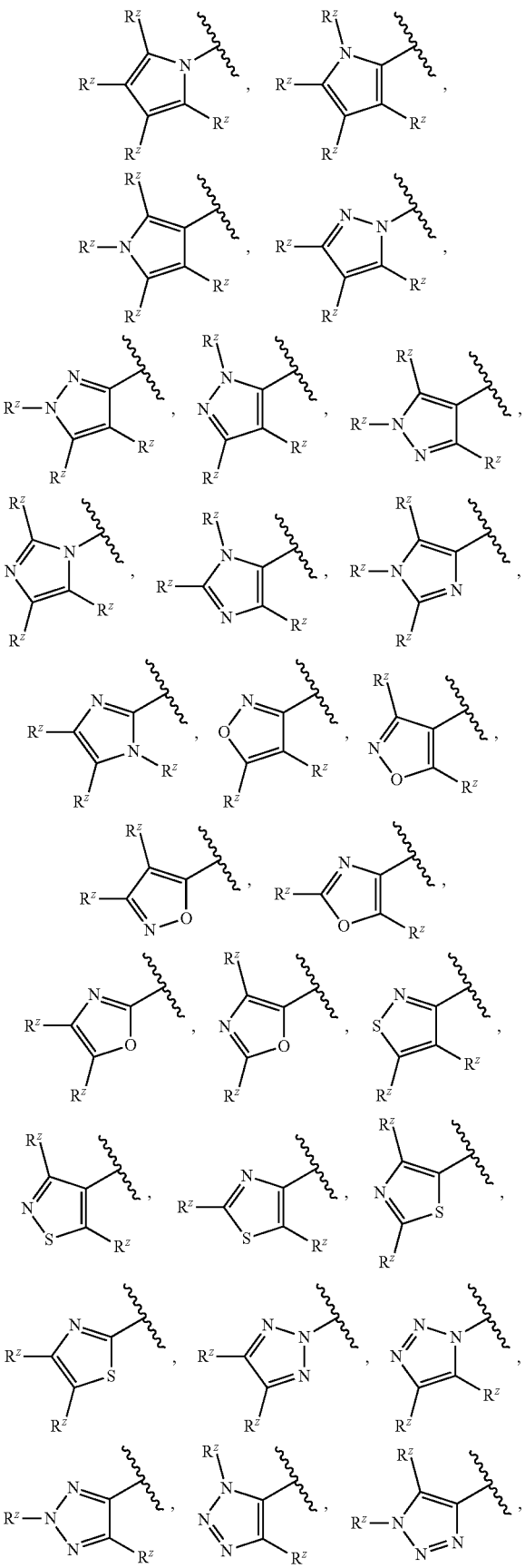

-continued

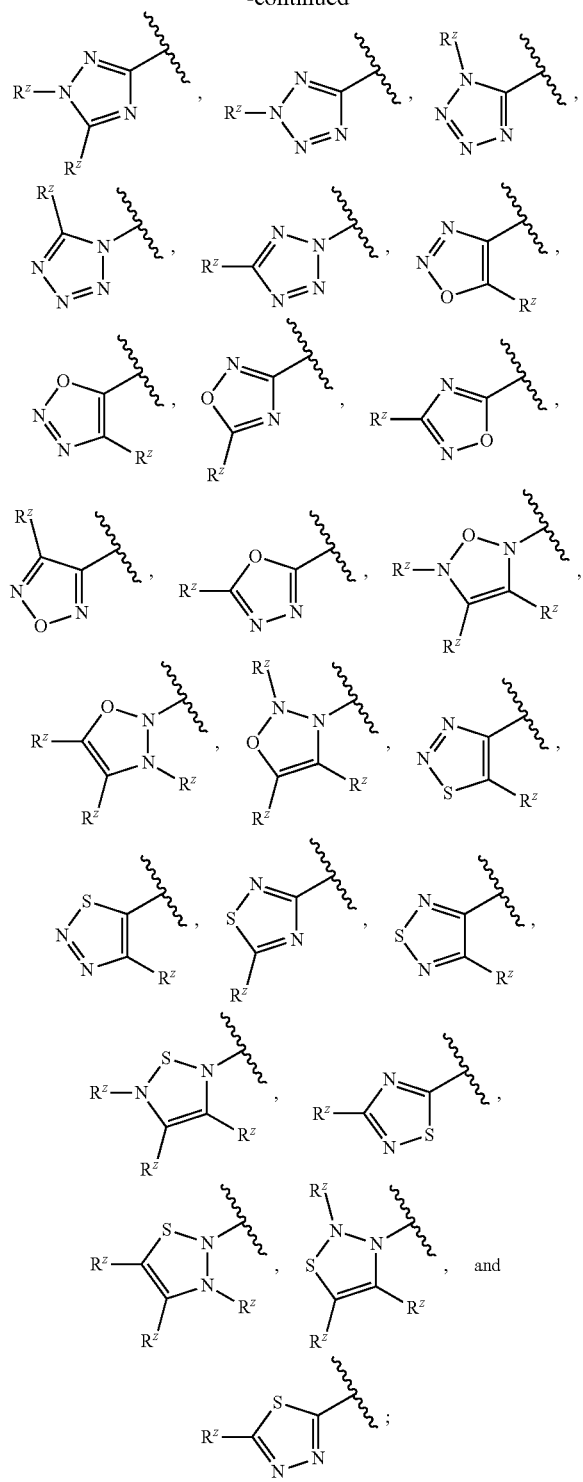

wherein
each $R^z$ is independently hydrogen, halogen, —CN, —OR$^3$, —SR$^3$, —S(=O)$_2$R$^3$, —N(R$^3$)$_2$, —C(=O)OR$^3$, substituted or unsubstituted C$_1$-C$_6$alkyl, substituted or unsubstituted C$_1$-C$_6$haloalkyl, substituted or unsubstituted C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted aralkyl, substituted or unsubstituted aryl, or substituted or unsubstituted heteroaryl; and each $R^3$ is independently hydrogen, substituted or unsubstituted C$_1$-C$_6$alkyl, substituted or unsubstituted C$_1$-C$_6$haloalkyl, substituted or unsubstituted C$_1$-C$_6$heteroalkyl, substituted or unsubstituted C$_3$-C$_{10}$cycloalkyl, or substituted or unsubstituted C$_2$-C$_{10}$heterocycloalkyl.

In some embodiments of a compound of Formula (I), $R^1$ is C$_1$-C$_6$alkyl substituted with a substituted or unsubstituted monocyclic 6-membered heteroaryl ring containing at least one N atom. In some embodiments of a compound of Formula (I), $R^1$ is C$_1$-C$_6$alkyl substituted with a substituted or unsubstituted monocyclic 6-membered heteroaryl ring containing 1 or 2 N atoms. In some embodiments of a compound of Formula (I), $R^1$ is C$_1$-C$_6$alkyl substituted with 6-membered heteroaryl ring selected from substituted or unsubstituted pyridinyl, substituted or unsubstituted pyrazinyl, substituted or unsubstituted pyrimidinyl, or substituted or unsubstituted pyridazinyl. In some embodiments of a compound of Formula (I), $R^1$ is C$_1$-C$_6$alkyl substituted with 6-membered heteroaryl ring selected from

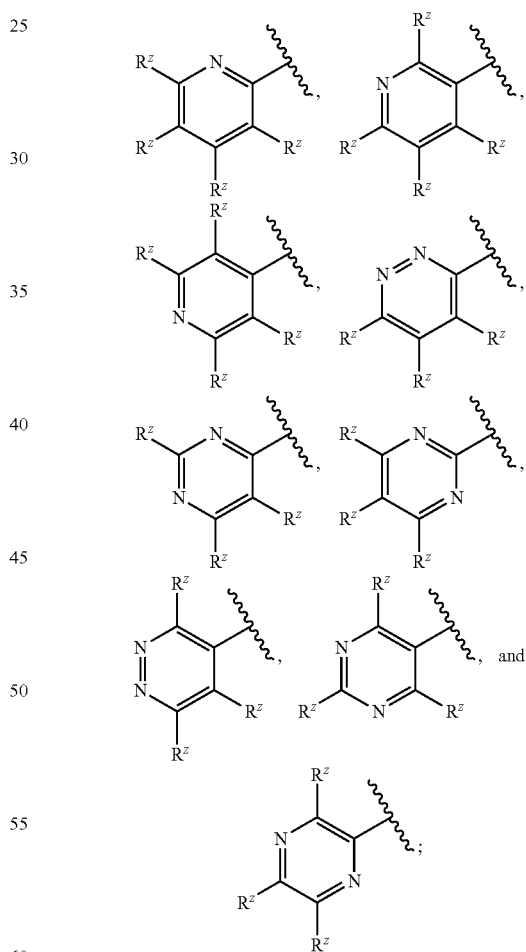

wherein
each $R^z$ is independently hydrogen, halogen, —CN, —OR$^3$, —SR$^3$, —S(=O)$_2$R$^3$, —N(R$^3$)$_2$, —C(=O)OR$^3$, substituted or unsubstituted C$_1$-C$_6$alkyl, substituted or unsubstituted C$_1$-C$_6$haloalkyl, substituted or unsubstituted C$_1$-C$_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl; and each $R^3$ is independently hydrogen, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, or substituted or unsubstituted $C_2$-$C_{10}$heterocycloalkyl.

In some embodiments of a compound of Formula (I), $R^1$ is $C_1$-$C_6$alkyl substituted with halogen, —CN, —$OR^3$, —$SR^3$, —S(=O) $R^3$, —S(=O)$_2$$R^3$, —N($R^3$)$_2$, —C(=O)$OR^3$, —C(=O)N($R^3$)$_2$, —$CR^3$=C($R^3$)$_2$, —C≡$CR^3$, substituted or unsubstituted $C_3$-$C_{10}$cycloalkyl, substituted or unsubstituted $C_2$-$C_{10}$heterocycloalkyl, or substituted or unsubstituted aryl; each $R^3$ is independently hydrogen, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, or substituted or unsubstituted $C_2$-$C_{10}$heterocycloalkyl.

In some embodiments of a compound of Formula (I), n is 0, 1, 2, or 3. In some embodiments of a compound of Formula (I), n is 0, 1, or 2. In some embodiments of a compound of Formula (I), n is 1 or 2. In some embodiments of a compound of Formula (I), n is 0 or 1. In some embodiments of a compound of Formula (I), n is 0.

In another aspect, the present disclosure provides a compound of Formula (Ia), or a pharmaceutically acceptable salt or a pharmaceutically acceptable solvate thereof:

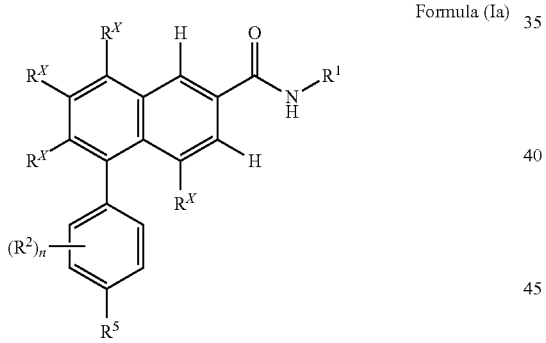

Formula (Ia)

wherein, each $R^X$ is independently hydrogen, halogen, nitro, oxo, thioxo, imino, oximo, —$OR^3$, —$SR^3$, —CN, —C(=O)$R^2$, —S(=O)$R^3$, —S(=O)$_2$$R^3$, —N($R^3$)$_2$, —$NR^3$S(=O)$_2$$R^3$, —$NR^3$C(=O)$R^3$, —$NR^3$C(=O)$OR^3$, substituted or unsubstituted $C_1$-$C_6$ alkyl, substituted or unsubstituted $C_1$-$C_6$haloalkyl, substituted or unsubstituted $C_2$-$C_4$alkenyl, substituted or unsubstituted $C_2$-$C_4$alkynyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;

$R^1$ is substituted or unsubstituted $C_1$-$C_6$alkyl, substituted or unsubstituted $C_1$-$C_6$haloalkyl, substituted or unsubstituted $C_2$-$C_4$alkenyl, substituted or unsubstituted $C_2$-$C_4$alkynyl, substituted or unsubstituted $C_3$-$C_{10}$cycloalkyl, substituted or unsubstituted $C_2$-$C_{10}$heterocycloalkyl, substituted or unsubstituted $C_1$-$C_6$heteroalkyl, or —S(=O)$_2$$R^4$;

each $R^2$ is independently —$N_3$, —CN, —$OR^3$, —$SR^3$, —S(=O)$_2$$R^3$, —N($R^3$)$_2$, —C(=O)$OR^3$, F, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;

each $R^3$ is independently hydrogen, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;

$R^4$ is substituted or unsubstituted $C_1$-$C_6$alkyl, substituted or unsubstituted $C_1$-$C_6$haloalkyl, substituted or unsubstituted $C_3$-$C_{10}$cycloalkyl, or —$NH_2$;

$R^5$ is F, —$SF_5$, substituted or unsubstituted $C_1$-$C_6$alkyl, substituted or unsubstituted $C_1$-$C_6$haloalkyl, substituted or unsubstituted $C_1$-$C_6$alkyloxy, or substituted or unsubstituted $C_1$-$C_6$alkylthio;

each -- is independently a single or double bond; and n is 0, 1, 2, 3, or 4.

In some embodiments of a compound of Formula (Ia), each $R^X$ is independently hydrogen, halogen, —OH, —$NH_2$, —$CH_3$, —$CH_2CH_3$, cyclopropyl, —$CF_3$, —$OCH_3$, —$OCH_2CH_3$, cyclopropyloxy, or —$OCF_3$;

$R^1$ is substituted or unsubstituted $C_1$-$C_6$alkyl, wherein if $C_1$-$C_6$alkyl is substituted, then it is substituted with 1 or 2 substituents each independently selected from —OH, —$NH_2$, azetidinyl, pyridyl, and aminopyridyl;

$R^2$ is F;

$R^5$ is —$CF_3$; and n is 0 or 1.

In some embodiments of a compound of Formula (Ia), each $R^X$ is independently hydrogen, F, Cl, Br, I, —$CH_3$, —$CH_2CH_3$, cyclopropyl, —OH, —$OCH_3$, —$OCH_2CH_3$, —$OCF_3$, —$SCH_3$, cyclopropyloxy, —$NH_2$, —NHC(=O)$CH_3$, —N($CH_3$)C(=O)$CH_3$, —NHS(=O)$_2$$CH_3$, —N($CH_3$)S(=O)$_2$$CH_3$, —S(=O)$CH_3$, or —S(=O)$_2$$CH_3$. In some embodiments of a compound of Formula (Ia), each $R^X$ is independently hydrogen, F, Cl, —$CH_3$, —$CH_2CH_3$, cyclopropyl, —OH, —$OCH_3$, —$OCH_2CH_3$, —$OCH_2F$, —$OCHF_2$, —$OCF_3$, —$SCH_3$, cyclopropyloxy, —$NH_2$, —NHC(=O)$CH_3$, —N($CH_3$)C(=O)$CH_3$, —NHS(=O)$_2$$CH_3$, —N($CH_3$)S(=O)$_2$$CH_3$, —S(=O)$CH_3$, or —S(=O)$_2$$CH_3$. In some embodiments of a compound of Formula (Ia), each $R^X$ is independently hydrogen, halogen, —OH, —$NH_2$, —$CH_3$, —$CH_2CH_3$, cyclopropyl, —$CF_3$, —$OCH_3$, —$OCH_2CH_3$, cyclopropyloxy, or —$OCF_3$. In some embodiments of a compound of Formula (Ia), each $R^X$ is independently hydrogen, F, Cl, —CN, —$CH_3$, —OH, —$OCH_3$, —$OCH_2F$, —$OCHF_2$, or —$OCF_3$. In some embodiments of a compound of Formula (Ia), each $R^X$ is independently hydrogen, halogen, —$OCH_3$, —$OCH_2CH_3$, cyclopropyloxy, or —$OCF_3$. In some embodiments of a compound of Formula (Ia), each $R^X$ is independently hydrogen, F, Cl, or —$CH_3$. In some embodiments of a compound of Formula (Ia), each $R^X$ is hydrogen.

In some embodiments of a compound of Formula (Ia), $R^1$ is substituted or unsubstituted $C_1$-$C_6$alkyl. In some embodiments of a compound of Formula (Ia), $R^1$ is $C_1$-$C_6$alkyl substituted with substituted or unsubstituted $C_3$-$C_{10}$cycloalkyl or substituted or unsubstituted $C_2$-$C_{10}$heterocycloalkyl. In some embodiments of a compound of Formula (Ia), $R^1$ is $C_1$-$C_6$alkyl substituted with a substituted or unsubstituted monocyclic 6-membered heteroaryl ring containing at least one N atom. In some embodiments of a compound of Formula (Ia), $R^1$ is $C_1$-$C_6$alkyl substituted with a substituted or unsubstituted monocyclic 6-membered heteroaryl ring containing 1 or 2 N atoms. In some embodiments of a compound of Formula (Ia), $R^1$ is $C_1$-$C_6$alkyl substituted with 6-membered heteroaryl ring selected from substituted or unsubstituted pyridinyl, substituted or unsubstituted pyrazinyl, substituted or unsubstituted pyrimidinyl, or substituted or unsubstituted pyridazinyl. In some embodiments of a compound of Formula (Ia), $R^1$ is $C_1$-$C_6$alkyl substituted with substituted or unsubstituted pyridinyl. In some embodiments of a compound of Formula (Ia), $R^1$ is $C_1$-$C_6$alkyl substituted with substituted or unsubstituted pyridin-2-yl, substituted or unsubstituted pyridin-3-yl, or substituted or unsubstituted pyridin-4-yl. In some embodiments of a compound of Formula (Ia), $R^1$ is $C_1$-$C_6$alkyl substituted with pyridin-2-yl, pyridin-3-yl, or pyridin-4-yl. In some embodiments of a compound of Formula (Ia), $R^1$ is $C_1$-$C_6$alkyl substituted with substituted or unsubstituted pyridin-2-yl or substituted or unsubstituted pyridin-3-yl. In some embodiments of a compound of Formula (Ia), $R^1$ is $C_1$-$C_6$alkyl substituted with pyridin-2-yl or pyridin-3-yl substituted with 1, 2, or 3 substituents each independently selected from F, Cl, —OH, —CN, and —NH$_2$. In some embodiments of a compound of Formula (Ia), $R^1$ is $C_1$-$C_6$alkyl substituted with pyridin-2-yl or pyridin-3-yl substituted with —OH, —CN, or —NH$_2$. In some embodiments of a compound of Formula (Ia), $R^1$ is $C_1$-$C_6$alkyl substituted with pyridin-2-yl or pyridin-3-yl substituted with —NH$_2$. In some embodiments of a compound of Formula (Ia), $R^1$ is $C_1$-$C_6$alkyl substituted with 6-aminopyridin-2-yl or 2-aminopyridin-3-yl.

In some embodiments of a compound of Formula (Ia), $R^1$ is $C_1$-$C_6$alkyl substituted with 1, 2, 3, or 4 substituents each independently selected from halogen, —CN, —OR$^3$, —N(R$^3$)$_2$, —C(═O)OR$^3$, —C(═O)N(R$^3$)$_2$, substituted or unsubstituted $C_3$-$C_{10}$cycloalkyl, substituted or unsubstituted $C_2$-$C_{10}$heterocycloalkyl, substituted or unsubstituted aryl, or substituted or unsubstituted heteroaryl; wherein each R$^3$ is independently hydrogen, substituted or unsubstituted $C_1$-$C_6$alkyl, substituted or unsubstituted $C_1$-$C_6$haloalkyl, or substituted or unsubstituted $C_1$-$C_6$heteroalkyl, substituted or unsubstituted $C_3$-$C_{10}$cycloalkyl, or substituted or unsubstituted $C_2$-$C_{10}$heterocycloalkyl. In some embodiments of a compound of Formula (Ia), $R^1$ is $C_1$-$C_6$alkyl substituted with 1, 2, 3, or 4 substituents each independently selected from F, Cl, cyclopropyloxy, cyclobutyloxy, cyclopentyloxy, oxetanyloxy, tetrahydrofuranyloxy, tetrahydropyranyloxy, azetidinyl, pyrrolidinyl, pyridinyl, pyrimidinyl, —CN, —OH, —OCH$_3$, —OCH$_2$CH$_3$, —OCH$_2$CH$_2$OH, —OCH$_2$CN, —OCF$_3$, —CO$_2$H, —CO$_2$CH$_3$, —CO$_2$CH$_2$CH$_3$, —C(═O)NH$_2$, —C(═O)NHCH$_3$, —C(═O)N(CH$_3$)$_2$, —NH$_2$, —NHCH$_3$, —N(CH$_3$)$_2$, —NHC(═O)CH$_3$, —N(CH$_3$)C(═O)CH$_3$, —NHC(═O)OCH$_3$, —N(CH$_3$)C(═O)OCH$_3$, —S(═O)CH$_3$, —S(═O)$_2$CH$_3$, —NHS(═O)$_2$CH$_3$, or —N(CH$_3$)S(═O)$_2$CH$_3$. In some embodiments of a compound of Formula (Ia), $R^1$ is substituted or unsubstituted $C_1$-$C_6$alkyl, wherein if $C_1$-$C_6$alkyl is substituted, then it is substituted with 1 or 2 substituents each independently selected from —OH, —NH$_2$, azetidinyl, pyridyl, and aminopyridyl. In some embodiments of a compound of Formula (Ia), $R^1$ is $C_1$-$C_6$alkyl substituted with 1, 2, or 3 substituents each independently selected from F, Cl, azetidinyl, pyridinyl, —CN, —OH, —OCH$_3$, —OCF$_3$, or —NH$_2$. In some embodiments of a compound of Formula (Ia), $R^1$ is $C_1$-$C_6$alkyl substituted with azetidinyl, —OH or —NH$_2$. In some embodiments of a compound of Formula (Ia), $R^1$ is $C_1$-$C_6$alkyl substituted with —OH or —NH$_2$. In some embodiments of a compound of Formula (Ia), $R^1$ is $C_1$-$C_6$alkyl substituted with azetidinyl. In some embodiments of a compound of Formula (Ia), $R^1$ is $C_1$-$C_6$alkyl substituted with substituted or unsubstituted pyridinyl and —OH. In some embodiments of a compound of Formula (Ia), $R^1$ is $C_1$-$C_6$alkyl substituted with pyridinyl and —OH. In some embodiments of a compound of Formula (Ia), $R^1$ is $C_1$-$C_6$alkyl substituted with pyridin-2-yl and —OH.

In some embodiments of a compound of Formula (Ia), each $R^2$ is independently F, —CH$_3$, —CH$_2$CH$_3$, —OH, or —OCH$_3$. In some embodiments of a compound of Formula (Ia), each $R^2$ is independently F or —OCF$_3$. In some embodiments of a compound of Formula (Ia), each $R^2$ is F.

In some embodiments of a compound of Formula (Ia), $R^5$ is —F or —SF$_5$. In some embodiments of a compound of Formula (Ia), $R^5$ is —F. In some embodiments of a compound of Formula (Ia), $R^5$ is —SF$_5$. In some embodiments of a compound of Formula (Ia), $R^5$ is substituted or unsubstituted $C_1$-$C_4$haloalkyl, substituted $C_1$-$C_4$alkyloxy, or substituted $C_1$-$C_4$alkylthio. In some embodiments of a compound of Formula (Ia), $R^5$ is $C_1$-$C_6$haloalkyl, substituted $C_1$-$C_6$alkyloxy, or substituted $C_1$-$C_6$alkylthio. In some embodiments of a compound of Formula (Ia), $R^5$ is $C_1$-$C_4$haloalkyl. In some embodiments of a compound of Formula (Ia), $R^5$ is $C_1$-$C_4$alkyloxy, or $C_1$-$C_4$alkylthio, each independently substituted with one of more F. In some embodiments of a compound of Formula (Ia), $R^5$ is —CH$_2$F, —CHF$_2$, —CF$_3$, —CH$_2$CH$_2$F, —CH$_2$CHF$_2$, —CF$_2$CH$_3$, —CH$_2$CF$_3$, —OCH$_2$F, —OCHF$_2$, —OCF$_3$, —OCH$_2$CH$_2$F, —OCH$_2$CHF$_2$, —OCF$_2$CH$_3$, —OCH$_2$CF$_3$, —SCH$_2$F, —SCHF$_2$, —SCF$_3$, —SCH$_2$CH$_2$F, —SCH$_2$CHF$_2$, —SCF$_2$CH$_3$, or —SCH$_2$CF$_3$. In some embodiments of a compound of Formula (Ia), $R^5$ is —CHF$_2$, —CF$_3$, —OCHF$_2$, —OCF$_3$, —SCHF$_2$, or —SCF$_3$. In some embodiments of a compound of Formula (Ia), $R^5$ is —CF$_3$.

In some embodiments of a compound of Formula (Ia), n is 0, 1, 2, or 3. In some embodiments of a compound of Formula (Ia), n is 0, 1, or 2. In some embodiments of a compound of Formula (Ia), n is 1 or 2. In some embodiments of a compound of Formula (Ia), n is 0 or 1. In some embodiments of a compound of Formula (Ia), n is 0.

In another aspect, the present disclosure provides a compound of Formula (II), or a pharmaceutically acceptable salt or a pharmaceutically acceptable solvate thereof:

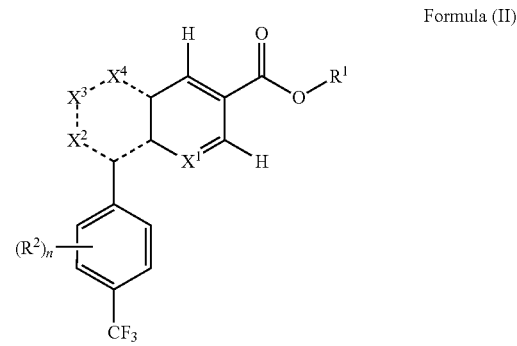

Formula (II)

wherein,
each $X^1$ and $X^2$ is independently N, $NR^X$, C(=O), or $CR^X$;
each $X^3$ and $X^4$ is independently N, $NR^X$, C(=O), or $CR^X$; or if both $X^3$ and $X^4$ are each independently $NR^X$ or $CR^X$, then the two $R^X$ are taken together with the intervening atoms to which they are attached to form a 5-membered heterocyclic ring;
each $R^X$ is independently hydrogen, halogen, nitro, oxo, thioxo, imino, oximo, —$OR^3$, —$SR^3$, —CN, —C(=O)$R^2$, —S(=O)$R^3$, —S(=O)$_2R^3$, —N($R^3$)$_2$, —$NR^3$S(=O)$_2R^3$, —$NR^3$C(=O)$R^3$, —$NR^3$C(=O)$OR^3$, substituted or unsubstituted $C_1$-$C_6$ alkyl, substituted or unsubstituted $C_1$-$C_6$haloalkyl, substituted or unsubstituted $C_2$-$C_4$alkenyl, substituted or unsubstituted $C_2$-$C_4$alkynyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;
$R^1$ is substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;
each $R^2$ is independently —$N_3$, —CN, —$OR^3$, —$SR^3$, —S(=O)$_2R^3$, —N($R^3$)$_2$, —C(=O)$OR^3$, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;
each $R^3$ is independently hydrogen, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;
$R^4$ is substituted or unsubstituted $C_1$-$C_6$alkyl, substituted or unsubstituted $C_3$-$C_{10}$cycloalkyl, or —$NH_2$;
each -- is independently a single or double bond; and
n is 0, 1, 2, 3, or 4.

In some embodiments of a compound of Formula (II), each $X^1$ and $X^2$ is $CR^X$. In some embodiments of a compound of Formula (II), $X^1$ is N and $X^2$ is $CR^X$. In some embodiments of a compound of Formula (II), $X^1$ is $CR^X$ and $X^2$ is N. In some embodiments of a compound of Formula (II), each $X^1$ and $X^2$ is N.

In some embodiments of a compound of Formula (II), each $X^3$ and $X^4$ is $CR^X$. In some embodiments of a compound of Formula (II), $X^3$ is N and $X^4$ is $CR^X$. In some embodiments of a compound of Formula (II), $X^3$ is $CR^X$ and $X^4$ is N. In some embodiments of a compound of Formula (II), each $X^3$ and $X^4$ is N. In some embodiments of a compound of Formula (II), $X^3$ is $NR^X$ and $X^4$ is C(=O).

In some embodiments of a compound of Formula (II), each $R^X$ is independently hydrogen, halogen, —$OR^3$, —$SR^3$, —CN, —S(=O)$R^3$, —S(=O)$_2R^3$, —N($R^3$)$_2$, —$NR^3$S(=O)$_2R^3$, —$NR^3$C(=O)$R^3$, substituted or unsubstituted $C_1$-$C_6$alkyl, substituted or unsubstituted $C_1$-$C_6$haloalkyl, substituted or unsubstituted $C_2$-$C_4$alkenyl, substituted or unsubstituted $C_2$-$C_4$alkynyl, or substituted or unsubstituted $C_1$-$C_6$heteroalkyl; and each $R^3$ is independently hydrogen, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, or substituted or unsubstituted $C_2$-$C_{10}$heterocycloalkyl. In some embodiments of a compound of Formula (II), each $R^X$ is independently hydrogen, halogen, —$OR^3$, —$SR^3$, —S(=O)$R^3$, —S(=O)$_2R^3$, —N($R^3$)$_2$, —$NR^3$S(=O)$_2R^3$, —$NR^3$C(=O)$R^3$, substituted or unsubstituted $C_1$-$C_6$alkyl, substituted or unsubstituted $C_1$-$C_6$haloalkyl, substituted or unsubstituted $C_2$-$C_4$alkynyl; and each $R^3$ is independently hydrogen, substituted or unsubstituted $C_1$-$C_6$alkyl, substituted or unsubstituted $C_1$-$C_6$haloalkyl, or substituted or unsubstituted $C_3$-$C_{10}$cycloalkyl. In some embodiments of a compound of Formula (II), each $R^X$ is independently hydrogen, F, Cl, Br, I, —$CH_3$, —$CH_2CH_3$, —$CH_2OH$, —$CH_2CH_2OH$, —$CH_2CN$, —$CH_2CO_2H$, —$CH_2CO_2CH_3$, —$CH_2CO_2CH_2CH_3$, —$CH_2C$(=O)$NH_2$, —$CH_2C$(=O)$NHCH_3$, —$CH_2C$(=O)$N(CH_3)_2$, —$CH_2NH_2$, —$CH_2NHCH_3$, —$CH_2N(CH_3)_2$, —$CH_2F$, —$CHF_2$, —$CF_3$, —CH=$CH_2$, —C≡CH, cyclopropyloxy, cyclobutyloxy, cyclopentyloxy, oxetanyloxy, tetrahydrofuranyloxy, tetrahydropyranyloxy, azetidinyl, pyrrolidinyl, tetrazolyl, —CN, —OH, —$OCH_3$, —$OCH_2CH_3$, —$OCH_2CH_2OH$, —$OCH_2CN$, —$OCF_3$, —$CO_2H$, —$CO_2CH_3$, —$CO_2CH_2CH_3$, —C(=O)$NH_2$, —C(=O)$NHCH_3$, —C(=O)$N(CH_3)_2$, —$NH_2$, —$NHCH_3$, —$N(CH_3)_2$, —NHC(=O)$CH_3$, —$N(CH_3)$C(=O)$CH_3$, —NHC(=O)$OCH_3$, —$N(CH_3)$C(=O)$OCH_3$, —S(=O)$CH_3$, —S(=O)$_2CH_3$, —NHS(=O)$_2CH_3$, or —$N(CH_3)$S(=O)$_2CH_3$. In some embodiments of a compound of Formula (II), each $R^X$ is independently hydrogen, Cl, —$CH_3$, —$CH_2CH_3$, —OH, or —$OCH_3$. In some embodiments of a compound of Formula (II), each $R^X$ is independently hydrogen, halogen, —$OCH_3$, —$OCH_2CH_3$, cyclopropyloxy, or —$OCF_3$. In some embodiments of a compound of Formula (II), each $R^X$ is independently hydrogen or halogen. In some embodiments of a compound of Formula (II), each $R^X$ is independently hydrogen, F, or Cl. In some embodiments of a compound of Formula (II), each $R^X$ is hydrogen.

In some embodiments of a compound of Formula (II), each $X^3$ and $X^4$ is independently $NR^X$ or $CR^X$, wherein the two $R^X$ are taken together with the intervening atoms to which they are attached to form a 5-membered heterocyclic ring. In some embodiments of a compound of Formula (II), when the two $R^X$ are taken together with the intervening atoms to which they are attached to form a 5-membered heterocyclic ring, the 5-membered heterocyclic ring is selected from:

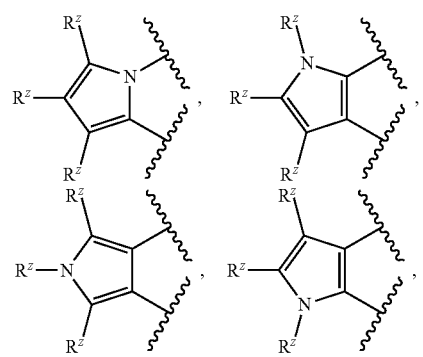

-continued
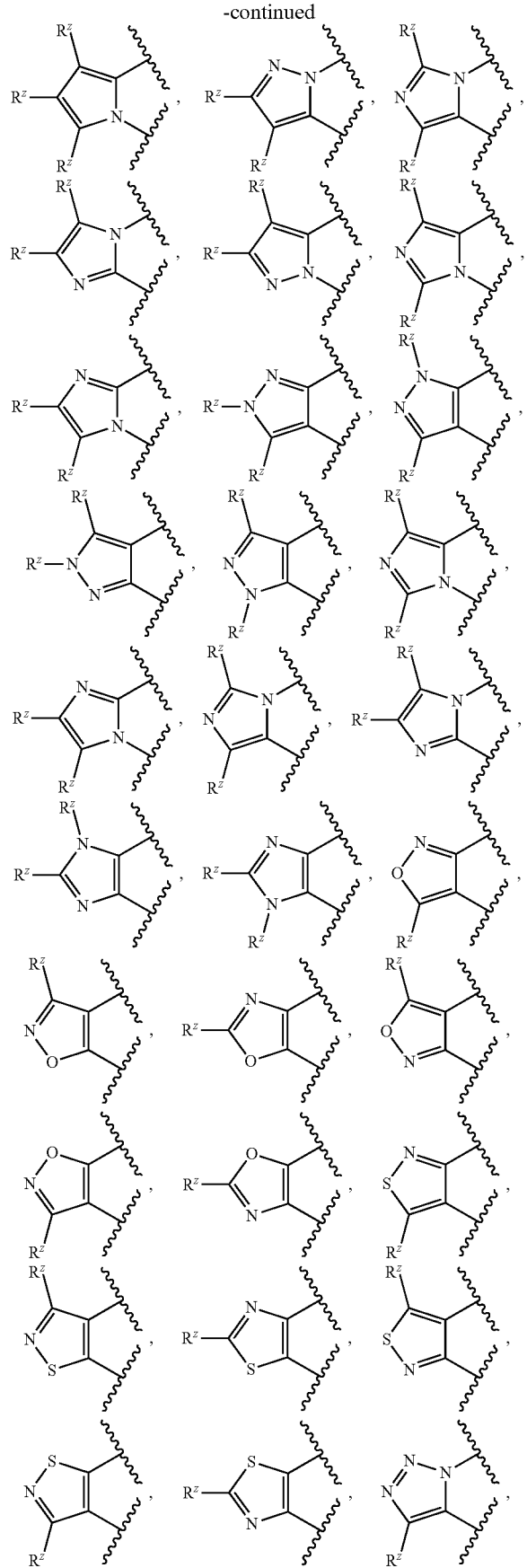
-continued
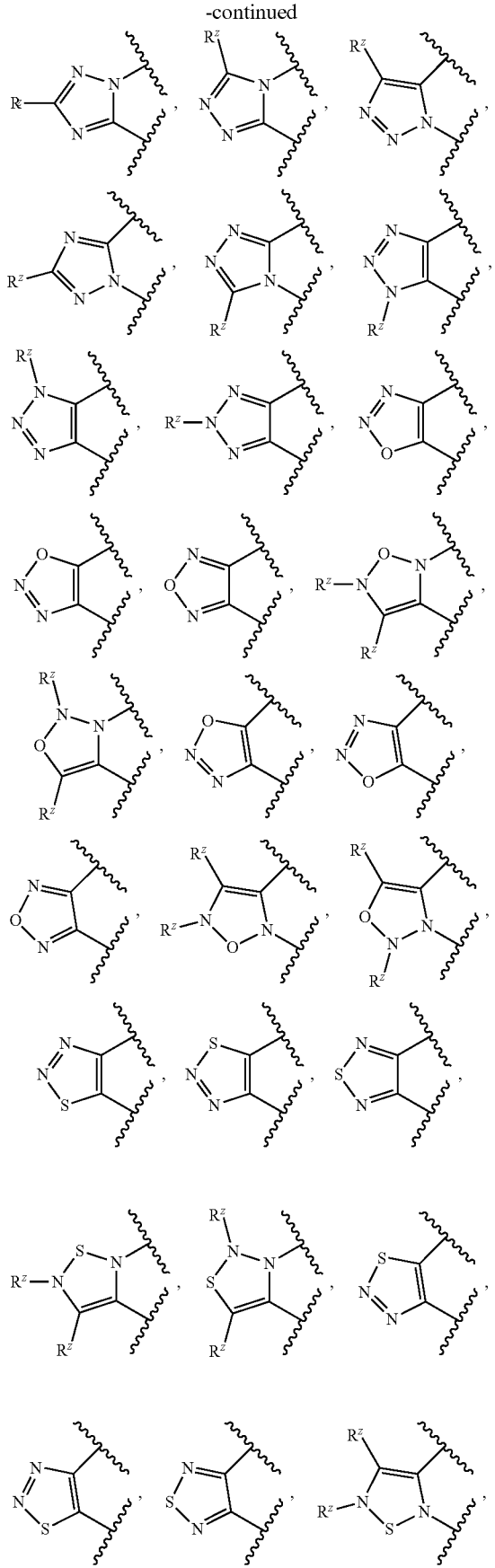

-continued

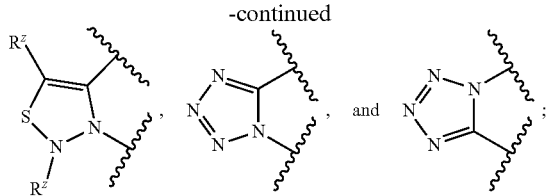

wherein
each $R^z$ is independently hydrogen, halogen, —CN, —OR$^3$, —SR$^3$, —S(=O)$_2$R$^3$, —N(R$^3$)$_2$, —C(=O)OR$^3$, substituted or unsubstituted C$_1$-C$_6$alkyl, substituted or unsubstituted C$_1$-C$_6$haloalkyl, substituted or unsubstituted C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted aralkyl, substituted or unsubstituted aryl, or substituted or unsubstituted heteroaryl; and each $R^3$ is independently hydrogen, substituted or unsubstituted C$_1$-C$_6$alkyl, substituted or unsubstituted C$_1$-C$_6$haloalkyl, substituted or unsubstituted C$_1$-C$_6$heteroalkyl, substituted or unsubstituted C$_3$-C$_{10}$cycloalkyl, or substituted or unsubstituted C$_2$-C$_{10}$heterocycloalkyl.

In some embodiments of a compound of Formula (II), when the two $R^X$ are taken together with the intervening atoms to which they are attached to form a 5-membered heterocyclic ring, the 5-membered heterocyclic ring is selected from:

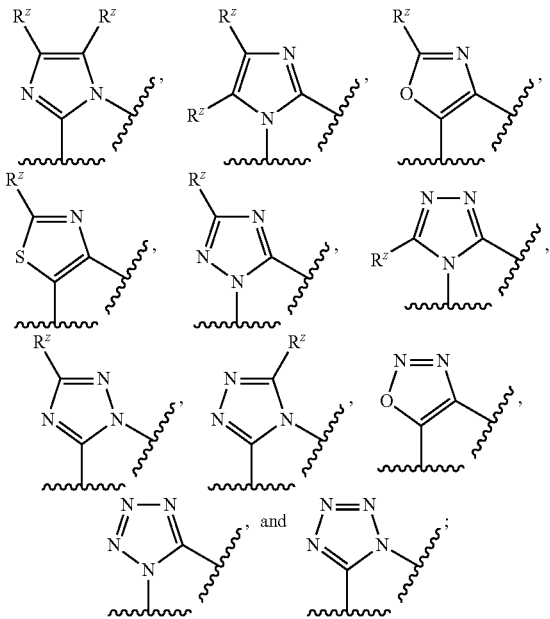

wherein
each $R^z$ is independently hydrogen, halogen, —CN, —OR$^3$, —SR$^3$, —S(=O)$_2$R$^3$, —N(R$^3$)$_2$, —C(=O)OR$^3$, substituted or unsubstituted C$_1$-C$_6$alkyl, substituted or unsubstituted C$_1$-C$_6$haloalkyl, substituted or unsubstituted C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted aralkyl, substituted or unsubstituted aryl, or substituted or unsubstituted heteroaryl; and each $R^3$ is independently hydrogen, substituted or unsubstituted C$_1$-C$_6$alkyl, substituted or unsubstituted C$_1$-C$_6$haloalkyl, substituted or unsubstituted C$_1$-C$_6$heteroalkyl, substituted or unsubstituted C$_3$-C$_{10}$cycloalkyl, or substituted or unsubstituted C$_2$-C$_{10}$heterocycloalkyl.

In some embodiments of a compound of Formula (II), when the two $R^X$ are taken together with the intervening atoms to which they are attached to form a 5-membered heterocyclic ring, the 5-membered heterocyclic ring is selected from:

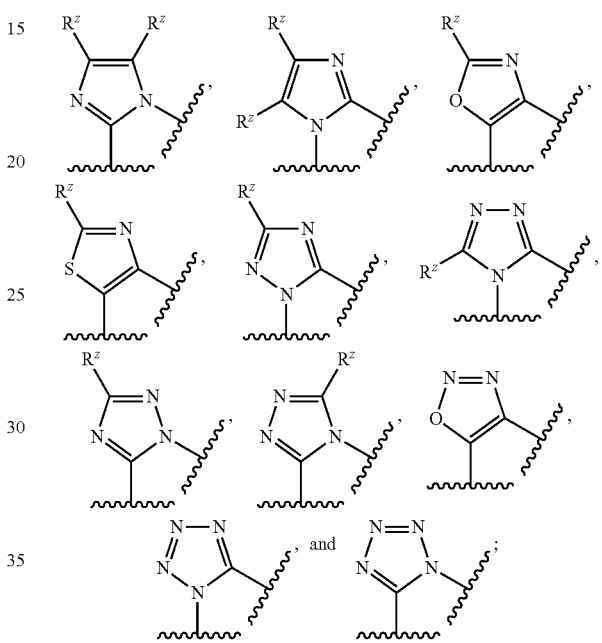

wherein
each $R^z$ is independently hydrogen, F, Cl, —CN, or —NH$_2$.

In some embodiments of a compound of Formula (II), when the two $R^X$ are taken together with the intervening atoms to which they are attached to form a 5-membered heterocyclic ring, the 5-membered heterocyclic ring is selected from:

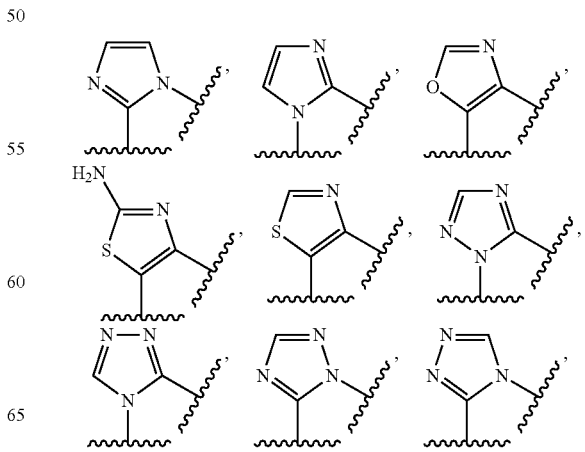

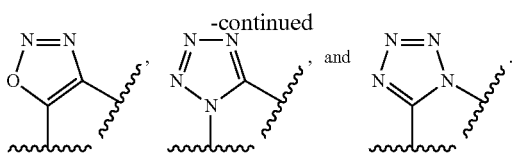

In some embodiments of a compound of Formula (II), $R^1$ is substituted or unsubstituted $C_1$-$C_6$alkyl. In some embodiments of a compound of Formula (II), $R^1$ is —$CH_3$, —$CH_2CH_3$, —$CH_2CH_2CH_3$, —$CH(CH_3)_2$, —$CH_2CH_2CH_2CH_3$, —$CH_2CH(CH_3)_2$, —$CH(CH_3)$ $(CH_2CH_3)$, —$C(CH_3)_3$, —$CH_2CH_2OH$, —$CH_2CH_2OCH_3$, or —$CH_2CF_3$.

In some embodiments of a compound of Formula (II), n is 0, 1, 2, or 3. In some embodiments of a compound of Formula (II), n is 0, 1, or 2. In some embodiments of a compound of Formula (II), n is 1 or 2. In some embodiments of a compound of Formula (II), n is 0 or 1. In some embodiments of a compound of Formula (II), n is 0.

In another aspect, the present disclosure provides a compound of Formula (III), or a pharmaceutically acceptable salt or a pharmaceutically acceptable solvate thereof:

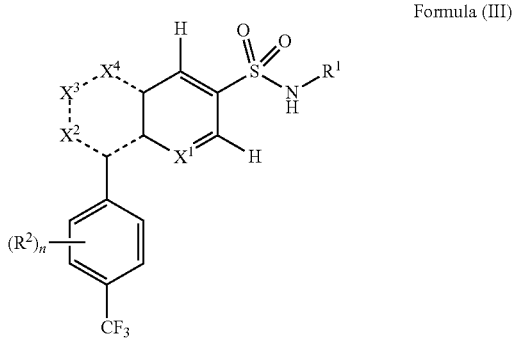

Formula (III)

wherein, each $X^1$ and $X^2$ is independently N, $NR^X$, C(=O), or $CR^X$;

each $X^3$ and $X^4$ is independently N, $NR^X$, C(=O), or $CR^X$; or if both $X^3$ and $X^4$ are each independently $NR^X$ or $CR^X$, then the two $R^X$ are taken together with the intervening atoms to which they are attached to form a 5-membered heterocyclic ring;

each $R^X$ is independently hydrogen, halogen, nitro, oxo, thioxo, imino, oximo, —$OR^3$, —$SR^3$, —CN, —C(=O)$R^2$, —S(=O)$R^3$, —S(=O)$_2R^3$, —N($R^3$)$_2$, —$NR^3S$(=O)$_2R^3$, —$NR^3$C(=O)$R^3$, —$NR^3$C(=O)O$R^3$, substituted or unsubstituted $C_1$-$C_6$ alkyl, substituted or unsubstituted $C_1$-$C_6$haloalkyl, substituted or unsubstituted $C_2$-$C_4$alkenyl, substituted or unsubstituted $C_2$-$C_4$alkynyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;

$R^1$ is substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, or substituted or unsubstituted $C_2$-$C_{10}$heterocycloalkyl;

each $R^2$ is independently —$N_3$, —CN, —$OR^3$, —$SR^3$, —S(=O)$_2R^3$, —N($R^3$)$_2$, —C(=O)O$R^3$, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;

each $R^3$ is independently hydrogen, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;

$R^4$ is substituted or unsubstituted $C_1$-$C_6$alkyl, substituted or unsubstituted $C_3$-$C_{10}$cycloalkyl, or —$NH_2$;

each -- is independently a single or double bond; and n is 0, 1, 2, 3, or 4.

In some embodiments of a compound of Formula (III), each $X^1$ and $X^2$ is $CR^X$. In some embodiments of a compound of Formula (III), $X^1$ is N and $X^2$ is $CR^X$. In some embodiments of a compound of Formula (III), $X^1$ is $CR^X$ and $X^2$ is N. In some embodiments of a compound of Formula (III), each $X^1$ and $X^2$ is N.

In some embodiments of a compound of Formula (III), each $X^3$ and $X^4$ is $CR^X$. In some embodiments of a compound of Formula (III), $X^3$ is N and $X^4$ is $CR^X$. In some embodiments of a compound of Formula (III), $X^3$ is $CR^X$ and $X^4$ is N. In some embodiments of a compound of Formula (III), each $X^3$ and $X^4$ is N. In some embodiments of a compound of Formula (III), $X^3$ is $NR^X$ and $X^4$ is C(=O).

In some embodiments of a compound of Formula (III), each $R^X$ is independently hydrogen, halogen, —$OR^3$, —$SR^3$, —CN, —S(=O)$R^3$, —S(=O)$_2R^3$, —N($R^3$)$_2$, —$NR^3S$(=O)$_2R^3$, —$NR^3$C(=O)$R^3$, substituted or unsubstituted $C_1$-$C_6$alkyl, substituted or unsubstituted $C_1$-$C_6$haloalkyl, substituted or unsubstituted $C_2$-$C_4$alkenyl, substituted or unsubstituted $C_2$-$C_4$alkynyl, or substituted or unsubstituted $C_1$-$C_6$heteroalkyl; and each $R^3$ is independently hydrogen, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, or substituted or unsubstituted $C_2$-$C_{10}$heterocycloalkyl. In some embodiments of a compound of Formula (III), each $R^X$ is independently hydrogen, halogen, —$OR^3$, —$SR^3$, —S(=O)$R^3$, —S(=O)$_2R^3$, —N($R^3$)$_2$, —$NR^3S$(=O)$_2R^3$, —$NR^3$C(=O)$R^3$, substituted or unsubstituted $C_1$-$C_6$alkyl, substituted or unsubstituted $C_1$-$C_6$haloalkyl, or substituted or unsubstituted $C_2$-$C_4$alkynyl; and each $R^3$ is independently hydrogen, substituted or unsubstituted $C_1$-$C_6$alkyl, substituted or unsubstituted $C_1$-$C_6$haloalkyl, or substituted or unsubstituted $C_3$-$C_{10}$cycloalkyl. In some embodiments of a compound of Formula (III), each $R^X$ is independently hydrogen, F, Cl, Br, I, —$CH_3$, —$CH_2CH_3$, —$CH_2OH$, —$CH_2CH_2OH$, —$CH_2CN$, —$CH_2CO_2H$, —$CH_2CO_2CH_3$, —$CH_2CO_2CH_2CH_3$, —$CH_2C$(=O)$NH_2$, —$CH_2C$(=O)$NHCH_3$, —$CH_2C$(=O)N($CH_3$)$_2$, —$CH_2NH_2$, —$CH_2NHCH_3$, —$CH_2N$($CH_3$)$_2$, —$CH_2F$, —$CHF_2$, —$CF_3$, —CH=$CH_2$, —C≡CH, cyclopropyloxy, cyclobutyloxy, cyclopentyloxy, oxetanyloxy, tetrahydrofuranyloxy, tetrahydropyranyloxy, azetidinyl, pyrrolidinyl, tetrazolyl, —CN, —OH, —$OCH_3$, —$OCH_2CH_3$, —$OCH_2CH_2OH$, —$OCH_2CN$, —$OCF_3$, —$CO_2H$, —$CO_2CH_3$, —CO$_2$CH$_2$CH$_3$, —C(=O)NH$_2$, —C(=O)NHCH$_3$, —C(=O)N(CH$_3$)$_2$, —NH$_2$, —NHCH$_3$, —N(CH$_3$)$_2$, —NHC(=O)CH$_3$, —N(CH$_3$)C(=O)CH$_3$, —NHC(=O)OCH$_3$, —N(CH$_3$)C(=O)OCH$_3$, —S(=O)CH$_3$, —S(=O)$_2$CH$_3$, —NHS(=O)$_2$CH$_3$, or —N(CH$_3$)S(=O)$_2$CH$_3$. In some embodiments of a compound of Formula (III), each R$^X$ is independently hydrogen, Cl, —CH$_3$, —CH$_2$CH$_3$, —OH, or —OCH$_3$. In some embodiments of a compound of Formula (III), each R$^X$ is independently hydrogen, halogen, —OCH$_3$, —OCH$_2$CH$_3$, cyclopropyl oxy, or —OCF$_3$. In some embodiments of a compound of Formula (III), each R$^X$ is independently hydrogen or halogen. In some embodiments of a compound of Formula (III), each R$^X$ is independently hydrogen, F, or Cl. In some embodiments of a compound of Formula (III), each R$^X$ is hydrogen.

In some embodiments of a compound of Formula (III), each X$^3$ and X$^4$ is independently NR$^X$ or CR$^X$, wherein the two R$^X$ are taken together with the intervening atoms to which they are attached to form a 5-membered heterocyclic ring. In some embodiments of a compound of Formula (III), when the two R$^X$ are taken together with the intervening atoms to which they are attached to form a 5-membered heterocyclic ring, the 5-membered heterocyclic ring is selected from:

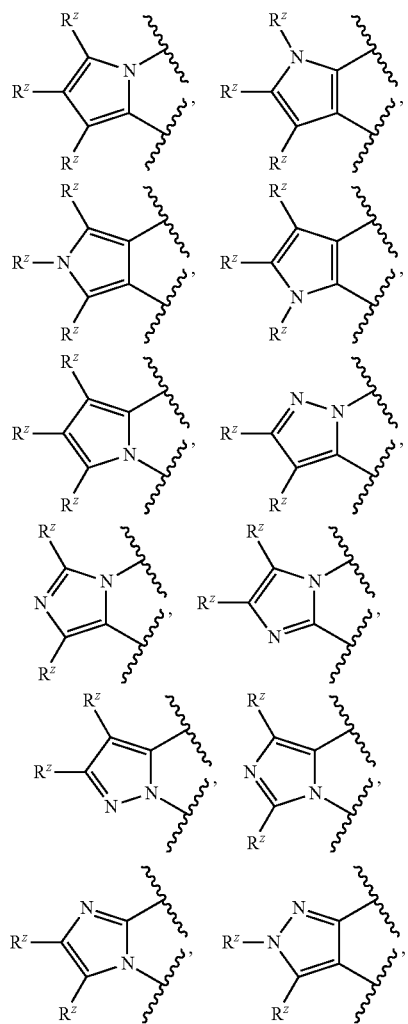

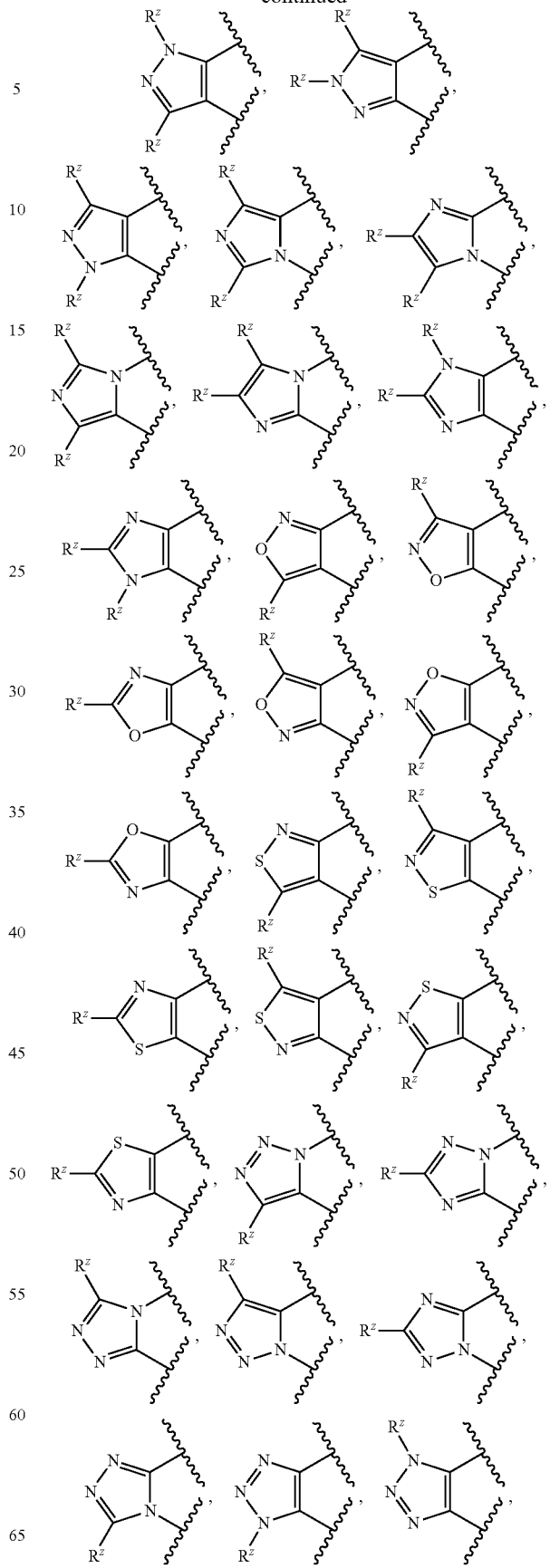

-continued

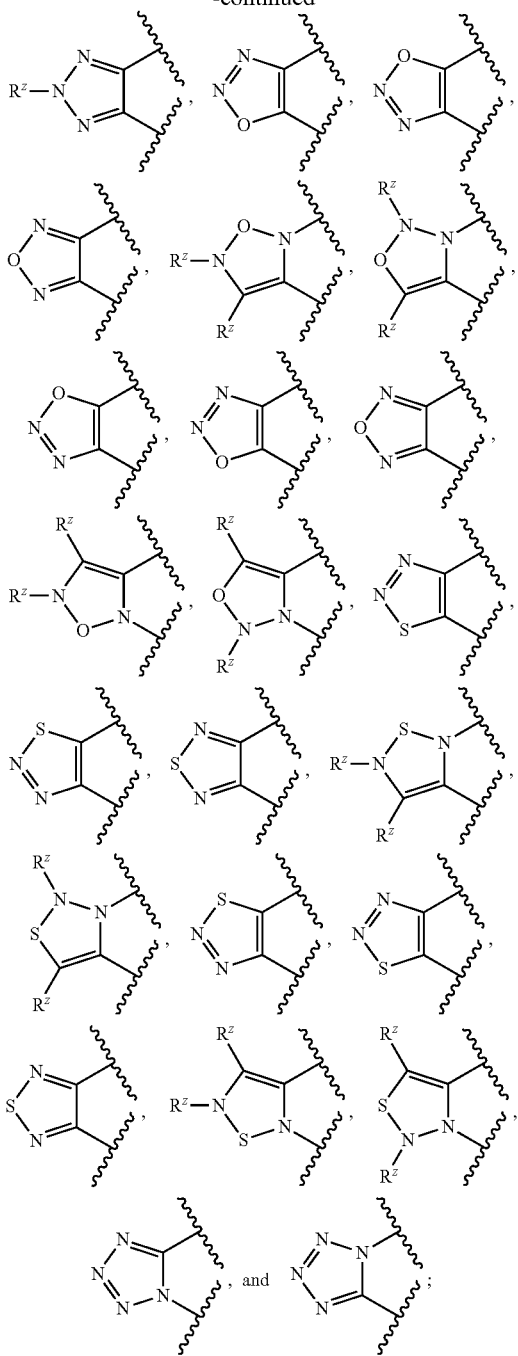

wherein
each $R^z$ is independently hydrogen, halogen, —CN, —OR$^3$, —SR$^3$, —S(=O)$_2$R$^3$, —N(R$^3$)$_2$, —C(=O)OR$^3$, substituted or unsubstituted C$_1$-C$_6$alkyl, substituted or unsubstituted C$_1$-C$_6$haloalkyl, substituted or unsubstituted C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted aralkyl, substituted or unsubstituted aryl, or substituted or unsubstituted heteroaryl; and each R$^3$ is independently hydrogen, substituted or unsubstituted C$_1$-C$_6$alkyl, substituted or unsubstituted C$_1$-C$_6$haloalkyl, substituted or unsubstituted C$_1$-C$_6$heteroalkyl, substituted or unsubstituted C$_3$-C$_{10}$cycloalkyl, or substituted or unsubstituted C$_2$-C$_{10}$heterocycloalkyl.

In some embodiments of a compound of Formula (III), when the two $R^x$ are taken together with the intervening atoms to which they are attached to form a 5-membered heterocyclic ring, the 5-membered heterocyclic ring is selected from:

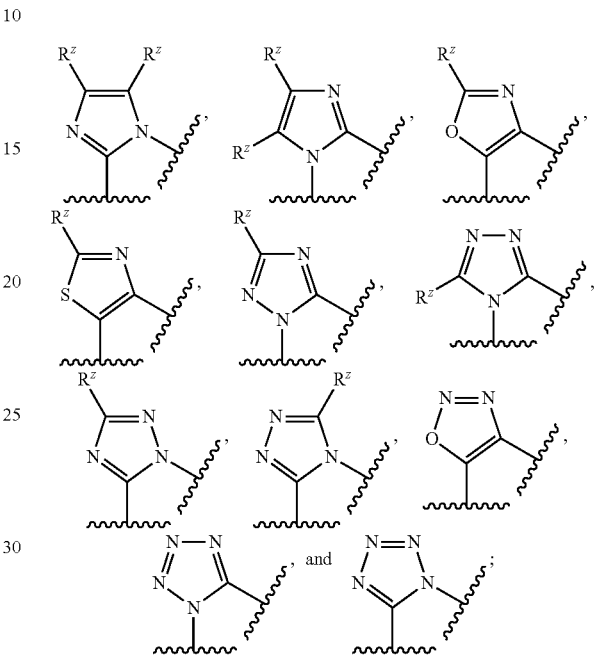

wherein
each $R^z$ is independently hydrogen, halogen, —CN, —OR$^3$, —SR$^3$, —S(=O)$_2$R$^3$, —N(R$^3$)$_2$, —C(=O)OR$^3$, substituted or unsubstituted C$_1$-C$_6$alkyl, substituted or unsubstituted C$_1$-C$_6$haloalkyl, substituted or unsubstituted C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted aralkyl, substituted or unsubstituted aryl, or substituted or unsubstituted heteroaryl; and each R$^3$ is independently hydrogen, substituted or unsubstituted C$_1$-C$_6$alkyl, substituted or unsubstituted C$_1$-C$_6$haloalkyl, substituted or unsubstituted C$_1$-C$_6$heteroalkyl, substituted or unsubstituted C$_3$-C$_{10}$cycloalkyl, or substituted or unsubstituted C$_2$-C$_{10}$heterocycloalkyl.

In some embodiments of a compound of Formula (III), when the two $R^x$ are taken together with the intervening atoms to which they are attached to form a 5-membered heterocyclic ring, the 5-membered heterocyclic ring is selected from:

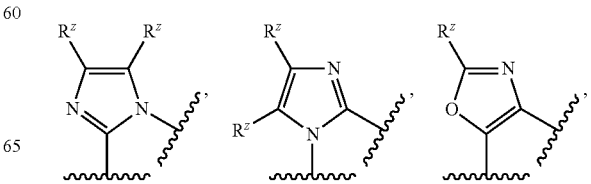

-continued

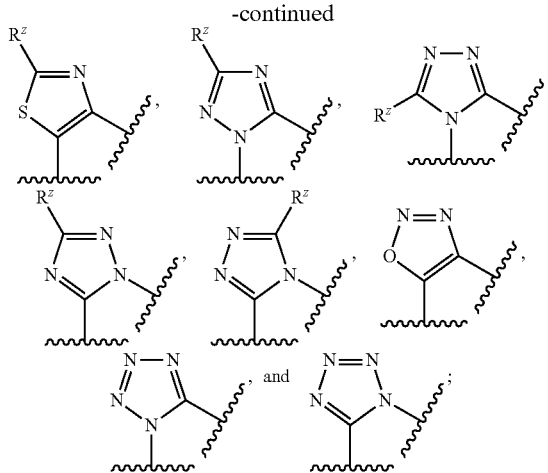

wherein
each $R^z$ is independently hydrogen, F, Cl, —CN, or —NH$_2$.

In some embodiments of a compound of Formula (III), when the two $R^X$ are taken together with the intervening atoms to which they are attached to form a 5-membered heterocyclic ring, the 5-membered heterocyclic ring is selected from:

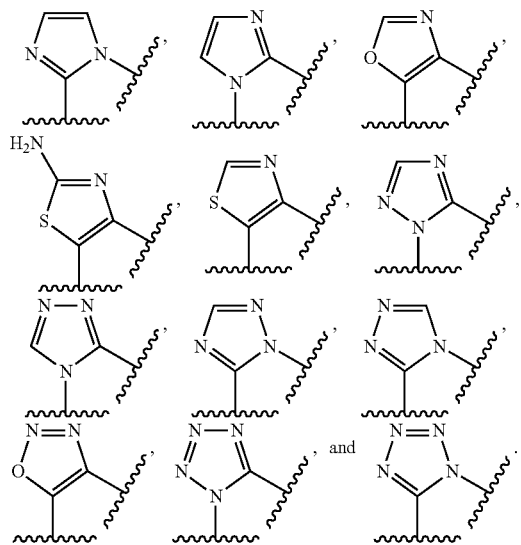

In some embodiments of a compound of Formula (III), $R^1$ is substituted or unsubstituted $C_1$-$C_6$alkyl. In some embodiments of a compound of Formula (III), $R^1$ is —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH(CH$_3$)$_2$, —CH(CH$_3$) (CH$_2$CH$_3$), —C(CH$_3$)$_3$, —CH$_2$CH$_2$OH, —CH$_2$CH$_2$OCH$_3$, or —CH$_2$CF$_3$.

In some embodiments of a compound of Formula (III), n is 0, 1, 2, or 3. In some embodiments of a compound of Formula (III), n is 0, 1, or 2. In some embodiments of a compound of Formula (III), n is 1 or 2. In some embodiments of a compound of Formula (III), n is 0 or 1. In some embodiments of a compound of Formula (III), n is 0.

In another aspect, the present disclosure provides a compound of Formula (IV), or a pharmaceutically acceptable salt or a pharmaceutically acceptable solvate thereof:

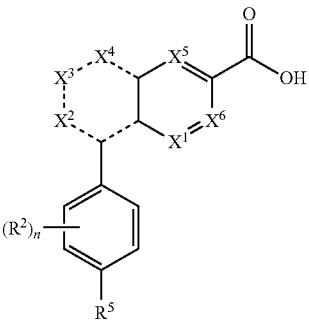

Formula (IV)

wherein,
each $X^1$, $X^2$, $X^5$, and $X^6$, is independently N, NR$^X$, C(=O), or CR$^X$;

each $X^3$ and $X^4$ is independently N, NR$^X$, C(=O), or CR$^X$; or if both $X^3$ and $X^4$ are each independently NR$^X$ or CR$^X$, then the two $R^X$ are taken together with the intervening atoms to which they are attached to form a 5-membered heterocyclic ring;

each $R^X$ is independently hydrogen, halogen, nitro, oxo, thioxo, imino, oximo, —OR$^3$, —SR$^3$, —CN, —C(=O)R$^2$, —S(=O)R$^3$, —S(=O)$_2$R$^3$, —N(R$^3$)$_2$, —NR$^3$S(=O)$_2$R$^3$, —NR$^3$C(=O)R$^3$, —NR$^3$C(=O)OR$^3$, substituted or unsubstituted $C_1$-$C_6$ alkyl, substituted or unsubstituted $C_1$-$C_6$haloalkyl, substituted or unsubstituted $C_2$-$C_4$alkenyl, substituted or unsubstituted $C_2$-$C_4$alkynyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;

each $R^2$ is independently —CN, —OR$^3$, —SR$^3$, —S(=O)$_2$R$^3$, —N(R$^3$)$_2$, —C(=O)OR$^3$, —N$_3$, F, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;

each $R^3$ is independently hydrogen, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or unsubstituted heteroaryl;

$R^5$ is F, —SF$_5$, substituted $C_1$-$C_6$alkyl, substituted or unsubstituted $C_1$-$C_6$haloalkyl, substituted $C_1$-$C_6$alkyloxy, or substituted $C_1$-$C_6$alkylthio;

each -- is independently a single or double bond; and n is 0, 1, 2, 3, or 4.

In some embodiments, a compound of Formula (IV) is not 4-(4-(trifluoromethyl)phenyl)quinazoline-7-carboxylic acid.

In another aspect, the present disclosure provides a compound of Formula (V), or a pharmaceutically acceptable salt or a pharmaceutically acceptable solvate thereof:

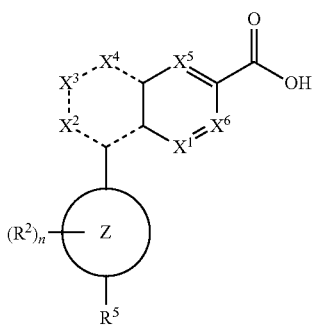

Formula (V)

wherein, each $X^1$, $X^2$, $X^5$, and $X^6$, is independently N, $NR^X$, C(=O), or $CR^X$;

each $X^3$ and $X^4$ is independently N, $NR^X$, C(=O), or $CR^X$; or if both $X^3$ and $X^4$ are each independently $NR^X$ or $CR^X$, then the two $R^X$ are taken together with the intervening atoms to which they are attached to form a 5-membered heterocyclic ring;

each $R^X$ is independently hydrogen, halogen, nitro, oxo, thioxo, imino, oximo, $-OR^3$, $-SR^3$, $-CN$, $-C(=O)R^2$, $-S(=O)R^3$, $-S(=O)_2R^3$, $-N(R^3)_2$, $-NR^3S(=O)_2R^3$, $-NR^3C(=O)R^3$, $-NR^3C(=O)OR^3$, substituted or unsubstituted $C_1$-$C_6$ alkyl, substituted or unsubstituted $C_1$-$C_6$haloalkyl, substituted or unsubstituted $C_2$-$C_4$alkenyl, substituted or unsubstituted $C_2$-$C_4$alkynyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;

Ring Z is a substituted monocyclic 5-membered heterocyclic ring containing at least one N, O, or S atom or a substituted monocyclic 6-membered heterocyclic ring containing at least one N atom;

each $R^2$ is independently $-CN$, $-OR^3$, $-SR^3$, $-S(=O)_2R^3$, $-N(R^3)_2$, $-C(=O)OR^3$, $-N_3$, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;

each $R^3$ is independently hydrogen, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aralkyl, substituted or unsubstituted aryl, or substituted or unsubstituted heteroaryl;

$R^5$ is F, $-SF_5$, substituted $C_1$-$C_6$alkyl, substituted or unsubstituted $C_1$-$C_6$haloalkyl, substituted $C_1$-$C_6$alkyloxy, or substituted $C_1$-$C_6$alkylthio;

each -- is independently a single or double bond; and n is 0, 1, 2, 3, or 4.

In some embodiments of a compound of Formula (V), when $X^1$, $X^3$, $X^5$, and $X^6$ is CH; and $X^2$ and $X^4$ is N, then ring Z is not pyrazole.

In some embodiments of a compound of Formula (V),

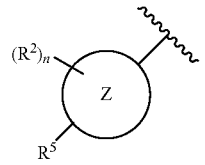

is a substituted monocyclic 5-membered heterocyclic ring containing at least one N, O, or S atom. In some embodiments of a compound of Formula (V),

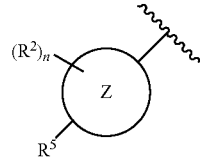

is a substituted monocyclic 5-membered heterocyclic ring containing at containing 1-4 N atoms, 0-2 O atoms, and 0-2 S atoms.

In some embodiments of a compound of Formula (V),

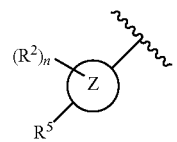

is substituted pyrrolidinyl, substituted imidazolidinyl, substituted pyrazolidinyl, substituted oxazolidinyl, substituted isoxazolidinyl, substituted thiazolidinyl, or substituted isothiazolidinyl. In some embodiments of a compound of Formula (V),

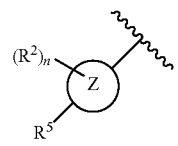

is substituted furanyl, substituted pyrrolyl, substituted thiophenyl, substituted imidazolyl, substituted pyrazolyl, substituted oxazolyl, substituted isoxazolyl, substituted thiazolyl, substituted isothiazolyl, substituted triazolyl, substituted tetrazolyl, substituted oxadiazolyl, substituted thiadiazolyl, or substituted dithiazolyl. In some embodiments of a compound of Formula (V),

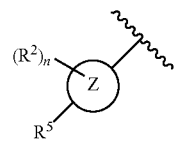

is substituted furanyl, substituted thiophenyl, substituted imidazolyl, substituted oxazolyl, substituted isoxazolyl, substituted thiazolyl, substituted isothiazolyl, substituted oxadiazolyl, substituted thiadiazolyl, or substituted dithiazolyl. In some embodiments of a compound of Formula (V),

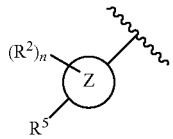

is substituted thiophenyl, substituted thiazolyl, or substituted thiadiazolyl. In some embodiments of a compound of Formula (V),

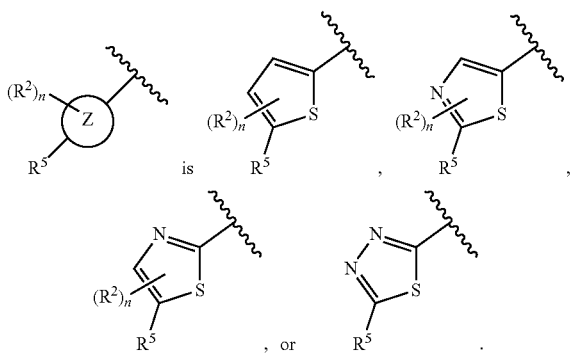

In some embodiments of a compound of Formula (V),

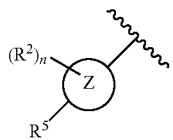

is a substituted monocyclic 6-membered heteroaryl ring containing at least one N atom. In some embodiments of a compound of Formula (V),

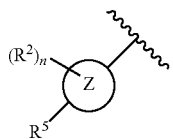

is a substituted monocyclic 6-membered heteroaryl ring containing 1, 2, or 3 N atoms. In some embodiments of a compound of Formula (V),

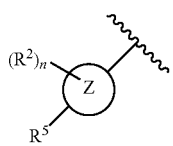

is substituted pyridinyl, substituted pyrazinyl, substituted pyrimidinyl, substituted pyridazinyl, or substituted triazinyl. In some embodiments of a compound of Formula (V),

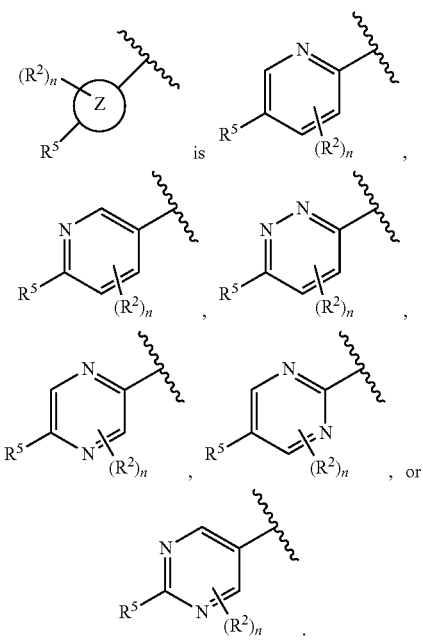

In some embodiments of a compound of Formula (V),

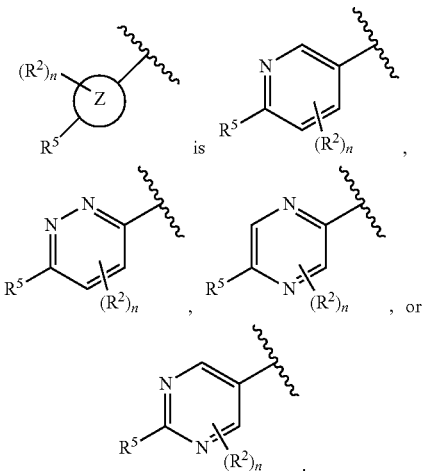

In some embodiments, a compound of Formula (V) has a structure of Formula (Va), or a pharmaceutically acceptable salt or a pharmaceutically acceptable solvate thereof:

Formula (Va)

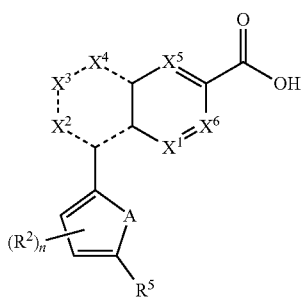

wherein,

A is —S—, —CH=N— or —N=CH—.

In some embodiments of a compound of Formula (IV), Formula (V), or Formula (Va), each $X^1$ and $X^2$ is $CR^X$. In some embodiments of a compound of Formula (IV), Formula (V), or Formula (Va), $X^1$ is N and $X^2$ is $CR^X$. In some embodiments of a compound of Formula (IV), Formula (V), or Formula (Va), $X^1$ is $CR^X$ and $X^2$ is N. In some embodiments of a compound of Formula (IV), Formula (V), or Formula (Va), $X^1$ is $CR^X$ and $X^2$ is N. In some embodiments of a compound of Formula (IV), Formula (V), or Formula (Va), each $X^1$ and $X^2$ is N.

In some embodiments of a compound of Formula (IV), Formula (V), or Formula (Va), each $X^5$ and $X^6$ is $CR^X$. In some embodiments of a compound of Formula (IV), Formula (V), or Formula (Va), $X^5$ is N and $X^6$ is $CR^X$. In some embodiments of a compound of Formula (IV), Formula (V), or Formula (Va), $X^5$ is $CR^X$ and $X^6$ is N. In some embodiments of a compound of Formula (IV), Formula (V), or Formula (Va), each $X^5$ and $X^6$ is N.

In some embodiments of a compound of Formula (IV), Formula (V), or Formula (Va), each $X^3$ and $X^4$ is $CR^X$. In some embodiments of a compound of Formula (IV), Formula (V), or Formula (Va), $X^3$ is N and $X^4$ is $CR^X$. In some embodiments of a compound of Formula (IV), Formula (V), or Formula (Va), $X^3$ is $CR^X$ and $X^4$ is N. In some embodiments of a compound of Formula (IV), Formula (V), or Formula (Va), $X^3$ is $NR^X$ and $X^4$ is $C(=O)$.

In some embodiments, a compound of Formula (IV) has a structure of Formula (IVa):

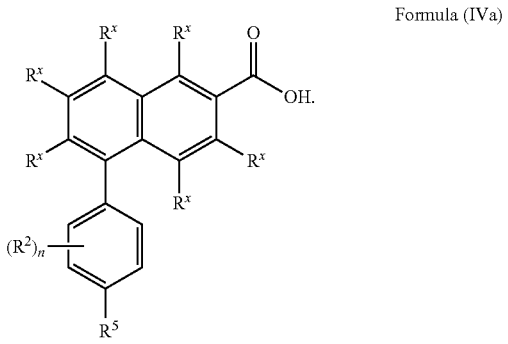

Formula (IVa)

In some embodiments, a compound of Formula (IV) has a structure of Formula (IVb):

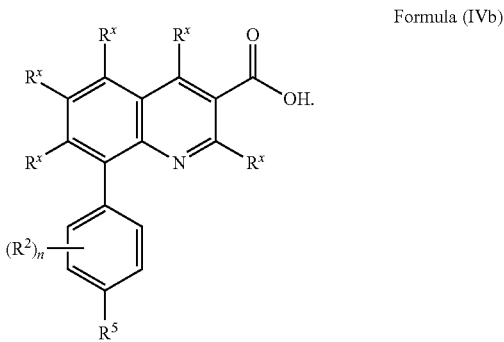

Formula (IVb)

In some embodiments, a compound of Formula (Va) has a structure of Formula (Vb), or a pharmaceutically acceptable salt or a pharmaceutically acceptable solvate thereof:

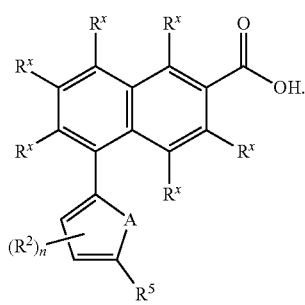

Formula (Vb)

In some embodiments of a compound of Formula (IV), Formula (IVa), Formula (IVb), Formula (V), Formula (Va), or Formula (Vb), each $R^X$ is independently hydrogen, halogen, —$OR^3$, —$SR^3$, —CN, —$S(=O)R^3$, —$S(=O)_2R^3$, —$N(R^3)_2$, —$NR^3S(=O)_2R^3$, —$NR^3C(=O)R^3$, substituted or unsubstituted $C_1$-$C_6$alkyl, substituted or unsubstituted $C_1$-$C_6$haloalkyl, substituted or unsubstituted $C_2$-$C_4$alkenyl, substituted or unsubstituted $C_2$-$C_4$alkynyl, or substituted or unsubstituted $C_1$-$C_6$heteroalkyl; and each $R^3$ is independently hydrogen, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, or substituted or unsubstituted $C_2$-$C_{10}$heterocycloalkyl. In some embodiments of a compound of Formula (IV), Formula (IVa), Formula (IVb), Formula (V), Formula (Va), or Formula (Vb), each $R^X$ is independently hydrogen, halogen, —$OR^3$, —$SR^3$, —$S(=O)R^3$, —$S(=O)_2R^3$, —$N(R^3)_2$, —$NR^3S(=O)_2R^3$, —$NR^3C(=O)R^3$, substituted or unsubstituted $C_1$-$C_6$alkyl, substituted or unsubstituted $C_1$-$C_6$haloalkyl, or substituted or unsubstituted $C_2$-$C_4$alkynyl; and each $R^3$ is independently hydrogen, substituted or unsubstituted $C_1$-$C_6$alkyl, substituted or unsubstituted $C_1$-$C_6$haloalkyl, or substituted or unsubstituted $C_3$-$C_{10}$cycloalkyl. In some embodiments of a compound of Formula (IV), Formula (IVa), Formula (IVb), Formula (V), Formula (Va), or Formula (Vb), each $R^X$ is independently hydrogen, Cl, or —OH. In some embodiments of a compound of Formula (IV), Formula (IVa), Formula (IVb), Formula (V), Formula (Va), or Formula (Vb), each $R^X$ is independently hydrogen, Cl, —$CH_3$, —$CH_2CH_3$, —$CH_2CH_2CH_3$, or —$CH(CH_3)_2$. In some embodiments of a compound of Formula (IV), Formula (IVa), Formula (IVb), Formula (V), Formula (Va), or Formula (Vb), each $R^X$ is independently hydrogen, —$OCH_3$, —$OCH_2CH_3$, —$OCH_2CH_2CH_3$, or —$OCH(CH_3)_2$, —$OCF_3$, —$OCH_2CF_3$, cyclopropyloxy, or cyclobutyloxy. In some embodiments of a compound of Formula (IV), Formula (IVa), Formula (IVb), Formula (V), Formula (Va), or Formula (Vb), each $R^X$ is independently hydrogen, —$OCH_3$, —$OCH_2CH_3$, —$OCF_3$, or cyclopropyl oxy. In some embodiments of a compound of Formula (IV), Formula (IVa), Formula (IVb), Formula (V), Formula (Va), or Formula (Vb), each $R^X$ is independently hydrogen or halogen. In some embodiments of a compound of Formula (IV), Formula (IVa), Formula (IVb), Formula (V), Formula (Va), or Formula (Vb), each $R^X$ is independently hydrogen, F, or Cl. In some embodiments of a compound of Formula (IV), Formula (IVa), Formula (IVb), Formula (V), Formula (Va), or Formula (Vb), each $R^X$ is hydrogen.

In some embodiments of a compound of Formula (IV) or Formula (V), each $X^3$ and $X^4$ is independently $NR^X$ or $CR^X$, wherein the two $R^X$ are taken together with the intervening atoms to which they are attached to form a 5-membered heterocyclic ring. In some embodiments of a compound of Formula (IV) or Formula (V), when the two $R^X$ are taken together with the intervening atoms to which they are attached to form a 5-membered heterocyclic ring, the 5-membered heterocyclic ring is selected from:
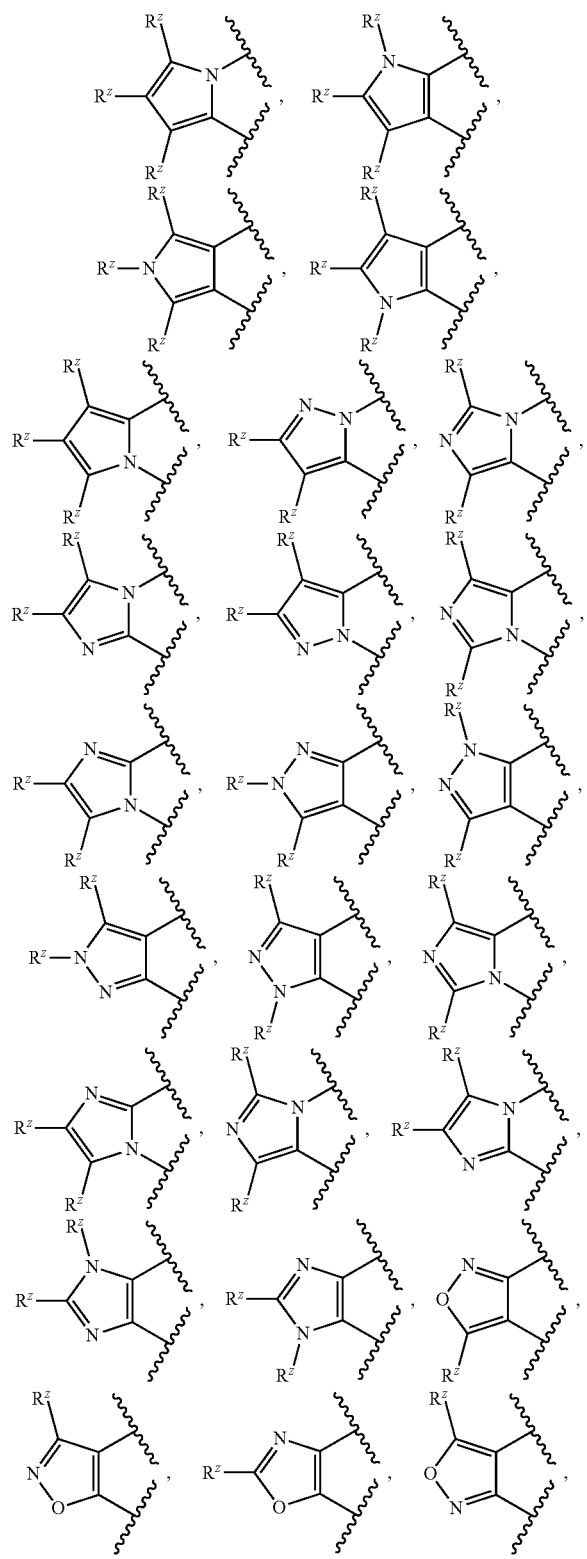
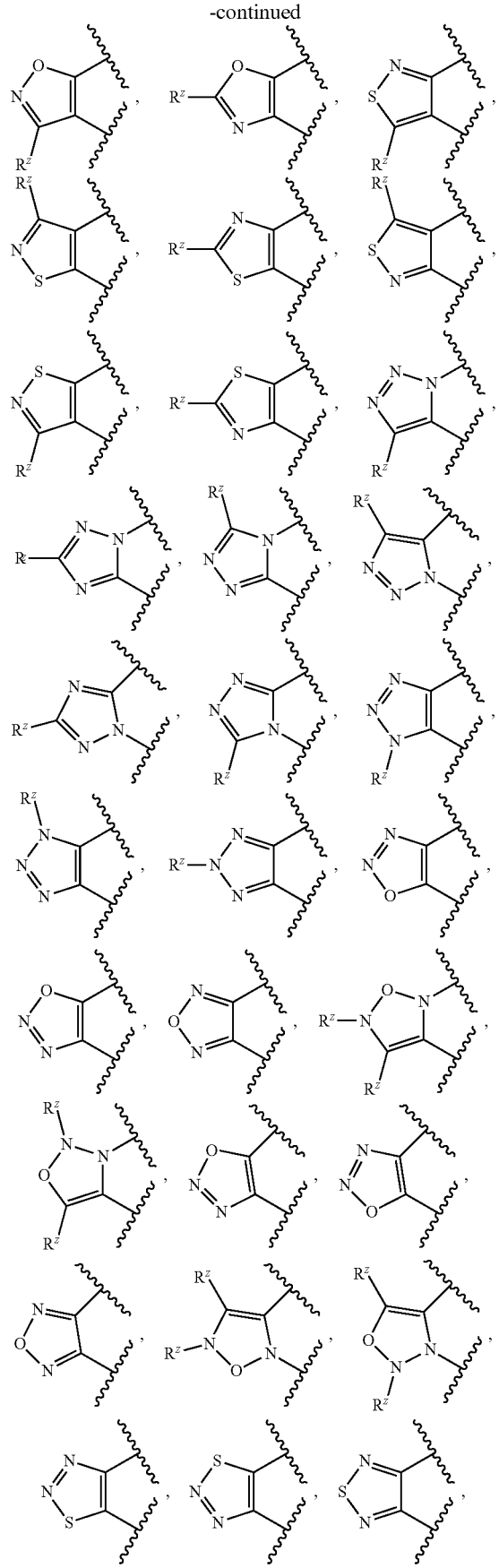
-continued -continued

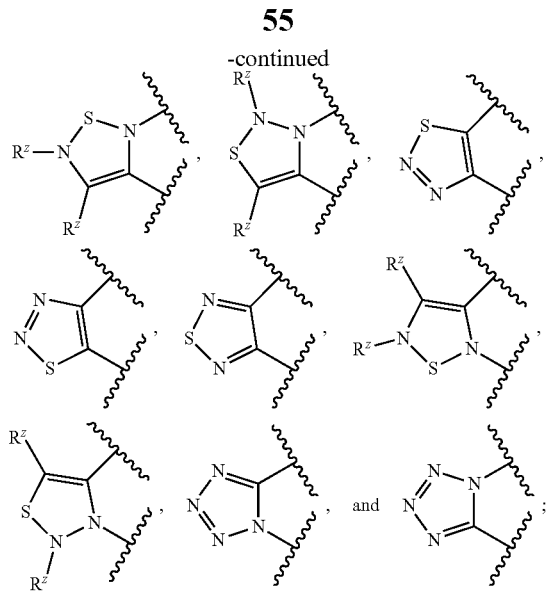

wherein each $R^z$ is independently hydrogen, halogen, —CN, —OR$^3$, —SR$^3$, —S(=O)$_2$R$^3$, —N(R$^3$)$_2$, —C(=O)OR$^3$, substituted or unsubstituted C$_1$-C$_6$alkyl, substituted or unsubstituted C$_1$-C$_6$haloalkyl, substituted or unsubstituted C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted aralkyl, substituted or unsubstituted aryl, or substituted or unsubstituted heteroaryl; and each $R^3$ is independently hydrogen, substituted or unsubstituted C$_1$-C$_6$alkyl, substituted or unsubstituted C$_1$-C$_6$haloalkyl, substituted or unsubstituted C$_1$-C$_6$heteroalkyl, substituted or unsubstituted C$_3$-C$_{10}$cycloalkyl, or substituted or unsubstituted C$_2$-C$_{10}$heterocycloalkyl.

In some embodiments of a compound of Formula (IV) or Formula (V), when the two $R^x$ are taken together with the intervening atoms to which they are attached to form a 5-membered heterocyclic ring, the 5-membered heterocyclic ring is selected from:

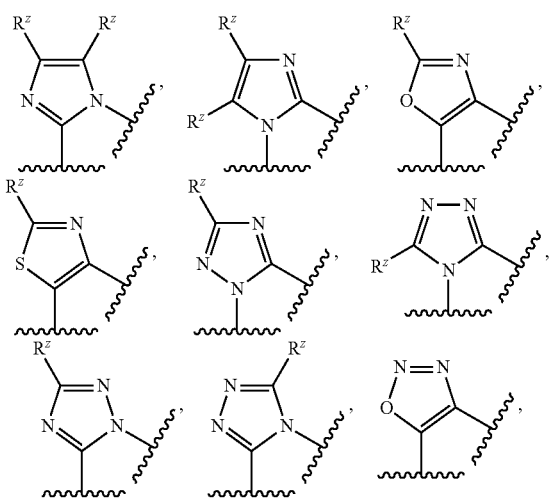

-continued

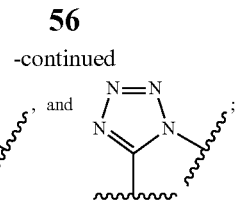

wherein each $R^z$ is independently hydrogen, halogen, —CN, —OR$^3$, —SR$^3$, —S(=O)$_2$R$^3$, —N(R$^3$)$_2$, —C(=O)OR$^3$, substituted or unsubstituted C$_1$-C$_6$alkyl, substituted or unsubstituted C$_1$-C$_6$haloalkyl, substituted or unsubstituted C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted aralkyl, substituted or unsubstituted aryl, or substituted or unsubstituted heteroaryl; and each $R^3$ is independently hydrogen, substituted or unsubstituted C$_1$-C$_6$alkyl, substituted or unsubstituted C$_1$-C$_6$haloalkyl, substituted or unsubstituted C$_1$-C$_6$heteroalkyl, substituted or unsubstituted C$_3$-C$_{10}$cycloalkyl, or substituted or unsubstituted C$_2$-C$_{10}$heterocycloalkyl.

In some embodiments of a compound of Formula (IV) or Formula (V), when the two $R^x$ are taken together with the intervening atoms to which they are attached to form a 5-membered heterocyclic ring, the 5-membered heterocyclic ring is selected from:

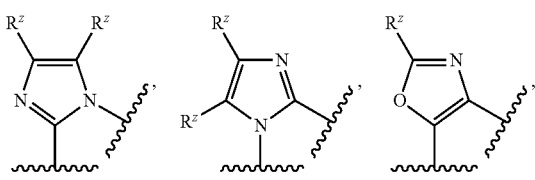

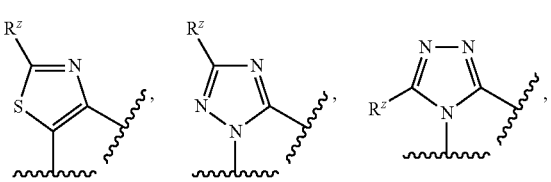

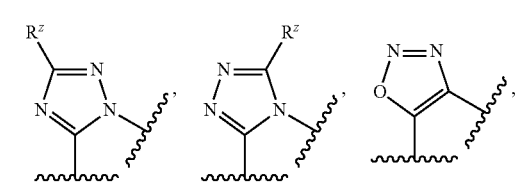

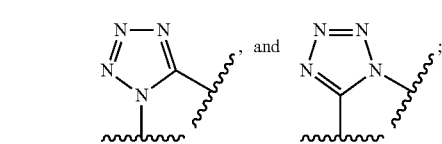

wherein
each $R^z$ is independently hydrogen, F, Cl, —CN, or —NH$_2$.

In some embodiments of a compound of Formula (IV) or Formula (V), when the two $R^x$ are taken together with the intervening atoms to which they are attached to form a 5-membered heterocyclic ring, the 5-membered heterocyclic ring is selected from:

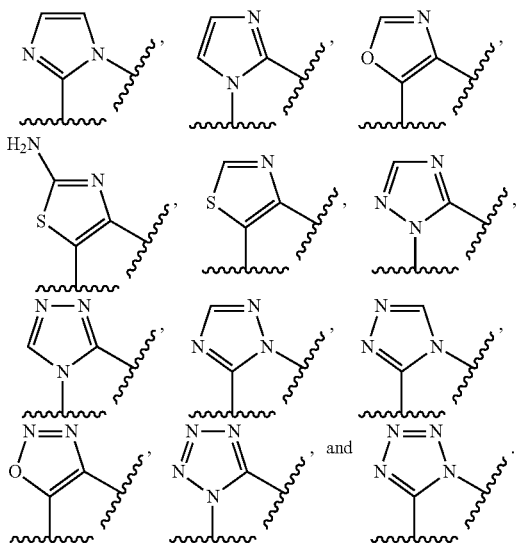

In some embodiments of a compound of Formula (IV), Formula (IVa), Formula (IVb), Formula (V), Formula (Va), or Formula (Vb), $R^5$ is —F or —SF$_5$. In some embodiments of a compound of Formula (IV), Formula (IVa), Formula (IVb), Formula (V), Formula (Va), or Formula (Vb), $R^5$ is —F. In some embodiments of a compound of Formula (IV), Formula (IVa), Formula (IVb), Formula (V), Formula (Va), or Formula (Vb), $R^5$ is —SF$_5$. In some embodiments of a compound of Formula (IV), Formula (IVa), Formula (IVb), Formula (V), Formula (Va), or Formula (Vb), $R^5$ is substituted or unsubstituted C$_1$-C$_6$haloalkyl, substituted C$_1$-C$_6$alkyloxy, or substituted C$_1$-C$_6$alkylthio. In some embodiments of a compound of Formula (IV), Formula (IVa), Formula (IVb), Formula (V), Formula (Va), or Formula (Vb), $R^5$ is C$_1$-C$_6$haloalkyl, substituted C$_1$-C$_6$alkyloxy, or substituted C$_1$-C$_6$alkylthio. In some embodiments of a compound of Formula (IV), Formula (IVa), Formula (IVb), Formula (V), Formula (Va), or Formula (Vb), $R^5$ is C$_1$-C$_6$alkyloxy, or C$_1$-C$_6$alkylthio, each of which is independently substituted with one of more F. In some embodiments of a compound of Formula (IV), Formula (IVa), Formula (IVb), Formula (V), Formula (Va), or Formula (Vb), $R^5$ is —CH$_2$F, —CHF$_2$, —CF$_3$, —CH$_2$CH$_2$F, —CH$_2$CHF$_2$, —CF$_2$CH$_3$, —CH$_2$CF$_3$, —OCH$_2$F, —OCHF$_2$, —OCF$_3$, —OCH$_2$CH$_2$F, —OCH$_2$CHF$_2$, —OCF$_2$CH$_3$, —OCH$_2$CF$_3$, —SCH$_2$F, —SCHF$_2$, —SCF$_3$, —SCH$_2$CH$_2$F, —SCH$_2$CHF$_2$, —SCF$_2$CH$_3$, or —SCH$_2$CF$_3$. In some embodiments of a compound of Formula (IV), Formula (IVa), Formula (IVb), Formula (V), Formula (Va), or Formula (Vb), $R^5$ is —CHF$_2$, —CF$_3$, —OCHF$_2$, —OCF$_3$, —SCHF$_2$, or —SCF$_3$. In some embodiments of a compound of Formula (IV), Formula (IVa), Formula (IVb), Formula (V), Formula (Va), or Formula (Vb), $R^5$ is C$_1$-C$_6$haloalkyl. In some embodiments of a compound of Formula (IV), Formula (IVa), Formula (IVb), Formula (V), Formula (Va), or Formula (Vb), $R^5$ is —CF$_3$.

In some embodiments of a compound of Formula (IV), Formula (IVa), Formula (IVb), Formula (V), Formula (Va), or Formula (Vb), each $R^2$ is independently —CN, —OR$^3$, —SR$^3$, —S(=O)$_2$R$^3$, —N(R$^3$)$_2$, —C(=O)OR$^3$, —N$_3$, substituted or unsubstituted C$_1$-C$_6$alkyl, substituted or unsubstituted C$_1$-C$_6$haloalkyl, substituted or unsubstituted C$_1$-C$_6$heteroalkyl, substituted or unsubstituted C$_3$-C$_{10}$cycloalkyl, or substituted or unsubstituted C$_2$-C$_{10}$heterocycloalkyl; and each $R^3$ is independently hydrogen, substituted or unsubstituted C$_1$-C$_6$alkyl, substituted or unsubstituted C$_1$-C$_6$haloalkyl, substituted or unsubstituted C$_1$-C$_6$heteroalkyl, substituted or unsubstituted C$_3$-C$_{10}$cycloalkyl, or substituted or unsubstituted C$_2$-C$_{10}$heterocycloalkyl.

In some embodiments of a compound of Formula (IV), Formula (IVa), Formula (IVb), Formula (V), Formula (Va), or Formula (Vb), each $R^2$ is independently —CH$_3$, —CH$_2$CH$_3$, —CH$_2$OH, —CH$_2$CH$_2$OH, —CH$_2$CN, —CH$_2$CO$_2$H, —CH$_2$CO$_2$CH$_3$, —CH$_2$CO$_2$CH$_2$CH$_3$, —CH$_2$C(=O)NH$_2$, —CH$_2$C(=O)NHCH$_3$, —CH$_2$C(=O)N(CH$_3$)$_2$, —CH$_2$NH$_2$, —CH$_2$NHCH$_3$, —CH$_2$N(CH$_3$)$_2$, —CH$_2$F, —CHF$_2$, —CF$_3$, cyclopropyloxy, cyclobutyloxy, cyclopentyloxy, oxetanyloxy, tetrahydrofuranyloxy, tetrahydropyranyloxy, azetidinyl, pyrrolidinyl, —CN, —OH, —OCH$_3$, —OCH$_2$CH$_3$, —OCH$_2$CH$_2$OH, —OCH$_2$CN, —OCF$_3$, —CO$_2$H, —CO$_2$CH$_3$, —CO$_2$CH$_2$CH$_3$, —NH$_2$, —NHCH$_3$, —N(CH$_3$)$_2$, or —S(=O)$_2$CH$_3$. In some embodiments of a compound of Formula (IV), Formula (IVa), Formula (IVb), Formula (V), Formula (Va), or Formula (Vb), each $R^2$ is independently —CH$_3$, —CH$_2$CH$_3$, —OH, or —OCH$_3$. In some embodiments of a compound of Formula (IV), Formula (IVa), Formula (IVb), Formula (V), Formula (Va), or Formula (Vb), each $R^2$ is —CH$_3$. In some embodiments of a compound of Formula (IV), Formula (IVa), or Formula (IVb), each $R^2$ is F.

In some embodiments of a compound of Formula (IV), Formula (IVa), Formula (IVb), Formula (V), Formula (Va), or Formula (Vb), n is 0, 1, 2, or 3. In some embodiments of a compound of Formula (IV), Formula (IVa), Formula (IVb), Formula (V), Formula (Va), or Formula (Vb), n is 0, 1, or 2. In some embodiments of a compound of Formula (IV), Formula (IVa), Formula (IVb), Formula (V), Formula (Va), or Formula (Vb), n is 1 or 2. In some embodiments of a compound of Formula (IV), Formula (IVa), Formula (IVb), Formula (V), Formula (Va), or Formula (Vb), n is 0 or 1. In some embodiments of a compound of Formula (IV), Formula (IVa), Formula (IVb), Formula (V), Formula (Va), or Formula (Vb), n is 0.

In another aspect, the present disclosure provides a compound or a pharmaceutically acceptable salt or a pharmaceutically acceptable solvate thereof, wherein the compound is a compound from Table 1, or a pharmaceutically acceptable salt or a pharmaceutically acceptable solvate thereof.

TABLE 1

| Compound No. | Structure | Name |
|---|---|---|
| 1 | 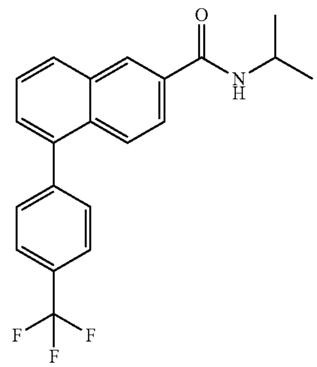 [SMILES: CC(C)NC(=O)c1ccc2c(-c3ccc(C(F)(F)F)cc3)cccc2c1] | N-isopropyl-5-(4-(trifluoromethyl)phenyl)-2-naphthamide |
| 2 | 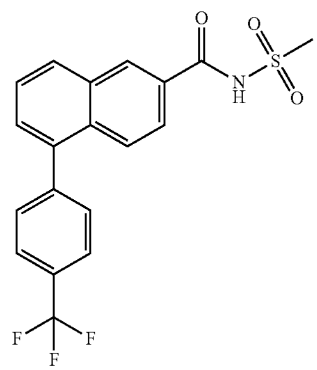 [SMILES: CS(=O)(=O)NC(=O)c1ccc2c(-c3ccc(C(F)(F)F)cc3)cccc2c1] | N-(methylsulfonyl)-5-(4-(trifluoromethyl)phenyl)-2-naphthamide |
| 3 | 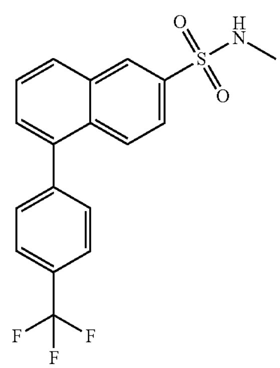 [SMILES: CNS(=O)(=O)c1ccc2c(-c3ccc(C(F)(F)F)cc3)cccc2c1] | N-methyl-5-(4-(trifluoromethyl)phenyl)naphthalene-2-sulfonamide |
| 4 | 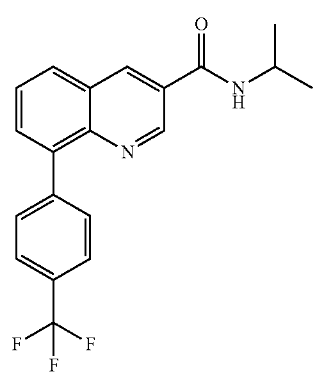 [SMILES: CC(C)NC(=O)c1cnc2c(-c3ccc(C(F)(F)F)cc3)cccc2c1] | N-isopropyl-8-(4-(trifluoromethyl)phenyl)quinoline-3-carboxamide |

TABLE 1-continued

| Compound No. | Structure | Name |
|---|---|---|
| 5 | 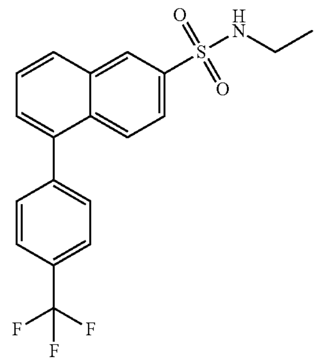 [SMILES: CCNS(=O)(=O)c1ccc2c(-c3ccc(C(F)(F)F)cc3)cccc2c1] | N-ethyl-5-(4-(trifluoromethyl)phenyl)naphthalene-2-sulfonamide |
| 6 | 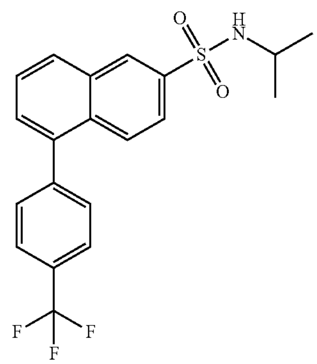 [SMILES: CC(C)NS(=O)(=O)c1ccc2c(-c3ccc(C(F)(F)F)cc3)cccc2c1] | N-isopropyl-5-(4-(trifluoromethyl)phenyl)naphthalene-2-sulfonamide |
| 7 | 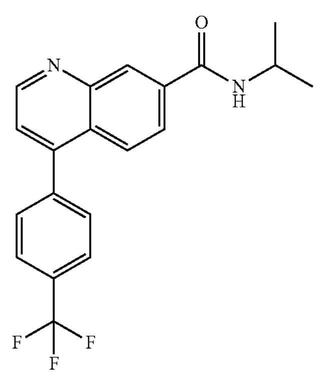 | N-isopropyl-4-[4-(trifluoromethyl)phenyl]quinoline-7-carboxamide |
| 8 | 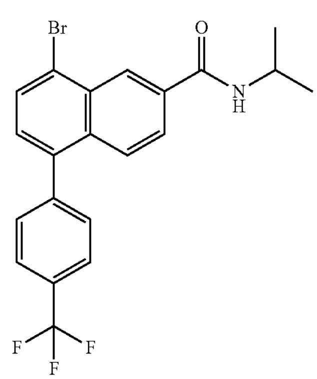 [SMILES: CC(C)NC(=O)c1ccc2c(-c3ccc(C(F)(F)F)cc3)ccc(Br)c2c1] | 8-bromo-N-isopropyl-5-(4-(trifluoromethyl)phenyl)-2-naphthamide |

TABLE 1-continued

| Compound No. | Structure | Name |
|---|---|---|
| 9 | 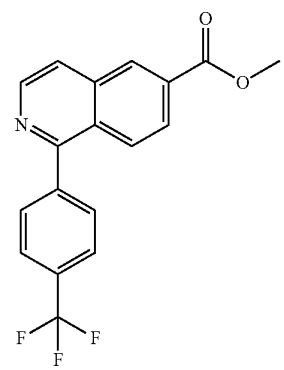 [SMILES: COC(=O)c1ccc2c(-c3ccc(C(F)(F)F)cc3)nccc2c1] | methyl 1-[4-(trifluoromethyl)phenyl]isoquinoline-6-carboxylate |
| 10 | 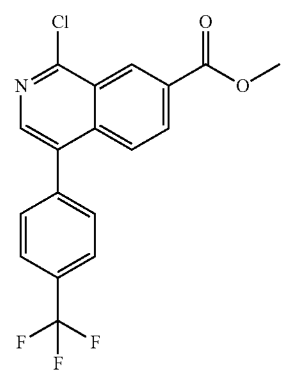 [SMILES: COC(=O)c1ccc2c(-c3ccc(C(F)(F)F)cc3)cnc(Cl)c2c1] | methyl 1-chloro-4-[4-(trifluoromethyl)phenyl]isoquinoline-7-carboxylate |
| 11 | 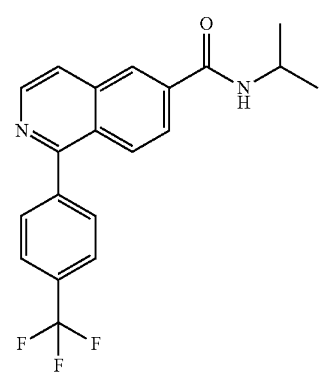 [SMILES: CC(C)NC(=O)c1ccc2c(-c3ccc(C(F)(F)F)cc3)nccc2c1] | N-isopropyl-1-[4-(trifluoromethyl)phenyl]isoquinoline-6-carboxylate |
| 12 | 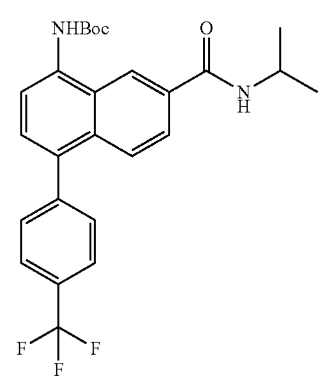 [SMILES: CC(C)NC(=O)c1ccc2c(-c3ccc(C(F)(F)F)cc3)ccc(NC(=O)OC(C)(C)C)c2c1] | tert-butyl (7-(isopropylcarbamoyl)-4-(4-(trifluoromethyl)phenyl)naphthalen-1-yl)carbamate |

TABLE 1-continued

| Compound No. | Structure | Name |
|---|---|---|
| 13 | 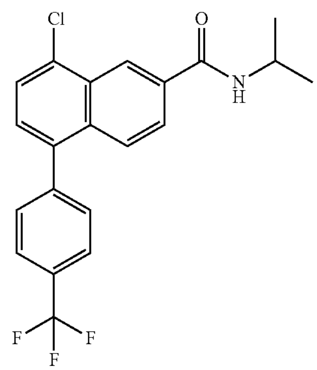 [SMILES: CC(C)NC(=O)c1ccc2c(-c3ccc(C(F)(F)F)cc3)ccc(Cl)c2c1] | 8-chloro-N-isopropyl-5-(4-(trifluoromethyl)phenyl)-2-naphthamide |
| 14 | 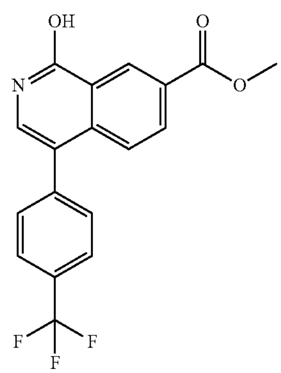 [SMILES: COC(=O)c1ccc2c(-c3ccc(C(F)(F)F)cc3)cnc(O)c2c1] | methyl 1-oxo-4-[4-(trifluoromethyl)phenyl]-2H-isoquinoline-7-carboxylate |
| 15 | 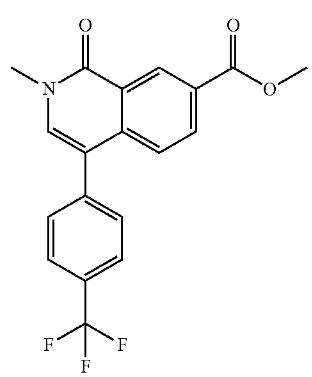 | methyl 2-methyl-1-oxo-4-[4-(trifluoromethyl)phenyl]isoquinoline-7-carboxylate |
| 16 | 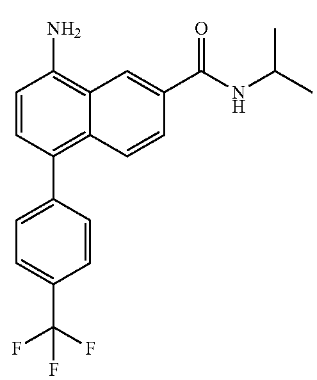 [SMILES: CC(C)NC(=O)c1ccc2c(-c3ccc(C(F)(F)F)cc3)ccc(N)c2c1] | 8-amino-N-isopropyl-5-(4-(trifluoromethyl)phenyl)-2-naphthamide |

TABLE 1-continued

| Compound No. | Structure | Name |
|---|---|---|
| 17 | 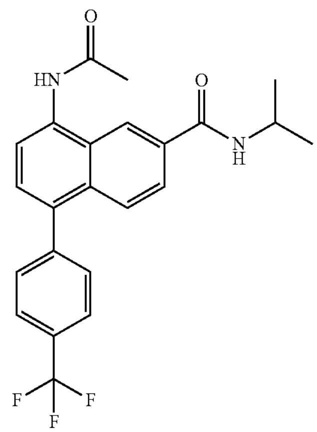 [SMILES: CC(=O)Nc1ccc(-c2ccc(C(F)(F)F)cc2)c2ccc(C(=O)NC(C)C)cc12] | 8-acetamido-N-isopropyl-5-(4-(trifluoromethyl)phenyl)-2-naphthamide |
| 18 | 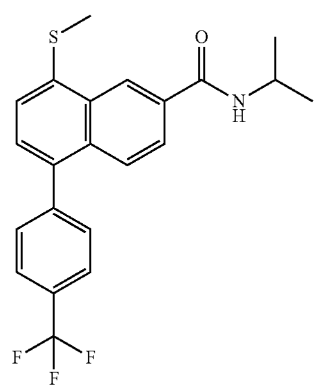 [SMILES: CSc1ccc(-c2ccc(C(F)(F)F)cc2)c2ccc(C(=O)NC(C)C)cc12] | N-isopropyl-8-methylsulfanyl-5-[4-(trifluoromethyl)phenyl]naphthalene-2-carboxamide |
| 19 | 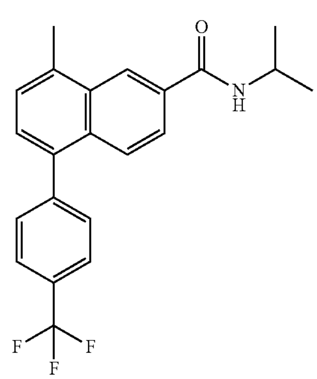 [SMILES: Cc1ccc(-c2ccc(C(F)(F)F)cc2)c2ccc(C(=O)NC(C)C)cc12] | N-isopropyl-8-methyl-5-[4-(trifluoromethyl)phenyl]naphthalene-2-carboxamide |

TABLE 1-continued

| Compound No. | Structure | Name |
|---|---|---|
| 20 | 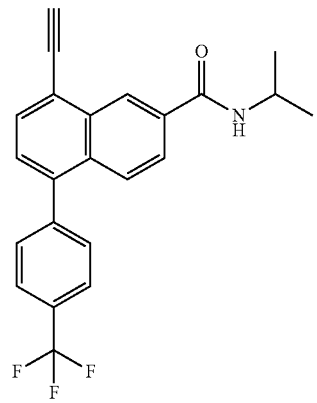 [SMILES: C#Cc1ccc(-c2ccc(C(F)(F)F)cc2)c2ccc(C(=O)NC(C)C)cc12] | 8-ethynyl-N-isopropyl-5-[4-(trifluoromethyl)phenyl]naphthalene-2-carboxamide |
| 21 | 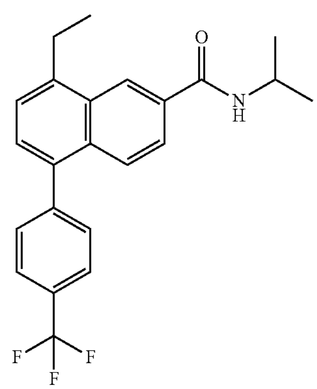 [SMILES: CCc1ccc(-c2ccc(C(F)(F)F)cc2)c2ccc(C(=O)NC(C)C)cc12] | 8-ethyl-N-isopropyl-5-[4-(trifluoromethyl)phenyl]naphthalene-2-carboxamide |
| 22 | 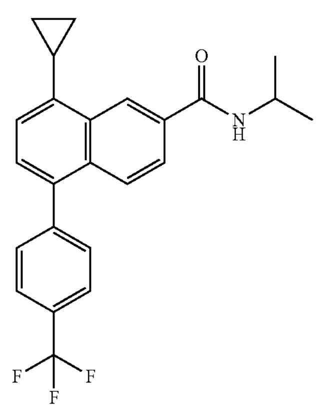 [SMILES: CC(C)NC(=O)c1ccc2c(-c3ccc(C(F)(F)F)cc3)ccc(C3CC3)c2c1] | 8-cyclopropyl-N-isopropyl-5-(4-(trifluoromethyl)phenyl)-2-naphthamide |

TABLE 1-continued

| Compound No. | Structure | Name |
|---|---|---|
| 23 | 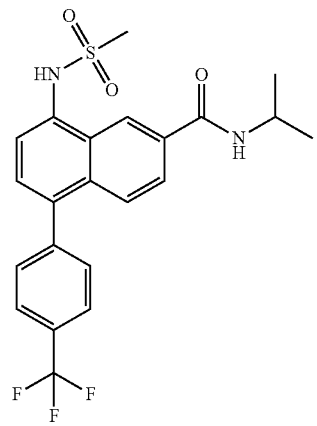 [SMILES: CC(C)NC(=O)c1ccc2c(-c3ccc(C(F)(F)F)cc3)ccc(NS(C)(=O)=O)c2c1] | N-isopropyl-8-(methyl-sulfonamido)-5-(4-(trifluoromethyl)phenyl)-2-naphthamide |
| 24 | 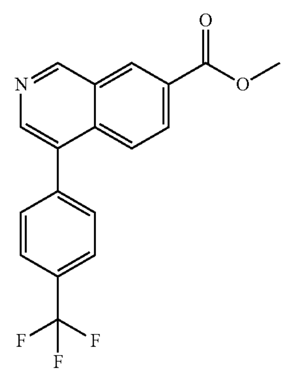 [SMILES: COC(=O)c1ccc2c(-c3ccc(C(F)(F)F)cc3)cncc2c1] | methyl 4-[4-(trifluoromethyl)phenyl]isoquinoline-7-carboxylate |
| 25 | 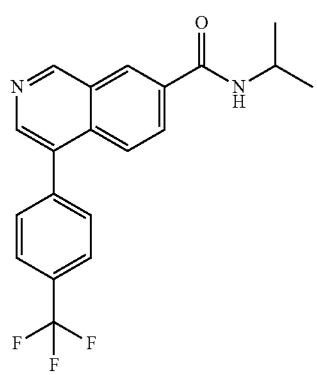 [SMILES: CC(C)NC(=O)c1ccc2c(-c3ccc(C(F)(F)F)cc3)cncc2c1] | N-isopropyl-4-[4-(trifluoromethyl)phenyl]isoquinoline-7-carboxamide |
| 26 | 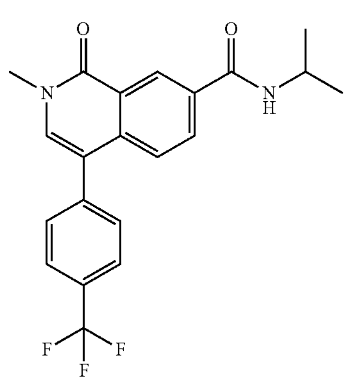 [SMILES: CC(C)NC(=O)c1ccc2c(-c3ccc(C(F)(F)F)cc3)cn(C)c(=O)c2c1] | N-isopropyl-2-methyl-1-oxo-4-(4-(trifluoromethyl)phenyl)-1,2-dihydroisoquinoline-7-carboxamide |

TABLE 1-continued

| Compound No. | Structure | Name |
|---|---|---|
| 27 | 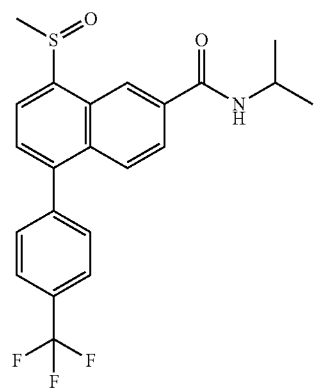 [SMILES: CC(C)NC(=O)c1ccc2c(-c3ccc(C(F)(F)F)cc3)ccc(S(C)=O)c2c1] | N-isopropyl-8-methylsulfinyl-5-[4-(trifluoromethyl)phenyl]naphthalene-2-carboxamide |
| 28 | 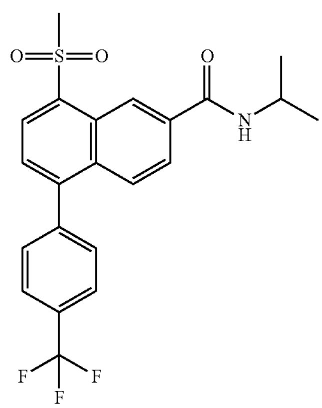 [SMILES: CC(C)NC(=O)c1ccc2c(-c3ccc(C(F)(F)F)cc3)ccc(S(C)(=O)=O)c2c1] | N-isopropyl-8-methylsulfonyl-5-[4-(trifluoromethyl)phenyl]naphthalene-2-carboxamide |
| 29 | 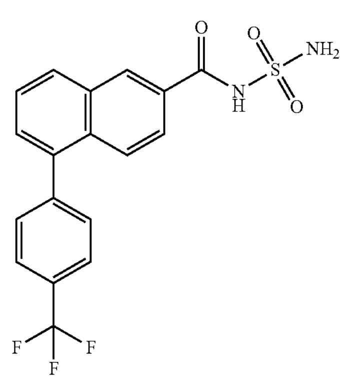 [SMILES: NS(=O)(=O)NC(=O)c1ccc2c(-c3ccc(C(F)(F)F)cc3)cccc2c1] | N-sulfamoyl-5-(4-(trifluoromethyl)phenyl)-2-naphthamide |

TABLE 1-continued

| Compound No. | Structure | Name |
|---|---|---|
| 30 | 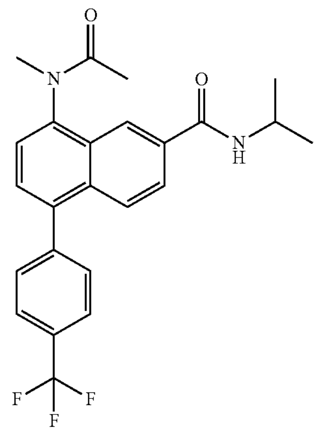 [SMILES: CC(=O)N(C)c1ccc(-c2ccc(C(F)(F)F)cc2)c2ccc(C(=O)NC(C)C)cc12] | N-isopropyl-8-(N-methyl-acetamido)-5-(4-(trifluoromethyl)phenyl)-2-naphthamide |
| 31 | 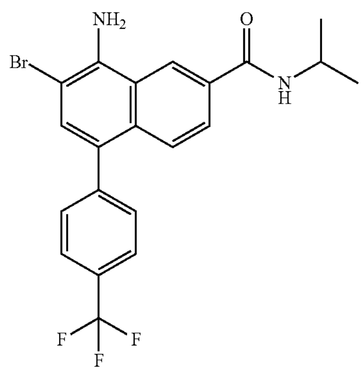 [SMILES: CC(C)NC(=O)c1ccc2c(-c3ccc(C(F)(F)F)cc3)cc(Cl)c(N)c2c1] | 8-amino-7-bromo-N-isopropyl-5-(4-(trifluoromethyl)phenyl)-2-naphthamide |
| 32 | 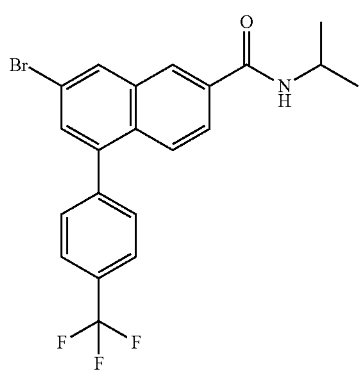 | 7-bromo-N-isopropyl-5-[4-(trifluoromethyl)phenyl]naphthalene-2-carboxamide |
| 33 | 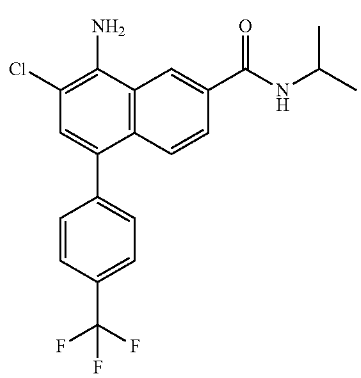 | 8-amino-7-chloro-N-isopropyl-5-(4-(trifluoromethyl)phenyl)-2-naphthamide |

TABLE 1-continued

| Compound No. | Structure | Name |
|---|---|---|
| 34 | 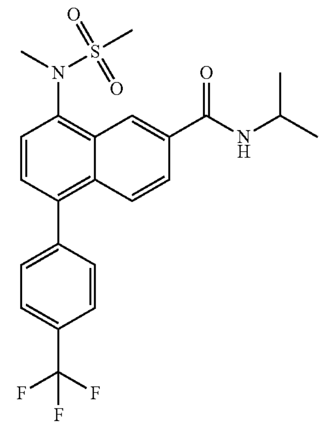 [SMILES: CC(C)NC(=O)c1ccc2c(-c3ccc(C(F)(F)F)cc3)ccc(N(C)S(C)(=O)=O)c2c1] | N-isopropyl-8-(N-methylmethyl-sulfonamido)-5-(4-(trifluoromethyl)phenyl)-2-naphthamide |
| 35 | 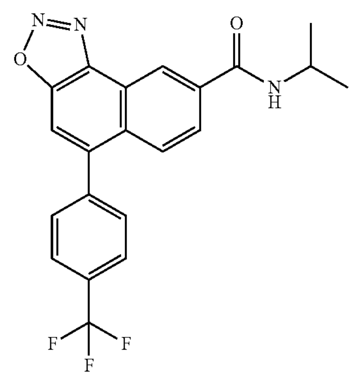 [SMILES: CC(C)NC(=O)c1ccc2c(-c3ccc(C(F)(F)F)cc3)cc3onnc3c2c1] | N-isopropyl-5-[4-(trifluoromethyl)phenyl]benzo[e][1,2,3]benzoxadiazole-8-carboxamide |
| 36 | 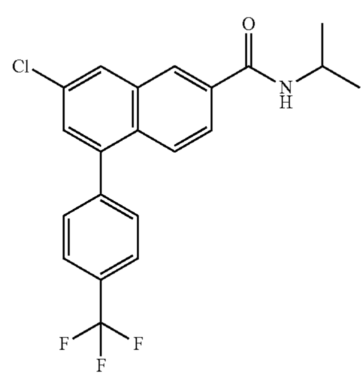 [SMILES: CC(C)NC(=O)c1ccc2c(-c3ccc(C(F)(F)F)cc3)cc(Cl)cc2c1] | 7-chloro-N-isopropyl-5-(4-(trifluoromethyl)phenyl)-2-naphthamide |
| 37 | 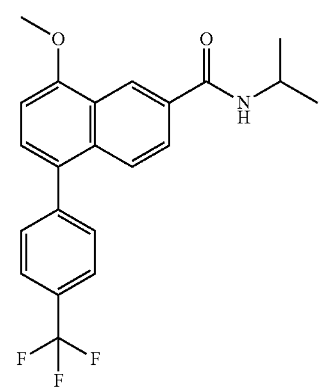 [SMILES: COc1ccc(-c2ccc(C(F)(F)F)cc2)c2ccc(C(=O)NC(C)C)cc12] | N-isopropyl-8-methoxy-5-[4-(trifluoromethyl)phenyl]naphthalene-2-carboxamide |

TABLE 1-continued

| Compound No. | Structure | Name |
|---|---|---|
| 38 | 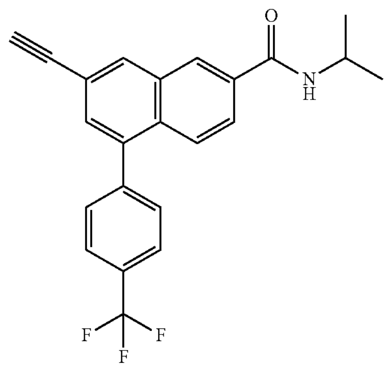 [SMILES: C#Cc1cc(-c2ccc(C(F)(F)F)cc2)c2ccc(C(=O)NC(C)C)cc2c1] | 7-ethynyl-N-isopropyl-5-(4-(trifluoromethyl)phenyl)-2-naphthamide |
| 39 | 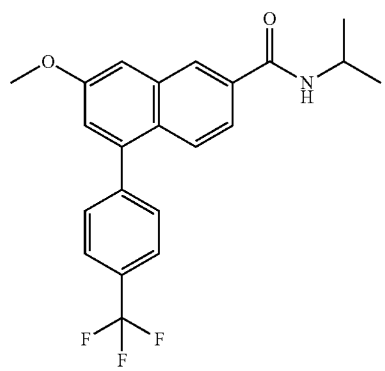 [SMILES: COc1cc(-c2ccc(C(F)(F)F)cc2)c2ccc(C(=O)NC(C)C)cc2c1] | N-isopropyl-7-methoxy-5-[4-(trifluoromethyl)phenyl]naphthalene-2-carboxamide |
| 40 | 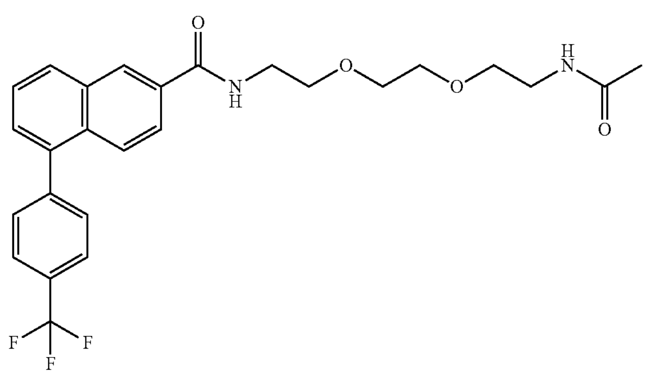 [SMILES: CC(=O)NCCOCCOCCNC(=O)c1ccc2c(-c3ccc(C(F)(F)F)cc3)cccc2c1] | N-(2-(2-(2-acetamido-ethoxy)ethoxy)ethyl)-5-(4-(trifluoromethyl)phenyl)-2-naphthamide |
| 41 | 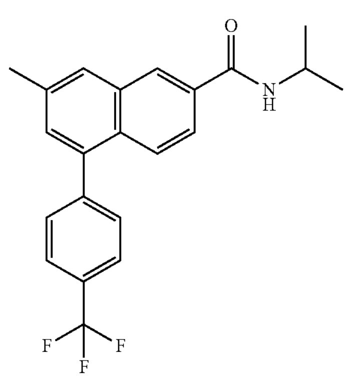 [SMILES: Cc1cc(-c2ccc(C(F)(F)F)cc2)c2ccc(C(=O)NC(C)C)cc2c1] | N-isopropyl-7-methyl-5-(4-(trifluoromethyl)phenyl)-2-naphthamide |

TABLE 1-continued
| Compound No. | Structure | Name |
|---|---|---|
| 42 | 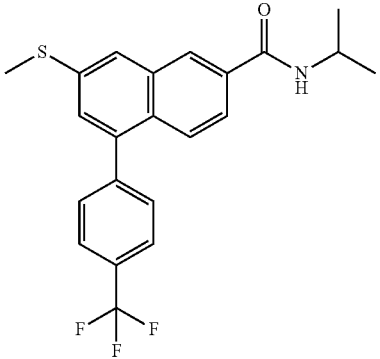 [SMILES: CSc1cc(-c2ccc(C(F)(F)F)cc2)c2ccc(C(=O)NC(C)C)cc2c1] | N-isopropyl-7-(methylthio)-5-(4-(trifluoromethyl)phenyl)-2-naphthamide |
| 43 | 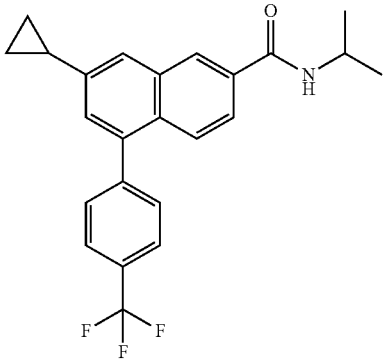 [SMILES: CC(C)NC(=O)c1ccc2c(-c3ccc(C(F)(F)F)cc3)cc(C3CC3)cc2c1] | 7-cyclopropyl-N-isopropyl-5-[4-(trifluoromethyl)phenyl]naphthalene-2-carboxamide |
| 44 | 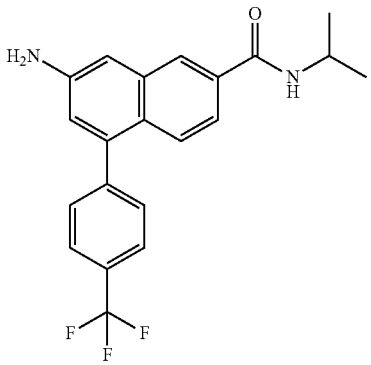 [SMILES: CC(C)NC(=O)c1ccc2c(-c3ccc(C(F)(F)F)cc3)cc(N)cc2c1] | 7-amino-N-isopropyl-5-[4-(trifluoromethyl)phenyl]naphthalene-2-carboxamide |
| 45 | 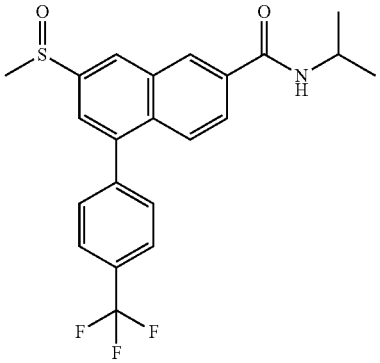 [SMILES: CC(C)NC(=O)c1ccc2c(-c3ccc(C(F)(F)F)cc3)cc(S(C)=O)cc2c1] | N-isopropyl-7-methylsulfinyl-5-[4-(trifluoromethyl)phenyl]naphthalene-2-carboxamide |

TABLE 1-continued

| Compound No. | Structure | Name |
|---|---|---|
| 46 | 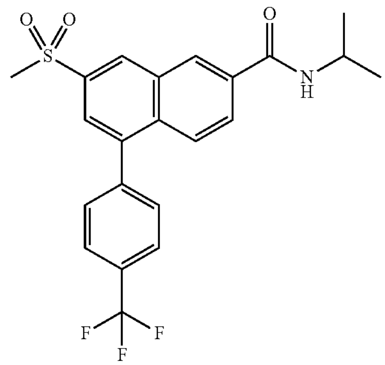 [SMILES: CC(C)NC(=O)c1ccc2c(-c3ccc(C(F)(F)F)cc3)cc(S(C)(=O)=O)cc2c1] | N-isopropyl-7-methylsulfonyl-5-[4-(trifluoromethyl)phenyl]naphthalene-2-carboxamide |
| 47 | 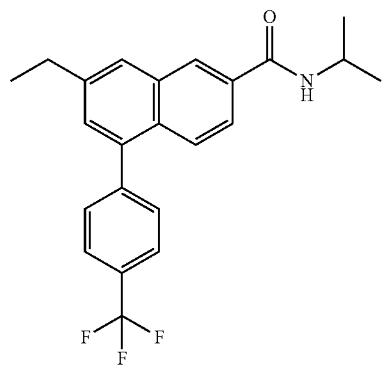 [SMILES: CCc1cc(-c2ccc(C(F)(F)F)cc2)c2ccc(C(=O)NC(C)C)cc2c1] | 7-ethyl-N-isopropyl-5-(4-(trifluoromethyl)phenyl)-2-naphthamide |
| 48 | 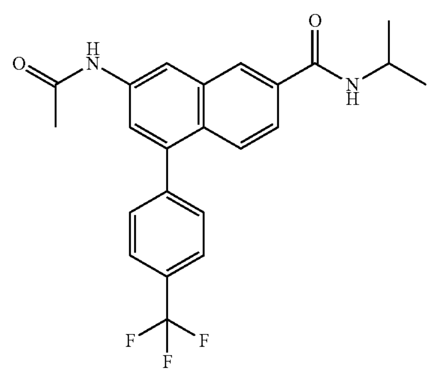 [SMILES: CC(=O)Nc1cc(-c2ccc(C(F)(F)F)cc2)c2ccc(C(=O)NC(C)C)cc2c1] | 7-acetamido-N-isopropyl-5-(4-(trifluoromethyl)phenyl)-2-naphthamide |
| 49 | 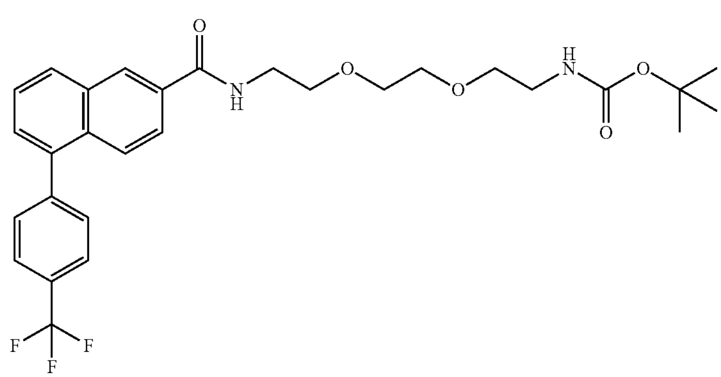 [SMILES: CC(C)(C)OC(=O)NCCOCCOCCNC(=O)c1ccc2c(-c3ccc(C(F)(F)F)cc3)cccc2c1] | tert-butyl (2-(2-(2-(5-(4-(trifluoromethyl)phenyl)-2-naphthamido)ethoxy)ethoxy)ethyl)carbamate |

TABLE 1-continued

| Compound No. | Structure | Name |
|---|---|---|
| 50 | 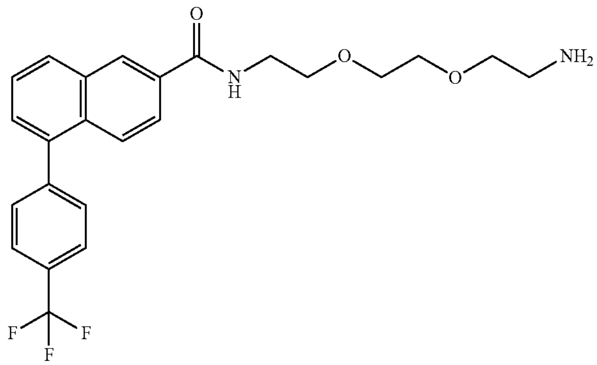 [SMILES: NCCOCCOCCNC(=O)c1ccc2c(-c3ccc(C(F)(F)F)cc3)cccc2c1] | N-(2-(2-(2-aminoethoxy)ethoxy)ethyl)-5-(4-(trifluoromethyl)phenyl)-2-naphthamide |
| 51 | 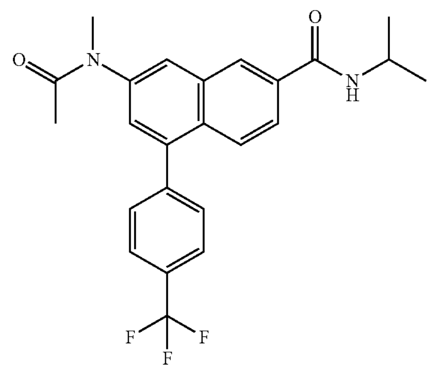 [SMILES: CC(=O)N(C)c1cc(-c2ccc(C(F)(F)F)cc2)c2ccc(C(=O)NC(C)C)cc2c1] | N-isopropyl-7-(N-methylacetamido)-5-(4-(trifluoromethyl)phenyl)-2-naphthamide |
| 52 | 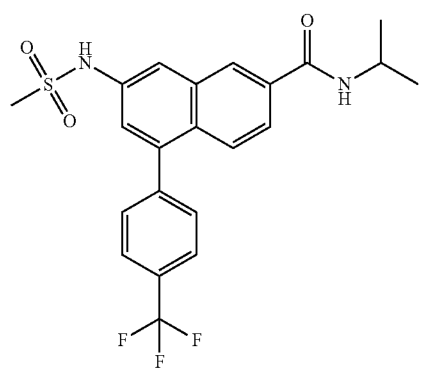 [SMILES: CC(C)NC(=O)c1ccc2c(-c3ccc(C(F)(F)F)cc3)cc(NS(C)(=O)=O)cc2c1] | N-isopropyl-7-(methylsulfonamido)-5-(4-(trifluoromethyl)phenyl)-2-naphthamide |
| 53 | 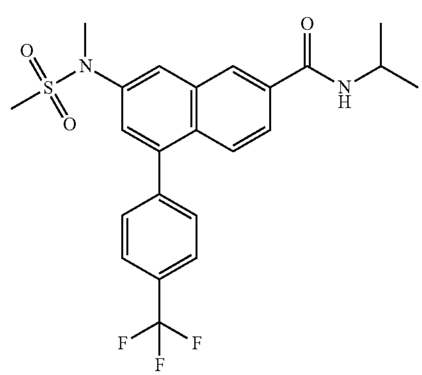 [SMILES: CC(C)NC(=O)c1ccc2c(-c3ccc(C(F)(F)F)cc3)cc(N(C)S(C)(=O)=O)cc2c1] | N-isopropyl-7-(N-methylmethylsulfonamido)-5-(4-(trifluoromethyl)phenyl)-2-naphthamide |

TABLE 1-continued
| Compound No. | Structure | Name |
|---|---|---|
| 54 | 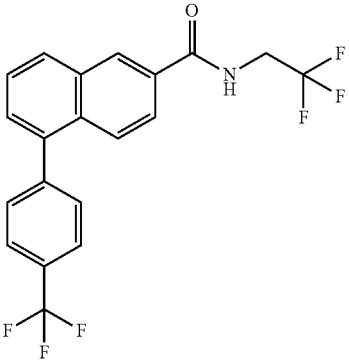 [SMILES: O=C(NCC(F)(F)F)c1ccc2c(-c3ccc(C(F)(F)F)cc3)cccc2c1] | N-(2,2,2-trifluoroethyl)-5-(4-(trifluoromethyl)phenyl)-2-naphthamide |
| 55 | 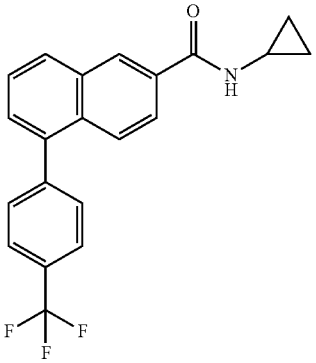 [SMILES: O=C(NC1CC1)c1ccc2c(-c3ccc(C(F)(F)F)cc3)cccc2c1] | N-cyclopropyl-5-(4-(trifluoromethyl)phenyl)-2-naphthamide |
| 56 | 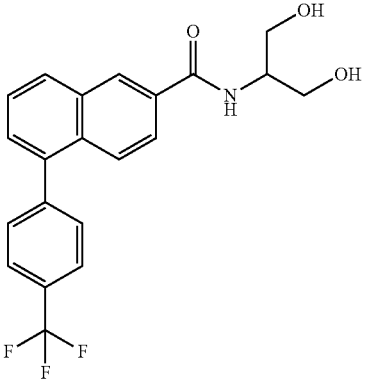 [SMILES: O=C(NC(CO)CO)c1ccc2c(-c3ccc(C(F)(F)F)cc3)cccc2c1] | N-(1,3-dihydroxy-propan-2-yl)-5-(4-(trifluoromethyl)phenyl)-2-naphthamide |
| 57 | 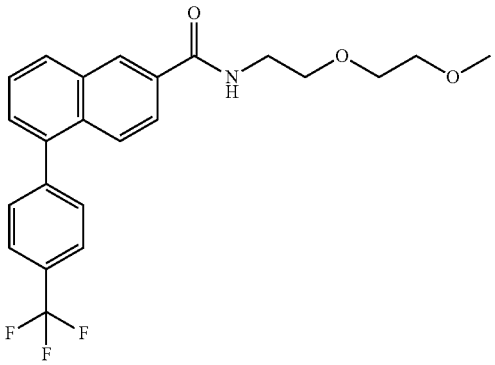 [SMILES: COCCOCCNC(=O)c1ccc2c(-c3ccc(C(F)(F)F)cc3)cccc2c1] | N-(2-(2-methoxy-ethoxy)ethyl)-5-(4-(trifluoromethyl)phenyl)-2-naphthamide |

TABLE 1-continued

| Compound No. | Structure | Name |
|---|---|---|
| 58 | 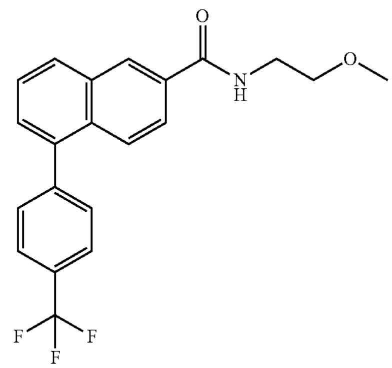 [SMILES: COCCNC(=O)c1ccc2c(-c3ccc(C(F)(F)F)cc3)cccc2c1] | N-(2-methoxyethyl)-5-(4-(trifluoromethyl)phenyl)-2-naphthamide |
| 59 | 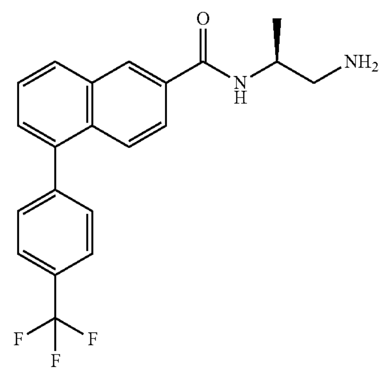 [SMILES: C[C@@H](CN)NC(=O)c1ccc2c(-c3ccc(C(F)(F)F)cc3)cccc2c1] | (S)-N-(1-aminopropan-2-yl)-5-(4-(trifluoromethyl)phenyl)-2-naphthamide |
| 60 | 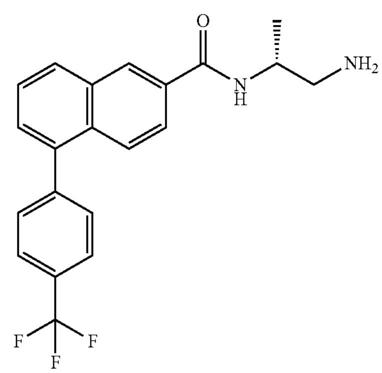 [SMILES: C[C@H](CN)NC(=O)c1ccc2c(-c3ccc(C(F)(F)F)cc3)cccc2c1] | (R)-N-(1-aminopropan-2-yl)-5-(4-(trifluoromethyl)phenyl)-2-naphthamide |
| 61 | 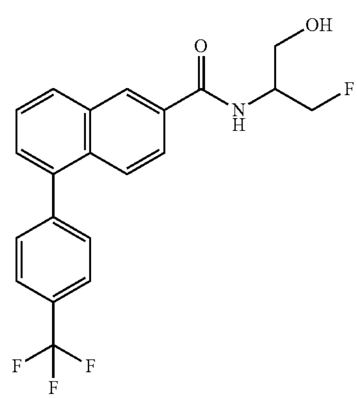 [SMILES: O=C(NC(CO)CF)c1ccc2c(-c3ccc(C(F)(F)F)cc3)cccc2c1] | N-(1-fluoro-3-hydroxypropan-2-yl)-5-(4-(trifluoromethyl)phenyl)-2-naphthamide |

TABLE 1-continued

| Compound No. | Structure | Name |
|---|---|---|
| 62 | 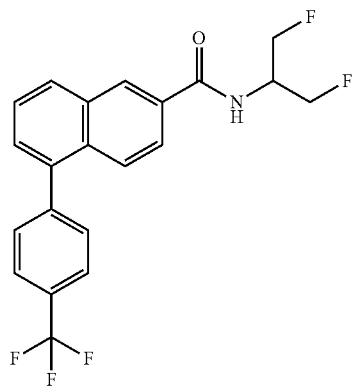 [SMILES: O=C(NC(CF)CF)c1ccc2c(-c3ccc(C(F)(F)F)cc3)cccc2c1] | N-(1,3-difluoro-propan-2-yl)-5-(4-(trifluoromethyl)phenyl)-2-naphthamide |
| 63 | 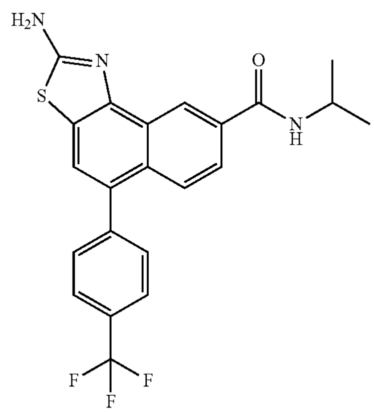 [SMILES: CC(C)NC(=O)c1ccc2c(-c3ccc(C(F)(F)F)cc3)cc3sc(N)nc3c2c1] | 2-amino-N-isopropyl-5-(4-(trifluoromethyl)phenyl)naphtho[1,2-d]thiazole-8-carboxamide |
| 64 | 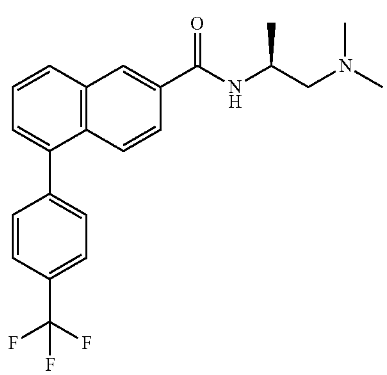 [SMILES: C[C@@H](CN(C)C)NC(=O)c1ccc2c(-c3ccc(C(F)(F)F)cc3)cccc2c1] | (S)-N-(1-(dimethylamino)propan-2-yl)-5-(4-(trifluoromethyl)phenyl)-2-naphthamide |
| 65 | 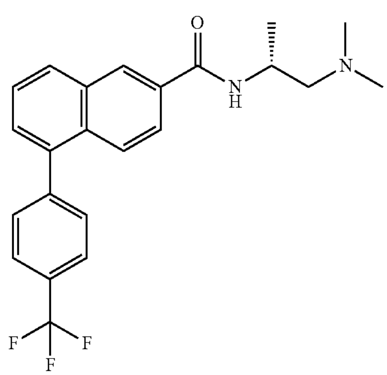 [SMILES: C[C@H](CN(C)C)NC(=O)c1ccc2c(-c3ccc(C(F)(F)F)cc3)cccc2c1] | (R)-N-(1-(dimethylamino)propan-2-yl)-5-(4-(trifluoromethyl)phenyl)-2-naphthamide |

TABLE 1-continued

| Compound No. | Structure | Name |
|---|---|---|
| 66 | 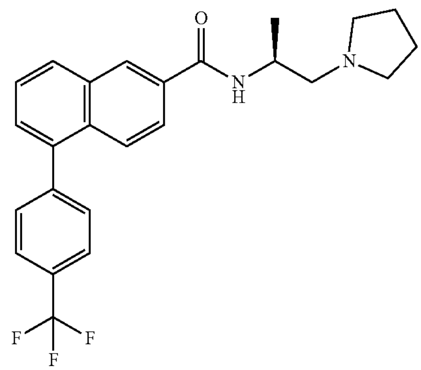 [SMILES: C[C@@H](CN1CCCC1)NC(=O)c1ccc2c(-c3ccc(C(F)(F)F)cc3)cccc2c1] | (S)-N-(1-(pyrrolidin-1-yl)propan-2-yl)-5-(4-(trifluoromethyl)phenyl)-2-naphthamide |
| 67 | 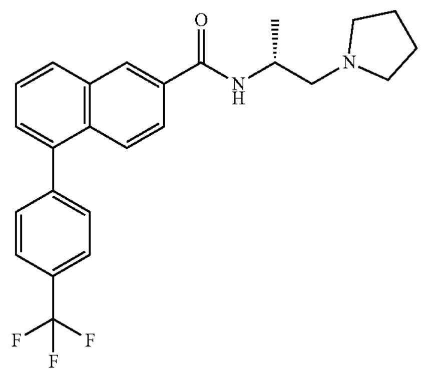 [SMILES: C[C@H](CN1CCCC1)NC(=O)c1ccc2c(-c3ccc(C(F)(F)F)cc3)cccc2c1] | (R)-N-(1-(pyrrolidin-1-yl)propan-2-yl)-5-(4-(trifluoromethyl)phenyl)-2-naphthamide |
| 68 | 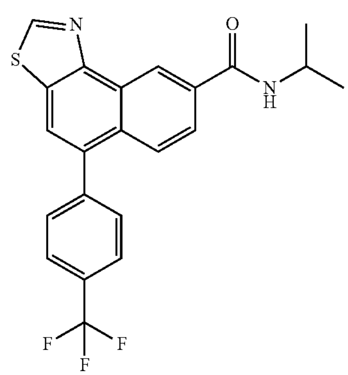 [SMILES: CC(C)NC(=O)c1ccc2c(-c3ccc(C(F)(F)F)cc3)cc3scnc3c2c1] | N-isopropyl-5-(4-(trifluoromethyl)phenyl)naphtho[1,2-d]thiazole-8-carboxamide |
| 69 | 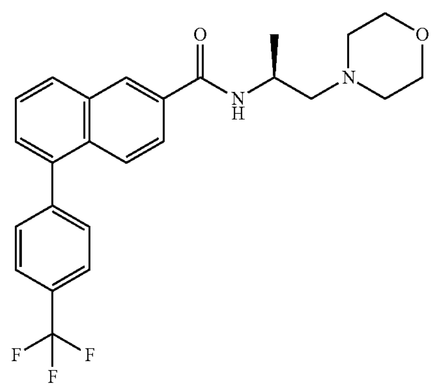 [SMILES: C[C@@H](CN1CCOCC1)NC(=O)c1ccc2c(-c3ccc(C(F)(F)F)cc3)cccc2c1] | (S)-N-(1-morpholinopropan-2-yl)-5-(4-((trifluoromethyl)phenyl)-2-naphthamide |

TABLE 1-continued

| Compound No. | Structure | Name |
|---|---|---|
| 70 | 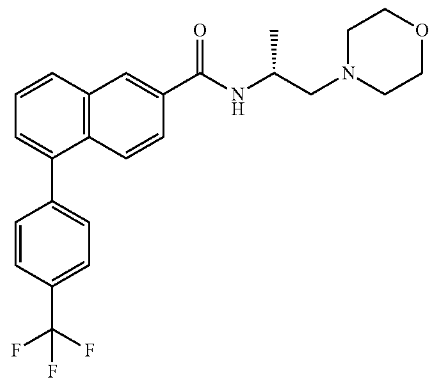 [SMILES: C[C@H](CN1CCOCC1)NC(=O)c1ccc2c(-c3ccc(C(F)(F)F)cc3)cccc2c1] | (R)-N-(1-morpholinopropan-2-yl)-5-(4-(trifluoromethyl)phenyl)-2-naphthamide |
| 71 | 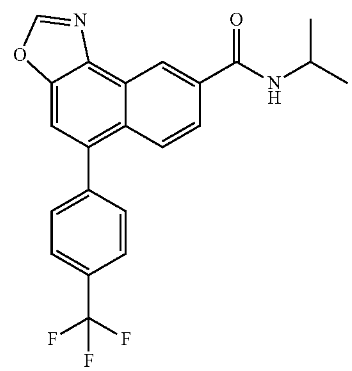 [SMILES: CC(C)NC(=O)c1ccc2c(-c3ccc(C(F)(F)F)cc3)cc3ocnc3c2c1] | N-isopropyl-5-(4-(trifluoromethyl)phenyl)naphtho[1,2-d]oxazole-8-carboxamide |
| 72 | 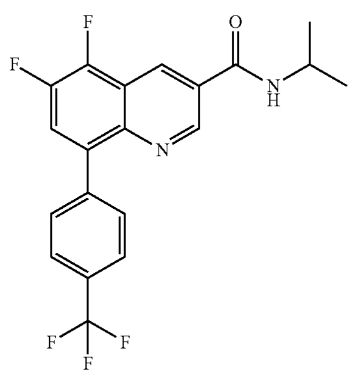 [SMILES: CC(C)NC(=O)c1cnc2c(-c3ccc(C(F)(F)F)cc3)cc(F)c(F)c2c1] | 5,6-Difluoro-N-isopropyl-8-(4-(trifluoromethyl)phenyl)quinoline-3-carboxamide |
| 73 | 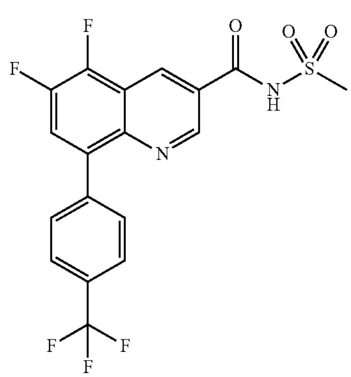 [SMILES: CS(=O)(=O)NC(=O)c1cnc2c(-c3ccc(C(F)(F)F)cc3)cc(F)c(F)c2c1] | 5,6-Difluoro-N-(methylsulfonyl)-8-(4-(trifluoromethyl)phenyl)quinoline-3-carboxamide |

TABLE 1-continued

| Compound No. | Structure | Name |
|---|---|---|
| 74 | 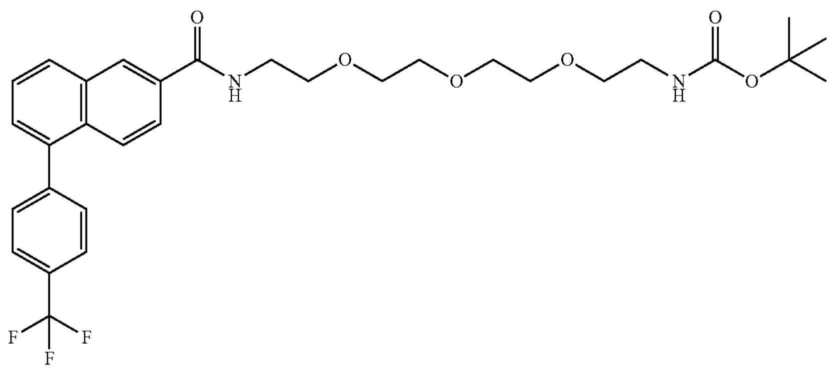 [SMILES: CC(C)(C)OC(=O)NCCOCCOCCOCCNC(=O)c1ccc2c(-c3ccc(C(F)(F)F)cc3)cccc2c1] | tert-butyl (1-oxo-1-(5-(4-(trifluoromethyl)phenyl)naphthalen-2-yl)-5,8,11-trioxa-2-azatridecan-13-yl)carbamate |
| 75 | 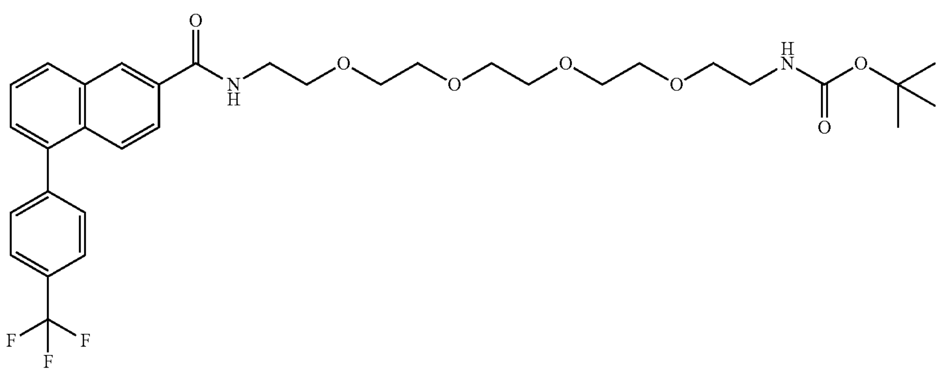 [SMILES: CC(C)(C)OC(=O)NCCOCCOCCOCCOCCNC(=O)c1ccc2c(-c3ccc(C(F)(F)F)cc3)cccc2c1] | tert-butyl (1-oxo-1-(5-(4-(trifluoromethyl)phenyl)naphthalen-2-yl)-5,8,11,14-tetraoxa-2-azahexadecan-16-yl)carbamate |
| 76 | 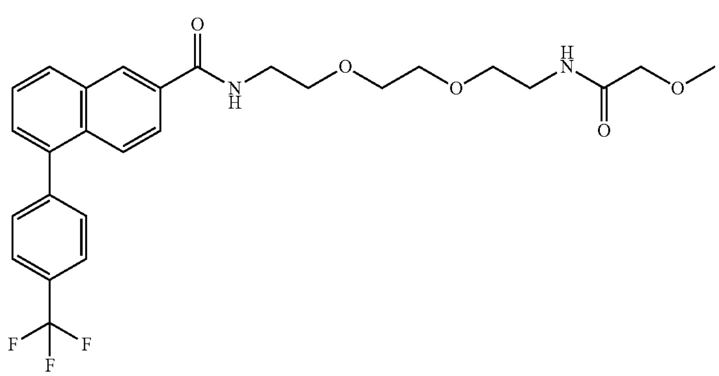 [SMILES: COCC(=O)NCCOCCOCCNC(=O)c1ccc2c(-c3ccc(C(F)(F)F)cc3)cccc2c1] | N-(4-oxo-2,8,11-trioxa-5-azatridecan-13-yl)-5-(4-(trifluoromethyl)phenyl)-2-naphthamide |
| 77 | 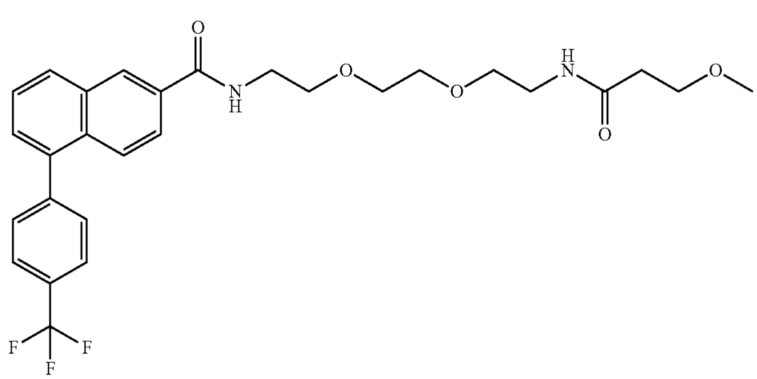 [SMILES: COCCC(=O)NCCOCCOCCNC(=O)c1ccc2c(-c3ccc(C(F)(F)F)cc3)cccc2c1] | N-(5-oxo-2,9,12-trioxa-6-azatetradecan-14-yl)-5-(4-(trifluoromethyl)phenyl)-2-naphthamide |

TABLE 1-continued

| Compound No. | Structure | Name |
|---|---|---|
| 78 | 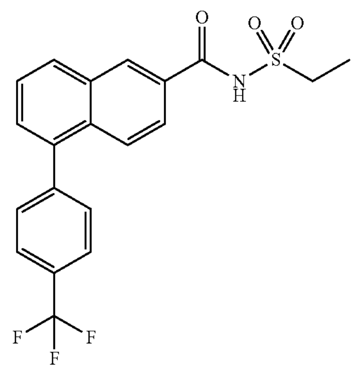 [SMILES: CCS(=O)(=O)NC(=O)c1ccc2c(-c3ccc(C(F)(F)F)cc3)cccc2c1] | N-(ethylsulfonyl)-5-(4-(trifluoromethyl)phenyl)-2-naphthamide |
| 79 | 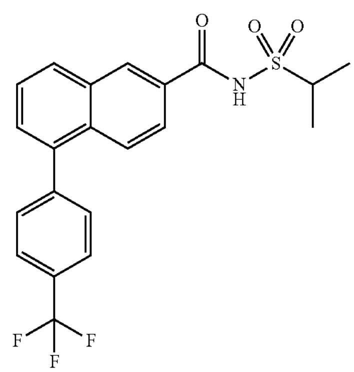 [SMILES: CC(C)S(=O)(=O)NC(=O)c1ccc2c(-c3ccc(C(F)(F)F)cc3)cccc2c1] | N-(isopropylsulfonyl)-5-(4-(trifluoromethyl)phenyl)-2-naphthamide |
| 80 | 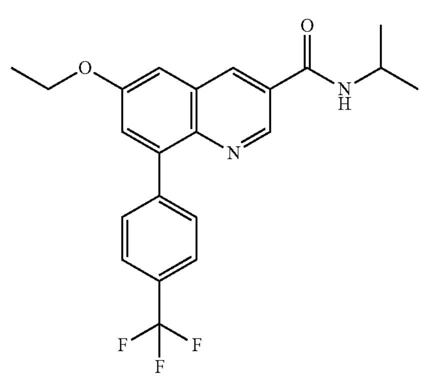 [SMILES: CCOc1cc(-c2ccc(C(F)(F)F)cc2)c2ncc(C(=O)NC(C)C)cc2c1] | 6-ethoxy-N-isopropyl-8-(4-(trifluoromethyl)phenyl)quinoline-3-carboxamide |
| 81 | 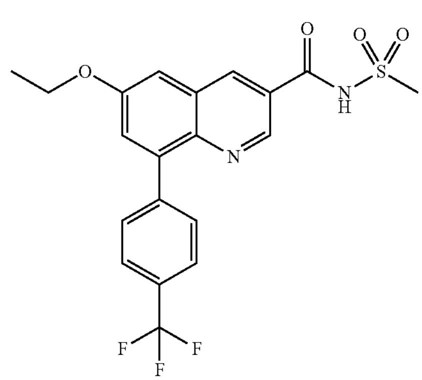 [SMILES: CCOc1cc(-c2ccc(C(F)(F)F)cc2)c2ncc(C(=O)NS(C)(=O)=O)cc2c1] | 6-ethoxy-N-(methylsulfonyl)-8-(4-(trifluoromethyl)phenyl)quinoline-3-carboxamide |

TABLE 1-continued

| Compound No. | Structure | Name |
|---|---|---|
| 82 | 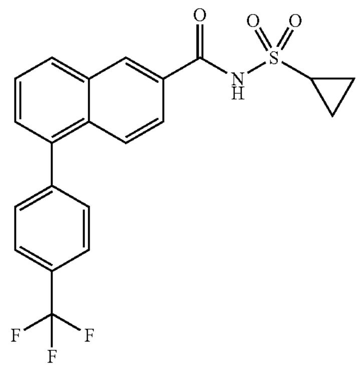 [SMILES: O=C(NS(=O)(=O)C1CC1)c1ccc2c(-c3ccc(C(F)(F)F)cc3)cccc2c1] | N-(cyclopropylsulfonyl)-5-(4-(trifluoromethyl)phenyl)-2-naphthamide |
| 83 | 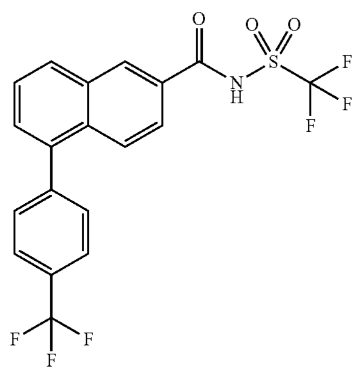 [SMILES: O=C(NS(=O)(=O)C(F)(F)F)c1ccc2c(-c3ccc(C(F)(F)F)cc3)cccc2c1] | 5-(4-(trifluoromethyl)phenyl)-N-((trifluoromethyl)sulfonyl)-2-naphthamide |
| 84 | 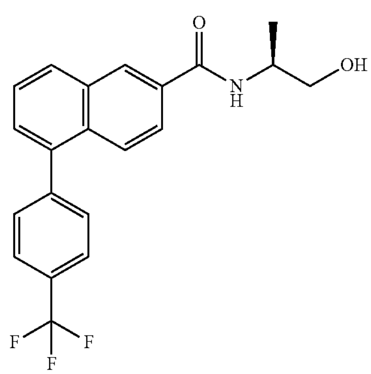 [SMILES: C[C@@H](CO)NC(=O)c1ccc2c(-c3ccc(C(F)(F)F)cc3)cccc2c1] | (S)-N-(1-hydroxypropan-2-yl)-5-(4-(trifluoromethyl)phenyl)-2-naphthamide |
| 85 | 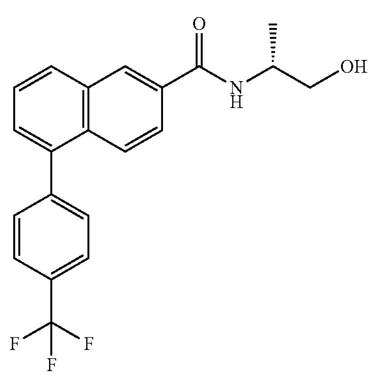 [SMILES: C[C@H](CO)NC(=O)c1ccc2c(-c3ccc(C(F)(F)F)cc3)cccc2c1] | (R)-N-(1-hydroxypropan-2-yl)-5-(4-(trifluoromethyl)phenyl)-2-naphthamide |

TABLE 1-continued

| Compound No. | Structure | Name |
|---|---|---|
| 86 | 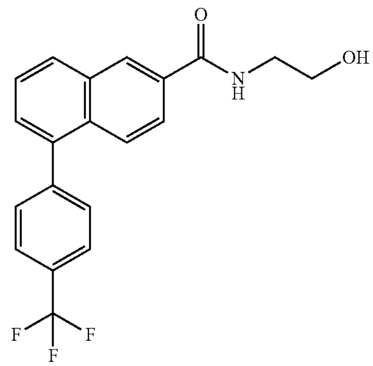 [SMILES: O=C(NCCO)c1ccc2c(-c3ccc(C(F)(F)F)cc3)cccc2c1] | N-(2-hydroxyethyl)-5-(4-(trifluoromethyl)phenyl)-2-naphthamide |
| 87 | 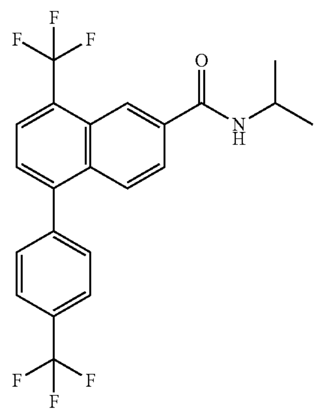 [SMILES: CC(C)NC(=O)c1ccc2c(-c3ccc(C(F)(F)F)cc3)ccc(C(F)(F)F)c2c1] | N-isopropyl-8-(trifluoromethyl)-5-(4-(trifluoromethyl)phenyl)-2-naphthamide |
| 88 | 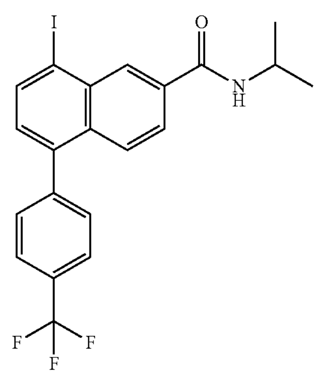 [SMILES: CC(C)NC(=O)c1ccc2c(-c3ccc(C(F)(F)F)cc3)ccc(I)c2c1] | 8-iodo-N-isopropyl-5-(4-(trifluoromethyl)phenyl)-2-naphthamide |
| 89 | 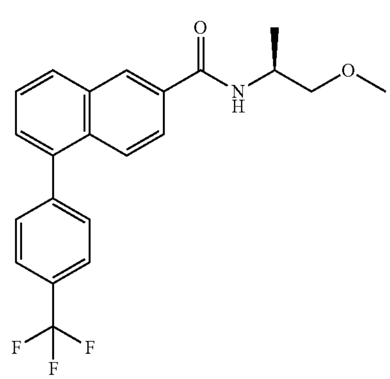 [SMILES: COC[C@H](C)NC(=O)c1ccc2c(-c3ccc(C(F)(F)F)cc3)cccc2c1] | (S)-N-(1-methoxy-propan-2-yl)-5-(4-(trifluoromethyl)phenyl)-2-naphthamide |

TABLE 1-continued

| Compound No. | Structure | Name |
|---|---|---|
| 90 | 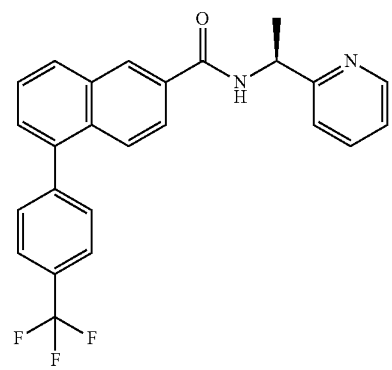 [SMILES: C[C@H](NC(=O)c1ccc2c(-c3ccc(C(F)(F)F)cc3)cccc2c1)c1ccccn1] | (S)-N-(1-(pyridin-2-yl)ethyl)-5-(4-(trifluoromethyl)phenyl)-2-naphthamide |
| 91 | 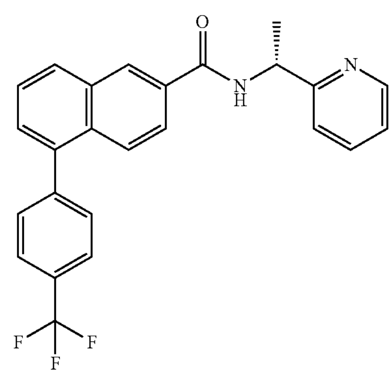 | (R)-N-(1-(pyridin-2-yl)ethyl)-5-(4-(trifluoromethyl)phenyl)-2-naphthamide |
| 92 | 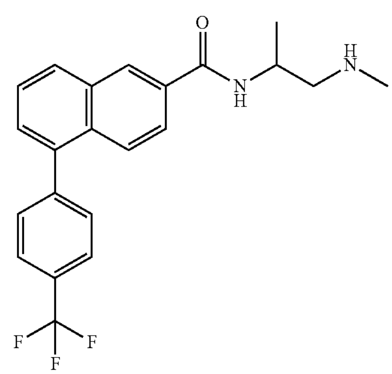 [SMILES: CNCC(C)NC(=O)c1ccc2c(-c3ccc(C(F)(F)F)cc3)cccc2c1] | N-(1-(methylamino)propan-2-yl)-5-(4-(trifluoromethyl)phenyl)-2-naphthamide |
| 93 | 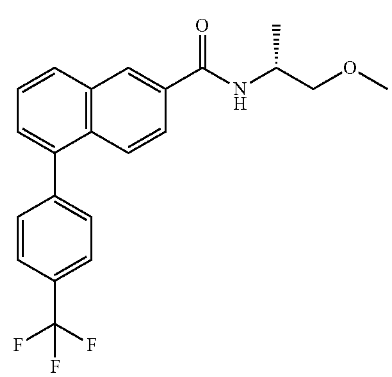 [SMILES: COC[C@@H](C)NC(=O)c1ccc2c(-c3ccc(C(F)(F)F)cc3)cccc2c1] | (R)-N-(1-methoxypropan-2-yl)-5-(4-(trifluoromethyl)phenyl)-2-naphthamide |

TABLE 1-continued

| Compound No. | Structure | Name |
|---|---|---|
| 94 | 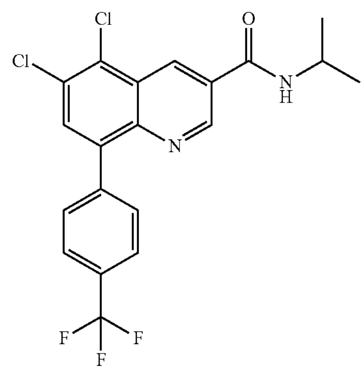 [SMILES: CC(C)NC(=O)c1cnc2c(-c3ccc(C(F)(F)F)cc3)cc(Cl)c(Cl)c2c1] | 5,6-Dichloro-N-isopropyl-8-(4-(trifluoromethyl)phenyl)quinoline-3-carboxamide |
| 95 | 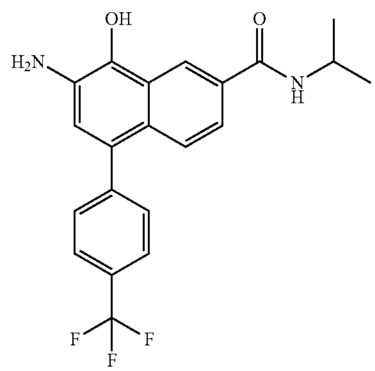 [SMILES: CC(C)NC(=O)c1ccc2c(-c3ccc(C(F)(F)F)cc3)cc(N)c(O)c2c1] | 7-amino-8-hydroxy-N-isopropyl-5-(4-(trifluoromethyl)phenyl)-2-naphthamide |
| 96 | 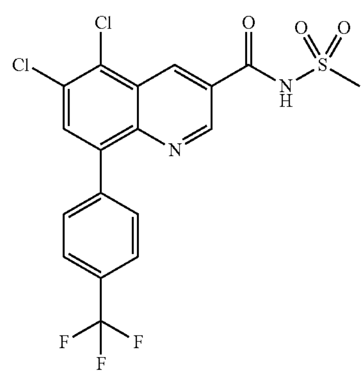 [SMILES: CS(=O)(=O)NC(=O)c1cnc2c(-c3ccc(C(F)(F)F)cc3)cc(Cl)c(Cl)c2c1] | 5,6-dichloro-N-(methylsulfonyl)-8-(4-(trifluoromethyl)phenyl)quinoline-3-carboxamide |
| 97 | 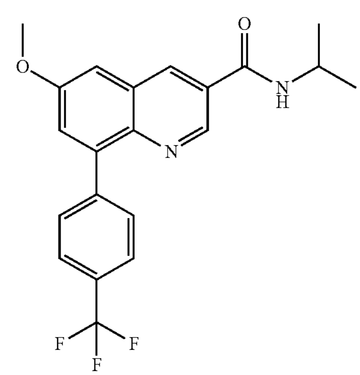 [SMILES: COc1cc(-c2ccc(C(F)(F)F)cc2)c2ncc(C(=O)NC(C)C)cc2c1] | N-isopropyl-6-methoxy-8-[4-(trifluoromethyl)phenyl]quinoline-3-carboxamide |

TABLE 1-continued

| Compound No. | Structure | Name |
|---|---|---|
| 98 | 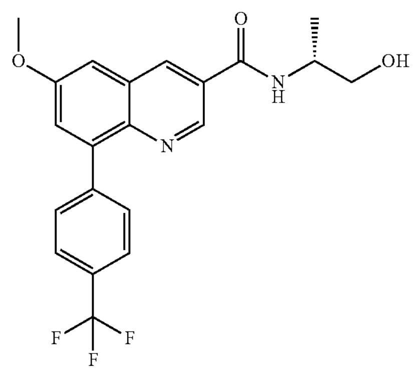 [SMILES: COc1cc(-c2ccc(C(F)(F)F)cc2)c2ncc(C(=O)N[C@H](C)CO)cc2c1] | N-[(1R)-2-hydroxy-1-methyl-ethyl]-6-methoxy-8-[4-(trifluoromethyl)phenyl]quinoline-3-carboxamide |
| 99 | 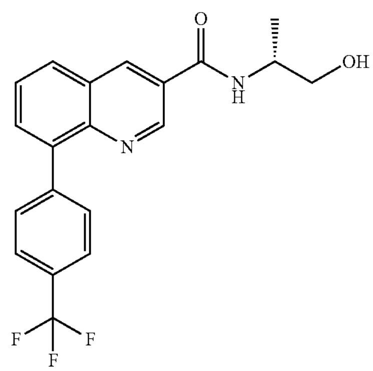 [SMILES: C[C@H](CO)NC(=O)c1cnc2c(-c3ccc(C(F)(F)F)cc3)cccc2c1] | (R)-N-(1-hydroxypropan-2-yl)-8-(4-(trifluoromethyl)phenyl)quinoline-3-carboxamide |
| 100 | 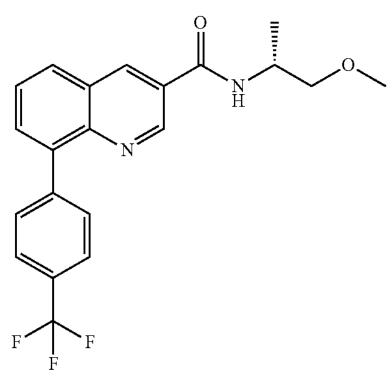 [SMILES: COC[C@@H](C)NC(=O)c1cnc2c(-c3ccc(C(F)(F)F)cc3)cccc2c1] | (R)-N-(1-methoxypropan-2-yl)-8-(4-(trifluoromethyl)phenyl)quinoline-3-carboxamide |
| 101 | 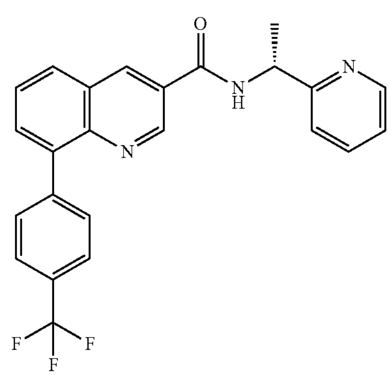 [SMILES: C[C@@H](NC(=O)c1cnc2c(-c3ccc(C(F)(F)F)cc3)cccc2c1)c1ccccn1] | (R)-N-(1-(pyridin-2-yl)ethyl)-8-(4-(trifluoromethyl)phenyl)quinoline-3-carboxamide |

TABLE 1-continued

| Compound No. | Structure | Name |
|---|---|---|
| 102 | 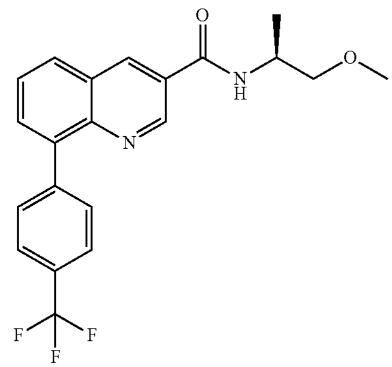 [SMILES: COC[C@H](C)NC(=O)c1cnc2c(-c3ccc(C(F)(F)F)cc3)cccc2c1] | (S)-N-(1-methoxy-propan-2-yl)-8-(4-(trifluoromethyl)phenyl)quinoline-3-carboxamide |
| 103 | 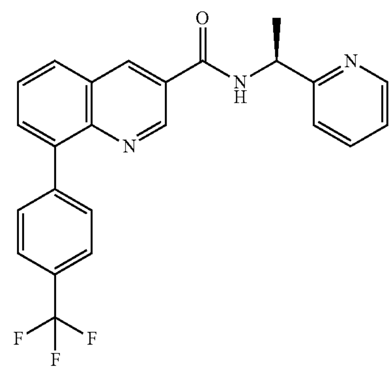 [SMILES: C[C@H](NC(=O)c1cnc2c(-c3ccc(C(F)(F)F)cc3)cccc2c1)c1ccccn1] | (S)-N-(1-(pyridin-2-yl)ethyl)-8-(4-(trifluoromethyl)phenyl)quinoline-3-carboxamide |
| 104 | 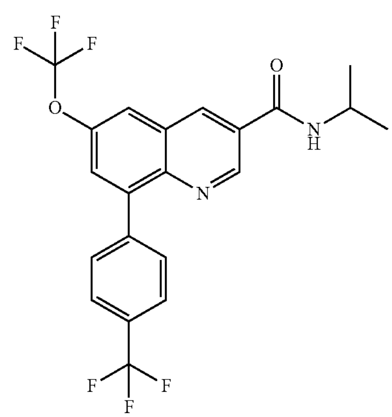 [SMILES: CC(C)NC(=O)c1cnc2c(-c3ccc(C(F)(F)F)cc3)cc(OC(F)(F)F)cc2c1] | N-isopropyl-6-(trifluoromethoxy)-8-[4-(trifluoromethyl)phenyl]quinoline-3-carboxamide |
| 105 | 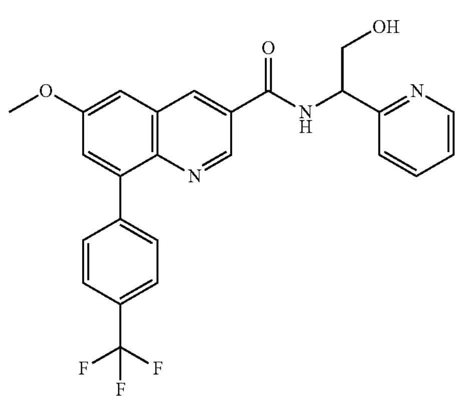 [SMILES: COc1cc(-c2ccc(C(F)(F)F)cc2)c2ncc(C(=O)NC(CO)c3ccccn3)cc2c1] | N-[2-hydroxy-1-(2-pyridyl)ethyl]-6-methoxy-8-[4-(trifluoromethyl)phenyl]quinoline-3-carboxamide |

TABLE 1-continued
| Compound No. | Structure | Name |
|---|---|---|
| 106 | 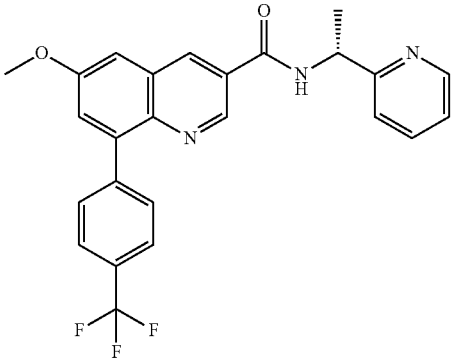 [SMILES: COc1cc(-c2ccc(C(F)(F)F)cc2)c2ncc(C(=O)N[C@H](C)c3ccccn3)cc2c1] | 6-methoxy-N-[(1R)-1-(2-pyridyl)ethyl]-8-[4-((trifluoromethyl)phenyl]quinoline-3-carboxamide |
| 107 | 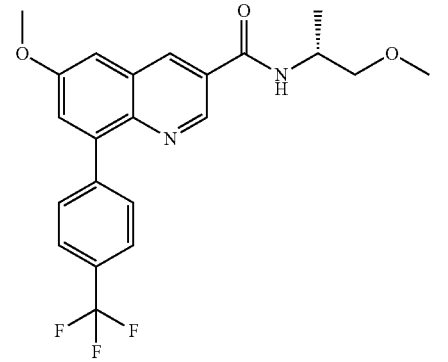 [SMILES: COC[C@@H](C)NC(=O)c1cnc2c(-c3ccc(C(F)(F)F)cc3)cc(OC)cc2c1] | 6-methoxy-N-[(1R)-2-methoxy-1-methyl-ethyl]-8-[4-(trifluoromethyl)phenyl]quinoline-3-carboxamide |
| 108 | 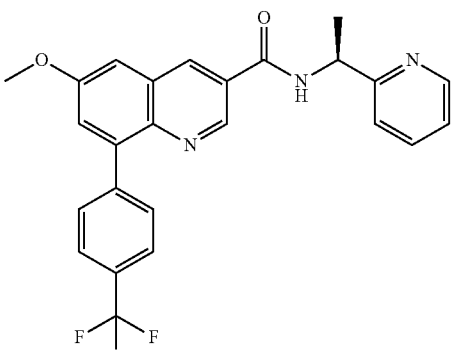 | 6-methxoy-N-[(1S)-1-(2-pyridyl)ethyl]-8-[4-(trifluoromethyl)phenyl]quinoline-3-carboxamide |
| 109 | 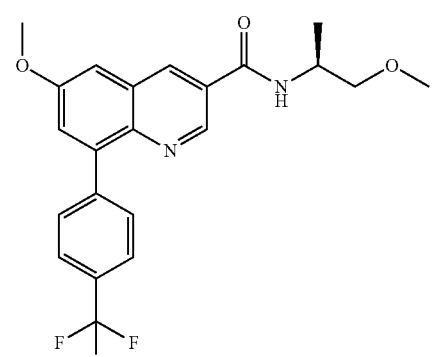 | 6-methoxy-N-[(1S)-2-methoxy-1-methyl-ethyl]-8-[4-(trifluoromethyl)phenyl]quinoline-3-carboxamide |

TABLE 1-continued

| Compound No. | Structure | Name |
|---|---|---|
| 110 | 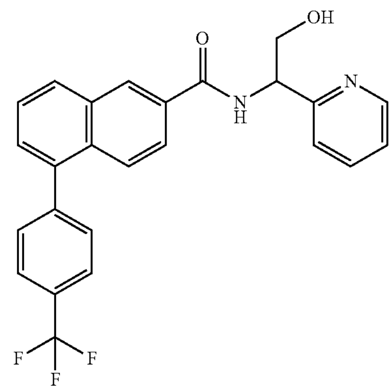 [SMILES: O=C(NC(CO)c1ccccn1)c1ccc2c(-c3ccc(C(F)(F)F)cc3)cccc2c1] | N-(2-hydroxy-1-(pyridin-2-yl)ethyl)-5-(4-(trifluoromethyl)phenyl)-2-naphthamide |
| 111 | 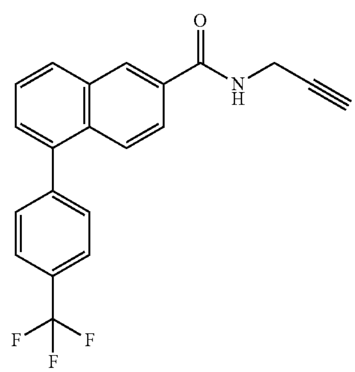 [SMILES: C#CCNC(=O)c1ccc2c(-c3ccc(C(F)(F)F)cc3)cccc2c1] | N-(prop-2-yn-1-yl)-5-(4-(trifluoromethyl)phenyl)-2-naphthamide |
| 112 | 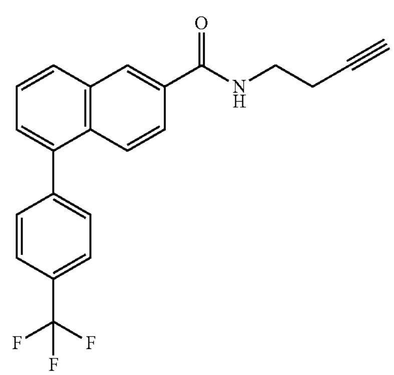 [SMILES: C#CCCNC(=O)c1ccc2c(-c3ccc(C(F)(F)F)cc3)cccc2c1] | N-(but-3-yn-1-yl)-5-(4-(trifluoromethyl)phenyl)-2-naphthamide |
| 113 | 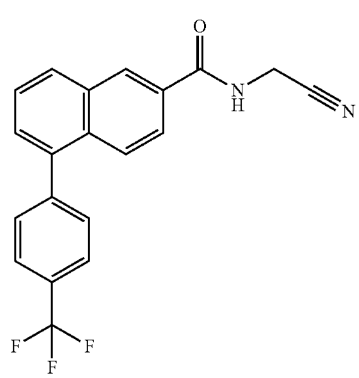 [SMILES: N#CCNC(=O)c1ccc2c(-c3ccc(C(F)(F)F)cc3)cccc2c1] | N-(cyanomethyl)-5-(4-(trifluoromethyl)phenyl)-2-naphthamide |

TABLE 1-continued

| Compound No. | Structure | Name |
|---|---|---|
| 114 | 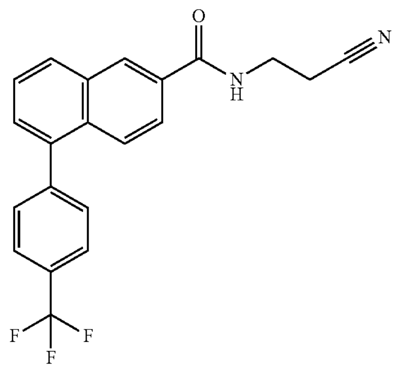 [SMILES: N#CCCNC(=O)c1ccc2c(-c3ccc(C(F)(F)F)cc3)cccc2c1] | N-(2-cyanoethyl)-5-(4-(trifluoromethyl)phenyl)-2-naphthamide |
| 115 | 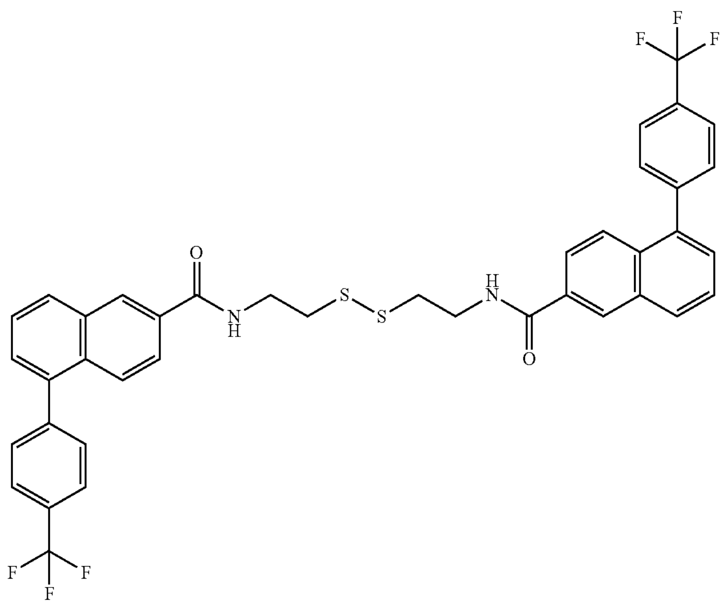 [SMILES: O=C(NCCSSCCNC(=O)c1ccc2c(-c3ccc(C(F)(F)F)cc3)cccc2c1)c1ccc2c(-c3ccc(C(F)(F)F)cc3)cccc2c1] | N,N'-(disulfanediylbis(ethane-2,1-diyl))bis(5-(4-(trifluoromethyl)phenyl)-2-naphthamide) |
| 116 | 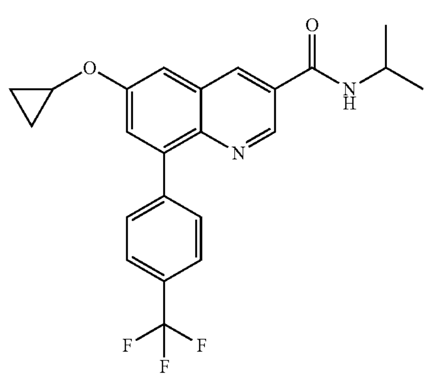 [SMILES: CC(C)NC(=O)c1cnc2c(-c3ccc(C(F)(F)F)cc3)cc(OC3CC3)cc2c1] | 6-cyclopropoxy-N-isopropyl-8-(4-(trifluoromethyl)phenyl)quinoline-3-carboxamide |

TABLE 1-continued

| Compound No. | Structure | Name |
|---|---|---|
| 117 | 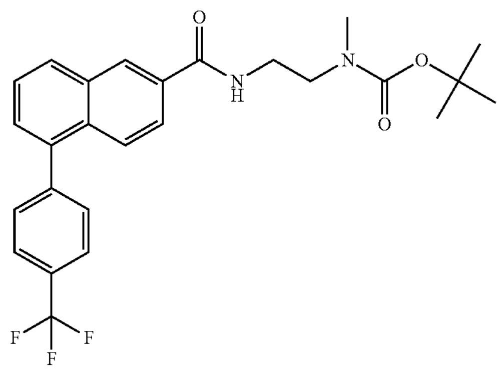 [SMILES: CN(CCNC(=O)c1ccc2c(-c3ccc(C(F)(F)F)cc3)cccc2c1)C(=O)OC(C)(C)C] | tert-butyl methyl (2-(5-(4-(trifluoromethyl)phenyl)-2-naphthamido)ethyl)carbamate |
| 118 | 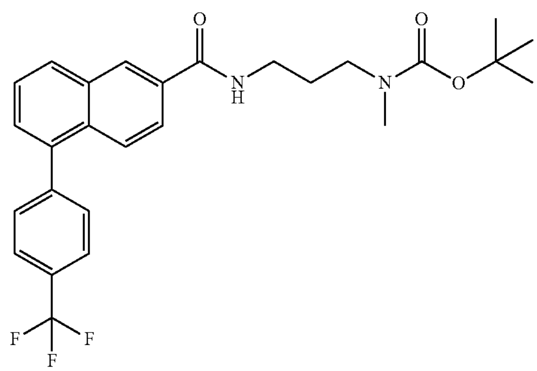 [SMILES: CN(CCCNC(=O)c1ccc2c(-c3ccc(C(F)(F)F)cc3)cccc2c1)C(=O)OC(C)(C)C] | tert-butyl methyl(3-(5-(4-(trifluoromethyl)phenyl)-2-naphthamido)propyl)carbamate |
| 119 | 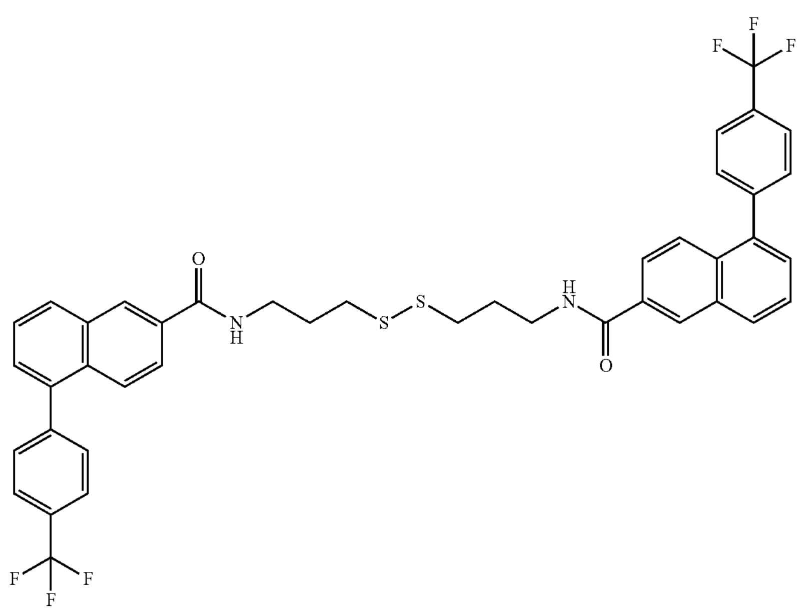 [SMILES: O=C(NCCCSSCCCNC(=O)c1ccc2c(-c3ccc(C(F)(F)F)cc3)cccc2c1)c1ccc2c(-c3ccc(C(F)(F)F)cc3)cccc2c1] | N,N'-(disulfanediylbis(propane-3,1-diyl))bis(5-(4-(trifluoromethyl)phenyl)-2-naphthamide) |

TABLE 1-continued

| Compound No. | Structure | Name |
|---|---|---|
| 120 | 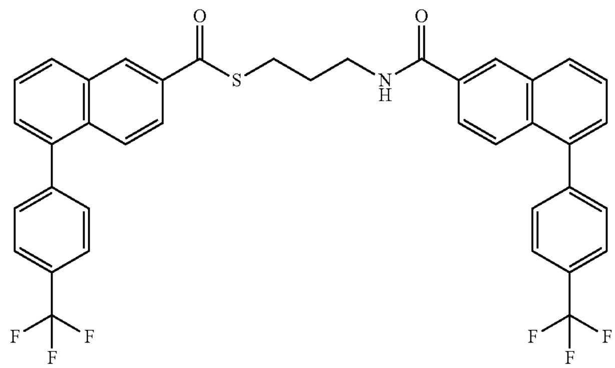 [SMILES: O=C(NCCCSC(=O)c1ccc2c(-c3ccc(C(F)(F)F)cc3)cccc2c1)c1ccc2c(-c3ccc(C(F)(F)F)cc3)cccc2c1] | S-(3-(5-(4-(trifluoromethyl)phenyl)-2-naphthamido)propyl) 5-(4-(trifluoromethyl)phenyl)naphthalene-2-carbothioate |
| 121 | 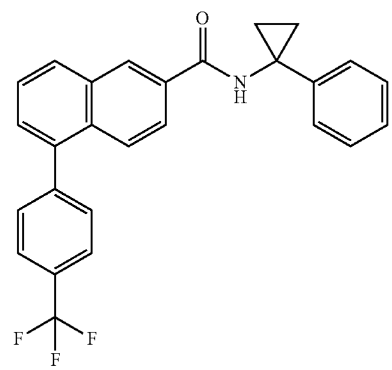 [SMILES: O=C(NC1(c2ccccc2)CC1)c1ccc2c(-c3ccc(C(F)(F)F)cc3)cccc2c1] | N-(1-phenylcyclopropyl)-5-[4-(trifluoromethyl)phenyl]naphthalene-2-carboxamide |
| 122 | 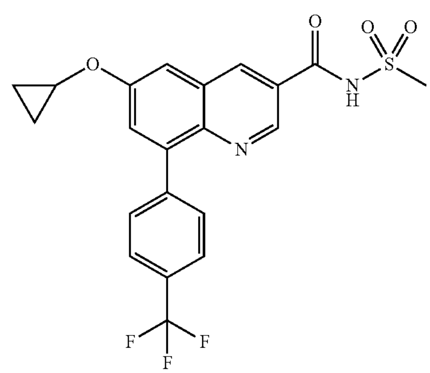 [SMILES: CS(=O)(=O)NC(=O)c1cnc2c(-c3ccc(C(F)(F)F)cc3)cc(OC3CC3)cc2c1] | 6-cyclopropoxy-N-(methylsulfonyl)-8-(4-(trifluoromethyl)phenyl)quinoline-3-carboxamide |
| 123 | 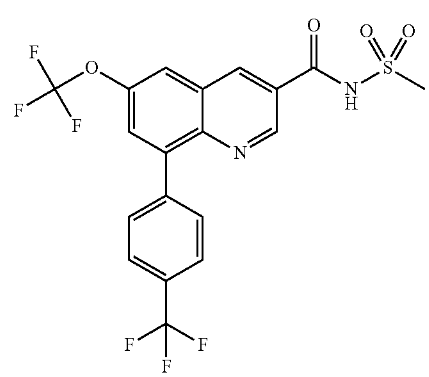 [SMILES: CS(=O)(=O)NC(=O)c1cnc2c(-c3ccc(C(F)(F)F)cc3)cc(OC(F)(F)F)cc2c1] | N-(methylsulfonyl)-6-(trifluoromethoxy)-8-(4-(trifluoromethyl)phenyl)quinoline-3-carboxamide |

TABLE 1-continued

| Compound No. | Structure | Name |
|---|---|---|
| 124 | 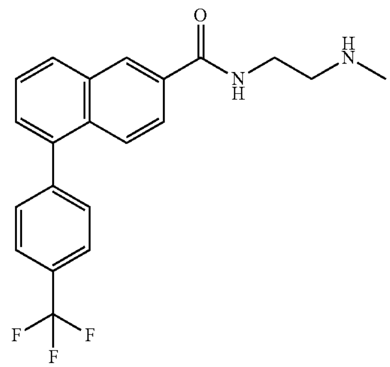 [SMILES: CNCCNC(=O)c1ccc2c(-c3ccc(C(F)(F)F)cc3)cccc2c1] | N-(2-(methylamino)ethyl)-5-(4-(trifluoromethyl)phenyl)-2-naphthamide |
| 125 | 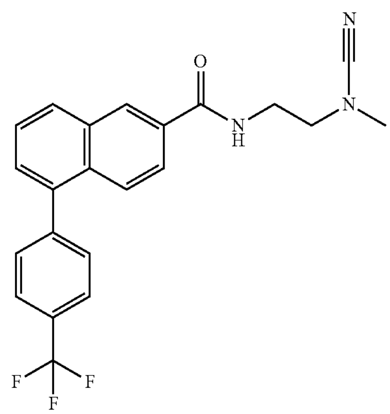 [SMILES: CN(C#N)CCNC(=O)c1ccc2c(-c3ccc(C(F)(F)F)cc3)cccc2c1] | N-(2-(N-methyl-cyanamido)ethyl)-5-(4-(trifluoromethyl)phenyl)-2-naphthamide |
| 126 | 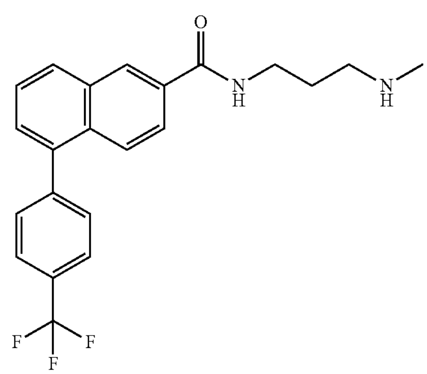 [SMILES: CNCCCNC(=O)c1ccc2c(-c3ccc(C(F)(F)F)cc3)cccc2c1] | N-(3-(methylamino)propyl)-5-(4-(trifluoromethyl)phenyl)-2-naphthamide |
| 127 | 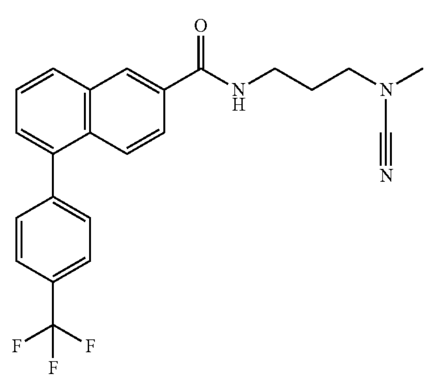 [SMILES: CN(C#N)CCCNC(=O)c1ccc2c(-c3ccc(C(F)(F)F)cc3)cccc2c1] | N-(3-(N-methylcyanamido)propyl)-5-(4-(trifluoromethyl)phenyl)-2-naphthamide |

TABLE 1-continued

| Compound No. | Structure | Name |
|---|---|---|
| 128 | 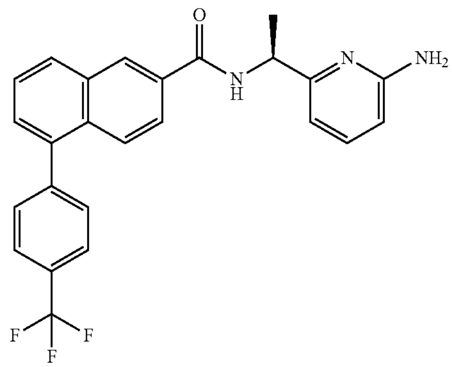 [SMILES: C[C@H](NC(=O)c1ccc2c(-c3ccc(C(F)(F)F)cc3)cccc2c1)c1cccc(N)n1] | (S)-N-(1-(6-aminopyridin-2-yl)ethyl)-5-(4-(trifluoromethyl)phenyl)-2-naphthamide |
| 129 | 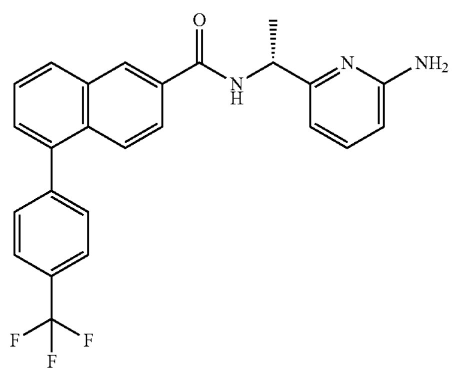 [SMILES: C[C@@H](NC(=O)c1ccc2c(-c3ccc(C(F)(F)F)cc3)cccc2c1)c1cccc(N)n1] | (R)-N-(1-(6-aminopyridin-2-yl)ethyl)-5-(4-(trifluoromethyl)phenyl)-2-naphthamide |

In another aspect, the present disclosure provides a compound or a pharmaceutically acceptable salt or a pharmaceutically acceptable solvate thereof, wherein the compound is a compound from Table 2, or a pharmaceutically acceptable salt or a pharmaceutically acceptable solvate thereof.

TABLE 2

| Compound No. | Structure | Name |
|---|---|---|
| 130 | 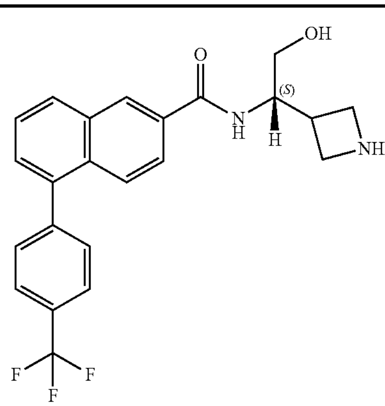 | N-[(1S)-1-(azetidin-3-yl)-2-hydroxy-ethyl]-5-[4-(trifluoromethyl)phenyl]naphthalene-2-carboxamide |

TABLE 2-continued

| Compound No. | Structure | Name |
|---|---|---|
| 131 | 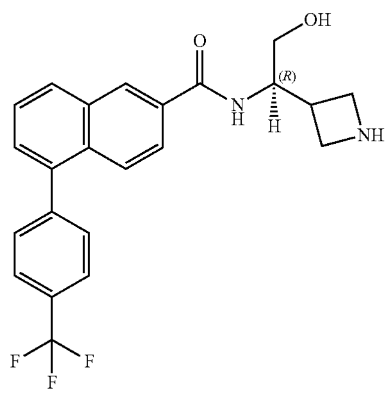 | N-[(1R)-1-(azetidin-3-yl)-2-hydroxy-ethyl]-5-[4-(trifluoromethyl)phenyl]napthalene-2-carboxamide |
| 132 | 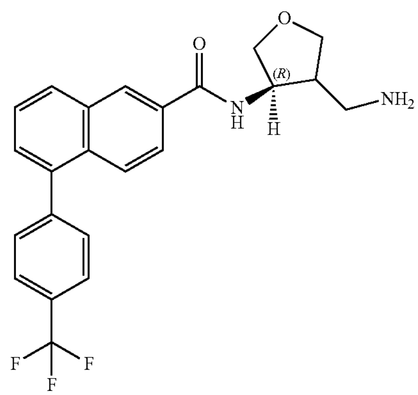 | N-[(3R)-4-(aminomethyl)tetrahydrofuran-3-yl]-5-[4-(trifluoromethyl)phenyl]naphthalene-2-carboxamide |
| 133 | 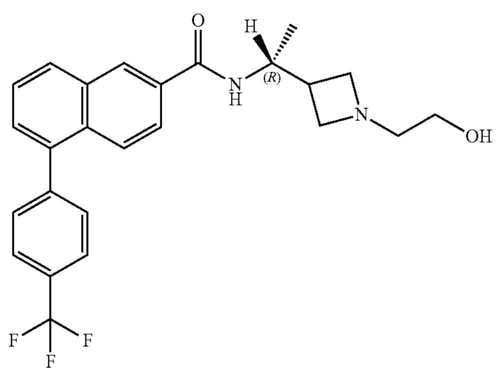 | (R)-N-(1-(1-(2-hydroxyethyl)azetidin-3-yl)ethyl)-5-(4-(trifluoromethyl)phenyl)-2-naphthamide |
| 134 | 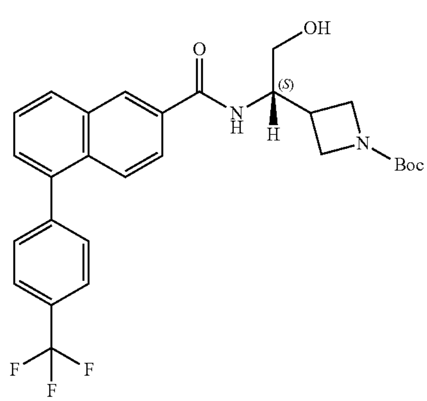 | tert-butyl 3-[(1S)-2-hydroxy-1-[[5-[4-(trifluoromethyl)phenyl]naphthalene-2-carbonyl]amino]ethyl]azetidine-1-carboxylate |

TABLE 2-continued

| Compound No. | Structure | Name |
|---|---|---|
| 135 | 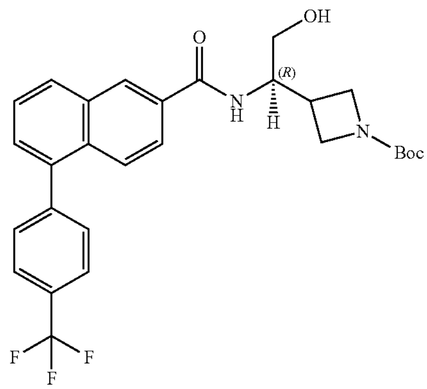 | tert-butyl 3-[(1R)-2-hydroxy-1-[[5-[4-(trifluoromethyl)phenyl]naphthalene-2-carbonyl]amino]ethyl]azetidine-1-carboxylate |
| 136 | 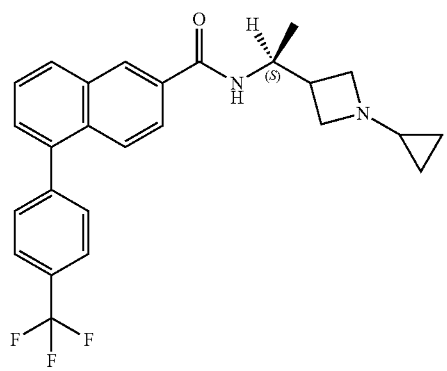 | N-[(1S)-1-(1-cyclopropylazetidin-3-yl)ethyl]-5-[4-(trifluoromethyl)phenyl]naphthalene-2-carboxamide |
| 137 | 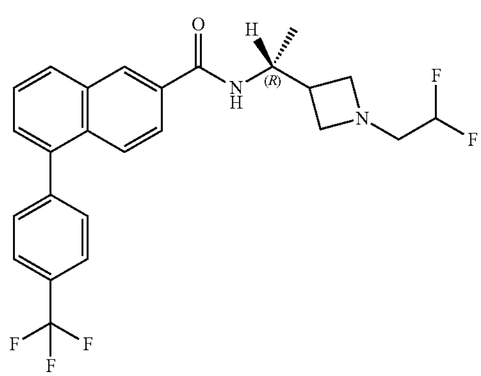 | (R)-N-(1-(1-(2,2-difluoroethyl)azetidin-3-yl)ethyl)-5-(4-(trifluoromethyl)phenyl)-2-naphthamide |
| 138 | 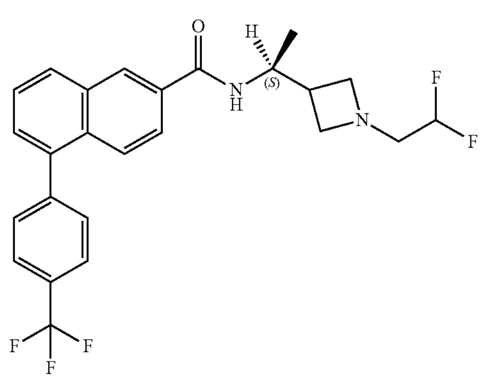 | N-[(1S)-1-[1-(2,2-difluoroethyl)azetidin-3-yl]ethyl]-5-[4-(trifluoromethyl)phenyl]naphthalene-2-carboxamide |

TABLE 2-continued

| Compound No. | Structure | Name |
|---|---|---|
| 139 | 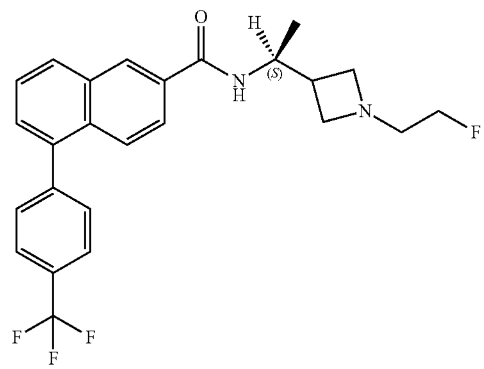 | N-[(1S)-1-[1-(2-fluoroethyl)azetidin-3-yl]ethyl]-5-[4-(trifluoromethyl)phenyl]naphthalene-2-carboxamide |
| 140 | 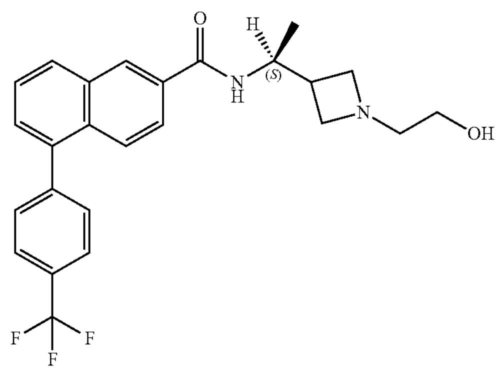 | N-[(1S)-1-[1-(2-hydroxyethyl)azetidin-3-yl]ethyl]-5-[4-(trifluoromethyl)phenyl]naphthalene-2-carboxamide |
| 141 | 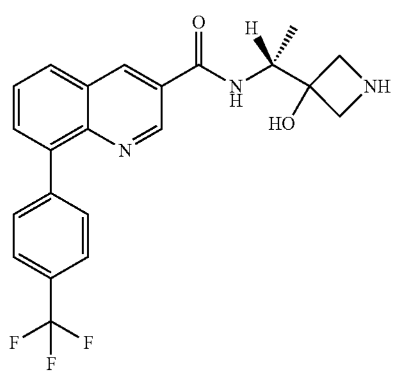 [SMILES: C[C@@H](NC(=O)c1cnc2c(-c3ccc(C(F)(F)F)cc3)cccc2c1)C1(O)CNC1] | (R)-N-(1-(3-hydroxyazetidin-3-yl)ethyl)-8-(4-(trifluoromethyl)phenyl)quinoline-3-carboxamide |
| 142 | 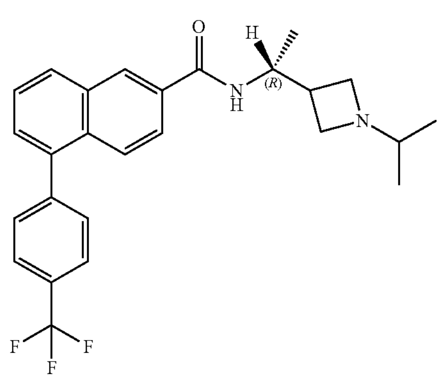 | N-[(1R)-1-(1-isopropylazetidin-3-yl)ethyl]-5-[4-(trifluoromethyl)phenyl]naphthalene-2-carboxamide |

TABLE 2-continued

| Compound No. | Structure | Name |
|---|---|---|
| 143 | 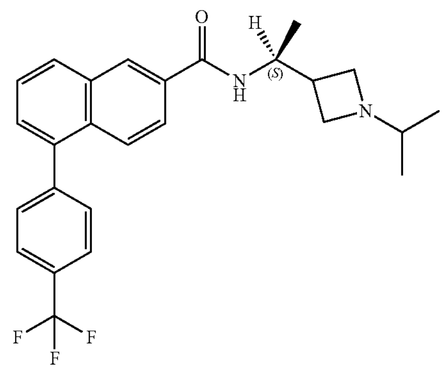 | N-[(1S)-1-(1-isopropylazetidin-3-yl)ethyl]-5-[4-(trifluoromethyl)phenyl]naphthalene-2-carboxamide |
| 144 | 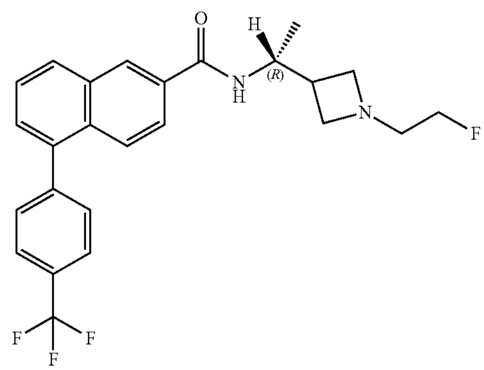 | (R)-N-(1-(1-(2-fluoroethyl)azetidin-3-yl)ethyl)-5-(4-(trifluoromethyl)phenyl)-2-naphthamide |
| 145 | 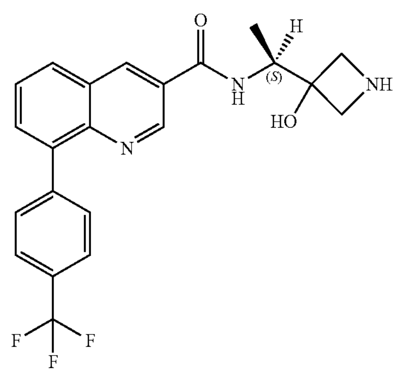 | N-[(1S)-1-(3-hydroxyazetidin-3-yl)ethyl]-8-[4-(trifluoromethyl)phenyl]quinoline-3-carboxamide |
| 146 | 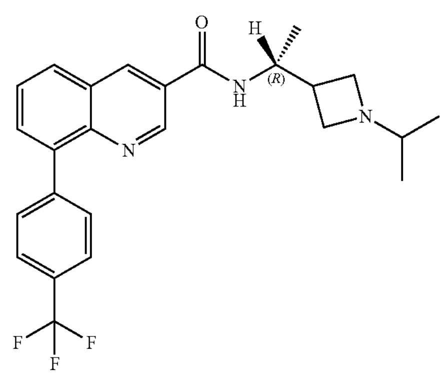 | N-[(1R)-1-(1-Isopropylazetidin-3-yl)ethyl]-8-[4-(trifluoromethyl)phenyl]quinoline-3-carboxamide |

TABLE 2-continued

| Compound No. | Structure | Name |
|---|---|---|
| 147 | 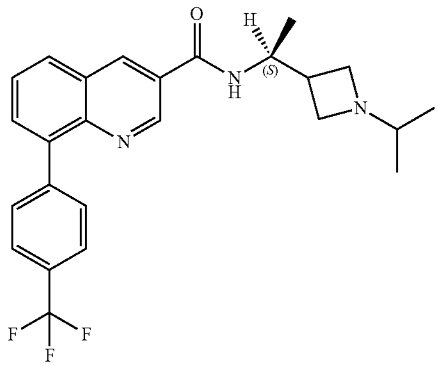 | N-[(1S)-1-(1-Isopropylazetidin-3-yl)ethyl]-8-[4-(trifluoromethyl)phenyl]quinoline-3-carboxamide |
| 148 | 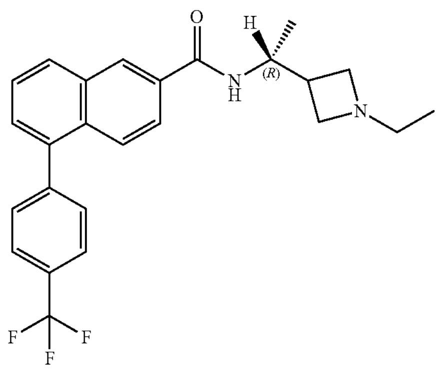 | N-[(1R)-1-(1-Ethylazetidin-3-yl)ethyl]-5-[4-(trifluoromethyl)phenyl]naphthalene-2-carboxamide |
| 149 | 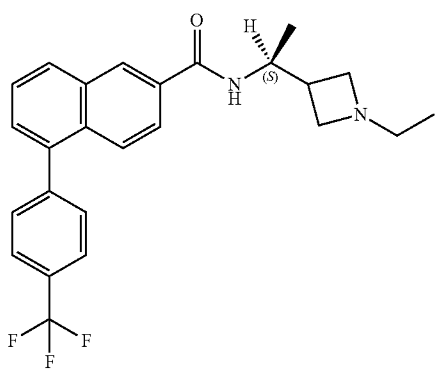 | N-[(1S)-1-(1-Ethylazetidin-3-yl)ethyl]-5-[4-(trifluoromethyl)phenyl]naphthalene-2-carboxamide |
| 150 | 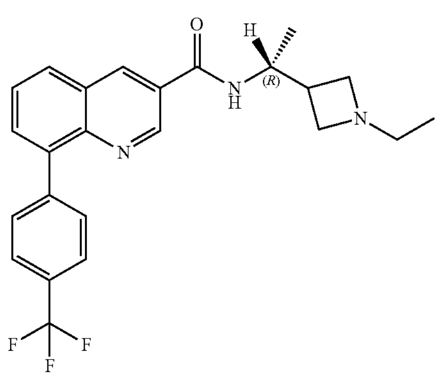 | N-[(1R)-1-(1-Ethylazetidin-3-yl)ethyl]-8-[4-(trifluoromethyl)phenyl]quinoline-3-carboxamide |

TABLE 2-continued

| Compound No. | Structure | Name |
|---|---|---|
| 151 | 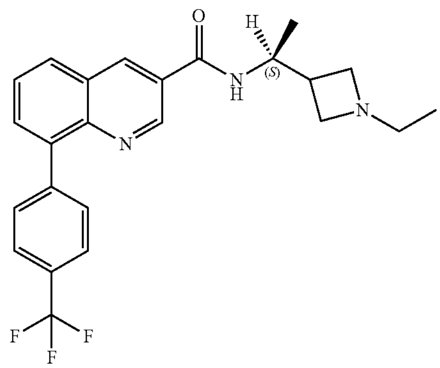 | N-[(1S)-1-(1-Ethylazetidin-3-yl)ethyl]-8-[4-(trifluoromethyl)phenyl]quinoline-3-carboxamide |
| 152 | 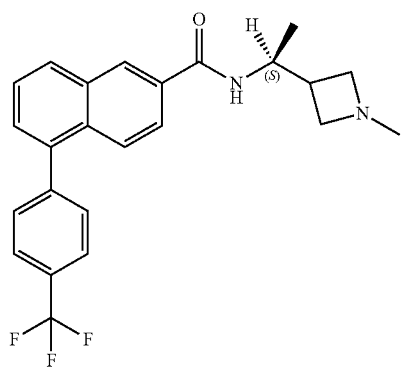 | N-[(1S)-1-(1-methylazetidin-3-yl)ethyl]-5-[4-(trifluoromethyl)phenyl]naphthalene-2-carboxamide |
| 153 | 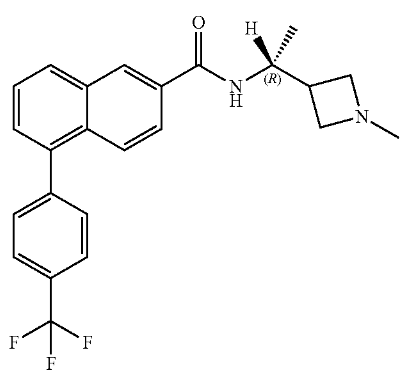 | N-[(1R)-1-(1-methylazetidin-3-yl)ethyl]-5-[4-(trifluoromethyl)phenyl]naphthalene-2-carboxamide |
| 154 | 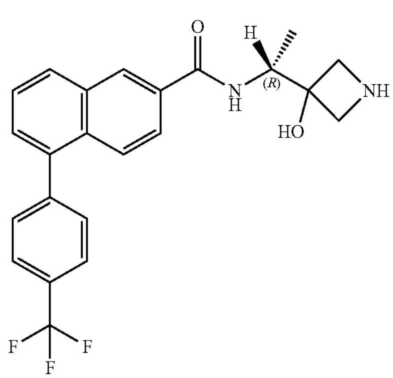 | (R)-N-(1-(3-hydroxyazetidin-3-yl)ethyl)-5-(4-(trifluoromethyl)phenyl)-2-naphthamide |

TABLE 2-continued
| Compound No. | Structure | Name |
|---|---|---|
| 155 | 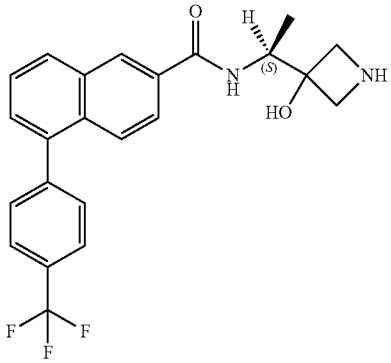 | (S)-N-(1-(3-hydroxyazetidin-3-yl)ethyl)-5-(4-(trifluoromethyl)phenyl)-2-naphthamide |
| 156 | 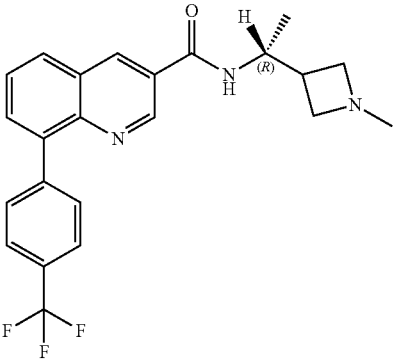 | N-[(1R)-1-(1-methylazetidin-3-yl)ethyl]-8-[4-(trifluoromethyl)phenyl]quinoline-3-carboxamide |
| 157 | 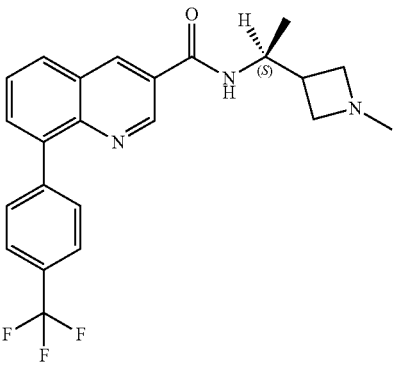 | N-[(1S)-1-(1-Methylazetidin-3-yl)ethyl]-8-[4-(trifluoromethyl)phenyl]quinoline-3-carboxamide |
| 158 | 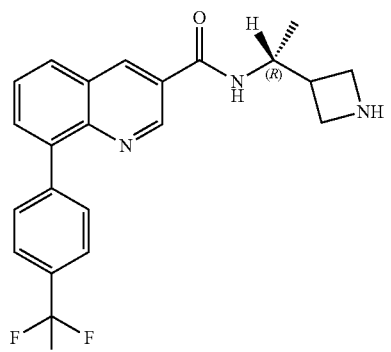 | N-[(1R)-1-(Azetidin-3-yl)ethyl]-8-[4-(trifluoromethyl)phenyl]quinoline-3-carboxamide |

TABLE 2-continued

| Compound No. | Structure | Name |
|---|---|---|
| 159 | 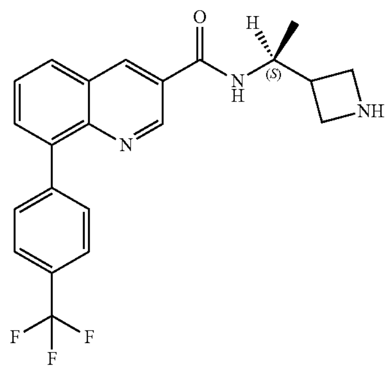 | N-[(1S)-1-(Azetidin-3-yl)ethyl]-8-[4-(trifluoromethyl)phenyl]quinoline-3-carboxamide |
| 160 | 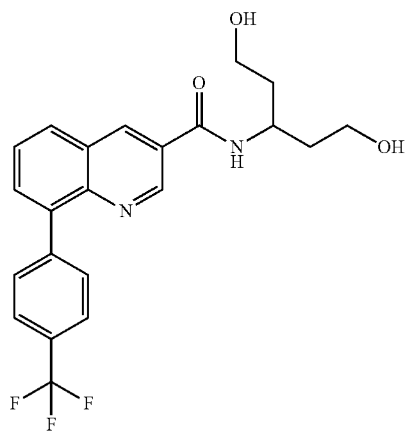 [SMILES: O=C(NC(CCO)CCO)c1cnc2c(-c3ccc(C(F)(F)F)cc3)cccc2c1] | N-(1,5-dihydroxypentan-3-yl)-8-(4-(trifluoromethyl)phenyl)quinoline-3-carboxamide |
| 161 | 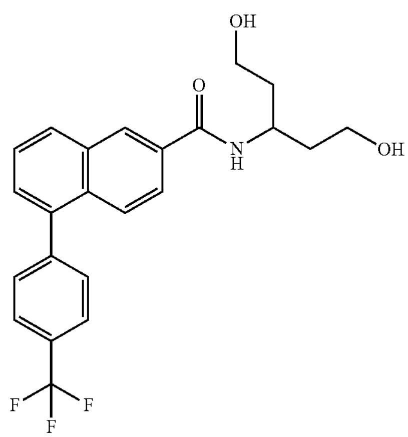 [SMILES: O=C(NC(CCO)CCO)c1ccc2c(-c3ccc(C(F)(F)F)cc3)cccc2c1] | N-(1,5-dihydroxypropan-3-yl)-5-(4-(trifluoromethyl)phenyl)-2-naphthamide |
| 162 | 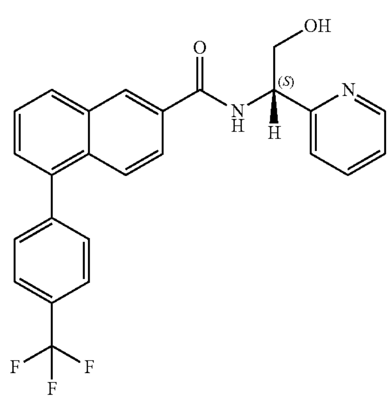 | N-[(1S)-2-hydroxy-1-(2-pyridyl)ethyl]-5-[4-(trifluoromethyl)phenyl]naphthalene-2-carboxamide |

TABLE 2-continued

| Compound No. | Structure | Name |
|---|---|---|
| 163 | 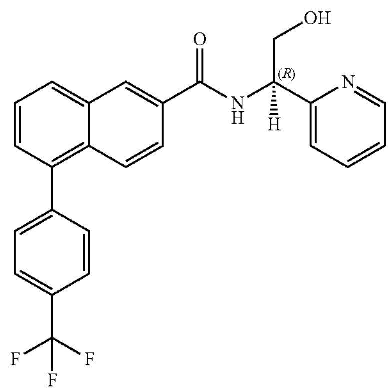 | N-[(1S)-2-hydroxy-1-(2-pyridyl)ethyl]-5-[4-(trifluoromethyl)phenyl]naphthalene-2-carboxamide |
| 164 | 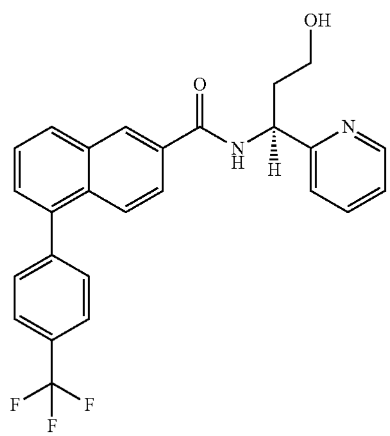 [SMILES: O=C(N[C@@H](CCO)c1ccccn1)c1ccc2c(-c3ccc(C(F)(F)F)cc3)cccc2c1] | (S)-N-(3-hydroxy-1-(pyridin-2-yl)propyl)-5-(4-(trifluoromethyl)phenyl)-2-naphthamide |
| 165 | 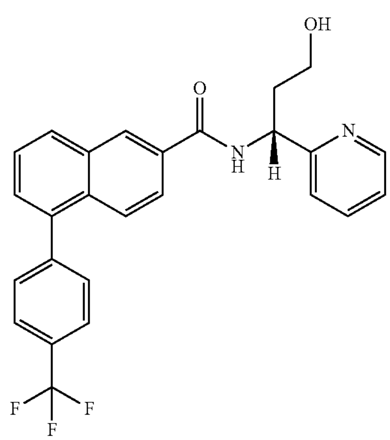 [SMILES: O=C(N[C@H](CCO)c1ccccn1)c1ccc2c(-c3ccc(C(F)(F)F)cc3)cccc2c1] | (R)-N-(3-hydroxy-1-(pyridin-2-yl)propyl)-5-(4-(trifluoromethyl)phenyl)-2-naphthamide |

TABLE 2-continued
| Compound No. | Structure | Name |
|---|---|---|
| 166 | 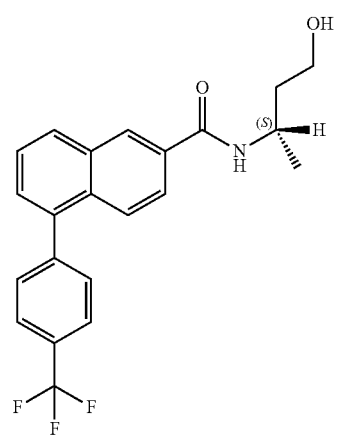 | N-[(1S)-3-hydroxy-1-methyl-propyl]-5-[4-(trifluoromethyl)phenyl]naphthalene-2-carboxamide |
| 167 | 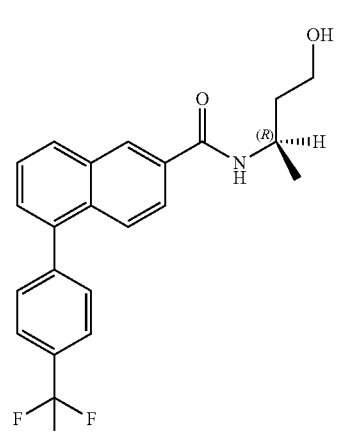 | N-[(1R)-3-hydroxy-1-methyl-propyl]-5-[4-(trifluoromethyl)phenyl]naphthalene-2-carboxamide |
| 168 | 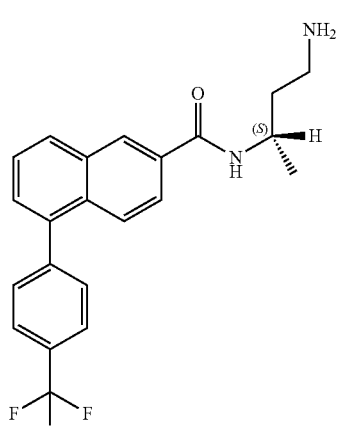 | (S)-N-(4-aminobutan-2-yl)-5-(4-(trifluoromethyl)phenyl)-2-naphthamide |

TABLE 2-continued

| Compound No. | Structure | Name |
| --- | --- | --- |
| 169 | 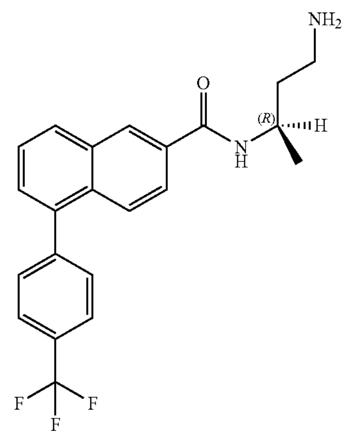 | (R)-N-(4-aminobutan-2-yl)-5-(4-(trifluoromethyl)phenyl)-2-naphthamide |
| 170 | 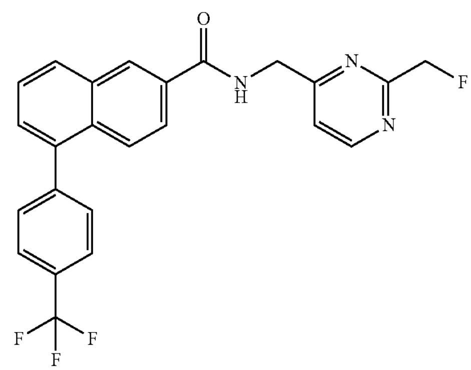 [SMILES: O=C(NCc1ccnc(CF)n1)c1ccc2c(-c3ccc(C(F)(F)F)cc3)cccc2c1] | N-((2-fluoromethyl)pyrimidin-4-yl)methyl)-5-(4-(trifluoromethyl)phenyl)-2-naphthamide |
| 171 | 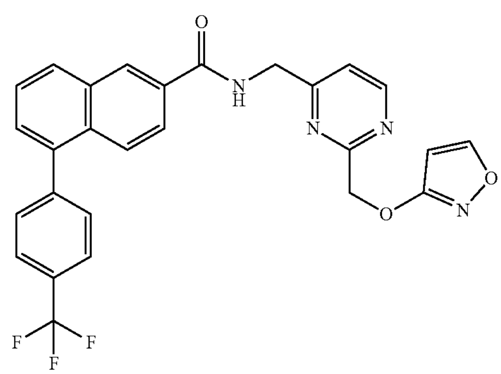 [SMILES: O=C(NCc1ccnc(COc2ccon2)n1)c1ccc2c(-c3ccc(C(F)(F)F)cc3)cccc2c1] | N-((2-((Isoxazol-3-yloxy)methyl)pyrimidin-4-yl)methyl)-5-(4-(trifluoromethyl)phenyl)-2-naphthamide |
| 172 | 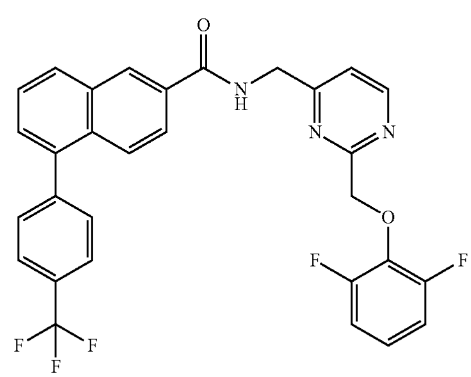 | N-((2-((2,6-difluorophenoxy)methyl)pyrimidin-4-yl)methyl)-5-(4-(trifluoromethyl)phenyl)-2-naphthamide |

TABLE 2-continued

| Compound No. | Structure | Name |
|---|---|---|
| 173 | 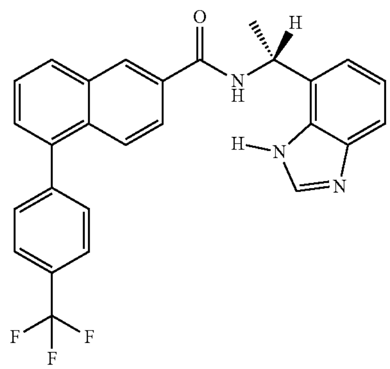 [SMILES: C[C@@H](NC(=O)c1ccc2c(-c3ccc(C(F)(F)F)cc3)cccc2c1)c1cccc2nc[nH]c12] | N-[(1R)-1-(3H-benzimidazol-4-yl)ethyl]-5-[4-(trifluoromethyl)phenyl]naphthalene-2-carboxamide |
| 174 | 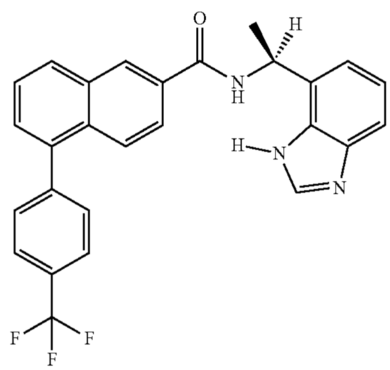 | N-[(1S)-1-(3H-benzimidazol-4-yl)ethyl]-5-[4-(trifluoromethyl)phenyl]naphthalene-2-carboxamide |
| 175 | 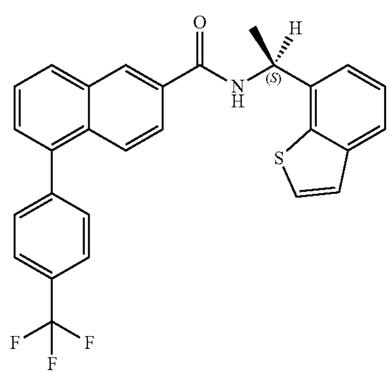 | N-[(1S)-1-(benzothiophen-7-yl)ethyl]-5-[4-(trifluoromethyl)phenyl]naphthalene-2-carboxamide |
| 176 | 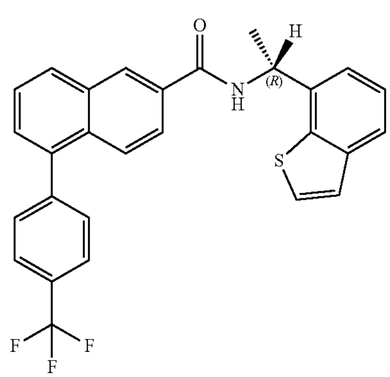 | N-[(1R)-1-(benzothiophen-7-yl)ethyl]-5-[4-(trifluoromethyl)phenyl]naphthalene-2-carboxamide |

TABLE 2-continued

| Compound No. | Structure | Name |
| --- | --- | --- |
| 177 | 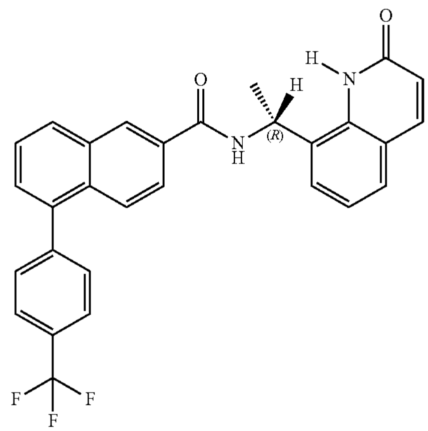 | N-[(1R)-1-(2-oxo-1H-quinolin-8-yl)ethyl]-5-[4-(trifluoromethyl)phenyl]naphthalene-2-carboxamide |
| 178 | 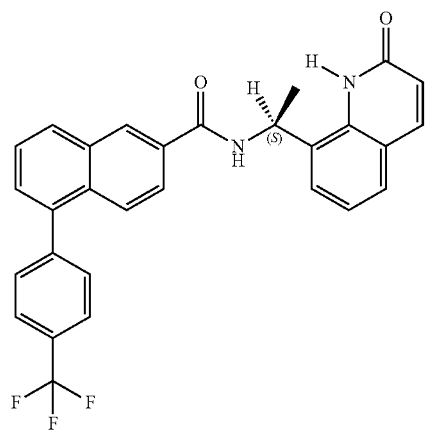 | N-[(1S)-1-(2-oxo-1H-quinolin-8-yl)ethyl]-5-[4-(trifluoromethyl)phenyl]naphthalene-2-carboxamide |
| 179 | 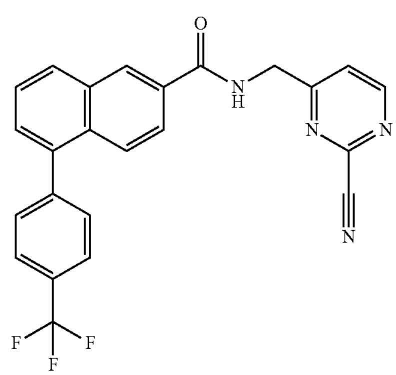 | N-((2-cyanopyrimidin-4-yl)methyl)-5-(4-(trifluoromethyl)phenyl)-2-naphthamide |
| 180 | 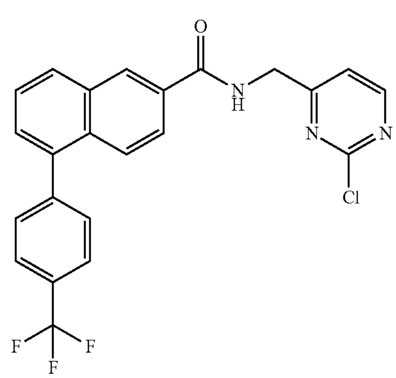 | N-((2-chloropyrimidin-4-yl)methyl)-5-(4-(trifluoromethyl)phenyl)-2-naphthalene-2-carboxamide |

TABLE 2-continued
| Compound No. | Structure | Name |
|---|---|---|
| 181 | 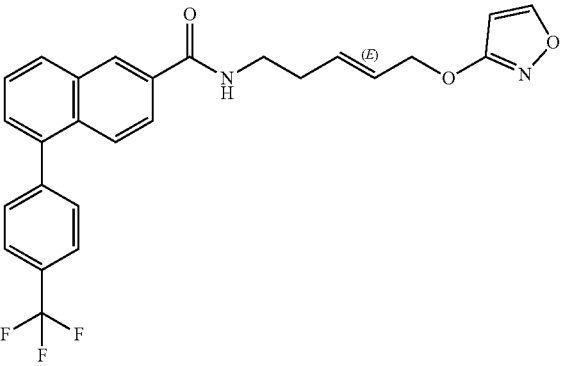 [SMILES: O=C(NCC/C=C/COc1ccon1)c1ccc2c(-c3ccc(C(F)(F)F)cc3)cccc2c1] | N-[(E)-5-isoxazol-3-yloxypent-3-enyl]-5-[4-(trifluoromethyl)phenyl]naphthalene-2-carboxamide |
| 182 | 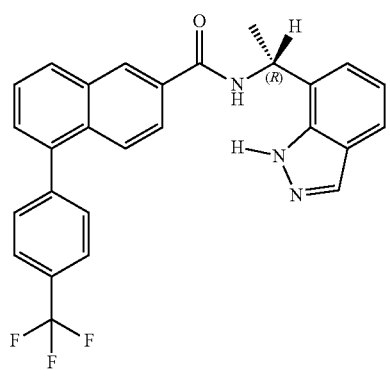 | N-[(1R)-1-(1H-indazol-7-yl)ethyl]-5-[4-(trifluoromethyl)phenyl]naphthalene-2-carboxamide |
| 183 | 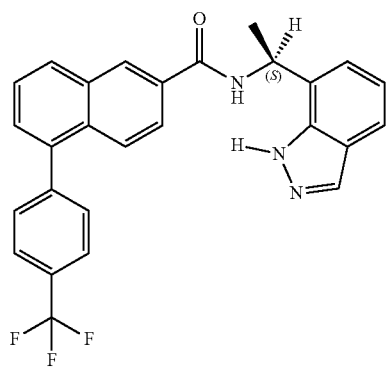 | N-[(1S)-1-(1H-indazol-7-yl)ethyl]-5-[4-(trifluoromethyl)phenyl]naphthalene-2-carboxamide |
| 184 | 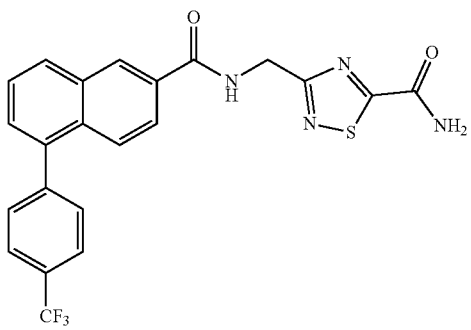 [SMILES: NC(=O)c1nc(CNC(=O)c2ccc3c(-c4ccc(C(F)(F)F)cc4)cccc3c2)ns1] | 3-((5-(4-(Trifluoromethyl)phenyl)-2-naphthamido)methyl)-1,2,4-thiadiazole-5-carboxamide |

TABLE 2-continued

| Compound No. | Structure | Name |
|---|---|---|
| 185 | 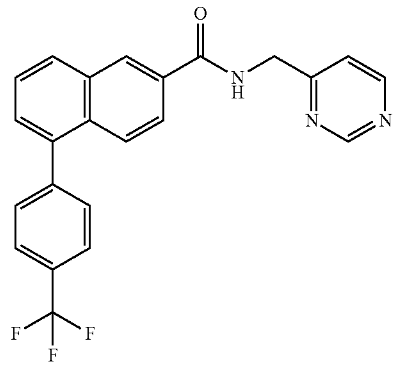 [SMILES: O=C(NCc1ccncn1)c1ccc2c(-c3ccc(C(F)(F)F)cc3)cccc2c1] | N-(pyrimidin-4-ylmethyl)-5-(4-(trifluoromethyl)phenyl)-2-naphthamide |
| 186 | 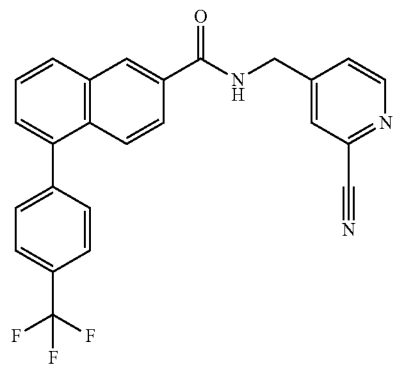 | N-((2-cyanopyridin-4-yl)methyl)-5-(4-(trifluoromethyl)phenyl)-2-naphthamide |
| 187 | 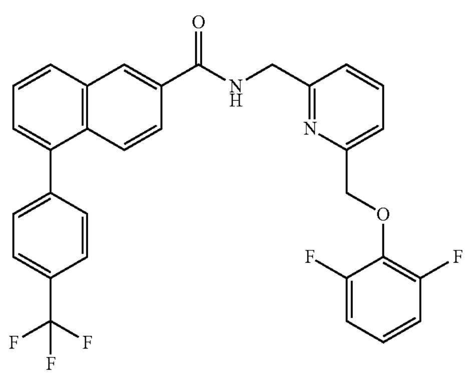 [SMILES: O=C(NCc1cccc(COc2c(F)cccc2F)n1)c1ccc2c(-c3ccc(C(F)(F)F)cc3)cccc2c1] | N-((6-((2,6-difluorophenoxy)methyl)pyridin-2-yl)methyl)-5-(4-(trifluoromethyl)phenyl)-2-naphthamide |
| 188 | 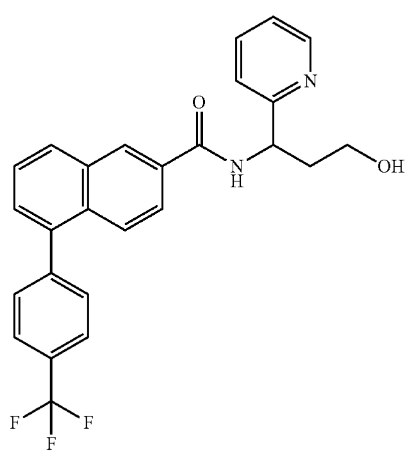 [SMILES: O=C(NC(CCO)c1ccccn1)c1ccc2c(-c3ccc(C(F)(F)F)cc3)cccc2c1] | N-[3-hydroxy-1-(2-pyridyl)propyl]-5-[4-(trifluoromethyl)phenyl]naphthalene-2-carboxamide |

TABLE 2-continued
| Compound No. | Structure | Name |
|---|---|---|
| 189 | 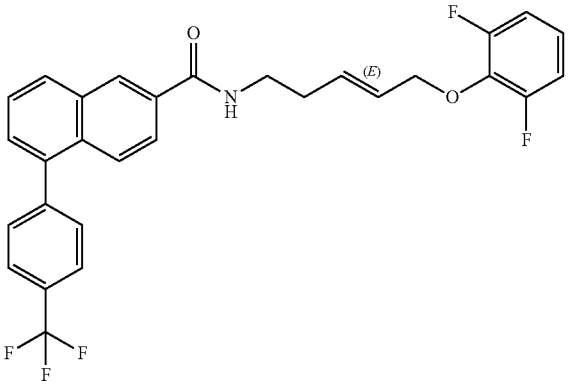 [SMILES: O=C(NCC/C=C/COc1c(F)cccc1F)c1ccc2c(-c3ccc(C(F)(F)F)cc3)cccc2c1] | N-[(E)-5-(2,6-difluorophenoxy)pent-3-enyl]-5-[4-(trifluoromethyl)phenyl]naphthalene-2-carboxamide |
| 190 | 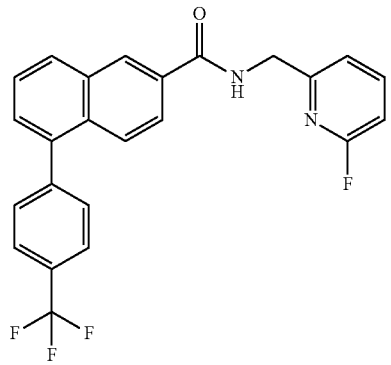 [SMILES: O=C(NCc1cccc(F)n1)c1ccc2c(-c3ccc(C(F)(F)F)cc3)cccc2c1] | N-((6-fluoropyridin-2-yl)methyl)-5-(4-(trifluoromethyl)phenyl)-2-naphthamide |
| 191 | 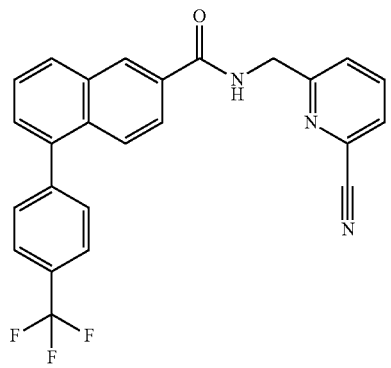 [SMILES: N#Cc1cccc(CNC(=O)c2ccc3c(-c4ccc(C(F)(F)F)cc4)cccc3c2)n1] | N-((6-cyanopyridin-2-yl)methyl)-5-(4-(trifluoromethyl)phenyl)-2-naphthamide |
| 192 | 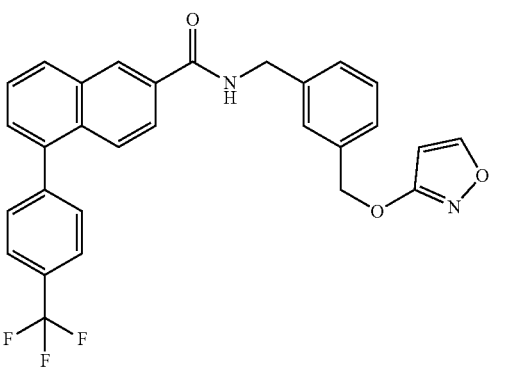 | N-(3-((isoxazol-3-yloxy)methyl)benzyl)-5-(4-(trifluoromethyl)phenyl)-2-naphthamide |

TABLE 2-continued

| Compound No. | Structure | Name |
|---|---|---|
| 193 | 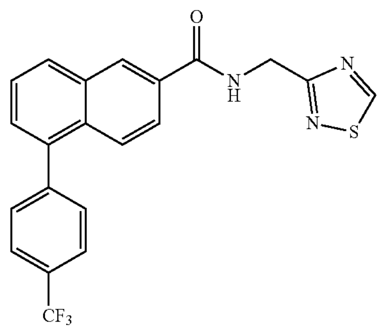 [SMILES: O=C(NCc1ncsn1)c1ccc2c(-c3ccc(C(F)(F)F)cc3)cccc2c1] | N-((1,2,4-thiadiazol-3-yl)methyl)-5-(4-(trifluoromethyl)phenyl)-2-naphthamide |
| 194 | 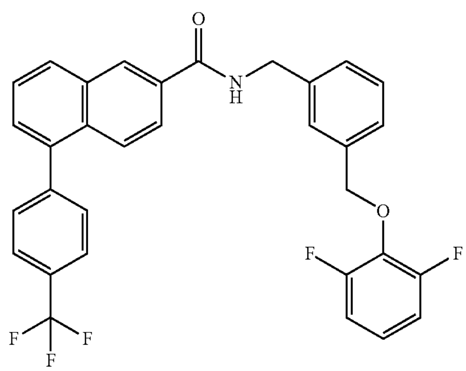 [SMILES: O=C(NCc1cccc(COc2c(F)cccc2F)c1)c1ccc2c(-c3ccc(C(F)(F)F)cc3)cccc2c1] | N-(3-((2,6-difluorophenoxy)methyl)benzyl)-5-(4-(trifluoromethyl)phenyl)-2-naphthamide |
| 195 | 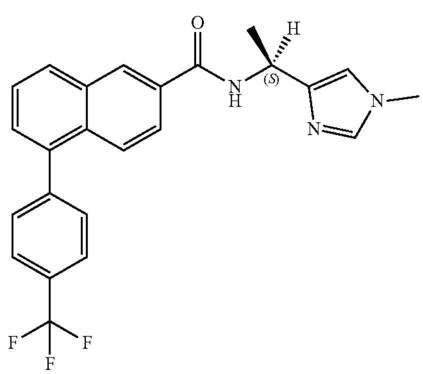 | (S)-N-(1-(1-methyl-1H-imidazol-4-yl)ethyl)-5-(4-(trifluoromethyl)phenyl)-2-naphthamide |
| 196 | 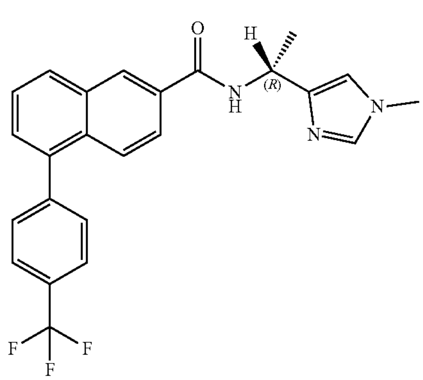 | (R)-N-(1-(1-methyl-1H-imidazol-4-yl)ethyl)-5-(4-(trifluoromethyl)phenyl)-2-naphthamide |

TABLE 2-continued

| Compound No. | Structure | Name |
|---|---|---|
| 197 | 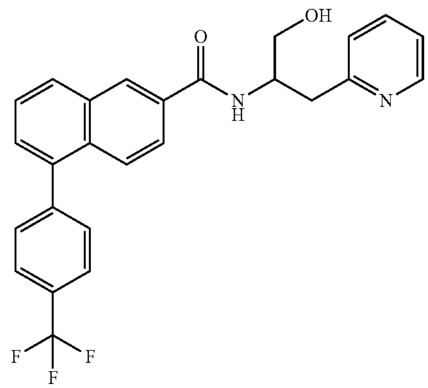 [SMILES: O=C(NC(CO)Cc1ccccn1)c1ccc2c(-c3ccc(C(F)(F)F)cc3)cccc2c1] | N-(1-hydroxy-3-(pyridin-2-yl)propan-2-yl)-5-(4-(trifluoromethyl)phenyl)-2-naphthamide |
| 198 | 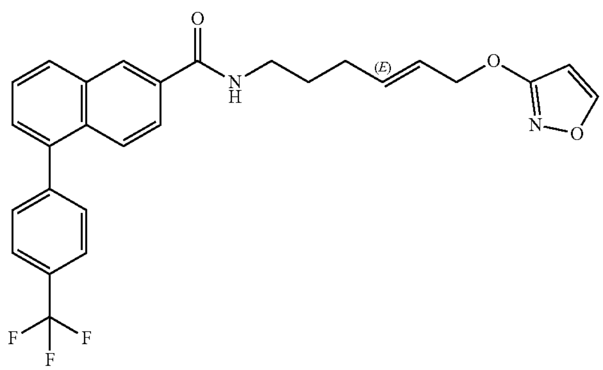 [SMILES: O=C(NCCC/C=C/COc1ccon1)c1ccc2c(-c3ccc(C(F)(F)F)cc3)cccc2c1] | N-[(E)-6-isoxazol-3-yloxyhex-4-enyl]-5-[4-(trifluoromethyl)phenyl]naphthalene-2-carboxamide |
| 199 | 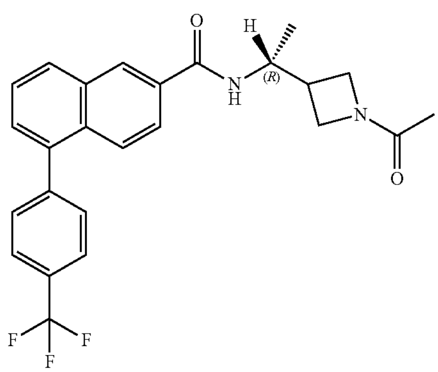 | (R)-N-(1-(1-acetylazetidin-3-yl)ethyl)-5-(4-(trifluoromethyl)phenyl)-2-naphthamide |
| 200 | 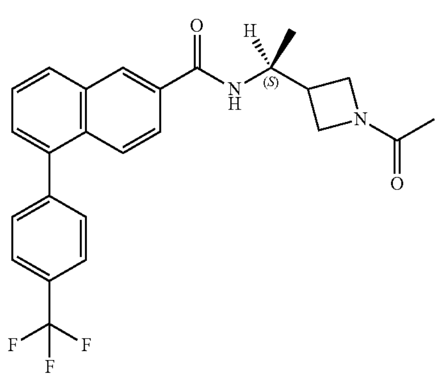 | (S)-N-(1-(1-acetylazetidin-3-yl)ethyl)-5-(4-(trifluoromethyl)phenyl)-2-naphthamide |

TABLE 2-continued

| Compound No. | Structure | Name |
|---|---|---|
| 201 | 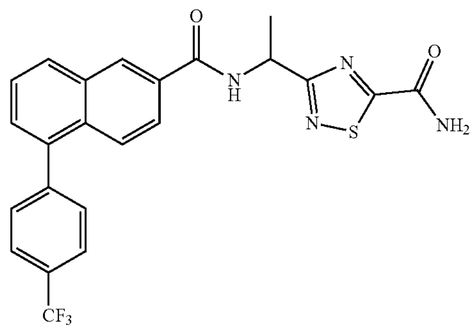 [SMILES: CC(NC(=O)c1ccc2c(-c3ccc(C(F)(F)F)cc3)cccc2c1)c1nsc(C(N)=O)n1] | 3-(1-(5-(4-(Trifluoromethyl)phenyl)-2-naphthamido)ethyl)-1,2,4-thiadiazole-5-carboxamide |
| 202 | 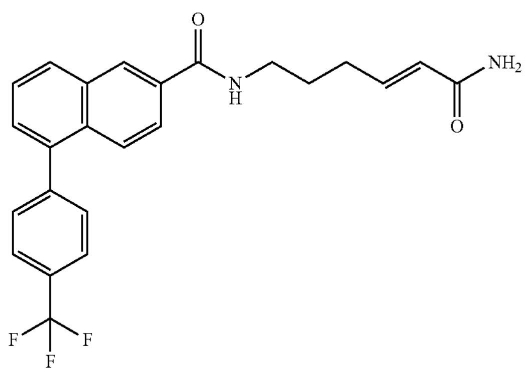 [SMILES: NC(=O)/C=C/CCCNC(=O)c1ccc2c(-c3ccc(C(F)(F)F)cc3)cccc2c1] | N-[(E)-6-amino-6-oxo-hex-4-enyl]-5-[4-(trifluoromethyl)phenyl]naphthalene-2-carboxamide |
| 203 | 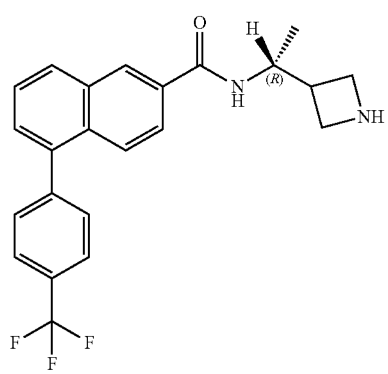 | (R)-N-(1-(azetidin-3-yl)ethyl)-5-(4-(trifluoromethyl)phenyl)-2-naphthamide |
| 204 | 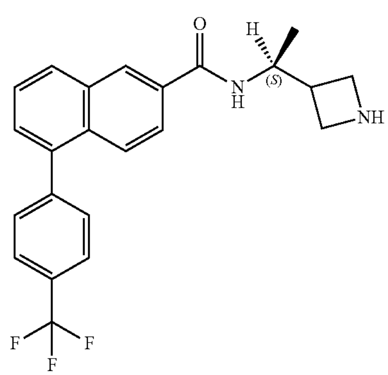 | (S)-N-(1-(azetidin-3-yl)ethyl)-5-(4-(trifluoromethyl)phenyl)-2-naphthamide |

TABLE 2-continued
| Compound No. | Structure | Name |
|---|---|---|
| 205 | 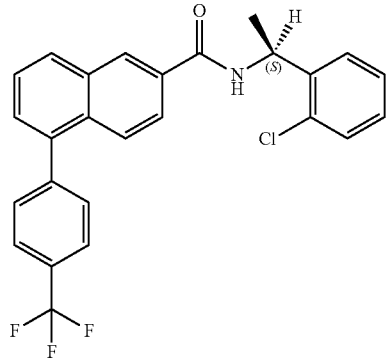 | (S)-N-(1-(2-chlorophenyl)ethyl)-5-(4-(trifluoromethyl)phenyl)-2-naphthamide |
| 206 | 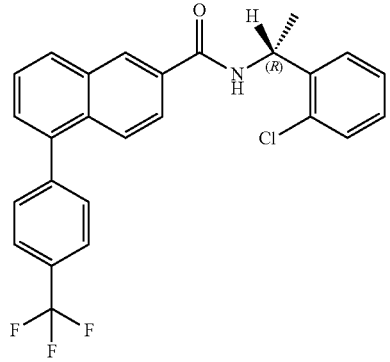 | (R)-N-(1-(2-chlorophenyl)ethyl)-5-(4-(trifluoromethyl)phenyl)-2-naphthamide |
| 207 | 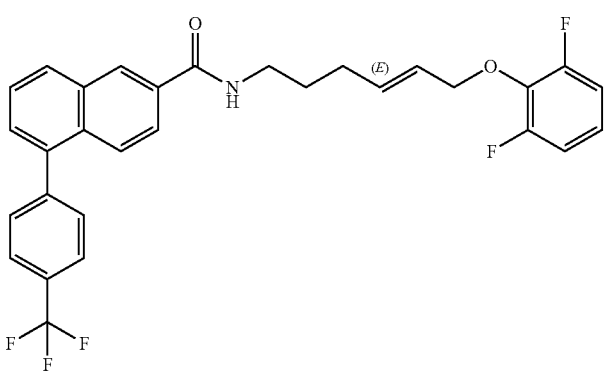 [SMILES: O=C(NCCC/C=C/COc1c(F)cccc1F)c1ccc2c(-c3ccc(C(F)(F)F)cc3)cccc2c1] | N-[(E)-6-(2,6-difluorophenoxy)hex-4-enyl]-5-[4-(trifluoromethyl)phenyl]naphthalene-2-carboxamide |
| 208 | 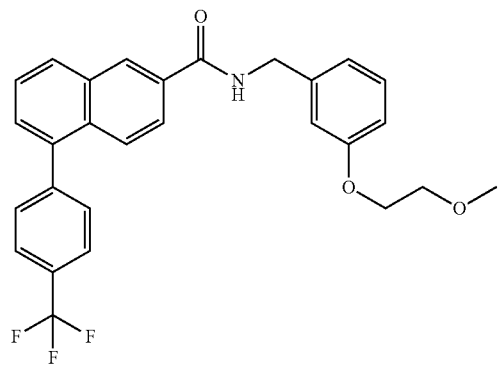 [SMILES: COCCOc1cccc(CNC(=O)c2ccc3c(-c4ccc(C(F)(F)F)cc4)cccc3c2)c1] | N-(3-(2-methoxyethoxy)benzyl)-5-(4-(trifluoromethyl)phenyl)-2-naphthamide |

TABLE 2-continued

| Compound No. | Structure | Name |
|---|---|---|
| 209 | 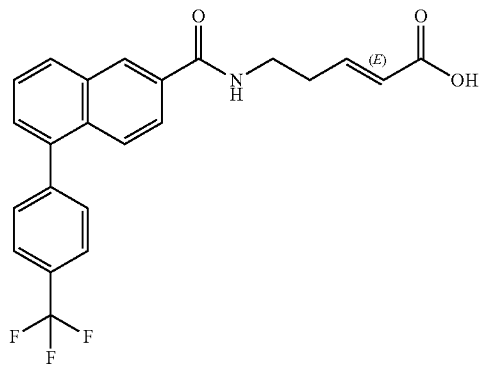 [SMILES: O=C(O)/C=C/CCNC(=O)c1ccc2c(-c3ccc(C(F)(F)F)cc3)cccc2c1] | (E)-5-[[5-[4-(trifluoromethyl)phenyl]napthalene-2-carbonyl]amino]pent-2-enoic acid |
| 210 | 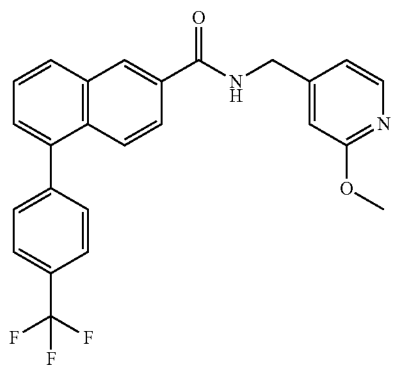 [SMILES: COc1cc(CNC(=O)c2ccc3c(-c4ccc(C(F)(F)F)cc4)cccc3c2)ccn1] | N-((2-methoxypyridin-4-yl)methyl)-5-(4-(trifluoromethyl)phenyl)-2-naphthamide |
| 211 | 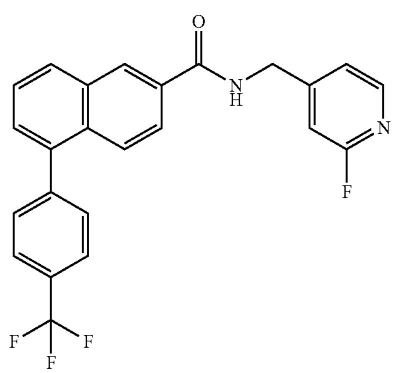 [SMILES: O=C(NCc1ccnc(F)c1)c1ccc2c(-c3ccc(C(F)(F)F)cc3)cccc2c1] | N-((2-fluoropyridin-4-yl)methyl)-5-(4-(trifluoromethyl)phenyl)-2-naphthamide |
| 212 | 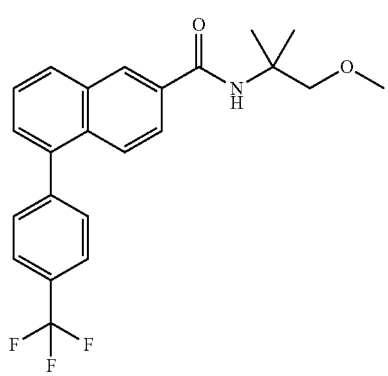 [SMILES: COCC(C)(C)NC(=O)c1ccc2c(-c3ccc(C(F)(F)F)cc3)cccc2c1] | N-(1-methoxy-2-methylpropan-2-yl)-5-(4-(trifluoromethyl)phenyl)-2-naphthamide |

TABLE 2-continued

| Compound No. | Structure | Name |
|---|---|---|
| 213 | 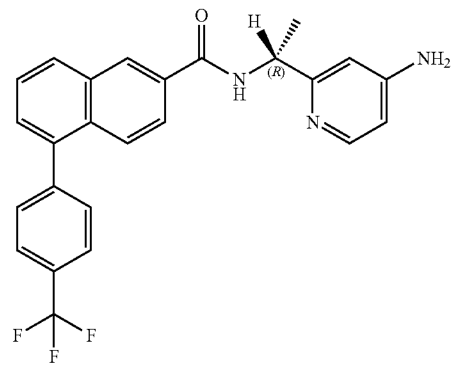 | (R)-N-(1-(4-aminopyridin-2-yl)ethyl)-5-(4-(trifluoromethyl)phenyl)-2-naphthamide |
| 214 | 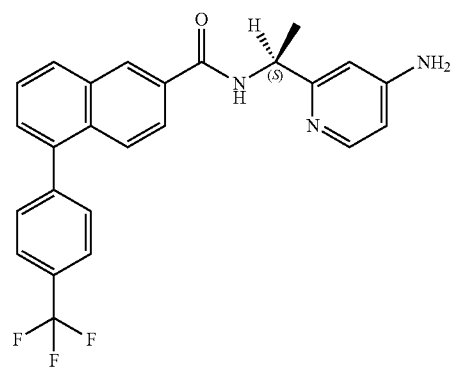 | (S)-N-(1-(4-aminopyridin-2-yl)ethyl)-5-(4-(trifluoromethyl)phenyl)-2-naphthamide |
| 215 | 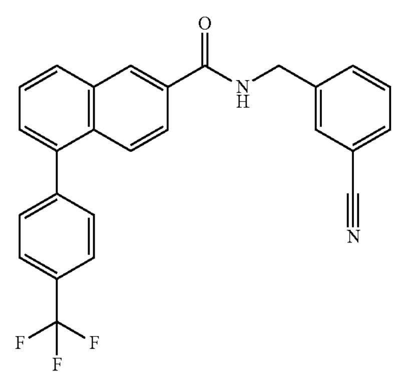 | N-(3-cyanobenzyl)-5-(4-(trifluoromethyl)phenyl)-2-naphthamide |
| 216 | 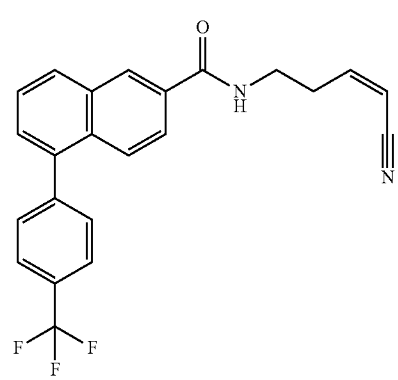 [SMILES: N#C/C=C\CCNC(=O)c1ccc2c(-c3ccc(C(F)(F)F)cc3)cccc2c1] | N-[(Z)-4-cyanobut-3-enyl]-5-[4-(trifluoromethyl)phenyl]naphthalene-2-carboxamide |

TABLE 2-continued
| Compound No. | Structure | Name |
|---|---|---|
| 217 | 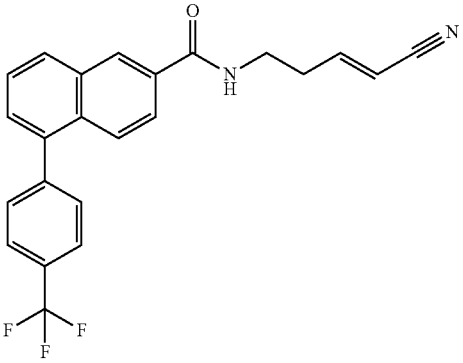 [SMILES: N#C/C=C/CCNC(=O)c1ccc2c(-c3ccc(C(F)(F)F)cc3)cccc2c1] | N-[(E)-4-cyanobut-3-enyl]-5-[4-(trifluoromethyl)phenyl]naphthalene-2-carboxamide |
| 218 | 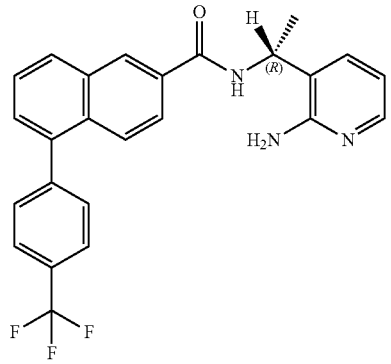 | (R)-N-[1-(2-amino-3-pyridyl)ethyl]-5-[4-(trifluoromethyl)phenyl]naphthalene-2-carboxamide |
| 219 | 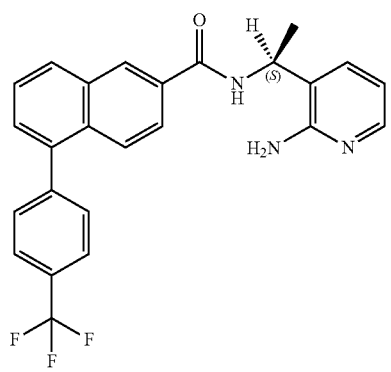 | (S)-N-(1-(2-aminopyridin-3-yl)ethyl)-5-(4-(trifluoromethyl)phenyl)-2-naphthamide |
| 220 | 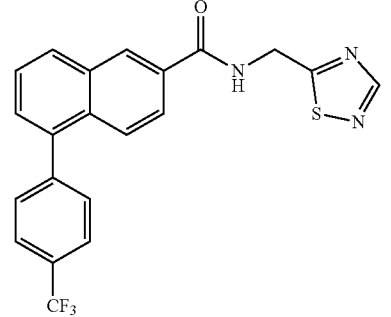 [SMILES: O=C(NCc1ncns1)c1ccc2c(-c3ccc(C(F)(F)F)cc3)cccc2c1] | N-((1,2,4-thiadiazol-5-yl)methyl)-5-(4-(trifluoromethyl)phenyl)-2-naphthamide |

TABLE 2-continued

| Compound No. | Structure | Name |
|---|---|---|
| 221 | 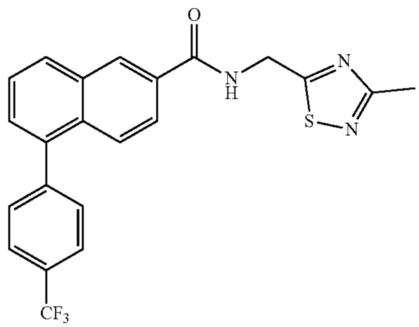 [SMILES: Cc1nsc(CNC(=O)c2ccc3c(-c4ccc(C(F)(F)F)cc4)cccc3c2)n1] | N-((3-methyl-1,2,4-thiadiazol-5-yl)methyl)-5-(4-(trifluoromethyl)phenyl)-2-naphthamide |
| 222 | 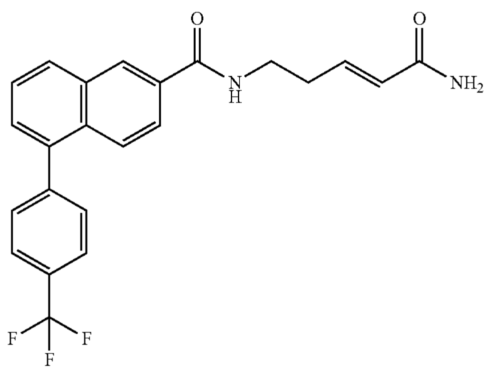 [SMILES: NC(=O)/C=C/CCNC(=O)c1ccc2c(-c3ccc(C(F)(F)F)cc3)cccc2c1] | N-[(E)-5-amino-5-oxo-pent-3-enyl]-5-[4-(trifluoromethyl)phenyl]naphthalene-2-carboxamide |
| 223 | 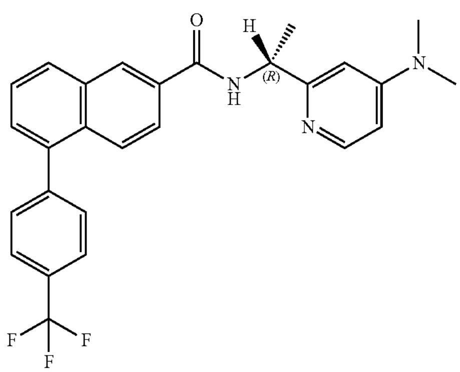 | (R)-N-(1-(4-(dimethylamino)pyridin-2-yl)ethyl)-5-(4-(trifluoromethyl)phenyl)-2-naphthamide |
| 224 | 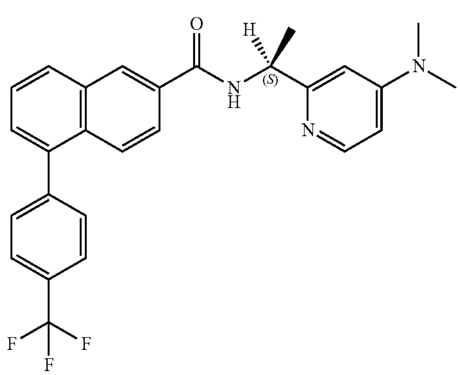 | (S)-N-(1-(4-(dimethylamino)pyridin-2-yl)ethyl)-5-(4-(trifluoromethyl)phenyl)-2-naphthamide |

TABLE 2-continued

| Compound No. | Structure | Name |
|---|---|---|
| 225 | 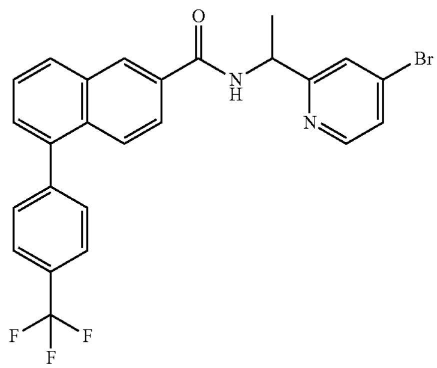 [SMILES: CC(NC(=O)c1ccc2c(-c3ccc(C(F)(F)F)cc3)cccc2c1)c1cc(Br)ccn1] | N-(1-(4-bromopyridin-2-yl)ethyl)-5-(4-(trifluoromethyl)phenyl)-2-naphthamide |
| 226 | 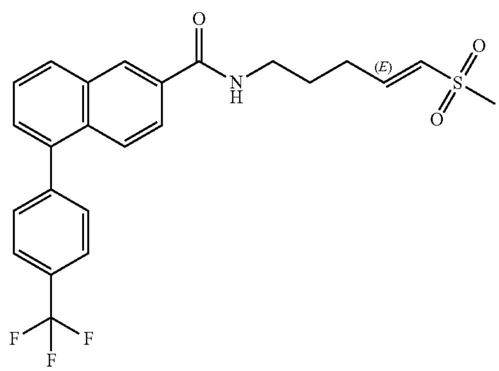 [SMILES: CS(=O)(=O)/C=C/CCCNC(=O)c1ccc2c(-c3ccc(C(F)(F)F)cc3)cccc2c1] | N-[(E)-5-methylsulfonylpent-2-enyl]-5-[4-(trifluoromethyl)phenyl]naphthalene-2-carboxamide |
| 227 | 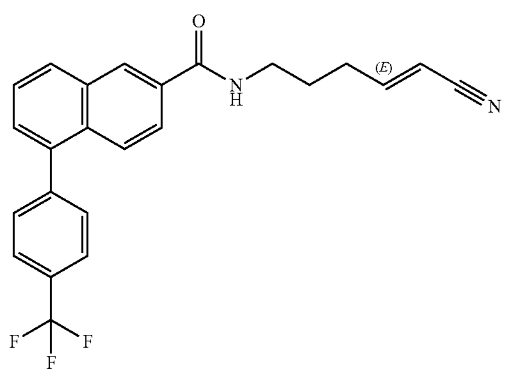 [SMILES: N#C/C=C/CCCNC(=O)c1ccc2c(-c3ccc(C(F)(F)F)cc3)cccc2c1] | N-[(E)-5-cyanopent-4-enyl]-5-[4-(trifluoromethyl)phenyl]naphthalene-2-carboxamide |
| 228 | 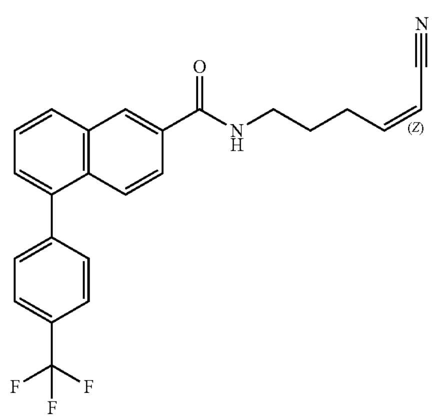 [SMILES: N#C/C=C\CCCNC(=O)c1ccc2c(-c3ccc(C(F)(F)F)cc3)cccc2c1] | N-[(Z)-5-cyanopent-4-enyl]-5-[4-(trifluoromethyl)phenyl]naphthalene-2-carboxamide |

TABLE 2-continued

| Compound No. | Structure | Name |
|---|---|---|
| 229 | 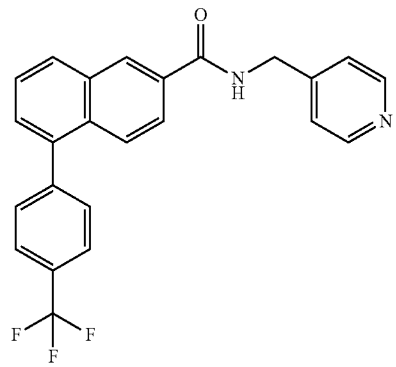 [SMILES: O=C(NCc1ccncc1)c1ccc2c(-c3ccc(C(F)(F)F)cc3)cccc2c1] | N-(pyridin-4-ylmethyl)-5-(4-(trifluoromethyl)phenyl)-2-naphthamide |
| 230 | 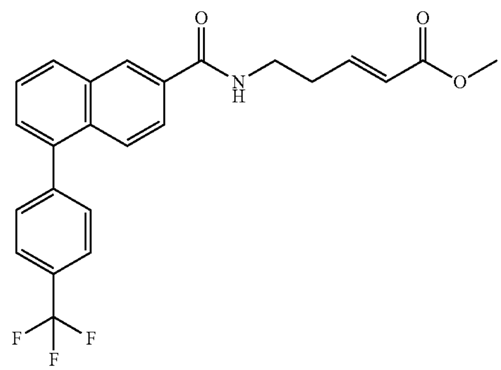 [SMILES: COC(=O)/C=C/CCNC(=O)c1ccc2c(-c3ccc(C(F)(F)F)cc3)cccc2c1] | methyl (E)-5-[[5-[4-(trifluoromethyl)phenyl]naphthalene-2-carbonyl]amino]pent-2-enoate |
| 231 | 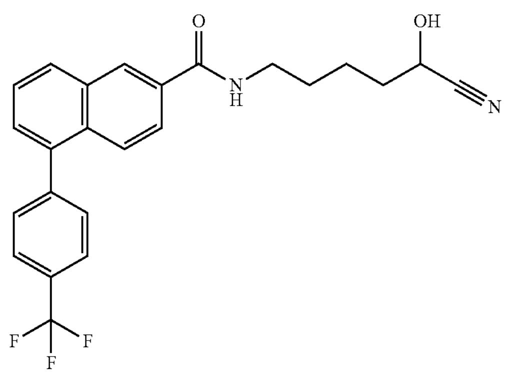 [SMILES: N#CC(O)CCCCNC(=O)c1ccc2c(-c3ccc(C(F)(F)F)cc3)cccc2c1] | N-(5-cyano-5-hydroxy-pentyl)-5-[4-(trifluoromethyl)phenyl]naphthalene-2-carboxamide |
| 232 | 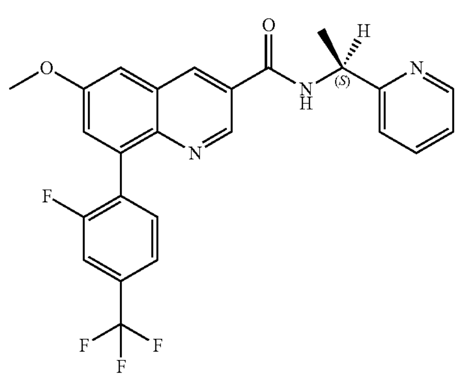 | (S)-8-(2-Fluoro-4-(trifluoromethyl)phenyl)-6-methoxy-N-(1-(pyridin-2-yl)ethyl)quinoline-3-carboxamide |

TABLE 2-continued

| Compound No. | Structure | Name |
|---|---|---|
| 233 | 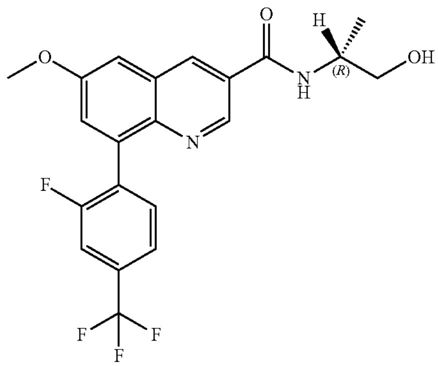 | (R)-8-(2-Fluoro-4-(trifluoromethyl)phenyl)-N-(1-hydroxypropan-2-yl)-6-methoxyquinoline-3-carboxamide |
| 234 | 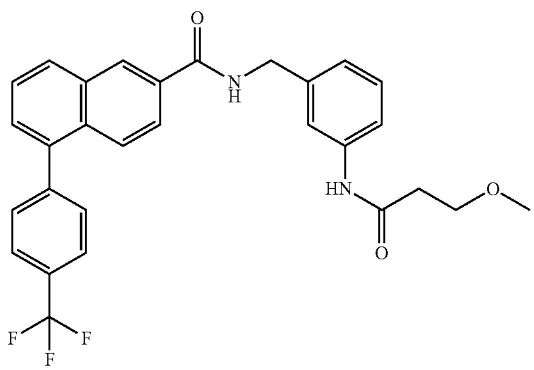 [SMILES: COCCC(=O)Nc1cccc(CNC(=O)c2ccc3c(-c4ccc(C(F)(F)F)cc4)cccc3c2)c1] | N-(3-(3-methoxypropanamido)benzyl)-5-(4-(trifluoromethyl)phenyl)-2-naphthamide |
| 235 | 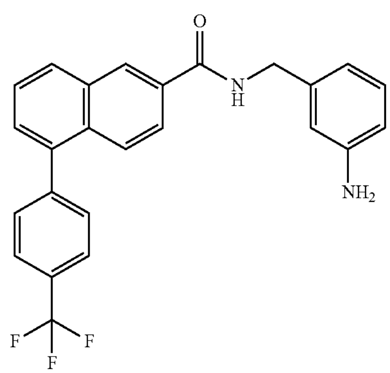 [SMILES: Nc1cccc(CNC(=O)c2ccc3c(-c4ccc(C(F)(F)F)cc4)cccc3c2)c1] | N-(3-aminobenzyl)-5-(4-(trifluoromethyl)phenyl)-2-naphthamide |
| 236 | 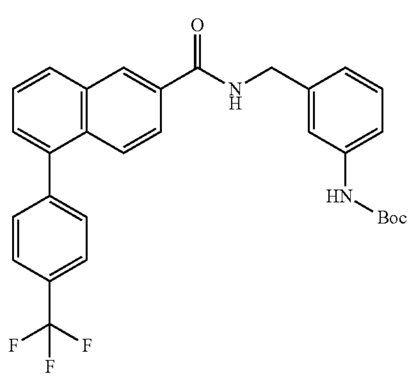 [SMILES: CC(C)(C)OC(=O)Nc1cccc(CNC(=O)c2ccc3c(-c4ccc(C(F)(F)F)cc4)cccc3c2)c1] | tert-butyl (3-((5-(4-(trifluoromethyl)phenyl)-2-naphthamido)methyl)phenyl)carbamate |

TABLE 2-continued

| Compound No. | Structure | Name |
|---|---|---|
| 237 | 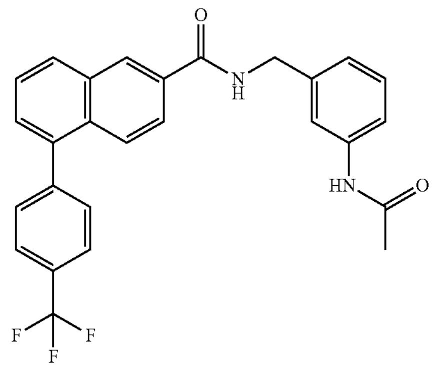 [SMILES: CC(=O)Nc1cccc(CNC(=O)c2ccc3c(-c4ccc(C(F)(F)F)cc4)cccc3c2)c1] | N-(3-acetamidobenzyl)-5-(4-(trifluoromethyl)phenyl)-2-naphthamide |
| 238 | 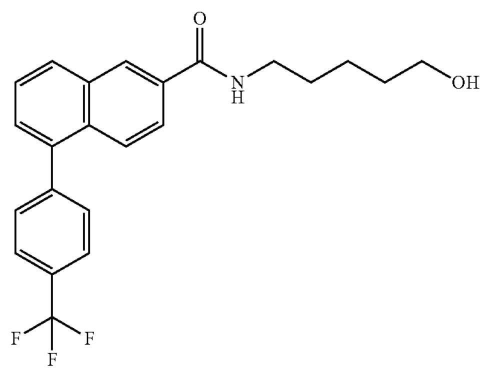 [SMILES: O=C(NCCCCCO)c1ccc2c(-c3ccc(C(F)(F)F)cc3)cccc2c1] | N-(5-hydroxypentyl)-5-[4-(trifluoromethyl)phenyl]naphthalene-2-carboxamide |
| 239 | 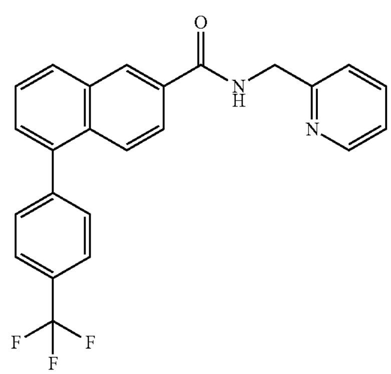 [SMILES: O=C(NCc1ccccn1)c1ccc2c(-c3ccc(C(F)(F)F)cc3)cccc2c1] | N-(pyridin-2-ylmethyl)-5-(4-(trifluoromethyl)phenyl)-2-naphthamide |
| 240 | 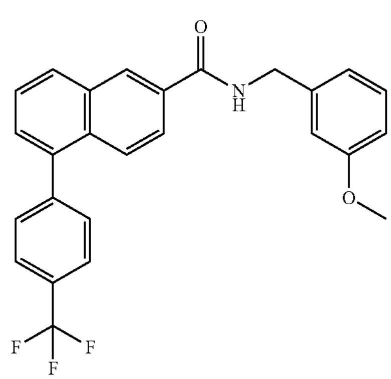 [SMILES: COc1cccc(CNC(=O)c2ccc3c(-c4ccc(C(F)(F)F)cc4)cccc3c2)c1] | N-(3-methoxybenzyl)-5-(4-(trifluoromethyl)phenyl)-2-naphthamide |

TABLE 2-continued

| Compound No. | Structure | Name |
|---|---|---|
| 241 | 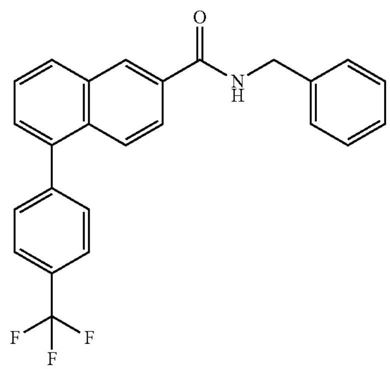 [SMILES: O=C(NCc1ccccc1)c1ccc2c(-c3ccc(C(F)(F)F)cc3)cccc2c1] | N-benzyl-5-(4-(trifluoromethyl)phenyl)-2-naphthamide |
| 242 | 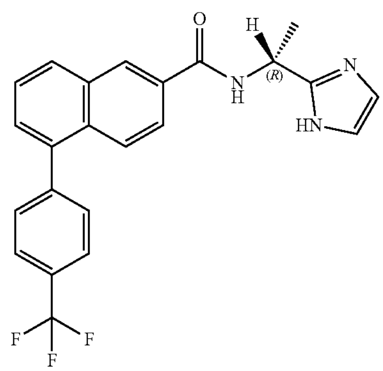 | (R)-N-(1-(1H-imidazol-2-yl)ethyl)-5-(4-(trifluoromethyl)phenyl)-2-naphthamide |
| 243 | 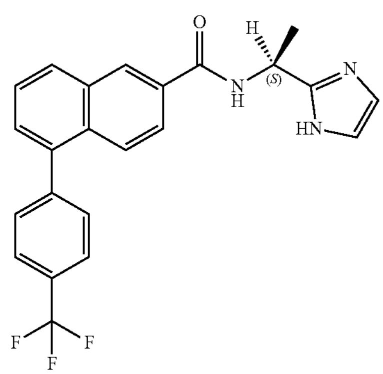 | (S)-N-(1-(1H-imidazol-2-yl)ethyl)-5-(4-(trifluoromethyl)phenyl)-2-naphthamide |
| 244 | 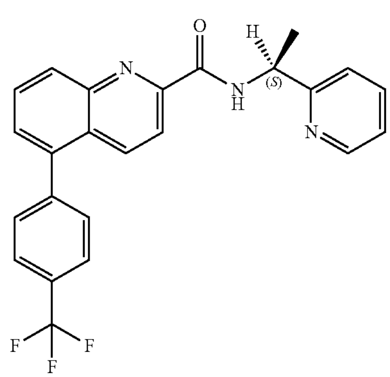 | (S)-N-(1-(Pyridin-2-yl)ethyl)-5-(4-(trifluoromethyl)phenyl)quinoline-2-carboxamide |

TABLE 2-continued

| Compound No. | Structure | Name |
|---|---|---|
| 245 | 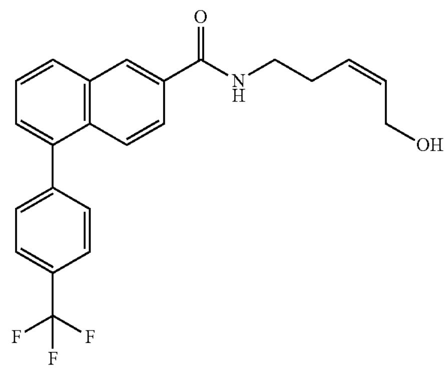 [SMILES: O=C(NCC/C=C\CO)c1ccc2c(-c3ccc(C(F)(F)F)cc3)cccc2c1] | N-[(E)-5-hydroxypent-3-enyl]-5-[4-(trifluoromethyl)phenyl]napthalene-2-carboxamide |
| 246 | 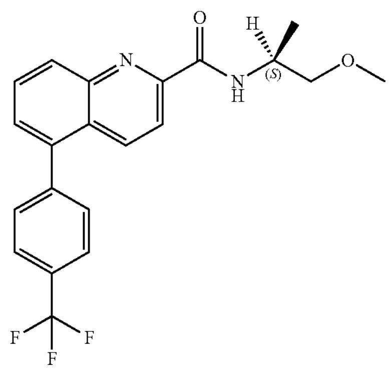 | (S)-N-(1-Methoxypropan-2-yl)-5-(4-(trifluoromethyl)phenyl)quinoline-2-carboxamide |
| 247 | 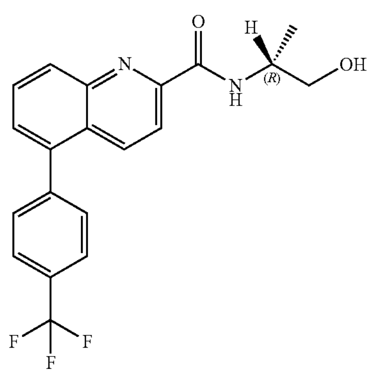 | (R)-N-(1-Hydroxypropan-2-yl)-5-(4-(trifluoromethyl)phenyl)quinoline-2-carboxamide |
| 248 | 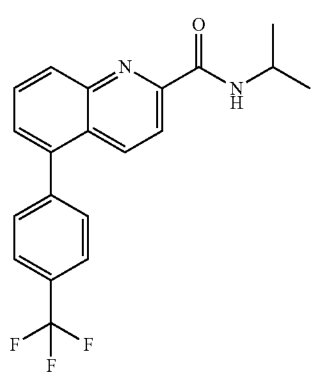 [SMILES: CC(C)NC(=O)c1ccc2c(-c3ccc(C(F)(F)F)cc3)cccc2n1] | N-isopropyl-5-(4-(trifluoromethyl)phenyl)quinoline-2-carboxamide |

TABLE 2-continued
| Compound No. | Structure | Name |
|---|---|---|
| 249 | 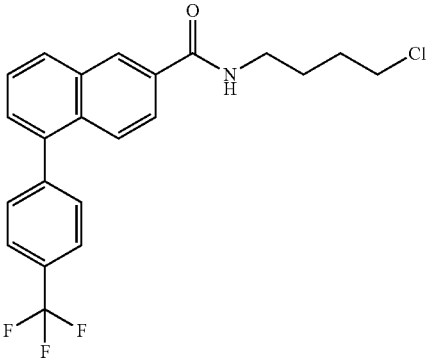 [SMILES: O=C(NCCCCCl)c1ccc2c(-c3ccc(C(F)(F)F)cc3)cccc2c1] | N-(4-chlorobutyl)-5-(4-(trifluoromethyl)phenyl)-2-naphthamide |
| 250 | 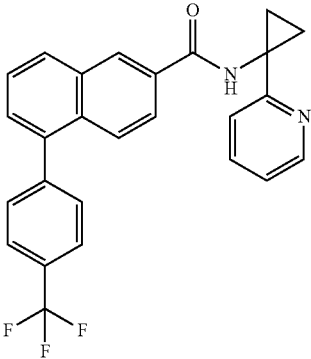 [SMILES: O=C(NC1(c2ccccn2)CC1)c1ccc2c(-c3ccc(C(F)(F)F)cc3)cccc2c1] | N-(1-(pyridin-2-yl)cyclopropyl)-5-(4-(trifluoromethyl)phenyl)-2-napthamide |
| 251 | 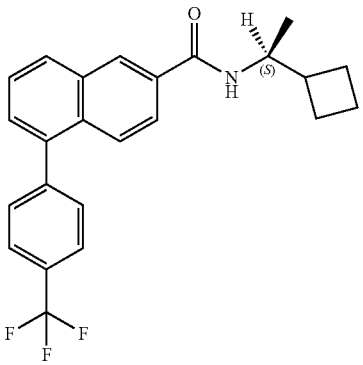 | (S)-N-(1-cyclobutylethyl)-5-(4-(trifluoromethyl)phenyl)-2-naphthamide |
| 252 | 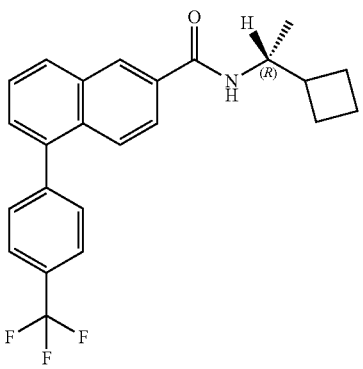 | (S)-N-(1-cyclobutylethyl)-5-(4-(trifluoromethyl)phenyl)-2-naphthamide |

TABLE 2-continued

| Compound No. | Structure | Name |
|---|---|---|
| 253 | 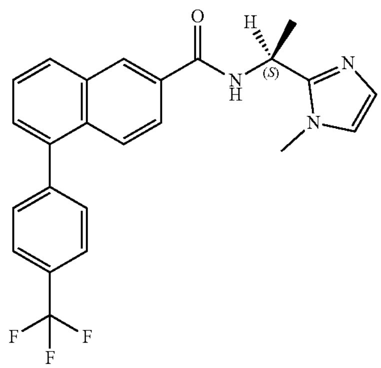 | (S)-N-(1-(1-methyl-1H-imidazol-2-yl)ethyl)-5-(4-(trifluoromethyl)phenyl)-2-naphthamide |
| 254 | 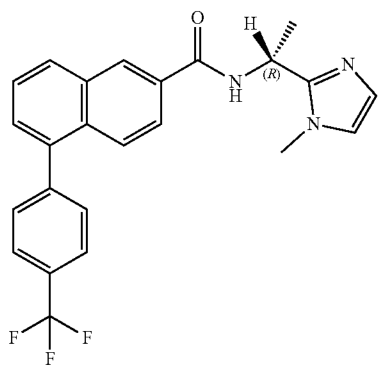 | (R)-N-(1-(1-methyl-1H-imidazol-2-yl)ethyl)-5-(4-(trifluoromethyl)phenyl)-2-naphthamide |
| 255 | 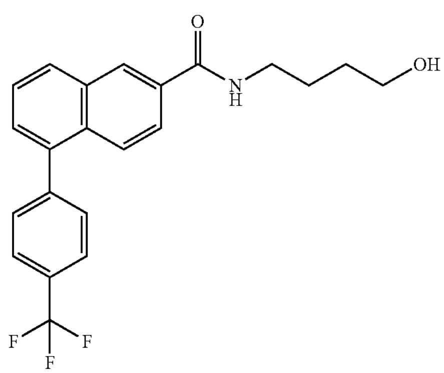 [SMILES: O=C(NCCCCO)c1ccc2c(-c3ccc(C(F)(F)F)cc3)cccc2c1] | N-(4-hydroxybutyl)-5-(4-(trifluoromethyl)phenyl)-2-naphthamide |
| 256 | 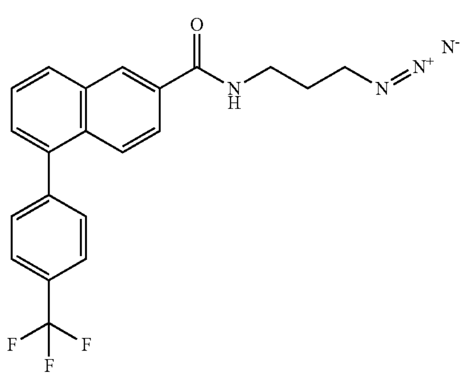 | N-(3-azidophenyl)-5-(4-(trifluoromethyl)phenyl)-2-naphthamide |

TABLE 2-continued

| Compound No. | Structure | Name |
|---|---|---|
| 257 | 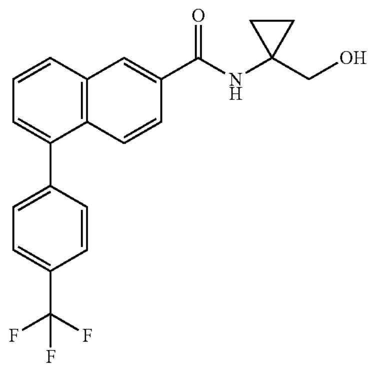 [SMILES: O=C(NC1(CO)CC1)c1ccc2c(-c3ccc(C(F)(F)F)cc3)cccc2c1] | N-(1-(hydroxymethyl)cyclopropyl)-5-(4-(trifluoromethyl)phenyl)-2-naphthamide |
| 258 | 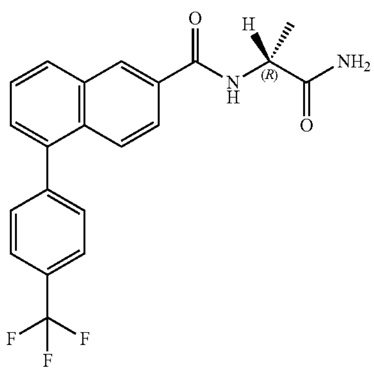 | (R)-N-(1-amino-1-oxopropan-2-yl)-5-(4-(trifluoromethyl)phenyl)-2-naphthamide |
| 259 | 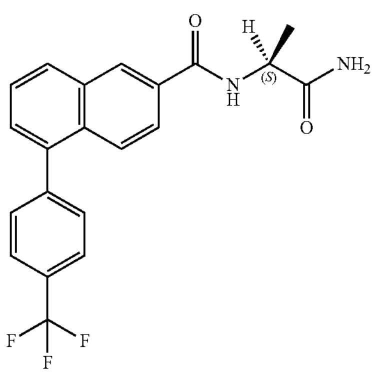 | (S)-N-(1-amino-1-oxopropan-2-yl)-5-(4-(trifluoromethyl)phenyl)-2-naphthamide |
| 260 | 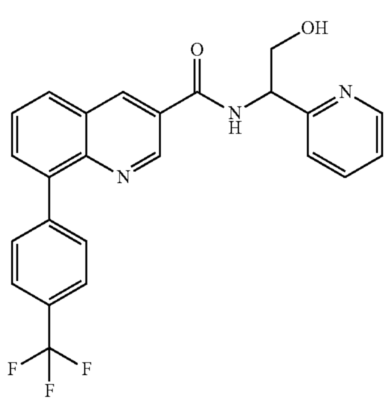 [SMILES: O=C(NC(CO)c1ccccn1)c1cnc2c(-c3ccc(C(F)(F)F)cc3)cccc2c1] | N-[2-hydroxy-1-(2-pyridyl)ethyl]-8-[4-(trifluoromethyl)phenyl]-quinoline-3-carboxamide |

TABLE 2-continued
| Compound No. | Structure | Name |
|---|---|---|
| 261 | 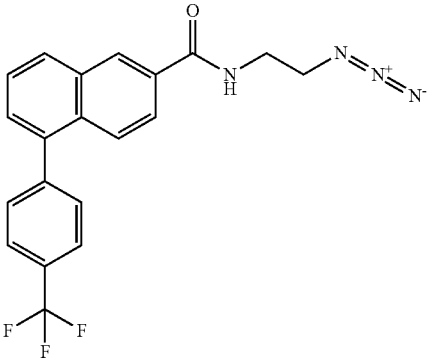 [SMILES: [N-]=[N+]=NCCNC(=O)c1ccc2c(-c3ccc(C(F)(F)F)cc3)cccc2c1] | N-(2-azidoethyl)-5-(4-(trifluoromethyl)phenyl)-2-naphthamide |
| 262 | 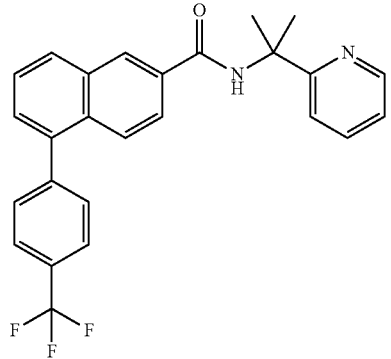 [SMILES: CC(C)(NC(=O)c1ccc2c(-c3ccc(C(F)(F)F)cc3)cccc2c1)c1ccccn1] | N-(2-(pyridin-2-yl)propan-2-yl)-5-(4-(trifluoromethyl)phenyl)-2-naphthamide |
| 263 | 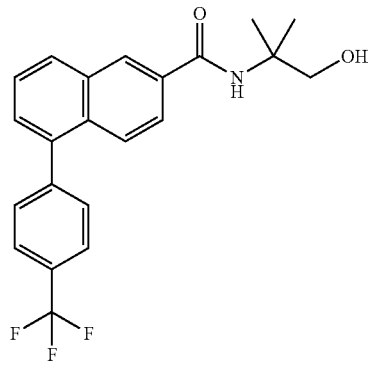 | N-(1-hydroxy-2-methylpropan-2-yl)-5-(4-(trifluoromethyl)phenyl)-2-naphthamide |
| 264 | 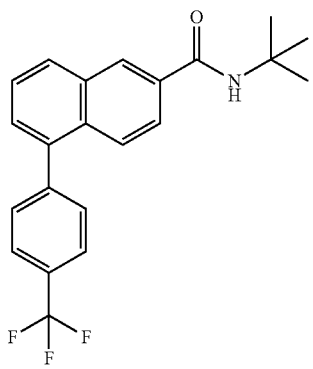 [SMILES: CC(C)(C)NC(=O)c1ccc2c(-c3ccc(C(F)(F)F)cc3)cccc2c1] | N-(tert-butyl)-5-(4-(trifluoromethyl)phenyl)-2-naphthamide |

TABLE 2-continued

| Compound No. | Structure | Name |
|---|---|---|
| 265 | 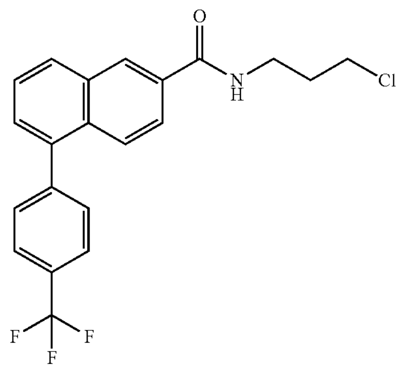 [SMILES: O=C(NCCCCl)c1ccc2c(-c3ccc(C(F)(F)F)cc3)cccc2c1] | N-(3-chloropropyl)-5-(4-(trifluoromethyl)phenyl)-2-naphthamide |
| 266 | 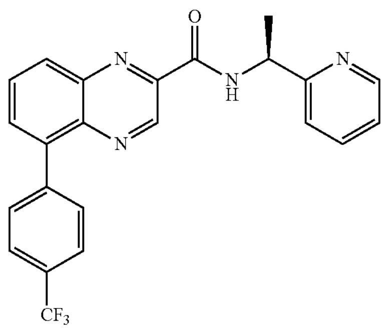 [SMILES: C[C@H](NC(=O)c1cnc2c(-c3ccc(C(F)(F)F)cc3)cccc2n1)c1ccccn1] | (S)-N-(1-(pyridin-2-yl)ethyl)-5-(4-(trifluoromethyl)phenyl)quinoxaline-2-carboxamide |
| 267 | 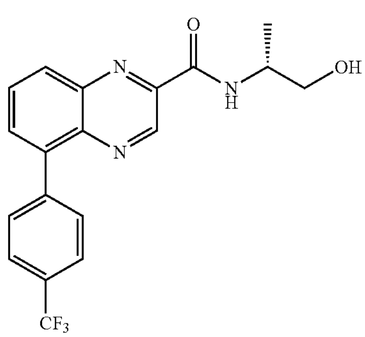 [SMILES: C[C@H](CO)NC(=O)c1cnc2c(-c3ccc(C(F)(F)F)cc3)cccc2n1] | (R)-N-(1-hydroxypropan-2-yl)-5-(4-(trifluoromethyl)phenyl)quinoxaline-2-carboxamide |
| 268 | 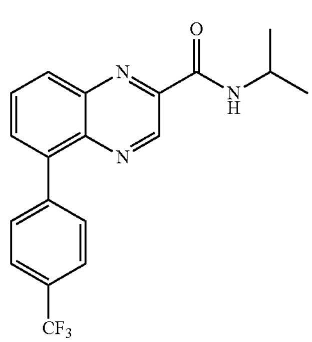 [SMILES: CC(C)NC(=O)c1cnc2c(-c3ccc(C(F)(F)F)cc3)cccc2n1] | N-Isopropyl-5-(4-(trifluoromethyl)phenyl)quinoxaline-2-carboxamide |

TABLE 2-continued

| Compound No. | Structure | Name |
|---|---|---|
| 269 | 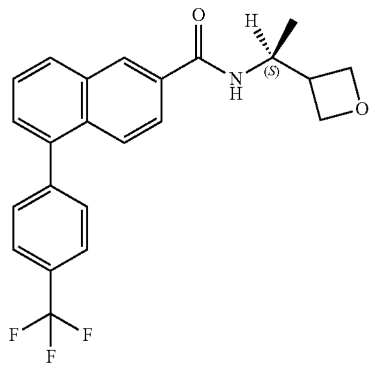 | (S)-N-(1-(oxetan-3-yl)ethyl)-5-(4-(trifluoromethyl)phenyl)-2-naphthamide |
| 270 | 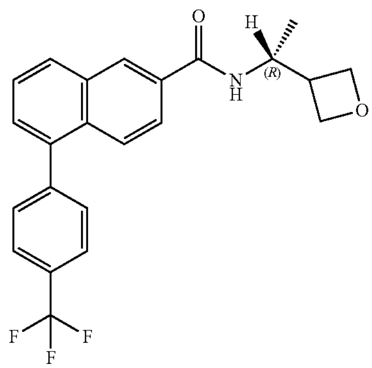 | (R)-N-(1-(oxetan-3-yl)ethyl)-5-(4-(trifluoromethyl)phenyl)-2-naphthamide |
| 271 | 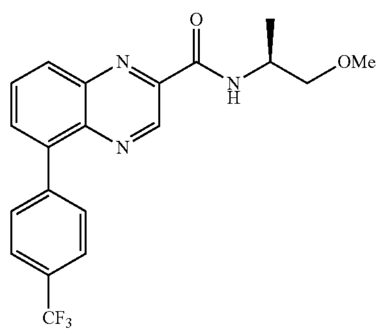 [SMILES: COC[C@H](C)NC(=O)c1cnc2c(-c3ccc(C(F)(F)F)cc3)cccc2n1] | (S)-N-(1-methoxypropan-2-yl)-5-(4-(trifluoromethyl)phenyl)quinoxaline-2-carboxamide |
| 272 | 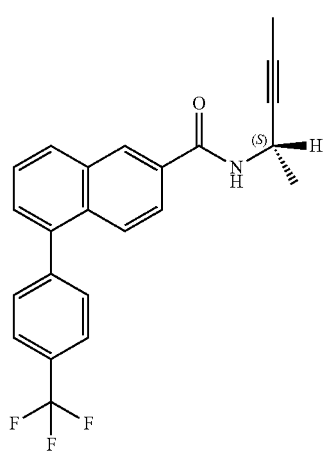 | (S)-N-(pent-3-yn-2-yl)-5-(4-(trifluoromethyl)phenyl)-2-naphthamide |

TABLE 2-continued

| Compound No. | Structure | Name |
|---|---|---|
| 273 | 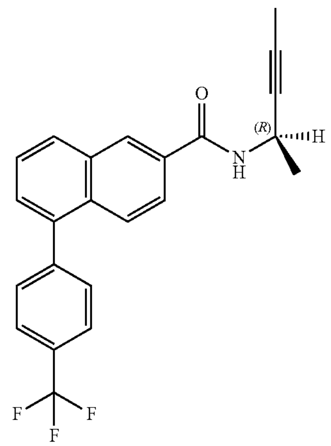 | (R)-N-(pent-3-yn-2-yl)-5-(4-(trifluoromethyl)phenyl)-2-naphthamide |
| 274 | 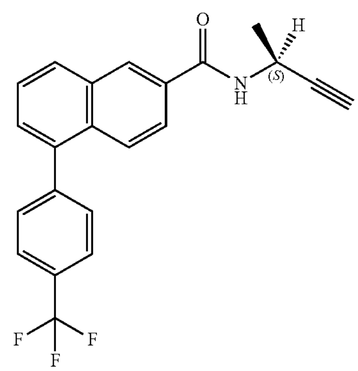 | (S)-N-(but-3-yn-2-yl)-5-(4-(trifluoromethyl)phenyl)-2-naphthamide |
| 275 | 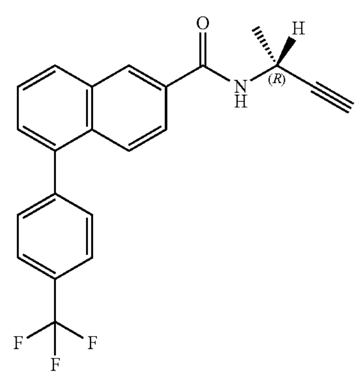 | (R)-N-(but-3-yn-2-yl)-5-(4-(trifluoromethyl)phenyl)-2-naphthamide |
| 276 | 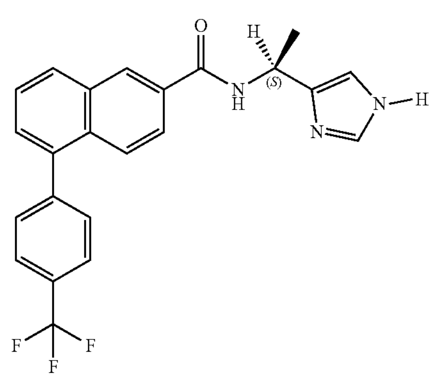 | (S)-N-(1-(1H-imidazol-4-yl)ethyl)-5-(4-(trifluoromethyl)phenyl)-2-naphthamide |

TABLE 2-continued

| Compound No. | Structure | Name |
|---|---|---|
| 277 | 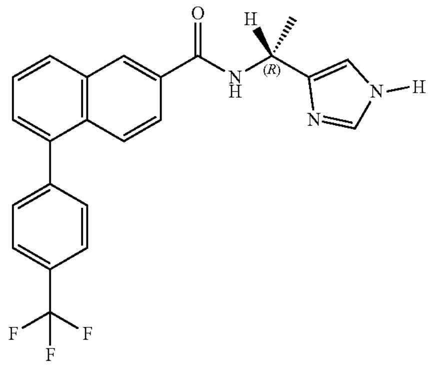 | (R)-N-(1-(1H-imidazol-4-yl)ethyl)-5-(4-(trifluoromethyl)phenyl)-2-naphthamide |
| 278 | 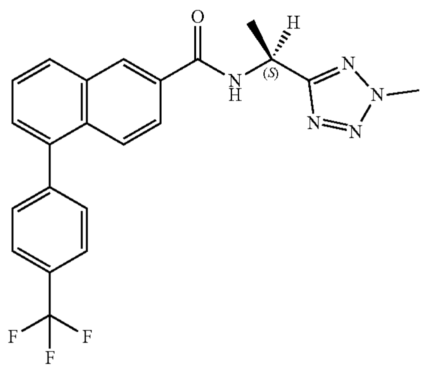 | (S)-N-(1-(2-methyl-2H-tetrazol-5-yl)ethyl)-5-(4-(trifluoromethyl)phenyl)-2-naphthamide |
| 279 | 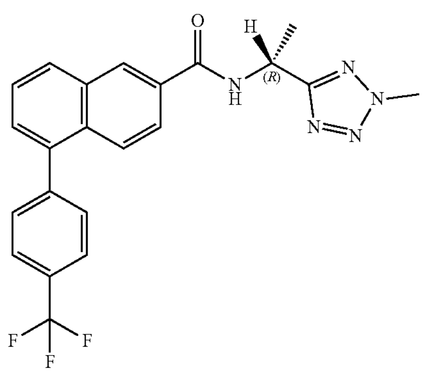 | (R)-N-(1-(2-methyl-2H-tetrazol-5-yl)ethyl)-5-(4-(trifluoromethyl)phenyl)-2-naphthamide |
| 280 | 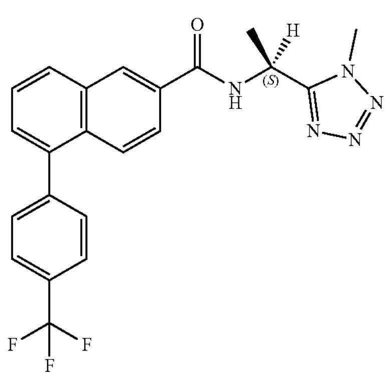 | (S)-N-(1-(1-methyl-1H-tetrazol-5-yl)ethyl)-5-(4-(trifluoromethyl)phenyl)-2-naphthamide |

TABLE 2-continued

| Compound No. | Structure | Name |
|---|---|---|
| 281 | 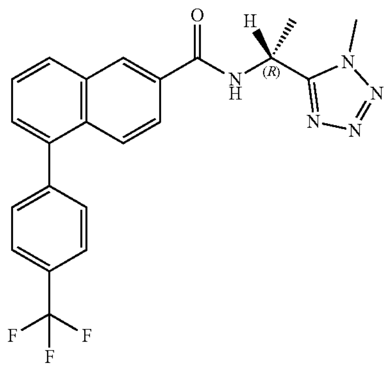 | (R)-N-(1-(1-methyl-1H-tetrazol-5-yl)ethyl)-5-(4-(trifluoromethyl)phenyl)-2-naphthamide |
| 282 | 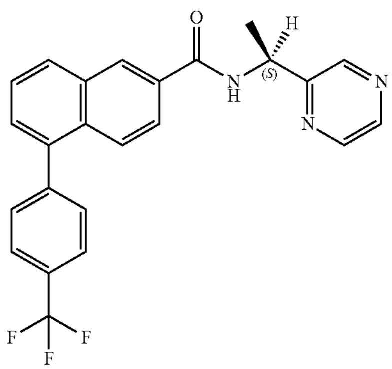 | (S)-N-(1-(pyrazin-2-yl)ethyl)-5-(4-(trifluoromethyl)phenyl)-2-naphthamide |
| 283 | 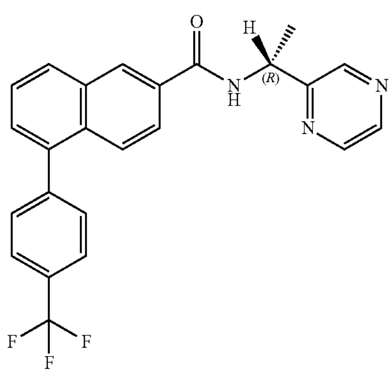 | (R)-N-(1-(pyrazin-2-yl)ethyl)-5-(4-(trifluoromethyl)phenyl)-2-naphthamide |
| 284 | 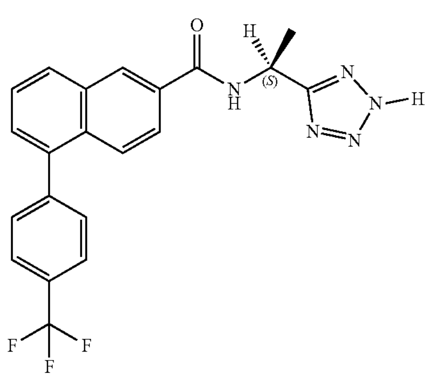 | (S)-N-(1-(2H-tetrazol-5-yl)ethyl)-5-(4-(trifluoromethyl)phenyl)-2-naphthamide |

TABLE 2-continued

| Compound No. | Structure | Name |
|---|---|---|
| 285 | 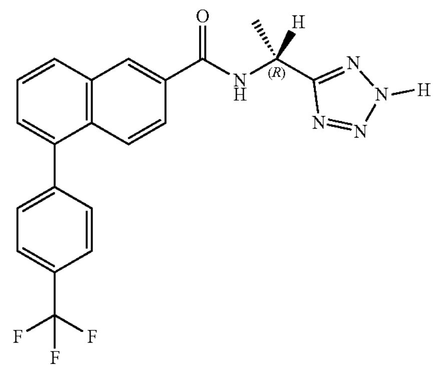 | (R)-N-(1-(2H-tetrazol-5-yl)ethyl)-5-(4-(trifluoromethyl)phenyl)-2-naphthamide |
| 286 | 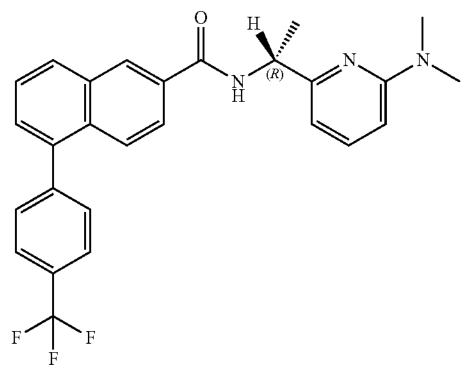 | (R)-N-(1-(6-(dimethylamino)pyridin-2-yl)ethyl)-5-(4-(trifluoromethyl)phenyl)-2-naphthamide |
| 287 | 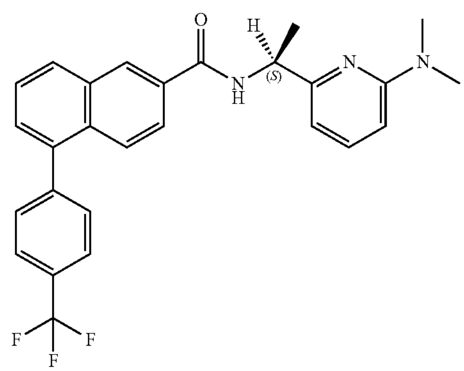 | (S)-N-(1-(6-(dimethylamino)pyridin-2-yl)ethyl)-5-(4-(trifluoromethyl)phenyl)-2-naphthamide |
| 288 | 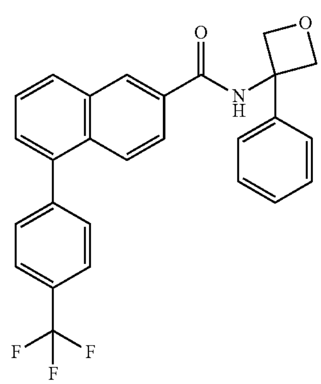 [SMILES: O=C(NC1(c2ccccc2)COC1)c1ccc2c(-c3ccc(C(F)(F)F)cc3)cccc2c1] | N-(3-phenyloxetan-3-yl)-5-(4-(trifluoromethyl)phenyl)-2-naphthamide |

TABLE 2-continued
| Compound No. | Structure | Name |
|---|---|---|
| 289 | 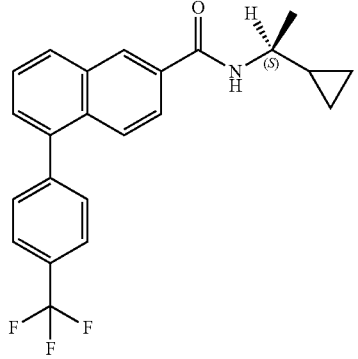 | (S)-N-(1-cyclopropylethyl)-5-(4-(trifluoromethyl)phenyl)-2-naphthamide |
| 290 | 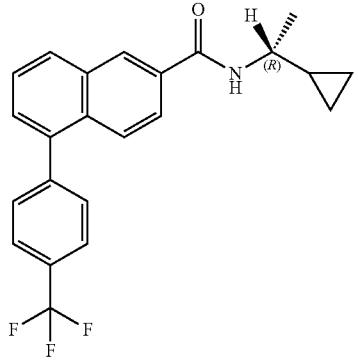 | (R)-N-(1-cyclopropylethyl)-5-(4-(trifluoromethyl)phenyl)-2-naphthamide |
| 291 | 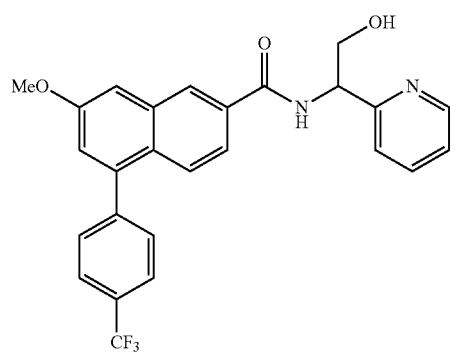 [SMILES: COc1cc(-c2ccc(C(F)(F)F)cc2)c2ccc(C(=O)NC(CO)c3ccccn3)cc2c1] | N-(2-Hydroxy-1-(pyridin-2-yl)ethyl)-7-methoxy-5-(4-(trifluoromethyl)phenyl)-2-naphthamide |
| 292 | 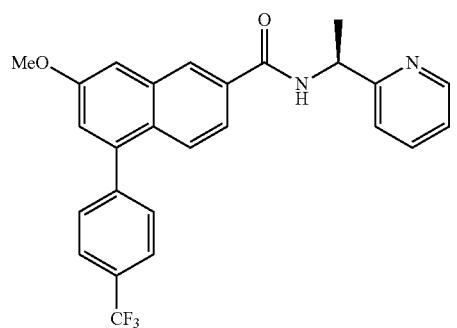 | (S)-7-Methoxy-N-(1-(pyridin-2-yl)ethyl)-5-(4-(trifluoromethyl)phenyl)-2-naphthamide |

TABLE 2-continued

| Compound No. | Structure | Name |
|---|---|---|
| 293 | 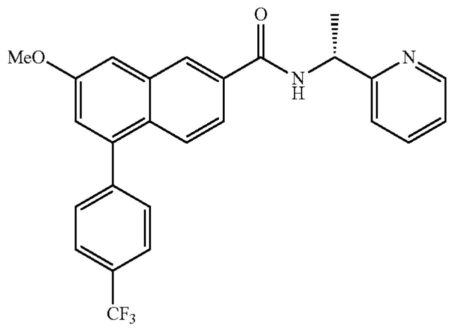 [SMILES: COc1cc(-c2ccc(C(F)(F)F)cc2)c2ccc(C(=O)N[C@H](C)c3ccccn3)cc2c1] | (R)-7-Methoxy-N-(1-(pyridin-2-yl)ethyl)-5-(4-(trifluoromethyl)phenyl)-2-naphthamide |
| 294 | 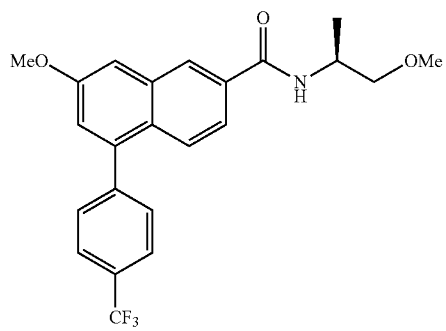 [SMILES: COC[C@H](C)NC(=O)c1ccc2c(-c3ccc(C(F)(F)F)cc3)cc(OC)cc2c1] | (S)-7-Methoxy-N-(1-methoxypropan-2-yl)-5-(4-(trifluoromethyl)phenyl)-2-naphthamide |
| 295 | 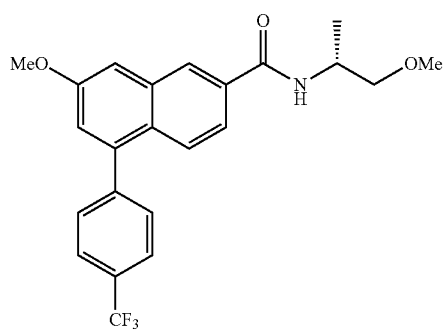 [SMILES: COC[C@@H](C)NC(=O)c1ccc2c(-c3ccc(C(F)(F)F)cc3)cc(OC)cc2c1] | (R)-7-Methoxy-N-(1-methoxypropan-2-yl)-5-(4-(trifluoromethyl)phenyl)-naphthamide |
| 296 | 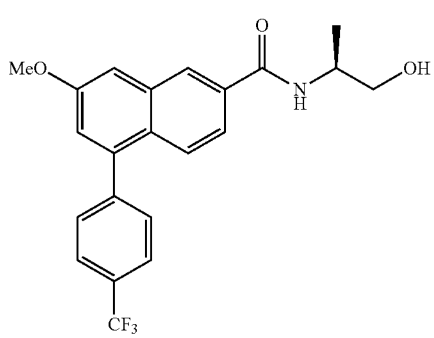 [SMILES: COc1cc(-c2ccc(C(F)(F)F)cc2)c2ccc(C(=O)N[C@@H](C)CO)cc2c1] | (S)-N-(1-Hydroxypropan-2-yl)-7-methoxy-5-(4-(trifluoromethyl)phenyl)-2-naphthamide |

TABLE 2-continued

| Compound No. | Structure | Name |
|---|---|---|
| 297 | 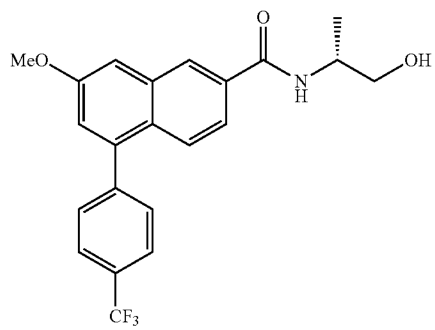 [SMILES: COc1cc(-c2ccc(C(F)(F)F)cc2)c2ccc(C(=O)N[C@H](C)CO)cc2c1] | (R)-N-(1-Hydroxypropan-2-yl)-7-methoxy-5-(4-(trifluoromethyl)phenyl)-2-naphthamide |
| 298 | 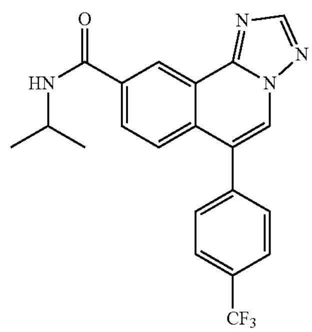 [SMILES: CC(C)NC(=O)c1ccc2c(-c3ccc(C(F)(F)F)cc3)cn3ncnc3c2c1] | N-Isopropyl-6-(4-(trifluoromethyl)phenyl)-[1,2,4]triazolo[5,1-a]isoquinoline-9-carboxamide |
| 299 | 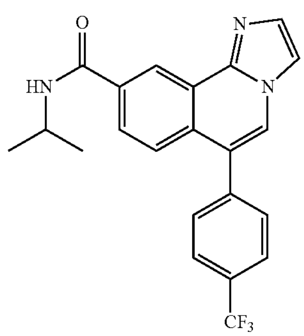 [SMILES: CC(C)NC(=O)c1ccc2c(-c3ccc(C(F)(F)F)cc3)cn3ccnc3c2c1] | N-Isopropyl-6-(4-(trifluoromethyl)phenyl)imidazo[2,1-a]isoquinoline-9-carboxamide |
| 300 | 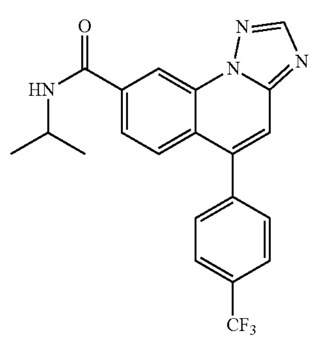 [SMILES: CC(C)NC(=O)c1ccc2c(-c3ccc(C(F)(F)F)cc3)cc3ncnn3c2c1] | N-Isopropyl-5-(4-(trifluoromethyl)phenyl)-[1,2,4]triazolo[1,5-a]quinoline-8-carboxamide |

TABLE 2-continued

| Compound No. | Structure | Name |
|---|---|---|
| 301 | 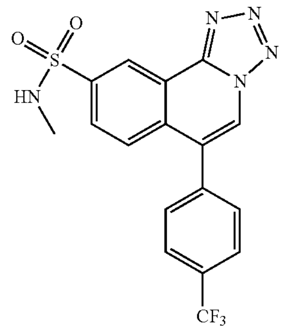 [SMILES: CNS(=O)(=O)c1ccc2c(-c3ccc(C(F)(F)F)cc3)cn3nnnc3c2c1] | N-Methyl-6-(4-(trifluoromethyl)phenyl)tetrazolo[5,1-a]isoquinoline-9-sulfonamide |
| 302 | 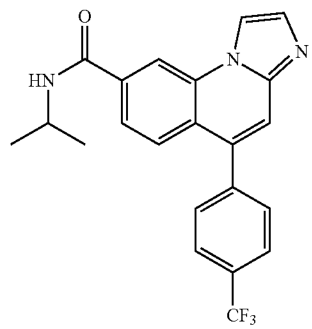 [SMILES: CC(C)NC(=O)c1ccc2c(-c3ccc(C(F)(F)F)cc3)cc3nccn3c2c1] | N-Isopropyl-5-(4-(trifluoromethyl)phenyl)imidazo[1,2-a]quinoline-8-carboxamide |
| 303 | 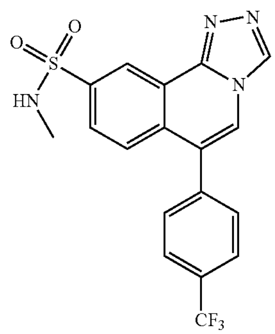 [SMILES: CNS(=O)(=O)c1ccc2c(-c3ccc(C(F)(F)F)cc3)cn3cnnc3c2c1] | N-Methyl-6-(4-(trifluoromethyl)phenyl)-[1,2,4]triazolo[3,4-a]isoquinoline-9-sulfonamide |
| 304 | 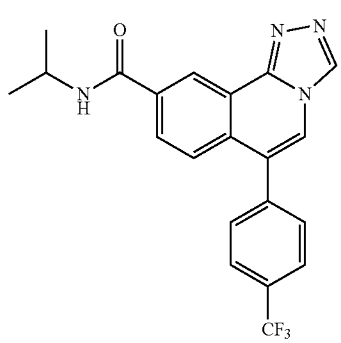 [SMILES: CC(C)NC(=O)c1ccc2c(-c3ccc(C(F)(F)F)cc3)cn3cnnc3c2c1] | N-Isopropyl-6-(4-(trifluoromethyl)phenyl)-[1,2,4]triazolo[3,4-a]isoquinoline-9-carboxamide |

TABLE 2-continued
| Compound No. | Structure | Name |
|---|---|---|
| 305 | 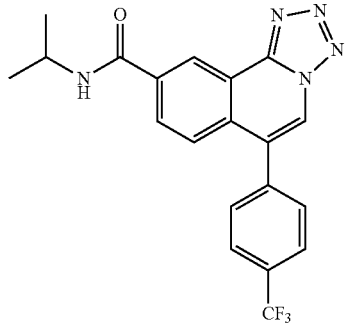 [SMILES: CC(C)NC(=O)c1ccc2c(-c3ccc(C(F)(F)F)cc3)cn3nnnc3c2c1] | N-Isopropyl-6-(4-(trifluoromethyl)phenyl)tetrazolo[5,1-a]isoquinoline-9-carboxamide |
| 306 | 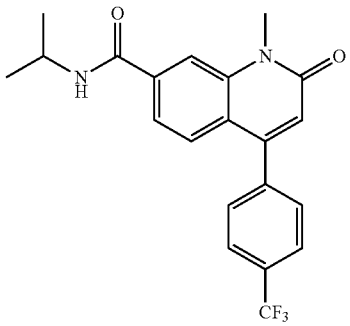 [SMILES: CC(C)NC(=O)c1ccc2c(-c3ccc(C(F)(F)F)cc3)cc(=O)n(C)c2c1] | N-Isopropyl-1-methyl-2-oxo-4-(4-(trifluoromethyl)phenyl)-1,2-dihydroquinoline-7-carboxamide |
| 307 | 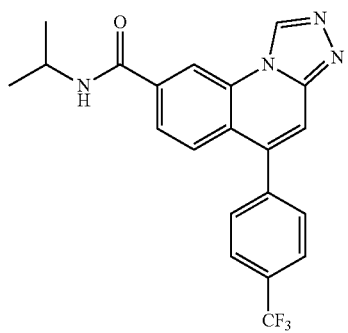 [SMILES: CC(C)NC(=O)c1ccc2c(-c3ccc(C(F)(F)F)cc3)cc3nncn3c2c1] | N-Isopropyl-5-(4-(trifluoromethyl)phenyl)-[1,2,4]triazolo[4,3-a]quinoline-8-carboxamide |
| 308 | 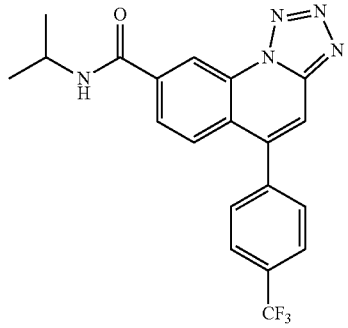 [SMILES: CC(C)NC(=O)c1ccc2c(-c3ccc(C(F)(F)F)cc3)cc3nnnn3c2c1] | N-Isopropyl-5-(4-(trifluoromethyl)phenyl)tetrazolo[1,5-a]quinoline-8-carboxamide |

TABLE 2-continued

| Compound No. | Structure | Name |
|---|---|---|
| 309 | 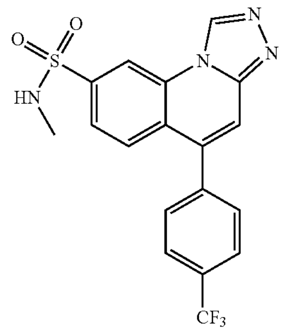 | N-Methyl-5-(4-(trifluoromethyl)phenyl)-[1,2,4]triazolo[4,3-a]quinoline-8-sulfonamide |
| 310 | 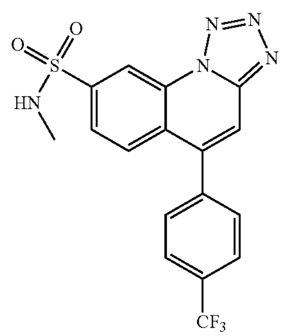 [SMILES: CNS(=O)(=O)c1ccc2c(-c3ccc(C(F)(F)F)cc3)cc3nncn3c2c1] | N-Methyl-5-(4-(trifluoromethyl)phenyl)tetrazolo[1,5-a]quinoline-8-sulfonamide |
| 311 | 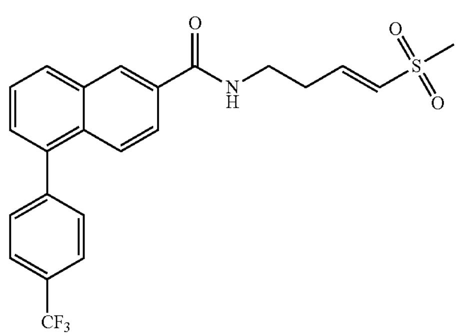 [SMILES: CS(=O)(=O)/C=C/CCNC(=O)c1ccc2c(-c3ccc(C(F)(F)F)cc3)cccc2c1] | (E)-N-(4-(Methylsulfonyl)but-3-en-1-yl)-5-(4-(trifluoromethyl)phenyl)-2-naphthamide |
| 312 | 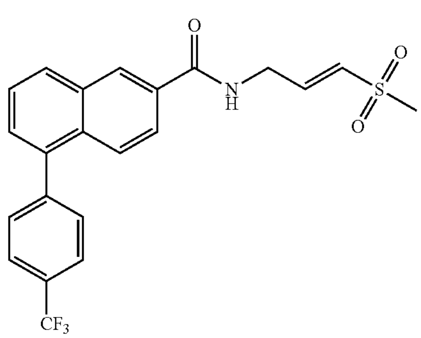 [SMILES: CS(=O)(=O)/C=C/CNC(=O)c1ccc2c(-c3ccc(C(F)(F)F)cc3)cccc2c1] | (E)-N-(3-(Methylsulfonyl)allyl)-5-(4-(trifluoromethyl)phenyl)-2-naphthamide |

TABLE 2-continued

| Compound No. | Structure | Name |
|---|---|---|
| 313 | 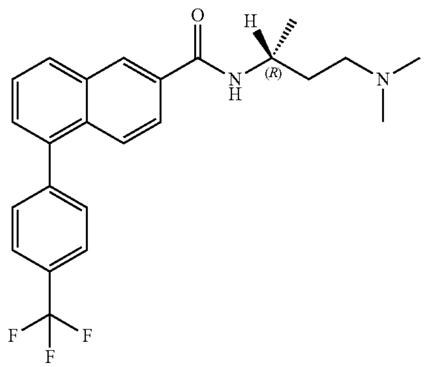 | N-[(1R)-3-(dimethylamino)-1-methyl-propyl]-5-[4-(trifluoromethyl)phenyl]naphthalene-2-carboxamide |
| 314 | 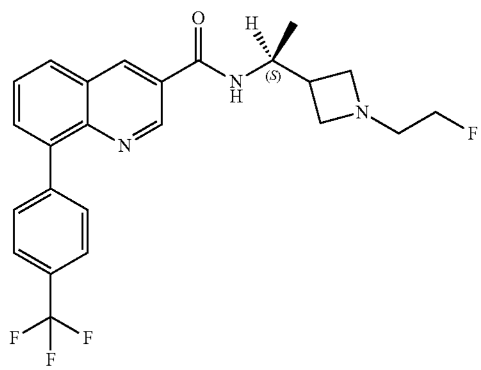 | N-[(1S)-1-[1-(2-fluoroethyl)azetidin-3-yl]ethyl]-8-[4-(trifluoromethyl)phenyl]quinoline-3-carboxamide |
| 315 | 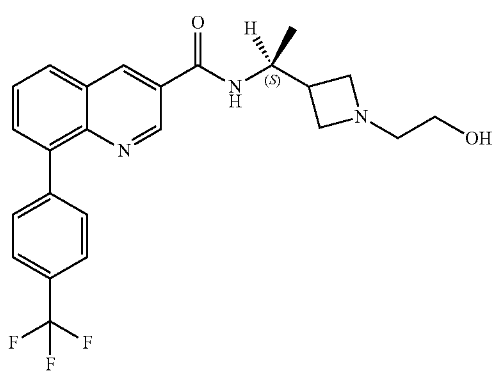 | N-[(1S)-1-[1-(2-hydroxyethyl)azetidin-3-yl]ethyl]-8-[4-(trifluoromethyl)phenyl]quinoline-3-carboxamide |
| 316 | 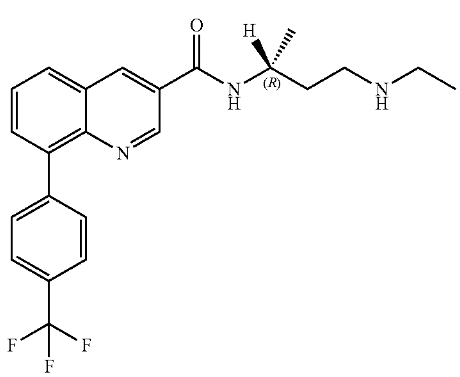 | N-[(1R)-3-(ethylamino)-1-methyl-propyl]-8-[4-(trifluoromethyl)phenyl]quinoline-3-carboxamide |

TABLE 2-continued

| Compound No. | Structure | Name |
|---|---|---|
| 317 | 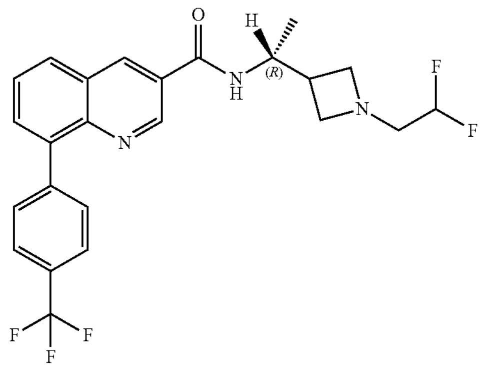 | (R)-N-(1-(1-(2,2-difluoroethyl)azetidin-3-yl)ethyl)-8-(4-(trifluoromethyl)phenyl)quinoline-3-carboxamide |
| 318 | 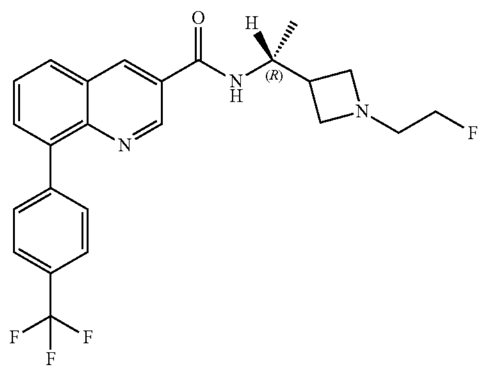 | (R)-N-(1-(1-(2-fluoroethyl)azetidin-3-yl)ethyl)-8-(4-(trifluoromethyl)phenyl)quinoline-3-carboxamide |
| 319 | 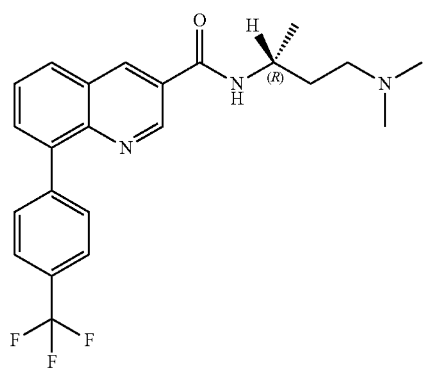 | N-[(1R)-3-(Dimethylamino)-1-methyl-propyl]-8-[4-(trifluoromethyl)phenyl]quinoline-3-carboxamide |
| 320 | 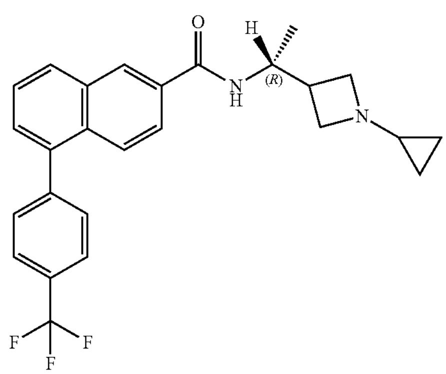 | (R)-N-(1-(1-cyclopropylazetidin-3-yl)ethyl)-5-(4-(trifluoromethyl)phenyl)-2-naphthamide |

In another aspect, the present disclosure provides a compound or a pharmaceutically acceptable salt or a pharmaceutically acceptable solvate thereof, wherein the compound is a compound from Table 3, or a pharmaceutically acceptable salt or a pharmaceutically acceptable solvate thereof.

TABLE 3

| Compound No. | Structure | Name |
| --- | --- | --- |
| 321 | 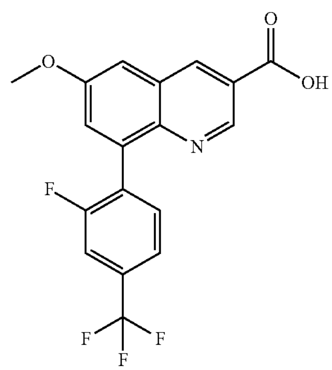 [SMILES: COc1cc(-c2ccc(C(F)(F)F)cc2F)c2ncc(C(=O)O)cc2c1] | 8-(2-Fluoro-4-(trifluoromethyl)phenyl)-6-methoxyquinoline-3-carboxylic acid |
| 322 | 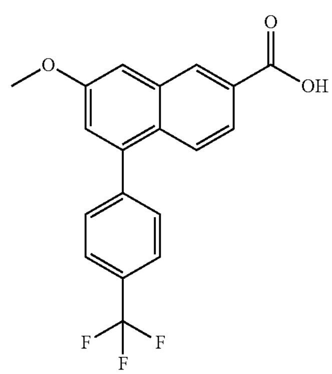 [SMILES: COc1cc(-c2ccc(C(F)(F)F)cc2)c2ccc(C(=O)O)cc2c1] | 7-Methoxy-5-(4-(trifluoromethyl)phenyl)-2-naphthoic acid |
| 323 | 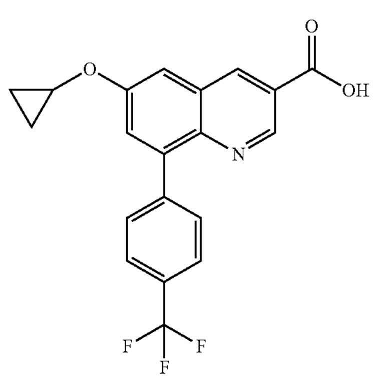 [SMILES: O=C(O)c1cnc2c(-c3ccc(C(F)(F)F)cc3)cc(OC3CC3)cc2c1] | 6-Cyclopropoxy-8-(4-(trifluoromethyl)phenyl)quinoline-3-carboxylic acid |

TABLE 3-continued
| Compound No. | Structure | Name |
|---|---|---|
| 324 | 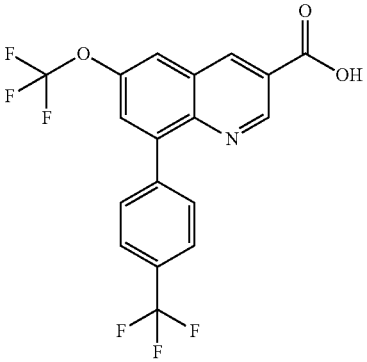 [SMILES: O=C(O)c1cnc2c(-c3ccc(C(F)(F)F)cc3)cc(OC(F)(F)F)cc2c1] | 6-(Trifluoromethoxy)-8-[4-trifluoromethyl)phenyl]quinoline-3-carboxylic acid |
| 325 | 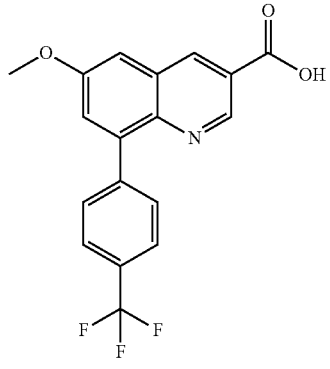 [SMILES: COc1cc(-c2ccc(C(F)(F)F)cc2)c2ncc(C(=O)O)cc2c1] | 6-Methoxy-8-(4-(trifluoromethyl)phenyl)quinoline-3-carboxylic acid |
| 326 | 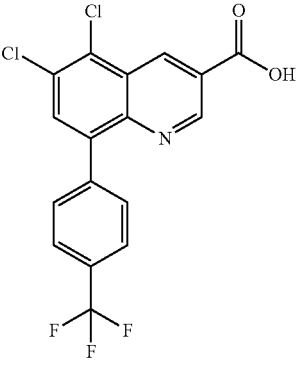 [SMILES: O=C(O)c1cnc2c(-c3ccc(C(F)(F)F)cc3)cc(Cl)c(Cl)c2c1] | 5,6-Dichloro-8-(4-(trifluoromethyl)phenyl)quinoline-3-carboxylic acid |
| 327 | 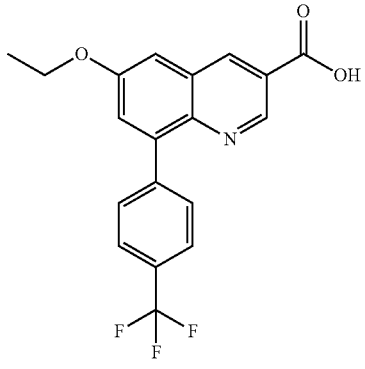 [SMILES: CCOc1cc(-c2ccc(C(F)(F)F)cc2)c2ncc(C(=O)O)cc2c1] | 6-Ethoxy-8-(4-(trifluoromethyl)phenyl)quinoline-3-carboxylic acid |

TABLE 3-continued

| Compound No. | Structure | Name |
|---|---|---|
| 328 | 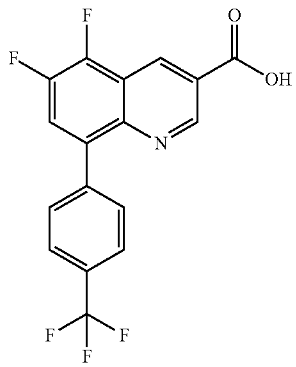 [SMILES: O=C(O)c1cnc2c(-c3ccc(C(F)(F)F)cc3)cc(F)c(F)c2c1] | 5,6-Difluoro-8-(4-(trifluoromethyl)phenyl)quinoline-3-carboxylic acid |
| 329 | 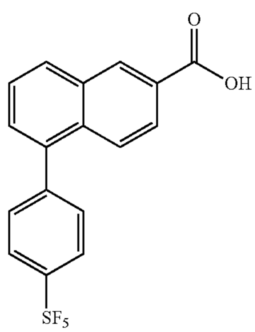 | 5-[4-(pentafluoro-sulfanyl)phenyl]naphthalene-2-carboxylic acid |
| 330 | 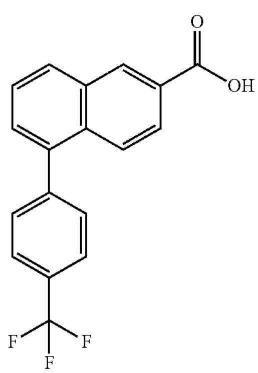 [SMILES: O=C(O)c1ccc2c(-c3ccc(C(F)(F)F)cc3)cccc2c1] | 5-[4-(Trifluoromethyl)phenyl]naphthalene-2-carboxylic acid |
| 331 | 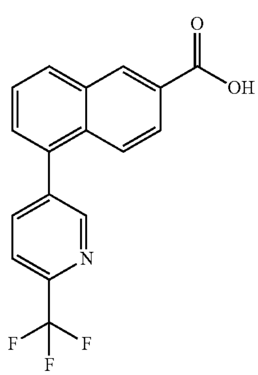 [SMILES: O=C(O)c1ccc2c(-c3ccc(C(F)(F)F)nc3)cccc2c1] | 5-(6-(trifluoromethyl)pyridin-3-yl)-2-naphthoic acid |

TABLE 3-continued
| Compound No. | Structure | Name |
|---|---|---|
| 332 | 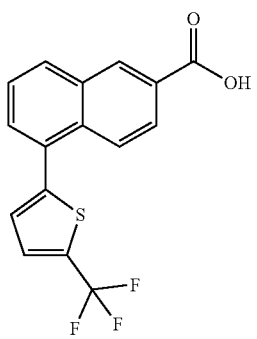 [SMILES: O=C(O)c1ccc2c(-c3ccc(C(F)(F)F)s3)cccc2c1] | 5-[5-(trifluoromethyl)-2-thienyl]naphthalene-2-carboxylic acid |
| 333 | 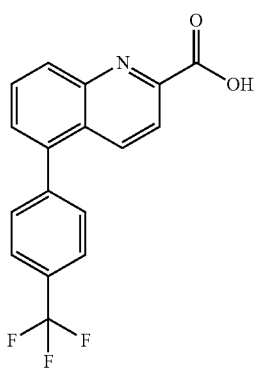 | 5-(4-(trifluoromethyl)phenyl)quinoline-2-carboxylic acid |
| 334 | 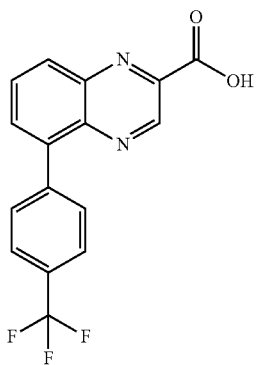 | 5-(4-(trifluoromethyl)phenyl)quinoxaline-2-carboxylic acid |
| 335 | 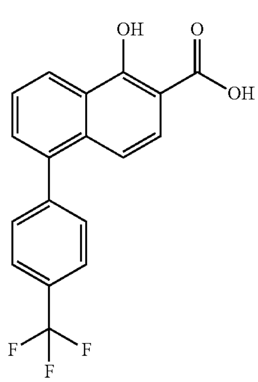 [SMILES: O=C(O)c1ccc2c(-c3ccc(C(F)(F)F)cc3)cccc2c1O] | 1-hydroxy-5-(4-(trifluoromethyl)phenyl)-2-naphthoic acid |

TABLE 3-continued

| Compound No. | Structure | Name |
|---|---|---|
| 336 | 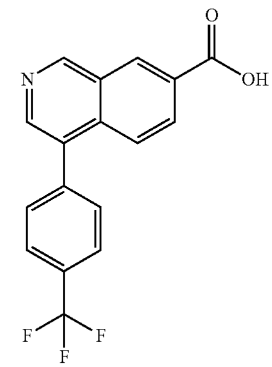 | 4-[4-(trifluoromethyl)phenyl]isoquinoline-7-carboxylic acid |
| 337 | 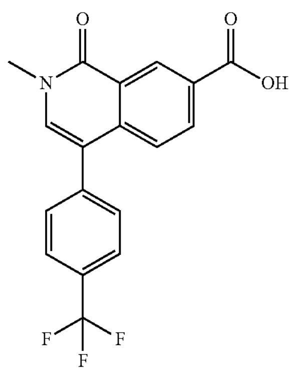 [SMILES: Cn1cc(-c2ccc(C(F)(F)F)cc2)c2ccc(C(=O)O)cc2c1=O] | 2-methyl-1-oxo-4-(4-(trifluoromethyl)phenyl)-1,2-dihydroisoquinoline-7-carboxylic acid |
| 338 | 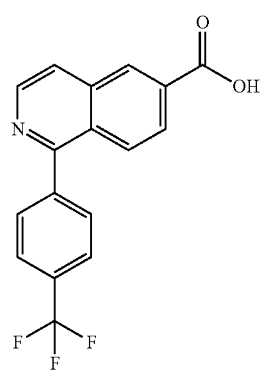 [SMILES: O=C(O)c1ccc2c(-c3ccc(C(F)(F)F)cc3)nccc2c1] | 1-(4-(trifluoromethyl)phenyl)isoquinoline-6-carboxylic acid |
| 339 | 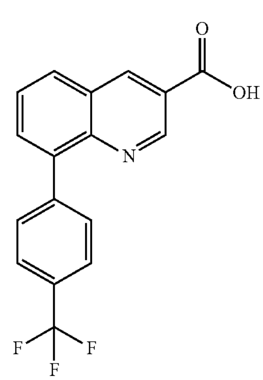 [SMILES: O=C(O)c1cnc2c(-c3ccc(C(F)(F)F)cc3)cccc2c1] | 8-(4-(trifluoromethyl)phenyl)quinoline-3-carboxylic acid |

Preparation of the Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, PA), Aldrich Chemical (Milwaukee, WI, including Sigma Chemical and Fluka), Apin Chemicals Ltd. (Milton Park, UK), Avocado Research (Lancashire, U.K.), BDH Inc. (Toronto, Canada), Bionet (Cornwall, U.K.), Chemservice Inc. (West Chester, PA), Crescent Chemical Co. (Hauppauge, NY), Eastman Organic Chemicals, Eastman Kodak Company (Rochester, NY), Fisher Scientific Co. (Pittsburgh, PA), Fisons Chemicals (Leicestershire, UK), Frontier Scientific (Logan, UT), ICN Biomedicals, Inc. (Costa Mesa, CA), Key Organics (Cornwall, U.K.), Lancaster Synthesis (Windham, NH), Maybridge Chemical Co. Ltd. (Cornwall, U.K.), Parish Chemical Co. (Orem, UT), Pfaltz & Bauer, Inc. (Waterbury, CN), Polyorganix (Houston, TX), Pierce Chemical Co. (Rockford, IL), Riedel de Haen AG (Hanover, Germany), Spectrum Quality Product, Inc. (New Brunswick, NJ), TCI America (Portland, OR), Trans World Chemicals, Inc. (Rockville, MD), and Wako Chemicals USA, Inc. (Richmond, VA).

Methods known to one of ordinary skill in the art are identified through various reference books and databases. Suitable reference books and treatise that detail the synthesis of reactants useful in the preparation of compounds described herein, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Additional suitable reference books and treatise that detail the synthesis of reactants useful in the preparation of compounds described herein, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2000) John Wiley & Sons, in over 55 volumes; and "Chemistry of Functional Groups" John Wiley & Sons, in 73 volumes.

In some instances, specific and analogous reactants are identified through the indices of known chemicals prepared by the Chemical Abstract Service of the American Chemical Society, which are available in most public and university libraries, as well as through on-line databases (the American Chemical Society, Washington, D.C., is contacted for more details). Chemicals that are known but not commercially available in catalogs are prepared by custom chemical synthesis houses, where many of the standard chemical supply houses (e.g., those listed above) provide custom synthesis services. A reference for the preparation and selection of pharmaceutical salts of the compounds described herein is P. H. Stahl & C. G. Wermuth "Handbook of Pharmaceutical Salts", Verlag Helvetica Chimica Acta, Zurich, 2002.

In some embodiments, the compounds disclosed herein are prepared as described in the Examples section.

Further Forms of Compounds Disclosed Herein

Isomers

Furthermore, in some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers. The compounds described herein include all possible tautomers within the formulas described herein. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers, and recovering the optically pure enantiomers. In some embodiments, disclosed herein are dissociable complexes (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that does not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. In some embodiments, examples of isotopes that are incorporated into compounds of the disclosure include isotopes of hydrogen, carbon, nitrogen, oxygen, phosphorous, sulfur, fluorine, and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds described herein, and the metabolites, pharmaceutically acceptable salts, esters, prodrugs, solvates, hydrates, or derivatives thereof which contain the aforementioned isotopes and/or other isotopes of other atoms are within the scope of this disclosure. Certain isotopically-labeled compounds, for example those into which radioactive isotopes such as $^3$H and $^{14}$C are incorporated, are useful in drug and/or substrate tissue distribution assays. Tritiated, i. e., $^3$H and carbon-14, i. e., $^{14}$C, isotopes are particularly preferred for their ease of preparation and detectability. Further, substitution with heavy isotopes such as deuterium, i.e., $^2$H, produces certain therapeutic advantages resulting from greater metabolic stability, for example increased in vivo half-life or reduced dosage requirements. In some embodiments, the isotopically labeled compounds, pharmaceutically acceptable salt, ester, prodrug, solvate, hydrate or derivative thereof is prepared by any suitable method.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds of the disclosure, or by separately reacting a purified compound in its free form with a suitable acid or base, and isolating the salt thus formed.

Solvates

In some embodiments, the compounds described herein exist as solvates. The disclosure provides for methods of treating diseases by administering such solvates. The disclosure further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. In some embodiments, solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran, or methanol. In some embodiments, the compounds provided herein exist in unsolvated as well as solvated forms. In general, the solvated forms are considered equivalent to the unsolvated forms for the purposes of the compounds and methods provided herein.

Prodrugs

In some embodiments, the compounds described herein exist in prodrug form. The disclosure provides for methods of treating diseases by administering such prodrugs. The disclosure further provides for methods of treating diseases by administering such prodrugs as pharmaceutical compositions.

In some embodiments, prodrugs include compounds wherein an amino acid residue, or a polypeptide chain of two or more (e. g., two, three, or four) amino acid residues is covalently joined through an amide or ester bond to a free amino, hydroxy, or carboxylic acid group of compounds of the present disclosure. The amino acid residues include, but are not limited to, the 20 naturally occurring amino acids and also includes 4-hydroxyproline, hydroxylysine, demosine, isodemosine, 3-methylhistidine, norvaline, beta-alanine, gamma-aminobutyric acid, cirtulline, homocysteine, homoserine, ornithine, and methionine sulfone. In other embodiments, prodrugs include compounds wherein a nucleic acid residue, or an oligonucleotide of two or more (e. g., two, three or four) nucleic acid residues is covalently joined to a compound of the present disclosure.

Pharmaceutically acceptable prodrugs of the compounds described herein also include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, metal salts, and sulfonate esters. In some embodiments, compounds having free amino, amido, hydroxy, or carboxylic groups are converted into prodrugs. For instance, free carboxyl groups are derivatized as amides or alkyl esters. In certain instances, all of these prodrug moieties incorporate groups including, but not limited to, ether, amine, and carboxylic acid functionalities.

Hydroxy prodrugs include esters such as, though not limited to, acyloxyalkyl (e.g. acyloxymethyl, acyloxyethyl) esters, alkoxycarbonyloxyalkyl esters, alkyl esters, aryl esters, sulfonate esters, sulfate esters and disulfide containing esters, ethers, amides, carbamates, hemisuccinates, dimethylaminoacetates, and phosphoryloxymethyloxycarbonyls, as outlined in *Advanced Drug Delivery Reviews* 1996, 19, 115.

Amine derived prodrugs include, but are not limited to, the following groups and combinations of groups:

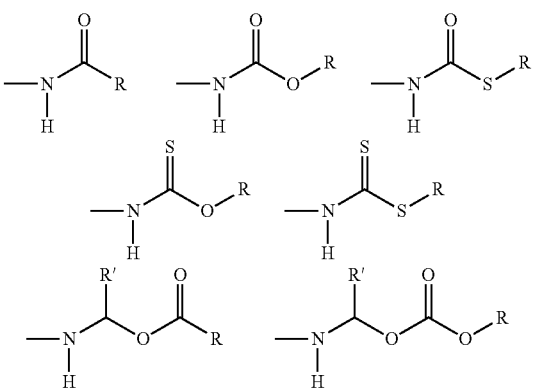

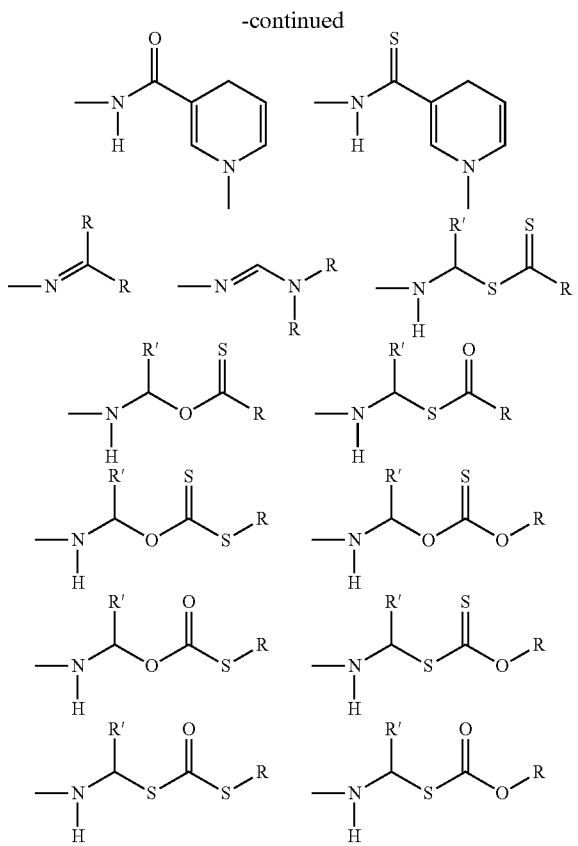

as well as sulfonamides and phosphonamides.

In certain instances, sites on any aromatic ring portions are susceptible to various metabolic reactions, therefore incorporation of appropriate substituents on the aromatic ring structures reduce, minimize, or eliminate this metabolic pathway.

Metabolites

In some embodiments, compounds described herein are susceptible to various metabolic reactions. Therefore, in some embodiments, incorporation of appropriate substituents into the structure will reduce, minimize, or eliminate a metabolic pathway. In specific embodiments, the appropriate substituent to decrease or eliminate the susceptibility of an aromatic ring to metabolic reactions is, by way of example only, a halogen or an alkyl group.

In additional or further embodiments, the compounds described herein are metabolized upon administration to an organism in need to produce a metabolite that is then used to produce a desired effect, including a desired therapeutic effect.

Pharmaceutical Compositions

In certain embodiments, the compound as described herein is administered as a pure chemical. In other embodiments, the compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in *Remington; The Science and Practice of Pharmacy* (Gennaro, 21$^{st}$ Ed. Mack Pub. Co., Easton, PA (2005)), the disclosure of which is hereby incorporated herein by reference in its entirety.

Accordingly, provided herein is a pharmaceutical composition comprising at least one compound described herein, or a stereoisomer, pharmaceutically acceptable salt, hydrate, solvate, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a pharmaceutically acceptable carrier and a compound of Formula (I), Formula (Ia), Formula (II), Formula (III), Formula (IV), Formula (IVa), Formula (IVb), Formula (V), Formula (Va), or Formula (Vb), or a pharmaceutically acceptable salt or a pharmaceutically acceptable solvate thereof.

Another embodiment provides a pharmaceutical composition consisting essentially of a pharmaceutically acceptable carrier and a compound of Formula (I), Formula (Ia), Formula (II), Formula (III), Formula (IV), Formula (IVa), Formula (IVb), Formula (V), Formula (Va), or Formula (Vb), or a pharmaceutically acceptable salt or a pharmaceutically acceptable solvate thereof.

In certain embodiments, the compound as described herein is substantially pure, in that it contains less than about 5%, or less than about 1%, or less than about 0.1%, of other organic small molecules, such as contaminating intermediates or by-products that are created, for example, in one or more of the steps of a synthesis method.

These formulations include those suitable for oral, rectal, topical, buccal, parenteral (e.g., subcutaneous, intramuscular, intradermal, or intravenous), rectal, vaginal, or aerosol administration, although the most suitable form of administration in any given case will depend on the degree and severity of the condition being treated and on the nature of the particular compound being used. For example, disclosed compositions are formulated as a unit dose, and/or are formulated for oral or subcutaneous administration.

In some instances, exemplary pharmaceutical compositions are used in the form of a pharmaceutical preparation, for example, in solid, semisolid, or liquid form, which includes one or more of a disclosed compound, as an active ingredient, in admixture with an organic or inorganic carrier or excipient suitable for external, enteral, or parenteral applications. In some embodiments, the active ingredient is compounded, for example, with the usual non-toxic, pharmaceutically acceptable carriers for tablets, pellets, capsules, suppositories, solutions, emulsions, suspensions, and any other form suitable for use. The active object compound is included in the pharmaceutical composition in an amount sufficient to produce the desired effect upon the process or condition of the disease.

For preparing solid compositions such as tablets in some instances, the principal active ingredient is mixed with a pharmaceutical carrier, e.g., conventional tableting ingredients such as corn starch, lactose, sucrose, sorbitol, talc, stearic acid, magnesium stearate, dicalcium phosphate, or gums, and other pharmaceutical diluents, e.g., water, to form a solid preformulation composition containing a homogeneous mixture of a disclosed compound or a non-toxic pharmaceutically acceptable salt or a non-toxic pharmaceutically acceptable solvate thereof. When referring to these preformulation compositions as homogeneous, it is meant that the active ingredient is dispersed evenly throughout the composition so that the composition is readily subdivided into equally effective unit dosage forms such as tablets, pills, and capsules.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions also comprise buffering agents in some embodiments. Solid compositions of a similar type are also employed as fillers in soft and hard-filled gelatin capsules using such excipients as lactose or milk sugars, as well as high molecular weight polyethylene glycols and the like.

In some instances, a tablet is made by compression or molding, optionally with one or more accessory ingredients. Compressed tablets are prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets are made by molding in a suitable machine a mixture of the subject composition moistened with an inert liquid diluent. Tablets, and other solid dosage forms, such as dragees, capsules, pills and granules, are optionally be scored or prepared with coatings and shells, such as enteric coatings and other coatings well known in the pharmaceutical-formulating art.

Compositions for inhalation or insufflation include solutions and suspensions in pharmaceutically acceptable, aqueous or organic solvents, or mixtures thereof, and powders. Liquid dosage forms for oral administration include pharmaceutically acceptable emulsions, microemulsions, solutions, suspensions, syrups and elixirs. In addition to the subject composition, the liquid dosage forms contain optionally inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, optionally contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

In some embodiments, formulations for rectal or vaginal administration are presented as a suppository, which are prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent.

Dosage forms for transdermal administration of a subject composition include powders, sprays, ointments, pastes, creams, lotions, gels, solutions, patches and inhalants. The active component is optionally mixed under sterile conditions with a pharmaceutically acceptable carrier, and with any preservatives, buffers, or propellants which are required in some embodiments.

In some embodiments, the ointments, pastes, creams and gels contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

In some embodiments, powders and sprays contain, in addition to a subject composition, excipients such as lactose, talc, silicic acid, aluminum hydroxide, calcium silicates and polyamide powder, or mixtures of these substances. Sprays additionally contain customary propellants, such as chlorofluorohydrocarbons and volatile unsubstituted hydrocarbons, such as butane and propane.

Compositions and compounds disclosed herein are alternatively administered by aerosol. This is accomplished by preparing an aqueous aerosol, liposomal preparation or solid particles containing the compound. A non-aqueous (e.g., fluorocarbon propellant) suspension could be used. Sonic nebulizers are used because they minimize exposing the agent to shear, which result in degradation of the compounds contained in the subject compositions in some embodiments. Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions suitable for parenteral administration comprise a subject composition in combination with one or more pharmaceutically-acceptable sterile isotonic aqueous or non-aqueous solutions, dispersions, suspensions or emulsions, or sterile powders which are reconstituted into sterile injectable solutions or dispersions just prior to use, which optionally contain antioxidants, buffers, bacteriostats, solutes which render the formulation isotonic with the blood of the intended recipient or suspending or thickening agents.

Examples of suitable aqueous and non-aqueous carriers employed in the pharmaceutical compositions include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. In some embodiments, proper fluidity is maintained, for example, by the use of coating materials, such as lecithin, by the maintenance of the required particle size in the case of dispersions, and by the use of surfactants Also contemplated are enteral pharmaceutical formulations including a disclosed compound and an enteric material; and a pharmaceutically acceptable carrier or excipient thereof. Enteric materials refer to polymers that are substantially insoluble in the acidic environment of the stomach, and that are predominantly soluble in intestinal fluids at specific pHs. The small intestine is the part of the gastrointestinal tract (gut) between the stomach and the large intestine, and includes the duodenum, jejunum, and ileum. The pH of the duodenum is about 5.5, the pH of the jejunum is about 6.5 and the pH of the distal ileum is about 7.5. Accordingly, enteric materials are not soluble, for example, until a pH of about 5.0, of about 5.2, of about 5.4, of about 5.6, of about 5.8, of about 6.0, of about 6.2, of about 6.4, of about 6.6, of about 6.8, of about 7.0, of about 7.2, of about 7.4, of about 7.6, of about 7.8, of about 8.0, of about 8.2, of about 8.4, of about 8.6, of about 8.8, of about 9.0, of about 9.2, of about 9.4, of about 9.6, of about 9.8, or of about 10.0. Exemplary enteric materials include cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, cellulose acetate maleate, cellulose acetate butyrate, cellulose acetate propionate, copolymer of methylmethacrylic acid and methyl methacrylate, copolymer of methyl acrylate, methylmethacrylate and methacrylic acid, copolymer of methylvinyl ether and maleic anhydride (Gantrez ES series), ethyl methylacrylate-methylmethacrylate-chlorotrimethylammonium ethyl acrylate copolymer, natural resins such as zein, shellac and copal collophorium, and several commercially available enteric dispersion systems (e.g., Eudragit L30D55, Eudragit FS30D, Eudragit L100, Eudragit S100, Kollicoat EMM30D, Estacryl 30D, Coateric, and Aquateric). The solubility of each of the above materials is either known or is readily determinable in vitro. The foregoing is a list of possible materials, but one of skill in the art with the benefit of the disclosure will recognize that it is not comprehensive and that there are other enteric materials that meet the objectives of the present disclosure.

In some embodiments, the doses of the composition comprising at least one compound as described herein differ, depending upon the patient's (e.g., human) condition, that is, stage of the disease, general health status, age, and other factors that a person skilled in the medical art will use to determine dose.

In some instances, pharmaceutical compositions are administered in a manner appropriate to the disease to be treated (or prevented) as determined by persons skilled in the medical arts. An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic and/or prophylactic benefit (e.g., an improved clinical outcome, such as more frequent complete or partial remissions, or longer disease-free and/or overall survival, or a lessening of symptom severity. Optimal doses are generally determined using experimental models and/or clinical trials. In some embodiments, the optimal dose depends upon the body mass, weight, or blood volume of the patient.

In some embodiments, oral doses typically range from about 1.0 mg to about 1000 mg, one to four times, or more, per day.

The Hippo Signaling Network

The Hippo signaling network (also known as the Salvador/Warts/Hippo (SWH) pathway) is a master regulator of cell proliferation, death, and differentiation. In some embodiments, the main function of the Hippo signaling pathway is to regulate negatively the transcriptional co-activators Yes-associated protein (YAP) and its paralogue, the transcriptional coactivator with PDZ-binding motif (TAZ; also known as WWTR1) (FIG. 1). The Hippo kinase cascade phosphorylates and inhibits YAP/TAZ by promoting its cytoplasmic retention and degradation, thereby inhibiting the growth promoting function regulated under the YAP/TAZ control. In an un-phosphorylated/de-phosphorylated state, YAP, also known as YAP1 or YAP65, together with TAZ, are transported into the nucleus where they interact with TEAD family of transcription factors to upregulate genes that promote proliferation and migration, and inhibit apoptosis. In some instances, unregulated upregulation of these genes involved in proliferation, migration, and anti-apoptosis leads to development of cancer. In some instances, overexpression of YAP/TAZ is associated with cancer.

Additional core members of the Hippo signaling pathway comprise the serine/threonine kinases MST1/2 (homologues of Hippo/Hpo in Drosophila), Lats1/2 (homologues of Warts/Wts), and their adaptor proteins Sav1 (homologue of Salvador/Sav) and Mob (MOBKL1A and MOBKL1B; homologues of Mats), respectively (FIG. 1). In general, MST1/2 kinase complexes with the scaffold protein Sav1, which in turn phosphorylates and activates Lats1/2 kinase. Lats1/2 is also activated by the scaffold protein Mob. The activated Lats1/2 then phosphorylates and inactivates YAP or its paralog TAZ. The phosphorylation of YAP/TAZ leads to their nuclear export, retention within the cytoplasm, and degradation by the ubiquitin proteasome system.

In some instances, Lats1/2 phosphorylates YAP at the [HXRXXS] consensus motifs. YAP comprises five [HXRXXS] consensus motifs, wherein X denotes any amino acid residue. In some instances, Lats1/2 phosphorylates YAP at one or more of the consensus motifs. In some instances, Lats1/2 phosphorylates YAP at all five of the consensus motifs. In some instances, Lats1/2 phosphorylate at the S127 amino acid position. The phosphorylation of YAP S127 promotes 14-3-3 protein binding and results in cytoplasmic sequestration of YAP. Mutation of YAP at the S127 position thereby disrupts its interaction with 14-3-3 and subsequently promotes nuclear translocation.

Additional phosphorylation occurs at the S381 amino acid position in YAP. Phosphorylation of YAP at the S381 position and on the corresponding site in TAZ primes both proteins for further phosphorylation events by CK1δ/ε in the degradation motif, which then signals for interaction with the β-TRCP E3 ubiquitin ligase, leading to polyubiquitination and degradation of YAP.

In some instances, Lats1/2 phosphorylates TAZ at the [HXRXXS] consensus motifs. TAZ comprises four [HXRXXS] consensus motifs, wherein X denotes any amino acid residues. In some instances, Lats1/2 phosphorylates TAZ at one or more of the consensus motifs. In some instances, Lats1/2 phosphorylates TAZ at all four of the consensus motifs. In some instances, Lats1/2 phosphorylate at the S89 amino acid position. The phosphorylation of TAZ S89 promotes 14-3-3 protein binding and results in cytoplasmic sequestration of TAZ. Mutation of TAZ at the S89 position thereby disrupts its interaction with 14-3-3 and subsequently promotes nuclear translocation.

In some embodiments, phosphorylated YAP/TAZ accumulates in the cytoplasm, and undergoes $SCF^{\beta-TRCP}$-mediated ubiquitination and subsequent proteasomal degradation. In some instances, the Skp, Cullin, F-box containing complex (SCF complex) is a multi-protein E3 ubiquitin ligase complex that comprises a F-box family member protein (e.g. Cdc4), Skp1, a bridging protein, and RBX1, which contains a small RING Finger domain which interacts with E2-ubiquitin conjugating enzyme. In some cases, the F-box family comprises more than 40 members, in which exemplary members include F-box/WD repeat-containing protein 1A (FBXW1A, βTrCP1, Fbxw1, hsSlimb, plkappaBalpha-E3 receptor subunit) and S-phase kinase-associated proteins 2 (SKP2). In some embodiments, the SCF complex (e.g. SCF$^{\beta TrCP1}$) interacts with an E1 ubiquitin-activating enzyme and an E2 ubiquitin-conjugating enzyme to catalyze the transfer of ubiquitin to the YAP/TAZ substrate. Exemplary E1 ubiquitin-activating enzymes include those encoded by the following genes: UBA1, UBA2, UBA3, UBA5, UBA5, UBA7, ATG7, NAE1, and SAE1. Exemplary E2 ubiquitin-conjugating enzymes include those encoded by the following genes: UBE2A, UBE2B, UBE2C, UBE2D1, UBE2D2, UBE2D3, UBE2E1, UBE2E2, UBE2E3, UBE2F, UBE2G1, UBE2G2, UBE2H, UBE2I, UBE2J1, UBE2J2, UBE2K, UBE2L3, UBE2L6, UBE2M, UBE2N, UBE2O, UBE2Q1, UBE2Q2, UBE2R1, UBE2R2, UBE2S, UBE2T, UBE2U, UBE2V1, UBE2V2, UBE2Z, ATG2, BIRC5, and UFC1. In some embodiments, the ubiquitinated YAP/TAZ further undergoes the degradation process through the 26S proteasome.

In some embodiments, the Hippo pathway is regulated upstream by several different families of regulators (FIG. 1). In some instances, the Hippo pathway is regulated by the G-protein and its coupled receptors, the Crumbs complex, regulators upstream of the MST kinases, and the adherens junction.

YAP/TAZ Interaction with TEAD

In some embodiments, un-phosphorylated and/or dephosphorylated YAP/TAZ accumulates in the nucleus. Within the nucleus, YAP/TAZ interacts with the TEAD family of transcription factors (e.g. TEAD1, TEAD2, TEAD3, or TEAD4) to activate genes involved in anti-apoptosis and proliferation, such as for example CTFG, Cyr61, and FGF1.

In some embodiments, the compounds disclosed herein modulate the interaction between YAP/TAZ and TEAD. In some embodiments, the compounds disclosed herein bind to TEAD, YAP, or TAZ and prevent the interaction between YAP/TAZ and TEAD.

YAP/TAZ Regulation Mediated by G-Proteins/GPCRs

Figure 2:
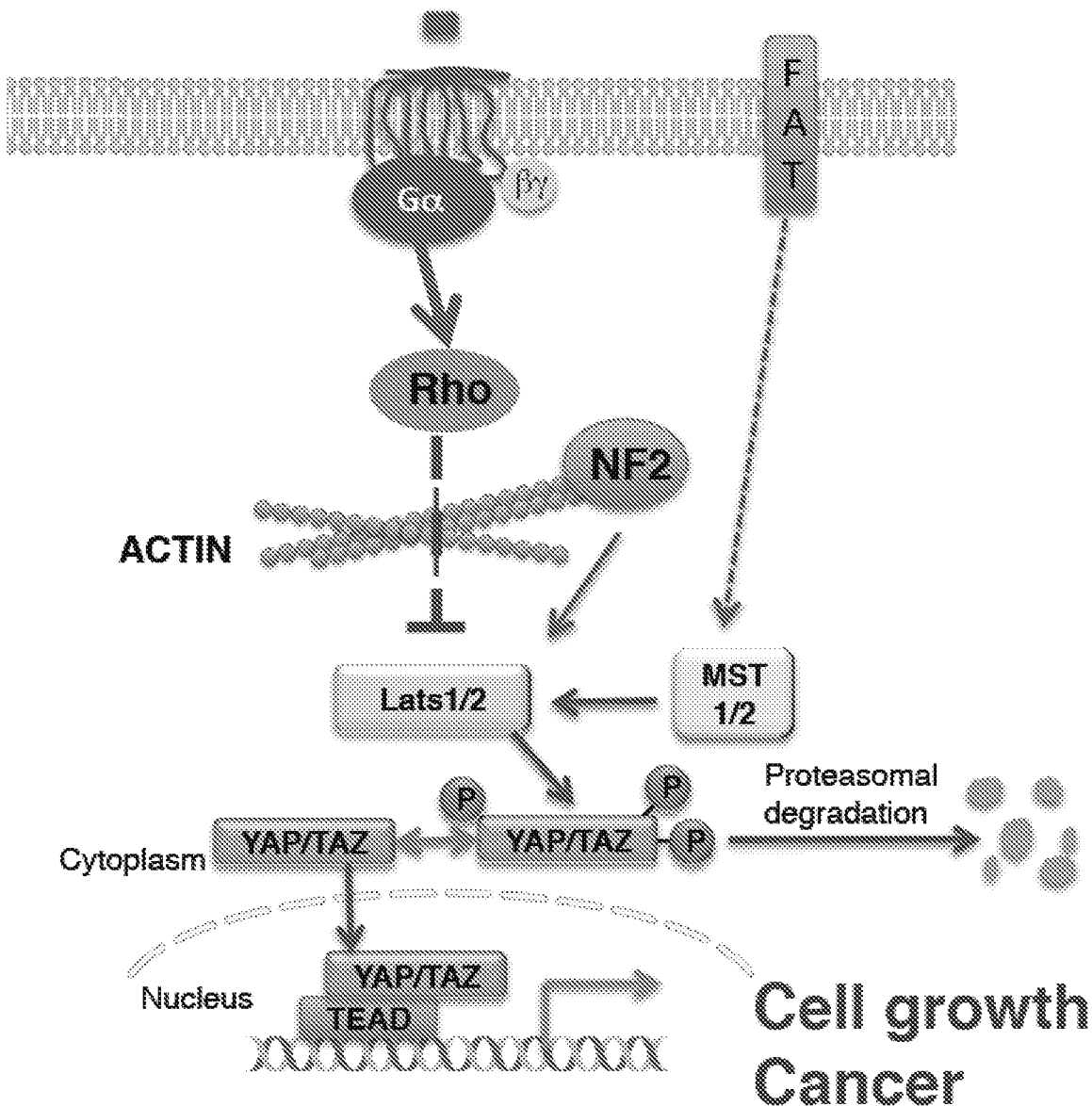
FIG. 2 illustrates a schematic representation of the Hippo signaling pathway regulated by G alpha proteins.

In some embodiments, the Hippo pathway is regulated by the G protein-coupled receptor (GPCR) and G protein (also known as guanine nucleotide-binding proteins) family of proteins (FIG. 2). G proteins are molecular switches that transmit extracellular stimuli into the cell through GPCRs. In some instances, there are two classes of G proteins: monomeric small GTPases and heterotrimeric G protein complexes. In some instances, the latter class of complexes comprise of alpha ($G_\alpha$), beta ($G_\beta$), and gamma ($G_\gamma$) subunits. In some cases, there are several classes of $G_\alpha$ subunits: $G_{q/11}\alpha$, $G_{12/13}\alpha$, $G_{i/o}\alpha$ (G inhibitory, G other), and $G_s\alpha$ (G stimulatory).

In some instances, $G_i\alpha$ (G inhibitory), $G_o\alpha$ (G other), $G_{q/11}\alpha$, and $G_{12/13}\alpha$ coupled GPCRs activate YAP/TAZ and promote nuclear translocation. In other instances, $G_s\alpha$ (G stimulatory) coupled GPCRs suppress YAP/TAZ activity, leading to YAP/TAZ degradation.

In some cases, $G_i\alpha$ (G inhibitory), $G_o\alpha$ (G other), $G_{q/11}\alpha$, and $G_{12/13}\alpha$ coupled GPCRs activate YAP/TAZ through repression of Lats1/2 activities. In contrast, $G_s\alpha$, in some embodiments, induces Lats1/2 activity, thereby promoting YAP/TAZ degradation.

$G_q$ Family $G_q\alpha$ (also known as $G_{q/11}$ protein), participates in the inositol trisphosphate ($IP_3$) signal transduction pathway and calcium ($Ca^{2+}$) release from intracellular storage through the activation of phospholipase C (PLC). The activated PLC hydrolyzes phosphatidylinositol 4,5-bisphosphate ($PIP_2$) to diacyl glycerol (DAG) and $IP_3$. In some instances, $IP_3$ then diffuses through the cytoplasm into the ER or the sarcoplasmic reticulum (SR) in the case of muscle cells, and then binds to inositol trisphosphate receptor (InsP3R), which is a $Ca^{2+}$ channel. In some cases, the binding triggers the opening of the $Ca^{2+}$ channel, and thereby increases the release of $Ca^{2+}$ into the cytoplasm.

In some embodiments, the GPCRs that interact with $G_q\alpha$ include, but are not limited to, 5-hydroxytryptamine receptor (5-HT receptor) types $5-HT_2$ and $5-HT_3$; alpha-1 adrenergic receptor; vasopressin type 1 receptors 1A and 1B; angiotensin II receptor type 1; calcitonin receptor; histamine H1 receptor; metabotropic glutamate receptor, group I; muscarinic receptors $M_1$, $M_3$, and $M_5$; and trace amine-associated receptor 1.

In some instances, there are several types of $G_q\alpha$: $G_q$, $G_{q/11}$, $G_{q/14}$, and $G_{q/15}$. The $G_q$ protein is encoded by GNAQ. $G_{q/11}$ is encoded by GNA11. $G_{q/14}$ is encoded by GNA14. $G_{q/15}$ is encoded by GNA15.

In some instances, mutations or modifications of the $G_q\alpha$ genes have been associated with cancer. Indeed, studies have shown that mutations in $G_q\alpha$ promote uveal melanoma (UM) tumorigenesis. In some instances, about 80% of UM cases have been detected to contain a mutation in GNAQ and/or GNA11.

In some instances, mutations or modifications of the $G_q\alpha$ genes have been associated with congenital diseases. In some instances, mutations of $G_q\alpha$ have been observed in congenital diseases such as Port-Wine Stain and/or Sturge-Weber Syndrome. In some instances, about 92% of Port-Wine stain cases harbors a mutation in GNAQ. In some instances, about 88% of Sturge-Weber Syndrome harbors a mutation in GNAQ.

$G_{12/13}$ Family $G_{12/13}\alpha$ modulates actin cytoskeletal remodeling in cells and regulates cell processes through guanine nucleotide exchange factors (GEFs). GEFs participate in the activation of small GTPases which acts as molecular switches in a variety of intracellular signaling pathways. Examples of small GTPases include the Ras-related GTPase superfamily (e.g. Rho family such as Cdc42), which is involved in cell differentiation, proliferation, cytoskeletal organization, vesicle trafficking, and nuclear transport.

In some embodiments, the GPCRs that interact with $G_{12/13}\alpha$ include, but are not limited to, purinergic receptors (e.g. $P2Y_1$, $P2Y_2$, $P2Y_4$, $P2Y_6$); muscarinic acetylcholine receptors M1 and M3; receptors for thrombin [protease-activated receptor (PAR)-1, PAR-2]; thromboxane (TXA2); sphingosine 1-phosphate (e.g. $S1P_2$, $S1P_3$, $S1P_4$ and $S1P_5$); lysophosphatidic acid (e.g. $LPA_1$, $LPA_2$, $LPA_3$); angiotensin II (AT1); serotonin ($5-HT_{2c}$ and $5-HT_4$); somatostatin ($sst_5$); endothelin ($ET_A$ and $ET_B$); cholecystokinin ($CCK_1$); $V_{1a}$ vasopressin receptors; $D_5$ dopamine receptors; fMLP formyl peptide receptors; $GAL_2$ galanin receptors; $EP_3$ prostanoid receptors; $A_1$ adenosine receptors; $\alpha_1$ adrenergic receptors; $BB_2$ bombesin receptors; $B_2$ bradykinin receptors; calcium-sensing receptors; KSHV-ORF74 chemokine receptors; $NK_1$ tachykinin receptors; and thyroid-stimulating hormone (TSH) receptors.

In some instances, $G_{12/13}\alpha$ is further subdivided into $G_{12}$ and $G_{13}$ types which are encoded by GNA12 and GNA13, respectively.

$G_{i/o}$ Family $G_{i/o}\alpha$ (G inhibitory, G other) (also known as $G_i/G_0$ or $G_i$ protein) suppresses the production of 3',5'-cyclic AMP (cAMP) from adenosine triphosphate (ATP) through an inhibition of adenylate cyclase activity, which converts ATP to cAMP.

In some embodiments, the GPCRs that interact with $G_i\alpha$ include, but are not limited to, 5-hydroxytryptamine receptor (5-HT receptor) types $5\text{-}HT_1$ and $5\text{-}HT_5$; muscarinic acetylcholine receptors such as $M_2$ and $M_4$; adenosine receptors such as $A_1$ and $A_3$; adrenergic receptors such as $\alpha_{2A}$, $\alpha_{2B}$, and $\alpha_{2C}$; apelin receptors; calcium-sensing receptor; cannabinoid receptors CB1 and CB2; chemokine CXCR4 receptor; dopamines $D_2$, $D_3$, and $D_4$; $GABA_B$ receptor; glutamate receptors such as metabotropic glutamate receptor 2 (mGluR2), metabotropic glutamate receptor 3 (mGluR3), metabotropic glutamate receptor 4 (mGluR4), metabotropic glutamate receptor 6 (mGluR6), metabotropic glutamate receptor 7 (mGluR7), and metabotropic glutamate receptor 8 (mGluR8); histamine receptors such as $H_3$ and $H_4$ receptors; melatonin receptors such as melatonin receptor type 1 (MT1), melatonin receptor type 2 (MT2), and melatonin receptor type 3 (MT3); niacin receptors such as NIACR1 and NIACR2; opioid receptors such as δ, κ, μ, and nociceptin receptors; prostaglandin receptors such as prostaglandin E receptor 1 ($EP_1$), prostaglandin E receptor 3 ($EP_3$), prostaglandin F receptor (FP), and thromboxane receptor (TP); somatostatin receptors sst1, sst2, sst3, sst4, and sst5; and trace amine-associated receptor 8.

In some instances, there are several types of $G_i\alpha$: $G_i\alpha1$, $G_i\alpha2$, $G_i\alpha3$, $G_i\alpha4$, $G_o\alpha$, $G_t$, $G_{gust}$, and $G_z$. $G_i\alpha1$ is encoded by GNAI1. $G_i\alpha2$ is encoded by GNAI2. $G_i\alpha3$ is encoded by GNAI3. $G_o\alpha$, the $a_o$ subunit, is encoded by GNAO1. $G_t$ is encoded by GNAT1 and GNAT2. $G_{gust}$ is encoded by GNATS. $G_z$ is encoded by GNAZ.

$G_s$ Family $G_s\alpha$ (also known as G stimulatory, $G_s$ alpha subunit, or $G_s$ protein) activates the cAMP-dependent pathway through the activation of adenylate cyclase, which convers adenosine triphosphate (ATP) to 3',5'-cyclic AMP (cAMP) and pyrophosphate. In some embodiments, the GPCRs that interact with $G_s\alpha$ include, but are not limited to, 5-hydroxytryptamine receptor (5-HT receptor) types $5\text{-}HT_4$, $5\text{-}HT_6$, and $5\text{-}HT_7$; adrenocorticotropic hormone receptor (ACTH receptor) (also known as melanocortin receptor 2 or MC2R); adenosine receptor types $A_{2a}$ and $A_{2b}$; arginine vasopressin receptor 2 (AVPR2); β-adrenergic receptors $\beta_1$, $\beta_2$, and $\beta_3$; calcitonin receptor; calcitonin gene-related peptide receptor; corticotropin-releasing hormone receptor; dopamine receptor $D_1$-like family receptors such as $D_1$ and $D_5$; follicle-stimulating hormone receptor (FSH-receptor); gastric inhibitory polypeptide receptor; glucagon receptor; histamine $H_2$ receptor; luteinizing hormone/choriogonadotropin receptor; melanocortin receptors such as MC1R, MC2R, MC3R, MC4R, and MC5R; parathyroid hormone receptor 1; prostaglandin receptor types $D_2$ and $I_2$; secretin receptor; thyrotropin receptor; trace amine-associated receptor 1; and box jellyfish opsin.

In some instances, there are two types of $G_s\alpha$: $G_s$ and $G_{olf}$. $G_s$ is encoded by GNAS. $G_{olf}$ is encoded by GNAL.

Additional Regulators of the Hippo Signaling Network

In some embodiments, the additional regulator of the Hippo signaling pathway is the Crumbs (Crb) complex. The Crumbs complex is a key regulator of cell polarity and cell shape. In some instances, the Crumbs complex comprises transmembrane CRB proteins which assemble multi-protein complexes that function in cell polarity. In some instances, CRB complexes recruit members of the Angiomotin (AMOT) family of adaptor proteins that interact with the Hippo pathway components. In some instances, studies have shown that AMOT directly binds to YAP, promotes YAP phosphorylation, and inhibits its nuclear localization.

In some instances, the additional regulator of the Hippo signaling pathway comprises regulators of the MST kinase family. MST kinases monitor actin cytoskeletal integrity. In some instances, the regulators include TAO kinases and cell polarity kinase PAR-1.

In some instances, the additional regulator of the Hippo signaling pathway comprises molecules of the adherens junction. In some instances, E-Cadherin (E-cad) suppresses YAP nuclear localization and activity through regulating MST activity. In some embodiments, E-cad-associated protein α-catenin regulates YAP through sequestering YAP/14-3-3 complexes in the cytoplasm. In other instances, Ajuba protein family members interact with Lats1/2 kinase activity, thereby preventing inactivation of YAP/TAZ.

In some embodiments, additional proteins that interact with YAP/TAZ either directly or indirectly include, but are not limited to, Merlin, protocadherin Fat 1, MASK1/2, HIPK2, PTPN14, RASSF, PP2A, Salt-inducible kinases (SIKs), Scribble (SCRIB), the Scribble associated proteins Discs large (Dlg), KIBRA, PTPN14, NPHP3, LKB1, Ajuba, and ZO1/2.

In some embodiments, the compounds described herein are inhibitors of transcriptional coactivator with PDZ binding motif/Yes-associated protein transcriptional coactivator (TAZ/YAP). In some embodiments, the compounds described herein increase the phosphorylation of transcriptional coactivator with PDZ binding motif/Yes-associated protein transcriptional coactivator (TAZ/YAP) or decrease the dephosphorylation of transcriptional coactivator with PDZ binding motif/Yes-associated protein transcriptional coactivator (TAZ/YAP). In some embodiments, the compounds increase the ubiquitination of transcriptional coactivator with PDZ binding motif/Yes-associated protein transcriptional coactivator (TAZ/YAP) or decrease the deubiquitination of transcriptional coactivator with PDZ binding motif/Yes-associated protein transcriptional coactivator (TAZ/YAP).

In some embodiments, the compounds disclosed herein are inhibitors of one or more of the proteins encompassed by, or related to, the Hippo pathway. In some instances, the one or more proteins comprise a protein shown in FIGS. 1 and/or 2. In some embodiments, an inhibitor of the Hippo pathway is an inhibitor of a G-protein and/or its coupled GPCR. In some embodiments, an inhibitor of the Hippo pathway is an inhibitor of a G-protein. In some embodiments, an inhibitor of the Hippo pathway is an inhibitor of the $G_q\alpha$ family proteins such as $G_q$, $G_{q/11}$, $G_{q/14}$, and $G_{q/15}$; the $G_{12/13}\alpha$ family of proteins such as $G_{12}$ and $G_{13}$; or the $G_i\alpha$ family of proteins such as $G_i\alpha1$, $G_i\alpha2$, $G_i\alpha3$, $G_i\alpha4$, $G_o\alpha$, $G_t$, $G_{gust}$, and $G_z$. In some embodiments, an inhibitor of the Hippo pathway is an inhibitor of $G_q$. In some embodiments, an inhibitor of the Hippo pathway is an inhibitor of $G_{q/11}$. In some embodiments, an inhibitor of the Hippo pathway is an inhibitor of $G_{q/14}$. In some embodiments, an inhibitor of the Hippo pathway is an inhibitor of $G_{q/15}$. In some embodiments, an inhibitor of the Hippo pathway is an inhibitor of $G_{12}$. In some embodiments, an inhibitor of the Hippo pathway is an inhibitor of $G_{13}$. In some embodiments, an inhibitor of the Hippo pathway is an inhibitor of $G_i\alpha1$. In some embodiments, an inhibitor of the Hippo pathway is an inhibitor of $G_i\alpha2$. In some embodiments, an inhibitor of the Hippo pathway is an inhibitor of $G_i\alpha3$. In some embodiments, an inhibitor of the Hippo pathway is an inhibitor of $G_i\alpha4$. In some embodiments, an inhibitor of the Hippo pathway is an inhibitor of $G_o\alpha$. In some embodiments, an inhibitor of the Hippo pathway is an inhibitor of $G_t$. In some embodiments, an inhibitor of the Hippo pathway is an inhibitor of $G_{gust}$. In some embodiments, an inhibitor of the Hippo pathway is an inhibitor of $G_z$.

In some embodiments, an inhibitor of the Hippo pathway is an inhibitor of a core protein of the Hippo pathway. In some embodiments, an inhibitor of the Hippo pathway is an inhibitor of Sav1. In some embodiments, an inhibitor of the Hippo pathway is an inhibitor of Mob. In some embodiments, an inhibitor of the Hippo pathway is an inhibitor of YAP. In some embodiments, an inhibitor of the Hippo pathway is an inhibitor of TAZ. In some embodiments, an inhibitor of the Hippo pathway is an inhibitor of TEAD.

In some embodiments, an inhibitor of the Hippo pathway is an inhibitor of a protein associated with the ubiquitination and proteasomal degradation pathway. In some embodiments, an inhibitor of the Hippo pathway is an inhibitor of a proteasomal degradation pathway protein (e.g. 26 S proteasome).

In some embodiments, an inhibitor of the Hippo pathway is an inhibitor of a protein of the Ras superfamily of proteins. In some embodiments, an inhibitor of the Hippo pathway is an inhibitor of a protein of the Rho family of proteins. In some embodiments, an inhibitor of the Hippo pathway is an inhibitor of Cdc42.

Cdc42 is a member of the Ras superfamily of small GTPases. Specifically, Cdc42 belongs to the Rho family of GTPases, in which the family members participate in diverse and critical cellular processes such as gene transcription, cell-cell adhesion, and cell cycle progression. Cdc42 is involved in cell growth and polarity, and in some instances, Cdc42 is activated by guanine nucleotide exchange factors (GEFs). In some cases, an inhibitor of Cdc42 is a compound disclosed herein.

In some embodiments, an inhibitor of the Hippo pathway is an inhibitor of a deubiquitinating enzyme. In some embodiments, an inhibitor of the Hippo pathway is an inhibitor of a cysteine protease or a metalloprotease. In some embodiments, an inhibitor of the Hippo pathway is an inhibitor of an ubiquitin-specific protease. USP47 is a member of the ubiquitin-specific protease (USP/UBP) superfamily of cysteine proteases. In some embodiments, the compounds disclosed herein are inhibitors of USP47.

Further embodiments provided herein include combinations of one or more of the particular embodiments set forth above.

Diseases

Cancer

In some embodiments, the compounds disclosed herein are useful for treating cancer. In some embodiments, the cancer is mediated by activation of transcriptional coactivator with PDZ binding motif/Yes-associated protein transcription coactivator (TAZ/YAP). In some embodiments, the cancer is mediated by modulation of the interaction of YAP/TAZ with TEAD. In some embodiments, the cancer is characterized by a mutant Gα-protein. In some embodiments, the mutant Gα-protein is selected from G12, G13, Gq, G11, Gi, Go, and Gs. In some embodiments, the mutant Gα-protein is G12. In some embodiments, the mutant Gα-protein is G13. In some embodiments, the mutant Gα-protein is Gq. In some embodiments, the mutant Gα-protein is G11. In some embodiments, the mutant Gα-protein is Gi. In some embodiments, the mutant Gα-protein is Go. In some embodiments, the mutant Gα-protein is Gs.

In some embodiments, the cancer is a solid tumor. In some instances, the cancer is a hematologic malignancy. In some instances, the solid tumor is a sarcoma or carcinoma. In some instances, the solid tumor is a sarcoma. In some instances, the solid tumor is a carcinoma.

Exemplary sarcoma includes, but is not limited to, alveolar rhabdomyosarcoma, alveolar soft part sarcoma, ameloblastoma, angiosarcoma, chondrosarcoma, chordoma, clear cell sarcoma of soft tissue, dedifferentiated liposarcoma, desmoid, desmoplastic small round cell tumor, embryonal rhabdomyosarcoma, epithelioid fibrosarcoma, epithelioid hemangioendothelioma, epithelioid sarcoma, esthesioneuroblastoma, Ewing sarcoma, extrarenal rhabdoid tumor, extraskeletal myxoid chondrosarcoma, extraskeletal osteosarcoma, fibrosarcoma, giant cell tumor, hemangiopericytoma, infantile fibrosarcoma, inflammatory myofibroblastic tumor, Kaposi sarcoma, leiomyosarcoma of bone, liposarcoma, liposarcoma of bone, malignant fibrous histiocytoma (MFH), malignant fibrous histiocytoma (MFH) of bone, malignant mesenchymoma, malignant peripheral nerve sheath tumor, mesenchymal chondrosarcoma, myxofibrosarcoma, myxoid liposarcoma, myxoinflammatory fibroblastic sarcoma, neoplasms with perivascular epithelioid cell differentiation, osteosarcoma, parosteal osteosarcoma, neoplasm with perivascular epithelioid cell differentiation, periosteal osteosarcoma, pleomorphic liposarcoma, pleomorphic rhabdomyosarcoma, PNET/extraskeletal Ewing tumor, rhabdomyosarcoma, round cell liposarcoma, small cell osteosarcoma, solitary fibrous tumor, synovial sarcoma, and telangiectatic osteosarcoma.

Exemplary carcinoma includes, but is not limited to, adenocarcinoma, squamous cell carcinoma, adenosquamous carcinoma, anaplastic carcinoma, large cell carcinoma, small cell carcinoma, anal cancer, appendix cancer, bile duct cancer (i.e., cholangiocarcinoma), bladder cancer, brain tumor, breast cancer, cervical cancer, colon cancer, cancer of Unknown Primary (CUP), esophageal cancer, eye cancer, fallopian tube cancer, gastroenterological cancer, kidney cancer, liver cancer, lung cancer, medulloblastoma, melanoma, oral cancer, ovarian cancer, pancreatic cancer, parathyroid disease, penile cancer, pituitary tumor, prostate cancer, rectal cancer, skin cancer, stomach cancer, testicular cancer, throat cancer, thyroid cancer, uterine cancer, vaginal cancer, and vulvar cancer. In some instances, the liver cancer is primary liver cancer.

In some instances, the cancer is selected from uveal melanoma, mesothelioma, esophageal cancer, liver cancer, breast cancer, hepatocellular carcinoma, lung adenocarcinoma, glioma, colon cancer, colorectal cancer, gastric cancer, medulloblastoma, ovarian cancer, esophageal squamous cell carcinoma, sarcoma, Ewing sarcoma, head and neck cancer, prostate cancer, and meningioma. In some cases, the cancer is uveal melanoma, mesothelioma, esophageal cancer, liver cancer, breast cancer, hepatocellular carcinoma, lung adenocarcinoma, glioma, colon cancer, colorectal cancer, gastric cancer, medulloblastoma, ovarian cancer, esophageal squamous cell carcinoma, sarcoma, Ewing sarcoma, head and neck cancer, prostate cancer, or meningioma. In some cases, the cancer is uveal melanoma, mesothelioma, esophageal cancer, or liver cancer. In some cases, the cancer is uveal melanoma. In some cases, the cancer is mesothelioma. In some cases, the cancer is esophageal cancer. In some cases, the cancer is liver cancer. In some cases, the cancer is primary liver cancer.

In some instances, the cancer is a hematologic malignancy. In some embodiments, a hematologic malignancy is a leukemia, a lymphoma, a myeloma, a non-Hodgkin's lymphoma, a Hodgkin's lymphoma, a T-cell malignancy, or a B-cell malignancy. In some instances, a hematologic malignancy is a T-cell malignancy. Exemplary T-cell malignancy includes, but is not limited to, peripheral T-cell lymphoma not otherwise specified (PTCL-NOS), anaplastic large cell lymphoma, angioimmunoblastic lymphoma, cutaneous T-cell lymphoma, adult T-cell leukemia/lymphoma (ATLL), blastic NK-cell lymphoma, enteropathy-type T-cell lymphoma, hematosplenic gamma-delta T-cell lymphoma, lymphoblastic lymphoma, nasal NK/T-cell lymphomas, and treatment-related T-cell lymphomas.

In some instances, a hematologic malignancy is a B-cell malignancy. Exemplary B-cell malignancy includes, but is not limited to, chronic lymphocytic leukemia (CLL), small lymphocytic lymphoma (SLL), high risk CLL, and a non-CLL/SLL lymphoma. In some embodiments, the cancer is follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis.

In some instances, the cancer is a relapsed or refractory cancer. In some embodiments, the relapsed or refractory cancer is a relapsed or refractory solid tumor. In some embodiments, the relapsed or refractory solid tumor is a relapsed or refractory sarcoma or a relapsed or refractory carcinoma. In some embodiments, the relapsed or refractory carcinoma includes adenocarcinoma, squamous cell carcinoma, adenosquamous carcinoma, anaplastic carcinoma, large cell carcinoma, small cell carcinoma, anal cancer, appendix cancer, bile duct cancer (i.e., cholangiocarcinoma), bladder cancer, brain tumor, breast cancer, cervical cancer, colon cancer, cancer of Unknown Primary (CUP), esophageal cancer, eye cancer, fallopian tube cancer, gastroenterological cancer, kidney cancer, liver cancer, lung cancer, medulloblastoma, melanoma, oral cancer, ovarian cancer, pancreatic cancer, parathyroid disease, penile cancer, pituitary tumor, prostate cancer, rectal cancer, skin cancer, stomach cancer, testicular cancer, throat cancer, thyroid cancer, uterine cancer, vaginal cancer, and vulvar cancer.

In some instances, the relapsed or refractory cancer is selected from relapsed or refractory uveal melanoma, mesothelioma, esophageal cancer, liver cancer, breast cancer, hepatocellular carcinoma, lung adenocarcinoma, glioma, colon cancer, colorectal cancer, gastric cancer, medulloblastoma, ovarian cancer, esophageal squamous cell carcinoma, sarcoma, Ewing sarcoma, head and neck cancer, prostate cancer, and meningioma. In some cases, the relapsed or refractory cancer is relapsed or refractory uveal melanoma, mesothelioma, esophageal cancer, liver cancer, breast cancer, hepatocellular carcinoma, lung adenocarcinoma, glioma, colon cancer, colorectal cancer, gastric cancer, medulloblastoma, ovarian cancer, esophageal squamous cell carcinoma, sarcoma, Ewing sarcoma, head and neck cancer, prostate cancer, or meningioma. In some cases, the relapsed or refractory cancer is relapsed or refractory uveal melanoma, mesothelioma, esophageal cancer, or liver cancer. In some cases, the relapsed or refractory cancer is relapsed or refractory uveal melanoma. In some cases, the relapsed or refractory cancer is relapsed or refractory mesothelioma. In some cases, the relapsed or refractory cancer is relapsed or refractory esophageal cancer. In some cases, the relapsed or refractory cancer is relapsed or refractory liver cancer. In some cases, the relapsed or refractory cancer is relapsed or refractory primary liver cancer.

In some instances, the relapsed or refractory cancer is a relapsed or refractory hematologic malignancy. In some embodiments, a relapsed or refractory hematologic malignancy is a relapsed or refractory leukemia, a relapsed or refractory lymphoma, a relapsed or refractory myeloma, a relapsed or refractory non-Hodgkin's lymphoma, a relapsed or refractory Hodgkin's lymphoma, a relapsed or refractory T-cell malignancy, or a relapsed or refractory B-cell malignancy. In some instances, a relapsed or refractory hematologic malignancy is a relapsed or refractory T-cell malignancy. In some instances, a relapsed or refractory hematologic malignancy is a relapsed or refractory B-cell malignancy, such as for example, chronic lymphocytic leukemia (CLL), small lymphocytic lymphoma (SLL), high risk CLL, or a non-CLL/SLL lymphoma. In some embodiments, the cancer is follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis.

In some instances, the cancer is a metastasized cancer. In some instances, the metastasized cancer is a metastasized solid tumor. In some instances, the metastasized solid tumor is a metastasized sarcoma or a metastasized carcinoma. In some embodiments, the metastasized carcinoma includes adenocarcinoma, squamous cell carcinoma, adenosquamous carcinoma, anaplastic carcinoma, large cell carcinoma, small cell carcinoma, anal cancer, appendix cancer, bile duct cancer (i.e., cholangiocarcinoma), bladder cancer, brain tumor, breast cancer, cervical cancer, colon cancer, cancer of Unknown Primary (CUP), esophageal cancer, eye cancer, fallopian tube cancer, gastroenterological cancer, kidney cancer, liver cancer, lung cancer, medulloblastoma, melanoma, oral cancer, ovarian cancer, pancreatic cancer, parathyroid disease, penile cancer, pituitary tumor, prostate cancer, rectal cancer, skin cancer, stomach cancer, testicular cancer, throat cancer, thyroid cancer, uterine cancer, vaginal cancer, and vulvar cancer.

In some instances, the metastasized cancer is selected from metastasized uveal melanoma, mesothelioma, esophageal cancer, liver cancer, breast cancer, hepatocellular carcinoma, lung adenocarcinoma, glioma, colon cancer, colorectal cancer, gastric cancer, medulloblastoma, ovarian cancer, esophageal squamous cell carcinoma, sarcoma, Ewing sarcoma, head and neck cancer, prostate cancer, and meningioma. In some cases, the metastasized cancer is metastasized uveal melanoma, mesothelioma, esophageal cancer, liver cancer, breast cancer, hepatocellular carcinoma, lung adenocarcinoma, glioma, colon cancer, colorectal cancer, gastric cancer, medulloblastoma, ovarian cancer, esophageal squamous cell carcinoma, sarcoma, Ewing sarcoma, head and neck cancer, prostate cancer, or meningioma. In some cases, the metastasized cancer is metastasized uveal melanoma, mesothelioma, esophageal cancer, or liver cancer. In some cases, the metastasized cancer is metastasized uveal melanoma. In some cases, the metastasized cancer is metastasized mesothelioma. In some cases, the metastasized cancer is metastasized esophageal cancer. In some cases, the metastasized cancer is metastasized liver cancer. In some cases, the metastasized cancer is metastasized primary liver cancer.

In some instances, the metastasized cancer is a metastasized hematologic malignancy. In some embodiments, the metastasized hematologic malignancy is a metastasized leukemia, a metastasized lymphoma, a metastasized myeloma, a metastasized non-Hodgkin's lymphoma, a metastasized Hodgkin's lymphoma, a metastasized T-cell malignancy, or a metastasized B-cell malignancy. In some instances, a metastasized hematologic malignancy is a metastasized T-cell malignancy. In some instances, a metastasized hematologic malignancy is a metastasized B-cell malignancy, such as for example, chronic lymphocytic leukemia (CLL), small lymphocytic lymphoma (SLL), high risk CLL, or a non-CLL/SLL lymphoma. In some embodiments, the cancer is follicular lymphoma (FL), diffuse large B-cell lymphoma (DLBCL), mantle cell lymphoma (MCL), Waldenstrom's macroglobulinemia, multiple myeloma, extranodal marginal zone B cell lymphoma, nodal marginal zone B cell lymphoma, Burkitt's lymphoma, non-Burkitt high grade B cell lymphoma, primary mediastinal B-cell lymphoma (PMBL), immunoblastic large cell lymphoma, precursor B-lymphoblastic lymphoma, B cell prolymphocytic leukemia, lymphoplasmacytic lymphoma, splenic marginal zone lymphoma, plasma cell myeloma, plasmacytoma, mediastinal (thymic) large B cell lymphoma, intravascular large B cell lymphoma, primary effusion lymphoma, or lymphomatoid granulomatosis.

In some embodiments, the cancer is selected from malignant peripheral nerve sheath tumor (MPNST), schwannoma, and cutaneous neurofibromas.

Congenital Diseases

In some embodiments, the compounds disclosed herein are useful for treating a congenital disease. In some embodiments, the congenital disease is mediated by activation of transcriptional coactivator with PDZ binding motif/Yes-associated protein transcription coactivator (TAZ/YAP). In some embodiments, the congenital disease is characterized by a mutant Gα-protein. In some embodiments, the mutant Gα-protein is selected from G12, G13, Gq, G11, Gi, Go, and Gs. In some embodiments, the mutant Gα-protein is G12. In some embodiments, the mutant Gα-protein is G13. In some embodiments, the mutant Gα-protein is Gq. In some embodiments, the mutant Ga-protein is G11. In some embodiments, the mutant Gα-protein is Gi. In some embodiments, the mutant Gα-protein is Go. In some embodiments, the mutant Gα-protein is Gs.

In some embodiments, the congenital disease is the result of a genetic abnormality, an intrauterine environment, errors related to morphogenesis, infection, epigenetic modifications on a parental germline, or a chromosomal abnormality. Exemplary congenital diseases include, but are not limited to, Sturge-Weber Syndrome, Port-Wine stain, Holt-Oram syndrome, abdominal wall defects, Becker muscular dystrophy (BMD), biotinidase deficiency, Charcot-Marie-Tooth (CMT), cleft lip, cleft palate, congenital adrenal hyperplasia, congenital heart defects, congenital hypothyroidism, congenital muscular dystrophy, cystic fibrosis, Down syndrome, Duchenne muscular dystrophy, Fragile X syndrome, Friedreich's ataxia, galactosemia, hemoglobinopathies, Krabbe disease, limb-girdle muscular dystrophy, medium chain acyl-CoA dehydrogenase deficiency, myasthenia gravis, neural tube defects, phenylketonuria, Pompe disease, severe combined immunodeficiency (SCID), Stickler syndrome (or hereditary progressive arthro-ophthalmopathy), spinal muscular atrophy, and trisomy 18. In some embodiments, the congenital disease is Sturge-Weber Syndrome or Port-Wine stain. In some embodiments, the congenital disease is Sturge-Weber Syndrome. In some embodiments, the congenital disease is Port-Wine stain.

EXAMPLES

These examples are provided for illustrative purposes only and not to limit the scope of the claims provided herein.

List of Abbreviations

As used above, and throughout the disclosure, the following abbreviations, unless otherwise indicated, shall be understood to have the following meanings:

| | |
|---|---|
| ACN or MeCN | acetonitrile |
| Ac | acetyl |
| Bn | benzyl |
| BOC or Boc | tert-butyl carbamate |
| t-Bu | tert-butyl |
| Cy | cyclohexyl |
| ° C. | degrees Celsius |
| DBA or dba | dibenzylideneacetone |
| DCE | dichloroethane (ClCH$_2$CH$_2$Cl) |
| DCM | dichloromethane (CH$_2$Cl$_2$) |
| DIAD | diisopropyl azodicarboxylate |
| DIPEA or DIEA | diisopropylethylamine |
| DMAP | 4-(N,N-dimethylamino)pyridine |
| DMF | dimethylformamide |
| DMA | N,N-dimethylacetamide |
| DMSO | dimethylsulfoxide |
| Dppf or dppf | 1,1'-bis(diphenylphosphino)ferrocene |
| EA or EtOAc | ethyl acetate |
| eq | equivalent(s) |
| Et | ethyl |
| Et$_2$O | diethyl ether |
| EtOH | ethanol |
| g | gram(s) |
| h | hour(s) |
| HPLC | high performance liquid chromatography |
| Hz | hertz |
| LAH | lithium aluminum anhydride |
| LCMS | liquid chromatography mass spectrometry |
| m/z | mass-to-charge ratio |
| M | molar |
| Me | methyl |
| MeI | methyl iodide |
| MeOH | methanol |
| mg | milligram(s) |
| MHz | megahertz |
| umol | micromole(s) |
| uL | microliter(s) |
| mL | milliliter(s) |
| mmol | millimole(s) |
| MS | mass spectroscopy |
| MsCl | methanesulfonyl chloride |
| MW | microwave radiation |
| NCS | N-chlorosuccinimide |
| NMM | N-methyl-morpholine |
| NMP | N-methyl-pyrrolidin-2-one |
| NMR | nuclear magnetic resonance |
| PE | petroleum ether |
| Ph | phenyl |
| prep-HPLC | preparative high pressure liquid chromatography |
| prep-TLC | preparative thin layer chromatography |
| Py | pyridine |
| RP-HPLC | reverse phase-high pressure liquid chromatography |
| RT | retention time |
| TEA | triethylamine |
| TFA | trifluoroacetic acid |

| | |
|---|---|
| THF | tetrahydrofuran |
| TLC | thin layer chromatography |
| TMSCl | trimethylsilyl chloride |
| Xantphos | 4,5-bis(diphenylphosphino)-9,9-dimethylxanthene |
| XPhos | 2-dicyclohexylphosphino-2',4',6'-triisopropylbiphenyl |
| XPhos Pd G II | chloro(2-dicyclohexylphosphino-2',4',6'-triisopropyl-1,1'-biphenyl)[2-(2'-amino-1,1'-biphenyl)]palladium(II) |

I. Chemical Synthesis

Unless otherwise noted, reagents and solvents were used as received from commercial suppliers. Anhydrous solvents and oven-dried glassware were used for synthetic transformations sensitive to moisture and/or oxygen. Yields were not optimized. Reaction times were approximate and were not optimized. Column chromatography and thin layer chromatography (TLC) were performed on silica gel unless otherwise noted. Same compounds can have different annotation.

Example 1: N-isopropyl-5-(4-(trifluoromethyl)phenyl)-2-naphthamide (Compound 1)

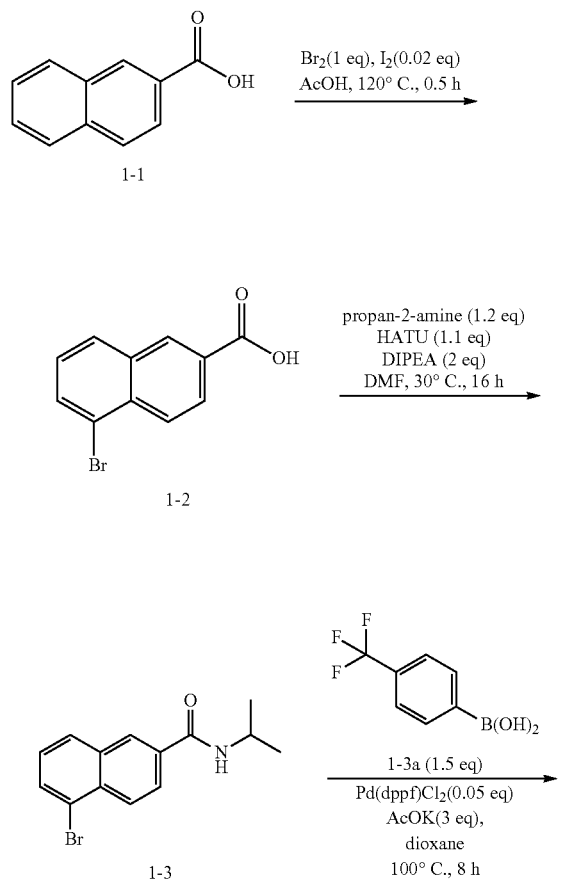

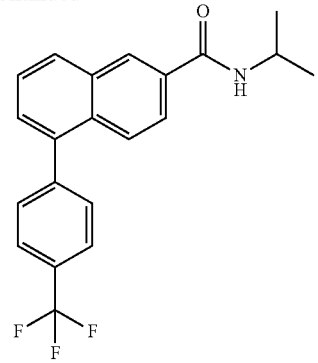

Compound 1

Step 1: 5-bromo-2-naphthoic Acid

To a boiling solution of compound 1-1 (4 g, 23.23 mmol, 1 eq) in AcOH (20 mL) is added Br$_2$ (3.71 g, 23.23 mmol, 1.20 mL, 1 eq) containing I$_2$ (117.9 mg, 0.46 mmol, 93 uL, 0.02 eq). After the addition, the solution was refluxed at 120° C. for 0.5 hr. A white precipitate was formed during cooling. The mixture was filtered, washed with acetic acid (15 mL) and then water (15 mL). The collected filter cake was triturated in methanol (50 mL) and filtered, dried under vacuum to give compound 1-2 (2.4 g, 9.56 mmol, 41.15% yield) as a white solid, which was used directly without purification. $^1$H NMR (400 MHz, DMSO-d$_6$) δ 8.68 (d, J=1.5 Hz, 1H), 8.21 (t, J=8.0 Hz, 2H), 8.17-8.11 (m, 1H), 8.03 (d, J=7.0 Hz, 1H), 7.54 (t, J=8.0 Hz, 1H).

Step 2: 5-bromo-N-isopropyl-2-naphthamide

To a solution of compound 1-2 (1 g, 3.98 mmol, 1 eq) in DMF (5 mL) were added DIPEA (1.03 g, 7.97 mmol, 1.39 mL, 2 eq and HATU (1.67 g, 4.38 mmol, 1.1 eq) at 30° C. After stirring for 10 min, propan-2-amine (282.5 mg, 4.78 mmol, 0.41 mL, 1.2 eq) was added and the solution was stirred at 30° C. for 16 hr. LCMS showed 47% of desired product was detected. The solution was diluted with 50 mL of EA, washed with 0.5 M HCl (20 mL*2) and brine (20 mL) twice in turns, dried over anhydrous Na$_2$SO$_4$, filtered and concentrated to give a residue. The residue was purified by column chromatography (SiO$_2$, Petroleum ether/Ethyl acetate=100/0 to 2:1) to give compound 1-3 (0.6 g, 2.05 mmol, 51.56% yield) as a white solid. $^1$H NMR (400 MHz, CDCl$_3$) δ 8.35-8.25 (m, 2H), 7.95-7.84 (m, 3H), 7.41 (t, J=7.8 Hz, 1H), 6.09 (br s, 1H), 4.38 (qd, J=6.6, 13.7 Hz, 1H), 1.35 (d, J=6.5 Hz, 6H).

Step 3: N-isopropyl-5-(4-(trifluoromethyl)phenyl)-2-naphthamide

A mixture of compound 1-3 (0.2 g, 0.68 mmol, 1 eq), 1-3a (195.0 mg, 1.03 mmol, 1.5 eq), Pd(dppf)Cl$_2$ (25.04 mg, 34.2 umol, 0.05 eq) and KOAc (201.5 mg, 2.05 mmol, 3 eq) in dioxane (5 mL) was bubbled with nitrogen for 1 min, sealed and stirred at 100° C. for 8 hr. LCMS showed 48% of desired product was formed. The mixture was filtered and concentrated to give a residue. The residue was purified by prep-HPLC. The desired fractions were collected and most of organic solvent was removed under vacuum. The remained mixture was lyophilized to dryness to give the title compound (176.88 mg, 0.49 mmol, 71.48% yield) as a white solid. LCMS (ESI): RT=0.826 min, mass calc. for $C_{21}H_{18}F_3NO$ 357.13, m/z found 358.0 [M+1]$^+$; $^1$H NMR (400 MHz, DMSO-d$_6$) δ 8.55 (s, 1H), 8.45 (d, J=7.5 Hz, 1H), 8.12 (d, J=8.0 Hz, 1H), 7.97-7.90 (m, 3H), 7.80 (d, J=8.5 Hz, 1H), 7.78-7.66 (m, 3H), 7.59 (d, J=7.0 Hz, 1H), 4.24-4.07 (m, 1H), 1.22 (d, J=6.5 Hz, 6H).

Example 2: N-(methylsulfonyl)-5-(4-(trifluoromethyl)phenyl)-2-naphthamide (Compound 2)

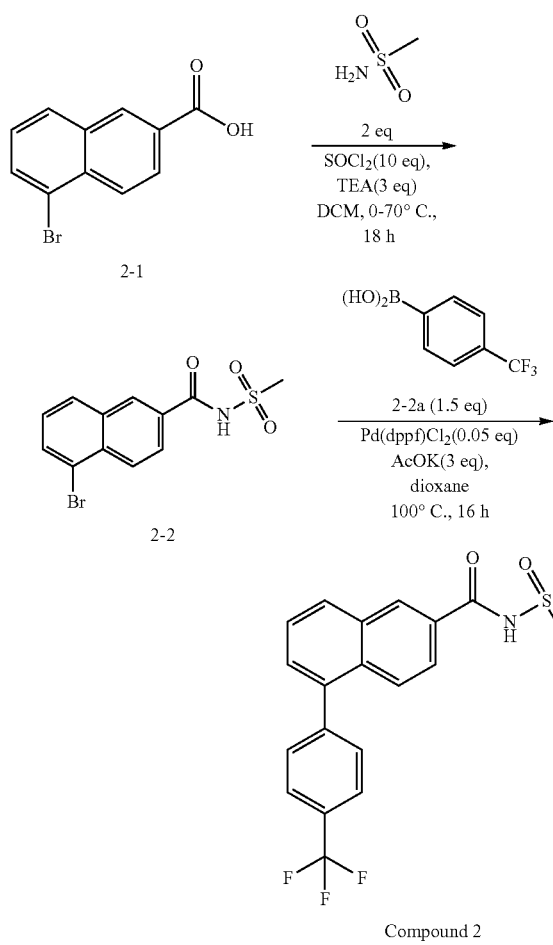

Compound 2

Step 1: 5-bromo-N-(methylsulfonyl)-2-naphthamide

A mixture of compound 2-1 (0.3 g, 1.19 mmol, 1 eq) and SOCl$_2$ (1.42 g, 11.95 mmol, 0.87 mL, 10 eq) in DCM (5 mL) was stirred at 70° C. for 2 h. Then the solution was concentrated to give residue, which was quickly dissolved in DCM (5 mL). After cooling to 0° C., TEA (362.7 mg, 3.58 mmol, 0.50 L, 3 eq) and methanesulfonamide (227.3 mg, 2.39 mmol, 2 eq) were added and the resulting mixture was at 25° C. for 16 hr. LCMS showed 46% of desired product was detected. The mixture was quenched with water (5 mL) and diluted with EA (60 mL) and separated. The organic layer was washed with brine (10 mL*3), dried by anhydrous Na$_2$SO$_4$, filtered and concentrated to give a residue. The residue was triturated with a mixture solution of Ethyl acetate:Petroleum ether=1:1 (20 mL) to give compound 2-2 (0.4 g, crude) as a white solid, which was used directly without further purification. $^1$H NMR showed it was a 1:1 mixture of starting material and desired product. $^1$H NMR (400 MHz, DMSO-d$_6$) δ 8.55 (s, 1H), 8.47 (s, 1H), 8.24-8.16 (m, 2H), 8.11-8.01 (m, 4H), 7.88 (dd, J=7.4, 11.7 Hz, 2H), 7.43 (q, J=8.2 Hz, 2H), 2.89 (s, 3H).

Step 2: N-(methylsulfonyl)-5-(4-(trifluoromethyl)phenyl)-2-naphthamide

A mixture of compound 2-2 (0.3 g, 0.91 mmol, 1 eq), 2-2a (260.4 mg, 1.37 mmol, 1.5 eq), Pd(dppf)Cl$_2$ (33.4 mg, 46 umol, 0.05 eq) and AcOK (269.1 mg, 2.74 mmol, 3 eq) in dioxane (10 mL) was bubbled with nitrogen for 1 min, sealed and stirred at 100° C. for 16 hr. LCMS showed the reaction was complete and 40% of desired product was formed. The reaction was filtered and concentrated to give a residue. The residue was purified by prep-HPLC to give the crude product (20 mg). Then it was purified again by prep-HPLC to give the title compound (5.31 mg, 12.27 umol, 1.34% yield) as a white solid. LCMS (ESI): RT=1.411 min, mass calc. for $C_{19}H_{14}F_3NO_3S$ 393.06, m/z found 394.0 [M+1]$^+$; $^1$H NMR (400 MHz, CD$_3$OD) δ 8.63 (d, J=1.5 Hz, 1H), 8.08 (d, J=8.3 Hz, 1H), 8.03-7.97 (m, 1H), 7.89-7.80 (m, 3H), 7.72-7.62 (m, 3H), 7.59-7.54 (m, 1H), 3.30 (s, 3H), 3.23 (s, 1H).

Example 3: N-methyl-5-(4-(trifluoromethyl)phenyl)naphthalene-2-sulfonamide (Compound 3)

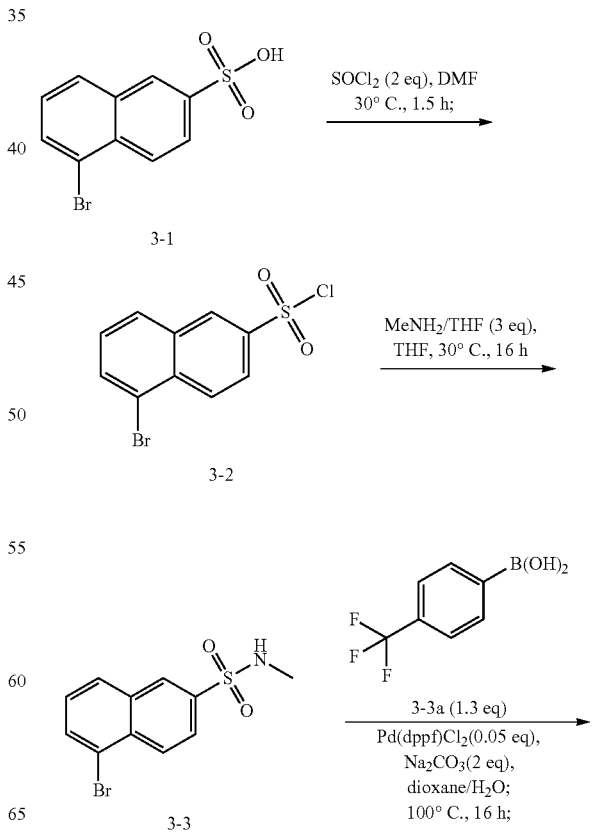

-continued

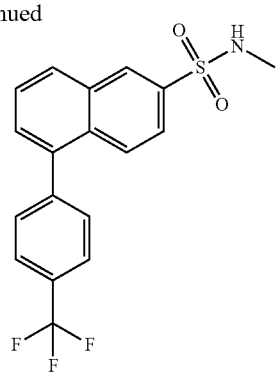

Compound 3

Step 1: 5-bromonaphthalene-2-sulfonyl Chloride

To a solution of compound 3-1 (300 mg, 1.04 mmol, 1 eq) in DMF (1 mL) at 30° C. was added $SOCl_2$ (248.6 mg, 2.09 mmol, 0.15 mL, 2 eq) drop-wise. The reaction mixture was then stirred at 30° C. for 1.5 h. The mixture was poured into the ice-water (20 mL), and then extracted with EA (20 mL*3). The combined organic layer was washed with brine (20 mL), dried over anhydrous $Na_2SO_4$, filtered and concentrated under reduced pressure to give compound 3-2 (310 mg, 1.01 mmol, 97.1% yield) as a yellow solid, which was used directly for next step.

Step 2: 5-bromo-N-methylnaphthalene-2-sulfonamide

To a solution of $MeNH_2$ (2.0 M in THF, 1.52 mL, 3 eq) in THF (1 mL) at 30° C. was added compound 3-2 (310 mg, 1.01 mmol, 1 eq) in THF (2 mL) drop-wise. The reaction mixture was stirred at 30° C. for 16 h. The mixture was diluted with water (20 mL), and extracted with EA (20 mL*3). The combined organic layer was washed with brine (20 mL), dried over anhydrous $Na_2SO_4$, filtered and concentrated under reduced pressure to give compound 3-3 (270 mg, 0.81 mmol, 79.8% yield) as a yellow solid. LCMS (ESI): RT=0.706 min, mass calc. for $C_{11}H_{10}BrNO_2S$ 298.96, m/z found 299.7[M+1]$^+$; $^1$H NMR (400 MHz, CDCl$_3$) δ 8.36 (d, J=1.8 Hz, 1H), 8.33 (d, J=9.0 Hz, 1H), 7.91-7.84 (m, 3H), 7.40 (t, J=7.8 Hz, 1H), 4.38 (d, J=4.8 Hz, 1H), 2.64 (d, J=5.5 Hz, 3H).

Step 3: N-methyl-5-(4-(trifluoromethyl)phenyl) naphthalene-2-sulfonamide

The mixture of compound 3-3 (100 mg, 0.33 mmol, 1 eq), compound 3-3a (82.3 mg, 0.43 mmol, 1.3 eq), Pd(dppf)Cl$_2$ (12.2 mg, 16.7 umol, 0.05 eq) and $Na_2CO_3$ (70.6 mg, 0.67 mmol, 2 eq) in dioxane (5 mL) and Water (1 mL) at 30° C. was degassed and purged with $N_2$ for 3 times, and then stirred at 100° C. under $N_2$ for 16 h. LCMS showed starting material was consumed completely and 72% of desired product was formed. The mixture was concentrated to give a residue. The residue was purified by prep-TLC (PE:EA=1:1) to give the title compound (90.9 mg, 0.24 mmol, 73.2% yield) as a white solid. LCMS (ESI): RT=0.810 min, mass calc. for $C_{18}H_{14}F_3NO_2S$ 365.07, m/z found 365.9[M+1]$^+$; $^1$H NMR (400 MHz, DMSO-d$_6$) δ 8.54 (d, J=1.5 Hz, 1H), 8.29 (d, J=8.0 Hz, 1H), 7.98-7.90 (m, 3H), 7.84-7.74 (m, 4H), 7.69 (d, J=7.0 Hz, 1H), 7.63 (brs, 1H), 2.45 (s, 3H).

Example 4: N-isopropyl-8-(4-(trifluoromethyl)phenyl)quinoline-3-carboxamide (Compound 4)

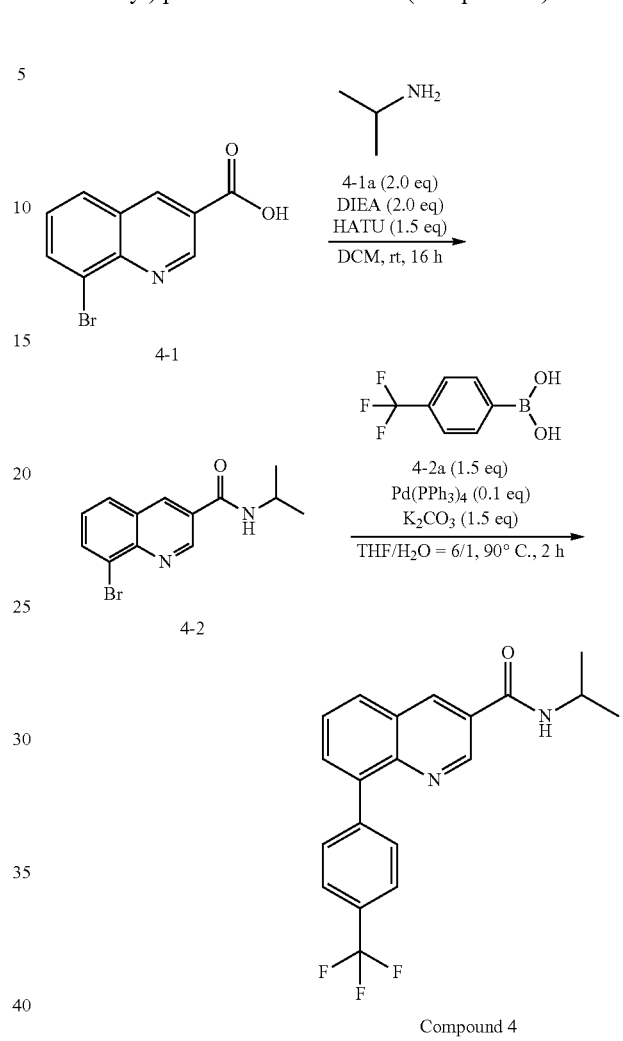

Compound 4

Step 1: 8-bromo-N-isopropylquinoline-3-carboxamide

To a solution of compound 4-1 (100 mg, 0.40 mmol, 1 eq) in DCM (2 mL) were added HATU (226.3 mg, 0.60 mmol, 1.5 eq), DIEA (102.5 mg, 0.80 mmol, 0.14 mL, 2 eq) and compound 4-1a (46.9 mg, 0.80 mmol, 68 uL, 2 eq). The mixture was stirred at 25° C. for 16 hr. LCMS indicated that 66% of desired product was detected. The reaction mixture was diluted with EA (20 mL). The organic phase was washed with brine (5 mL), dried over $Na_2SO_4$, filtered and concentrated in vacuum. The crude product was purified by column chromatography (Petroleum ether/Ethyl acetate=1/0 to 9:1). The compound 4-2 (55 mg, 0.18 mmol, 47.3% yield) was obtained as a white solid. $^1$H NMR (400 MHz, CDCl$_3$) δ 9.33 (d, J=2.26 Hz, 1H), 8.58 (d, J=2.02 Hz, 1H), 8.15 (dd, J=7.40, 1.13 Hz, 1H), 7.90 (dd, J=8.16, 1.13 Hz, 1H), 7.49 (t, J=7.92 Hz, 1H), 6.08 (br s, 1H) 4.28-4.46 (m, 1H), 1.34 (d, J=6.52 Hz, 7H).

Step 2: N-isopropyl-8-(4-(trifluoromethyl) phenyl) quinoline-3-carboxamide

To a solution of compound 4-2 (50 mg, 0.17 mmol, 1 eq) in THF (3 mL) and $H_2O$ (0.5 mL) were added Pd(PPh$_3$)$_4$ (19.7 mg, 17 umol, 0.1 eq), $K_2CO_3$ (35.36 mg, 0.25 mmol, 1.5 eq) and compound 4-2a (48.6 mg, 0.25 mmol, 1.5 eq). The mixture was stirred at 90° C. for 2 hr. LCMS showed that 42% of desired product was detected. The reaction mixture was filtered and the filter was concentrated in vacuum. The crude product was purified by prep-HPLC. The title compound (25.14 mg, 70.15 umol, 41.1% yield) was obtained as a white solid. LCMS (ESI): RT=0.786 min, mass calcd. For $C_{20}H_{17}F_3N_2O$, 358.13 m/z found 359.0 $[M+H]^+$; $^1H$ NMR (400 MHz, $CDCl_3$) δ 9.26 (d, J=2.26 Hz, 1H), 8.66 (d, J=2.26 Hz, 1H), 7.99 (dd, J=8.02, 1.25 Hz, 1H), 7.81-7.87 (m, 3H), 7.76-7.80 (m, 2H), 7.70-7.75 (m, 1H), 6.08 (br d, J=6.27 Hz, 1H), 4.35-4.44 (m, 1H), 1.35 (d, J=6.52 Hz, 6H).

Example 5: N-ethyl-5-(4-(trifluoromethyl)phenyl) naphthalene-2-sulfonamide (Compound 5)

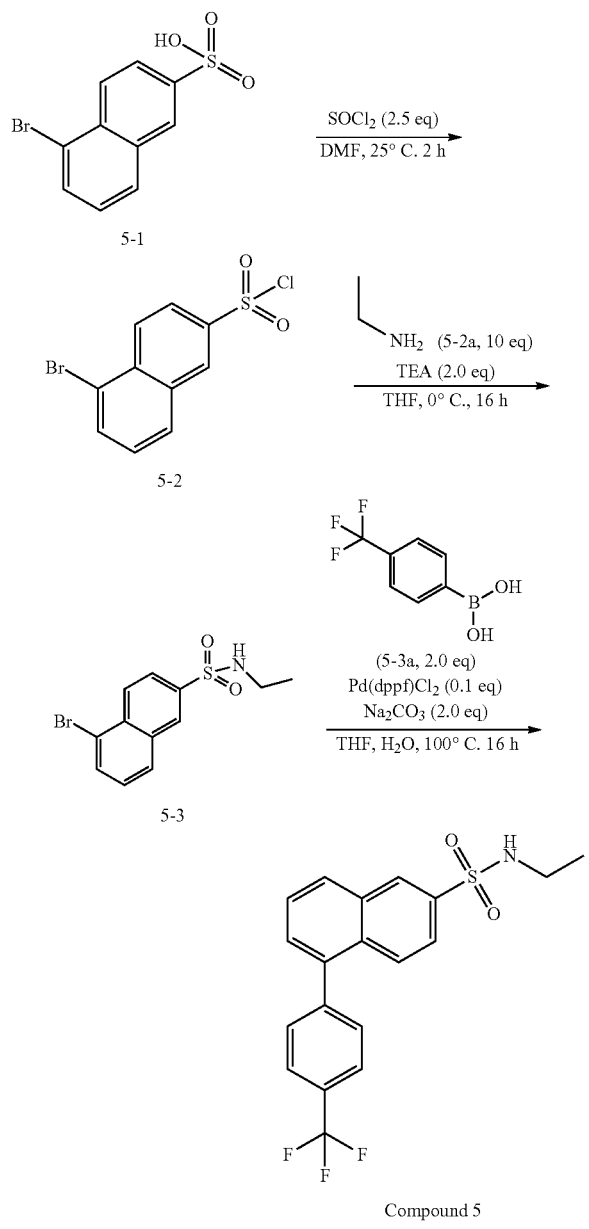

Compound 5

Step 1: 5-bromonaphthalene-2-sulfonyl Chloride

To a solution of compound 5-1 (500 mg, 1.74 mmol, 1.0 eq) in DMF (5 mL) was added $SOCl_2$ (517.9 mg, 4.35 mmol, 0.31 mL, 2.5 eq) dropwise at 25° C. The mixture was stirred at 25° C. for 2 hr. The reaction mixture was poured into water (20 mL) and extracted with DCM (20 mL*3). The combined organic layers were washed with brine (10 mL), dried over $Na_2SO_4$, filtered and concentrated under reduced pressure to give compound 5-2 (500 mg, crude) as a yellow oil, which was used into the next step without further purification.

Step 2: 5-bromo-N-ethylnaphthalene-2-sulfonamide

To a solution of compound 5-2 (200 mg, 0.65 mmol, 1.0 eq) in THF (5 mL) were added TEA (132.4 mg, 1.31 mmol, 0.18 mL, 2.0 eq) and 5-2a (295.0 mg, 6.55 mmol, 0.43 mL, 10.0 eq). The mixture was stirred at 25° C. for 16 hr. LCMS showed the reactant 2 was consumed completely, and 50% desired MS was detected. The reaction mixture was poured into water (10 mL) and extracted with EA (20 mL*3). The combined organic layers were washed with brine (10 mL), dried over $Na_2SO_4$, filtered and concentrated under reduced pressure to give compound 5-3 (150 mg, crude) as a yellow solid, which was used into the next step without further purification. LCMS (ESI): RT=0.734 min, mass calcd. for $C_{12}H_{12}BrNO_2S$, 312.98, m/z found 313.8 $[M+H]^+$.

Step 3: N-ethyl-5-(4-(trifluoromethyl)phenyl)naphthalene-2-sulfonamide

To a solution of compound 5-3 (150 mg, 0.48 mmol, 1.0 eq) in $H_2O$ (1 mL) and THF (5 mL) were added $Pd(dppf)Cl_2$ (34.9 mg, 47.7 umol, 0.1 eq), $Na_2CO_3$ (101.2 mg, 0.95 mmol, 2.0 eq) and 5-3a (181.3 mg, 0.95 mmol, 2.0 eq). The mixture was stirred at 100° C. for 16 hr. LCMS showed the reactant 5-3 was consumed completely, and ~50% desired MS was detected. The reaction was monitored by HPLC. The reaction mixture was concentrated in vacuum. The residue was purified by prep-HPLC to give the title compound (19.52 mg, 51.5 umol, 10.8% yield) as a white solid. LCMS (ESI): RT=0.828 min, mass calcd. for $C_{19}H_{16}F_3NO_2S$ 379.09, m/z found 379.9 $[M+H]^+$; $^1H$ NMR (400 MHz, $CDCl_3$) δ 8.52 (d, J=1.8 Hz, 1H), 8.04 (d, J=8.0 Hz, 1H), 7.95 (d, J=8.8 Hz, 1H), 7.84-7.76 (m, 3H), 7.73-7.66 (m, 1H), 7.64-7.57 (m, 3H), 4.41 (br d, J=5.8 Hz, 1H), 3.13-3.03 (m, 2H), 1.13 (t, J=7.2 Hz, 3H).

Example 6: N-isopropyl-5-(4-(trifluoromethyl)phenyl)naphthalene-2-sulfonamide (Compound 6)

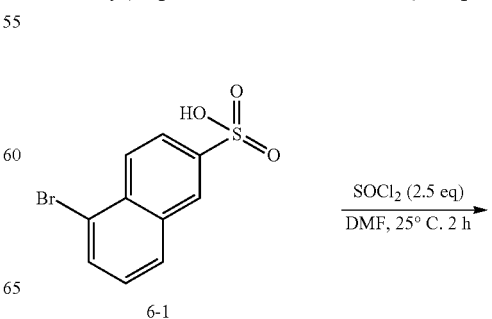

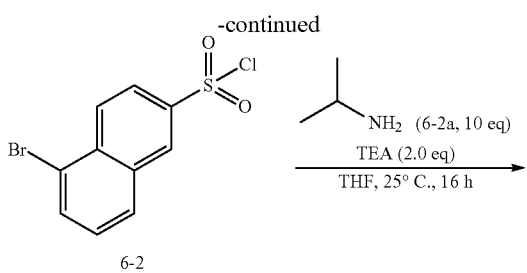

6-2

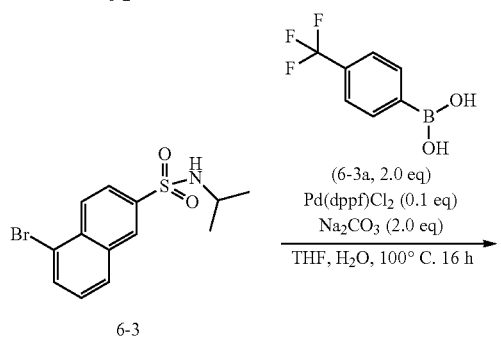

6-3

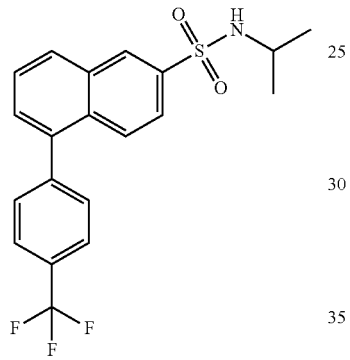

Compound 6

Step 1: 5-bromonaphthalene-2-sulfonyl Chloride

To a solution of compound 6-1 (500 mg, 1.74 mmol, 1.0 eq) in DMF (5 mL) was added $SOCl_2$ (517.9 mg, 4.35 mmol, 0.31 mL, 2.5 eq) dropwise at 25° C. The mixture was stirred at 25° C. for 2 hr. The reaction mixture was poured into water (20 mL) and extracted with DCM (20 mL*3). The combined organic layers were washed with brine (10 mL), dried over $Na_2SO_4$ filtered and concentrated under reduced pressure to give a residue. The crude product was used into the next step without further purification. Compound 6-2 (500 mg, crude) was obtained as a yellow oil.

Step 2: 5-bromo-N-isopropylnaphthalene-2-sulfonamide

To a solution of compound 6-2 (200 mg, 0.65 mmol, 1.0 eq) in THF (5 mL) were added TEA (132.4 mg, 1.31 mmol, 0.18 mL, 2.0 eq) and 6-2a (386.9 mg, 6.55 mmol, 0.56 mL, 10.0 eq). The mixture was stirred at 25° C. for 16 hr. LCMS showed the reactant was consumed completely, and 50% desired MS was detected. The reaction mixture was poured into water (10 mL) and extracted with EA (20 mL*3). The combined organic layers were washed with brine (10 mL), dried over $Na_2SO_4$, filtered and concentrated under reduced pressure to give a residue. The crude product was used into the next step without further purification. Compound 6-3 (160 mg, crude) was obtained as a yellow solid. LCMS (ESI): RT=0.765 min, mass calcd. for $C_{13}H_{14}BrNO_2S$, 326.99, m/z found 329.7 $[M+H]^+$.

Step 3: N-isopropyl-5-(4-(trifluoromethyl)phenyl)naphthalene-2-sulfonamide

To a solution of compound 6-3 (160 mg, 0.49 mmol, 1.0 eq) in $H_2O$ (1 mL) and THF (5 mL) were added $Pd(dppf)Cl_2$ (35.6 mg, 48.75 umol, 0.1 eq), $Na_2CO_3$ (103.3 mg, 0.97 mmol, 2.0 eq) and 6-3a (185.1 mg, 0.97 mmol, 2.0 eq). The mixture was stirred at 100° C. for 16 hr. The reaction mixture was concentrated in vacuum. The residue was purified by prep-HPLC to give the title compound (27.02 mg, 68.68 umol, 14.1% yield) as a white solid. LCMS (ESI): RT=0.849 min, mass calcd. for $C_{20}H_{18}F_3NO_2S$ 393.10, m/z found 393.9 $[M+H]^+$; $^1H$ NMR (400 MHz, $CDCl_3$) δ 8.54 (d, J=1.8 Hz, 1H), 8.04 (d, J=8.3 Hz, 1H), 7.94 (d, J=9.0 Hz, 1H), 7.84-7.76 (m, 3H), 7.73-7.66 (m, 1H), 7.64-7.56 (m, 3H), 4.40 (br d, J=7.3 Hz, 1H), 3.61-3.49 (m, 1H), 2.78 (s, 1H), 1.11 (d, J=6.5 Hz, 6H).

Example 7: N-isopropyl-4-[4-(trifluoromethyl)phenyl]quinoline-7-carboxamide (Compound 7)

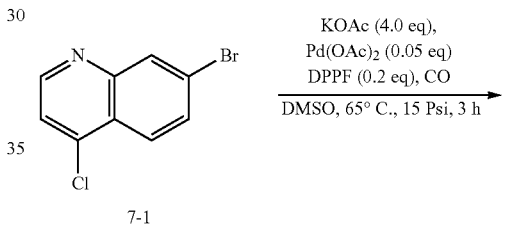

7-1

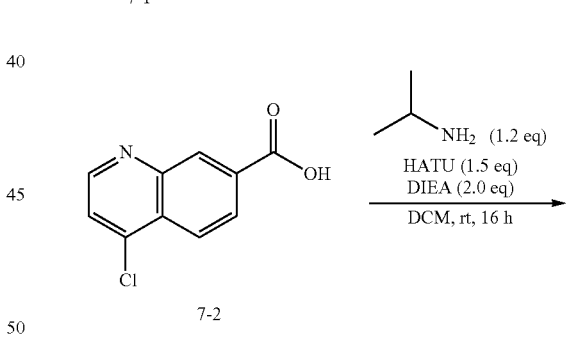

7-2

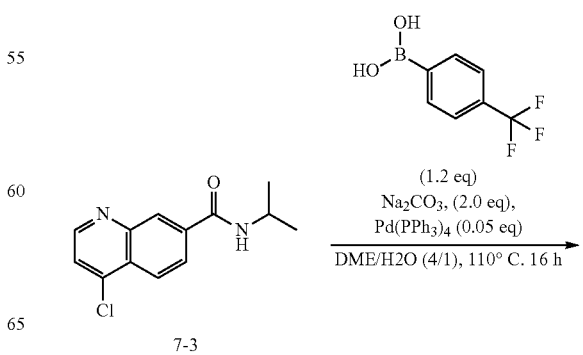

7-3

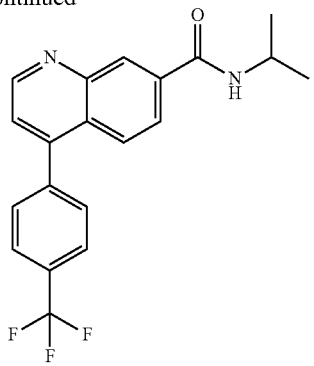

Compound 7

Step 1: 4-chloroquinoline-7-carboxylic Acid

To a solution of compound 7-1 (0.2 g, 0.82 mmol, 1 eq), KOAc (323.7 mg, 3.30 mmol, 4 eq) and DPPF (91.4 mg, 0.16 mmol, 0.2 eq) in DMSO (4 mL) was added Pd(OAc)$_2$ (9.2 mg, 41.2 umol, 0.05 eq) under N$_2$. The suspension was degassed under vacuum and purged with CO several times. The mixture was stirred under CO (15 psi) at 65° C. for 3 hours. LCMS showed that 30% of desired product was detected. The reaction was diluted with EA (40 mL) and washed with brine (2*10 mL). The organic layer was dried over Na2SO4 and concentrated. The residue was triturated with EA (20 mL) and filtered to give compound 7-2 (98 mg, 0.46 mmol, 55.92% yield) as a pink solid.

Step 2: 4-chloro-N-isopropyl-quinoline-7-carboxamide

To a solution of compound 7-2 (98 mg, 0.47 mmol, 1 eq) and HATU (269.2 mg, 0.70 mmol, 1.5 eq) in DCM (5 mL) was added propan-2-amine (33.4 mg, 0.56 mmol, 48.6 uL, 1.2 eq) and DIEA (122 mg, 0.94 mmol, 0.16 mL, 2 eq). The reaction was stirred at 25° C. for 16 hr. LCMS showed that 93% of desired product was detected. The reaction was diluted with DCM (20 mL) and washed with water (2*10 mL). The organic layer was dried over Na$_2$SO$_4$ and concentrated. The residue was purified by column chromatography on silica gel (EA:PE=1:1 to 1:0) to give compound 7-3 (40 mg, 0.16 mmol, 33.02% yield) as a yellow solid. $^1$H NMR (400 MHz, CDCl$_3$) δ 8.85 (d, J=4.4 Hz, 1H), 8.40 (d, J=1.2 Hz, 1H), 8.31 (d, J=8.8 Hz, 1H), 8.12 (dd, J=8.8, 1.6 Hz, 1H), 7.57 (d, J=4.8 Hz, 1H), 6.19 (br, 1H), 4.40-4.25 (m, 1H), 1.33 (d, J=6.8 Hz, 6H).

Step 3: N-isopropyl-4-[4-(trifluoromethyl)phenyl]quinoline-7-carboxamide

To a solution of compound 7-3 (40 mg, 0.16 mmol, 1 eq) in DME (2.4 mL) was added Pd(PPh$_3$)$_4$ (9.2 mg, 8.0 umol, 0.05 eq). And then Na$_2$CO$_3$ (34.0 mg, 0.32 mmol, 2 eq) in H$_2$O (0.6 mL) and [4-(trifluoromethyl)phenyl]boronic acid (38.1 mg, 0.2 mmol, 1.25 eq) was added. The suspension was degassed under vacuum and purged with N$_2$ several times. The mixture was stirred under N$_2$ at 110° C. for 16 hours. LCMS showed that 30% of starting material was remained and 16% of desired product was detected. The reaction was diluted with EA (15 mL) and washed with water (2*6 mL). The organic layer was dried over Na$_2$SO$_4$ and concentrated. The residue was purified by prep-HPLC to give the title compound (2.03 mg, 5.66 umol, 3.52% yield) as a white solid. LCMS (ESI): RT=0.709 min, mass calcd for C$_{20}$H$_{17}$F$_3$N$_2$O 358.13, m/z found 359.0 [M+H]$^+$; $^1$H NMR (400 MHz, CHLOROFORM-d) δ 9.05 (d, J=4.2 Hz, 1H), 8.47 (d, J=1.5 Hz, 1H), 8.02 (dd, J=8.6, 1.6 Hz, 1H), 7.92 (d, J=8.8 Hz, 1H), 7.85 (d, J=8.0 Hz, 2H), 7.66 (d, J=8.0 Hz, 2H), 7.43 (d, J=4.2 Hz, 1H), 6.20 (d, J=7.6 Hz, 1H), 4.32-4.43 (m, 1H), 1.35 (d, J=6.5 Hz, 6H).

Example 8: 8-bromo-N-isopropyl-5-(4-(trifluoromethyl)phenyl)-2-naphthamide (Compound 8)

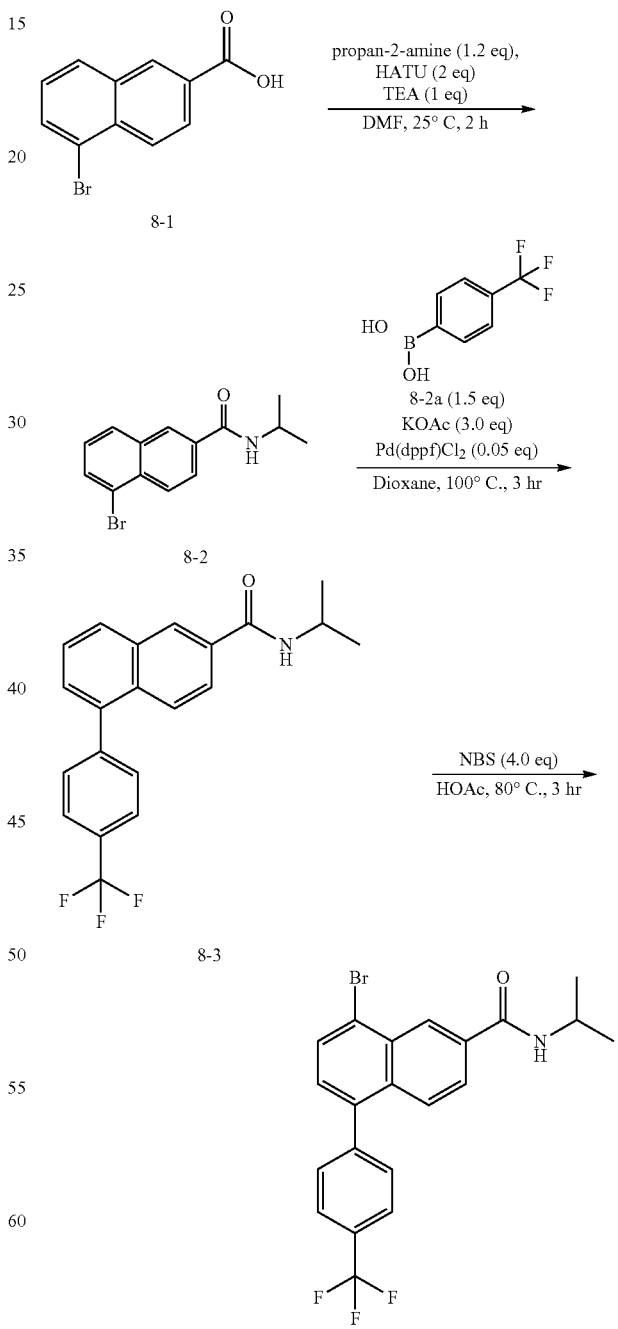

Compound 8

Step 1: 5-bromo-N-isopropyl-2-naphthamide

To a mixture of compound 8-1 (11 g, 43.81 mmol, 1 eq) in DMF (10 mL) was added HATU (33.32 g, 87.62 mmol, 2 eq) and Et₃N (4.43 g, 43.81 mmol, 6.10 mL, 1 eq). The mixture was stirred for 0.5 hrs at 25° C. Then propan-2-amine (3.11 g, 52.57 mmol, 4.52 mL, 1.2 eq) was added to the mixture. The mixture was stirred for 1.5 hrs at 25° C. LCMS showed the reaction was finished. The mixture was quenched by H₂O (30 mL), and the mixture was extracted with EA (20 mL*3). The combined organic phase was washed with brine (20 mL*3), dried with anhydrous Na₂SO₄, filtered and concentrated in vacuum. The residue was purified by column chromatography (SiO₂, Petroleum ether/Ethyl acetate=50/1 to 5:1). Compound 8-2 (11 g, 37.65 mmol, 85.9% yield) was obtained as a yellow solid.

Step 2: N-isopropyl-5-(4-(trifluoromethyl)phenyl)-2-naphthamide

A mixture of compound 8-2 (1 g, 3.42 mmol, 1 eq), compound 8-2a (975.0 mg, 5.13 mmol, 1.5 eq), KOAc (1.01 g, 10.2 mmol, 3 eq), Pd(dppf)Cl₂ (125.2 mg, 0.17 mmol, 0.05 eq) in dioxane (15 mL) was degassed and purged with N₂ for 3 times, and then the mixture was stirred at 100° C. for 3 hr under N₂ atmosphere. The residue was poured into H₂O (50 mL) and stirred for 5 min. The aqueous phase was extracted with EA (30 mL*3). The combined organic phase was washed with brine (50 mL), dried with anhydrous Na₂SO₄, filtered and concentrated in vacuo to give crude product. The residue was purified by flash silica gel chromatography. Compound 8-3 (920 mg, 2.57 mmol, 75.2% yield) was obtained as a white solid.

Step 3: 8-bromo-N-isopropyl-5-(4-(trifluoromethyl)phenyl)-2-naphthamide

To a solution of compound 8-3 (150 mg, 0.41 mmol, 1 eq) in HOAc (5 mL) was added NBS (298.8 mg, 1.68 mmol, 4 eq). The mixture was stirred at 80° C. for 3 hr. The mixture was cooled to rt. Then iced water (20 mL) was added and the mixture was neutralized to pH=7.5 with aq. NaOH (2 M). The aqueous phase was extracted with ethyl acetate (15 mL*3). The combined organic phase was washed with brine (30 mL), dried with anhydrous Na₂SO₄, filtered and concentrated in vacuum. The residue was purified by prep-HPLC to give the title compound (42.7 mg, 96.9 umol, 23% yield) as a white solid. LCMS (ESI): RT=0.938 min, mass calcd for $C_{21}H_{17}BrF_3NO$ 436.26, m/z found 437.7 [M+H]⁺; ¹H NMR (400 MHz, DMSO-d₆) δ 8.73 (d, J=1.3 Hz, 1H), 8.64 (d, J=7.5 Hz, 1H), 8.07 (d, J=7.5 Hz, 1H), 8.01 (dd, J=1.5, 8.8 Hz, 1H), 7.94 (d, J=8.0 Hz, 2H), 7.83 (d, J=8.8 Hz, 1H), 7.74 (d, J=8.0 Hz, 2H), 7.50 (d, J=7.8 Hz, 1H), 4.18 (qd, J=6.7, 13.8 Hz, 1H), 1.22 (d, J=6.5 Hz, 6H).

Example 9: Methyl 1-[4-(trifluoromethyl)phenyl]isoquinoline-6-carboxylate (Compound 9)

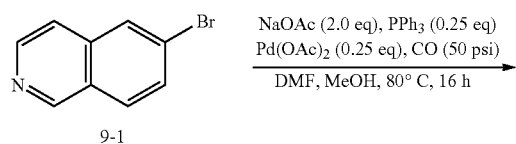

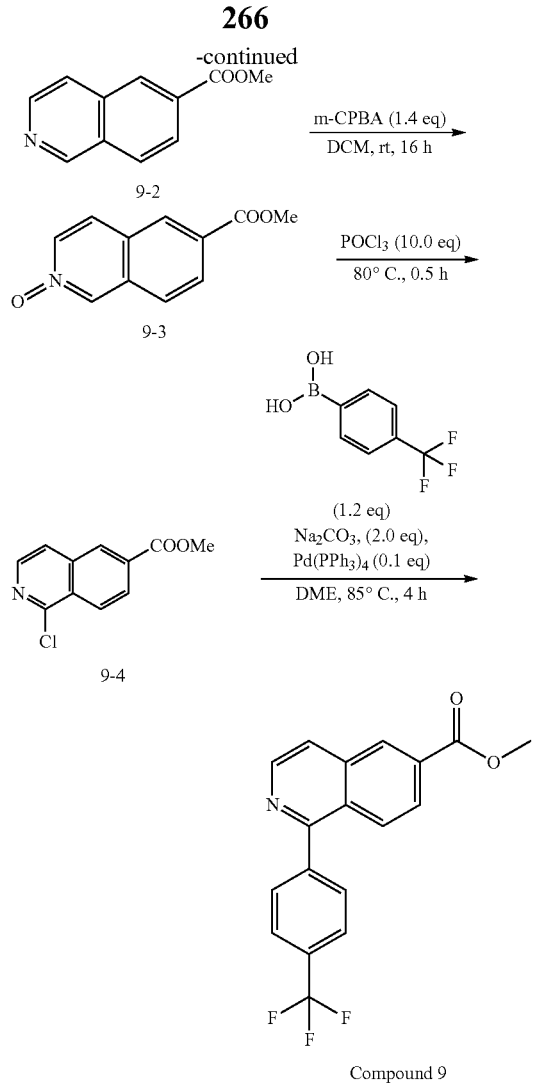

Compound 9

Step 1: Methyl isoquinoline-6-carboxylate

To a solution of compound 9-1 (2 g, 9.6 mmol, 1 eq), NaOAc (1.58 g, 19.2 mmol, 2 eq) and PPh₃ (630.3 mg, 2.4 mmol, 0.25 eq) in DMF (20 mL) and MeOH (20 mL) was added Pd(OAc)₂ (539.5 mg, 2.4 mmol, 0.25 eq). The suspension was degassed under vacuum and purged with CO several times. The mixture was stirred under CO (50 psi) at 80° C. for 16 hours. LCMS showed that 76% of desired product was detected. The MeOH was removed. The residue was diluted with EA (30 mL) and washed with brine (2*15 mL). The organic layer was dried over Na₂SO₄ and concentrated. The crude product was used for next step directly. Compound 9-2 (1.6 g, 8.55 mmol, 88.91% yield) was obtained as a yellow solid.

Step 2: Methyl 2-oxidoisoquinolin-2-ium-6-carboxylate

To a solution of compound 9-2 (1.3 g, 6.9 mmol, 1 eq) in DCM (15 mL) was added m-CPBA (1.95 g, 9.6 mmol, 1.38 eq) in portions at 0° C. The reaction was stirred at 25° C. for 16 hr. LCMS showed that 40% of desired product was detected. The reaction was diluted with EA (50 mL) and washed with Sat.Na₂CO₃ (3*15 mL). The organic layer was dried over Na$_2$SO$_4$ and concentrated. The compound 9-3 (0.7 g, 2.72 mmol, 39.19% yield) was used for next step directly as a yellow solid. LCMS confirmed that desired product was obtained.

Step 3: Methyl 2-oxidoisoquinolin-2-ium-6-carboxylate

Compound 9-3 (0.7 g, 3.4 mmol, 1 eq) was added into POCl$_3$ (3 mL) in portions, and the reaction was heated at 80° C. for 0.5 hr. LCMS showed that 29% of desired product was detected. The reaction was poured into water (10 mL), adjusted pH to 7 with Sat.NaHCO$_3$ and extracted with EA (2*15 mL). The organic layer was dried over Na$_2$SO$_4$ and concentrated. The crude product was purified by column chromatography on silica gel (EA:PE=1:10~1:5) to give compound 9-4 (260 mg, 0.94 mmol, 17.03% yield) as a white solid. $^1$H NMR (400 MHz, CDCl$_3$) δ 8.59 (d, J=1.25 Hz, 1H), 8.44-8.35 (m, 2H) 8.27 (dd, J=8.78, 1.51 Hz, 1H), 7.72 (d, J=5.52 Hz, 1H).

Step 4: Methyl 1-[4-(trifluoromethyl)phenyl]isoquinoline-6-carboxylate

A mixture of compound 9-4 (60 mg, 0.27 mmol, 1 eq), [4-(trifluoromethyl)phenyl]boronic acid (61.7 mg, 0.32 mmol, 1.2 eq), Na$_2$CO$_3$ (57.3 mg, 0.54 mmol, 2 eq) and Pd(PPh$_3$)$_4$ (31.8 mg, 27 umol, 0.1 eq) in DME (3 mL) was de-gassed and then heated at 85° C. for 4 hours under N$_2$. LCMS showed that 28% of desired product was detected. The reaction was concentrated. The residue was diluted with EA (20 mL) and washed with brine (2*10 mL). The organic layer was dried over Na$_2$SO$_4$ and concentrated. The crude product was purified by prep-HPLC to give the title compound (12 mg, 35.35 umol, 13.06% yield) as a white solid. LCMS (ESI): RT=0.815 min, mass calcd for C$_{18}$H$_{12}$F$_3$NO$_2$ 331.08, m/z found 331.9 [M+H]$^+$; $^1$H NMR (400 MHz, DMSO-d$_6$) δ 8.80 (s, 1H), 8.75 (d, J=5.52 Hz, 1H), 8.17 (d, J=5.77 Hz, 1H), 8.12 (s, 2H), 7.90-8.00 (m, 4H), 3.96 (s, 3H).

Example 10: Methyl 1-chloro-4-[4-(trifluoromethyl)phenyl]isoquinoline-7-carboxylate (Compound 10)

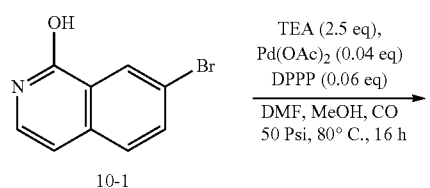

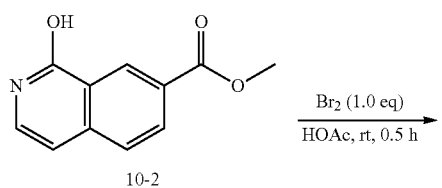

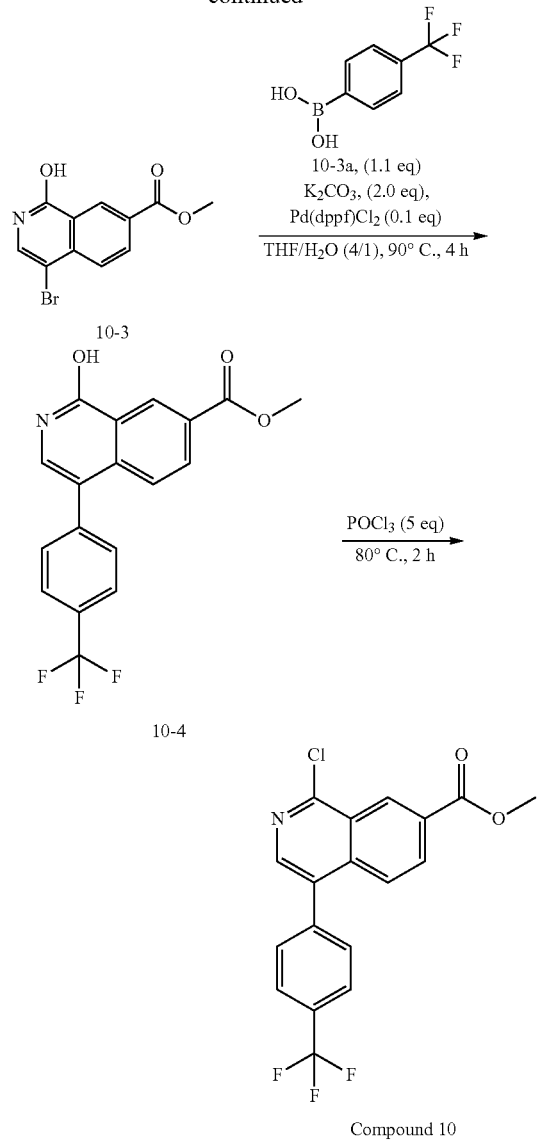

Compound 10

Step 1: Methyl 1-hydroxyisoquinoline-7-carboxylate

To a solution of compound 10-1 (0.5 g, 2.23 mmol, 1 eq), Et$_3$N (564.5 mg, 5.58 mmol, 0.77 mL, 2.5 eq) and DPPP (55.2 mg, 0.13 mmol, 0.06 eq) in DMF (5 mL) and MeOH (5 mL) was added Pd(OAc)$_2$ (20 mg, 89.26 umol, 0.04 eq) under N$_2$. The suspension was degassed under vacuum and purged with CO several times. The mixture was stirred under CO (50 psi) at 80° C. for 16 hours. LCMS showed that 94% of desired product was detected. The reaction was filtered and removed the MeOH. The residue was diluted with EA (40 mL) and washed with brine (3*20 mL). The organic layer was dried over Na$_2$SO$_4$ and concentrated. The compound 10-2 (400 mg, 1.97 mmol, 88.21% yield) was used for next step directly as an off-white solid. HNMR confirmed that desired product was obtained. $^1$H NMR (400 MHz, CDCl$_3$) δ 11.08 (br s, 1H), 9.08 (d, J=1.76 Hz, 1H), 8.28 (dd, J=8.41, 1.88 Hz, 1H), 7.61 (d, J=8.28 Hz, 1H), 6.58 (d, J=7.28 Hz, 1H), 4.02-3.87 (m, 3H).

Step 2: methyl 4-bromo-1-hydroxy-isoquinoline-7-carboxylate

A mixture of $Br_2$ (220.2 mg, 1.38 mmol, 71.04 uL, 1 eq) and HOAc (2 mL) was added dropwise to a mixture of compound 10-2 (280 mg, 1.38 mmol, 1 eq) and HOAc (10 mL) and stirred at 25° C. for 30 minutes. LCMS showed that 53% of starting material was remained and 45% of desired product was detected. The reaction was diluted with water (20 mL) and filtered. The compound 10-3 (350 mg, 1.24 mmol, 89.95% yield) was obtained as a yellow solid which was used for next step directly without further purification.

Step 3: Methyl 1-hydroxy-4-[4-(trifluoromethyl)phenyl]isoquinoline-7-carboxylate To a solution of compound 10-3 (330 mg, 1.17 mmol, 1 eq), compound 10-3a (244.40 mg, 1.29 mmol, 1.1 eq) and $K_2CO_3$ (323.3 mg, 2.34 mmol, 2 eq) in THF (8 mL) and $H_2O$ (2 mL) was added Pd(dppf)$Cl_2$ (85.6 mg, 0.11 mmol, 0.1 eq) under $N_2$. The suspension was degassed under vacuum and purged with $N_2$ several times. The mixture was stirred under $N_2$ at 90° C. for 4 hours. LCMS showed that 36% of desired product was consumed. The reaction was concentrated. The residue was diluted with EA (15 mL) and washed with water (2*5 mL). The organic layer was dried over $Na_2SO_4$ and concentrated. The crude product was purified by column chromatography on silica gel (EA:PE=1:10-1:5) to give compound 10-4 (70 mg, 177.37 umol, 15.16% yield) as a white solid.

Step 4: Methyl 1-chloro-4-[4-(trifluoromethyl)phenyl]isoquinoline-7-carboxylate A solution of compound 10-4 (70 mg, 0.2 mmol, 1 eq) in $POCl_3$ (1.5 mL) was heated at 80° C. for 2 hr. LCMS showed that 81% of desired product was detected. The reaction was poured into water (5 mL), adjusted pH to 7 with Sat-.NaHCO$_3$ and extracted with EA (2*10 mL). The organic layer was dried over $Na_2SO_4$ and concentrated. The residue was purified by column chromatography on silica gel (EA:PE=1:10) to give the title compound (46 mg, 0.12 mmol, 59.90% yield) as a white solid. LCMS (ESI): RT=0.946 min, mass calcd for $C_{18}H_{11}ClF_3NO_2$ 365.04, m/z found 365.9 $[M+H]^+$; $^1H$ NMR (400 MHz, CDCl$_3$) δ 9.19 (d, J=1.00 Hz, 1H), 8.38-8.30 (m, 2H), 7.90 (d, J=8.78 Hz, 1H), 7.85 (d, J=8.03 Hz, 2H), 7.64 (d, J=8.03 Hz, 2H), 4.06 (s, 3H).

Example 11: N-isopropyl-1-[4-(trifluoromethyl)phenyl]isoquinoline-6-carboxamide (Compound 11)

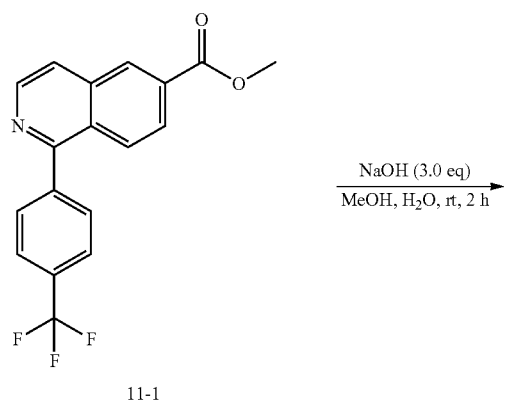

11-1

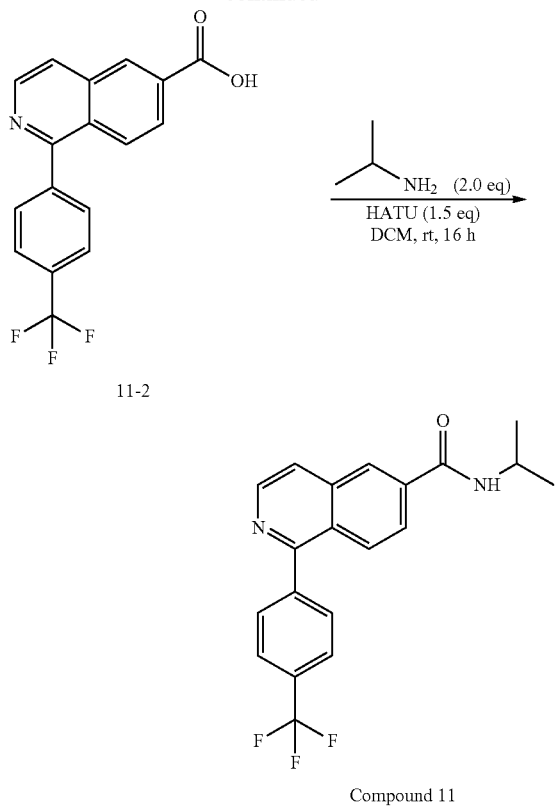

11-2

Compound 11

Step 1: 1-[4-(trifluoromethyl)phenyl]isoquinoline-6-carboxylic Acid

To a solution of compound 11-1 (45 mg, 0.13 mmol, 1 eq) in MeOH (3 mL) and $H_2O$ (3 mL) was added NaOH (16.3 mg, 0.4 mmol, 3 eq). The reaction was stirred at 25° C. for 2 hr. LCMS showed that 90% of desired product was detected. The reaction was concentrated. The residue was adjusted pH to 4-5 with 1N aq.HCl and extracted with EA (20 mL). The organic layer was dried over $Na_2SO_4$ and concentrated. Compound 11-2 (40 mg, 0.11 mmol, 83.5% yield) as a white solid was used for next step directly.

Step 2: N-isopropyl-1-[4-(trifluoromethyl)phenyl]isoquinoline-6-carboxamide

To a solution of compound 11-2 (40 mg, 0.12 mmol, 1 eq) and HATU (71.9 mg, 0.18 mmol, 1.5 eq) in DCM (2 mL) was added isopropylamine (14.9 mg, 0.25 mmol, 22 uL, 2 eq). The reaction was stirred at 25° C. for 16 hr. LCMS showed that 71% desired product was detected. The reaction was diluted with EA (30 mL) and washed with brine (3*10 mL). The organic layer was dried over $Na_2SO_4$ and concentrated. The residue was purified by prep-HPLC to give the title compound (14.67 mg, 40.94 umol, 32.47% yield) as a white solid. LCMS (ESI): RT=0.737 min, mass calcd for $C_{20}H_{17}F_3N_2O$ 358.13, m/z found 359.0 $[M+H]^+$; $^1H$ NMR (400 MHz, DMSO-d$_6$) δ 8.70 (d, J=5.52 Hz, 1H), 8.62 (d, J=7.78 Hz, 1H), 8.54 (s, 1H), 8.05-8.00 (m, 3H), 7.94 (q, J=8.28 Hz, 4H), 4.26-4.10 (m, 1H), 1.22 (d, J=6.53 Hz, 6H).

Example 12: Tert-Butyl (7-(isopropylcarbamoyl)-4-(4-(trifluoromethyl)phenyl)naphthalen-1-yl)carbamate (Compound 12)

Example 13: 8-chloro-N-isopropyl-5-(4-(trifluoromethyl)phenyl)-2-naphthamide (Compound 13)

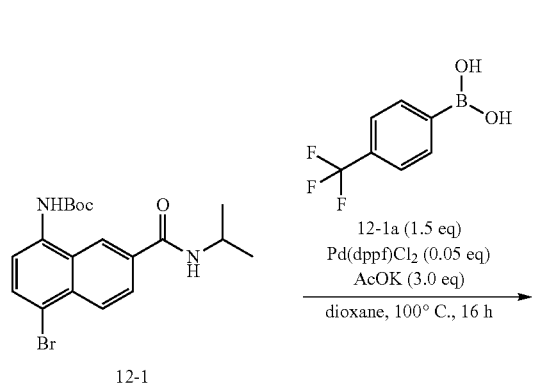

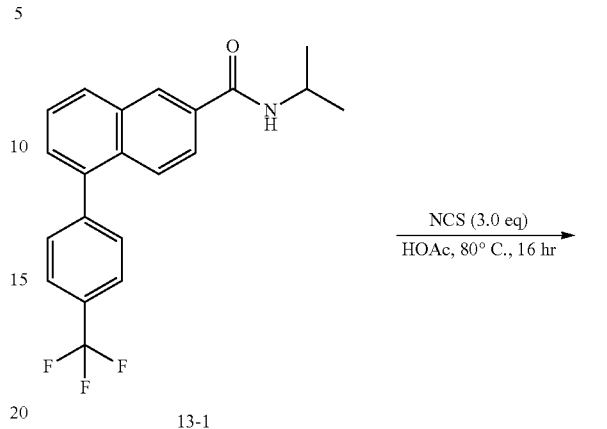

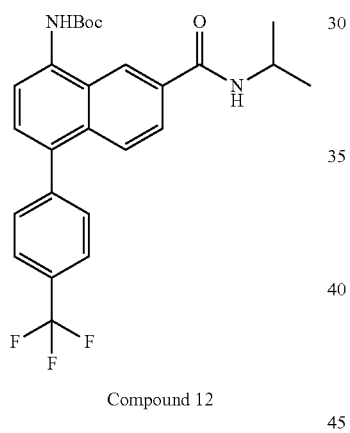

Compound 12

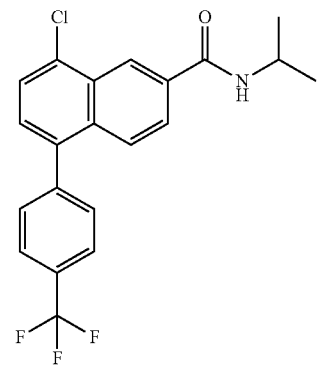

Compound 13

To a solution of compound 12-1 (220 mg, 0.54 mmol, 1 eq) in dioxane (2 mL) were added Pd(dppf)Cl$_2$ (19.8 mg, 27.0 umol, 0.05 eq), AcOK (159.0 mg, 1.62 mmol, 3 eq) and compound 12-1a (153.9 mg, 0.81 mmol, 1.5 eq). The mixture was stirred at 100° C. for 16 hr. LCMS showed that the starting material was consumed completely and 70% of desired product was detected. The reaction mixture was filtered and concentrated in vacuum. The residue was diluted with EA (20 mL), washed with brine (5 mL*2), dried over Na$_2$SO$_4$, filtered and concentrated in vacuum. The crude product was purified by column chromatography (SiO$_2$, Petroleum ether/Ethyl acetate=1/0 to 4:1). The title compound (300 mg, 0.55 mmol, 53.8% yield) was obtained as a white solid. LCMS (ESI): RT=0.935 min, mass calcd. For C$_{26}$H$_{27}$F$_3$N$_2$O$_3$, 472.20 m/z found 495.1 [M+Na]$^+$; $^1$H NMR (400 MHz, CHLOROFORM-d) δ 8.55 (s, 1H), 8.07 (br d, J=7.78 Hz, 1H), 7.86 (d, J=8.78 Hz, 1H), 7.75 (d, J=8.04 Hz, 2H), 7.64 (d, J=9.04 Hz, 1H), 7.57 (d, J=8.04 Hz, 2H), 7.48 (d, J=8.04 Hz, 1H), 7.13 (br s, 1H), 6.07 (br d, J=8.28 Hz, 1H), 4.36 (dq, J=13.62, 6.76 Hz, 1H), 1.59 (s, 9H), 1.32 (d, J=6.54 Hz, 6H).

To a solution of compound 13-1 (300 mg, 0.83 mmol, 1 eq) in HOAc (5 mL) was added NCS (336.2 mg, 2.52 mmol, 3 eq). The mixture was stirred at 80° C. for 16 hr. Then iced water (20 mL) was added and the mixture was neutralized to pH=7.5 with aq. NaOH (2 M), The aqueous phase was extracted with ethyl acetate (15 mL*3). The combined organic phase was washed with brine (30 mL), dried with anhydrous Na$_2$SO$_4$, filtered and concentrated in vacuum. The residue was purified by prep-HPLC to give 85 mg crude product. And then the crude product was purified by chiral SFC to give the title compound (51.8 mg, 0.13 mmol, 15.7% yield) as a white solid. LCMS (ESI): RT=0.934 min, mass calc. for C$_{21}$H$_{17}$ClF$_3$NO 391.1, m/z found 391.9 [M+H]$^+$; $^1$H NMR (400 MHz, DMSO-d$_6$) δ 8.77 (d, J=1.5 Hz, 1H), 8.66 (d, J=7.8 Hz, 1H), 8.02 (dd, J=1.8, 8.8 Hz, 1H), 7.93 (d, J=8.0 Hz, 2H), 7.86 (dd, J=8.4, 13.9 Hz, 2H), 7.73 (d, J=8.0 Hz, 2H), 7.57 (d, J=7.8 Hz, 1H), 4.23-4.10 (m, 1H), 1.22 (d, J=6.5 Hz, 6H), 1.16 (d, J=6.5 Hz, 1H).

Example 14: Methyl 1-oxo-4-[4-(trifluoromethyl)phenyl]-2H-isoquinoline-7-carboxylate (Compound 14)

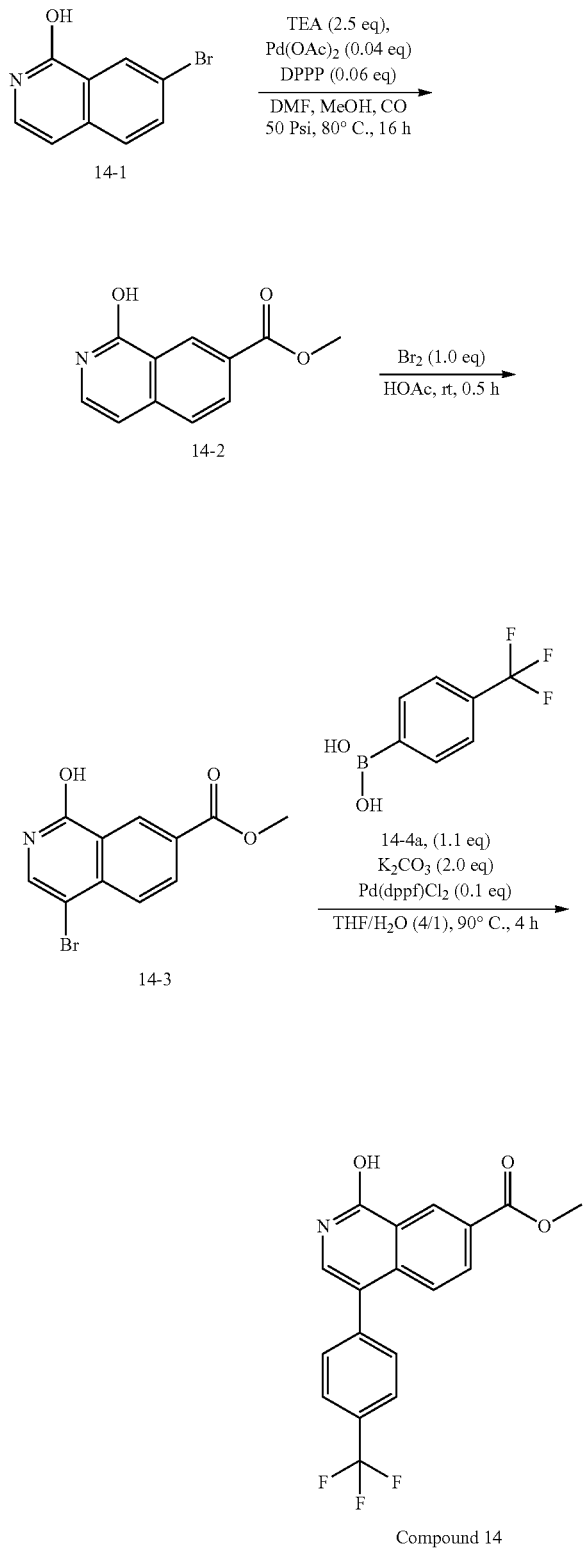

Step 1: Methyl 1-hydroxyisoquinoline-7-carboxylate

To a solution of compound 14-1 (0.5 g, 2.23 mmol, 1 eq), $Et_3N$ (564.5 mg, 5.58 mmol, 0.8 mL, 2.5 eq) and DPPP (55.2 mg, 0.13 mmol, 0.06 eq) in DMF (5 mL) and MeOH (5 mL) was added $Pd(OAc)_2$ (20 mg, 89.3 umol, 0.04 eq) under $N_2$. The suspension was degassed under vacuum and purged with CO several times. The mixture was stirred under CO (50 psi) at 80° C. for 16 hours. LCMS showed that 94% of desired product was detected. The reaction was filtered and removed the MeOH. The residue was diluted with EA (40 mL) and washed with brine (3*20 mL). The organic layer was dried over $Na_2SO_4$ and concentrated. The compound 14-2 (400 mg, 1.97 mmol, 88.2% yield) was used for next step directly as an off-white solid. HNMR confirmed that desired product was obtained. $^1H$ NMR (400 MHz, CHLOROFORM-d) 11.08 (br s, 1H), 9.08 (d, J=1.76 Hz, 1H), 8.28 (dd, J=8.41, 1.88 Hz, 1H), 7.61 (d, J=8.28 Hz, 1H), 6.58 (d, J=7.28 Hz, 1H), 4.02-3.87 (m, 3H).

Step 2: Methyl 4-bromo-1-hydroxy-isoquinoline-7-carboxylate

A mixture of $Br_2$ (220.2 mg, 1.38 mmol, 71 uL, 1 eq) and HOAc (2 mL) was added dropwise to a mixture of compound 14-2 (280 mg, 1.38 mmol, 1 eq) and HOAc (10 mL) and stirred at 25° C. for 30 minutes. LCMS showed that 53% of starting material was remained and 45% of desired product was detected. The reaction was diluted with water (20 mL) and filtered. The compound 14-3 (350 mg, 1.24 mmol, 89.9% yield) was used for next step directly as a yellow solid.

Step 3: Methyl 1-oxo-4-[4-(trifluoromethyl)phenyl]-2H-isoquinoline-7-carboxylate To a solution of compound 14-3 (1.9 g, 6.74 mmol, 1 eq), compound 14-4a (1.41 g, 7.41 mmol, 1.1 eq) and $K_2CO_3$ (1.86 g, 13.47 mmol, 2 eq) in THF (40 mL) and $H_2O$ (10 mL) was added $Pd(dppf)Cl_2$ (492.8 mg, 0.67 mmol, 0.1 eq) under $N_2$. The suspension was degassed under vacuum and purged with $N_2$ several times. The mixture was stirred under $N_2$ at 90° C. for 4 hours. LCMS showed that 36% of desired product was consumed. The reaction was concentrated. The residue was diluted with EA (100 mL) and washed with water (2*30 mL). The organic layer was dried over $Na_2SO_4$ and concentrated. The crude product was purified by column chromatography on silica gel (EA:PE=1:10~1:5) to give the title compound (480 mg, 1.24 mmol, 18.47% yield) as a white solid. LCMS (ESI): RT=0.802 min, mass calcd for $C_{18}H_{12}F_3NO_3$ 347.08, m/z found 347.9 $[M+H]^+$; $^1H$ NMR (400 MHz, DMSO-$d_6$) δ 11.85 (br, 1H), 8.89 (s, 1H), 8.20 (dd, J=8.4, 1.0 Hz, 2H), 7.88 (d, J=8.0 Hz, 2H), 7.70 (d, J=8.0 Hz, 2H), 7.62 (d, J=8.4 Hz, 1H), 7.40 (s, 1H), 3.92 (s, 3H).

Example 15: Methyl 2-methyl-1-oxo-4-[4-(trifluoromethyl)phenyl]isoquinoline-7-carboxylate (Compound 15)

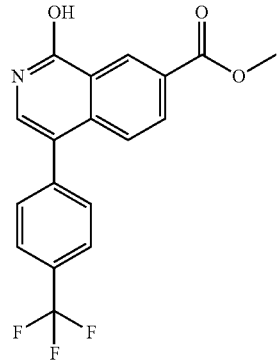

15-1

Cs₂CO₃ (1.5 eq)
MeI (1.3 eq)
DMF, 50° C., 3 h

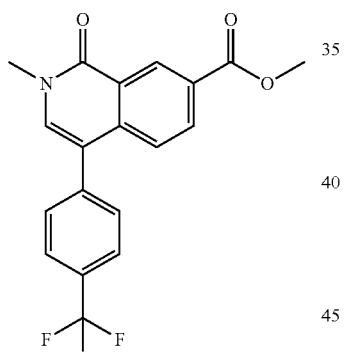

Compound 15

To a solution of compound 15-1 (50 mg, 0.14 mmol, 1 eq) and Cs₂CO₃ (70.4 mg, 0.21 mmol, 1.5 eq) in DMF (2 mL) was added MeI (26.5 mg, 0.18 mmol, 11.6 uL, 1.3 eq). The reaction was heated at 50° C. for 3 hr. LCMS showed that desired product was detected and HPLC showed that 80% of desired product was detected. The reaction was diluted with EA (15 mL) and washed with brine (2*10 mL). The organic layer was dried over Na₂SO₄ and concentrated. The residue was purified by prep-HPLC to give the title compound (25 mg, 69.19 umol, 48% yield) as a white solid. LCMS (ESI): RT=0.837 min, mass calc. for $C_{19}H_{14}F_3NO_3$ 361.09, m/z found 362.1 [M+1]⁺; ¹H NMR (400 MHz, CDCl₃) δ 9.20 (d, J=2.0 Hz, 1H), 8.23 (d, J=8.4, 2.0 Hz, 1H), 7.77 (d, J=8.4 Hz, 2H), 7.60-7.50 (m, 3H), 7.18 (s, 1H), 3.99 (s, 3H), 3.70 (s, 3H).

Example 16: 8-amino-N-isopropyl-5-(4-(trifluoromethyl)phenyl)-2-naphthamide (Compound 16)

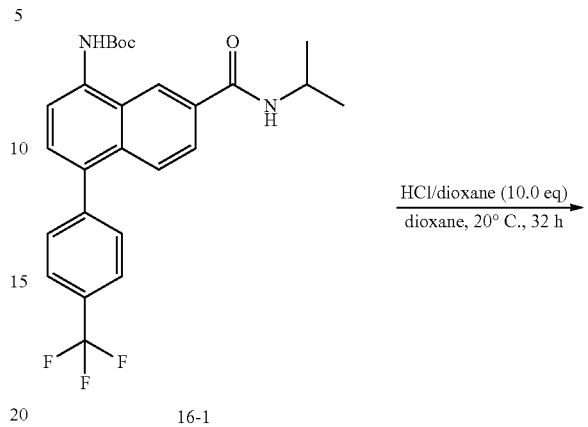

16-1

HCl/dioxane (10.0 eq)
dioxane, 20° C., 32 h

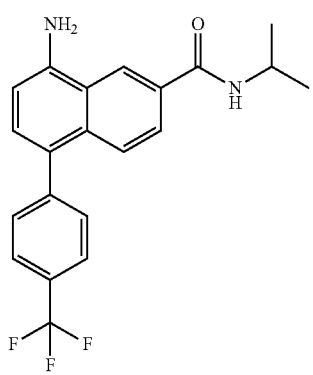

Compound 16

To a solution of compound 16-1 (20 mg, 42.3 umol, 1 eq) in dioxane (0.5 mL) was added HCl/dioxane (4 M, 0.1 mL, 10 eq). The mixture was stirred at 20° C. for 32 h. LCMS showed that the starting material was consumed completely and 76% of desired product was detected. The reaction mixture was concentrated in vacuum. The crude product was purified by prep-HPLC. The title compound (8 mg, 21.5 umol, 50.8% yield) was obtained as a light yellow solid. LCMS (ESI): RT=0.826 min, mass calcd. For $C_{21}H_{19}F_3N_2O$, 372.14 m/z found 372.9 [M+H]⁺; ¹H NMR (400 MHz, CHLOROFORM-d) δ 8.48 (s, 1H) 7.78 (d, J=8.76 Hz, 1H) 7.66 (br d, J=7.88 Hz, 2H) 7.61 (br d, J=8.88 Hz, 1H) 7.48 (br d, J=7.88 Hz, 2H) 7.26 (d, J=7.64 Hz, 1H) 6.96 (d, J=7.50 Hz, 1H) 6.12 (br d, J=7.38 Hz, 1H) 4.20-4.30 (m, 1H) 1.21 (d, J=6.50 Hz, 6H).

Example 17: 8-acetamido-N-isopropyl-5-(4-(trifluoromethyl)phenyl)-2-naphthamide (Compound 17)

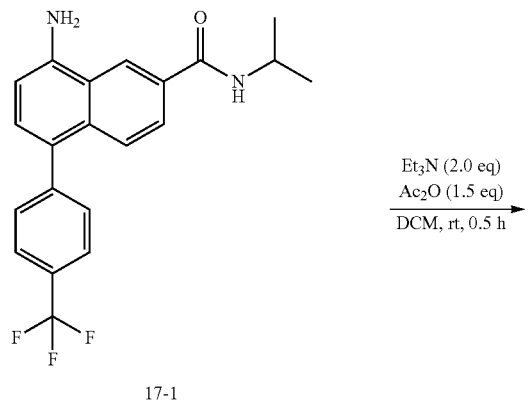

17-1

Et₃N (2.0 eq)
Ac₂O (1.5 eq)
———————→
DCM, rt, 0.5 h

Example 18: N-isopropyl-8-methylsulfanyl-5-[4-(trifluoromethyl)phenyl]naphthalene-2-carboxamide (Compound 18)

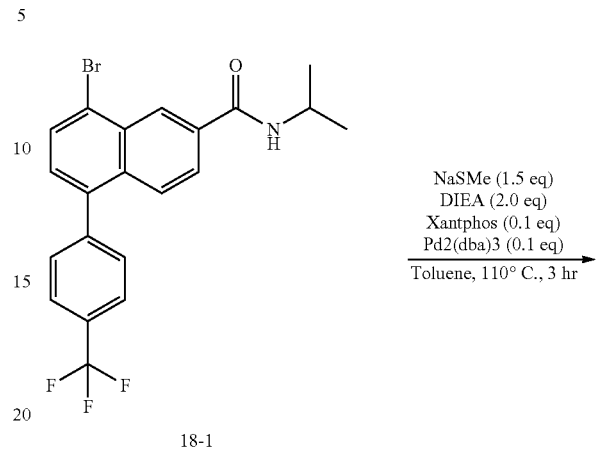

18-1

NaSMe (1.5 eq)
DIEA (2.0 eq)
Xantphos (0.1 eq)
Pd2(dba)3 (0.1 eq)
———————→
Toluene, 110° C., 3 hr

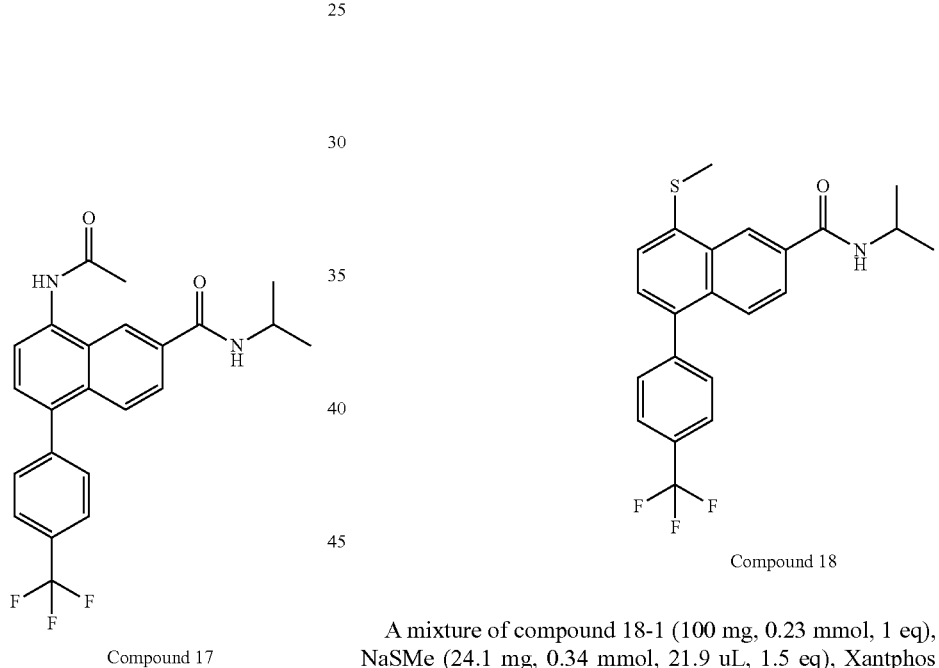

Compound 17

Compound 18

To a solution of compound 17-1 (50 mg, 0.14 mmol, 1 eq) in DCM (1 mL) was added TEA (27.2 mg, 0.27 mmol, 37.4 uL, 2 eq) and acetyl acetate (20.6 mg, 0.2 mmol, 18.9 uL, 1.5 eq). The mixture was stirred at 20° C. for 1 hr. LCMS showed that 85% of desired product was detected. The reaction mixture was concentrated in vacuum. The crude product was purified by prep-HPLC. The title compound (28 mg, 64.9 umol, 48.3% yield) was obtained as a white solid. LCMS (ESI): RT=0.787 min, mass calcd. For $C_{23}H_{21}F_3N_2O_2$, 414.16 m/z found 437.0 [M+Na]⁺; ¹H NMR (400 MHz, CHLOROFORM-d) δ 8.49 (s, 1H), 7.91-8.12 (m, 2H), 7.70-7.82 (m, 3H), 7.60 (br s, 1H), 7.51 (br d, J=7.76 Hz, 2H), 7.44 (br d, J=7.76 Hz, 1H), 6.24 (br d, J=7.64 Hz, 1H), 4.33 (dq, J=13.59, 6.74 Hz, 1H), 2.39 (s, 3H), 1.32 (d, J=6.50 Hz, 6H).

A mixture of compound 18-1 (100 mg, 0.23 mmol, 1 eq), NaSMe (24.1 mg, 0.34 mmol, 21.9 uL, 1.5 eq), Xantphos (13.2 mg, 22.9 umol, 0.1 eq), Pd₂(dba)₃ (20.9 mg, 22.9 umol, 0.1 eq) and DIPEA (59.2 mg, 0.46 mmol, 79.8 uL, 2 eq) in toluene (10 mL) was degassed and purged with N₂ for 3 times, and then the mixture was stirred at 110° C. for 3 hr under N₂ atmosphere. The residue was poured into H₂O (50 mL) and stirred for 5 min. The aqueous phase was extracted with EA (30 mL*3). The combined organic phase was washed with brine (50 mL), dried with anhydrous Na₂SO₄, filtered and concentrated in vacuum. The residue was purified by prep-HPLC to give the title compound (42.8 mg, 0.11 mmol, 46.2% yield) as a white solid. LCMS (ESI): RT=0.927 min, mass calc. for $C_{22}H_{20}F_3NOS$ 403.1, m/z found 404.0 [M+H]⁺; ¹H NMR (400 MHz, DMSO-d₆) δ 8.72 (d, J=1.4 Hz, 1H), 8.56 (d, J=7.6 Hz, 1H), 7.98 (dd, J=1.6, 8.9 Hz, 1H), 7.92 (d, J=8.1 Hz, 2H), 7.83 (d, J=8.9 Hz, 1H), 7.72 (d, J=8.0 Hz, 2H), 7.59-7.52 (m, 2H), 4.17 (q, J=6.7, 13.8 Hz, 1H), 2.69 (s, 3H), 1.22 (d, J=6.6 Hz, 6H).

Example 19: N-isopropyl-8-methyl-5-[4-(trifluoromethyl)phenyl]naphthalene-2-carboxamide (Compound 19)

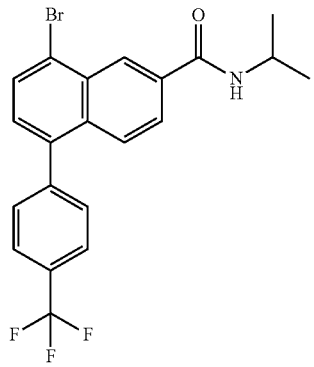

19-1

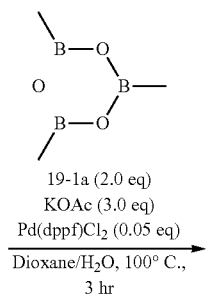

19-1a (2.0 eq)
KOAc (3.0 eq)
Pd(dppf)Cl₂ (0.05 eq)
Dioxane/H₂O, 100° C.,
3 hr

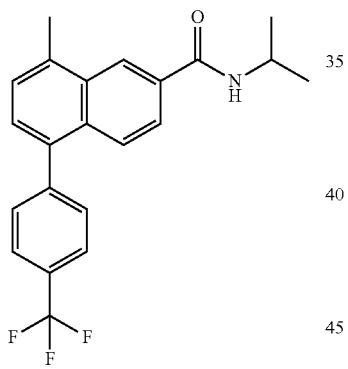

Compound 19

To a mixture of compound 19-1 (0.05 g, 0.11 mmol, 1 eq) and 19-1a (28.7 mg, 0.22 mmol, 32 uL, 2 eq) in dioxane (5 mL) and H₂O (1 mL) was added KOAc (33.7 mg, 0.34 mmol, 3 eq), Pd(dppf)Cl₂ (4.1 mg, 5.7 umol, 0.05 eq) under N₂. The mixture was stirred for 3 hrs at 100° C. LCMS showed the reaction was complete. The mixture was quenched by EA (30 mL), and the mixture was extracted with EA (20 mL*3). The combined organic phase was washed with brine (20 mL*3), dried with anhydrous Na₂SO₄, filtered and concentrated in vacuum. The residue was purified by prep-HPLC. The title compound (6.38 mg, 17.1 umol, 14.9% yield) was obtained as a white solid. LCMS (ESI): RT=0.915 min, mass calc. for: $C_{22}H_{20}F_3NO$ 371.40, m/z found 372.0 [M+H]⁺; ¹H NMR (400 MHz, CD₃OD) δ 8.65 (s, 1H), 7.90-7.82 (m, 4H), 7.67 (d, J=8.1 Hz, 2H), 7.52 (d, J=7.3 Hz, 1H), 7.45 (d, J=7.1 Hz, 1H), 4.35-4.26 (m, 1H), 2.85 (s, 3H), 1.33 (d, J=6.6 Hz, 6H).

Example 20: 8-ethynyl-N-isopropyl-5-[4-(trifluoromethyl)phenyl]naphthalene-2-carboxamide (Compound 20)

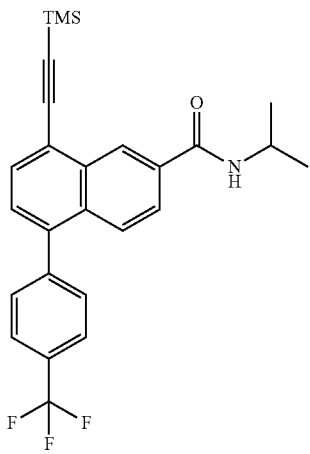

20-1

TBAF (1 M)
DCM, r.t, 10 min

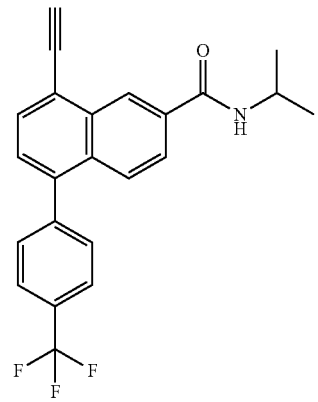

Compound 20

To a mixture of compound 20-1 (0.03 g, 66.1 umol, 1 eq) in DCM (1 mL) was added TBAF (1 M, 66.1 uL, 1 eq). The mixture was stirred for 10 mins at 25° C. LCMS showed the reaction was complete. The mixture was quenched by H₂O (30 mL), and the mixture was extracted with EA (20 mL*3). The combined organic phase was washed with brine (20 mL*3), dried with anhydrous Na₂SO₄, filtered and concentrated in vacuum. The residue was purified by prep-HPLC. The title compound (8.9 mg, 23.3 umol, 35.2% yield) was obtained as a white solid. LCMS (ESI): RT=0.908 min, mass calc. for: $C_{23}H_{18}F_3NO$ 381.39, m/z found 382.0 [M+H]⁺; ¹H NMR (400 MHz, CD₃OD) δ 8.92 (s, 1H), 7.91-7.85 (m, 5H), 7.70 (br d, J=7.9 Hz, 2H), 7.54 (d, J=7.4 Hz, 1H), 4.30 (td, J=6.6, 13.2 Hz, 1H), 4.14 (s, 1H), 1.32 (d, J=6.6 Hz, 6H).

Example 21: 8-ethyl-N-isopropyl-5-[4-(trifluoromethyl)phenyl]naphthalene-2-carboxamide (Compound 21)

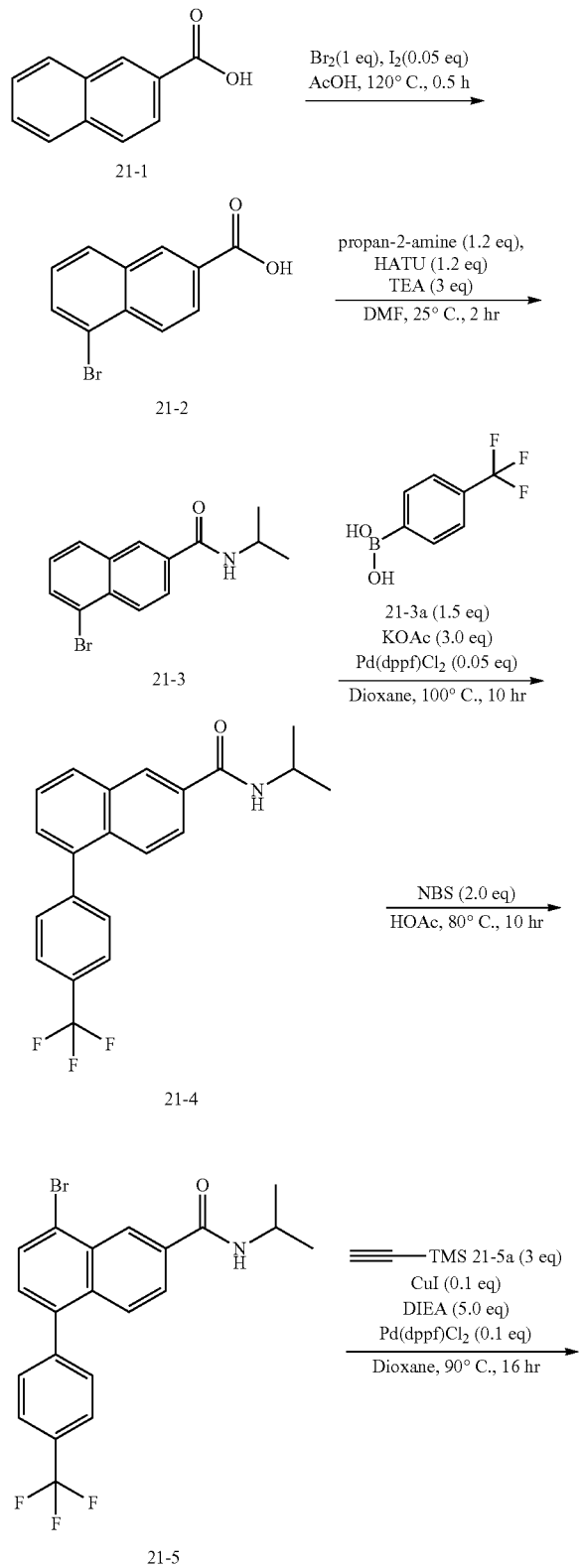

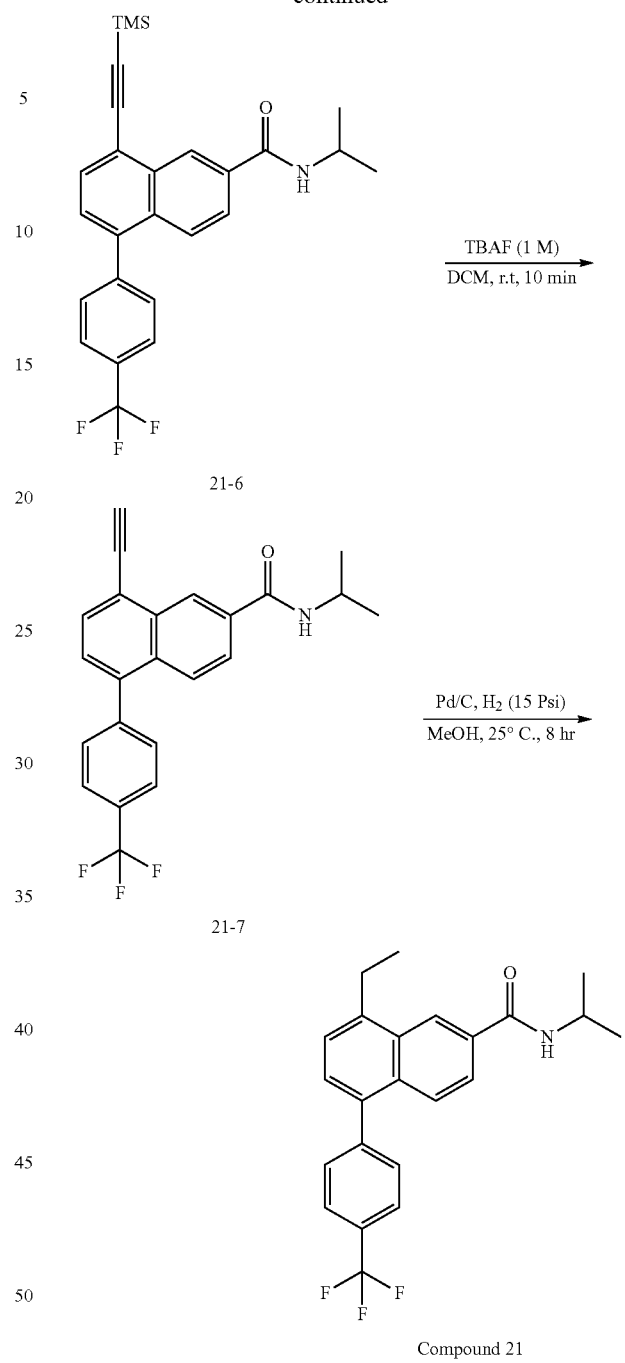

Step 1: 5-bromonaphthalene-2-carboxylic Acid

To a mixture of compound 21-1 (5 g, 29.04 mmol, 1 eq) in AcOH (50 mL) was added I₂ (368.5 mg, 1.45 mmol, 0.29 mL, 0.05 eq) and Br₂ (4.64 g, 29.04 mmol, 1.50 mL, 1 eq) under N₂. The mixture was stirred for 0.5 hrs at 120° C. The mixture was quenched by H₂O (100 mL), and the mixture was filtered and the filtered cake was washed with PE (100 mL*3). The crude product was used into the next step without further purification. Compound 21-2 (18 g, crude) was obtained as a white solid.

Step 2: 5-bromo-N-isopropyl-naphthalene-2-carboxamide

To a mixture of compound 21-2 (9 g, 35.85 mmol, 1 eq) in DMF (10 mL) was added HATU (16.36 g, 43.01 mmol, 1.2 eq) and Et₃N (10.88 g, 107.54 mmol, 14.97 mL, 3 eq). The mixture was stirred for 0.5 hrs at 25° C. Then propan-2-amine (2.54 g, 43.01 mmol, 3.70 mL, 1.2 eq) was added to the mixture. The mixture was stirred for 1.5 hrs at 25° C. The mixture was quenched by H₂O (30 mL), and the mixture was extracted with EA (20 mL*3). The combined organic phase was washed with brine (20 mL*3), dried with anhydrous Na₂SO₄, filtered and concentrated in vacuum. The residue was purified by column chromatography (SiO₂, Petroleum ether/Ethyl acetate=50/1 to 5:1). Compound 21-3 (20 g, 51.34 mmol, 71.6% yield) was obtained as a white solid.

Step 3: N-isopropyl-5-[4-(trifluoromethyl)phenyl]naphthalene-2-carboxamide

To a mixture of compound 21-3 (6 g, 20.54 mmol, 1 eq) and [4-(trifluoromethyl)phenyl]boronic acid 21-3a (5.85 g, 30.80 mmol, 1.5 eq) in dioxane (5 mL) was added KOAc (6.05 g, 61.61 mmol, 3 eq), Pd(dppf)Cl₂ (751.3 mg, 1.03 mmol, 0.05 eq) under N₂. The mixture was stirred for 10 hrs at 100° C. The mixture was quenched by EA (30 mL), and the mixture was filtered and the filtered cake was washed with EA (20 mL*3). The combined organic phase was washed with brine (20 mL*3), dried with anhydrous Na₂SO₄, filtered and concentrated in vacuum. The residue was purified by column chromatography (SiO₂, Petroleum ether/Ethyl acetate=50/1 to 10:1) to give the residue. Compound 21-4 (6.12 g, 17.13 mmol, 27.8% yield) was obtained as a white solid.

Step 4: 8-bromo-N-isopropyl-5-[4-(trifluoromethyl)phenyl]naphthalene-2-carboxamide To a mixture of compound 21-4 (2.5 g, 7.0 mmol, 1 eq) in AcOH (10 mL) was added NBS (2.49 g, 13.99 mmol, 2 eq) under N₂. The mixture was stirred for 10 hrs at 80° C. The mixture was quenched by NaOH (4 M, 100 mL) and the mixture was extracted with EA (30 mL*3). The combined organic phase was washed with brine (20 mL*3), dried with anhydrous Na₂SO₄, filtered and concentrated in vacuum. The residue was purified by column chromatography (SiO₂, Petroleum ether/Ethyl acetate=50/1 to 5:1). Compound 21-5 (3 g, 6.8 mmol, 48.6% yield) was obtained as a yellow solid.

Step 5: N-isopropyl-5-[4-(trifluoromethyl)phenyl]-8-(2-trimethylsilylethynyl)naphthalene-2-carboxamide To a mixture of compound 21-5 (0.2 g, 0.45 mmol, 1 eq) and ethynyl(trimethyl)silane 21-5a (135.0 mg, 1.3 mmol, 0.19 mL, 3 eq) in dioxane (2 mL) was added Pd(dppf)Cl₂ (33.5 mg, 45.8 mmol, 0.1 eq), CuI (8.7 mg, 45.8 umol, 0.1 eq) and DIPEA (296.2 mg, 2.2 mmol, 0.39 mL, 5 eq). The mixture was stirred for 10 hrs at 100° C. LCMS showed the reaction was complete. The mixture was quenched by EA (30 mL), and the mixture was filtered and the filtered cake was washed with EA (20 mL*3). The combined organic phase was washed with brine (20 mL*3), dried with anhydrous Na₂SO₄, filtered and concentrated in vacuum. The residue was purified by column chromatography (SiO₂, Petroleum ether/Ethyl acetate=50/1 to 8:1). Compound 21-6 (0.15 g, 0.33 mmol, 72.1% yield) was obtained as a yellow solid.

Step 6: 8-ethynyl-N-isopropyl-5-[4-(trifluoromethyl)phenyl]naphthalene-2-carboxamide To a mixture of compound 21-6 (0.1 g, 0.22 mmol, 1 eq) in DCM (1 mL) was added TBAF (1 M, 0.22 mL, 1 eq). The mixture was stirred for 10 mins at 25° C. The mixture was quenched by H₂O (30 mL), and the mixture was extracted with EA (20 mL*3). The combined organic phase was washed with brine (20 mL*3), dried with anhydrous Na₂SO₄, filtered and concentrated in vacuum. The residue was purified by column chromatography (SiO₂, Petroleum ether/Ethyl acetate=50/1 to 8:1). Compound 21-7 (61 mg, 0.15 mmol, 72.5% yield) was obtained as a yellow solid.

Step 7: 8-ethyl-N-isopropyl-5-[4-(trifluoromethyl)phenyl]naphthalene-2-carboxamide To a solution of compound 21-7 (30 mg, 0.078 mmol, 1 eq) in MeOH (2 mL) was added Pd/C (30 mg, 10% wet) under N₂. The suspension was degassed under vacuum and purged with H₂ several times. The mixture was stirred under H₂ (15 psi) at 25° C. for 8 hrs. LCMS showed the reaction was complete. The reaction solution was filtered and the filtered was concentrated in vacuum. The residue was purified by prep-HPLC. The title compound (9.5 mg, 24.6 umol, 31.3% yield) was obtained as a white solid. LCMS (ESI): RT=0.939 min, mass calc. for: $C_{23}H_{22}F_3NO$ 385.17, m/z found 386.0 [M+H]⁺; ¹H NMR (400 MHz, DMSO) δ 8.66 (s, 1H), 8.50 (d, J=7.6 Hz, 1H), 7.96-7.88 (m, 3H), 7.81 (d, J=8.9 Hz, 1H), 7.71 (d, J=8.0 Hz, 2H), 7.58-7.47 (m, 2H), 4.19 (br d, J=7.1 Hz, 1H), 3.24 (q, J=7.4 Hz, 2H), 1.39 (t, J=7.4 Hz, 3H), 1.23 (d, J=6.6 Hz, 6H).

Example 22: 8-cyclopropyl-N-isopropyl-5-(4-(trifluoromethyl)phenyl)-2-naphthamide (Compound 22)

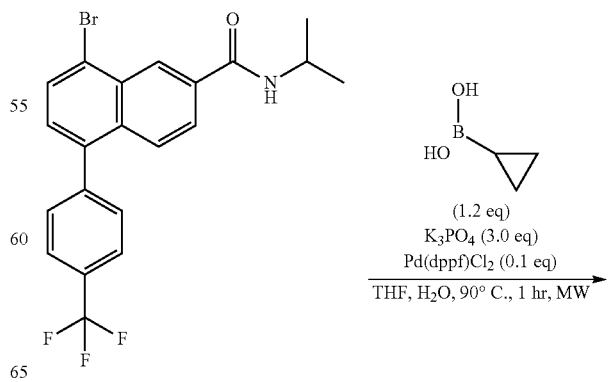

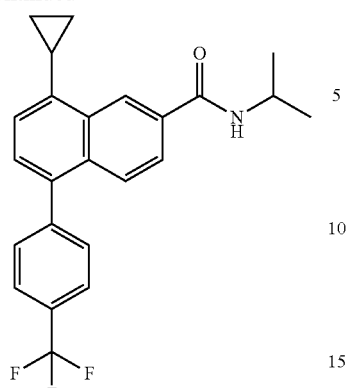

Compound 22

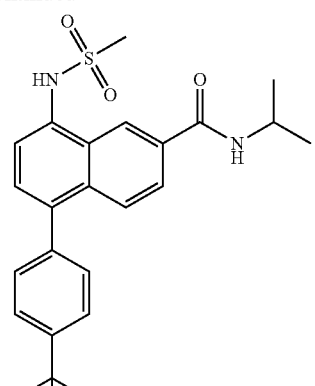

Compound 23

A mixture of compound 22-1 (100 mg, 0.22 mmol, 1 eq), cyclopropylboronic acid (23.6 mg, 0.27 mmol, 1.2 eq), $K_3PO_4$ (145.9 mg, 0.68 mmol, 3 eq), $H_2O$ (4.1 mg, 0.22 mmol, 4.13 uL, 1 eq) and Pd(dppf)Cl$_2$ (16.77 mg, 22.9 umol, 0.1 eq) in THF (5 mL) was the mixture was stirred at 90° C. for 1 hr under $N_2$ atmosphere with microwave. LC-MS and HPLC showed the desired compound was detected. The reaction mixture was diluted with $H_2O$ (5 mL) and the mixture was extracted with EA (6 mL*3). The combined organic phase was washed with brine (6 mL*2), dried with anhydrous $Na_2SO_4$, filtered and concentrated in vacuum. The residue was purified by prep-HPLC. The title compound (35 mg, 87.1 umol, 38.0% yield) was obtained as white solid. LCMS (ESI): RT=0.953 min, mass calc. for $C_{24}H_{22}F_3NO$ 397.17, m/z found 398.0 [M+H]$^+$; $^1$H NMR (400 MHz, DMSO-d$_6$) δ=0.82-0.86 (m, 2H) 1.13-1.18 (m, 2H) 1.23 (d, J=6.50 Hz, 6H) 2.59-2.65 (m, 1H) 4.15-4.22 (m, 1H) 7.38 (d, J=7.50 Hz, 1H) 7.45-7.49 (m, 1H) 7.70 (d, J=8.00 Hz, 2H) 7.81 (d, J=8.88 Hz, 1H) 7.88-7.98 (m, 3H) 8.49 (d, J=7.75 Hz, 1H) 8.98 (s, 1H).

To a solution of compound 23-1 (30 mg, 80.6 umol, 1 eq) in DCM (1 mL) were added TEA (24.5 mg, 0.24 mmol, 34 uL, 3 eq) and methanesulfonyl chloride (0.34 g, 2.97 mmol, 0.2 mL, 36 eq) at 0° C. The mixture was stirred at 20° C. for 4 hr. LCMS showed that the starting material was consumed completely and ~50% of desired mass was detected. The reaction mixture was concentrated in vacuum. The crude product was purified by prep-HPLC. The title compound (10 mg, 22.2 umol, 27.5% yield) was obtained as a light yellow solid. LCMS (ESI): RT=0.819 min, mass calcd. For $C_{22}H_{21}F_3N_2O_3S$, 450.12 m/z found 473.0 [M+Na]$^+$; $^1$H NMR (400 MHz, CDCl$_3$) δ 8.73-8.76 (m, 1H) 7.88-7.92 (m, 1H) 7.77-7.84 (m, 4H) 7.59 (d, J=8.00 Hz, 2H) 7.52 (d, J=7.75 Hz, 2H) 6.29 (br d, J=7.50 Hz, 1H) 4.31-4.40 (m, 1H) 3.14 (s, 3H) 1.32 (d, J=6.50 Hz, 6H).

Example 23: N-isopropyl-8-(methylsulfonamido)-5-(4-(trifluoromethyl)phenyl)-2-naphthamide (Compound 23)

Example 24: Methyl 4-[4-(trifluoromethyl)phenyl]isoquinoline-7-carboxylate (Compound 24)

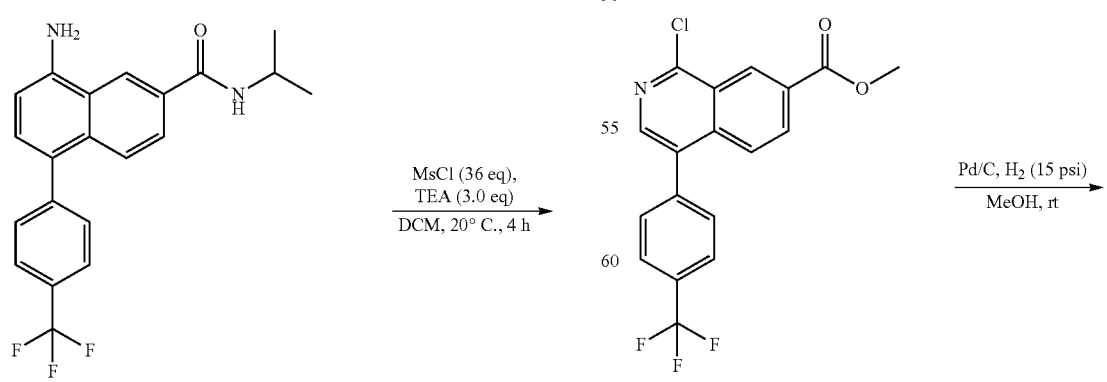

287
-continued

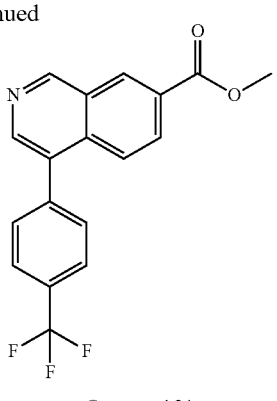

Compound 24

To a solution of compound 24-1 (140 mg, 0.38 mmol, 1 eq) in MeOH (3 mL) was added Pd/C (50 mg, 50% purity) under $N_2$. The suspension was degassed under vacuum and purged with $H_2$ several times. The mixture was stirred under $H_2$ (15 psi) at 25° C. for 3 hours. LCMS showed that 84% of desired product was detected. The reaction mixture was filtered and concentrated. 20 mg crude product was purified by prep-HPLC to give the title compound (4.42 mg, 12.67 umol, 3.3% yield) as a white solid. LCMS (ESI): RT=0.786 min, mass calcd for $C_{18}H_{12}F_3NO_2$ 330.08, m/z found 331.9 [M+H]$^+$; $^1$H NMR (400 MHz, CHLOROFORM-d) δ 9.43 (s, 1H), 8.85 (d, J=1.38 Hz, 1H), 8.61 (s, 1H), 8.30 (dd, J=8.88, 1.75 Hz, 1H), 7.92 (d, J=8.88 Hz, 1H), 7.85 (d, J=8.00 Hz, 2H), 7.67 (d, J=8.00 Hz, 2H), 4.00-4.09 (m, 3H).

Example 25: N-isopropyl-4-[4-(trifluoromethyl) phenyl]isoquinoline-7-carboxamide (Compound 25)

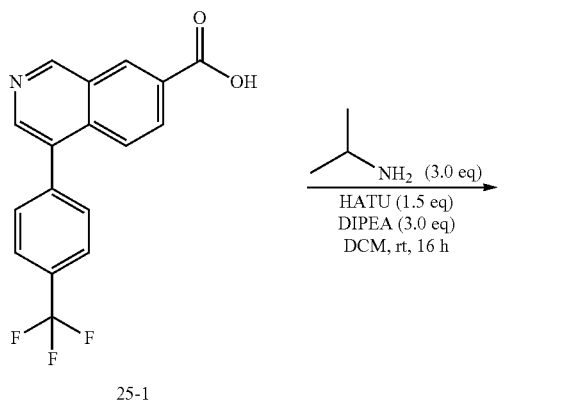

25-1

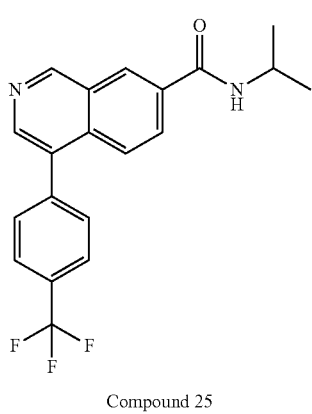

Compound 25

288

To a solution of compound 25-1 (50 mg, 0.16 mmol, 1 eq) and DIEA (61.1 mg, 0.47 mmol, 82 uL, 3 eq) in DCM (4 mL) was added isopropylamine (27.9 mg, 0.47 mmol, 41 uL, 3 eq) followed by HATU (89.8 mg, 0.24 mmol, 1.5 eq). The reaction was stirred at 25° C. for 16 hr. LCMS showed that 45% of desired product was detected. The reaction was diluted with DCM (15 mL) and washed with water (2*5 mL). The organic layer was dried over $Na_2SO_4$ and concentrated. The residue was purified by prep-HPLC to give the title compound (2.33 mg, 6.24 umol, 3.9% yield) as a white solid. LCMS (ESI): RT=0.722 min, mass calcd for $C_{20}H_{17}F_3N_2O$ 358.13, m/z found 359.0 [M+H]$^+$; $^1$H NMR (400 MHz, CDCl$_3$) δ 9.41 (s, 1H), 8.58 (s, 1H), 8.47 (s, 1H), 8.09 (dd, J=8.91, 1.63 Hz, 1H), 7.92 (d, J=8.78 Hz, 1H), 7.84 (d, J=8.03 Hz, 2H), 7.67 (d, J=8.03 Hz, 2H), 6.09 (s, 1H), 4.33-4.47 (m, 1H), 1.36 (d, J=6.53 Hz, 6H).

Example 26: N-isopropyl-2-methyl-1-oxo-4-(4-(trifluoromethyl)phenyl)-1,2-dihydroisoquinoline-7-carboxamide (Compound 26)

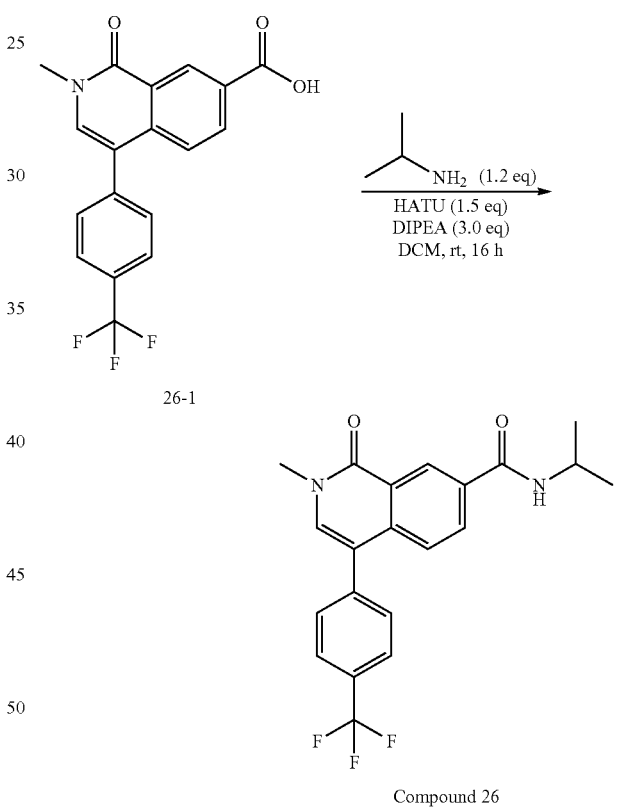

To a solution of compound 26-1 (13 mg, 37.4 umol, 1 eq) and isopropylamine (2.6 mg, 44.9 umol, 4 uL, 1.2 eq) in DCM (2 mL) was added HATU (21.3 mg, 56.1 umol, 1.5 eq) and DIEA (14.5 mg, 0.11 mmol, 19.5 uL, 3 eq). The reaction was stirred at 25° C. for 16 hr. LCMS showed that 58% of desired product was detected. The reaction was diluted with EA (20 mL) and washed with brine (2*10 mL). The organic layer was dried over $Na_2SO_4$ and concentrated. The residue was purified by prep-HPLC to give the title compound (3.15 mg, 8.11 umol, 21.6% yield) as a white solid. HNMR and LCMS confirmed that desired product was obtained. LCMS (ESI): RT=0.782 min, mass calc. for $C_{21}H_{19}F_3N_2O_2$ 388.14, m/z found 389.1 [M+1]⁺; ¹H NMR (400 MHz, CHLOROFORM-d) δ 8.76 (d, J=1.88 Hz, 1H), 8.23 (dd, J=8.51, 2.00 Hz, 1H), 7.78 (d, J=8.13 Hz, 2H), 7.58 (dd, J=12.26, 8.38 Hz, 3H), 7.18 (s, 1H), 6.26 (br d, J=6.63 Hz, 1H), 4.30-4.41 (m, 1H), 3.72 (s, 3H), 1.33 (d, J=6.63 Hz, 6H).

Example 27: N-isopropyl-8-methylsulfinyl-5-[4-(trifluoromethyl)phenyl]naphthalene-2-carboxamide (Compound 27)

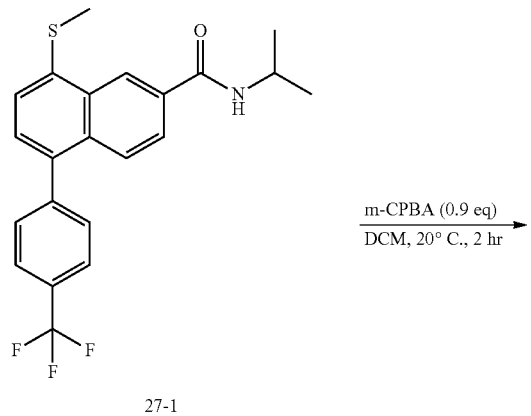

Example 28: N-isopropyl-8-methylsulfonyl-5-[4-(trifluoromethyl)phenyl]naphthalene-2-carboxamide (Compound 28)

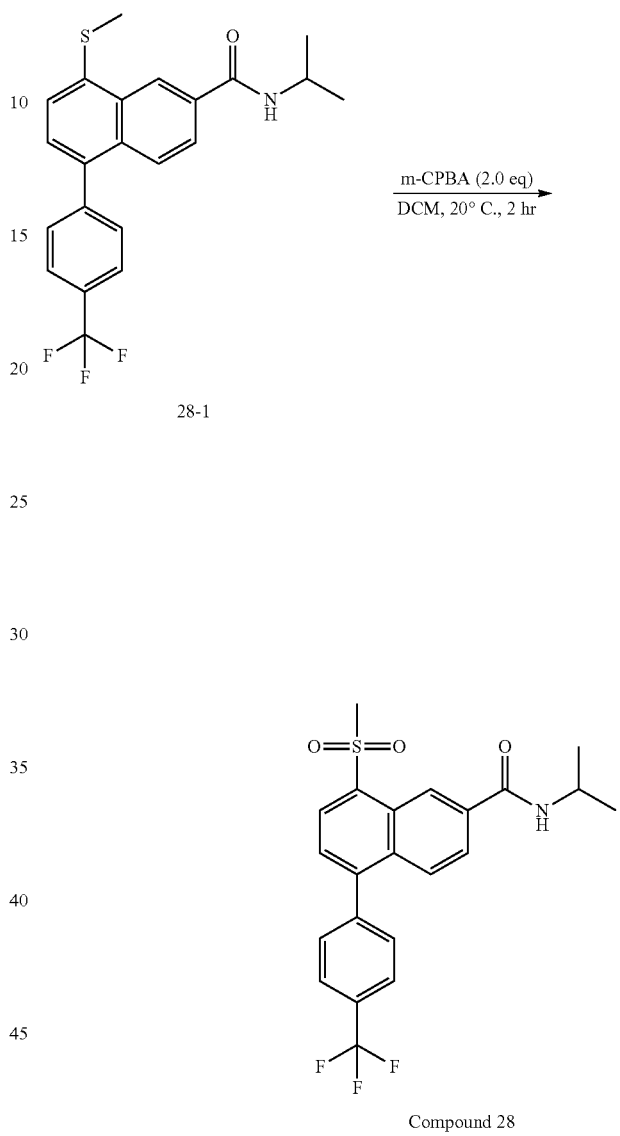

To a solution of compound 27-1 (120 mg, 0.3 mmol, 1 eq) in DCM (3 mL) was added m-CPBA (47.1 mg, 0.3 mmol, 0.9 eq). The mixture was stirred at 20° C. for 2 hr. LCMS showed reactant was consumed completely and ~83% of desired compound was detected (m/z=441.9; RT: 0.78 min). The reaction mixture was diluted with DCM (30 mL). This solution was washed sequentially with saturated Na₂SO₃ (20 mL*2), NaHCO₃ (20 mL*2), and brine (30 mL). The organic phase was dried over anhydrous Na₂SO₄, filtered and concentrated in vacuum. The residue was purified by prep-HPLC to give the title compound (65.8 mg, 0.2 mmol, 52.7% yield) as a white solid. LCMS (ESI): RT=0.790 min, mass calc. for C₂₂H₂₀F₃NO₂S 419.1, m/z found 442.0 [M+Na]⁺; ¹H NMR (400 MHz, DMSO-d₆) δ 8.59 (d, J=7.6 Hz, 1H), 8.48 (d, J=1.3 Hz, 1H), 8.23 (d, J=7.5 Hz, 1H), 8.06 (dd, J=1.6, 9.0 Hz, 1H), 7.99-7.89 (m, 3H), 7.86-7.74 (m, 3H), 4.17 (m, 1H), 2.93 (s, 3H), 1.23 (dd, J=2.6, 6.6 Hz, 6H).

To a solution of compound 28-1 (120 mg, 0.3 mmol, 1 eq) in DCM (3 mL) was added m-CPBA (104.8 mg, 0.6 mmol, 2 eq). The mixture was stirred at 20° C. for 2 hr. LCMS showed reactant was consumed completely and ~72% of desired compound was detected (m/z=436.0; RT: 0.82 min). The reaction mixture was diluted with DCM (30 mL). This solution was washed sequentially with saturated Na₂SO₃ (20 mL*2), NaHCO₃ (20 mL*2), and brine (30 mL). The organic phase was dried over anhydrous Na₂SO₄, filtered and concentrated in vacuum. The residue was purified by prep-HPLC to give the title compound (45.8 mg, 0.1 mmol, 35.4% yield) as a white solid. LCMS (ESI): RT=0.825 min, mass calc. for C₂₂H₂₀F₃NO₃S 435.1, m/z found 436.0 [M+H]⁺; ¹H NMR (400 MHz, DMSO-d₆) δ 9.14 (d, J=1.3 Hz, 1H), 8.58 (d, J=7.6 Hz, 1H), 8.38 (d, J=7.6 Hz, 1H), 8.06 (dd, J=1.6, 8.9 Hz, 1H), 8.00-7.91 (m, 3H), 7.78 (t, J=7.5 Hz, 3H), 4.26-4.10 (m, 1H), 3.49 (s, 3H), 1.23 (d, J=6.6 Hz, 6H).

Example 29: N-sulfamoyl-5-(4-(trifluoromethyl)phenyl)-2-naphthamide (Compound 29)

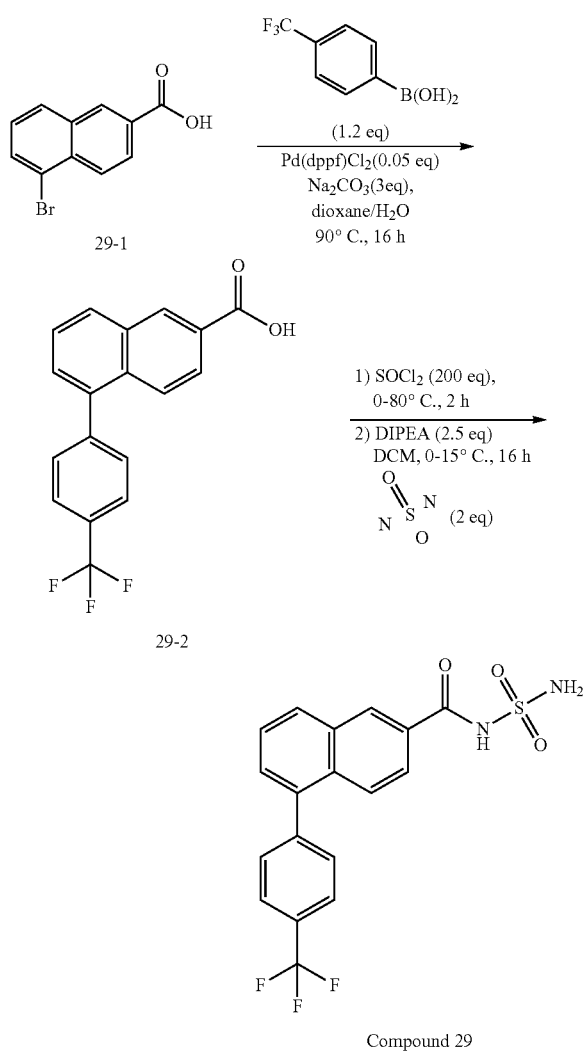

Compound 29

Step 1: 5-(4-(trifluoromethyl)phenyl)-2-naphthoic Acid

To a mixture of compound 29-1 (0.5 g, 1.99 mmol, 1 eq), [4-(trifluoromethyl)phenyl]boronic acid (453.9 mg, 2.39 mmol, 1.2 eq) and Na$_2$CO$_3$ (633.2 mg, 5.97 mmol, 3 eq) in dioxane (7 mL) and H$_2$O (1.3 mL) was added Pd(dppf)Cl$_2$ (72.9 mg, 99 umol, 0.05 eq) at 20° C. The mixture was degassed and refilled with nitrogen for three times and then stirred at 90° C. for 16 hr. LCMS showed no starting material was remained, 48% of desired product was detected. The mixture was concentrated to remove organic solvent, diluted with water (10 mL), adjusted to pH~11 with 1 M NaOH and extracted with EA (15 mL*2). The separated aqueous layer was adjusted to pH~2 with 1 M HCl and extracted with EA (25 mL*3). However, the combined organic layer was dried (Na$_2$SO$_4$), filtered and concentrated to give only 50 mg of residue. Then the above parts were combined, concentrated, diluted with a 7:1 solution of DCM:MeOH (30 mL) and filtered. The filtrate was concentrated to give a residue. The residue was purified by prep-HPLC to give compound 29-2 (0.21 g, 0.66 mmol, 33.3% yield) as a gray solid. $^1$H NMR (400 MHz, DMSO-d$_6$) δ 8.69 (s, 1H), 8.21 (d, J=8.1 Hz, 1H), 8.00 (dd, J=1.6, 8.8 Hz, 1H), 7.92 (d, J=8.1 Hz, 2H), 7.82 (d, J=8.9 Hz, 1H), 7.78-7.67 (m, 3H), 7.62 (d, J=6.5 Hz, 1H).

Step 2: N-sulfamoyl-5-(4-(trifluoromethyl)phenyl)-2-naphthamide

A solution of compound 29-2 (80 mg, 0.25 mmol, 1 eq) and SOCl$_2$ (6.02 g, 50.59 mmol, 3.7 mL, 200 eq) was heated at 80° C. for 2 h and then concentrated under vacuum to give a residue, which was quickly dissolved in DCM (3 mL). The resulting solution was drop-wise added to a solution of sulfamide (48.6 mg, 0.51 mmol, 30 uL, 2 eq) and DIPEA (81.7 mg, 0.63 mmol, 0.1 mL, 2.5 eq) in DCM (3 mL) at 0° C. Then the resulting mixture was stirred at 15° C. for 16 hr. LCMS showed no starting material was remained and 53% of desired product was detected. The mixture was quenched with 1 mL of water and then concentrated to give a residue. The residue was purified by prep-HPLC to give the title compound (28.1 mg, 69 umol, 27.3% yield) as a white solid. LCMS (ESI): RT=1.615 min, mass calc. for C$_{18}$H$_{13}$F$_3$O$_3$S 394.06, m/z found 395.0 [M+H]$^+$. NMR (400 MHz, DMSO-d6) δ 12.08 (s, 1H), 8.70 (d, J=1.3 Hz, 1H), 8.36 (s, 1H), 8.16 (d, J=8.3 Hz, 1H), 7.99-7.92 (m, 3H), 7.85 (d, J=9.0 Hz, 1H), 7.78-7.71 (m, 3H), 7.67-7.56 (m, 3H).

Example 30: N-isopropyl-8-(N-methylacetamido)-5-(4-(trifluoromethyl)phenyl)-2-naphthamide (Compound 30)

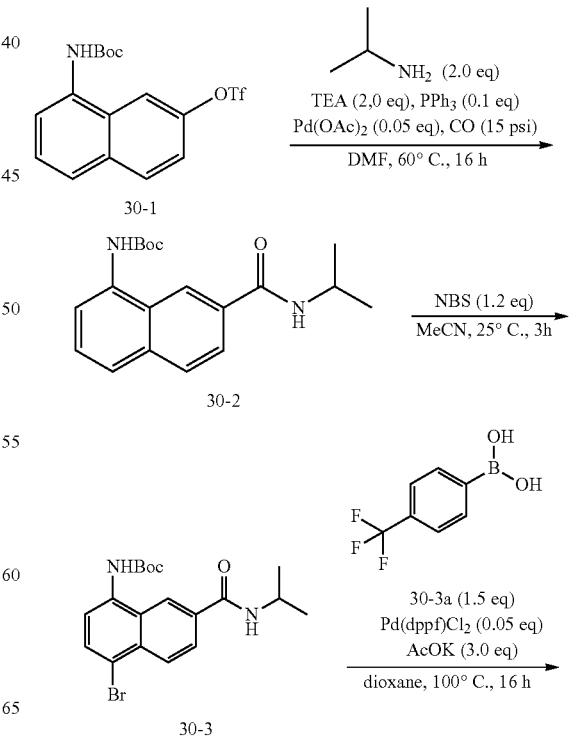

-continued

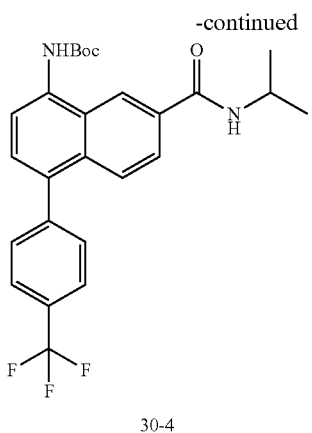

30-4

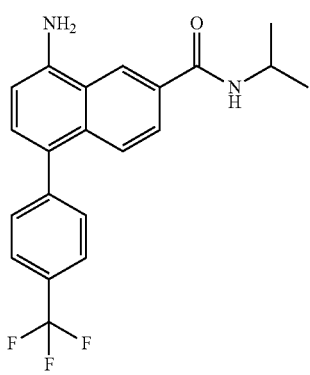

30-5

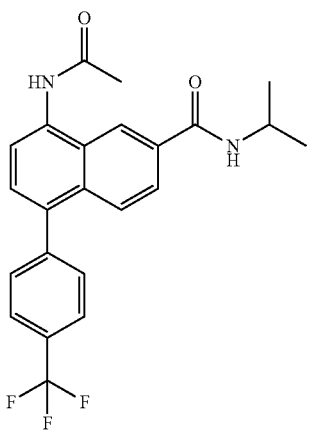

30-6

-continued

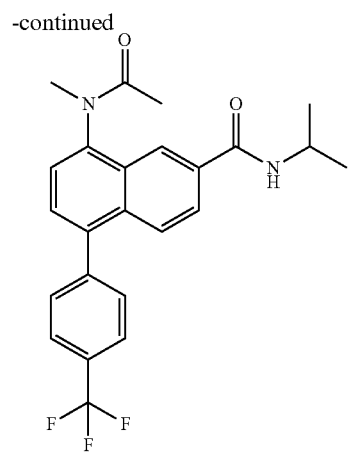

Compound 30

Step 1: Tert-Butyl (7-(isopropylcarbamoyl)naphthalen-1-yl)carbamate

To a solution of compound 30-1 (2.0 g, 5.11 mmol, 1 eq) in DMF (20 mL) were added TEA (1.03 g, 10.22 mmol, 1.4 mL, 2 eq), PPh$_3$ (134.0 mg, 0.51 mmol, 0.1 eq), Pd(OAc)$_2$ (57.4 mg, 0.26 mmol, 0.05 eq) and propan-2-amine (604.1 mg, 10.22 mmol, 0.88 mL, 2 eq). The reaction mixture was purged with CO, then heated to 60° C. and stirred for 16 hr under CO atmosphere. LCMS showed that 45% of desired product was detected. The reaction mixture was filtered and concentrated in vacuum. The residue was diluted with EA (20 mL) and washed with brine (5 mL*2), dried over Na$_2$SO$_4$, filtered and concentrated. The crude product was purified by column chromatography (SiO$_2$, Petroleum ether/Ethyl acetate=1/0 to 4:1). Compound 30-2 (700 mg, 2.07 mmol, 40.5% yield) was obtained as a white solid. $^1$H NMR (400 MHz, CDCl$_3$) δ 8.46 (s, 1H), 7.98 (br d, J=7.04 Hz, 1H), 7.86 (d, J=8.54 Hz, 1H), 7.70 (dd, J=8.54, 1.25 Hz, 1H), 7.62 (d, J=8.28 Hz, 1H), 7.50-7.56 (m, 1H), 7.12 (br s, 1H), 6.18 (br d, J=7.04 Hz, 1H), 4.29-4.42 (m, 1H), 1.57 (s, 9H), 1.31 (d, J=6.54 Hz, 6H).

Step 2: Tert-Butyl (4-bromo-7-(isopropylcarbamoyl) naphthalen-1-yl)carbamate To a solution of compound 30-2 (500 mg, 1.52 mmol, 1 eq) in MeCN (5 mL) was added NBS (325.2 mg, 1.83 mmol, 1.2 eq). The mixture was stirred at 25° C. for 1.5 hr. LCMS showed that 97% of desired product was detected. The reaction mixture was concentrated in vacuum. The residue was diluted with EA (20 mL), washed with brine (5 mL*2) and the organic phase was dried over Na$_2$SO$_4$, filtered and concentrated in vacuum. The crude product was purified by column chromatography (SiO$_2$, Petroleum ether/Ethyl acetate=1/0 to 4:1). Compound 30-3 (420 mg, 1.03 mmol, 67.7% yield) was obtained as a yellow solid.

Step 3: Tert-Butyl (7-(isopropylcarbamoyl)-4-(4-(trifluoromethyl)phenyl)naphthalen-1-yl)carbamate To a solution of compound 30-3 (220 mg, 0.54 mmol, 1 eq) in dioxane (2 mL) were added Pd(dppf)Cl$_2$ (19.8 mg, 27.0 umol, 0.05 eq), AcOK (159.0 mg, 1.62 mmol, 3 eq) and compound 30-3a (153.9 mg, 0.81 mmol, 1.5 eq). The mixture was stirred at 100° C. for 16 hr. LCMS showed that the starting material was consumed completely and 70% of desired product was detected. The reaction mixture was filtered and concentrated in vacuum. The residue was diluted with EA (20 mL), washed with brine (5 mL*2), dried over $Na_2SO_4$, filtered and concentrated in vacuum. The crude product was purified by column chromatography ($SiO_2$, Petroleum ether/Ethyl acetate=1/0 to 4:1). Compound 30-4 (300 mg, 0.55 mmol, 53.8% yield) was obtained as a white solid. LCMS (ESI): RT=0.935 min, mass calcd. For $C_{26}H_{27}F_3N_2O_3$, 472.20 m/z found 495.1 [M+Na]$^+$; $^1$H NMR (400 MHz, CDCl$_3$) δ 8.55 (s, 1H), 8.07 (br d, J=7.78 Hz, 1H), 7.86 (d, J=8.78 Hz, 1H), 7.75 (d, J=8.04 Hz, 2H), 7.64 (d, J=9.04 Hz, 1H), 7.57 (d, J=8.04 Hz, 2H), 7.48 (d, J=8.04 Hz, 1H), 7.13 (br s, 1H), 6.07 (br d, J=8.28 Hz, 1H), 4.36 (dq, J=13.62, 6.76 Hz, 1H), 1.59 (s, 9H), 1.32 (d, J=6.54 Hz, 6H).

Step 4: 8-amino-N-isopropyl-5-(4-(trifluoromethyl)phenyl)-2-naphthamide

To a solution of compound 30-4 (20 mg, 42.3 umol, 1 eq) in dioxane (0.5 mL) was added HCl/dioxane (4 M, 0.1 mL, 10 eq). The mixture was stirred at 20° C. for 32 h. LCMS showed that the starting material was consumed completely and 76% of desired product was detected. The reaction mixture was concentrated in vacuum. The crude product was purified by prep-HPLC. Compound 30-5 (8 mg, 21.5 umol, 50.8% yield) was obtained as a light yellow solid. LCMS (ESI): RT=0.826 min, mass calcd. For $C_{21}H_{19}F_3N_2O$, 372.14 m/z found 372.9 [M+H]$^+$; $^1$H NMR (400 MHz, CDCl$_3$) δ 8.48 (s, 1H) 7.78 (d, J=8.76 Hz, 1H) 7.66 (br d, J=7.88 Hz, 2H) 7.61 (br d, J=8.88 Hz, 1H) 7.48 (br d, J=7.88 Hz, 2H) 7.26 (d, J=7.64 Hz, 1H) 6.96 (d, J=7.50 Hz, 1H) 6.12 (br d, J=7.38 Hz, 1H) 4.20-4.30 (m, 1H) 1.21 (d, J=6.50 Hz, 6H).

Step 5: 8-acetamido-N-isopropyl-5-(4-(trifluoromethyl)phenyl)-2-naphthamide

To a solution of compound 30-5 (50 mg, 0.14 mmol, 1 eq) in DCM (1 mL) was added TEA (27.2 mg, 0.27 mmol, 37.4 uL, 2 eq) and acetyl acetate (20.6 mg, 0.2 mmol, 18.9 uL, 1.5 eq). The mixture was stirred at 20° C. for 1 hr. LCMS showed that 85% of desired product was detected. The reaction mixture was concentrated in vacuum. The crude product was purified by prep-HPLC. 30-6 (28 mg, 64.9 umol, 48.3% yield) was obtained as a white solid. LCMS (ESI): RT=0.787 min, mass calcd. For $C_{23}H_{21}F_3N_2O_2$, 414.16 m/z found 437.0 [M+Na]$^+$; $^1$H NMR (400 MHz, CDCl$_3$) δ 8.49 (s, 1H), 7.91-8.12 (m, 2H), 7.70-7.82 (m, 3H), 7.60 (br s, 1H), 7.51 (br d, J=7.76 Hz, 2H), 7.44 (br d, J=7.76 Hz, 1H), 6.24 (br d, J=7.64 Hz, 1H), 4.33 (dq, J=13.59, 6.74 Hz, 1H), 2.39 (s, 3H), 1.32 (d, J=6.50 Hz, 6H).

Step 6: N-isopropyl-8-(N-methylacetamido)-5-(4-(trifluoromethyl)phenyl)-2-naphthamide To a solution of compound 30-6 (5 mg, 12.1 umol, 1 eq) in DMF (0.2 mL) were added $K_2CO_3$ (8.34 mg, 60.3 umol, 5 eq) and MeI (0.89 g, 6.27 mmol, 0.39 mL, 520 eq). The mixture was stirred at 20° C. for 4 hr. LCMS showed that 56% of desired product was detected. The reaction mixture was filtered. The crude product was purified by prep-HPLC. The title compound (3.5 mg, 8.2 umol, 67.7% yield) was obtained as a white solid. LCMS (ESI): RT=0.824 min, mass calcd. For $C_{24}H_{23}F_3N_2O_2$, 428.17 m/z found 429.1 [M+H]$^+$; $^1$H NMR (400 MHz, CDCl$_3$) δ 8.28 (s, 1H), 7.93 (s, 2H), 7.81 (d, J=8.00 Hz, 2H), 7.62 (d, J=7.88 Hz, 2H), 7.51 (q, J=7.50 Hz, 2H), 6.19 (br d, J=7.63 Hz, 1H), 4.30-4.43 (m, 1H), 3.44 (s, 3H), 1.87 (s, 3H), 1.34 (d, J=6.63 Hz, 6H).

Example 31: 8-amino-7-bromo-N-isopropyl-5-(4-(trifluoromethyl)phenyl)-2-naphthamide (Compound 31)

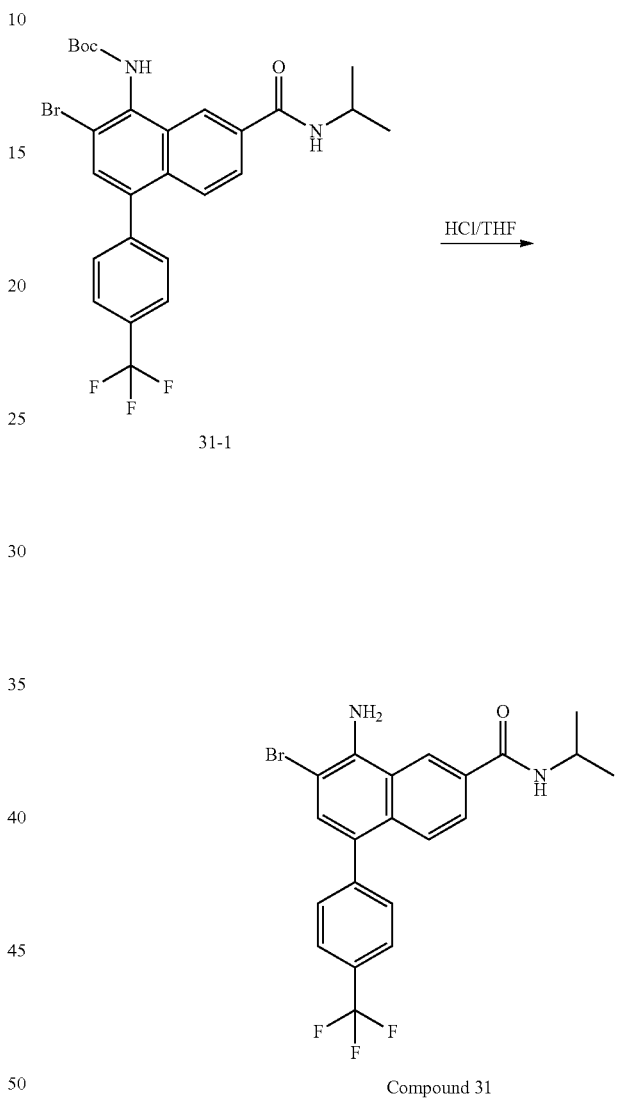

The mixture of compound 31-1 (0.41 g, 0.74 mmol, 1 eq) in HCl/EtOAc (4 M, 7.44 mL, 40 eq) was stirred at 25° C. for 2 hr. LCMS showed the reaction was complete. The mixture was concentrated in vacuum to afford the crude product (0.35 g, crude, HCl) as white solid. The crude product was used into the next step without more purification. The crude product (40 mg) was purified by Prep-HPLC to give the title compound (14.7 mg, 30.1 umol, HCl) as a white solid. LCMS (ESI): RT=1.069 min, mass calc. for $C_{21}H_{18}BrF_3N_2O$ 450.06, m/z found 453.4 [M+H]$^+$; $^1$H NMR (400 MHz, DMSO-d$_6$) δ 8.80 (d, J=1.3 Hz, 1H), 8.28 (d, J=7.6 Hz, 1H), 7.91 (dd, J=1.5, 8.9 Hz, 1H), 7.86 (d, J=8.1 Hz, 2H), 7.74 (d, J=8.9 Hz, 1H), 7.67 (d, J=8.0 Hz, 2H), 7.53 (s, 1H), 4.17 (qd, J=6.8, 13.8 Hz, 1H), 1.24 (d, J=6.5 Hz, 6H).

Example 32: 7-bromo-N-isopropyl-5-[4-(trifluoromethyl)phenyl]naphthalene-2-carboxamide (Compound 32)

Example 33: 8-amino-7-chloro-N-isopropyl-5-(4-(trifluoromethyl)phenyl)-2-naphthamide (Compound 33)

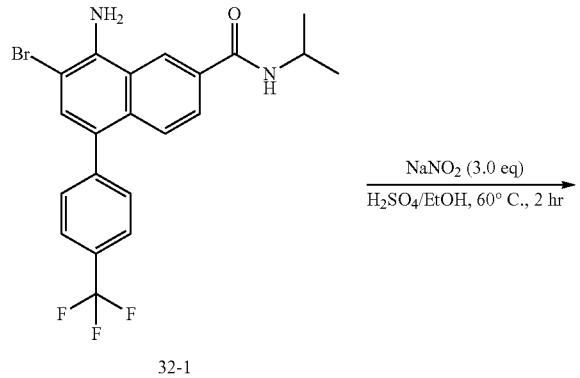

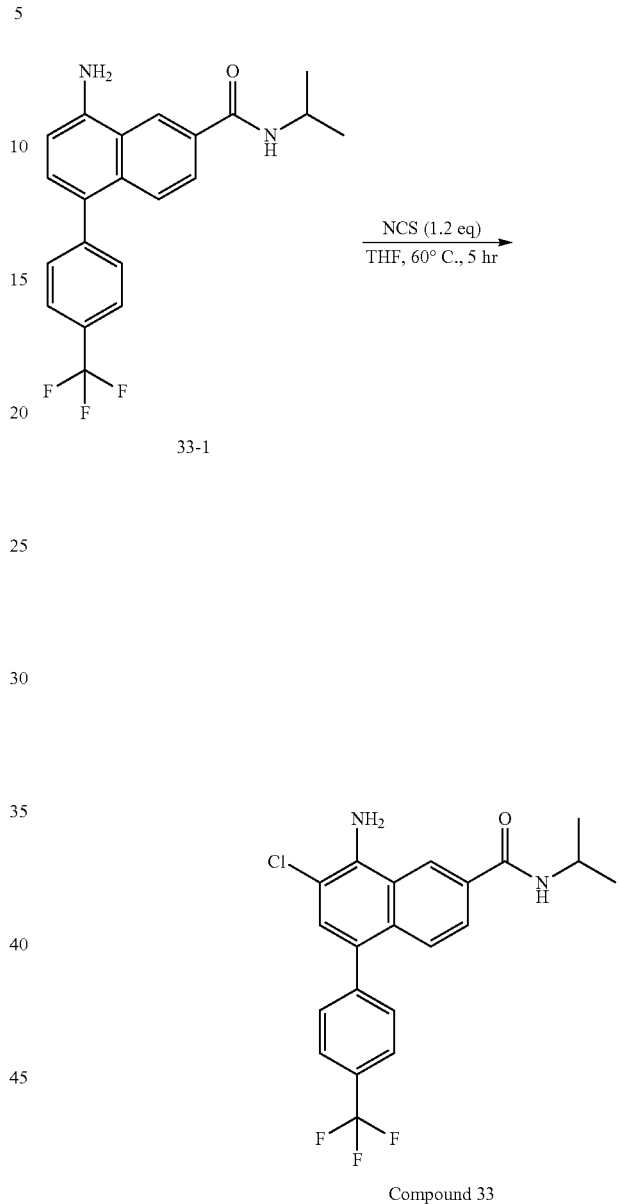

To a solution of compound 32-1 (650 mg, 1.44 mmol, 1 eq) in EtOH (2 mL) was added $H_2SO_4$ (1.20 g, 12.19 mmol, 0.65 mL, 8.47 eq) and sodium nitrite (298.1 mg, 4.32 mmol, 3 eq). The mixture was stirred at 60° C. for 2 hr. The reaction mixture was diluted with $H_2O$ (5 mL) and the mixture was extracted with EA (5 mL*3). The combined organic phase was washed with brine (5 mL*3), dried with anhydrous $Na_2SO_4$, filtered and concentrated in vacuum. The residue was purified by column chromatography ($SiO_2$, Petroleum ether/Ethyl acetate=0/1 to 1:1) to give the crude product (180 mg, 0.30 mmol, 20.9% yield) as a white solid. 40 mg of the crude product were purified by prep-HPLC to give the title compound (26 mg) as white solid. LCMS (ESI): RT=0.949 min, mass calc. for $C_{21}H_{17}BrF_3NO$ 435.04, m/z found 437.7 [M+H]$^+$; $^1$H NMR (400 MHz, DMSO-$d_6$) δ 1.08-1.29 (m, 1H) 1.21 (d, J=6.53 Hz, 5H) 4.15 (dq, J=13.80, 6.69 Hz, 1H) 7.67-7.79 (m, 1H) 7.71 (d, J=2.01 Hz, 1H) 7.76 (d, J=8.53 Hz, 2H) 7.89-7.99 (m, 3H) 8.39-8.52 (m, 3H).

To a mixture of compound 33-1 (0.05 g, 0.13 mmol, 1 eq) in THF (2 mL) was added NCS (21.5 mg, 0.16 mmol, 1.2 eq) under $N_2$. The mixture was stirred for 0.5 hrs at 25° C. LCMS showed the reaction was complete. The mixture was quenched by HCl (4 M, 20 mL) and the mixture was extracted with EA (10 mL*3). The combined organic phase was washed with brine (10 mL*3), dried with anhydrous $Na_2SO_4$, filtered and concentrated in vacuum. The residue was purified by prep-HPLC to give the title compound (6.8 mg, 15.2 umol, 11.3% yield, HCl) as a light yellow solid. LCMS (ESI): RT=0.903 min, mass calc. for $C_{21}H_{18}ClF_3N_2O$ 406.83, m/z found 406.9 [M+H]$^+$; $^1$H NMR (400 MHz, CD$_3$OD) δ 8.68 (s, 1H), 7.93-7.80 (m, 5H), 7.66 (br d, J=8.0 Hz, 2H), 7.48 (s, 1H), 7.51-7.46 (m, 1H), 4.29 (td, J=6.6, 13.2 Hz, 1H), 1.33 (d, J=6.5 Hz, 7H).

Example 34: N-isopropyl-8-(N-methylmethylsulfonamido)-5-(4-(trifluoromethyl)phenyl)-2-naphthamide (Compound 34)

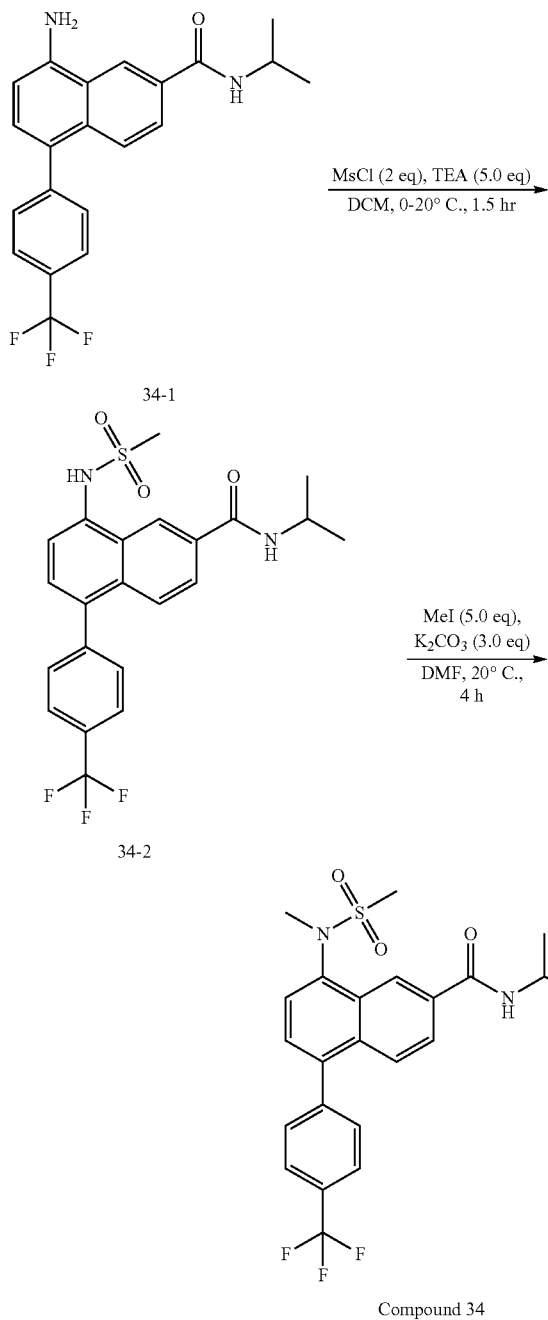

Step 1: N-isopropyl-8-(methylsulfonamido)-5-(4-(trifluoromethyl)phenyl)-2-naphthamide To a solution of compound 34-1 (120 mg, 0.32 mmol, 1 eq) in DCM (1 mL) were added TEA (163 mg, 0.64 mmol, 0.2 mL, 5 eq) and methanesulfonyl chloride (0.07 g, 4.02 mmol, 50 uL, 2 eq) at 0° C. The mixture was stirred at 20° C. for 1.5 hr. LCMS showed that the starting material was consumed completely and 20% desired product was detected. The reaction mixture was concentrated in vacuum. The crude product was purified by prep-HPLC. Compound 34-2 (14 mg, 31.08 umol, 9.6% yield) was obtained as a white solid. LCMS (ESI): RT=0.813 min, mass calcd. For $C_{22}H_{21}F_3N_2O_3S$, 450.12 m/z found 473.0 [M+Na]$^+$.

Step 2: N-isopropyl-8-(N-methylmethylsulfonamido)-5-(4-(trifluoromethyl)phenyl)-2-naphthamide To a solution of compound 34-2 (14 mg, 31 umol, 1 eq) in DMF (1 mL) were added $K_2CO_3$ (12.9 mg, 93 umol, 3 eq) and MeI (2.5 mg, 15 umol, 5 eq). The mixture was stirred at 20° C. for 4 hr. LCMS showed that the starting material was consumed completely and 82% of desired product was detected. The reaction mixture was filtered and concentrated in vacuum. The crude product was purified by prep-HPLC. The title compound (5 mg, 10.33 umol, 33.2% yield) was obtained as a white solid. LCMS (ESI): RT=0.829 min, mass calcd. For $C_{23}H_{23}F_3N_2O_3S$, 464.14 m/z found 487.0 [M+Na]$^+$; $^1$H NMR (400 MHz, CDCl$_3$) δ 8.66 (s, 1H), 7.87 (s, 2H), 7.80 (d, J=8.0 Hz, 2H), 7.65 (d, J=7.5 Hz, 1H), 7.59 (d, J=8.0 Hz, 2H), 7.51 (d, J=7.5 Hz, 1H), 6.14 (br d, J=7.3 Hz, 1H), 4.40-4.30 (m, 1H), 3.49 (s, 3H), 3.13 (s, 3H), 1.37-1.31 (m, 6H).

Example 35: N-isopropyl-5-[4-(trifluoromethyl)phenyl]benzo[e][1,2,3]benzoxadiazole-8-carboxamide (Compound 35)

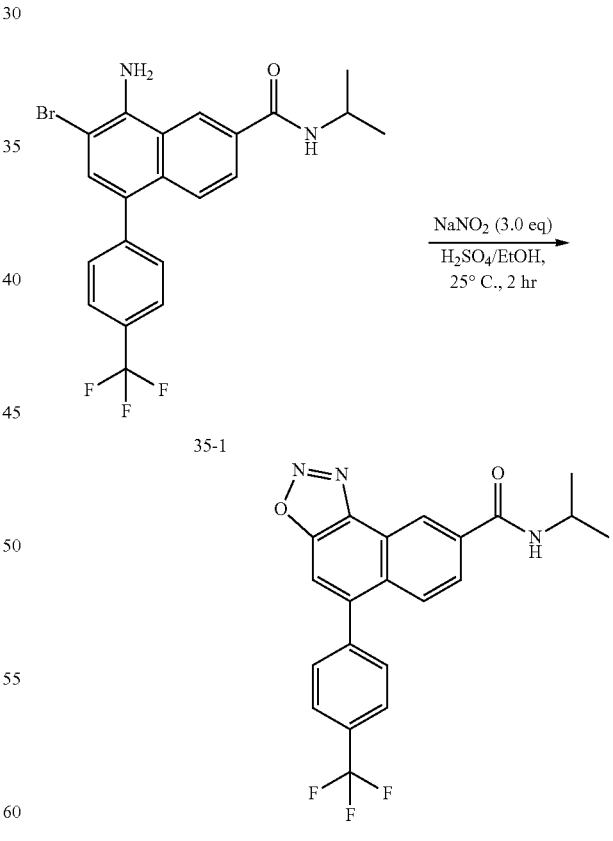

To a solution of compound 35-1 (500 mg, 1.11 mmol, 1 eq) in EtOH (5 mL) was added $H_2SO_4$ (184.0 mg, 1.84 mmol, 0.1 mL, 1.66 eq) and sodium nitrite (229.3 mg, 3.32 mmol, 3.0 eq). The mixture was stirred at 25° C. for 2 hr. The reaction mixture was diluted with H₂O (20 mL) and the mixture was adjusted pH to 8 with NaOH (4M). The mixture was extracted with EA (30 mL*3). The combined organic phase was washed with brine (20 mL*2), dried with anhydrous Na₂SO₄, filtered and concentrated in vacuum. The residue was purified by column chromatography (SiO₂, Petroleum ether/Ethyl acetate=1/0 to 3:1) to give the title compound (210 mg, 0.52 mmol, 47.4% yield) as a red solid. LCMS (ESI): RT=0.785 min, mass calc. for $C_{21}H_{16}F_3N_3O_2$ 399.12, m/z found 400.0 [M+H]⁺; ¹H NMR (400 MHz, CDCl₃) δ 1.23 (d, J=6.53 Hz, 6H) 4.20-4.30 (m, 1H) 5.91 (br d, J=7.03 Hz, 1H) 6.63 (s, 1H) 7.32-7.40 (m, 2H) 7.45 (d, J=8.03 Hz, 2H) 7.71 (d, J=8.03 Hz, 2H) 7.80 (d, J=1.25 Hz, 1H).

Example 36: 7-chloro-N-isopropyl-5-(4-(trifluoromethyl)phenyl)-2-naphthamide (Compound 36)

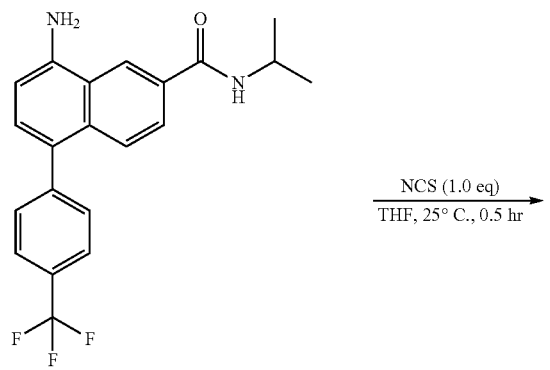

Step 1: 8-amino-7-chloro-N-isopropyl-5-(4-(trifluoromethyl)phenyl)-2-naphthamide To a mixture of compound 36-1 (0.05 g, 0.13 mmol, 1 eq) in THF (3 mL) was added NCS (17.9 mg, 0.13 mmol, 1 eq). The mixture was stirred for 0.5 hrs at 25° C. LCMS showed the reaction was complete. The mixture was quenched by HCl (4 M, 10 mL), and the mixture was extracted with EA (10 mL*3). The combined organic phase was washed with brine (10 mL*3), dried with anhydrous Na₂SO₄, filtered and concentrated in vacuum. The residue was purified by column chromatography (SiO₂, Petroleum ether/Ethyl acetate=50/1 to 5:1). Compound 36-2 (30 mg, 73.3 umol, 54.6% yield) was obtained as a yellow solid.

Step 2: 7-chloro-N-isopropyl-5-(4-(trifluoromethyl)phenyl)-2-naphthamide

To a mixture of compound 36-2 (0.02 g, 49.1 umol, 1 eq) in EtOH (2 mL) and H₂SO₄ (4.9 mg, 49.1 umol, 2.67 uL, 1 eq) was added NaNO₂ (16.9 mg, 0.24 mmol, 5 eq) and H₂O (4.4 mg, 0.24 mmol, 4.4 uL, 5 eq). The mixture was stirred for 0.5 hrs at 25° C. LCMS showed the reaction was complete. The mixture was quenched by H₂O (10 mL), and the mixture was extracted with EA (10 mL*3). The combined organic phase was washed with brine (10 mL*3), dried with anhydrous Na₂SO₄, filtered and concentrated in vacuum. The residue was purified by prep-HPLC to give the title compound (2.7 mg, 7.0 umol, 14.3% yield) as a white solid. LCMS (ESI): RT=0.933 min, mass calc. for $C_{21}H_{17}ClF_3NO$ 391.81, m/z found 391.9 [M+H]⁺; ¹H NMR (400 MHz, CD₃OD) δ 8.40 (d, J=1.5 Hz, 1H), 8.11 (d, J=1.8 Hz, 1H), 7.92-7.85 (m, 3H), 7.85-7.80 (m, 1H), 7.71 (d, J=8.0 Hz, 2H), 7.56 (d, J=2.0 Hz, 1H), 4.35-4.23 (m, 1H), 1.31 (d, J=6.5 Hz, 6H).

Example 37: N-isopropyl-8-methoxy-5-[4-(trifluoromethyl)phenyl]naphthalene-2-carboxamide (Compound 37)

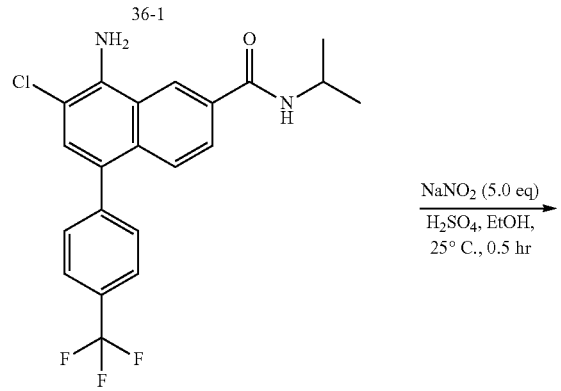

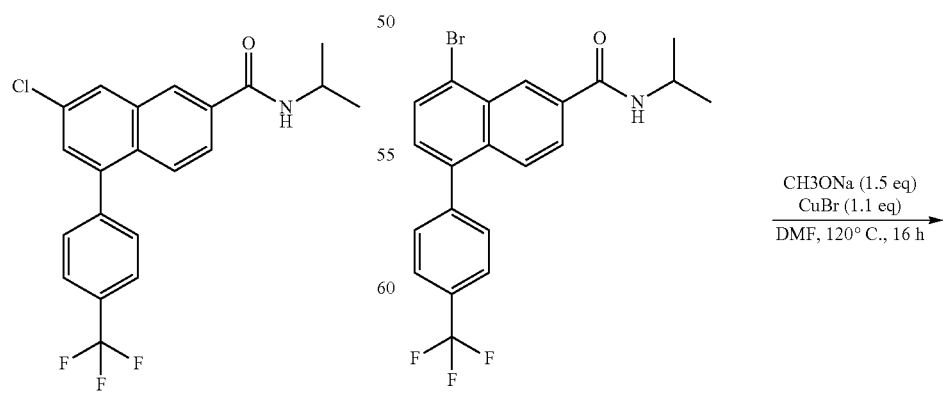

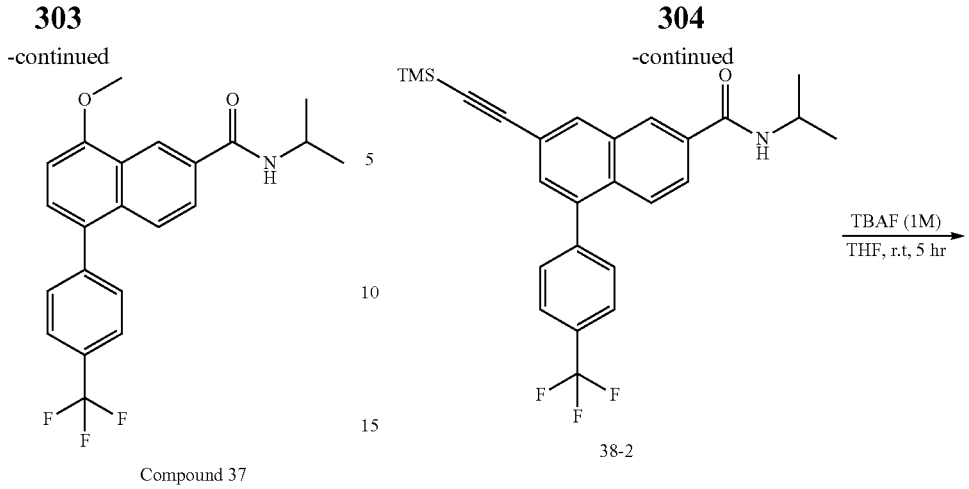

Compound 37

To a solution of compound 37-1 (200 mg, 0.5 nmol, 1 eq) and CuBr (72.3 mg, 0.5 mmol, 15.4 uL, 1.1 eq) in DMF (3 mL) was added $CH_3ONa$ (0.13 M, 5.3 mL, 1.5 eq). The mixture was stirred at 120° C. for 16 hr. LCMS showed reactant was consumed completely and ~74% of desired compound was detected (m/z=388.0; RT: 0.89 min). Then ice water (20 mL) was added and the mixture was neutralized to pH=4~5 with aq.HCl (2 M), The aqueous phase was extracted with ethyl acetate (25 mL*3). The combined organic phase was washed with brine (40 mL), dried with anhydrous $Na_2SO_4$, filtered and concentrated in vacuum. The residue was purified by prep-HPLC to give the title compound (61.6 mg, 0.2 mmol, 34.7% yield) as a white solid. LCMS (ESI): RT=0.900 min, mass calc. for $C_{22}H_{20}F_3NO_2$ 387.1, m/z found 388.0 [M+H]$^+$; $^1$H NMR (400 MHz, DMSO-$d_6$) δ 8.78 (s, 1H), 8.53 (d, J=7.0 Hz, 1H), 7.99-7.86 (m, 2H), 7.79 (d, J=8.5 Hz, 1H), 7.70 (d, J=7.3 Hz, 2H), 7.52 (d, J=8.0 Hz, 1H), 7.16 (d, J=8.0 Hz, 1H), 4.22-4.13 (m, 1H), 4.16 (m, 1H), 4.08 (s, 3H), 1.21 (d, J=6.0 Hz, 6H).

Example 38: 7-ethynyl-N-isopropyl-5-(4-(trifluoromethyl)phenyl)-2-naphthamide (Compound 38)

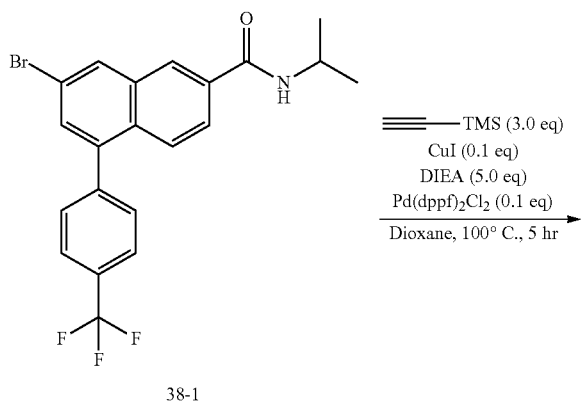

38-1

Step 1: N-isopropyl-5-(4-(trifluoromethyl)phenyl)-7-((trimethylsilyl)ethynyl)-2-naphthamide A mixture of compound 38-1 (50 mg, 0.11 mmol, 1 eq), ethynyl(trimethyl)silane (33.7 mg, 0.34 mmol, 47.6 uL, 3 eq), Pd(dppf)Cl$_2$ (8.3 mg, 11.4 umol, 0.1 eq), CuI (2.1 mg, 11.4 umol, 0.1 eq) and DIPEA (74.0 mg, 0.57 mmol, 99.8 uL, 5 eq) in dioxane (2 mL) was degassed and purged with N$_2$ for 3 times, and then the mixture was stirred at 100° C. for 3 hr under N$_2$ atmosphere. LC-MS showed the desired compound was detected. The reaction mixture was diluted with H$_2$O (10 mL) and the mixture was extracted with EA (10 mL*3). The combined organic phase was washed with brine (10 mL*2), dried with anhydrous Na$_2$SO$_4$, filtered and concentrated in vacuum. Compound 38-2 (80 mg, crude) was obtained as yellow solid, which was used into the next step without further purification.

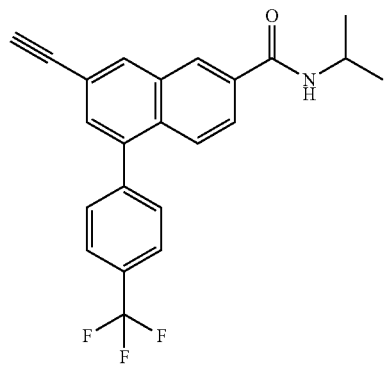

Compound 38

Step 2: 7-ethynyl-N-isopropyl-5-(4-(trifluoromethyl)phenyl)-2-naphthamide

To a solution of compound 38-2 (80 mg, 0.17 mmol, 1 eq) in THF (5 mL) was added TBAF (1 M, 0.17 mL, 1.0 eq). The mixture was stirred at 25° C. for 10 min. LC-MS showed the desired compound was detected. The reaction mixture was diluted with H₂O (10 mL) and the mixture was extracted with EA (10 mL*3). The combined organic phase was washed with brine (10 mL*2), dried with anhydrous Na₂SO₄, filtered and concentrated in vacuum. The residue was purified by prep-HPLC to give the title compound (5 mg, 12.9 umol, 7.3% yield) as white solid. LCMS (ESI): RT=0.909 min, mass calc. for $C_{23}H_{18}F_3NO$ 381.39, m/z found 381.9 [M+H]⁺; ¹H NMR (400 MHz, CD₃OD) δ 8.43 (d, J=1.6 Hz, 1H), 8.21 (s, 1H), 7.94-7.81 (m, 4H), 7.70 (d, J=8.0 Hz, 2H), 7.58 (d, J=1.5 Hz, 1H), 4.33-4.24 (m, 1H), 3.71 (s, 1H), 1.31 (d, J=6.6 Hz, 6H).

Example 39: N-isopropyl-7-methoxy-5-[4-(trifluoromethyl)phenyl]naphthalene-2-carboxamide (Compound 39)

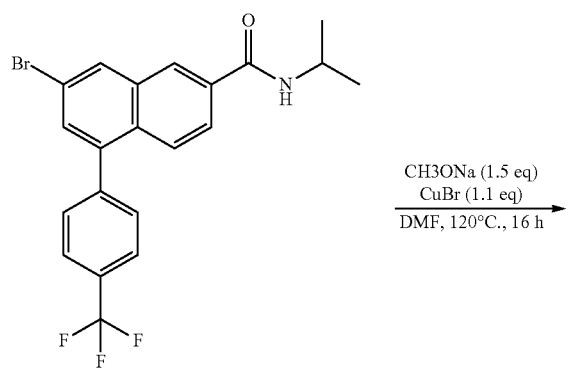

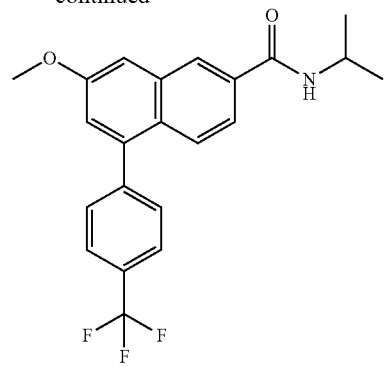

Compound 39

To a solution of compound 39-1 (100 mg, 0.2 mmol, 1 eq) and CuBr (36.2 mg, 0.3 mmol, 8 uL, 1.1 eq) in DMF (2 mL) was added CH₃ONa (0.13 M, 2.6 mL, 1.5 eq). The mixture was stirred at 120° C. for 16 hr. LCMS showed reactant was consumed completely and ~67% of desired compound was detected (m/z=388.0; RT: 0.89 min). Then iced water (20 mL) was added and the mixture was neutralized to pH=4~5 with aq.HCl (2 M), The aqueous phase was extracted with ethyl acetate (25 mL*3). The combined organic phase was washed with brine (40 mL), dried with anhydrous Na₂SO₄, filtered and concentrated in vacuum. The residue was purified by prep-HPLC to give the title compound (26.7 mg, 68.9 umol, 30.1% yield) as a white solid. LCMS (ESI): RT=0.901 min, mass calc. for $C_{22}H_{20}F_3NO_2$ 387.1, m/z found 388.0 [M+H]⁺; ¹H NMR (400 MHz, CD₃OD) δ 8.33 (s, 1H), 7.83 (d, J=8.0 Hz, 2H), 7.74-7.61 (m, 4H), 7.43 (d, J=2.3 Hz, 1H), 7.19 (d, J=2.5 Hz, 1H), 4.27 (m, 1H), 4.01-3.94 (m, 1H), 3.97 (s, 2H), 1.29 (d, J=6.8 Hz, 6H).

Example 40: N-(2-(2-(2-acetamidoethoxy)ethoxy)ethyl)-5-(4-(trifluoromethyl)phenyl)-2-naphthamide (Compound 40)

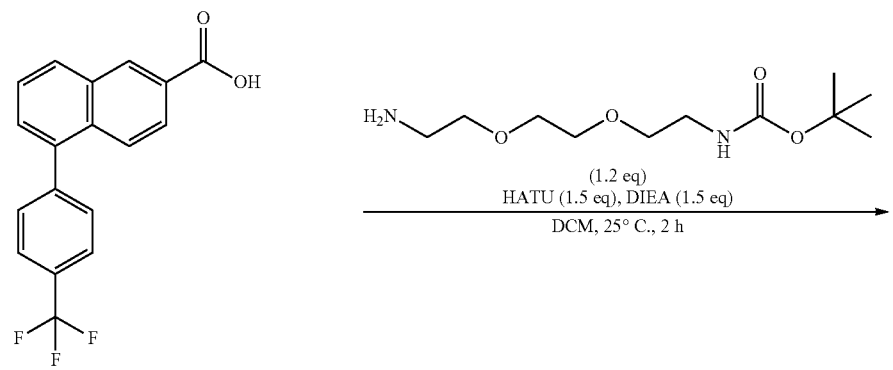

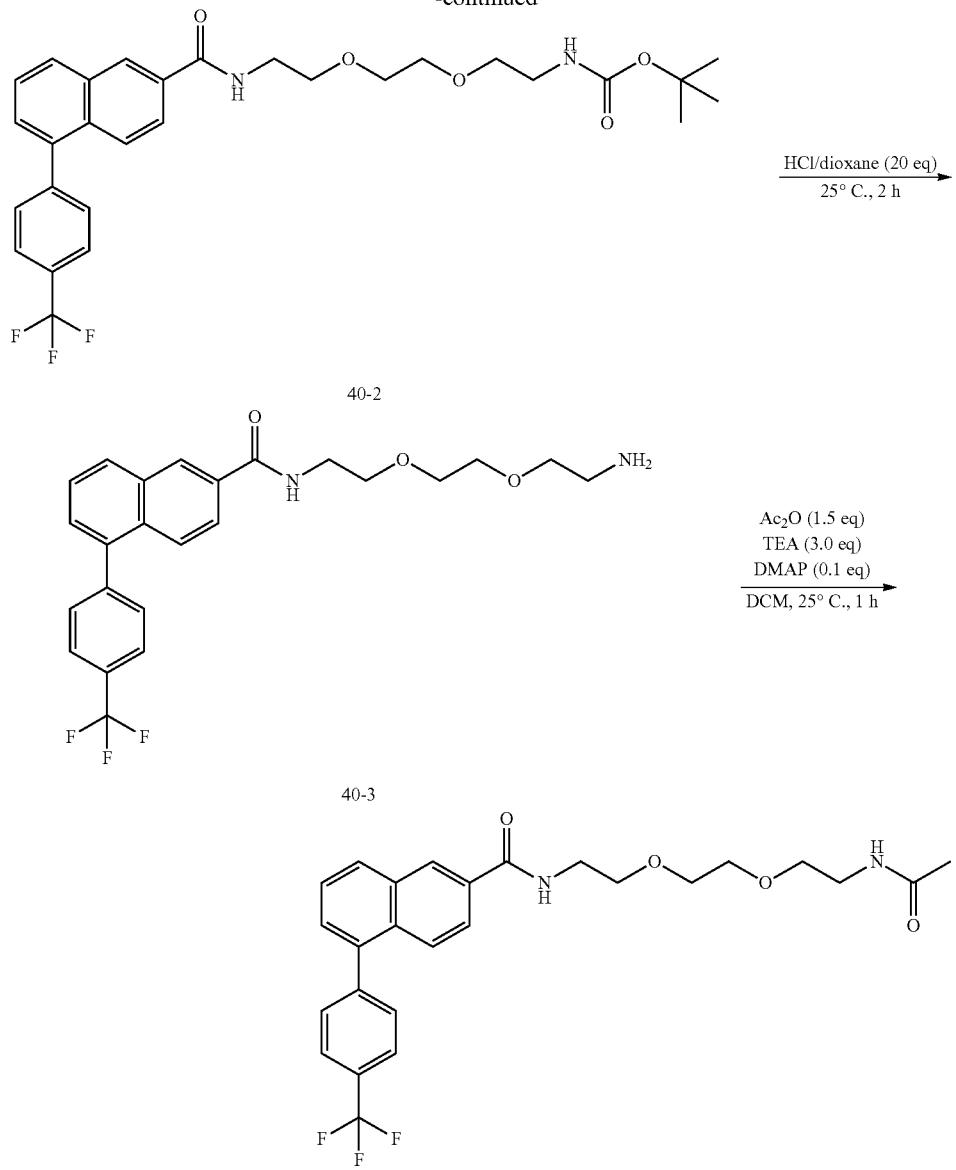

Compound 40

Step 1: Tert-Butyl (2-(2-(2-(5-(4-(trifluoromethyl)phenyl)-2-naphthamido)ethoxy)ethoxy)ethyl)carbamate To a solution of compound 40-1 (0.05 g, 0.16 mmol, 1 eq) and tert-butyl N-[2-[2-(2-aminoethoxy)ethoxy]ethyl]carbamate (47.1 mg, 0.19 mmol, 1.2 eq) in DCM (2 mL) was added HATU (90.2 mg, 0.24 mmol, 1.5 eq) and DIEA (30.7 mg, 0.24 mmol, 41.3 uL, 1.5 eq). The mixture was stirred at 25° C. for 2 hr. LCMS showed the starting material was consumed and the desired mass was detected. To work up the reaction, H₂O (25 mL) was added to the solution. The mixture was extracted with ethyl acetate (30 mL*3). The combined organic layers were washed with brine (60 mL*2), dried over anhydrous Na₂SO₄, filtered and concentrated in vacuum. The residue was purified by column chromatography (SiO₂, Petroleum ether/Ethyl acetate=1/1 to =0:1). Compound 40-2 (0.3 g, crude) was obtained as a white solid.

Step 2: N-(2-(2-(2-aminoethoxy)ethoxy)ethyl)-5-(4-(trifluoromethyl)phenyl)-2-naphthamide To a solution of compound 40-2 (0.3 g, 0.55 mmol, 1 eq) was added HCl/dioxane (3 mL). The mixture was stirred at 25° C. for 2 hr. LCMS showed the starting material was consumed and the desired mass was detected. The reaction mixture was concentrated in vacuum to give crude product. The reaction mixture was used to the net step without purification. Compound 40-3 (0.2 g, 0.45 mmol, 81.6% yield) was obtained as a white solid.

Step 3: N-(2-(2-(2-acetamidoethoxy)ethoxy)ethyl)-5-(4-(trifluoromethyl)phenyl)-2-naphthamide To a solution of compound 40-3 (0.06 g, 0.13 mmol, 1 eq) in DCM (2 mL) was added Ac₂O (20.6 mg, 0.20 mmol, 18.9 uL, 1.5 eq), DMAP (16.4 mg, 0.13 mmol, 0.1 eq) and TEA (40.8 mg, 0.40 mmol, 56.1 uL, 3 eq). The mixture was stirred at 25° C. for 1 hr. LCMS showed the starting material was consumed and the desired mass was detected. H$_2$O (20 mL) was added to the solution. The mixture was extracted with ethyl acetate (25 mL*3). The combined organic layers were washed with brine (40 mL*2), dried over anhydrous Na$_2$SO$_4$, filtered and concentrated in vacuum. The residue was purified by prep-HPLC. The title compound (19.9 mg, 40.9 umol, 30.4% yield) was obtained as a white solid. LCMS (ESI): RT=0.794 min, mass calc. for C$_{26}$H$_{27}$F$_3$N$_2$O$_4$ 488.5, m/z found 389.1 [M+H]$^+$; $^1$H NMR (400 MHz, DMSO-d$_6$) δ 8.77 (br t, J=5.4 Hz, 1H), 8.57 (s, 1H), 8.12 (d, J=8.3 Hz, 1H), 7.92 (d, J=8.0 Hz, 3H), 7.81 (d, J=9.0 Hz, 1H), 7.77-7.77 (m, 1H), 7.78-7.67 (m, 2H), 7.60 (d, J=7.3 Hz, 1H), 3.60-3.55 (m, 5H), 3.55-3.52 (m, 2H), 3.51-3.44 (m, 2H), 3.40 (t, J=5.9 Hz, 2H), 3.21-3.12 (m, 1H), 3.21-3.12 (m, 1H), 1.78 (s, 3H).

Example 41: N-isopropyl-7-methyl-5-(4-(trifluoromethyl)phenyl)-2-naphthamide (Compound 41)

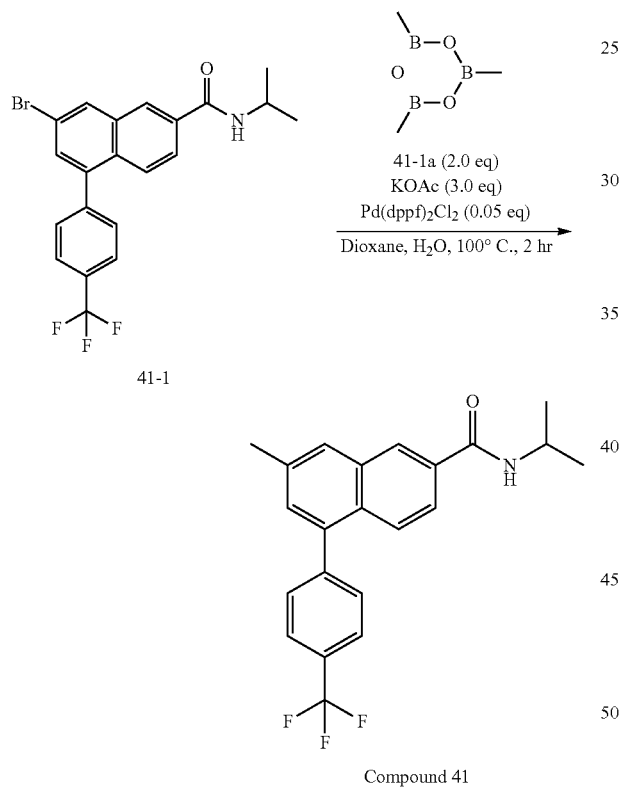

Compound 41

A mixture of compound 41-1 (50 mg, 0.11 mmol, 1 eq), compound 41-1a (28.7 mg, 0.22 mmol, 32 uL, 2 eq), KOAc (33.7 mg, 0.34 mmol, 3 eq) and Pd(dppf)Cl$_2$ (4.1 mg, 5.7 umol, 0.05 eq) in dioxane (5 mL) and H$_2$O (1 mL) was degassed and purged with N$_2$ for 3 times, and then the mixture was stirred at 100° C. for 2 hr under N$_2$ atmosphere. LC-MS showed the desired compound was detected. The reaction mixture was diluted with H$_2$O (20 mL) and the mixture was adjusted pH to 4 with HCl (4 M). The mixture was extracted with EA (30 mL*3). The combined organic phase was washed with brine (20 mL*3), dried with anhydrous Na$_2$SO$_4$, filtered and concentrated in vacuum. The residue was purified by prep-HPLC. The title compound (6 mg, 15.9 umol, 13.9% yield) was obtained as white solid. LCMS (ESI): RT=1.037 min, mass calc. for C$_{22}$H$_{20}$F$_3$NO 371.4, m/z found 372.1 [M+H]$^+$; $^1$H NMR (400 MHz, CD$_3$OD) δ 8.36 (s, 1H), 7.88-7.80 (m, 4H), 7.79 (s, 2H), 7.68 (d, J=8.0 Hz, 2H), 7.42 (d, J=1.3 Hz, 1H), 4.28 (td, J=6.6, 13.2 Hz, 1H), 4.36-4.21 (m, 1H), 2.59 (s, 3H), 1.31 (d, J=6.5 Hz, 6H).

Example 42: N-isopropyl-7-(methylthio)-5-(4-(trifluoromethyl)phenyl)-2-naphthamide (Compound 42)

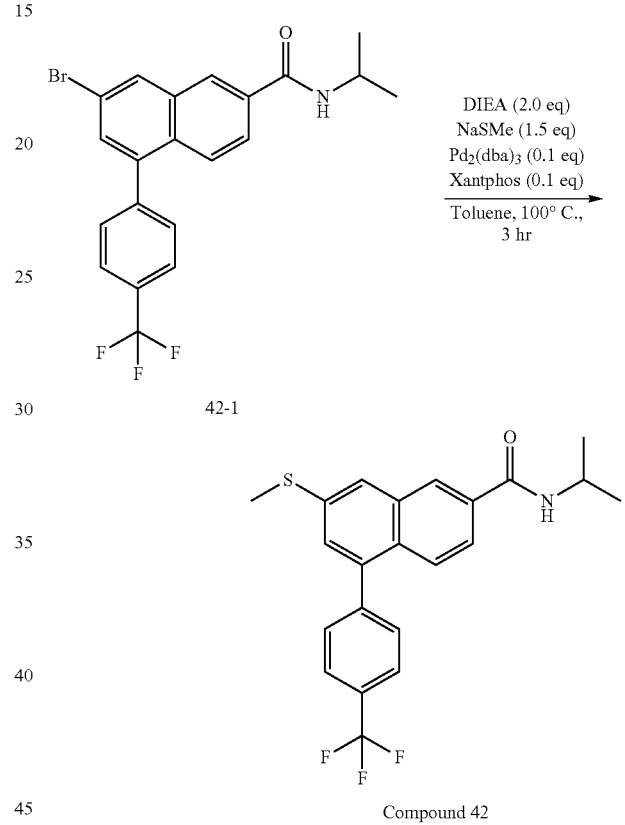

Compound 42

A mixture of compound 42-1 (50 mg, 0.11 mmol, 1 eq), sodium methanethiolate (12 mg, 0.17 mmol, 10.9 uL, 1.5 eq), Pd$_2$(dba)$_3$ (10.5 mg, 11.4 umol, 0.1 eq), Xantphos (6.6 mg, 11.4 umol, 0.1 eq) and DIPEA (29.6 mg, 0.22 mmol, 39.9 uL, 2 eq) in toluene (3 mL) was degassed and purged with N$_2$ for 3 times, and then the mixture was stirred at 100° C. for 3 hr under N$_2$ atmosphere. LC-MS showed the desired compound was detected. The reaction mixture was diluted with H$_2$O (20 mL) and the mixture was extracted with EA (30 mL*3). The combined organic phase was washed with brine (20 mL*3), dried with anhydrous Na$_2$SO$_4$, filtered and concentrated in vacuum. The residue was purified by prep-HPLC. The title compound (4.3 mg, 10.7 umol, 9.3% yield) was obtained as white solid. LCMS (ESI): RT=0.925 min, mass calc. for C$_{22}$H$_{20}$F$_3$NOS 403.46, m/z found 403.9 [M+H]$^+$; $^1$H NMR (400 MHz, CD$_3$OD) δ 8.36 (s, 1H), 7.89-7.82 (m, 3H), 7.81-7.73 (m, 2H), 7.69 (br d, J=7.8 Hz, 2H), 7.42 (d, J=1.8 Hz, 1H), 4.28 (td, J=6.6, 13.2 Hz, 1H), 2.66 (s, 3H), 1.31 (d, J=6.5 Hz, 8H).

311

Example 43: 7-cyclopropyl-N-isopropyl-5-[4-(trifluoromethyl)phenyl]naphthalene-2-carboxamide (Compound 43)

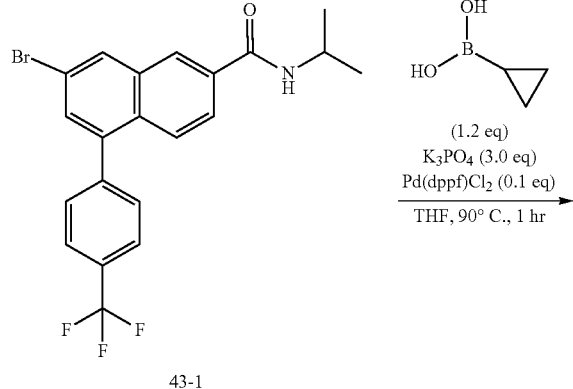

43-1

Compound 43

A mixture of compound 43-1 (50 mg, 0.11 mmol, 1 eq), cyclopropylboronic acid (11.8 mg, 0.13 mmol, 1.2 eq), Pd(dppf)Cl$_2$ (8.3 mg, 0.01 mmol, 0.1 eq), H$_2$O (2.0 mg, 0.11 mmol, 2.0 uL, 1 eq) and K$_3$PO$_4$ (72.9 mg, 0.34 mmol, 3 eq) in THF (5 mL) was degassed and purged with N$_2$ for 3 times, and then the mixture was stirred at 90° C. for 1 hr under N$_2$ atmosphere. LC-MS and HPLC showed the desired compound was detected. The reaction mixture was diluted with H$_2$O (10 mL) and the mixture was extracted with EA (10 mL*3). The combined organic phase was washed with brine (10 mL*2), dried with anhydrous Na$_2$SO$_4$, filtered and concentrated in vacuum. The residue was purified by prep-HPLC and SFC. The title compound (5 mg, 12.4 umol, 10.8% yield) was obtained as white solid. LCMS (ESI): RT=1.054 min, mass calc. for C$_{24}$H$_{22}$F$_3$NO 397.43, m/z found 398.2 [M+H]$^+$; $^1$H NMR (400 MHz, CD$_3$OD) δ 0.73-0.80 (m, 2H), 0.96-1.03 (m, 2H), 1.19 (d, J=6.53 Hz, 6H), 2.00-2.11 (m, 1H), 4.12-4.20 (m, 1H), 7.17 (d, J=1.76 Hz, 1H), 7.56 (d, J=8.03 Hz, 2H), 7.62-7.67 (m, 3H), 7.73 (d, J=8.03 Hz, 2H), 8.24 (s, 1H).

312

Example 44: 7-amino-N-isopropyl-5-[4-(trifluoromethyl)phenyl]naphthalene-2-carboxamide (Compound 44)

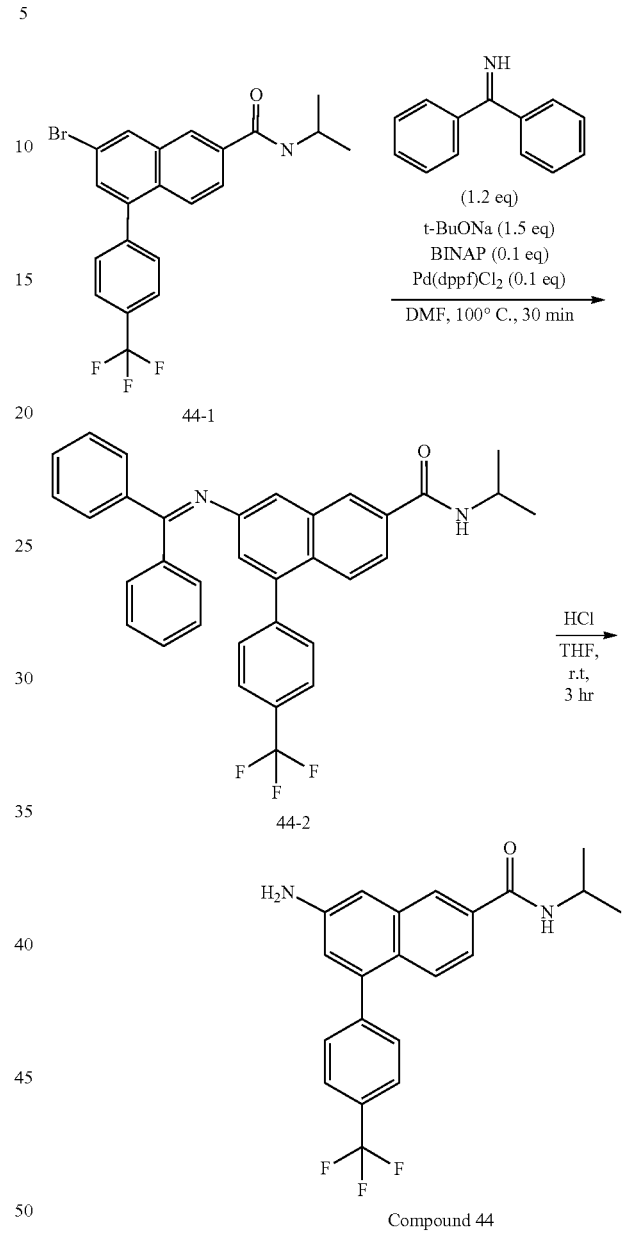

44-1

44-2

Compound 44

Step 1: 7-(benzhydrylideneamino)-N-isopropyl-5-[4-(trifluoromethyl)phenyl]naphthalene-2-carboxamide A mixture of compound 44-1 (140 mg, 0.32 mmol, 1 eq), diphenylmethanimine (69.7 mg, 0.38 mmol, 64.6 uL, 1.2 eq), t-BuONa (46.2 mg, 0.48 mmol, 1.5 eq), Pd(dppf)Cl$_2$ (23.4 mg, 0.03 mol, 0.1 eq) and BINAP (19.9 mg, 0.03 mol, 0.1 eq) in DMF (3 mL) was degassed and purged with N$_2$ for 3 times, and then the mixture was stirred at 100° C. for 30 min with microwave. LC-MS showed the desired compound was detected. The reaction mixture was diluted with H$_2$O (10 mL) and the mixture was extracted with EA (10 mL*3). The combined organic phase was washed with brine (10 mL*5), dried with anhydrous Na$_2$SO$_4$, filtered and concentrated in vacuum. The residue was purified by column chromatography (SiO$_2$, Petroleum ether/Ethyl acetate=1/0 to 4:1). Compound 44-2 (140 mg, 0.14 mmol, 44.7% yield) was obtained as yellow solid. LCMS (ESI): RT=1.008 min, mass calc. for C$_{34}$H$_{27}$F$_3$N$_2$O, 536.59, m/z found 537.0 [M+H]$^+$.

Step 2: 7-amino-N-isopropyl-5-[4-(trifluoromethyl)phenyl]naphthalene-2-carboxamide To a solution of compound 44-2 (140 mg, 0.26 mmol, 1 eq) in THF (3 mL) was added HCl (12 M, 0.14 mL, 6.44 eq) and the mixture was stirred at 25° C. for 3 hr. LC-MS showed the desired compound was detected. The reaction mixture was diluted with H$_2$O (2 mL) and the mixture was adjusted pH to 7 with NaHCO$_3$. The mixture was extracted with EA (10 mL*3). The combined organic phase was washed with brine (10 mL*2), dried with anhydrous Na$_2$SO$_4$, filtered and concentrated in vacuum. The residue was purified by column chromatography (SiO$_2$, Petroleum ether/Ethyl acetate=1/0 to 1:1) and prep-HPLC. The title compound (65 mg, 0.17 mmol, 66.2% yield) was obtained as red solid. LCMS (ESI): RT=0.778 min, mass calc. for C$_{21}$H$_{19}$F$_3$N$_2$O 372.38, m/z found 373.0 [M+H]$^+$; $^1$H NMR (400 MHz, DMSO-d$_6$) δ 1.21 (d, J=6.63 Hz, 6H) 2.29-2.40 (m, 1H) 4.10-4.19 (m, 1H) 7.19 (s, 1H) 7.16-7.18 (m, 1H) 7.40 (br s, 1H) 7.57-7.73 (m, 4H) 7.92 (d, J=8.13 Hz, 2H) 8.30 (s, 1H) 8.36 (br d, J=7.75 Hz, 1H).

Example 45: N-isopropyl-7-methylsulfinyl-5-[4-(trifluoromethyl)phenyl]naphthalene-2-carboxamide (Compound 45)

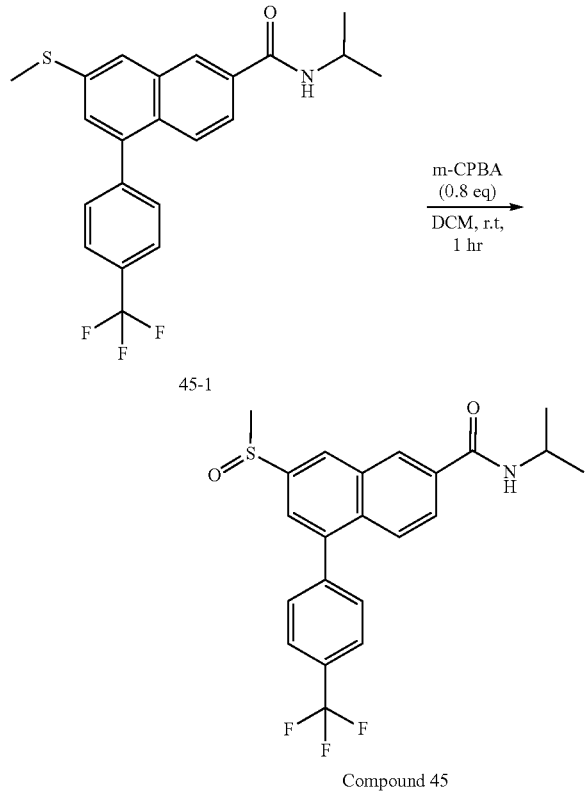

Compound 45

A mixture of compound 45-1 (15 mg, 0.03 mmol, 1 eq) and m-CPBA (6.4 mg, 0.02 mmol, 0.8 eq), in DCM (2 mL) was stirred at 25° C. for 1 hr. LC-MS showed the desired compound was detected. The reaction mixture was diluted with H$_2$O (6 mL) and the mixture was extracted with EA (8 mL*3). The combined organic phase was washed with brine (8 mL*2), dried with anhydrous Na$_2$SO$_4$, filtered and concentrated in vacuum. The residue was purified by prep-HPLC. The title compound (2 mg, 4.7 umol, 12.8% yield) was obtained as white solid. LCMS (ESI): RT=0.780 min, mass calc. for C$_{22}$H$_{20}$F$_3$NO$_2$S 419.46, m/z found 420.0 [M+H]$^+$; $^1$H NMR (400 MHz, CD$_3$OD) δ 1.21 (d, J=6.53 Hz, 6H) 2.85 (s, 3H) 4.18 (quin, J=6.59 Hz, 1H) 7.61-7.71 (m, 2H) 7.68-7.69 (m, 1H) 7.76-7.85 (m, 3H) 7.87-7.95 (m, 1H) 8.33 (s, 1H) 8.48 (d, J=1.26 Hz, 1H).

Example 46: N-isopropyl-7-methylsulfonyl-5-[4-(trifluoromethyl)phenyl]naphthalene-2-carboxamide (Compound 46)

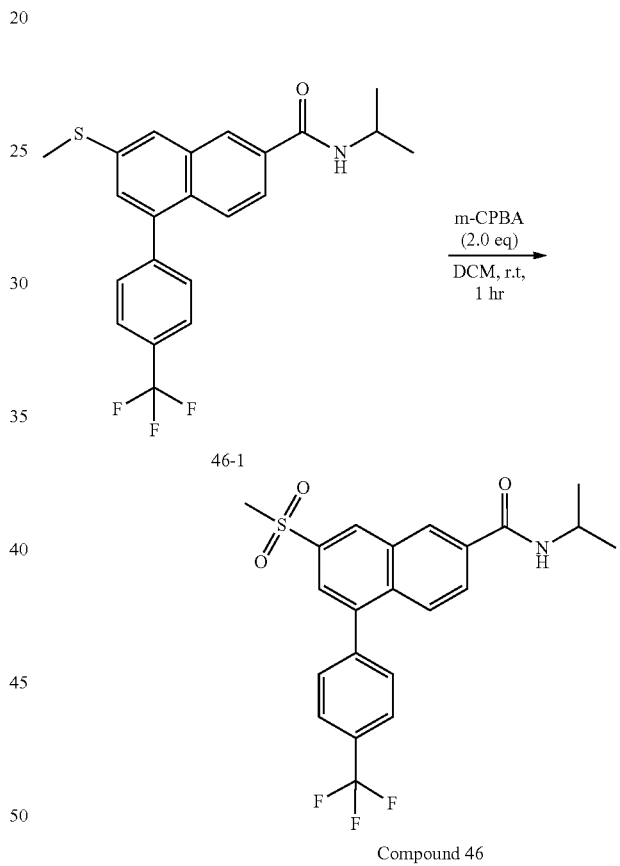

Compound 46

A mixture of compound 46-1 (15 mg, 0.03 mmol, 1 eq) and m-CPBA (16.0 mg, 0.07 mmol, 2 eq) in DCM (2 mL) was stirred at 25° C. for 1 hr. LC-MS showed the desired compound was detected. The reaction mixture was diluted with H$_2$O (6 mL) and the mixture was extracted with EA (8 mL*3). The combined organic phase was washed with brine (8 mL*2), dried with anhydrous Na$_2$SO$_4$, filtered and concentrated in vacuum. The residue was purified by prep-HPLC. The title compound (7 mg, 15.9 umol, 42.8% yield) was obtained as white solid. LCMS (ESI): RT=0.828 min, mass calc. for C$_{22}$H$_{20}$F$_3$NO$_3$S 435.46, m/z found 436.0 [M+H]$^+$; $^1$H NMR (400 MHz, CD$_3$OD) δ 1.31-1.34 (m, 1H) 1.32-1.32 (m, 1H) 1.32-1.32 (m, 1H) 3.29 (s, 3H) 4.24-4.33 (m, 1H) 7.77 (d, J=8.03 Hz, 2H) 7.92 (d, J=8.03 Hz, 2H)

7.97 (d, J=8.78 Hz, 1H) 8.01 (d, J=1.76 Hz, 1H) 8.10 (dd, J=8.78, 1.76 Hz, 1H) 8.55 (br d, J=7.28 Hz, 1H) 8.67 (d, J=1.51 Hz, 1H) 8.75 (s, 1H).

Example 47: 7-ethyl-N-isopropyl-5-(4-(trifluoromethyl)phenyl)-2-naphthamide (Compound 47)

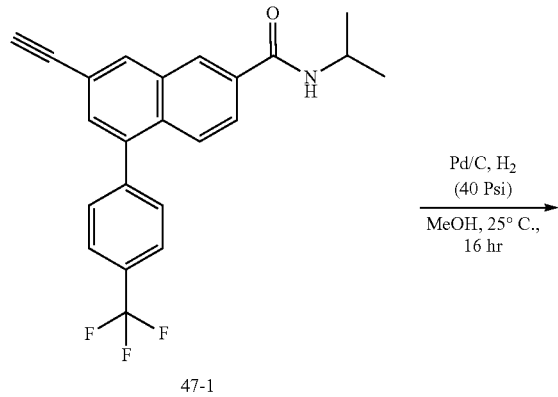

Example 48: 7-acetamido-N-isopropyl-5-(4-(trifluoromethyl)phenyl)-2-naphthamide (Compound 48)

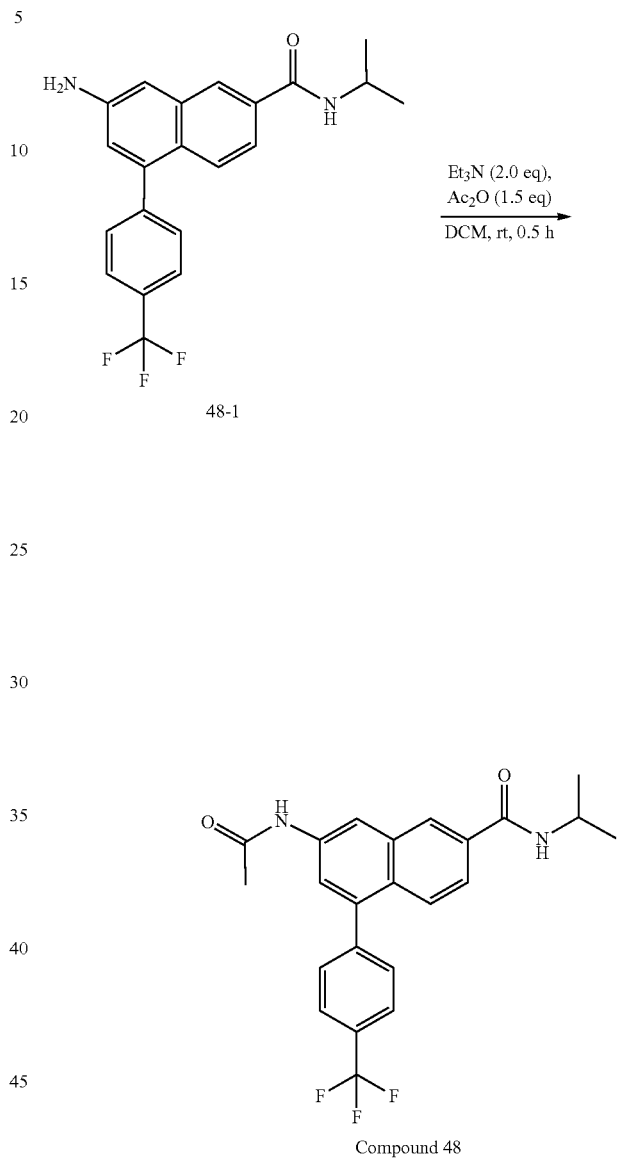

A mixture of compound 47-1 (80 mg, 0.20 mmol, 1 eq), Pd/C (35 mg, 10%, 1.00 eq) and H$_2$ (0.42 mg, 0.20 mmol, 1 eq) in MeOH (5 mL) was degassed and purged with H$_2$ for 3 times, and then the mixture was stirred at 25° C. for 1 hr under H$_2$ atmosphere. LC-MS showed the desired compound was detected. The reaction mixture was diluted with H$_2$O (10 mL) and the mixture was extracted with EA (10 mL*3). The combined organic phase was washed with brine (10 mL*2), dried with anhydrous Na$_2$SO$_4$, filtered and concentrated in vacuum. The residue was purified by prep-HPLC. The title compound (9 mg, 23.1 umol, 11.0% yield) was obtained as white solid. LCMS (ESI): RT=1.072 min, mass calc. for C$_{23}$H$_{22}$F$_3$NO 385.42, m/z found 386.1 [M+H]$^+$; $^1$H NMR (400 MHz, CD$_3$OD) δ=8.40 (s, 1H), 7.85 (br d, J=9.3 Hz, 3H), 7.80 (s, 2H), 7.69 (d, J=7.8 Hz, 2H), 7.46 (d, J=1.5 Hz, 1H), 4.29 (td, J=6.6, 13.1 Hz, 1H), 2.91 (q, J=7.5 Hz, 2H), 1.39 (t, J=7.5 Hz, 3H), 1.33-1.33 (m, 1H), 1.32 (d, J=6.8 Hz, 5H).

The mixture of compound 48-1 (20 mg, 53.7 umol, 1 eq), TEA (10.9 mg, 0.10 mmol, 14.9 uL, 2 eq) and Ac$_2$O (8.22 mg, 80.5 umol, 7.55 uL, 1.5 eq) in DCM (1 mL) was stirred at 25° C. for 30 min. LC-MS showed the desired compound was detected. The reaction mixture was diluted with H$_2$O (10 mL) and the mixture was extracted with EA (10 mL*3). The combined organic phase was washed with brine (10 mL*2), dried with anhydrous Na$_2$SO$_4$, filtered and concentrated in vacuum. The residue was purified by prep-HPLC. The title compound (12 mg, 28.9 umol, 53.9% yield) was obtained as a white solid. LCMS (ESI): RT=0.803 min, mass calc. for C$_{23}$H$_{21}$F$_3$N$_2$O$_2$ 414.42, m/z found 415.0 [M+H]$^+$; $^1$H NMR (400 MHz, CD$_3$OD) δ 8.42 (d, J=2.0 Hz, 1H), 8.36 (s, 1H), 8.37-8.33 (m, 1H), 7.85 (d, J=8.3 Hz, 2H), 7.77 (s, 1H), 7.77 (br d, J=19.6 Hz, 1H), 7.69 (d, J=8.0 Hz, 2H), 7.64 (d, J=2.0 Hz, 1H), 7.65-7.62 (m, 1H), 4.27 (quin, J=6.6 Hz, 1H), 2.21 (s, 3H), 1.30 (d, J=6.5 Hz, 6H).

Example 49: Tert-Butyl (2-(2-(2-(5-(4-(trifluoromethyl)phenyl)-2-naphthamido)ethoxy)ethoxy)ethyl)carbamate (Compound 49)

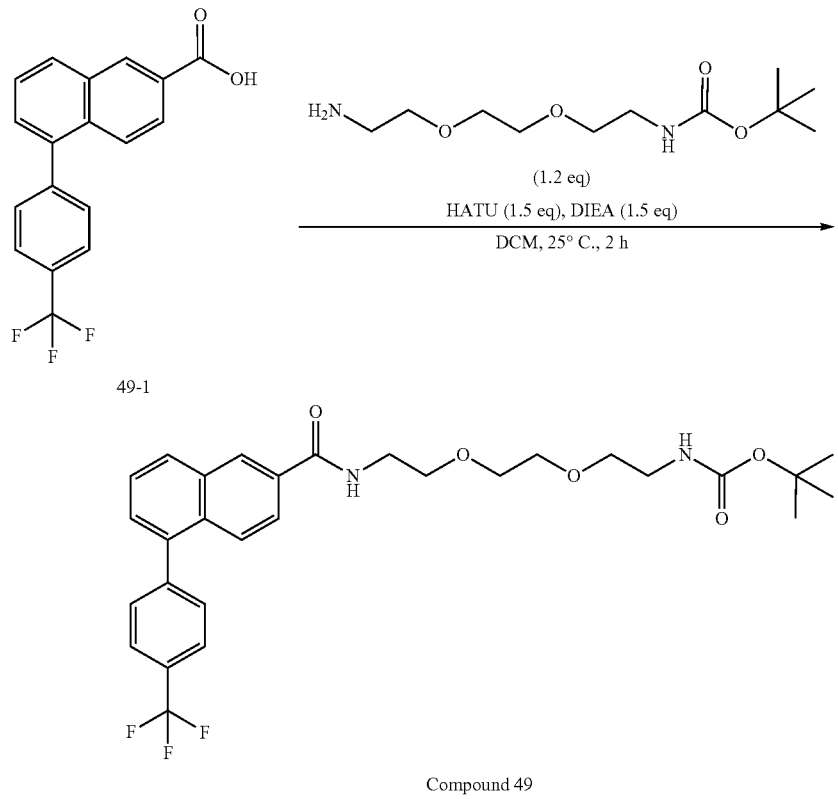

To a solution of compound 49-1 (50 mg, 0.16 mmol, 1 eq) and tert-butyl N-[2-[2-(2-aminoethoxy)ethoxy]ethyl]carbamate (47.1 mg, 0.19 mmol, 1.2 eq) in DCM (1 mL) was added HATU (90.2 mg, 0.24 mmol, 1.5 eq) and DIEA (30.7 mg, 0.24 mmol, 41.3 uL, 1.5 eq). The mixture was stirred at 25° C. for 2 hr. LCMS showed the starting material was consumed and the desired mass wad detected. H₂O (30 mL) was added to the solution. The mixture was extracted with ethyl acetate (35 mL*3). The combined organic layers were washed with brine (60 mL*2), dried over anhydrous Na₂SO₄, filtered and concentrated in vacuum. The residue was purified by prep-HPLC. The title compound (16.8 mg, 30.6 umol, 19.3% yield) was obtained as a white solid.

LCMS (ESI): RT=0.889 min, mass calc. for $C_{29}H_{33}F_3N_2O_5$ 546.58, m/z found 569.1 [M+Na]⁺; ¹H NMR (400 MHz, DMSO-d₆) δ 8.74 (br t, J=5.5 Hz, 1H), 8.56 (s, 1H), 8.12 (d, J=8.3 Hz, 1H), 8.15-8.09 (m, 1H), 7.96-7.90 (m, 3H), 7.81 (d, J=8.8 Hz, 1H), 7.77-7.67 (m, 3H), 7.60 (d, J=7.0 Hz, 1H), 6.76 (br s, 1H), 3.62-3.46 (m, 8H), 3.41-3.35 (m, 3H), 3.05 (q, J=5.9 Hz, 2H), 1.36 (s, 9H).

Example 50: N-(2-(2-(2-aminoethoxy)ethoxy)ethyl)-5-(4-(trifluoromethyl)phenyl)-2-naphthamide (Compound 50)

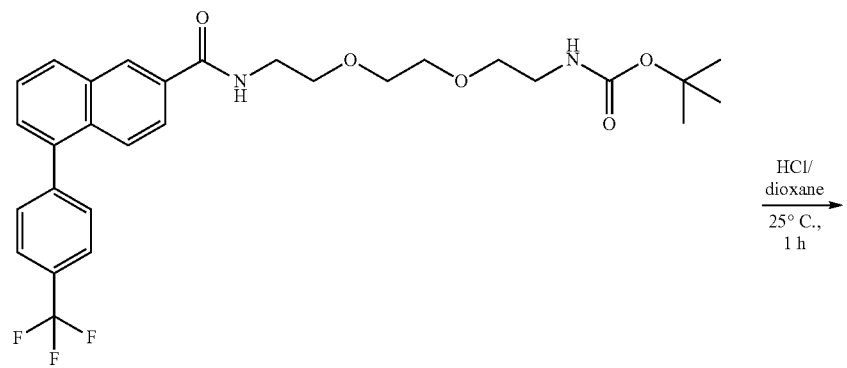

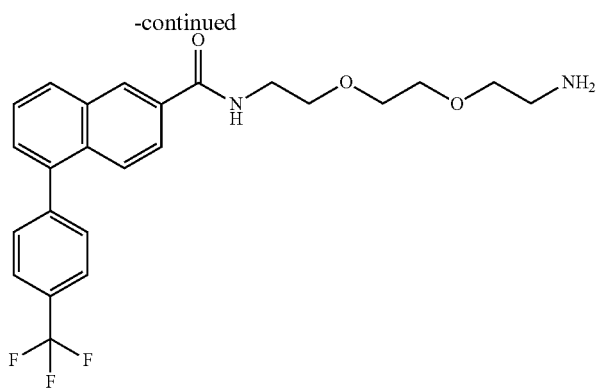

Compound 50

Compound 50-1 (50 mg, 91.5 umol, 1 eq) was added to HCl/dioxane (4 mL). The reaction mixture was stirred at 25° C. for 1 hr. LCMS showed the starting material was consumed and the desired mass was detected. The reaction mixture was concentrated under reduced pressure to remove the solvent. The residue was purified by prep-HPLC. The title compound (7.72 mg, 17.3 umol, 18.9% yield) was obtained as a white solid. LCMS (ESI): RT=0.727 min, mass calc. for $C_{24}H_{25}F_3N_2O_3$ 446.46, m/z found 447.0 [M+H]$^+$; $^1$H NMR (400 MHz, DMSO-d$_6$) δ 8.84 (br t, J=5.4 Hz, 1H), 8.60 (d, J=1.3 Hz, 1H), 8.12 (d, J=8.3 Hz, 1H), 8.04-8.00 (m, 1H), 7.98-7.89 (m, 4H), 7.81 (d, J=8.8 Hz, 1H), 7.77-7.67 (m, 3H), 7.62-7.58 (m, 1H), 3.63-3.59 (m, 8H), 3.54-3.48 (m, 2H), 2.94 (br d, J=5.3 Hz, 2H).

Example 51: N-isopropyl-7-(N-methylacetamido)-5-(4-(trifluoromethyl)phenyl)-2-naphthamide (Compound 51)

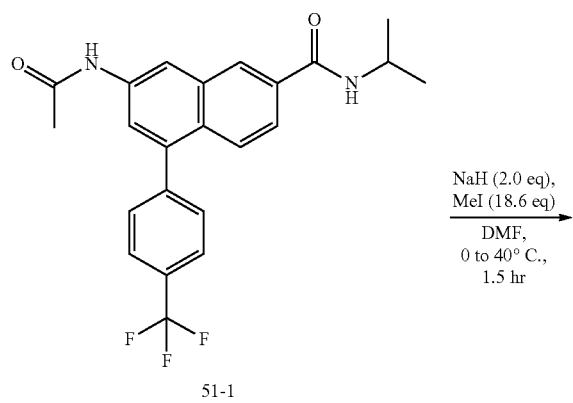

51-1

NaH (2.0 eq),
MeI (18.6 eq)
DMF,
0 to 40° C.,
1.5 hr

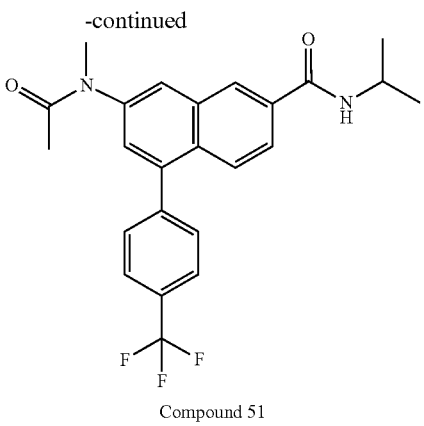

Compound 51

To a solution of compound 51-1 (66 mg, 0.15 mmol, 1 eq) in DMF (5 mL) was added NaH (12.7 mg, 0.31 mmol, 60%, 2 eq) at 0° C. The mixture was stirred at 0° C. for 30 min. Then MeI (0.42 g, 2.96 mmol, 0.18 mL, 18.6 eq) was added at the mixture and the mixture was stirred at 40° C. for 1 hr. LC-MS showed the desired compound was detected. The reaction mixture was diluted with H$_2$O (10 mL) and the mixture was extracted with EA (10 mL*3). The combined organic phase was washed with brine (10 mL*3), dried with anhydrous Na$_2$SO$_4$, filtered and concentrated in vacuum. The residue was purified by prep-HPLC. The title compound (12 mg, 27.4 umol, 17.2% yield) was obtained as a white solid. LCMS (ESI): RT=0.808 min, mass calc. for $C_{24}H_{23}F_3N_2O_2$ 428.45, m/z found 429.0 [M+H]$^+$; $^1$H NMR (400 MHz, CD$_3$OD) δ 8.49 (s, 1H), 8.04 (br s, 1H), 7.97-7.86 (m, 4H), 7.75 (br d, J=7.8 Hz, 2H), 7.55 (d, J=1.8 Hz, 1H), 4.29 (td, J=6.6, 13.2 Hz, 1H), 3.41 (br s, 1H), 3.43-3.38 (m, 1H), 3.43-3.37 (m, 1H), 2.07-1.90 (m, 3H), 1.32 (d, J=6.5 Hz, 6H).

Example 52: N-isopropyl-7-(methylsulfonamido)-5-(4-(trifluoromethyl)phenyl)-2-naphthamide (Compound 52)

Example 53: N-isopropyl-7-(N-methylmethylsulfonamido)-5-(4-(trifluoromethyl)phenyl)-2-naphthamide (Compound 53)

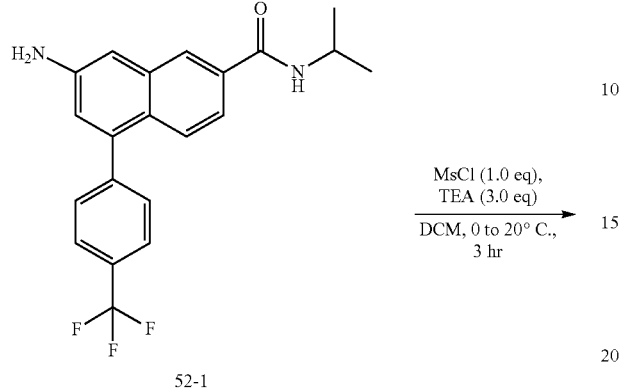

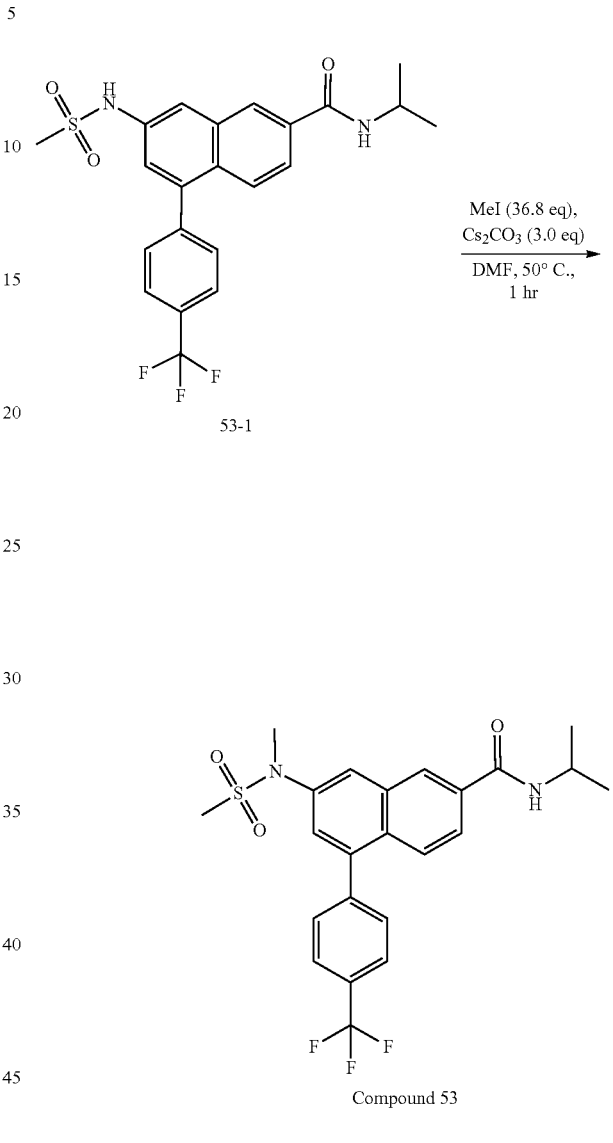

Methanesulfonyl chloride (9.23 mg, 80.5 umol, 6.2 uL, 1 eq) was added to the mixture of compound 52-1 (30 mg, 80.5 umol, 1 eq) and TEA (24.46 mg, 0.24 mmol, 33.6 uL, 3 eq) in DCM (1 mL) at 0° C., then the mixture was stirred at 20° C. for 3 hr. LC-MS showed the desired compound was detected. The reaction mixture was diluted with H$_2$O (10 mL) and the mixture was extracted with EA (15 mL*3). The combined organic phase was washed with brine (10 mL*3), dried with anhydrous Na$_2$SO$_4$, filtered and concentrated in vacuum. The residue was purified by prep-HPLC. The title compound (10 mg, 21.9 umol, 27.2% yield) was obtained as white solid. LCMS (ESI): RT=0.808 min, mass calc. for C$_{22}$H$_{21}$F$_3$N$_2$O$_3$S 450.47, m/z found 451.2 [M+H]$^+$; $^1$H NMR (400 MHz, CD$_3$OD) δ 8.27 (s, 1H), 7.82 (d, J=2.0 Hz, 1H), 7.75 (d, J=8.0 Hz, 2H), 7.69-7.67 (m, 2H), 7.59 (d, J=8.0 Hz, 2H), 7.32 (d, J=2.3 Hz, 1H), 4.16 (quin, J=6.5 Hz, 1H), 2.98 (s, 3H), 1.19 (d, J=6.8 Hz, 6H).

To a solution of compound 53-1 (38 mg, 84.3 umol, 1 eq) in DMF (2 mL) was added Cs$_2$CO$_3$ (82.4 mg, 0.25 mmol, 3 eq) and MeI (0.44 g, 3.10 mmol, 0.19 mL, 36.8 eq). The mixture was stirred at 50° C. for 1 hr. LC-MS showed the desired compound was detected. The reaction mixture was diluted with H$_2$O (10 mL) and the mixture was extracted with EA (10 mL*3). The combined organic phase was washed with brine (10 mL*3), dried with anhydrous Na$_2$SO$_4$, filtered and concentrated in vacuum. The residue was purified by prep-HPLC. The title compound (10 mg, 21.5 umol, 25.5% yield) was obtained as white solid. LCMS (ESI): RT=0.844 min, mass calc. for C$_{23}$H$_{23}$F$_3$N$_2$O$_3$S 464.50, m/z found 465.0 [M+H]$^+$; $^1$H NMR (400 MHz, CD$_3$OD) δ 8.48 (s, 1H), 8.13 (d, J=2.0 Hz, 1H), 7.93-7.82 (m, 4H), 7.73 (d, J=8.0 Hz, 2H), 7.67 (d, J=2.3 Hz, 1H), 4.29 (q, J=6.6 Hz, 1H), 3.49 (s, 2H), 3.46 (s, 1H), 3.00 (s, 1H), 3.04-2.93 (m, 1H), 3.06-2.93 (m, 1H), 3.05-2.89 (m, 1H), 1.32 (d, J=6.5 Hz, 4H), 1.34-1.28 (m, 1H), 1.35-1.28 (m, 1H).

Example 54: N-(2,2,2-trifluoroethyl)-5-(4-(trifluoromethyl)phenyl)-2-naphthamide (Compound 54)

Example 55: N-cyclopropyl-5-(4-(trifluoromethyl)phenyl)-2-naphthamide (Compound 55)

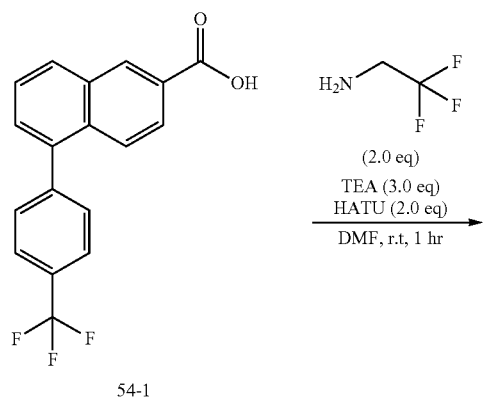

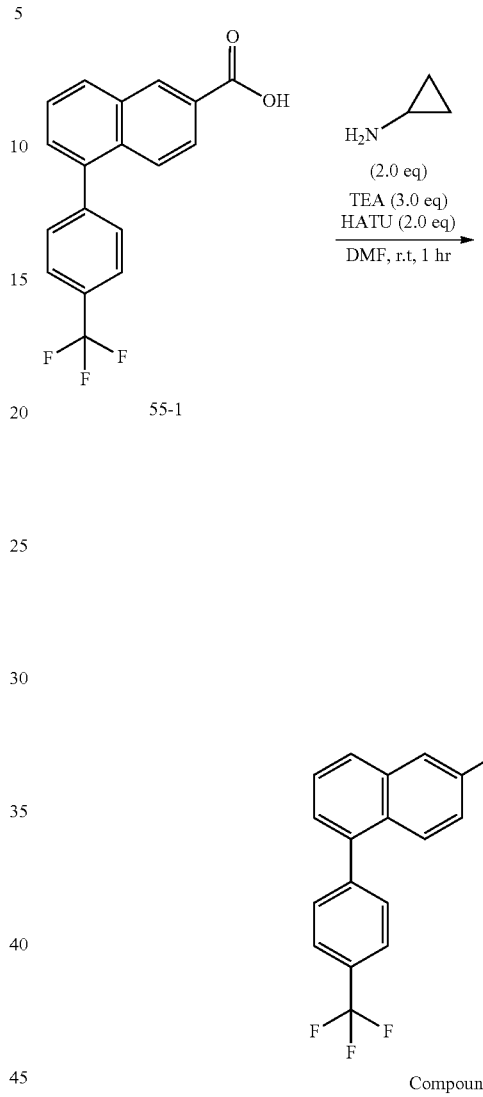

To a mixture of compound 54-1 (0.05 g, 0.15 mmol, 1 eq) in DMF (2 mL) was added HATU (120.2 mg, 0.31 mmol, 2 eq) and Et$_3$N (47.9 mg, 0.47 mmol, 66 uL, 3 eq). The mixture was stirred for 0.5 hrs at 25° C. Then 2,2,2-trifluoroethanamine (31.3 mg, 0.31 mmol, 24.8 uL, 2 eq) was added to the mixture. The mixture was stirred for 1.5 hrs at 25° C. LCMS showed the reaction was complete. The mixture was quenched by H$_2$O (30 mL), and the mixture was extracted with EA (20 mL*3). The combined organic phase was washed with brine (20 mL*3), dried with anhydrous Na$_2$SO$_4$, filtered and concentrated in vacuum. The residue was purified by prep-HPLC. The title compound (19 mg, 48 umol, 30.3% yield) was obtained as a white solid. LCMS (ESI): RT=0.895 min, mass calc. for: C$_{20}$H$_{13}$F$_6$NO 397.31, m/z found 397.9 [M+H]$^+$; $^1$H NMR (400 MHz, DMSO-d6) δ 9.33 (t, J=6.3 Hz, 1H), 8.63 (d, J=1.5 Hz, 1H), 8.16 (d, J=8.0 Hz, 1H), 7.99-7.91 (m, 3H), 7.85 (d, J=9.0 Hz, 1H), 7.77-7.70 (m, 3H), 7.63 (dd, J=1.0, 7.0 Hz, 1H), 4.22-4.12 (m, 2H).

To a mixture of compound 55-1 (0.05 g, 0.15 mmol, 1 eq) in DMF (2 mL) was added HATU (120.2 mg, 0.31 mmol, 2 eq) and Et$_3$N (47.9 mg, 0.47 mmol, 66 uL, 3 eq). The mixture was stirred for 0.5 hrs at 25° C. Then cyclopropanamine (18 mg, 0.31 mmol, 21.9 uL, 2 eq) was added to the mixture. The mixture was stirred for 1.5 hrs at 25° C. LCMS showed the reaction was complete. The mixture was quenched by H$_2$O (30 mL), and the mixture was extracted with EA (20 mL*3). The combined organic phase was washed with brine (20 mL*3), dried with anhydrous Na$_2$SO$_4$, filtered and concentrated in vacuum. The residue was purified by prep-HPLC. The title compound (23 mg, 64.9 umol, 41.1% yield) was obtained as a white solid. LCMS (ESI): RT=0.854 min, mass calc. for: C$_{21}$H$_{16}$F$_3$NO 355.35, m/z found 355.9 [M+H]$^+$; $^1$H NMR (400 MHz, DMSO-d6) δ 8.67 (br d, J=3.5 Hz, 1H), 8.52 (s, 1H), 8.11 (br d, J=8.0 Hz, 1H), 7.92 (br d, J=8.5 Hz, 3H), 7.83-7.66 (m, 4H), 7.58 (br d, J=6.8 Hz, 1H), 2.92 (td, J=3.5, 7.0 Hz, 1H), 0.80-0.68 (m, 2H), 0.63 (br d, J=3.0 Hz, 2H).

Example 56: N-(1,3-dihydroxypropan-2-yl)-5-(4-(trifluoromethyl)phenyl)-2-naphthamide (Compound 56)

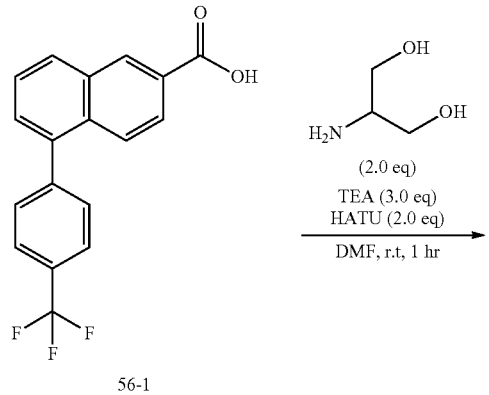

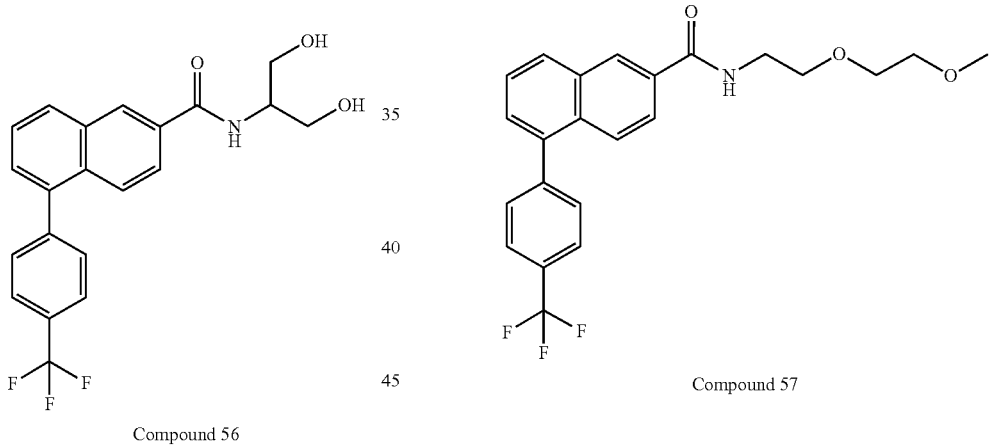

Compound 56

To a mixture of compound 56-1 (0.05 g, 0.15 mmol, 1 eq) in DMF (2 mL) was added HATU (120.2 mg, 0.31 mmol, 2 eq) and Et$_3$N (47.9 mg, 0.47 mmol, 66.0 uL, 3 eq). The mixture was stirred for 0.5 hrs at 25° C. Then 2-aminopropane-1,3-diol (28.8 mg, 0.31 mmol, 2 eq) was added to the mixture. The mixture was stirred for 1.5 hrs at 25° C. LCMS showed the reaction was complete. The mixture was quenched by H$_2$O (30 mL), and the mixture was extracted with EA (20 mL*3). The combined organic phase was washed with brine (20 mL*3), dried with anhydrous Na$_2$SO$_4$, filtered and concentrated in vacuum. The residue was purified by prep-HPLC. The title compound (5.9 mg, 15.1 umol, 9.5% yield) was obtained as a white solid. LCMS (ESI): RT=0.756 min, mass calc. for: C$_{21}$H$_{18}$F$_3$NO$_3$ 389.37, m/z found 390.0 [M+H]$^+$; $^1$H NMR (400 MHz, CD$_3$OD) δ 8.54 (s, 1H), 8.09 (d, J=8.3 Hz, 1H), 7.94-7.84 (m, 4H), 7.72-7.65 (m, 3H), 7.58 (d, J=6.8 Hz, 1H), 4.25 (t, J=5.6 Hz, 1H), 3.80 (d, J=5.8 Hz, 4H).

Example 57: N-(2-(2-methoxyethoxy)ethyl)-5-(4-(trifluoromethyl)phenyl)-2-naphthamide (Compound 57)

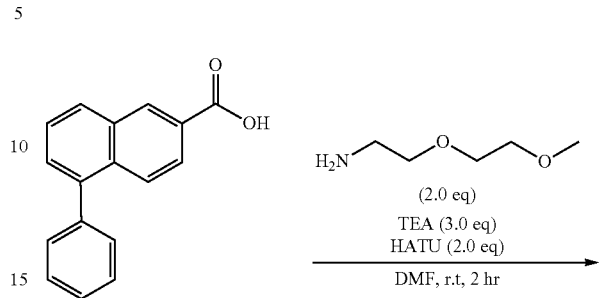

Compound 57

To a mixture of compound 57-1 (0.05 g, 0.15 mmol, 1 eq) in DMF (2 mL) was added HATU (120.2 mg, 0.31 mmol, 2 eq) and Et$_3$N (47.9 mg, 0.47 mmol, 66.0 uL, 3 eq). The mixture was stirred for 0.5 hrs at 25° C. Then 2-(2-methoxyethoxy)ethanamine (37.6 mg, 0.31 mmol, 2 eq) was added to the mixture. The mixture was stirred for 1.5 hrs at 25° C. LCMS showed the reaction was complete. The mixture was quenched by H$_2$O (30 mL), and the mixture was extracted with EA (20 mL*3). The combined organic phase was washed with brine (20 mL*3), dried with anhydrous Na$_2$SO$_4$, filtered and concentrated in vacuum. The residue was purified by prep-HPLC. The title compound (9.56 mg, 22.9 umol, 14.4% yield) was obtained as a white solid. LCMS (ESI): RT=0.843 min, mass calc. for: C$_{23}$H$_{22}$F$_3$NO$_3$ 417.42, m/z found 440.0 [M+Na]$^+$; $^1$H NMR (400 MHz, DMSO-d$_6$) δ 8.75 (t, J=5.8 Hz, 1H), 8.59-8.55 (m, 1H), 8.12 (d, J=8.3 Hz, 1H), 7.96-7.90 (m, 3H), 7.83-7.68 (m, 4H), 7.60 (d, J=7.0 Hz, 1H), 3.61-3.54 (m, 4H), 3.52-3.44 (m, 4H), 3.24 (s, 3H).

Example 58: N-(2-methoxyethyl)-5-(4-(trifluoromethyl)phenyl)-2-naphthamide (Compound 58)

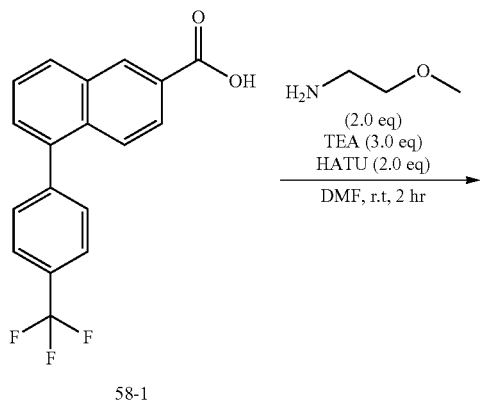

58-1

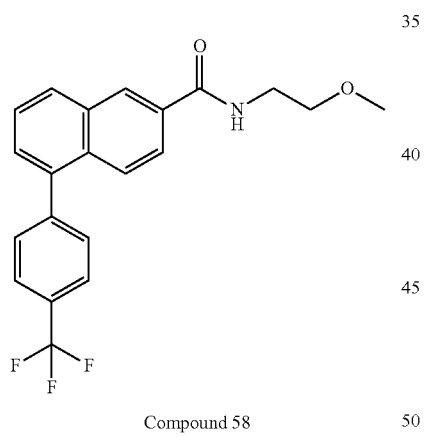

Compound 58

To a mixture of compound 58-1 (0.05 g, 0.15 mmol, 1 eq) in DMF (2 mL) was added HATU (120.2 mg, 0.31 mmol, 2 eq) and Et₃N (47.9 mg, 0.47 mmol, 66.0 uL, 3 eq). The mixture was stirred for 0.5 hrs at 25° C. Then 2-methoxyethanamine (23.7 mg, 0.31 mmol, 27.4 uL, 2 eq) was added to the mixture. The mixture was stirred for 1.5 hrs at 25° C. LCMS showed the reaction was complete. The mixture was quenched by H₂O (30 mL), and the mixture was extracted with EA (20 mL*3). The combined organic phase was washed with brine (20 mL*3), dried with anhydrous Na₂SO₄, filtered and concentrated in vacuum. The residue was purified by prep-HPLC. The title compound (21.1 mg, 56.5 umol, 35.7% yield) was obtained as a white solid.

LCMS (ESI): RT=0.840 min, mass calc. for: $C_{21}H_{18}F_3NO_2$ 373.37, m/z found 373.9 [M+H]⁺; ¹H NMR (400 MHz, CD₃OD) δ 8.49 (s, 1H), 8.08 (d, J=8.3 Hz, 1H), 7.91-7.83 (m, 4H), 7.74-7.65 (m, 3H), 7.58 (dd, J=1.0, 7.0 Hz, 1H), 3.64 (s, 4H), 3.42 (s, 3H).

Example 59: (S)—N-(1-aminopropan-2-yl)-5-(4-(trifluoromethyl)phenyl)-2-naphthamide (Compound 59) and (R)—N-(1-aminopropan-2-yl)-5-(4-(trifluoromethyl)phenyl)-2-naphthamide (Compound 60)

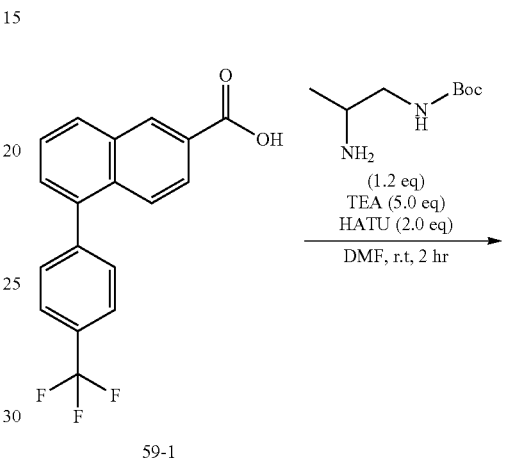

59-1

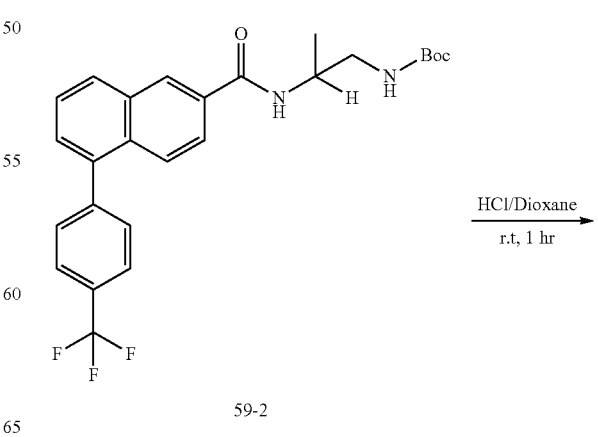

59-2

-continued

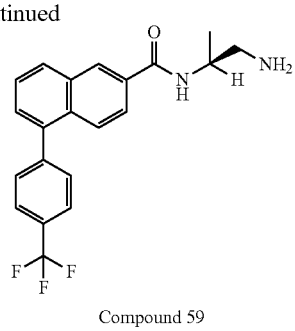

Compound 59

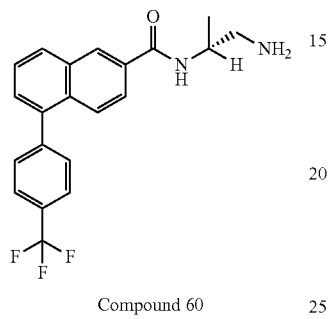

Compound 60

Step 1: Tert-Butyl (2-(5-(4-(trifluoromethyl)phenyl)-2-naphthamido)propyl)carbamate To a mixture of compound 59-1 (0.1 g, 0.31 mmol, 1 eq) in DMF (10 mL) was added HATU (240.4 mg, 0.63 mmol, 2 eq) and Et$_3$N (159.9 mg, 1.58 mmol, 0.22 mL, 5 eq). The mixture was stirred for 0.5 hrs at 25° C. Then tert-butyl N-(2-aminopropyl)carbamate (66.1 mg, 0.37 mmol, 1.2 eq) was added to the mixture. The mixture was stirred for 1.5 hrs at 25° C. LCMS showed the reaction was complete. The mixture was quenched by H$_2$O (30 mL), and the mixture was extracted with EA (20 mL*3). The combined organic phase was washed with brine (20 mL*3), dried with anhydrous Na$_2$SO$_4$, filtered and concentrated in vacuum. The residue was purified by column chromatography (SiO$_2$, Petroleum ether/Ethyl acetate=50/1 to 1:1). Compound 59-2 (0.08 g, 0.16 mmol, 53.5% yield) was obtained as a yellow solid.

Step 2: (S)—N-(1-aminopropan-2-yl)-5-(4-(trifluoromethyl)phenyl)-2-naphthamide and (R)—N-(1-aminopropan-2-yl)-5-(4-(trifluoromethyl)phenyl)-2-naphthamide To a solution of compound 59-2 (80 mg, 0.16 mmol, 1 eq) in MeOH (1 mL) was added HCl/dioxane (4 M, 3.00 mL, 70.87 eq). The mixture was stirred for 1 hr at 25° C. LCMS showed the reaction was complete. The mixture was quenched by H$_2$O (30 mL), and the mixture was extracted with EA (20 mL*3). The combined organic phase was washed with brine (20 mL*3), dried with anhydrous Na$_2$SO$_4$, filtered and concentrated in vacuum. The residue was purified by prep-HPLC to afford the racemic compounds (61 mg). The racemic compounds were separated by SFC. Compound 59 (18.8 mg, 50.6 umol, 29.9% yield) was obtained as a white solid. LCMS (ESI): RT=0.727 min, mass calc. for: C$_{21}$H$_{19}$F$_3$N$_2$O 372.38, m/z found 373.0 [M+H]$^+$; $^1$H NMR (400 MHz, CD$_3$OD) δ 8.40 (s, 1H), 7.96 (d, J=8.3 Hz, 1H), 7.81-7.70 (m, 4H), 7.59-7.53 (m, 3H), 7.45 (d, J=6.9 Hz, 1H), 4.13 (q, J=6.8 Hz, 1H), 2.73 (d, J=6.5 Hz, 2H), 1.19 (d, J=6.8 Hz, 3H). Compound 60 (16.1 mg, 43.2 umol, 25.5% yield) was obtained as a white solid. LCMS (ESI): RT=0.735 min, mass calc. for: C$_{21}$H$_{19}$F$_3$N$_2$O 372.38, m/z found 373.0 [M+H]$^+$; $^1$H NMR (400 MHz, CD$_3$OD) δ 8.39 (s, 1H), 7.96 (d, J=8.3 Hz, 1H), 7.81-7.70 (m, 4H), 7.60-7.53 (m, 3H), 7.45 (d, J=6.8 Hz, 1H), 4.12 (q, J=6.7 Hz, 1H), 2.72 (d, J=6.3 Hz, 2H), 1.19 (d, J=6.8 Hz, 3H).

Example 60: N-(1-fluoro-3-hydroxypropan-2-yl)-5-(4-(trifluoromethyl)phenyl)-2-naphthamide (Compound 61) and N-(1,3-difluoropropan-2-yl)-5-(4-(trifluoromethyl)phenyl)-2-naphthamide (Compound 62)

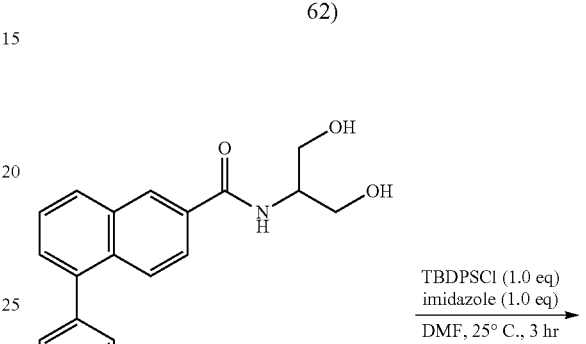

61-1

61-2

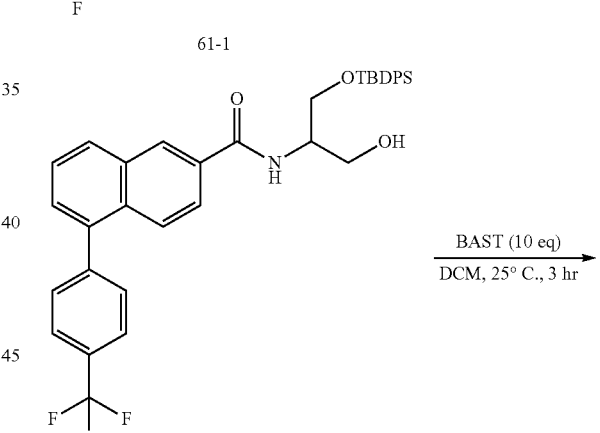

61-3

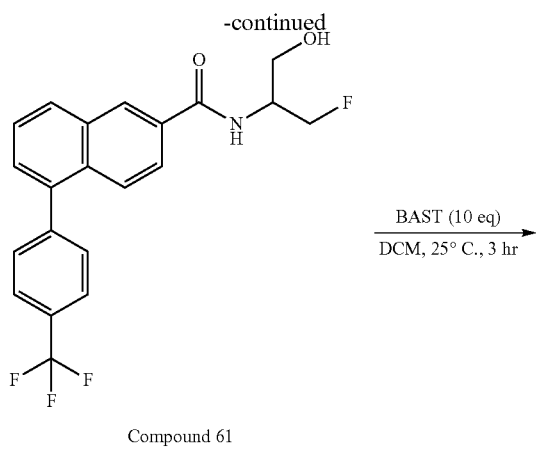

Compound 61

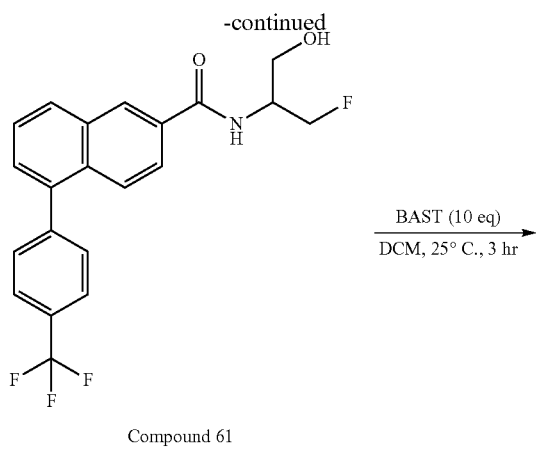

Compound 62

Step 1: N-(1-((tert-butyldiphenylsilyl)oxy)-3-hydroxypropan-2-yl)-5-(4-(trifluoromethyl)phenyl)-2-naphthamide To a solution of compound 61-1 (1.86 g, 4.78 mmol, 1 eq) in DCM (5 mL) was added imidazole (325.3 mg, 4.78 mmol, 1 eq) and TBDPSCl (1.31 g, 4.78 mmol, 1.23 mL, 1 eq). The mixture was stirred for 3 hrs at 25° C. The mixture was quenched by H₂O (30 mL), and the mixture was extracted with EA (20 mL*3). The combined organic phase was washed with brine (20 mL*3), dried with anhydrous Na₂SO₄, filtered and concentrated in vacuum. The residue was used to the next step without further purification. Compound 61-2 (1.6 g, 2.55 mmol, 53.3% yield) was obtained as a yellow oil.

Step 2: N-(1-((tert-butyldiphenylsilyl)oxy)-3-fluoropropan-2-yl)-5-(4-(trifluoromethyl)phenyl)-2-naphthamide To a solution of compound 61-2 (0.8 g, 1.27 mmol, 1 eq) in DCM (5 mL) was added BAST (2.82 g, 12.74 mmol, 2.79 mL, 10 eq). The mixture was stirred for 3 hrs at 25° C. The mixture was quenched by H₂O (30 mL), and the mixture was extracted with EA (20 mL*3). The combined organic phase was washed with brine (20 mL*3), dried with anhydrous Na₂SO₄, filtered and concentrated in vacuum. The residue was used to the next step without further purification. Compound 61-3 (0.81 g, crude) was obtained as a yellow oil.

Step 3: N-(1-fluoro-3-hydroxypropan-2-yl)-5-(4-(trifluoromethyl)phenyl)-2-naphthamide To a solution of compound 61-3 (0.6 g, 0.95 mmol, 1 eq) in THF (1 mL) was added TBAF (1 M, 4.76 mL, 5 eq). The mixture was stirred for 3 hrs at 25° C. LCMS showed the reaction was complete. The mixture was quenched by H₂O (30 mL), and the mixture was extracted with EA (20 mL*3). The combined organic phase was washed with brine (20 mL*3), dried with anhydrous Na₂SO₄, filtered and concentrated in vacuum. The residue was purified by column chromatography (SiO₂, Petroleum ether/Ethyl acetate=50/1 to 1:1). Compound 61 (0.212 g, 0.54 mmol, 56.8% yield) was obtained as a yellow oil. LCMS (ESI): RT=0.768 min, mass calc. for: $C_{21}H_{17}F_4NO_2$ 391.36, m/z found 372.0 [M-FH]⁺; ¹H NMR (400 MHz, CD₃OD) δ 8.58 (s, 1H), 8.07 (d, J=7.7 Hz, 1H), 8.00 (d, J=8.9 Hz, 1H), 7.86 (d, J=8.3 Hz, 3H), 7.73-7.66 (m, 3H), 7.59 (d, J=6.8 Hz, 1H), 4.67-4.58 (m, 1H), 4.53-4.42 (m, 2H), 3.77 (t, J=4.8 Hz, 2H).

Step 4: N-(1,3-difluoropropan-2-yl)-5-(4-(trifluoromethyl)phenyl)-2-naphthamide To a solution of compound 61 (0.1 g, 0.25 mmol, 1 eq) in DCM (5 mL) was added BAST (565.3 mg, 2.56 mmol, 0.55 mL, 10 eq). The mixture was stirred for 3 hrs at 25° C. LCMS and HPLC showed the reaction was complete. The mixture was quenched by H₂O (30 mL), and the mixture was extracted with EA (20 mL*3). The combined organic phase was washed with brine (20 mL*3), dried with anhydrous Na₂SO₄, filtered and concentrated in vacuum. The residue was purified by prep-HPLC. Compound 62 (4.38 mg, 10.5 umol, 4.1% yield) was obtained as a white solid. LCMS (ESI): RT=0.885 min, mass calc. for: $C_{21}H_{16}F_5NO$ 393.35, m/z found 373.9 [M-FH]⁺; ¹H NMR (400 MHz, CD₃OD) δ 8.58 (s, 1H), 8.07 (d, J=8.3 Hz, 1H), 7.99 (dd, J=1.5, 9.0 Hz, 1H), 7.91-7.80 (m, 3H), 7.74-7.64 (m, 3H), 7.59 (d, J=6.3 Hz, 1H), 4.75-4.46 (m, 5H), 3.30-3.25 (m, 1H), 3.22 (s, 1H).

Example 61: 2-amino-N-isopropyl-5-(4-(trifluoromethyl)phenyl)naphtho[1,2-d]thiazole-8-carboxamide (Compound 63)

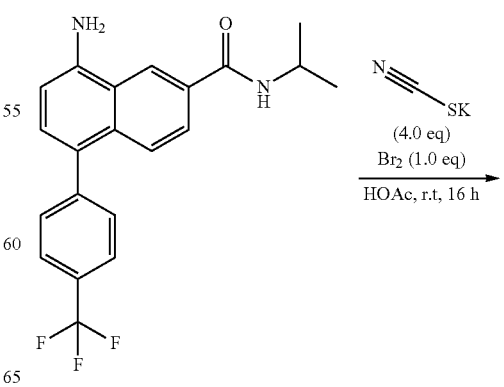

63-1

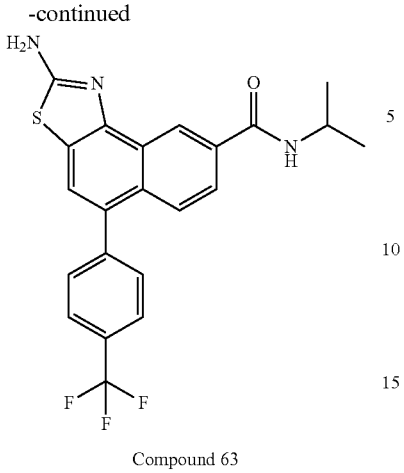

Compound 63

To a solution of compound 63-1 (50 mg, 0.13 mmol, 1 eq) and thiocyanatopotassium (52.2 mg, 0.54 mmol, 52.2 uL, 4 eq) in HOAc (2 mL) was added $Br_2$ (21.5 mg, 0.13 mmol, 6.9 uL, 1 eq). The mixture was stirred at 19° C. for 16 hr. LCMS showed the starting material was consumed and the desired mass was detected. $H_2O$ (15 mL) was added to the solution. The mixture was extracted with ethyl acetate (25 mL*3). The combined organic layers were washed with brine (30 mL*2), dried over anhydrous $Na_2SO_4$, filtered and concentrated in vacuum. The residue was purified by prep-HPLC. The title compound (1.67 mg, 3.6 umol, 2.6% yield, HCl) was obtained as a white solid. LCMS (ESI): RT=0.821 min, mass calc. for $C_{22}H_{18}F_3N_3OS$ 429.46, m/z found 430.0 $[M+H]^+$; $^1H$ NMR (400 MHz, $CD_3OD$) δ 8.91 (s, 1H), 7.96-7.93 (m, 3H), 7.90-7.87 (m, 1H), 7.88 (d, J=7.8 Hz, 1H), 7.72 (d, J=8.0 Hz, 2H), 4.30 (q, J=6.6 Hz, 1H), 1.33 (d, J=6.6 Hz, 7H).

Example 62: (S)—N-(1-(dimethylamino)propan-2-yl)-5-(4-(trifluoromethyl)phenyl)-2-naphthamide (Compound 64) and (R)—N-(1-(dimethylamino)propan-2-yl)-5-(4-(trifluoromethyl)phenyl)-2-naphthamide (Compound 65)

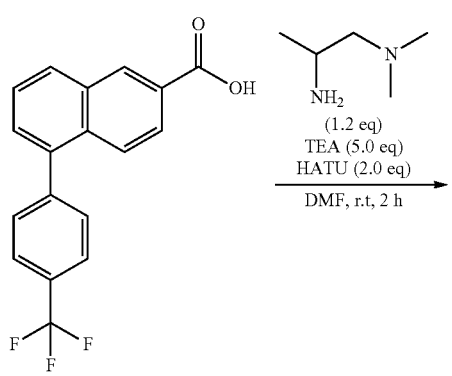

64-1

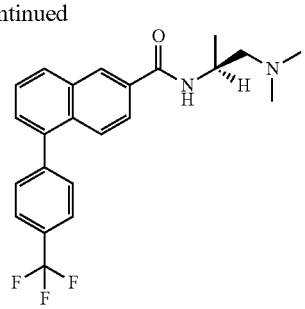

Compound 64

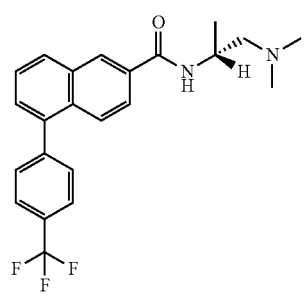

Compound 65

To a mixture of compound 64-1 (0.2 g, 0.63 mmol, 1 eq) in DMF (10 mL) was added HATU (480.8 mg, 1.26 mmol, 2 eq) and $Et_3N$ (319.9 mg, 3.16 mmol, 0.44 mL, 5 eq). The mixture was stirred for 0.5 hrs at 25° C. Then N1,N1-dimethylpropane-1,2-diamine (77.5 mg, 0.75 mmol, 1.2 eq) was added to the mixture. The mixture was stirred for 1.5 hrs at 25° C. LCMS showed the reaction was complete. The mixture was quenched by $H_2O$ (30 mL), and the mixture was extracted with EA (20 mL*3). The combined organic phase was washed with brine (20 mL*3), dried with anhydrous $Na_2SO_4$, filtered and concentrated in vacuum. The residue was purified by prep-HPLC to afford the racemic compounds (51 mg). The racemic compounds were separated by SFC. Compound 64 (10.8 mg, 27.1 umol, 4.2% yield) was obtained as a white solid. LCMS (ESI): RT=0.747 min, mass calc. for: $C_{23}H_{23}F_3N_2O$ 400.44, m/z found 401.0 $[M+H]^+$; $^1H$ NMR (400 MHz, $CD_3OD$) δ 8.40 (s, 1H), 7.96 (br d, J=8.0 Hz, 1H), 7.82-7.71 (m, 4H), 7.60-7.52 (m, 3H), 7.48-7.43 (m, 1H), 4.30 (td, J=6.2, 8.3 Hz, 1H), 2.57 (dd, J=9.0, 12.5 Hz, 1H), 2.25 (dd, J=5.4, 12.7 Hz, 1H), 2.23-2.19 (m, 6H), 1.17 (d, J=6.5 Hz, 3H). Compound 65 (13.8 mg, 34.6 umol, 5.4% yield) was obtained as a white solid. LCMS (ESI): RT=0.736 min, mass calc. for: $C_{23}H_{23}F_3N_2O$ 400.44, m/z found 401.0 $[M+H]^+$; $^1H$ NMR (400 MHz, $CD_3OD$) δ 8.40 (s, 1H), 7.95 (t, J=6.5 Hz, 1H), 7.82-7.69 (m, 4H), 7.60-7.51 (m, 3H), 7.45 (br t, J=6.8 Hz, 1H), 4.30 (br d, J=8.3 Hz, 1H), 2.60-2.52 (m, 1H), 2.27-2.23 (m, 1H), 2.22 (d, J=3.5 Hz, 6H), 1.17 (d, J=6.5 Hz, 3H).

Example 63: (S)—N-(1-(pyrrolidin-1-yl)propan-2-yl)-5-(4-(trifluoromethyl)phenyl)-2-naphthamide (Compound 66) and (R)—N-(1-(pyrrolidin-1-yl)propan-2-yl)-5-(4-(trifluoromethyl)phenyl)-2-naphthamide (Compound 67)

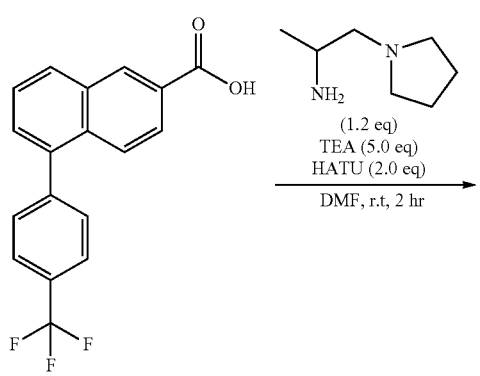

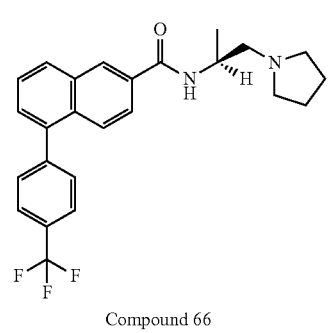

Compound 66

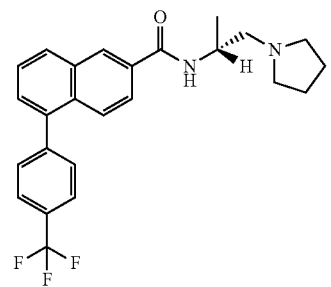

Compound 67

To a mixture of compound 66-1 (0.12 g, 0.37 mmol, 1 eq) in DMF (10 mL) was added HATU (288.5 mg, 0.75 mmol, 2 eq) and Et₃N (191.9 mg, 1.90 mmol, 0.26 mL, 5 eq). The mixture was stirred for 0.5 hrs at 25° C. Then 1-pyrrolidin-1-ylpropan-2-amine (58.3 mg, 0.45 mmol, 1.2 eq) was added to the mixture. The mixture was stirred for 1.5 hrs at 25° C. LCMS showed the reaction was complete. The mixture was quenched by H₂O (30 mL), and the mixture was extracted with EA (20 mL*3). The combined organic phase was washed with brine (20 mL*3), dried with anhydrous Na₂SO₄, filtered and concentrated in vacuum. The residue was purified by prep-HPLC to afford the racemic compounds (42 mg). The racemic compounds were separated by SFC. Compound 66 (4.8 mg, 11.2 umol, 2.9% yield) was obtained as a white solid. LCMS (ESI): RT=0.768 min, mass calc. for: $C_{25}H_{25}F_3N_2O$ 426.47, m/z found 427.1 [M+H]⁺; ¹H NMR (400 MHz, CD₃OD) δ 8.43-8.38 (m, 1H), 7.96 (d, J=8.3 Hz, 1H), 7.82-7.71 (m, 4H), 7.61-7.53 (m, 3H), 7.46 (d, J=6.5 Hz, 1H), 4.35-4.26 (m, 1H), 2.73 (dd, J=8.7, 12.4 Hz, 1H), 2.62-2.54 (m, 2H), 2.51 (br dd, J=1.9, 6.9 Hz, 2H), 2.45-2.40 (m, 1H), 1.71 (br s, 4H), 1.19 (d, J=6.5 Hz, 3H). Compound 67 (6.2 mg, 14.1 umol, 3.7% yield) was obtained as a white solid. LCMS (ESI): RT=0.757 min, mass calc. for: $C_{25}H_{25}F_3N_2O$ 426.47, m/z found 427.0 [M+H]⁺; ¹H NMR (400 MHz, CD₃OD) δ 8.40 (d, J=1.5 Hz, 1H), 7.96 (d, J=8.3 Hz, 1H), 7.82-7.72 (m, 4H), 7.61-7.53 (m, 3H), 7.46 (d, J=6.7 Hz, 1H), 4.35-4.26 (m, 1H), 2.73 (dd, J=8.8, 12.3 Hz, 1H), 2.62-2.55 (m, 2H), 2.54-2.47 (m, 2H), 2.44 (dd, J=5.3, 12.3 Hz, 1H), 1.71 (br s, 4H), 1.19 (d, J=6.5 Hz, 3H).

Example 64: N-isopropyl-5-(4-(trifluoromethyl)phenyl)naphtho[1,2-d]thiazole-8-carboxamide (Compound 68)

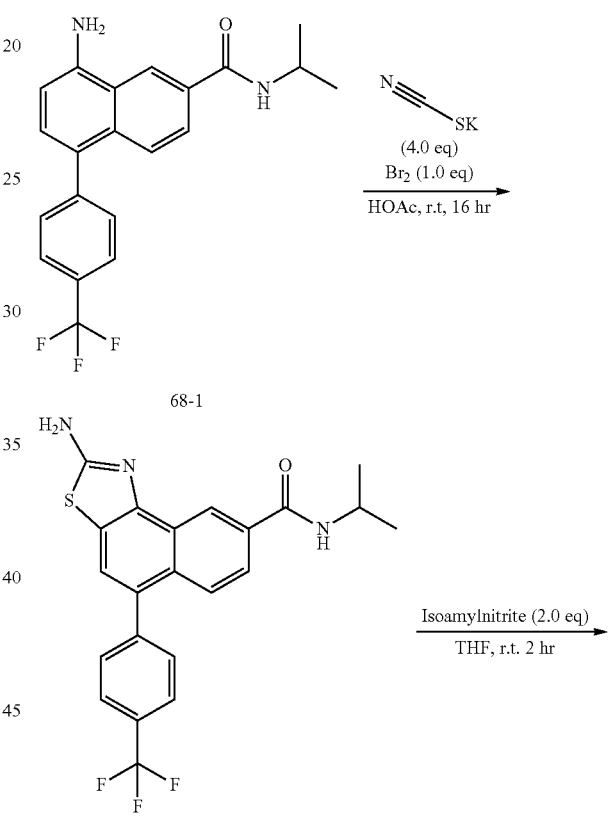

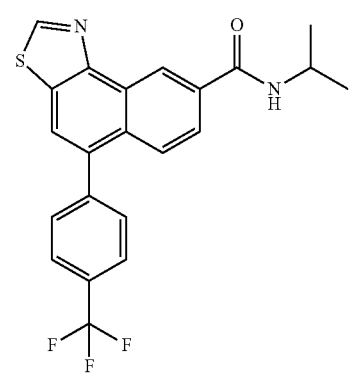

Compound 68

Step 1: 2-amino-N-isopropyl-5-(4-(trifluoromethyl) phenyl)naphtho[1,2-d]thiazole-8-carboxamide To a solution of compound 68-1 (0.2 g, 0.53 mmol, 1 eq) and thiocyanatopotassium (208.7 mg, 2.15 mmol, 0.20 mL, 4 eq) in HOAc (2 mL) was added Br$_2$ (85.8 mg, 0.53 mmol, 27.6 uL, 1 eq). The mixture was stirred at 19° C. for 16 hr. LCMS showed the starting material was consumed and the desired mass was detected. H$_2$O (5 mL) was added to the solution. The mixture was extracted with ethyl acetate (10 mL*3). The combined organic layers were washed with brine (15 mL*2), dried over anhydrous Na$_2$SO$_4$, filtered and concentrated in vacuum. Compound 68-2 (200 mg, 0.46 mmol, 86.7% yield) was obtained as a white solid.

Step 2: N-isopropyl-5-(4-(trifluoromethyl)phenyl) naphtho[1,2-d]thiazole-8-carboxamide To a solution of compound 68-2 (0.15 g, 0.34 mmol, 1 eq) in THF (3 mL) was added isopentyl nitrite (81.8 mg, 0.69 mmol, 94.0 uL, 2 eq). The mixture was stirred at 19° C. for 2 hr. LCMS showed the starting material was consumed and the desired mass was detected. H$_2$O (30 mL) was added to the solution. The mixture was extracted with ethyl acetate (35 mL*3). The combined organic layers were washed with brine (60 mL*2), dried over anhydrous Na$_2$SO$_4$, filtered and concentrated in vacuum. The residue was purified by prep-HPLC. The title compound (36.27 mg, 87.5 umol, 25.0% yield) was obtained as a brown solid. LCMS (ESI): RT=0.879 min, mass calc. for C$_{22}$H$_{17}$F$_3$N$_2$OS 414.44, m/z found 415.0 [M+H]$^+$; $^1$H NMR (400 MHz, DMSO-d$_6$) δ 9.65 (s, 1H), 9.37 (d, J=1.5 Hz, 1H), 8.70 (d, J=7.8 Hz, 1H), 8.34 (s, 1H), 8.05 (dd, J=1.8, 8.8 Hz, 1H), 7.96 (d, J=8.3 Hz, 2H), 7.88 (d, J=8.8 Hz, 1H), 7.80 (d, J=8.0 Hz, 2H), 4.21 (qd, J=6.7, 13.9 Hz, 1H), 1.24 (d, J=6.5 Hz, 7H).

Example 65: (S)—N-(1-morpholinopropan-2-yl)-5-(4-(trifluoromethyl)phenyl)-2-naphthamide (Compound 69) and (R)—N-(1-morpholinopropan-2-yl)-5-(4-(trifluoromethyl)phenyl)-2-naphthamide (Compound 70)

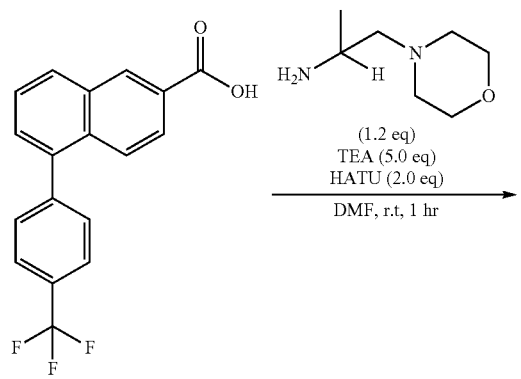

69-1

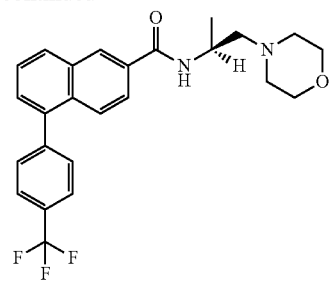

Compound 69

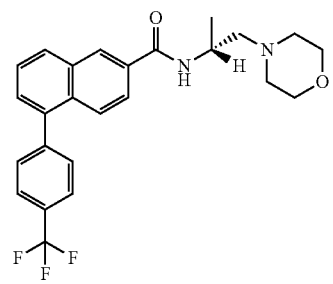

Compound 70

To a mixture of compound 69-1 (0.2 g, 0.63 mmol, 1 eq) in DMF (3 mL) was added HATU (480.8 mg, 1.26 mmol, 2 eq) and Et$_3$N (319.9 mg, 3.16 mmol, 0.44 mL, 5 eq). The mixture was stirred for 0.5 hrs at 25° C. Then 1-morpholino-propan-2-amine (109.4 mg, 0.75 mmol, 1.2 eq) was added to the mixture. The mixture was stirred for 1.5 hrs at 25° C. LCMS and HPLC showed the reaction was complete. The mixture was quenched by H$_2$O (30 mL), and the mixture was extracted with EA (20 mL*3). The combined organic phase was washed with brine (20 mL*3), dried with anhydrous Na$_2$SO$_4$, filtered and concentrated in vacuum. The residue was purified by prep-HPLC to afford the racemic compounds (50 mg). The racemic compounds were separated by SFC. Compound 69 (12.5 mg, 26.9 umol, 4.2% yield) was obtained as a white solid. LCMS (ESI): RT=0.751 min, mass calc. for: C$_{25}$H$_{25}$F$_3$N$_2$O$_2$ 442.47, m/z found 443.0 [M+H]$^+$; $^1$H NMR (400 MHz, CD$_3$OD) δ 8.36 (s, 1H), 7.97 (br d, J=8.1 Hz, 1H), 7.82-7.70 (m, 4H), 7.65-7.52 (m, 3H), 7.51-7.42 (m, 1H), 3.61 (br s, 4H), 3.55-3.41 (m, 1H), 3.35-3.26 (m, 1H), 2.81 (br d, J=6.5 Hz, 1H), 2.67-2.45 (m, 4H), 1.09-0.99 (m, 3H). Compound 70 (10.2 mg, 23.0 umol, 3.6% yield) was obtained as a white solid. LCMS (ESI): RT=0.760 min, mass calc. for: C$_{25}$H$_{25}$F$_3$N$_2$O$_2$ 442.47, m/z found 443.0 [M+H]$^+$; $^1$H NMR (400 MHz, CD$_3$OD) δ 8.49 (s, 1H), 8.09 (br d, J=8.0 Hz, 1H), 7.95-7.80 (m, 4H), 7.78-7.65 (m, 3H), 7.63-7.57 (m, 1H), 3.81-3.68 (m, 4H), 3.61 (dd, J=8.0 7.1, 13.6 Hz, 1H), 3.42 (br dd, J=8.0 6.5, 13.6 Hz, 1H), 2.93 (br d, J=8.0 6.9 Hz, 1H), 2.81-2.58 (m, 4H), 1.19-1.11 (m, 3H).

Example 66: N-isopropyl-5-(4-(trifluoromethyl)phenyl)naphtho[1,2-d]oxazole-8-carboxamide (Compound 71)

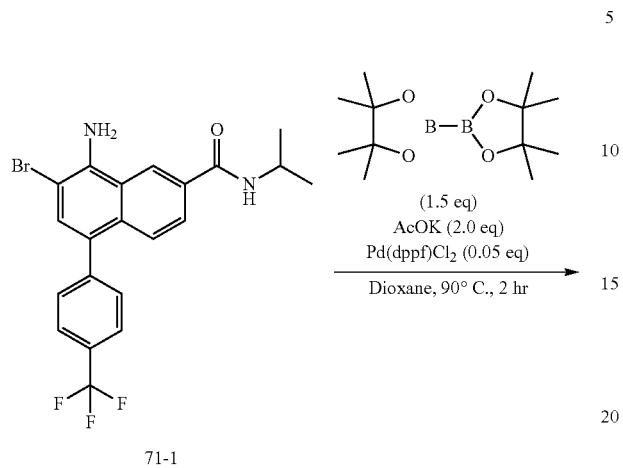

71-1

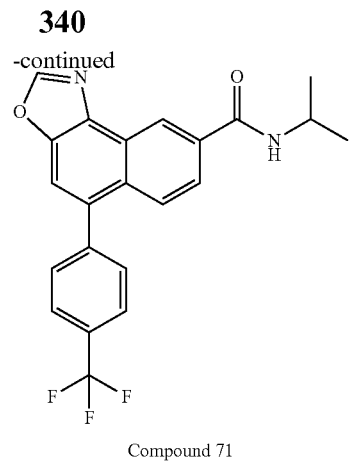

Compound 71

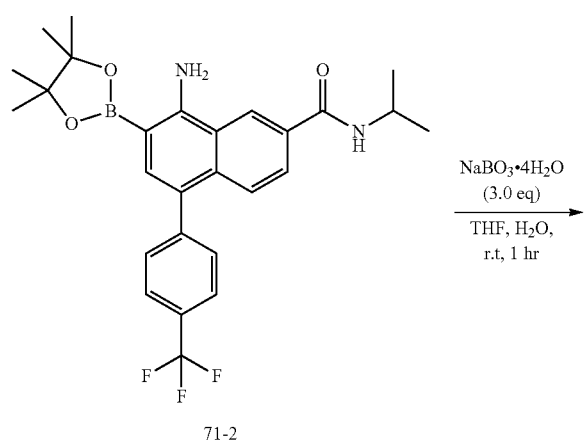

71-2

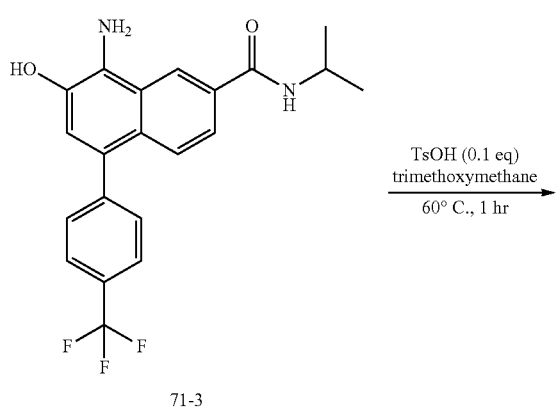

71-3

Step 1: 8-amino-N-isopropyl-7-(4,4,5,5-tetramethyl-1,3,2-dioxaborolan-2-yl)-5-(4-(trifluoromethyl)phenyl)-2-naphthamide To a solution of compound 71-1 (200 mg, 0.44 mmol, 1 eq) and 4,4,5,5-tetramethyl-2-(4,4,5,5-tetramethyl-1,3,2-dioxaborolan-2-yl)-1,3,2-dioxaborolane (168.8 mg, 0.66 mmol, 1.5 eq) in dioxane (2 mL) was added AcOK (86.9 mg, 0.88 mmol, 2 eq) and Pd(dppf)Cl$_2$ (16.2 mg, 22.1 umol, 0.05 eq). The mixture was stirred at 90° C. for 2 hr. LCMS showed the starting material was consumed and the desired mass was detected. H$_2$O (15 mL) was added to the solution. The mixture was extracted with ethyl acetate (25 mL*3). The combined organic layers were washed with brine (40 mL*2), dried over anhydrous Na$_2$SO$_4$, filtered and concentrated in vacuum. The residue was purified by column chromatography (SiO$_2$, Petroleum ether/Ethyl acetate=1/0 to 1:1). Compound 71-2 (100 mg, crude) was obtained as a yellow oil.

Step 2: 8-amino-7-hydroxy-N-isopropyl-5-(4-(trifluoromethyl)phenyl)-2-naphthamide To a solution of compound 71-2 (100 mg, 0.20 mmol, 1 eq) in THF (2 mL) was added sodium 3-oxidodioxaborirane tetrahydrate (92.6 mg, 0.60 mmol, 0.11 mL, 3 eq) and H$_2$O (0.5 mL). The mixture was stirred at 25° C. for 1 hr. LCMS showed the starting material was consumed and the desired mass was detected. H$_2$O (15 mL) was added to the solution. The mixture was extracted with ethyl acetate (25 mL*3). The combined organic layers were washed with brine (50 mL*2), dried over anhydrous Na$_2$SO$_4$, filtered and concentrated in vacuum. Compound 71-3 (90 mg, crude) was obtained as a brown solid.

Step 3: N-isopropyl-5-(4-(trifluoromethyl)phenyl)naphtho[1,2-d]oxazole-8-carboxamide To a solution of compound 71-3 (90 mg, 0.23 mmol, 1 eq) in trimethoxymethane (491.8 mg, 4.63 mmol, 0.50 mL, 20 eq) was added TsOH (3.9 mg, 23.1 umol, 0.1 eq). The mixture was stirred at 60° C. for 1 hr. LCMS showed the starting material was consumed and the desired mass was detected. H$_2$O (3 mL) was added to the solution. The mixture was extracted with ethyl acetate (5 mL*3). The combined organic layers were washed with brine (6 mL*2), dried over anhydrous Na$_2$SO$_4$, filtered and concentrated in vacuum. The residue was purified by prep-HPLC to afford product (5 mg). HPLC showed the ~54% desired product was detected. The product was purified by SFC. The title compound (1 mg, 2.4 umol, 1.0% yield) was obtained as a white solid. LCMS (ESI): RT=0.856 min, mass calc. for $C_{22}H_{17}F_3N_2O_2$ 398.38, m/z found 399.0 [M+H]$^+$; $^1$H NMR (400 MHz, CD$_3$OD) δ 8.93 (s, 1H), 8.60 (s, 1H), 7.84 (s, 3H), 7.78 (d, J=8.1 Hz, 2H), 7.64 (d, J=8.1 Hz, 2H), 4.20 (quin, J=6.6 Hz, 1H), 1.22 (d, J=6.6 Hz, 8H).

Example 67: 5,6-Difluoro-N-isopropyl-8-(4-(trifluoromethyl)phenyl)quinoline-3-carboxamide (Compound 72)

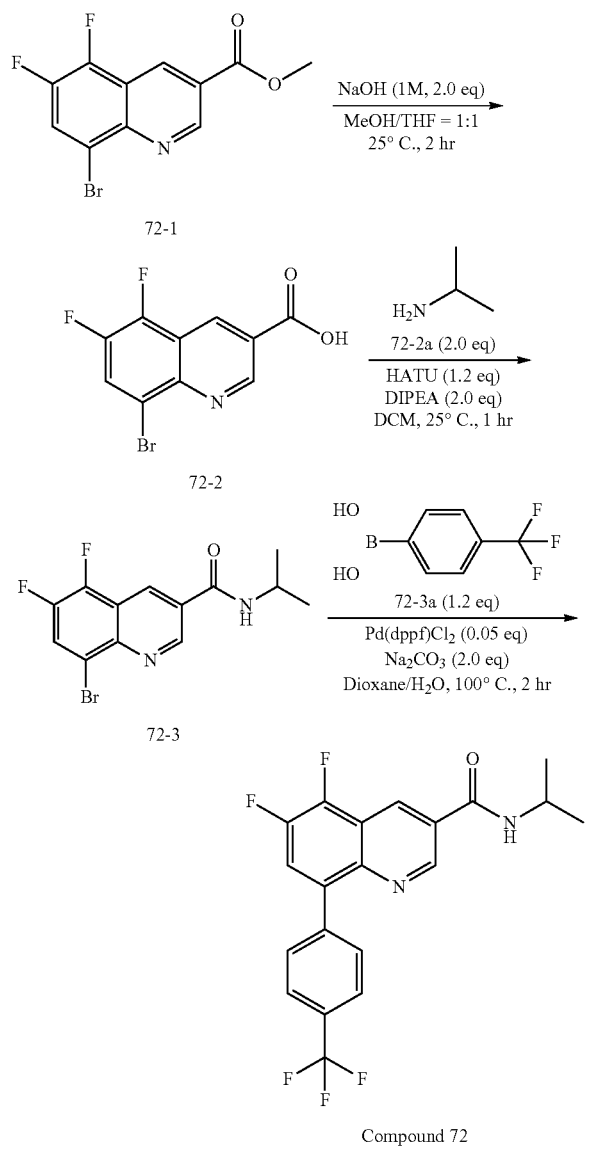

Compound 72

Step 1: 8-Bromo-5,6-difluoroquinoline-3-carboxylic Acid

A solution of compound 72-1 (140 mg, 0.46 mmol, 1.0 eq) in MeOH (2 mL) and THF (2 mL) was added a solution of NaOH (1 M, 0.93 mL, 2.0 eq) dropwise. The reaction mixture was stirred at 25° C. for 2 hours. The reaction mixture was adjusted with HCl (1M) to pH=2, and then the resultant mixture was extracted with EA (20 mL*3). The combined organic layers were dried over Na$_2$SO$_4$, filtered and concentrated to dryness under reduced pressure to give compound 72-2 (120 mg, 89% yield) as a white solid.

Step 2: 8-bromo-5,6-difluoro-N-isopropylquinoline-3-carboxamide

To a solution of compound 72-2 (30 mg, 0.10 mmol, 1.0 eq), DIPEA (27 mg, 0.20 mmol, 2.0 eq) and compound 72-2a (12.3 mg, 0.20 mmol, 2.0 eq) in DCM (2 mL) was added HATU (47.5 mg, 0.12 mmol, 1.2 eq). The reaction was stirred at 25° C. for 1 hr. The reaction mixture was concentrated under reduced pressure. The mixture was diluted with water (20 mL) and the resultant mixture was extracted with EA (30 mL*3). The combined organic layers were dried over Na$_2$SO$_4$, filtered and concentrated to dryness under reduced pressure. The residue was purified by column chromatography over silica gel (petroleum ether: ethyl acetate=1:0 to 3:1) to give compound 72-3 (30 mg, 87% yield) as a white solid.

Step 3: 5,6-Difluoro-N-isopropyl-8-(4-(trifluoromethyl)phenyl)quinoline-3-carboxamide To a solution of compound 72-3 (30 mg, 91 umol, 1.0 eq), compound 72-3a (21 mg, 0.11 mmol, 1.2 eq) and Na$_2$CO$_3$ (19 mg, 0.18 mmol, 2.0 eq) in Dioxane (2 mL) and H$_2$O (0.4 mL) was added Pd(dppf)Cl$_2$ (3.3 mg, 4.6 umol, 0.05 eq) under N$_2$. The reaction mixture was stirred at 100° C. for 2 hours under N$_2$. LC-MS showed starting material was consumed completely and one main peak with desired MS was detected. The reaction mixture was concentrated under reduced pressure. The mixture was diluted with water (20 mL) and the resultant mixture was extracted with EA (30 mL*3). The combined organic layers were dried over Na$_2$SO$_4$, filtered and concentrated to dryness under reduced pressure. The residue was purified by prep-HPLC to give the title compound (12.80 mg, 35% yield) as a white solid. LCMS (ESI): RT=0.890 min, mass calcd. for $C_{20}H_{15}F_5N_2O$ 394.11, m/z found 394.9 [M+H]$^+$; $^1$H NMR (400 MHz, CDCl$_3$) δ 9.28 (d, J=2.0 Hz, 1H), 8.83 (d, J=2.0 Hz, 1H), 7.77 (s, 4H), 7.72 (dd, J=8.5, 10.8 Hz, 1H), 6.11 (d, J=7.3 Hz, 1H), 4.44-4.32 (m, 1H), 1.35 (d, J=6.5 Hz, 6H).

Example 68: 5,6-Difluoro-N-(methylsulfonyl)-8-(4-(trifluoromethyl)phenyl)quinoline-3-carboxamide (Compound 73)

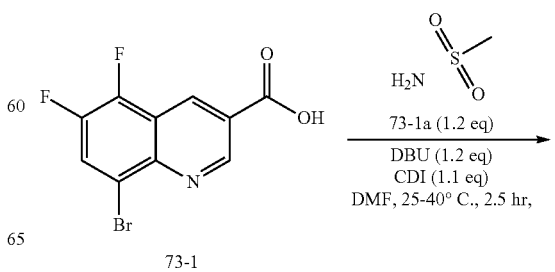

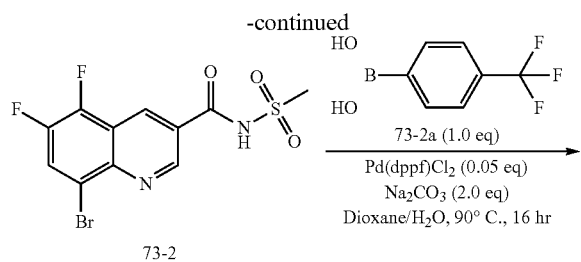

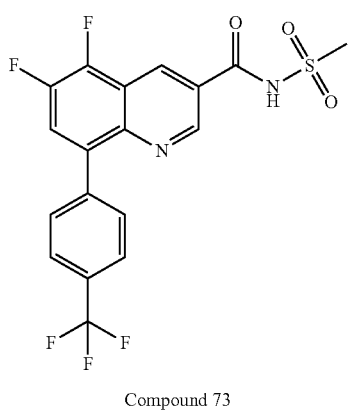

Compound 73

Step 1: 8-Bromo-5,6-difluoro-N-(methylsulfonyl)quinoline-3-carboxamide

To a solution of compound 73-1 (20 mg, 69 umol, 1.0 eq) in DMF (0.5 mL) was added CDI (12 mg, 76 umol, 1.1 eq). The reaction mixture was stirred at 40° C. for 30 min. The reaction was cooled to 25° C., and then DBU (13 mg, 83 umol, 1.2 eq) and compound 73-1a (8 mg, 83 umol, 1.2 eq) were added. The reaction was stirred at 25° C. for 2 hours. LC-MS showed the starting material was consumed completely and one main peak with desired MS was detected. The reaction mixture was concentrated under reduced pressure. The mixture was diluted with water (10 mL) and the resultant mixture was extracted with EA (20 mL*3). The combined organic layers were dried over $Na_2SO_4$, filtered and concentrated to dryness under reduced pressure to give compound 73-2 (22 mg, crude) as a yellow solid.

Step 2: 5,6-Difluoro-N-(methylsulfonyl)-8-(4-(trifluoromethyl)phenyl)quinoline-3-carboxamide To a solution of compound 73-2 (30 mg, 82 umol, 1.0 eq), compound 73-2a (16 mg, 82 umol, 1.0 eq) and $Na_2CO_3$ (17.4 mg, 0.16 mmol, 2.0 eq) in Dioxane (2 mL) and $H_2O$ (0.4 mL) was added $Pd(dppf)Cl_2$ (3.0 mg, 4.1 umol, 0.05 eq) under $N_2$. The reaction mixture was stirred at 90° C. for 16 hours under $N_2$. LC-MS showed the starting material was consumed completely and one main peak with desired MS was detected. The reaction mixture was concentrated under reduced pressure. The mixture was diluted with water (10 mL) and the resultant mixture was extracted with EA (20 mL*3). The combined organic layers were dried over $Na_2SO_4$, filtered and concentrated to dryness under reduced pressure. The residue was purified by prep-HPLC to give the title compound (2.66 mg, 6.9% yield, HCl) as a white solid. LCMS (ESI): RT=0.946 min, mass calcd. for $C_{18}H_{11}F_5N_2O_3S$ 430.04, m/z found 431.0 [M+H]$^+$; $^1$H NMR (500 MHz, DMSO-d$_6$) δ 9.29 (dd, J=2.1, 12.7 Hz, 2H), 8.25 (dd, J=8.5, 11.3 Hz, 1H), 7.90 (s, 4H), 3.47-3.45 (m, 1H), 3.46 (s, 4H).

Example 69: Tert-Butyl (1-oxo-1-(5-(4-(trifluoromethyl)phenyl)naphthalen-2-yl)-5,8,11-trioxa-2-azatridecan-13-yl)carbamate (Compound 74)

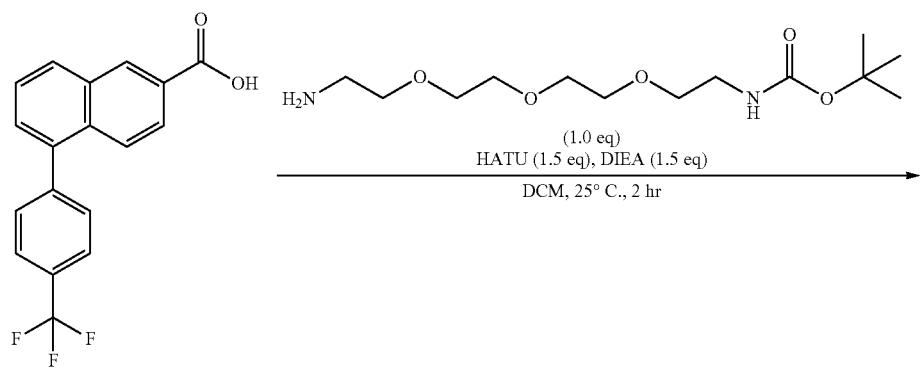

74-1

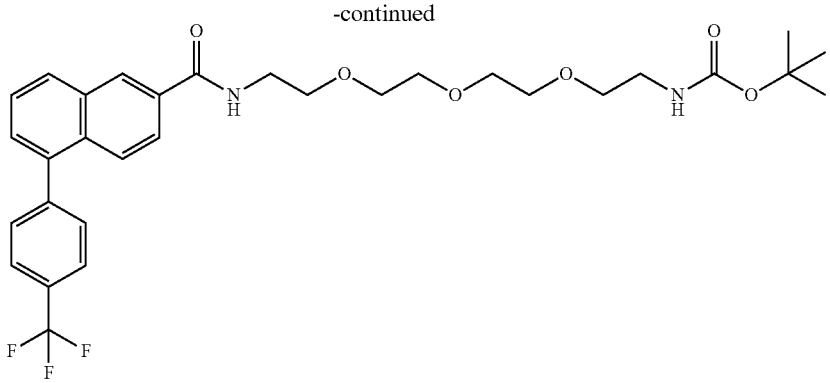

Compound 74

The mixture of compound 74-1 (50 mg, 0.15 mmol, 1 eq), HATU (90.1 mg, 0.23 mmol, 1.5 eq) and DIEA (30.6 mg, 0.23 mmol, 41.3 uL, 1.5 eq) in DCM (2 mL) was stirred at 25° C. for 1 hr. Then tert-butyl N-[2-[2-[2-(2-aminoethoxy)ethoxy]ethoxy]ethyl]carbamate (46.2 mg, 0.15 mmol, 1 eq) was added at the mixture and the mixture was stirred at 25° C. for 1 hr. LC-MS and HPLC showed the desired compound was detected. The reaction mixture was diluted with H₂O (10 mL) and the mixture was extracted with EA (10 mL*3). The combined organic phase was washed with brine (10 mL*3), dried with anhydrous Na₂SO₄, filtered and concentrated in vacuum. The residue was purified by prep-HPLC. The title compound (30 mg, 50.7 umol, 32.1% yield) was obtained as yellow solid. LCMS (ESI): RT=0.828 min, mass calc. for $C_{31}H_{37}F_3N_2O_6$ 590.63, m/z found 613.1 [M+Na]⁺; ¹H NMR (400 MHz, CD₃OD) δ 1.33-1.46 (m, 9H), 3.17 (t, J=5.57 Hz, 2H), 3.45 (t, J=5.50 Hz, 2H), 3.54-3.59 (m, 2H), 3.62 (br s, 1H), 3.63-3.69 (m, 1H), 3.63-3.68 (m, 1H), 3.63-3.68 (m, 1H), 3.70-3.71 (m, 2H), 3.71-3.75 (m, 2H), 4.78-4.95 (m, 9H), 7.58 (dd, J=7.07, 0.94 Hz, 1H), 7.65-7.72 (m, 3H), 7.82-7.93 (m, 1H), 7.83-7.91 (m, 3H), 8.08 (d, J=8.26 Hz, 1H), 8.50 (s, 1H).

Example 70: Tert-Butyl (1-oxo-1-(5-(4-(trifluoromethyl)phenyl)naphthalen-2-yl)-5,8,11,14-tetraoxa-2-azahexadecan-16-yl)carbamate (Compound 75)

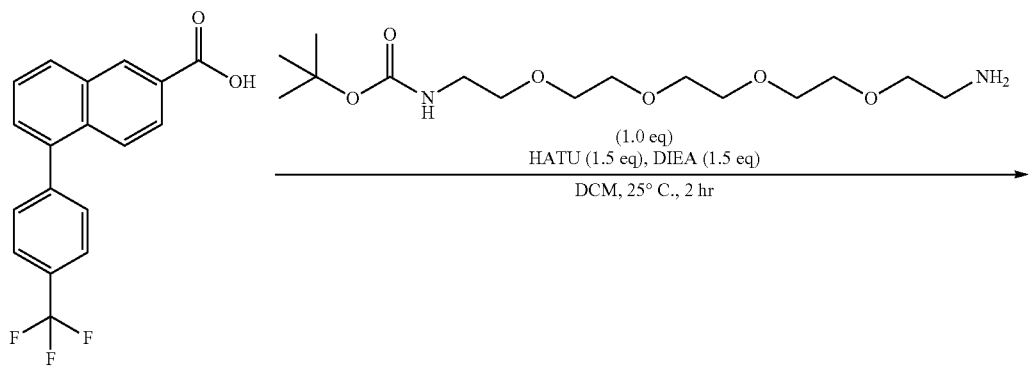

75-1

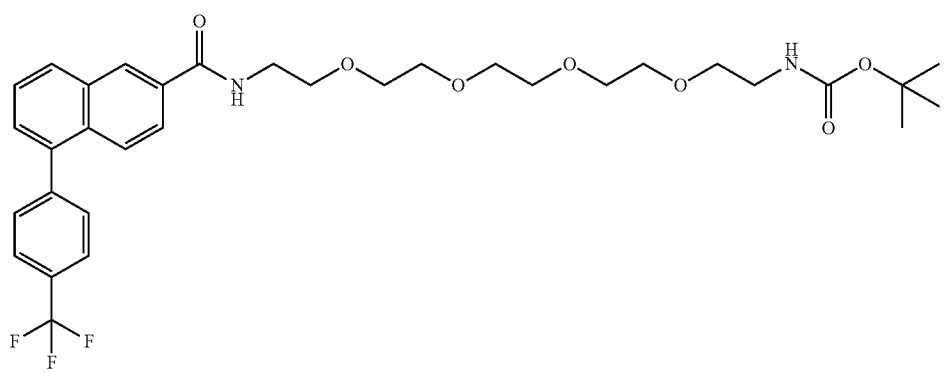

Compound 75

The mixture of compound 75-1 (50 mg, 0.15 mmol, 1 eq), DIEA (30.6 mg, 0.23 mmol, 41.3 uL, 1.5 eq) and HATU (90.1 mg, 0.23 mmol, 1.5 eq) in DCM (1 mL) was stirred at 25° C. for 1 hr. Then tert-butyl N-[2-[2-[2-[2-(2-aminoethoxy)ethoxy]ethoxy]ethoxy]ethyl]carbamate (53.1 mg, 0.15 mmol, 1 eq) was added at the mixture and the mixture was stirred at 25° C. for 1 hr. LC-MS and HPLC showed the desired compound was detected. The reaction mixture was diluted with H₂O (10 mL) and the mixture was extracted with EA (10 mL*3). The combined organic phase was washed with brine (10 mL*3), dried with anhydrous Na₂SO₄, filtered and concentrated in vacuum. The residue was purified by prep-HPLC. The title compound (25 mg, 39.3 umol, 24.9% yield) was obtained as yellow oil. LCMS (ESI): RT=0.886 min, mass calc. for $C_{33}H_{41}F_3N_2O_7$ 634.68, m/z found 657.1 [M+Na]⁺; ¹H NMR (400 MHz, CD₃OD) δ 1.43 (s, 9H), 3.18 (t, J=5.52 Hz, 2H), 3.44 (t, J=5.52 Hz, 2H), 3.49-3.54 (m, 2H), 3.54-3.59 (m, 2H), 3.59-3.63 (m, 2H), 3.64-3.68 (m, 4H), 3.69 (s, 3H), 3.71-3.76 (m, 2H), 7.59 (d, J=7.03 Hz, 1H), 7.64-7.74 (m, 3H), 7.81-7.94 (m, 4H), 8.09 (d, J=8.28 Hz, 1H), 8.51 (s, 1H).

Example 71: N-(4-oxo-2,8,11-trioxa-5-azatridecan-13-yl)-5-(4-(trifluoromethyl)phenyl)-2-naphthamide (Compound 76)

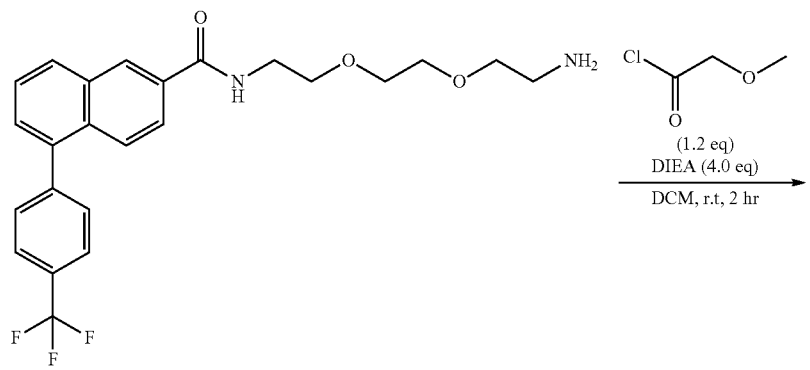

76-1

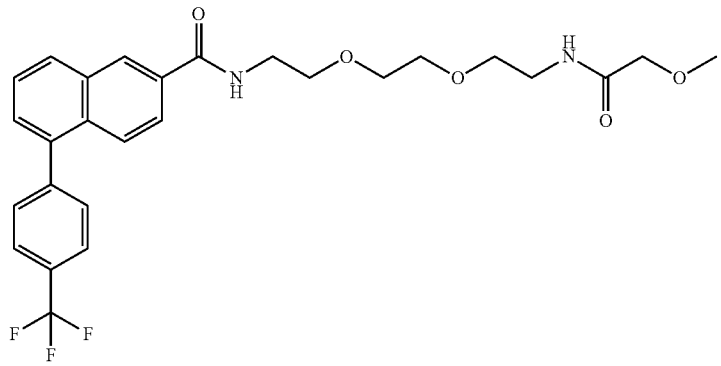

Compound 76

The mixture of compound 76-1 (50 mg, 0.11 mmol, 1 eq), 2-methoxyacetyl chloride (14.5 mg, 0.13 mmol, 12.2 uL, 1.2 eq) and DIEA (57.9 mg, 0.44 mmol, 78.0 uL, 4 eq) in DCM (3 mL) was stirred at 25° C. for another 2 hr. LC-MS showed the desired compound was detected. The reaction mixture was diluted with H₂O (10 mL) and the mixture was extracted with EA (10 mL*3). The combined organic phase was washed with brine (10 mL*2), dried with anhydrous Na₂SO₄, filtered and concentrated in vacuum. The residue was purified by prep-HPLC. The title compound (12 mg, 22.6 umol, 20.2% yield) was obtained as yellow oil. LCMS (ESI): RT=0.828 min, mass calc. for $C_{27}H_{29}F_3N_2O_5$ 518.52, m/z found 519.2 [M+H]⁺; ¹H NMR (400 MHz, CD₃OD) δ 8.50 (s, 1H), 8.08 (d, J=8.3 Hz, 1H), 7.90-7.83 (m, 4H), 7.72-7.65 (m, 3H), 7.58 (dd, J=0.9, 7.1 Hz, 1H), 3.84 (s, 2H), 3.75-3.71 (m, 2H), 3.70-3.65 (m, 6H), 3.61-3.56 (m, 2H), 3.44-3.39 (m, 2H), 3.37 (s, 3H), 3.33 (td, J=1.6, 3.3 Hz, 5H).

Example 72: N-(5-oxo-2,9,12-trioxa-6-azatetradecan-14-yl)-5-(4-(trifluoromethyl)phenyl)-2-naphthamide (Compound 77)

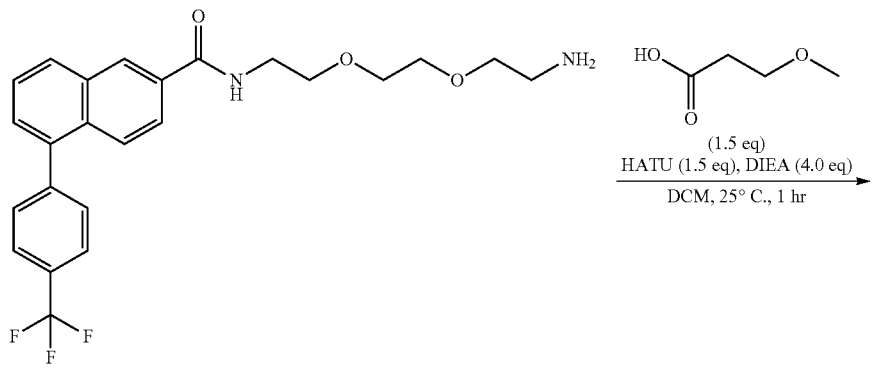

77-1

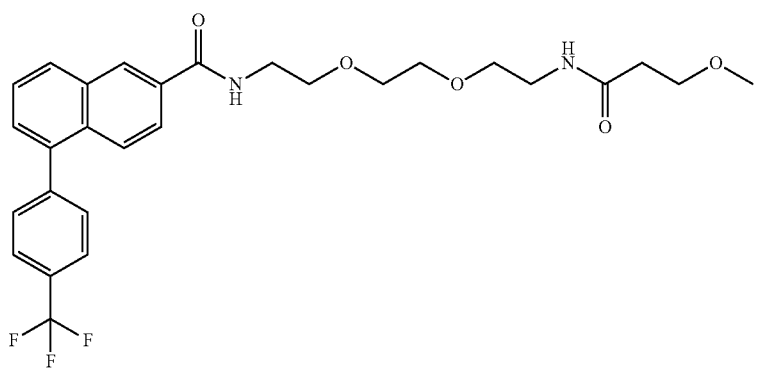

Compound 77

The mixture of 3-methoxypropanoic acid (17.4 mg, 0.16 mmol, 15.7 uL, 1.5 eq), HATU (63.8 mg, 0.16 mmol, 1.5 eq) and DIEA (57.9 mg, 0.44 mmol, 78.0 uL, 4 eq) in DCM (2 mL) was stirred at 25° C. for 1 hr. Then compound 77-1 (50 mg, 0.11 mmol, 1 eq) was added at the mixture and the mixture was stirred for another 1 hr. LC-MS showed the desired compound was detected. The reaction mixture was diluted with $H_2O$ (10 mL) and the mixture was extracted with EA (30 mL*3). The combined organic phase was washed with brine (10 mL*2), dried with anhydrous $Na_2SO_4$, filtered and concentrated in vacuum. The residue was purified by prep-HPLC. The title compound (10 mg, 18.5 umol, 16.6% yield) was obtained as yellow oil. LCMS (ESI): RT=0.899 min, mass calc. for $C_{28}H_{31}F_3N_2O_5$ 532.56, m/z found 533.2 [M+H]$^+$; $^1$H NMR (400 MHz, $CD_3OD$) δ 8.50 (d, J=1.3 Hz, 1H), 8.08 (d, J=8.1 Hz, 1H), 7.89-7.83 (m, 4H), 7.72-7.67 (m, 1H), 7.66 (s, 1H), 7.72-7.65 (m, 1H), 7.58 (dd, J=1.1, 7.1 Hz, 1H), 3.76-3.63 (m, 8H), 3.61-3.54 (m, 1H), 3.57 (td, J=5.9, 7.5 Hz, 3H), 3.36 (t, J=5.5 Hz, 2H), 3.34-3.32 (m, 3H), 3.29 (s, 3H), 2.41 (t, J=6.1 Hz, 2H).

Example 73: N-(ethylsulfonyl)-5-(4-(trifluoromethyl)phenyl)-2-naphthamide (Compound 78)

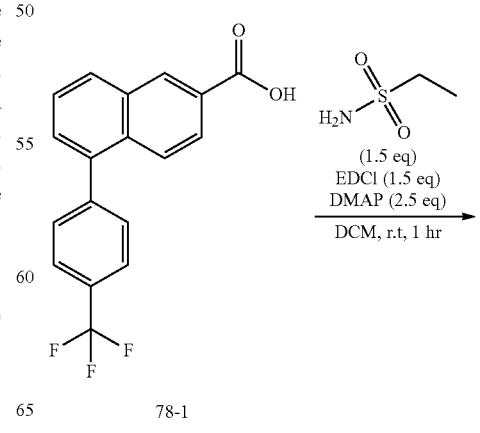

78-1

-continued

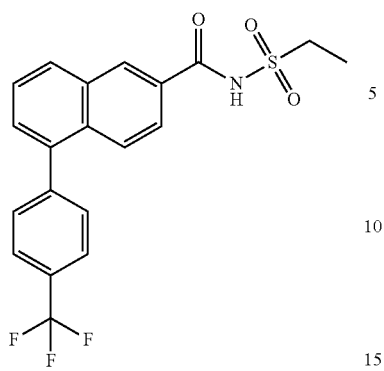

Compound 78

-continued

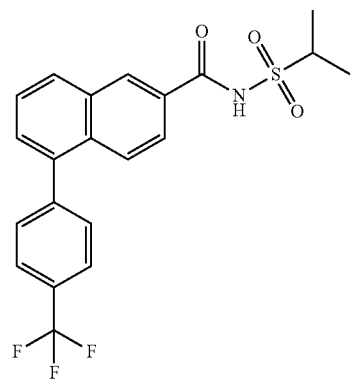

Compound 79

To a solution of 78-1 (100 mg, 0.31 mmol, 1 eq) and ethylsulfonamide (51.7 mg, 0.47 mmol, 1.5 eq) in DCM (2 mL) was added EDCI (90.9 mg, 0.47 mmol, 1.5 eq) and DMAP (96.5 mg, 0.79 mmol, 2.5 eq). The mixture was stirred at 19° C. for 1 hr. LCMS and HPLC showed the starting material was consumed. H$_2$O (8 mL) was added to the solution. The mixture was extracted with ethyl acetate (10 mL*3). The combined organic layers were washed with brine (15 mL*2), dried over anhydrous Na$_2$SO$_4$, filtered and concentrated in vacuum. The residue was purified by prep-HPLC to afford the crude product (18 mg). The residue was purified by SFC. The title compound (7.2 mg, 17.7 umol, 5.6% yield) was obtained as a white solid. $^1$H NMR (400 MHz, DMSO-d$_6$) δ 8.63 (s, 1H), 8.12 (d, J=8.3 Hz, 1H), 8.07-8.02 (m, 1H), 7.91 (d, J=8.0 Hz, 2H), 7.77-7.71 (m, 3H), 7.64 (s, 1H), 7.54 (s, 1H), 3.18 (q, J=7.1 Hz, 2H), 1.15 (t, J=7.4 Hz, 3H).

To a solution of compound 79-1 (50 mg, 0.15 mmol, 1 eq) and propane-2-sulfonamide (29.2 mg, 0.23 mmol, 1.5 eq) in DCM (2 mL) was added EDCI (45.4 mg, 0.23 mmol, 1.5 eq) and DMAP (48.2 mg, 0.39 mmol, 2.5 eq). The mixture was stirred at 19° C. for 1 hr. LCMS showed the starting material was consumed. H$_2$O (10 mL) was added to the solution. The mixture was extracted with ethyl acetate (10 mL*3). The combined organic layers were washed with brine (12 mL*2), dried over anhydrous Na$_2$SO$_4$, filtered and concentrated in vacuum. The residue was purified by prep-HPLC. The title compound (12.3 mg, 29.2 umol, 18.4% yield) was obtained as a white solid. $^1$H NMR (400 MHz, DMSO-d$_6$) δ 12.28-12.20 (m, 1H), 8.75 (s, 1H), 8.20 (d, J=7.8 Hz, 1H), 7.98-7.92 (m, 3H), 7.86 (s, 1H), 7.75 (d, J=7.8 Hz, 3H), 7.69-7.65 (m, 1H), 3.92-3.83 (m, 1H), 1.35 (d, J=6.8 Hz, 6H).

Example 75: 6-ethoxy-N-isopropyl-8-(4-(trifluoromethyl)phenyl)quinoline-3-carboxamide (Compound 80)

Example 74: N-(isopropylsulfonyl)-5-(4-(trifluoromethyl)phenyl)-2-naphthamide (Compound 79)

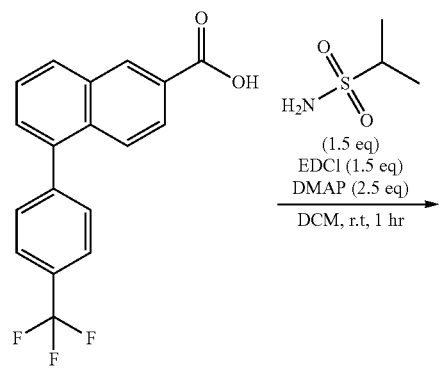

79-1

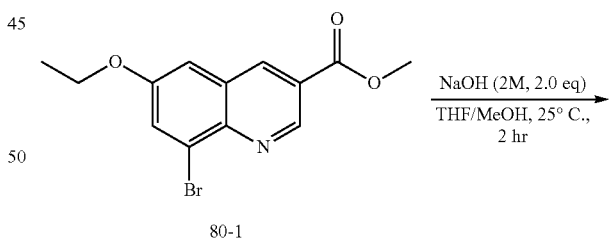

80-1

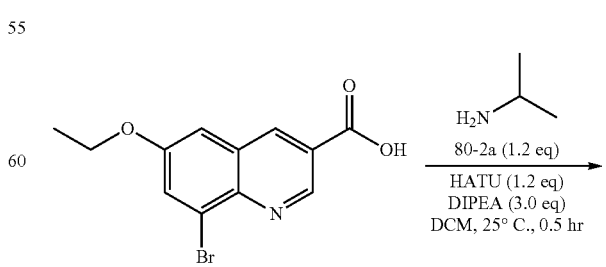

80-2

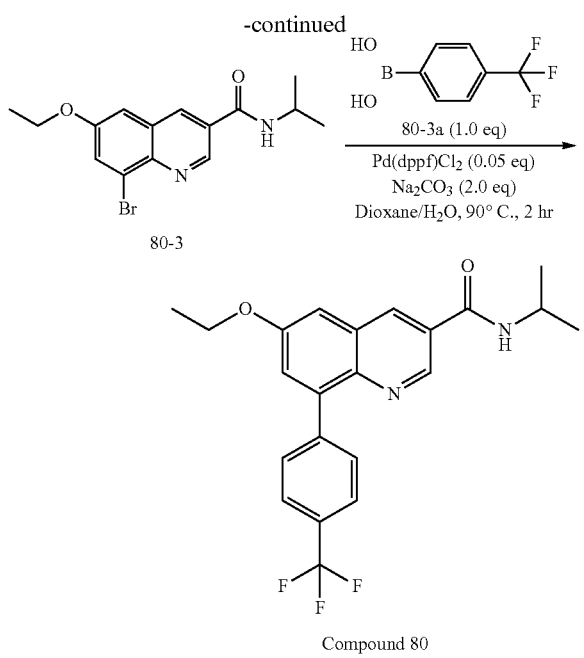

Compound 80

Step 1: 8-Bromo-6-ethoxyquinoline-3-carboxylic Acid

To a solution of compound 80-1 (150 mg, 0.484 mmol, 1.0 eq) in THF (1.5 mL) and MeOH (1.5 mL) was added a solution of NaOH (2 M, 0.48 mL, 2.0 eq) dropwise. The reaction mixture was stirred at 25° C. for 2 hours. LC-MS showed starting material was consumed completely and one main peak with desired MS was detected. The reaction mixture was concentrated under reduced pressure. The residue was diluted with water (10 mL), and then the residue was adjusted with HCl (1M) to pH=6. The resultant mixture was extracted with EA (40 mL*3). The combined organic layers were dried over Na$_2$SO$_4$, filtered and concentrated to dryness under reduced pressure to give compound 80-2 (130 mg, 90% yield) as a white solid. LCMS (ESI): RT=0.829 min, mass calcd. C$_{12}$H$_{10}$BrNO$_3$ 294.98, m/z found 296.0 [M+H]$^+$.

Step 2: 8-Bromo-6-ethoxy-N-isopropylquinoline-3-carboxamide

To a solution of compound 80-2 (40.0 mg, 0.13 mmol, 1 eq), compound 80-2a (9.6 mg, 0.16 mmol, 1.2 eq) and DIPEA (52.3 mg, 0.40 mmol, 3.0 eq) in DCM (2 mL) was added HATU (61.6 mg, 0.16 mmol, 1.2 eq). The reaction mixture was stirred at 25° C. for 0.5 hour. LC-MS showed starting material was consumed completely and one main peak with desired MS was detected. The mixture was diluted with water (10 mL) and the resultant mixture was extracted with DCM (20 mL*3). The combined organic layers were dried over Na$_2$SO$_4$, filtered and concentrated to dryness under reduced pressure. The residue was purified by column chromatography over silica gel (petroleum ether:ethyl acetate=1:0 to 1:1) to give compound 80-3 (40 mg, 87% yield) as a white solid.

Step 3: 6-Ethoxy-N-isopropyl-8-(4-(trifluoromethyl)phenyl)quinoline-3-carboxamide To a solution of compound 80-3 (40 mg, 0.12 mmol, 1.0 eq), compound 80-3a (23 mg, 0.12 mmol, 1.0 eq) and Na$_2$CO$_3$ (25 mg, 0.24 mmol, 2.0 eq) in Dioxane (2 mL) and H$_2$O (0.4 mL) was added Pd(dppf)Cl$_2$ (4.3 mg, 5.9 umol, 0.05 eq). The reaction mixture was stirred at 90° C. for 2 hrs under N$_2$. LC-MS showed starting material was consumed completely and one main peak with desired MS was detected. The reaction mixture was concentrated under reduced pressure. The mixture was diluted with water (10 mL) and the resultant mixture was extracted with EA (20 mL*3). The combined organic layers were dried over Na$_2$SO$_4$, filtered and concentrated to dryness under reduced pressure. The residue was purified by prep-HPLC to give the title compound (20.00 mg, 41% yield) as a white solid. LCMS (ESI): RT=1.008 min, mass calcd. for C$_{22}$H$_{21}$F$_3$N$_2$O$_2$ 402.16, m/z found 403.1 [M+H]$^+$; $^1$H NMR (400 MHz, CDCl$_3$) δ 9.05 (d, J=2.3 Hz, 1H), 8.53 (d, J=2.1 Hz, 1H), 7.83-7.78 (m, 2H), 7.78-7.73 (m, 2H), 7.48 (d, J=2.8 Hz, 1H), 7.18 (d, J=2.8 Hz, 1H), 6.05 (d, J=7.5 Hz, 1H), 4.43-4.32 (m, 1H), 4.21 (q, J=6.9 Hz, 2H), 1.53 (t, J=6.9 Hz, 3H), 1.33 (d, J=6.5 Hz, 6H).

Example 76: 6-ethoxy-N-(methylsulfonyl)-8-(4-(trifluoromethyl)phenyl)quinoline-3-carboxamide (Compound 81)

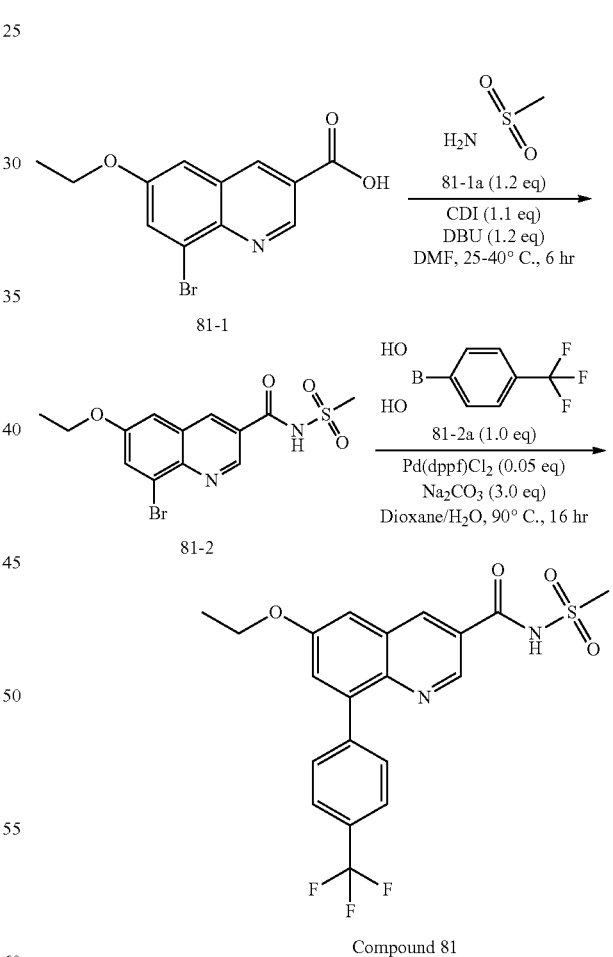

Compound 81

Step 1: 8-Bromo-6-ethoxy-N-(methylsulfonyl)quinoline-3-carboxamide

To a solution of compound 81-1 (40 mg, 0.14 mmol, 1 eq) in DMF (1 mL) was added CDI (24 mg, 0.15 mol, 1.1 eq).

The reaction mixture was stirred at 40° C. for 30 min. The reaction was cooled to 25° C., and then DBU (25 mg, 0.16 mmol, 1.2 eq) and compound 81-1a (15 mg, 0.16 mmol, 1.2 eq) were added. The reaction was stirred at 25° C. for 5.5 hours. The reaction mixture was concentrated under reduced pressure. The reaction mixture was adjusted with HCl (1M) to pH=4. The mixture was diluted with water (10 mL) and the resultant mixture was extracted with EA (30 mL*3). The combined organic layers were dried over Na$_2$SO$_4$, filtered and concentrated to dryness under reduced pressure. The residue was purified by column chromatography over silica gel (DCM:MeOH=1:0 to 10:1) to give compound 81-2 (40 mg, crude) as a white solid.

Step 2: 6-ethoxy-N-(methylsulfonyl)-8-(4-(trifluoromethyl)phenyl)quinoline-3-carboxamide To a solution of compound 81-2 (40 mg, 0.11 mmol, 1 eq), compound 81-2a (20 mg, 0.11 mmol, 1.0 eq) and Na$_2$CO$_3$ (34 mg, 0.32 mmol, 3.0 eq) in Dioxane (2 mL) and H$_2$O (0.4 mL) was added Pd(dppf)Cl$_2$ (3.9 mg, 5.4 umol, 0.05 eq). The reaction mixture was stirred at 90° C. for 16 hours under N$_2$. LC-MS showed starting material was consumed completely and one main peak with desired MS was detected. The reaction mixture was concentrated under reduced pressure. The residue was diluted with water (5 mL), and then the residue was adjusted with HCl (1M) to pH=5. The resultant mixture was extracted with EA (20 mL*3). The combined organic layers were dried over Na$_2$SO$_4$, filtered and concentrated to dryness under reduced pressure. The residue was purified by prep-HPLC to give the title compound (10.10 mg, 19% yield) as a white solid. LCMS (ESI): RT=0.959 min, mass calcd. for C$_{20}$H$_{17}$F$_3$N$_2$O$_4$S 438.09, m/z found 439.0 [M+H]$^+$; $^1$H NMR (400 MHz, DMSO-d$_6$) δ 12.54 (br s, 1H), 9.08 (d, J=2.1 Hz, 1H), 8.93 (d, J=2.3 Hz, 1H), 7.92-7.82 (m, 4H), 7.63-7.59 (m, 2H), 4.27 (q, J=7.0 Hz, 2H), 3.45 (s, 3H), 1.45 (t, J=6.9 Hz, 3H).

Example 77: N-(cyclopropylsulfonyl)-5-(4-(trifluoromethyl)phenyl)-2-naphthamide (Compound 82)

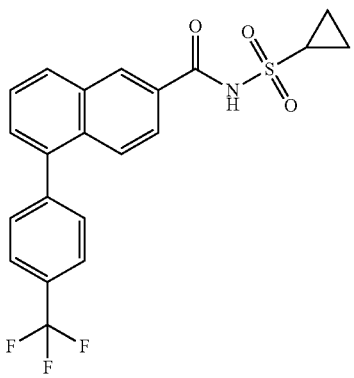

Compound 82

To a solution of compound 82-1 (50 mg, 0.15 mmol, 1 eq) and cyclopropanesulfonamide (28.7 mg, 0.23 mmol, 1.5 eq) in DCM (2 mL) was added EDCI (45.4 mg, 0.23 mmol, 1.5 eq) and DMAP (48.2 mg, 0.39 mmol, 2.5 eq). The mixture was stirred at 19° C. for 1 hr. LCMS showed the starting material was consumed. H$_2$O (10 mL) was added to the solution. The mixture was extracted with ethyl acetate (15 mL*3). The combined organic layers were washed with brine (15 mL*2), dried over anhydrous Na$_2$SO$_4$, filtered and concentrated in vacuum. HPLC showed ~100% of desired mass was detected. The residue was purified by prep-HPLC. The title compound (14.6 mg, 34.9 umol, 22.1% yield) was obtained as a white solid. LCMS (ESI): RT=0.874 min, mass calc. for C$_{21}$H$_{16}$F$_3$NO$_3$S 419.42, m/z found 419.8 [M+H]$^+$; $^1$H NMR (400 MHz, DMSO-d$_6$) δ 8.70 (d, J=1.5 Hz, 1H), 8.17 (d, J=8.3 Hz, 1H), 7.99 (dd, J=1.8, 8.9 Hz, 1H), 7.93 (d, J=8.1 Hz, 2H), 7.82 (d, J=8.9 Hz, 1H), 7.75 (d, J=8.1 Hz, 2H), 7.73-7.68 (m, 1H), 7.65-7.60 (m, 1H), 3.19-3.09 (m, 1H), 1.16-1.01 (m, 4H).

Example 78: 5-(4-(trifluoromethyl)phenyl)-N-((trifluoromethyl)sulfonyl)-2-naphthamide (Compound 83)

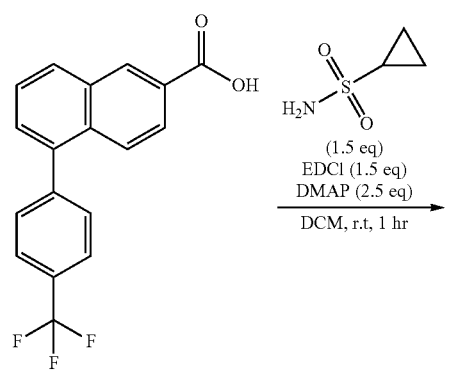

82-1

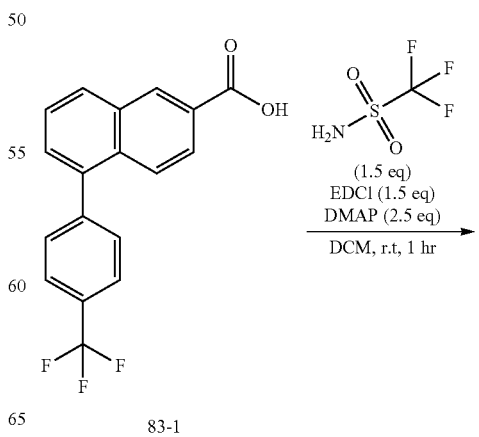

83-1

-continued

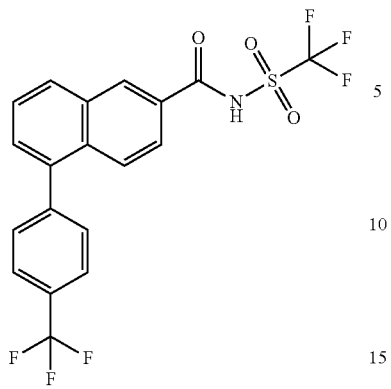

Compound 83

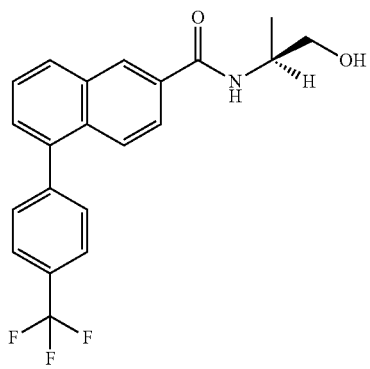

Compound 84

To a solution of compound 83-1 (50 mg, 0.15 mmol, 1 eq) and trifluoromethanesulfonamide (35.3 mg, 0.23 mmol, 1.5 eq) in DCM (2 mL) was added EDCI (45.4 mg, 0.23 mmol, 1.5 eq) and DMAP (48.2 mg, 0.39 mmol, 2.5 eq). The mixture was stirred at 19° C. for 1 hr. LCMS showed the starting material was consumed. H$_2$O (9 mL) was added to the solution. The mixture was extracted with ethyl acetate (12 mL*3). The combined organic layers were washed with brine (15 mL*2), dried over anhydrous Na$_2$SO$_4$, filtered and concentrated in vacuum. The residue was purified by prep-HPLC. The title compound (6.0 mg, 13.4 umol, 8.4% yield) was obtained as a white solid. $^1$H NMR (400 MHz, DMSO-d$_6$) δ 8.81-8.78 (m, 1H), 8.61 (d, J=1.3 Hz, 1H), 8.15 (d, J=8.0 Hz, 1H), 8.02 (dd, J=1.6, 8.9 Hz, 1H), 7.91 (d, J=8.3 Hz, 2H), 7.79-7.71 (m, 3H), 7.69-7.60 (m, 1H), 7.55 (d, J=6.0 Hz, 1H), 7.26-6.94 (m, 1H).

Example 79: (S)—N-(1-hydroxypropan-2-yl)-5-(4-(trifluoromethyl)phenyl)-2-naphthamide (Compound 84)

The mixture of compound 84-1 (60 mg, 0.18 mmol, 1 eq), HATU (108.2 mg, 0.28 mmol, 1.5 eq) and DIEA (73.5 mg, 0.56 mmol, 99.1 uL, 3 eq) in DCM (3 mL) was stirred at 25° C. for 1 hr. Then (2S)-2-aminopropan-1-ol (14.2 mg, 0.18 mmol, 14.7 uL, 1 eq) was added at the mixture and the mixture was stirred at 25° C. for another 1 hr. LC-MS showed the desired compound was detected. The reaction mixture was diluted with H$_2$O (10 mL) and the mixture was extracted with EA (15 mL*3). The combined organic phase was washed with brine (10 mL*3), dried with anhydrous Na$_2$SO$_4$, filtered and concentrated in vacuum. The residue was purified by prep-HPLC. The title compound (50 mg, 0.13 mmol, 69.8% yield) was obtained as white solid. LCMS (ESI): RT=0.931 min, mass calcd for C$_{21}$H$_{18}$F$_3$NO$_2$ 373.37, m/z found 374.1 [M+H]$^+$, $^1$H NMR (400 MHz, DMSO-d$_6$) δ 8.57 (d, J=1.5 Hz, 1H), 8.34 (d, J=8.0 Hz, 1H), 8.12 (d, J=8.3 Hz, 1H), 7.96-7.90 (m, 3H), 7.81 (d, J=8.8 Hz, 1H), 7.78-7.67 (m, 3H), 7.62-7.56 (m, 1H), 4.12-4.04 (m, 1H), 3.52 (br dd, J=5.9, 10.7 Hz, 1H), 2.45 (br s, 1H), 1.18 (d, J=6.8 Hz, 3H).

Example 80: (R)—N-(1-hydroxypropan-2-yl)-5-(4-(trifluoromethyl)phenyl)-2-naphthamide (Compound 85)

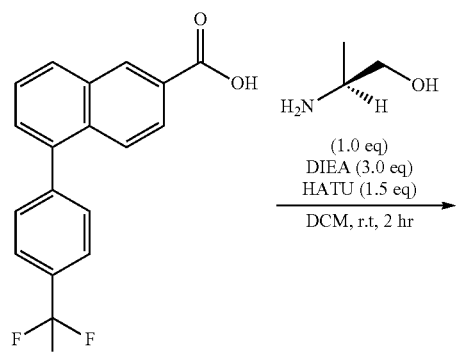

84-1

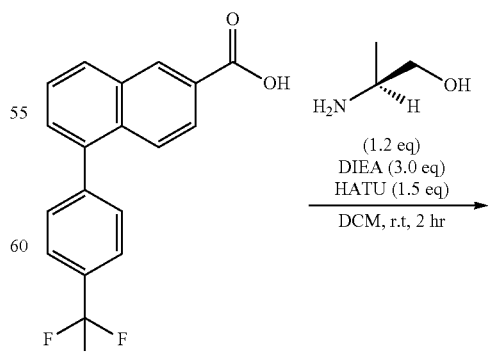

85-1

359
-continued

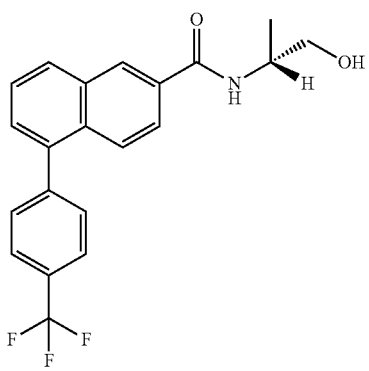

Compound 85

The mixture of compound 85-1 (70 mg, 0.22 mmol, 1 eq), HATU (126.2 mg, 0.33 mmol, 1.5 eq) and DIEA (85.8 mg, 0.66 mmol, 0.11 mL, 3 eq) in DCM (3 mL) was stirred at 25° C. for 1 hr. Then 2-aminopropan-1-ol (19.9 mg, 0.26 mmol, 21.1 uL, 1.2 eq) was added at the mixture and the mixture was stirred at 25° C. for another 1 hr. LC-MS showed the desired compound was detected. The reaction mixture was diluted with H$_2$O (10 mL) and the mixture was extracted with EA (10 mL*3). The combined organic phase was washed with brine (10 mL*3), dried with anhydrous Na$_2$SO$_4$, filtered and concentrated in vacuum. The residue was purified by prep-HPLC. The title compound (52 mg, 0.13 mmol, 62.3% yield) was obtained as white solid. LCMS (ESI): RT=0.924 min, mass calcd for C$_{21}$H$_{18}$F$_3$NO$_2$ 373.37, m/z found 374.1 [M+H]$^+$, NMR (400 MHz, DMSO-d$_6$) δ 8.57 (s, 1H), 8.34 (d, J=8.0 Hz, 1H), 8.11 (s, 1H), 7.96-7.90 (m, 3H), 7.81 (d, J=8.8 Hz, 1H), 7.76-7.67 (m, 3H), 7.59 (d, J=6.5 Hz, 1H), 4.11-4.03 (m, 1H), 4.12 (s, 1H), 3.57-3.47 (m, 1H), 3.52 (dd, J=5.8, 10.5 Hz, 1H), 3.41 (br s, 1H), 1.18 (d, J=6.8 Hz, 3H).

Example 81: N-(2-hydroxyethyl)-5-(4-(trifluoromethyl)phenyl)-2-naphthamide (Compound 86)

360
-continued

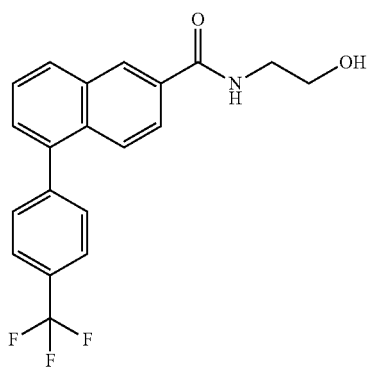

Compound 86

The mixture of compound 86-1 (70 mg, 0.22 mmol, 1 eq), HATU (126.2 mg, 0.33 mmol, 1.5 eq) and DIEA (85.8 mg, 0.66 mmol, 0.11 mL, 3 eq) in DCM (2 mL) was stirred at 25° C. for 1 hr, Then 2-aminoethanol (16.2 mg, 0.26 mmol, 16.0 uL, 1.2 eq) was added at the mixture and the mixture was stirred for another 1 hr. LC-MS showed the desired compound was detected. The reaction mixture was diluted with H$_2$O (10 mL) and the mixture was extracted with EA (10 mL*3). The combined organic phase was washed with brine (10 mL*3), dried with anhydrous Na$_2$SO$_4$, filtered and concentrated in vacuum. The residue was purified by prep-HPLC. The title compound (36 mg, 0.10 mmol, 45.2% yield) was obtained as white solid. LCMS (ESI): RT=0.898 min, mass calcd for C$_{20}$H$_{16}$F$_3$NO$_2$ 359.34, m/z found 360.1 [M+H]$^+$, $^1$H NMR (400 MHz, DMSO-d$_6$) δ 8.67 (br t, J=5.5 Hz, 1H), 8.58 (d, J=1.5 Hz, 1H), 8.12 (d, J=8.3 Hz, 1H), 7.98-7.89 (m, 3H), 7.81 (d, J=8.8 Hz, 1H), 7.77-7.67 (m, 3H), 7.59 (dd, J=1.0, 7.0 Hz, 1H), 4.78 (br s, 1H), 3.61-3.51 (m, 2H), 3.45-3.39 (m, 2H).

Example 82: N-isopropyl-8-(trifluoromethyl)-5-(4-(trifluoromethyl)phenyl)-2-naphthamide (Compound 87) and 8-iodo-N-isopropyl-5-(4-(trifluoromethyl)phenyl)-2-naphthamide (Compound 88)

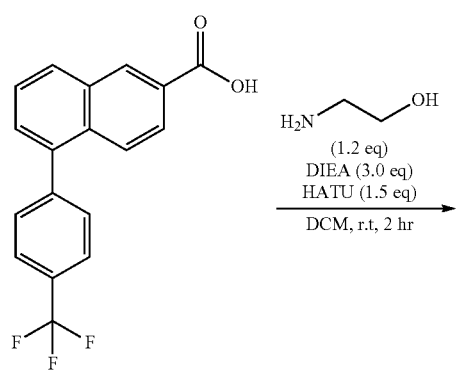

86-1

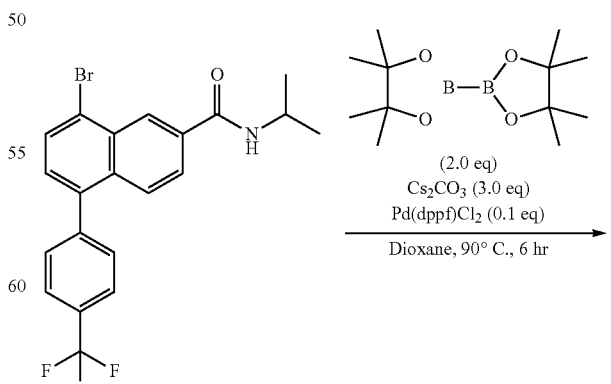

87-1

-continued

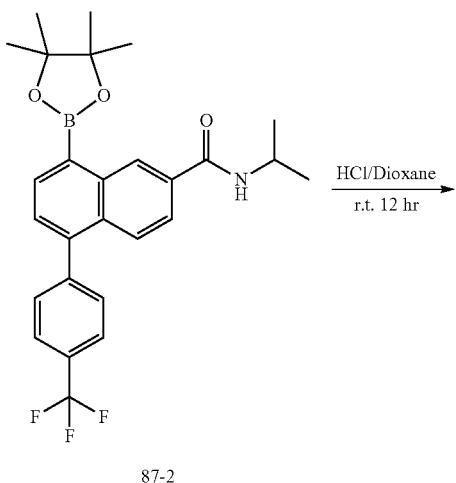

87-2

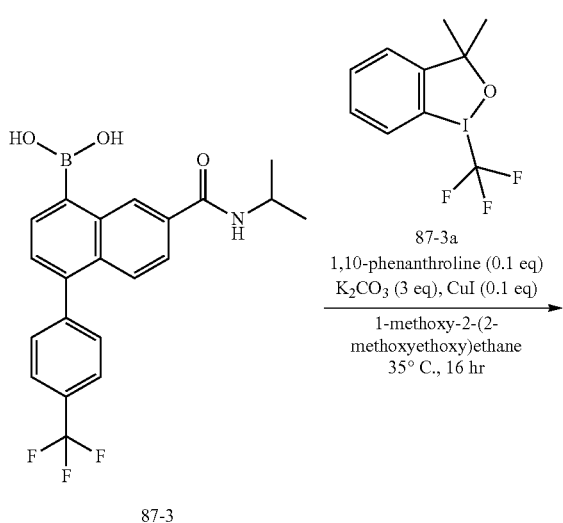

87-3

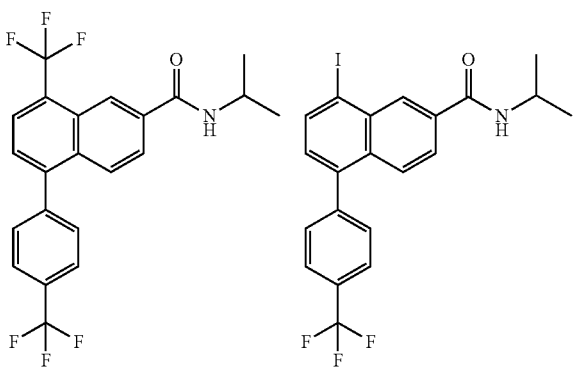

Compound 87     Compound 88

Step 1: N-isopropyl-8-(trifluoromethyl)-5-(4-(trifluoromethyl)phenyl)-2-naphthamide To a mixture of compound 87-1 (0.4 g, 0.91 mmol, 1 eq) and 4,4,5,5-tetramethyl-2-(4,4,5,5-tetramethyl-1,3,2-dioxaborolan-2-yl)-1,3,2-dioxaborolane (465.6 mg, 1.83 mmol, 2 eq) in dioxane (3 mL) was added $Cs_2CO_3$ (896.2 mg, 2.75 mmol, 3 eq) and $Pd(dppf)Cl_2$ (67.0 mg, 91.6 umol, 0.1 eq) at 25° C. under $N_2$. The mixture was heated to 90° C. and stirred for 6 hrs. LCMS showed the starting material was consumed completely and one main peak with desired mass. The reaction mixture was filtered and the filter was concentrated to give the crude compound. The residue was purified by column chromatography ($SiO_2$, Petroleum ether/Ethyl acetate=5/1 to 3:1) to give compound 87-2 (250 mg, 0.20 mmol, 22.5% yield) as a yellow solid.

Step 2: (7-(isopropylcarbamoyl)-4-(4-(trifluoromethyl)phenyl)naphthalen-1-yl)boronic Acid To a solution of compound 87-2 (0.2 g, 0.41 mmol, 1 eq) in dioxane (2 mL) was added HCl/dioxane (1 M, 2.07 mL, 5 eq) at 25° C. The mixture was stirred at 25° C. for 12 hrs. LCMS showed the starting material was consumed completely and one main peak with desired mass. The reaction mixture was quenched by addition of water (10 mL) and extracted with EA (20 mL*2). The combined organic layers were washed with brine (10 mL), dried over $Na_2SO_4$, filtered and concentrated under reduced pressure to give a residue. The residue was purified by column chromatography ($SiO_2$, Petroleum ether/Ethyl acetate=10/1 to 0:1) to give compound 87-3 (50 mg, 53.5 umol, 12.9% yield) as yellow oil.

Step 3: N-isopropyl-8-(trifluoromethyl)-5-(4-(trifluoromethyl)phenyl)-2-naphthamide and 8-iodo-N-isopropyl-5-(4-(trifluoromethyl)phenyl)-2-naphthamide To a mixture of compound 87-3 (20 mg, 49.8 umol, 1 eq) and compound 87-3a (24.6 mg, 74.7 umol, 1.5 eq) in 1-methoxy-2-(2-methoxyethoxy)ethane (1 mL) were added 1,10-phenanthroline (0.89 mg, 4.9 umol, 0.1 eq), CuI (0.94 mg, 5 umol, 0.1 eq) and $K_2CO_3$ (20.6 mg, 0.15 mmol, 3 eq) at 25° C. under $N_2$. The mixture was heated to 35° C. and stirred for 16 hrs. LCMS showed the starting material was consumed completely and one main peak with desired mass. The reaction mixture was quenched by addition water (10 mL) and extracted with EA (20 mL*2). The combined organic layers were washed with brine (10 mL), dried over $Na_2SO_4$, filtered and concentrated under reduced pressure to give a residue. The residue was purified by prep-HPLC. Compound 87 (4 mg, 9.4 umol, 18.8% yield) as a white solid. LCMS (ESI): RT=0.929 min, mass calc. for $C_{22}H_{17}F_6NO$, 425.37, m/z found 425.9[M+H]$^+$; $^1$H NMR (400 MHz, DMSO-$d_6$) δ 8.66 (s, 1H), 8.60 (br d, J=7.6 Hz, 1H), 8.16 (d, J=7.6 Hz, 1H), 8.09 (dd, J=1.3, 8.9 Hz, 1H), 7.96 (d, J=8.0 Hz, 2H), 7.90 (d, J=8.9 Hz, 1H), 7.77 (d, J=8.0 Hz, 2H), 7.71 (d, J=7.6 Hz, 1H), 4.17 (qd, J=6.9, 13.9 Hz, 1H), 1.21 (d, J=6.5 Hz, 6H). Compound 88 (3.5 mg, 7.0 umol, 14.0% yield) as a white solid. LCMS (ESI): RT=0.949 min, mass calc. for $C_{21}H_{17}F_3INO$, 483.27, m/z found 483.8 [M+H]$^+$; $^1$H NMR (400 MHz, DMSO-d$_6$) δ 8.63-8.56 (m, 2H), 8.31 (d, J=7.5 Hz, 1H), 7.96 (dd, J=1.4, 8.8 Hz, 1H), 7.92 (d, J=8.1 Hz, 2H), 7.76 (d, J=8.8 Hz, 1H), 7.72 (br d, J=7.9 Hz, 2H), 7.31 (d, J=7.6 Hz, 1H), 4.17 (qd, J=6.7, 13.7 Hz, 1H), 1.22 (d, J=6.5 Hz, 6H).

Example 83: (S)—N-(1-methoxypropan-2-yl)-5-(4-(trifluoromethyl)phenyl)-2-naphthamide (Compound 89) and (R)—N-(1-methoxypropan-2-yl)-5-(4-(trifluoromethyl)phenyl)-2-naphthamide (Compound 93)

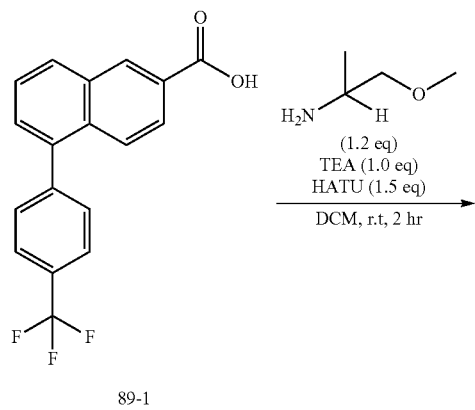

89-1

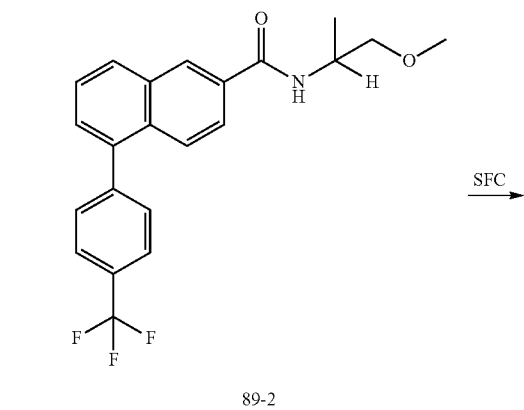

89-2

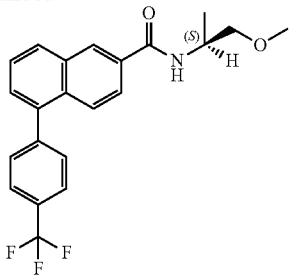

Compound 89

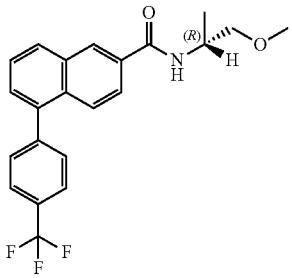

Compound 93

The mixture of compound 89-1 (200 mg, 0.63 mmol, 1 eq), TEA (63.9 mg, 0.63 mmol, 88 uL, 1 eq) and HATU (360.6 mg, 0.94 mmol, 1.5 eq) in DCM (5 mL) was stirred at 25° C. for 1 hr. Then 1-methoxypropan-2-amine (67.6 mg, 0.75 mmol, 80 uL, 1.2 eq) was added at the mixture and the mixture was stirred at 25° C. for another 1 hr. LC-MS showed the desired compound was detected. The reaction mixture was diluted with H$_2$O (10 mL) and the mixture was extracted with EA (10 mL*3). The combined organic phase was washed with brine (10 mL*3), dried with anhydrous Na$_2$SO$_4$, filtered and concentrated in vacuum. The residue was purified by column chromatography (SiO$_2$, Petroleum ether/Ethyl acetate=1/0 to 1:1) to give compound 89-2 (90 mg) as a white solid, which was further separated by SFC to give the title compounds. Compound 89 (28 mg, 70.8 umol, 11.2% yield) was obtained as white solid. LCMS (ESI): RT=0.991 min, mass calcd for $C_{22}H_{20}F_3NO_2$ 387.39, m/z found 388.1 [M+H]$^+$; $^1$H NMR (400 MHz, DMSO-d$_6$) δ 8.56 (d, J=1.5 Hz, 1H), 8.46 (d, J=8.1 Hz, 1H), 8.13 (d, J=8.3 Hz, 1H), 7.96-7.90 (m, 3H), 7.81 (d, J=8.9 Hz, 1H), 7.77-7.72 (m, 2H), 7.69 (d, J=8.1 Hz, 1H), 7.60 (dd, J=0.9, 7.1 Hz, 1H), 4.27 (spt, J=6.9 Hz, 1H), 3.49-3.42 (m, 1H), 3.35 (br s, 1H), 3.30 (s, 3H), 1.19 (d, J=6.8 Hz, 3H). Compound 93 (18 mg, 46.4 umol, 72.0% yield) was obtained as white solid. LCMS (ESI): RT=0.875 min, mass calcd for $C_{22}H_{20}F_3NO_2$ 387.39, m/z found 388.0 [M+H]$^+$; $^1$H NMR (400 MHz, CD$_3$OD) δ 8.36 (s, 1H), 7.96 (d, J=8.1 Hz, 1H), 7.77-7.72 (m, 4H), 7.60-7.53 (m, 3H), 7.47-7.44 (m, 1H), 4.29 (sxt, J=6.4 Hz, 1H), 3.47-3.41 (m, 1H), 3.39-3.33 (m, 1H), 3.30 (s, 3H), 1.18 (d, J=6.8 Hz, 3H).

Example 84: (S)—N-(1-(pyridin-2-yl)ethyl)-5-(4-(trifluoromethyl)phenyl)-2-naphthamide (Compound 90) and (R)—N-(1-(pyridin-2-yl)ethyl)-5-(4-(trifluoromethyl)phenyl)-2-naphthamide (Compound 91)

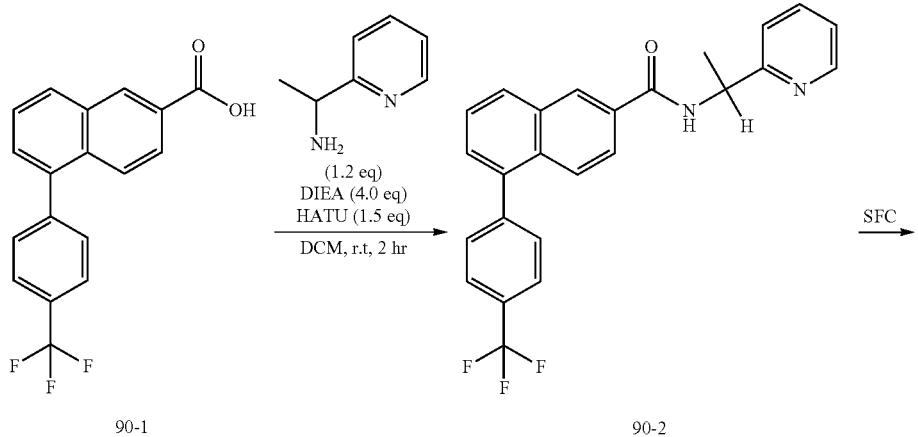

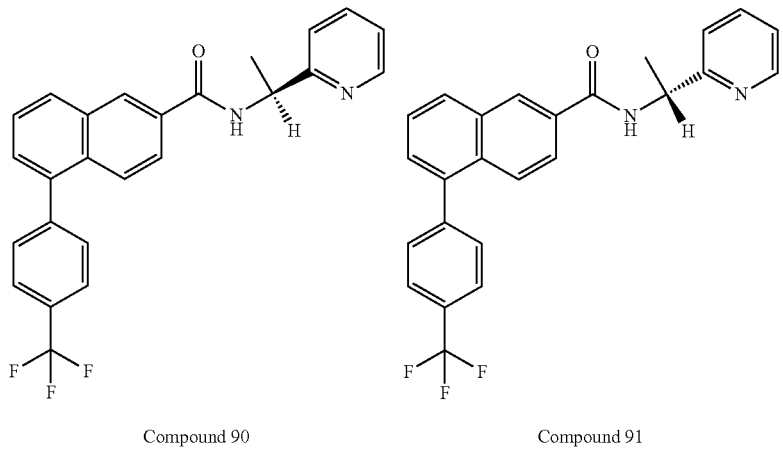

Compound 90          Compound 91

Step 1: N-(1-(pyridin-2-yl)ethyl)-5-(4-(trifluoromethyl)phenyl)-2-naphthamide

The mixture of compound 90-1 (200 mg, 0.63 mmol, 1 eq), HATU (360.6 mg, 0.94 mmol, 1.5 eq) and DIEA (326.9 mg, 2.53 mmol, 0.44 mL, 4 eq) in DCM (3 mL) was stirred at 25° C. for 1 hr. Then 1-(2-pyridyl)ethanamine (92.7 mg, 0.75 mmol, 1.2 eq) was added to the mixture and the mixture was stirred at 25° C. for another 1 hr. LC-MS showed the desired compound was detected. The reaction mixture was diluted with $H_2O$ (10 mL) and the mixture was extracted with EA (10 mL*3). The combined organic phase was washed with brine (10 mL*2), dried with anhydrous $Na_2SO_4$, filtered and concentrated in vacuum. The residue was purified by column chromatography ($SiO_2$, Petroleum ether/Ethyl acetate=1/0 to 1:1). Compound 90-2 (200 mg, 0.46 mmol, 72.9% yield) was obtained as yellow oil.

Step 2: (S)—N-(1-(pyridin-2-yl)ethyl)-5-(4-(trifluoromethyl)phenyl)-2-naphthamide and (R)—N-(1-(pyridin-2-yl)ethyl)-5-(4-(trifluoromethyl)phenyl)-2-naphthamide Compound 90-2 (90 mg, 0.21 mmol, 1 eq) was purified by SFC. Compound 90 (20 mg, 47.5 umol, 22.2% yield) was obtained as white solid. LCMS (ESI): RT=0.881 min, mass calcd for $C_{25}H_{19}F_3N_2O$ 420.43, m/z found 421.1 $[M+H]^+$; $^1$H NMR (400 MHz, $CD_3OD$) δ 8.56-8.51 (m, 2H), 8.08 (d, J=8.3 Hz, 1H), 7.93-7.78 (m, 5H), 7.72-7.63 (m, 3H), 7.56 (d, J=6.1 Hz, 1H), 7.51 (d, J=19 Hz, 1H), 7.31 (dd, J=4.8, 6.6 Hz, 1H), 5.32 (q, J=7.0 Hz, 1H), 1.63 (d, J=7.0 Hz, 3H). Compound 91 (30 mg, 71.3 umol, 33.3% yield) was obtained as white solid. LCMS (ESI): RT=0.896 min, mass calcd for $C_{25}H_{19}F_3N_2O$ 420.43, m/z found 421.1 $[M+H]^+$; $^1$H NMR (400 MHz, $CD_3OD$) δ 8.57-8.54 (m, 2H), 8.08 (d, J=7.9 Hz, 1H), 7.95-7.81 (m, 4H), 7.95-7.79 (m, 1H), 7.70-7.64 (m, 2H), 7.71-7.64 (m, 1H), 7.61-7.55 (m, 1H), 7.58 (t, J=7.9 Hz, 1H), 7.40 (dd, J=5.5, 6.8 Hz, 1H), 5.37-5.28 (m, 1H), 1.65 (d, J=7.5 Hz, 3H).

Example 85: N-(1-(methylamino)propan-2-yl)-5-(4-(trifluoromethyl)phenyl)-2-naphthamide (Compound 92)

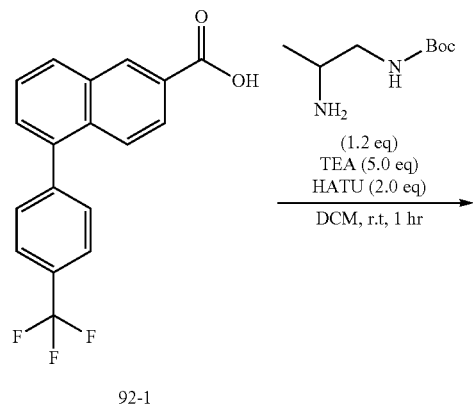

92-1

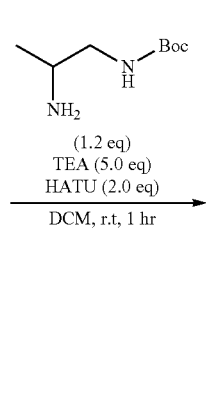

92-2

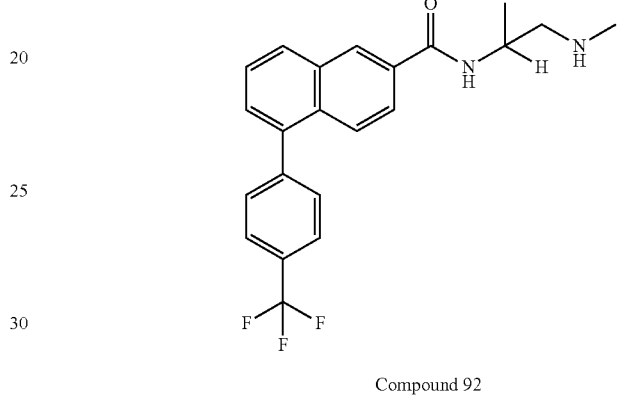

92-3

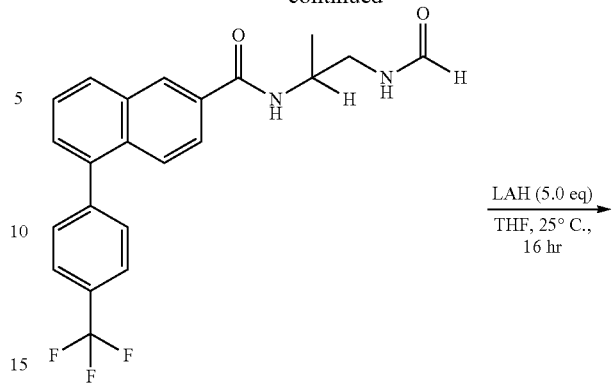

92-4

Compound 92

Step 1: Tert-Butyl (2-(5-(4-(trifluoromethyl)phenyl)-2-naphthamido)propyl)carbamate To a solution of compound 92-1 (0.5 g, 1.58 mmol, 1 eq) in DMF (2 mL) was added HATU (1.20 g, 3.16 mmol, 2 eq) and TEA (799.8 mg, 7.90 mmol, 1.10 mL, 5 eq). The mixture was stirred for 0.5 hours at 25° C. tert-butyl N-(2-aminopropyl)carbamate (330.5 mg, 1.90 mmol, 1.2 eq) was added to the mixture and the mixture was stirred for 0.5 hr at 25° C. LCMS showed the reaction was complete. The mixture was quenched by $H_2O$ (15 mL), and the mixture was extracted with EA (10 mL*3). The combined organic phase was washed with brine (15 mL*3), dried with anhydrous $Na_2SO_4$, filtered and concentrated in vacuum. The residue was used to the next step without further purification. Compound 92-2 (0.650 g, crude) was obtained as a yellow oil.

Step 2: N-(1-aminopropan-2-yl)-5-(4-(trifluoromethyl)phenyl)-2-naphthamide

To a solution of compound 92-2 (0.65 g, 1.38 mmol, 1 eq) in MeOH (3 mL) was added HCl/dioxane (4 M, 2.60 mL, 7.56 eq). The mixture was stirred for 1 hr at 25° C. The mixture was quenched by $H_2O$ (25 mL) and adjusted pH to 8 with NaOH (4M). The mixture was extracted with EA (15 mL*3). The combined organic phase was washed with brine (10 mL*3), dried with anhydrous $Na_2SO_4$, filtered and concentrated in vacuum. The residue was purified by column chromatography ($SiO_2$, Petroleum ether/Ethyl acetate=10/1 to 0:1). Compound 92-3 (0.45 g, 1.21 mmol, 87.8% yield) was obtained as a yellow solid.

Step 3: N-(1-formamidopropan-2-yl)-5-(4-(trifluoromethyl)phenyl)-2-naphthamide To a mixture of compound 92-3 (0.1 g, 0.26 mmol, 1 eq) was added ethyl formate (198.9 mg, 2.69 mmol, 0.21 mL, 10 eq) and the mixture was stirred for 48 hrs at 80° C. LCMS showed the reaction had desired MS. The mixture was concentrated in vacuum. The residue was purified by column chromatography (SiO$_2$, Petroleum ether/Ethyl acetate=5/1 to 0:1) to give compound 92-4 (0.01 g, 24.9 umol, 9.3% yield) was obtained as a yellow solid.

Step 4: N-(1-(methylamino)propan-2-yl)-5-(4-(trifluoromethyl)phenyl)-2-naphthamide To a solution of compound 92-4 (0.02 g, 49.9 umol, 1 eq) in THF (1 mL) was added LiAlH$_4$ (9.4 mg, 0.24 mmol, 5 eq). The mixture was stirred for 16 hrs at 25° C. LCMS showed the reaction was complete. The mixture was quenched by H$_2$O (30 mL), and the mixture was extracted with EA (20 mL*3). The combined organic phase was washed with brine (20 mL*3), dried with anhydrous Na$_2$SO$_4$, filtered and concentrated in vacuum. The residue was purified by prep-HPLC. Compound (8 mg) was obtained as a yellow solid. The residue was purified by prep-HPLC. The title compound (1.2 mg, HCl) was obtained as a colorless oil. LCMS (ESI): RT=0.738 min, mass calcd for C$_{22}$H$_{21}$F$_3$N$_2$O 386.41, m/z found 387.0 [M+H]$^+$, $^1$H NMR (400 MHz, CD$_3$OD) δ 8.57 (s, 1H), 8.10 (d, J=8.0 Hz, 1H), 7.95 (d, J=1.8 Hz, 1H), 7.93-7.83 (m, 3H), 7.74-7.66 (m, 3H), 7.65-7.58 (m, 1H), 3.28-3.13 (m, 2H), 2.82-2.75 (m, 3H), 1.43 (d, J=6.8 Hz, 3H), 1.20 (s, 1H).

Example 86: 5,6-Dichloro-N-isopropyl-8-(4-(trifluoromethyl)phenyl)quinoline-3-carboxamide (Compound 94)

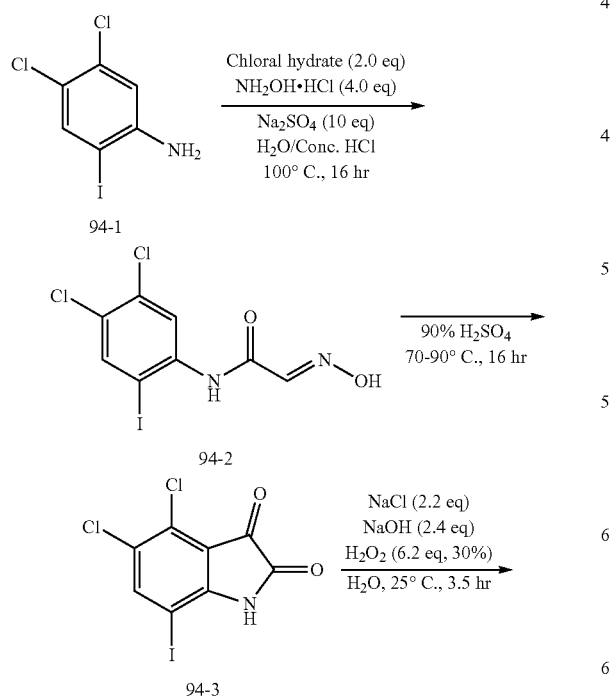

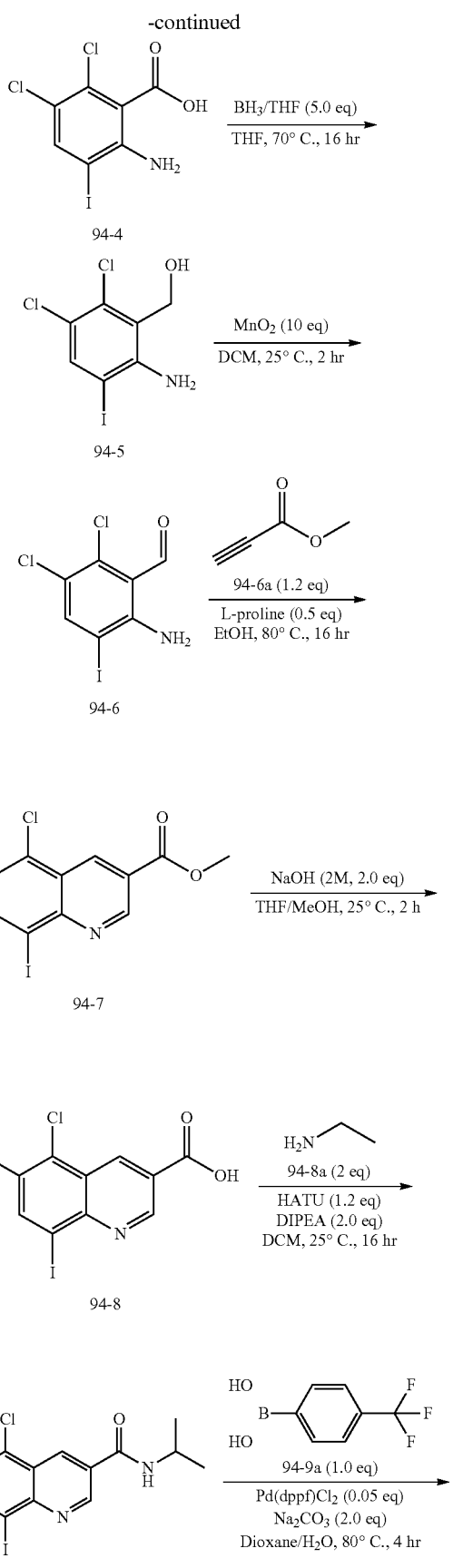

-continued

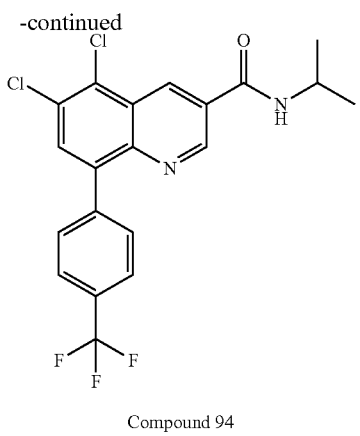

Compound 94

Step 1: (2E)-N-(4,5-Dichloro-2-iodophenyl)-2-(hydroxyimino)acetamide

To a solution of compound 94-1 (8.0 g, 28 mmol, 1.0 eq) in H₂O (160 mL) were added con.HCl (1.28 mL), Na₂SO₄ (39.5 g, 0.28 mol, 10 eq), chloral hydrate (9.2 g, 55.5 mmol, 2.0 eq) and hydroxylamine hydrochloride (7.7 g, 111 mol, 4.0 eq). The reaction mixture was stirred at 100° C. for 16 hours. The reaction mixture was extracted with EA (100 mL*3). The combined organic layers were dried over Na₂SO₄, filtered and concentrated to dryness under reduced pressure. The residue was purified by column chromatography over silica gel (petroleum ether:ethyl acetate=1:0 to 3:1) to give compound 94-2 (1.7 g, 17% yield) as a brown solid.

Step 2: 4,5-Dichloro-7-iodoindoline-2,3-dione

Compound 94-2 (1.7 g, 4.74 mmol, 1.0 eq) was added to 90% aqueous H₂SO₄ (20 mL) by portion at 70° C. The mixture was stirred at 90° C. for 16 hours. The reaction mixture was poured into ice-water, and then the resultant mixture was extracted with EA (30 mL*3). The combined organic layers were dried over Na₂SO₄, filtered and concentrated to dryness under reduced pressure to give compound 94-3 (1.5 g, crude) as a red solid. $^1$H NMR (400 MHz, DMSO-d₆) δ 11.25 (s, 1H), 8.20 (s, 1H).

Step 3: 2-Amino-5,6-dichloro-3-iodobenzoic Acid

A solution of compound 94-3 (1.5 g, 4.4 mmol, 1.0 eq), NaCl (564 mg, 9.65 mmol, 2.2 eq) and NaOH (420 mg, 0.70 mmol, 2.4 eq) in H₂O (75 mL) was stirred at 25° C. for 0.5 hour. H₂O₂ (2.61 mL, 27.2 mmol, 30%, 6.2 eq) was added slowly, followed by an aqueous NaOH solution (420 mg NaOH in H₂O (75 mL)). The reaction mixture was stirred at 25° C. for 3 hours. The reaction mixture was adjusted with HCl (1M) to pH=5. The suspension was extracted with EA (30 mL*3). The combined organic layers were dried over Na₂SO₄, filtered and concentrated to dryness under reduced pressure to give compound 94-4 (920 mg, crude) as a gray solid. $^1$H NMR (400 MHz, DMSO-d₆) δ 7.92 (s, 1H).

Step 4: (2-amino-5,6-dichloro-3-iodophenyl)methanol

To a solution of compound 94-4 (920 mg, 2.77 mmol, 1.0 eq) in THF (1.0 mL) was added BH₃·THF (1 M, 14 mL, 5.0 eq) at 25° C. The reaction mixture was stirred 70° C. for 16 hours. The reaction mixture was cooled to 0° C., and then MeOH (20 mL) was added. The mixture was stirred for 10 min, and then the reaction mixture was concentrated under reduced pressure. The residue was purified by column chromatography over silica gel (petroleum ether:ethyl acetate=1:0 to 3:1) to give compound 94-5 (750 mg, 85% yield) as a white solid. $^1$H NMR (400 MHz, CDCl₃) δ 7.72 (s, 1H), 4.97 (s, 2H).

Step 5: 2-Amino-5,6-dichloro-3-iodobenzaldehyde

To a solution of compound 94-5 (750 mg, 2.36 mmol, 1.0 eq) in DCM (10 mL) was added MnO₂ (2.05 g, 23.59 mmol, 10 eq). The reaction was stirred at 25° C. for 2 hours. The reaction mixture was filtered, and then the filtrate was concentrated under reduce pressure to give compound 94-6 (720 mg, 96% yield) as a yellow solid. $^1$H NMR (400 MHz, CDCl₃) δ 10.39 (s, 1H), 7.91 (s, 1H).

Step 6: Methyl 5,6-dichloro-8-iodoquinoline-3-carboxylate

A mixture of compound 94-6 (720 mg, 2.28 mmol, 1.0 eq), compound 94-6a (230 mg, 2.73 mmol, 1.2 eq) and L-proline (131 mg, 1.14 mmol, 0.5 eq) in EtOH (10 mL) was stirred at 80° C. for 16 hours. LC-MS showed starting material was consumed completely and one main peak with desired MS was detected. The reaction mixture was concentrated under reduced pressure. The mixture was diluted with water (20 mL) and the resultant mixture was extracted with DCM (30 mL*3). The combined organic layers were dried over Na₂SO₄, filtered and concentrated to dryness under reduced pressure. The residue was purified by column chromatography over silica gel (petroleum ether:ethyl acetate=1:0 to 5:1) to give compound 94-7 (800 mg, 91% yield) as a yellow solid.

Step 7: 5,6-Dichloro-8-iodoquinoline-3-carboxylic Acid

To a solution of methyl compound 94-7 (300 mg, 0.78 mmol, 1.0 eq) in THF (2 mL) and MeOH (2 mL) was added a solution of NaOH (1 M, 1.6 mL, 2 eq) dropwise. The reaction mixture was stirred at 25° C. for 2 hours. LC-MS showed starting material was consumed completely and one main peak with desired MS was detected. The reaction mixture was acidified with HCl (1M) to pH=5, and then the suspension was extracted with EA (25 mL*3). The combined organic layers were concentrated under reduce pressure to give compound 94-8 (270 mg, 97% yield) as a yellow solid.

Step 8: 5,6-Dichloro-8-iodoquinoline-3-carboxylic Acid

To a solution of compound 94-8 (50.0 mg, 0.14 mmol, 1.0 eq), DIPEA (35.1 mg, 0.27 mmol, 2.0 eq) and compound 94-8a (16 mg, 0.272 mmol, 2.0 eq) in DCM (2 mL) was added HATU (62.0 mg, 0.16 mmol, 1.2 eq). The reaction was stirred at 25° C. for 16 hours. LC-MS showed starting material was remained and one main peak with desired MS was detected. The reaction mixture was concentrated under reduced pressure. The mixture was diluted with water (20 mL) and the resultant mixture was extracted with EA (30 mL*3). The combined organic layers were dried over Na₂SO₄, filtered and concentrated to dryness under reduced pressure. The residue was purified by column chromatography over silica gel (petroleum ether:ethyl acetate=1:0 to 1:1) to give compound 94-9 (45 mg, 80% yield) as a light yellow solid.

Step 9: 5,6-Dichloro-N-isopropyl-8-(4-(trifluoromethyl)phenyl)quinoline-3-carboxamide To a solution of compound 94-9 (45.0 mg, 0.11 mmol, 1 eq), compound 94-9a (20.9 mg, 0.11 mmol, 1.0 eq) and $Na_2CO_3$ (23.3 mg, 0.22 mmol, 2.0 eq) in Dioxane (2.5 mL) and $H_2O$ (0.5 mL) was added $Pd(dppf)Cl_2$ (4.0 mg, 5.5 umol, 0.05 eq) under $N_2$. The reaction mixture was degassed under vacuum and purged with $N_2$ several times. The mixture was stirred under $N_2$ at 80° C. for 4 hours. LC-MS showed starting material was consumed completely and one main peak with desired MS was detected. The reaction mixture was concentrated under reduced pressure. The mixture was diluted with water (5 mL) and the resultant mixture was extracted with EA (30 mL*3). The combined organic layers were dried over $Na_2SO_4$, filtered and concentrated to dryness under reduced pressure. The residue was purified by prep-HPLC to give the title compound (17.5 mg, 35% yield) as a white solid. LCMS (ESI): RT=1.075 min, mass calcd. for $C_{20}H_{15}Cl_2F_3N_2O$ 426.05, m/z found 427.0 [M+H]$^+$; $^1$H NMR (400 MHz, $CDCl_3$) δ 9.28 (d, J=2.3 Hz, 1H), 8.96 (d, J=2.3 Hz, 1H), 7.88 (s, 1H), 7.77 (s, 4H), 6.16 (d, J=7.0 Hz, 1H), 4.44-4.33 (m, 1H), 1.36 (d, J=6.5 Hz, 6H).

Example 87: 7-amino-8-hydroxy-N-isopropyl-5-(4-(trifluoromethyl)phenyl)-2-naphthamide (Compound 95)

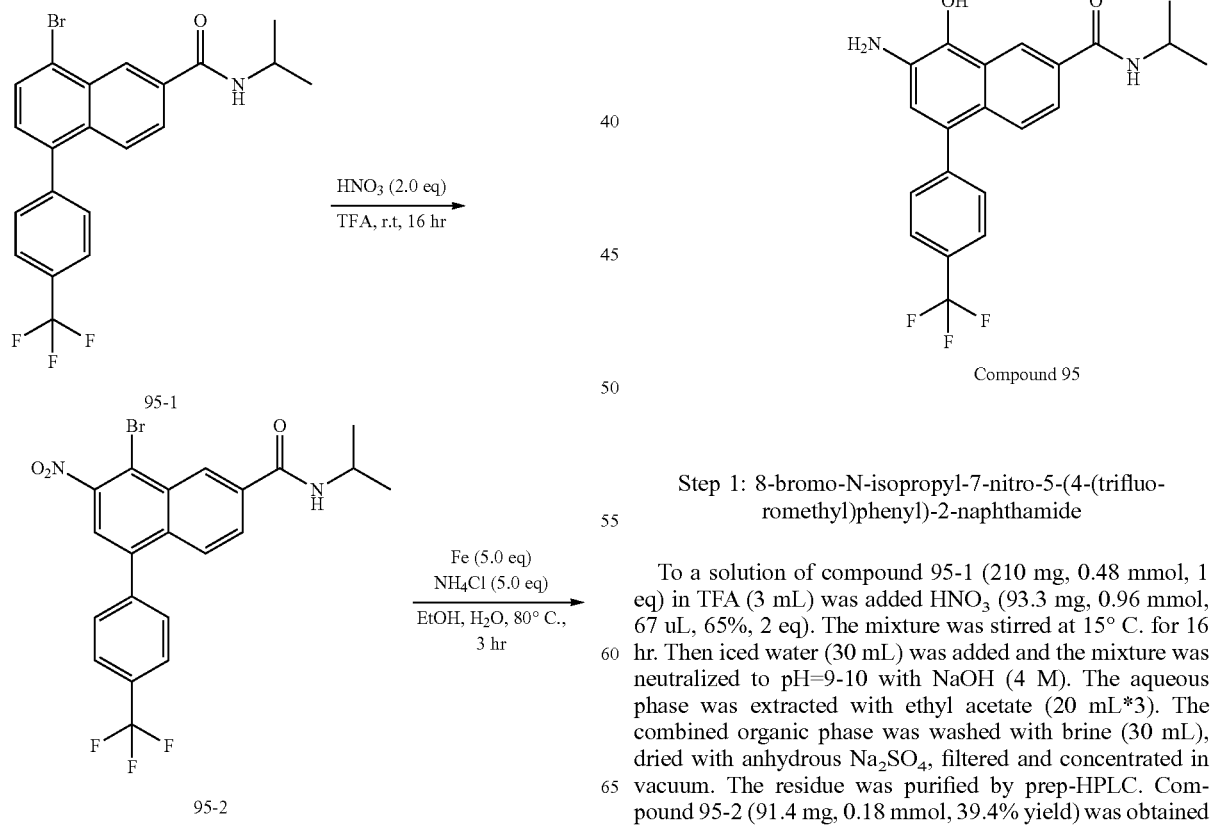

Step 1: 8-bromo-N-isopropyl-7-nitro-5-(4-(trifluoromethyl)phenyl)-2-naphthamide

To a solution of compound 95-1 (210 mg, 0.48 mmol, 1 eq) in TFA (3 mL) was added $HNO_3$ (93.3 mg, 0.96 mmol, 67 uL, 65%, 2 eq). The mixture was stirred at 15° C. for 16 hr. Then iced water (30 mL) was added and the mixture was neutralized to pH=9-10 with NaOH (4 M). The aqueous phase was extracted with ethyl acetate (20 mL*3). The combined organic phase was washed with brine (30 mL), dried with anhydrous $Na_2SO_4$, filtered and concentrated in vacuum. The residue was purified by prep-HPLC. Compound 95-2 (91.4 mg, 0.18 mmol, 39.4% yield) was obtained as a white solid.

Step 2: 7-amino-8-bromo-N-isopropyl-5-(4-(trifluoromethyl)phenyl)-2-naphthamide A mixture of compound 95-2 (85 mg, 0.17 mmol, 1 eq), Fe (49.3 mg, 0.88 mmol, 5 eq), NH$_4$Cl (47.2 mg, 0.88 mmol, 31 uL, 5 eq) in a mixture of EtOH (5 mL) and H$_2$O (1 mL) was stirred at 80° C. for 3 hr. The reaction mixture was filtered and the cake was washed with EtOH (10 mL*3), the filter was concentrated in vacuum to give crude product. The crude product was used for next step without further purification. Compound 95-3 (76.4 mg, crude) was obtained as a yellow solid.

Step 3: 7-amino-N-isopropyl-8-(4,4,5,5-tetramethyl-1,3,2-dioxaborolan-2-yl)-5-(4-(trifluoromethyl)phenyl)-2-naphthamide A mixture of compound 95-3 (75 mg, 0.16 mmol, 1 eq), 4,4,5,5-tetramethyl-2-(4,4,5,5-tetramethyl-1,3,2-dioxaborolan-2-yl)-1,3,2-dioxaborolane (63.3 mg, 0.24 mmol, 1.5 eq), KOAc (48.9 mg, 0.49 mmol, 3 eq), Pd(dppf)Cl$_2$ (6.08 mg, 8.3 umol, 0.05 eq) in dioxane (5 mL) was degassed and purged with N$_2$ for 3 times, and then the mixture was stirred at 110° C. for 3 hr under N$_2$ atmosphere. The residue was poured into H$_2$O (30 mL) and stirred for 5 min. The aqueous phase was extracted with EA (10 mL*3). The combined organic phase was washed with brine (20 mL), dried with anhydrous Na$_2$SO$_4$, filtered and concentrated in vacuum. The residue was purified by flash silica gel chromatography. Compound 95-4 (68 mg, 0.11 mmol, 71.4% yield) was obtained as a yellow solid.

Step 4: 7-amino-8-hydroxy-N-isopropyl-5-(4-(trifluoromethyl)phenyl)-2-naphthamide To a solution of compound 95-4 (50 mg, 0.10 mmol, 1 eq) in THF (1 mL) and LEO (0.5 mL) was added sodium 3-oxidodioxaborirane tetrahydrate (46.3 mg, 0.30 mmol, 58 uL, 3 eq). The mixture was stirred at 10° C. for 1 hr. The residue was poured into H$_2$O (20 mL) and stirred for 5 min. The aqueous phase was extracted with EA (10 mL*3). The combined organic phase was washed with brine (20 mL), dried with anhydrous Na$_2$SO$_4$, filtered and concentrated in vacuum. The residue was purified by prep-HPLC. The title compound (23.8 mg, 54.9 umol, 54.7% yield, HCl) was obtained as a white solid. LCMS (ESI): RT=0.765 min, mass calcd for C$_{21}$H$_{19}$F$_3$N$_2$O$_2$ 388.38, m/z found 398.2 [M+H]$^+$; $^1$H NMR (400 MHz, DMSO-d$_6$) δ 10.48 (br s, 1H), 8.54 (s, 1H), 8.23 (br d, J=8.0 Hz, 1H), 7.88 (d, J=8.0 Hz, 2H), 7.70-7.61 (m, 1H), 7.50 (d, J=8.0 Hz, 2H), 7.00 (d, J=9.0 Hz, 1H), 6.66 (s, 1H), 4.12 (qd, J=6.5, 13.6 Hz, 1H), 1.22-1.12 (m, 1H), 1.17 (d, J=6.5 Hz, 5H).

Example 88: 5,6-dichloro-N-(methylsulfonyl)-8-(4-(trifluoromethyl)phenyl)quinoline-3-carboxamide (Compound 96)

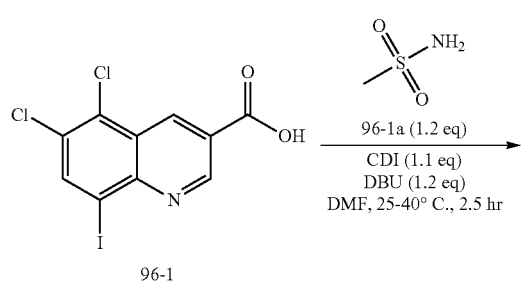

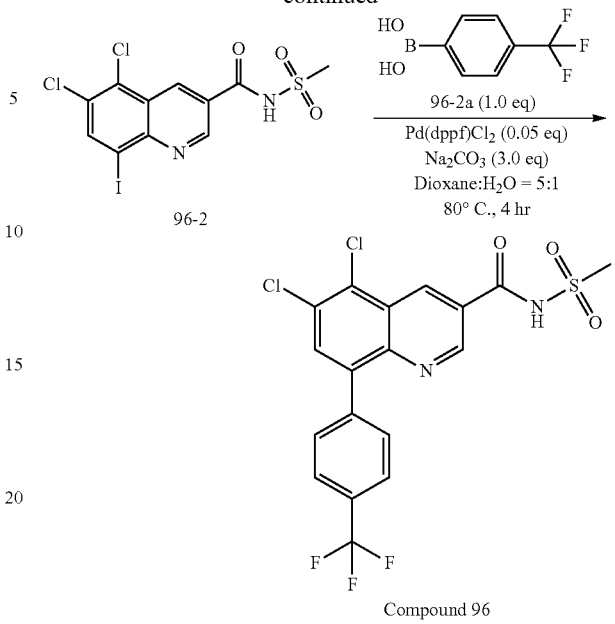

Step 1: 5,6-Dichloro-8-iodo-N-(methylsulfonyl)quinoline-3-carboxamide

To a solution of compound 96-1 (50.0 mg, 0.13 mmol, 1.0 eq) in DMF (1 mL) was added CDI (24.2 mg, 0.14 mmol, 1.1 eq). The reaction mixture was stirred at 40° C. for 30 min. The reaction was cooled to 25° C., and then DBU (24.8 mg, 0.16 mmol, 1.2 eq) and compound 96-1a (15.5 mg, 0.16 mmol, 1.2 eq) were added. The reaction was stirred at 25° C. for 2 hours. LC-MS showed starting material was consumed completely and one main peak with desired MS was detected. The reaction mixture was concentrated under reduced pressure. The mixture was diluted with water (10 mL) and the resultant mixture was extracted with EA (20 mL*3). The combined organic layers were dried over Na$_2$SO$_4$, filtered and concentrated to dryness under reduced pressure. The residue was triturated with DCM (2 mL) and filtered to give compound 96-2 (35 mg, 57% yield) as a white solid.

Step 2: 5,6-dichloro-N-(methylsulfonyl)-8-(4-(trifluoromethyl)phenyl)quinoline-3-carboxamide To a solution of compound 96-2 (35 mg, 78 mmol, 1.0 eq), compound 96-2a (15 mg, 78 mmol, 1.0 eq) and Na$_2$CO$_3$ (25.0 mg, 0.23 mmol, 3.0 eq) in Dioxane (2 mL) and H$_2$O (0.4 mL) was added Pd(dppf)Cl$_2$ (2.9 mg, 3.9 umol, 0.05 eq) under N$_2$. The suspension was degassed under vacuum and purged with N$_2$ several times. The mixture was stirred under N$_2$ at 80° C. for 4 hours. LC-MS showed starting material was consumed completely and one main peak with desired MS was detected. The suspension was adjusted with HCl (1M) to pH=5. The mixture was diluted with water (5 mL) and the resultant mixture was extracted with EA (20 mL*3). The combined organic layers were dried over Na$_2$SO$_4$, filtered and concentrated to dryness under reduced pressure. The residue was purified by prep-HPLC to give the title compound (9.6 mg, 24% yield) as a white solid. LCMS (ESI): RT=1.011 min, mass calcd. for C$_{18}$H$_{11}$Cl$_2$F$_3$N$_2$O$_3$S 461.98, m/z found 462.9 [M+H]$^+$; $^1$H NMR (400 MHz, DMSO-d$_6$) δ 9.33 (d, J=2.3 Hz, 1H), 9.27 (d, J=2.0 Hz, 1H), 8.23 (s, 1H), 7.89 (s, 4H), 3.45 (s, 3H).

Example 89: N-isopropyl-6-methoxy-8-[4-(trifluoromethyl)phenyl]quinoline-3-carboxamide (Compound 97)

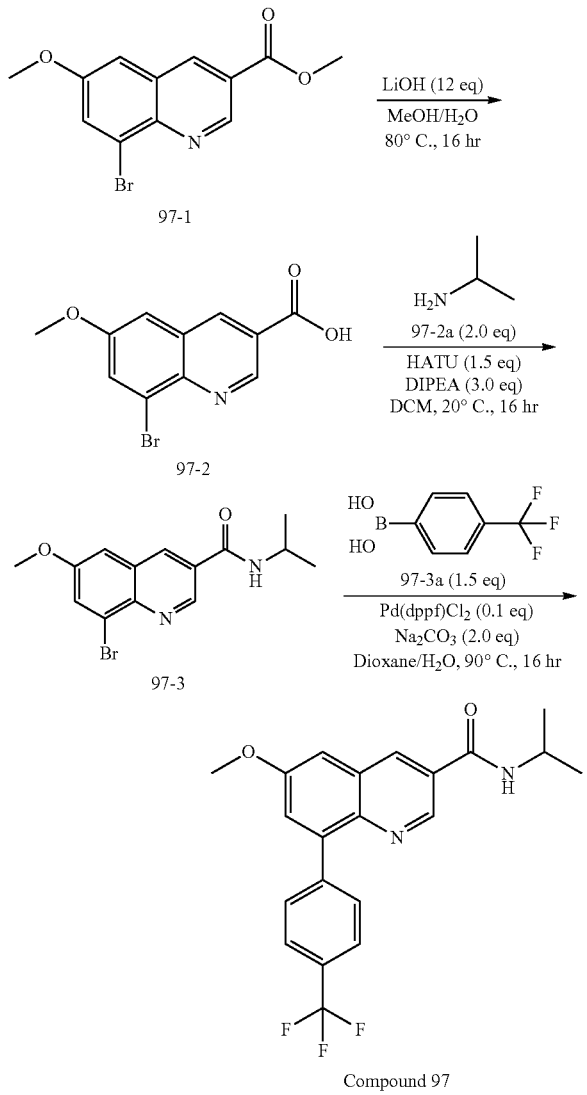

Compound 97

Step 1: 8-Bromo-6-methoxy-quinoline-3-carboxylic Acid

To a mixture of compound 97-1 (200 mg, 0.68 mmol, 1.0 eq) and H2O (1 mL) in MeOH (3 mL) was added LiOH·H$_2$O (340 mg, 8.1 mmol, 12.0 eq). The mixture was stirred at 80° C. for 16 hr. LCMS showed desired product. The mixture was adjusted to pH=7 with citric acid. The mixture was extracted with EA (20 mL*3). The organic phases were combined, dried over Na$_2$SO$_4$, filtered and concentrated under reduced pressure to give a residue. Compound 97-2 (140 mg, 63.9% yield) was obtained as a yellow solid. LCMS (ESI): RT=0.681 min, mass calcd. For C$_{11}$H$_8$BrNO$_3$, 280.97 m/z found 283.7 [M+H]$^+$.

Step 2: 8-Bromo-N-isopropyl-6-methoxy-quinoline-3-carboxamide

To a mixture of compound 97-2 (30 mg, 0.11 mmol, 1.0 eq) and DIEA (41.2 mg, 0.32 mmol, 3.0 eq) in DCM (2 mL) was added HATU (60.7 mg, 0.16 mmol, 1.5 eq). The mixture was stirred at 20° C. for 1 hr. Compound 97-2a (12.6 mg, 0.213 mmol, 2.0 eq) was added. The mixture was stirred at 20° C. for 15 hr. LCMS showed desired product. The mixture was diluted with H$_2$O (10 mL) and extracted with DCM (20 mL*3). The organic phases were combined, dried over Na$_2$SO$_4$, filtered and concentrated under pressure to give a residue. The residue was purified by flash silica gel chromatography. Compound 97-3 (13 mg, 37.1% yield) was obtained as a yellow solid. LCMS (ESI): RT=0.700 min, mass calcd. For C$_{14}$H$_{15}$BrN$_2$O$_2$, 322.03 m/z found 324.8 [M+H]$^+$.

Step 3: N-isopropyl-6-methoxy-8-[4-(trifluoromethyl)phenyl]quinoline-3-carboxamide To a mixture of compound 97-3 (13 mg, 40 umol, 1.0 eq), compound 97-3a (11.5 mg, 60 umol, 1.5 eq), H$_2$O (0.5 mL) and Na$_2$CO$_3$ (12.8 mg, 0.12 mmol, 3.0 eq) in dioxane (2 mL) was added Pd(dppf)Cl$_2$ (3.0 mg, 4 umol, 0.1 eq). The mixture was degassed and purged with N$_2$ for 3 times. The mixture was stirred at 90° C. for 16 hr under N$_2$ atmosphere. LCMS showed desired product. The mixture was filtered. The filtrate diluted with H$_2$O (2 mL) and extracted with EA (5 mL*3). The organic phases were combined, dried over Na$_2$SO$_4$, filtered and concentrated under reduced pressure to give a residue. The residue was purified by prep-HPLC. The title compound (10.86 mg, 69.5% yield) was obtained as a white solid. LCMS (ESI): RT=0.845 min, mass calcd. For C$_{21}$H$_{19}$F$_3$N$_2$O$_2$, 388.14 m/z found 388.9 [M+H]$^+$. $^1$H NMR (400 MHz, CDCl$_3$) δ 8.98 (s, 1H), 8.47 (s, 1H), 7.73-7.67 (m, 4H), 7.40 (s, 1H), 7.13 (s, 1H), 5.99 (d, J=7.2 Hz, 1H), 4.33-4.23 (m, 1H), 3.96-3.88 (m, 3H), 1.28-1.23 (m, 6H).

Example 90: N-[(1R)-2-hydroxy-1-methyl-ethyl]-6-methoxy-8-[4-(trifluoromethyl)phenyl]quinoline-3-carboxamide (Compound 98)

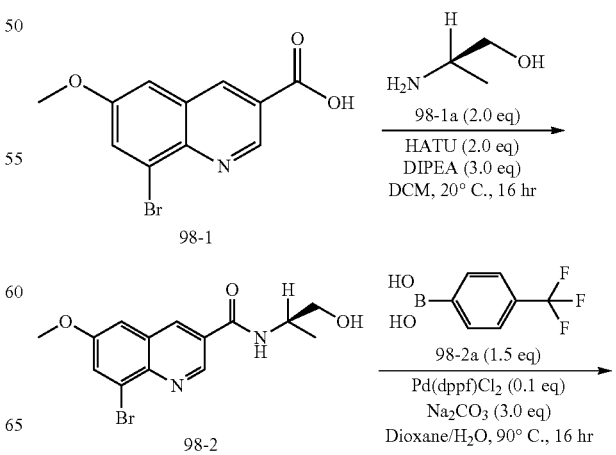

-continued

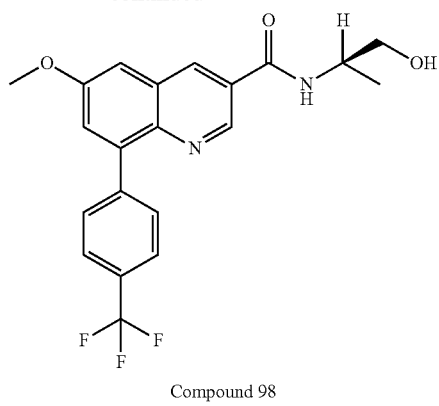

Compound 98

Step 1: 8-Bromo-N-[(1R)-2-hydroxy-1-methyl-ethyl]-6-methoxy-quinoline-3-carboxamide To a mixture of compound 98-1 (80 mg, 0.284 mmol, 1.0 eq), DIEA (110 mg, 0.851 mmol, 3.0 eq) and compound 98-1a (42.6 mg, 0.567 mmol, 2.0 eq) in DCM (2 mL) was added HATU (216 mg, 0.567 mmol, 2.0 eq). The mixture was stirred at 20° C. for 16 hr. LCMS showed desired product. The mixture was diluted with H$_2$O (10 mL) and extracted with EA (20 mL*3). The organic phases were combined, dried over Na$_2$SO$_4$, filtered and concentrated under reduced pressure to give a residue. The residue was purified by flash silica gel chromatography. Compound 98-2 (66 mg, 63.81% yield) was obtained as a yellow solid. LCMS (ESI): RT=0.638 min, mass calcd. For C$_{14}$H$_{15}$BrN$_2$O$_3$, 338.03 m/z found 340.8 [M+H]$^+$.

Step 2: N-[(1R)-2-hydroxy-1-methyl-ethyl]-6-methoxy-8-[4-(trifluoromethyl)phenyl]quinoline-3-carboxamide To a mixture of compound 98-2 (60 mg, 0.177 mmol, 1.0 eq), compound 98-2a (50.4 mg, 0.265 mmol, 1.5 eq), Na$_2$CO$_3$ (56.2 mg, 0.531 mmol, 3.0 eq) and H$_2$O (0.5 mL) in dioxane (2 mL) was added Pd(dppf)Cl$_2$ (13 mg, 18 umol, 0.1 eq). The mixture was degassed and purged with N$_2$ for 3 times. The mixture was stirred at 90° C. for 16 hr under N$_2$ atmosphere. LCMS and HPLC showed desired product. The mixture was diluted with H$_2$O (10 mL) and extracted with EA (20 mL*3). The organic phases were combined, dried over Na$_2$SO$_4$, filtered and concentrated under reduced pressure to give a residue. The residue was purified by prep-HPLC. The title compound (8.28 mg, 10% yield) was obtained as a light yellow solid. LCMS (ESI): RT=0.775 min, mass calcd. For C$_{21}$H$_{19}$F$_3$N$_2$O$_3$, 404.13 m/z found 404.9 [M+H]$^+$. $^1$H NMR (400 MHz, CDCl$_3$) δ 9.11 (d, J=2 Hz, 1H), 8.58 (d, J=2.4 Hz, 1H), 7.83-7.76 (m, 4H), 7.50 (d, J=2.8 Hz, 1H), 7.22 (d, J=2.4 Hz, 1H), 6.51-6.49 (m, 1H), 4.39 (m, 1H), 4.01 (s, 3H), 3.89-3.86 (m, 1H), 3.75-3.71 (m, 1H), 2.43 (m, 1H), 1.39-1.36 (m, 3H).

Example 91: (R)—N-(1-hydroxypropan-2-yl)-8-(4-(trifluoromethyl)phenyl)quinoline-3-carboxamide (Compound 99)

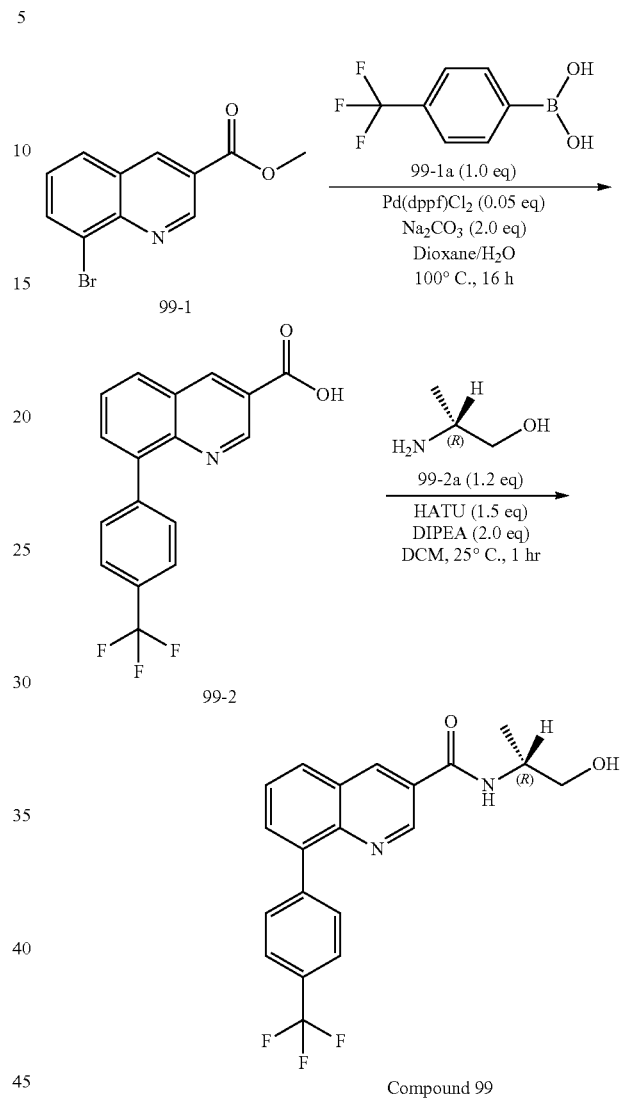

Compound 99

Step 1: 8-(4-(trifluoromethyl)phenyl)quinoline-3-carboxylic Acid

To a solution of compound 99-1 (500.0 mg, 1.88 mmol, 1.0 eq), compound 99-1a (356.8 mg, 1.88 mmol, 1.0 eq) and Na$_2$CO$_3$ (398.3 mg, 3.76 mmol, 2.0 eq) in Dioxane (7.5 mL) and H$_2$O (1.5 mL) was added Pd(dppf)Cl$_2$ (68.7 mg, 93 umol, 0.05 eq). The reaction mixture was stirred at 100° C. for 16 hours under N$_2$. LC-MS showed starting material was consumed completely and one main peak with desired MS was detected. The reaction mixture was concentrated under reduced pressure. The mixture was diluted with water (20 mL) and the resultant mixture was extracted with EA (40 mL). The aqueous layers were acidified with HCl (1M) to pH=5, and then the suspension was extracted with EA (40 mL*3). The combined organic layers were dried over Na$_2$SO$_4$, filtered and concentrated to dryness under reduced pressure to give compound 99-2 (550 mg, crude) as a brown solid.

Step 2: (R)—N-(1-hydroxypropan-2-yl)-8-(4-(trifluoromethyl)phenyl)quinoline-3-carboxamide To a solution of compound 99-2 (50.0 mg, 0.15 mmol, 1.0 eq), compound 99-2a (14.2 mg, 0.18 mmol, 1.2 eq) and DIPEA (40.7 mg, 0.31 mmol, 2.0 eq) in DCM (3 mL) was added HATU (89.9 mg, 0.23 mmol, 1.5 eq). The reaction mixture was stirred at 25° C. for 1 hour. LC-MS showed starting material was consumed completely and one main peak with desired MS was detected. The reaction mixture was concentrated under reduced pressure. The mixture was diluted with water (10 mL) and the resultant mixture was extracted with EA (20 mL*3). The combined organic layers were dried over Na$_2$SO$_4$, filtered and concentrated to dryness under reduced pressure. The residue was purified by prep-HPLC to give the title compound (17.41 mg, 29% yield) as a white solid. LCMS (ESI): RT=0.870 min, mass calcd. for C$_{20}$H$_{17}$F$_3$N$_2$O$_2$ 374.12, m/z found 375.0 [M+H]$^+$; $^1$H NMR (400 MHz, CDCl$_3$) δ 9.27 (d, J=2.3 Hz, 1H), 8.66 (d, J=2.3 Hz, 1H), 7.96 (dd, J=1.1, 8.2 Hz, 1H), 7.85-7.73 (m, 5H), 7.73-7.68 (m, 1H), 6.59 (d, J=7.0 Hz, 1H), 4.45-4.32 (m, 1H), 3.92-3.80 (m, 1H), 3.76-3.63 (m, 1H), 2.59 (s, 1H), 1.36 (d, J=6.8 Hz, 3H).

Example 92: (R)—N-(1-methoxypropan-2-yl)-8-(4-(trifluoromethyl)phenyl)quinoline-3-carboxamide (Compound 100)

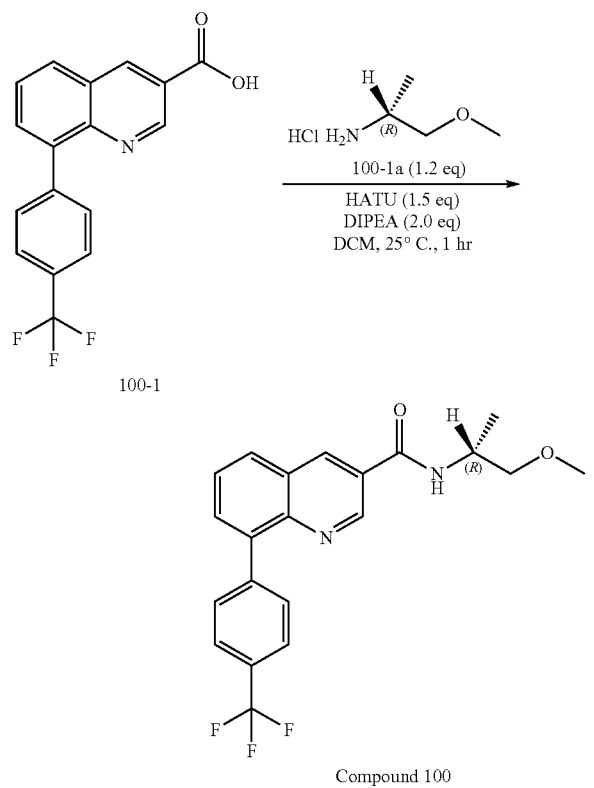

Compound 100

To a solution of compound 100-1 (50.0 mg, 0.15 mmol, 1.0 eq), compound 100-1a (23.7 mg, 0.18 mmol, 1.2 eq) and DIPEA (61.1 mg, 0.47 mmol, 3.0 eq) in DCM (3 mL) was added HATU (89.9 mg, 0.23 mmol, 1.5 eq). The reaction mixture was stirred at 25° C. for 1 hour. LC-MS showed starting material was consumed completely and one main peak with desired MS was detected. The reaction mixture was concentrated under reduced pressure. The mixture was diluted with water (10 mL) and the resultant mixture was extracted with EA (20 mL*3). The combined organic layers were dried over Na$_2$SO$_4$, filtered and concentrated to dryness under reduced pressure. The residue was purified by prep-HPLC to give the title compound (19.7 mg, 32% yield) as a white solid. LCMS (ESI): RT°=0.930 min, mass calcd. for C$_{21}$H$_{19}$F$_3$N$_2$O$_2$ 388.13, m/z found 389.0 [M+H]$^+$; $^1$H NMR (400 MHz, CDCl$_3$) δ 9.28 (d, J=2.4 Hz, 1H), 8.67 (d, J=2.3 Hz, 1H), 7.99 (dd, J=1.4, 8.1 Hz, 1H), 7.85-7.75 (m, 5H), 7.74-7.68 (m, 1H), 6.61 (d, J=7.5 Hz, 1H), 4.49-4.39 (m, 1H), 3.60-3.55 (m, 1H), 3.51-3.47 (m, 1H), 3.42 (s, 3H), 1.37 (d, J=6.9 Hz, 3H).

Example 93: (R)—N-(1-(pyridin-2-yl)ethyl)-8-(4-(trifluoromethyl)phenyl)quinoline-3-carboxamide (Compound 101)

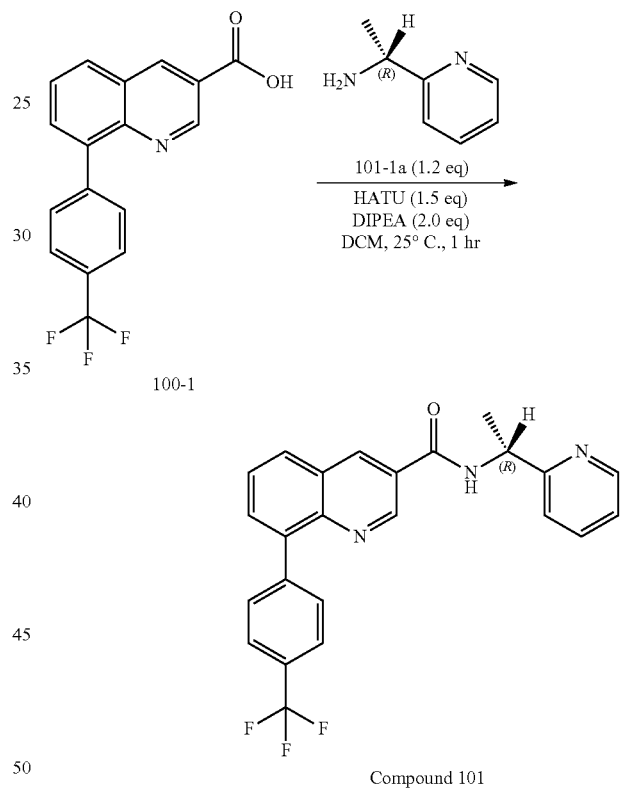

Compound 101

To a solution of compound 101-1 (50.0 mg, 0.15 mmol, 1.0 eq), compound 101-1a (23.1 mg, 0.18 mmol, 1.2 eq) and DIPEA (40.7 mg, 0.31 mmol, 2.0 eq) in DCM (3 mL) was added HATU (89.9 mg, 0.23 mmol, 1.5 eq). The reaction mixture was stirred at 25° C. for 1 hour. LC-MS showed starting material was consumed completely and one main peak with desired MS was detected. The reaction mixture was concentrated under reduced pressure. The mixture was diluted with water (10 mL) and the resultant mixture was extracted with EA (20 mL*3). The combined organic layers were dried over Na$_2$SO$_4$, filtered and concentrated to dryness under reduced pressure. The residue was purified by prep-HPLC to give the title compound (27.8 mg, 41% yield) as a white solid. LCMS (ESI): RT=0.841 min, mass calcd. for C$_{24}$H$_{18}$F$_3$N$_3$O 421.14 m/z found 422.1 [M+H]$^+$; $^1$H NMR (400 MHz, CDCl₃) δ 9.42 (d, J=2.3 Hz, 1H), 8.78 (d, J=2.3 Hz, 1H), 8.60 (d, J=4.5 Hz, 1H), 8.22 (br d, J=6.8 Hz, 1H), 8.02 (dd, J=1.3, 8.0 Hz, 1H), 7.87-7.82 (m, 3H), 7.81-7.77 (m, 2H), 7.77-7.69 (m, 2H), 7.35 (d, J=7.8 Hz, 1H), 7.28-7.25 (m, 1H), 5.41 (quin, J=6.8 Hz, 1H), 1.67 (s, 3H).

Example 94: (S)—N-(1-methoxypropan-2-yl)-8-(4-(trifluoromethyl)phenyl)quinoline-3-carboxamide (Compound 102)

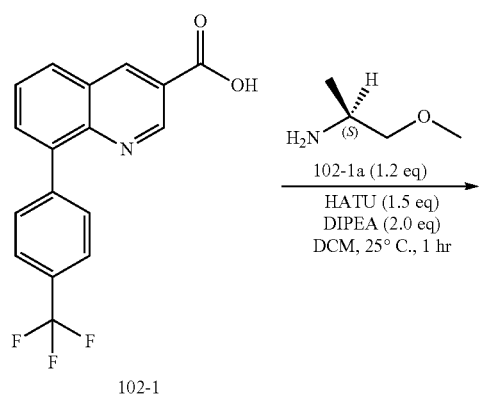

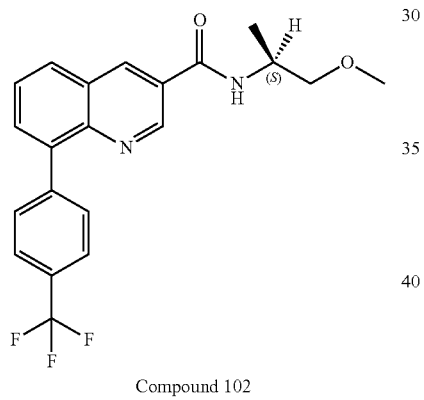

Compound 102

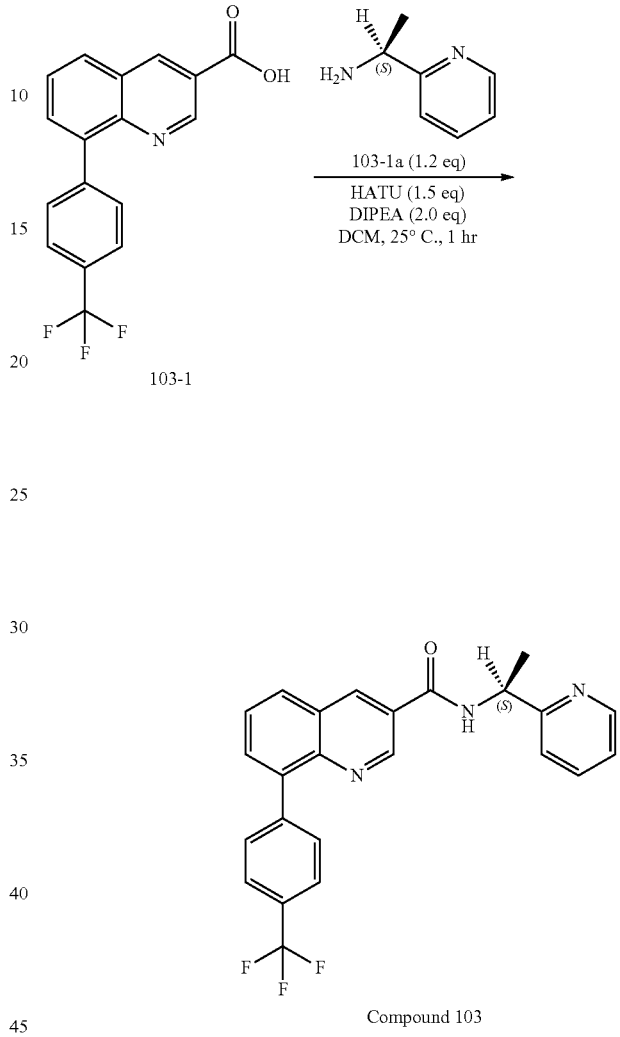

Example 95: (S)—N-(1-(pyridin-2-yl)ethyl)-8-(4-(trifluoromethyl)phenyl)quinoline-3-carboxamide (Compound 103)

To a solution of compound 102-1 (50.0 mg, 0.15 mmol, 1.0 eq), compound 102-1a (16.8 mg, 0.18 mmol, 1.2 eq) and DIPEA (40.7 mg, 0.31 mmol, 2.0 eq) in DCM (3 mL) was added HATU (89.9 mg, 0.23 mmol, 1.5 eq). The reaction mixture was stirred at 25° C. for 1 hour. LC-MS showed starting material was consumed completely and one main peak with desired MS was detected. The reaction mixture was concentrated under reduced pressure. The mixture was diluted with water (10 mL) and the resultant mixture was extracted with EA (20 mL*3). The combined organic layers were dried over Na₂SO₄, filtered and concentrated to dryness under reduced pressure. The residue was purified by prep-HPLC to give the title compound (18.9 mg, 30% yield) as a white solid. LCMS (ESI): RT=0.940 min, mass calcd. for $C_{21}H_{19}F_3N_2O_2$ 388.13, m/z found 389.0 [M+H]⁺; ¹H NMR (400 MHz, CDCl₃) δ 9.28 (d, J=2.3 Hz, 1H), 8.67 (d, J=2.3 Hz, 1H), 7.99 (dd, J=1.3, 8.0 Hz, 1H), 7.86-7.74 (m, 5H), 7.74-7.68 (m, 1H), 6.60 (d, J=8.0 Hz, 1H), 4.50-4.39 (m, 1H), 3.59-3.54 (m, 1H), 3.51-3.46 (m, 1H), 3.42 (s, 3H), 1.37 (d, J=6.8 Hz, 3H).

To a solution of compound 103-1 (50.0 mg, 0.15 mmol, 1.0 eq), compound 103-1a (23.1 mg, 0.18 mmol, 1.2 eq) and DIPEA (40.7 mg, 0.31 mmol, 2.0 eq) in DCM (3 mL) was added HATU (89.9 mg, 0.23 mmol, 1.5 eq). The reaction mixture was stirred at 25° C. for 1 hour. LC-MS showed starting material was consumed completely and one main peak with desired MS was detected. The reaction mixture was concentrated under reduced pressure. The mixture was diluted with water (10 mL) and the resultant mixture was extracted with EA (20 mL*3). The combined organic layers were dried over Na₂SO₄, filtered and concentrated to dryness under reduced pressure. The residue was purified by prep-HPLC to give the title compound (26.2 mg, 39% yield) as a white solid. LCMS (ESI): RT=0.846 min, mass calcd. for $C_{24}H_{18}F_3N_3O$ 421.14 m/z found 422.1 [M+H]⁺; ¹H NMR (400 MHz, CDCl₃) δ 9.42 (d, J=2.3 Hz, 1H), 8.78 (d, J=2.3 Hz, 1H), 8.60 (d, J=4.5 Hz, 1H), 8.22 (br d, J=7.0 Hz, 1H), 8.03 (dd, J=1.3, 8.3 Hz, 1H), 7.87-7.77 (m, 5H), 7.77-7.70 (m, 2H), 7.35 (d, J=7.8 Hz, 1H), 7.28-7.25 (m, 1H), 5.41 (quin, J=6.8 Hz, 1H), 1.66 (d, J=6.8 Hz, 3H).

Example 96: N-isopropyl-6-(trifluoromethoxy)-8-[4-(trifluoromethyl)phenyl]quinoline-3-carboxamide (Compound 104)

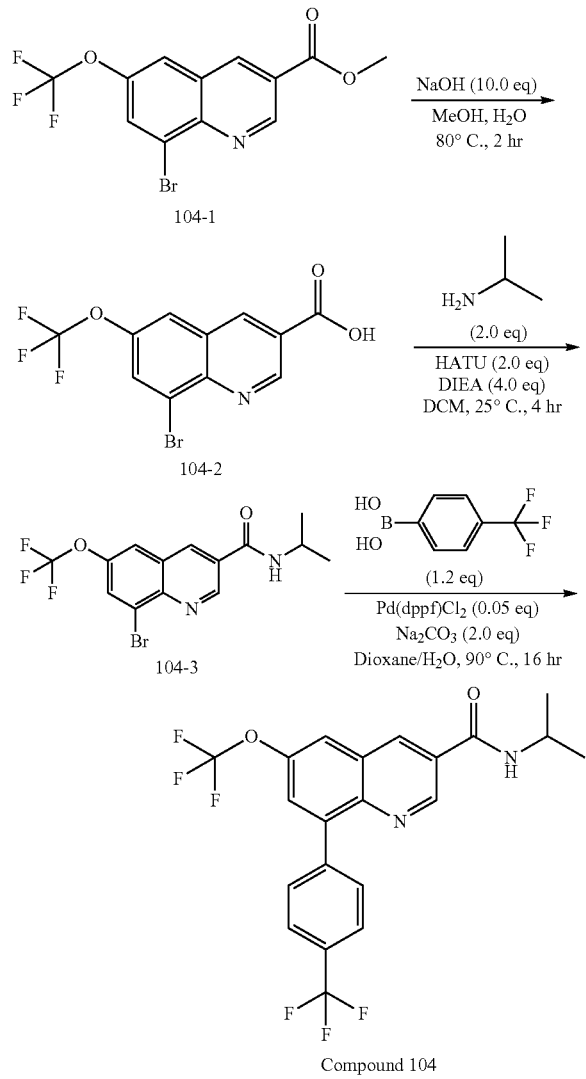

Step 1: 8-bromo-6-(trifluoromethoxy)quinoline-3-carboxylic Acid

To a mixture of compound 104-1 (380 mg, 1.1 mmol, 1.0 eq) and H$_2$O (2 mL) in MeOH (8 mL) was added NaOH (434.1 mg, 10.8 mmol, 10 eq). The mixture was stirred at 80° C. for 2 hr. LCMS showed desired product. The mixture was concentrated under reduced pressure to give a residue. The residue dissolved with H$_2$O (5 mL). The mixture pH was adjusted to pH=6 by sat.citric acid, extracted with EA (20 mL*3). The organic phases were combined, dried over Na$_2$SO$_4$, filtered and concentrated under reduced pressure to give a residue. Compound 104-2 (330 mg, 0.98 mmol, 90.5% yield) was obtained as a yellow solid. LCMS (ESI): RT=0.769 min, mass calc. for C$_{11}$H$_5$BrF$_3$NO$_3$ 334.94, m/z found 335.8 [M+H]$^+$.

Step 2: 8-bromo-N-isopropyl-6-(trifluoromethoxy)quinoline-3-carboxamide

To a mixture of compound 104-2 (50 mg, 0.14 mmol, 1 eq) and DIEA (76.9 mg, 0.59 mmol, 0.10 mL, 4 eq) in DCM (3 mL) was added HATU (113.1 mg, 0.29 mmol, 2 eq). The mixture was stirred at 25° C. for 1 hr. propan-2-amine (17.5 mg, 0.29 mmol, 25.5 uL, 2 eq) was added. The mixture was stirred at 25° C. for 2 hr. LCMS showed desired product. The mixture diluted with H2O (10 mL) and extracted with EA (20 mL*3). The organic phases were combined, dried over Na$_2$SO$_4$, filtered and concentrated under reduced pressure to give a residue. The residue was purified by flash silica gel chromatography. Compound 104-3 (55 mg, 0.14 mmol, 94.0% yield) was obtained as a yellow solid. LCMS (ESI): RT=0.787 min, mass calc. for C$_{14}$H$_{12}$BrF$_3$N$_2$O$_2$ 377.16, m/z found 378.8 [M+H]$^+$; $^1$H NMR (400 MHz, CDCl$_3$) δ 9.35 (m, 1H), 8.58 (m, 1H), 8.03 (m, 1H), 7.74 (s, 1H), 6.08 (s, 1H), 4.42-4.33 (m, 1H), 1.35-1.32 (m, 6H).

Step 3: N-isopropyl-6-(trifluoromethoxy)-8-[4-(trifluoromethyl)phenyl]quinoline-3-carboxamide To a mixture of compound 104-3 (50 mg, 0.13 mmol, 1 eq), [4-(trifluoromethyl)phenyl]boronic acid (30.2 mg, 0.15 mmol, 1.2 eq), H$_2$O (1 mL) and Na$_2$CO$_3$ (28.1 mg, 0.26 mmol, 2 eq) in dioxane (4 mL) was added Pd(dppf)Cl$_2$ (4.8 mg, 6.6 umol, 0.05 eq). The mixture was degassed and purged with N$_2$ for 3 times. The mixture was stirred at 90° C. for 16 hr under N$_2$ atmosphere. LCMS showed desired product. The mixture was filtered. The filtrate was diluted with H2O (10 mL) and extracted with EA (20 mL*3). The organic phases were combined, dried over Na2S04, filtered and concentrated under reduced pressure to give a residue. The residue was purified by prep-HPLC. The title compound (21 mg, 47.5 umol, 35.8% yield) was obtained as a white solid. LCMS (ESI): RT=0.915 min, mass calc. for C$_{21}$H$_{16}$F$_6$N$_2$O$_2$ 442.35, m/z found 442.9 [M+H]$^+$; $^1$H NMR (400 MHz, CDCl$_3$) δ 9.26 (m, 1H), 8.62 (m, 1H), 7.83-7.77 (m, 5H), 7.69-7.68 (m, 1H), 6.07-6.06 (m, 1H), 4.42-4.34 (m, 1H), 1.35-1.33 (m, 6H).

Example 97: N-[2-hydroxy-1-(2-pyridyl)ethyl]-6-methoxy-8-[4-(trifluoromethyl)phenyl]quinoline-3-carboxamide (Compound 105)

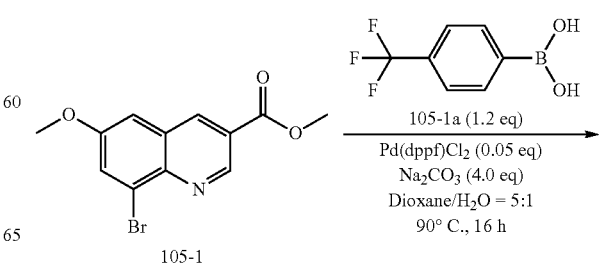

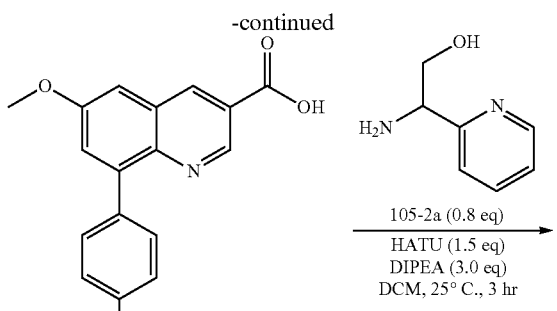

Compound 105

Step 1: 6-methoxy-8-[4-(trifluoromethyl)phenyl]quinoline-3-carboxylic Acid

To a mixture of compound 105-1 (500.0 mg, 1.7 mmol, 1.0 eq), compound 105-1a (384.8 mg, 2.0 mmol, 1.2 eq), $Na_2CO_3$ (715.8 mg, 6.7 mmol, 4.0 eq) and $H_2O$ (2 mL) in dioxane (10 mL) was added Pd(dppf)$Cl_2$ (61.8 mg, 84 umol, 0.05 eq). The mixture was degassed and purged with $N_2$ for 3 times. The mixture was stirred at 90° C. for 16 hr under $N_2$ atmosphere. LCMS showed desired product. The mixture pH was adjusted to pH=6 by sat.citric acid. The mixture was diluted with $H_2O$ (10 mL) and extracted with EA (20 mL*3). The organic phases were combined, dried over $Na_2SO_4$, filtered and concentrated under reduced pressure to give a residue. Compound 105-2 (780 mg, crude) was obtained as a black solid. LCMS (ESI): RT=0.831 min, mass calc. for $C_{18}H_{12}F_3NO_3$ 347.08, m/z found 347.9 [M+H]$^+$.

Step 2: N-[2-hydroxy-1-(2-pyridyl)ethyl]-6-methoxy-8-[4-(trifluoromethyl)phenyl]quinoline-3-carboxamide To a compound 105-2 (50.0 mg, 0.144 mmol, 1.0 eq) and DIEA (55.8 mg, 0.432 mmol, 3.0 eq) in DCM (3 mL) was added HATU (82.1 mg, 0.216 mmol, 1.5 eq). The mixture was stirred at 25° C. for 1 hr. Compound 105-2a (24.0 mg, 0.114 mmol, 0.8 eq, 2HCl) was added. The mixture was stirred at 25° C. for 2 hr. LCMS showed desired product. The mixture was diluted with $H_2O$ (10 mL) and extracted with EA (20 mL*3). The organic phases were combined, dried over $Na_2SO_4$, filtered and concentrated under reduced pressure to give a residue. The residue was purified by prep-HPLC. The title compound (15.7 mg, 23.4% yield) was obtained as a white solid. LCMS (ESI): RT=0.731 min, mass calc. for $C_{25}H_{20}F_3N_3O_3$ 467.15, m/z found 468.0 [M+H]$^+$; $^1$H NMR (400 MHz, CDCl$_3$) δ 9.23 (m, 1H), 8.64 (m, 1H), 8.59-8.58 (m, 1H), 8.17 (m, 1H), 7.83-7.76 (m, 5H), 7.54-7.50 (m, 2H), 7.32 (m, 1H), 7.24 (m, 1H), 5.44-5.41 (m, 1H), 4.20-4.16 (m, 3H), 4.10-4.02 (m, 3H).

Example 98: 6-methoxy-N-[(1R)-1-(2-pyridyl)ethyl]-8-[4-(trifluoromethyl)phenyl]quinoline-3-carboxamide (Compound 106)

Compound 106

To a mixture of compound 106-1 (70.0 mg, 0.201 mmol, 1.0 eq) and DIEA (104.2 mg, 0.806 mmol, 4.0 eq) in DCM (3 mL) was added HATU (114.9 mg, 0.30 mmol, 1.5 eq). The mixture was stirred at 25° C. for 1 hr. Compound 106-1a (29.5 mg, 0.24 mmol, 1.2 eq) was added. The mixture was stirred at 25° C. for 2 hr. LCMS showed desired product. The mixture was diluted with $H_2O$ (10 mL) and extracted with EA (20 mL*3). The organic phases were combined, dried over $Na_2SO_4$, filtered and concentrated under reduced pressure to give a residue. The residue was purified by prep-HPLC. The title compound (33.5 mg, 36.9% yield) was obtained as a white solid. LCMS (ESI): RT=0.756 min, mass calc. for $C_{25}H_{20}F_3N_3O_2$ 451.15, m/z found 452.0 [M+H]$^+$; NMR (400 MHz, CDCl$_3$) δ 9.23 (m, 1H), 8.66 (m, 1H), 8.58 (m, 1H), 8.44 (m, 1H), 7.82-7.75 (m, 2H), 7.73-7.72 (m, 3H), 7.48 (m, 1H), 7.35-7.33 (m, 1H), 7.25-7.24 (m, 2H), 5.43-5.36 (m, 1H), 4.00 (s, 3H), 1.65-1.63 (m, 3H).

Example 99: 6-methoxy-N-[(1R)-2-methoxy-1-methyl-ethyl]-8-[4-(trifluoromethyl)phenyl]quinoline-3-carboxamide (Compound 107)

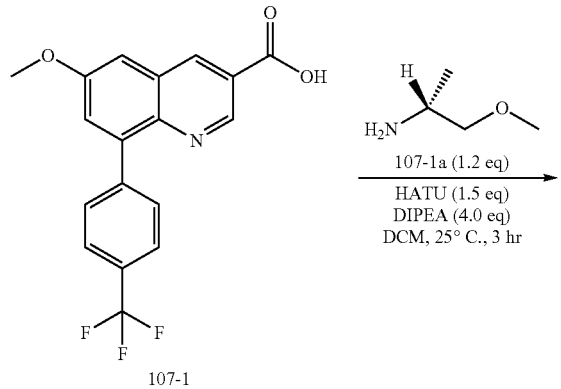

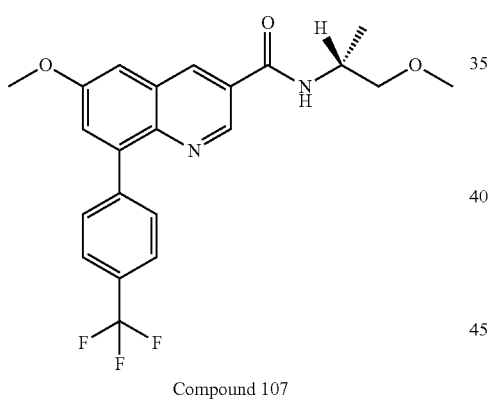

Compound 107

Example 100: 6-methoxy-N-[(1S)-1-(2-pyridyl)ethyl]-8-[4-(trifluoromethyl)phenyl]quinoline-3-carboxamide (Compound 108)

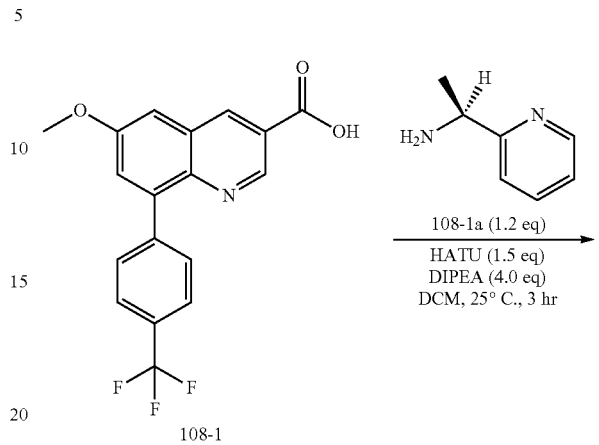

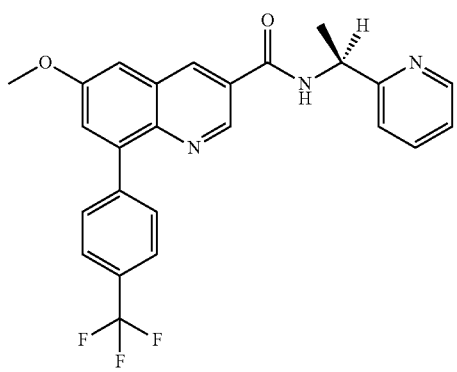

Compound 108

To a mixture of compound 107-1 (70.0 mg, 0.20 mmol, 1.0 eq) and DIEA (104.2 mg, 0.80 mmol, 4.0 eq) in DCM (3 mL) was added HATU (114.9 mg, 0.30 mmol, 1.5 eq). The mixture was stirred at 25° C. for 1 hr. Compound 107-1a (21.5 mg, 0.24 mmol, 1.2 eq) was added. The mixture was stirred at 25° C. for 2 hr. LCMS showed desired product. The mixture was diluted with $H_2O$ (10 mL) and extracted with EA (20 mL*3). The organic phases were combined, dried over $Na_2SO_4$, filtered and concentrated under reduced pressure to give a residue. The residue was purified by prep-HPLC. The title compound (26.9 mg, 31.6% yield) was obtained as a white solid. LCMS (ESI): RT=0.832 min, mass calc. for $C_{22}H_{21}F_3N_2O_3$ 418.15, m/z found 419.0 $[M+H]^+$; $^1H$ NMR (400 MHz, CDCl$_3$) δ 9.10 (m, 1H), 8.57 (m, 1H), 7.81-7.75 (m, 4H), 7.48 (m, 1H), 7.22 (m, 1H), 6.60-6.58 (m, 1H), 4.46-4.43 (m, 1H), 4.00 (s, 3H), 3.58-3.55 (m, 1H), 3.50-3.46 (m, 1H), 3.42 (s, 3H), 1.36-1.35 (m, 3H).

To a mixture of compound 108-1 (70.0 mg, 0.20 mmol, 1.0 eq) and DIEA (104.2 mg, 0.80 mmol, 4.0 eq) in DCM (3 mL) was added HATU (114.9 mg, 0.30 mmol, 1.5 eq). The mixture was stirred at 25° C. for 1 hr. Compound 108-1a (29.5 mg, 0.24 mmol, 1.2 eq) was added. The mixture was stirred at 25° C. for 2 hr. LCMS showed desired product. The filtrate was diluted with $H_2O$ (10 mL) and extracted with EA (20 mL*3). The organic phases were combined, dried over $Na_2SO_4$, filtered and concentrated under reduced pressure to give a residue. The residue was purified by prep-HPLC. The title compound (20.4 mg, 22.4% yield) was obtained as a white solid. LCMS (ESI): RT=0.753 min, mass calc. for $C_{25}H_{20}F_3N_3O_2$ 451.15, m/z found 452.0 $[M+H]^+$; $^1H$ NMR (400 MHz, CDCl$_3$) δ 9.23 (m, 1H), 8.66 (m, 1H), 8.58 (m, 1H), 8.44 (m, 1H), 7.82-7.75 (m, 2H), 7.73-7.72 (m, 3H), 7.48 (m, 1H), 7.34-7.32 (m, 1H), 7.25-7.24 (m, 1H), 5.43-5.36 (m, 1H), 4.00 (s, 3H), 1.65-1.63 (m, 3H).

Example 101: 6-methoxy-N-[(1S)-2-methoxy-1-methyl-ethyl]-8-[4-(trifluoromethyl)phenyl]quinoline-3-carboxamide (Compound 109)

Example 102: N-(2-hydroxy-1-(pyridin-2-yl)ethyl)-5-(4-(trifluoromethyl)phenyl)-2-naphthamide (Compound 110)

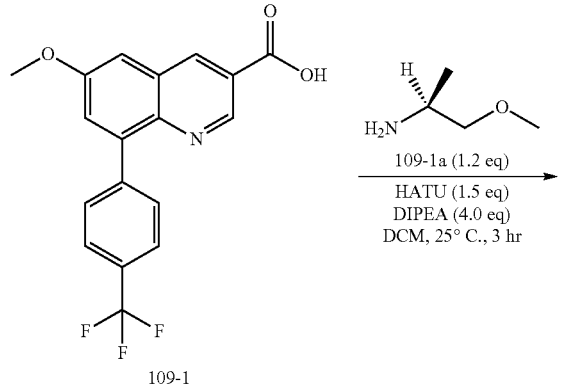

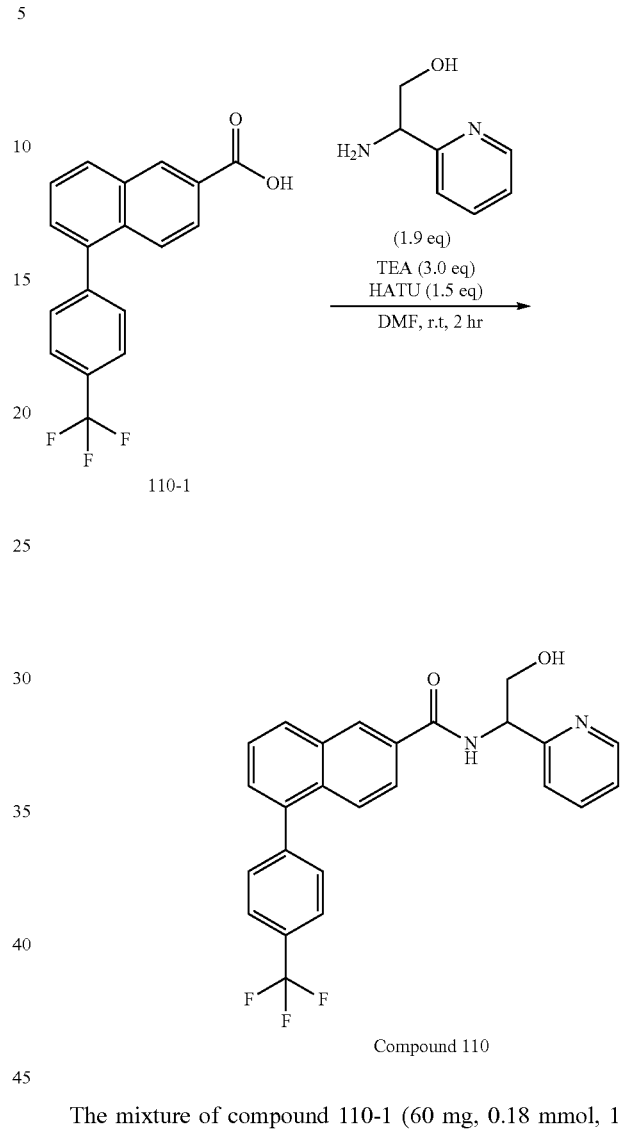

To a mixture of compound 109-1 (70.0 mg, 0.20 mmol, 1.0 eq) and DIEA (104.2 mg, 0.80 mmol, 4.0 eq) in DCM (3 mL) was added HATU (114.9 mg, 0.30 mmol, 1.5 eq). The mixture was stirred at 25° C. for 1 hr. Compound 109-1a (21.5 mg, 0.24 mmol, 1.2 eq) was added. The mixture was stirred at 25° C. for 2 hr. LCMS showed desired product. The mixture was diluted with $H_2O$ (10 mL) and extracted with EA (20 mL*3). The organic phases were combined, dried over $Na_2SO_4$, filtered and concentrated under reduced pressure to give a residue. The residue was purified by prep-HPLC. The title compound (9.8 mg, 11.4% yield) was obtained as a white solid. LCMS (ESI): RT=0.831 min, mass calc. for $C_{22}H_{21}F_3N_2O_3$ 418.15, m/z found 419.0 [M+H]$^+$; $^1$H NMR (400 MHz, CDCl$_3$) δ 9.10 (m, 1H), 8.56-8.55 (m, 1H), 7.81-7.74 (m, 4H), 7.48-7.47 (m, 1H), 7.21-7.20 (m, 1H), 6.61-6.59 (m, 1H), 4.46-4.43 (m, 1H), 3.99 (s, 3H), 3.57-3.54 (m, 1H), 3.49-3.46 (m, 1H), 3.42 (s, 3H), 1.36-1.35 (m, 3H).

The mixture of compound 110-1 (60 mg, 0.18 mmol, 1 eq), TEA (57.5 mg, 0.56 mmol, 79.2 uL, 3 eq) and HATU (108.2 mg, 0.28 mmol, 1.5 eq) in DCM (2 mL) was stirred at 25° C. for 1 hr. Then 2-amino-2-pyridin-2-yl-ethanol (50 mg, 0.36 mmol, 1.9 eq, 2HCl) was added at the mixture and the mixture was stirred at 25° C. for another 1 hr. LC-MS showed the desired compound was detected. The reaction mixture was diluted with $H_2O$ (10 mL) and the mixture was extracted with EA (10 mL*3). The combined organic phase was washed with brine (10 mL*2), dried with anhydrous $Na_2SO_4$, filtered and concentrated in vacuum. The residue was purified by prep-HPLC. The title compound (50 mg, 0.11 mmol, 60.3% yield) was obtained as white solid. LCMS (ESI): RT=0.865 min, mass calcd for $C_{25}H_{19}F_3N_2O_2$ 436.43 m/z found 437.1[M+H]$^+$, $^1$H NMR (400 MHz, DMSO-d$_6$) δ 8.90 (d, J=7.8 Hz, 1H), 8.68 (d, J=1.5 Hz, 1H), 8.55 (d, J=4.0 Hz, 1H), 8.16 (d, J=8.3 Hz, 1H), 7.99 (dd, J=1.8, 8.8 Hz, 1H), 7.93 (d, J=8.0 Hz, 2H), 7.83 (d, J=8.8 Hz, 1H), 7.81-7.69 (m, 4H), 7.62-7.59 (m, 1H), 7.47 (d, J=8.0 Hz, 1H), 7.28 (dd, J=4.9, 6.7 Hz, 1H), 5.25-5.18 (m, 1H), 5.00 (t, J=5.9 Hz, 1H), 3.93-3.80 (m, 2H).

Example 103: N-(prop-2-yn-1-yl)-5-(4-(trifluoromethyl)phenyl)-2-naphthamide (Compound 111)

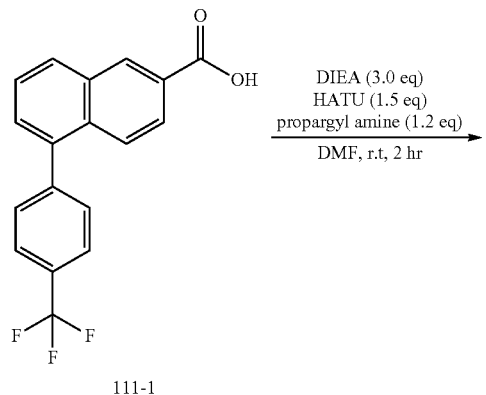

Example 104: N-(but-3-yn-1-yl)-5-(4-(trifluoromethyl)phenyl)-2-naphthamide (Compound 112)

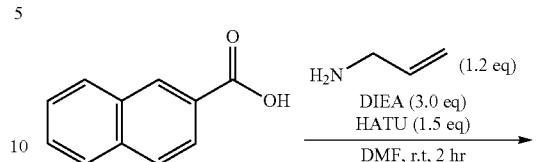

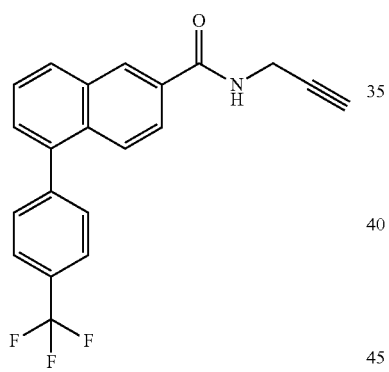

Compound 111

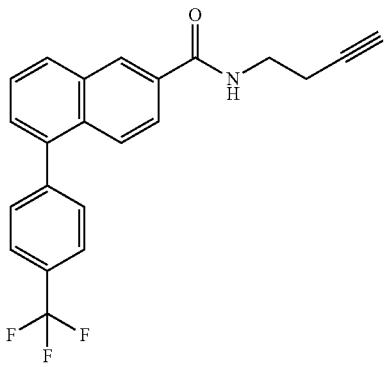

Compound 112

The mixture of compound 111-1 (50 mg, 0.15 mmol, 1 eq), DIPEA (61.2 mg, 0.47 mmol, 82.6 uL, 3 eq) and HATU (90.1 mg, 0.23 mmol, 1.5 eq) in DMF (2 mL) was stirred at 25° C. for 1 hr. Then prop-2-yn-1-amine (10.4 mg, 0.18 mmol, 12.1 uL, 1.2 eq) was added at the mixture and the mixture was stirred at 25° C. for another 1 hr. LC-MS and HPLC showed the desired compound was detected. The reaction mixture was diluted with H$_2$O (10 mL) and the mixture was extracted with EA (10 mL*3). The combined organic phase was washed with brine (10 mL*2), dried with anhydrous Na$_2$SO$_4$, filtered and concentrated in vacuum. The residue was purified by prep-HPLC. The title compound (8 mg, 22.4 umol, 14.1% yield) was obtained as white solid. LCMS (ESI): RT=0.859 min, mass calcd for C$_{21}$H$_{14}$F$_3$NO 353.34 m/z found 353.9[M+H]$^+$; $^1$H NMR (400 MHz, CD$_3$OD) δ 8.50 (s, 1H), 8.09 (d, J=8.1 Hz, 1H), 7.92-7.82 (m, 4H), 7.72-7.66 (m, 3H), 7.59 (d, J=6.4 Hz, 1H), 4.24 (d, J=2.4 Hz, 2H), 2.65 (t, J=2.5 Hz, 1H).

The mixture of compound 112-1 (50 mg, 0.15 mmol, 1 eq), HATU (90.1 mg, 0.23 mmol, 1.5 eq) and DIPEA (61.2 mg, 0.47 mmol, 82.6 uL, 3 eq) in DMF (2 mL) was stirred at 25° C. for 1 hr. Then but-3-yn-1-amine (20 mg, 0.18 mmol, 1.2 eq, HCl) was added at the mixture and the mixture was stirred at 25° C. for another 1 hr. LC-MS and HPLC showed the desired compound was detected. The reaction mixture was diluted with H$_2$O (10 mL) and the mixture was extracted with EA (10 mL*3). The combined organic phase was washed with brine (10 mL*2), dried with anhydrous Na$_2$SO$_4$, filtered and concentrated in vacuum. The residue was purified by prep-HPLC. The title compound (10 mg, 27.2 umol, 17.2% yield) was obtained as white solid. LCMS (ESI): RT=0.879 min, mass calcd for C$_{22}$H$_{16}$F$_3$NO 367.36 m/z found 367.9[M+H]$^+$; $^1$H NMR (400 MHz, DMSO-d$_6$) δ 8.93 (t, J=5.7 Hz, 1H), 8.61 (d, J=1.3 Hz, 1H), 8.18 (d, J=8.3 Hz, 1H), 8.02-7.95 (m, 3H), 7.87 (d, J=8.9 Hz, 1H), 7.82-7.71 (m, 3H), 7.65 (d, J=6.5 Hz, 1H), 3.55-3.45 (m, 3H), 2.92 (t, J=2.6 Hz, 1H), 2.54-2.50 (m, 2H).

Example 105: N-(cyanomethyl)-5-(4-(trifluoromethyl)phenyl)-2-naphthamide (Compound 113)

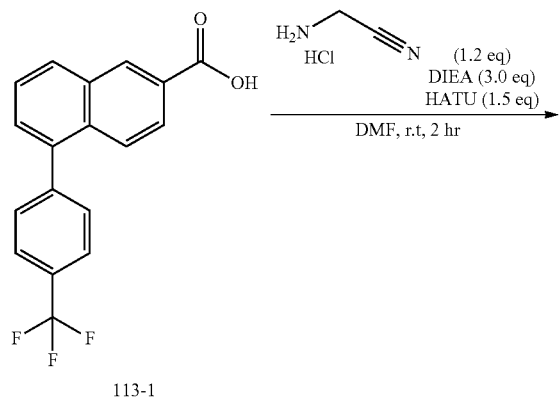

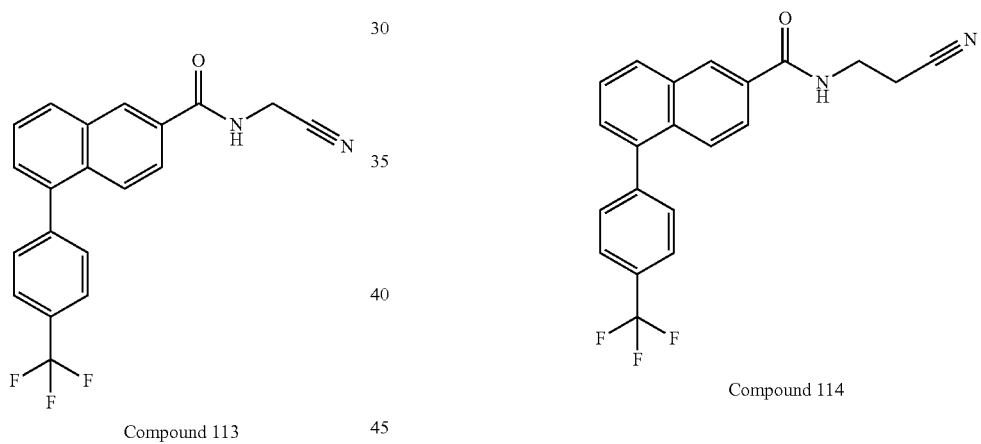

Compound 113

The mixture of compound 113-1 (50 mg, 0.15 mmol, 1 eq), DIPEA (61.2 mg, 0.47 mmol, 82.6 uL, 3 eq) and HATU (90.1 mg, 0.23 mmol, 1.5 eq) in DMF (1 mL) was stirred at 25° C. for 1 hr. Then 2-aminoacetonitrile (17.5 mg, 0.18 mmol, 1.2 eq, HCl) was added at the mixture and the mixture was stirred for another 1 hr. LC-MS and HPLC showed the desired compound was detected. The reaction mixture was diluted with H$_2$O (10 mL) and the mixture was extracted with EA (10 mL*3). The combined organic phase was washed with brine (10 mL*2), dried with anhydrous Na$_2$SO$_4$, filtered and concentrated in vacuum. The residue was purified by prep-HPLC. The title compound (32 mg, 89.4 umol, 56.5% yield) was obtained as white solid. LCMS (ESI): RT=0.958 min, mass calcd for C$_{20}$H$_{13}$F$_3$N$_2$O 354.33 m/z found 355.0[M+H]$^+$; $^1$H NMR (400 MHz, CDCl$_3$) δ 8.34 (d, J=1.6 Hz, 1H), 7.92 (d, J=8.3 Hz, 1H), 7.82 (d, J=8.9 Hz, 1H), 7.73-7.67 (m, 3H), 7.59-7.44 (m, 4H), 6.67 (br t, J=5.4 Hz, 1H), 4.40 (d, J=5.8 Hz, 2H).

Example 106: N-(2-cyanoethyl)-5-(4-(trifluoromethyl)phenyl)-2-naphthamide (Compound 114)

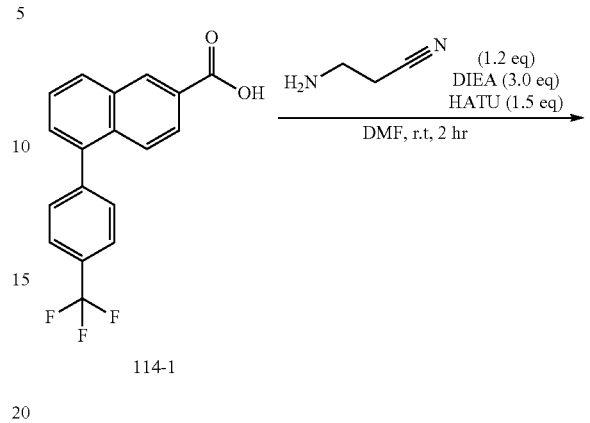

114-1

Compound 114

The mixture of compound 114-1 (50 mg, 0.15 mmol, 1 eq), DIPEA (61.2 mg, 0.47 mmol, 82.6 uL, 3 eq) and HATU (90.1 mg, 0.23 mmol, 1.5 eq) in DMF (1 mL) was stirred at 25° C. for 1 hr. Then 3-aminopropanenitrile (13.3 mg, 0.18 mmol, 14 uL, 1.2 eq) was added at the mixture and the mixture was stirred at 25° C. for another 1 hr. LC-MS and HPLC showed the desired compound was detected. The reaction mixture was diluted with H$_2$O (10 mL) and the mixture was extracted with EA (10 mL*3). The combined organic phase was washed with brine (10 mL*2), dried with anhydrous Na$_2$SO$_4$, filtered and concentrated in vacuum. The residue was purified by prep-HPLC. The title compound (27 mg, 73.3 umol, 46.3% yield) was obtained as white solid. LCMS (ESI): RT=0.960 min, mass calcd for C$_{21}$H$_{15}$F$_3$N$_2$O 368.35 m/z found 369.0[M+H]$^+$; $^1$H NMR (400 MHz, DMSO-d$_6$) δ 9.08 (t, J=5.6 Hz, 1H), 8.58 (d, J=1.3 Hz, 1H), 8.14 (d, J=8.3 Hz, 1H), 7.98-7.89 (m, 3H), 7.84 (d, J=8.9 Hz, 1H), 7.77-7.68 (m, 3H), 7.61 (d, J=6.4 Hz, 1H), 3.60-3.59 (m, 1H), 3.59-3.54 (m, 1H), 3.55-3.53 (m, 1H), 3.59-3.53 (m, 1H), 3.57 (q, J=6.3 Hz, 1H), 2.83 (t, J=6.4 Hz, 2H).

Example 107: N,N'-(disulfanediylbis(ethane-2,1-diyl))bis(5-(4-(trifluoromethyl)phenyl)-2-naphthamide) (Compound 115)

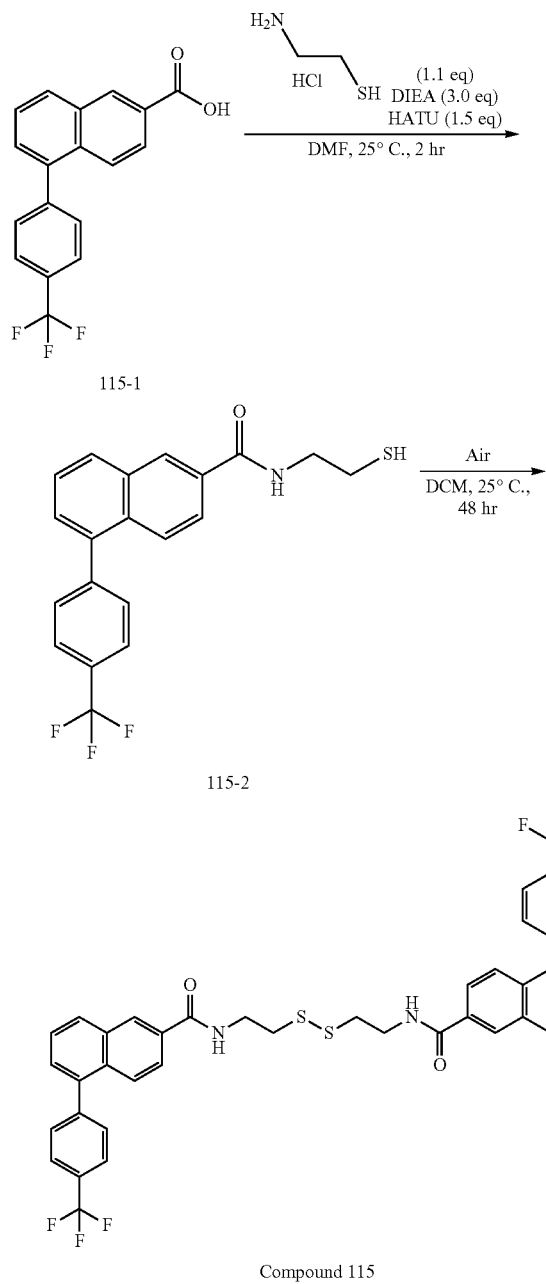

Step 1: N-(2-mercaptoethyl)-5-(4-(trifluoromethyl)phenyl)-2-naphthamide

The mixture of compound 115-1 (50 mg, 0.15 mmol, 1 eq), HATU (90.1 mg, 0.23 mmol, 1.5 eq) and DIPEA (61.2 mg, 0.47 mmol, 82.6 uL, 3 eq) in DCM (2 mL) was stirred at 25° C. for 1 hr. Then 2-aminoethanethiol (19.7 mg, 0.17 mmol, 1.1 eq, HCl) was added into the mixture and the mixture was stirred at 25° C. for another 1 hr. LC-MS showed the desired compound was detected. Compound 115-2 (59 mg, crude) was used into the next step without further purification.

Step 2: N,N'-(disulfanediylbis(ethane-2,1-diyl))bis(5-(4-(trifluoromethyl)phenyl)-2-naphthamide)

The mixture of compound 115-2 (59 mg, 0.15 mmol, 1 eq) in DCM (2 mL) was stirred at 25° C. for 48 hr. LC-MS and HPLC showed the desired compound was detected. The reaction mixture was diluted with $H_2O$ (10 mL) and the mixture was extracted with EA (10 mL*3). The combined organic phase was washed with brine (10 mL*2), dried with anhydrous $Na_2SO_4$, filtered and concentrated in vacuum. The residue was purified by prep-HPLC. The title compound (20 mg, 25.3 umol, 16.1% yield) was obtained as a yellow solid. LCMS (ESI): RT=1.165 min, mass calcd for $C_{40}H_{30}F_6N_2O_2S_2$ 748.80 m/z found 748.9[M+H]$^+$; $^1$H NMR (400 MHz, DMSO-$d_6$) δ 8.91 (br t, J=5.4 Hz, 2H), 8.55 (s, 2H), 8.10 (d, J=8.3 Hz, 2H), 7.96-7.86 (m, 6H), 7.79 (d, J=8.8 Hz, 2H), 7.75-7.64 (m, 6H), 7.58 (d, J=6.8 Hz, 2H), 3.65 (q, J=6.2 Hz, 4H), 3.01 (br t, J=6.8 Hz, 4H).

Example 108: 6-cyclopropoxy-N-isopropyl-8-(4-(trifluoromethyl)phenyl)quinoline-3-carboxamide (Compound 116)

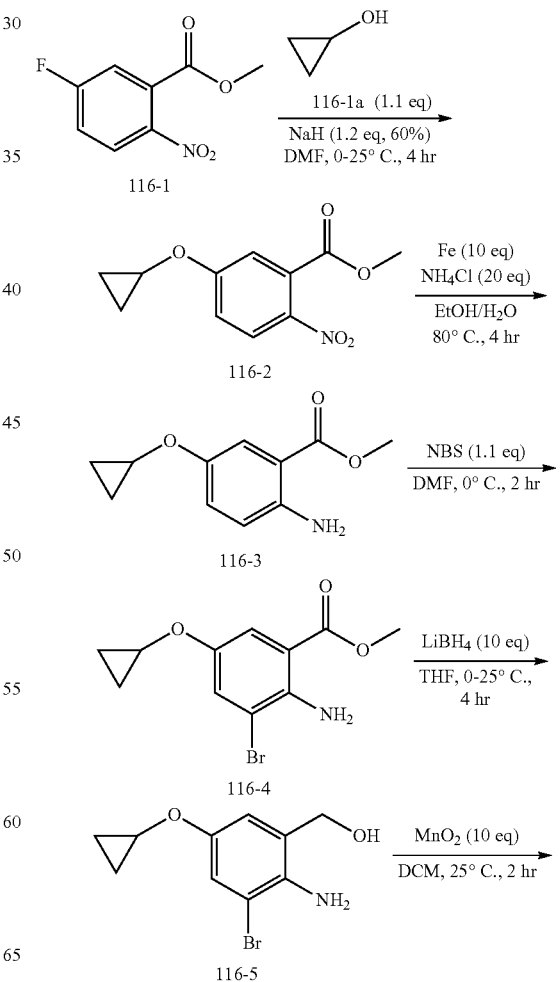

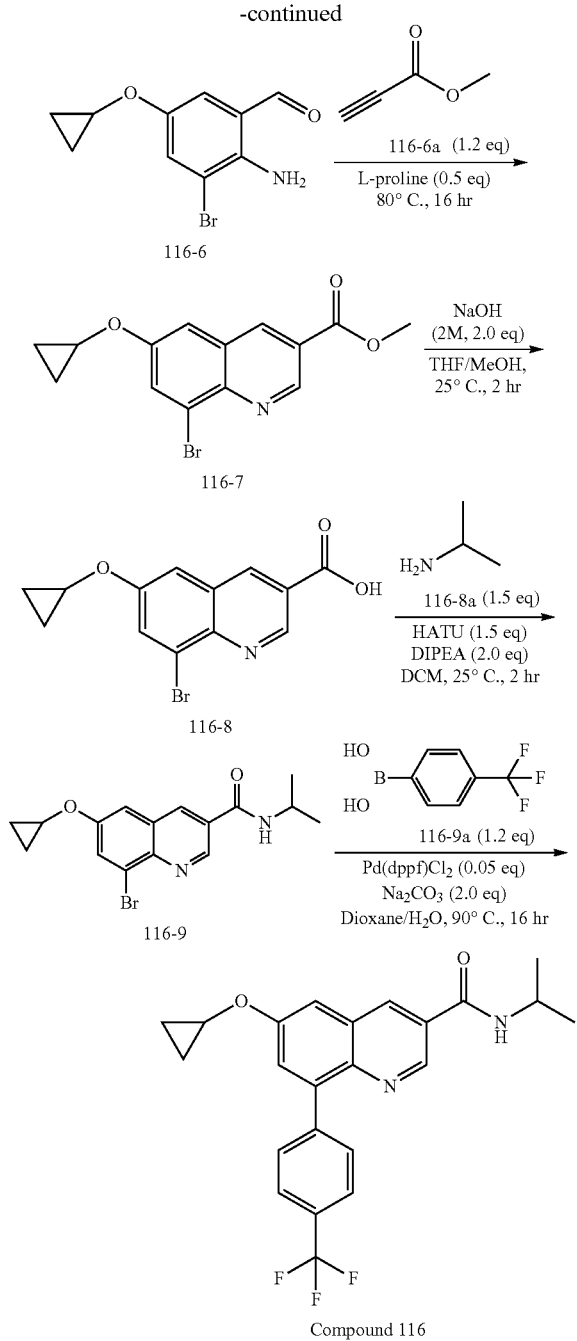

Compound 116

Step 1: methyl 5-cyclopropoxy-2-nitrobenzoate

To a solution of compound 116-1a (577.4 mg, 9.9 mmol, 1.1 eq) in DMF (15 mL) was added NaH (433.8 mg, 10.8 mmol, 60%, 1.2 eq) at 0° C. The reaction mixture was stirred at 0° C. for 30 min. After compound 116-1 (1.8 g, 9.0 mmol, 1.0 eq) in DMF (3 mL) was added dropwise slowly, the reaction mixture was stirred at 25° C. for 3.5 hours. The reaction mixture was concentrated under reduced pressure. The mixture was diluted with water (20 mL) and the resultant mixture was extracted with EA (50 mL*3). The combined organic layers were dried over $Na_2SO_4$, filtered and concentrated to dryness under reduced pressure. The residue was purified by column chromatography over silica gel (petroleum ether:ethyl acetate=1:0 to 10:1) to give compound 116-2 (1.1 g, 53% yield) as yellow oil.

Step 2: methyl 2-amino-5-cyclopropoxybenzoate

To a solution of compound 116-2 (1.5 g, 6.3 mmol, 1.0 eq) in EtOH (30 mL) and $H_2O$ (6 mL) were added Fe (3.53 g, 63.2 mmol, 10 eq) and $NH_4Cl$ (6.77 g, 126 mmol, 20 eq). The reaction mixture was stirred at 80° C. for 4 hours. LC-MS showed starting material was consumed completely and one main peak with desired MS was detected. The suspension was filtered, washed with EA (50 mL) and water (30 mL). The filtrate was separated, and then the organic layer was dried over $Na_2SO_4$, filtered and concentrated to dryness under reduced pressure to give compound 116-3 (1.2 g, 91% yield) as yellow oil.

Step 3: Methyl 2-amino-3-bromo-5-cyclopropoxybenzoate

To a solution of compound 116-3 (1.2 g, 5.8 mmol, 1.0 eq) in DMF (10 mL) was added NBS (1.13 g, 6.4 mmol, 1.1 eq) at 0° C. The reaction mixture was stirred at 25° C. for 2 hours. The mixture was diluted with water (20 mL) and the resultant mixture was extracted with EA (50 mL*3). The combined organic layers were dried over $Na_2SO_4$, filtered and concentrated to dryness under reduced pressure. The residue was purified by column chromatography over silica gel (petroleum ether:ethyl acetate=1:0 to 10:1) to give compound 116-4 (790 mg, 47% yield) as colorless oil. LCMS (ESI): RT=0.959 min, mass calcd. for $C_{11}H_{12}BrNO_3$ 285.00, m/z found 287.9 $[M+H]^+$.

Step 4: (2-amino-3-bromo-5-cyclopropoxyphenyl)methanol

To a solution of compound 116-4 (790.0 mg, 2.76 mmol, 1.0 eq) in THF (12 mL) was added $LiBH_4$ (601.4 mg, 27.6 mmol, 10 eq) at 0° C. The reaction mixture was stirred at 25° C. for 4 hours. LC-MS showed starting material was consumed completely and one main peak with desired MS was detected. The reaction mixture was poured into $H_2O$ (30 mL), and then the mixture was extracted with EA (50 mL). The combined organic layers were dried over $Na_2SO_4$, filtered and concentrated to dryness under reduced pressure. The residue was purified by column chromatography over silica gel (petroleum ether:ethyl acetate=1:0 to 5:1) to give compound 116-5 (700 mg, 97% yield) as a white solid.

Step 5: 2-amino-3-bromo-5-cyclopropoxybenzaldehyde

To a solution of compound 116-5 (700.0 mg, 2.71 mmol, 1.0 eq) in DCM (15 mL) was added $MnO_2$ (2.36 g, 27.1 mmol, 10 eq). The reaction mixture was stirred at 25° C. for 2 hours. The mixture was filtered and the filtrate was concentrated under reduce pressure. The residue was purified by column chromatography over silica gel (petroleum ether:ethyl acetate=1:0 to 10:1) to give compound 116-6 (480 mg, 69% yield) as yellow oil.

Step 6: methyl 8-bromo-6-cyclopropoxyquinoline-3-carboxylate

To a solution of compound 116-6 (480.0 mg, 1.87 mmol, 1.0 eq) and compound 116-6a (189.0 mg, 2.25 mmol, 1.2 eq) in EtOH (8 mL) was added L-proline (108.8 mg, 0.937 mmol, 0.5 eq). The reaction mixture was stirred at 80° C. for 16 hours. The reaction mixture was concentrated under reduced pressure. The mixture was diluted with water (10 mL) and the resultant mixture was extracted with EA (30 mL*3). The combined organic layers were dried over $Na_2SO_4$, filtered and concentrated to dryness under reduced pressure. The residue was purified by column chromatography over silica gel (petroleum ether:ethyl acetate=1:0 to 5:1) to give compound 116-7 (560 mg, 92% yield) as a light yellow solid.

Step 7: 8-bromo-6-cyclopropoxyquinoline-3-carboxylic Acid

To a solution of compound 116-7 (150 mg, 0.47 mmol, 1.0 eq) in THF (1.5 mL) and MeOH (0.5 mL) was added NaOH (2 M, 0.46 mL, 2.0 eq) dropwise. The reaction mixture was stirred at 25° C. for 2 hours. The reaction mixture was adjusted with HCl (1M) to pH=6, and then $H_2O$ (5 mL) was added. The suspension was extracted with EA (50 mL*3). The combined organic layers were dried over $Na_2SO_4$, filtered and concentrated to dryness under reduced pressure to give compound 116-8 (140 mg, 97% yield) as a light yellow solid.

Step 8: 8-bromo-6-cyclopropoxy-N-isopropylquinoline-3-carboxamide

To a solution of compound 116-8 (40.0 mg, 0.13 mmol, 1.0 eq), compound 116-8a (11.5 mg, 0.195 mmol, 1.5 eq) and DIPEA (33.5 mg, 0.26 mmol, 2.0 eq) in DCM (1 mL) was added HATU (74.0 mg, 0.15 mmol, 1.5 eq). The reaction mixture was stirred at 25° C. for 2 hours. LC-MS showed starting material was consumed completely and one main peak with desired MS was detected. The reaction mixture was concentrated under reduced pressure. The mixture was diluted with water (30 mL) and the resultant mixture was extracted with EA (50 mL*3). The combined organic layers were dried over $Na_2SO_4$, filtered and concentrated to dryness under reduced pressure. The residue was purified by column chromatography over silica gel (petroleum ether:ethyl acetate=1:0 to 3:1) to give compound 9 (40 mg, 88% yield) as a white solid.

Step 9: 6-cyclopropoxy-N-isopropyl-8-(4-(trifluoromethyl)phenyl)quinoline-3-carboxamide To a solution of compound 116-9 (40.0 mg, 0.11 mmol, 1.0 eq), compound 116-9a (26.1 mg, 0.14 mmol, 1.2 eq) and $Na_2CO_3$ (24.2 mg, 0.23 mmol, 2.0 eq) in Dioxane (2 mL) and $H_2O$ (0.4 mL) was added Pd(dppf)$Cl_2$ (4.1 mg, 5.7 umol, 0.05 eq). The reaction mixture was stirred at 90° C. for 16 hours under $N_2$. LC-MS showed starting material was consumed completely and one main peak with desired MS was detected. The reaction mixture was concentrated under reduced pressure. The mixture was diluted with water (10 mL) and the resultant mixture was extracted with EA (30 mL*3). The combined organic layers were dried over $Na_2SO_4$, filtered and concentrated to dryness under reduced pressure. The residue was purified by prep-HPLC to give compound the title compound (6.86 mg, 14% yield) as a white solid. LCMS (ESI): RT=1.024 min, mass calcd. for $C_{23}H_{21}F_3N_2O_2$ 414.16, m/z found 415.0 $[M+H]^+$; $^1H$ NMR (400 MHz, $CDCl_3$) δ 9.09 (d, J=2.3 Hz, 1H), 8.58 (d, J=2.3 Hz, 1H), 7.84-7.73 (m, 4H), 7.55 (d, J=2.8 Hz, 1H), 7.49 (d, J=2.8 Hz, 1H), 6.07 (d, J=7.1 Hz, 1H), 4.45-4.33 (m, 1H), 3.97-3.91 (m, 1H), 1.34 (d, J=6.5 Hz, 6H), 0.97-0.89 (m, 4H).

Example 109: Tert-Butyl methyl(2-(5-(4-(trifluoromethyl)phenyl)-2-naphthamido)ethyl)carbamate (Compound 117)

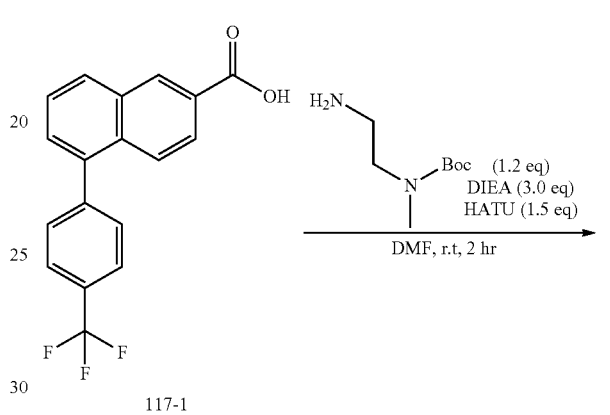

117-1

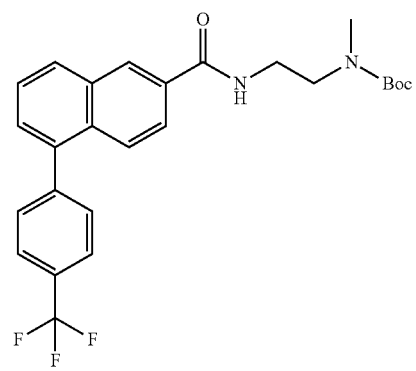

Compound 117

The mixture of compound 117-1 (0.03 g, 94.8 umol, 1 eq), HATU (54.1 mg, 0.14 mmol, 1.5 eq) and DIPEA (36.7 mg, 0.28 mmol, 49.5 uL, 3 eq) in DMF (1 mL) was stirred at 25° C. for 1 hr. tert-butyl N-(2-aminoethyl)-N-methyl-carbamate (19.8 mg, 0.11 mmol, 20.3 uL, 1.2 eq) was added into the reaction. The mixture was stirred at 25° C. for another 1 hr. LCMS showed the reaction was complete. The mixture was partitioned between EA (5 mL) and brine (5 mL). The organic layer was washed with brine (5 mL), dried over anhydrous Na$_2$SO$_4$ and concentrated in vacuum to afford the crude product. The crude product was purified by prep-HPLC. The title compound (6 mg, 12.5 umol, 13.2% yield) was obtained as white solid. LCMS (ESI): RT=0.878 min, mass calcd for C$_{26}$H$_{27}$F$_3$N$_2$O$_3$. $^1$H NMR (400 MHz, CD$_3$OD) δ 8.48 (br d, J=14.6 Hz, 1H), 8.07 (d, J=8.0 Hz, 1H), 7.93-7.82 (m, 4H), 7.74-7.64 (m, 3H), 7.59 (d, J=6.5 Hz, 1H), 3.64-3.58 (m, 1H), 3.58-3.54 (m, 1H), 3.65-3.51 (m, 2H), 2.97 (br s, 3H), 1.39 (br d, J=18.8 Hz, 9H).

Example 110: Tert-Butyl methyl(3-(5-(4-(trifluoromethyl)phenyl)-2-naphthamido)propyl)carbamate (Compound 118)

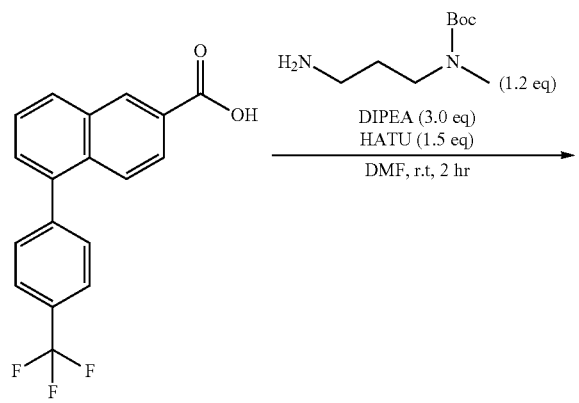

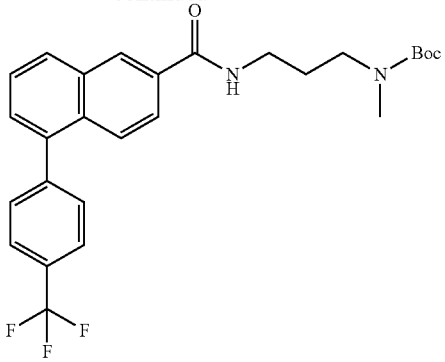

Compound 118

The mixture of compound 118-1 (0.03 g, 94.8 umol, 1 eq), DIPEA (36.7 mg, 0.28 mmol, 49.5 uL, 3 eq) and HATU (54.1 mg, 0.14 mmol, 1.5 eq) in DMF (1 mL) was stirred at 25° C. for 1 hr. Then tert-butyl N-(3-aminopropyl)-N-methyl-carbamate (21.4 mg, 0.11 mmol, 1.2 eq) was added at the mixture and the mixture was stirred for another 1 hr. LC-MS and HPLC showed the reaction was complete. The reaction mixture was diluted with H$_2$O (10 mL) and the mixture was extracted with EA (10 mL*3). The combined organic phase was washed with brine (10 mL*4), dried with anhydrous Na$_2$SO$_4$, filtered and concentrated in vacuum. The residue was purified by prep-HPLC. The title compound (7 mg, 14.2 umol, 15% yield) was obtained as brown solid. LCMS (ESI): RT=1.069 min, mass calcd for C$_{27}$H$_{29}$F$_3$N$_2$O$_3$ 486.53 m/z found 487.1[M+H]$^+$; $^1$H NMR (400 MHz, CD$_3$OD) δ 8.40 (s, 1H), 7.98 (d, J=8.3 Hz, 1H), 7.82-7.72 (m, 4H), 7.64-7.55 (m, 3H), 7.48 (d, J=7.0 Hz, 1H), 3.37 (t, J=6.9 Hz, 2H), 3.30 (t, J=7.1 Hz, 2H), 2.82 (br s, 3H), 1.82 (br s, 2H), 1.37 (br d, J=8.9 Hz, 9H).

Example 111: N,N'-(disulfanediylbis(propane-3,1-diyl))bis(5-(4-(trifluoromethyl)phenyl)-2-naphthamide) (Compound 119)

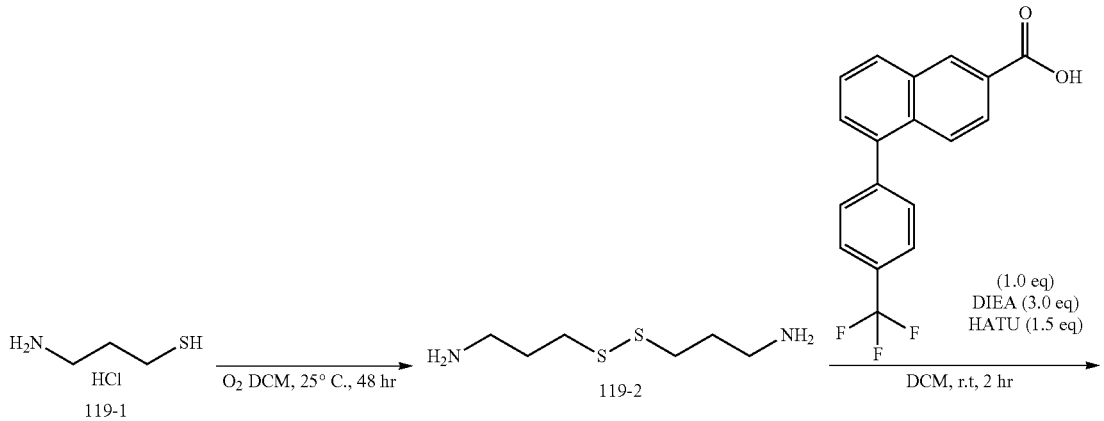

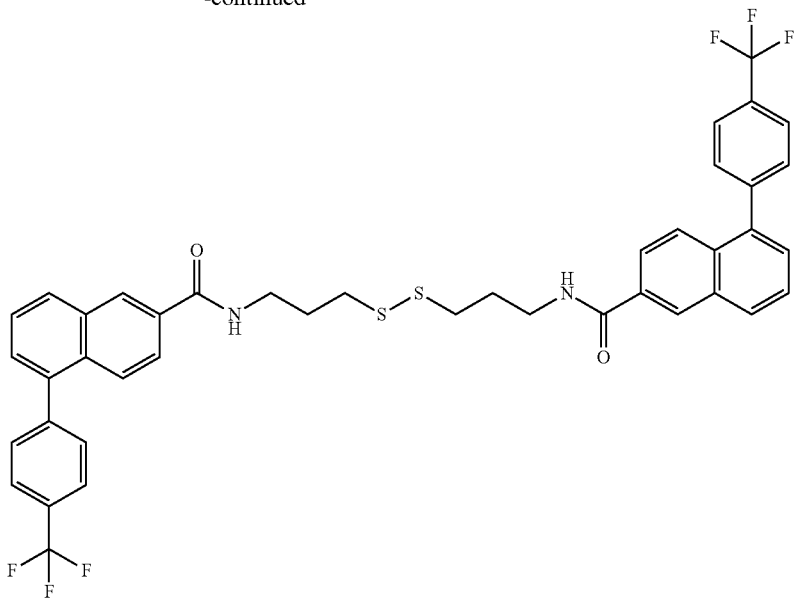

Compound 119

The mixture of compound 119-1 (50 mg, 391.74 umol, 1 eq, HCl) in DCM (2 mL) was stirred at 25° C. for 48 hr under O₂ atmosphere. Compound 119-2 (crude) was used into the next step without further purification.

Step 2: N,N'-(disulfanediylbis(propane-3,1-diyl))bis (5-(4-(trifluoromethyl)phenyl)-2-naphthamide)

The mixture of 5-[4-(trifluoromethyl)phenyl]naphthalene-2-carboxylic acid (55.8 mg, 0.17 mmol, 1 eq), HATU (100.6 mg, 0.26 mmol, 1.5 eq), compound 119-2 (35 mg, 0.19 mmol, 1.1 eq) and DIPEA (68.4 mg, 0.52 mmol, 92.2 uL, 3 eq) in DCM (2 mL) was stirred at 25° C. for 2 hr. LC-MS and HPLC showed the desired compound was detected. The reaction mixture was diluted with H₂O (10 mL) and the mixture was extracted with EA (10 mL*3). The combined organic phase was washed with brine (10 mL*2), dried with anhydrous Na₂SO₄, filtered and concentrated in vacuum. The residue was purified by prep-HPLC. The title compound (10 mg, 12.7 umol, 7.2% yield) was obtained as a white solid. LCMS (ESI): RT=1.172 min, mass calcd for C₄₂H₃₄F₆N₂O₂S₂ 776.85 m/z found 777.0[M+H]⁺; ¹H NMR (400 MHz, DMSO-d₆) δ 8.79 (br s, 2H), 8.55 (s, 2H), 8.12 (d, J=8.3 Hz, 2H), 7.94-7.88 (m, 6H), 7.80 (d, J=8.9 Hz, 2H), 7.76-7.66 (m, 6H), 7.59 (br d, J=7.0 Hz, 2H), 3.43 (br d, J=5.8 Hz, 4H), 2.85 (t, J=7.1 Hz, 4H), 2.06-1.91 (m, 5H).

Example 112: S-(3-(5-(4-(trifluoromethyl)phenyl)-2-naphthamido)propyl) 5-(4-(trifluoromethyl)phenyl)naphthalene-2-carbothioate (Compound 120)

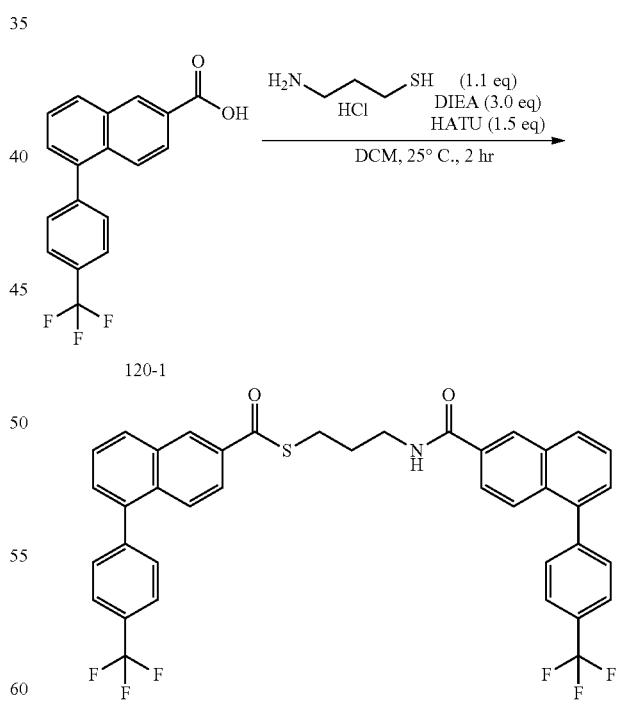

Compound 120

A mixture of compound 120-1 (50 mg, 0.15 mmol, 1 eq), 3-aminopropane-1-thiol (22.2 mg, 0.17 mmol, 1.1 eq, HCl), HATU (90.1 mg, 0.23 mmol, 1.5 eq) and DIPEA (61.2 mg, 0.47 mmol, 82.6 uL, 3 eq) in DCM (2 mL) was stirred at 25°

C. for 2 hr. LC-MS and HPLC showed the desired compound was detected. The reaction mixture was diluted with H₂O (10 mL) and the mixture was extracted with EA (10 mL*3). The combined organic phase was washed with brine (10 mL*2), dried with anhydrous Na₂SO₄, filtered and concentrated in vacuum. The crude product was washed with MeCN (5 mL) and filtered. The filter cake was concentrated in vacuum. The title compound (10 mg, 14.4 umol, 9.1% yield) was obtained as a white solid. LCMS (ESI): RT=1.225 min, mass calcd for C₃₉H₂₇F₆NO₂S 687.69 m/z found 688.0[M+H]⁺; ¹H NMR (400 MHz, DMSO-di) δ 8.80 (t, J=5.6 Hz, 1H), 8.72 (d, J=1.8 Hz, 1H), 8.58 (d, J=1.3 Hz, 1H), 8.28 (d, J=8.3 Hz, 1H), 8.12 (d, J=8.3 Hz, 1H), 7.98-7.86 (m, 7H), 7.82 (d, J=8.8 Hz, 1H), 7.77-7.70 (m, 5H), 7.71-7.65 (m, 2H), 7.59 (d, J=6.0 Hz, 1H), 3.48 (q, J=6.5 Hz, 2H), 3.22 (t, J=7.0 Hz, 2H), 2.04-1.93 (m, 2H).

Example 113: N-(1-phenylcyclopropyl)-5-[4-(trifluoromethyl)phenyl]naphthalene-2-carboxamide (Compound 121)

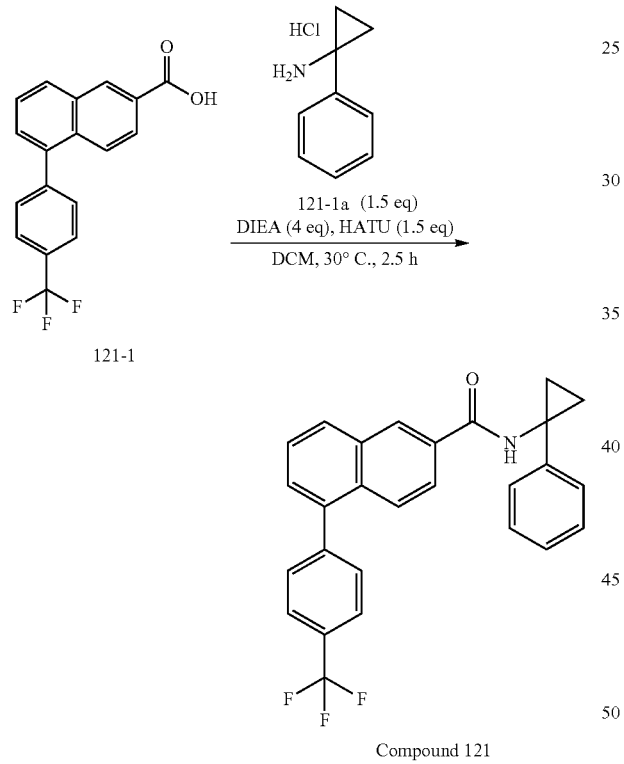

Compound 121

To a solution of compound 121-1 (20 mg, 63.2 umol, 1 eq) in DCM (1 mL) were added DIEA (32.7 mg, 0.25 mmol, 44 uL, 4 eq) and HATU (36.1 mg, 94.8 umol, 1.5 eq). The mixture was stirred at 30° C. for 0.5 h. Compound 121-1a (16.1 mg, 94.8 umol, 1.5 eq, HCl) was added into the mixture. The mixture was stirred at 30° C. for 2 h. LCMS detected desired compound. The mixture was diluted with H₂O (10 mL), extracted with EA (20 mL*3). The combined organic layers were washed with brine (10 mL), dried over Na₂SO₄, filtered and concentrated. The residue was checked by HPLC. The residue was purified by prep-HPLC to give the title compound (24.2 mg, 56.1 umol, 88.7% yield) as a white solid. LCMS (ESI): RT=1.056 min, mass calc. for C₂₇H₂₀F₃NO 431.15, m/z found 432.0 [M+H]⁺; ¹H NMR (400 MHz, CDCl₃) δ 8.38 (d, J=1.4 Hz, 1H), 7.98 (d, J=8.3 Hz, 1H), 7.90-7.74 (m, 4H), 7.64-7.57 (m, 3H), 7.50 (dd, J=1.1, 7.1 Hz, 1H), 7.38-7.28 (m, 4H), 7.23-7.18 (m, 1H), 6.97 (s, 1H), 1.48-1.40 (m, 4H).

Example 114: 6-cyclopropoxy-N-(methylsulfonyl)-8-(4-(trifluoromethyl)phenyl)quinoline-3-carboxamide (Compound 122)

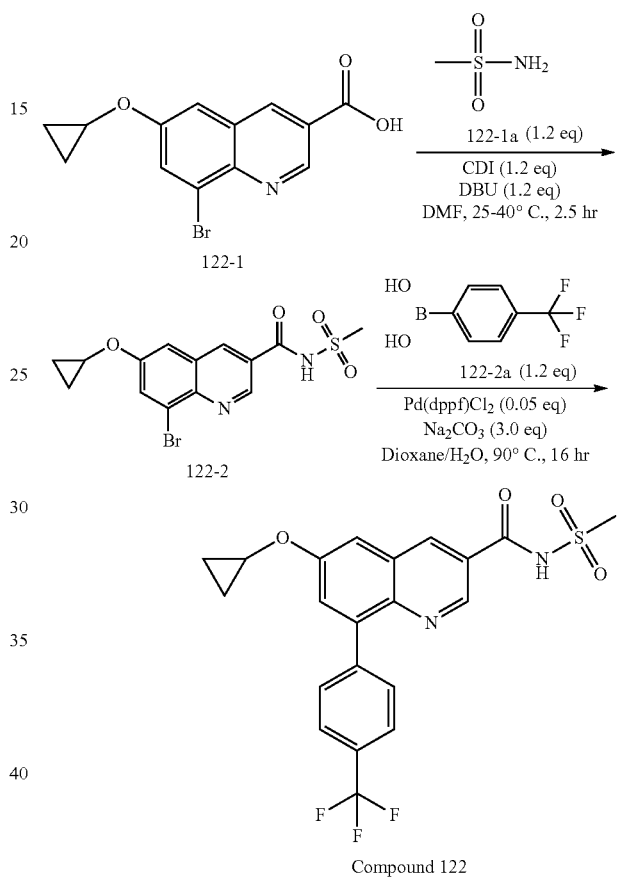

Compound 122

Step 1: 8-bromo-6-cyclopropoxy-N-(methylsulfonyl)quinoline-3-carboxamide

To a solution of compound 122-1 (50.0 mg, 0.16 mmol, 1.0 eq) in DMF (1 mL) was added CDI (31.5 mg, 0.19 mmol, 1.2 eq). The reaction mixture was stirred at 40° C. for 30 min. The reaction was cooled to 25° C., and then DBU (29.6 mg, 0.19 mmol, 1.2 eq) and compound 122-1a (18.5 mg, 0.19 mmol, 1.2 eq) were added. The reaction was stirred at 25° C. for 2 hours. LC-MS showed starting material was consumed completely and one main peak with desired MS was detected. The reaction mixture was concentrated under reduced pressure. The mixture was diluted with water (10 mL) and the resultant mixture was extracted with EA (20 mL*3). The combined organic layers were dried over Na₂SO₄, filtered and concentrated to dryness under reduced pressure. The residue was purified by column chromatography over silica gel (DCM:MeOH=20:1) to give compound 122-2 (35 mg, 53% yield) as a white solid. LCMS (ESI): RT=0.831 min, mass calcd. for C₁₄H₁₃BrN₂O₄S, 383.98, m/z found 386.8 [M+H]⁺.

Step 2: 6-cyclopropoxy-N-(methylsulfonyl)-8-(4-(trifluoromethyl)phenyl)quinoline-3-carboxamide To a solution of compound 122-2 (35.0 mg, 90 umol, 1.0 eq), compound 122-2a (20.7 mg, 0.11 mmol, 1.2 eq) and $Na_2CO_3$ (28.8 mg, 0.27 mmol, 3.0 eq) in Dioxane (2 mL) and $H_2O$ (0.4 mL) was added Pd(dppf)$Cl_2$ (3.3 mg, 4.5 umol, 0.05 eq) under $N_2$. The reaction mixture was stirred at 90° C. for 16 hours under $N_2$. LC-MS showed starting material was consumed completely and one main peak with desired MS was detected. The reaction mixture was adjusted with HCl (1M) to pH=5. The resultant mixture was extracted with EA (30 mL*3). The combined organic layers were dried over $Na_2SO_4$, filtered and concentrated to dryness under reduced pressure. The residue was purified by prep-HPLC to give the title compound (2.23 mg, 5% yield, HCl) as a white solid. LCMS (ESI): RT=0.979 min, mass calcd. for $C_{21}H_{17}F_3N_2O_4S$ 450.09, m/z found 451.0 [M+H]$^+$; $^1$H NMR (400 MHz, DMSO-$d_6$) δ 9.09 (d, J=2.0 Hz, 1H), 9.00 (d, J=2.0 Hz, 1H), 7.92-7.81 (m, 5H), 7.63 (d, J=2.8 Hz, 1H), 4.14-4.06 (m, 1H), 3.44 (s, 3H), 0.99-0.88 (m, 2H), 0.85-0.76 (m, 2H).

Example 115: N-(methylsulfonyl)-6-(trifluoromethoxy)-8-(4-(trifluoromethyl)phenyl)quinoline-3-carboxamide (Compound 123)

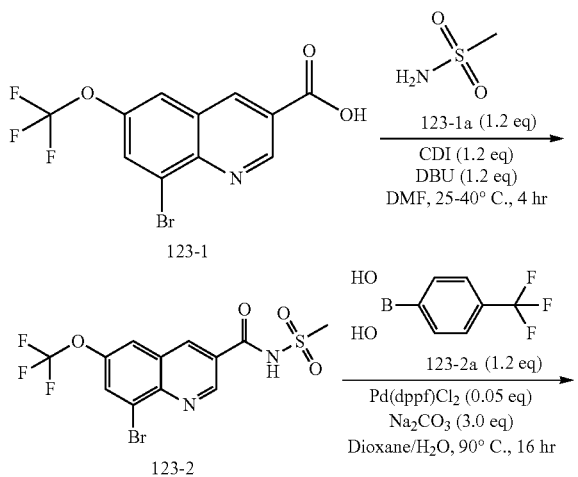

Compound 123

Step 1: 8-bromo-N-(methylsulfonyl)-6-(trifluoromethoxy)quinoline-3-carboxamide To a solution of compound 123-1 (80.0 mg, 0.24 mmol, 1.0 eq) in DMF (1 mL) was added CDI (46.3 mg, 0.28 mmol, 1.2 eq). The reaction mixture was stirred at 40° C. for 30 min. The reaction was cooled to 25° C., and then DBU (43.4 mg, 0.28 mmol, 1.2 eq) and compound 123-1a (27.1 mg, 0.28 mmol, 1.2 eq) were added. The reaction was stirred at 25° C. for 3 hours. LC-MS showed starting material was remained and one peak with desired MS was detected. The reaction mixture was concentrated under reduced pressure. The mixture was diluted with water (3 mL) and the mixture was adjusted with HCl (1M) to pH=5. The resultant mixture was extracted with EA (20 mL*3). The combined organic layers were dried over $Na_2SO_4$, filtered and concentrated to dryness under reduced pressure. The residue was purified by column chromatography over silica gel (DCM:MeOH=10:1) to give compound 123-2 (80 mg, crude) as yellow oil.

Step 2: N-(methylsulfonyl)-6-(trifluoromethoxy)-8-(4-(trifluoromethyl)phenyl)quinoline-3-carboxamide To a solution of compound 123-2 (80.0 mg, 0.19 mmol, 1.0 eq), compound 123-2a (44.1 mg, 0.23 mmol, 1.2 eq) and $Na_2CO_3$ (61.5 mg, 0.58 mmol, 3.0 eq) in Dioxane (2 mL) and $H_2O$ (0.4 mL) was added Pd(dppf)$Cl_2$ (7.0 mg, 9.7 umol, 0.05 eq) under $N_2$. The reaction mixture was stirred at 90° C. for 16 hours under $N_2$. LC-MS showed starting material was consumed completely and one main peak with desired MS was detected. The reaction mixture was adjusted with HCl (1M) to pH=5. The resultant mixture was extracted with EA (30 mL*3). The combined organic layers were dried over $Na_2SO_4$, filtered and concentrated to dryness under reduced pressure. The residue was purified by prep-HPLC to give the title compound (19.45 mg, 19% yield, HCl) as a light yellow solid. LCMS (ESI): RT=0.993 min, mass calcd. for $C_{19}H_{12}F_6N_2O_4S$ 478.04, m/z found 478.9 [M+H]$^+$; $^1$H NMR (400 MHz, DMSO-$d_6$) δ 9.29 (d, J=2.3 Hz, 1H), 9.15 (d, J=2.3 Hz, 1H), 8.31 (d, J=1.3 Hz, 1H), 8.00 (d, J=2.5 Hz, 1H), 7.95-7.85 (m, 4H), 3.44 (s, 3H).

Example 116: N-(2-(methylamino)ethyl)-5-(4-(trifluoromethyl)phenyl)-2-naphthamide (Compound 124)

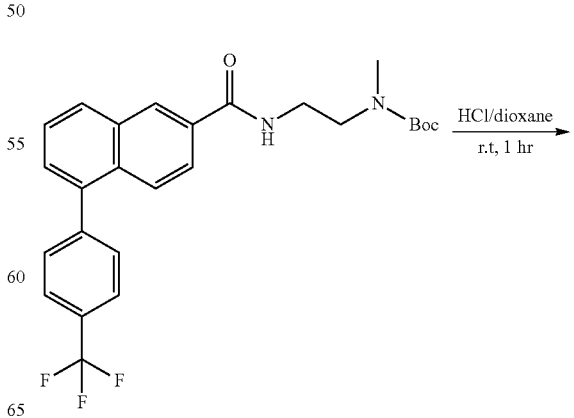

124-1

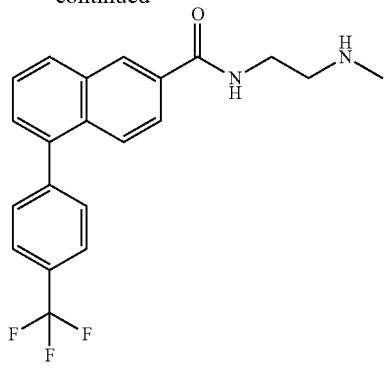

Compound 124

The mixture of compound 124-1 (0.02 g, 42.3 umol, 1 eq) in HCl/dioxane (4 M, 0.52 mL, 50 eq) was stirred at 25° C. for 1 hr. LC-MS and HPLC showed the desired compound was detected. The mixture was concentrated in vacuum to afford the crude product. The crude product was purified by prep-HPLC. The title compound (5 mg, 12.2 umol, 28.8% yield, HCl) was obtained as white solid. LCMS (ESI): RT=0.850 min, mass calcd for $C_{21}H_{19}F_3N_2O$ 372.38 m/z, found 373.0 [M+H]$^+$; $^1$H NMR (400 MHz, CD$_3$OD) δ 8.46 (d, J=1.5 Hz, 1H), 7.99 (d, J=8.3 Hz, 1H), 7.86-7.81 (m, 1H), 7.79-7.71 (m, 3H), 7.61-7.55 (m, 3H), 7.51-7.46 (m, 1H), 3.67 (t, J=5.7 Hz, 2H), 3.21-3.17 (m, 3H), 2.71-2.63 (m, 3H).

Example 117: N-(2-(N-methylcyanamido)ethyl)-5-(4-(trifluoromethyl)phenyl)-2-naphthamide (Compound 125)

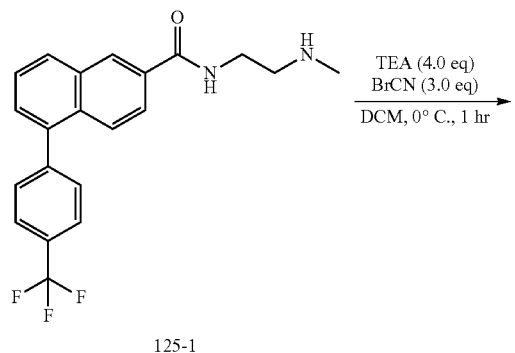

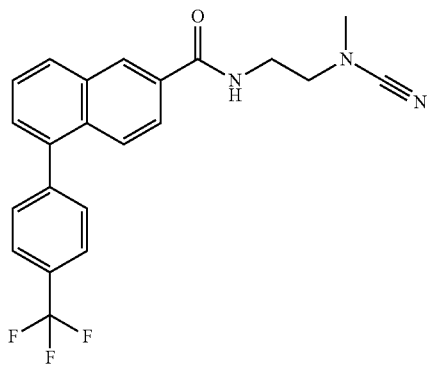

Compound 125

The mixture of compound 125-1 (40 mg, 0.10 mmol, 1 eq), TEA (43.4 mg, 0.42 mmol, 59.8 uL, 4 eq) and BrCN (34.1 mg, 0.32 mmol, 23.7 uL, 3 eq) in DCM (2 mL) was stirred at 0° C. for 1 hr. LC-MS and HPLC showed the desired compound was detected. The reaction mixture was diluted with H$_2$O (10 mL) and the mixture was extracted with EA (10 mL*3). The combined organic phase was washed with brine (10 mL*2), dried with anhydrous Na$_2$SO$_4$, filtered and concentrated in vacuum. The residue was purified by prep-HPLC. The title compound (6 mg, 14.9 umol, 13.9% yield) was obtained as white solid. LCMS (ESI): RT=0.946 min, mass calcd for $C_{22}H_{18}F_3N_3O$ 397.39 m/z, found 398.0 [M+H]$^+$; $^1$H NMR (400 MHz, CD$_3$OD) δ 8.51 (s, 1H), 8.09 (d, J=8.1 Hz, 1H), 7.93-7.83 (m, 4H), 7.73-7.65 (m, 3H), 7.58 (d, J=6.3 Hz, 1H), 3.70 (t, J=5.7 Hz, 2H), 3.36 (t, J=5.8 Hz, 2H), 3.00 (s, 3H).

Example 118: N-(3-(methylamino)propyl)-5-(4-(trifluoromethyl)phenyl)-2-naphthamide (Compound 126)

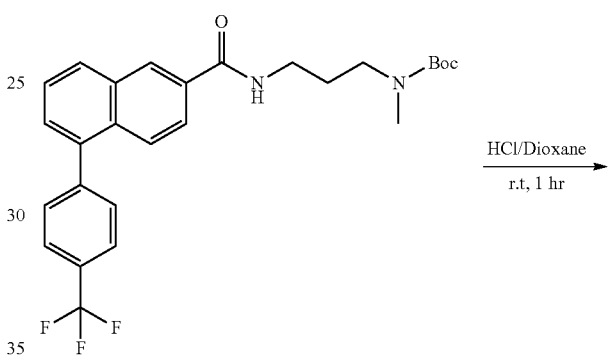

126-1

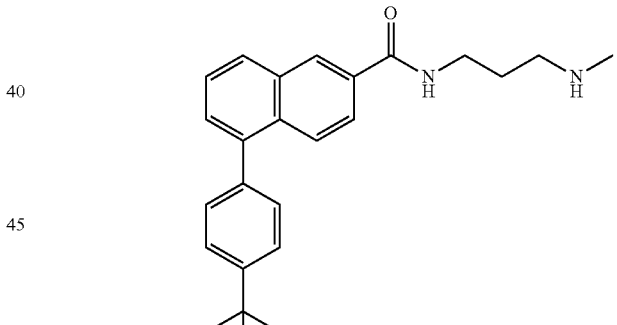

Compound 126

The mixture of compound 126-1 (0.05 g, 0.10 mmol, 1 eq) in HCl/dioxane (4 M, 1.28 mL, 50 eq) was stirred at 25° C. for 1 hr. The reaction mixture was concentrated under reduced pressure to give a residue. The residue was partitioned between EA (5 mL) and saturated NaHCO$_3$ (5 mL). The organic layer was washed with brine (5 mL), dried over anhydrous Na$_2$SO$_4$ and concentrated in vacuum to afford the crude product. The crude product was purified by column chromatography (SiO$_2$, EA:PE=1:0 to 1:1). The title compound (38 mg, 96.3 umol, 93.7% yield) was obtained as white solid. LCMS (ESI): RT=0.845 min, mass calcd for $C_{22}H_{21}F_3N_2O$ 386.41 m/z, found 387.0 [M+H]$^+$; $^1$H NMR (400 MHz, CD$_3$OD) δ 8.54 (s, 1H), 8.10 (d, J=8.3 Hz, 1H), 7.95-7.83 (m, 4H), 7.73-7.66 (m, 3H), 7.60 (d, J=6.5 Hz, 1H), 3.63-3.55 (m, 2H), 3.12 (t, J=7.3 Hz, 2H), 2.77 (s, 3H), 2.06 (quin, J=6.9 Hz, 2H).

Example 119: N-(3-(N-methylcyanamido)propyl)-5-(4-(trifluoromethyl)phenyl)-2-naphthamide (Compound 127)

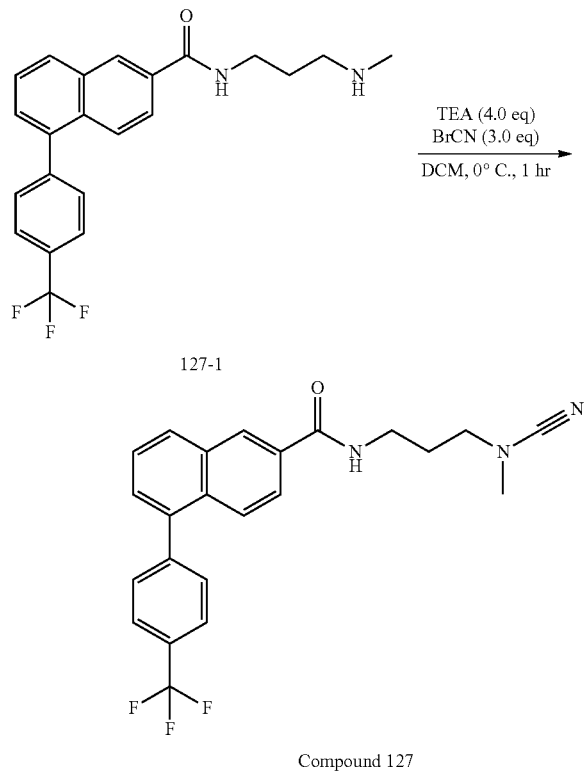

The mixture of compound 127-1 (100 mg, 0.25 mmol, 1 eq), BrCN (82.2 mg, 0.77 mmol, 57.1 uL, 3 eq) and TEA (104.7 mg, 1.04 mmol, 0.14 mL, 4 eq) in DCM (2 mL) was stirred at 0° C. for 1 hr. LC-MS and HPLC showed the desired compound was detected. The reaction mixture was diluted with H$_2$O (10 mL) and the mixture was extracted with EA (10 mL*3). The combined organic phase was washed with brine (10 mL*2), dried with anhydrous Na$_2$SO$_4$, filtered and concentrated in vacuum. The residue was purified by prep-HPLC. The title compound (18 mg, 43.3 umol, 16.7% yield) was obtained as brown solid. LCMS (ESI): RT=0.960 min, mass calcd for C$_{23}$H$_{20}$F$_3$N$_3$O 411.42 m/z, found 412.0 [M+H]$^+$; $^1$H NMR (400 MHz, CD$_3$OD) δ 8.47 (d, J=1.5 Hz, 1H), 8.07-8.03 (m, 1H), 7.88-7.80 (m, 5H), 7.67-7.61 (m, 3H), 7.55-7.51 (m, 1H), 3.54 (t, J=6.9 Hz, 2H), 3.37-3.31 (m, 1H), 3.16 (t, J=7.0 Hz, 2H), 2.91 (s, 3H), 2.01 (quin, J=7.0 Hz, 2H).

Example 120: (S)—N-(1-(6-aminopyridin-2-yl)ethyl)-5-(4-(trifluoromethyl)phenyl)-2-naphthamide (Compound 128) and (R)—N-(1-(6-aminopyridin-2-yl)ethyl)-5-(4-(trifluoromethyl)phenyl)-2-naphthamide (Compound 129)

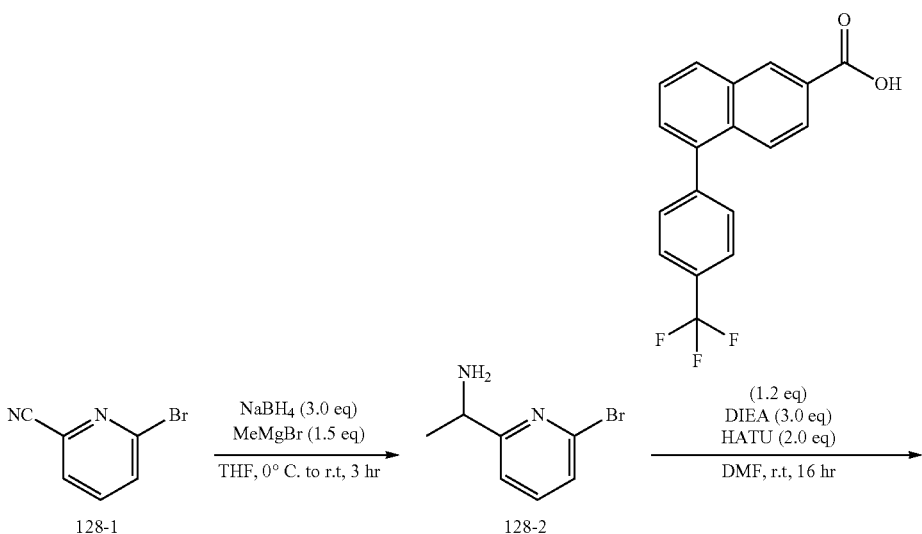

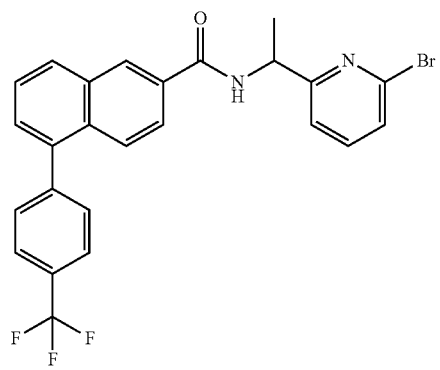

128-3

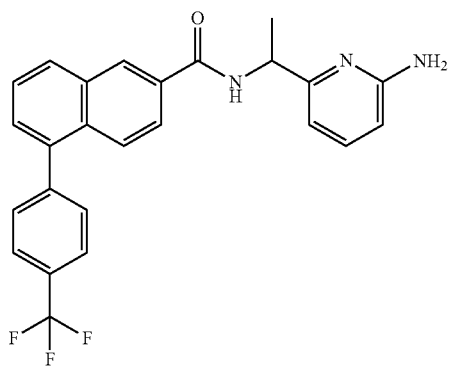

128-4

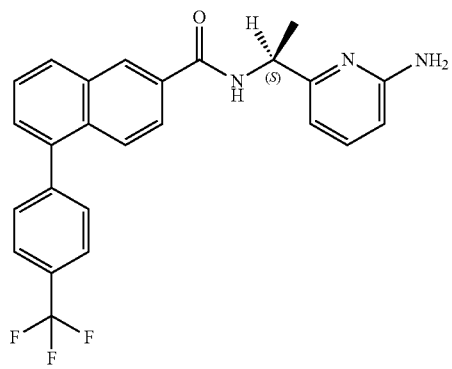

Compound 128

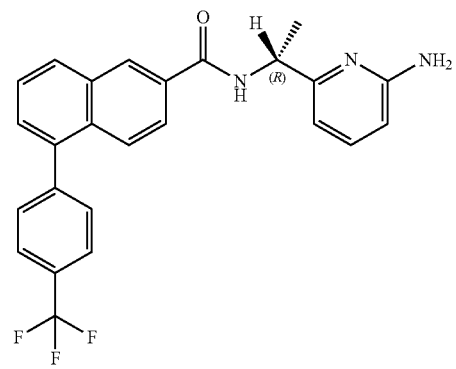

Compound 129

Step 1: 1-(6-bromopyridin-2-yl)ethanamine

To a solution of compound 128-1 (9.5 g, 51.91 mmol, 1 eq) in dry THF (150 mL) was added dropwise MeMgBr (3 M, 25.96 mL, 1.5 eq) at 0° C. under $N_2$ atmosphere. After the addition, the reaction mixture was stirred 25° C. for 0.5 hr. The suspension was then treated with MeOH (31.34 g, 978.16 mmol, 39.58 mL, 18.84 eq) and $NaBH_4$ (5.89 g, 155.73 mmol, 3 eq). The reaction was stirred at 25° C. for 2.5 hrs. The reaction mixture was poured into NaOH (120 mL, 2M) at 0° C. and stirred for 5 min. The aqueous phase was extracted with EA (60 mL*3). The combined organic phase was washed with brine (100 mL), dried with anhydrous $Na_2SO_4$, filtered and concentrated in vacuum. The residue was purified by flash silica gel chromatography. Compound 128-2 (1.1 g, 3.99 mmol, 7.6% yield) was obtained as a yellow oil.

Step 2: N-(1-(6-bromopyridin-2-yl)ethyl)-5-(4-(trifluoromethyl)phenyl)-2-naphthamide A mixture of compound 5-(4-(trifluoromethyl)phenyl)-2-naphthoic acid (1.51 g, 4.77 mmol, 1.2 eq), HATU (3.03 g, 7.96 mmol, 2 eq) in DMF (15 mL) was added DIPEA (1.54 g, 11.94 mmol, 2.08 mL, 3 eq) at 25° C. After addition, the mixture was stirred at 25° C. for 1 hr, and then 128-2 (800 mg, 3.98 mmol, 1 eq) (in DMF (3 mL)) was added. The resulting mixture was stirred at 25° C. for 15 hr. The residue was poured into $H_2O$ (30 mL) and stirred for 5 min. The aqueous phase was extracted with EA (15 mL*3). The combined organic phase was washed with brine (20 mL), dried with anhydrous $Na_2SO_4$, filtered and concentrated in vacuum. The residue was purified by flash silica gel chromatography. Compound 128-3 (386 mg, 0.74 mmol, 18.8% yield) was obtained as a yellow solid.

Step 3: (S)—N-(1-(6-aminopyridin-2-yl)ethyl)-5-(4-(trifluoromethyl)phenyl)-2-naphthamide and (R)—N-(1-(6-aminopyridin-2-yl)ethyl)-5-(4-(trifluoromethyl)phenyl)-2-naphthamide A mixture of compound 128-3 (300 mg, 0.60 mmol, 1 eq), $NH_3 \cdot H_2O$ (842.2 mg, 6.01 mmol, 0.92 mL, 25%, 10 eq), $Cu_2O$ (85.9 mg, 0.60 mmol, 61.4 uL, 1 eq) in ethylene glycol (2 mL) were loaded in a sealed reaction tube. The reaction temperature was increased to 70° C. and the reaction mixture was stirred at 70° C. for 16 hr. The residue was poured into $H_2O$ (20 mL) and stirred for 5 min. The aqueous phase was extracted with EA (10 mL*3). The combined organic phase was washed with brine (20 mL), dried with anhydrous $Na_2SO_4$, filtered and concentrated in vacuum. The residue was purified by flash silica gel chromatography to give 152 mg of the product. The product was purified by chiral SFC. Compound 128 (48.6 mg, 0.10 mmol, 18% yield) was obtained as a white solid. LCMS (ESI): RT=0.768 min, mass calcd for $C_{25}H_{20}F_3N_3O$ 435.44 m/z found 436.0 [M+H]$^+$; $^1$H NMR (400 MHz, DMSO-d$_6$) δ 8.85 (d, J=7.8 Hz, 1H), 8.63 (s, 1H), 8.15 (d, J=8.0 Hz, 1H), 8.00-7.89 (m, 3H), 7.81 (d, J=9.0 Hz, 1H), 7.77-7.67 (m, 3H), 7.59 (d, J=6.3 Hz, 1H), 7.33 (t, J=7.7 Hz, 1H), 6.55 (d, J=7.3 Hz, 1H), 6.31 (d, J=8.3 Hz, 1H), 5.89 (s, 2H), 5.01 (quin, J=7.2 Hz, 1H), 1.48 (d, J=7.0 Hz, 3H). Compound 129 (47.4 mg, 0.10 mmol, 18.1% yield) was obtained as a white solid. LCMS (ESI): RT=0.774 min, mass calcd for $C_{25}H_{20}F_3N_3O$ 435.44 m/z found 436.0 [M+H]$^+$; $^1$H NMR (400 MHz, DMSO-d$_6$) δ 8.85 (d, J=7.8 Hz, 1H), 8.63 (s, 1H), 8.15 (d, J=8.0 Hz, 1H), 8.00-7.89 (m, 3H), 7.81 (d, J=9.0 Hz, 1H), 1.11-7.67 (m, 3H), 7.59 (d, J=6.3 Hz, 1H), 7.33 (t, J=1.1 Hz, 1H), 6.55 (d, J=7.3 Hz, 1H), 6.31 (d, J=8.3 Hz, 1H), 5.89 (s, 2H), 5.01 (quin, J=7.2 Hz, 1H), 1.48 (d, J=7.0 Hz, 3H).

Example 121: N-[(1S)-1-(azetidin-3-yl)-2-hydroxyethyl]-5-[4-(trifluoromethyl)phenyl]naphthalene-2-carboxamide (Compound 130) and tert-butyl 3-[(1S)-2-hydroxy-1-[[5-[4-(trifluoromethyl)phenyl]naphthalene-2-carbonyl] amino]ethyl]azetidine-1-carboxylate (Compound 134)

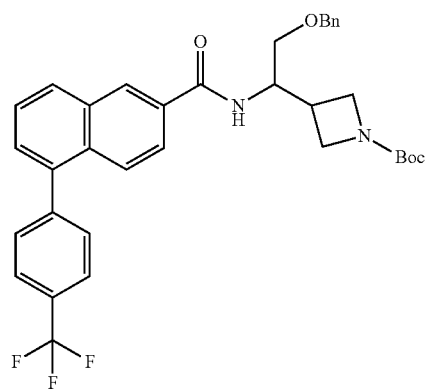

121-6a

SFC

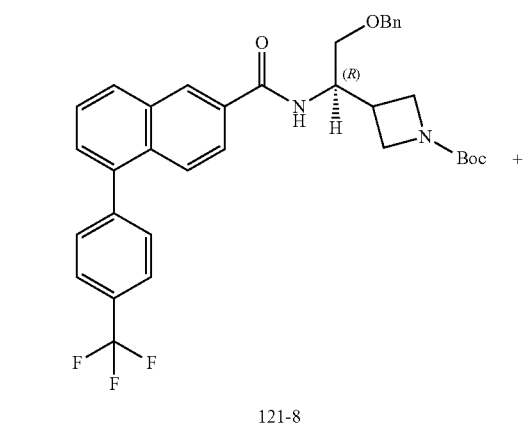

121-8

+

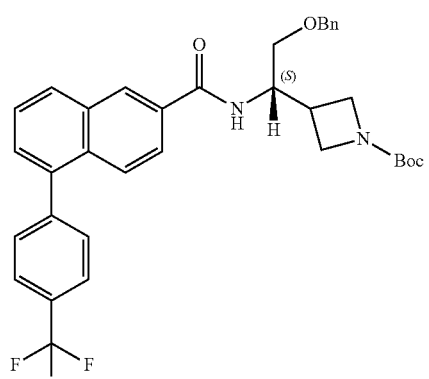

121-9

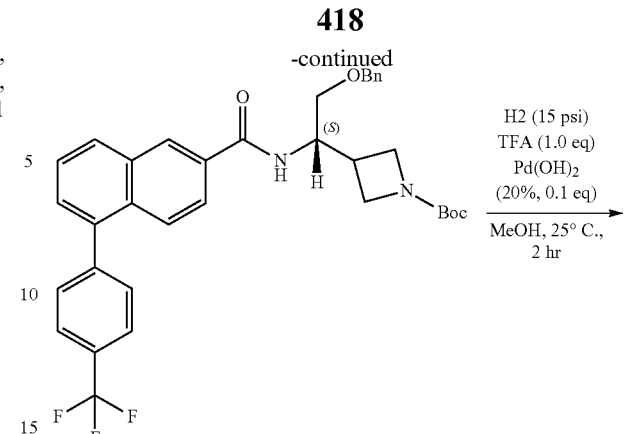

121-9

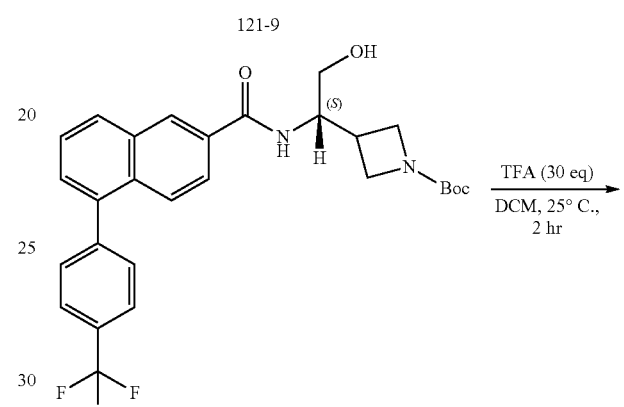

Compound 134

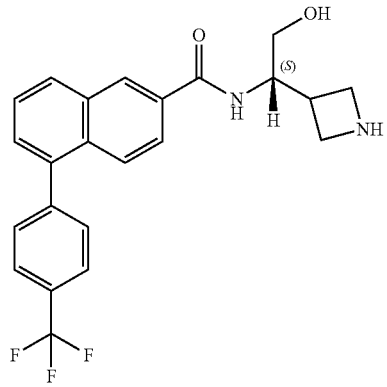

Compound 130

Tert-Butyl 3-[(1R)-2-benzyloxy-1-[[5-[4-(trifluoromethyl)phenyl]naphthalene-2-carbonyl]amino]ethyl]azetidine-1-carboxylate and tert-butyl 3-[(1S)-2-benzyloxy-1-[[5-[4-(trifluoromethyl)phenyl]naphthalene-2-carbonyl] amino]ethyl]azetidine-1-carboxylate The separated method of compound 121-6a (150 mg, 0.24 mmol, 1 eq) was developed by SFC. The product was checked by LCMS. The racemate was separated by chiral SFC (column: DAICEL CHIRALCEL OD-H (250 mm*30 mm, 5 um); mobile phase: [0.1% NH$_3$H$_2$O ETOH]; B %: 25%-25%, min). Compound 121-8 (65 mg, 0.10 mmol, 42.4% yield) was obtained as colorless oil. Compound 121-9 (65 mg, 0.10 mmol, 42.9% yield) was obtained as colorless oil.

Tert-Butyl 3-[(1S)-2-hydroxy-1-[[5-[4-(trifluoromethyl)phenyl]naphthalene-2-carbonyl]amino]ethyl]azetidine-1-carboxylate (Compound 134)

To a solution of compound 121-9 (65 mg, 0.10 mmol, 1 eq) in MeOH (2 mL) were added Pd(OH)$_2$ (7.5 mg, 10.7 umol, 20%, 0.1 eq) and TFA (12.2 mg, 0.10 mmol, 8 uL, 1 eq). The mixture was degassed and purged with H$_2$ for 3 times and stirred at 25° C. for 2 hr under H$_2$ atmosphere (15 psi). The reaction mixture was filtered and the filtrate was concentrated in vacuum. The crude product was purified by prep-TLC (PE/EA=1/2). The desired compound (43 mg, 82.7 umol, 76.9% yield) was obtained as a white solid. LCMS (ESI): RT=0.982 min, mass calcd. For C$_{28}$H$_{29}$F$_3$N$_2$O$_4$, 514.21 m/z found 515.3 [M+H]$^+$. $^1$H NMR (400 MHz, CDCl$_3$) δ 8.37 (d, J=1.3 Hz, 1H), 7.99 (d, J=8.3 Hz, 1H), 7.90-7.85 (m, 1H), 7.83-7.75 (m, 3H), 7.65-7.58 (m, 3H), 7.52 (dd, J=0.9, 6.9 Hz, 1H), 6.71 (br d, J=8.5 Hz, 1H), 4.49 (td, J=4.3, 8.4 Hz, 1H), 4.06 (td, J=8.6, 11.2 Hz, 2H), 3.93 (dd, J=5.8, 8.8 Hz, 1H), 3.88-3.74 (m, 3H), 3.05-2.88 (m, 1H), 2.52-2.30 (m, 1H), 1.43 (s, 9H).

N-[(1S)-1-(azetidin-3-yl)-2-hydroxy-ethyl]-5-[4-(trifluoromethyl)phenyl]naphthalene-2-carboxamide (Compound 130)

To a solution of Compound 134 (35 mg, 68.0 umol, 1 eq) in DCM (2 mL) was added TFA (232.6 mg, 2.04 mmol, 0.15 mL, 30 eq). The mixture was stirred at 25° C. for 2 hr. The reaction mixture was concentrated in vacuum. The residue was quenched with saturated aq.NaHCO$_3$ (5 mL), extracted with EA (10 mL*3). The combined organic phase was washed with H$_2$O (5 mL), brine (5 mL) and dried over Na$_2$SO$_4$, filtered and concentrated in vacuum. The crude product was checked by LCMS, HPLC and purified by prep-HPLC. Compound 130 (4.0 mg, 8.8 umol, 13.0% yield, HCl) was obtained as colorless oil. LCMS (ESI): RT=0.748 min, mass calcd. For C$_{23}$H$_{21}$F$_3$N$_2$O$_2$, 414.16 m/z found 415.0 [M+H]$^+$. $^1$H NMR (400 MHz, CD$_3$OD) δ 8.57 (d, J=1.3 Hz, 1H), 8.11 (d, J=8.0 Hz, 1H), 7.96-7.83 (m, 4H), 7.76-7.66 (m, 3H), 7.63-7.57 (m, 1H), 4.53 (td, J=5.5, 8.7 Hz, 1H), 4.22-4.08 (m, 4H), 3.79-3.63 (m, 2H), 3.46-3.35 (m, 1H).

Example 122: N-[(1R)-1-(azetidin-3-yl)-2-hydroxy-ethyl]-5-[4-(trifluoromethyl)phenyl]naphthalene-2-carboxamide (Compound 131), N-[(3R)-4-(aminomethyl)tetrahydrofuran-3-yl]-5-[4-(trifluoromethyl)phenyl]naphthalene-2-carboxamide (Compound 132), and tert-butyl 3-[(1R)-2-hydroxy-1-[[5-[4-(trifluoromethyl)phenyl]naphthalene-2-carbonyl] amino]ethyl]azetidine-1-carboxylate (Compound 135)

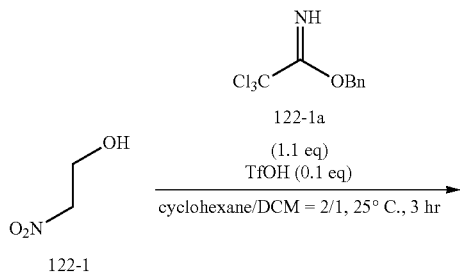

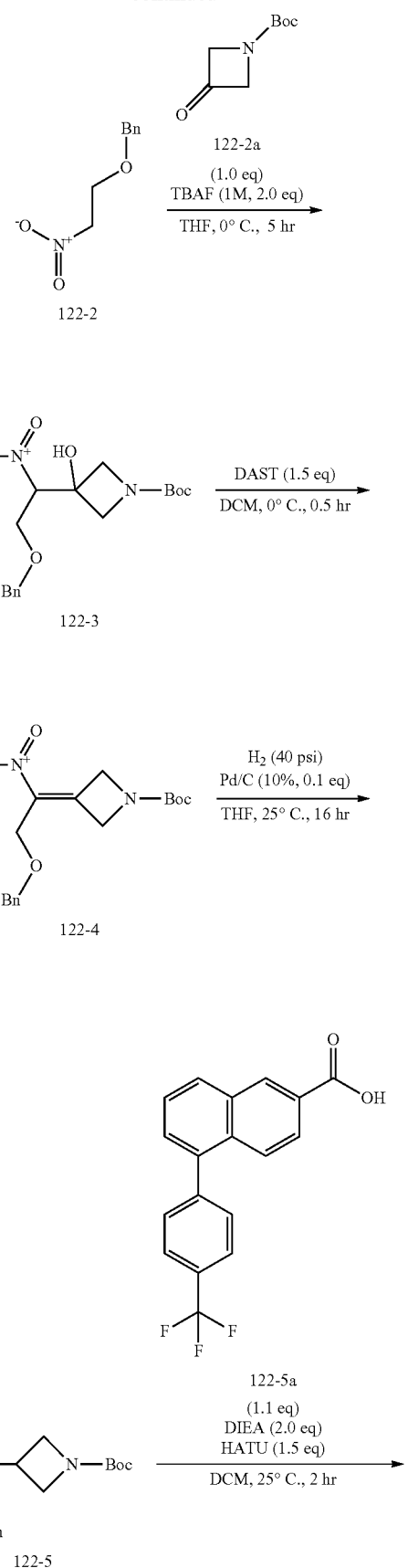

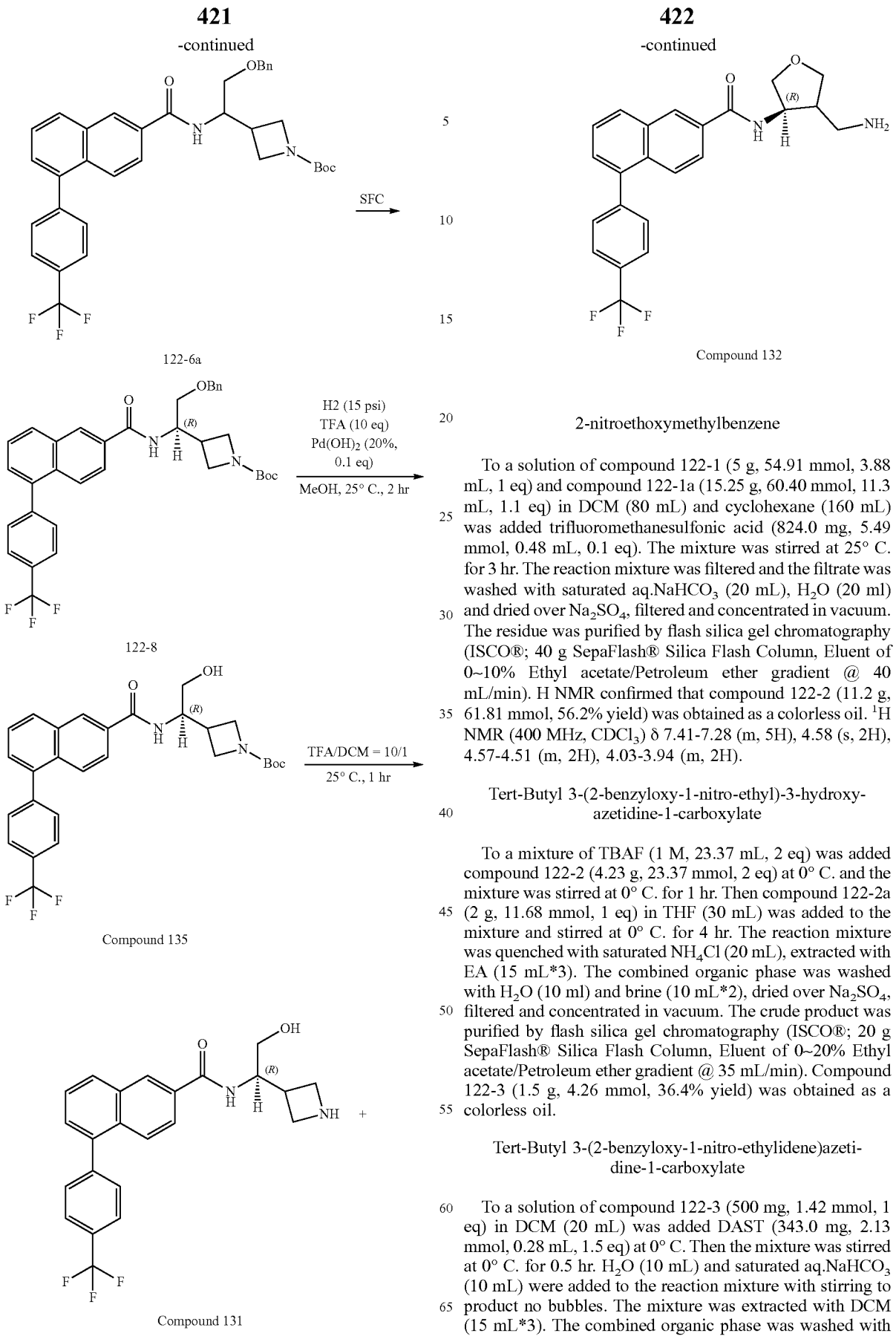

2-nitroethoxymethylbenzene

To a solution of compound 122-1 (5 g, 54.91 mmol, 3.88 mL, 1 eq) and compound 122-1a (15.25 g, 60.40 mmol, 11.3 mL, 1.1 eq) in DCM (80 mL) and cyclohexane (160 mL) was added trifluoromethanesulfonic acid (824.0 mg, 5.49 mmol, 0.48 mL, 0.1 eq). The mixture was stirred at 25° C. for 3 hr. The reaction mixture was filtered and the filtrate was washed with saturated aq.NaHCO$_3$ (20 mL), H$_2$O (20 ml) and dried over Na$_2$SO$_4$, filtered and concentrated in vacuum. The residue was purified by flash silica gel chromatography (ISCO®; 40 g SepaFlash® Silica Flash Column, Eluent of 0~10% Ethyl acetate/Petroleum ether gradient @ 40 mL/min). H NMR confirmed that compound 122-2 (11.2 g, 61.81 mmol, 56.2% yield) was obtained as a colorless oil. $^1$H NMR (400 MHz, CDCl$_3$) δ 7.41-7.28 (m, 5H), 4.58 (s, 2H), 4.57-4.51 (m, 2H), 4.03-3.94 (m, 2H).

Tert-Butyl 3-(2-benzyloxy-1-nitro-ethyl)-3-hydroxy-azetidine-1-carboxylate

To a mixture of TBAF (1 M, 23.37 mL, 2 eq) was added compound 122-2 (4.23 g, 23.37 mmol, 2 eq) at 0° C. and the mixture was stirred at 0° C. for 1 hr. Then compound 122-2a (2 g, 11.68 mmol, 1 eq) in THF (30 mL) was added to the mixture and stirred at 0° C. for 4 hr. The reaction mixture was quenched with saturated NH$_4$Cl (20 mL), extracted with EA (15 mL*3). The combined organic phase was washed with H$_2$O (10 ml) and brine (10 mL*2), dried over Na$_2$SO$_4$, filtered and concentrated in vacuum. The crude product was purified by flash silica gel chromatography (ISCO®; 20 g SepaFlash® Silica Flash Column, Eluent of 0~20% Ethyl acetate/Petroleum ether gradient @ 35 mL/min). Compound 122-3 (1.5 g, 4.26 mmol, 36.4% yield) was obtained as a colorless oil.

Tert-Butyl 3-(2-benzyloxy-1-nitro-ethylidene)azetidine-1-carboxylate

To a solution of compound 122-3 (500 mg, 1.42 mmol, 1 eq) in DCM (20 mL) was added DAST (343.0 mg, 2.13 mmol, 0.28 mL, 1.5 eq) at 0° C. Then the mixture was stirred at 0° C. for 0.5 hr. H$_2$O (10 mL) and saturated aq.NaHCO$_3$ (10 mL) were added to the reaction mixture with stirring to product no bubbles. The mixture was extracted with DCM (15 mL*3). The combined organic phase was washed with H$_2$O (10 mL), brine (10 mL) and dried over Na$_2$SO$_4$, filtered and concentrated in vacuum. The residue was purified by flash silica gel chromatography. Compound 122-4 (815 mg, 2.44 mmol, 85.8% yield) was obtained as a yellow oil.

Tert-Butyl 3-(1-amino-2-benzyloxy-ethyl)azetidine-1-carboxylate

To a solution of compound 122-4 (800 mg, 2.39 mmol, 1 eq) in THF (5 mL) was added Pd/C (381.9 mg, 0.36 mmol, 10%, 0.1 eq). The mixture was degassed and purged with $H_2$ for 3 times and stirred at 25° C. for 16 hr under $H_2$ atmosphere (40 psi). The reaction mixture was filtered and the filtrate was concentrated in vacuum. The crude product was used for the next step directly. Compound 122-5 (610 mg, crude) was obtained as a yellow oil.

Tert-Butyl 3-[2-benzyloxy-1-[[5-[4-(trifluoromethyl)phenyl]naphthalene-2-carbonyl]amino]ethyl]azetidine-1-carboxylate To a solution of compound 122-5a (227.0 mg, 0.72 mmol, 1.1 eq) in DCM (3 mL) were added HATU (409.5 mg, 1.08 mmol, 1.5 eq), mixture of compound 122-5 (220 mg, 0.72 mmol, 1 eq) and DIEA (185.5 mg, 1.44 mmol, 0.25 mL, 2 eq). The mixture was stirred at 25° C. for 2 hr. The reaction mixture was concentrated in vacuum. Then the residue was diluted with EA (15 mL*3) washed with $H_2O$ (10 ml) and brine (10 mL*2), dried over $Na_2SO_4$, filtered and concentrated in vacuum. The residue was purified by flash silica gel. Then the crude product was purified by perp-HPLC (column: Welch Xtimate C18 150*25 mm*5 um; mobile phase: [water (0.05% HCl)-ACN]; B %: 65%-95%, 8.5 min). Compound 122-6a (110 mg, 0.17 mmol, 24.8% yield) was obtained as a white solid. $^1$H NMR (400 MHz, $CDCl_3$) δ 8.34 (s, 1H), 8.00 (d, J=8.1 Hz, 1H), 7.88 (d, J=8.9 Hz, 1H), 7.82-7.75 (m, 3H), 7.67-7.59 (m, 3H), 7.52 (d, J=6.8 Hz, 1H), 7.40-7.29 (m, 5H), 6.67 (br d, J=9.0 Hz, 1H), 4.67-4.59 (m, 1H), 4.59-4.48 (m, 2H), 4.06-3.90 (m, 3H), 3.80-3.71 (m, 1H), 3.67-3.58 (m, 2H), 3.07-2.94 (m, 1H), 1.42 (s, 9H).

Tert-Butyl 3-[(1R)-2-benzyloxy-1-[[5-[4-(trifluoromethyl)phenyl]naphthalene-2-carbonyl]amino]ethyl]azetidine-1-carboxylate The separated method of compound 122-6a (150 mg, 0.24 mmol, 1 eq) was developed by SFC. The product was checked by LCMS. The racemate was separated by chiral SFC (column: DAICEL CHIRALCEL OD-H (250 mm*30 mm, 5 um); mobile phase: [0.1% $NH_3H_2O$ ETOH]; B %: 25%-25%, min). Compound 122-8 (65 mg, 0.10 mmol, 42.4% yield) was obtained as colorless oil.

Tert-Butyl 3-[(1R)-2-hydroxy-1-[[5-[4-(trifluoromethyl)phenyl]naphthalene-2-carbonyl]amino]ethyl]azetidine-1-carboxylate (Compound 135)

To a solution of compound 122-8 (65 mg, 0.10 mmol, 1 eq) in MeOH (2 mL) was added $Pd(OH)_2$ (7.5 mg, 10 umol, 20%, 0.1 eq) and TFA (122.5 mg, 1.07 mmol, 79 uL, 10 eq). The mixture was degassed and purged with Eh for 3 times and stirred at 25° C. for 2 hr under Eh atmosphere (15 psi). The reaction mixture was filtered and the filtrate was concentrated in vacuum. The crude product was purified by prep-TLC (PE/EA=1/2). LCMS and H NMR confirmed that Compound 135 (42 mg, 81.6 umol, 75.9% yield) was obtained as a white solid. LCMS (ESI): RT=0.927 min, mass calcd. For $C_{28}H_{29}F_3N_2O_4$, 514.21 m/z found 515.1 [M+H]$^+$. $^1$H NMR (400 MHz, $CDCl_3$) δ 8.37 (s, 1H), 7.99 (d, J=8.3 Hz, 1H), 7.91-7.85 (m, 1H), 7.84-7.76 (m, 3H), 7.67-7.59 (m, 3H), 7.52 (d, J=7.0 Hz, 1H), 6.67 (br d, J=8.4 Hz, 1H), 4.56-4.44 (m, 1H), 4.07 (td, J=8.7, 11.3 Hz, 2H), 3.93 (dd, J=5.7, 8.8 Hz, 1H), 3.87-3.75 (m, 3H), 3.05-2.92 (m, 1H), 2.33 (br s, 1H), 1.43 (s, 9H).

N-[(1R)-1-(azetidin-3-yl)-2-hydroxy-ethyl]-5-[4-(trifluoromethyl)phenyl]naphthalene-2-carboxamide (Compound 131) and N-[(3R)-4-(aminomethyl) tetrahydrofuran-3-yl]-5-[4-(trifluoromethyl)phenyl] naphthalene-2-carboxamide (Compound 132)

To a solution of Compound 135 (30 mg, 58.3 umol, 1 eq) in DCM (2.5 mL) was added TFA (385 mg, 3.38 mmol, 0.25 mL). The mixture was stirred at 25° C. for 1 hr. The reaction mixture was concentrated in vacuum. The residue was adjusted pH=8 with saturated aq.$NaHCO_3$, extracted with EA (15 mL*3). The combined organic phase was washed with $H_2O$ (10 mL), brine (10 mL) and dried over $Na_2SO_4$, filtered and concentrated in vacuum. The crude product was checked by LCMS, HPLC and purified by prep-HPLC (column: Welch Xtimate C18 150*25 mm*5 um; mobile phase: [water (0.05% HCl)-ACN]; B %: 20%-50%, 8.5 min). Compound 132 (6.6 mg, 14.1 umol, 24.2% yield, HCl) was obtained as colorless oil. LCMS (ESI): RT=0.724 min, mass calcd. For $C_{23}H_{21}F_3N_2O_2$, 414.16 m/z found 415.1 [M+H]$^+$. $^1$H NMR (400 MHz, $CD_3OD$) δ 8.47 (d, J=1.8 Hz, 1H), 8.15 (d, J=8.3 Hz, 1H), 8.00 (d, J=9.0 Hz, 1H), 7.87 (d, J=8.0 Hz, 2H), 7.80-7.72 (m, 2H), 7.72-7.67 (m, 3H), 3.98-3.92 (m, 1H), 3.91-3.85 (m, 2H), 3.85-3.74 (m, 2H), 3.74-3.61 (m, 2H), 2.57-2.45 (m, 1H). $^{13}$C NMR (101 MHz, $CD_3OD$) δ 160.80, 143.68, 138.90, 132.99, 132.94, 130.33, 129.70, 129.28, 129.03, 127.03, 126.57, 126.10, 125.22, 125.18, 123.19, 60.56, 59.27, 52.63, 48.09, 47.88, 47.66, 40.46, 34.16. Compound 131 (2.8 mg, 6.2 umol, 10.7% yield, HCl) was obtained as colorless oil. LCMS (ESI): RT=0.741 min, mass calcd. For $C_{23}H_{21}F_3N_2O_2$, 414.16 m/z found 415.0 [M+H]$^+$. $^1$H NMR (400 MHz, $CD_3OD$) δ 8.54 (d, J=1.5 Hz, 1H), 8.09 (d, J=8.3 Hz, 1H), 7.94-7.81 (m, 4H), 7.72-7.65 (m, 3H), 7.58 (dd, J=0.8, 7.0 Hz, 1H), 4.51 (td, J=5.5, 8.9 Hz, 1H), 4.21-4.07 (m, 4H), 3.77-3.64 (m, 2H), 3.43-3.33 (m, 1H). $^{13}$C NMR (101 MHz, $CD_3OD$) δ 169.23, 138.63, 133.10, 132.52, 131.23, 130.31, 129.24, 128.73, 128.26, 126.17, 125.44, 125.10, 125.06, 124.23, 61.83, 53.22, 49.27, 49.07, 48.24, 47.88, 34.35.

Example 123: (R)—N-(1-(1-(2-hydroxyethyl)azetidin-3-yl)ethyl)-5-(4-(trifluoromethyl)phenyl)-2-naphthamide (Compound 133)

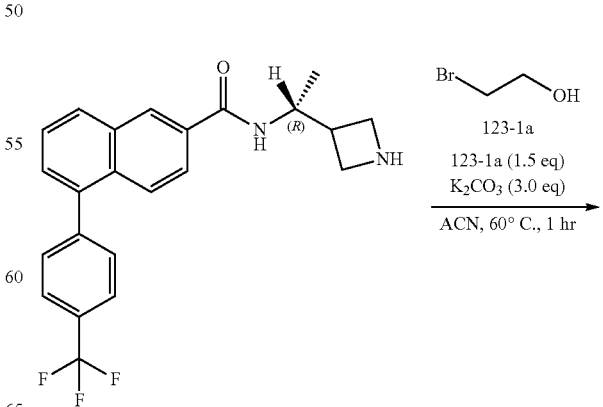

123-1

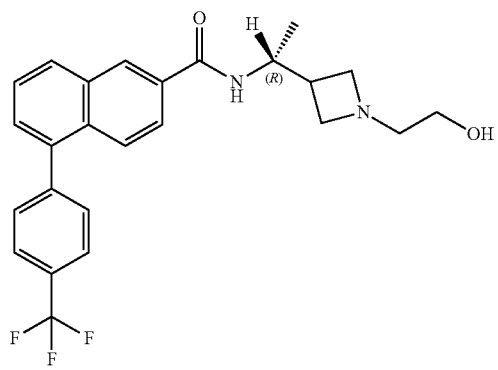

Compound 133

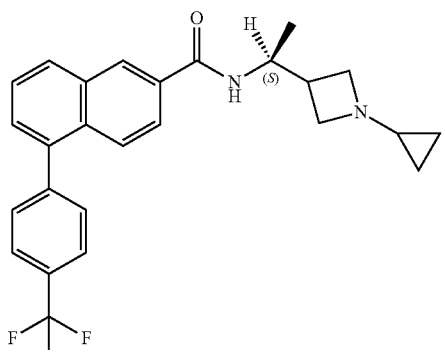

Compound 136

To a solution of 123-1 (50.0 mg, 0.13 mmol, 1.0 eq) and K$_2$CO$_3$ (52.0 mg, 0.38 mmol, 3.0 eq) in ACN (1 mL) was added 123-1a (23.5 mg, 0.19 mmol, 13 uL, 1.5 eq) at 30° C. The reaction was stirred at 60° C. for 1 h. The reaction was concentrated under reduced pressure to give a residue, which was purified by prep-HPLC: (column: Welch Xtimate C18 150*25 mm*5 um; mobile phase: [water (0.05% HCl)-ACN]; B %: 20%-50%, 8.5 min]; B %: 65%-95%, 7.8 min) to give Compound 133 (2.8 mg, 6 umol, 4.8% yield, HCl) as a yellow solid. LCMS (ESI): RT=0.862 min, mass calc. for C$_{25}$H$_{25}$F$_3$N$_2$O$_2$ 442.19, m/z found 443.3 [M+H]$^+$; $^1$H NMR (400 MHz, DMSO-d$_6$) δ 11.01-10.23 (m, 1H), 8.61 (brs, 1H), 8.53 (brd, J=7.4 Hz, 1H), 8.11 (d, J=8.1 Hz, 1H), 7.97 (dd, J=1.8, 8.9 Hz, 1H), 7.89 (d, J=8.1 Hz, 2H), 7.79 (d, J=8.8 Hz, 1H), 7.73-7.67 (m, 3H), 7.57 (dd, J=1.0, 7.0 Hz, 1H), 4.53-4.29 (m, 1H), 4.27-3.95 (m, 4H), 3.88 (brs, 1H), 3.64 (brd, J=4.3 Hz, 2H), 3.07-2.99 (m, 2H), 1.22-1.13 (m, 3H).

Example 124: N-[(1S)-1-(1-cyclopropylazetidin-3-yl)ethyl]-5-[4-(trifluoromethyl)phenyl]naphthalene-2-carboxamide (Compound 136)

To a mixture of 124-1 (60 mg, 0.15 mmol, 1 eq) and 124-1a (19.4 mg, 0.23 mmol, 1.5 eq) in DCM (5 mL) was added Cu(OAc)$_2$ (54.7 mg, 0.30 mmol, 2 eq) and DIPEA (38.9 mg, 0.30 mmol, 52.5 uL, 2 eq) in one portion at 25° C. The suspension was degassed under vacuum and purged with O$_2$ several times. The mixture was stirred under O$_2$ (15 psi) at 25° C. for 18 hrs. The reaction mixture was filtered and the cake was washed with EA (10 mL*2). The filtrate was concentrated in vacuo to give crude product. The crude product was purified by prep-HPLC (column: Waters Xbridge C18 150*50 mm*10 um; mobile phase: [water (0.04% NH3H2O)-ACN]; B %: 54%-84%, 11 min) to afford Compound 136 (5.6 mg, 12.5 umol, 8.3% yield) as a white solid. LCMS (ESI): RT=0.804 min, mass calcd for C$_{26}$H$_{25}$F$_3$N$_2$O 438.19, m/z found 439.3 [M+H]$^+$; $^1$H NMR (400 MHz, DMSO-d$_6$) δ 8.52 (d, J=1.0 Hz, 1H), 8.43 (d, J=8.3 Hz, 1H), 8.11 (d, J=8.3 Hz, 1H), 7.91 (d, J=8.0 Hz, 3H), 7.80 (d, J=8.8 Hz, 1H), 7.77-7.65 (m, 3H), 7.58 (d, J=6.3 Hz, 1H), 4.31-4.14 (m, 1H), 3.32-3.22 (m, 2H), 3.02 (t, J=6.5 Hz, 1H), 2.93 (t, J=6.7 Hz, 1H), 2.48-2.42 (m, 1H), 1.80 (m, 1H), 1.10 (d, J=6.8 Hz, 3H), 0.28 (m, 2H), 0.17 (m, 2H).

Example 125: (R)—N-(1-(1-(2,2-difluoroethyl)azetidin-3-yl)ethyl)-5-(4-(trifluoromethyl)phenyl)-2-naphthamide (Compound 137)

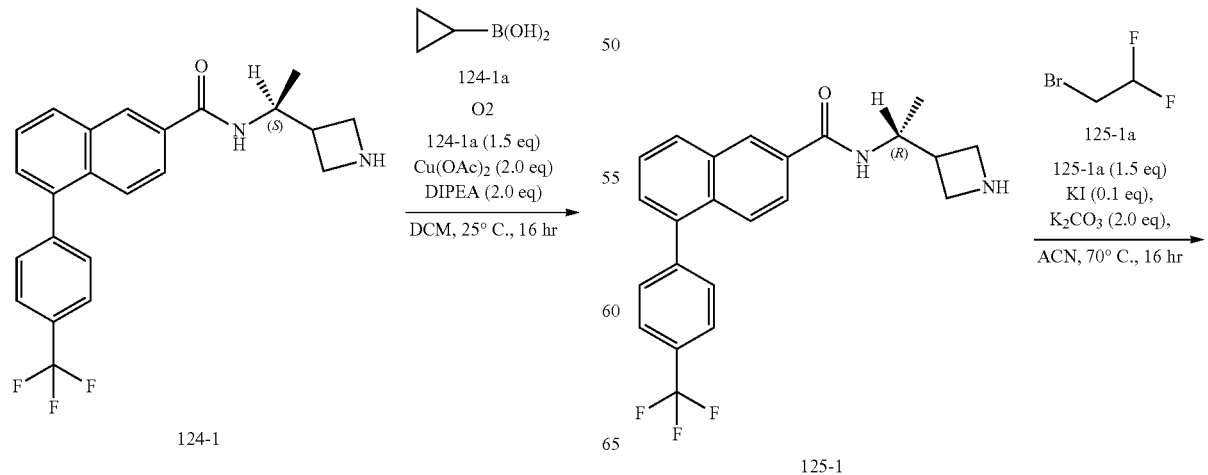

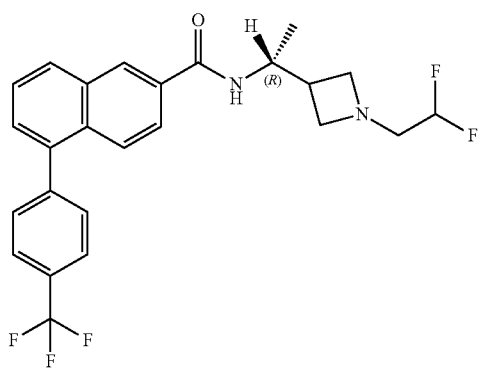

Compound 137

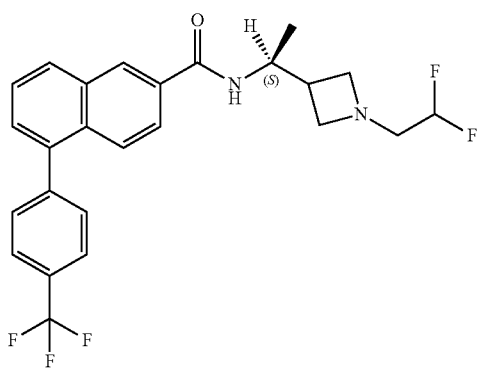

Compound 138

To a solution of 125-1 (50 mg, 0.13 mmol, 1 eq), KI (2.1 mg, 12.6 umol, 0.1 eq) and $K_2CO_3$ (52.0 mg, 0.38 mmol, 3 eq) in ACN (3 mL) at 30° C. was added 125-1a (27.3 mg, 0.19 mmol, 1.5 eq), and the mixture was stirred at 70° C. for 16 h. The reaction mixture was filtered to remove the solid and the filtrate was concentrated under reduced pressure to give a residue. The residue was purified by prep-HPLC (column: Welch Xtimate C18 150*25 mm*5 um; mobile phase: [water (0.04% $NH_3H_2O$+10 mM $NH_4HCO_3$)-ACN]; B %: 58%-88%, 11 min) to give Compound 137 (31.1 mg, 67.4 umol, 53.7% yield) as a white solid. LCMS (ESI): RT=0.783 min, mass calc. for $C_{25}H_{23}F_5N_2O$ 462.17, m/z found 463.1 $[M+H]^+$; $^1$H NMR (400 MHz, DMSO-$d_6$) δ 8.52 (d, J=1.1 Hz, 1H), 8.44 (d, J=8.4 Hz, 1H), 8.12 (d, J=8.3 Hz, 1H), 7.91 (d, J=8.3 Hz, 3H), 7.81 (d, J=8.9 Hz, 1H), 7.73 (d, J=8.0 Hz, 2H), 7.69 (t, J=7.7 Hz, 1H), 7.58 (d, J=6.6 Hz, 1H), 6.11-5.74 (m, 1H), 4.34-4.19 (m, 1H), 3.39 (br d, J=8.0 Hz, 2H), 3.07 (t, J=6.8 Hz, 1H), 2.99 (t, J=6.8 Hz, 1H), 2.76 (dt, J=4.1, 16.1 Hz, 2H), 2.62-2.56 (m, 1H), 1.10 (d, J=6.5 Hz, 3H).

Example 126: N-[(1S)-1-[1-(2,2-difluoroethyl)azetidin-3-yl]ethyl]-5-[4-(trifluoromethyl)phenyl]naphthalene-2-carboxamide (Compound 138)

To a solution of 126-1 (60 mg, 0.15 mmol, 1 eq) in MeCN (3 mL) was added K2CO3 (52.0 mg, 0.38 mmol, 2.5 eq) and 126-1a (32.7 mg, 0.23 mmol, 1.5 eq). The mixture was stirred at 70° C. for 16 hr. The reaction mixture was diluted with $H_2O$ (30 mL) and stirred for 5 min. The aqueous phase was extracted with EA (15 mL*3). The combined organic phase was washed with brine (20 mL), dried with anhydrous $Na_2SO_4$, filtered and concentrated in vacuum. The residue was purified by prep-HPLC (column: Waters Xbridge 150*25 mm*5 um; mobile phase: [water (0.04% NH3H2O)-ACN]; B %: 60%-90%, 7.8 min) to afford Compound 138 (10.6 mg, 22.9 umol, 15.2% yield) as a white solid. LCMS (ESI): RT=0.808 min, mass calcd for $C_{25}H_{23}F_5N_2O$ 462.17, m/z found 463.3 $[M+H]^+$; $^1$H NMR (400 MHz, DMSO-$d_6$) δ 8.52 (d, J=1.5 Hz, 1H), 8.44 (d, J=8.3 Hz, 1H), 8.12 (d, J=8.0 Hz, 1H), 7.91 (d, J=8.5 Hz, 3H), 7.81 (d, J=9.0 Hz, 1H), 7.76-7.66 (m, 3H), 7.58 (dd, J=1.0, 7.0 Hz, 1H), 6.10-5.75 (m, 1H), 4.32-4.20 (m, 1H), 3.44-3.38 (m, 1H), 3.12-2.94 (m, 2H), 2.76 (m, 2H), 2.63-2.55 (m, 1H), 1.10 (d, J=6.8 Hz, 3H).

Example 127: N-[(1S)-1-[1-(2-fluoroethyl)azetidin-3-yl]ethyl]-5-[4-(trifluoromethyl)phenyl]naphthalene-2-carboxamide (Compound 139)

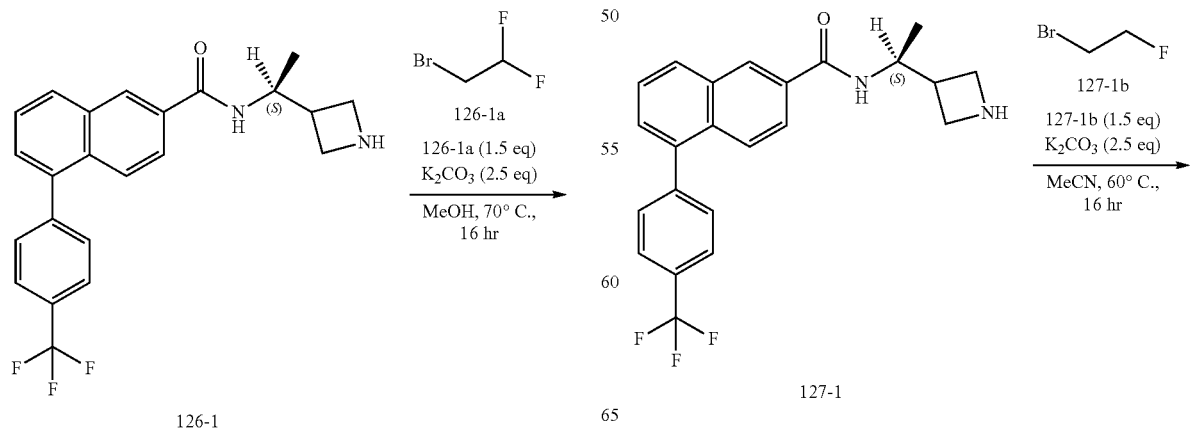

429

-continued

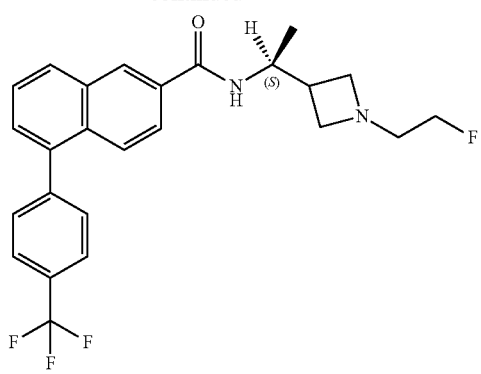

Compound 139

To a solution of 127-1 (60 mg, 0.15 mmol, 1 eq) in MeCN (3 mL) was added $K_2CO_3$ (52.0 mg, 0.38 mmol, 2.5 eq) and 1-bromo-2-fluoro-ethane (28.68 mg, 0.23 mmol, 1.5 eq). The mixture was stirred at 70° C. for 16 hr. The reaction mixture was diluted with $H_2O$ (30 mL) and stirred for 5 min. The aqueous phase was extracted with EA (15 mL*3). The combined organic phase was washed with brine (20 mL), dried with anhydrous $Na_2SO_4$, filtered and concentrated in vacuum. The residue was purified by prep-HPLC (column: Waters Xbridge C18 150*50 mm*10 um; mobile phase: [water (0.04% NH3H2O)-ACN]; B %: 48%-78%, 11 min) to afford Compound 139 (11.2 mg, 24.7 umol, 16.4% yield) as a yellow solid. LCMS (ESI): RT=0.788 min, mass calcd for $C_{25}H_{24}F_4N_2O$ 444.18, m/z found 445.3 $[M+H]^+$; $^1H$ NMR (400 MHz, DMSO-$d_6$) δ 8.53 (d, J=1.1 Hz, 1H), 8.46 (d, J=8.3 Hz, 1H), 8.12 (d, J=8.3 Hz, 1H), 7.96-7.88 (m, 3H), 7.81 (d, J=8.9 Hz, 1H), 7.76-7.66 (m, 3H), 7.58 (d, J=6.4 Hz, 1H), 4.43 (t, J=4.8 Hz, 1H), 4.36-4.21 (m, 2H), 3.35-3.27 (m, 2H), 2.99 (t, J=6.6 Hz, 1H), 2.90 (t, J=6.8 Hz, 1H), 2.66 (t, J=4.8 Hz, 1H), 2.62-2.53 (m, 2H), 1.11 (d, J=6.6 Hz, 3H).

Example 128: N-[(1S)-1-[1-(2-hydroxyethyl)azetidin-3-yl]ethyl]-5-[4-(trifluoromethyl)phenyl]naphthalene-2-carboxamide (Compound 140)

430

-continued

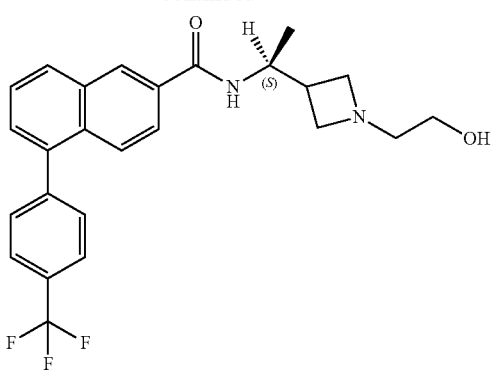

Compound 140

To a solution of 128-1 (60 mg, 0.15 mmol, 1 eq) in DMF (2 mL) was added $K_2CO_3$ (52.0 mg, 0.38 mmol, 2.5 eq) and 2-bromoethanol (28.2 mg, 0.23 mmol, 16.0 uL, 1.5 eq). The mixture was stirred at 25° C. for 16 hr. The reaction mixture was diluted with $H_2O$ (30 mL) and stirred for 5 min. The aqueous phase was extracted with EA (15 mL*3). The combined organic phase was washed with brine (20 mL), dried with anhydrous $Na_2SO_4$, filtered and concentrated in vacuum. The residue was purified by prep-HPLC (column: Welch Xtimate C18 150*25 mm*5 um; mobile phase: [water (0.05% HCl)-ACN]; B %: 25%-55%, 8.5 min) to afford Compound 140 (14.6 mg, 30.5 umol, 20.2% yield, HCl) as a white solid. LCMS (ESI): RT=0.783 min, mass calcd for $C_{25}H_{25}F_3N_2O_2$ 442.19, m/z found 443.2 $[M+H]^+$; $^1H$ NMR (400 MHz, DMSO-$d_6$) δ 8.60 (s, 1H), 8.49 (d, J=8.0 Hz, 1H), 8.11 (d, J=8.3 Hz, 1H), 8.00-7.85 (m, 3H), 7.80 (d, J=8.8 Hz, 1H), 7.75-7.65 (m, 3H), 7.58 (d, J=7.3 Hz, 1H), 4.36 (m, 1H), 4.26-3.75 (m, 4H), 3.64 (s, 2H), 3.38-3.19 (m, 3H), 1.17 (d, J=6.0 Hz, 1H), 1.23-1.10 (m, 1H), 1.23-1.10 (m, 1H).

Example 129: (R)—N-(1-(3-hydroxyazetidin-3-yl)ethyl)-8-(4-(trifluoromethyl)phenyl)quinoline-3-carboxamide (Compound 141)

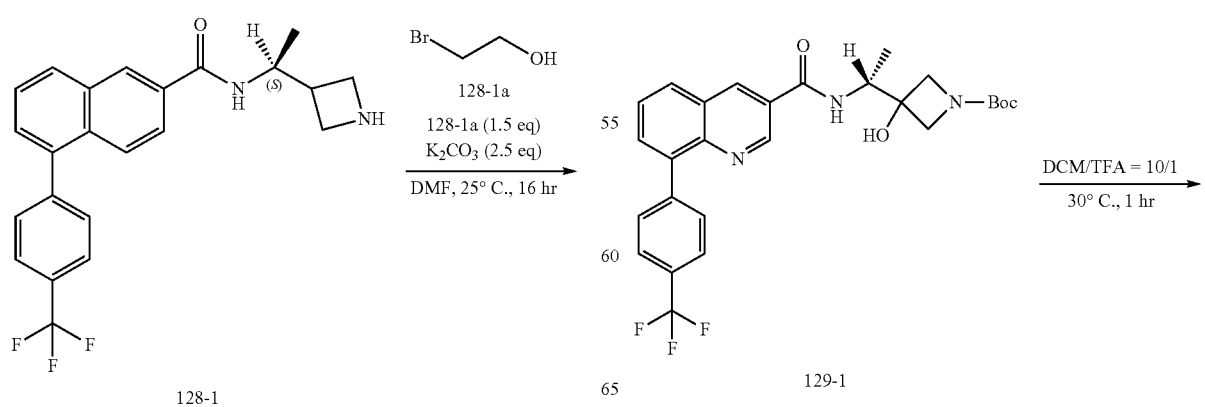

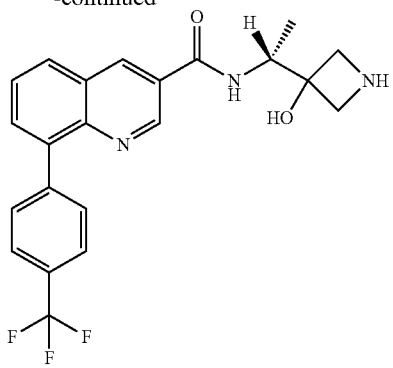

Compound 141

To a solution of 129-1 in DCM (1 mL) at 30° C. was added TFA (154.0 mg, 1.4 mmol, 0.1 mL, 12.2 eq). The mixture was stirred at 30° C. for 1 h. The reaction mixture was concentrated under reduced pressure to give a residue, which was basified with $NH_3 \cdot H_2O$ to pH=9 and concentrated under reduced pressure to give a residue, which was purified by prep-HPLC (column: Waters Xbridge C18 150*50 mm*10 um; mobile phase: [water (0.04% $NH_3H_2O+10$ mM $NH_4HCO_3$)-ACN]; B %: 33%-63%, 11 min) to give Compound 141 (14.9 mg, 35 umol, 32.0% yield) as a white solid. LCMS (ESI): RT=0.825 min, mass calc. for $C_{22}H_{20}F_3N_3O_2$ 415.15, m/z found 416.2 [M+H]$^+$; $^1$H NMR (400 MHz, DMSO-d6) δ 9.25 (d, J=2.0 Hz, 1H), 8.93 (d, J=1.9 Hz, 1H), 8.48 (brd, J=8.8 Hz, 1H), 8.18 (d, J=7.8 Hz, 1H), 7.95-7.89 (m, 2H), 7.87 (d, J=8.6 Hz, 4H), 7.82-7.78 (m, 1H), 5.59 (brs, 1H), 4.49-4.40 (m, 1H), 3.44 (brs, 2H), 3.32 (brs, 2H), 1.16 (d, J=6.8 Hz, 3H).

Example 130: N-[(1R)-1-(1-isopropylazetidin-3-yl) ethyl]-5-[4-(trifluoromethyl)phenyl]naphthalene-2-carboxamide (Compound 142) and N-[(1S)-1-(1-isopropylazetidin-3-yl)ethyl]-5-[4-(trifluoromethyl) phenyl]naphthalene-2-carboxamide (Compound 143)

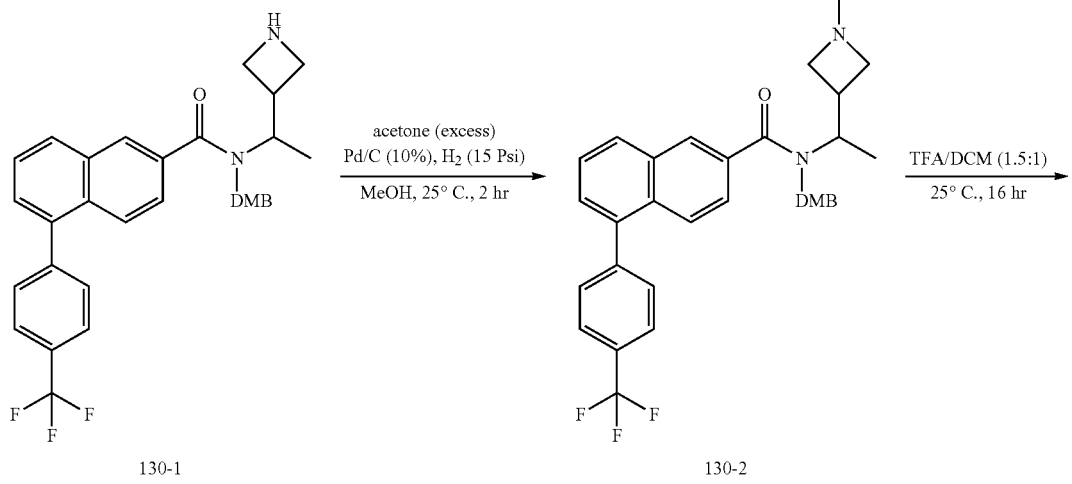

130-1      130-2

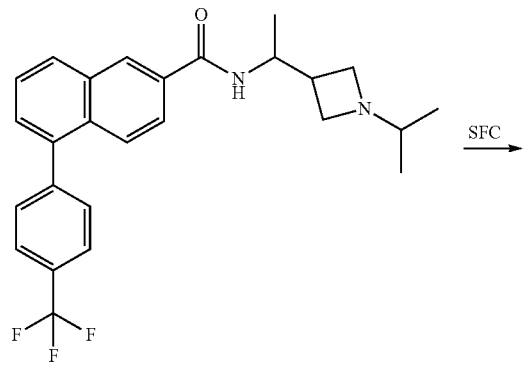

130-3

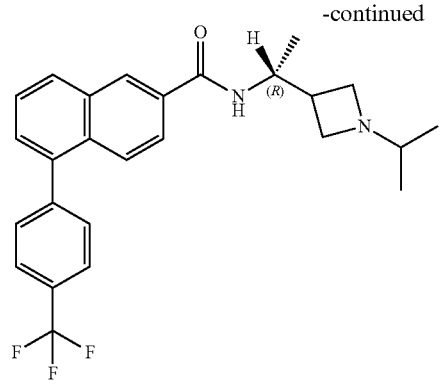

Compound 142

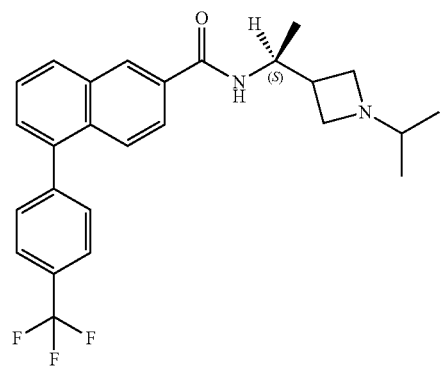

Compound 143

N-[(2,4-Dimethoxyphenyl)methyl]-N-[1-(1-isopropylazetidin-3-yl)ethyl]-5-[4-(trifluoromethyl)phenyl]naphthalene-2-carboxamide To a solution of 130-1 (200 mg, 0.36 mmol, 1 eq) in MeOH (15 mL) was added acetone (264.2 mg, 4.55 mmol, 0.33 mL, 12.4 eq) and Pd/C (150 mg, 10%). The suspension was degassed under vacuum and purged with $H_2$ several times. The mixture was stirred under $H_2$ (15 psi) at 25° C. for 2 hrs. The reaction mixture was filtered and concentrated under reduced pressure to give a residue. The crude product was used into the next step without further purification. Compound 130-2 (200 mg, 0.33 mmol, 92.8% yield) was obtained as a white solid. LCMS (ESI): RT=0.969 min, mass calcd for $C_{35}H_{37}F_3N_2O_3$ 590.28 m/z found 591.2 [M+H]$^+$.

N-[1-(1-Isopropylazetidin-3-yl)ethyl]-5-[4-(trifluoromethyl)phenyl]naphthalene-2-carboxamide To a solution of 130-2 (260 mg, 0.44 mmol, 1 eq) in DCM (2 mL) was added TFA (7.8 g, 68.5 mmol, 5.0 mL, 155.7 eq). The mixture was stirred at 25° C. for 16 hr. The reaction mixture was concentrated under reduced pressure to give a residue. The residue was purified by prep-HPLC (column: Welch Xtimate C18 150*25 mm*5 um; mobile phase: [water (0.05% HCl)-ACN]; B %: 40%-70%, 5 min) to give 130-3 (90 mg, 0.20 mmol, 46.4% yield) as a white solid. LCMS (ESI): RT=0.881 min, mass calcd for $C_{26}H_{27}F_3N_2O$, 440.21 m/z found 441.1[M+H]$^+$.

N-[(1R)-1-(1-isopropylazetidin-3-yl)ethyl]-5-[4-(trifluoromethyl)phenyl]naphthalene-2-carboxamide (Compound 142) and N-[(1S)-1-(1-isopropylazetidin-3-yl)ethyl]-5-[4-(trifluoromethyl)phenyl]naphthalene-2-carboxamide (Compound 143)

130-3 (90 mg) was purified by prep-SFC (column: DAICEL CHIRALPAK AS (250 mm*30 mm, 10 um); mobile phase: [0.1% NH$_3$H$_2$O IPA]; B %: 20%-20%, min) to give Compound 143 (14.5 mg, 32.7 umol, 16.0% yield) and Compound 142 (17.2 mg, 38.7 umol, 18.9% yield) as two white solids. Compound 143 LCMS (ESI): RT=0.883 min, mass calcd for $C_{26}H_{27}F_3N_2O$ 440.21 m/z found 441.1[M+H]$^+$. $^1$H NMR (400 MHz, CD$_3$OD) δ 8.50-8.40 (m, 1H), 8.06 (d, J=8.3 Hz, 1H), 7.88-7.80 (m, 4H), 7.69-7.63 (m, 3H), 7.55 (dd, J=1.0, 7.1 Hz, 1H), 4.38-4.21 (m, 1H), 3.57-3.46 (m, 2H), 3.07 (t, J=7.8 Hz, 1H), 2.95 (t, J=7.8 Hz, 1H), 2.72-2.58 (m, 1H), 2.43 (spt, J=6.2 Hz, 1H), 1.22-1.18 (m, 3H), 0.95 (dd, J=4.0, 6.3 Hz, 6H). Compound 142 LCMS (ESI): RT=0.883 min, mass calcd for $C_{26}H_{27}F_3N_2O$ 440.21 m/z found 441.1[M+H]$^+$. $^1$H NMR (400 MHz, CD$_3$OD) δ 8.48 (s, 1H), 8.07 (d, J=8.3 Hz, 1H), 7.90-7.80 (m, 4H), 7.70-7.64 (m, 3H), 7.56 (dd, J=1.0, 7.1 Hz, 1H), 4.47-4.34 (m, 1H), 3.97-3.82 (m, 2H), 3.63 (br t, J=8.4 Hz, 1H), 3.51 (br t, J=8.5 Hz, 1H), 2.97 (td, J=6.3, 12.6 Hz, 1H), 2.85 (sxt, J=8.3 Hz, 1H), 1.25 (d, 6.8 Hz, 3H), 1.11 (dd, J=1.3, 6.4 Hz, 6H).

Example 131: (R)—N-(1-(1-(2-fluoroethyl)azetidin-3-yl)ethyl)-5-(4-(trifluoromethyl)phenyl)-2-naphthamide (Compound 144)

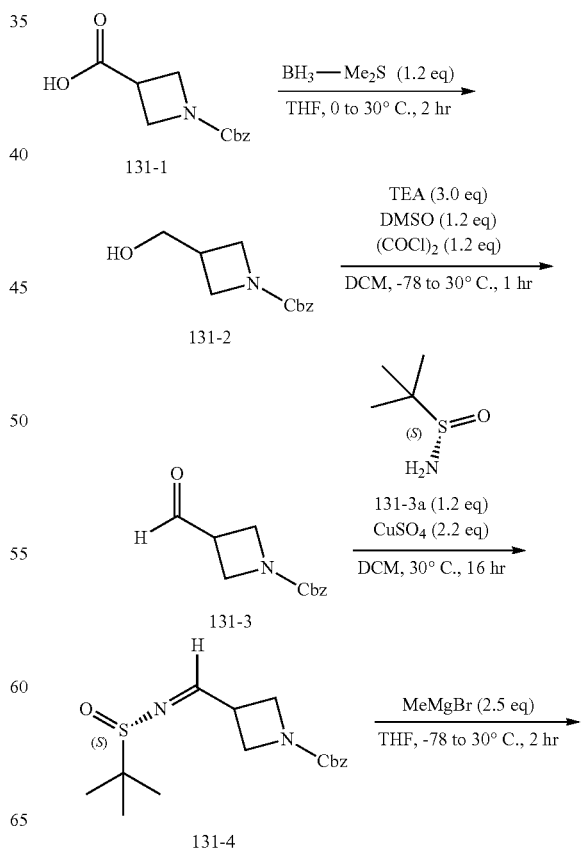

435

-continued

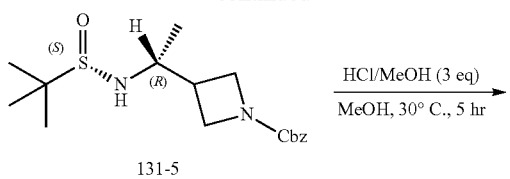
131-5

HCl/MeOH (3 eq)
MeOH, 30° C., 5 hr
→

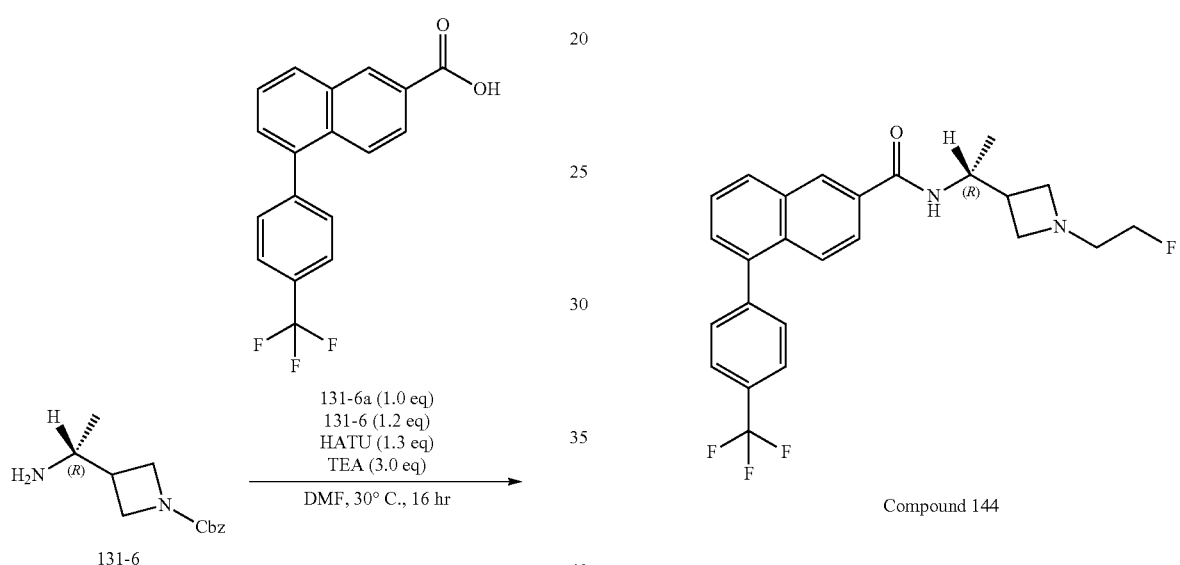

436

-continued

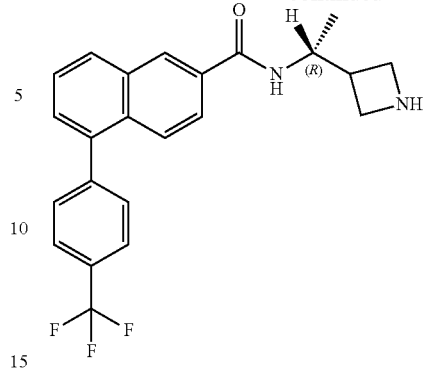
131-8

131-8a (1.5 eq)
K₂CO₃ (3 eq)
ACN, 70° C., 16 h
→

Compound 144

Benzyl 3-(hydroxymethyl)azetidine-1-carboxylate

To a solution of 131-1 (5 g, 21.26 mmol, 1 eq) in THF (50 mL) at 0° C. was added BH₃-Me₂S (10 M, 2.55 mL, 1.2 eq) drop-wise, and the mixture was stirred at 30° C. for 2 h. The mixture was quenched at 0° C. with saturated NH₄Cl (50 mL) and then combined with that of page ES8223-963. The combined mixture was diluted with water (100 mL) and extracted with EA (100 mL*3). The combined organic layers were washed with brine (100 mL), dried over anhydrous Na₂SO₄, filtered and concentrated under reduced pressure to give a residue. The residue was purified by flash silica gel chromatography (ISCO®; 80 g SepaFlash® Silica Flash Column, Eluent of 0~100% Ethyl acetate/Petroleum ether gradient @ 60 mL/min) to give 131-2 (8.5 g, 38.42 mmol, 90.7% yield) as colorless oil. ¹H NMR (400 MHz, CDCl₃) δ 7.41-7.29 (m, 5H), 5.10 (s, 2H), 4.08 (t, J=8.6 Hz, 2H), 3.84-3.72 (m, 4H), 2.82-2.69 (m, 1H), 1.81 (br s, 1H).

Benzyl 3-formylazetidine-1-carboxylate

To a solution of (COCl)₂ (1.38 g, 10.85 mmol, 0.95 mL, 1.2 eq) in DCM (40 mL) at −78° C. was added DMSO (847.5 mg, 10.85 mmol, 0.85 mL, 1.2 eq) drop-wise, and the mixture was stirred at −78° C. for 0.5 h. And then 131-2 (2 g, 9.04 mmol, 1 eq) in DCM (10 mL) and TEA (2.74 g, 27.12 mmol, 3.77 mL, 3 eq) successively was added into the above

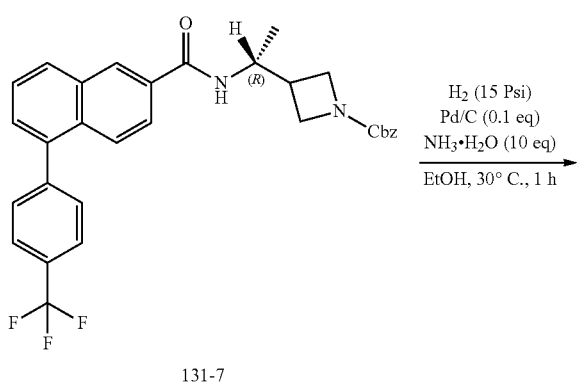
131-7

H₂ (15 Psi)
Pd/C (0.1 eq)
NH₃·H₂O (10 eq)
EtOH, 30° C., 1 h
→ mixture at −78° C. The resulting mixture was stirred at 30° C. for 0.5 h. The mixture was poured into water (100 mL) at 0° C. slowly and then extracted with EA (100 mL*3). The combined organic layers were washed with brine (100 mL), dried over anhydrous $Na_2SO_4$, filtered and concentrated under reduced pressure to give 131-3 (3.96 g, 18.06 mmol, 100.00% yield) as yellow oil, which was used directly for next step.

(S)-benzyl 3-(((tert-butylsulfinyl)imino)methyl)azetidine-1-carboxylate

To a solution of 131-3 (1.98 g, 9.03 mmol, 1 eq) and 131-3a (1.31 g, 10.84 mmol, 1.2 eq) in DCM (100 mL) at 30° C. was added $CuSO_4$ (3.17 g, 19.87 mmol, 3.05 mL, 2.2 eq) drop-wise, and the mixture was stirred at 30° C. for 16 h. The mixture was filtered by celite to remove the solid. The filtrate was concentrated to give a residue. The residue was purified by flash silica gel chromatography (ISCO®; 40 g SepaFlash® Silica Flash Column, Eluent of 0~50% Ethyl acetate/Petroleum ether gradient @ 40 mL/min) to give 131-4 (4.8 g, 14.89 mmol, 82.4% yield) as colorless oil.

Benzyl 3-((R)-1-((S)-1,1-dimethylethylsulfinamido)ethyl)azetidine-1-carboxylate To a solution of 131-4 (2.4 g, 7.44 mmol, 1 eq) in DCM (30 mL) at −78° C. was added MeMgBr (3 M, 6.20 mL, 2.5 eq) drop-wise, and the mixture was stirred at −78° C. for 0.5 h and then at 30° C. for another 1.5 h. The mixture was quenched with saturated NH4Cl solution (10 mL) at 0° C., then diluted with water (40 mL) and then extracted with EA (50 mL*3). The combined organic layers were washed with brine (40 mL), dried over anhydrous $Na_2SO_4$, filtered and concentrated under reduced pressure to give a residue. The residue was purified by flash silica gel chromatography (ISCO®; 20 g SepaFlash® Silica Flash Column, Eluent of 0~100% Ethyl acetate/Petroleum ether gradient @35 mL/min) to give 2.4 g of desired product as isomer mixture. The 2.4 g of desired product was purified further by prep-HPLC (column: YMC-Triart Prep C18 150*40 mm*7 um; mobile phase: [water (0.04% $NH_3H_2O$+10 mM $NH_4HCO_3$)-ACN]; B %: 43%-43%, 10 min) to give 131-5 (1.7 g, 4.72 mmol, 31.7% yield) as colorless oil.

(R)-benzyl 3-(1-aminoethyl)azetidine-1-carboxylate

To a solution of 131-5 (1.7 g, 5.02 mmol, 1 eq) in MeOH (20 mL) at 30° C. was added HCl/MeOH (4 M, 3.77 mL, 3 eq) drop-wise, and the mixture was stirred at 30° C. for 5 h. To the mixture was added $Na_2CO_3$ powder (2 g), and then the mixture was diluted with EA (20 mL) and then filtered to remove the solid. The filtrate was concentrated under reduced pressure to give 131-6 (1.10 g, 4.69 mmol, 93.5% yield) as colorless oil, which was used directly for next step.

(R)-benzyl 3-(1-(5-(4-(trifluoromethyl)phenyl)-2-naphthamido)ethyl)azetidine-1-carboxylate To a solution of 131-6a (300 mg, 0.95 mmol, 1 eq), 131-6 (266.7 mg, 1.14 mmol, 1.2 eq) and HATU (468.9 mg, 1.23 mmol, 1.3 eq) in DMF (3 mL) at 30° C. was added TEA (288.0 mg, 2.85 mmol, 0.40 mL, 3 eq), and the mixture was stirred at 30° C. for 16 h. The reaction mixture was diluted with water (20 mL) and extracted with EA (20 mL*3). The combined organic layers were washed with brine (20 mL), dried over anhydrous $Na_2SO_4$, filtered and concentrated under reduced pressure to give a residue. The residue was purified by flash silica gel chromatography (ISCO®; 12 g SepaFlash® Silica Flash Column, Eluent of 0~60% Ethyl acetate/Petroleum ether gradient @ 30 mL/min) to give 7 (450 mg, 0.80 mmol, 84.6% yield) as a white solid. LCMS (ESI): RT=0.994 min, mass calc. for $C_{31}H_{27}F_3N_2O_3$ 532.20, m/z found 533.1 $[M+H]^+$.

(R)—N-(1-(azetidin-3-yl)ethyl)-5-(4-(trifluoromethyl)phenyl)-2-naphthamide

To a solution of 131-7 (400 mg, 0.75 mmol, 1 eq) and $NH_3·H_2O$ (1.05 g, 7.51 mmol, 1.16 mL, 25% solution, 10 eq) in EtOH (10 mL) at 30° C. was added Pd/C (79.9 mg, 75.1 umol, 10%, 0.1 eq), and the mixture was purged and degassed with $H_2$ for 3 times and then stirred at 30° C. under $H_2$ (15 Psi) for 1 h. The reaction mixture was filtered to remove Pd/C and the filtrate was concentrated under reduced pressure to give 131-8 (290 mg, 0.68 mmol, 91.1% yield) as a white solid, which was used directly for next step. LCMS (ESI): RT=0.756 min, mass calc. for $C_{23}H_{21}F_3N_2O$, 398.16, m/z found 399.0 $[M+H]^+$.

(R)—N-(1-(1-(2-fluoroethyl)azetidin-3-yl)ethyl)-5-(4-(trifluoromethyl)phenyl)-2-naphthamide To a solution of 131-8 (50 mg, 0.13 mmol, 1 eq) and $K_2CO_3$ (52.0 mg, 0.38 mmol, 3 eq) in ACN (3 mL) at 30° C. was added 131-8a (23.9 mg, 0.19 mmol, 1.5 eq), and the mixture was stirred at 70° C. for 16 h. The reaction mixture was filtered to remove the solid and the filtrate was concentrated under reduced pressure to give a residue. The residue was purified by prep-HPLC (column: Welch Xtimate C18 150*25 mm*5 um; mobile phase: [water (0.05% HCl)-ACN]; B %: 25%-55%, 8.5 min) to give Compound 144 (31.8 mg, 64.7 umol, 51.5% yield, HCl) as a white solid (hygroscopic). LCMS (ESI): RT=0.792 min, mass calc. for $C_{25}H_{24}F_4N_2O$ 444.18, m/z found 445.0 $[M+H]^+$; $^1H$ NMR (400 MHz, DMSO-$d_6$) δ 8.59 (d, J=1.3 Hz, 1H), 8.45 (d, J=7.8 Hz, 1H), 8.12 (d, J=8.3 Hz, 1H), 7.95 (dd, J=1.9, 8.9 Hz, 1H), 7.90 (d, J=8.0 Hz, 2H), 7.80 (d, J=8.8 Hz, 1H), 7.74-7.68 (m, 3H), 7.59 (dd, J=1.3, 7.0 Hz, 1H), 4.80-4.76 (m, 1H), 4.69-4.63 (m, 1H), 4.41 (brs, 1H), 4.23-3.93 (m, 4H), 3.63-3.45 (m, 2H), 3.05-3.04 (m, 1H), 1.19 (brd, J=6.8 Hz, 3H).

Example 132: N-[(1S)-1-(3-hydroxyazetidin-3-yl)ethyl]-8-[4-(trifluoromethyl)phenyl]quinoline-3-carboxamide (Compound 145)
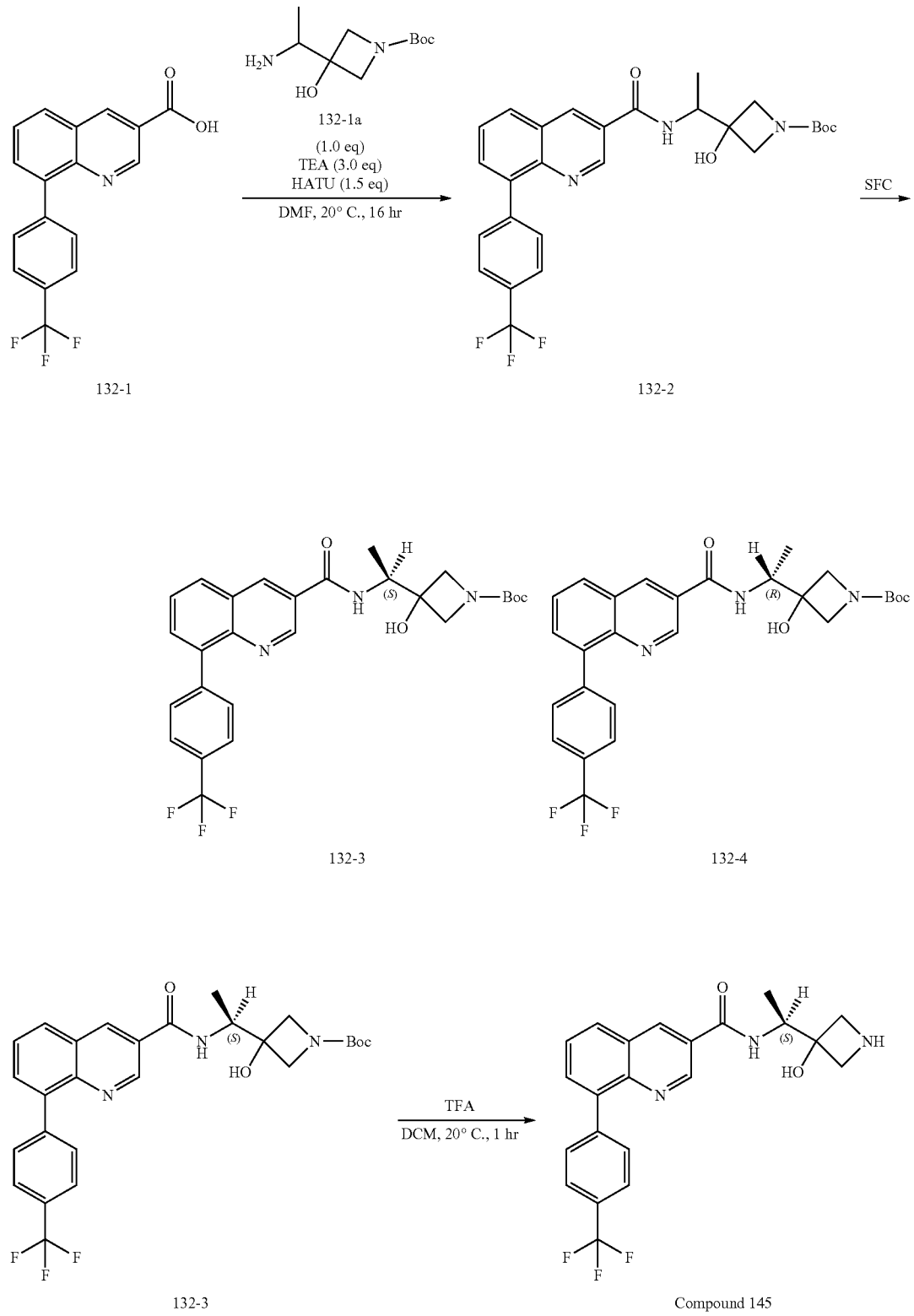

tert-butyl3-hydroxy-3-(1-(8-(4-(trifluoromethyl)phenyl)quinoline-3-carboxamido)ethyl)azetidine-1-carboxylate To a solution of 132-1 (90.0 mg, 0.28 mmol, 1 eq) and HATU (161.8 mg, 0.43 mmol, 1.5 eq) in DMF (1 mL) at 20° C. were added 132-1a (61.4 mg, 0.28 mmol, 1.0 eq) and TEA (86.1 mg, 0.85 mmol, 0.12 mL, 3.0 eq). The mixture was stirred at 20° C. for 16 h. The reaction mixture was diluted with water (20 mL) and extracted with EA (20 mL*3). The combined organic layers were washed with water (20 mL*2) and brine (20 mL*2), dried over $Na_2SO_4$, filtered and concentrated under reduced pressure to give a residue, which was purified by flash silica gel chromatography (ISCO®; 4 g SepaFlash® Silica Flash Column, Eluent of 0~75% Ethyl acetate/Petroleum ether gradient @ 20 mL/min) to give 132-2 (82.0 mg, 0.14 mmol, 49.9% yield) was obtained as colorless oil. LCMS (ESI): RT=0.910 min, mass calcd. for $C_{27}H_{28}F_3N_3O_4$ 515.20, m/z found 516.1 [M+H]$^+$.

(S)-tert-butyl3-hydroxy-3-(1-(8-(4-(trifluoromethyl)phenyl)quinoline-3-carboxamido)ethyl)azetidine-1-carboxylate 132-2 (82.0 mg, 0.16 mmol, 1.0 eq) was purified by SFC: (column: DAICEL CHIRALPAK AD (250 mm*30 mm, 10 um); mobile phase: [0.1% $NH_3H_2O$ ETOH]; B %: 30%-30%, min) to give 132-3 (38.0 mg, 72 umol, 45.5% yield) and 132-4 (40.0 mg, 57 umol, 35.6% yield) was obtained as a white solid. LCMS (ESI): RT=0.908 min, mass calcd. for $C_{27}H_{28}F_3N_3O_4$ 515.20, m/z found 516.1 [M+H]$^+$.

N-[(1S)-1-(3-hydroxyazetidin-3-yl)ethyl]-8-[4-(trifluoromethyl)phenyl]quinoline-3-carboxamide To a solution of 132-3 (38.0 mg, 73.7 umol, 1 eq) in DCM (0.6 mL) at 20° C. was added TFA (0.50 mg, 4.42 umol, 3.27e−1 uL, 0.06 eq). The mixture was stirred at 30° C. for 1 h. The reaction mixture was concentrated under reduced pressure to give a residue which was basified with $NH_3 \cdot H_2O$ to pH=9. The residue was purified by prep-HPLC: (column: Waters Xbridge C18 150*50 mm*10 um; mobile phase: [water (0.04% $NH_3H_2O$ 10 mM $NH_4HCO_3$)-ACN]; B %: 32%-62%, 11 min) to give Compound 145 (9.8 mg, 23.7 umol, 32.1% yield) was obtained as colorless oil. LCMS (ESI): RT=0.738 min, mass calcd. for $C_{22}H_{20}F_3N_3O_2$ 415.15, m/z found 416.0 [M+H]$^+$; $^1$H NMR (400 MHz, CDCl$_3$) δ 9.28 (d, J=1.8 Hz, 1H), 8.66 (d, J=1.5 Hz, 1H), 7.92 (brd, J=8.0 Hz, 1H), 7.82-7.71 (m, 5H), 7.69-7.64 (m, 1H), 7.22 (brd, J=8.5 Hz, 1H), 4.71 (brs, 1H), 4.62-4.51 (m, 1H), 3.96-3.56 (m, 4H), 1.30 (br d, J=6.8 Hz, 3H).

Example 133: N-[(1R)-1-(1-Isopropylazetidin-3-yl)ethyl]-8-[4-(trifluoromethyl)phenyl]quinoline-3-carboxamide (Compound 146) and N-[(1S)-1-(1-Isopropylazetidin-3-yl)ethyl]-8-[4-(trifluoromethyl)phenyl]quinoline-3-carboxamide (Compound 147)

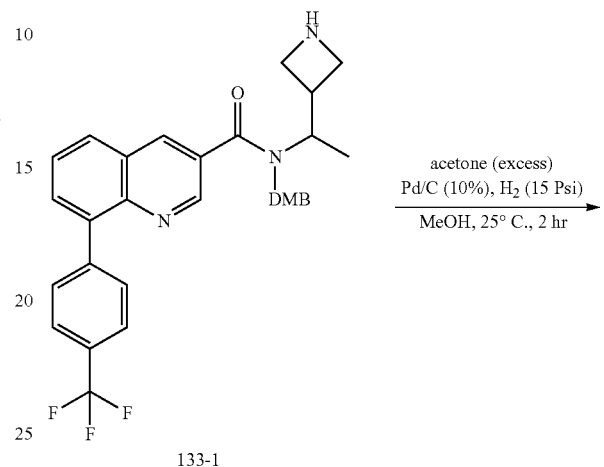

133-1

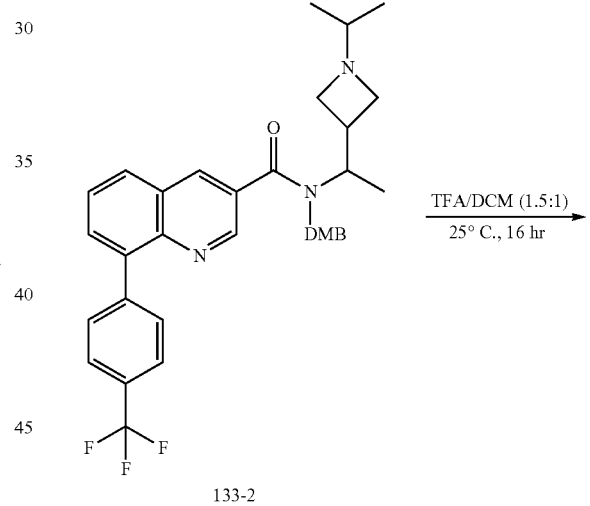

133-2

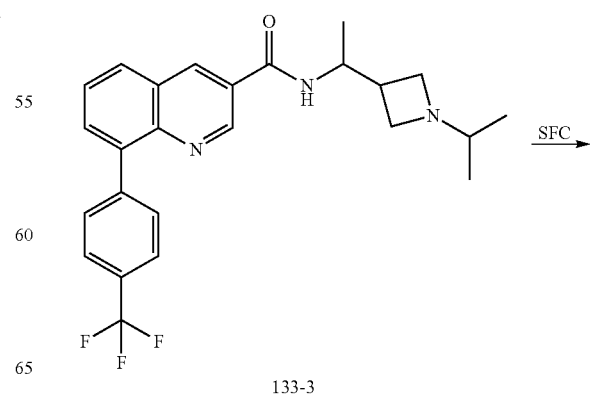

133-3

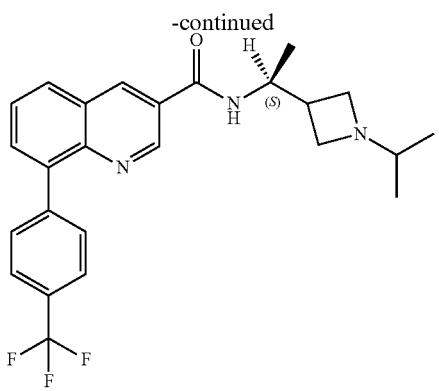

Compound 147

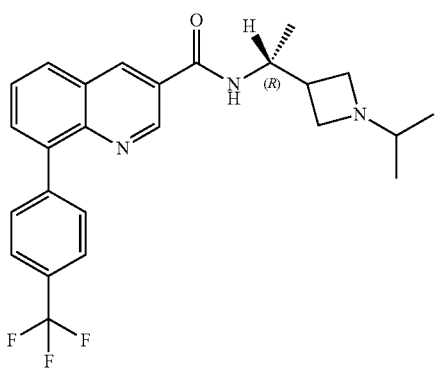

Compound 146

N-[(2,4-Dimethoxyphenyl)methyl]-N-[1-(1-isopropylazetidin-3-yl)ethyl]-8-[4-(trifluoromethyl)phenyl]quinoline-3-carboxamide To a solution of 133-1 (0.1 g, 0.18 mmol, 1 eq) and acetone (105.7 mg, 1.81 mmol, 10 eq) in MeOH (6 mL) was added Pd/C (200 mg, 10%). The suspension was degassed under vacuum and purged with $H_2$ several times. The mixture was stirred under $H_2$ (15 psi) at 25° C. for 2 hours. The reaction mixture was concentrated under reduced pressure to give a residue. The crude product was used into the next step without further purification. Compound 133-2 (90 mg, crude) was obtained as a white solid. LCMS (ESI): RT=0.944 min, mass calcd for $C_{34}H_{36}F_3N_3O_3$ 591.27 m/z found 592.2 $[M+H]^+$.

N-[1-(1-Isopropylazetidin-3-yl)ethyl]-8-[4-(trifluoromethyl)phenyl]quinoline-3-carboxamide To a solution of 133-2 (170 mg, 0.28 mmol, 1 eq) in DCM (2 mL) was added TFA (5.1 g, 44.76 mmol, 3.31 mL, 155.7 eq). The mixture was stirred at 25° C. for 16 hr. The reaction mixture was concentrated under reduced pressure to give a residue. The residue was purified by prep-HPLC (column: Welch Xtimate C18 150*25 mm*5 um; mobile phase: [water (0.05% HCl)-ACN]; B %: 20%-50%, 8.5 min) to give 3 (60 mg, 47.3% yield) as a white solid. LCMS (ESI): RT=0.842 min, mass calcd for $C_{25}H_{26}F_3N_3O$, 441.20 m/z found 442.1$[M+H]^+$.

N-[(1R)-1-(1-Isopropylazetidin-3-yl)ethyl]-8-[4-(trifluoromethyl)phenyl]quinoline-3-carboxamide (Compound 146) and N-[(1S)-1-(1-Isopropylazetidin-3-yl)ethyl]-8-[4-(trifluoromethyl)phenyl]quinoline-3-carboxamide (Compound 147)

133-3 (60 mg) was purified by prep-SFC (column: DAICEL CHIRALPAK AD-H (250 mm*30 mm, 5 um); mobile phase: [0.1% $NH_3H_2O$ ETOH]; B %: 25%-25%, min) to give Compound 147 (3.7 mg, 8.3 umol, 6.1% yield) and Compound 146 (4.4 mg, 9.8 umol, 7.2% yield) as two white solids. Compound 147 LCMS (ESI): RT=0.853 min, mass calcd for $C_{25}H_{26}F_3N_3O$ 441.20 m/z found 442.1 $[M+H]^+$. $^1$H NMR (400 MHz, $CD_3OD$) δ 9.24 (d, J=2.3 Hz, 1H), 8.89 (d, J=2.3 Hz, 1H), 8.13 (dd, J=1.2, 8.2 Hz, 1H), 7.92 (dd, J=1.3, 7.2 Hz, 1H), 7.85-7.76 (m, 5H), 4.49 (s, 1H), 4.30-4.18 (m, 2H), 4.16-4.08 (m, 1H), 4.02 (t, J=9.2 Hz, 1H), 3.53-3.35 (m, 1H), 3.11-2.93 (m, 1H), 1.30 (d, J=6.9 Hz, 3H), 1.25 (d, J=6.5 Hz, 6H). Compound 146 LCMS (ESI): RT=0.856 min, mass calcd for $C_{25}H_{26}F_3N_3O$ 441.20 m/z found 442.1 $[M+H]^+$. $^1$H NMR (400 MHz, $CD_3OD$) δ9.21 (d, J=2.3 Hz, 1H), 8.82 (d, J=2.3 Hz, 1H), 8.11 (dd, J=1.3, 8.1 Hz, 1H), 7.91 (dd, J=1.4, 7.1 Hz, 1H), 7.87-7.82 (m, 2H), 7.81-7.76 (m, 3H), 4.62 (s, 1H), 4.45-4.26 (m, 1H), 3.68 (q, J=8.4 Hz, 2H), 3.20 (t, J=8.0 Hz, 1H), 2.80-2.60 (m, 2H), 1.23 (d, J=6.6 Hz, 3H), 1.02 (dd, J=3.3, 6.3 Hz, 6H).

Example 134: N-[(1R)-1-(1-Ethylazetidin-3-yl)ethyl]-5-[4-(trifluoromethyl)phenyl]naphthalene-2-carboxamide (Compound 148) and N-[(1S)-1-(1-Ethylazetidin-3-yl)ethyl]-5-[4-(trifluoromethyl)phenyl]naphthalene-2-carboxamide (Compound 149)

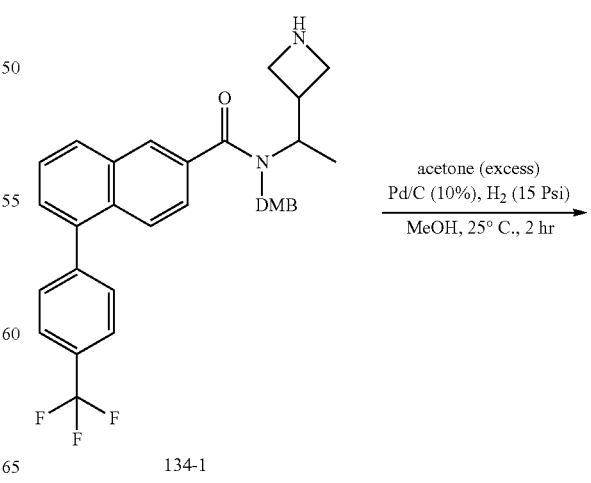

134-1

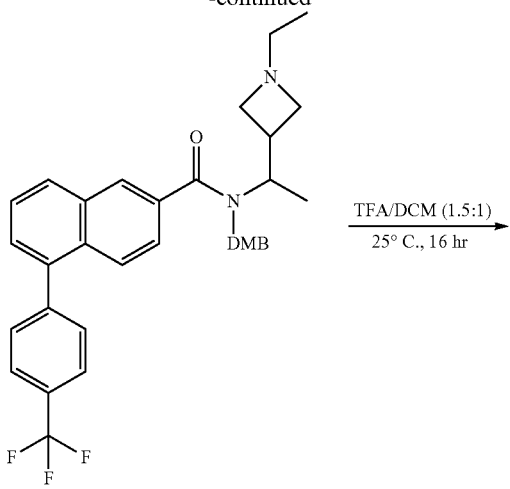

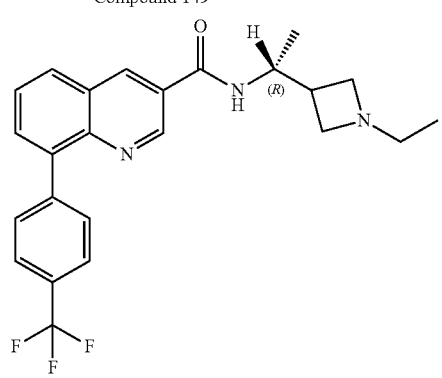

N-[(2,4-Dimethoxyphenyl)methyl]-N-[1-(1-ethyl-azetidin-3-yl)ethyl]-5-[4-(trifluoromethyl)phenyl]naphthalene-2-carboxamide To a solution of 134-1 (150 mg, 0.27 mmol, 1 eq) in MeOH (15 mL) was added acetaldehyde (150.3 mg, 3.4 mmol, 0.19 mL, 12.48 eq) and Pd/C (150 mg, 10%). The suspension was degassed under vacuum and purged with $H_2$ several times. The mixture was stirred under $H_2$ (15 psi) at 25° C. for 2 hours. The reaction mixture was filtered and concentrated under reduced pressure to give a residue. The crude product was used into the next step without further purification. 134-2 (160 mg, crude) was obtained as a white solid. LCMS (ESI): RT=0.946 min, mass calcd for $C_{34}H_{35}F_3N_2O_3$ 576.26 m/z found 577.2 [M+H]$^+$.

N-[1-(1-Ethylazetidin-3-yl)ethyl]-5-[4-(trifluoromethyl)phenyl]naphthalene-2-carboxamide To a solution of 134-2 (200 mg, 0.34 mmol, 1 eq) in DCM (2 mL) was added TFA (6.16 g, 54.03 mmol, 4 mL, 155.7 eq). The mixture was stirred at 25° C. for 16 hr. The reaction mixture was concentrated under reduced pressure to give a residue. The residue was purified by prep-HPLC (column: Welch Xtimate C18 150*25 mm*5 um; mobile phase: [water (0.05% HCl)-ACN]; B %: 22%-52%, 9.5 min) to give 134-3 (40 mg, 93 umol, 27.04% yield) as a white solid. LCMS (ESI): RT=0.873 min, mass calcd for $C_{25}H_{25}F_3N_2O$, 426.19 m/z found 427.1 [M+H]$^+$.

N-[(1R)-1-(1-Ethylazetidin-3-yl)ethyl]-5-[4-(trifluoromethyl)phenyl]naphthalene-2-carboxamide (Compound 148) and N-[(1S)-1-(1-Ethylazetidin-3-yl)ethyl]-5-[4-(trifluoromethyl)phenyl]naphthalene-2-carboxamide (Compound 149)

134-3 (40 mg) was purified by prep-SFC (column: DAICEL CHIRALPAK IG (250 mm*30 mm, 10 um); mobile phase: [0.1% $NH_3H_2O$ ETOH]; B %: 25%-25%, min) to give Compound 149 (6.6 mg, 15.4 umol, 16.5% yield) LCMS (ESI): RT=0.785 min, mass calcd for $C_{25}H_{25}F_3N_2O$ 426.19 m/z found 427.0 [M+H]$^+$. $^1$H NMR (400 MHz, $CD_3OD$) δ 8.51 (d, J=1.0 Hz, 1H), 8.08 (d, J=8.3 Hz, 1H), 7.92-7.82 (m, 4H), 7.67 (td, J=3.5, 8.0 Hz, 3H), 7.58 (dd, J=1.0, 7.0 Hz, 1H), 4.50 (s, 1H), 4.33-3.94 (m, 4H), 3.25 (q, J=6.9 Hz, 2H), 3.11 (sxt, J=8.4 Hz, 1H), 1.28 (d, J=6.8 Hz, 3H), 1.21 (t, J=7.3 Hz, 3H) and Compound 148 (8.3 mg, 19.5 umol, 20.8% yield) LCMS (ESI): RT=0.895 min, mass calcd for $C_{25}H_{25}F_3N_2O$ 426.19 m/z found 427.0 [M+H]$^+$. NMR (400 MHz, $CD_3OD$) δ 8.45 (s, 1H), 8.06 (d, J=8.0 Hz, 1H), 7.88-7.80 (m, 4H), 7.70-7.62 (m, 3H), 7.56 (dd, J=1.0, 7.0 Hz, 1H), 4.39-4.27 (m, 1H), 3.55-3.41 (m, 2H), 3.04 (t, J=1.1 Hz, 1H), 2.92 (t, J=7.7 Hz, 1H), 2.76-2.64 (m, 1H), 2.51 (q, J=7.1 Hz, 2H), 1.20 (d, J=6.8 Hz, 3H), 0.97 (t, J=7.2 Hz, 3H).

Example 135: N-[(1R)-1-(1-Ethylazetidin-3-yl)ethyl]-8-[4-(trifluoromethyl)phenyl]quinoline-3-carboxamide (Compound 150) and N-[(1S)-1-(1-Ethylazetidin-3-yl)ethyl]-8-[4-(trifluoromethyl)phenyl]quinoline-3-carboxamide (Compound 151)

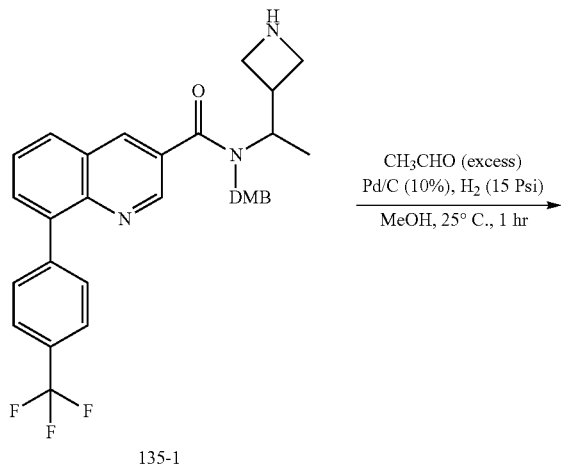

135-1

CH₃CHO (excess)
Pd/C (10%), H₂ (15 Psi)
MeOH, 25° C., 1 hr

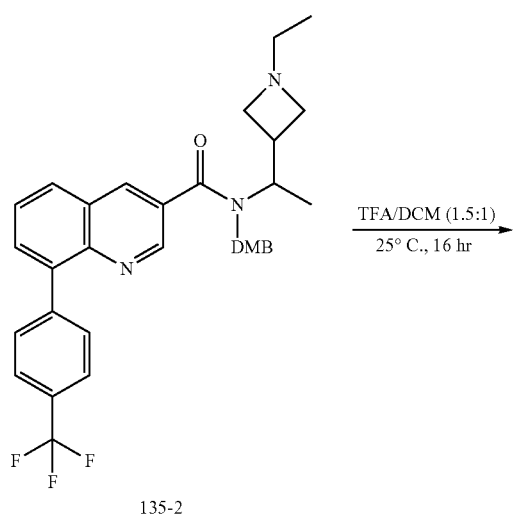

135-2

TFA/DCM (1.5:1)
25° C., 16 hr

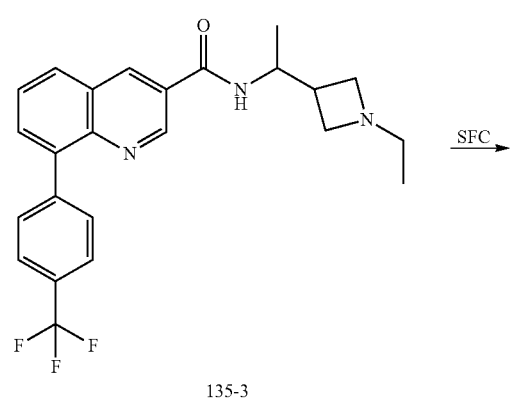

135-3

SFC

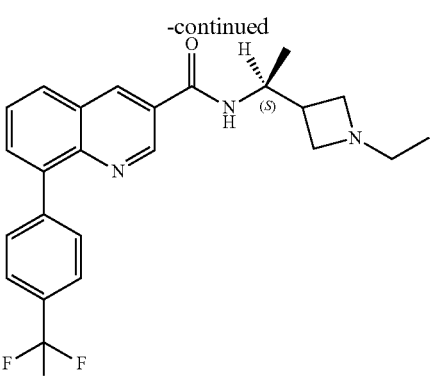

Compound 151

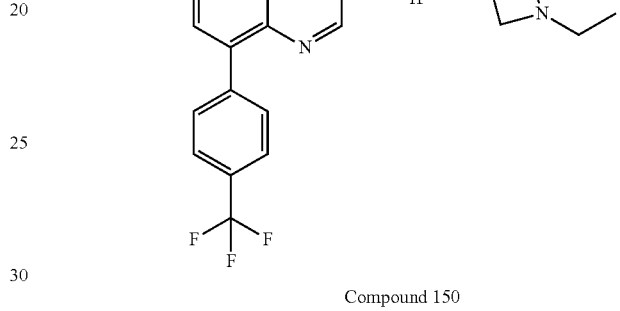

Compound 150

N-[(2,4-Dimethoxyphenyl)methyl]-N-[1-(1-ethylazetidin-3-yl)ethyl]-8-[4-(trifluoromethyl)phenyl]quinoline-3-carboxamide To a solution of 135-1 (150 mg, 0.27 mmol, 1 eq) in MeOH (5 mL) was added Pd/C (50 mg, 10%), H₂ and acetaldehyde (60.1 mg, 1.3 mmol, 76.5 uL, 5 eq). The suspension was degassed under vacuum and purged with H₂ several times. The mixture was stirred under H₂ (15 psi) at 25° C. for 1 hr. The reaction mixture was filtered and concentrated under reduced pressure to give a residue. The crude product was used into the next step without further purification. LCMS (ESI): RT=0.920 min, mass calcd for $C_{33}H_{34}F_3N_3O_3$ 577.26 m/z found 578.1[M+H]⁺.

N-[1-(1-Ethylazetidin-3-yl)ethyl]-8-[4-(trifluoromethyl)phenyl]quinoline-3-carboxamide To a solution of 135-2 (160 mg, 0.27 mol, 1 eq) in DCM (0.5 mL) was added TFA (4.81 g, 42.17 mmol, 3.12 mL, 152.2 eq). The mixture was stirred at 25° C. for 16 hr. The reaction mixture was concentrated under reduced pressure to give a residue. The residue was purified by prep-HPLC (column: Welch Xtimate C18 150*25 mm*5 um; mobile phase: [water (0.05% HCl)-ACN]; B %: 20%-50%, 8.5 min) to give 135-3 (40 mg, 93.58 umol, 33.78% yield) as a white solid. LCMS (ESI): RT=0.842 min, mass calcd for $C_{24}H_{24}F_3N_3O$, 427.19 m/z found 728.1 [M+H]⁺.

N-[(1R)-1-(1-Ethylazetidin-3-yl)ethyl]-8-[4-(trifluoromethyl)phenyl]quinoline-3-carboxamide (Compound 150) and N-[(1S)-1-(1-Ethylazetidin-3-yl)ethyl]-8-[4-(trifluoromethyl)phenyl]quinoline-3-carboxamide (Compound 151)

135-3 (40 mg) was purified by prep-SFC (column: DAICEL CHIRALPAK AD-H (250 mm*30 mm, 5 um); mobile phase: [0.1% NH₃H₂O ETOH]; B %: 25%-25%, min) to give Compound 151 (10.2 mg, 23.8 umol, 25.5% yield) and Compound 150 (13.1 mg, 30.7 umol, 32.9% yield) as two white solids. Compound 151 LCMS (ESI): RT=0.761 min, mass calcd for C₂₄H₂₄F₃N₃O 427.19 m/z found 428.0 [M+H]⁺. ¹H NMR (400 MHz, CD₃OD) δ9.20 (d, J=2.3 Hz, 1H), 8.79 (d, J=2.3 Hz, 1H), 8.10 (dd, J=1.1, 8.2 Hz, 1H), 7.89 (dd, J=1.3, 7.3 Hz, 1H), 7.85-7.81 (m, 2H), 7.80-7.74 (m, 3H), 4.40-4.29 (m, 1H), 3.61-3.47 (m, 2H), 3.09 (t, J=7.7 Hz, 1H), 2.97 (t, J=7.7 Hz, 1H), 2.80-2.67 (m, 1H), 2.54 (q, J=7.1 Hz, 2H), 1.21 (d, J=6.8 Hz, 3H), 0.98 (t, J=12 Hz, 3H). Compound 150 LCMS (ESI): RT=0.759 min, mass calcd for C₂₄H₂₄F₃N₃O 427.19 m/z found 428.0 [M+H]⁺. ¹H NMR (400 MHz, CD₃OD) δ9.24 (d, J=2.0 Hz, 1H), 8.90 (d, J=1.8 Hz, 1H), 8.13 (dd, J=1.1, 8.2 Hz, 1H), 7.91 (dd, J=1.4, 7.2 Hz, 1H), 7.85-7.81 (m, 2H), 7.81-7.75 (m, 3H), 4.51 (s, 1H), 4.33-3.68 (m, 4H), 3.27 (s, 2H), 3.17-3.09 (m, 1H), 1.29 (d, J=7.0 Hz, 3H), 1.22 (t, J=12 Hz, 3H).

Example 136: N-[(1S)-1-(1-methylazetidin-3-yl)ethyl]-5-[4-(trifluoromethyl)phenyl]naphthalene-2-carboxamide (Compound 152) and N-[(1R)-1-(1-methylazetidin-3-yl)ethyl]-5-[4-(trifluoromethyl)phenyl]naphthalene-2-carboxamide (Compound 153)

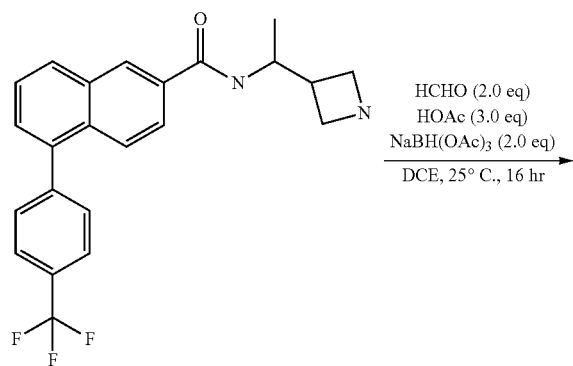

136-1

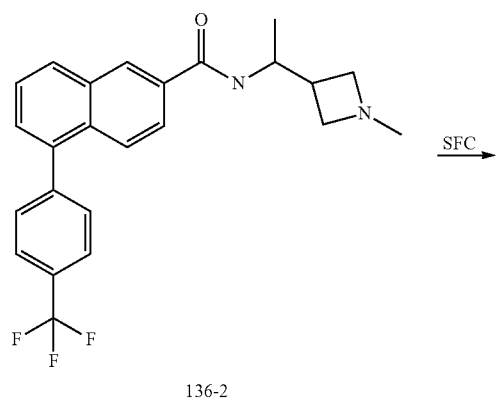

136-2

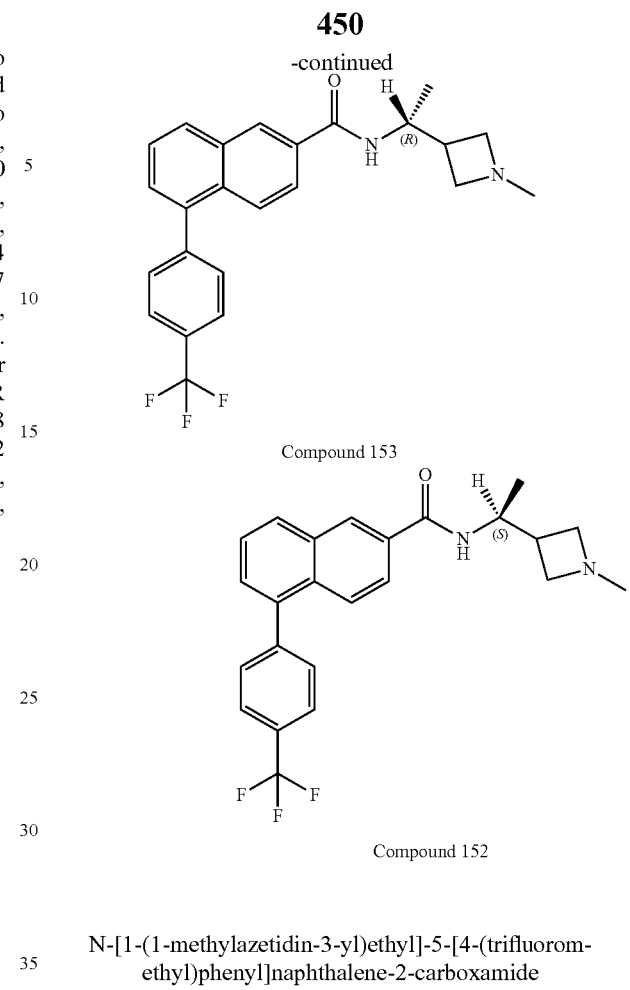

Compound 153

Compound 152

N-[1-(1-methylazetidin-3-yl)ethyl]-5-[4-(trifluoromethyl)phenyl]naphthalene-2-carboxamide To a solution of 136-1 (150 mg, 0.38 mmol, 1 eq) and HCHO (61.1 mg, 0.75 mmol, 56.1 uL, 2 eq) in DCE (3 mL) was added HOAc (67.8 mg, 1.13 mmol, 64.6 uL, 3 eq) and stirred at 25° C. for 1 hr, and then NaBH(OAc)₃ (159.6 mg, 0.75 mmol, 2 eq) was added. The resulting mixture was stirred at 25° C. for 15 hr. Then iced water (30 mL) was added and the mixture was neutralized to pH=9~10 with aq.NaOH (2 M). The aqueous phase was extracted with EA (20 mL*3). The combined organic phase was washed with brine (30 mL), dried with anhydrous Na₂SO₄, filtered and concentrated in vacuo to give residue. The residue was purified by flash silica gel chromatography (12 g Sepa-Flash® Silica Flash Column, EA/PE: 0~30%) to afford 106 mg the crude product. And the crude product was purified by prep-HPLC (column: Welch Xtimate C18 150*25 mm*5 um; mobile phase: [water (0.05% HCl)-ACN]; B %: 25%-55%, 11.5 min) to give 136-2 (32 mg, 77.6 umol, 20.6% yield) as a white solid.

N-[(1R)-1-(1-methylazetidin-3-yl)ethyl]-5-[4-(trifluoromethyl)phenyl]naphthalene-2-carboxamide (Compound 153) and N-[(1S)-1-(1-methylazetidin-3-yl)ethyl]-5-[4-(trifluoromethyl)phenyl]naphthalene-2-carboxamide (Compound 152)

Compound N-[1-(1-methylazetidin-3-yl)ethyl]-5-[4-(trifluoromethyl)phenyl]naphthalene-2-carboxamide (30 mg, 72.7 umol, 1 eq) was separated by SFC (column: DAICEL CHIRALPAK IC (250 mm*30 mm, 5 um); mobile phase: [0.1% NH3H2O IPA]; B %: 35%-35%, min) to afford Compound 153 (5.4 mg, 12.7 umol, 17.5% yield) as a yellow solid. LCMS (ESI): RT=0.787 min, mass calcd for $C_{24}H_{23}F_3N_2O$ 412.18, m/z found 413.2 [M+H]$^+$. $^1$H NMR (400 MHz, CD$_3$OD) δ 8.51 (s, 1H), 8.08 (d, J=8.1 Hz, 1H), 7.90-7.81 (m, 4H), 7.71-7.64 (m, 3H), 7.58 (dd, J=1.1, 7.1 Hz, 1H), 4.50 (s, 1H), 4.34 (s, 2H), 4.16-3.88 (m, 2H), 3.17-3.09 (m, 1H), 2.93 (s, 3H), 1.29-1.24 (m, 3H) and Compound 152 (5.2 mg, 12.5 umol, 17.2% yield) as a yellow solid. LCMS (ESI): RT=0.794 min, mass calcd for $C_{24}H_{23}F_3N_2O$ 412.18, m/z found 413.1 [M+H]$^+$; $^1$H NMR (400 MHz, CD$_3$OD) δ 8.46 (s, 1H), 8.07 (d, J=7.8 Hz, 1H), 7.88-7.82 (m, 4H), 7.71-7.64 (m, 3H), 7.57 (dd, J=1.1, 7.0 Hz, 1H), 4.45-4.34 (m, 1H), 3.68 (m, 2H), 3.39-3.33 (m, 1H), 3.25 (t, J=8.1 Hz, 1H), 2.84-2.73 (m, 1H), 2.47 (s, 3H), 1.90 (s, 1H), 1.21 (d, J=6.8 Hz, 3H).

Example 137: (R)—N-(1-(3-hydroxyazetidin-3-yl)ethyl)-5-(4-(trifluoromethyl)phenyl)-2-naphthamide (Compound 154) and (S)—N-(1-(3-hydroxyazetidin-3-yl)ethyl)-5-(4-(trifluoromethyl)phenyl)-2-naphthamide (Compound 155)

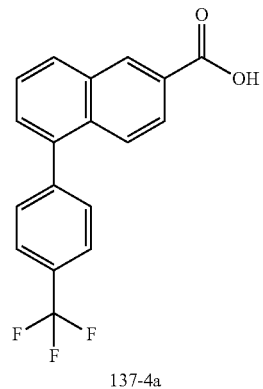

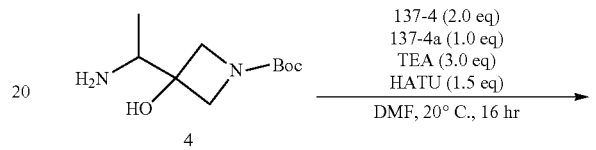

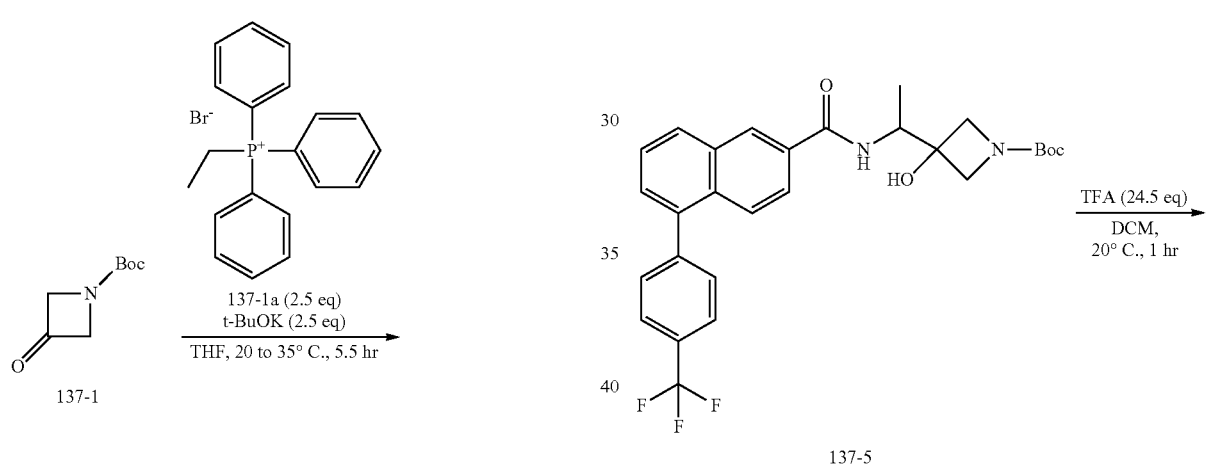

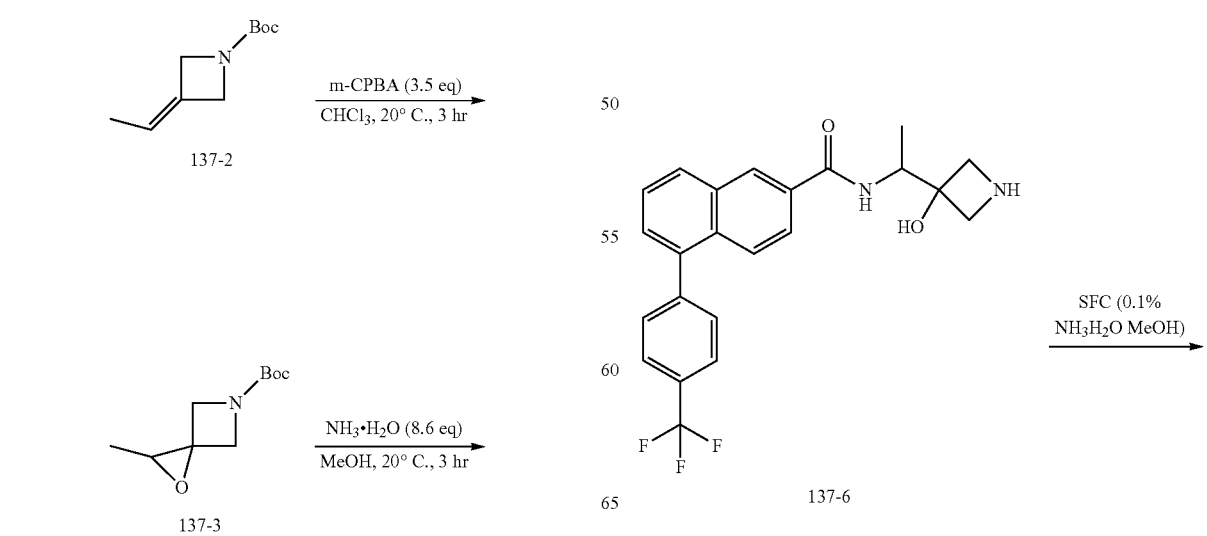

-continued

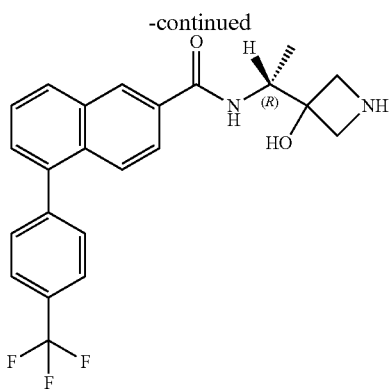

Compound 154

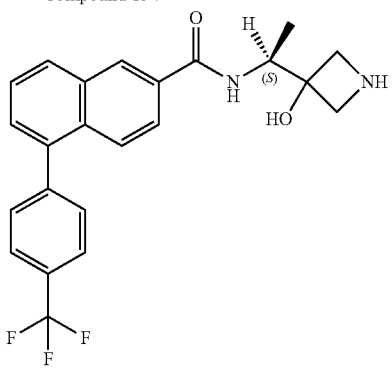

Compound 155

Tert-Butyl 3-ethylideneazetidine-1-carboxylate

To a solution of 137-1a (3.25 g, 8.76 mmol, 2.5 eq) and t-BuOK (983.2 mg, 8.76 mmol, 2.5 eq) in THF (10 mL) at 20° C. was purged and degassed with $N_2$ and then stirred at 20° C. for 1 h. Then 137-1 (600.0 mg, 3.50 mmol, 1 eq) was added into the reaction at 20° C. and purged and degassed with $N_2$ and then stirred at 35° C. for 4.5 h. The residue was diluted with water (20 mL), and then extracted with EA (20 mL*3). The combined organic layers were washed with water (20 mL*2) and brine (20 mL), dried over anhydrous $Na_2SO_4$, filtered and concentrated under reduced pressure to give a residue, which was purified by flash silica gel chromatography (ISCO®; 20 g SepaFlash® Silica Flash Column, Eluent of 0-20% Ethyl acetate/Petroleum ether gradient @35 mL/min) to give compound 137-2 (288.0 mg, 1.57 mmol, 44.8% yield) as colorless oil. $^1$H NMR (400 MHz, CDCl$_3$) δ 5.37-5.28 (m, 1H), 4.46-4.40 (m, 4H), 1.56-1.53 (m, 3H), 1.46 (s, 9H).

Tert-Butyl 2-methyl-1-oxa-5-azaspiro[2.3]hexane-5-carboxylate

To a solution of 137-2 (150.0 mg, 0.82 mmol, 1 eq) in CHCl$_3$ (2 mL) at 20° C. was added m-CPBA (581.7 mg, 2.86 mmol, 85%, 3.5 eq) and then stirred at 20° C. for 3 h. The reaction mixture was diluted with $Na_2SO_3$ (4 ml) and DCM (50 mL), and then washed with saturated $Na_2CO_3$ solution (14 mL*4). The combined organic layers were washed with $H_2O$ (20 mL*2) and brine (20 mL), dried over anhydrous $Na_2SO_4$, filtered and concentrated under reduced pressure to give compound 137-3 (174.0 mg, crude) as colorless oil. $^1$H NMR (400 MHz, CDCl$_3$) δ 4.19-4.08 (m, 4H), 3.10 (q, J=5.3 Hz, 1H), 1.47 (s, 9H), 1.25 (d, J=5.3 Hz, 3H).

Tert-Butyl 3-(1-aminoethyl)-3-hydroxyazetidine-1-carboxylate

To a solution of 137-3 (150.0 m 0.75 mmol, 1 eq) in MeOH (2 mL) at 20° C. was added $NH_3 \cdot H_2O$ (910.0 mg, 6.49 mmol, 1 mL, 25% solution, 8.6 eq) and then the reaction was stirred at 20° C. for 3 h. The reaction mixture was concentrated under reduced pressure to give compound 137-4 (130.0 mg, 0.60 mmol, 79.8% yield) as a white solid.

Tert-Butyl 2-methyl-1-oxa-5-azaspiro[2.3]hexane-5-carboxylate

To a solution of 137-4a (95.1 mg, 0.30 mmol, 1 eq) and HATU (171.4 mg, 0.45 mmol, 1.5 eq) in DMF (1 mL) at 20° C. were added 137-4 (130.0 mg, 0.60 mmol, 2 eq) and TEA (91.2 mg, 0.90 mmol, 0.13 mL, 3 eq). The mixture was stirred at 20° C. for 16 h. The reaction mixture was concentrated under reduced pressure to give a residue, which was purified by prep-HPLC: (column: Welch Xtimate C18 150*25 mm*5 um; mobile phase: [water (0.05% HCl)-ACN]; B %: 45%-75%, 8.5 min) to give compound 137-5 (27.0 mg, 50 umol, 16.7% yield) as a white solid. LCMS (ESI): RT=0.955 min, mass calc. for $C_{28}H_{29}F_3N_2O_4$ 514.21, m/z found 515.1 [M+H]$^+$; NMR (400 MHz, CDCl$_3$) δ 8.37 (s, 1H), 8.00 (d, J=8.3 Hz, 1H), 7.89 (d, J=8.5 Hz, 1H), 7.79 (brd, J=8.0 Hz, 3H), 7.66-7.60 (m, 3H), 7.55-7.51 (m, 1H), 6.58 (brs, 1H), 4.43 (brs, 1H), 4.05 (d, J=9.3 Hz, 1H), 3.98 (brd, J=9.3 Hz, 1H), 3.85 (brd, J=11.0 Hz, 2H), 1.45 (s, 9H), 1.40 (brd, J=6.5 Hz, 3H).

N-(1-(3-hydroxyazetidin-3-yl)ethyl)-5-(4-(trifluoromethyl)phenyl)-2-naphthamide

To a solution of 137-5 (17.0 mg, 33.0 umol, 1 eq) in DCM (0.6 mL) at 20° C. was added TFA (92.4 mg, 0.81 mmol, 60 uL, 24.5 eq). The mixture was stirred at 20° C. for 1 h. The reaction was combined with ES10388-363. The reaction was concentrated under reduced pressure to give a residue, which was purified by prep-HPLC (column: Waters Xbridge C18 150*50 mm*10 um; mobile phase: [water (0.04% $NH_3H_2O$ 10 mM $NH_4HCO_3$)-ACN]; B %: 43%-73%, 11 min) to give compound 137-6 (22.0 mg, 51 umol, 77.9% yield) as a white solid. LCMS (ESI): RT=0.773 min, mass calc. for $C_{23}H_{21}F_3N_2O_2$ 414.16, m/z found 415.0 [M+H]$^+$.

(S)—N-(1-(3-hydroxyazetidin-3-yl)ethyl)-5-(4-(trifluoromethyl)phenyl)-2-naphthamide (Compound 155) and (R)—N-(1-(3-hydroxyazetidin-3-yl)ethyl)-5-(4-(trifluoromethyl)phenyl)-2-naphthamide (Compound 154)

The 137-6 (20.0 mg, 48.26 umol, 1 eq) was separated by SFC (column: Phenomenex-Cellulose-2 (250 mm*30 mm, 10 um); mobile phase: [0.1% $NH_3H_2O$ MEOH]; B %: 50%-50%, min) to give 6 mg sample and 5 mg sample. The 6 mg sample was purified by prep-HPLC: (column: Waters Xbridge C18 150*50 mm*10 um; mobile phase: [water (0.04% $NH_3H_2O$+10 mM $NH_4HCO_3$)-ACN]; B %: 43%-73%, 11 min) to give Compound 154 (2.7 mg, 6 umol, 12.7% yield) as a white solid. LCMS (ESI): RT=0.771 min, mass calc. for $C_{23}H_{21}F_3N_2O_2$ 414.16, m/z found 415.0 [M+H]$^+$; $^1$H NMR (400 MHz, CDCl$_3$) δ 8.38 (s, 1H), 7.98 (brd, J=8.3 Hz, 1H), 7.88-7.84 (m, 1H), 7.81-7.76 (m, 3H), 7.63-7.57 (m, 3H), 7.50 (brd, J=6.8 Hz, 1H), 6.95 (brd, J=8.1 Hz, 1H), 4.61-4.49 (m, 1H), 3.88-3.74 (m, 2H), 3.61 (brdd, J=8.8, 16.2 Hz, 2H), 1.33 (brd, J=6.5 Hz, 3H). The 5 mg sample was purified by prep-HPLC: (column: Waters Xbridge C18 150*50 mm*10 um; mobile phase: [water (0.04% NH$_3$H$_2$O+10 mM NH$_4$HCO$_3$)-ACN]; B %: 43%-73%, 11 min) to give Compound 155 (1.5 mg, 4 umol, 7.5% yield) as a white solid. LCMS (ESI): RT=0.774 min, mass calc. for C$_{23}$H$_{21}$F$_3$N$_2$O$_2$ 414.16, m/z found 415.0 [M+H]$^+$; $^1$H NMR (400 MHz, CDCl$_3$) δ 8.38 (s, 1H), 7.99 (brd, J=8.3 Hz, 1H), 7.89-7.83 (m, 1H), 7.82-7.76 (m, 3H), 7.63-7.57 (m, 3H), 7.53-7.49 (m, 1H), 6.93 (brd, J=7.5 Hz, 1H), 4.60-4.50 (m, 1H), 3.89-3.73 (m, 2H), 3.68-3.54 (m, 2H), 1.34 (brd, J=6.6 Hz, 3H).

Example 138: N-[(1R)-1-(1-methylazetidin-3-yl)ethyl]-8-[4-(trifluoromethyl)phenyl]quinoline-3-carboxamide (Compound 156) and N-[(1S)-1-(1-Methylazetidin-3-yl)ethyl]-8-[4-(trifluoromethyl)phenyl]quinoline-3-carboxamide (Compound 157)

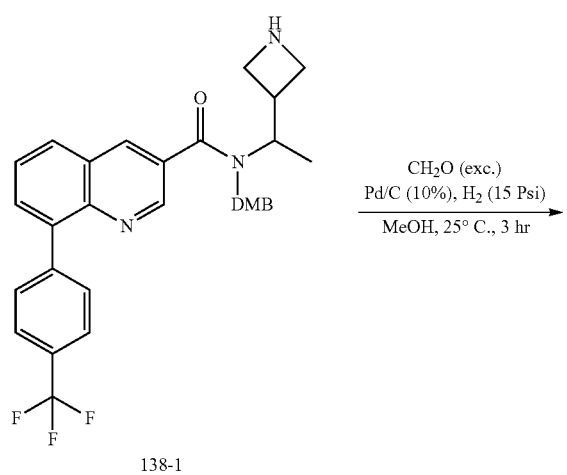

138-1

CH$_2$O (exc.)
Pd/C (10%), H$_2$ (15 Psi)
────────────────
MeOH, 25° C., 3 hr

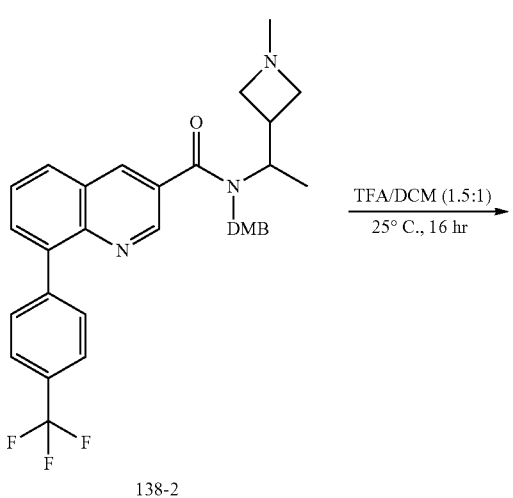

138-2

TFA/DCM (1.5:1)
────────────────
25° C., 16 hr

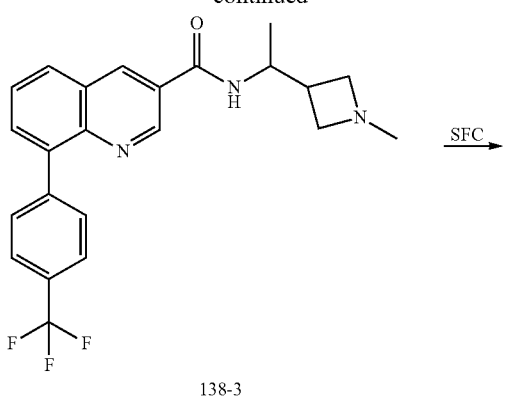

138-3

SFC →

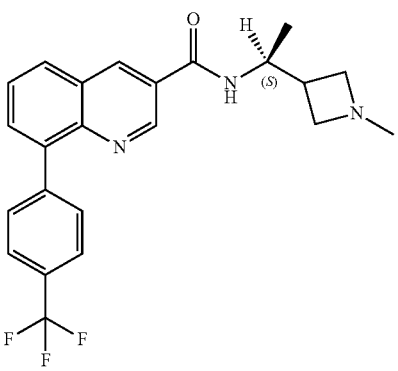

Compound 157

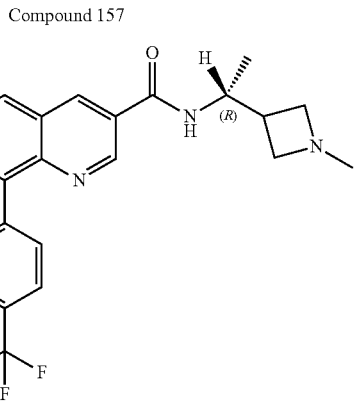

Compound 156

N-[(2,4-Dimethoxyphenyl)methyl]-N-[1-(1-methyl-azetidin-3-yl)ethyl]-8-[4-(trifluoromethyl)phenyl]quinoline-3-carboxamide To a solution of 138-1 (150 mg, 0.27 mmol, 1 eq) in MeOH (5 mL) was added Pd/C (50 mg, 10%) and formaldehyde (4.90 g, 60.44 mmol, 4.50 mL, 221.4 eq). The suspension was degassed under vacuum and purged with H$_2$ several times. The mixture was stirred under H$_2$ (15 psi) at 25° C. for 3 hrs. The reaction mixture was filtered and concentrated under reduced pressure to give a residue. The residue was purified by column chromatography (SiO$_2$, Ethyl acetate:Methanol=100/1 to 1/2) to give 138-2 (70 mg, 0.12 mmol, 45.5% yield) as a white solid. LCMS (ESI): RT=0.839 min, mass calcd for C$_{32}$H$_{32}$F$_3$N$_3$O$_3$ 563.24 m/z found 564.1 [M+H]$^+$.

N-[1-(1-Methylazetidin-3-yl)ethyl]-8-[4-(trifluoromethyl)phenyl]quinoline-3-carboxamide To a solution of 138-2 (70 mg, 0.12 mmol, 1 eq) in DCM (0.5 mL) was added TFA (2.16 g, 18.91 mmol, 1.40 mL, 152.2 eq). The mixture was stirred at 25° C. for 16 hr. The reaction mixture was concentrated under reduced pressure to give a residue. The residue was purified by prep-HPLC (column: Welch Xtimate C18 150*25 mm*5 um; mobile phase: [water (0.05% HCl)-ACN]; B %: 20%-50%, 8.5 min) to give 138-3 (20 mg, 48.3 umol, 38.9% yield) as a white solid. LCMS (ESI): RT=0.825 min, mass calcd for $C_{23}H_{22}F_3N_3O$, 413.17 m/z found 414.1 [M+H]$^+$.

N-[(1S)-1-(1-Methylazetidin-3-yl)ethyl]-8-[4-(trifluoromethyl)phenyl]quinoline-3-carboxamide (Compound 157) and N-[(1R)-1-(1-methylazetidin-3-yl)ethyl]-8-[4-(trifluoromethyl)phenyl]quinoline-3-carboxamide (Compound 156)

138-3 (30 mg) was purified by prep-SFC (column: DAICEL CHIRALPAK AD-H (250 mm*30 mm, 5 um); mobile phase: [0.1% NH$_3$H$_2$O ETOH]; B %: 25%-25%, min) to give Compound 157 (6.5 mg, 15.4 umol, 21.3% yield) and Compound 156 (10.8 mg, 25.2 umol, 34.7% yield) as two white solid. Compound 157 LCMS (ESI): RT=0.824 min, mass calcd for $C_{23}H_{22}F_3N_3O$ 413.17 m/z found 414.1 [M+H]$^+$. $^1$H NMR (400 MHz, CD$_3$OD) δ 9.22 (d, J=2.3 Hz, 1H), 8.85 (d, J=2.3 Hz, 1H), 8.11 (dd, J=1.1, 8.1 Hz, 1H), 7.91 (dd, J=1.2, 7.2 Hz, 1H), 7.85-7.81 (m, 2H), 7.80-7.76 (m, 3H), 4.52-4.40 (m, 1H), 4.01 (q, J=8.8 Hz, 2H), 3.90-3.82 (m, 1H), 3.74 (t, J=8.9 Hz, 1H), 3.04-2.91 (m, 1H), 2.75 (s, 3H), 1.26 (d, J=6.6 Hz, 3H). Compound 156 LCMS (ESI): RT=0.830 min, mass calcd for $C_{23}H_{22}F_3N_3O$ 413.17 m/z found 414.0 [M+H]$^+$. $^1$H NMR (400 MHz, CD$_3$OD) δ9.20 (d, J=2.1 Hz, 1H), 8.80 (d, J=2.3 Hz, 1H), 8.10 (d, J=7.5 Hz, 1H), 7.92-7.87 (m, 1H), 7.86-7.81 (m, 2H), 7.80-7.74 (m, 3H), 4.46-4.27 (m, 1H), 3.62 (q, J=8.5 Hz, 2H), 3.27 (t, J=7.8 Hz, 1H), 3.16 (t, J=7.8 Hz, 1H), 2.81-2.68 (m, 1H), 2.42 (s, 3H), 1.22 (d, J=6.6 Hz, 3H).

Example 139: N-[(1R)-1-(Azetidin-3-yl)ethyl]-8-[4-(trifluoromethyl)phenyl]quinoline-3-carboxamide (Compound 158) and N-[(1S)-1-(Azetidin-3-yl)ethyl]-8-[4-(trifluoromethyl)phenyl]quinoline-3-carboxamide (Compound 159)

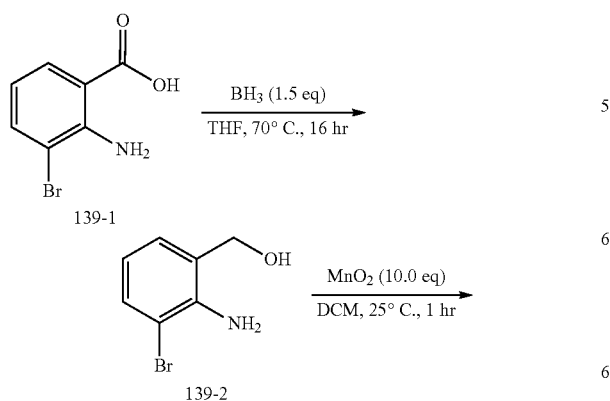

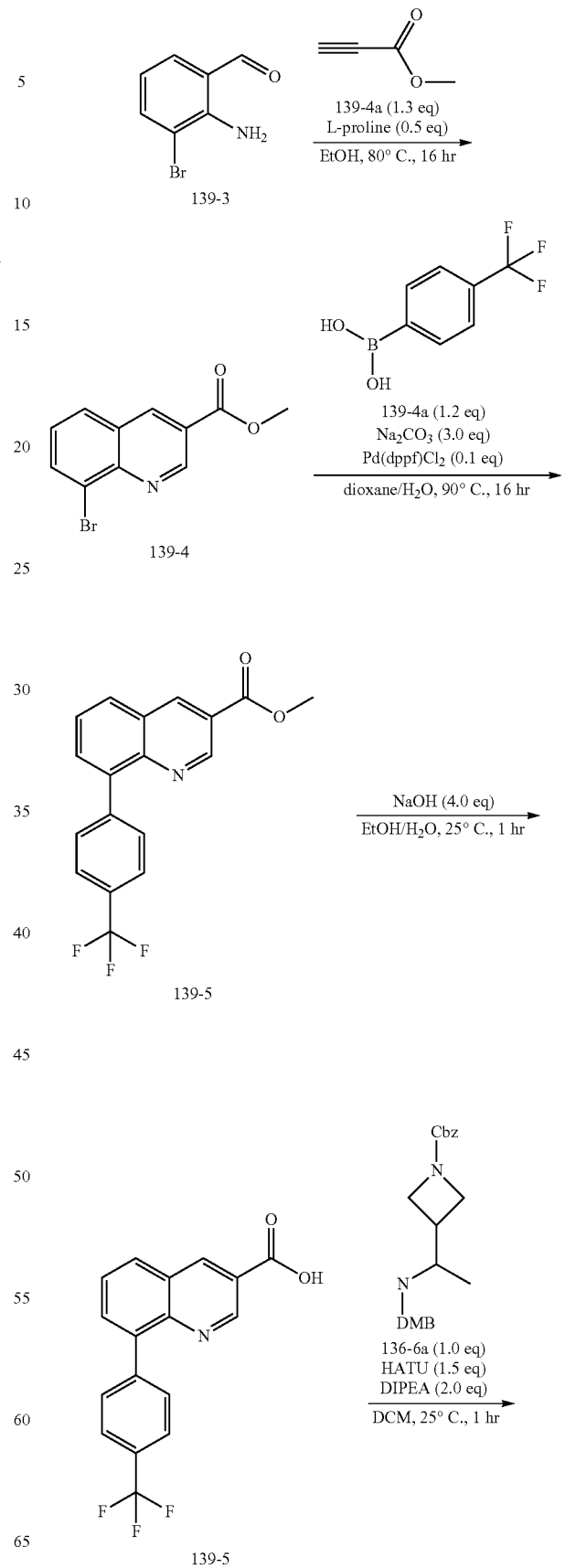

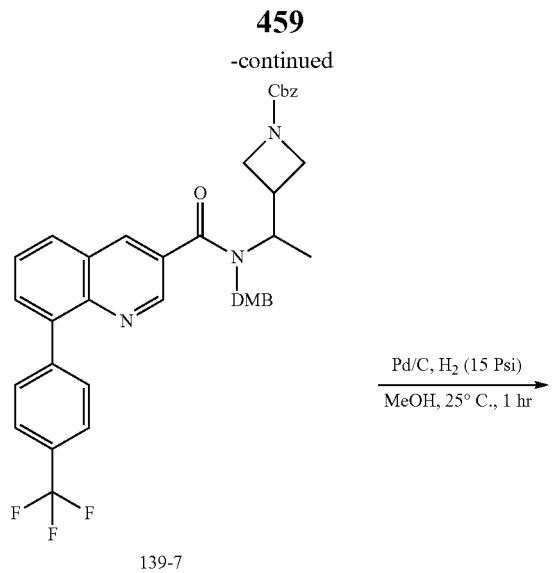

139-7

Pd/C, H₂ (15 Psi)
―――――――――→
MeOH, 25° C., 1 hr

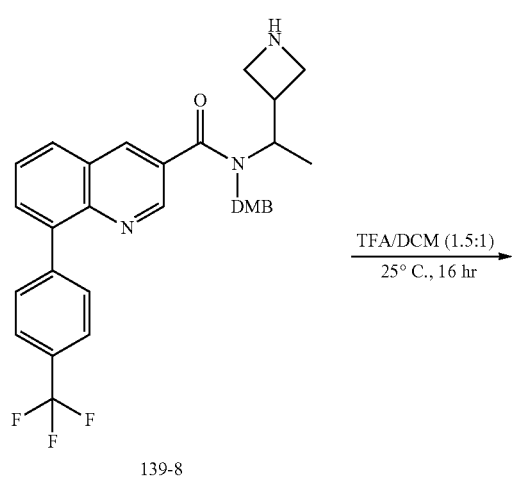

139-8

TFA/DCM (1.5:1)
―――――――――→
25° C., 16 hr

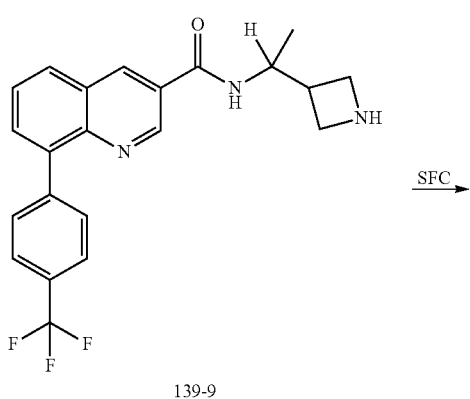

139-9

SFC →

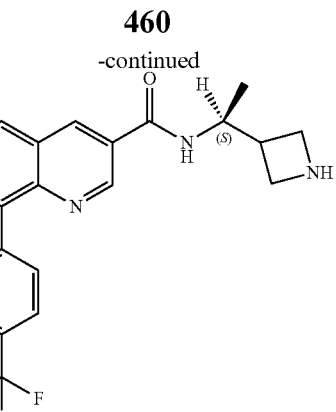

Compound 159

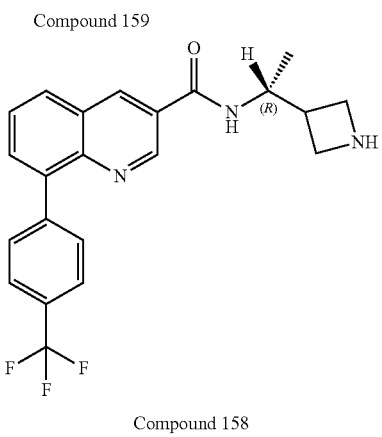

Compound 158

(2-Amino-3-bromo-phenyl)methanol

To a solution of 139-1 (1.2 g, 5.55 mmol, 1 eq) in THF (5 mL) was added BH₃·THF (1 M, 8.33 mL, 1.5 eq) at 0° C. The mixture was stirred under at 70° C. for 16 hours. The reaction mixture was filtered and concentrated under reduced pressure to give a residue. The residue was purified by column chromatography (SiO₂, Petroleum ether/Ethyl acetate=100/1 to 1/1) to give 139-2 (1.1 g, 5.44 mmol, 98% yield) as a white solid. LCMS (ESI): RT=0.699 min, mass calcd for C₇H₈BrNO 200.98 m/z found 203.0 [M+H]⁺.

2-Amino-3-bromo-benzaldehyde

To a solution of 139-2 (1.10 g, 5.44 mmol, 1 eq) in DCM (15 mL) was added MnO₂ (4.73 g, 54.44 mmol, 10 eq). The mixture was stirred at 25° C. for 1 hr. The reaction mixture was filtered and concentrated under reduced pressure to give 139-3 (1 g, crude) as a black oil.

Methyl 8-bromoquinoline-3-carboxylate

To a solution of 139-3 (1.0 g, 5.00 mmol, 1 eq) in EtOH (10 mL) was added L-proline (287.7 mg, 2.50 mmol, 0.5 eq) and 139-3a (546.3 mg, 6.5 mmol, 0.54 mL, 1.3 eq). The mixture was stirred at 80° C. for 16 hr. The reaction mixture was concentrated under reduced pressure to give a residue. The residue was purified by column chromatography (SiO₂, Petroleum ether/Ethyl acetate=100/1 to 3/1) to give 139-4 (1.2 g, 4.51 mmol, 90% yield) as a light yellow solid.

Methyl 8-[4-(trifluoromethyl)phenyl]quinoline-3-carboxylate

To a solution of methyl 139-4 (0.7 g, 2.63 mmol, 1 eq) in dioxane (8 mL) and H₂O (1 mL) was added Pd(dppf)Cl₂

(192.4 mg, 0.26 mmol, 0.1 eq), 139-4a (599.5 mg, 3.16 mmol, 1.2 eq) and $Na_2CO_3$ (836.4 mg, 7.89 mmol, 3.0 eq). The mixture was stirred at 90° C. for 16 hr under $N_2$. The reaction mixture was filtered and concentrated under reduced pressure to give a residue. The residue was purified by column chromatography ($SiO_2$, Petroleum ether/Ethyl acetate=100/1 to 5/1) to give methyl 139-5 (800 mg, 2.25 mmol, 85.3% yield) as a white solid. LCMS (ESI): RT=1.029 min, mass calcd for $C_{18}H_{12}F_3NO_2$ 331.08 m/z found 332.0 [M+H]$^+$.

8-[4-(Trifluoromethyl)phenyl]quinoline-3-carboxylic acid

To a solution of 139-5 (800 mg, 2.41 mmol, 1 eq) in MeOH (6 mL) was added a solution of NaOH (386.3 mg, 9.66 mmol, 4.0 eq) in $H_2O$ (3 mL). The mixture was stirred at 25° C. for 1 hr. The pH of the reaction mixture was adjusted with HCl (2M) to 4~5. The mixture was concentrated under reduced pressure to remove MeOH, then diluted with $H_2O$ (20 mL) and extracted with EtOAc (20 mL*3). The combined organic layers were dried over $Na_2SO_4$, filtered and concentrated under reduced pressure to give a residue. The crude product was used into the next step without further purification. Compound 139-6 (750 mg, crude) was obtained as a white solid.

Benzyl 3-[1-[(2,4-dimethoxyphenyl)methyl-[8-[4-(trifluoromethyl)phenyl]quinoline-3-carbonyl]amino]ethyl]azetidine-1-carboxylat To a solution of 139-6 (0.6 g, 1.89 mmol, 1 eq) in DCM (6 mL) was added HATU (1.08 g, 2.84 mmol, 1.5 eq), DIPEA (488.8 mg, 3.78 mmol, 0.65 mL, 2.0 eq) and 139-6a (799.8 mg, 2.08 mmol, 1.1 eq). The mixture was stirred at 25° C. for 1 hr. The reaction mixture was concentrated under reduced pressure to give a residue. The residue was purified by column chromatography ($SiO_2$, Petroleum ether/Ethyl acetate=100/1 to 1/1) to give 139-7 (1.2 g, 1.56 mmol, 82.6% yield) as a colorless oil. LCMS (ESI): RT=1.096 min, mass calcd for $C_{39}H_{36}F_3N_3O_5$ 683.26 m/z found 684.1 [M+H]$^+$.

N-[1-(Azetidin-3-yl)ethyl]-N-[(2,4-dimethoxyphenyl)methyl]-8-[4-(trifluoromethyl)phenyl]quinoline-3-carboxamide To a solution of 139-7 (0.7 g, 1.0 mmol, 1 eq) in MeOH (30 mL) was added Pd/C (0.3 g, 10%) under $N_2$. The suspension was degassed under vacuum and purged with $H_2$ several times. The mixture was stirred under $H_2$ (15 psi) at 25° C. for 1 hr. The reaction mixture was filtered and concentrated under reduced pressure to give a residue. The crude product was used into the next step without further purification. Compound 139-8 (540 mg, crude) was obtained as a white solid. LCMS (ESI): RT=0.903 min, mass calcd for $C_{31}H_{30}F_3N_3O_3$ 549.22 m/z found 550.1 [M+H]$^+$.

N-[1-(Azetidin-3-yl)ethyl]-8-[4-(trifluoromethyl)phenyl]quinoline-3-carboxamide To a solution of 139-8 (200 mg, 0.36 mmol, 1 eq) in DCM (0.5 mL) was added TFA (10.27 g, 90.04 mmol, 6.67 mL, 247.4 eq). The mixture was stirred at 25° C. for 16 hr. The reaction mixture was concentrated under reduced pressure to give a residue. The residue was purified by prep-HPLC (column: Welch Xtimate C18 150*25 mm*5 um; mobile phase: [water (0.05% HCl)-ACN]; B %: 20%-50%, 8.5 min) to give 139-9 (30 mg, 75.11 umol, 20.64% yield) as a white solid. LCMS (ESI): RT=0.820 min, mass calcd for $C_{22}H_{20}F_3N_3O$, 399.16 m/z found 400.1 [M+H]$^+$.

N-[(1R)-1-(Azetidin-3-yl)ethyl]-8-[4-(trifluoromethyl)phenyl]quinoline-3-carboxamide (Compound 158) and N-[(1S)-1-(Azetidin-3-yl)ethyl]-8-[4-(trifluoromethyl)phenyl]quinoline-3-carboxamide (Compound 159)

139-9 (40 mg) was purified by was purified by prep-SFC (column: DAICEL CHIRALPAK AD (250 mm*30 mm, 10 um); mobile phase: [0.1% $NH_3H_2O$ IPA]; B %: 40%-40%, min) to give Compound 159 (4.0 mg, 10.1 umol, 10.1% yield) and Compound 158 (4.1 mg, 10.2 umol, 10.2% yield) as two white solids. Compound 159 LCMS (ESI): RT=0.826 min, mass calcd for $C_{22}H_{20}F_3N_3O$ 399.16 m/z found 400.0 [M+H]$^+$. $^1$H NMR (400 MHz, $CD_3OD$) δ 9.23-9.18 (m, 1H), 8.81 (d, J=2.3 Hz, 1H), 8.11 (dd, J=1.1, 8.2 Hz, 1H), 7.90 (dd, J=1.3, 7.3 Hz, 1H), 7.85-7.82 (m, 2H), 7.80-7.76 (m, 3H), 4.51-4.40 (m, 1H), 3.77-3.65 (m, 3H), 3.60 (t, J=8.2 Hz, 1H), 3.08-2.92 (m, 1H), 1.22 (d, J=6.5 Hz, 3H). Compound 158 LCMS (ESI): RT=0.824 min, mass calcd for $C_{22}H_{20}F_3N_3O$ 399.16 m/z found 400.0 [M+H]$^+$. NMR (400 MHz, $CD_3OD$) δ 9.21 (d, J=2.3 Hz, 1H), 8.82 (d, J=2.0 Hz, 1H), 8.10 (dd, J=1.1, 8.2 Hz, 1H), 7.90 (dd, J=1.3, 7.0 Hz, 1H), 7.85-7.81 (m, 2H), 7.81-7.77 (m, 3H), 4.52-4.41 (m, 1H), 3.75 (d, J=7.3 Hz, 3H), 3.69-3.61 (m, 1H), 3.08-2.92 (m, 1H), 1.23 (d, J=6.5 Hz, 3H).

Example 140: N-(1,5-dihydroxypentan-3-yl)-8-(4-(trifluoromethyl)phenyl)quinoline-3-carboxamide (Compound 160)

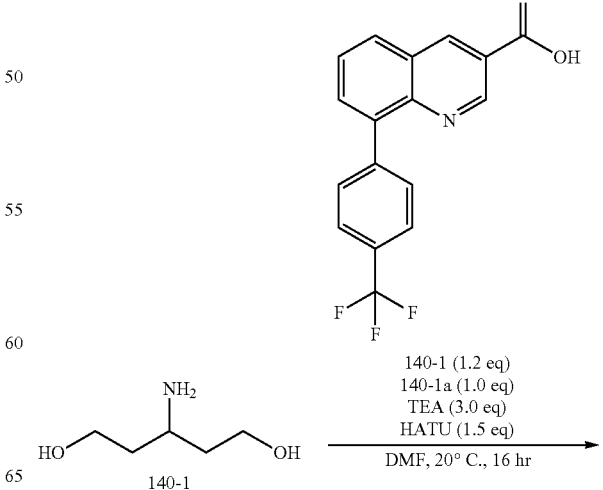

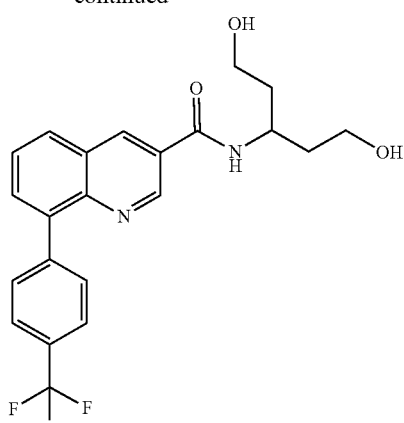

Compound 160

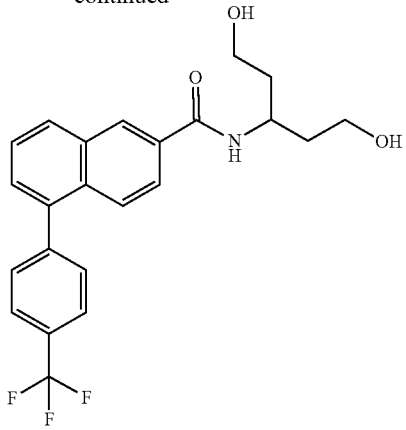

Compound 161

To a solution of 140-1a (30.0 mg, 95 umol, 1 eq) and HATU (53.9 mg, 0.14 mmol, 1.5 eq) in DMF (1 mL) at 20° C. was added 140-1 (13.5 mg, 0.11 mmol, 1.2 eq) and TEA (28.7 mg, 0.28 mmol, 39 uL, 3 eq). The mixture was stirred at 20° C. for 16 h. The reaction mixture was concentrated to give a residue, which was purified by prep-HPLC (column: Xtimate C18 100*30 mm*3 um; mobile phase: [water (0.05% HCl)-ACN]; B %: 25%-55%, 8.5 min) to give Compound 160 (3.9 mg, 9 umol, 9.6% yield) as colorless oil. LCMS (ESI): RT=0.841 min, mass calc. for $C_{22}H_{21}F_3N_2O_3$ 418.15, m/z found 419.0 [M+H]$^+$; 1H NMR (400 MHz, CD$_3$OD) δ 9.31 (q, J=2.2 Hz, 2H), 8.34 (dd, J=1.3, 8.3 Hz, 1H), 8.11-8.05 (m, 1H), 8.02-7.96 (m, 1H), 7.92-7.86 (m, 2H), 7.84 (d, J=8.3 Hz, 2H), 4.43 (tt, J=4.7, 9.0 Hz, 1H), 3.73-3.65 (m, 4H), 1.98-1.82 (m, 4H).

To a solution of 141-1a (120.0 mg, 0.38 mmol, 1 eq) and HATU (216.4 mg, 0.57 mmol, 1.5 eq) in DMF (1 mL) at 20° C. was added 141-1 (54.3 mg, 0.46 mmol, 1.2 eq) and TEA (115.2 mg, 1.14 mmol, 0.16 mL, 3 eq). The mixture was stirred at 20° C. for 16 h. The reaction mixture was concentrated to give a residue, which was purified by prep-HPLC (column: Welch Xtimate C18 150*25 mm*5 um; mobile phase: [water (0.05% HCl)-ACN]; B %: 35%-65%, 8.5 min) to give Compound 161 (10.2 mg, 24 umol, 6.4% yield) as a white solid. LCMS (ESI): RT=0.886 min, mass calc. for $C_{23}H_{22}F_3NO_3$ 417.16, m/z found 418.0 [M+H]$^+$; 1H NMR (400 MHz, CD$_3$OD) δ 8.47 (s, 1H), 8.07 (d, J=8.0 Hz, 1H), 7.86 (s, 2H), 7.84 (d, J=8.0 Hz, 2H), 7.69-7.64 (m, 3H), 7.56 (dd, J=1.0, 7.0 Hz, 1H), 4.40 (tt, J=4.6, 9.0 Hz, 1H), 3.72-3.66 (m, 4H), 1.97-1.81 (m, 4H).

Example 142: N-[(1S)-2-hydroxy-1-(2-pyridyl)ethyl]-5-[4-(trifluoromethyl)phenyl]naphthalene-2-carboxamide (Compound 162) and N-[(1R)-2-hydroxy-1-(2-pyridyl)ethyl]-5-[4-(trifluoromethyl)phenyl]naphthalene-2-carboxamide (Compound 163)

Example 141: N-(1,5-dihydroxypentan-3-yl)-5-(4-(trifluoromethyl)phenyl)-2-naphthamide (Compound 161)

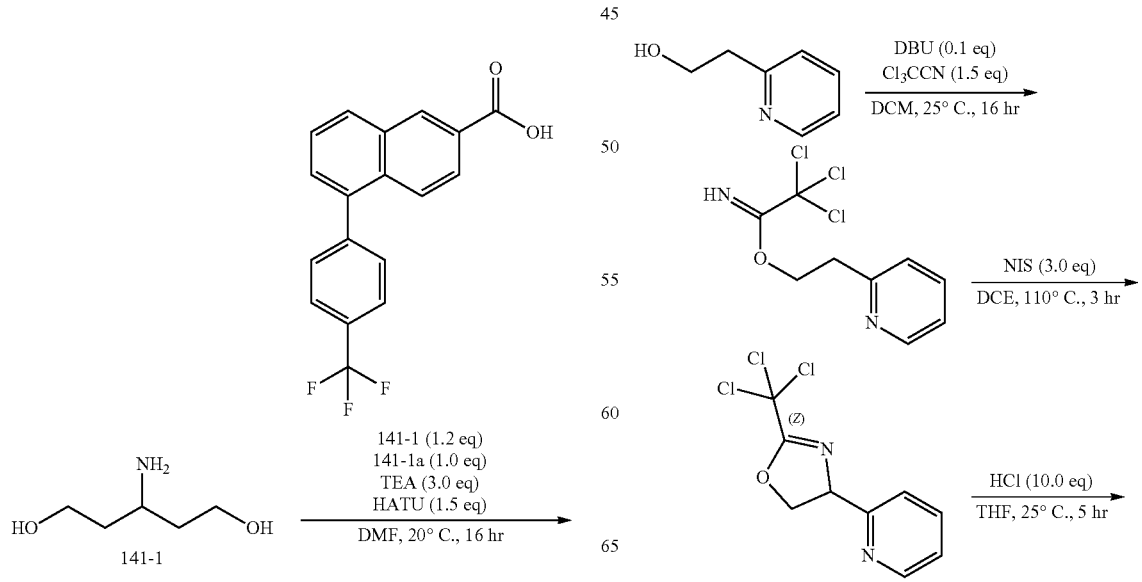

465
-continued

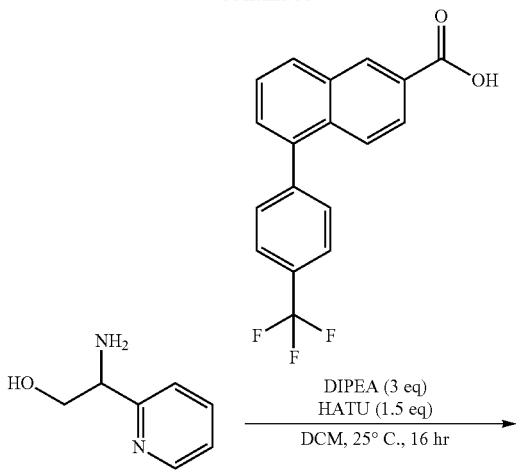

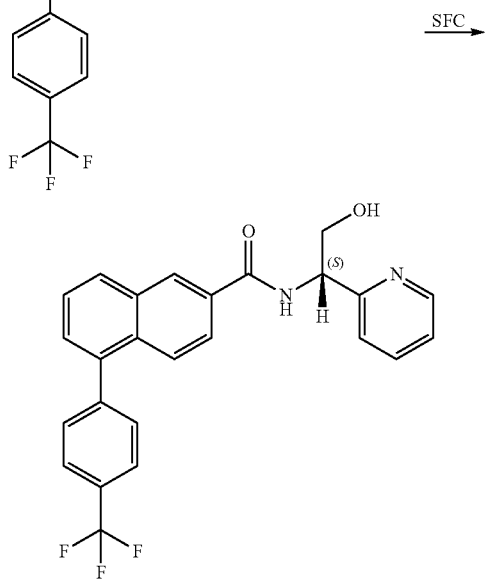

Compound 162

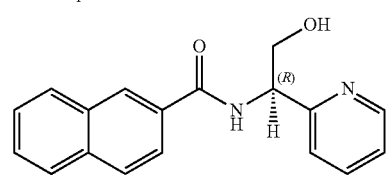

Compound 163

466

2-(2-pyridyl)ethyl 2,2,2-trichloroethanimidate

The mixture of 2-(2-pyridyl)ethanol (200 mg, 1.62 mmol, 0.18 mL, 1 eq), 2,2,2-trichloroacetonitrile (351.7 mg, 2.44 mmol, 0.24 mL, 1.5 eq) and DBU (24.7 mg, 0.16 mmol, 24.4 uL, 0.1 eq) in DCM (16 mL) was stirred at 25° C. for 16 hr. The reaction mixture was diluted with H$_2$O (10 mL) and the mixture was extracted with EA (20 mL*3). The combined organic phase was washed with brine (10 mL*2), dried with anhydrous Na$_2$SO$_4$, filtered and concentrated in vacuum. The residue was purified by column chromatography (SiO$_2$, Petroleum ether/Ethyl acetate=1/0 to 1/1). Compound 2-(2-pyridyl)ethyl 2,2,2-trichloroethanimidate (300 mg, 1.12 mmol, 69.0% yield) was obtained as yellow oil.

4-(2-pyridyl)-2-(trichloromethyl)-4,5-dihydrooxazole

A mixture of 2-(2-pyridyl)ethyl 2,2,2-trichloroethanimidate (200 mg, 0.74 mmol, 1 eq) and NIS (504.5 mg, 2.24 mmol, 3 eq) in DCE (5 mL) in glass vial (purged with N$_2$, sealed with PTFE cap) was heated at 110° C. for 3 hrs. The mixture was used into the next step without further purification.

2-amino-2-(2-pyridyl)ethanol

HCl (12 M, 0.62 mL, 10 eq) was added at the mixture of 4-(2-pyridyl)-2-(trichloromethyl)-4,5-dihydrooxazole (198 mg, 0.74 mmol, 1 eq) in THF (10 mL) was stirred at 25° C. for 5 hr. The reaction mixture was concentrated under reduced pressure to give a residue. Compound 2-amino-2-(2-pyridyl)ethanol (100 mg, crude, HCl) was obtained as brown oil, which was used into the next step without further purification.

N-[2-hydroxy-1-(2-pyridyl)ethyl]-5-[4-(trifluoromethyl)phenyl]naphthalene-2-carboxamide The mixture of 5-[4-(trifluoromethyl)phenyl]naphthalene-2-carboxylic acid (100 mg, 0.31 mmol, 1 eq), 2-amino-2-(2-pyridyl)ethanol (66.2 mg, 0.37 mmol, 1.2 eq, HCl), DIPEA (122.5 mg, 0.94 mmol, 0.16 mL, 3 eq) and HATU (180.3 mg, 0.47 mmol, 1.5 eq) in DCM (2 mL) was stirred at 25° C. for 2 hr. The reaction mixture was diluted with H$_2$O (10 mL) and the mixture was extracted with EA (20 mL*3). The combined organic phase was washed with brine (10 mL*2), dried with anhydrous Na$_2$SO$_4$, filtered and concentrated in vacuum. The residue was purified by prep-HPLC (column: Welch Xtimate C18 150*25 mm*5 um; mobile phase: [water (0.05% HCl)-ACN]; B %: 28%-58%, 8.5 min). Compound N-[2-hydroxy-1-(2-pyridyl)ethyl]-5-[4-(trifluoromethyl)phenyl]naphthalene-2-carboxamide (80 mg, 0.18 mmol, 57.4% yield) was obtained as brown solid.

N-[(1S)-2-hydroxy-1-(2-pyridyl)ethyl]-5-[4-(trifluoromethyl)phenyl]naphthalene-2-carboxamide (Compound 162) and N-[(1R)-2-hydroxy-1-(2-pyridyl)ethyl]-5-[4-(trifluoromethyl)phenyl]naphthalene-2-carboxamide (Compound 163)

The racemic compound N-[2-hydroxy-1-(2-pyridyl)ethyl]-5-[4-(trifluoromethyl)phenyl]naphthalene-2-carboxamide (80 mg, 0.18 mmol, 1 eq) was purified by prep-SFC (column: DAICEL CHIRALPAK AD (250 mm*30 mm, 10 um); mobile phase: [0.1% NH$_3$H$_2$O IPA]; B %: 35%-35%, min). Compound 163 (12.2 mg, 27.8 umol, 15.2% yield)

was obtained as white solid. LCMS (ESI): RT=0.857 min, mass calcd for $C_{25}H_{19}F_3N_2O_2$ 436.43 m/z found 437.0[M+H]$^+$. $^1$H NMR (400 MHz, CDCl$_3$) δ 4.07-4.17 (m, 1H) 4.16-4.24 (m, 1H) 5.41-5.49 (m, 1H) 7.30-7.38 (m, 1H) 7.51 (dd, J=7.13, 1.00 Hz, 1H) 7.56-7.63 (m, 4H) 7.75-7.91 (m, 1H) 7.75-7.85 (m, 2H) 7.76-7.82 (m, 1H) 7.86 (s, 1H) 7.88-7.93 (m, 1H) 8.02 (d, J=8.13 Hz, 1H) 8.16 (br d, J=6.88 Hz, 1H) 8.49 (s, 1H) 8.59 (br d, J=4.63 Hz, 1H). Compound 162 (14.2 mg, 32.2 umol, 17.6% yield) was obtained as white solid. LCMS (ESI): RT=0.857 min, mass calcd for $C_{25}H_{19}F_3N_2O_2$ 436.43 m/z found 437.0[M+H]$^+$. $^1$H NMR (400 MHz, CDCl$_3$) δ 4.04-4.14 (m, 1H) 4.16-4.24 (m, 1H) 5.41-5.46 (m, 1H) 7.32 (dd, J=6.57, 5.07 Hz, 1H) 7.49-7.58 (m, 2H) 7.58-7.65 (m, 4H) 7.75-7.83 (m, 3H) 7.88 (s, 2H) 8.01 (d, J=7.88 Hz, 1H) 8.07 (br d, J=7.38 Hz, 1H) 8.47 (s, 1H) 8.58 (d, J=4.25 Hz, 1H).

Example 143: (S)—N-(3-hydroxy-1-(pyridin-2-yl)propyl)-5-(4-(trifluoromethyl)phenyl)-2-naphthamide (Compound 164) and (R)—N-(3-hydroxy-1-(pyridin-2-yl)propyl)-5-(4-(trifluoromethyl)phenyl)-2-naphthamide (Compound 165)

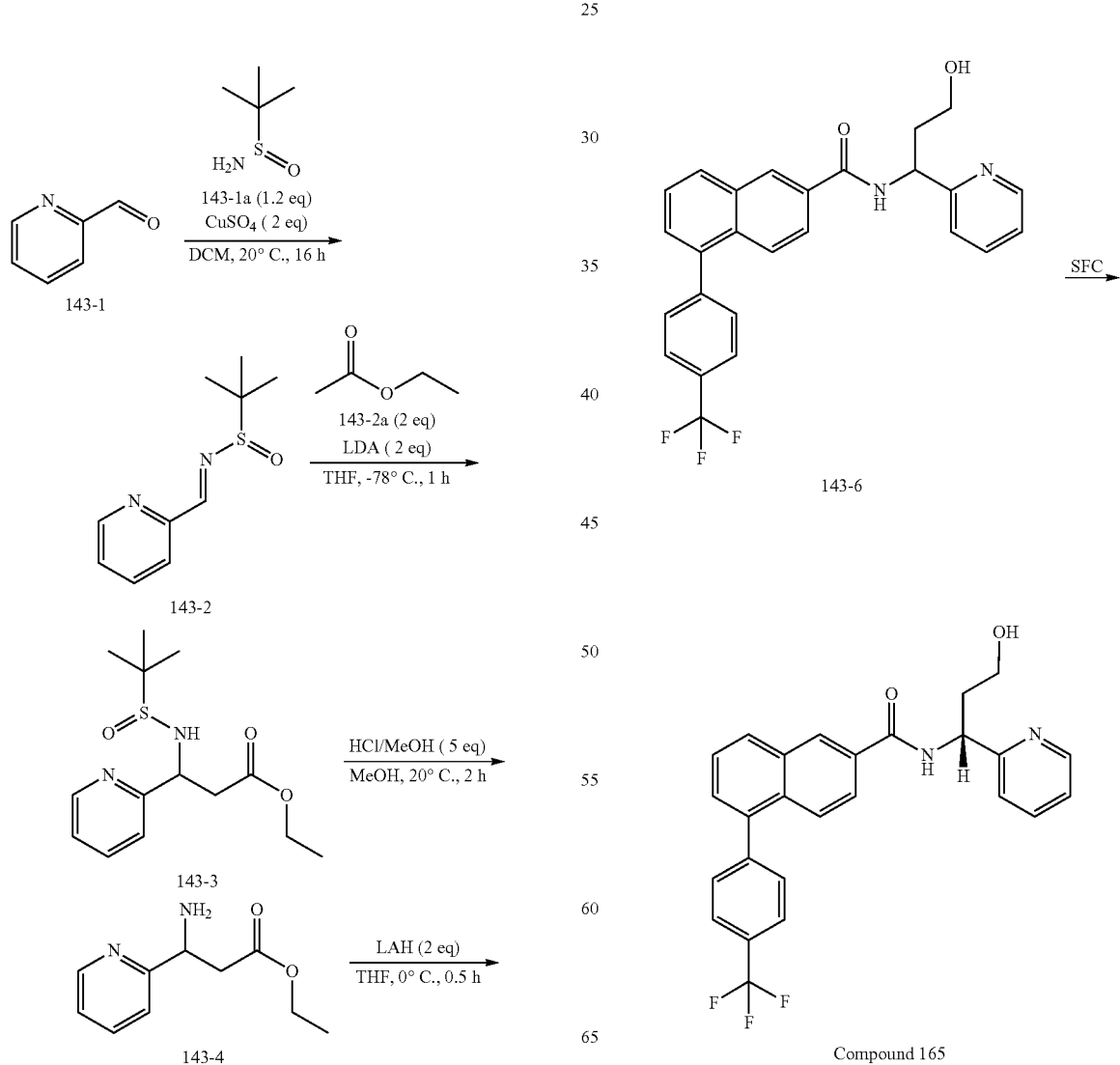

Compound 165

469
-continued

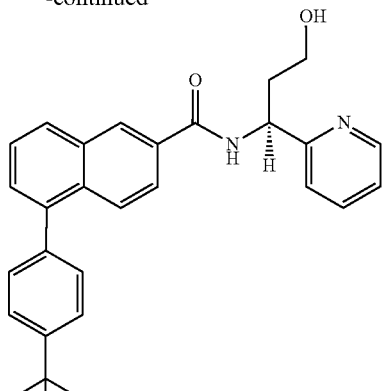

Compound 164

(E)-2-methyl-N-(pyridin-2-ylmethylene)propane-2-sulfinamide

To a solution of 143-1 (3 g, 28.01 mmol, 1 eq) and 143-1a (4.07 g, 33.61 mmol, 1.2 eq) in DCM (56 mL) at 20° C. was added CuSO$_4$ (8.94 g, 56.02 mmol, 8.60 mL, 2 eq). The reaction was stirred at 20° C. for 16 h. The reaction mixture was filtered to remove the solid and the filtrate was concentrated under reduced pressure to give the residue. The residue was diluted with water (100 mL), and then extracted with EA (100 mL*3). The combined organic layers were washed with water (50 mL) and brine (50 mL), dried over anhydrous Na$_2$SO$_4$, filtered and concentrated under reduced pressure to give 143-2 (4.32 g, 20.54 mmol, 73.3% yield) as yellow oil, which was used for next step directly. LCMS (ESI): RT=0.640 min, mass calc. for C$_{10}$H$_{14}$N$_2$OS 210.08, m/z found 210.9 [M+H]$^+$.

Ethyl 3-(1,1-dimethylethylsulfinamido)-3-(pyridin-2-yl)propanoate

To a solution of 143-2a (838.8 mg, 9.52 mmol, 0.93 mL, 2 eq) in THF (5 mL) at −78° C. was added LDA (2 M, 4.76 mL, 2 eq) drop-wise, and the resulting mixture was stirred at −78° C. for 0.5 h. And then the solution of 143-2 (1 g, 4.76 mmol, 1 eq) in THF (5 mL) was added into the above mixture at −78° C. The reaction mixture was stirred at −78° C. for another 0.5 h. The reaction mixture was quenched with saturated NH$_4$Cl solution (20 mL) and then extracted with EA (20 mL*3). The combined organic layers were washed with brine (20 mL), dried over anhydrous Na$_2$SO$_4$, filtered and concentrated under reduced pressure to give a residue. The residue was purified by flash silica gel chromatography (ISCO®; 12 g SepaFlash® Silica Flash Column, Eluent of 0~20% Ethylacetate/Petroleum ether gradient @ 30 mL/min) to give 143-3 (1.2 g, 3.98 mmol, 83.6% yield) as a yellow solid. LCMS (ESI): RT=0.708 min, mass calc. for C$_{14}$H$_{22}$N$_2$O$_3$S, 298.14, m/z found 298.9 [M+H]$^+$.

Ethyl 3-amino-3-(pyridin-2-yl)propanoate

To a solution of 143-3 (300 mg, 1.01 mmol, 1 eq) in MeOH (2 mL) at 20° C. was added HCl/MeOH (4 M, 1.26

470 mL, 5 eq). The reaction mixture was stirred at 20° C. for 2 h. The reaction mixture was concentrated under reduced pressure to give 143-4 (195 mg, 1.00 mmol, 99.9% yield) as a yellow solid, which was used directly for next step.

3-amino-3-(pyridin-2-yl)propan-1-ol

To a solution of 143-4 (195 mg, 1.00 mmol, 1 eq) in THF (3 mL) at 0° C. was added LAH (76.2 mg, 2.01 mmol, 2 eq). The reaction mixture was stirred at 0° C. for 0.5 h. The reaction mixture was quenched with water (0.08 mL), then 2 N NaOH (0.1 mL) and then water (0.24 mL), and then diluted with EA (20 mL). The resulting mixture was dried over anhydrous Na$_2$SO$_4$, and filtered to remove the solid. The filtrate was concentrated under reduced pressure to give 143-5 (150 mg, 0.99 mmol, 98.2% yield) as yellow oil, which was used directly for next step.

N-(3-hydroxy-1-(pyridin-2-yl)propyl)-5-(4-(trifluoromethyl)phenyl)-2-naphthamide To a solution of 143-5a (150 mg, 0.47 mmol, 1 eq), 143-5 (144.4 mg, 0.95 mmol, 2 eq) and HATU (234.4 mg, 0.62 mmol, 1.3 eq) in DMF (2 mL) at 20° C. was added TEA (144.0 mg, 1.42 mmol, 0.20 mL, 3 eq). The reaction mixture was stirred at 20° C. for 16 h. The reaction mixture was concentrated under reduced pressure to give a residue. The residue was purified by prep-HPLC (column: Waters Xbridge BEH C18 100*25 mm*5 um; mobile phase: [water (0.05% ammonia hydroxide v/v)-ACN]; B %: 35%-75%, 9.5 min) to give 143-6 (130 mg, 0.29 mmol, 60.9% yield) as colorless oil.

(S)—N-(3-hydroxy-1-(pyridin-2-yl)propyl)-5-(4-(trifluoromethyl)phenyl)-2-naphthamide (Compound 164) and (R)—N-(3-hydroxy-1-(pyridin-2-yl)propyl)-5-(4-(trifluoromethyl)phenyl)-2-naphthamide (Compound 165)

The sample 143-6 (80 mg, 0.18 mmol, 1 eq) was purified by SFC (column: DAICEL CHIRALPAK AD (250 mm*30 mm, 10 um); mobile phase: [0.1% NH$_3$H$_2$O ETOH]; B %: 55%-55%, min) to give Compound 165 (31.7 mg, 70.5 umol, 39.7% yield) as a white solid and Compound 164 (30.8 mg, 68.4 umol, 38.5% yield) as a white solid. Compound 165 LCMS (ESI): RT=0.796 min, mass calc. for C$_{26}$H$_{21}$F$_3$N$_2$O$_2$ 450.16, m/z found 450.9 [M+H]$^+$; $^1$H NMR (400 MHz, CD$_3$OD) δ 8.58-8.48 (m, 2H), 8.08 (d, J=8.1 Hz, 1H), 7.93-7.79 (m, 5H), 7.71-7.64 (m, 3H), 7.55 (dd, J=7.4, 16.8 Hz, 2H), 7.32 (dd, J=5.4, 7.0 Hz, 1H), 5.42 (dd, J=5.9, 8.4 Hz, 1H), 3.76-3.63 (m, 2H), 2.28-2.16 (m, 2H). Compound 164 LCMS (ESI): RT=0.799 min, mass calc. for C$_{26}$H$_{21}$F$_3$N$_2$O$_2$ 450.16, m/z found 451.0 [M+H]$^+$; $^1$H NMR (400 MHz, CD$_3$OD) δ 8.57-8.51 (m, 2H), 8.08 (d, J=8.3 Hz, 1H), 7.93-7.79 (m, 5H), 7.71-7.63 (m, 3H), 7.60-7.51 (m, 2H), 7.33 (ddd, J=1.0, 5.0, 7.5 Hz, 1H), 5.42 (dd, J=5.9, 8.4 Hz, 1H), 3.76-3.63 (m, 2H), 2.30-2.13 (m, 2H).

Example 144: N-[(1S)-3-hydroxy-1-methyl-propyl]-5-[4-(trifluoromethyl)phenyl]naphthalene-2-carboxamide (Compound 166) and N-[(1R)-3-hydroxy-1-methyl-propyl]-5-[4-(trifluoromethyl)phenyl]naphthalene-2-carboxamide (Compound 167)

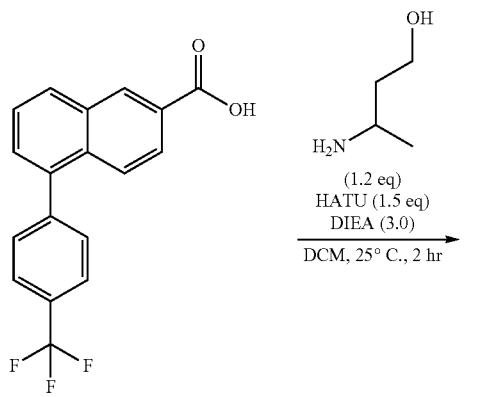

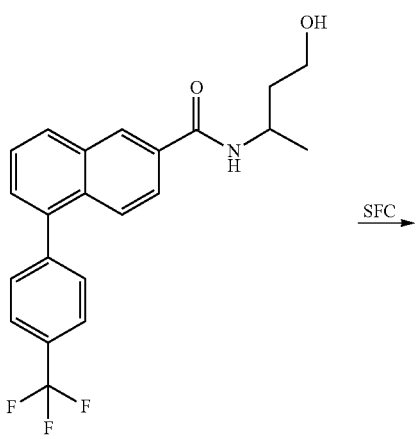

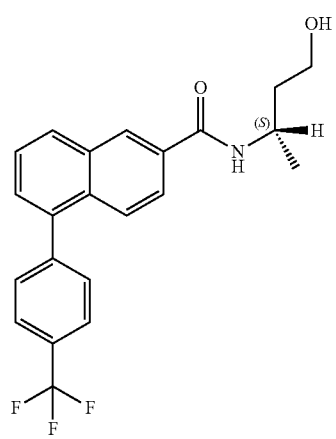

Compound 166

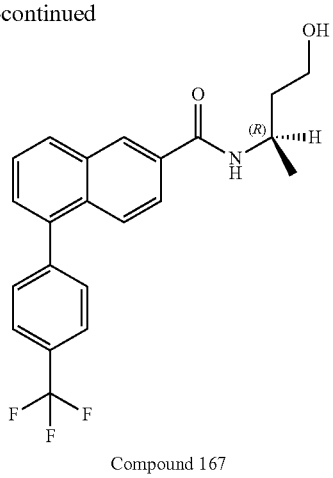

Compound 167

N-(3-hydroxy-1-methyl-propyl)-5-[4-(trifluoromethyl)phenyl]naphthalene-2-carboxamide The mixture of 5-[4-(trifluoromethyl)phenyl]naphthalene-2-carboxylic acid (90 mg, 0.28 mmol, 1 eq), 3-aminobutan-1-ol (30.4 mg, 0.34 mmol, 1.2 eq), HATU (162.3 mg, 0.42 mmol, 1.5 eq) and DIPEA (110.3 mg, 0.85 mmol, 0.14 mL, 3 eq) in DCM (5 mL) was stirred at 25° C. for 2 hr. The reaction mixture was diluted with H$_2$O (10 mL) and the mixture was extracted with EA (20 mL*3). The combined organic phase was washed with brine (10 mL*2), dried with anhydrous Na$_2$SO$_4$, filtered and concentrated in vacuum. The residue was purified by column chromatography (SiO$_2$, Petroleum ether/Ethyl acetate=1/0 to 1/1). Compound N-(3-hydroxy-1-methyl-propyl)-5-[4-(trifluoromethyl)phenyl]naphthalene-2-carboxamide (100 mg, 0.25 mmol, 90.7% yield) was obtained as white solid.

N-[(1S)-3-hydroxy-1-methyl-propyl]-5-[4-(trifluoromethyl)phenyl]naphthalene-2-carboxamide (Compound 166) and N-[(1R)-3-hydroxy-1-methyl-propyl]-5-[4-(trifluoromethyl)phenyl]naphthalene-2-carboxamide (Compound 167)

The racemic compound N-(3-hydroxy-1-methyl-propyl)-5-[4-(trifluoromethyl)phenyl]naphthalene-2-carboxamide (90 mg, 0.23 mmol) was separated by SFC (column: DAICEL CHIRALPAK IC (250 mm*30 mm, 5 um); mobile phase: [0.1% NH$_3$H$_2$O IPA]; B %: 35%-35%, min). Compound 167 (12.0 mg, 30.7 umol, 13.2% yield) was obtained as yellow solid. LCMS (ESI): RT=0.923 min, mass calcd for C$_{22}$H$_{20}$F$_3$NO$_2$ 387.39 m/z found 388.0[M+H]$^+$, $^1$H NMR (400 MHz, DMSO-d$_6$) δ ppm 1.21 (d, J=6.63 Hz, 3H) 1.62-1.82 (m, 2H) 3.45-3.54 (m, 2H) 4.14-4.24 (m, 1H) 4.47 (t, J=5.07 Hz, 1H) 7.59 (d, J=6.50 Hz, 1H) 7.66-7.77 (m, 3H) 7.81 (d, J=8.88 Hz, 1H) 7.88-7.97 (m, 3H) 8.12 (d, J=8.25 Hz, 1H) 8.43 (d, J=8.13 Hz, 1H) 8.54 (d, J=1.25 Hz, 1H). Compound 166 (15.4 mg, 39.8 umol, 17.14% yield) was obtained as yellow solid. LCMS (ESI): RT=0.927 min, mass calcd for C$_{22}$H$_{20}$F$_3$NO$_2$ 387.39 m/z found 338.0[M+H]$^+$. $^1$H NMR (400 MHz, DMSO-d$_6$) δ ppm 1.20 (d, J=6.63 Hz, 3H) 1.62-1.82 (m, 2H) 3.49 (br t, J=6.25 Hz, 2H) 4.14-4.23 (m, 1H) 4.49 (br s, 1H) 7.58 (d, J=7.00 Hz, 1H) 7.65-7.76 (m, 3H) 7.80 (d, J=8.88 Hz, 1H) 7.88-7.95 (m, 3H) 8.12 (d, J=8.13 Hz, 1H) 8.43 (d, J=8.13 Hz, 1H) 8.54 (d, J=1.00 Hz, 1H).

Example 145: (S)—N-(4-aminobutan-2-yl)-5-(4-(trifluoromethyl)phenyl)-2-naphthamide (Compound 168) and (R)—N-(4-aminobutan-2-yl)-5-(4-(trifluoromethyl)phenyl)-2-naphthamide (Compound 169)
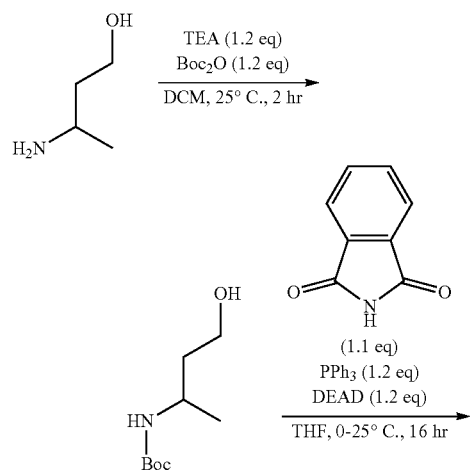
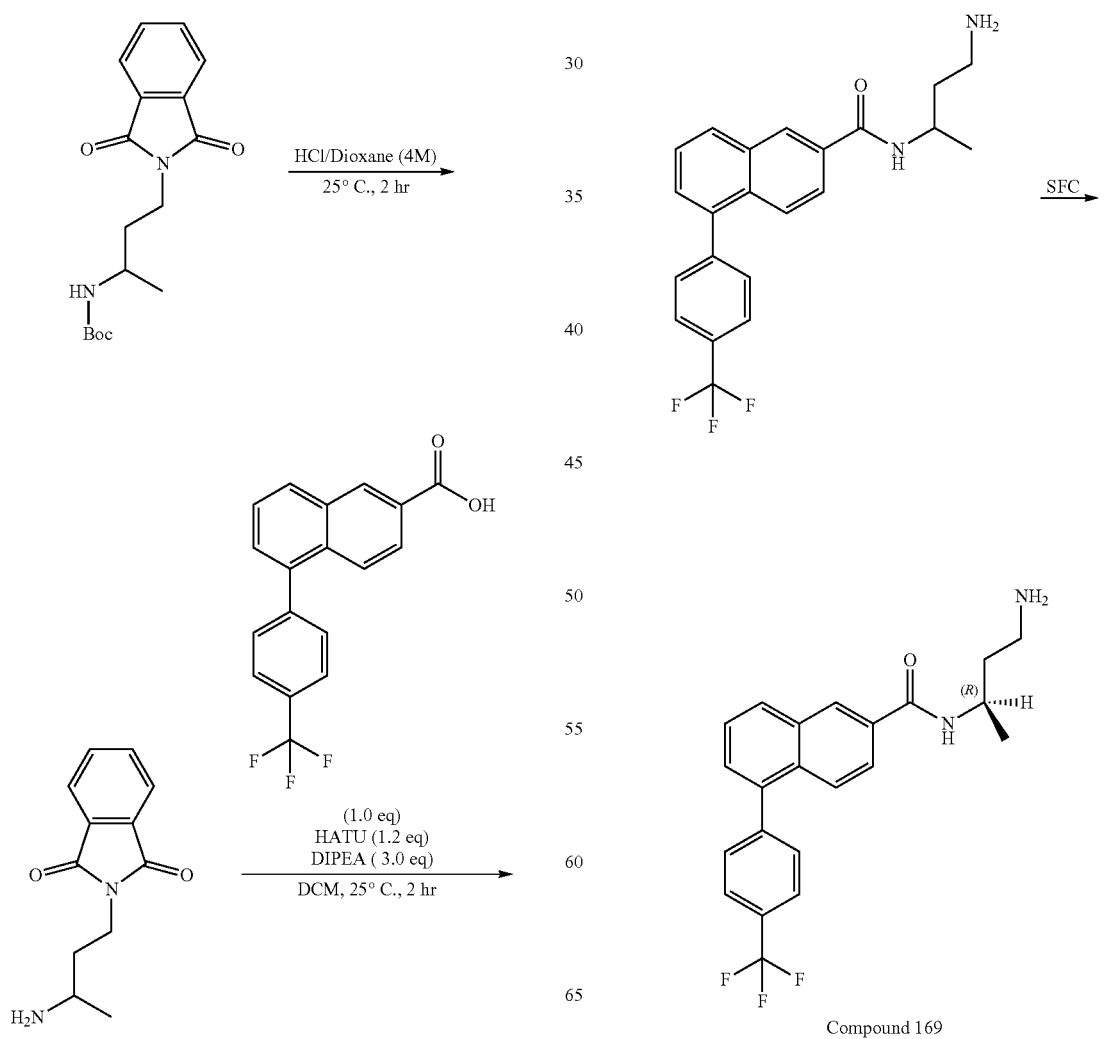
Compound 169

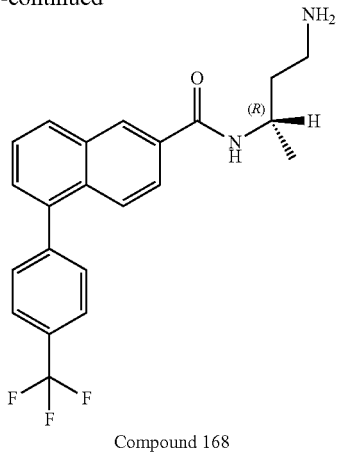

Compound 168

Tert-Butyl (4-hydroxybutan-2-yl)carbamate

To a solution of 3-aminobutan-1-ol (300 mg, 3.37 mmol, 1 eq) and TEA (408 mg, 4.04 mmol, 1.2 eq) in DCM (5 mL) was added Boc$_2$O (881 mg, 4.04 mmol, 1.2 eq). The reaction mixture was stirred at 25° C. for 2 hrs. The reaction mixture was concentrated under reduced pressure. The mixture was diluted with water (10 mL) and the resultant mixture was extracted with EA (20 mL*3). The combined organic layers were dried over Na$_2$SO$_4$, filtered and concentrated to dryness under reduced pressure. The residue was purified by column chromatography over silica gel (petroleum ether:ethyl acetate=1:0 to 1:1) to afford tert-Butyl (4-hydroxybutan-2-yl)carbamate (530 mg, 83% yield) as colorless oil. $^1$H NMR (400 MHz, CDCl$_3$) δ 4.42 (br s, 1H), 3.91 (br s, 1H), 3.64 (dd, J=2.9, 7.9 Hz, 2H), 1.88-1.76 (m, 1H), 1.46 (s, 9H), 1.38-1.27 (m, 1H), 1.20 (d, J=6.5 Hz, 3H).

Tert-Butyl (4-(1,3-dioxoisoindolin-2-yl)butan-2-yl)carbamate

To a solution of tert-butyl N-(3-hydroxy-1-methyl-propyl)carbamate (430 mg, 2.27 mmol, 1 eq), isoindoline-1,3-dione (367 mg, 2.50 mmol, 1.1 eq) and PPh$_3$ (715 mg, 2.73 mmol, 1.2 eq) in THF (5 mL) was added DEAD (474 mg, 2.73 mmol, 1.2 eq) dropwise at 0° C. The reaction mixture was stirred at 25° C. for 16 hrs. The reaction mixture was concentrated under reduced pressure. The mixture was diluted with water (30 mL) and the resultant mixture was extracted with EA (50 mL*3). The combined organic layers were dried over Na$_2$SO$_4$, filtered and concentrated to dryness under reduced pressure. The residue was purified by column chromatography over silica gel (petroleum ether: ethyl acetate=1:0 to 2:1) to afford tert-Butyl (4-(1,3-dioxoisoindolin-2-yl)butan-2-yl)carbamate (700 mg, 78% yield) as a white solid.

2-(3-Aminobutyl)isoindoline-1,3-dione

A solution of tert-butyl N-[3-(1,3-dioxoisoindolin-2-yl)-1-methyl-propyl]carbamate (120 mg, 0.37 mmol, 1 eq) in 4M of HCl/dioxane (3 mL) was stirred at 25° C. for 2 hrs. The reaction mixture was concentrated under reduced pressure to give 2-(3-Aminobutyl)isoindoline-1,3-dione (85 mg, crude, HCl) as a white solid.

N-(4-(1,3-Dioxoisoindolin-2-yl)butan-2-yl)-5-(4-(trifluoromethyl)phenyl)-2-naphthamide To a solution of 5-[4-(trifluoromethyl)phenyl]naphthalene-2-carboxylic acid (100 mg, 0.31 mmol, 1 eq), 2-(3-aminobutyl)isoindoline-1,3-dione (80.5 mg, 0.31 mmol, 1 eq, HCl) and DIPEA (122.5 mg, 0.94 mmol, 3 eq) in DCM (3 mL) was added HATU (144.2 mg, 0.38 mmol, 1.2 eq). The reaction mixture was stirred at 25° C. for 2 hrs. The reaction mixture was concentrated under reduced pressure. The mixture was diluted with water (30 mL) and the resultant mixture was extracted with EA (50 mL*3). The combined organic layers were dried over Na$_2$SO$_4$, filtered and concentrated to dryness under reduced pressure. The residue was purified by column chromatography over silica gel (petroleum ether:ethyl acetate=1:0 to 2:1) to afford N-(4-(1,3-Dioxoisoindolin-2-yl)butan-2-yl)-5-(4-(trifluoromethyl)phenyl)-2-naphthamide (150 mg, 90% yield) as a white solid.

N-(4-Aminobutan-2-yl)-5-(4-(trifluoromethyl)phenyl)-2-naphthamide

NH$_2$NH$_2$·H$_2$O (126.0 mg, 2.52 mmol, 10 eq) was added to a solution of N-[3-(1,3-dioxoisoindolin-2-yl)-1-methyl-propyl]-5-[4-(trifluoromethyl)phenyl]naphthalene-2-carboxamide (130 mg, 0.25 mmol, 1 eq) in EtOH (8 mL). The reaction mixture was stirred at 25° C. for 5 hrs. The reaction mixture was concentrated under reduced pressure. The mixture was diluted with water (10 mL) and the resultant mixture was extracted with EA (20 mL*3). The combined organic layers were dried over Na$_2$SO$_4$, filtered and concentrated to dryness under reduced pressure. The residue was purified by prep-HPLC (column: Welch Xtimate C18 150*25 mm*5 um; mobile phase: [water (0.05% HCl)-ACN]; B %: 20%-50%, 8.5 min) to give N-(4-Aminobutan-2-yl)-5-(4-(trifluoromethyl)phenyl)-2-naphthamide (75 mg, 70% yield, HCl) as a white solid. LCMS (ESI): RT=0.839 min, mass calcd for C$_{22}$H$_{21}$F$_3$N$_2$O, 368.16 m/z, found 387.1 [M+H]$^+$.

(S)—N-(4-aminobutan-2-yl)-5-(4-(trifluoromethyl)phenyl)-2-naphthamide (Compound 168) and (R)—N-(4-aminobutan-2-yl)-5-(4-(trifluoromethyl)phenyl)-2-naphthamide (Compound 169)

N-(3-Amino-1-methyl-propyl)-5-[4-(trifluoromethyl)phenyl]naphthalene-2-carboxamide (75 mg, 0.17 mmol, 1 eq, HCl) was separate by SFC (column: Daicel ChiralPak IG (250*30 mm, 10 um); mobile phase: [0.1% NH$_3$H$_2$O MEOH]; B %: 20%-20%, min). The pure fractions were collected and the volatiles were removed under vacuum. The residue was re-suspended in water (10 mL) and ACN (1 mL), and then the resulting mixture were lyophilized to dryness to remove the solvent residue completely to give Compound 169 (R)—N-(4-aminobutan-2-yl)-5-(4-(trifluoromethyl)phenyl)-2-naphthamide (22.04 mg, 57 umol, 32% yield) as a light yellow solid and Compound 168 (S)—N-(4-aminobutan-2-yl)-5-(4-(trifluoromethyl)phenyl)-2-naphthamide (21.54 mg, 55 umol, 31% yield) as a light yellow solid. Compound 169 LCMS (ESI): RT=0.845 min, mass calcd for C$_{22}$H$_{21}$F$_3$N$_2$O 368.16 m/z, found 387.0 [M+H]$^+$, $^1$H NMR (400 MHz, DMSO-d$_6$) δ 8.60-8.52 (m, 2H), 8.13 (d, J=8.0 Hz, 1H), 7.92 (br d, J=8.0 Hz, 3H), 7.81 (d, J=8.8 Hz, 1H), 7.77-7.66 (m, 3H), 7.59 (d, J=6.3 Hz, 1H), 4.25-4.12 (m, 1H), 2.61 (t, J=6.8 Hz, 2H), 1.72-1.53 (m, 2H), 1.20 (d, J=6.8 Hz, 3H). Compound 168 LCMS (ESI): RT=0.836 min, mass calcd for $C_{22}H_{21}F_3N_2O$ 368.16 m/z, found 387.1 [M+H]$^+$, $^1$H NMR (400 MHz, DMSO-d$_6$) δ 8.62-8.51 (m, 2H), 8.13 (d, J=8.3 Hz, 1H), 7.96-7.88 (m, 3H), 7.81 (d, J=9.0 Hz, 1H), 7.77-7.66 (m, 3H), 7.62-7.56 (m, 1H), 4.31-4.10 (m, 1H), 2.63 (t, J=6.9 Hz, 2H), 1.73-1.55 (m, 2H), 1.21 (d, J=6.5 Hz, 3H).

Example 146: N-((2-(fluoromethyl)pyrimidin-4-yl)methyl)-5-(4-(trifluoromethyl)phenyl)-2-naphthamide (Compound 170)

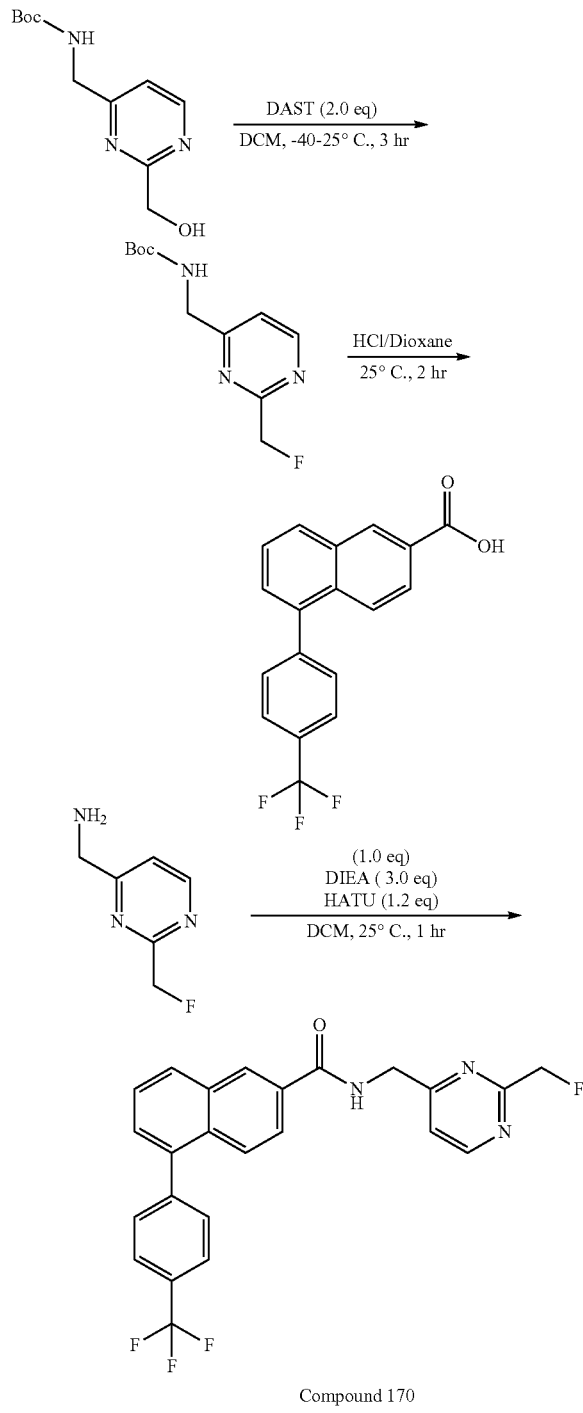

Compound 170

Tert-Butyl ((2-(fluoromethyl)pyrimidin-4-yl)methyl)carbamate

To a solution of tert-butyl N-[[2-(hydroxymethyl)pyrimidin-4-yl]methyl]carbamate (20 mg, 83 umol, 1 eq) in DCM (0.5 mL) was added N-ethyl-N-(trifluoro-sulfanyl) ethanamine (26.9 mg, 0.16 mmol, 2 eq) at −40° C. The reaction mixture was allowed to warm up to 25° C. and stirred at 25° C. for 3 hrs. The reaction mixture was concentrated under reduced pressure. The residue was purified by Pre-TLC (Petroleum ether:Ethyl acetate=1:1) to obtain the title compound as a white solid. Compound tert-butyl N-[[2-(fluoromethyl)pyrimidin-4-yl]methyl]carbamate (8 mg, 33 umol, 39.6% yield) was obtained as a white solid.

(2-(Fluoromethyl)pyrimidin-4-yl)methanamine

A solution of tert-butyl N-[[2-(fluoromethyl)pyrimidin-4-yl]methyl]carbamate (8 mg, 33 umol, 1 eq) in 4M of HCl/dioxane (1 mL) was stirred at 25° C. for 2 hrs. The reaction mixture was concentrated under reduced pressure. Compound [2-(fluoromethyl)pyrimidin-4-yl]methanamine (5.8 mg, crude, HCl) was obtained as a yellow solid.

N-((2-(fluoromethyl)pyrimidin-4-yl)methyl)-5-(4-(trifluoromethyl)phenyl)-2-naphthamide To a solution of 5-[4-(trifluoromethyl)phenyl]naphthalene-2-carboxylic acid (10 mg, 31 umol, 1 eq) and DIPEA (12.2 mg, 94 umol, 3 eq) in DCM (1 mL) was added HATU (14.4 mg, 38 umol, 1.2 eq). The reaction mixture was stirred at 25° C. for 15 min. After [2-(fluoromethyl)pyrimidin-4-yl]methanamine (5.6 mg, 31 umol, 1 eq, HCl) was added, the reaction mixture was stirred at 25° C. for 45 min. The reaction mixture was concentrated under reduced pressure. The mixture was diluted with water (10 mL) and the resultant mixture was extracted with DCM (20 mL*3). The combined organic layers were dried over Na$_2$SO$_4$, filtered and concentrated to dryness under reduced pressure. The residue was purified by prep-HPLC (column: Welch Xtimate C18 150*25 mm*5 um; mobile phase: [water (0.05% HCl)-ACN]; B %: 55%-85%, 8.5 min) to give the title compound as a light yellow solid. Compound N-[[2-(fluoromethyl)pyrimidin-4-yl]methyl]-5-[4-(trifluoromethyl)phenyl]naphthalene-2-carboxamide (1.3 mg, 3.1 umol, 9.7% yield) was obtained as a white solid. LCMS (ESI): RT=0.935 min, mass calcd for $C_{24}H_{17}F_4N_3O$ 439.13 m/z, found 440.0 [M+H]$^+$, $^1$H NMR (400 MHz, CD$_3$OD) δ 8.77 (d, J=5.3 Hz, 1H), 8.57 (s, 1H), 8.10 (d, J=8.3 Hz, 1H), 7.97-7.92 (m, 1H), 7.92-7.87 (m, 1H), 7.85 (d, J=8.1 Hz, 2H), 7.73-7.66 (m, 3H), 7.59 (d, J=6.5 Hz, 1H), 7.50 (d, J=5.4 Hz, 1H), 5.60-5.46 (m, 2H), 4.76 (s, 2H).

Example 147: N-((2-((Isoxazol-3-yloxy)methyl)pyrimidin-4-yl)methyl)-5-(4-(trifluoromethyl)phenyl)-2-naphthamide (Compound 171)

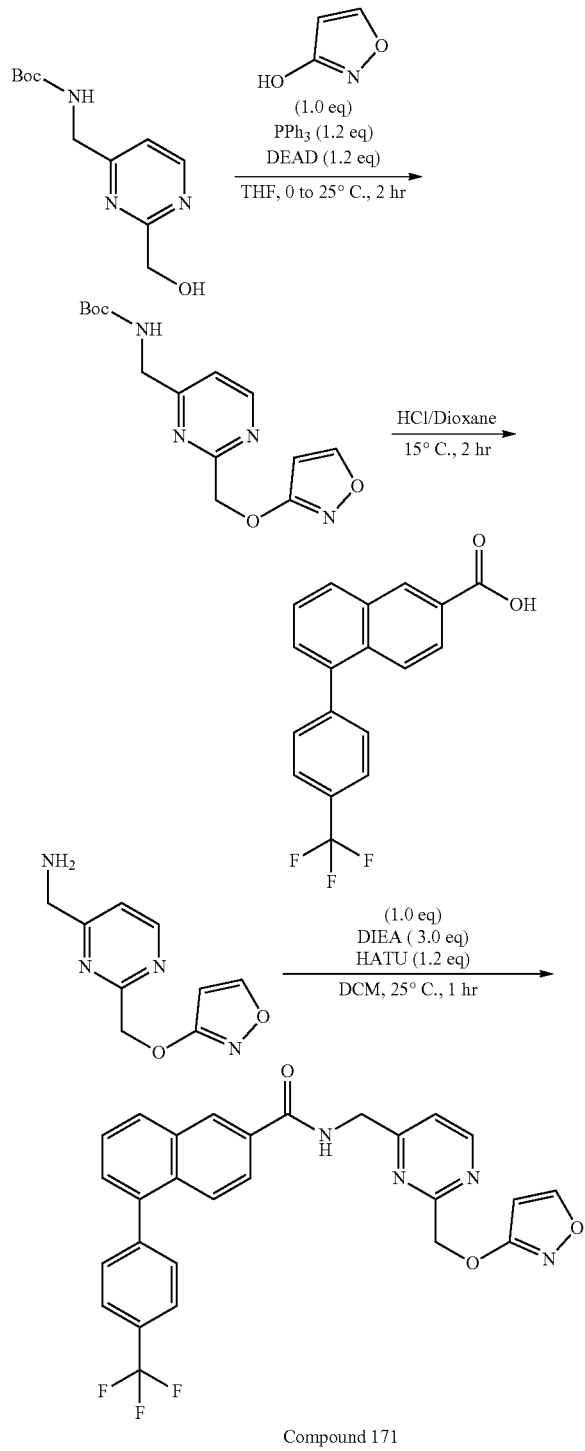 [SMILES: CC(C)(C)OC(=O)NCc1ccnc(CO)n1 ; Oc1ccon1 ; CC(C)(C)OC(=O)NCc1ccnc(COc2ccon2)n1 ; NCc1ccnc(COc2ccon2)n1 ; O=C(O)c1ccc2c(-c3ccc(C(F)(F)F)cc3)cccc2c1 ; O=C(NCc1ccnc(COc2ccon2)n1)c1ccc2c(-c3ccc(C(F)(F)F)cc3)cccc2c1]

Compound 171

Tert-Butyl ((2-((isoxazol-3-yloxy)methyl)pyrimidin-4-yl)methyl)carbamate

DEAD (26.2 mg, 0.15 mmol, 1.2 eq) was added to a solution of tert-butyl N-[[2-(hydroxymethyl)pyrimidin-4-yl]methyl]carbamate (30.0 mg, 0.12 mmol, 1 eq), isoxazol-3-ol (12.8 mg, 0.15 mmol, 1.2 eq) and PPh$_3$ (39.4 mg, 0.15 mmol, 1.2 eq) in THF (1 mL) dropwise at 0° C. under N$_2$. The reaction mixture allowed to warm up to 25° C. and stirred at 25° C. for 2 hrs. The reaction mixture was concentrated under reduced pressure. The mixture was diluted with water (10 mL) and the resultant mixture was extracted with EA (20 mL*3). The combined organic layers were dried over Na$_2$SO$_4$, filtered and concentrated to dryness under reduced pressure. The residue was purified by Pre-TLC (Ethyl acetate) to obtain the title compound as a light yellow solid. Compound tert-butyl N-[[2-(isoxazol-3-yloxymethyl)pyrimidin-4-yl]methyl]carbamate (15 mg, 41.6 umol, 33.2% yield) was obtained as a light yellow solid.

(2-((Isoxazol-3-yloxy)methyl)pyrimidin-4-yl)methanamine

A mixture of tert-butyl N-[[2-(isoxazol-3-yloxymethyl)pyrimidin-4-yl]methyl]carbamate (15.0 mg, 49 umol, 1 eq) in 4M of HCl/dioxane (1 mL) was stirred at 15° C. for 2 hrs. The reaction mixture was concentrated under reduced pressure. Compound [2-(isoxazol-3-yloxymethyl)pyrimidin-4-yl]methanamine (10 mg, 41 umol, 84.1% yield, HCl) was obtained as a yellow solid.

N-((2-((Isoxazol-3-yloxy)methyl)pyrimidin-4-yl)methyl)-5-(4-(trifluoromethyl)phenyl)-2-naphthamide To a solution of 5-[4-(trifluoromethyl)phenyl]naphthalene-2-carboxylic acid (12.0 mg, 38 umol, 1 eq), [2-(isoxazol-3-yloxymethyl)pyrimidin-4-yl]methanamine (10.0 mg, 41 umol, 1.1 eq, HCl) and DIPEA (14.7 mg, 0.11 mmol, 3 eq) in DCM (1 mL) was added HATU (17.3 mg, 45.5 umol, 1.2 eq). The reaction mixture was stirred at 25° C. for 1 hr. The reaction mixture was concentrated under reduced pressure. The mixture was diluted with water (10 mL) and the resultant mixture was extracted with EA (20 mL*3). The combined organic layers were dried over Na$_2$SO$_4$, filtered and concentrated to dryness under reduced pressure. The residue was purified by prep-HPLC (column: Waters Xbridge BEH C18 100*25 mm*5 um; mobile phase: [water (0.05% ammonia hydroxide v/v)-ACN]; B %: 40%-70%, 9.5 min) to give the title compound (2.5 mg, 5 umol, 13.1% yield). LCMS (ESI): RT=0.951 min, mass calcd for C$_{27}$H$_{19}$F$_3$N$_4$O$_3$ 540.14 m/z, found 505.1 [M+H]$^+$, $^1$H NMR (400 MHz, CDCl$_3$) δ 8.76 (d, J=5.3 Hz, 1H), 8.47 (s, 1H), 8.11 (d, J=1.5 Hz, 1H), 8.04 (d, J=8.3 Hz, 1H), 7.94-7.89 (m, 1H), 7.88-7.83 (m, 1H), 7.80 (d, J=8.0 Hz, 2H), 7.68-7.60 (m, 3H), 7.59-7.51 (m, 2H), 7.36-7.31 (m, 1H), 7.33 (d, J=5.3 Hz, 1H), 6.12 (d, J=1.5 Hz, 1H), 5.56 (s, 2H), 4.85 (d, J=5.0 Hz, 2H).

Example 148: N-((2-((2,6-difluorophenoxy)methyl)pyrimidin-4-yl)methyl)-5-(4-(trifluoromethyl)phenyl)-2-naphthamide (Compound 172)

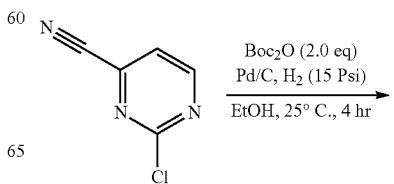

481

-continued

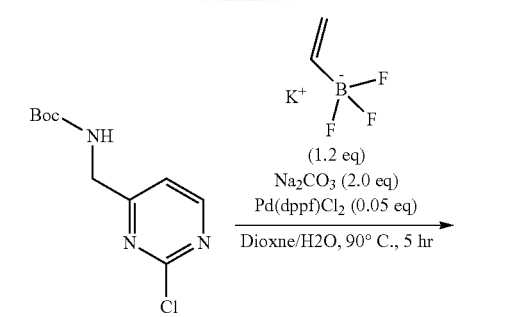

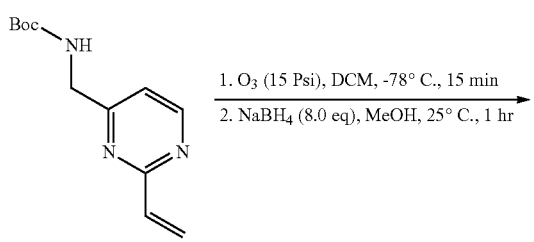

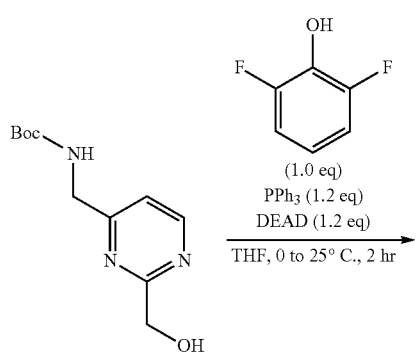

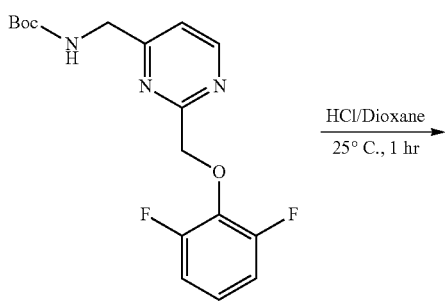

482

-continued

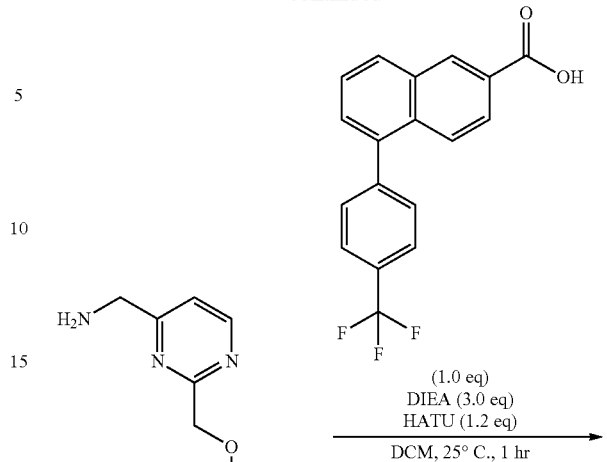

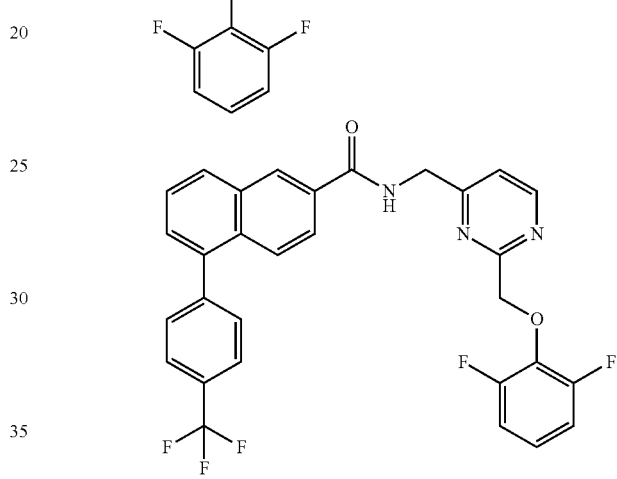

Compound 172

Tert-Butyl ((2-chloropyrimidin-4-yl)methyl)carbamate

A solution of 2-chloropyrimidine-4-carbonitrile (1 g, 7.17 mmol, 1 eq), Boc$_2$O (3.13 g, 14.33 mmol, 3.29 mL, 2 eq) and Pd/C (200 mg, 10%) in EtOH (60 mL) was stirred at 25° C. for 4 hrs under H$_2$ (15 Psi). The reaction mixture was filtered and the filtrate was concentrated under reduce pressure. The residue was purified by column chromatography over silica gel (petroleum ether:ethyl acetate=1:0 to 3:1) to afford the title compound as a light yellow solid. Compound tert-butyl N-[(2-chloropyrimidin-4-yl)methyl]carbamate (630 mg, 2.15 mmol, 29.9% yield) was obtained as a light yellow solid

Tert-Butyl ((2-vinylpyrimidin-4-yl)methyl)carbamate

To a solution of tert-butyl N-[(2-chloropyrimidin-4-yl)methyl]carbamate (700 mg, 2.87 mmol, 1 eq), potassium trifluoro(vinyl)borate (461.7 mg, 3.45 mmol, 1.2 eq) and Na$_2$CO$_3$ (608.9 mg, 5.75 mmol, 2 eq) in Dioxane (10 mL) and H$_2$O (2 mL) was added Pd(dppf)Cl$_2$ (105.0 mg, 0.14 mmol, 0.05 eq) under N$_2$. The suspension was degassed under vacuum and purged with N$_2$ several times. The mixture was stirred at 90° C. for 5 hrs under N$_2$. The reaction mixture was concentrated under reduced pressure. The mixture was diluted with water (10 mL) and the resultant mixture was extracted with EA (20 mL*3). The combined organic layers were dried over Na$_2$SO$_4$, filtered and concentrated to dryness under reduced pressure. The residue was purified by column chromatography over silica gel (petroleum ether:ethyl acetate=1:0 to 3:1) to afford the title compound as a light yellow solid. Compound tert-butyl N-[(2-vinylpyrimidin-4-yl)methyl]carbamate (530 mg, 2.25 mmol, 78.4% yield) was obtained as a light yellow solid.

Tert-Butyl ((2-(hydroxymethyl)pyrimidin-4-yl)methyl)carbamate tert-butyl N-[(2-vinylpyrimidin-4-yl)methyl]carbamate (530 mg, 2.25 mmol, 1 eq) was dissolved in DCM (10 mL) and cooled to −78° C. Ozone was bubbled through the solution for 15 min and the reaction was allowed to warm to 25° C. as then purged with N2. NaBH4 (681.7 mg, 18.02 mmol, 8 eq) in MeOH (4 mL) was added and the reaction allowed to stir for 1 hr at 25° C. The reaction mixture was concentrated under reduced pressure. The mixture was diluted with water (10 mL) and the resultant mixture was extracted with EA (20 mL*3). The combined organic layers were dried over Na$_2$SO$_4$, filtered and concentrated to dryness under reduced pressure. The residue was purified by column chromatography over silica gel (petroleum ether: ethyl acetate=1:0 to 2:3) to afford the title compound. Compound tert-butyl N-[[2-(hydroxymethyl)pyrimidin-4-yl]methyl]carbamate (75 mg, 0.31 mmol, 13.9% yield) was obtained as a white solid.

Tert-Butyl ((2-((2,6-difluorophenoxy)methyl)pyrimidin-4-yl)methyl)carbamate

DEAD (26.2 mg, 0.15 mmol, 27.3 uL, 1.2 eq) was added to a solution of tert-butyl N-[[2-(hydroxymethyl)pyrimidin-4-yl]methyl]carbamate (30 mg, 0.12 mmol, 1 eq), 2,6-difluorophenol (16.3 mg, 0.12 mmol, 1 eq) and PPh$_3$ (39.4 mg, 0.15 mmol, 1.2 eq) in THF (1 mL) dropwise at 0° C. under N$_2$. The reaction mixture allowed to warm up to 25° C. and stirred at 25° C. for 2 hrs. The reaction mixture was concentrated under reduced pressure. The mixture was diluted with water (10 mL) and the resultant mixture was extracted with EA (20 mL*3). The combined organic layers were dried over Na$_2$SO$_4$, filtered and concentrated to dryness under reduced pressure. The residue was purified by Pre-TLC (Petroleum ether:Ethyl acetate=2:1) to obtain the title compound as a white solid. Compound tert-butyl N-[[2-[(2,6-difluorophenoxy)methyl]pyrimidin-4-yl]methyl]carbamate (40 mg, 88.8 umol, 70.8% yield) was obtained as a white solid.

(2-((2,6-difluorophenoxy)methyl)pyrimidin-4-yl)methanamine

A mixture of tert-butyl N-[[2-[(2,6-difluorophenoxy)methyl]pyrimidin-4-yl]methyl]carbamate (40 mg, 0.11 mmol, 1 eq) in 4M of HCl/dioxane (2 mL) was stirred at 25° C. for 3 hrs. The reaction mixture was concentrated under reduced pressure. Compound [2-[(2,6-difluorophenoxy)methyl]pyrimidin-4-yl]methanamine (32 mg, crude, HCl) was obtained as a yellow solid.

N-((2-((2,6-difluorophenoxy)methyl)pyrimidin-4-yl)methyl)-5-(4-(trifluoromethyl)phenyl)-2-naphthamide To a solution of N-methyl-2-[5-[4-(trifluoromethyl)phenyl]-2-naphthyl]ethanamine (20 mg, 60.7 umol, 1 eq) and KOAc (11.9 mg, 0.12 mmol, 2 eq) in MeOH (0.5 mL) was added carbonitride. To a solution of 5-[4-(trifluoromethyl)phenyl]naphthalene-2-carboxylic acid (30 mg, 94.8 umol, 1 eq), [2-[(2,6-difluorophenoxy)methyl]pyrimidin-4-yl]methanamine (30.0 mg, 0.10 mmol, 1.1 eq, HCl) and DIPEA (36.7 mg, 0.28 mmol, 49.5 uL, 3 eq) in DCM (1 mL) was added HATU (43.2 mg, 0.11 mmol, 1.2 eq). The reaction mixture was stirred at 25° C. for 1 hr. The reaction mixture was concentrated under reduced pressure. The mixture was diluted with water (10 mL) and the resultant mixture was extracted with EA (20 mL*3). The combined organic layers were dried over Na$_2$SO$_4$, filtered and concentrated to dryness under reduced pressure. The residue was purified by prep-HPLC (column: Waters Xbridge BEH C18 100*25 mm*5 um; mobile phase: [water (0.05% ammonia hydroxide v/v)-ACN]; B %: 56%-86%, 9.5 min) to give the title compound (9.9 mg, 17.7 umol, 18.7% yield). LCMS (ESI): RT=1.021 min, mass calcd for C$_{30}$H$_{20}$F$_5$N$_3$O$_2$ 549.49 m/z, found 550.1 [M+H]$^+$. $^1$H NMR (400 MHz, CDCl$_3$) δ 8.74 (d, J=5.1 Hz, 1H), 8.48 (s, 1H), 8.02 (d, J=8.3 Hz, 1H), 7.93-7.85 (m, 2H), 7.79 (d, J=8.0 Hz, 2H), 7.70 (br t, J=4.5 Hz, 1H), 7.66-7.60 (m, 3H), 7.53 (d, J=7.0 Hz, 1H), 7.32 (d, J=5.0 Hz, 1H), 6.95-6.78 (m, 3H), 5.44 (s, 2H), 4.85 (d, J=4.9 Hz, 2H).

Example 149: N-[(1R)-1-(3H-benzimidazol-4-yl)ethyl]-5-[4-(trifluoromethyl)phenyl]naphthalene-2-carboxamide (Compound 173) and N-[(1S)-1-(3H-benzimidazol-4-yl)ethyl]-5-[4-(trifluoromethyl)phenyl]naphthalene-2-carboxamide (Compound 174)

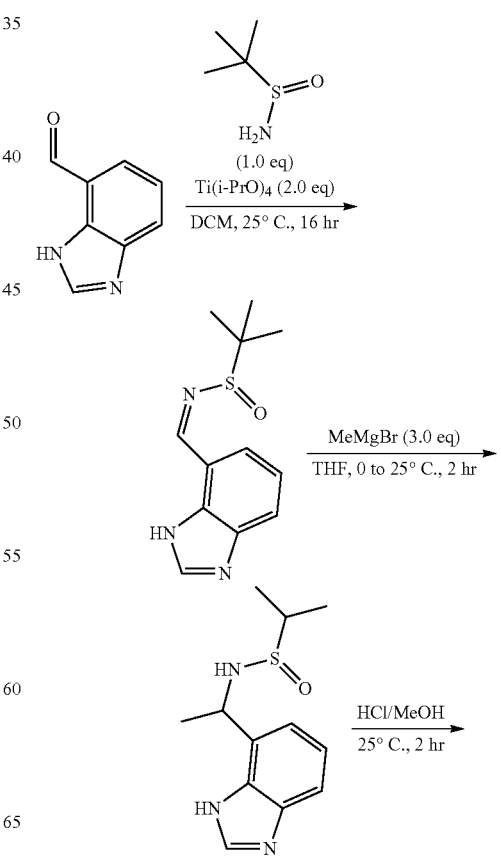

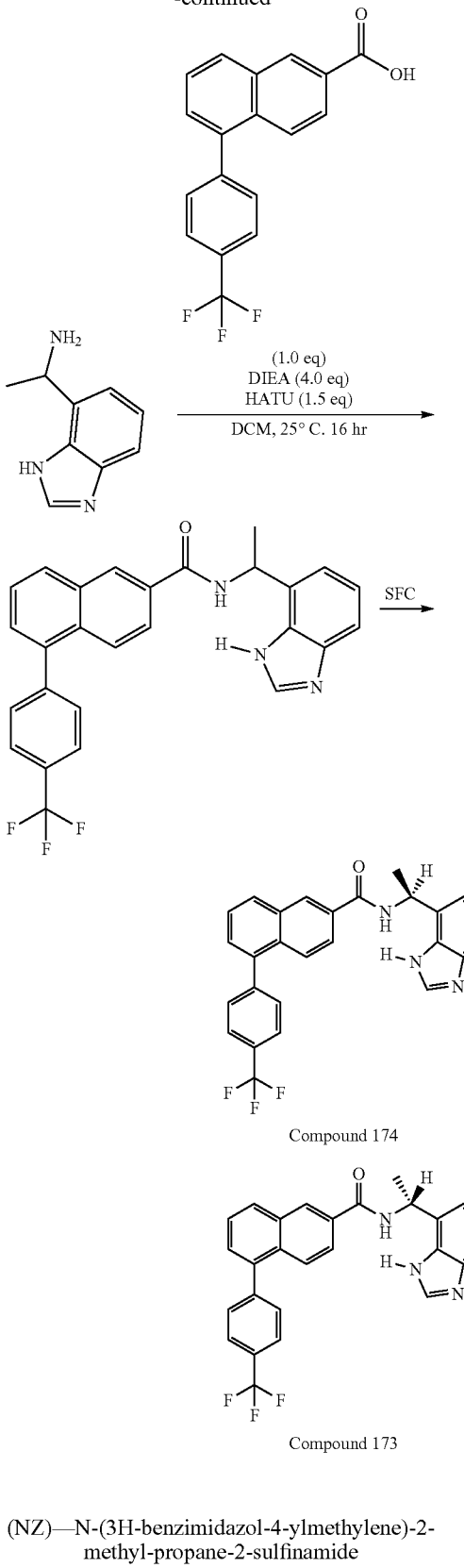

(NZ)—N-(3H-benzimidazol-4-ylmethylene)-2-methyl-propane-2-sulfinamide

The mixture of 3H-benzimidazole-4-carbaldehyde (50 mg, 0.34 mmol, 1 eq), Ti(i-PrO)$_4$ (194.4 mg, 0.68 mmol, 0.20 mL, 2 eq) and 2-methylpropane-2-sulfinamide (41.4 mg, 0.34 mmol, 1 eq) in DCM (2 mL) was stirred at 25° C. for 16 hr. The reaction mixture was diluted with H$_2$O (5 mL) and the mixture was extracted with EA (20 mL*3). The combined organic phase was washed with brine (10 mL*2), dried with anhydrous Na$_2$SO$_4$, filtered and concentrated in vacuum. The residue was purified by column chromatography (SiO$_2$, Petroleum ether/Ethyl acetate=1/0 to 0/1, EA:MeOH=1:1). Compound (NZ)—N-(3H-benzimidazol-4-ylmethylene)-2-methyl-propane-2-sulfinamide (60 mg, 0.24 mmol, 70.3% yield) was obtained as yellow oil.

N-[1-(3H-benzimidazol-4-yl)ethyl]-2-methyl-propane-2-sulfinamide

To a solution of (NE)-N-(3H-benzimidazol-4-ylmethylene)-2-methyl-propane-2-sulfinamide (60 mg, 0.24 mmol, 1 eq) in THF (2 mL) was added MeMgBr (3 M, 0.24 mL, 3 eq) at 0° C. The mixture was stirred at 25° C. for 2 hr. The reaction mixture was diluted with NH$_4$Cl (2 mL), H$_2$O (10 ml) and the mixture was extracted with EA (10 mL*3). The combined organic phase was washed with brine (10 mL*2), dried with anhydrous Na$_2$SO$_4$, filtered and concentrated in vacuum. The residue was purified by column chromatography (SiO$_2$, EA:MeOH=1/0 to 1/1). Compound N-[1-(3H-benzimidazol-4-yl)ethyl]-2-methyl-propane-2-sulfinamide (60 mg, 0.22 mmol, 93.9% yield) was obtained as yellow oil.

Intermediate 4: 1-(3H-benzimidazol-4-yl)ethanamine

The mixture of N-[1-(3H-benzimidazol-4-yl)ethyl]-2-methyl-propane-2-sulfinamide (60 mg, 0.22 mmol, 1 eq) in HCl/dioxane (4 M, 3.69 mL, 65.32 eq) was stirred at 25° C. for 2 hr. The reaction mixture was concentrated under reduced pressure to remove solvent. Compound 1-(3H-benzimidazol-4-yl)ethanamine (50 mg, crude, HCl) was obtained as yellow oil.

N-[1-(3H-benzimidazol-4-yl)ethyl]-5-[4-(trifluoromethyl)phenyl]naphthalene-2-carboxamide The mixture of 5-[4-(trifluoromethyl)phenyl]naphthalene-2-carboxylic acid (64.0 mg, 0.20 mmol, 1 eq), DIPEA (104.6 mg, 0.80 mmol, 0.14 mL, 4 eq), 1-(3H-benzimidazol-4-yl)ethanamine (40 mg, 0.20 mmol, 1 eq, HCl) and HATU (115.4 mg, 0.30 mmol, 1.5 eq) in DCM (2 mL) was stirred at 25° C. for 16 hr. The reaction mixture was diluted with H$_2$O (10 mL) and the mixture was extracted with EA (20 mL*3). The combined organic phase was washed with brine (10 mL*2), dried with anhydrous Na$_2$SO$_4$, filtered and concentrated in vacuum. The residue was purified by prep-HPLC (column: Waters Xbridge BEH C18 150*25 mm*5 um; mobile phase: [water (0.05% ammonia hydroxide v/v)-ACN]; B %: 55%-85%, 8.8 min). Compound N-[1-(3H-benzimidazol-4-yl)ethyl]-5-[4-(trifluoromethyl)phenyl]naphthalene-2-carboxamide (30 mg, 64.6 umol, 31.9% yield) was obtained as white solid.

N-[(1R)-1-(3H-benzimidazol-4-yl)ethyl]-5-[4-(trifluoromethyl)phenyl]naphthalene-2-carboxamide (Compound 173) and N-[(1S)-1-(3H-benzimidazol-4-yl)ethyl]-5-[4-(trifluoromethyl)phenyl]naphthalene-2-carboxamide (Compound 174)

The racemic compound N-[1-(3H-benzimidazol-4-yl)ethyl]-5-[4-(trifluoromethyl)phenyl]naphthalene-2-carboxamide (30 mg, 65.2 umol, 1 eq) was purified by SFC (column: DAICEL CHIRALPAK IC (250 mm*30 mm, 10 um); mobile phase: [Neu-ETOH]; B %: 40%-40%, min). Compound 174 (17.1 mg, 36.9 umol, 56.5% yield) was obtained as white solid. LCMS (ESI): RT=0.886 min, mass calcd for $C_{27}H_{20}F_3N_3O$ 459.46 m/z found 460.1[M+H]+. $^1$H NMR (400 MHz, DMSO-d$_6$) δ ppm 1.59 (d, J=6.88 Hz, 3H) 5.61-5.80 (m, 1H) 7.09-7.24 (m, 2H) 7.42 (br s, 1H) 7.56 (dd, J=7.07, 1.06 Hz, 1H) 7.64-7.74 (m, 3H) 7.79 (d, J=8.88 Hz, 1H) 7.86-7.96 (m, 3H) 8.13 (d, J=8.25 Hz, 1H) 8.23 (s, 1H) 8.61 (d, J=1.50 Hz, 1H) 9.28 (br s, 1H) 12.53 (br s, 1H) 12.40-12.64 (m, 1H). Compound 173 (13.6 mg, 29.7 umol, 45.6% yield) was obtained as white solid. LCMS (ESI): RT=0.893 min, mass calcd for $C_{27}H_{20}F_3N_3O$ 459.46 m/z found 460.1[M+H]+. $^1$H NMR (400 MHz, DMSO-d$_6$) δ ppm 1.59 (d, J=7.00 Hz, 3H) 5.71 (br s, 1H) 7.09-7.16 (m, 1H) 7.15-7.22 (m, 1H) 7.43 (br d, J=8.25 Hz, 1H) 7.57 (dd, J=7.13, 1.13 Hz, 1H) 7.64-7.74 (m, 3H) 7.79 (d, J=9.01 Hz, 1H) 7.85-7.97 (m, 3H) 8.13 (d, J=8.13 Hz, 1H) 8.23 (s, 1H) 8.62 (d, J=1.50 Hz, 1H) 9.32 (br s, 1H) 12.50 (br s, 1H).

Example 150: N-[(1S)-1-(benzothiophen-7-yl)ethyl]-5-[4-(trifluoromethyl)phenyl]naphthalene-2-carboxamide (Compound 175) and N-[(1R)-1-(benzothiophen-7-yl)ethyl]-5-[4-(trifluoromethyl)phenyl]naphthalene-2-carboxamide (Compound 176)

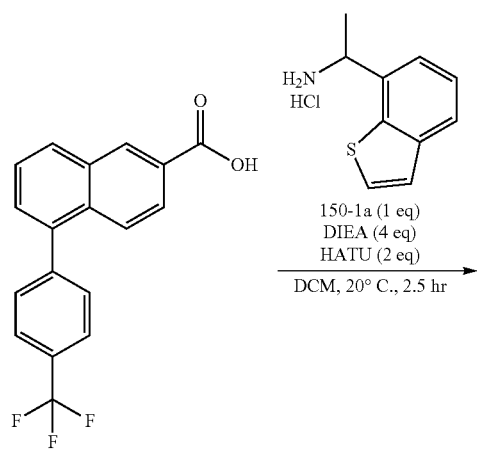

150-1

150-1a (1 eq)
DIEA (4 eq)
HATU (2 eq)
DCM, 20° C., 2.5 hr

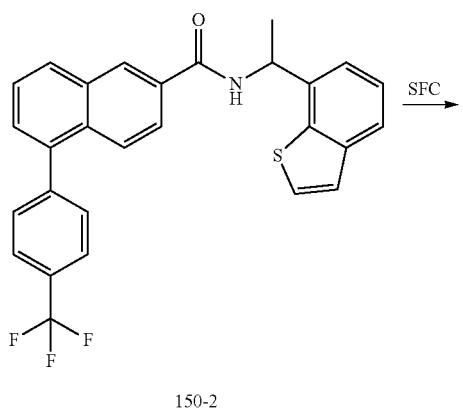

150-2

SFC

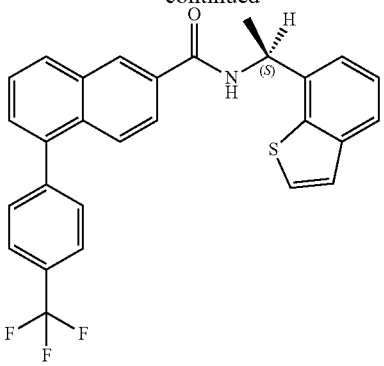

Compound 175

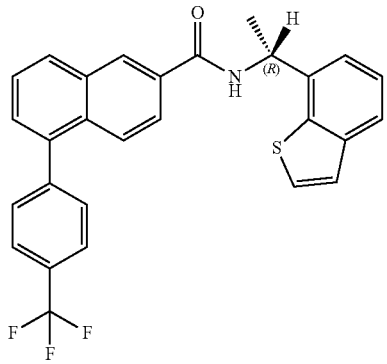

Compound 176

N-[1-(benzothiophen-7-yl)ethyl]-5-[4-(trifluoromethyl)phenyl]naphthalene-2-carboxamide To a solution of 150-1 (80 mg, 0.25 mmol, 1 eq) in DCM (2 mL) were added DIEA (130.8 mg, 1.01 mmol, 0.18 mL, 4 eq) and HATU (192.4 mg, 0.51 mmol, 2 eq). The mixture was stirred at 20° C. for 0.5 h. 150-1a (54.1 mg, 0.25 mmol, 1 eq, HCl) was added into the mixture. The mixture was stirred at 20° C. for 2 h. The mixture was diluted with H$_2$O (15 mL), extracted with EA (30 mL*3). The combined organic layer was washed with brine (20 mL), dried over Na$_2$SO$_4$, filtered and concentrated. The residue was checked by HPLC and purified by prep-HPLC (column: Waters Xbridge BEH C18 150*25 mm*5 um; mobile phase: [water (0.05% ammonia hydroxide v/v)-ACN]; B %: 70%-100%, 9.5 min) to give 150-2 (65 mg, 0.14 mmol, 54.0% yield) as a white solid.

N-[(1S)-1-(benzothiophen-7-yl)ethyl]-5-[4-(trifluoromethyl)phenyl]naphthalene-2-carboxamide (Compound 175) and N-[(1R)-1-(benzothiophen-7-yl)ethyl]-5-[4-(trifluoromethyl)phenyl]naphthalene-2-carboxamide (Compound 176)

150-2 (60 mg, 0.13 mmol, 1 eq) was purified by SFC. The residue was purified by SFC (column: DAICEL CHIRALPAK AD (250 mm*50 mm, 10 um); mobile phase: [0.1% NH$_3$H$_2$O IPA]; B %: 35%-35%, min) to give Compound 175 (15.5 mg, 32.6 umol, 25.9% yield) as a light yellow solid (RT=2.873 min) and Compound 176 (17.6 mg, 37.1 umol, 29.4% yield) as a light yellow solid. (RT=3.280 min). Compound 175 LCMS (ESI): RT=1.081 min, mass calc. for $C_{28}H_{20}F_3NOS$ 475.52, m/z found 476.1 [M+H]$^+$; $^1$H NMR (400 MHz, CDCl$_3$) δ 8.40 (s, 1H), 7.97 (d, J=8.3 Hz, 1H), 7.90-7.72 (m, 5H), 7.66-7.55 (m, 3H), 7.54-7.36 (m, 5H), 6.66 (br d, J=7.1 Hz, 1H), 5.69 (t, J=7.0 Hz, 1H), 1.83 (d, J=6.9 Hz, 3H). Compound 176 LCMS (ESI): RT=1.076 min, mass calc. for $C_{28}H_{20}F_3NOS$ 475.52, m/z found 476.1 [M+H]$^+$; $^1$H NMR (400 MHz, CDCl$_3$) δ 8.40 (s, 1H), 7.98 (d, J=8.3 Hz, 1H), 7.91-7.71 (m, 5H), 7.67-7.55 (m, 3H), 7.54-7.37 (m, 5H), 6.65 (br d, J=7.4 Hz, 1H), 5.69 (t, J=7.0 Hz, 1H), 1.83 (d, J=6.9 Hz, 3H).

Example 151: N-[(1R)-1-(2-oxo-1H-quinolin-8-yl)ethyl]-5-[4-(trifluoromethyl)phenyl]naphthalene-2-carboxamide (Compound 177) and N-[(1S)-1-(2-oxo-1H-quinolin-8-yl)ethyl]-5-[4-(trifluoromethyl)phenyl]naphthalene-2-carboxamide (Compound 178)

N-[1-(2-oxo-1H-quinolin-8-yl)ethyl]-5-[4-(trifluoromethyl)phenyl]naphthalene-2-carboxamide The mixture of 5-[4-(trifluoromethyl)phenyl]naphthalene-2-carboxylic acid (33.6 mg, 0.10 mmol, 1 eq), 8-(1-aminoethyl)-1H-quinolin-2-one (20 mg, 0.10 mmol, 1 eq), DIPEA (41.2 mg, 0.31 mmol, 55.5 uL, 3 eq) and HATU (48.4 mg, 0.12 mmol, 1.2 eq) in DCM (2 mL) was stirred at 25° C. for 2 hr. The reaction mixture was diluted with H$_2$O (5 mL) and the mixture was extracted with EA (10 mL*3). The combined organic phase was washed with brine (10 mL*2), dried with anhydrous Na$_2$SO$_4$, filtered and concentrated in vacuum. The residue was purified by prep-HPLC (column: Waters Xbridge BEH C18 150*25 mm*5 um; mobile phase: [water (0.05% ammonia hydroxide v/v)-ACN]; B %: 54%-84%, 9.5 min). Compound N-[1-(2-oxo-1H-quinolin-8-yl)ethyl]-5-[4-(trifluoromethyl)phenyl]naphthalene-2-carboxamide (5.1 mg, 10.3 umol, 9.7% yield) was obtained as white solid.

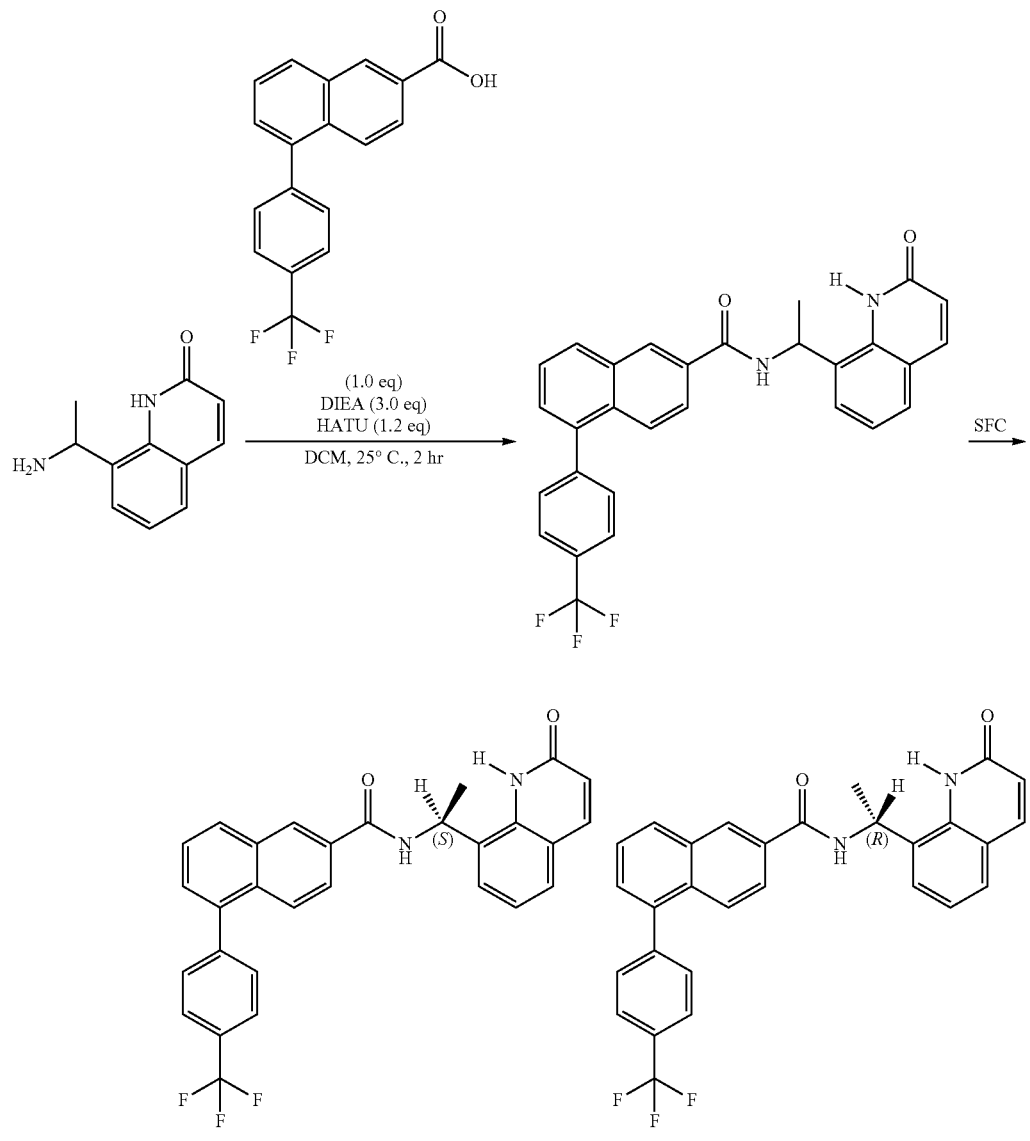

Compound 178

Compound 177

N-[(1R)-1-(2-oxo-1H-quinolin-8-yl)ethyl]-5-[4-(trifluoromethyl)phenyl]naphthalene-2-carboxamide (Compound 177) and N-[(1S)-1-(2-oxo-1H-quinolin-8-yl)ethyl]-5-[4-(trifluoromethyl)phenyl]naphthalene-2-carboxamide (Compound 178)

The racemic compound N-[1-(2-oxo-1H-quinolin-8-yl)ethyl]-5-[4-(trifluoromethyl)phenyl]naphthalene-2-carboxamide (12 mg, 24.67 umol, 1 eq) was purified by SFC (column: DAICEL CHIRALPAK AS-H (250 mm*30 mm, 5 um); mobile phase: [0.1% $NH_3H_2O$ ETOH]; B %: 30%-30%, min). Compound 178 (4.1 mg, 8.0 umol, 32.7% yield) was obtained as a white solid. LCMS (ESI): RT=0.972 min, mass calcd for $C_{29}H_{21}F_3N_2O_2$ 486.48 m/z found 487.1[M+H]$^+$, 1H NMR (400 MHz, CDCl$_3$) δ ppm 1.80 (d, J=7.03 Hz, 3H) 5.69-5.76 (m, 1H) 6.62 (d, J=9.54 Hz, 1H) 7.03 (br s, 1H) 7.13-7.17 (m, 1H) 7.37-7.41 (m, 1H) 7.43-7.49 (m, 4H) 7.60 (d, J=7.28 Hz, 1H) 7.67 (d, J=9.54 Hz, 3H) 7.72 (s, 2H) 7.80 (br d, J=8.03 Hz, 1H) 8.39 (s, 1H) 11.16 (br s, 1H). Compound 177 (3.2 mg, 6.4 umol, 26.0% yield) was obtained as a white solid. LCMS (ESI): RT=0.971 min, mass calcd for $C_{29}H_{21}F_3N_2O_2$ 486.48 m/z found 487.1[M+H]$^+$, $^1$H NMR (400 MHz, CDCl$_3$) δ ppm 1.88 (d, J=7.03 Hz, 2H) 1.85-1.91 (m, 1H) 5.73-5.82 (m, 1H) 6.70 (d, J=9.54 Hz, 1H) 7.21-7.25 (m, 1H) 7.43-7.47 (m, 1H) 7.49 (s, 1H) 7.48-7.50 (m, 1H) 7.53 (br d, J=8.28 Hz, 3H) 7.67-7.79 (m, 2H) 7.67-7.76 (m, 1H) 7.69-7.76 (m, 1H) 7.76-7.76 (m, 1H) 7.76-7.79 (m, 1H) 7.80-7.87 (m, 2H) 8.47 (s, 1H) 11.35 (br s, 1H).

Example 152: N-((2-cyanopyrimidin-4-yl)methyl)-5-(4-(trifluoromethyl)phenyl)-2-naphthamide (Compound 179)

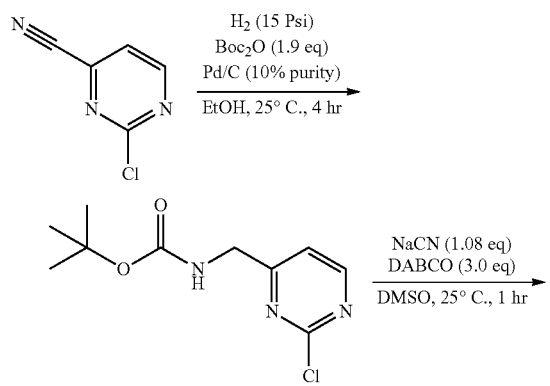

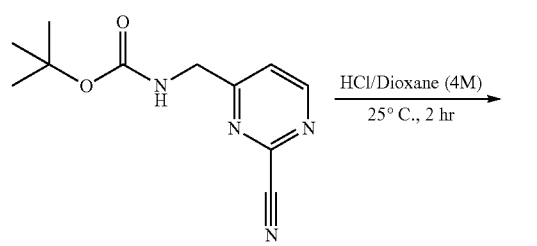

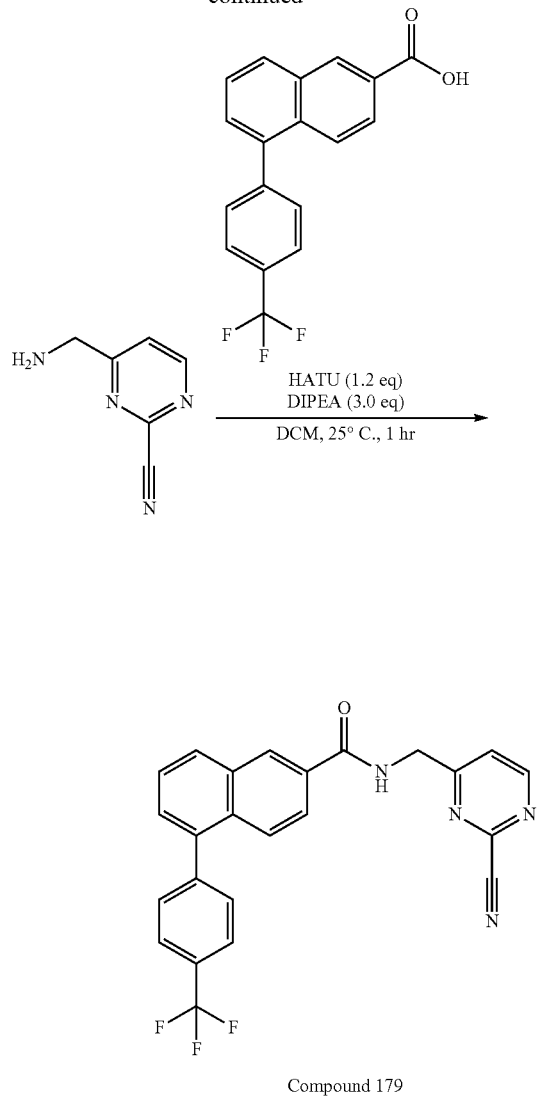

Compound 179

Tert-Butyl ((2-Chloropyrimidin-4-yl)methyl)carbamate

A solution of 2-chloropyrimidine-4-carbonitrile (1.00 g, 7.17 mmol, 1 eq), Boc$_2$O (2.97 g, 13.62 mmol, 3.13 mL, 1.9 eq) and Pd/C (300 mg, 10%) in EtOH (20 mL) was stirred at 25° C. for 4 hrs under H$_2$ (15 Psi). The reaction mixture was filtered and the filtrate was concentrated under reduce pressure. The residue was purified by column chromatography over silica gel (petroleum ether:ethyl acetate=1:0 to 3:1) to afford tert-butyl ((2-Chloropyrimidin-4-yl)methyl)carbamate (230 mg, 12.2% yield) as a light yellow solid. LCMS (ESI): RT=0.766 min, mass calcd for C10H14ClN3O2 243.08 m/z, found 244.0 [M+H]$^+$.

Tert-Butyl ((2-cyanopyrimidin-4-yl)methyl)carbamate

To a mixture of tert-butyl N-[(2-chloropyrimidin-4-yl)methyl]carbamate (230 mg, 0.94 mmol, 1 eq) in DMSO (2 mL) were added DABCO (317.6 mg, 2.83 mmol, 3 eq) and NaCN (50 mg, 1.02 mmol, 1.08 eq). The reaction mixture was stirred at 25° C. for 1 hour. The reaction mixture was concentrated under reduced pressure. The mixture was diluted with water (10 mL) and the resultant mixture was extracted with EA (20 mL*3). The combined organic layers were dried over $Na_2SO_4$, filtered and concentrated to dryness under reduced pressure. The residue was purified by column chromatography over silica gel (petroleum ether: ethyl acetate=1:0 to 3:1) to afford tert-butyl (2-cyanopyrimidin-4-yl)methyl)carbamate (105 mg, 47.4% yield) as an orange solid.

4-(aminomethyl)pyrimidine-2-carbonitrile

A mixture of tert-butyl N-[(2-cyanopyrimidin-4-yl)methyl]carbamate (20 mg, 85.3 umol, 1 eq) in HCl/dioxane (1 mL) was stirred at 25° C. for 2 hrs. The reaction mixture was concentrated under reduced pressure to give 4-(aminomethyl)pyrimidine-2-carbonitrile (14 mg, crude, HCl) as a red solid.

N-((2-cyanopyrimidin-4-yl)methyl)-5-(4-(trifluoromethyl)phenyl)-2-naphthamide

To a solution of 5-[4-(trifluoromethyl)phenyl]naphthalene-2-carboxylic acid (30 mg, 94.8 umol, 1 eq), 4-(aminomethyl)pyrimidine-2-carbonitrile (14.0 mg, 0.10 mmol, 1.1 eq, HCl) and HATU (43.2 mg, 0.11 mmol, 1.2 eq) in DCM (1 mL) was added DIPEA (36.7 mg, 0.28 mmol, 3 eq). The reaction mixture was stirred at 25° C. for 1 hr. The reaction mixture was concentrated under reduced pressure. The mixture was diluted with water (10 mL) and the resultant mixture was extracted with EA (20 mL*3). The combined organic layers were dried over $Na_2SO_4$, filtered and concentrated to dryness under reduced pressure. The residue was purified by prep-HPLC (column: Waters Xbridge BEH C18 150*25 mm*5 um; mobile phase: [water (0.05% ammonia hydroxide v/v)-ACN]; B %: 55%-85%, 9.5 min) to obtain N-((2-cyanopyrimidin-4-yl)methyl)-5-(4-(trifluoromethyl)phenyl)-2-naphthamide (8.3 mg, 20.0% yield) as a white solid. LCMS (ESI): RT=0.974 min, mass calcd for $C_{24}H_{15}F_3N_4O$ 432.12 m/z, found 433.0 [M+H]$^+$, $^1$H NMR (400 MHz, CDCl$_3$) δ 8.82 (d, J=5.0 Hz, 1H), 8.47 (d, J=1.3 Hz, 1H), 8.03 (d, J=8.0 Hz, 1H), 7.96-7.90 (m, 1H), 7.89-7.84 (m, 1H), 7.79 (d, J=8.0 Hz, 2H), 7.68-7.60 (m, 4H), 7.55 (d, J=6.5 Hz, 1H), 7.38-7.31 (m, 1H), 4.88 (d, J=5.5 Hz, 2H).

Example 153: N-((2-chloropyrimidin-4-yl)methyl)-5-(4-(trifluoromethyl)phenyl)-2-naphthamide (Compound 180)

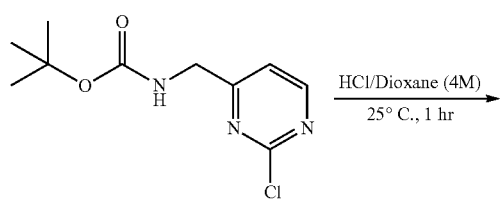

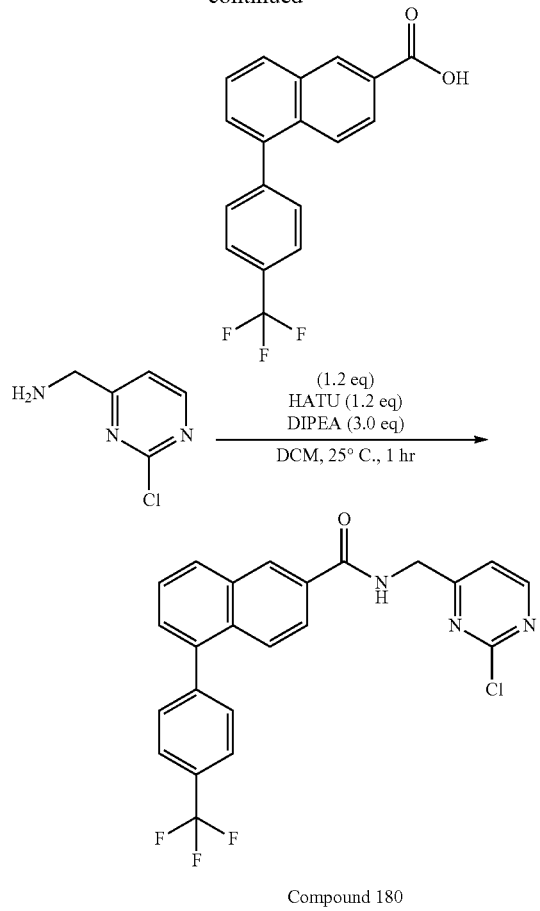

Compound 180

(2-chloropyrimidin-4-yl)methanamine

A solution of tert-butyl N-[(2-chloropyrimidin-4-yl)methyl]carbamate (30 mg, 0.12 mmol, 1 eq) in HCl/dioxane (1 mL) was stirred at 25° C. for 1 hr. The reaction mixture was concentrated under reduce pressure to give (2-chloropyrimidin-4-yl)methanamine (25 mg, crude, HCl) as a white solid.

N-((2-chloropyrimidin-4-yl)methyl)-5-(4-(trifluoromethyl)phenyl)-2-naphthamide

A solution of 5-[4-(trifluoromethyl)phenyl]naphthalene-2-carboxylic acid (30 mg, 94.8 umol, 1 eq), (2-chloropyrimidin-4-yl)methanamine (20.4 mg, 0.11 mmol, 1.2 eq, HCl) and HATU (43.2 mg, 0.11 mmol, 1.2 eq) in DCM (1 mL) was added DIPEA (36.7 mg, 0.28 mmol, 49.5 uL, 3 eq). The reaction mixture was stirred at 25° C. for 1 hr. The reaction mixture was concentrated under reduced pressure. The mixture was diluted with water (10 mL) and the resultant mixture was extracted with EA (20 mL*3). The combined organic layers were dried over $Na_2SO_4$, filtered and concentrated to dryness under reduced pressure. The residue was purified by prep-HPLC (column: Xtimate C18 10µ 250 mm*50 mm; mobile phase: [water (0.05% ammonia hydroxide v/v)-ACN]; B %: 65%-95%, 7.8 min) to give the title compound (18.1 mg, 43.2% yield) as a white solid. LCMS (ESI): RT=1.003 min, mass calcd for $C_{23}H_{15}ClF_3N_3O$ 441.09 m/z, found 442.0 [M+H]$^+$. $^1$H NMR (400 MHz, CDCl$_3$) δ 8.62 (d, J=5.1 Hz, 1H), 8.47 (d, J=1.6 Hz, 1H), 8.02 (d, J=8.1 Hz, 1H), 7.94-7.89 (m, 1H), 7.88-7.84 (m, 1H), 7.79 (d, J=8.1 Hz, 2H), 7.67-7.60 (m, 3H), 7.54 (dd, J=7.1, 1.1 Hz, 1H), 7.39-7.32 (m, 2H), 4.82 (d, J=5.4 Hz, 2H).

Example 154: N-[(E)-5-isoxazol-3-yloxypent-3-enyl]-5-[4-(trifluoromethyl)phenyl]naphthalene-2-carboxamide (Compound 181)

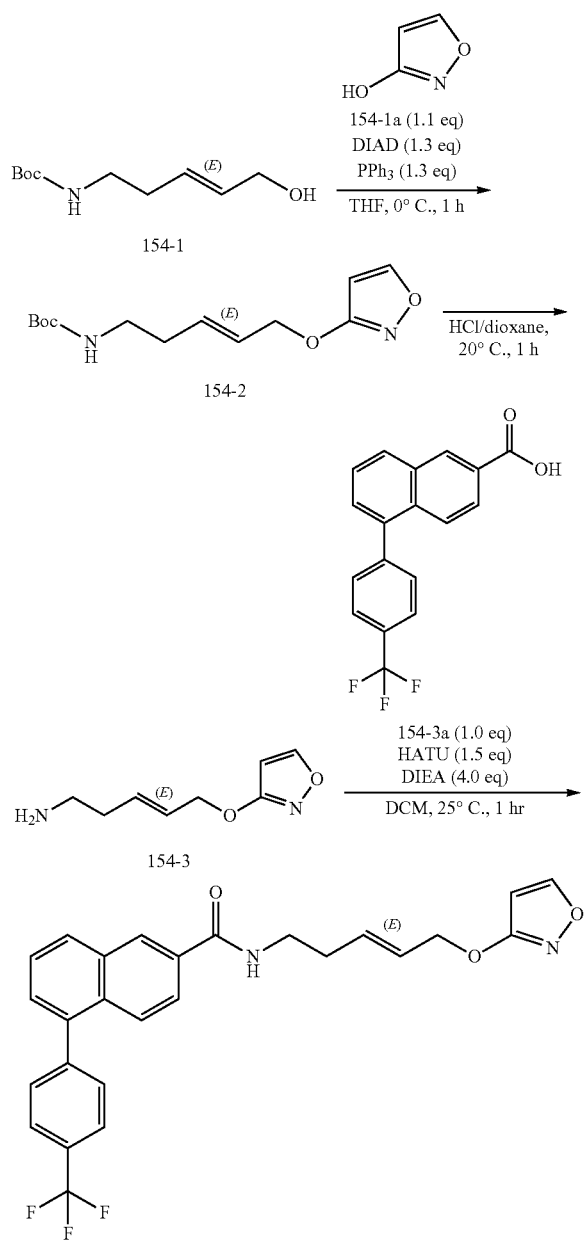

Compound 181

Tert-Butyl N-[(E)-5-isoxazol-3-yloxypent-3-enyl] carbamate

To a solution of compound 154-1 (70 mg, 0.34 mmol, 1 eq), 154-1a (32.5 mg, 0.38 mmol, 1.1 eq) and PPh$_3$ (118.5 mg, 0.45 mmol, 1.3 eq) in THF (1 mL) was added DIAD (91.4 mg, 0.45 mmol, 87 uL, 1.3 eq) at 0° C. The reaction was stirred at 0° C. for 1 hr. The reaction mixture was concentrated. The crude product was triturated with EA/PE (1:2, 1 mL) and filtered to give compound 154-2 (50 mg, crude) as colorless oil, which was used for next step directly.

(E)-5-isoxazol-3-yloxypent-3-en-1-amine

A solution of compound 154-2 (50 mg, 0.18 mmol, 1 eq) in HCl/dioxane (0.5 mL) was stirred at 20° C. for 1 hr. The reaction was concentrated to give compound 154-3 (40 mg, crude, HCl) as yellow oil, which was used for next step directly.

N-[(E)-5-isoxazol-3-yloxypent-3-enyl]-5-[4-(trifluoromethyl)phenyl]naphthalene-2-carboxamide To a solution of compound 154-3a (61.8 mg, 0.19 mmol, 1 eq), HATU (111.4 mg, 0.29 mmol, 1.5 eq) and compound 154-3 (40 mg, 0.19 mmol, 1 eq, HCl) in DCM (2 mL) was added DIEA (101.0 mg, 0.78 mmol, 0.13 mL, 4 eq). The reaction was stirred at 25° C. for 1 hr. The reaction was diluted with EA (15 mL) and washed with H$_2$O (2*5 mL). The organic layer was dried over Na$_2$SO$_4$ and concentrated. The crude product was purified by Prep.HPLC (column: Waters Xbridge Prep OBD C18 100*19 mm*5 um; mobile phase: [water (0.05% ammonia hydroxide v/v)-ACN]; B %: 55%-85%, 7.8 min) to give the title compound (6.5 mg, 13.82 umol, 7.07% yield) as a white solid. LCMS (ESI): RT=0.936 min, mass calcd. For C$_{26}$H$_{21}$F$_3$N$_2$O$_3$, 466.15 m/z found 467.1 [M+H]$^+$. $^1$H NMR (400 MHz, CDCl$_3$) δ 8.37 (s, 1H), 8.00 (d, J=8.0 Hz, 1H), 7.91-7.83 (m, 1H), 7.79 (d, J=7.8 Hz, 3H), 7.69 (d, J=2.5 Hz, 1H), 7.65-7.59 (m, 3H), 7.51 (d, J=6.0 Hz, 1H), 6.44 (br s, 1H), 5.86-5.77 (m, 1H), 5.73 (d, J=2.5 Hz, 1H), 5.68-5.56 (m, 1H), 4.49 (d, J=6.0 Hz, 2H), 3.62 (q, J=6.5 Hz, 2H), 2.45 (q, J=6.9 Hz, 2H).

Example 155: N-[(1R)-1-(1H-indazol-7-yl)ethyl]-5-[4-(trifluoromethyl)phenyl]naphthalene-2-carboxamide (Compound 182) and N-[(1S)-1-(1H-indazol-7-yl)ethyl]-5-[4-(trifluoromethyl)phenyl]naphthalene-2-carboxamide (Compound 183)

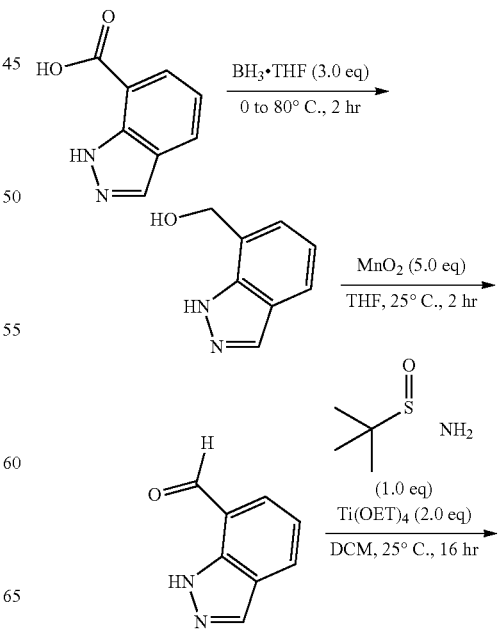

-continued

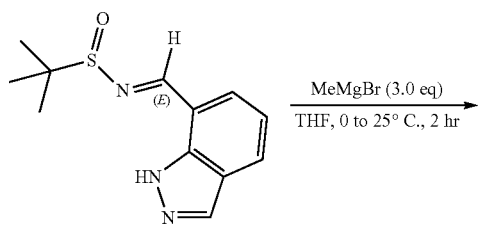

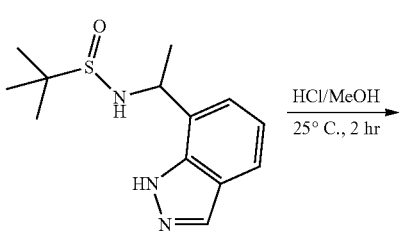

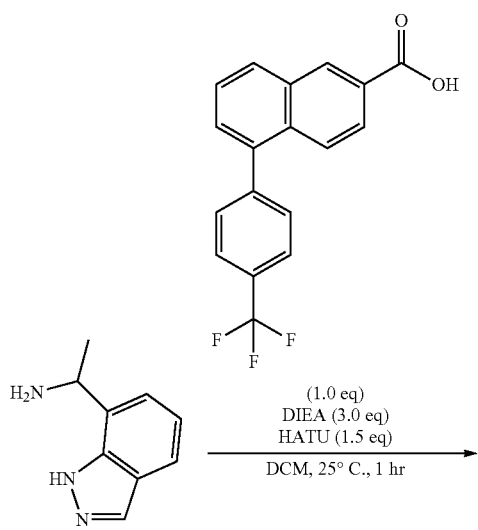

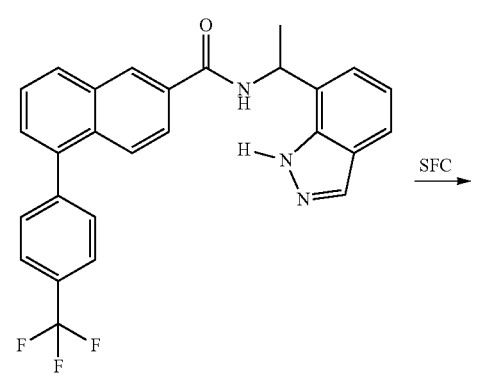

-continued

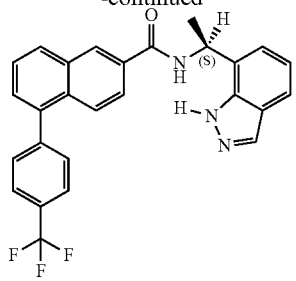

Compound 183

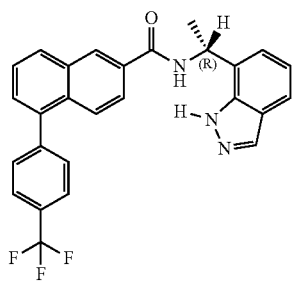

Compound 182

1H-indazol-7-ylmethanol 1H-indazole-7-carboxylic acid (1 g, 6.17 mmol, 1 eq) was added at $BH_3 \cdot THF$ (1 M, 18.50 mL, 3 eq) at 0° C. Then the mixture was stirred at 80° C. for 2 hr. The reaction mixture was diluted with $H_2O$ (10 mL) and the mixture was extracted with EA (20 mL*3). The combined organic phase was washed with brine (10 mL*2), dried with anhydrous $Na_2SO_4$, filtered and concentrated in vacuum. No purification. Compound 1H-indazol-7-ylmethanol (900 mg, crude) was obtained as white solid, which was used into the next step without further purification.

1H-indazole-7-carbaldehyde

The mixture of 1H-indazol-7-ylmethanol (800 mg, 5.40 mmol, 1 eq) and $MnO_2$ (2.35 g, 27.00 mmol, 5 eq) in THF (2 mL) was stirred at 25° C. for 2 hr. The resulting product was dissolved in EA and filtered to remove the insoluble. The filter liquor was concentrated in vacuo. The residue was purified by column chromatography ($SiO_2$, Petroleum ether/Ethyl acetate=1/0 to 5:1). Compound 1H-indazole-7-carbaldehyde (180 mg, 1.23 mmol, 22.81% yield) was obtained as white solid.

(NZ)—N-(1H-indazol-7-ylmethylene)-2-methyl-propane-2-sulfinamide

The mixture of 1H-indazole-7-carbaldehyde (100 mg, 0.68 mmol, 1 eq), 2-methylpropane-2-sulfinamide (82.9 mg, 0.68 mmol, 1 eq) and $Ti(OEt)_4$ (312.1 mg, 1.37 mmol, 0.28 mL, 2 eq) in DCM (1 mL) was stirred at 25° C. for 16 hr. The reaction mixture was diluted with $H_2O$ (5 mL) and the mixture was extracted with EA (20 mL*3). The combined organic phase was washed with brine (10 mL*2), dried with anhydrous $Na_2SO_4$, filtered and concentrated in vacuum. The residue was purified by column chromatography ($SiO_2$, Petroleum ether/Ethyl acetate=1/0 to 3:1). Compound (NZ)—N-(1H-indazol-7-ylmethylene)-2-methyl-propane-2-sulfinamide (150 mg, 0.60 mmol, 87.9% yield) was obtained as yellow solid.

N-[1-(1H-indazol-7-yl)ethyl]-2-methyl-propane-2-sulfinamide

MeMgBr (3 M, 0.40 mL, 3 eq) was added at the mixture of (NZ)—N-(1H-indazol-7-ylmethylene)-2-methyl-propane-2-sulfinamide (100 mg, 0.40 mmol, 1 eq) in THF (2 mL) at 0° C. dropwise. Then the mixture was stirred at 25° C. for 2 hr. The reaction mixture was diluted with H$_2$O (2 mL), NaOH (2M, 2 ml), H$_2$O (10 mL) and the mixture was extracted with EA (20 mL*3). The combined organic phase was washed with brine (10 mL*2), dried with anhydrous Na$_2$SO$_4$, filtered and concentrated in vacuum. No purification. Compound N-[1-(1H-indazol-7-yl)ethyl]-2-methyl-propane-2-sulfinamide (100 mg, crude) was obtained as yellow oil, which was used into the next step without further purification.

1-(1H-indazol-7-yl)ethanamine

The mixture of N-[1-(1H-indazol-7-yl)ethyl]-2-methyl-propane-2-sulfinamide (100 mg, 0.37 mmol, 1 eq) in HCl/MeOH (4 M, 2 mL, 21.23 eq) was stirred at 25° C. for 2 hr. The reaction mixture was diluted with NaOH (4M 10 mL), H$_2$O (10 ml) and the mixture was extracted with EA (20 mL*3). The combined organic phase was washed with brine (10 mL*2), dried with anhydrous Na$_2$SO$_4$, filtered and concentrated in vacuum. Compound 1-(1H-indazol-7-yl)ethanamine (60 mg, crude) was obtained as yellow oil, which was used into the next step without further purification.

N-[1-(1H-indazol-7-yl)ethyl]-5-[4-(trifluoromethyl)phenyl]naphthalene-2-carboxamide The mixture of 5-[4-(trifluoromethyl)phenyl]naphthalene-2-carboxylic acid (117.7 mg, 0.37 mmol, 1 eq), 1-(1H-indazol-7-yl)ethanamine (60.0 mg, 0.37 mmol, 1 eq), DIPEA (144.3 mg, 1.12 mmol, 0.19 mL, 3 eq) and HATU (212.2 mg, 0.55 mmol, 1.5 eq) in DCM (2 mL) was stirred at 25° C. for 16 hr. The reaction mixture was diluted with H$_2$O (10 mL) and the mixture was extracted with EA (20 mL*3). The combined organic phase was washed with brine (10 mL*2), dried with anhydrous Na$_2$SO$_4$, filtered and concentrated in vacuum. The residue was purified by prep-HPLC (column: Waters Xbridge 150*50 10u; mobile phase: [water (0.05% ammonia hydroxide v/v)-ACN]; B %: 65%-95%, 7.8 min). Compound N-[1-(1H-indazol-7-yl)ethyl]-5-[4-(trifluoromethyl)phenyl]naphthalene-2-carboxamide (70 mg, 0.15 mmol, 40.9% yield) was obtained as white solid.

N-[(1R)-1-(1H-indazol-7-yl)ethyl]-5-[4-(trifluoromethyl)phenyl]naphthalene-2-carboxamide (Compound 182) and N-[(1S)-1-(1H-indazol-7-yl)ethyl]-5-[4-(trifluoromethyl)phenyl]naphthalene-2-carboxamide (Compound 183)

The racemic compound (70 mg, 0.15 mmol, 1 eq) was purified by SFC (column: DAICEL CHIRALPAK AD-H (250 mm*30 mm, 5 um); mobile phase: [0.1% NH$_3$H$_2$O MEOH]; B %: 45%-45%, min). Compound 182 (22.3 mg, 46.7 umol, 30.6% yield) was obtained as white solid. LCMS (ESI): RT=1.017 min, mass calcd for C$_{27}$H$_{20}$F$_3$N$_3$O 459.46 m/z found 460.0[M+H]$^+$, $^1$H NMR (400 MHz, CDCl$_3$) δ 11.79 (br s, 1H), 8.37 (d, J=1.5 Hz, 1H), 8.09 (s, 1H), 7.94 (d, J=8.3 Hz, 1H), 7.85-7.71 (m, 5H), 7.62-7.55 (m, 3H), 7.50 (dd, J=1.3, 7.0 Hz, 1H), 7.42 (d, J=7.0 Hz, 1H), 7.17 (t, J=7.7 Hz, 1H), 6.57 (br d, J=9.3 Hz, 1H), 6.03 (br d, J=2.3 Hz, 1H), 1.92 (d, J=7.0 Hz, 3H), 1.59 (br s, 2H). Compound 183 (20.2 mg, 41.4 umol, 27.1% yield) was obtained as white solid. LCMS (ESI): RT=1.015 min, mass calcd for C$_{27}$H$_{20}$F$_3$N$_3$O 459.46 m/z found 460.0[M+H]$^+$, $^1$H NMR (400 MHz, CDCl$_3$) δ 11.77 (br s, 1H), 8.37 (d, J=1.5 Hz, 1H), 8.09 (s, 1H), 7.95 (d, J=8.3 Hz, 1H), 7.85-7.71 (m, 5H), 7.63-7.55 (m, 3H), 7.50 (dd, J=1.3, 7.0 Hz, 1H), 7.42 (d, J=13 Hz, 1H), 7.17 (t, J=7.5 Hz, 1H), 6.56 (br d, J=9.8 Hz, 1H), 6.08-5.98 (m, 1H), 1.92 (d, J=7.0 Hz, 3H).

Example 156: 3-((5-(4-(Trifluoromethyl)phenyl)-2-naphthamido)methyl)-1,2,4-thiadiazole-5-carboxamide (Compound 184)

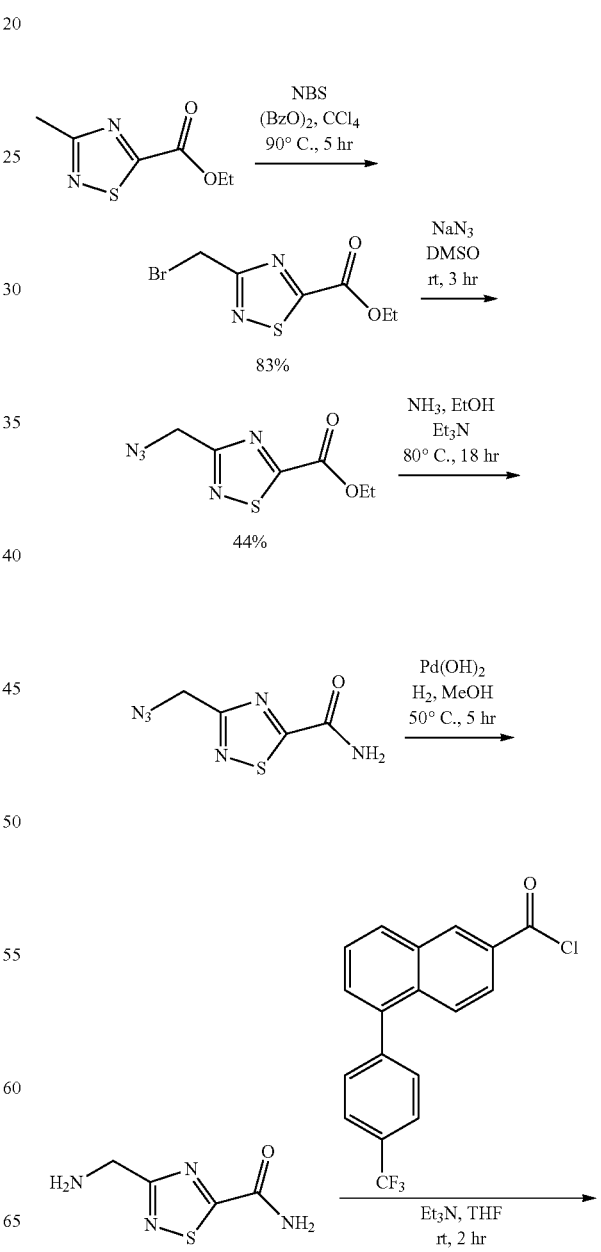

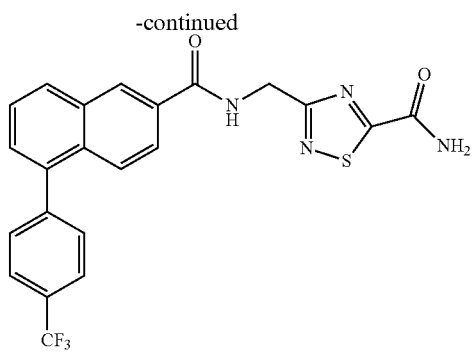

55%
Compound 184

Ethyl 3-(bromomethyl)-1,2,4-thiadiazole-5-carboxylate

Ethyl 3-methyl-1,2,4-thiadiazole-5-carboxylate (6.33 g, 1 equiv.), synthesized according to WO2008023157, NBS (14.14 g, 2 equiv.), benzoyl peroxide (5.77 g, 0.6 equiv.), and $CCl_4$ (130 mL) were heated to 90° C. for 5 hr. Upon completion, the mixture was cooled to rt, diluted with EtOAc and washed with sat. aq. $NH_4Cl$, $H_2O$, and brine. The organic layer was dried with $Na_2SO_4$, concentrated, and purified by FCC, 0 to 30% EtOAc in Hex gradient to give the desired product (7.72 g, 83%). LCMS [M+H]$^+$=251.

Ethyl 3-(azidomethyl)-1,2,4-thiadiazole-5-carboxylate

Ethyl 3-(bromomethyl)-1,2,4-thiadiazole-5-carboxylate (1.3 g, 1 equiv.), $NaN_3$ (0.7 g, 3 equiv.), and DMSO (5 mL) were stirred at rt for 3 hr. Upon completion, the mixture was diluted with EtOAc and washed with sat. aq. $NH_4Cl$, $H_2O$, and brine. The organic layer was dried with $Na_2SO_4$, concentrated, and purified by FCC, 0 to 100% DCM in Hex gradient to give the desired product (0.49 g, 44%). LCMS [M+H]$^+$=214.

3-(Azidomethyl)-1,2,4-thiadiazole-5-carboxamide

Ethyl 3-(azidomethyl)-1,2,4-thiadiazole-5-carboxylate (0.47 g, 1 equiv.), $Et_3N$ (0.6 mL), $NH_3$ in EtOH (1.65 mL, 2M), and EtOH (5 mL) were heated to 80° C. for 18 hr in a sealed vessel. Upon completion, the mixture was diluted with EtOAc and washed with sat. aq. $NH_4Cl$, $H_2O$, and brine. The organic layer was dried with $Na_2SO_4$, concentrated, and used directly in the next step without further purification. LCMS [M+H]$^+$=185.

3-(Aminomethyl)-1,2,4-thiadiazole-5-carboxamide 3-(Azidomethyl)-1,2,4-thiadiazole-5-carboxamide (213 mg, 1 equiv.), Pd(OH)$_2$ (25 mg), and MeOH (10 mL) were carefully purged with $H_2$. The reaction was stirred under positive pressure $H_2$ at 50° C. for 5 hr. The reaction was cooled to rt, filtered over celite and concentrated to five the desired product, which was used without further purification. LCMS [M+H]$^+$=159.

3-((5-(4-(Trifluoromethyl)phenyl)-2-naphthamido)methyl)-1,2,4-thiadiazole-5-carboxamide 3-(Aminomethyl)-1,2,4-thiadiazole-5-carboxamide (22 mg, 4 equiv.), 5-(4-(trifluoromethyl)phenyl)-2-naphthoyl chloride (10 mg, 1 equiv.), $Et_3N$ (0.04 mL, 8 equiv.), and THF (1 mL) were stirred at rt for 2 hr. The mixture was concentrated and purified by FCC 0 to 60% EtOAc in DCM gradient to give the desired product (8 mg, 55%). LCMS [M+H]$^+$=457.

Example 157: N-(pyrimidin-4-ylmethyl)-5-(4-(trifluoromethyl)phenyl)-2-naphthamide (Compound 185)

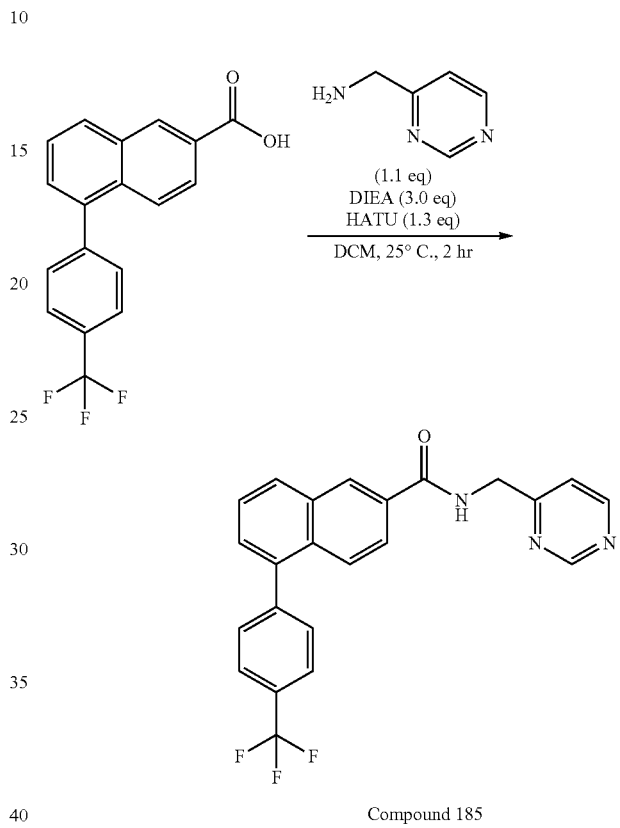

Compound 185

N-(pyrimidin-4-ylmethyl)-5-(4-(trifluoromethyl)phenyl)-2-naphthamide

The mixture of 5-[4-(trifluoromethyl)phenyl]naphthalene-2-carboxylic acid (30 mg, 94.8 umol, 1 eq), HATU (46.8 mg, 0.12 mmol, 1.3 eq) and DIPEA (36.7 mg, 0.28 mmol, 49.5 uL, 3 eq) in DCM (2 mL) was stirred at 25° C. for 1 hr. Then pyrimidin-4-ylmethanamine (11.3 mg, 0.10 mmol, 1.1 eq) was added into the mixture and the mixture was stirred at 25° C. for another 1 hr. The reaction mixture was diluted with $H_2O$ (10 mL) and the mixture was extracted with EA (10 mL*3). The combined organic phase was washed with brine (10 mL*2), dried with anhydrous $Na_2SO_4$, filtered and concentrated in vacuum. The residue was purified by prep-HPLC (column: Waters Xbridge 150*25 5u; mobile phase: [water (0.05% ammonia hydroxide v/v)-ACN]; B %: 46%-76%, 9 min). The title compound (7.5 mg, 17.9 umol, 18.8% yield) was obtained as a yellow solid. LCMS (ESI): RT=0.926 min, mass calcd for $C_{23}H_{16}F_3N_3O$ 407.39 m/z found 408.0 [M+H]$^+$. $^1$H NMR (400 MHz, CDCl$_3$) δ 9.15 (s, 1H), 8.66 (d, J=5.1 Hz, 1H), 8.41 (s, 1H), 7.95 (d, J=8.1 Hz, 1H), 7.83 (s, 2H), 7.71 (d, J=8.0 Hz, 2H), 7.59-7.55 (m, 2H), 7.55-7.51 (m, 2H), 7.45 (d, J=6.9 Hz, 1H), 7.33 (d, J=5.0 Hz, 1H), 4.77 (d, J=4.9 Hz, 2H).

Example 158: N-((2-cyanopyridin-4-yl)methyl)-5-(4-(trifluoromethyl)phenyl)-2-naphthamide (Compound 186)

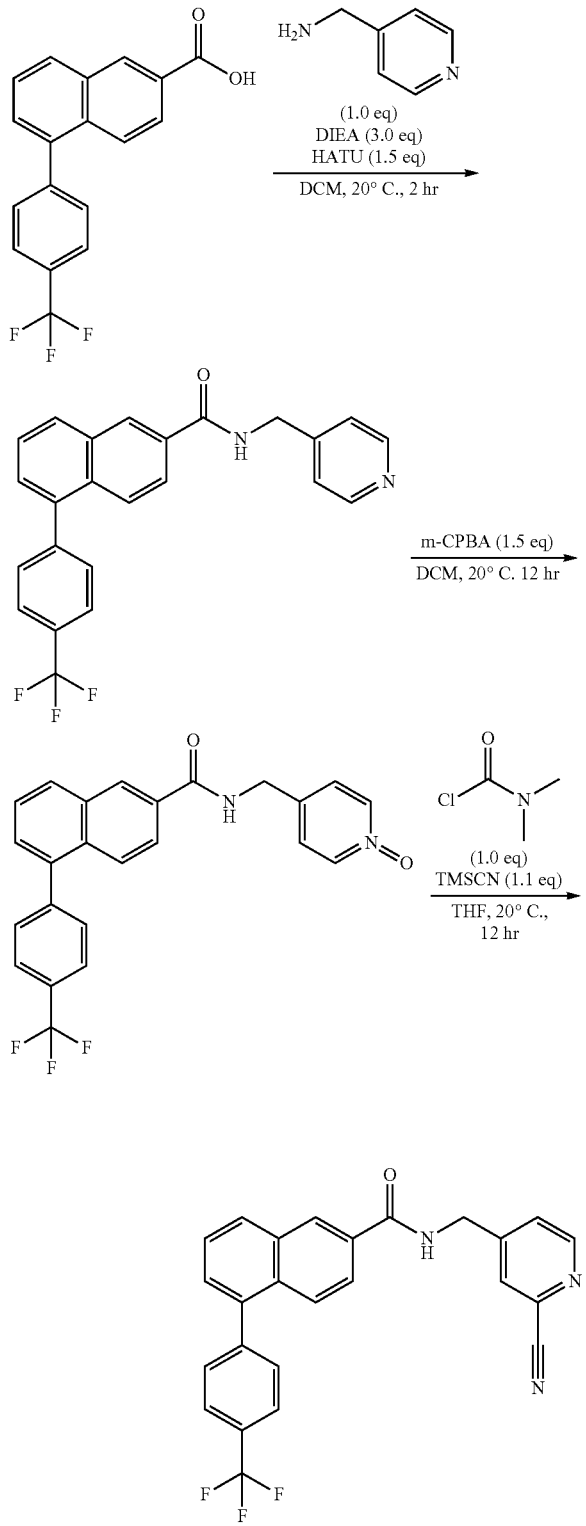

Compound 186

N-(pyridin-4-ylmethyl)-5-(4-(trifluoromethyl)phenyl)-2-naphthamide

The mixture of 5-[4-(trifluoromethyl)phenyl]naphthalene-2-carboxylic acid (200 mg, 0.63 mmol, 1 eq), HATU (360.6 mg, 0.94 mmol, 1.5 eq) and DIPEA (245.1 mg, 1.90 mmol, 0.33 mL, 3 eq) in DCM (3 mL) was stirred at 20° C. for 1 hr. Then 4-pyridylmethanamine (68.3 mg, 0.63 mmol, 63.9 uL, 1 eq) was added into the mixture and the mixture was stirred at 20° C. for another 1 hr. The reaction mixture was diluted with $H_2O$ (20 mL) and extracted with EA (20 mL*3). The combined organic phase was washed with brine (10 mL*2), dried with anhydrous $Na_2SO_4$, filtered and concentrated in vacuum. The residue was purified by column chromatography ($SiO_2$, Petroleum ether/Ethyl acetate=1/0 to 1:1). Compound N-(4-pyridylmethyl)-5-[4-(trifluoromethyl)phenyl]naphthalene-2-carboxamide (256 mg, 0.62 mmol, 99.6% yield) was obtained as a white solid.

4-((5-(4-(trifluoromethyl)phenyl)-2-naphthamido)methyl)pyridine 1-oxide

To a solution of N-(4-pyridylmethyl)-5-[4-(trifluoromethyl)phenyl]naphthalene-2-carboxamide (100 mg, 0.24 mmol, 1 eq) in DCM (2 mL) was added m-CPBA (79.6 mg, 0.36 mmol, 80%, 1.5 eq). The mixture was stirred at 20° C. for 12 hr. The reaction mixture was diluted with $H_2O$ (10 mL) and extracted with EA (10 mL*3). The combined organic phase was washed with brine (10 mL*2), dried with anhydrous $Na_2SO_4$, filtered and concentrated in vacuum. The residue was purified by column chromatography ($SiO_2$, Ethyl acetate:Methanol=1/0 to 5:1). Compound N-[(1-oxidopyridin-1-ium-4-yl)methyl]-5-[4-(trifluoromethyl)phenyl]naphthalene-2-carboxamide (74 mg, 0.17 mmol, 71.2% yield) was obtained as a white solid.

N-((2-cyanopyridin-4-yl)methyl)-5-(4-(trifluoromethyl)phenyl)-2-naphthamide

To a solution of N-[(1-oxidopyridin-1-ium-4-yl)methyl]-5-[4-(trifluoromethyl)phenyl]naphthalene-2-carboxamide (74 mg, 0.17 mmol, 1 eq) in DCM (2 mL) was added TMSCN (19.1 mg, 0.19 mmol, 24.1 uL, 1.1 eq) and N,N-dimethylcarbamoyl chloride (18.8 mg, 0.17 mmol, 16.1 uL, 1 eq). The mixture was stirred at 20° C. for 12 hr. The reaction mixture was diluted with $H_2O$ (10 mL) and extracted with EA (10 mL*3). The combined organic phase was washed with brine (10 mL*2), dried with anhydrous $Na_2SO_4$, filtered and concentrated in vacuum. The residue was purified by prep-HPLC (column: Xtimate $C_{18}$ 150*25 mm*5 um; mobile phase: [water (10 mM $NH_4HCO_3$)-ACN]; B %: 50%-80%, 8.5 min). The title compound (6.0 mg, 13.9 umol, 7.9% yield) was obtained as a yellow solid. LCMS (ESI): RT=0.985 min, mass calcd for $C_{25}H_{16}F_3N_3O$ 431.41 m/z found 432.0 [M+H]$^+$. $^1$H NMR (400 MHz, $CD_3OD$) δ 8.55 (d, J=5.1 Hz, 1H), 8.45 (d, J=1.5 Hz, 1H), 7.98 (d, J=8.3 Hz, 1H), 7.85-7.80 (m, 1H), 7.80-7.76 (m, 2H), 7.74 (d, J=8.0 Hz, 2H), 7.60-7.58 (m, 2H), 7.58-7.54 (m, 2H), 7.48 (dd, J=1.1, 7.0 Hz, 1H), 4.61 (s, 2H).

Example 159: N-((6-((2,6-difluorophenoxy)methyl)pyridin-2-yl)methyl)-5-(4-(trifluoromethyl)phenyl)-2-naphthamide (Compound 187)

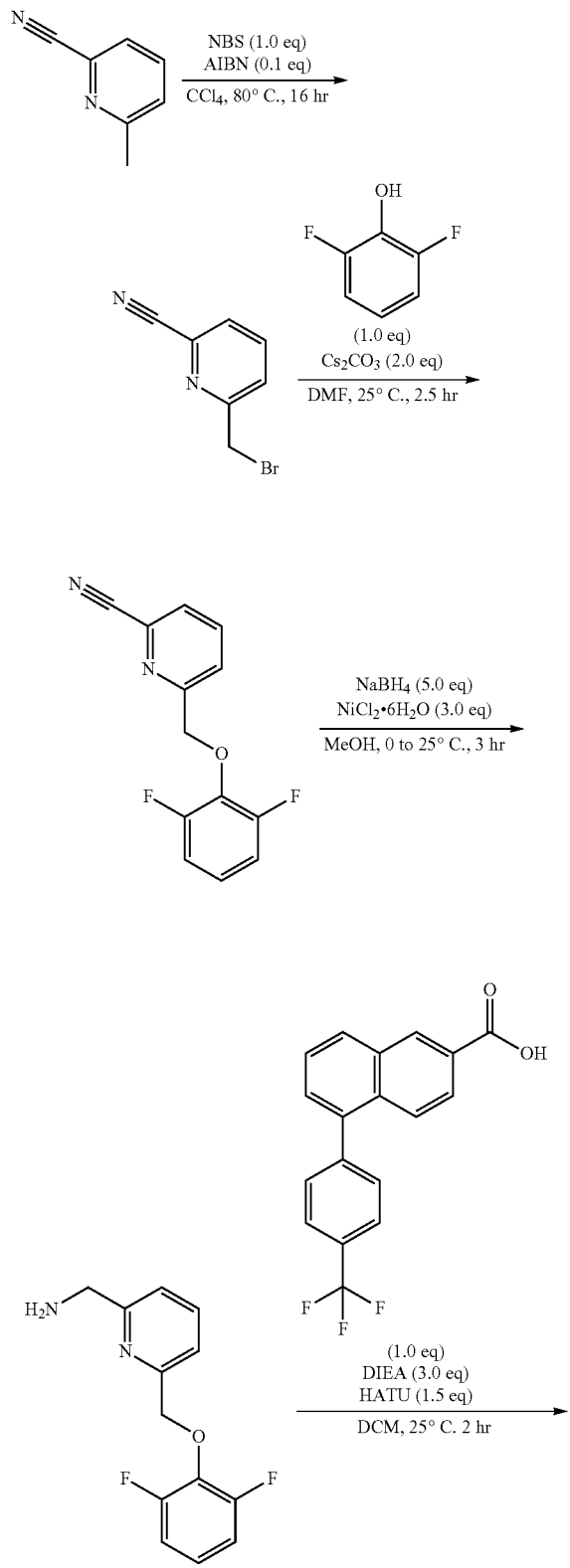

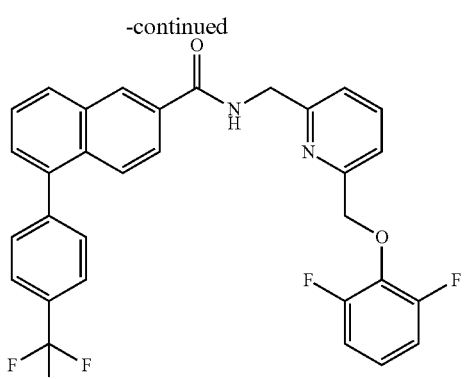

Compound 187

6-(bromomethyl)picolinonitrile

To a solution of 6-methylpyridine-2-carbonitrile (1 g, 8.46 mmol, 1 eq) in CCl$_4$ (15 mL) was added NBS (1.51 g, 8.46 mmol, 1 eq) and AIBN (139.0 mg, 0.84 mmol, 0.1 eq). The mixture was stirred at 80° C. for 16 hr. The reaction mixture was added H$_2$O (30 mL) and extracted with EA (30 mL*3). The combined organic layers were washed with brine (30 mL), dried with anhydrous Na$_2$SO$_4$, filtered and concentrated under reduced pressure to give a residue. The residue was purified by flash silica gel chromatography (40 g SepaFlash® Silica Flash Column, EA/PE: 0~10%) to afford two main spots. To afford 6-(bromomethyl)pyridine-2-carbonitrile (979 mg, crude) as yellow solid.

6-((2,6-difluorophenoxy)methyl)picolinonitrile

To a solution of 2,6-difluorophenol (200 mg, 1.54 mmol, 1 eq) in DMF (5 mL) was added Cs$_2$CO$_3$ (1.0 g, 3.0 mmol, 2 eq) at 25° C. The mixture was stirred at 25° C. for 0.5 hr. Then 6-(bromomethyl)pyridine-2-carbonitrile (644.4 mg, 1.5 mmol, 1 eq) was added into the reaction. The mixture was stirred at 25° C. for 2 hr. The mixture was added H$_2$O (20 mL) and extracted with EA (15 mL*3). The combined organic layers were washed with brine (20 mL), dried with anhydrous Na$_2$SO$_4$, filtered and concentrated under reduced pressure to give a residue. The residue was purified by flash silica gel chromatography (20 g SepaFlash® Silica Flash Column, EA/PE: 0~10%). To afford 6-[(2,6-difluorophenoxy)methyl]pyridine-2-carbonitrile (500 mg, 2.0 mmol, 87.1% yield) as white solid.

(6-((2,6-difluorophenoxy)methyl)pyridin-2-yl)methanamine

A mixture of 6-[(2,6-difluorophenoxy)methyl]pyridine-2-carbonitrile (500 mg, 2.03 mmol, 1 eq) and NiCl$_2$.6H$_2$O (1.45 g, 6.09 mmol, 3 eq) in MeOH (10 mL) was added NaBH$_4$ (384.1 mg, 10.15 mmol, 5 eq) at 0° C. After addition, the mixture was stirred at 25° C. for 3 hr. The filter was poured into H$_2$O (30 mL) and stirred for 5 min. The aqueous phase was extracted with EA (15 mL*3). The combined organic phase was washed with brine (20 mL), dried with anhydrous Na$_2$SO$_4$, filtered and concentrated in vacuo. The residue was purified by flash silica gel chromatography (20 g SepaFlash® Silica Flash Column, EA/PE: 0~30%). Compound [6-[(2,6-difluorophenoxy)methyl]-2-pyridyl]methanamine (355 mg, 1.42 mmol, 69.8% yield) was obtained as a yellow solid.

N-((6-((2,6-difluorophenoxy)methyl)pyridin-2-yl)methyl)-5-(4-(trifluoromethyl)phenyl)-2-naphthamide To a solution of 5-[4-(trifluoromethyl)phenyl]naphthalene-2-carboxylic acid (50 mg, 0.15 mmol, 1 eq) and HATU (90.1 mg, 0.23 mmol, 1.5 eq) in DCM (2 mL) was added DIPEA (61.3 mg, 0.47 mmol, 82.6 uL, 3 eq). After addition, the mixture was stirred at 25° C. for 0.5 hr, and then [6-[(2,6-difluorophenoxy)methyl]-2-pyridyl]methanamine (59.3 mg, 0.14 mmol, 0.9 eq) was added. The resulting mixture was stirred at 25° C. for 1.5 hr. The mixture was added H$_2$O (20 mL) and extracted with EA (15 mL*3). The combined organic layers were washed with brine (20 mL), dried with anhydrous Na$_2$SO$_4$, filtered and concentrated under reduced pressure to give a residue. The residue was purified by prep-HPLC (column: Waters Xbridge 150*50 10u; mobile phase: [water (0.05% ammonia hydroxide v/v)-ACN]; B %: 68%-98%, 7.8 min). The title compound (36.2 mg, 66.0 umol, 20.8% yield) was obtained as white solid. LCMS (ESI): RT=0.943 min, mass calcd for C$_{31}$H$_{21}$F$_5$N$_2$O$_2$ 548.50 m/z found 549.1 [M+H]$^+$. $^1$H NMR (400 MHz, DMSO-d$_6$) δ 9.36 (t, J=5.9 Hz, 1H), 8.65 (d, J=1.3 Hz, 1H), 8.14 (d, J=8.3 Hz, 1H), 8.00 (dd, J=1.8, 8.8 Hz, 1H), 7.92 (d, J=8.3 Hz, 2H), 7.89-7.81 (m, 2H), 7.77-7.68 (m, 3H), 7.64-7.58 (m, 1H), 7.48 (d, J=7.5 Hz, 1H), 7.35 (d, J=7.8 Hz, 1H), 7.21-7.08 (m, 3H), 5.23 (s, 2H), 4.61 (d, J=6.0 Hz, 2H).

Example 160: N-[3-hydroxy-1-(2-pyridyl)propyl]-5-[4-(trifluoromethyl)phenyl]naphthalene-2-carboxamide (Compound 188)

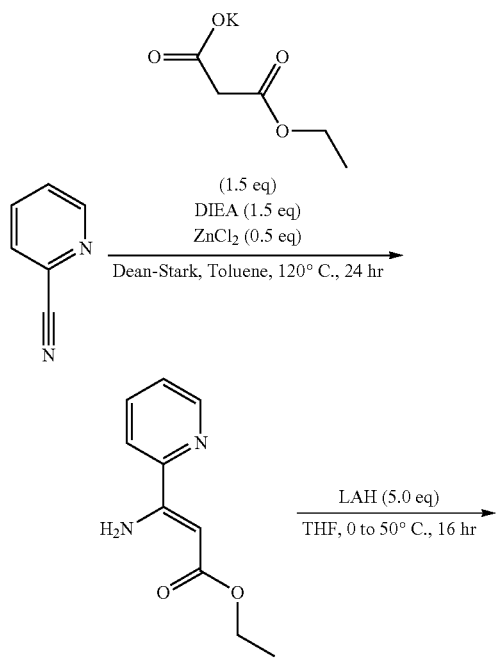

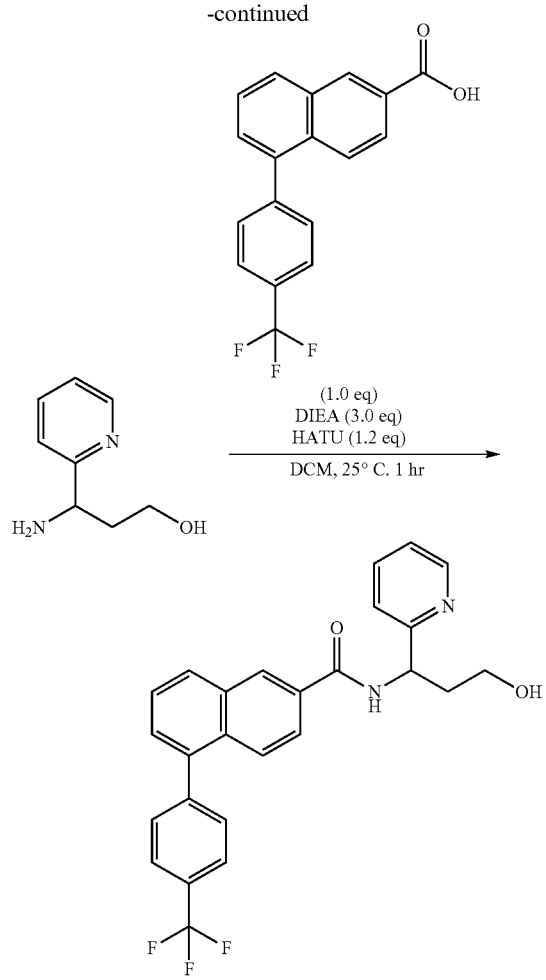

Compound 188

Ethyl (Z)-3-amino-3-(2-pyridyl)prop-2-enoate

A mixture of pyridine-2-carbonitrile (1 g, 9.61 mmol, 925.93 uL, 1 eq), potassium; 3-ethoxy-3-oxo-propanoate (2.45 g, 14.41 mmol, 1.5 eq), ZnCl$_2$ (654.5 mg, 4.80 mmol, 0.22 mL, 0.5 eq), DIPEA (1.49 g, 11.53 mmol, 2.01 mL, 1.2 eq) in toluene (20 mL) was stirred at 120° C. for 24 hr under N$_2$ atmosphere. The reaction mixture was diluted with NH$_4$Cl (20 mL). The combined organic phase dried with anhydrous Na$_2$SO$_4$, filtered and concentrated in vacuum. The residue was purified by column chromatography (SiO$_2$, Petroleum ether/Ethyl acetate=1/0 to 1:1). Compound ethyl (Z)-3-amino-3-(2-pyridyl)prop-2-enoate (1 g, 5.10 mmol, 53.0% yield) was obtained as yellow solid.

3-amino-3-(2-pyridyl)propan-1-ol

To a solution of ethyl (Z)-3-amino-3-(2-pyridyl)prop-2-enoate (150 mg, 0.78 mmol, 1 eq) in THF (1 mL) was added LiAlH$_4$ (148.08 mg, 3.90 mmol, 5 eq) at 0° C. The mixture was stirred at 50° C. for 16 hr. The reaction mixture was diluted with H$_2$O (0.5 mL), NaOH (2M, 0.25 mL), filtered and concentrated under reduced pressure to give a residue. Compound 3-amino-3-(2-pyridyl)propan-1-ol (40 mg, crude) was obtained as yellow oil, which was used into the next step without further purification.

N-[3-hydroxy-1-(2-pyridyl)propyl]-5-[4-(trifluoromethyl)phenyl]naphthalene-2-carboxamide The mixture of 5-[4-(trifluoromethyl)phenyl]naphthalene-2-carboxylic acid (83.1 mg, 0.26 mmol, 1 eq), 3-amino-3-(2-pyridyl)propan-1-ol (40 mg, 0.26 mmol, 1 eq), HATU (149.9 mg, 0.39 mmol, 1.5 eq) and DIPEA (135.8 mg, 1.05 mmol, 0.18 mL, 4 eq) in DCM (1 mL) was stirred at 25° C. for 16 hr. The reaction mixture was diluted with H$_2$O (10 mL) and the mixture was extracted with EA (20 mL*3). The combined organic phase was washed with brine (10 mL*2), dried with anhydrous Na$_2$SO$_4$, filtered and concentrated in vacuum. The residue was purified prep-HPLC (column: Welch Xtimate C18 150*25 mm*5 um; mobile phase: [water (0.05% HCl)-ACN]; B %: 23%-53%, 11.5 min). The title compound (1.5 mg, 3.0 umol, 1.1% yield, HCl) was obtained as yellow oil. LCMS (ESI): RT=0.860, mass calcd for C$_{26}$H$_{21}$F$_3$N$_2$O$_2$ 450.45 m/z found 451.1 [M+H]$^+$. $^1$H NMR (400 MHz, CD$_3$OD) δ ppm 2.25-2.47 (m, 2H) 3.74 (dt, J=11.10, 5.39 Hz, 1H) 3.82-3.89 (m, 1H) 5.51-5.56 (m, 1H) 7.62 (dd, J=7.07, 1.19 Hz, 1H) 7.68-7.74 (m, 3H) 7.87 (d, J=8.00 Hz, 2H) 7.89-7.93 (m, 2H) 7.99-8.03 (m, 1H) 8.12 (d, J=8.13 Hz, 1H) 8.18 (br d, J=8.26 Hz, 1H) 8.58-8.65 (m, 2H) 8.80 (d, J=5.75 Hz, 1H).

Example 161: N-[(E)-5-(2,6-difluorophenoxy)pent-3-enyl]-5-[4-(trifluoromethyl)phenyl]naphthalene-2-carboxamide (Compound 189)

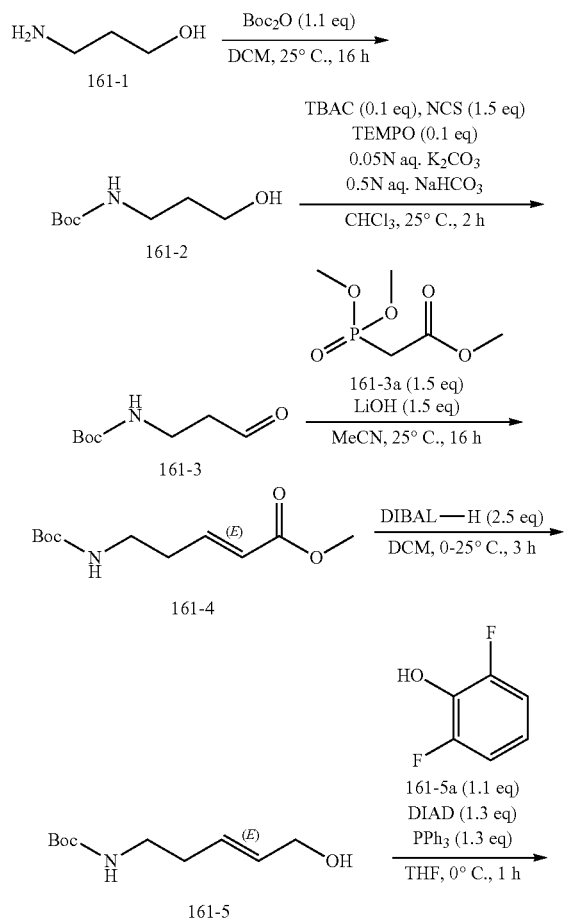

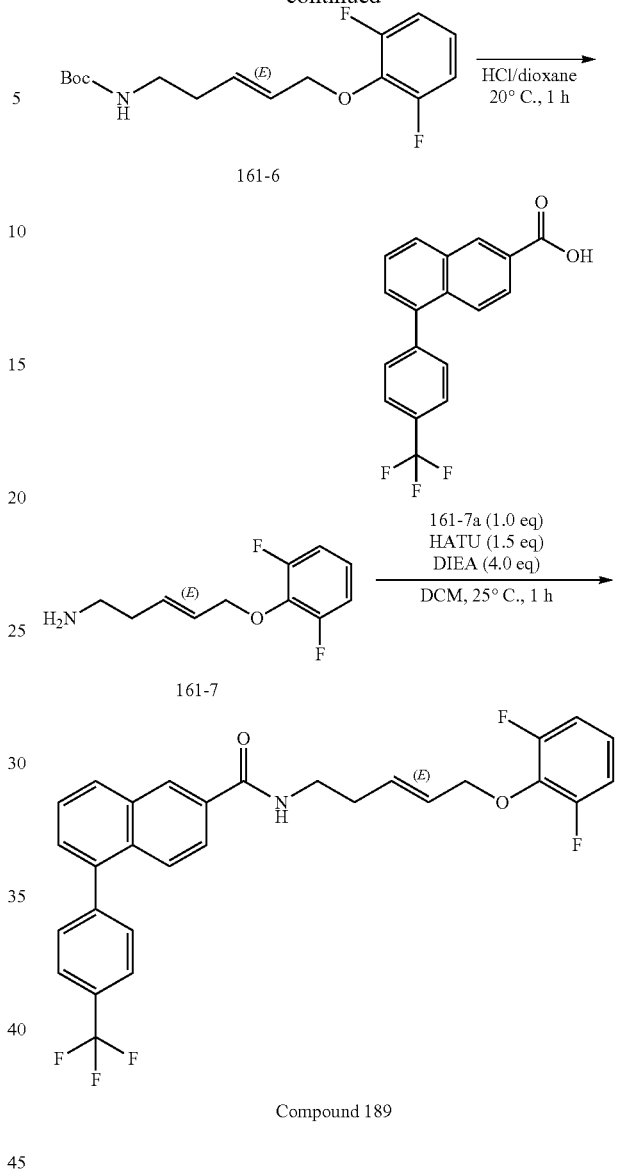

Compound 189

Tert-Butyl N-(3-hydroxypropyl)carbamate

To a solution of compound 161-1 (5 g, 66.5 mmol, 5.1 mL, 1 eq) in DCM (50 mL) was added dropwise a solution of Boc$_2$O (15.9 g, 73.2 mmol, 16.8 mL, 1.1 eq) in DCM (30 mL). The reaction was stirred at 25° C. for 16 hr. The reaction was washed with Sat.NaHCO$_3$ (15 mL) and brine (2*15 mL). The organic layer was dried over Na$_2$SO$_4$ and concentrated. Compound 161-2 (10 g, 57 mmol, 85.7% yield) was used for next step directly as colorless oil, which was confirmed by $^1$H NMR. $^1$H NMR (400 MHz, CDCl$_3$) δ 4.78 (br s, 1H), 3.66 (t, J=5.6 Hz, 2H), 3.29 (t, J=6.1 Hz, 2H), 2.74 (br s, 1H), 1.71-1.60 (m, 2H), 1.45 (s, 9H).

Tert-Butyl N-(3-oxopropyl)carbamate

To a suspension of compound 161-2 (1 g, 5.7 mmol, 0.98 mL, 1 eq), TBAC (158.6 mg, 0.57 mmol, 0.15 mL, 0.1 eq), NCS (1.14 g, 8.56 mmol, 1.5 eq) and TEMPO (89.7 mg, 0.57 mmol, 0.1 eq) in CHCl$_3$ (20 mL) was added a solution of NaHCO$_3$ (840 mg, 10 mmol, 0.38 mL, 1.75 eq) and K₂CO₃ (138 mg, 0.9 mmol, 1.75e-1 eq) in H₂O (20 mL). The reaction was stirred at 25° C. for 2 hr. The reaction was filtered and concentrated. The crude product was purified by column chromatography on silica gel (EA:PE=1:10) to give compound 161-3 (1 g, crude) as colorless oil, which was confirmed by ¹H NMR. ¹H NMR (400 MHz, CDCl₃) δ 9.82 (s, 1H), 4.94 (br d, J=9.6 Hz, 1H), 3.43 (br d, J=5.0 Hz, 2H), 2.75-2.71 (m, 2H), 1.44 (br s, 9H).

Methyl (E)-5-(tert-butoxycarbonylamino)pent-2-enoate

To a solution of compound 161-3 (1 g, 5.77 mmol, 1 eq) and compound 161-3a (1.58 g, 8.66 mmol, 1.25 mL, 1.5 eq) in MeCN (10 mL) was added LiOH·H₂O (363.4 mg, 8.66 mmol, 1.5 eq). The reaction was stirred at 25° C. for 16 hr. The reaction was concentrated. The residue was diluted with EA (30 mL) and washed with H₂O (2*10 mL). The organic layer was dried over Na₂SO₄ and concentrated. The crude product was purified by column chromatography on silica gel (EA:PE=1:5) to give compound 161-4 (0.3 g, 1.31 mmol, 22.7% yield) as colorless oil.

Tert-Butyl N-[(E)-5-hydroxypent-3-enyl]carbamate

To a solution of compound 161-4 (0.1 g, 0.43 mmol, 1 eq) in DCM (1 mL) was added DIBALH (1 M, 1.0 mL, 2.5 eq) at 0° C. The reaction was warmed to 25° C. for 3 hr. The reaction was diluted with DCM (10 mL) and washed with H₂O (2*5 mL). The organic layer was dried over Na₂SO₄ and concentrated. The crude product was purified by column chromatography on silica gel (EA:PE=1:3-1:1) to give compound 161-5 (55 mg, 0.27 mmol, 62.6% yield) as colorless oil, which was confirmed by ¹HNMR. ¹H NMR (400 MHz, CDCl₃) δ 5.80-5.57 (m, 2H), 4.56 (br s, 1H), 4.16-4.11 (m, 2H), 3.20 (br d, J=6.0 Hz, 2H), 2.25 (q, J=6.5 Hz, 2H), 1.53 (br s, 1H), 1.45 (s, 9H).

Tert-Butyl N-[(E)-5-(2,6-difluorophenoxy)pent-3-enyl]carbamate

To a solution of compound 161-5 (70 mg, 0.34 mmol, 1 eq), 161-5a (49.7 mg, 0.38 mmol, 1.1 eq) and PPh₃ (118.5 mg, 0.45 mmol, 1.3 eq) in THF (1 mL) was added DIAD (91.4 mg, 0.45 mmol, 87 uL, 1.3 eq) at 0° C. The reaction was stirred at 0° C. for 1 hr. The reaction mixture was concentrated. The residue was triturated with EA/PE (1:2, 1 mL) and filtered to give compound 161-6 (150 mg, crude) as yellow oil, which was used for next step directly.

(E)-5-(2,6-difluorophenoxy)pent-3-en-1-amine

A solution of compound 161-6 (150 mg, 0.47 mmol, 1 eq) in HCl/dioxane (1 mL) was stirred at 20° C. for 1 hr. The reaction was concentrated to give compound 161-7 (100 mg, 92.1 umol, 19.2% yield, HCl) as yellow oil, which was used for next step directly.

N-[(E)-5-(2,6-difluorophenoxy)pent-3-enyl]-5-[4-(trifluoromethyl)phenyl]naphthalene-2-carboxamide To a solution of compound 161-7a (29.1 mg, 92.1 umol, 1 eq), HATU (52.54 mg, 0.13 mmol, 1.5 eq) and compound 7 (100 mg, 92 umol, 1 eq, HCl) in DCM (2 mL) was added DIEA (47.62 mg, 0.36 mmol, 64 uL, 4 eq). The reaction was stirred at 25° C. for 1 hr. The reaction was diluted with EA (15 mL) and washed with H₂O (2*5 mL). The organic layer was dried over Na₂SO₄ and concentrated. The crude product was purified by Prep.HPLC (column: Waters Xbridge Prep OBD C18 100*19 mm*5 um; mobile phase: [water (0.05% ammonia hydroxide v/v)-ACN]; B %: 70%-100%, 7.8 min) to give the title compound (4.2 mg, 8 umol, 8.7% yield) as a white solid. LCMS (ESI): RT=1.082 min, mass calcd. For C₂₉H₂₂F₅NO₂, 511.16 m/z found 512.1 [M+H]⁺. ¹H NMR (400 MHz, CDCl₃) δ 8.35 (s, 1H), 7.99 (d, J=8.0 Hz, 1H), 7.90-7.85 (m, 1H), 7.81-7.73 (m, 3H), 7.65-7.57 (m, 3H), 7.51 (d, J=6.3 Hz, 1H), 6.95-6.78 (m, 3H), 6.30 (br s, 1H), 5.95-5.77 (m, 2H), 4.63 (d, J=5.3 Hz, 2H), 3.58 (q, J=6.4 Hz, 2H), 2.45 (q, J=6.4 Hz, 2H).

Example 162: N-((6-fluoropyridin-2-yl)methyl)-5-(4-(trifluoromethyl)phenyl)-2-naphthamide (Compound 190)

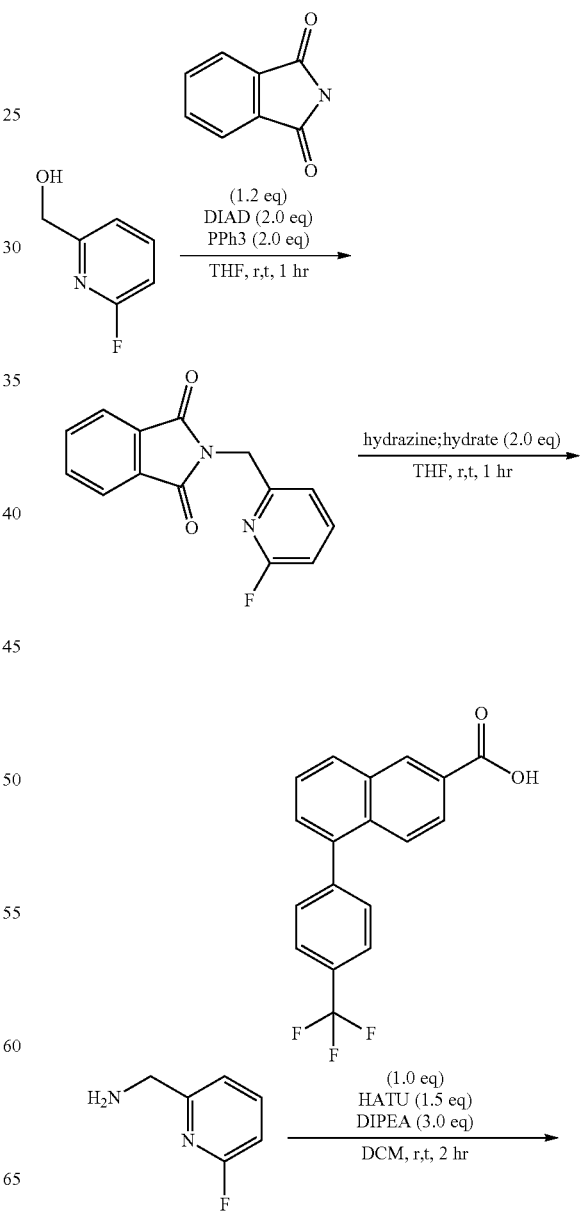

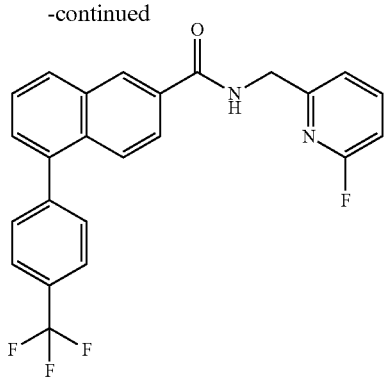

Compound 190

2-((6-fluoropyridin-2-yl)methyl)isoindoline-1,3-dione

A mixture of (6-fluoro-2-pyridyl)methanol (200 mg, 1.57 mmol, 1 eq), isoindoline-1,3-dione (277.7 mg, 1.89 mmol, 1.2 eq), DIAD (636 mg, 3.15 mmol, 0.61 mL, 2 eq), PPh$_3$ (825 mg, 3.15 mmol, 2 eq) in THF (3 mL) was degassed and purged with N$_2$ for 3 times, and then the mixture was stirred at 25° C. for 1 hr under N$_2$ atmosphere. The reaction mixture was diluted with H$_2$O (10 mL) and extracted with EA (10 mL*3). The combined organic phase was washed with brine (10 mL*2), dried with anhydrous Na$_2$SO$_4$, filtered and concentrated in vacuum. The residue was purified by column chromatography (SiO$_2$, Petroleum ether/Ethyl acetate=1/0 to 1:1). Compound 2-[(6-fluoro-2-pyridyl)methyl]isoindoline-1,3-dione (300 mg, 1.17 mmol, 74.4% yield) was obtained as a white solid.

6-fluoropyridin-2-yl)methanamine

To a solution of 2-[(6-fluoro-2-pyridyl)methyl]isoindoline-1,3-dione (300 mg, 1.17 mmol, 1 eq) in THF (4 mL) was added hydrazine hydrate (117 mg, 2.34 mmol, 0.11 mL, 2 eq). The mixture was stirred at 25° C. for 1 hr. The reaction mixture was diluted with H$_2$O (10 mL) and extracted with EA (10 mL*3). The combined organic phase was washed with brine (10 mL*2), dried with anhydrous Na$_2$SO$_4$, filtered and concentrated in vacuum. No purification. Compound (6-fluoro-2-pyridyl)methanamine (100 mg, 0.79 mmol, 67.7% yield) was obtained as yellow oil.

N-((6-fluoropyridin-2-yl)methyl)-5-(4-(trifluoromethyl)phenyl)-2-naphthamide The mixture of 5-[4-(trifluoromethyl)phenyl]naphthalene-2-carboxylic acid (75 mg, 0.23 mmol, 1 eq), HATU (135 mg, 0.35 mmol, 1.5 eq) and DIPEA (92 mg, 0.71 mmol, 0.12 mL, 3 eq) in DCM (2 mL) was stirred at 20° C. for 1 hr. Then (6-fluoro-2-pyridyl)methanamine (30 mg, 0.23 mmol, 1 eq) was added into the mixture and the mixture was stirred at 20° C. for another 1 hr. The reaction mixture was diluted with H$_2$O (10 mL) and extracted with EA (10 mL*3). The combined organic phase was washed with brine (10 mL*2), dried with anhydrous Na$_2$SO$_4$, filtered and concentrated in vacuum. The residue was purified by prep-HPLC (column: Xtimate C$_{18}$ 150*25 mm*5 um; mobile phase: [water (0.05% HCl)-ACN]; B %: 50%-80%, 11.5 min). The title compound (18 mg, 39.5 umol, 16.6% yield, HCl) was obtained as a white solid. LCMS (ESI): RT=0.997 min, mass calcd for C$_{24}$H$_{16}$F$_4$N$_2$O 424.39 m/z found 425.0 [M+H]$^+$. $^1$H NMR (400 MHz, CDCl$_3$) δ 8.48 (s, 1H), 8.04 (d, J=8.3 Hz, 1H), 7.92-7.89 (m, 2H), 7.88-7.82 (m, 1H), 7.80 (d, J=8.0 Hz, 2H), 7.67-7.62 (m, 3H), 7.55-7.52 (m, 1H), 7.39 (br s, 1H), 7.33-7.29 (m, 1H), 6.90 (dd, J=2.5, 8.1 Hz, 1H), 4.82 (d, J=5.1 Hz, 2H).

Example 163: N-((6-cyanopyridin-2-yl)methyl)-5-(4-(trifluoromethyl)phenyl)-2-naphthamide (Compound 191)

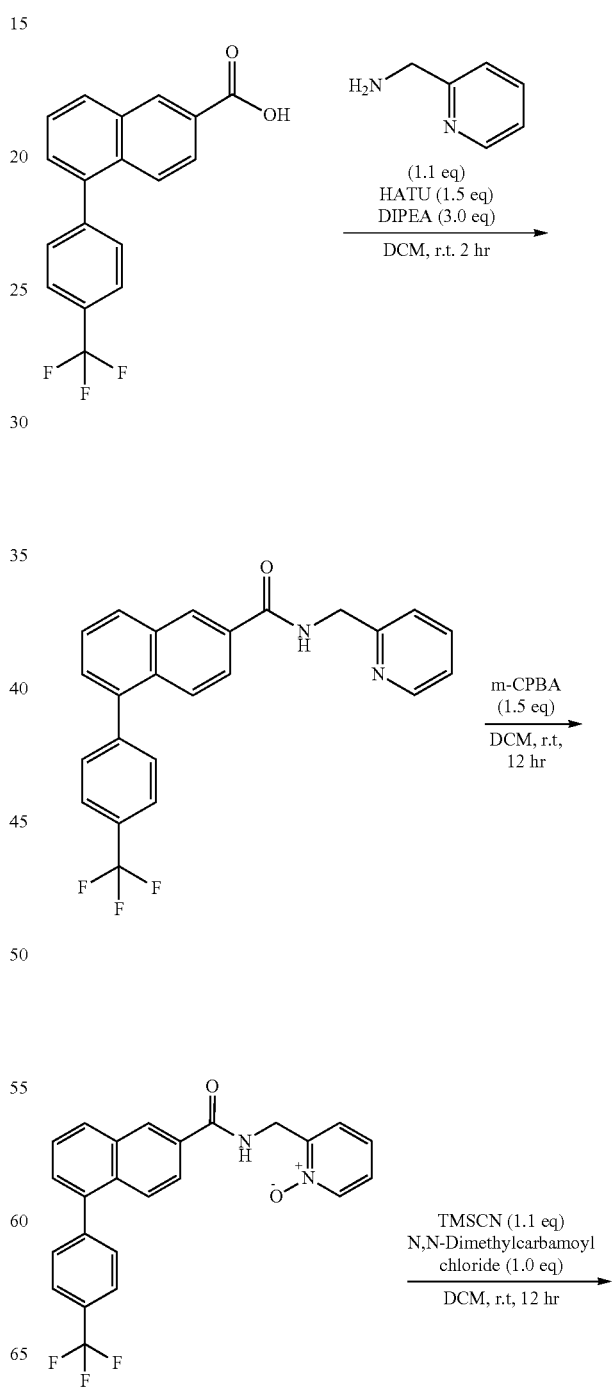

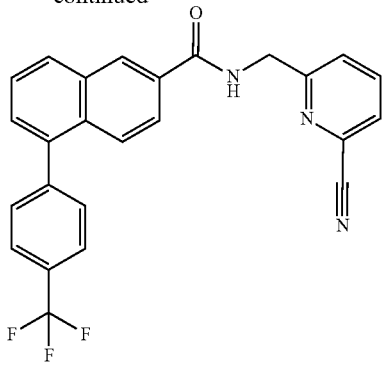

Compound 191

N-(pyridin-2-ylmethyl)-5-(4-(trifluoromethyl)phenyl)-2-naphthamide

The mixture of 5-[4-(trifluoromethyl)phenyl]naphthalene-2-carboxylic acid (200 mg, 0.63 mmol, 1 eq), HATU (360.6 mg, 0.94 mmol, 1.5 eq) and DIPEA (245.1 mg, 1.90 mmol, 0.3 mL, 3 eq) in DCM (3 mL) was stirred at 25° C. for 1 hr. Then 2-pyridylmethanamine (75.2 mg, 0.69 mmol, 70.9 uL, 1.1 eq) was added into the mixture and the mixture was stirred at 25° C. for another 1 hr. The reaction mixture was diluted with H₂O (10 mL) and extracted with EA (10 mL*3). The combined organic phase was washed with brine (10 mL*2), dried with anhydrous Na₂SO₄, filtered and concentrated in vacuum. The residue was purified by column chromatography (SiO₂, Petroleum ether/Ethyl acetate=1/0 to 1:1). Compound N-(2-pyridylmethyl)-5-[4-(trifluoromethyl)phenyl]naphthalene-2-carboxamide (200 mg, 0.49 mmol, 77.8% yield) was obtained as a white solid.

2-((5-(4-(trifluoromethyl)phenyl)-2-naphthamido)methyl)pyridine 1-oxide

The mixture of N-(2-pyridylmethyl)-5-[4-(trifluoromethyl)phenyl]naphthalene-2-carboxamide (100 mg, 0.24 mmol, 1 eq) and m-CPBA (74.9 mg, 0.36 mmol, 85%, 1.5 eq) in DCM (2 mL) was stirred at 20° C. for 12 hr. The reaction mixture was diluted with H₂O (10 mL) and extracted with EA (10 mL*3). The combined organic phase was washed with brine (10 mL*2), dried with anhydrous Na₂SO₄, filtered and concentrated in vacuum. The residue was purified by column chromatography (SiO₂, Ethyl acetate:Methanol=1/0 to 5:1). Compound N-[(1-oxidopyridin-1-ium-2-yl)methyl]-5-[4-(trifluoromethyl)phenyl]naphthalene-2-carboxamide (90 mg, 0.21 mmol, 86.5% yield) was obtained as a white solid.

N-((6-cyanopyridin-2-yl)methyl)-5-(4-(trifluoromethyl)phenyl)-2-naphthamide

The mixture of N-[(1-oxidopyridin-1-ium-2-yl)methyl]-5-[4-(trifluoromethyl)phenyl]naphthalene-2-carboxamide (90 mg, 0.21 Mmol, 1 eq), N,N-dimethylcarbamoyl chloride (22.9 mg, 0.21 Mmol, 19 uL, 1 eq) and TMSCN (23.2 mg, 0.23 mmol, 29 uL, 1.1 eq) in DCM (2 mL) was stirred at 20° C. for 12 hr. The reaction mixture was diluted with H₂O (10 mL) and extracted with EA (10 mL*3). The combined organic phase was washed with brine (10 mL*2), dried with anhydrous Na₂SO₄, filtered and concentrated in vacuum. The residue was purified by column chromatography (SiO₂, Petroleum ether/Ethyl acetate=1/0 to 1:1). The title compound (5.6 mg, 12.7 umol, 5.9% yield) was obtained as a yellow solid. LCMS (ESI): RT=0.992 min, mass calcd for $C_{25}H_{16}F_3N_3O$ 431.41 m/z found 432.0 [M+H]⁺, ¹H NMR (400 MHz, CD₃OD) δ 8.57 (d, J=1.8 Hz, 1H), 8.10 (d, J=8.3 Hz, 1H), 8.02-7.97 (m, 1H), 7.97-7.93 (m, 1H), 7.92-7.88 (m, 1H), 7.86 (d, J=8.0 Hz, 2H), 7.79 (d, J=7.5 Hz, 1H), 7.74 (d, J=8.0 Hz, 1H), 7.73-7.67 (m, 3H), 7.60 (dd, J=1.3, 7.0 Hz, 1H), 4.80 (s, 2H).

Example 164: N-(3-((isoxazol-3-yloxy)methyl)benzyl)-5-(4-(trifluoromethyl)phenyl)-2-naphthamide (Compound 192)

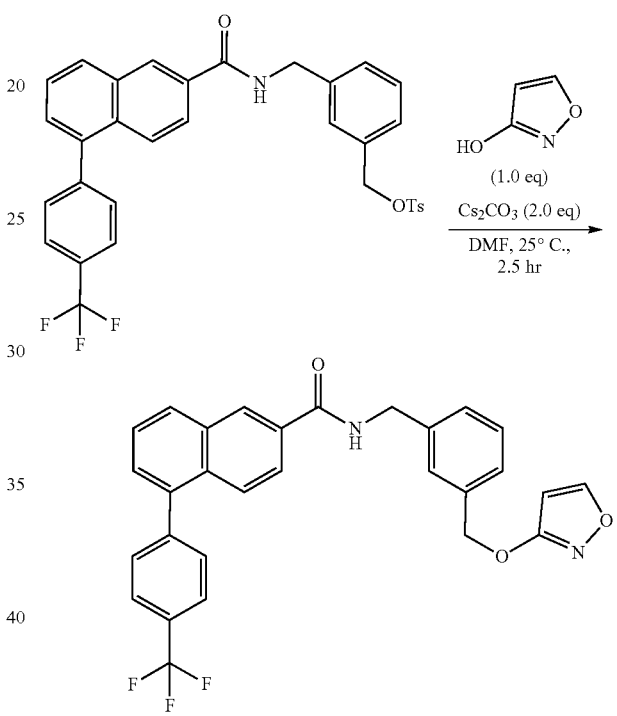

Compound 192

To a solution of [3-[[[5-[4-(trifluoromethyl)phenyl]naphthalene-2-carbonyl]amino]methyl]phenyl]methyl 4-methylbenzenesulfonate (50 mg, 84.7 umol, 1 eq) in DMF (1 mL) was added Cs₂CO₃ (55.2 mg, 0.16 mmol, 2 eq) at 25° C. The mixture was stirred at 25° C. for 0.5 hr. Then isoxazol-3-ol (7.21 mg, 84.7 umol, 1 eq) was added into the reaction. The mixture was stirred at 25° C. for 2 hr. The mixture was added H₂O (10 mL) and extracted with EA (15 mL*3). The combined organic layers were washed with brine (20 mL), dried with anhydrous Na₂SO₄, filtered and concentrated under reduced pressure to give a residue. The residue was purified by prep-HPLC (column: Xtimate C18 150*25 mm*5 um; mobile phase: [water (0.05% HCl)-ACN]; B %: 55%-85%, 11.5 min). The title compound (3.1 mg, 5.9 umol, 7.0% yield) was obtained as a white solid. LCMS (ESI): RT=0.980 min, mass calcd for $C_{29}H_{21}F_3N_2O_3$ 502.48 m/z found 503.1 [M+H]⁺, ¹H NMR (400 MHz, CD₃OD) δ 8.40 (s, 1H), 8.25 (s, 1H), 7.97 (br d, J=8.3 Hz, 1H), 7.84-7.71 (m, 4H), 7.62-7.53 (m, 3H), 7.46 (br d, J=7.1 Hz, 1H), 7.41 (s, 1H), 7.33-7.23 (m, 3H), 6.02 (s, 1H), 5.16 (s, 2H), 4.56 (s, 2H).

Example 165: N-((1,2,4-thiadiazol-3-yl)methyl)-5-(4-(trifluoromethyl)phenyl)-2-naphthamide (Compound 193)

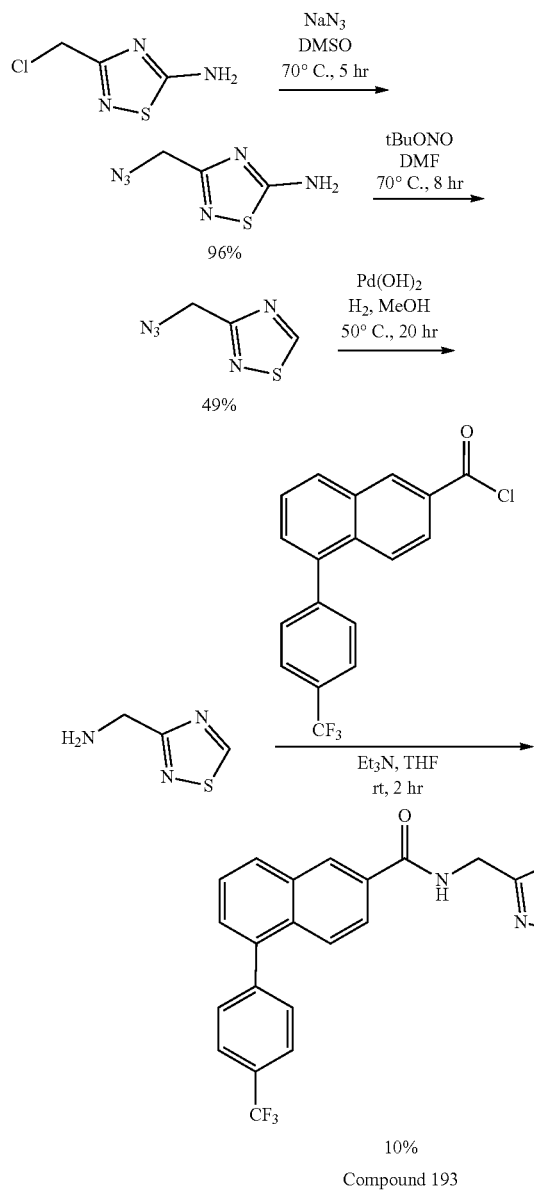

10%
Compound 193

3-(Azidomethyl)-1,2,4-thiadiazol-5-amine 3-(Chloromethyl)-1,2,4-thiadiazol-5-amine (500 mg, 3.34 mmol, 1 equiv.), synthesized according to WO2014072930, NaN$_3$ (434 mg, 6.68 mmol, 2 equiv.), and DMSO (6 mL) were heated to 70° C. The reaction was stirred at 70° C. for 5 hr. The mixture was cooled to rt, diluted with EtOAc, washed with H$_2$O, brine, dried with Na$_2$SO$_4$, concentrated, and used directly in the next step without further purification (500 mg, 3.2 mmol, 96%). LCMS [M+H]$^+$=157.

3-(Azidomethyl)-1,2,4-thiadiazole 3-(Azidomethyl)-1,2,4-thiadiazol-5-amine (500 mg, 3.2 mmol, 1 equiv.), tBuONO (3.8 mL, 32 mmol, 10 equiv.), and DMF (6 mL) were heated to 70° C. for 8 hr. The mixture was concentrated and purified by FCC, 0 to 40% EtOAc in Hex gradient to give the desired product, a pale yellow oil (220 mg, 1.56 mmol, 49%). LCMS [M+H]$^+$=142.

(1,2,4-Thiadiazol-3-yl)methanamine 3-(Azidomethyl)-1,2,4-thiadiazole (220 mg, 1.56 mmol, 1 equiv.), Pd(OH)$_2$ (25 mg), and MeOH (3 mL) were carefully purged with H$_2$. The reaction was stirred under positive pressure H$_2$ at 50° C. for 20 hr. The reaction was cooled to rt, filtered over celite and concentrated to five the desired product, which was used without further purification. LCMS [M+H]$^+$=116.

N-((1,2,4-thiadiazol-3-yl)methyl)-5-(4-(trifluoromethyl)phenyl)-2-naphthamide (1,2,4-Thiadiazol-3-yl)methanamine, (14 mg, 0.126 mmol, 2 equiv.), 5-(4-(trifluoromethyl)phenyl)-2-naphthoyl chloride (21 mg, 0.0629 mmol, 1 equiv.), Et$_3$N (0.02 mL, 0.126 mmol, 2 equiv.), and THF (1 mL) were stirred at rt for 2 hr. The mixture was concentrated and purified by FCC 0 to 30% THF in DCM gradient to give the desired product (2.7 mg, 10%). LCMS [M+H]$^+$=414.

Example 166: N-(3-((2,6-difluorophenoxy)methyl)benzyl)-5-(4-(trifluoromethyl)phenyl)-2-naphthamide (Compound 194)

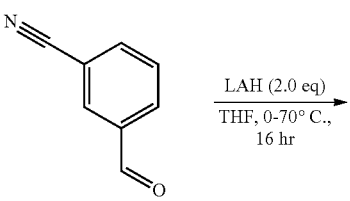

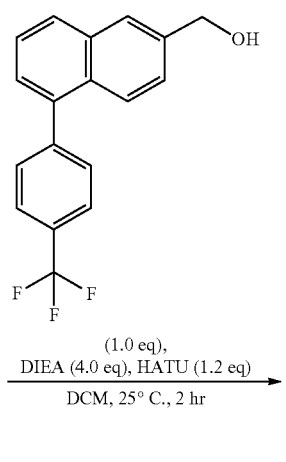

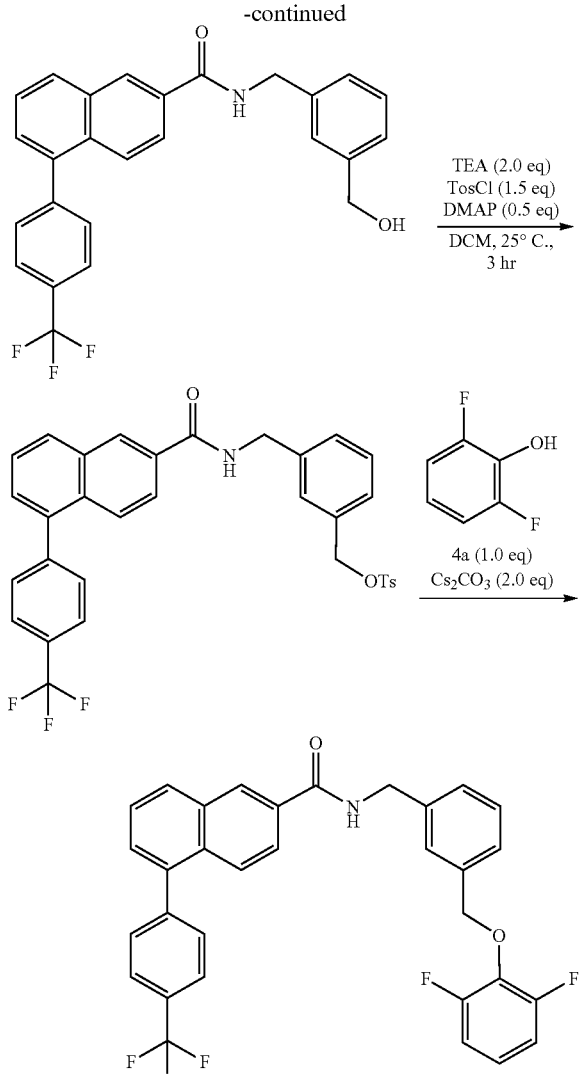

Compound 194

(3-(aminomethyl)phenyl)methanol

To a solution of 3-formylbenzonitrile (1 g, 7.63 mmol, 1 eq) in THF (30 mL) was added LiAlH$_4$ (578.8 mg, 15.25 mmol, 2 eq) at 0° C. dropwise under nitrogen atmosphere. After the complete addition the reaction mixture was heated up to reflux for 16 hr at 70° C. Worked up by addition of water (1 mL), 4M NaOH solution (1 mL) and water (3 mL), anhydrous Na$_2$SO$_4$ (10 g) again. The precipitate was filtered off and washed with EA (30 mL). The mixture was added H$_2$O (10 mL) and extracted with EA (15 mL*3). The combined organic layers were washed with brine (40 mL), dried with anhydrous Na$_2$SO$_4$, filtered and concentrated under reduced pressure to give a residue. The residue was purified by flash silica gel chromatography (12 g SepaFlash® Silica Flash Column, MeOH/EA: 0-20%). Compound (3-(aminomethyl)phenyl)methanol (593 mg, 3.24 mmol, 42.5% yield) was obtained as a yellow oil.

N-(3-(hydroxymethyl)benzyl)-5-(4-(trifluoromethyl)phenyl)-2-naphthamide

To a solution of 5-[4-(trifluoromethyl)phenyl]naphthalene-2-carboxylic acid (150 mg, 0.47 mmol, 1 eq) and HATU (216.4 mg, 0.56 mmol, 1.2 eq) in DCM (5 mL) was added DIPEA (245.1 mg, 1.90 mmol, 0.33 mL, 4 eq). After addition, the mixture was stirred at 25° C. for 0.5 hr, and then [3-(aminomethyl)phenyl]methanol (95.4 mg, 0.52 mmol, 1.1 eq) was added. The resulting mixture was stirred at 25° C. for 1.5 hr. The mixture was added H$_2$O (10 mL) and extracted with EA (15 mL*3). The combined organic layers were washed with brine (20 mL), dried with anhydrous Na$_2$SO$_4$, filtered and concentrated under reduced pressure to give a residue. The residue was purified by flash silica gel chromatography (12 g SepaFlash® Silica Flash Column, EA/PE: 0-50%). Compound N-[[3-(hydroxymethyl)phenyl]methyl]-5-[4-(trifluoromethyl)phenyl]naphthalene-2-carboxamide (293 mg, 0.60 mmol, 95.2% yield) was obtained as a white solid.

3-(((((5-(4-(trifluoromethyl)phenyl)naphthalen-2-yl)methyl)amino)methyl)benzyl-4-methylbenzenesulfonate To a solution of N-[[3-(hydroxymethyl)phenyl]methyl]-5-[4-(trifluoromethyl)phenyl]naphthalene-2-carboxamide (210 mg, 0.43 mmol, 1 eq) in THF (5 mL) was added TEA (87.8 mg, 0.86 mmol, 0.12 mL, 2 eq) and DMAP (26.5 mg, 0.21 mmol, 0.5 eq). After addition, the mixture was stirred at 25° C. for 0.5 hr, and then 4-methylbenzenesulfonyl chloride (124.1 mg, 0.65 mmol, 1.5 eq) was added. The mixture was stirred at 25° C. for 2.5 hr. The mixture was added H$_2$O (10 mL) and extracted with EA (15 mL*3). The combined organic layers were washed with brine (20 mL), dried with anhydrous Na$_2$SO$_4$, filtered and concentrated under reduced pressure to give a residue. The residue was purified by flash silica gel chromatography (12 g SepaFlash® Silica Flash Column, EA/PE: 0~50%). Compound 3-(((((5-(4-(trifluoromethyl)phenyl)naphthalen-2-yl)methyl)amino)methyl)benzyl-4-methylbenzenesulfonate (101.2 mg, 0.15 mmol, 35.5% yield) was obtained as a colorless oil.

N-(3-((2,6-difluorophenoxy)methyl)benzyl)-5-(4-(trifluoromethyl)phenyl)-2-naphthamide To a solution of 2,6-difluorophenol (11.0 mg, 84.8 umol, 1 eq) in DMF (1 mL) was added Cs$_2$CO$_3$ (55.2 mg, 0.16 mmol, 2 eq) at 25° C. The mixture was stirred at 25° C. for 0.5 hr. Then [3-[[[5-[4-(trifluoromethyl)phenyl]naphthalene-2-carbonyl]amino]methyl]phenyl]methyl 4-methylbenzenesulfonate (50.0 mg, 84.8 umol, 1 eq) was added into the reaction. The mixture was stirred at 25° C. for 2 hr. The mixture was added H$_2$O (10 mL) and extracted with EA (15 mL*3). The combined organic layers were washed with brine (20 mL), dried with anhydrous Na$_2$SO$_4$, filtered and concentrated under reduced pressure to give a residue. The residue was purified by prep-HPLC (column: Waters Xbridge 150*50 10u; mobile phase: [water (0.05% ammonia hydroxide v/v)-ACN]; B %: 70%-100%, 7.8 min). The title compound (12.2 mg, 21.7 umol, 25.6% yield) was obtained as a white solid. LCMS (ESI): RT=1.101 min, mass calcd for C$_{32}$H$_{22}$F$_5$NO$_2$ 547.51 m/z found 548.1 [M+H]$^+$, $^1$H NMR (400 MHz, DMSO-d$_6$) δ 9.34-9.23 (m, 1H), 8.61 (s, 1H), 8.13 (d, J=8.0 Hz, 1H), 7.98 (d, J=8.8 Hz, 1H), 7.92 (br d, J=7.9 Hz, 2H), 7.83 (d, J=8.9 Hz, 1H), 7.78-7.67 (m, 3H), 7.60 (d, J=7.0 Hz, 1H), 7.44 (s, 1H), 7.39-7.28 (m, 3H), 7.09 (br d, J=9.1 Hz, 3H), 5.14 (s, 2H), 4.55 (br d, J=5.6 Hz, 2H).

Example 167: (S)—N-(1-(1-methyl-1H-imidazol-4-yl)ethyl)-5-(4-(trifluoromethyl)phenyl)-2-naphthamide (Compound 195) and (R)—N-(1-(1-methyl-1H-imidazol-4-yl)ethyl)-5-(4-(trifluoromethyl)phenyl)-2-naphthamide (Compound 196)

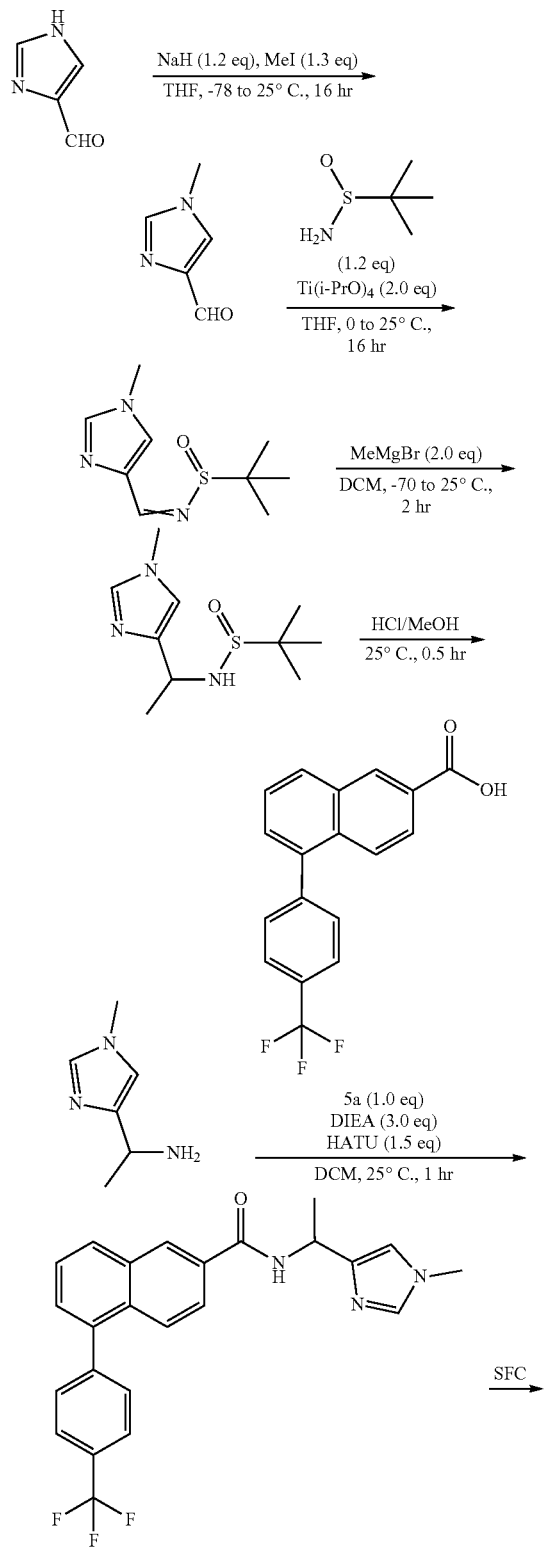

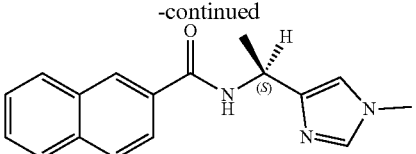

Compound 195

Compound 196

1-methyl-1H-imidazole-4-carbaldehyde

To a solution of 1H-imidazole-4-carbaldehyde (5 g, 52.04 mmol, 1 eq) in THF (30 mL) was added NaH (2.50 g, 62.44 mmol, 60%, 1.2 eq) −78° C., and then the suspension was allowed to 25° C. and stirred at 25° C. for 30 min. The reaction mixture was cooled to −78° C. and added MeI (10.06 g, 70.88 mmol, 4.41 mL, 1.36 eq) dropwise at −78° C. The mixture was gradually warmed to 25° C. and stirred at 25° C. for 16 hrs. The reaction mixture was quenched with MeOH (40 mL), and then the suspension was concentrated under reduce pressure. The residue was purified by column chromatography over silica gel (DCM:MeOH=1:0 to 10:1) to afford the title compound as a yellow solid. Compound 1-methylimidazole-4-carbaldehyde (900 mg, 8.17 mmol, 15.71% yield) was obtained as a yellow solid.

2-methyl-N-((1-methyl-1H-imidazol-4-yl)methylene)propane-2-sulfinamide

To a solution of 1-methylimidazole-4-carbaldehyde (700 mg, 6.36 mmol, 1 eq) and 2-methylpropane-2-sulfinamide (924.5 mg, 7.63 mmol, 1.2 eq) in THF (10 mL) was added Ti(i-PrO)$_4$ (3.61 g, 12.71 mmol, 3.75 mL, 2 eq) at 0° C. The reaction mixture was allowed to warm up to 25° C. and stirred at 25° C. for 16 hrs. The reaction mixture was poured into water (20 mL), and then the suspension was filtered and washed with EA (50 mL). The filtrate was separated and the organic layer was concentrated under reduce pressure. The residue was purified by column chromatography over silica gel (DCM:MeOH=1:0 to 20:1) to afford the title compound as colorless oil. Compound (NZ)-2-methyl-N-[(1-methylimidazol-4-yl)methylene]propane-2-sulfinamide (1.2 g, 5.63 mmol, 88.5% yield) was obtained as colorless oil.

2-methyl-N-(1-(1-methyl-1H-imidazol-4-yl)ethyl)propane-2-sulfinamide

To a solution of (NZ)-2-methyl-N-[(1-methylimidazol-4-yl)methylene]propane-2-sulfinamide (100 mg, 0.46 mmol, 1 eq) in DCM (2 mL) was added MeMgBr (3 M, 0.31 mL, 2 eq) at −70° C. The reaction mixture was allowed to warm up to 25° C. and stirred at 25° C. for 2 hrs. The suspension was poured into MeOH (10 mL), and then the suspension was concentrated under reduce pressure. The mixture was diluted with EA (30 mL) and filtered, and then the filtrate was concentrated under reduce pressure to give the title compound as light yellow oil. Compound 2-methyl-N-[1-(1-methylimidazol-4-yl)ethyl]propane-2-sulfinamide (150 mg, crude) was obtained as light yellow oil.

1-(1-methyl-1H-imidazol-4-yl)ethanamine

A solution of 2-methyl-N-[1-(1-methylimidazol-4-yl)ethyl]propane-2-sulfinamide (150 mg, 0.65 mmol, 1 eq) in HCl/MeOH (2 mL) was stirred at 25° C. for 0.5 hr. The reaction mixture was concentrated under reduced pressure to give the title compound as a yellow solid. Compound 1-(1-methylimidazol-4-yl)ethanamine (120 mg, crude, HCl) was obtained as a yellow solid.

N-(1-(1-methyl-1H-imidazol-4-yl)ethyl)-5-(4-(trifluoromethyl)phenyl)-2-naphthamide To a solution of 5-[4-(trifluoromethyl)phenyl]naphthalene-2-carboxylic acid (100 mg, 0.31 mmol, 1 eq), 1-(1-methylimidazol-4-yl)ethanamine (51.1 mg, 0.31 mmol, 1 eq, HCl) and DIPEA (122.5 mg, 0.94 mmol, 0.16 mL, 3 eq) in DCM (3 mL) was added HATU (180.3 mg, 0.47 mmol, 1.5 eq). The reaction mixture was stirred at 25° C. for 1 hr. The reaction mixture was concentrated under reduced pressure. The mixture was diluted with water (10 mL) and the resultant mixture was extracted with EA (30 mL*3). The combined organic layers were dried over Na$_2$SO$_4$, filtered and concentrated to dryness under reduced pressure. The residue was purified by prep-HPLC (column: Xtimate C18 150*25 mm*5 um; mobile phase: [water (0.05% HCl)-ACN]; B %: 28%-58%, 8.5 min to obtain the title compound as a white solid. Compound N-[1-(1-methylimidazol-4-yl)ethyl]-5-[4-(trifluoromethyl)phenyl]naphthalene-2-carboxamide (45 mg, 96.8 umol, 30.6% yield, HCl) was obtained as a white solid.

(S)—N-(1-(1-methyl-1H-imidazol-4-yl)ethyl)-5-(4-(trifluoromethyl)phenyl)-2-naphthamide (Compound 195) and (R)—N-(1-(1-methyl-1H-imidazol-4-yl)ethyl)-5-(4-(trifluoromethyl)phenyl)-2-naphthamide (Compound 196)

The racemic compound N-[1-(1-methylimidazol-4-yl)ethyl]-5-[4-(trifluoromethyl)phenyl]naphthalene-2-carboxamide (45 mg, 97.8 umol, 1 eq, HCl) was separated by SFC (column: DAICEL CHIRALPAK AD 250 mm*30 mm, 10 um); mobile phase: [0.1% NH$_3$H$_2$O MEOH]; B %: 55%-55%, min) to give Compound 195 (10.1 mg, 23.4 umol, 47.9% yield) as a light yellow solid. LCMS (ESI): RT=0.864 min, mass calcd for C$_{24}$H$_{20}$F$_3$N$_3$O 423.43 m/z found 424.1 [M+H]$^+$, $^1$H NMR (400 MHz, DMSO-d$_6$) δ 8.73 (d, J=8.3 Hz, 1H), 8.61 (d, J=1.3 Hz, 1H), 8.12 (d, J=8.3 Hz, 1H), 7.97 (dd, J=1.8, 8.9 Hz, 1H), 7.93 (d, J=8.3 Hz, 2H), 7.80 (d, J=8.9 Hz, 1H), 7.74 (d, J=8.0 Hz, 2H), 7.70 (t, J=7.6 Hz, 1H), 7.59 (d, J=7.0 Hz, 1H), 7.51 (s, 1H), 7.00 (s, 1H), 5.17 (quin, J=7.2 Hz, 1H), 3.61 (s, 3H), 1.49 (d, J=6.9 Hz, 3H). Compound 196 (6.7 mg, 15.5 umol, 31.7% yield) as a light yellow solid. LCMS (ESI): RT=0.869 min, mass calcd for C$_{24}$H$_{20}$F$_3$N$_3$O 423.43 m/z found 424.0 [M+H]$^+$, $^1$H NMR (400 MHz, DMSO-d$_6$) δ 8.73 (d, J=8.1 Hz, 1H), 8.61 (s, 1H), 8.12 (d, J=8.1 Hz, 1H), 7.97 (br d, J=8.9 Hz, 1H), 7.92 (d, J=8.1 Hz, 2H), 7.80 (d, J=8.9 Hz, 1H), 7.74 (br d, J=8.0 Hz, 2H), 7.69 (t, J=7.7 Hz, 1H), 7.59 (d, J=7.0 Hz, 1H), 7.51 (s, 1H), 7.00 (s, 1H), 5.17 (quin, J=7.1 Hz, 1H), 3.61 (s, 3H), 1.49 (d, J=6.9 Hz, 3H).

Example 168: N-(1-hydroxy-3-(pyridin-2-yl)propan-2-yl)-5-(4-(trifluoromethyl)phenyl)-2-naphthamide (Compound 197)

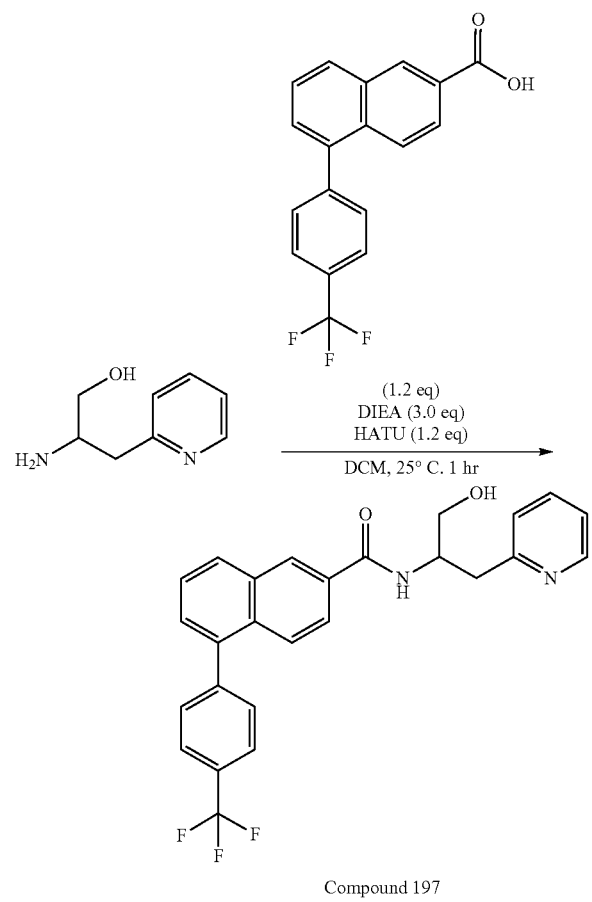

Compound 197

The mixture of 5-[4-(trifluoromethyl)phenyl]naphthalene-2-carboxylic acid (84.3 mg, 0.26 mmol, 1.2 eq), 2-amino-3-(2-pyridyl)propan-1-ol (50 mg, 0.22 mmol, 1 eq, 2HCl), HATU (101.3 mg, 0.26 mmol, 1.2 eq) and DIPEA (86.1 mg, 0.66 mmol, 0.11 mL, 3 eq) in DCM (1 mL) was stirred at 25° C. for 1 hr. The reaction mixture was diluted with H$_2$O (5 mL) and the mixture was extracted with EA (10 mL*3). The combined organic phase was washed with brine (10 mL*2), dried with anhydrous Na$_2$SO$_4$, filtered and concentrated in vacuum. The residue was purified by prep-HPLC (column: Waters Xbridge 150*50 10u; mobile phase: [water (0.05% ammonia hydroxide v/v)-ACN]; B %: 47%-77%, 8 min). The title compound (6.2 mg, 13.6 umol, 6.1% yield) was obtained as white solid. LCMS (ESI): RT=0.825 min: mass calcd for C$_{26}$H$_{21}$F$_3$N$_2$O$_2$ 450.45 m/z, found 451.1

[M+H]+, NMR (400 MHz, CDCl₃) δ 8.49 (br d, J=4.5 Hz, 1H), 8.30 (s, 1H), 7.90 (d, J=8.1 Hz, 1H), 7.82-7.75 (m, 2H), 7.75-7.68 (m, 3H), 7.61 (t, J=7.7 Hz, 1H), 7.56-7.49 (m, 3H), 7.42 (d, J=7.0 Hz, 1H), 7.24 (d, J=7.9 Hz, 1H), 7.17-7.11 (m, 1H), 4.46 (br d, J=5.8 Hz, 1H), 3.82-3.68 (m, 2H), 3.33-3.24 (m, 1H), 3.21-3.13 (m, 1H).

Example 169: N-[(E)-6-isoxazol-3-yloxyhex-4-enyl]-5-[4-(trifluoromethyl)phenyl]naphthalene-2-carboxamide (Compound 198)

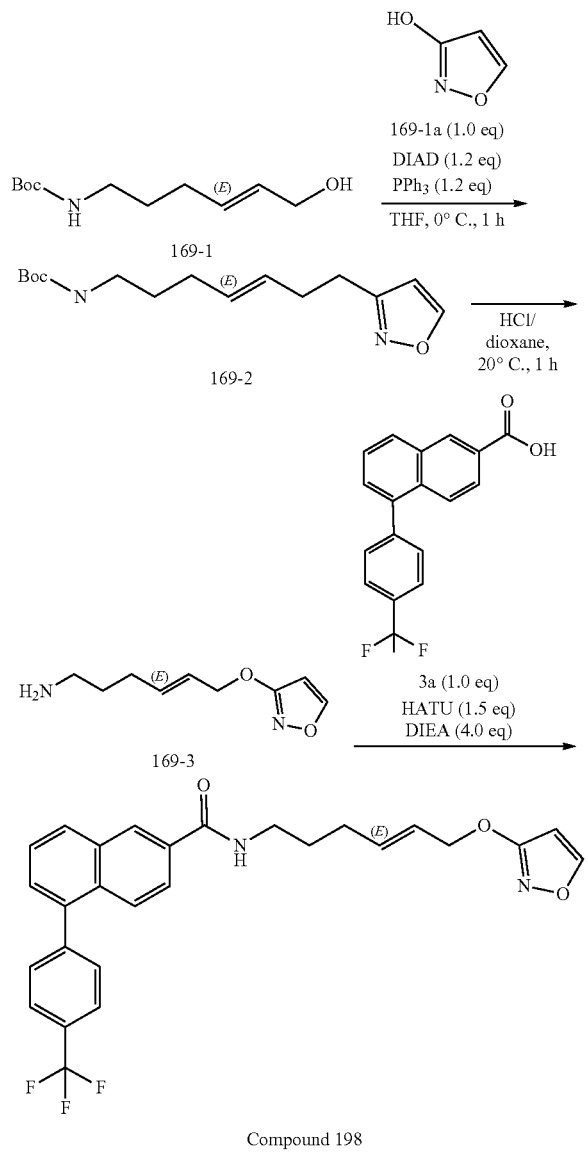

Compound 198

Tert-Butyl N-[(E)-6-isoxazol-3-yloxyhex-4-enyl] carbamate

To a solution of compound 169-1 (0.1 g, 0.46 mmol, 1 eq), compound 169-1a (39.5 mg, 0.46 mmol, 1 eq) and PPh₃ (146.2 mg, 0.55 mmol, 1.2 eq) in THF (1 mL) was added DIAD (112.7 mg, 0.55 mmol, 0.1 mL, 1.2 eq) at 0° C. The reaction was stirred at 0° C. for 1 hr. The reaction was quenched by H₂O (3 mL) and extracted with EA (2*5 mL). The organic layer was dried over Na₂SO₄ and concentrated. The crude product was purified by column chromatography on silica gel (EA:PE=1:3-1:0) to give 169-2 (20 mg, 49.5 umol, 10.6% yield) and was used for next step directly.

(E)-6-isoxazol-3-yloxyhex-4-en-1-amine

A solution of compound 169-2 (20 mg, 49.5 umol, 1 eq) in HCl/dioxane (0.5 mL, 4M) was stirred at 20° C. for 1 hr. The reaction was concentrated to give compound 169-3 (20 mg, crude, HCl), which was used for next step directly as colorless oil.

N-[(E)-6-isoxazol-3-yloxyhex-4-enyl]-5-[4-(trifluoromethyl)phenyl]naphthalene-2-carboxamide To a solution of compound 169-3a (28 mg, 88.5 umol, 1 eq), compound 169-3 (19.3 mg, 88.5 umol, 1 eq, HCl) and HATU (50.4 mg, 0.13 mmol, 1.5 eq) in DCM (1 mL) was added DIEA (45.7 mg, 0.35 mmol, 61.6 uL, 4 eq). The reaction was stirred at 20° C. for 1 hr. The reaction was diluted with DCM (10 mL) and washed with H₂O (2*5 mL). The organic layer was dried over Na₂SO₄ and concentrated. The residue was purified by Prep-HPLC (column: Waters Xbridge 150*50 10u; mobile phase: [water (0.05% ammonia hydroxide v/v)-ACN]; B %: 56%-56%, 12 min) to give the title compound (2.1 mg, 4.3 umol, 4.9% yield) as a white solid. LCMS (ESI): RT=0.948 min, mass calcd. for $C_{27}H_{23}F_3N_2O_3$ 480.17, m/z found 481.1 [M+H]+, ¹H NMR (400 MHz, CDCl₃) δ 8.37 (s, 1H), 7.99 (d, J=8.1 Hz, 1H), 7.90-7.85 (m, 1H), 7.83-7.75 (m, 4H), 7.67-7.58 (m, 3H), 7.51 (d, J=7.1 Hz, 1H), 6.43-6.34 (m, 1H), 5.86-5.75 (m, 2H), 5.63-5.48 (m, 1H), 4.47 (d, J=6.3 Hz, 2H), 3.53 (q, J=6.7 Hz, 2H), 2.21 (q, J=7.2 Hz, 2H), 1.79 (quin, J=7.3 Hz, 2H).

Example 170: (R)—N-(1-(1-acetylazetidin-3-yl)ethyl)-5-(4-(trifluoromethyl)phenyl)-2-naphthamide (Compound 199) and (S)—N-(1-(1-acetylazetidin-3-yl)ethyl)-5-(4-(trifluoromethyl)phenyl)-2-naphthamide (Compound 200)

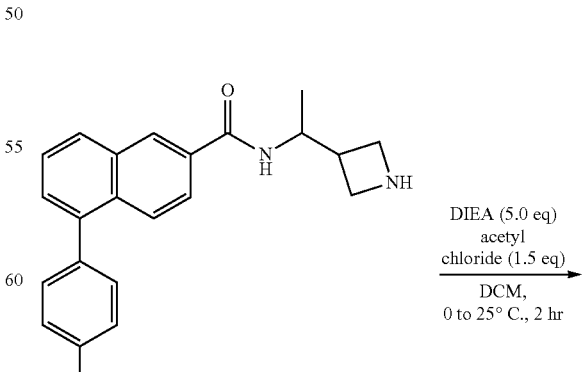

527
-continued

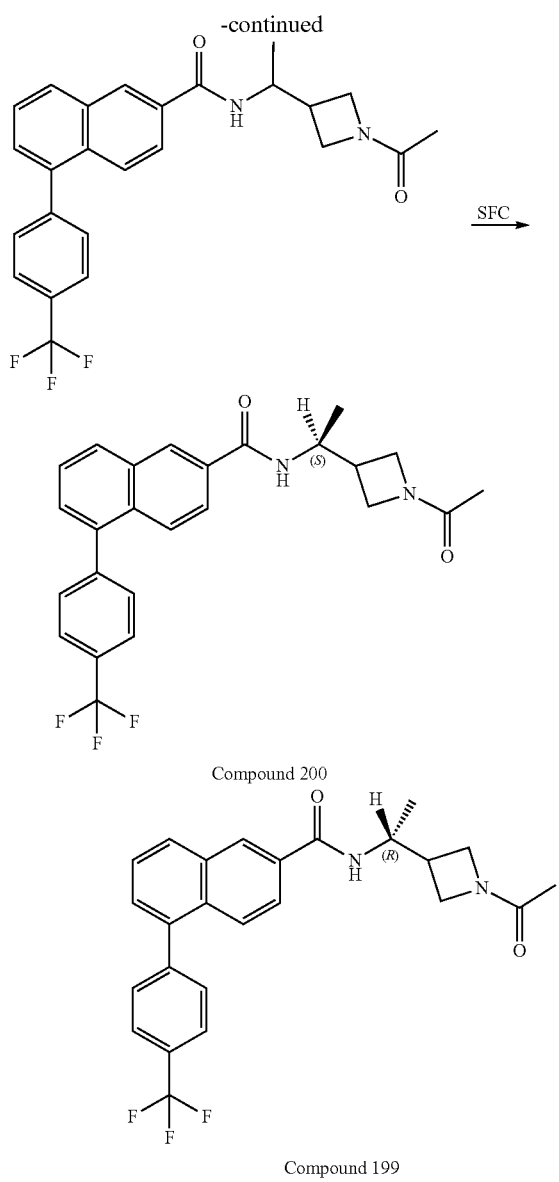

Compound 200

Compound 199

N-(1-(1-acetylazetidin-3-yl)ethyl)-5-(4-(trifluoromethyl)phenyl)-2-naphthamide

To a solution of N-[1-(azetidin-3-yl)ethyl]-5-[4-(trifluoromethyl)phenyl]naphthalene-2-carboxamide (200 mg, 0.50 mmol, 1 eq) and DIPEA (324.3 mg, 2.51 mmol, 0.43 mL, 5 eq) in DCM (5 mL) was added dropwise acetyl chloride (59.1 mg, 0.75 mmol, 53.7 uL, 1.5 eq) at 0° C. under $N_2$. After addition, the mixture was stirred at 25° C. for 2 hr. The residue was poured into $H_2O$ (30 mL) and stirred for 5 min. The aqueous phase was extracted with EA (15 mL*3). The combined organic phase was washed with brine (20 mL), dried with anhydrous $Na_2SO_4$, filtered and concentrated in vacuum. The residue was purified by flash silica gel chromatography (12 g SepaFlash® Silica Flash Column, EA/MeOH: 0~10%). Compound N-[1-(1-acetylazetidin-3-yl)ethyl]-5-[4-(trifluoromethyl)phenyl]naphthalene-2-carboxamide (135 mg, 0.29 mmol, 58.0% yield) was obtained as a yellow solid.

528

(R)—N-(1-(1-acetylazetidin-3-yl)ethyl)-5-(4-(trifluoromethyl)phenyl)-2-naphthamide (Compound 199) and (S)—N-(1-(1-acetylazetidin-3-yl)ethyl)-5-(4-(trifluoromethyl)phenyl)-2-naphthamide (Compound 200)

The racemic compound N-[1-(1-acetylazetidin-3-yl)ethyl]-5-[4-(trifluoromethyl)phenyl]naphthalene-2-carboxamide (95 mg, 0.21 mmol, 1 eq) was purified by SFC (column: DAICEL CHIRALPAK AS-H (250 mm*30 mm, 5 um); mobile phase: [0.1% $NH_3H_2O$ ETOH]; B %: 35%-35%, min). The compound was purified by SFC (column: DAICEL CHIRALPAK AS-H (250 mm*30 mm, 5 um); mobile phase: [0.1% $NH_3H_2O$ ETOH]; B %: 35%-35%, min). Compound 200 (23.4 mg, 52.6 umol, 24.3% yield) was obtained as a white solid. LCMS (ESI): RT=0.820 min, mass calcd for $C_{25}H_{23}F_3N_2O_2$ 440.46 m/z found 441.1 [M+H]$^+$, $^1$H NMR (400 MHz, DMSO-$d_6$) δ 8.59-8.49 (m, 2H), 8.12 (d, J=8.0 Hz, 1H), 7.92 (d, J=8.3 Hz, 3H), 7.81 (d, J=8.8 Hz, 1H), 7.77-7.66 (m, 3H), 7.59 (d, J=7.0 Hz, 1H), 4.39-4.26 (m, 1H), 4.21-4.08 (m, 1H), 3.97-3.78 (m, 2H), 3.71-3.55 (m, 1H), 2.78-2.68 (m, 1H), 1.72 (d, J=3.5 Hz, 3H), 1.15 (d, J=6.8 Hz, 3H). Compound 199 (25.8 mg, 58.5 umol, 27.1% yield) was obtained as a white solid. LCMS (ESI): RT=0.802 min, mass calcd for $C_{25}H_{23}F_3N_2O_2$ 440.46 m/z found 441.1 [M+H]$^+$, $^1$H NMR (400 MHz, DMSO-$d_6$) δ 8.59-8.48 (m, 2H), 8.12 (d, J=8.0 Hz, 1H), 7.91 (d, J=8.5 Hz, 3H), 7.81 (d, J=8.8 Hz, 1H), 7.76-7.66 (m, 3H), 7.58 (d, J=7.0 Hz, 1H), 4.38-4.25 (m, 1H), 4.20-4.08 (m, 1H), 3.96-3.78 (m, 2H), 3.70-3.56 (m, 1H), 2.78-2.68 (m, 1H), 1.72 (d, J=3.5 Hz, 3H), 1.15 (d, J=6.8 Hz, 3H).

Example 171: 3-(1-(5-(4-(Trifluoromethyl)phenyl)-2-naphthamido)ethyl)-1,2,4-thiadiazole-5-carboxamide (Compound 201)

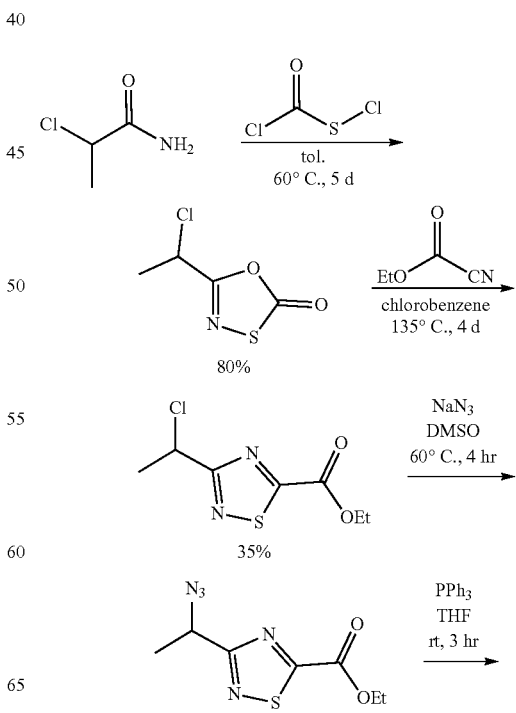

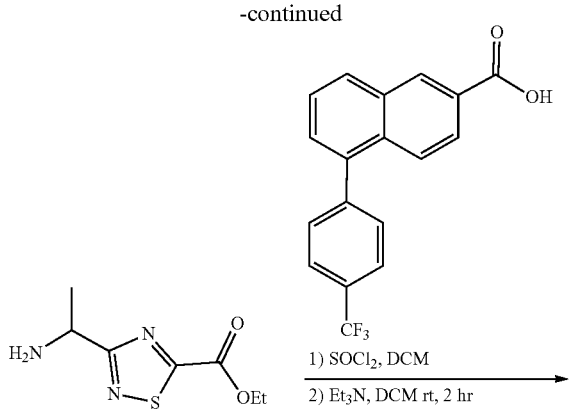

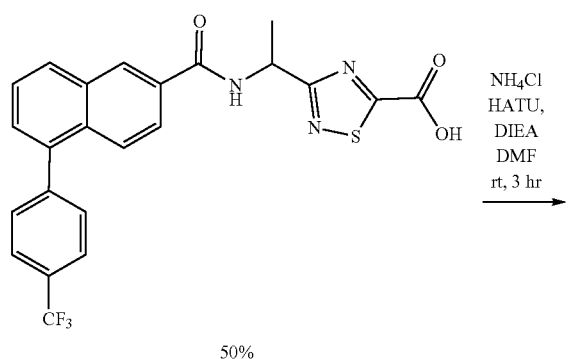

Compound 201

5-(1-Chloroethyl)-1,3,4-oxathiazol-2-one

2-Chloropropanamide (1.07 g, 10 mmol, 1 equiv.), chlorocarbonylsulfenyl chloride (4.2 mL, 50 mmol, 5 equiv.), and toluene (25 mL) were heated to 60° C. for 5 d. The mixture was concentrated and purified by FCC, 0 to 15% EtOAc in Hexane gradient to give 5-(1-chloroethyl)-1,3,4-oxathiazol-2-one (1.29 g, 8.1 mmol, 80%). LCMS [M+H]$^+$=166.

Ethyl 3-(1-chloroethyl)-1,2,4-thiadiazole-5-carboxylate 5-(1-Chloroethyl)-1,3,4-oxathiazol-2-one (828 mg, 5 mmol, 1 equiv.), ethyl cyanoformate (2.4 mL, 25 mmol, 5 equiv.), and chlorobenzene (12 mL) were heated at 135° C. for 4 d. The mixture was cooled, concentrated, and purified by FCC, 0 to 15% EtOAc in Hexane gradient to give ethyl 3-(1-chloroethyl)-1,2,4-thiadiazole-5-carboxylate, a yellow oil (380 mg, 35%). LCMS [M+H]$^+$=221.

Ethyl 3-(1-azidoethyl)-1,2,4-thiadiazole-5-carboxylate

Ethyl 3-(1-chloroethyl)-1,2,4-thiadiazole-5-carboxylate (220 mg, 1 mmol, 1 equiv.), NaN$_3$ (130 mg, 2 mmol, 2 equiv.), and DMSO (1 mL) were stirred at 60° C. until consumption of the acid as determined by LCMS, 4 hr. The reaction mixture was diluted with EtOAc and washed with sat. aq. NH$_4$Cl, H$_2$O, and brine. The organic layer was dried with Na$_2$SO$_4$, concentrated, and used in the next step without further purification. LCMS [M+H]$^+$=228.

Ethyl 3-(1-aminoethyl)-1,2,4-thiadiazole-5-carboxylate

Ethyl 3-(1-azidoethyl)-1,2,4-thiadiazole-5-carboxylate (113 mg, 0.5 mmol, 1 equiv.), PPh$_3$ (197 mg, 0.75 mmol, 1.5 equiv.), and THF (1 mL) were stirred at rt for 2 hr. H$_2$O was added to the reaction mixture and the reaction was further stirred for 1 hr. The mixture was extracted with EtOAc, dried with Na$_2$SO$_4$, and passed through a silica plug with EtOAc to give the desired product, which was used without further purification. LCMS [M+H]$^+$=202.

3-(1-(5-(4-(Trifluoromethyl)phenyl)-2-naphthamido)ethyl)-1,2,4-thiadiazole-5-carboxylic Acid 5-(4-(Trifluoromethyl)phenyl)-2-naphthoic acid (40 mg, 0.12 mmol, 1 equiv.), 1 drop DMF, and DCM (3 mL) were cooled to 0° C. (COCl)$_2$ (16 μL, 0.19 mmol, 1.5 equiv.) was added dropwise and stirred 1 hr. The mixture was concentrated and re-dissolved in 1 mL DCM and added to a mixture of ethyl 3-(1-aminoethyl)-1,2,4-thiadiazole-5-carboxylate (35 mg, 0.17 mmol, 1.4 equiv.), Et$_3$N (49 μL, 0.24 mmol, 2 equiv.), and THF (1 mL) at rt. The reaction was stirred 18 hr until consumption of the acid chloride as determined by LCMS. The mixture was diluted with EtOAc, carefully neutralized with 1N HCl(aq), and separated. The organic layer was washed with H$_2$O, brine, dried with Na$_2$SO$_4$, and concentrated. The residue was purified by FCC 0 to 20% MeOH in DCM gradient to give 3-(1-(5-(4-(trifluoromethyl)phenyl)-2-naphthamido)ethyl)-1,2,4-thiadiazole-5-carboxylic acid (30 mg, 50%). LCMS [M+H]$^+$=472.

3-(1-(5-(4-(Trifluoromethyl)phenyl)-2-naphthamido)ethyl)-1,2,4-thiadiazole-5-carboxamide 3-(1-(5-(4-(Trifluoromethyl)phenyl)-2-naphthamido)ethyl)-1,2,4-thiadiazole-5-carboxylic acid (30 mg, 1 equiv.), NH4Cl (10 mg, 3 equiv.), HATU (50 mg, 2 equiv.), and DMF were stirred at rt. DIEA (66 μL, 6 equiv.) was carefully added and the mixture was stirred at rt until consumption of the acid as determined by LCMS, 3 hr. The mixture was purified directly by prep HPLC to give the desired product (3 mg, 10%). LCMS [M+H]$^+$=471.

Example 172: N-[(E)-6-amino-6-oxo-hex-4-enyl]-5-[4-(trifluoromethyl)phenyl]naphthalene-2-carboxamide (Compound 202)

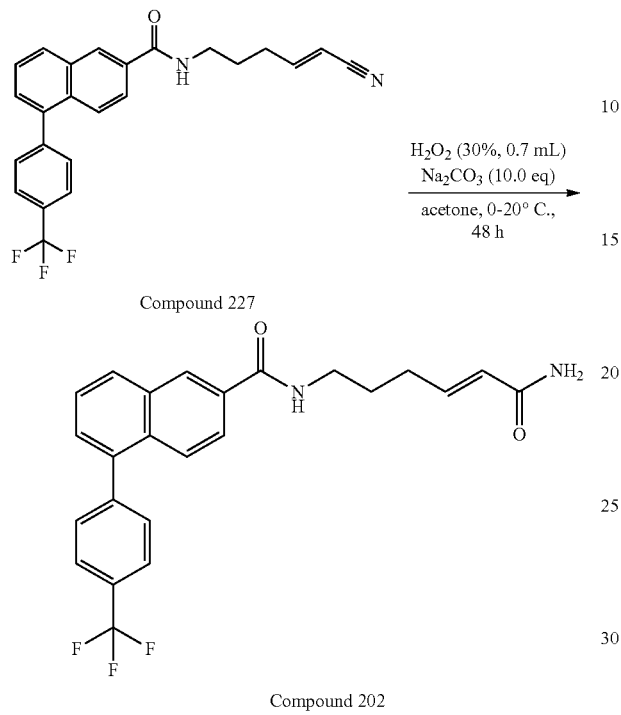

To a solution of Compound 227 (7 mg, 17.1 umol, 1 eq) in acetone (0.5 mL) were added Na$_2$CO$_3$ (18.1 mg, 0.17 mmol, 10 eq) and H$_2$O$_2$ (826.0 mg, 7.29 mmol, 0.7 mL, 30% solution) at 0° C. Then the mixture was stirred at 20° C. for 48 hr. The reaction mixture was concentrated in vacuum. The crude product was purified by prep-HPLC (column: Waters Xbridge 150*50 10u; mobile phase: [water (0.05% ammonia hydroxide v/v)-ACN]; B %: 45%-75%, 7.8 min) to give the title compound (2.3 mg, 5.3 umol, 18.4% yield). LCMS (ESI): RT=0.906 min, mass calcd. For C$_{24}$H$_{21}$F$_3$N$_2$O$_2$, 426.16 m/z found 427.0 [M+H]$^+$. $^1$H NMR (400 MHz, CDCl$_3$) δ 8.36 (s, 1H), 8.00 (br d, J=8.5 Hz, 1H), 7.87 (br d, J=8.8 Hz, 1H), 7.78 (br d, J=8.0 Hz, 3H), 7.65-7.59 (m, 3H), 7.51 (br d, J=7.0 Hz, 1H), 7.00-6.85 (m, 1H), 6.36 (br s, 1H), 5.94 (br d, J=15.6 Hz, 1H), 5.65-5.08 (m, 2H), 3.57 (q, J=6.7 Hz, 2H), 2.36 (q, J=7.3 Hz, 2H), 1.94-1.81 (m, 2H).

Example 173: (R)—N-(1-(azetidin-3-yl)ethyl)-5-(4-(trifluoromethyl)phenyl)-2-naphthamide (Compound 203) and (S)—N-(1-(azetidin-3-yl)ethyl)-5-(4-(trifluoromethyl)phenyl)-2-naphthamide (Compound 204)

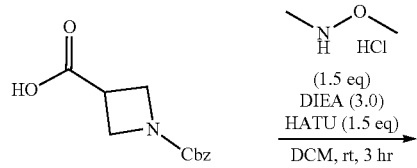

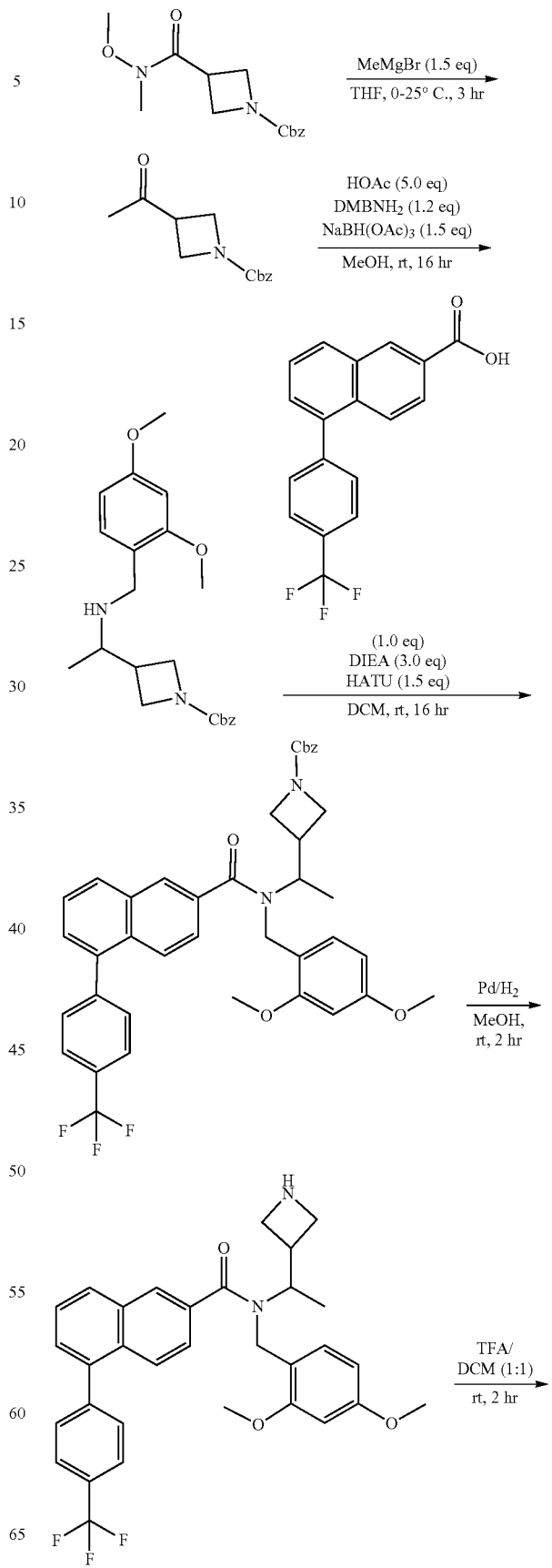

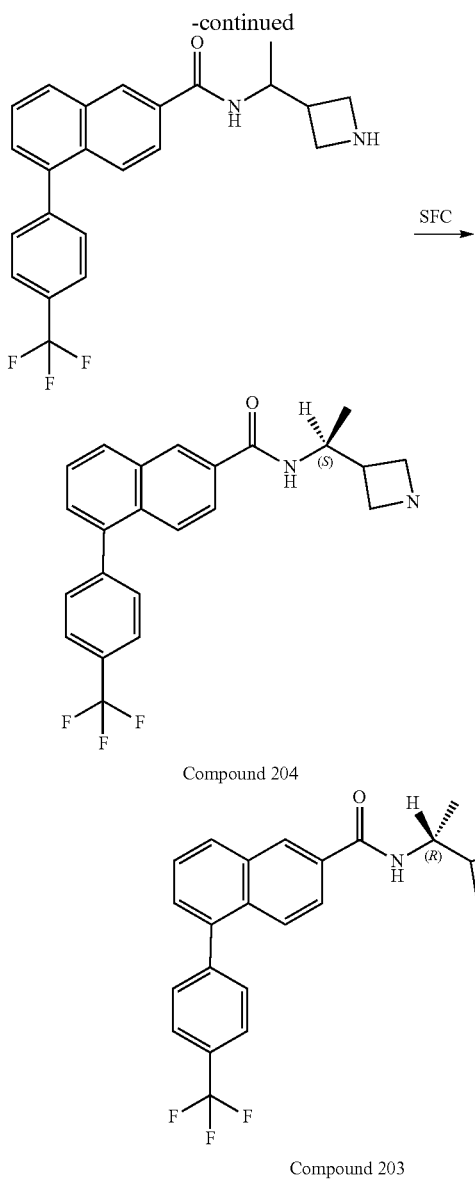

Compound 204

Compound 203

Benzyl 3-(methoxy(methyl)carbamoyl)azetidine-1-carboxylate

A mixture of 1-benzyloxycarbonylazetidine-3-carboxylic acid (5 g, 21.26 mmol, 1 eq), HATU (12.12 g, 31.88 mmol, 1.5 eq) in DCM (50 mL) was added DIPEA (8.24 g, 63.77 mmol, 11.11 mL, 3 eq) at 25° C. After addition, the mixture was stirred at 25° C. for 1 hr, and then N-methoxymethanamine (3.11 g, 31.88 mmol, 1.5 eq, HCl) was added. The resulting mixture was stirred at 25° C. for 2 hr. The residue was poured into H$_2$O (100 mL) and stirred for 5 min. The aqueous phase was extracted with EA (50 mL*3). The combined organic phase was washed with brine (120 mL), dried with anhydrous Na$_2$SO$_4$, filtered and concentrated in vacuum. The residue was purified by flash silica gel chromatography (80 g SepaFlash® Silica Flash Column, EA/PE: 0~40%). Compound benzyl 3-[methoxy(methyl)carbamoyl] azetidine-1-carboxylate (5.2 g, 18.68 mmol, 87.9% yield) was obtained as a yellow oil.

Benzyl 3-acetylazetidine-1-carboxylate

To a solution of benzyl 3-[methoxy(methyl)carbamoyl] azetidine-1-carboxylate (4.5 g, 16.17 mmol, 1 eq) in THF (80 mL) was added dropwise MeMgBr (3 M, 8.08 mL, 1.5 eq) at 0° C. under N$_2$. After addition, the mixture was stirred at 25° C. for 3 hr. The residue was poured into NH$_4$Cl (130 mL) at 0° C. and stirred for 5 min. The aqueous phase was extracted with EA (60 mL*3). The combined organic phase was washed with brine (120 mL), dried with anhydrous Na$_2$SO$_4$, filtered and concentrated in vacuum. The residue was purified by flash silica gel chromatography (80 g SepaFlash® Silica Flash Column, EA/PE: 0~40%). Compound benzyl 3-acetylazetidine-1-carboxylate (2.8 g, 12.00 mmol, 74.2% yield) was obtained as a colorless oil.

Benzyl 3-(1-((2,4-dimethoxybenzyl)amino)ethyl) azetidine-1-carboxylate

To a solution of benzyl 3-acetylazetidine-1-carboxylate (2.3 g, 9.86 mmol, 1 eq) and (2,4-dimethoxyphenyl)methanamine (1.98 g, 11.83 mmol, 1.78 mL, 1.2 eq) in MeOH (25 mL) was added HOAc (2.96 g, 49.30 mmol, 2.82 mL, 5 eq) and stirred at 25° C. for 1 hr, and then NaBH(OAc)$_3$ (3.13 g, 14.79 mmol, 1.5 eq) was added. The resulting mixture was stirred at 25° C. for 15 hr. Then iced water (30 mL) was added and the mixture was neutralized to pH=9~10 with aq.NaOH (2 M). The aqueous phase was extracted with EA (30 mL*3). The combined organic phase was washed with brine (60 mL), dried with anhydrous Na$_2$SO$_4$, filtered and concentrated in vacuo. The residue was purified by flash silica gel chromatography (40 g SepaFlash® Silica Flash Column, EA/PE: 0-80%). Compound benzyl 3-[1-[(2,4-dimethoxyphenyl)methylamino]ethyl]azetidine-1-carboxylate (1.3 g, 3.21 mmol, 32.5% yield) was obtained as a yellow oil.

Benzyl 3-(1-(N-(2,4-dimethoxybenzyl)-5-(4-(trifluoromethyl)phenyl)-2-naphthamido)ethyl)azetidine-1-carboxylate A mixture of 5-[4-(trifluoromethyl)phenyl]naphthalene-2-carboxylic acid (1.09 g, 3.43 mmol, 1.2 eq), HATU (1.63 g, 4.29 mmol, 1.5 eq) in DCM (20 mL) was added DIPEA (1.11 g, 8.58 mmol, 1.50 mL, 3 eq) at 25° C. After addition, the mixture was stirred at 25° C. for 1 hr, and then benzyl 3-[1-[(2,4-dimethoxyphenyl)methylamino]ethyl]azetidine-1-carboxylate (1.1 g, 2.86 mmol, 1 eq) (in DCM (5 mL)) was added. The resulting mixture was stirred at 25° C. for 15 hr. The residue was poured into H$_2$O (80 mL) and stirred for 5 min. The aqueous phase was extracted with EA (40 mL*3). The combined organic phase was washed with brine (100 mL), dried with anhydrous Na$_2$SO$_4$, filtered and concentrated in vacuum. The residue was purified by flash silica gel chromatography (40 g SepaFlash® Silica Flash Column, EA/PE: 0~30%). Compound benzyl 3-[1-[(2,4-dimethoxyphenyl)methyl-[5-[4-(trifluoromethyl)phenyl]naphthalene-2-carbonyl]amino]ethyl]azetidine-1-carboxylate (1.4 g, 1.91 mmol, 66.6% yield) was obtained as a colorless oil.

N-(1-(azetidin-3-yl)ethyl)-N-(2,4-dimethoxybenzyl)-5-(4-(trifluoromethyl)phenyl)-2-naphthamide To a solution of benzyl 3-[1-[(2,4-dimethoxyphenyl) methyl-[5-[4-(trifluoromethyl)phenyl]naphthalene-2-carbonyl]amino]ethyl]azetidine-1-carboxylate (1.2 g, 1.76 mmol, 1 eq) in MeOH (30 mL) was added Pd/C (200 mg, 10%)

under N$_2$. The suspension was degassed under vacuum and purged with H$_2$ several times. The mixture was stirred under H$_2$ (15 psi) at 25° C. for 2 hrs. The reaction mixture was filtered and the cake was washed with MeOH (10 mL*2). The filter was concentrated in vacuo to give product. The crude product was used for next step without further purification. Compound N-[1-(azetidin-3-yl)ethyl]-N-[(2,4-dimethoxyphenyl)methyl]-5-[4-(trifluoromethyl)phenyl] naphthalene-2-carboxamide (945 mg, crude) was obtained as a colorless oil.

N-(1-(azetidin-3-yl)ethyl)-5-(4-(trifluoromethyl) phenyl)-2-naphthamide

To a solution of N-[1-(azetidin-3-yl)ethyl]-N-[(2,4-dimethoxyphenyl)methyl]-5-[4-(trifluoromethyl)phenyl]naphthalene-2-carboxamide (140 mg, 0.25 mmol, 1 eq) in DCM (1 mL) was added TFA (4.62 g, 40.52 mmol, 3 mL, 158.77 eq). The mixture was stirred at 25° C. for 2 hr. The reaction mixture was filtered and the cake was washed with MeOH (10 mL*2). The filter was concentrated in vacuo to give product. The crude product was purified by prep-HPLC (column: Xtimate C18 150*25 mm*5 um; mobile phase: [water (0.05% HCl)-ACN]; B %: 25%-55%, 7.8 min). Compound N-[1-(azetidin-3-yl)ethyl]-5-[4-(trifluoromethyl)phenyl]naphthalene-2-carboxamide (88 mg, 0.22 mmol, 86.5% yield) was obtained as a white solid.

(R)—N-(1-(azetidin-3-yl)ethyl)-5-(4-(trifluoromethyl)phenyl)-2-naphthamide (Compound 203) and (S)—N-(1-(azetidin-3-yl)ethyl)-5-(4-(trifluoromethyl)phenyl)-2-naphthamide (Compound 204)

The racemic compound N-[1-(azetidin-3-yl)ethyl]-5-[4-(trifluoromethyl)phenyl]naphthalene-2-carboxamide (85 mg, 0.21 mmol, 1 eq) was purified by SFC (column: DAICEL CHIRALPAK IC (250 mm*30 mm, 10 um); mobile phase: [0.1% NH$_3$H$_2$O IPA]; B %: 50%-50%, min). Compound 204 (19.3 mg, 48.4 umol, 22.7% yield) was obtained as a white solid. LCMS (ESI): RT=0.744 min, mass calcd for C$_{23}$H$_{21}$F$_3$N$_2$O 398.42 m/z found 399.1 [M+H]$^+$, $^1$H NMR (400 MHz, DMSO-d$_6$) δ 8.72-8.62 (m, 2H), 8.15 (d, J=8.1 Hz, 1H), 8.02-7.88 (m, 3H), 7.82 (d, J=8.9 Hz, 1H), 7.78-7.67 (m, 3H), 7.60 (d, J=6.9 Hz, 1H), 4.42-4.30 (m, 1H), 4.01-3.87 (m, 3H), 3.84-3.72 (m, 1H), 3.05 (sxt, J=8.2 Hz, 1H), 1.14 (d, J=6.6 Hz, 3H). Compound 203 (23.6 mg, 59.2 umol, 27.7% yield) was obtained as a white solid. LCMS (ESI): RT=0.744 min, mass calcd for C$_{23}$H$_{21}$F$_3$N$_2$O 398.42 m/z found 399.1 [M+H]$^+$, $^1$H NMR (400 MHz, CD$_3$OD) δ 8.45 (s, 1H), 8.06 (d, J=8.3 Hz, 1H), 7.88-7.80 (m, 5H), 7.72-7.63 (m, 4H), 7.56 (d, J=7.0 Hz, 1H), 4.50-4.37 (m, 1H), 3.72-3.52 (m, 4H), 2.97 (sxt, J=8.0 Hz, 1H), 1.20 (D, J=6.6 Hz, 3H).

Example 174: (S)—N-(1-(2-chlorophenyl)ethyl)-5-(4-(trifluoromethyl)phenyl)-2-naphthamide (Compound 205) and (R)—N-(1-(2-chlorophenyl)ethyl)-5-(4-(trifluoromethyl)phenyl)-2-naphthamide (Compound 206)

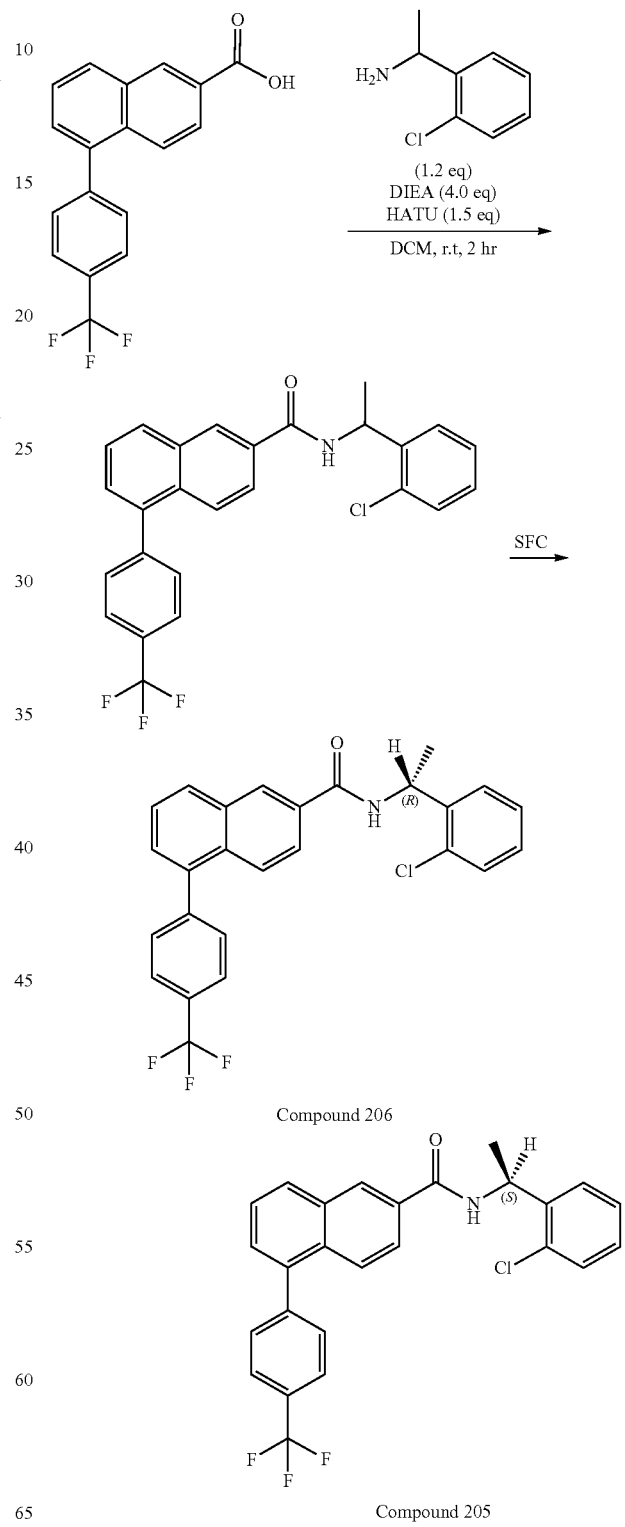

Compound 206

Compound 205

537

N-(1-(2-chlorophenyl)ethyl)-5-(4-(trifluoromethyl)phenyl)-2-naphthamide

The mixture of 5-[4-(trifluoromethyl)phenyl]naphthalene-2-carboxylic acid (100 mg, 0.31 mmol, 1 eq), 1-(2-chlorophenyl)ethanamine (59.0 mg, 0.37 mmol, 1.2 eq), HATU (180.3 mg, 0.47 mmol, 1.5 eq) and DIPEA (163.4 mg, 1.26 mmol, 0.22 mL, 4 eq) in DCM (5 mL) was stirred at 25° C. for 2 hr. The reaction mixture was diluted with $H_2O$ (10 mL) and the mixture was extracted with EA (20 mL*3). The combined organic phase was washed with brine (10 mL*2), dried with anhydrous $Na_2SO_4$, filtered and concentrated in vacuum. The residue was purified by column chromatography ($SiO_2$, Petroleum ether/Ethyl acetate=1/0 to 5:1). Compound N-[1-(2-chlorophenyl)ethyl]-5-[4-(trifluoromethyl)phenyl]naphthalene-2-carboxamide (106 mg, 0.22 mmol, 72.3% yield) was obtained as white solid.

(S)—N-(1-(2-chlorophenyl)ethyl)-5-(4-(trifluoromethyl)phenyl)-2-naphthamide (Compound 205) and (R)—N-(1-(2-chlorophenyl)ethyl)-5-(4-(trifluoromethyl)phenyl)-2-naphthamide (Compound 206)

The racemic compound N-[1-(2-chlorophenyl)ethyl]-5-[4-(trifluoromethyl)phenyl]naphthalene-2-carboxamide (90 mg, 0.19 mmol, 1 eq) was purified by SFC (column: DAICEL CHIRALPAK AS-H (250 mm*30 mm, 5 um); mobile phase: [Neu-ETOH]; B %: 35%-35%, min). Compound 205 (40 mg, 87.2 umol, 44.0% yield) was obtained as white solid. LCMS (ESI): RT=1.089 min, mass calcd for $C_{26}H_{19}ClF_3NO$ 453.88 m/z, found 454.0 [M+H]$^+$, $^1$H NMR (400 MHz, $CD_3Cl$) δ 8.38 (s, 1H), 7.98 (d, J=8.3 Hz, 1H), 7.88-7.76 (m, 4H), 7.64-7.57 (m, 3H), 7.53-7.39 (m, 3H), 7.28 (d, J=1.5 Hz, 1H), 7.25-7.21 (m, 1H), 7.32-7.21 (m, 1H), 6.80 (br d, J=7.5 Hz, 1H), 5.65 (t, J=7.2 Hz, 1H), 1.68 (d, J=7.0 Hz, 3H). Compound 206 (30 mg, 65.4 umol, 33.0% yield) was obtained as white solid. LCMS (ESI): RT=1.082 min, mass calcd for $C_{26}H_{19}ClF_3NO$ 453.88 m/z, found 454.0 [M+H]$^+$, $^1$H NMR (400 MHz, $CD_3Cl$) δ 8.39 (d, J=1.1 Hz, 1H), 7.97 (d, J=8.3 Hz, 1H), 7.88-7.77 (m, 3H), 7.64-7.58 (m, 3H), 7.50 (dd, J=1.1, 7.1 Hz, 1H), 7.45 (dd, J=1.8, 7.5 Hz, 1H), 7.40 (dd, J=1.5, 7.6 Hz, 1H), 7.30-7.27 (m, 1H), 7.25 (dd, J=1.9, 3.3 Hz, 1H), 7.24-7.20 (m, 1H), 6.84 (br d, J=7.5 Hz, 1H), 5.65 (quin, J=7.1 Hz, 1H), 1.67 (d, J=6.9 Hz, 3H).

Example 175: N-[(E)-6-(2,6-difluorophenoxy)hex-4-enyl]-5-[4-(trifluoromethyl)phenyl]naphthalene-2-carboxamide (Compound 207)

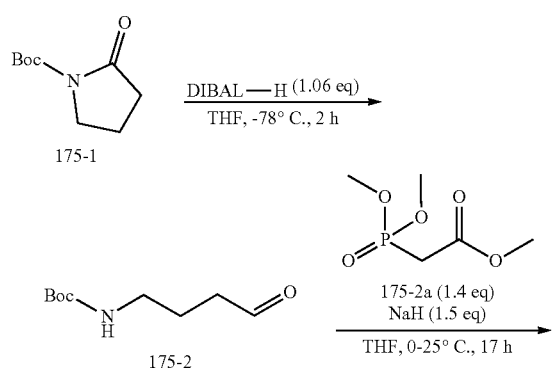

538

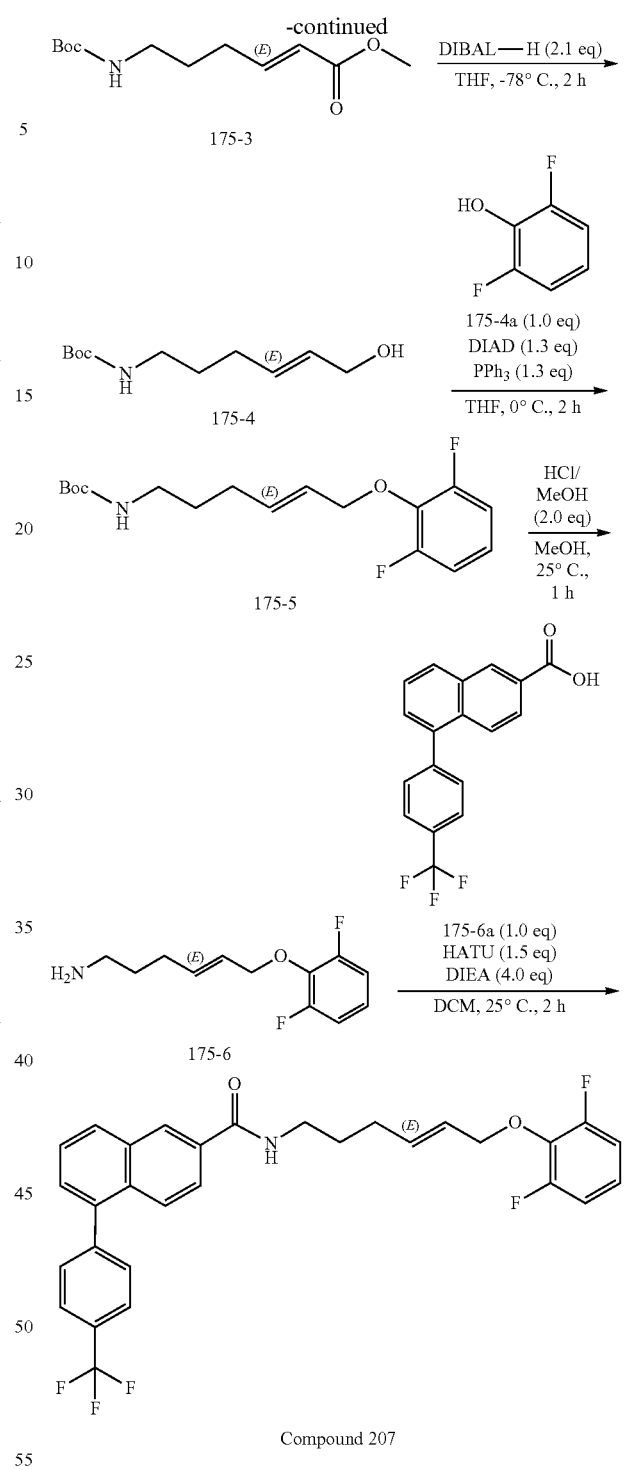

Tert-Butyl N-(4-oxobutyl)carbamate

To a solution of compound 175-1 (2 g, 10.8 mmol, 1.83 mL, 1 eq) in THF (30 mL) was added DIBAL-H (1 M, 11.43 mL, 1.06 eq) at −78° C. The reaction was stirred at −78° C. for 2 hr. The reaction was quenched by Sat. potassium sodium tartrate (30 mL), filtered and extracted with EA (3*50 mL). The organic layer was dried over $Na_2SO_4$ and concentrated to give compound 175-2 (2 g, crude) as colorless oil, which was used for next step directly.

Methyl
(E)-6-(tert-butoxycarbonylamino)hex-2-enoate

To a solution of compound 175-2a (2.7 g, 14.9 mmol, 2.16 mL, 1.4 eq) in THF (30 mL) was added NaH (640.8 mg, 16.0 mmol, 60%, 1.5 eq) at 0° C. The reaction was stirred at 25° C. for 1 hr. Compound 175-2 (2 g, 10.6 mmol, 1 eq) in THF (10 mL) was added to the solution at 0° C. and the reaction was stirred at 25° C. for 16 hr. The reaction was quenched by Sat.NH$_4$Cl (10 mL) and extracted with DCM (3*30 mL). The organic layer was dried over Na$_2$SO$_4$ and concentrated. The residue was purified by column chromatography on silica gel (EA:PE=1:5) to give compound 175-3 (1.2 g, 4.93 mmol, 46.2% yield) as colorless oil. $^1$H NMR (400 MHz, CDCl$_3$) δ 6.95 (td, J=6.8, 15.7 Hz, 1H), 5.90-5.78 (m, 1H), 4.55 (br s, 1H), 3.15 (br d, J=5.5 Hz, 2H), 2.29-2.20 (m, 2H), 1.82 (quin, J=7.1 Hz, 1H), 1.71-1.64 (m, 2H), 1.44 (s, 9H).

Tert-Butyl N-[(E)-6-hydroxyhex-4-enyl]carbamate

To a solution of compound 175-3 (0.2 g, 0.82 mmol, 1 eq) in DCM (4 mL) was added DIBAL-H (1 M, 1.73 mL, 2.1 eq) at −78° C. The reaction was stirred at −78° C. for 2 hr. The reaction was quenched by Sat. potassium sodium tartrate (20 mL) and filtered. The filtrated was extracted with DCM (2*30 mL). The organic layer was dried over Na$_2$SO$_4$ and concentrated to give compound 175-4 (150 mg, 0.69 mmol, 84.8% yield) as colorless oil, which was used for next step directly. $^1$H NMR (400 MHz, CDCl$_3$) δ 5.68-5.54 (m, 2H), 4.61-4.38 (m, 1H), 4.10-3.96 (m, 2H), 3.71-3.47 (m, 1H), 3.07 (br s, 2H), 2.10-1.98 (m, 2H), 1.53 (br s, 2H), 1.37 (s, 9H).

Tert-Butyl N-[(E)-6-(2,6-difluorophenoxy)hex-4-enyl]carbamate

To a solution of compound 175-4 (50 mg, 0.23 mmol, 1 eq), 175-4a (30.2 mg, 0.23 mmol, 1 eq) and PPh$_3$ (79.1 mg, 0.3 mmol, 1.3 eq) in THF (0.5 mL) was added DIAD (61.0 mg, 0.3 mmol, 58 uL, 1.3 eq) at 0° C. The reaction was stirred at 0° C. for 2 hr. The reaction was diluted with EA (10 mL) and washed with H$_2$O (2*5 mL). The organic layer was dried over Na$_2$SO$_4$ and concentrated. The crude product was purified by column chromatography on silica gel (EA:PE=1:10-1:3) to give compound 175-5 (25 mg, 52.7 umol, 22.7% yield) as colorless oil.

(E)-6-(2,6-difluorophenoxy)hex-4-en-1-amine

To a solution of compound 175-5 (25 mg, 52.6 umol, 1 eq) in MeOH (0.5 mL) was added HCl/MeOH (4 M, 26 uL, 2 eq). The reaction was stirred at 25° C. for 1 hr. The reaction was concentrated to give compound 175-6 (21 mg, 49.3 umol, 93.7% yield, HCl) as colorless oil, which was used for next step directly.

N-[(E)-6-(2,6-difluorophenoxy)hex-4-enyl]-5-[4-(trifluoromethyl)phenyl]naphthalene-2-carboxamide To a solution of compound 175-6a (15.6 mg, 49.3 umol, 1 eq), HATU (28.1 mg, 74.0 umol, 1.5 eq) and DIEA (25.5 mg, 0.19 mmol, 34 uL, 4 eq) in DCM (1 mL) was added compound 175-6 (21 mg, 49.3 umol, 1 eq, HCl). The reaction was stirred at 25° C. for 2 hr. The reaction was diluted with DCM (20 mL) and washed with H$_2$O (2*10 mL). The organic layer was dried over Na$_2$SO$_4$ and concentrated. The crude product was purified by prep-HPLC (column: Waters Xbridge 150*50 10u; mobile phase: [water (0.05% ammonia hydroxide v/v)-ACN]; B %: 73%-93%, 9.5 min) to give the title compound (8.0 mg, 15.1 umol, 30.6% yield) as a white solid. LCMS (ESI): RT=1.097 min, mass calcd. for $C_{30}H_{24}F_5NO_2$ 525.17, m/z found 526.1 [M+H]$^+$, $^1$H NMR (400 MHz, CDCl$_3$) δ 8.37 (s, 1H), 7.99 (d, J=8.0 Hz, 1H), 7.86 (d, J=8.8 Hz, 1H), 7.82-7.74 (m, 3H), 7.64-7.57 (m, 3H), 7.51 (d, J=7.0 Hz, 1H), 6.99-6.82 (m, 3H), 6.28 (brs, 1H), 5.87-5.75 (m, 2H), 4.61 (d, J=5.3 Hz, 2H), 3.56-3.46 (m, 2H), 2.27-2.14 (m, 2H), 1.84-1.74 (m, 2H).

Example 176: N-(3-(2-methoxyethoxy)benzyl)-5-(4-(trifluoromethyl)phenyl)-2-naphthamide (Compound 208)

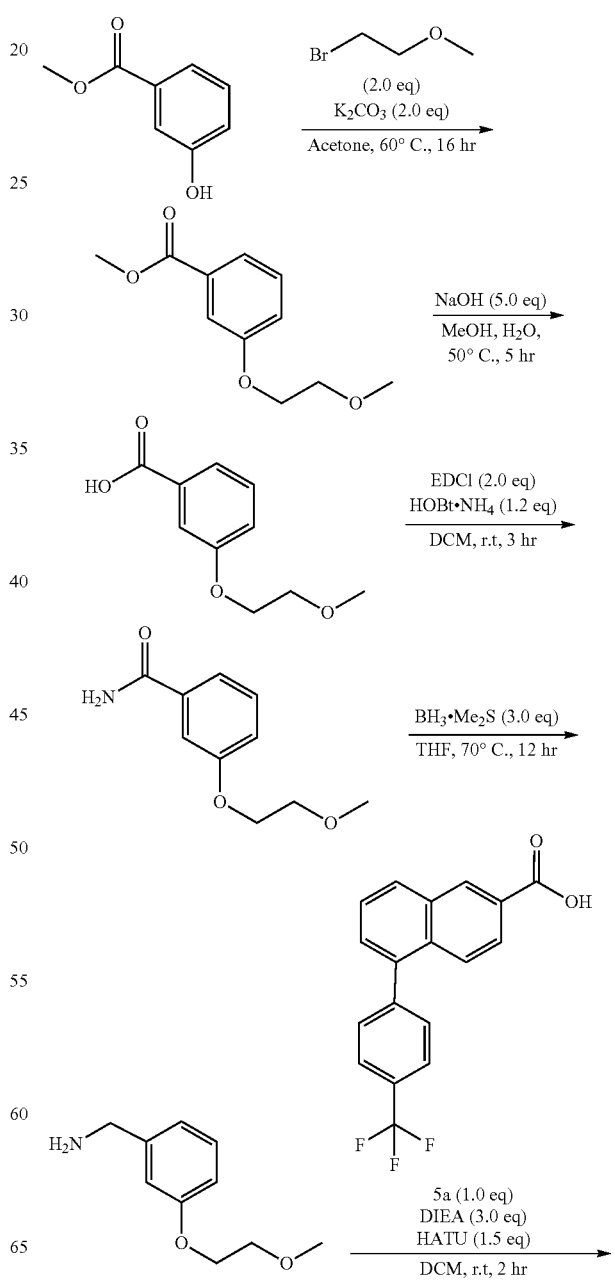

541

-continued

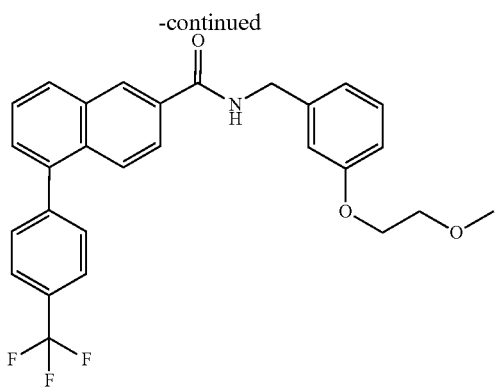

Compound 208

Methyl 3-(2-methoxyethoxy)benzoate

The mixture of methyl 3-hydroxybenzoate (1 g, 6.57 mmol, 1 eq), 1-bromo-2-methoxy-ethane (1.83 g, 13.15 mmol, 1.23 mL, 2 eq) and $K_2CO_3$ (1.82 g, 13.15 mmol, 2 eq) in ACETONE (10 mL) was stirred at 60° C. for 16 hr. The reaction mixture was diluted with $H_2O$ (70 mL) and extracted with DCM (20 mL*3). The combined organic layers were washed with brine (40 mL*2), dried with anhydrous $Na_2SO_4$, filtered and concentrated in vacuum. The residue was purified by column chromatography ($SiO_2$, Petroleum ether/Ethyl acetate=1/0 to 10:1). Compound methyl 3-(2-methoxyethoxy)benzoate (1.2 g, 5.71 mmol, 86.8% yield) was obtained as colorless oil.

3-(2-methoxyethoxy)benzoic Acid

To a solution of NaOH (1.14 g, 28.54 mmol, 5 eq) in $H_2O$ (5 mL) was added methyl 3-(2-methoxyethoxy)benzoate (1.2 g, 5.71 mmol, 1 eq). The mixture in THF (10 mL) was stirred at 50° C. for 5 hr. The reaction was cooled to 25° C. and adjusted with 4 M HCl to pH=1. The reaction mixture was diluted with $H_2O$ (70 mL) and extracted with DCM (20 mL*3). The combined organic layers were washed with brine (40 mL*2), dried with anhydrous $Na_2SO_4$, filtered and concentrated in vacuum. The residue was purified by column chromatography ($SiO_2$, Petroleum ether/Ethyl acetate=1/0 to 1:1). Compound 3-(2-methoxyethoxy)benzoic acid (850 mg, 4.33 mmol, 75.9% yield) was obtained as a white solid.

3-(2-methoxyethoxy)benzamide

The mixture of 3-(2-methoxyethoxy)benzoic acid (480 mg, 2.45 mmol, 1 eq) EDCI (937.9 mg, 4.89 mmol, 0.73 mL, 2 eq) in DCM (5 mL) was stirred at 20° C. for 1 hr. Then ammonium; 1-oxidobenzotriazole (446.6 mg, 2.94 mmol, 1.2 eq) was added into the mixture and the mixture was stirred at 20° C. for another 2 hr. The reaction mixture was diluted with $H_2O$ (10 mL) and extracted with EA (10 mL*3). The combined organic phase was washed with brine (10 mL*2), dried with anhydrous $Na_2SO_4$, filtered and concentrated in vacuum. The residue was purified by column chromatography ($SiO_2$, Ethyl acetate:Methanol=1/0 to 5:1). Compound 3-(2-methoxyethoxy)benzamide (234 mg, 1.20 mmol, 49.0% yield) was obtained as a white solid.

542

(3-(2-methoxyethoxy)phenyl)methanamine

The mixture of 3-(2-methoxyethoxy)benzamide (134 mg, 0.68 mmol, 1 eq) and $BH_3\text{-}Me_2S$ (10 M, 0.20 mL, 3 eq) in THF (2 mL) was stirred at 70° C. for 12 hr. The reaction mixture was quenched by addition 4 M HCl 40 mL at 0° C. The reaction was cooled to 25° C. and adjusted with 4 M NaOH to pH=11. Then the reaction mixture was diluted with (10 mL) and extracted with EA (10 mL*3). The combined organic phase was washed with brine (10 mL*2), dried with anhydrous $Na_2SO_4$, filtered and concentrated in vacuum. Compound [3-(2-methoxyethoxy)phenyl]methanamine (123 mg, crude) was obtained as colorless oil.

N-(3-(2-methoxyethoxy)benzyl)-5-(4-(trifluoromethyl)phenyl)-2-naphthamide

The mixture of 5-[4-(trifluoromethyl)phenyl]naphthalene-2-carboxylic acid (52.3 mg, 0.16 mmol, 1 eq), HATU (94.4 mg, 0.24 mmol, 1.5 eq) and DIPEA (64.1 mg, 0.49 mmol, 86.5 uL, 3 eq) in DCM (2 mL) was stirred at 25° C. for 1 hr. Then [3-(2-methoxyethoxy)phenyl]methanamine (30 mg, 0.16 mmol, 1.0 eq) was added into the mixture and the mixture was stirred at 25° C. for another 1 hr. The reaction mixture was diluted with $H_2O$ (10 mL) and extracted with EA (10 mL*3). The combined organic phase was washed with brine (10 mL*2), dried with anhydrous $Na_2SO_4$, filtered and concentrated in vacuum. The residue was purified by prep-HPLC (column: Xtimate $C_{18}$ 150*25 mm*5 um; mobile phase: [water (0.05% HCl)-ACN]; B %: 55%-85%, 8.5 min). The title compound (16.1 mg, 33.4 umol, 20.2% yield) was obtained as a white solid. LCMS (ESI): RT=1.033 min, mass calcd for $C_{28}H_{24}F_3NO_3$ 479.49 m/z found 480.1 [M+H]$^+$. $^1H$ NMR (400 MHz, $CD_3OD$) δ 8.31 (s, 1H), 7.88 (d, J=8.3 Hz, 1H), 7.80-7.76 (m, 1H), 7.75-7.71 (m, 1H), 7.69 (d, J=8.1 Hz, 2H), 7.55-7.49 (m, 3H), 7.42 (d, J=6.9 Hz, 1H), 7.24-7.16 (m, 1H), 6.89 (br s, 2H), 6.81-6.76 (m, 1H), 6.57 (br s, 1H), 4.59 (d, J=5.4 Hz, 2H), 4.08-3.97 (m, 2H), 3.70-3.62 (m, 2H), 3.36 (s, 3H).

Example 177: (E)-5-[[5-[4-(trifluoromethyl)phenyl]naphthalene-2-carbonyl]amino]pent-2-enoic Acid (Compound 209)

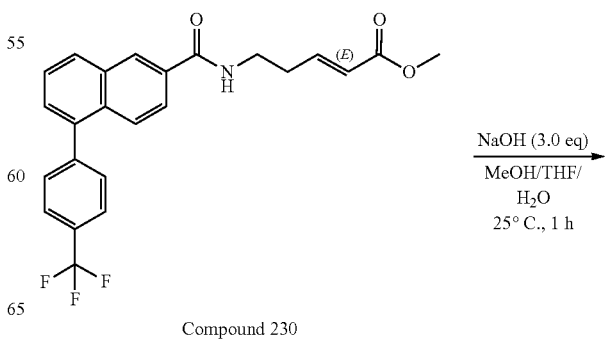

Compound 230

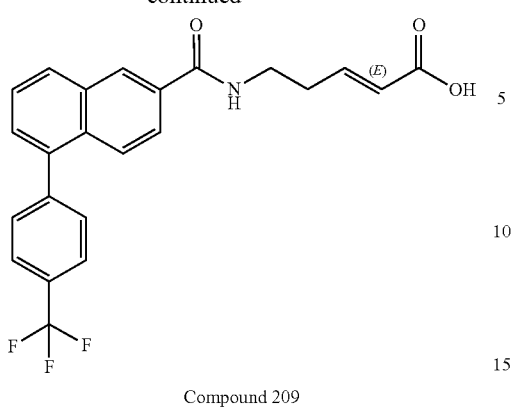

Compound 209

To a solution of Compound 230 (0.1 g, 0.23 mmol, 1 eq) in MeOH (2 mL), THF (2 mL) and H₂O (2 mL) was added NaOH (28.0 mg, 0.7 mmol, 3 eq). The reaction was stirred at 25° C. for 1 hr. The reaction mixture was concentrated. The residue was adjusted pH to 3-4 with 2N aq.HCl and extracted with EA (2*15 mL). The organic layer was dried over Na₂SO₄ and concentrated. The crude product was purified by prep. TLC (EA, UV) to give the title compound (20 mg, 47.9 umol, 20.4% yield) as a yellow solid. LCMS (ESI): RT=0.919 min, mass calcd. For $C_{23}H_{18}F_3NO_3$, 413.12 m/z found 414.1 [M+H]⁺. ¹H NMR (400 MHz, DMSO-d₆) δ 12.18 (brs, 1H), 8.79 (br t, J=5.6 Hz, 1H), 8.54 (s, 1H), 8.12 (d, J=8.3 Hz, 1H), 7.92 (br d, J=8.3 Hz, 3H), 7.81 (d, J=8.8 Hz, 1H), 7.74 (d, J=8.0 Hz, 2H), 7.69 (t, J=7.7 Hz, 1H), 7.59 (d, J=6.5 Hz, 1H), 6.92-6.77 (m, 1H), 5.85 (d, J=15.6 Hz, 1H), 3.46 (q, J=6.1 Hz, 2H), 2.54-2.52 (m, 2H).

Example 178: N-((2-methoxypyridin-4-yl)methyl)-5-(4-(trifluoromethyl)phenyl)-2-naphthamide (Compound 210)

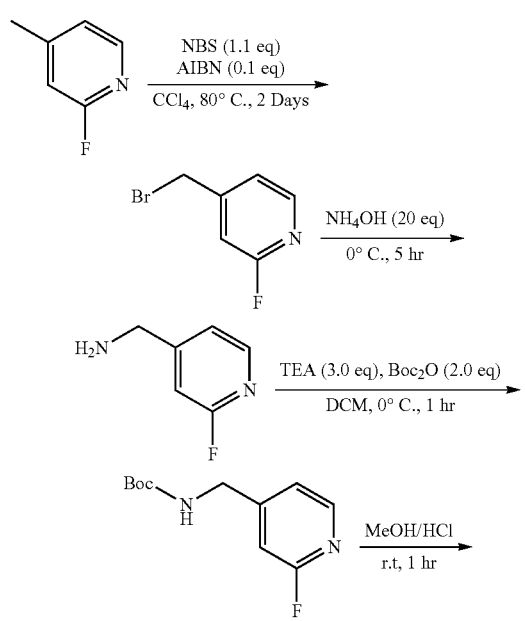

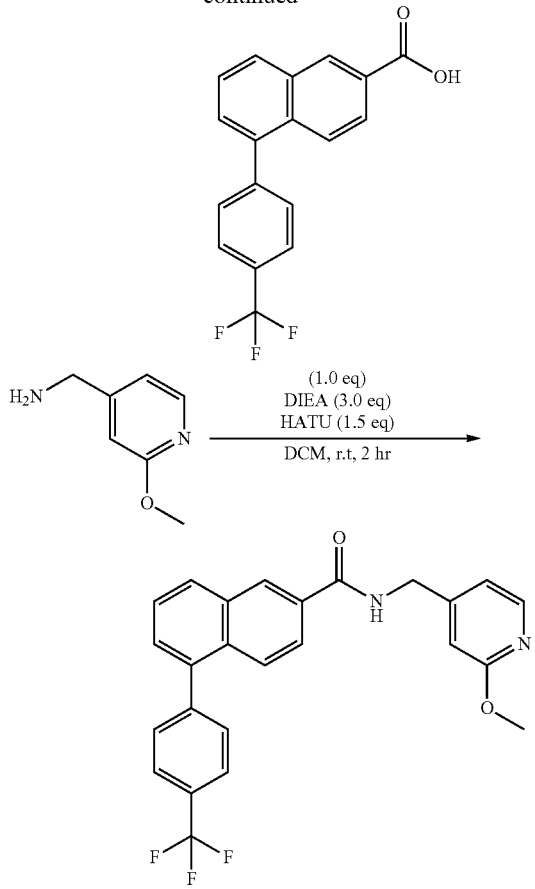

Compound 210

4-(bromomethyl)-2-fluoropyridine

The mixture of 2-fluoro-4-methyl-pyridine (2 g, 18.00 mmol, 1 eq), NBS (3.52 g, 19.80 mmol, 1.1 eq) and AIBN (295.5 mg, 1.80 mmol, 0.1 eq) in CCl₄ (20 mL) was stirred at 80° C. for 48 hr. The reaction mixture was diluted with H2O (60 mL) and extracted with DCM (10 mL*3). The combined organic phase was washed with brine (10 mL*2), dried with anhydrous Na₂SO₄, filtered and concentrated in vacuum. The residue was purified by column chromatography (SiO₂, Petroleum ether/Ethyl acetate=1/0 to 10:1). Compound 4-(bromomethyl)-2-fluoro-pyridine (1.9 g, 10.00 mmol, 55.5% yield) was obtained as a yellow oil and obtained as a yellow oil and used into the next step without further purification.

(2-fluoropyridin-4-yl)methanamine

The mixture of 4-(bromomethyl)-2-fluoro-pyridine (862 mg, 4.54 mmol, 1 eq) and NH₃·H₂O (11.36 g, 90.73 mmol, 12.48 mL, 28% solution, 20 eq) was stirred at 0° C. for 5 hr. Compound (2-fluoro-4-pyridyl)methanamine (527 mg, 4.18 mmol, 92.1% yield) was obtained as yellow oil and used into the next step without further purification.

Tert-Butyl ((2-fluoropyridin-4-yl)methyl)carbamate

The mixture of (2-fluoro-4-pyridyl)methanamine (527 mg, 4.18 mmol, 1 eq), TEA (1.27 g, 12.53 mmol, 1.74 mL, 3 eq) and Boc₂O (1.82 g, 8.36 mmol, 1.92 mL, 2 eq) in DCM (5 mL) was stirred at 0° C. for 1 hr. The reaction mixture was diluted with H₂O (10 mL) and extracted with EA (10 mL*3). The combined organic phase was washed with brine (10 mL*2), dried with anhydrous Na₂SO₄, filtered and concentrated in vacuum. The residue was purified by column chromatography (SiO₂, Petroleum ether/Ethyl acetate=1/0 to 10:1). Compound tert-butyl N-[(2-fluoro-4-pyridyl)methyl]carbamate (20 mg, 88.4 umol, 2.1% yield) was obtained as yellow oil.

(2-methoxypyridin-4-yl)methanamine

The mixture of tert-butyl N-[(2-fluoro-4-pyridyl)methyl] carbamate (20 mg, 88.4 umol, 1 eq) in MeOH/HCl (4 M, 0.44 mL, 20 eq) was stirred at 25° C. for 1 hr. The reaction mixture was filtered and concentrated in vacuum. Compound (2-methoxy-4-pyridyl)methanamine (12 mg, 68.7 umol, 77.7% yield, HCl) was obtained as yellow oil.

N-((2-methoxypyridin-4-yl)methyl)-5-(4-(trifluoromethyl)phenyl)-2-naphthamide

The mixture of 5-[4-(trifluoromethyl)phenyl]naphthalene-2-carboxylic acid (10.8 mg, 34.3 umol, 1 eq), HATU (19.6 mg, 51.5 umol, 1.5 eq) and DIPEA (13.3 mg, 0.10 mmol, 17.9 uL, 3 eq) in DCM (1 mL) was stirred at 25° C. for 1 hr. Then (2-methoxy-4-pyridyl)methanamine (6 mg, 34.3 umol, 1 eq, HCl) was added into the mixture and the mixture was stirred at 25° C. for another 1 hr. The reaction mixture was diluted with H₂O (10 mL) and extracted with EA (10 mL*3). The combined organic phase was washed with brine (10 mL*2), dried with anhydrous Na₂SO₄, filtered and concentrated in vacuum. The residue was purified by prep-HPLC (column: Xtimate C18 150*25 mm*5 um; mobile phase: [water (0.05% HCl)-ACN]; B %: 45%-75%, 11.5 min). The title compound (5.2 mg, 10.8 umol, 31.6% yield, HCl) was obtained as a white solid. LCMS (ESI): RT=0.953 min, mass calcd for C₂₅H₁₉F₃N₂O₂ 436.43 m/z found 437.0 [M+H]⁺, ¹H NMR (400 MHz, CD₃OD) δ 8.56 (s, 1H), 8.19-8.06 (m, 2H), 7.97-7.88 (m, 2H), 7.86 (br d, J=8.0 Hz, 2H), 7.74-7.66 (m, 3H), 7.60 (d, J=7.0 Hz, 1H), 7.16 (d, J=5.6 Hz, 1H), 7.06 (s, 1H), 4.71 (s, 2H), 4.01 (s, 3H).

Example 179: N-((2-fluoropyridin-4-yl)methyl)-5-(4-(trifluoromethyl)phenyl)-2-naphthamide (Compound 211)

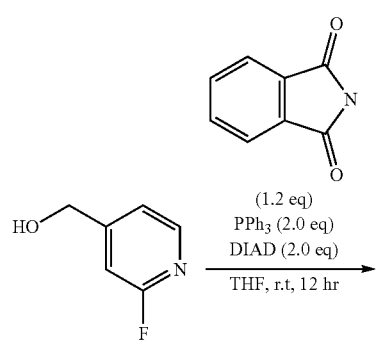

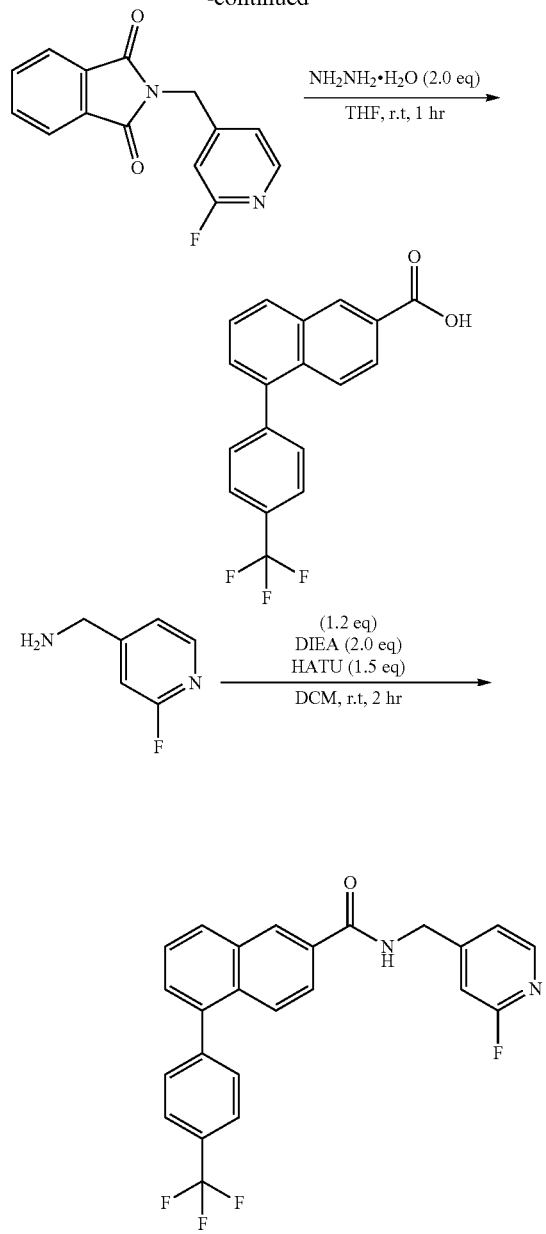

Compound 211

2-((2-fluoropyridin-4-yl)methyl)isoindoline-1,3-dione

DIAD (318.1 mg, 1.57 mmol, 0.30 mL, 2 eq) was added dropwise into a solution of isoindoline-1,3-dione (138.8 mg, 0.94 mmol, 1.2 eq), (2-fluoro-4-pyridyl)methanol (100 mg, 0.78 mmol, 1 eq) and PPh₃ (412.6 mg, 1.57 mmol, 2 eq) in THF (2 mL) at 0° C. under N₂. The resulting solution was stirred for 12 hr at 20° C. The reaction mixture was diluted with H₂O (10 mL) and extracted with EA (10 mL*3). The combined organic phase was washed with brine (10 mL*2), dried with anhydrous Na₂SO₄, filtered and concentrated in vacuum. The residue was purified by column chromatography (SiO₂, Petroleum ether/Ethyl acetate=1/0 to 10:1).

Compound 2-[(2-fluoro-4-pyridyl)methyl]isoindoline-1,3-dione (200 mg, 0.75 mmol, 96.2% yield) was obtained as a white solid.

(2-fluoropyridin-4-yl)methanamine

The mixture of 2-[(2-fluoro-4-pyridyl)methyl]isoindoline-1,3-dione (140 mg, 0.54 mmol, 1 eq) and hydrazine hydrate (54.7 mg, 1.09 mmol, 53.1 uL, 2 eq) in THF (2 mL) was stirred at 20° C. for 1 hr. The reaction mixture was diluted with $H_2O$ (10 mL) and extracted with EA (10 mL*3). The combined organic phase was washed with brine (10 mL*2), dried with anhydrous $Na_2SO_4$, filtered and concentrated in vacuum. Compound (2-fluoro-4-pyridyl)methanamine (68 mg, 0.53 mmol, 98.6% yield) was obtained as a white solid.

N-((2-fluoropyridin-4-yl)methyl)-5-(4-(trifluoromethyl)phenyl)-2-naphthamide The mixture of 5-[4-(trifluoromethyl)phenyl]naphthalene-2-carboxylic acid (142.0 mg, 0.44 mmol, 1 eq), HATU (256.2 mg, 0.67 mmol, 1.5 eq) and DIPEA (116.1 mg, 0.89 mmol, 0.15 mL, 2 eq) in DCM (3 mL) was stirred at 20° C. for 1 hr. Then (2-fluoro-4-pyridyl)methanamine (68 mg, 0.53 mmol, 1.2 eq) was added into the mixture and the mixture was stirred at 20° C. for another 1 hr. The reaction mixture was diluted with $H_2O$ (10 mL) and extracted with EA (10 mL*3). The combined organic phase was washed with brine (10 mL*2), dried with anhydrous $Na_2SO_4$, filtered and concentrated in vacuum. The residue was purified by prep-HPLC (column: Xtimate C18 150*25 mm*5 um; mobile phase: [water (0.05% HCl)-ACN]; B %: 45%-75%, 11.5 min). The title compound (3.5 mg, 7.5 umol, 1.6% yield, HCl) was obtained as a white solid. LCMS (ESI): RT=0.988 min, mass calcd for $C_{24}H_{16}F_4N_2O$ 424.39 m/z found 425.1 [M+H]$^+$, $^1$H NMR (400 MHz, CDCl$_3$) δ 8.37 (s, 1H), 8.13 (d, J=5.0 Hz, 1H), 7.93 (d, J=8.3 Hz, 1H), 7.85-7.81 (m, 1H), 7.78-7.74 (m, 1H), 7.71 (d, J=8.0 Hz, 2H), 7.59-7.52 (m, 3H), 7.49-7.45 (m, 1H), 7.13 (br d, J=5.0 Hz, 1H), 6.87 (s, 1H), 6.71 (br s, 1H), 4.70 (d, J=6.0 Hz, 2H).

Example 180: N-(1-methoxy-2-methylpropan-2-yl)-5-(4-(trifluoromethyl)phenyl)-2-naphthamide (Compound 212)

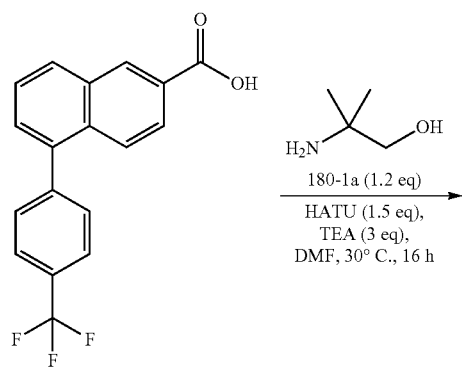

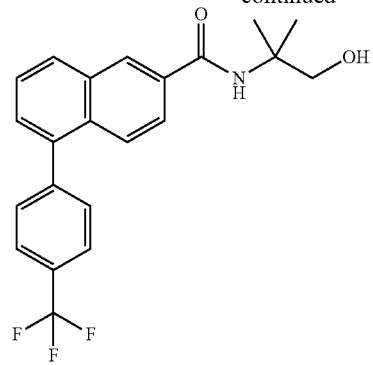

180-2

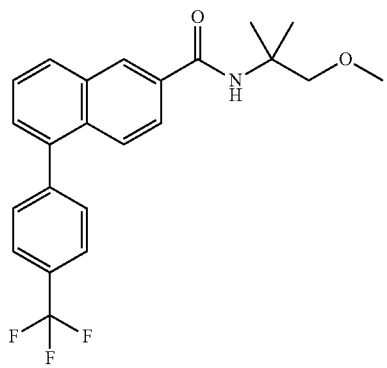

Compound 212

N-(1-hydroxy-2-methylpropan-2-yl)-5-(4-(trifluoromethyl)phenyl)-2-naphthamide To a solution of 180-1 (45 mg, 0.14 mmol, 1 eq) and HATU (81.2 mg, 0.21 mmol, 1.5 eq) in DMF (1 mL) at 30° C. was added 180-1a (15.2 mg, 0.17 mmol, 16 uL, 1.2 eq) and TEA (43.2 mg, 0.43 mmol, 59 uL, 3 eq). The mixture was stirred at 30° C. for 16 h. The reaction mixture was concentrated under reduced pressure to give a residue. The reaction mixture was diluted with water (20 mL) and extracted with EA (20 mL*3). The combined organic layers were washed with water (20 mL) and brine (20 mL), dried over $Na_2SO_4$, filtered and concentrated under reduced pressure to give a residue which was purified by flash silica gel chromatography (ISCO®; 12 g SepaFlash® Silica Flash Column, Eluent of 0~40% Ethylacetate/Petroleum ether gradient @ 20 mL/min) to give 180-2 (260 mg, 1.79 mmol, 46.9% yield) as a white solid. LCMS (ESI): RT=0.977 min, mass calc. for $C_{22}H_{20}F_3NO_2$ 387.14, m/z found 388.0 [M+H]$^+$.

N-(1-methoxy-2-methylpropan-2-yl)-5-(4-(trifluoromethyl)phenyl)-2-naphthamide To a solution of 180-2 (18 mg, 46 umol, 1 eq) and iodomethane (329.8 mg, 2.32 mmol, 0.14 mL, 50 eq) in THF (1 mL) at 0° C. was added NaH (14.9 mg, 0.37 mmol, 60%, 8 eq). The mixture was stirred at 20° C. for 4 h. The reaction mixture was concentrated under reduced pressure to give a residue. The reaction mixture was combined with ES10388-115-P1. The reaction was diluted with water (10 mL) and extracted with EA (10 mL*3). The combined organic layers were washed with water (20 mL) and brine (20 mL), dried over Na$_2$SO$_4$, filtered and concentrated under reduced pressure to give a residue which was purified by prep-HPLC: (column: Xtimate C18 150*25 mm*5 um; mobile phase: [water (0.05% HCl)-ACN]; B %: 55%-85%, 8.5 min) to give the title compound (10 mg, 24 umol, 52.5% yield) as a white solid. LCMS (ESI): RT=1.012 min, mass calc. for C$_{23}$H$_{22}$F$_3$NO$_2$ 401.16, m/z found 402.0 [M+H]$^+$; $^1$H NMR (400 MHz, CDCl$_3$) δ 8.33 (d, J=1.6 Hz, 1H), 7.99 (d, J=8.3 Hz, 1H), 7.88-7.82 (m, 1H), 7.79-7.75 (m, 3H), 7.62-7.58 (m, 3H), 7.49 (dd, J=1.2, 7.1 Hz, 1H), 6.51 (s, 1H), 3.50 (s, 2H), 3.45 (s, 3H), 1.53 (s, 6H).

Example 181: (R)—N-(1-(4-aminopyridin-2-yl) ethyl)-5-(4-(trifluoromethyl)phenyl)-2-naphthamide (Compound 213) and (S)—N-(1-(4-aminopyridin-2-yl)ethyl)-5-(4-(trifluoromethyl)phenyl)-2-naphthamide (Compound 214)

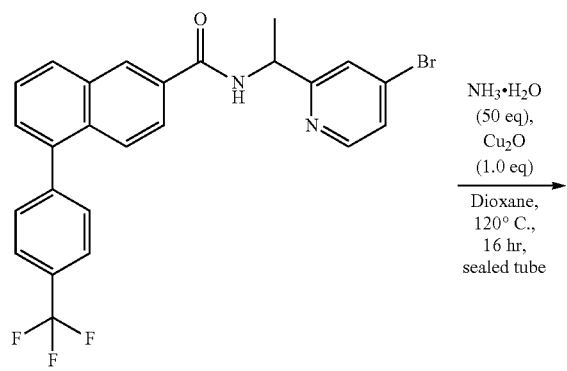

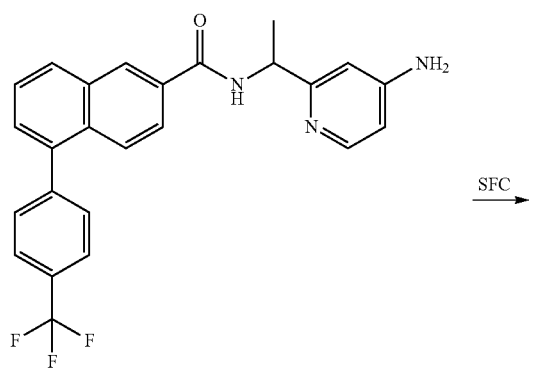

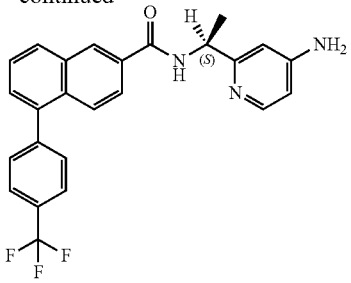

Compound 214

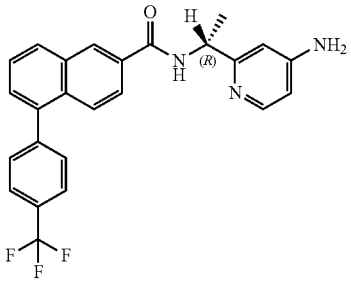

Compound 213

N-(1-(4-aminopyridin-2-yl)ethyl)-5-(4-(trifluoromethyl)phenyl)-2-naphthamide

To a solution of N-[1-(4-bromo-2-pyridyl)ethyl]-5-[4-(trifluoromethyl)phenyl]naphthalene-2-carboxamide (200 mg, 0.40 mmol, 1 eq) in dioxane (2 mL) was added NH$_3$·H$_2$O (2.73 g, 23.37 mmol, 3 mL, 30% solution, 58.34 eq) and Cu$_2$O (57.3 mg, 0.40 mmol, 40.9 uL, 1 eq). The mixture was stirred at 120° C. for 16 hr in a sealed tube. The mixture was added H$_2$O (10 mL) and extracted with EA (15 mL*3). The combined organic layers were washed with brine (30 mL), dried with anhydrous Na$_2$SO$_4$, filtered and concentrated under reduced pressure to give a residue. The residue was purified by prep-HPLC (column: Waters Xbridge 150*50 10u; mobile phase: [water (0.05% ammonia hydroxide v/v)-ACN]; B %: 50%-80%, 7.8 min). N-[1-(4-amino-2-pyridyl)ethyl]-5-[4-(trifluoromethyl)phenyl]naphthalene-2-carboxamide (82 mg, 0.18 mmol, 47.0% yield) was obtained as white solid (R)—N-(1-(4-aminopyridin-2-yl)ethyl)-5-(4-(trifluoromethyl)phenyl)-2-naphthamide (Compound 213) and (S)—N-(1-(4-aminopyridin-2-yl)ethyl)-5-(4-(trifluoromethyl)phenyl)-2-naphthamide (Compound 214)

The racemic compound N-[1-(4-amino-2-pyridyl)ethyl]-5-[4-(trifluoromethyl)phenyl]naphthalene-2-carboxamide (82 mg, 0.18 mmol, 1 eq) was purified by SFC (column: DAICEL CHIRALPAK AD (250 mm*30 mm, 10 um); mobile phase: [0.1% NH$_3$H$_2$O ETOH]; B %: 40%-40%, min). Compound 214 (32.4 mg, 74.4 umol, 39.5% yield) was obtained as a white solid. LCMS (ESI): RT=0.791 min, mass calcd for C$_{25}$H$_{20}$F$_3$N$_3$O 435.44 m/z found 436.0 [M+H]$^+$, $^1$H NMR (400 MHz, DMSO-d$_6$) δ 8.89 (br d, J=7.4 Hz, 1H), 8.66 (s, 1H), 8.14 (d, J=8.3 Hz, 1H), 8.02-7.88 (m, 4H), 7.82 (d, J=8.9 Hz, 1H), 7.77-7.67 (m, 3H), 7.59 (d, J=7.1 Hz, 1H), 6.52 (s, 1H), 6.34 (br d, J=5.5 Hz, 1H), 6.00 (br s, 2H), 5.10-4.98 (m, 1H), 1.49 (brd, J=6.8 Hz, 3H).

Compound 213 (30.7 mg, 70.5 umol, 37.4% yield) was obtained as a white solid. LCMS (ESI): RT=0.793 min, mass calcd for $C_{25}H_{20}F_3N_3O$ 435.44 m/z found 436.1 [M+H]$^+$, $^1$H NMR (400 MHz, DMSO-d$_6$) δ 8.89 (br d, J=7.9 Hz, 1H), 8.67 (s, 1H), 8.15 (d, J=8.3 Hz, 1H), 8.04-7.89 (m, 4H), 7.82 (d, J=9.0 Hz, 1H), 7.78-7.67 (m, 3H), 7.60 (d, J=7.3 Hz, 1H), 6.53 (s, 1H), 6.35 (br d, J=5.3 Hz, 1H), 5.98 (s, 2H), 5.11-5.00 (m, 1H), 1.49 (br d, J=6.9 Hz, 3H).

Example 182: N-(3-cyanobenzyl)-5-(4-(trifluoromethyl)phenyl)-2-naphthamide (Compound 215)

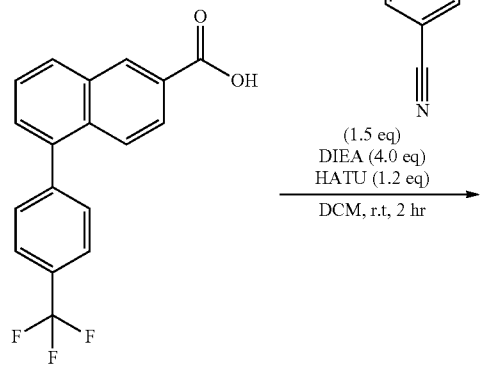

(1.5 eq)
DIEA (4.0 eq)
HATU (1.2 eq)
DCM, r.t, 2 hr

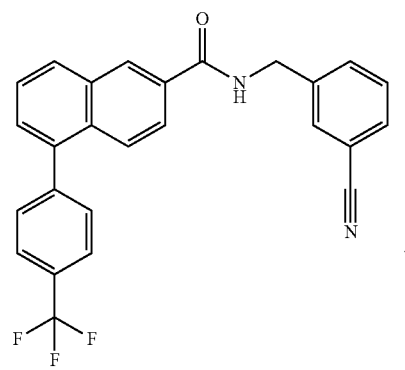

Compound 215

To a solution of 5-[4-(trifluoromethyl)phenyl]naphthalene-2-carboxylic acid (50 mg, 0.15 mmol, 1 eq) and HATU (72.1 mg, 0.18 mmol, 1.2 eq) in DCM (2 mL) was added DIPEA (81.7 mg, 0.63 mmol, 0.11 mL, 4 eq). After addition, the mixture was stirred at 25° C. for 0.5 hr, and then 3-(aminomethyl)benzonitrile (31.3 mg, 0.23 mmol, 1.5 eq) was added. The resulting mixture was stirred at 25° C. for 1.5 hr. The reaction mixture was added H$_2$O (20 mL) and extracted with EA (15 mL*3). The combined organic layers were washed with brine (20 mL), dried with anhydrous Na$_2$SO$_4$, filtered and concentrated under reduced pressure to give a residue. The residue was purified by prep-HPLC (column: Waters Xbridge 150*25 5u; mobile phase: [water (0.05% ammonia hydroxide v/v)-ACN]; B %: 60%-90%, 7.8 min). The title compound (41.7 mg, 96.8 umol, 61.2% yield) was obtained as a white solid. LCMS (ESI): RT=0.911 min, mass calcd for $C_{26}H_{17}F_3N_2O$ 430.42 m/z found 431.4 [M+H]$^+$, $^1$H NMR (400 MHz, DMSO-d$_6$) δ 9.34 (t, J=5.9 Hz, 1H), 8.62 (d, J=1.8 Hz, 1H), 8.14 (d, J=8.3 Hz, 1H), 7.98 (dd, J=1.8, 8.8 Hz, 1H), 7.92 (d, J=8.0 Hz, 2H), 7.86-7.78 (m, 2H), 7.77-7.68 (m, 5H), 7.63-7.54 (m, 2H), 4.59 (d, J=6.0 Hz, 2H).

Example 183: N—[(Z)-4-cyanobut-3-enyl]-5-[4-(trifluoromethyl)phenyl]naphthalene-2-carboxamide (Compound 216)

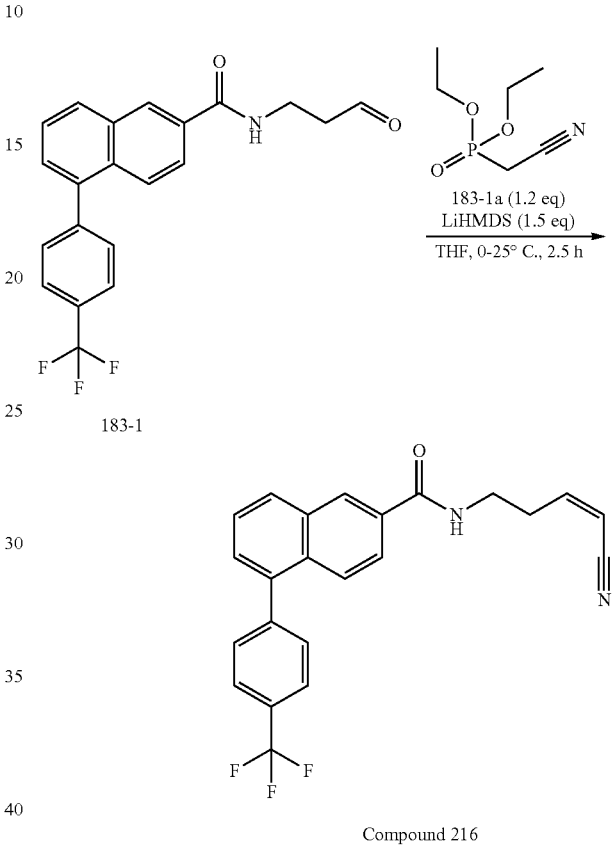

To a mixture of LHMDS (1 M, 1.0 mL, 1.5 eq) in THF (3 mL) was added compound 183-1a (143.1 mg, 0.81 mmol, 0.13 mL, 1.2 eq) at 0° C. and stirred for 30 min. Then compound 183-1 (250 mg, 0.67 mmol, 1 eq) in THF (3 mL) was added to the mixture and stirred for 2 hr at 25° C. The reaction mixture was quenched with saturated aq.NH$_4$Cl (4 mL), extracted with EA (5 mL*3). The combined organic phase was washed with H$_2$O (5 mL) and brine (5 mL), dried over Na$_2$SO$_4$, filtered and concentrated in vacuum. The crude product was purified by flash silica gel chromatography. Then the product was purified by SFC (column: Phenomenex-Amylose-1 (250 mm*30 mm, 5 um); mobile phase: [0.1% NH$_3$H$_2$O ETOH]; B %: 35%-35%, min). Compound 217 (68.81 mg, 0.17 mmol, 25.9% yield) was obtained. Compound 216 (27.0 mg, 67 umol, 10.0% yield) was obtained. Compound 216 LCMS (ESI): RT=0.858 min, mass calcd. For $C_{23}H_{17}F_3N_2O$, 394.13 m/z found 394.9 [M+H]$^+$. $^1$H NMR (400 MHz, CDCl$_3$) δ 8.39 (d, J=1.5 Hz, 1H), 8.00 (d, J=8.3 Hz, 1H), 7.94-7.86 (m, 1H), 7.78 (d, J=8.5 Hz, 3H), 7.68-7.59 (m, 3H), 7.52 (dd, J=1.3, 7.0 Hz, 1H), 6.65 (td, J=7.7, 11.0 Hz, 1H), 6.43 (br t, J=5.5 Hz, 1H), 5.46 (d, J=10.8 Hz, 1H), 3.75 (q, J=6.4 Hz, 2H), 2.90-2.75 (m, 2H).

Example 184: N-[(E)-4-cyanobut-3-enyl]-5-[4-(trifluoromethyl)phenyl]naphthalene-2-carboxamide (Compound 217)

N-(3-hydroxypropyl)-5-[4-(trifluoromethyl)phenyl]naphthalene-2-carboxamide

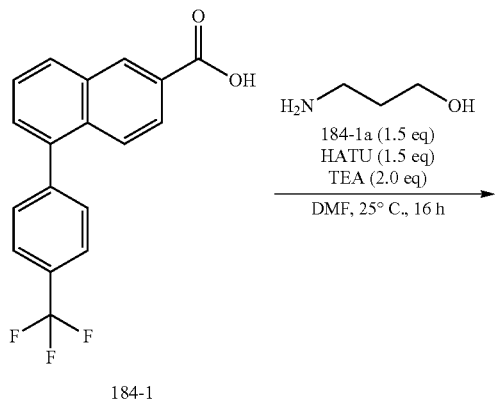

184-1

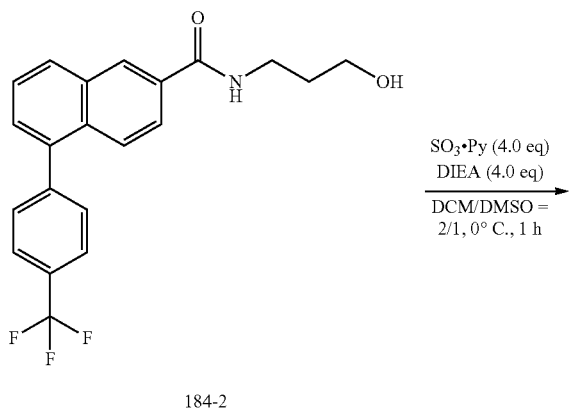

184-2

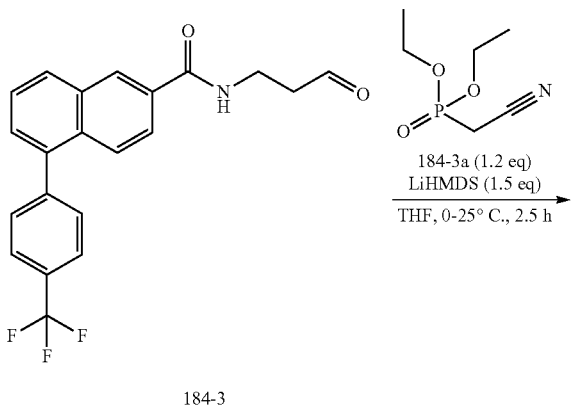

184-3

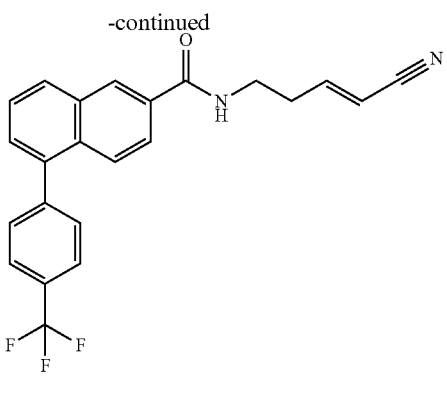

Compound 217

To a solution of compound 184-1 (400 mg, 1.26 mmol, 1 eq) in DMF (6 mL) were added HATU (721.3 mg, 1.90 mmol, 1.5 eq), compound 184-1a (142.5 mg, 1.90 mmol, 0.15 mL, 1.5 eq) and TEA (255.9 mg, 2.53 mmol, 0.35 mL, 2 eq). The mixture was stirred at 25° C. for 16 hr. The reaction mixture was quenched with H₂O (20 mL), extracted with EA (20 mL*3). The combined organic phase was washed with H₂O (10 mL) and brine (10 mL*3), dried over Na₂SO₄, filtered and concentrated in vacuum. The crude product was used for the next step directly. LCMS confirmed that compound 184-2 (430 mg, 0.97 mmol, 76.5% yield) was obtained as a white solid.

N-(3-oxopropyl)-5-[4-(trifluoromethyl)phenyl]naphthalene-2-carboxamide

To a solution of compound 184-2 (380 mg, 1.02 mmol, 1 eq) in DCM (5 mL) were added DMSO (2.5 mL), DIEA (526.1 mg, 4.07 mmol, 0.71 mL, 4 eq) and SO₃·Py (647.9 mg, 4.07 mmol, 4 eq). The mixture was stirred at 0° C. for 1 hr. The reaction mixture was concentrated in vacuum. The residue was diluted with H₂O (20 mL), extracted with EA (15 mL*3). The combined organic phase was washed with H₂O (5 mL) and brine (10 mL*3), dried over Na₂SO₄, filtered and concentrated in vacuum. The residue was purified by flash silica gel chromatography. HNMR confirmed that compound 184-3 (300 mg, 0.81 mmol, 79.3% yield) was obtained as a white solid. $^1$H NMR (400 MHz, CDCl₃) δ 9.90 (s, 1H), 8.34 (d, J=1.5 Hz, 1H), 7.99 (d, J=8.3 Hz, 1H), 7.90-7.84 (m, 1H), 7.82-7.74 (m, 3H), 7.65-7.58 (m, 3H), 7.51 (dd, J=1.1, 7.2 Hz, 1H), 6.85 (br s, 1H), 3.83 (q, J=6.0 Hz, 2H), 2.98-2.88 (m, 2H).

N-[(E)-4-cyanobut-3-enyl]-5-[4-(trifluoromethyl)phenyl]naphthalene-2-carboxamide To a mixture of LHMDS (1 M, 1.0 mL, 1.5 eq) in THF (3 mL) was added compound 184-3a (143.1 mg, 0.81 mmol, 0.13 mL, 1.2 eq) at 0° C. and stirred for 30 min. Then compound 184-3 (250 mg, 0.67 mmol, 1 eq) in THF (3 mL) was added to the mixture and stirred for 2 hr at 25° C. The reaction mixture was quenched with saturated aq.NH₄Cl (4 mL), extracted with EA (5 mL*3). The combined organic phase was washed with H₂O (5 mL) and brine (5 mL), dried over Na₂SO₄, filtered and concentrated in vacuum. The crude product was purified by flash silica gel chromatography. Then the product was purified by SFC (column: Phenomenex-Amylose-1 (250 mm*30 mm, 5 um); mobile phase: [0.1% NH₃H₂O ETOH]; B %: 35%-35%, min). Compound 217 (68.81 mg, 0.17 mmol, 25.9% yield) was obtained. Compound 216 (27.0 mg, 67 umol, 10.0% yield) was obtained. Compound 217 LCMS (ESI): RT=0.858 min, mass calcd. For C$_{23}$H$_{17}$F$_3$N$_2$O, 394.13 m/z found 394.9 [M+H]$^+$. $^1$H NMR (400 MHz, CDCl$_3$) δ 8.36 (d, J=1.8 Hz, 1H), 7.99 (d, J=8.3 Hz, 1H), 7.88 (d, J=9.0 Hz, 1H), 7.83-7.73 (m, 3H), 7.69-7.58 (m, 3H), 7.52 (dd, J=1.0, 7.0 Hz, 1H), 6.77 (td, J=7.2, 16.3 Hz, 1H), 6.46 (br t, J=5.5 Hz, 1H), 5.47 (td, J=1.3, 16.4 Hz, 1H), 3.67 (q, J=6.5 Hz, 2H), 2.65 (dq, J=1.4, 6.8 Hz, 2H).

Example 185: (R)—N-[1-(2-amino-3-pyridyl)ethyl]-5-[4-(trifluoromethyl)phenyl]naphthalene-2-carboxamide (Compound 218) and (S)—N-(1-(2-aminopyridin-3-yl)ethyl)-5-(4-(trifluoromethyl)phenyl)-2-naphthamide (Compound 219)

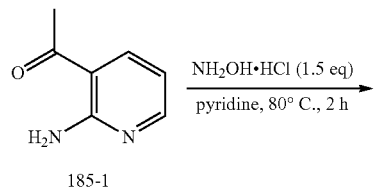

185-1

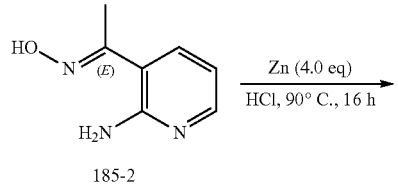

185-2

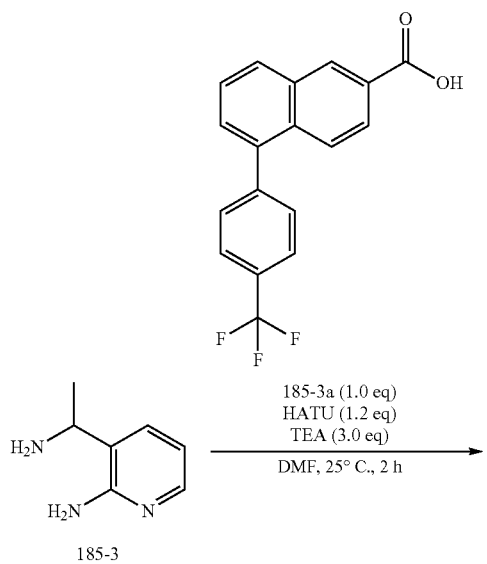

185-3

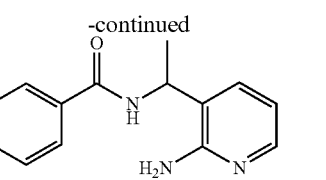

185-4

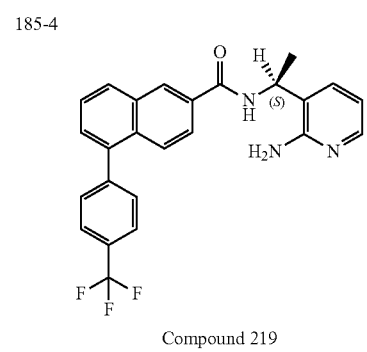

Compound 219

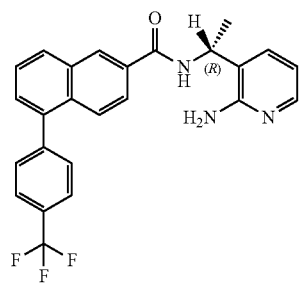

Compound 218

1-(2-amino-3-pyridyl)ethanone oxime

To a solution of compound 185-1 (0.3 g, 2.2 mmol, 1 eq) in Py (6 mL) was added NH$_2$OH·HCl (229.6 mg, 3.3 mmol, 1.5 eq). The reaction was heated at 80° C. for 2 hr. The reaction was concentrated. The residue was purified by column chromatography on silica gel (EA:PE=1:1) to give compound 185-2 (150 mg, 0.99 mmol, 45% yield) as a white solid. $^1$H NMR (400 MHz, CDCl$_3$) δ 13.23 (br s, 1H), 8.00 (dd, J=1.5, 5.0 Hz, 1H), 7.72 (dd, J=1.8, 7.8 Hz, 1H), 6.80 (br s, 2H), 6.72 (dd, J=5.1, 7.7 Hz, 1H), 2.38 (s, 3H).

3-(1-aminoethyl)pyridin-2-amine

To a mixture of compound 185-2 (0.15 g, 0.99 mmol, 1 eq) and Zn (259.5 mg, 3.97 mmol, 4 eq) was slowly added HCl (3 mL) with vigorous stirring. The mixture was heated at 90° C. for 16 hours. The reaction was adjusted pH to 9-10 with 2N aq.NaOH and extracted with EA (2*10 mL). The organic layer was dried over Na$_2$SO$_4$ and concentrated to give compound 185-3 (100 mg, crude), which was used for next step directly as a yellow solid. $^1$H NMR (400 MHz, DMSO-d$_6$) δ 7.76 (d, J=4.6 Hz, 1H), 7.58 (br s, 2H), 7.33 (br d, J=7.3 Hz, 1H), 6.53-6.44 (m, 1H), 6.01 (s, 2H), 4.00-3.90 (m, 1H), 1.22 (d, J=6.4 Hz, 3H).

N-[1-(2-amino-3-pyridyl)ethyl]-5-[4-(trifluoromethyl)phenyl]naphthalene-2-carboxamide To a solution of compound 185-3a (0.15 g, 0.47 mmol, 1 eq), HATU (216.4 mg, 0.56 mmol, 1.2 eq) and compound 185-3 (78 mg, 0.56 mmol, 1.2 eq) in DMF (4 mL) was added TEA (143.9 mg, 1.42 mmol, 0.19 mL, 3 eq). The reaction was stirred at 25° C. for 2 hr. The reaction was diluted with EA (30 mL) and washed with brine (2*10 mL). The organic layer was dried over $Na_2SO_4$ and concentrated. The crude product was purified by Prep.HPLC (column: Waters Xbridge 150*50 10u; mobile phase: [water (0.05% ammonia hydroxide v/v)-ACN]; B %: 51%-81%, 9.2 min) to give compound 185-4 (50 mg, 0.11 mmol, 23% yield) as a white solid. $^1$H NMR (400 MHz, $CDCl_3$) δ 8.34 (d, J=1.5 Hz, 1H), 8.04 (dd, J=1.5, 5.0 Hz, 1H), 7.97 (d, J=8.3 Hz, 1H), 7.88-7.84 (m, 1H), 7.80-7.73 (m, 3H), 7.64-7.57 (m, 3H), 7.56-7.50 (m, 2H), 6.68 (dd, J=5.0, 7.5 Hz, 1H), 6.35 (br d, J=9.0 Hz, 1H), 5.55-5.44 (m, 1H), 5.29 (s, 2H), 1.72 (d, J=6.8 Hz, 3H).

(R)—N-[1-(2-amino-3-pyridyl)ethyl]-5-[4-(trifluoromethyl)phenyl]naphthalene-2-carboxamide (Compound 218) and (S)—N-(1-(2-aminopyridin-3-yl)ethyl)-5-(4-(trifluoromethyl)phenyl)-2-naphthamide (Compound 219)

Compound 185-4 (40 mg, 91 umol, 1 eq) was separated by SFC (column: YMC CHIRAL Amylose-C (250 mm*30 mm, 10 um; mobile phase: [0.1% NH3H2O ETOH]; B %: 40%-40%, min) to give Compound 219 (5.5 mg, 12 umol, 13.7% yield) as a white solid and Compound 218 (7.3 mg, 16 umol, 18.1% yield) as a white solid. Compound 218 LCMS (ESI): RT=0.869 min, mass calcd. for $C_{25}H_{20}F_3N_3O$ 435.16 m/z found 436.1 $[M+H]^+$, $^1$H NMR (400 MHz, $CDCl_3$) δ 8.37 (s, 1H), 8.02-7.92 (m, 2H), 7.90-7.84 (m, 1H), 7.78 (br d, J=8.3 Hz, 3H), 7.67-7.56 (m, 4H), 7.52 (br d, J=7.0 Hz, 1H), 6.68 (br t, J=6.0 Hz, 1H), 6.53 (br s, 1H), 5.69 (br s, 2H), 5.54-5.43 (m, 1H), 1.73 (br d, J=6.6 Hz, 3H). Compound 219 LCMS (ESI): RT=0.870 min, mass calcd. for $C_{25}H_{20}F_3N_3O$ 435.16 m/z found 436.0 $[M+H]^+$, $^1$H NMR (400 MHz, $CDCl_3$) δ 8.37 (s, 1H), 8.02-7.92 (m, 2H), 7.90-7.84 (m, 1H), 7.78 (br d, J=8.3 Hz, 3H), 7.67-7.56 (m, 4H), 7.52 (br d, J=7.0 Hz, 1H), 6.68 (br t, J=6.0 Hz, 1H), 6.53 (br s, 1H), 5.69 (br s, 2H), 5.54-5.43 (m, 1H), 1.73 (br d, J=6.6 Hz, 3H).

Example 186: N-((1,2,4-thiadiazol-5-yl)methyl)-5-(4-(trifluoromethyl)phenyl)-2-naphthamide (Compound 220)

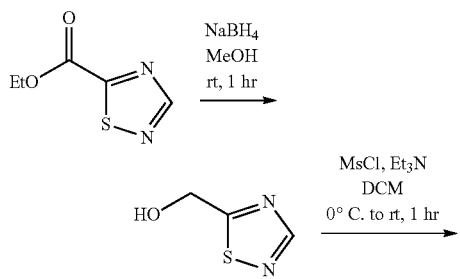

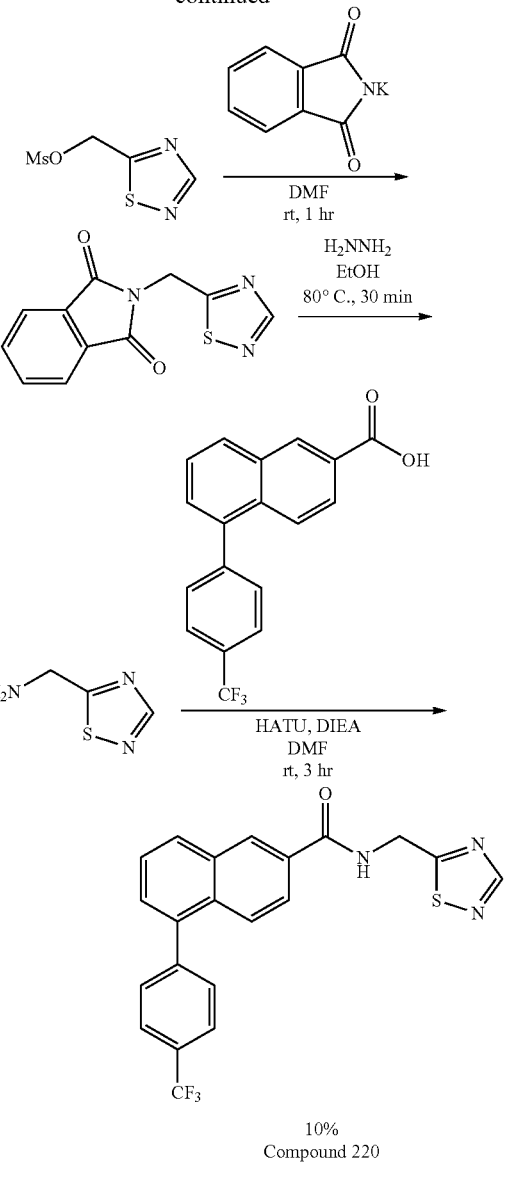

10%
Compound 220

(1,2,4-Thiadiazol-5-yl)methanol

Ethyl 1,2,4-thiadiazole-5-carboxylate (prepared following the procedure in WO2015130957) (183 mg, 1.2 mmol, 1 equiv.) was dissolved in MeOH (13 mL). $NaBH_4$ (81 mg, 2 mmol, 1.7 equiv.) was carefully added and stirred at rt for 1 hr. Upon completion, the reaction mixture was quenched with 3 mL $H_2O$ at 0° C. the mixture was concentrated and re-dissolved in a mixture of EtOAc and $H_2O$. The aqueous layer was washed with EtOAc, the combined organic layers were dried with $Na_2SO_4$, and concentrated. The crude material was used in the next step without further purification. LCMS $[M+H]^+$=117.

(1,2,4-Thiadiazol-5-yl)methyl methanesulfonate (1,2,4-Thiadiazol-5-yl)methanol (139 mg, 1 equiv.) was dissolved in DCM (3.5 mL) and MsCl (112 μL, 1.2 equiv.) was added at 0° C. $Et_3N$ (251 μL, 1.5 equiv.) was added slowly and the mixture was allowed to warm to rt and stir for a further 1 hr. Upon completion, the mixture was diluted with DCM and washed with H$_2$O, brine, dried with Na$_2$SO$_4$, and concentrated. The crude material was used in the next step without further purification. LCMS [M+H]$^+$=195.

2-((1,2,4-Thiadiazol-5-yl)methyl)isoindoline-1,3-dione (1,2,4-Thiadiazol-5-yl)methyl methanesulfonate (300 mg, 1.5 mmol, 1 equiv.), potassium 1,3-dioxoisoindolin-2-ide (344 mg, 1.9 mmol, 1.2 equiv.), and DMF (3 mL) were stirred at rt for 1 hr. The mixture was diluted with EtOAc, washed with sat NH$_4$Cl, H$_2$O, brine, dried with Na$_2$SO$_4$, and concentrated. The crude material was used in the next step without further purification. LCMS [M+H]$^+$=246.

(1,2,4-Thiadiazol-5-yl)methanamine 2-((1,2,4-Thiadiazol-5-yl)methyl)isoindoline-1,3-dione (370 mg, 1.5 mmol, 1 equiv.) and EtOH (3.3 mL) were stirred at rt. H$_2$NNH$_2$ (138 μL, 2.7 mmol, 1.8 equiv.) was added and the mixture was stirred at 80° C. for 30 min. Upon completion, the mixture was diluted with DCM and washed with H$_2$O, brine, dried with Na$_2$SO$_4$, and concentrated. The crude material was used in the next step without further purification. LCMS [M+H]$^+$=116.

N-((1,2,4-Thiadiazol-5-yl)methyl)-5-(4-(trifluoromethyl)phenyl)-2-naphthamide (1,2,4-Thiadiazol-5-yl)methanamine (70 mg, 0.6 mmol, 1 equiv.), 5-(4-(trifluoromethyl)phenyl)-2-naphthoic acid (212 mg, 0.7 mmol, 1.2 equiv.), HATU (347 mg, 0.9 mmol, 1.5 equiv.), DIEA (0.53 mL, 3 mmol, 5 equiv.), and DMF (1 mL) were stirred at rt for 1 hr. Upon completion, the reaction mixture was diluted with H$_2$O and stirred rapidly for 20 min. The resulting solid was filtered, rinsed with H$_2$O, and dried to give the desired amide product, colorless solid (26 mg, 10%). LCMS [M+H]$^+$=414. $^1$H NMR (600 MHz, DMSO-d$_6$) δ ppm 4.97 (d, J=5.50 Hz, 2H) 7.62-7.65 (m, 1H) 7.72-7.78 (m, 3H) 7.87 (d, J=9.17 Hz, 1H) 7.93 (d, J=8.07 Hz, 2H) 7.99 (dd, J=8.80, 1.83 Hz, 1H) 8.17 (d, J=8.07 Hz, 1H) 8.64-8.67 (m, 1H) 8.85 (s, 1H) 9.78 (t, J=5.50 Hz, 1H).

Example 187: N-((3-methyl-1,2,4-thiadiazol-5-yl)methyl)-5-(4-(trifluoromethyl)phenyl)-2-naphthamide (Compound 221)

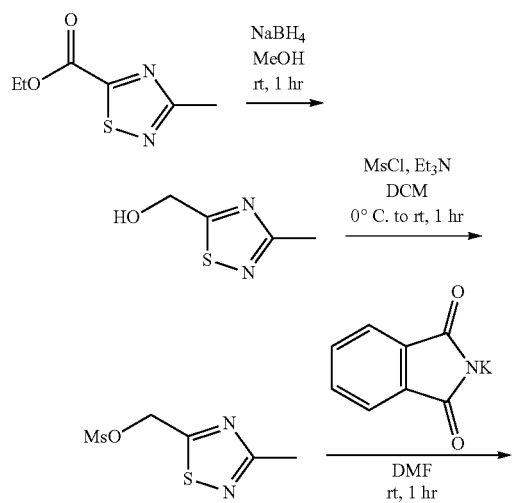

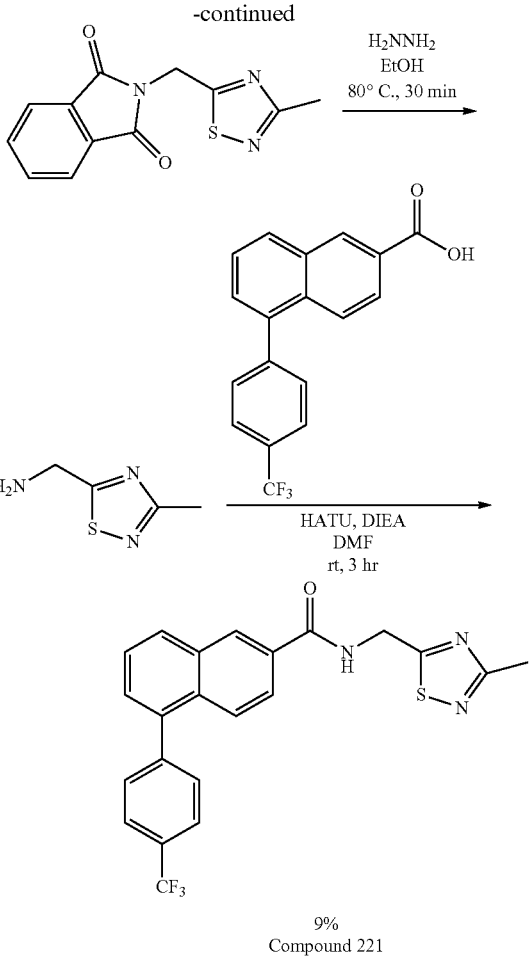

9% Compound 221

(3-Methyl-1,2,4-thiadiazol-5-yl)methanol

Ethyl 3-methyl-1,2,4-thiadiazole-5-carboxylate (prepared following the procedure in WO2008023157) (199 mg, 1.2 mmol, 1 equiv.) was dissolved in MeOH (13 mL). NaBH$_4$ (75 mg, 2 mmol, 1.7 equiv.) was carefully added and stirred at rt for 1 hr. Upon completion, the reaction mixture was quenched with 3 mL H$_2$O at 0° C. the mixture was concentrated and re-dissolved in a mixture of EtOAc and H$_2$O. The aqueous layer was washed with EtOAc, the combined organic layers were dried with Na$_2$SO$_4$, and concentrated. The crude material was used in the next step without further purification. LCMS [M+H]$^+$=131.

(3-Methyl-1,2,4-thiadiazol-5-yl)methyl methanesulfonate (3-Methyl-1,2,4-thiadiazol-5-yl)methanol (199 mg, 1 equiv.) was dissolved in DCM (5 mL) and MsCl (143 μL, 1.2 equiv.) was added at 0° C. Et$_3$N (320 μL, 1.5 equiv.) was added slowly and the mixture was allowed to warm to rt and stir for a further 1 hr. Upon completion, the mixture was diluted with DCM and washed with H$_2$O, brine, dried with Na$_2$SO$_4$, and concentrated. The crude material was used in the next step without further purification. LCMS [M+H]$^+$=209.

2-((3-Methyl-1,2,4-thiadiazol-5-yl)methyl)isoindoline-1,3-dione (3-Methyl-1,2,4-thiadiazol-5-yl)methyl methanesulfonate (100 mg, 0.5 mmol, 1 equiv.), potassium 1,3-dioxoisoindolin-2-ide (107 mg, 0.6 mmol, 1.2 equiv.), and DMF (1.5 mL) were stirred at rt for 1 hr. The mixture was diluted with EtOAc, washed with sat $NH_4Cl$, $H_2O$, brine, dried with $Na_2SO_4$, and concentrated. The crude material was used in the next step without further purification. LCMS $[M+H]^+$=260.

(3-Methyl-1,2,4-thiadiazol-5-yl)methanamine 2-((3-Methyl-1,2,4-thiadiazol-5-yl)methyl)isoindoline-1,3-dione (100 mg, 0.38 mmol, 1 equiv.) and EtOH (0.8 mL) were stirred at rt. $H_2NNH_2$ (34 μL, 0.69 mmol, 1.8 equiv.) was added and the mixture was stirred at 80° C. for 30 min. Upon completion, the mixture was diluted with DCM and washed with $H_2O$, brine, dried with $Na_2SO_4$, and concentrated. The crude material was used in the next step without further purification. LCMS $[M+H]^+$=130.

N-((3-Methyl-1,2,4-thiadiazol-5-yl)methyl)-5-(4-(trifluoromethyl)phenyl)-2-naphthamide (3-Methyl-1,2,4-thiadiazol-5-yl)methanamine (70 mg, 0.54 mmol, 1 equiv.), 5-(4-(trifluoromethyl)phenyl)-2-naphthoic acid (187 mg, 0.65 mmol, 1.2 equiv.), HATU (309 mg, 0.81 mmol, 1.5 equiv.), DIEA (0.3 mL, 1.6 mmol, 3 equiv.), and DMF (1 mL) were stirred at rt for 1 hr. Upon completion, the reaction mixture was diluted with $H_2O$ and stirred rapidly for 20 min. The resulting solid was filtered, rinsed with $H_2O$, and dried to give the desired amide product, colorless solid (20 mg, 9%). LCMS $[M+H]^+$=428. $^1$H NMR (600 MHz, DMSO-$d_6$) δ ppm 2.59 (s, 3H) 4.91 (d, J=5.87 Hz, 2H) 7.64 (dd, J=6.97, 1.10 Hz, 1H) 7.72-7.78 (m, 3H) 7.87 (d, J=8.80 Hz, 1H) 7.94 (d, J=8.07 Hz, 2H) 7.99 (dd, J=9.17, 1.83 Hz, 1H) 8.17 (d, J=8.44 Hz, 1H) 8.65 (d, J=1.47 Hz, 1H) 9.74 (t, J=5.87 Hz, 1H).

Example 188: N-[(E)-5-amino-5-oxo-pent-3-enyl]-5-[4-(trifluoromethyl)phenyl]naphthalene-2-carboxamide (Compound 222)

Compound 222

To a solution of Compound 217 (20 mg, 50 umol, 1 eq) in ACETONE (1 mL) were added $Na_2CO_3$ (26.8 mg, 0.25 mmol, 5 eq) and $H_2O_2$ (1.18 g, 10.41 mmol, 1 mL, 30% solution, 205 eq) at 0° C. Then the mixture was stirred at 25° C. for 16 hr. The reaction mixture was quenched with $H_2O$ (5 mL), extracted with EA (15 mL*3). The combined organic phase was washed with $H_2O$ (5 mL) and brine (5 mL), dried over $Na_2SO_4$, filtered and concentrated in vacuum. The crude product was purified by prep-HPLC (column: Waters Xbridge 150*50 10u; mobile phase: [water (0.05% ammonia hydroxide v/v)-ACN]; B %: 49%-49%, 8.5 min). LCMS and HNMR confirmed that the title compound (4.5 mg, 11 umol, 21.5% yield) was obtained as a white solid. LCMS (ESI): RT=0.785 min, mass calcd. For $C_{23}H_{19}F_3N_2O_2$, 412.14 m/z found 413.0 $[M+H]^+$. $^1$H NMR (400 MHz, CDCl$_3$) δ 8.35 (d, J=1.3 Hz, 1H), 7.99 (d, J=8.0 Hz, 1H), 7.87 (d, J=8.8 Hz, 1H), 7.82-7.74 (m, 3H), 7.65-7.58 (m, 3H), 7.52 (d, J=7.0 Hz, 1H), 6.98-6.86 (m, 1H), 6.51-6.42 (m, 1H), 5.97 (d, J=15.6 Hz, 1H), 5.69-5.15 (m, 2H), 3.69 (q, J=6.4 Hz, 2H), 2.71-2.52 (m, 2H).

Example 189: (R)—N-(1-(4-(dimethylamino)pyridin-2-yl)ethyl)-5-(4-(trifluoromethyl)phenyl)-2-naphthamide (Compound 223) and (S)—N-(1-(4-(dimethylamino)pyridin-2-yl)ethyl)-5-(4-(trifluoromethyl)phenyl)-2-naphthamide (Compound 224)

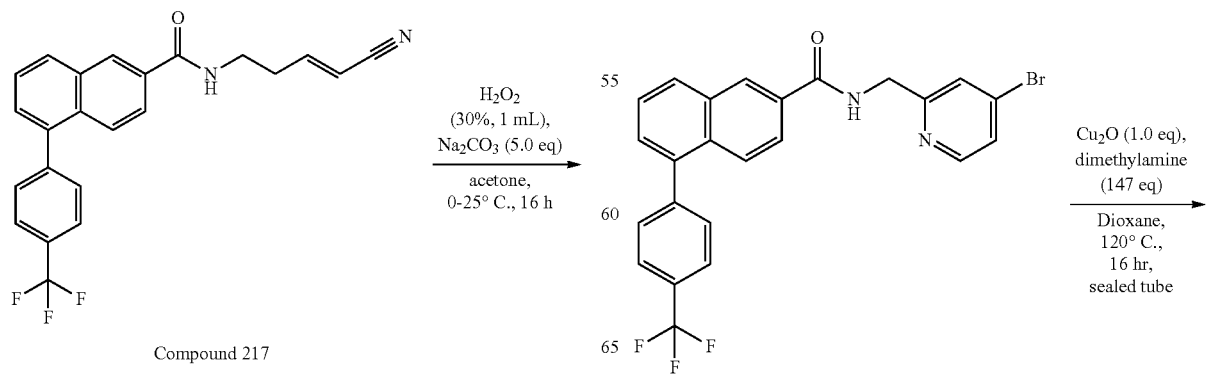

563

-continued

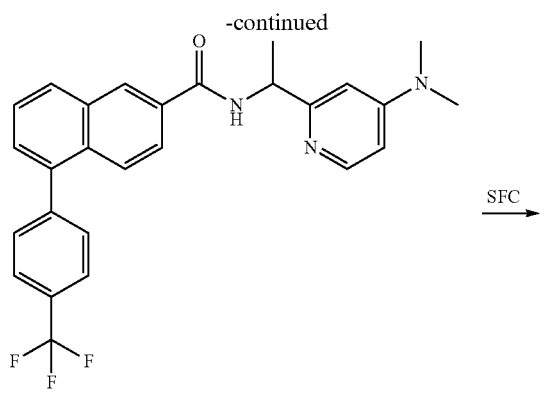

→ SFC

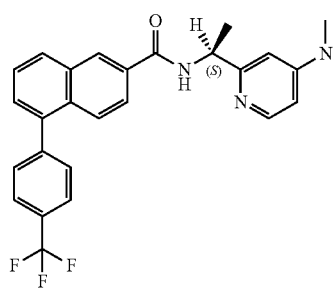

Compound 224

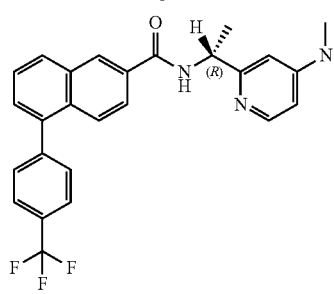

Compound 223

N-(1-(4-(dimethylamino)pyridin-2-yl)ethyl)-5-(4-(trifluoromethyl)phenyl)-2-naphthamide To a solution of N-[1-(4-bromo-2-pyridyl)ethyl]-5-[4-(trifluoromethyl)phenyl]naphthalene-2-carboxamide (200 mg, 0.40 mmol, 1 eq) in dioxane (2 mL) was added Me$_2$NH (2.67 g, 59.22 mmol, 3 mL, 147.8 eq) and Cu$_2$O (57.3 mg, 0.40 mmol, 40.9 uL, 1 eq). The mixture was stirred at 120° C. for 16 hr in a sealed tube. The mixture was added H$_2$O (10 mL) and extracted with EA (15 mL*3). The combined organic layers were washed with brine (30 mL), dried with anhydrous Na$_2$SO$_4$, filtered and concentrated under reduced pressure to give a residue. The residue was purified by flash silica gel chromatography (4 g SepaFlash® Silica Flash Column, EA/PE: 0~100%). Compound N-[1-[4-(dimethyl-

564 amino)-2-pyridyl]ethyl]-5-[4-(trifluoromethyl)phenyl]naphthalene-2-carboxamide (136 mg, 0.29 mmol, 72.5% yield) was obtained as a yellow oil.

(R)—N-(1-(4-(dimethylamino)pyridin-2-yl)ethyl)-5-(4-(trifluoromethyl)phenyl)-2-naphthamide (Compound 223) and (S)—N-(1-(4-(dimethylamino)pyridin-2-yl)ethyl)-5-(4-(trifluoromethyl)phenyl)-2-naphthamide (Compound 224)

The racemic compound N-[1-[4-(dimethylamino)-2-pyridyl]ethyl]-5-[4-(trifluoromethyl)phenyl]naphthalene-2-carboxamide (95 mg, 0.20 mmol, 1 eq) was purified by SFC (column: DAICEL CHIRALPAK AD-H (250 mm*30 mm, 5 um); mobile phase: [0.1% NH$_3$H$_2$O ETOH]; B %: 40%-40%, min). Compound 223 (33.6 mg, 72.4 umol, 35.3% yield) was obtained as a white solid. LCMS (ESI): RT=0.807 min, mass calcd for C$_{27}$H$_{24}$F$_3$N$_3$O 463.49 m/z, found 464.2 [M+H]$^+$, $^1$H NMR (400 MHz, DMSO-d$_6$) δ 8.87 (d, J=7.8 Hz, 1H), 8.61 (d, J=1.5 Hz, 1H), 8.13 (d, J=8.3 Hz, 1H), 8.07 (d, J=6.0 Hz, 1H), 7.98-7.87 (m, 3H), 7.81 (d, J=8.8 Hz, 1H), 7.77-7.65 (m, 3H), 7.58 (dd, J=1.1, 7.2 Hz, 1H), 6.68 (d, J=2.5 Hz, 1H), 6.49 (dd, J=2.6, 5.9 Hz, 1H), 5.13 (quin, J=7.2 Hz, 1H), 2.93 (s, 6H), 1.49 (d, J=7.0 Hz, 3H). Compound 224 (30.3 mg, 65.3 umol, 31.8% yield) was obtained as a white solid. LCMS (ESI): RT=0.812 min, mass calcd for C$_{27}$H$_{24}$F$_3$N$_3$O 463.49 m/z, found 464.2 [M+H]$^+$, NMR (400 MHz, DMSO-d$_6$) δ 8.88 (d, J=7.8 Hz, 1H), 8.62 (d, J=1.5 Hz, 1H), 8.14 (d, J=8.3 Hz, 1H), 8.08 (d, J=5.8 Hz, 1H), 7.99-7.89 (m, 3H), 7.82 (d, J=8.8 Hz, 1H), 7.77-7.65 (m, 3H), 7.59 (dd, J=1.0, 7.0 Hz, 1H), 6.69 (d, J=2.5 Hz, 1H), 6.50 (dd, J=2.6, 5.9 Hz, 1H), 5.18-5.11 (m, 1H), 2.94 (s, 6H), 1.50 (d, J=7.0 Hz, 3H).

Example 190: N-(1-(4-bromopyridin-2-yl)ethyl)-5-(4-(trifluoromethyl)phenyl)-2-naphthamide (Compound 225)

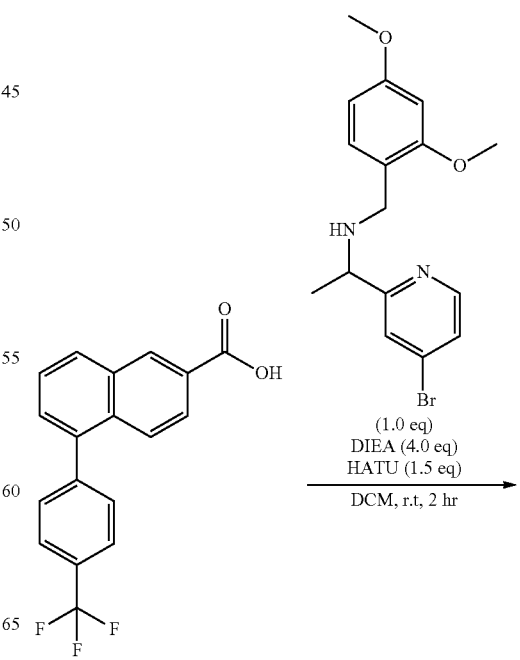

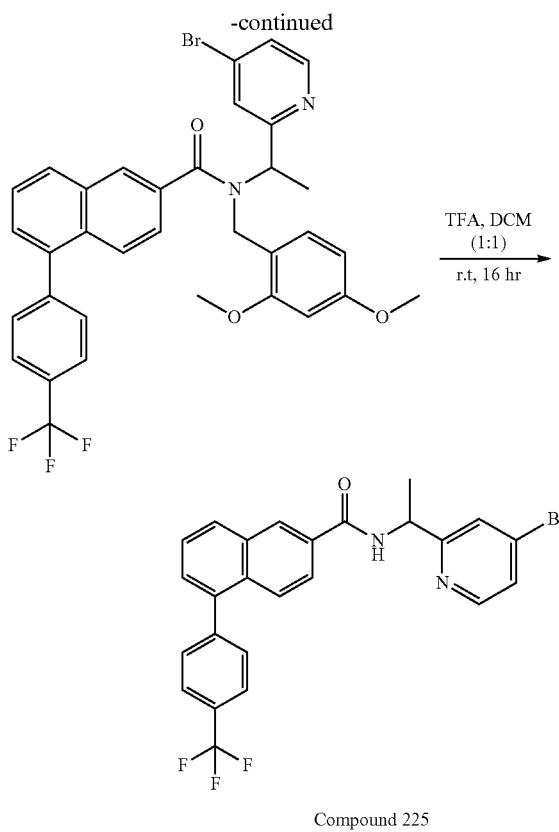

Compound 225

N-(1-(4-bromopyridin-2-yl)ethyl)-N-(2,4-dimethoxybenzyl)-5-(4-(trifluoromethyl)phenyl)-2-naphthamide To a solution of 5-[4-(trifluoromethyl)phenyl]naphthalene-2-carboxylic acid (1 g, 3.16 mmol, 1 eq) and HATU (1.80 g, 4.74 mmol, 1.5 eq) in DCM (20 mL) was added DIPEA (1.63 g, 12.65 mmol, 2.20 mL, 4 eq). After addition, the mixture was stirred at 25° C. for 0.5 hr, and then 1-(4-bromo-2-pyridyl)-N-[(2,4-dimethoxyphenyl)methyl]ethanamine (1.48 g, 3.16 mmol, 1 eq) was added. The resulting mixture was stirred at 25° C. for 1.5 hr. Then the mixture was added H₂O (30 mL) and extracted with EA (40 mL*3). The combined organic layers were washed with brine (50 mL), dried with anhydrous Na₂SO₄, filtered and concentrated under reduced pressure to give a residue. The residue was purified by flash silica gel chromatography (40 g SepaFlash® Silica Flash Column, EA/PE: 0~40%) to afford N-[1-(4-bromo-2-pyridyl)ethyl]-N-[(2,4-dimethoxyphenyl)methyl]-5-[4-(trifluoromethyl)phenyl]naphthalene-2-carboxamide (1.96 g, 2.99 mmol, 94.4% yield) as yellow oil.

N-(1-(4-bromopyridin-2-yl)ethyl)-5-(4-(trifluoromethyl)phenyl)-2-naphthamide To a solution of N-[1-(4-bromo-2-pyridyl)ethyl]-N-[(2,4-dimethoxyphenyl)methyl]-5-[4-(trifluoromethyl)phenyl]naphthalene-2-carboxamide (1.96 g, 3.02 mmol, 1 eq) in DCM (8 mL) was added TFA (38.50 g, 337.65 mmol, 25.00 mL, 111.89 eq). The mixture was stirred at 25° C. for 16 hr. The mixture was neutralized to pH=9~10 with aq.NaOH (4 M). The aqueous phase was extracted with EA (30 mL*3). The combined organic phase was washed with brine (50 mL), dried with anhydrous Na₂SO₄, filtered and concentrated in vacuo to give a residue. The residue was purified by flash silica gel chromatography (20 g SepaFlash® Silica Flash Column, EA/PE: 0-60%) to afford N-[1-(4-bromo-2-pyridyl)ethyl]-5-[4-(trifluoromethyl)phenyl]naphthalene-2-carboxamide (1.19 g, 2.36 mmol, 78.18% yield) as yellow solid. The compound N-[1-(4-bromo-2-pyridyl)ethyl]-5-[4-(trifluoromethyl)phenyl]naphthalene-2-carboxamide (60 mg, 0.11 mmol, 1 eq) was re-purified by flash silica gel chromatography (12 g SepaFlash® Silica Flash Column, EA/PE: 0-50%). The title compound (55 mg, 0.11 mmol, 92.5% yield) was obtained as a yellow solid. LCMS (ESI): RT=0.912 min, mass calcd for $C_{25}H_{18}BrF_3N_2O$ 499.32 m/z, found 501.0 [M+H]⁺, ¹H NMR (400 MHz, DMSO-d₆) δ 9.08 (d, J=7.8 Hz, 1H), 8.66 (d, J=1.5 Hz, 1H), 8.44 (d, J=5.3 Hz, 1H), 8.15 (d, J=8.0 Hz, 1H), 7.98 (dd, J=1.8, 9.0 Hz, 1H), 7.92 (d, J=8.3 Hz, 2H), 7.83 (d, J=8.8 Hz, 1H), 7.78-7.67 (m, 4H), 7.64-7.53 (m, 2H), 5.24 (quin, J=7.2 Hz, 1H), 1.55 (d, J=7.0 Hz, 3H).

Example 191: N-[(E)-5-methylsulfonylpent-4-enyl]-5-[4-(trifluoromethyl)phenyl]naphthalene-2-carboxamide (Compound 226)

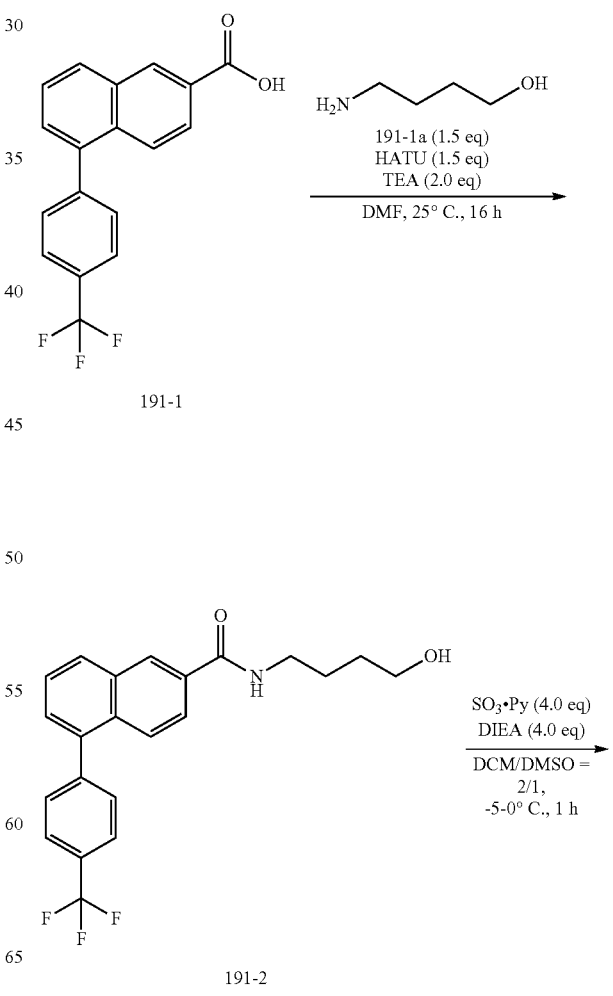

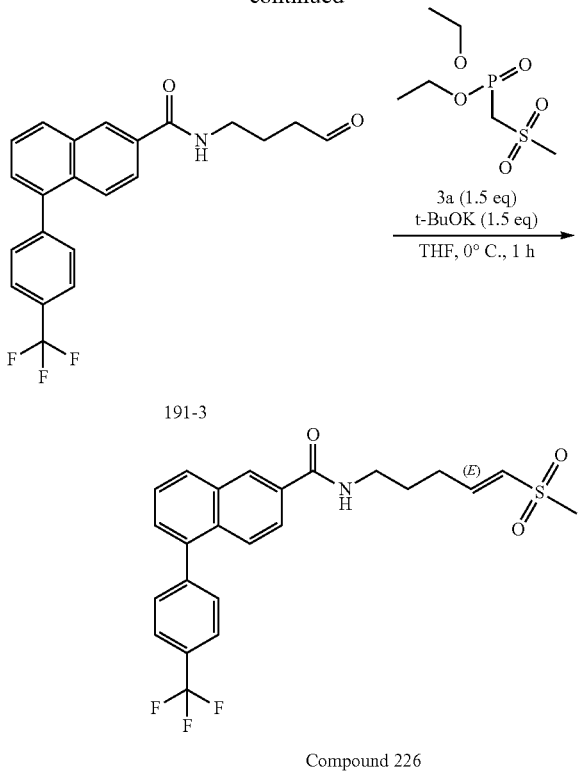

Compound 226

N-(4-hydroxybutyl)-5-[4-(trifluoromethyl)phenyl]naphthalene-2-carboxamide

To a solution of compound 191-1 (300 mg, 0.95 mmol, 1 eq) in DMF (5 mL) were added HATU (541.0 mg, 1.42 mmol, 1.5 eq), compound 191-1a (126.8 mg, 1.42 mmol, 0.13 mL, 1.5 eq) and TEA (191.9 mg, 1.90 mmol, 0.26 mL, 2 eq). The mixture was stirred at 25° C. for 16 hr. The reaction mixture was quenched with $H_2O$ (20 mL), extracted with EA (20 mL*3). The combined organic phase was washed with $H_2O$ (10 mL) and brine (10 mL*3), dried over $Na_2SO_4$, filtered and concentrated in vacuum. The crude product was used for the next step directly. LCMS confirmed that compound 191-2 (360 mg, 0.75 mmol, 79.3% yield) was obtained as a white solid.

N-(4-oxobutyl)-5-[4-(trifluoromethyl)phenyl]naphthalene-2-carboxamide

To a solution of compound 191-2 (310 mg, 0.80 mmol, 1 eq) in DCM (5 mL) and DMSO (2.5 mL) were added DIEA (413.6 mg, 3.20 mmol, 0.56 mL, 4 eq) and $SO_3$·Py (509.4 mg, 3.20 mmol, 4 eq) at 0° C. Then the mixture was stirred at 0° C. for 1 hr. The reaction mixture was concentrated in vacuum. The residue was diluted with $H_2O$ (20 mL), extracted with EA (15 mL*3). The combined organic phase was washed with $H_2O$ (5 mL) and brine (10 mL*3), dried over $Na_2SO_4$, filtered and concentrated in vacuum. The residue was purified by flash silica gel chromatography. HNMR confirmed that the compound 191-3 (230 mg, 0.42 mmol, 52.2% yield) was obtained as a white solid. $^1$H NMR (400 MHz, CDCl$_3$) δ 9.86 (s, 1H), 8.39 (d, J=1.5 Hz, 1H), 8.00 (d, J=8.0 Hz, 1H), 7.90-7.86 (m, 1H), 7.78 (d, J=8.0 Hz, 3H), 7.63-7.60 (m, 3H), 7.52-7.49 (m, 1H), 6.67 (br s, 1H), 3.57 (q, J=6.5 Hz, 2H), 2.68 (t, J=6.5 Hz, 2H), 2.03 (q, J=6.7 Hz, 2H).

N-[(E)-5-methylsulfonylpent-4-enyl]-5-[4-(trifluoromethyl)phenyl]naphthalene-2-carboxamide To a solution of compound 191-3a (44.8 mg, 0.19 mmol, 1.5 eq) in THF (1 mL) was added t-BuOK (21.8 mg, 0.19 mmol, 1.5 eq) at 0° C. Then compound 191-3 (50 mg, 0.13 mmol, 1 eq) in THF (1 mL) was added to the mixture and stirred at 0° C. for 1 hr. The reaction mixture was quenched with $H_2O$ (5 mL), extracted with EA (15 mL*3). The combined organic phase was washed with $H_2O$ (5 mL) and brine (5 mL), dried over $Na_2SO_4$, filtered and concentrated in vacuum. The crude product was purified by prep-HPLC (column: Waters Xbridge 150*50 10u; mobile phase: [water (0.05% ammonia hydroxide v/v)-ACN]; B %: 63%-63%, 8 min). The title compound (15.8 mg, 34 umol, 26.4% yield) was obtained as a white solid. LCMS (ESI): RT=0.878 min, mass calcd. For $C_{24}H_{22}F_3NO_3S$, 461.13 m/z found 462.0 $[M+H]^+$. $^1$H NMR (400 MHz, CDCl$_3$) δ 8.41-8.32 (m, 1H), 8.00 (d, J=8.3 Hz, 1H), 7.93-7.85 (m, 1H), 7.78 (d, J=7.8 Hz, 3H), 7.67-7.58 (m, 3H), 7.52 (dd, J=1.0, 7.0 Hz, 1H), 7.05-6.95 (m, 1H), 6.48 (d, J=15.3 Hz, 1H), 6.40 (br t, J=5.5 Hz, 1H), 3.58 (q, J=6.6 Hz, 2H), 2.94 (s, 3H), 2.43 (q, J=6.9 Hz, 2H), 1.90 (quin, J=7.2 Hz, 2H).

Example 192: N-[(E)-5-cyanopent-4-enyl]-5-[4-(trifluoromethyl)phenyl]naphthalene-2-carboxamide (Compound 227)

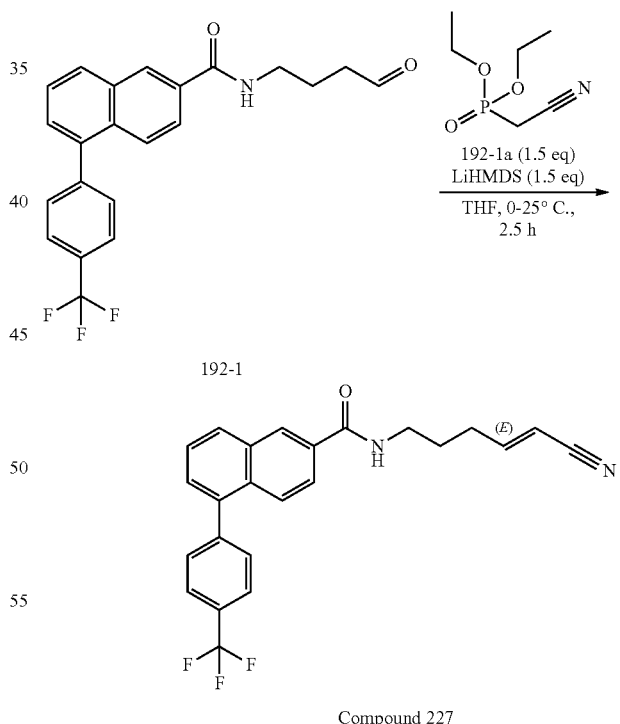

Compound 227

N-[(E)-5-cyanopent-4-enyl]-5-[4-(trifluoromethyl)phenyl]naphthalene-2-carboxamide To a solution of compound 192-1a (34.4 mg, 0.19 mmol, 31 uL, 1.5 eq) in THF (1 mL) was added LHMDS (1 M, 0.19 mL, 1.5 eq) at 0° C. and stirred at 0° C. for 30 min. Then compound 192-1 (50 mg, 0.13 mmol, 1 eq) in THF (1 mL) was added to the mixture and stirred at 25° C. for 2 hr. The reaction mixture was quenched with NH₄Cl (5 mL), extracted with EA (15 mL*3). The combined organic phase was washed with H₂O (5 mL) and brine (5 mL), dried over Na₂SO₄, filtered and concentrated in vacuum. The crude product was purified by flash silica gel chromatography. The crude product was purified by chiral SFC (column: DAICEL CHIRALCEL OJ-H (250 mm*30 mm, 5 um); mobile phase: [0.1% NH₃H₂O ETOH]; B %: 20%-20%, min). The title compound (14.9 mg, 36 umol, 27.8% yield) was obtained as a yellow solid. LCMS (ESI): RT=0.875 min, mass calcd. For C₂₄H₁₉F₃N₂O, 408.14 m/z found 409.0 [M+H]⁺. ¹H NMR (400 MHz, CDCl₃) δ 8.37 (s, 1H), 7.99 (br d, J=8.1 Hz, 1H), 7.93-7.86 (m, 1H), 7.79 (br d, J=6.5 Hz, 3H), 7.68-7.58 (m, 3H), 7.52 (d, J=7.0 Hz, 1H), 6.91-6.67 (m, 1H), 6.38 (br s, 1H), 5.44 (br d, J=16.5 Hz, 1H), 3.57 (q, J=6.4 Hz, 2H), 2.38 (q, J=7.2 Hz, 2H), 1.90-1.83 (m, 2H).

Example 193: N—[(Z)-5-cyanopent-4-enyl]-5-[4-(trifluoromethyl)phenyl]naphthalene-2-carboxamide (Compound 228)

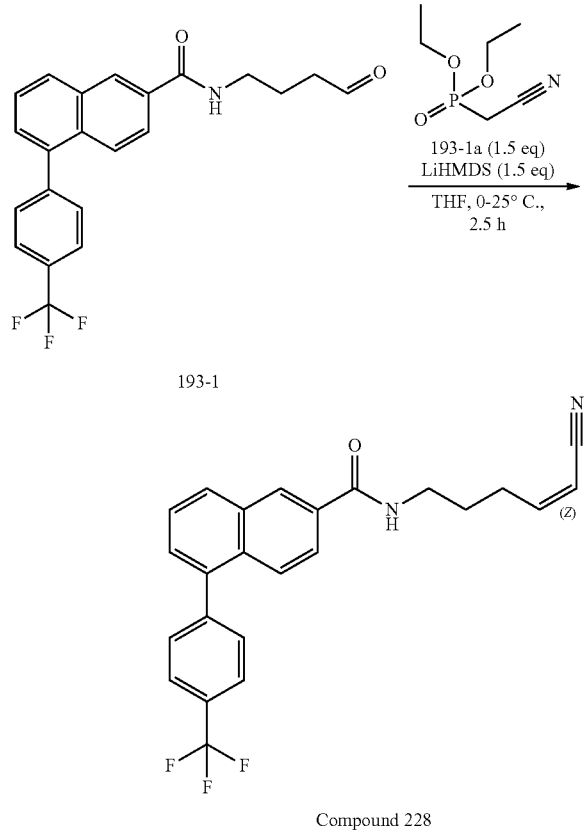

N—[(Z)-5-cyanopent-4-enyl]-5-[4-(trifluoromethyl)phenyl]naphthalene-2-carboxamide To a solution of compound 193-1a (34.4 mg, 0.19 mmol, 31 uL, 1.5 eq) in THF (1 mL) was added LHMDS (1 M, 0.19 mL, 1.5 eq) at 0° C. and stirred at 0° C. for 30 min. Then compound 193-1 (50 mg, 0.13 mmol, 1 eq) in THF (1 mL) was added to the mixture and stirred at 25° C. for 2 hr. The reaction mixture was quenched with NH₄Cl (5 mL), extracted with EA (15 mL*3). The combined organic phase was washed with H₂O (5 mL) and brine (5 mL), dried over Na₂SO₄, filtered and concentrated in vacuum. The crude product was purified by flash silica gel chromatography. The crude product was purified by chiral SFC (column: DAICEL CHIRALCEL OJ-H (250 mm*30 mm, 5 um); mobile phase: [0.1% NH₃H₂O ETOH]; B %: 20%-20%, min). The title compound (7.20 mg, 17 umol, 13.3% yield) was obtained as a yellow solid. LCMS (ESI): RT=0.875 min, mass calcd. For C₂₄H₁₉F₃N₂O, 408.14 m/z found 409.0 [M+H]⁺. ¹H NMR (400 MHz, CDCl₃) δ 8.42-8.42 (m, 1H), 8.41 (s, 1H), 8.00 (br d, J=8.1 Hz, 1H), 7.93-7.86 (m, 1H), 7.84-7.76 (m, 3H), 7.61 (br d, J=7.8 Hz, 3H), 7.51 (br d, J=6.9 Hz, 1H), 6.67-6.50 (m, 2H), 5.43 (br d, J=10.8 Hz, 1H), 3.58 (q, J=6.2 Hz, 2H), 2.59 (q, J=7.3 Hz, 2H), 1.95-1.88 (m, 2H).

Example 194: N-(pyridin-4-ylmethyl)-5-(4-(trifluoromethyl)phenyl)-2-naphthamide (Compound 229)

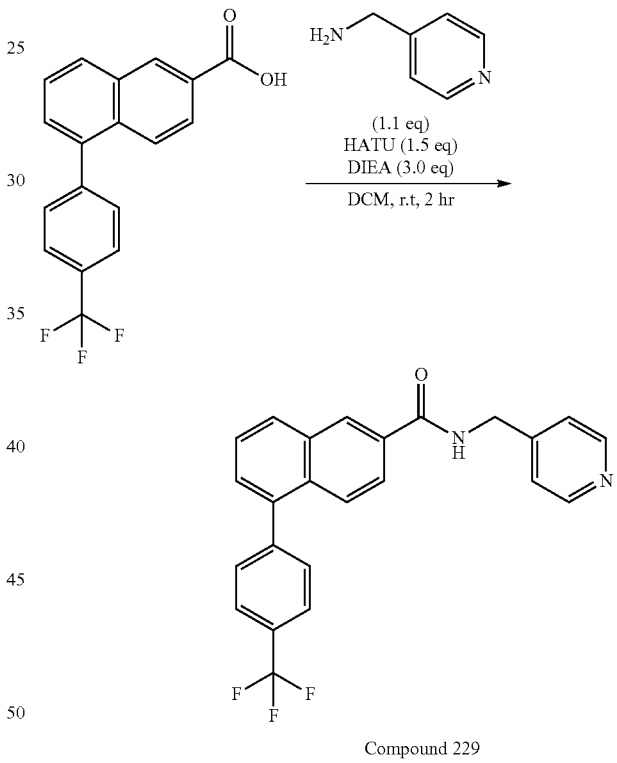

Compound 229

The mixture of 5-[4-(trifluoromethyl)phenyl]naphthalene-2-carboxylic acid (50 mg, 0.15 mmol, 1 eq), HATU (72.1 mg, 0.18 mmol, 1.2 eq) and DIPEA (61.3 mg, 0.47 mmol, 82 uL, 3 eq) in DCM (2 mL) was stirred at 25° C. for 1 hr. Then 4-pyridylmethanamine (18.8 mg, 0.17 mmol, 17 uL, 1.1 eq) was added into the mixture and the mixture was stirred at 25° C. for another 1 hr. The reaction mixture was diluted with H₂O (10 mL) and the mixture was extracted with EA (10 mL*3). The combined organic phase was washed with brine (10 mL*2), dried with anhydrous Na₂SO₄, filtered and concentrated in vacuum. The residue was purified by column chromatography (SiO₂, Petroleum ether/Ethyl acetate=1/0 to 5:1). The title compound (21.0 mg, 51.2 umol, 32.4% yield) was obtained as a white solid.

LCMS (ESI): RT=0.842 min, mass calcd for $C_{24}H_{17}F_3N_2O$ 406.40 m/z found 407.0 [M+H]$^+$, $^1$H NMR (400 MHz, CDCl$_3$) δ 8.58-8.49 (m, 3H), 8.10 (d, J=8.3 Hz, 1H), 7.92-7.84 (m, 1H), 7.97-7.83 (m, 3H), 7.73-7.66 (m, 3H), 7.60 (dd, J=0.9, 7.1 Hz, 1H), 7.47 (d, J=6.0 Hz, 2H), 4.71 (s, 2H).

Example 195: methyl (E)-5-[[5-[4-(trifluoromethyl) phenyl]naphthalene-2-carbonyl]amino]pent-2-enoate (Compound 230)

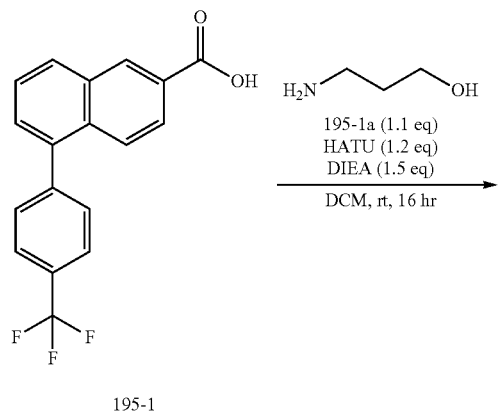

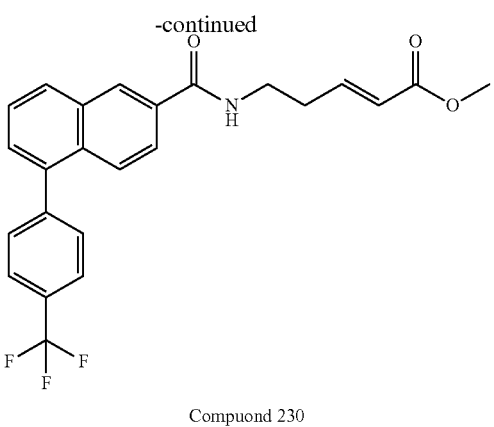

Compuond 230

N-(3-hydroxypropyl)-5-[4-(trifluoromethyl)phenyl] naphthalene-2-carboxamide

To a solution of compound 195-1 (0.6 g, 1.96 mmol, 1 eq), HATU (894.4 mg, 2.35 mmol, 1.2 eq) and compound 195-1a (161.9 mg, 2.16 mmol, 0.16 mL, 1.1 eq) in DMF (10 mL) was added TEA (297.5 mg, 2.94 mmol, 0.4 mL, 1.5 eq). The reaction was stirred at 25° C. for 16 hr. The reaction mixture was diluted with EA (30 mL) and washed with brine (2*10 mL). The organic layer was dried over Na$_2$SO$_4$ and concentrated. Compound 195-2 (720 mg, 1.93 mmol, 98.3% yield) was used for next step directly as a white solid.

N-(3-oxopropyl)-5-[4-(trifluoromethyl)phenyl]naphthalene-2-carboxamide

To a solution of compound 195-2 (0.7 g, 1.87 mmol, 1 eq) in DCM (10 mL) were added DIEA (1.21 g, 9.37 mmol, 1.63 mL, 5 eq), DMSO (5 mL) followed by SO3·Py (1.49 g, 9.37 mmol, 5 eq) at 0° C. The reaction was stirred at 0° C. for 1 hr. The reaction was diluted with EA (20 mL) and washed with brine (2*10 mL). The organic layer was dried over Na$_2$SO$_4$ and concentrated. The crude product was purified by column chromatography on silica gel (EA:PE=1:1) to give compound 195-3 (0.47 g, 1.27 mmol, 67.5% yield) as a white solid.

Methyl (E)-5-[[5-[4-(trifluoromethyl)phenyl]naphthalene-2-carbonyl]amino]pent-2-enoate To a solution of compound 195-3a (73.5 mg, 0.4 mmol, 58.3 uL, 1.5 eq) in THF (3 mL) was added drop-wise LiHMDS (1 M, 0.4 mL, 1.5 eq) at 0° C. After 10 min, compound 195-3 (0.1 g, 0.26 mmol, 1 eq) in THF (1 mL) was added. The reaction was warmed to 50° C. and stirred at 50° C. for 32 hr. The reaction was quenched by Sat.NH$_4$Cl (10 mL) and washed with EA (2*15 mL). The organic layer was dried over Na$_2$SO$_4$ and concentrated. The reaction was purified by Prep.HPLC (column: Waters Xbridge 150*50 10u; mobile phase: [water (0.05% ammonia hydroxide v/v)-ACN]; B %: 59%-89%, 7.8 min) to give the title compound (3.5 mg, 8.1 umol, 3% yield) as a white solid. LCMS (ESI): RT=0.984 min, mass calcd. For $C_{24}H_{20}F_3NO_3$, 427.14 m/z found 428.1 [M+Na]$^+$. $^1$H NMR (400 MHz, CDCl$_3$) δ 8.35 (s, 1H), 8.00 (d, J=7.4 Hz, 1H), 7.88 (d, J=8.9 Hz, 1H), 7.82-7.73 (m, 3H), 7.66-7.58 (m, 3H), 7.52 (d, J=6.9 Hz, 1H), 7.08-6.93 (m, 1H), 6.35 (br s, 1H), 5.97 (br d, J=14.9 Hz, 1H), 3.75 (s, 3H), 3.72-3.65 (m, 2H), 2.67-2.55 (m, 2H).

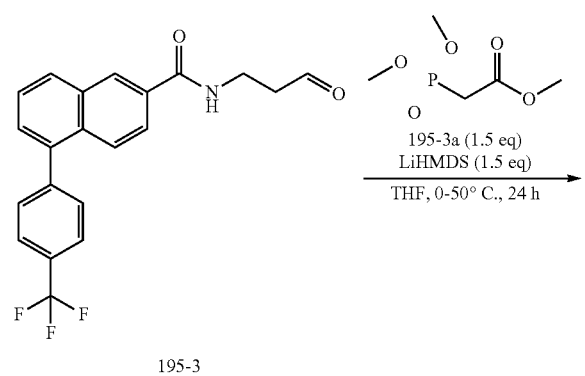

Example 196: N-(5-cyano-5-hydroxy-pentyl)-5-[4-(trifluoromethyl)phenyl]naphthalene-2-carboxamide (Compound 231)

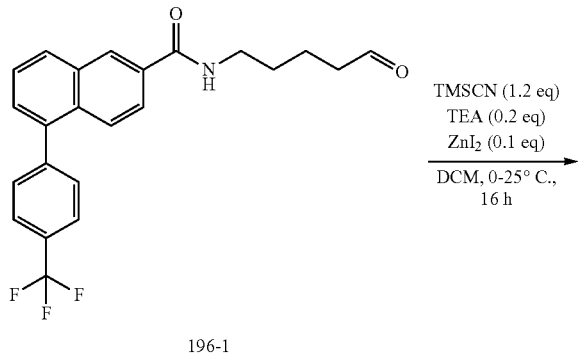

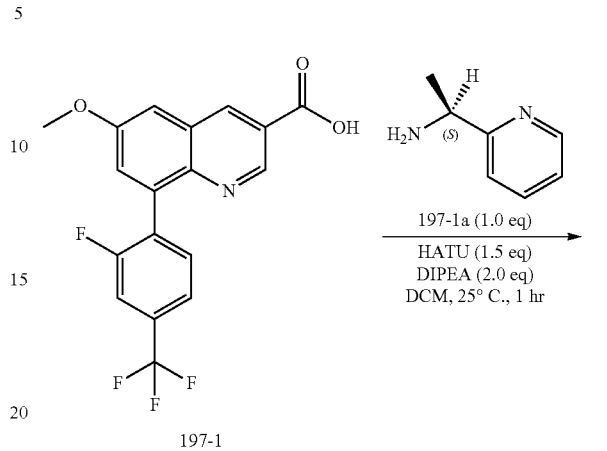

Example 197: (S)-8-(2-Fluoro-4-(trifluoromethyl)phenyl)-6-methoxy-N-(1-(pyridin-2-yl)ethyl)quinoline-3-carboxamide (Compound 232)

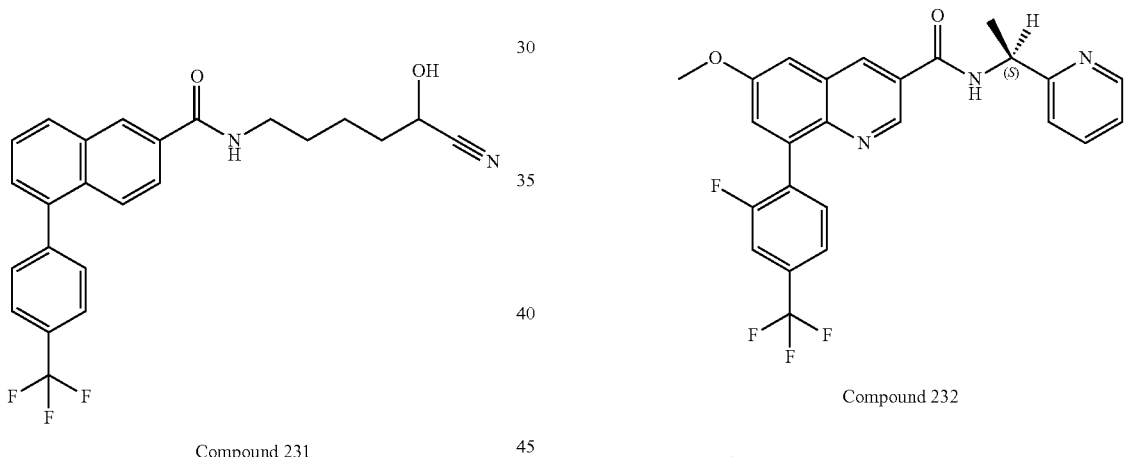

To a solution of compound 196-1 (200 mg, 0.50 mmol, 1 eq) in DCM (1 mL) were added TMSCN (59.6 mg, 0.60 mmol, 75 uL, 1.2 eq), diiodozinc (15.9 mg, 50 umol, 0.1 eq) and TEA (10.1 mg, 0.1 mmol, 14 uL, 0.2 eq) at 0° C. Then the mixture was stirred at 25° C. for 16 hr. The reaction mixture was concentrated in vacuum. The residue was diluted with EA (20 mL), washed with 1M.HCl (10 mL), $H_2O$ (5 mL) and brine (5 mL), dried over $Na_2SO_4$, filtered and concentrated in vacuum. The crude product was purified by flash silica gel chromatography. The title compound (130 mg, 0.30 mmol, 60.8% yield) was obtained as a white solid. LCMS (ESI): RT=0.879 min, mass calcd. For $C_{24}H_{21}F_3N_2O_2$, 426.16 m/z found 427.0 [M+H]$^+$; $^1$H NMR (400 MHz, CDCl$_3$) δ 8.36 (s, 1H), 7.97 (d, J=8.1 Hz, 1H), 7.89-7.83 (m, 1H), 7.80-7.72 (m, 3H), 7.64-7.56 (m, 3H), 7.50 (d, J=7.0 Hz, 1H), 7.53-7.47 (m, 1H), 6.54 (br s, 1H), 4.54 (q, J=6.2 Hz, 1H), 3.94 (d, J=6.4 Hz, 1H), 3.56 (br d, J=6.3 Hz, 2H), 2.05-1.88 (m, 2H), 1.80-1.71 (m, 2H), 1.69-1.60 (m, 2H).

To a solution of compound 197-1 (25.0 mg, 68.4 umol, 1.0 eq), compound 197-1a (8.3 mg, 68.4 umol, 1.0 eq) and DIPEA (17.6 mg, 0.13 mmol, 2.0 eq) in DCM (1 mL) was added HATU (39.0 mg, 0.10 mmol, 1.5 eq). The reaction mixture was stirred at 25° C. for 1 hour. The reaction mixture was concentrated under reduced pressure. The mixture was diluted with water (10 mL) and the resultant mixture was extracted with EA (20 mL*3). The combined organic layers were dried over $Na_2SO_4$, filtered and concentrated to dryness under reduced pressure. The residue was purified by prep-HPLC (column: Waters Xbridge 150*50 10u; mobile phase: [water (0.05% ammonia hydroxide v/v)-ACN]; B %: 55%-85%, 7.8 min) to give the title compound (8.85 mg, 27.5% yield) as a white solid. LCMS (ESI): RT=0.862 min, mass calcd. for $C_{25}H_{19}F_4N_3O_2$ 469.14, m/z found 470.0 [M+H]$^+$; $^1$H NMR (400 MHz, CDCl$_3$) δ 9.20 (d, J=2.3 Hz, 1H), 8.66 (d, J=2.3 Hz, 1H), 8.57 (d, J=4.5 Hz, 1H), 8.16 (d, J=7.0 Hz, 1H), 7.75-7.67 (m, 1H), 7.67-7.61 (m, 1H), 7.59-7.54 (m, 1H), 7.53-7.45 (m, 2H), 7.33 (d, J=7.8 Hz, 1H), 7.28 (d, J=2.8 Hz, 1H), 7.24 (dd, J=5.3, 7.0 Hz, 1H), 5.43-5.34 (m, 1H), 4.01 (s, 3H), 1.62 (s, 3H).

Example 198: (R)-8-(2-Fluoro-4-(trifluoromethyl)phenyl)-N-(1-hydroxypropan-2-yl)-6-methoxyquinoline-3-carboxamide (Compound 233)

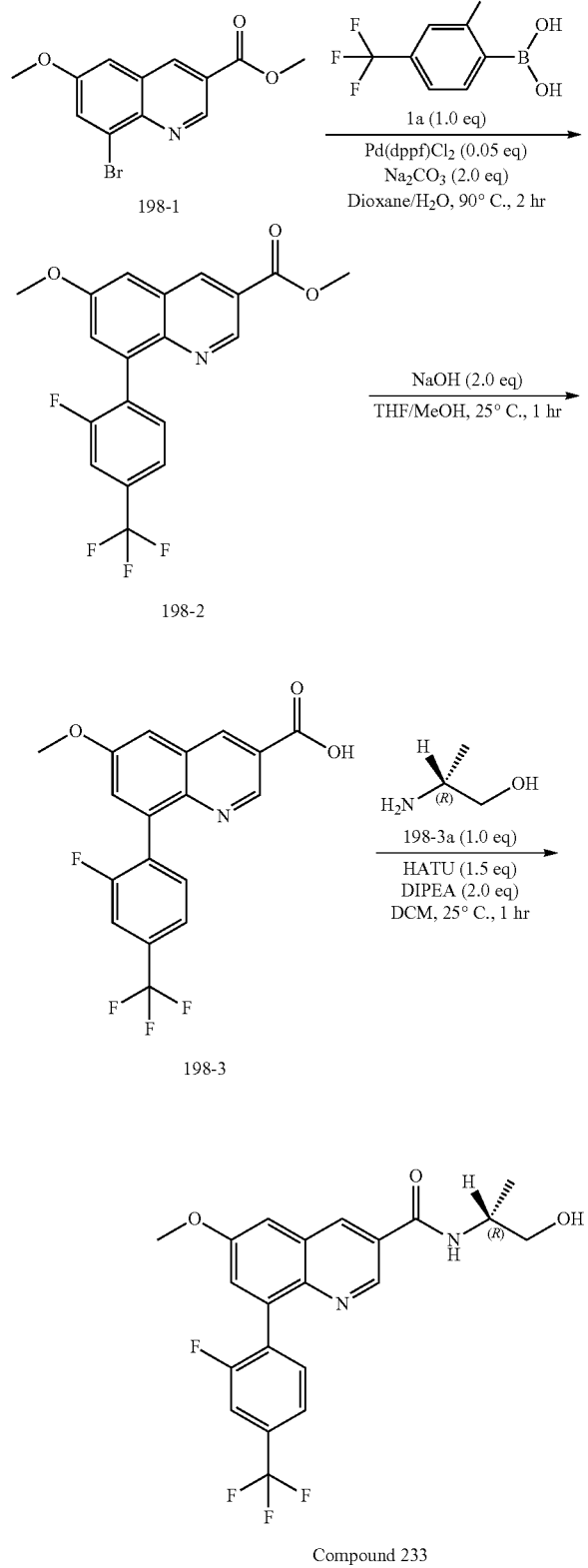

Methyl 8-(2-fluoro-4-(trifluoromethyl)phenyl)-6-methoxyquinoline-3-carboxylate To a solution of compound 198-1 (200.0 mg, 0.67 mmol, 1.0 eq), compound 198-1a (140.4 mg, 0.67 mmol, 1.0 eq) and $Na_2CO_3$ (143.1 mg, 1.35 mmol, 2.0 eq) in Dioxane (5 mL) and $H_2O$ (1 mL) was added $Pd(dppf)Cl_2$ (24.7 mg, 33.7 umol, 0.05 eq) under $N_2$. The reaction mixture was stirred at 90° C. for 2 hours under $N_2$. The reaction mixture was concentrated under reduced pressure. The mixture was diluted with water (30 mL) and the resultant mixture was extracted with EA (50 mL*3). The combined organic layers were dried over $Na_2SO_4$, filtered and concentrated to dryness under reduced pressure. The residue was purified by column chromatography over silica gel (petroleum ether: ethyl acetate=1:0 to 5:1) to give 198-2 (180 mg, 70.2 yield) as a white solid.

8-(2-Fluoro-4-(trifluoromethyl)phenyl)-6-methoxy-quinoline-3-carboxylic acid To a solution of compound 198-2 (150.0 mg, 0.39 mmol, 1.0 eq) in THF (0.6 mL) and MeOH (0.2 mL) was added NaOH (1 M, 0.79 mL, 2.0 eq). The reaction mixture was stirred at 25° C. for 1 hour. The reaction mixture was adjusted with HCl (1M) to pH=5, and then the suspension was extracted with EA (30 mL*3). The combined organic layers were dried over $Na_2SO_4$, filtered and concentrated to dryness under reduced pressure to give 198-3 (130 mg, 90.0% yield) as a white solid.

(R)-8-(2-Fluoro-4-(trifluoromethyl)phenyl)-N-(1-hydroxypropan-2-yl)-6-methoxyquinoline-3-carboxamide To a solution of compound 198-3 (25.0 mg, 68.4 umol, 1.0 eq), compound 198-3a (5.1 mg, 68.4 umol, 1.0 eq) and DIPEA (17.6 mg, 0.13 mmol, 2.0 eq) in DCM (1 mL) was added HATU (39.0 mg, 0.10 mmol, 1.5 eq). The reaction mixture was stirred at 25° C. for 1 hour. The reaction mixture was concentrated under reduced pressure. The mixture was diluted with water (10 mL) and the resultant mixture was extracted with EA (20 mL*3). The combined organic layers were dried over $Na_2SO_4$, filtered and concentrated to dryness under reduced pressure. The residue was purified by prep-HPLC (column: Waters Xbridge 150*50 10u; mobile phase: [water (0.05% ammonia hydroxide v/v)-ACN]; B %: 50%-80%, 7.8 min) to give the title compound (14.48 mg, 50.0% yield) as a white solid. LCMS (ESI): RT=0.887 min, mass calcd. for $C_{21}H_{18}F_4N_2O_3$ 422.13, m/z found 423.0 [M+H]$^+$; $^1$H NMR (400 MHz, CDCl$_3$) δ 9.05 (d, J=2.0 Hz, 1H), 8.54 (d, J=2.3 Hz, 1H), 7.64-7.58 (m, 1H), 7.57-7.53 (m, 1H), 7.51-7.45 (m, 2H), 7.21 (d, J=2.8 Hz, 1H), 6.57 (d, J=13 Hz, 1H), 4.42-4.30 (m, 1H), 3.98 (s, 3H), 3.88-3.78 (m, 1H), 3.72-3.64 (m, 1H), 2.68-2.60 (m, 1H), 1.34 (d, J=6.8 Hz, 3H).

Example 199: N-(3-(3-methoxypropanamido)benzyl)-5-(4-(trifluoromethyl)phenyl)-2-naphthamide (Compound 234)

Example 200: N-(3-aminobenzyl)-5-(4-(trifluoromethyl)phenyl)-2-naphthamide (Compound 235)

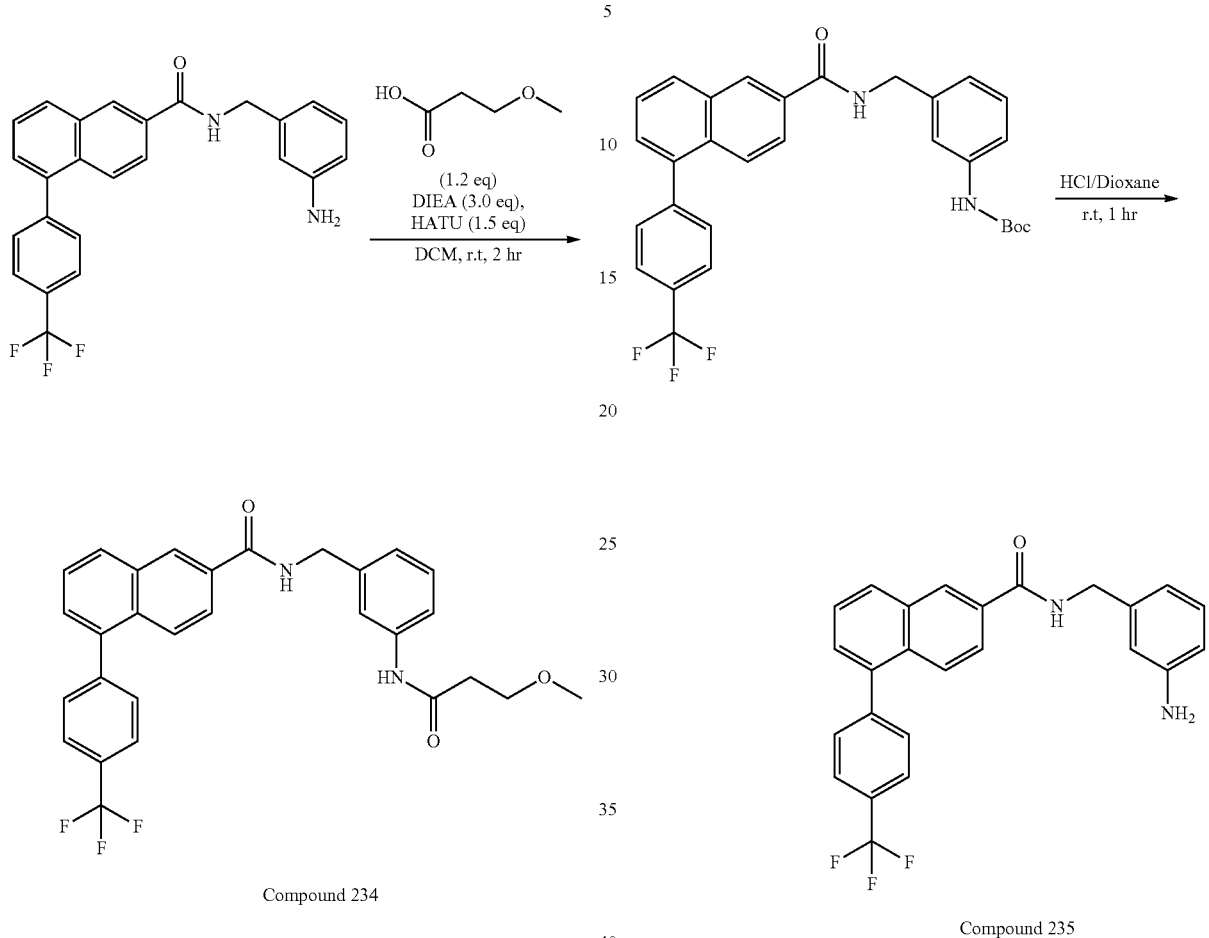

Compound 234

Compound 235

N-(3-(3-methoxypropanamido)benzyl)-5-(4-(trifluoromethyl)phenyl)-2-naphthamide The mixture of N-[(3-aminophenyl)methyl]-5-[4-(trifluoromethyl)phenyl]naphthalene-2-carboxamide (50 mg, 0.11 mmol, 1 eq), 3-methoxypropanoic acid (14.8 mg, 0.14 mmol, 13.3 uL, 1.2 eq), DIPEA (46.1 mg, 0.35 mmol, 62.1 uL, 3 eq) and HATU (67.8 mg, 0.17 mmol, 1.5 eq) in DCM (3 mL) was stirred at 25° C. for 2 hr. The reaction mixture was diluted with H$_2$O (10 mL) and the mixture was extracted with EA (10 mL*3). The combined organic phase was washed with brine (10 mL*3), dried with anhydrous Na$_2$SO$_4$, filtered and concentrated in vacuum. The residue was purified by prep-HPLC (column: Waters Xbridge 150*25 5u; mobile phase: [water (0.05% ammonia hydroxide v/v)-ACN]; B %: 50%-90%, 7.8 min). The title compound (35 mg, 68.4 umol, 57.5% yield) was obtained as white solid. LCMS (ESI): RT=0.980 min, mass calcd for C$_{29}$H$_{25}$F$_3$N$_2$O$_3$ 506.52 m/z, found 507.1 [M+H]$^+$, $^1$H NMR (400 MHz, CD$_3$Cl) δ 8.39 (s, 1H), 8.24 (br s, 1H), 7.98 (d, J=8.0 Hz, 1H), 7.89-7.80 (m, 2H), 7.77 (d, J=7.8 Hz, 2H), 7.61 (dt, J=3.0, 7.9 Hz, 4H), 7.50 (d, J=5.8 Hz, 1H), 7.43-7.38 (m, 1H), 7.34-7.29 (m, 1H), 7.15 (d, J=7.0 Hz, 1H), 6.60 (br d, J=5.3 Hz, 1H), 4.70 (d, J=5.5 Hz, 2H), 3.73 (t, J=5.6 Hz, 2H), 3.45 (s, 3H), 2.63 (t, J=5.6 Hz, 2H).

N-(3-aminobenzyl)-5-(4-(trifluoromethyl)phenyl)-2-naphthamide

The mixture of tert-butyl N-[3-[[[5-[4-(trifluoromethyl)phenyl]naphthalene-2-carbonyl]amino]methyl]phenyl]carbamate (400 mg, 0.76 mmol, 1 eq) and HCl/dioxane (4 M, 0.19 mL, 1 eq) in dioxane (3 mL) was stirred at 25° C. for 1 hr. The reaction mixture was concentrated under reduced pressure to remove solvent. Compound N-[(3-aminophenyl)methyl]-5-[4-(trifluoromethyl)phenyl]naphthalene-2-carboxamide (350 mg, crude, HCl) was obtained as yellow solid. The crude product (30 mg) was purified by prep-HPLC (column: Waters Xbridge 150*50 10u; mobile phase: [water (0.05% ammonia hydroxide v/v)-ACN]; B %: 57%-87%, 7.8 min). The title compound (10 mg, 23.3 umol, 32.6% yield) was obtained as white solid. LCMS (ESI): RT=0.888 min, mass calcd for C$_{25}$H$_{19}$F$_3$N$_2$O 420.43 m/z, found 421.1 [M+H]$^+$, $^1$H NMR (400 MHz, DMSO-d$_6$) δ 9.16 (t, J=5.7 Hz, 1H), 8.63 (s, 1H), 8.13 (d, J=8.1 Hz, 1H), 8.00 (d, J=9.5 Hz, 1H), 7.93 (d, J=8.1 Hz, 2H), 7.83 (d, J=8.9 Hz, 1H), 7.78-7.67 (m, 3H), 7.60 (d, J=6.9 Hz, 1H), 6.97 (t, J=7.6 Hz, 1H), 6.58-6.41 (m, 3H), 5.05 (s, 2H), 4.41 (d, J=5.9 Hz, 2H)

Example 201: Tert-Butyl (3-((5-(4-(trifluoromethyl)phenyl)-2-naphthamido)methyl)phenyl)carbamate (Compound 236)

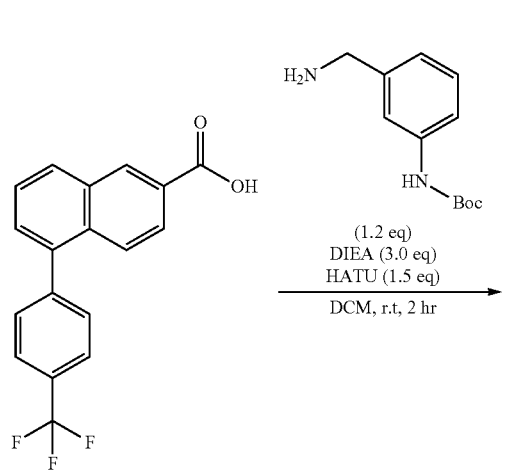

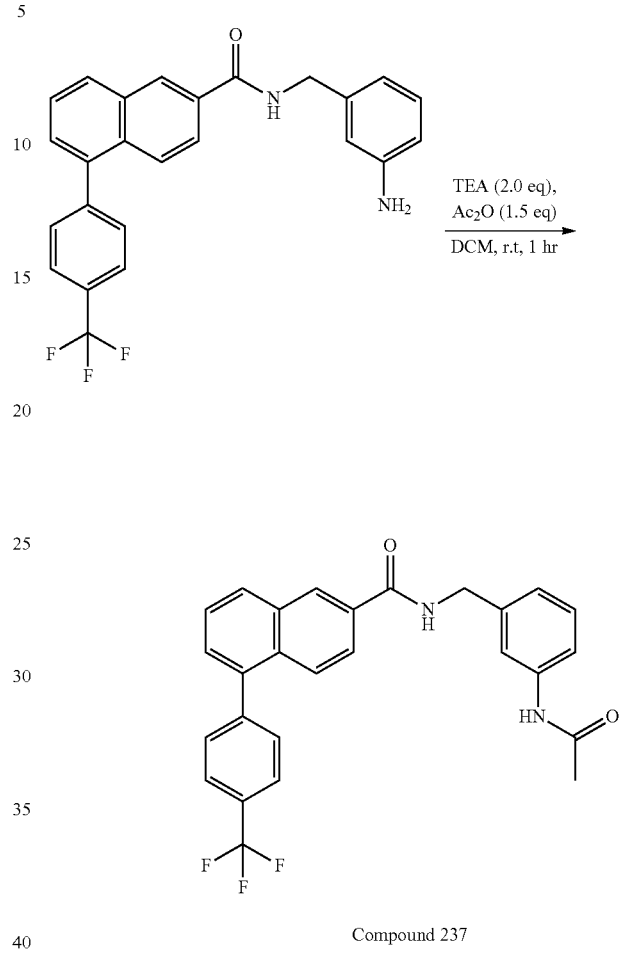

Compound 236

Tert-Butyl (3-((5-(4-(trifluoromethyl)phenyl)-2-naphthamido)methyl)phenyl)carbamate The mixture of 5-[4-(trifluoromethyl)phenyl]naphthalene-2-carboxylic acid (50 mg, 0.15 mmol, 1 eq), DIPEA (61.2 mg, 0.47 mmol, 82.6 uL, 3 eq) and HATU (90.1 mg, 0.23 mmol, 1.5 eq) in DCM (3 mL) was stirred at 25° C. for 1 hr. Then tert-butyl N-[3-(aminomethyl)phenyl]carbamate (42.1 mg, 0.18 mmol, 1.2 eq) was added at the mixture and the mixture was stirred at 25° C. for another 1 hr. The reaction mixture was diluted with H$_2$O (10 mL). The mixture was extracted with EA (10 mL*3). The combined organic phase was washed with brine (10 mL*2), dried with anhydrous Na$_2$SO$_4$, filtered and concentrated in vacuum. The residue was purified by prep-HPLC (column: Waters Xbridge 150*25 5u; mobile phase: [water (0.05% ammonia hydroxide v/v)-ACN]; B %: 70%-100%, 7 min). The title compound (30 mg, 57.0 umol, 36.0% yield) was obtained as white solid. LCMS (ESI): RT=0.967 min, mass calcd for C$_{30}$H$_{27}$F$_3$N$_2$O$_3$ 520.45 m/z, found 463.0 [M+H]$^+$, $^1$H NMR (400 MHz, CD$_3$Cl) δ 8.40 (s, 1H), 7.99 (d, J=8.3 Hz, 1H), 7.89-7.76 (m, 4H), 7.64-7.59 (m, 3H), 7.51 (d, J=7.0 Hz, 2H), 7.09 (d, J=7.1 Hz, 1H), 6.59 (br s, 1H), 6.52 (br s, 1H), 4.69 (d, J=5.6 Hz, 2H), 1.52 (s, 9H).

Example 202: N-(3-acetamidobenzyl)-5-(4-(trifluoromethyl)phenyl)-2-naphthamide (Compound 237)

Compound 237

N-(3-acetamidobenzyl)-5-(4-(trifluoromethyl)phenyl)-2-naphthamide

The mixture of N-[(3-aminophenyl)methyl]-5-[4-(trifluoromethyl)phenyl]naphthalene-2-carboxamide (50 mg, 0.11 mmol, 1 eq), TEA (24.0 mg, 0.23 mmol, 33.1 uL, 2 eq) and Ac$_2$O (18.2 mg, 0.17 mmol, 16.7 uL, 1.5 eq) in DCM (2 mL) was stirred at 25° C. for 1 hr. The reaction mixture was diluted with H$_2$O (10 mL) and the mixture was extracted with EA (20 mL*3). The combined organic phase was washed with brine (10 mL*2), dried with anhydrous Na$_2$SO$_4$, filtered and concentrated in vacuum. The residue was purified by prep-HPLC (column: Waters Xbridge 150*25 5u; mobile phase: [water (0.05% ammonia hydroxide v/v)-ACN]; B %: 65%-95%, 7 min). The title compound (15 mg, 32.1 umol, 27.0% yield) was obtained as white solid. LCMS (ESI): RT=0.967 min, mass calcd for C$_{27}$H$_{21}$F$_3$N$_2$O$_2$ 462.42 m/z, found 463.0 [M+H]$^+$, $^1$H NMR (400 MHz, CD$_3$Cl) δ 8.40 (s, 1H), 7.98 (d, J=8.3 Hz, 1H), 7.89-7.75 (m, 4H), 7.63-7.57 (m, 4H), 7.51 (d, J=6.3 Hz, 1H), 7.44 (br d, J=8.0 Hz, 1H), 7.32 (t, J=7.9 Hz, 1H), 7.15 (br d, J=7.5 Hz, 1H), 6.69 (br s, 1H), 4.69 (d, J=5.8 Hz, 2H), 2.17 (s, 3H), 1.59 (s, 4H).

Example 203: N-(5-hydroxypentyl)-5-[4-(trifluoromethyl)phenyl]naphthalene-2-carboxamide (Compound 238)

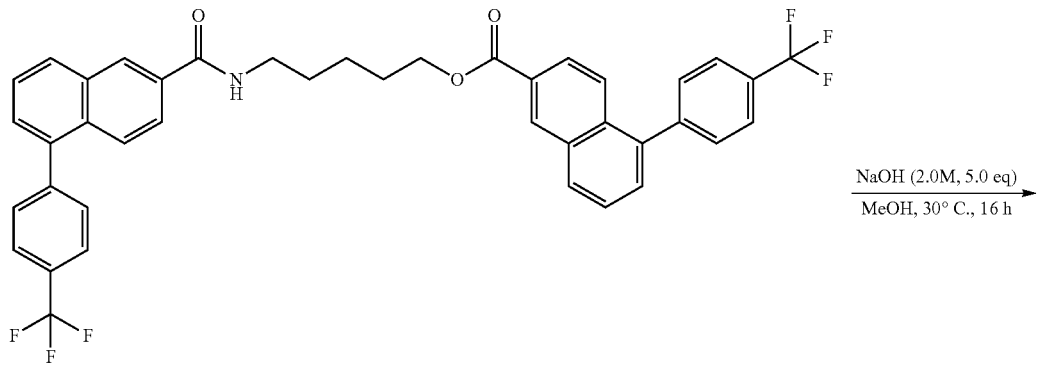

203-1

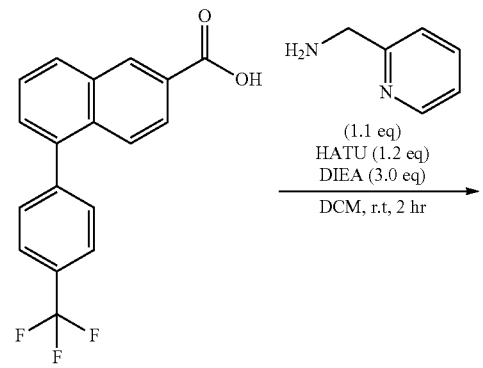

Compound 238

N-(5-hydroxypentyl)-5-[4-(trifluoromethyl)phenyl]naphthalene-2-carboxamide

To a solution of compound 203-1 (60 mg, 85 umol, 1 eq) in MeOH (1 mL) was added NaOH (2 M, 0.21 mL, 5 eq). The mixture was stirred at 30° C. for 16 hr. The reaction mixture was concentrated in vacuum. The aqueous phase was adjusted pH=6 with 1M.aq.HCl and extracted with EA (15 mL*3). The combined organic phase was washed with $H_2O$ (5 mL) and brine (5 mL), dried over $Na_2SO_4$, filtered and concentrated in vacuum. The crude product was purified by prep-HPLC (column: Waters Xbridge 150*25 5u; mobile phase: [water (0.05% ammonia hydroxide v/v)-ACN]; B %: 50%-80%, 7.8 min). The title compound (20 mg, 49 umol, 57.5% yield) was obtained as a white solid. LCMS (ESI): RT=0.825 min, mass calcd. For $C_{23}H_{22}F_3NO_2$, 401.16 m/z found 402.0 [M+H]$^+$. $^1$H NMR (400 MHz, CDCl$_3$) δ 8.37 (s, 1H), 7.98 (br d, J=8.1 Hz, 1H), 7.90-7.83 (m, 1H), 7.78 (br d, J=7.8 Hz, 3H), 7.60 (br d, J=7.6 Hz, 3H), 7.50 (br d, J=6.9 Hz, 1H), 6.42 (br s, 1H), 3.69 (t, J=6.3 Hz, 2H), 3.55 (q, J=6.6 Hz, 2H), 1.79-1.65 (m, 4H), 1.57-1.48 (m, 2H).

Example 204: N-(pyridin-2-ylmethyl)-5-(4-(trifluoromethyl)phenyl)-2-naphthamide (Compound 239)

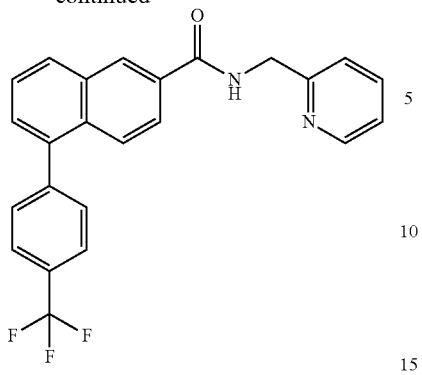

Compound 239

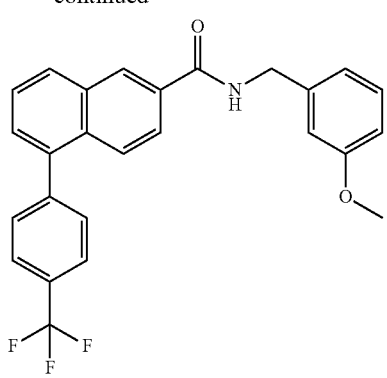

Compound 240

N-(pyridin-2-ylmethyl)-5-(4-(trifluoromethyl)phenyl)-2-naphthamide

The mixture of 5-[4-(trifluoromethyl)phenyl]naphthalene-2-carboxylic acid (50 mg, 0.15 mmol, 1 eq), HATU (72.1 mg, 0.18 mmol, 1.2 eq) and DIPEA (61.3 mg, 0.47 mmol, 82 uL, 3 eq) in DCM (2 mL) was stirred at 25° C. for 1 hr. Then 2-pyridylmethanamine (18.8 mg, 0.17 mmol, 17 uL, 1.1 eq) was added into the mixture and the mixture was stirred at 25° C. for another 1 hr. The reaction mixture was diluted with H$_2$O (10 mL) and the mixture was extracted with EA (10 mL*3). The combined organic phase was washed with brine (10 mL*2), dried with anhydrous Na$_2$SO$_4$, filtered and concentrated in vacuum. The residue was purified by prep-HPLC (column: Xtimate C18 150*25 mm*5 um; mobile phase: [water (10 mM NH$_4$HCO$_3$)-ACN]; B %: 51%-81%, 8.5 min). The title compound (17.6 mg, 43.4 umol, 27.4% yield) was obtained as a white solid. LCMS (ESI): RT=0.876 min, mass calcd for C$_{24}$H$_{17}$F$_3$N$_2$O 406.40 m/z found 407.0 [M+H]$^+$. $^1$H NMR (400 MHz, CD$_3$OD) δ 8.59-8.52 (m, 2H), 8.10 (d, J=8.1 Hz, 1H), 7.98-7.90 (m, 2H), 7.86 (d, J=8.0 Hz, 3H), 7.73-7.66 (m, 3H), 7.60 (dd, J=1.0, 7.1 Hz, 1H), 7.51 (d, J=7.9 Hz, 1H), 7.35 (dd, J=5.4, 7.1 Hz, 1H), 4.78 (s, 2H).

Example 205: N-(3-methoxybenzyl)-5-(4-(trifluoromethyl)phenyl)-2-naphthamide (Compound 240)

The mixture of 5-[4-(trifluoromethyl)phenyl]naphthalene-2-carboxylic acid (50 mg, 0.15 mmol, 1 eq), HATU (78.1 mg, 0.20 mmol, 1.3 eq) and DIPEA (61.3 mg, 0.47 mmol, 82.6 uL, 3 eq) in DCM (2 mL) was stirred at 25° C. for 1 hr. Then (3-methoxyphenyl)methanamine (23.8 mg, 0.17 mmol, 22.2 uL, 1.1 eq) was added into the mixture and the mixture was stirred at 25° C. for another 1 hr. The reaction mixture was diluted with H$_2$O (10 mL) and the mixture was extracted with EA (10 mL*3). The combined organic phase was washed with brine (10 mL*2), dried with anhydrous Na$_2$SO$_4$, filtered and concentrated in vacuum. The residue was purified by column chromatography (SiO$_2$, Petroleum ether/Ethyl acetate=1/0 to 3:1). The title compound (28.5 mg, 64.4 umol, 40.7% yield) was obtained as a white solid. LCMS (ESI): RT=1.038 min, mass calcd for C$_{26}$H$_{20}$F$_3$NO$_2$ 435.44 m/z found 436.0 [M+H]$^+$. $^1$H NMR (400 MHz, CD$_3$OD) δ 8.52 (d, J=1.5 Hz, 1H), 8.08 (d, J=8.3 Hz, 1H), 7.94-7.90 (m, 1H), 7.90-7.84 (m, 3H), 7.72-7.65 (m, 3H), 7.58 (dd, J=1.3, 7.0 Hz, 1H), 7.27 (t, J=8.2 Hz, 1H), 7.01-6.96 (m, 2H), 6.87-6.82 (m, 1H), 4.62 (s, 2H), 3.80 (s, 3H).

Example 206: N-benzyl-5-(4-(trifluoromethyl)phenyl)-2-naphthamide (Compound 241)

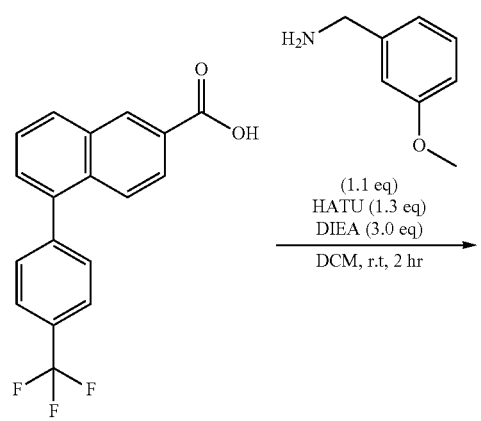

(1.1 eq)
HATU (1.3 eq)
DIEA (3.0 eq)
────────→
DCM, r.t, 2 hr

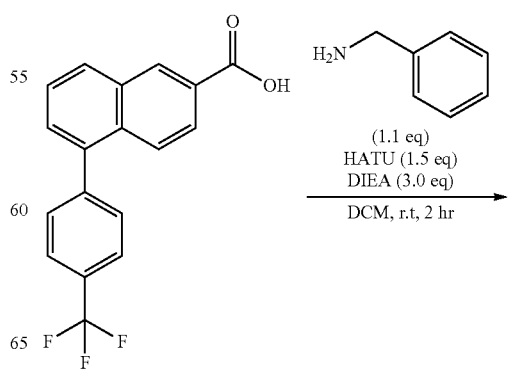

(1.1 eq)
HATU (1.5 eq)
DIEA (3.0 eq)
────────→
DCM, r.t, 2 hr

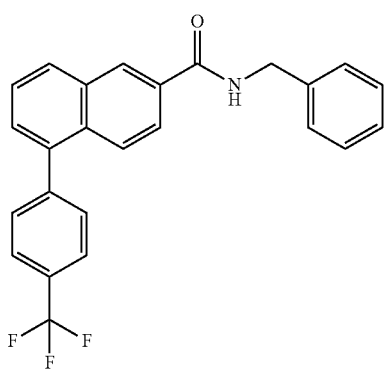

Compound 241

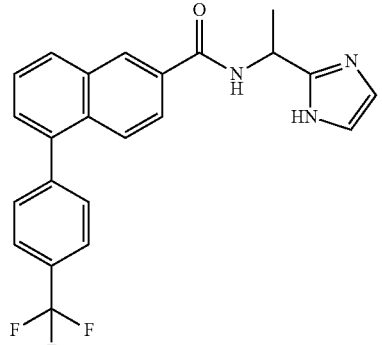

SFC

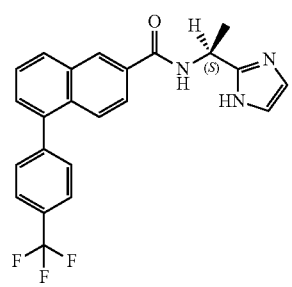

Compound 243

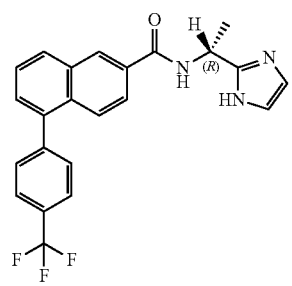

Compound 242

The mixture of 5-[4-(trifluoromethyl)phenyl]naphthalene-2-carboxylic acid (50 mg, 0.15 mmol, 1 eq), HATU (72.1 mg, 0.18 mmol, 1.2 eq) and DIPEA (61.2 mg, 0.47 mmol, 82 uL, 3 eq) in DCM (2 mL) was stirred at 25° C. for 1 hr. Then phenylmethanamine (18.6 mg, 0.17 mmol, 18 uL, 1.1 eq) was added into the mixture and the mixture was stirred at 25° C. for another 1 hr. The reaction mixture was diluted with H$_2$O (10 mL) and the mixture was extracted with EA (10 mL*3). The combined organic phase was washed with brine (10 mL*2), dried with anhydrous Na$_2$SO$_4$, filtered and concentrated in vacuum. The residue was purified by column chromatography (SiO$_2$, Petroleum ether/Ethyl acetate=1/0 to 5:1). The title compound (28.8 mg, 70.8 umol, 44.8% yield) was obtained as a white solid. LCMS (ESI): RT=1.048 min, mass calcd for C$_{25}$H$_{18}$F$_3$NO 405.41 m/z found 406.0 [M+H]$^+$. $^1$H NMR (400 MHz, CD$_3$OD) δ 8.52 (d, J=1.8 Hz, 1H), 8.08 (d, J=8.3 Hz, 1H), 7.94-7.90 (m, 1H), 7.89-7.83 (m, 1H), 7.89-7.83 (m, 2H), 7.71-7.64 (m, 3H), 7.58 (dd, J=1.3, 7.0 Hz, 1H), 7.44-7.39 (m, 2H), 7.38-7.33 (m, 2H), 7.30-7.25 (m, 1H), 4.62 (s, 2H).

Example 207: (R)—N-(1-(1H-imidazol-2-yl)ethyl)-5-(4-(trifluoromethyl)phenyl)-2-naphthamide (Compound 242) and (S)—N-(1-(1H-imidazol-2-yl)ethyl)-5-(4-(trifluoromethyl)phenyl)-2-naphthamide (Compound 243)

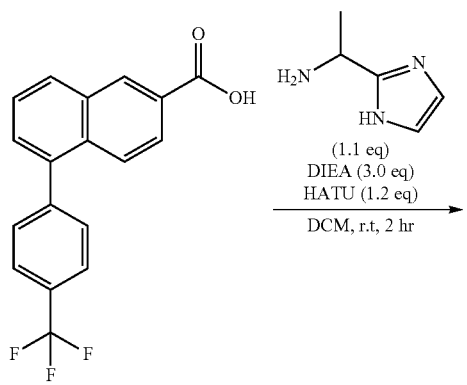

N-(1-(1H-imidazol-2-yl)ethyl)-5-(4-(trifluoromethyl)phenyl)-2-naphthamide

The mixture of 5-[4-(trifluoromethyl)phenyl]naphthalene-2-carboxylic acid (217.3 mg, 0.68 mmol, 1 eq), DIPEA (266.3 mg, 2.06 mmol, 0.35 mL, 3 eq) and HATU (391.8 mg, 1.03 mmol, 1.5 eq) in DCM (3 mL) was stirred at 25° C. for 1 hr. Then 1-(1H-imidazol-2-yl)ethanamine (84 mg, 0.75 mmol, 1.1 eq) was added into the mixture and the mixture was stirred at 25° C. for another 1 hr. The reaction mixture was diluted with H$_2$O (10 mL) and extracted with EA (10 mL*3). The combined organic phase was washed with brine (10 mL*2), dried with anhydrous Na$_2$SO$_4$, filtered and concentrated in vacuum. The residue was purified by prep-HPLC (column: Xtimate C$_{18}$ 150*25 mm*5 um; mobile phase: [water (0.05% HCl)-ACN]; B %: 22%-52%, 8.5 min). Compound N-[1-(1H-imidazol-2-yl)ethyl]-5-[4-(trifluoromethyl)phenyl]naphthalene-2-carboxamide (43.5 mg, 0.10 mmol, 15.4% yield) was obtained as a white solid.

(R)—N-(1-(1H-imidazol-2-yl)ethyl)-5-(4-(trifluoromethyl)phenyl)-2-naphthamide (Compound 242) and (S)—N-(1-(1H-imidazol-2-yl)ethyl)-5-(4-(trifluoromethyl)phenyl)-2-naphthamide (Compound 243)

The racemic compound N-[1-(1H-imidazol-2-yl)ethyl]-5-[4-(trifluoromethyl)phenyl]naphthalene-2-carboxamide (43.5 mg, 0.10 mmol, 1 eq) was purified by SFC was separated by SFC (column: YMC CHIRAL Amylose-C (250 mm*30 mm, 10 um; mobile phase: [0.1% NH$_3$H$_2$O ETOH]; B %: 40%-40%, min). Compound 242 (39.8 mg, 97.2 umol, 91.3% yield) was obtained as a white solid. LCMS (ESI): RT=0.850 min, mass calcd for C$_{23}$H$_{18}$F$_3$N$_3$O 409.40 m/z found 410.1 [M+H]$^+$, $^1$H NMR (400 MHz, CD$_3$OD) δ 8.45 (d, J=1.8 Hz, 1H), 7.97 (d, J=8.3 Hz, 1H), 7.85-7.80 (m, 1H), 7.77-7.71 (m, 3H), 7.60-7.54 (m, 3H), 7.47 (dd, J=1.0, 7.0 Hz, 1H), 7.01 (s, 2H), 5.34 (q, J=7.0 Hz, 1H), 1.61 (d, J=7.0 Hz, 3H). Compound 243 (6.4 mg, 15.0 umol, 14.1% yield) was obtained as a white solid. LCMS (ESI): RT=0.850 min, mass calcd for C$_{23}$H$_{18}$F$_3$N$_3$O 409.40 m/z found 410.1 [M+H]$^+$, $^1$H NMR (400 MHz, CD$_3$OD) δ 8.45 (d, J=1.5 Hz, 1H), 7.97 (d, J=8.3 Hz, 1H), 7.85-7.80 (m, 1H), 7.78-7.71 (m, 3H), 7.60-7.54 (m, 3H), 7.47 (dd, J=1.1, 7.2 Hz, 1H), 7.00 (s, 2H), 5.33 (q, J=7.0 Hz, 1H), 1.60 (d, J=7.0 Hz, 3H).

was purified by prep-HPLC (column: Waters Xbridge 150*50 10u; mobile phase: [water (0.05% ammonia hydroxide v/v)-ACN]; B %: 63%-93%, 7.8 min) to give the title compound (35.40 mg, 58.8% yield) as a white solid. LCMS (ESI): RT=0.892 min, mass calcd. for C$_{24}$H$_{18}$F$_3$N$_3$O 421.14, m/z found 422.0 [M+H]$^+$; $^1$H NMR (400 MHz, CDCl$_3$) δ 9.22 (d, J=8.0 Hz, 1H), 8.72-8.64 (m, 1H), 8.33-8.23 (m, 3H), 7.88-7.77 (m, 3H), 7.70 (dt, J=1.8, 7.7 Hz, 1H), 7.64-7.55 (m, 3H), 7.38 (d, J=7.8 Hz, 1H), 7.21-7.26 (m, 1H), 5.48-5.38 (m, 1H), 1.70 (d, J=6.8 Hz, 3H).

Example 209: N-[(E)-5-hydroxypent-3-enyl]-5-[4-(trifluoromethyl)phenyl]naphthalene-2-carboxamide (Compound 245)

Example 208: (S)—N-(1-(Pyridin-2-yl)ethyl)-5-(4-(trifluoromethyl)phenyl)quinoline-2-carboxamide (Compound 244)

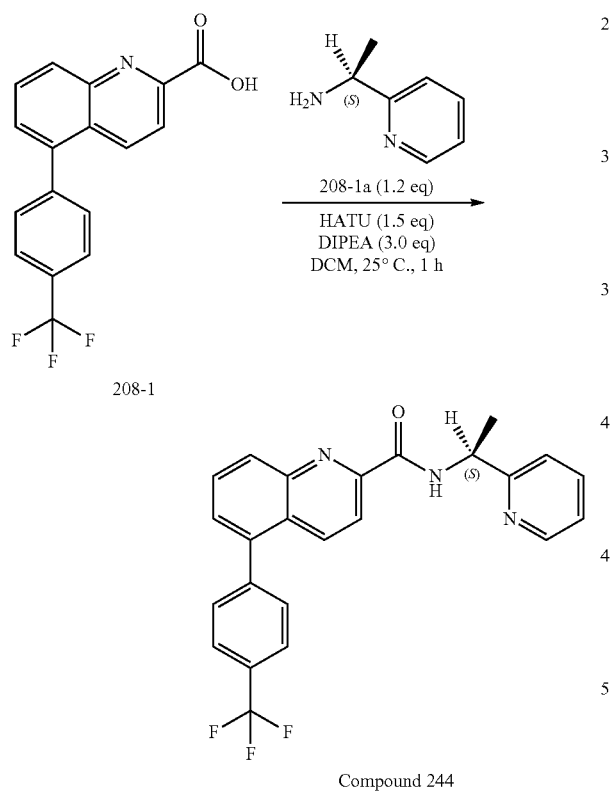

Compound 244

(S)—N-(1-(Pyridin-2-yl)ethyl)-5-(4-(trifluoromethyl)phenyl)quinoline-2-carboxamide To a solution of compound 208-1 (50.0 mg, 0.14 mmol, 1.0 eq, HCl), compound 208-1a (20.7 mg, 0.17 mmol, 1.2 eq) and DIPEA (54.8 mg, 0.42 mmol, 3.0 eq) in DCM (2 mL) was added HATU (80.6 mg, 0.21 mmol, 1.5 eq). The mixture was diluted with water (5 mL) and the resultant mixture was extracted with DCM (10 mL*3). The combined organic layers were dried over Na$_2$SO$_4$, filtered and concentrated to dryness under reduced pressure. The residue

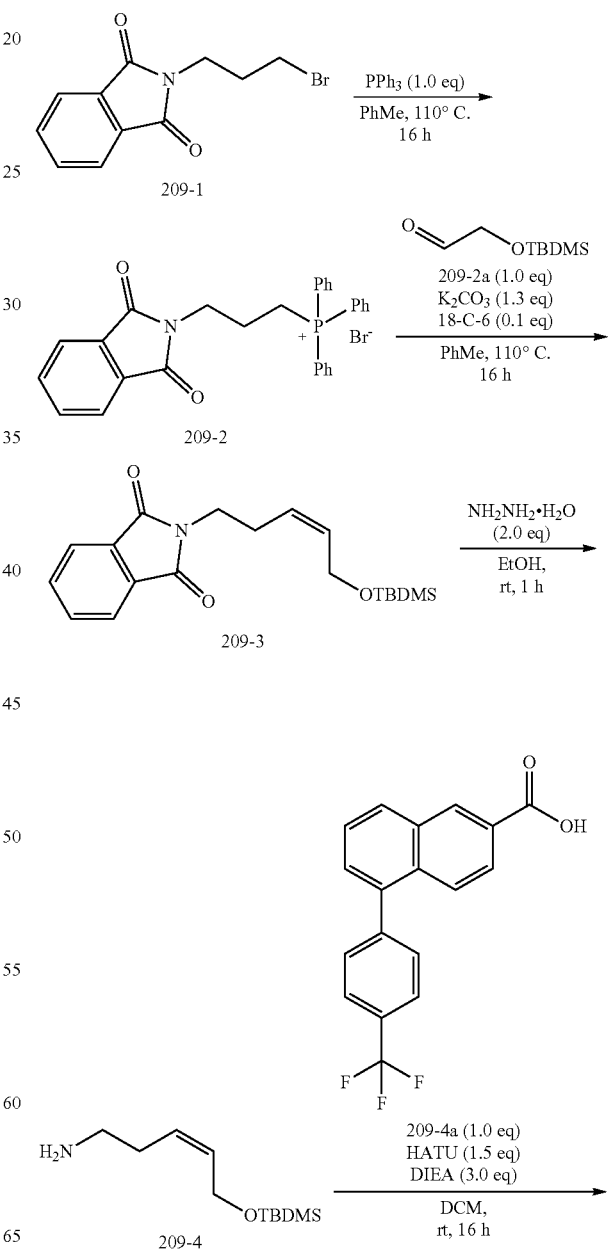

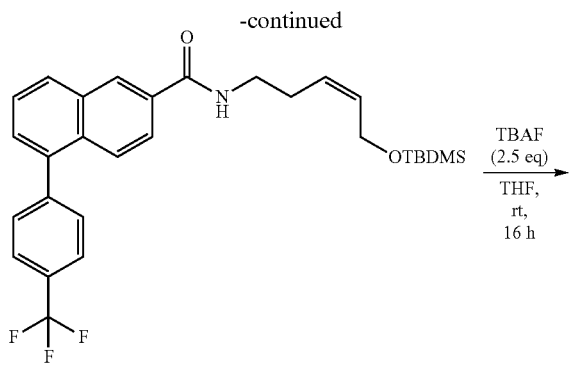

209-5

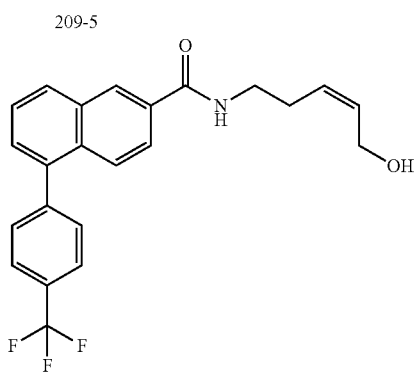

Compound 245

2-[3-[BLAH (triphenyl)-phosphanyl]propyl]isoindoline-1,3-dione

To a solution of compound 209-1 (2 g, 7.46 mmol, 1 eq) in toluene (30 mL) was added PPh₃ (1.96 g, 7.46 mmol, 1 eq). The reaction was heated at 110° C. for 16 hr. The reaction was filtered and dried under reduced pressure. Compound 209-2 (3.5 g, 6.60 mmol, 88.46% yield) was used for next step directly as a white solid. ¹H NMR (400 MHz, DMSO-d₆) δ 7.94-7.84 (m, 7H), 7.81-7.72 (m, 12H), 3.80-3.64 (m, 4H), 2.00-1.88 (m, 2H).

2-[(Z)-5-[tert-butyl(dimethyl)silyl]oxypent-3-enyl]isoindoline-1,3-dione

To a solution of compound 209-2 (0.3 g, 0.56 mmol, 1 eq) and compound 209-2a (98.5 mg, 0.56 mmol, 107.75 uL, 1 eq) in PhMe (10 mL) was added K₂CO₃ (101.6 mg, 0.73 mmol, 1.3 eq) and 18-CROWN-6 (14.9 mg, 56.5 umol, 0.1 eq). The reaction was heated at 110° C. for 16 hr. The reaction mixture was concentrated. The crude product was purified by column chromatography on silica gel (EA:PE=1:5) to give compound 209-3 (130 mg, 0.28 mmol, 49.8% yield) as colorless oil. ¹H NMR (400 MHz, CDCl₃) δ 7.83 (dd, J=3.1, 4.8 Hz, 2H), 7.70 (dd, J=3.0, 5.0 Hz, 2H), 5.64-5.55 (m, 1H), 5.49-5.36 (m, 1H), 4.15 (d, J=6.1 Hz, 2H), 3.73 (t, J=7.1 Hz, 2H), 2.45 (q, J=7.1 Hz, 2H), 0.84 (s, 8H), 0.00 (s, 6H)

(Z)-5-[tert-butyl(dimethyl)silyl]oxypent-3-en-1-amine

To a solution of compound 209-3 (120.0 mg, 0.34 mmol, 1 eq) in EtOH (3 mL) was added NH₂NH₂·H₂O (40.9 mg, 0.69 mmol, 39.7 uL, 85% solution, 2 eq). The reaction was stirred at 25° C. for 1 hr. The reaction was filtered and concentrated. Compound 209-4 (50 mg, 0.23 mmol, 66.8% yield) was used for next step directly as colorless oil.

N—[(Z)-5-[tert-butyl(dimethyl)silyl]oxypent-3-enyl]-5-[4-(trifluoromethyl)phenyl]naphthalene-2-carboxamide To a solution of compound 209-4a (73.4 mg, 0.23 mmol, 1 eq), HATU (132.3 mg, 0.34 mmol, 1.5 eq) and DIEA (90.0 mg, 0.69 mmol, 0.12 mL, 3 eq) in DCM (3 mL) was added compound 209-4 (50.0 mg, 0.23 mmol, 1 eq). The reaction was stirred at 25° C. for 16 hr. The reaction was diluted with DCM (20 mL) and washed with H₂O (2*5 mL). The organic layer was dried over Na₂SO₄ and concentrated. The crude product was purified by column chromatography on silica gel (EA:PE=1:5) to give compound 209-5 (100 mg, 0.18 mmol, 78.0% yield) as a white solid. ¹H NMR (400 MHz, CDCl₃) δ 8.37 (s, 1H), 7.99 (d, J=8.1 Hz, 1H), 7.89-7.83 (m, 1H), 7.81-7.74 (m, 3H), 7.65-7.59 (m, 3H), 7.51 (d, J=7.0 Hz, 1H), 6.45 (br s, 1H), 5.79-5.69 (m, 1H), 5.58-5.51 (m, 1H), 4.31-4.12 (m, 2H), 3.58 (q, J=6.3 Hz, 2H), 2.48 (q, J=7.0 Hz, 2H), 0.89-0.82 (m, 9H), 0.03 (s, 6H).

N-[(E)-5-hydroxypent-3-enyl]-5-[4-(trifluoromethyl)phenyl]naphthalene-2-carboxamide To a solution of compound 209-5 (90.0 mg, 0.17 mmol, 1 eq) in THF (2 mL) was added TBAF (1 M, 0.43 mL, 2.5 eq). The reaction was stirred at 25° C. for 1 hr. The reaction was concentrated. The crude product was purified by column chromatography on silica gel (EA:PE=1:10~1:0) to give the title compound (35 mg, 85.8 umol, 49.0% yield) as a white solid. LCMS (ESI): RT=0.932 min, mass calcd. For C₂₃H₂₀F₃NO₂, 399.14 m/z found 422.1 [M+Na]⁺. ¹H NMR (400 MHz, CDCl₃) δ 8.41 (s, 1H), 7.98 (d, J=8.1 Hz, 1H), 7.88-7.80 (m, 2H), 7.78 (br d, J=8.3 Hz, 2H), 7.64-7.56 (m, 3H), 7.50 (d, J=7.0 Hz, 1H), 6.77 (br s, 1H), 5.92-5.82 (m, 1H), 5.75-5.64 (m, 1H), 5.75-5.64 (m, 1H), 4.25 (br d, J=6.6 Hz, 2H), 3.59 (q, J=6.1 Hz, 2H), 2.52 (q, J=6.9 Hz, 2H), 1.64 (br s, 1H).

Example 210: (S)—N-(1-Methoxypropan-2-yl)-5-(4-(trifluoromethyl)phenyl)quinoline-2-carboxamide (Compound 246)

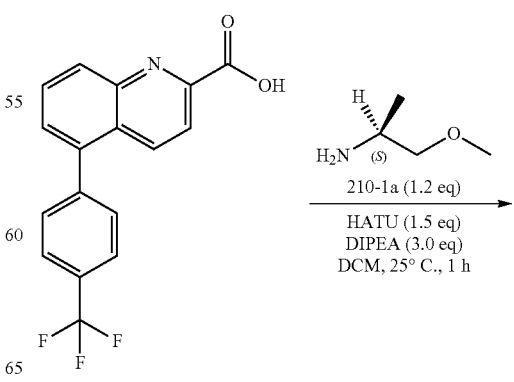

210-1

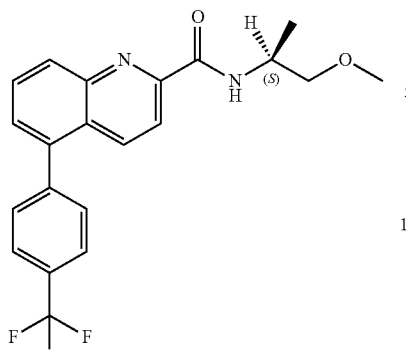

Compound 246

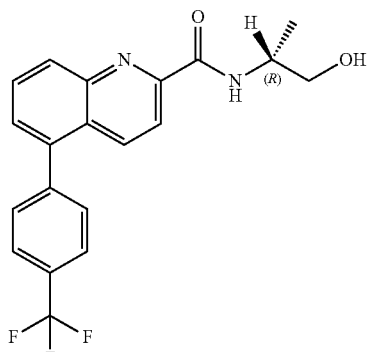

Compound 247

(S)—N-(1-Methoxypropan-2-yl)-5-(4-(trifluoromethyl)phenyl)quinoline-2-carboxamide To a solution of compound 210-1 (50.0 mg, 0.14 mmol, 1.0 eq, HCl), compound 210-1a (15.1 mg, 0.17 mmol, 1.2 eq) and DIPEA (54.8 mg, 0.42 mmol, 3.0 eq) in DCM (2 mL) was added HATU (80.6 mg, 0.21 mmol, 1.5 eq). The reaction mixture was stirred at 25° C. for 1 hour. The mixture was diluted with water (5 mL) and the resultant mixture was extracted with DCM (10 mL*3). The combined organic layers were dried over $Na_2SO_4$, filtered and concentrated to dryness under reduced pressure. The residue was purified by prep-HPLC (column: Waters Xbridge 150*50 10u; mobile phase: [water (0.05% ammonia hydroxide v/v)-ACN]; B %: 63%-93%, 7.8 min) to give the title compound (36.03 mg, 64.9% yield) as a white solid. LCMS (ESI): RT=1.011 min, mass calcd. for $C_{21}H_{19}F_3N_2O_2$ 388.14, m/z found 389.0 [M+H]$^+$; $^1$H NMR (400 MHz, CDCl$_3$) δ 8.37 (d, J=8.3 Hz, 1H), 8.33-8.26 (m, 2H), 8.21 (d, J=8.5 Hz, 1H), 7.87-7.78 (m, 3H), 7.63-7.55 (m, 3H), 4.51-4.38 (m, 1H), 3.57 (d, J=4.8 Hz, 2H), 3.45 (s, 3H), 1.39 (d, J=6.8 Hz, 3H).

Example 211: (R)—N-(1-Hydroxypropan-2-yl)-5-(4-(trifluoromethyl)phenyl)quinoline-2-carboxamide (Compound 247)

(R)—N-(1-Hydroxypropan-2-yl)-5-(4-(trifluoromethyl)phenyl)quinoline-2-carboxamide To a solution of compound 211-1 (50.0 mg, 0.14 mmol, 1.0 eq, HCl), compound 211-1a (12.7 mg, 0.17 mmol, 1.2 eq) and DIPEA (54.8 mg, 0.42 mmol, 3.0 eq) in DCM (2 mL) was added HATU (80.6 mg, 0.21 mmol, 1.5 eq). The reaction mixture was stirred at 25° C. for 1 hour. The mixture was diluted with water (5 mL) and the resultant mixture was extracted with DCM (10 mL*3). The combined organic layers were dried over $Na_2SO_4$, filtered and concentrated to dryness under reduced pressure. The residue was purified by prep-HPLC (column: Xtimate C18 150*25 mm*5 um; mobile phase: [water (0.05% HCl)-ACN]; B %: 54%-54%, 11 min) to give the title compound (6.84 mg, 11.4% yield, HCl) as a white solid. LCMS (ESI): RT=0.921 min, mass calcd. for $C_{20}H_{17}F_3N_2O_2$ 374.12, m/z found 375.0 [M+H]$^+$; $^1$H NMR (400 MHz, DMSO-d$_6$) δ 8.62 (d, J=8.5 Hz, 1H), 8.37 (d, J=8.8 Hz, 1H), 8.25 (d, J=8.5 Hz, 1H), 8.17 (d, J=8.8 Hz, 1H), 8.00-7.92 (m, 3H), 7.77 (d, J=8.0 Hz, 2H), 7.73 (dd, J=1.0, 7.3 Hz, 1H), 4.16-4.05 (m, 1H), 3.58-3.50 (m, 2H), 1.23 (d, J=6.8 Hz, 3H).

Example 212: N-isopropyl-5-(4-(trifluoromethyl)phenyl)quinoline-2-carboxamide (Compound 248)

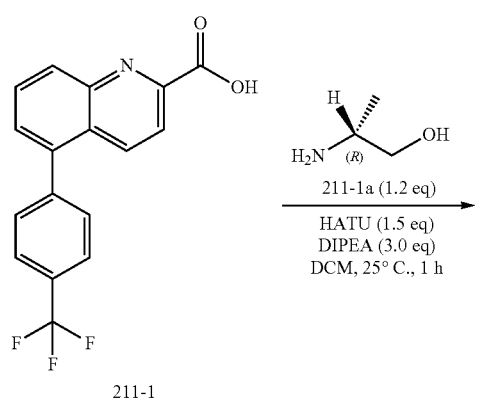

211-1

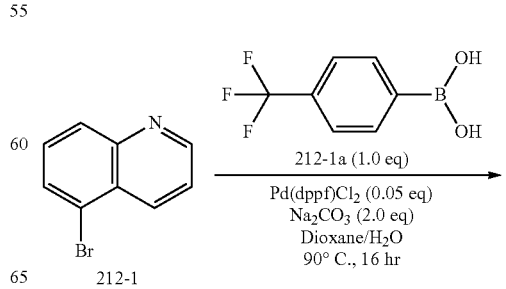

212-1

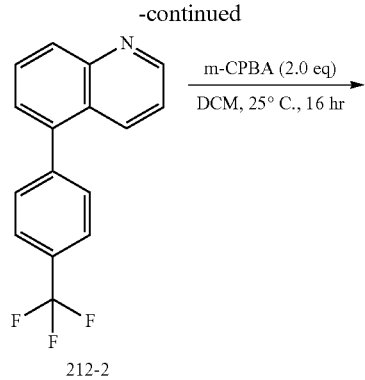

212-2

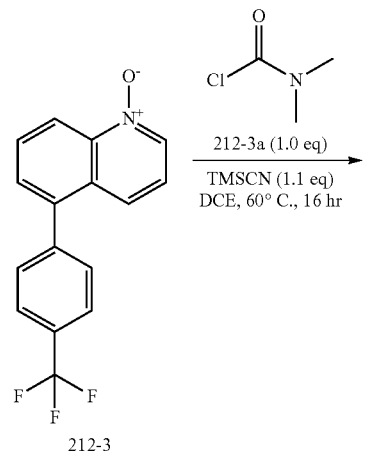

212-3

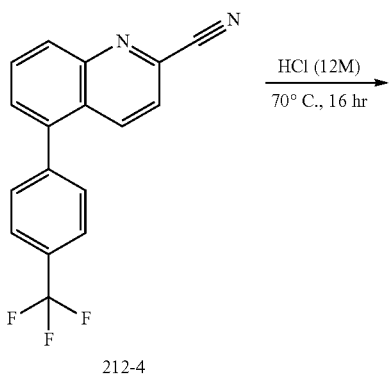

212-4

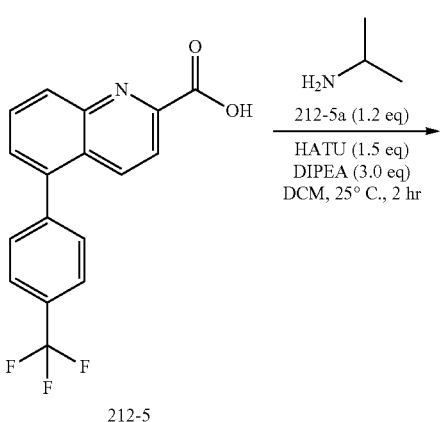

212-5

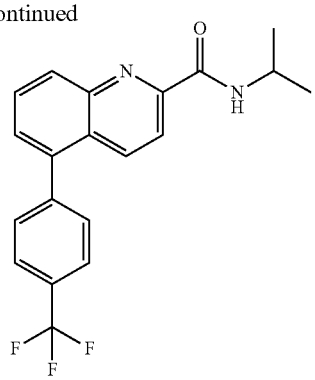

Compound 248

5-(4-(Trifluoromethyl)phenyl)quinoline

To a solution of compound 212-1 (500.0 mg, 2.40 mmol, 1.0 eq), compound 212-1a (456.4 mg, 2.40 mmol, 1.0 eq) and $Na_2CO_3$ (509.4 mg, 4.81 mmol, 2.0 eq) in Dioxane (10 mL) and $H_2O$ (2 mL) was added $Pd(dppf)Cl_2$ (87.9 mg, 0.12 mmol, 0.05 eq) under $N_2$. The reaction mixture was stirred at 90° C. for 16 hours under $N_2$. The reaction mixture was concentrated under reduced pressure. The mixture was diluted with water (20 mL) and the resultant mixture was extracted with EA (30 mL*3). The combined organic layers were dried over $Na_2SO_4$, filtered and concentrated to dryness under reduced pressure. The residue was purified by column chromatography over silica gel (petroleum ether: ethyl acetate=1:0 to 10:1) to give 212-2 (600 mg, 91.3% yield) as light yellow oil.

5-(4-(Trifluoromethyl)phenyl)quinoline 1-oxide

To a solution of compound 212-2 (500.0 mg, 1.83 mmol, 1.0 eq) in DCM (10 mL) was added w-CPBA (742.9 mg, 3.66 mmol, 85%, 2.0 eq). The reaction mixture was stirred at 25° C. for 16 hours. The mixture was diluted with NaOH (30 mL, 1M) and the resultant mixture was extracted with DCM (50 mL*2). The combined organic layers were washed with NaOH (25 mL, 1M), brine (25 mL), dried over $Na_2SO_4$, filtered and concentrated to dryness under reduced pressure to give 212-3 (480 mg, crude) as a white solid.

5-(4-(Trifluoromethyl)phenyl)quinoline-2-carbonitrile

To a solution of compound 212-3 (480.0 mg, 1.66 mmol, 1.0 eq) in DCE (6 mL) were added TMSCN (181.0 mg, 1.83 mmol, 1.1 eq) and compound 212-3a (178.4 mg, 1.66 mmol, 1.0 eq). The reaction mixture was stirred at 60° C. for 16 hours. The reaction mixture was concentrated under reduced pressure. The mixture was diluted with water (20 mL) and the resultant mixture was extracted with EA (30 mL*3). The combined organic layers were dried over $Na_2SO_4$, filtered and concentrated to dryness under reduced pressure. The residue was purified by column chromatography over silica gel (petroleum ether:ethyl acetate=1:0 to 10:1) to give 212-4 (450 mg, 90.9% yield) as a white solid.

5-(4-(Trifluoromethyl)phenyl)quinoline-2-carboxylic acid

A mixture of compound 212-4 (450.0 mg, 1.51 mmol, 1.0 eq) in con. HCl (5 mL, 12M) was stirred at 70° C. for 16 hours. The reaction mixture was cooled to 25° C., and then the suspension was filtered to give 212-5 (500 mg, crude) as a white solid.

N-isopropyl-5-(4-(trifluoromethyl)phenyl)quinoline-2-carboxamide

To a solution of compound 212-5 (50.0 mg, 0.14 mmol, 1.0 eq, HCl), compound 212-5a (10.0 mg, 0.17 mmol, 1.2 eq) and DIPEA (54.8 mg, 0.42 mmol, 3.0 eq) in DCM (2 mL) was added HATU (80.6 mg, 0.21 mmol, 1.5 eq). The reaction mixture was stirred at 25° C. for 2 hours. The mixture was diluted with water (5 mL) and the resultant mixture was extracted with DCM (10 mL*3). The combined organic layers were dried over Na$_2$SO$_4$, filtered and concentrated to dryness under reduced pressure. The residue was purified by prep-HPLC (column: Waters Xbridge 150*50 10u; mobile phase: [water (0.05% ammonia hydroxide v/v)-ACN]; B %: 65%-95%, 7.8 min) to give the title compound (29.20 mg, 57.6% yield) as a white solid. LCMS (ESI): RT=1.032 min, mass calcd. for C$_{20}$H$_{17}$F$_3$N$_2$O 358.13, m/z found 359.0 [M+H]$^+$; $^1$H NMR (400 MHz, CDCl$_3$) δ 8.29 (d, J=1.3 Hz, 2H), 8.19 (d, J=8.3 Hz, 1H), 8.12 (d, J=8.0 Hz, 1H), 7.86-7.77 (m, 3H), 7.63-7.55 (m, 3H), 4.43-4.28 (m, 1H), 1.37 (d, J=6.5 Hz, 6H).

Example 213: N-(4-chlorobutyl)-5-(4-(trifluoromethyl)phenyl)-2-naphthamide (Compound 249) and N-(4-hydroxybutyl)-5-(4-(trifluoromethyl)phenyl)-2-naphthamide (Compound 255)

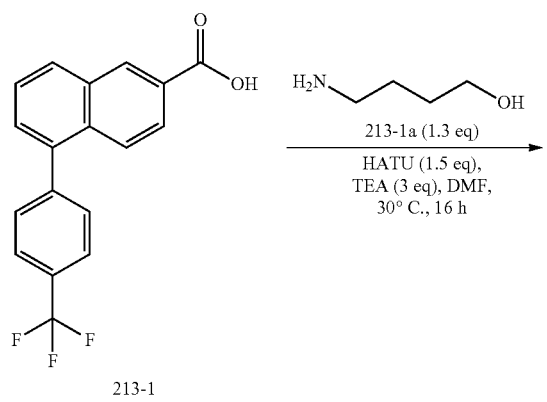

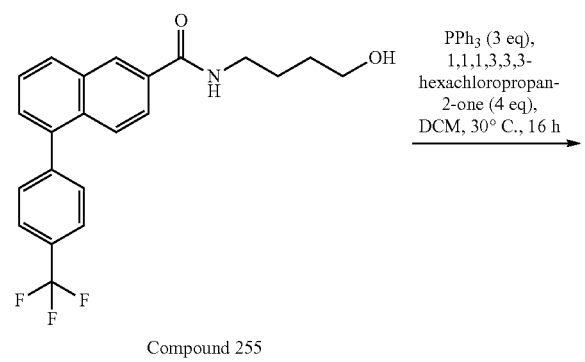

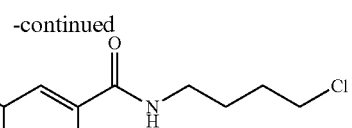

Compound 249

N-(4-hydroxybutyl)-5-(4-(trifluoromethyl)phenyl)-2-naphthamide (Compound 255)

To a solution of 213-1 (50 mg, 0.16 mmol, 1 eq), 213-1a (18.3 mg, 0.21 mmol, 19 uL, 1.3 eq) and HATU (90.2 mg, 0.24 mmol, 1.5 eq) in DMF (1 mL) at 30° C. was added TEA (48.0 mg, 0.47 mmol, 66 uL, 3 eq). The resulting mixture was stirred at 30° C. for 16 h. The reaction mixture was diluted with water (20 mL) and extracted with EA (20 mL*3). The combined organic layers were washed with brine (20 mL), dried over Na$_2$SO$_4$, filtered and concentrated under reduced pressure to give a residue. The residue was purified by flash silica gel chromatography (ISCO®; 4 g SepaFlash® Silica Flash Column, Eluent of 0~100% Ethylacetate/Petroleum ether gradient @ 20 mL/min) to give Compound 255 (50 mg, 0.13 mmol, 81.6% yield) as a white solid. LCMS (ESI): RT=0.814 min, mass calc. for C$_{22}$H$_{20}$F$_3$NO$_2$ 387.14, m/z found 388.0 [M+H]$^+$; $^1$H NMR (400 MHz, CDCl$_3$) δ 8.39 (d, J=1.8 Hz, 1H), 7.99 (d, J=8.3 Hz, 1H), 7.89-7.85 (m, 1H), 7.83-7.75 (m, 3H), 7.65-7.58 (m, 3H), 7.51 (dd, J=1.3, 7.0 Hz, 1H), 6.65 (brs, 1H), 3.77 (t, J=5.9 Hz, 2H), 3.59 (q, J=6.7 Hz, 2H), 1.86-1.77 (m, 2H), 1.77-1.70 (m, 2H).

N-(4-chlorobutyl)-5-(4-(trifluoromethyl)phenyl)-2-naphthamide (Compound 249)

To a solution of Compound 255 (30 mg, 77.4 umol, 1 eq) and PPh$_3$ (60.9 mg, 0.23 mmol, 3 eq) in DCM (2 mL) at 30° C. was added 1,1,1,3,3,3-hexachloropropan-2-one (82.0 mg, 0.31 mmol, 47 uL, 4 eq), and the mixture was stirred at 30° C. for 16 h. The mixture was concentrated to give a residue. The residue was purified by flash silica gel chromatography (ISCO®; 4 g SepaFlash® Silica Flash Column, Eluent of 0-50% Ethylacetate/Petroleum ether gradient @ 20 mL/min) to give Compound 249 (21.8 mg, 53.7 umol, 69.4% yield) as a white solid. LCMS (ESI): RT=0.921 min, mass calc. for C$_{22}$H$_{19}$ClF$_3$NO 405.11, m/z found 405.9 [M+H]$^+$; $^1$H NMR (400 MHz, CDCl$_3$) δ 8.37 (s, 1H), 7.99 (d, J=8.3 Hz, 1H), 7.91-7.85 (m, 1H), 7.78 (d, J=8.4 Hz, 3H), 7.66-7.58 (m, 3H), 7.51 (d, J=7.0 Hz, 1H), 6.34 (brs, 1H), 3.67-3.55 (m, 4H), 1.97-1.82 (m, 4H).

Example 214: N-(1-(pyridin-2-yl)cyclopropyl)-5-(4-(trifluoromethyl)phenyl)-2-naphthamide (Compound 250)

Example 215: (S)—N-(1-cyclobutylethyl)-5-(4-(trifluoromethyl)phenyl)-2-naphthamide (Compound 251) and (R)—N-(1-cyclobutylethyl)-5-(4-(trifluoromethyl)phenyl)-2-naphthamide (Compound 252)

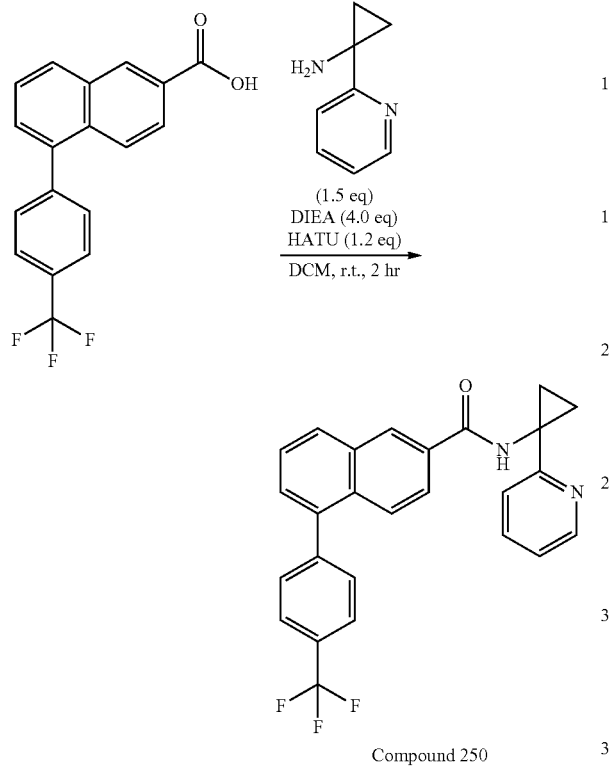

Compound 250

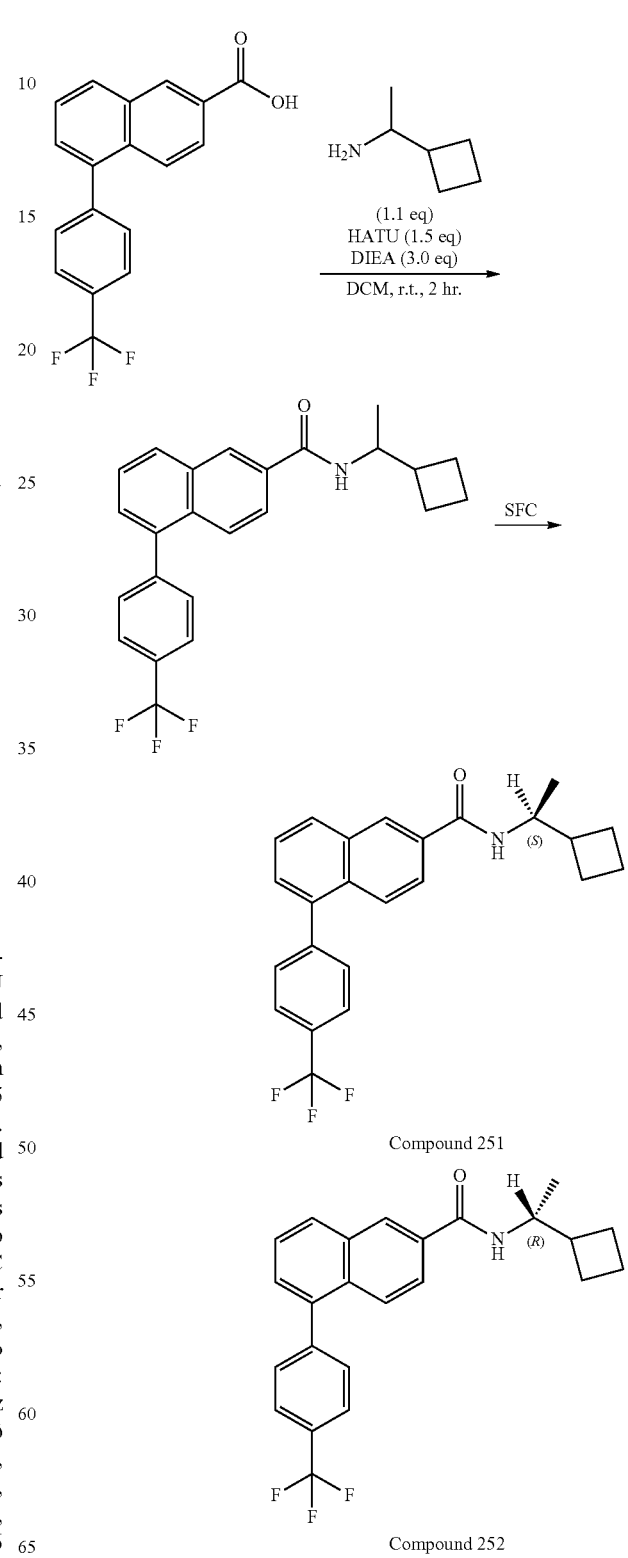

N-(1-(pyridin-2-yl)cyclopropyl)-5-(4-(trifluoromethyl)phenyl)-2-naphthamide

To a solution of 5-[4-(trifluoromethyl)phenyl]naphthalene-2-carboxylic acid (50 mg, 0.15 mmol, 1 eq) and HATU (72.1 mg, 0.18 mmol, 1.2 eq) in DCM (2 mL) was added DIPEA (61.3 mg, 0.47 mmol, 82.6 uL, 3 eq). After addition, the mixture was stirred at 25° C. for 0.5 hr, and then 1-(2-pyridyl)cyclopropanamine (127.2 mg, 0.23 mmol, 1.5 eq) was added. The resulting mixture was stirred at 25° C. for 1.5 hr. The reaction mixture was added $H_2O$ (20 mL) and extracted with EA (15 mL*3). The combined organic layers were washed with brine (20 mL), dried with anhydrous $Na_2SO_4$, filtered and concentrated under reduced pressure to give a residue. The residue was purified by prep-HPLC (column: Waters Xbridge 150*25 5u; mobile phase: [water (0.05% ammonia hydroxide v/v)-ACN]; B %: 60%-90%, 9.5 min). The title compound (26.3 mg, 60.8 umol, 38.4% yield) was obtained as a yellow solid. LCMS (ESI): RT=0.784 min, mass calcd for $C_{26}H_{19}F_3N_2O$ 432.44 m/z found 455.1 [M+Na]+, $^1$H NMR (400 MHz, DMSO-$d_6$) δ 9.47 (s, 1H), 8.67 (d, J=1.5 Hz, 1H), 8.46 (d, J=4.3 Hz, 1H), 8.15 (d, J=8.3 Hz, 1H), 8.00 (dd, J=1.8, 8.8 Hz, 1H), 7.93 (d, J=8.0 Hz, 2H), 7.84 (d, J=8.8 Hz, 1H), 7.77-7.66 (m, 4H), 7.61 (dd, J=1.0, 7.3 Hz, 1H), 7.38 (d, J=8.0 Hz, 1H), 7.16 (dt, J=1.0, 6.1 Hz, 1H), 1.63-1.54 (m, 2H), 1.35-1.28 (m, 2H).

N-(1-cyclobutylethyl)-5-(4-(trifluoromethyl)phenyl)-2-naphthamide

The mixture of 5-[4-(trifluoromethyl)phenyl]naphthalene-2-carboxylic acid (100 mg, 0.31 mmol, 1 eq), HATU (180.3 mg, 0.47 mmol, 1.5 eq) and DIPEA (122.5 mg, 0.94 mmol, 0.16 mL, 3 eq) in DCM (2 mL) was stirred at 25° C. for 1 hr. Then 1-cyclobutylethanamine (47.1 mg, 0.34 mmol, 1.1 eq, HCl) was added into the mixture and the mixture was stirred at 25° C. for another 1 hr. The reaction mixture was diluted with H₂O (10 mL) and the mixture was extracted with EA (10 mL*3). The combined organic phase was washed with brine (10 mL*2), dried with anhydrous Na₂SO₄, filtered and concentrated in vacuum. The residue was purified by column chromatography (SiO₂, Petroleum ether/Ethyl acetate=1:0 to 5:1). Compound N-(1-cyclobutylethyl)-5-[4-(trifluoromethyl)phenyl]naphthalene-2-carboxamide (99 mg, 0.24 mmol, 78.0% yield) was obtained as a white solid.

(S)—N-(1-cyclobutylethyl)-5-(4-(trifluoromethyl)phenyl)-2-naphthamide (Compound 251) and (R)—N-(1-cyclobutylethyl)-5-(4-(trifluoromethyl)phenyl)-2-naphthamide (Compound 252)

The racemic compound N-(1-cyclobutyl ethyl)-5-[4-(trifluoromethyl)phenyl]naphthalene-2-carboxamide (99 mg, 0.24 mmol, 1 eq) was separated by SFC (column: REGIS (s,s) WHELK-O1 (250 mm*30 mm, 5 um); mobile phase: [0.1% NH₃H₂O ETOH]; B %: 40%-40%, min). Compound 252 (10.7 mg, 26.8 umol, 10.7% yield) was obtained as a white solid. LCMS (ESI): RT=1.065 min, mass calcd for C₂₄H₂₂F₃NO 397.43 m/z found 398.0[M+H]⁺, ¹H NMR (400 MHz, CD₃OD) δ 8.43 (s, 1H), 8.06 (d, J=8.3 Hz, 1H), 7.90-7.78 (m, 4H), 7.73-7.61 (m, 3H), 7.56 (d, J=7.0 Hz, 1H), 4.23-4.09 (m, 1H), 2.50 (br d, J=6.0 Hz, 1H), 2.19-2.01 (m, 2H), 1.99-1.77 (m, 4H), 1.17 (d, J=6.5 Hz, 3H). Compound 251 (12.7 mg, 31.8 umol, 12.8% yield) was obtained as a white solid. LCMS (ESI): RT=1.068 min, mass calcd for C₂₄H₂₂F₃NO 397.43 m/z found 398.0 [M+H]⁺, ¹H NMR (400 MHz, CD₃OD) δ 8.45 (s, 1H), 8.07 (d, J=8.0 Hz, 1H), 7.90-7.82 (m, 4H), 7.72-7.64 (m, 3H), 7.57 (dd, J=1.3, 7.0 Hz, 1H), 4.23-4.13 (m, 1H), 2.58-2.45 (m, 1H), 2.16-2.02 (m, 2H), 1.97-1.79 (m, 4H), 1.18 (d, J=6.8 Hz, 3H).

Example 216: (S)—N-(1-(1-methyl-1H-imidazol-2-yl)ethyl)-5-(4-(trifluoromethyl)phenyl)-2-naphthamide (Compound 253) and (R)—N-(1-(1-methyl-1H-imidazol-2-yl)ethyl)-5-(4-(trifluoromethyl)phenyl)-2-naphthamide (Compound 254)

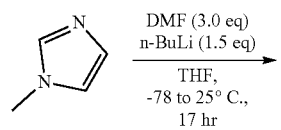

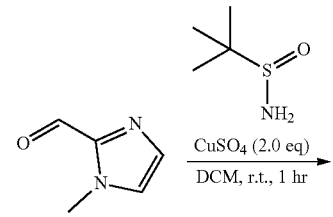

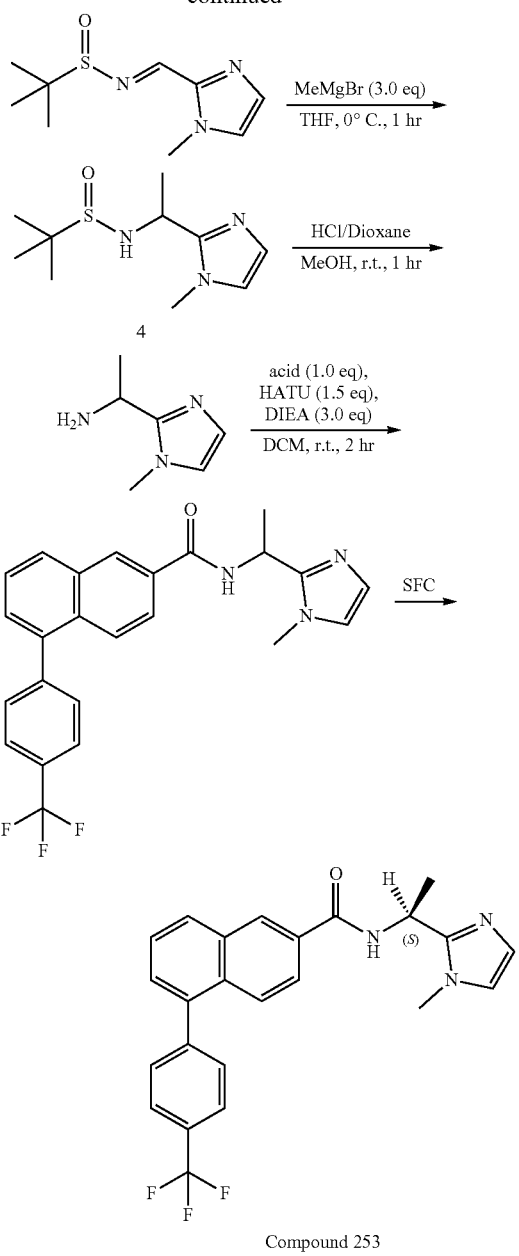

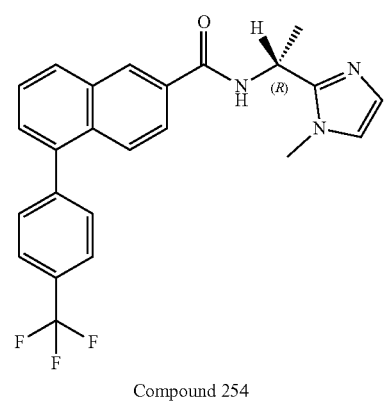

Compound 253

Compound 254

1-methyl-1H-imidazole-2-carbaldehyde

To a solution of 1-methylimidazole (3 g, 36.54 mmol, 2.91 mL, 1 eq) in THF (30 mL) was added n-BuLi (2.5 M, 21.92 mL, 1.5 eq) dropwise at −78° C. under $N_2$ atmosphere. After stirring 1 hr, DMF (8.01 g, 109.62 mmol, 8.43 mL, 3 eq) was added dropwise and the mixture was stirred for another 16 hr at 25° C. The reaction mixture was diluted with $H_2O$ (10 mL). The mixture was extracted with DCM (20 mL*3). The combined organic phase was washed with brine (10 mL*3), dried with anhydrous $Na_2SO_4$, filtered and concentrated in vacuum. The residue was purified by column chromatography ($SiO_2$, Petroleum ether/Ethyl acetate=1/0 to 1:1). Compound 1-methylimidazole-2-carbaldehyde (1 g, 9.08 mmol, 24.8% yield) was obtained as yellow oil.

(E)-2-methyl-N-((1-methyl-1H-imidazol-2-yl)methylene)propane-2-sulfinamide

The mixture of 1-methylimidazole-2-carbaldehyde (1 g, 9.08 mmol, 1 eq), $CuSO_4$ (2.90 g, 18.16 mmol, 2.79 mL, 2 eq) and 2-methylpropane-2-sulfinamide (660.4 mg, 5.45 mmol, 0.6 eq) in DCM (5 mL) was stirred at 25° C. for 1 hr. The reaction mixture was diluted with $H_2O$ (10 mL) and the mixture was extracted with EA (10 mL*3). The combined organic phase was washed with brine (10 mL*3), dried with anhydrous $Na_2SO_4$, filtered and concentrated in vacuum. The residue was purified by column chromatography ($SiO_2$, Petroleum ether/Ethyl acetate=1/0 to 0:1). Compound (NE)-2-methyl-N-[(1-methylimidazol-2-yl)methylene]propane-2-sulfinamide (500 mg, 2.34 mmol, 25.8% yield) was obtained as yellow oil.

2-methyl-N-(1-(1-methyl-1H-imidazol-2-yl)ethyl)propane-2-sulfinamide

To a solution of (NE)-2-methyl-N-[(1-methylimidazol-2-yl)methylene]propane-2-sulfinamide (500 mg, 2.34 mmol, 1 eq) in THF (3 mL) was added dropwise MeMgBr (3 M, 2.34 mL, 3 eq). The mixture was stirred at 0° C. for 1 hr. The reaction mixture was diluted with $H_2O$ (10 mL) and the mixture was extracted with EA (10 mL*3). The combined organic phase was washed with brine (10 mL*3), dried with anhydrous $Na_2SO_4$, filtered and concentrated in vacuum. The residue was purified by column chromatography ($SiO_2$, EA/MeOH=1/0 to 5:1). Compound 2-methyl-N-[1-(1-methylimidazol-2-yl)ethyl]propane-2-sulfinamide (90 mg, 0.39 mmol, 16.7% yield) was obtained as white solid.

1-(1-methyl-1H-imidazol-2-yl)ethanamine

The mixture of 2-methyl-N-[1-(1-methylimidazol-2-yl)ethyl]propane-2-sulfinamide (90 mg, 0.39 mmol, 1 eq) and HCl/dioxane (4 M, 98.11 uL, 1 eq) in MeOH (1 mL) was stirred at 25° C. for 1 hr. The reaction mixture was concentrated under reduced pressure to remove solvent. Compound 1-(1-methylimidazol-2-yl)ethanamine (50 mg, crude) was obtained as yellow solid.

N-(1-(1-methyl-1H-imidazol-2-yl)ethyl)-5-(4-(trifluoromethyl)phenyl)-2-naphthamide The mixture of 5-[4-(trifluoromethyl)phenyl]naphthalene-2-carboxylic acid (126.3 mg, 0.39 mmol, 1 eq), DIPEA (154.8 mg, 1.20 mmol, 0.20 mL, 3 eq) and HATU (227.8 mg, 0.59 mmol, 1.5 eq) in DCM (1 mL) was stirred at 25° C. for 1 hr. Then 1-(1-methylimidazol-2-yl)ethanamine (50 mg, 0.39 mmol, 1 eq) was added at the mixture and the mixture was stirred at 25° C. for another 1 hr. The reaction mixture was diluted with $H_2O$ (10 mL) and the mixture was extracted with EA (10 mL*3). The combined organic phase was washed with brine (10 mL*2), dried with anhydrous $Na_2SO_4$, filtered and concentrated in vacuum. The residue was purified by prep-HPLC (column: Waters Xbridge 150*25 5u; mobile phase: [water (0.05% ammonia hydroxide v/v)-ACN]; B %: 55%-85%, 7 min). Compound N-[1-(1-methylimidazol-2-yl)ethyl]-5-[4-(trifluoromethyl)phenyl]naphthalene-2-carboxamide (45 mg, 0.10 mmol, 26.6% yield) was obtained as white solid.

(S)—N-(1-(1-methyl-1H-imidazol-2-yl)ethyl)-5-(4-(trifluoromethyl)phenyl)-2-naphthamide (Compound 253) and (R)—N-(1-(1-methyl-1H-imidazol-2-yl)ethyl)-5-(4-(trifluoromethyl)phenyl)-2-naphthamide (Compound 254)

The compound N-[1-(1-methylimidazol-2-yl)ethyl]-5-[4-(trifluoromethyl)phenyl]naphthalene-2-carboxamide (45 mg, 0.10 mmol, 1 eq) was separated by SFC (column: DAICEL CHIRALPAK AD-H (250 mm*30 mm, 5 um); mobile phase: [0.1% $NH_3H_2O$ ETOH]; B %: 40%-40%, min). Compound 253 (15 mg, 35.4 umol, 33.3% yield) was obtained as white solid. LCMS (ESI): RT=0.868 min, mass calcd for $C_{24}H_{20}F_3N_3O$ 423.43 m/z found 424.0[M+H]$^+$, $^1$H NMR (400 MHz, $CD_3OD$) δ 8.52 (d, J=1.5 Hz, 1H), 8.07 (d, J=8.3 Hz, 1H), 7.92-7.82 (m, 4H), 7.70-7.64 (m, 3H), 7.57 (dd, J=1.3, 7.0 Hz, 1H), 7.05 (d, J=1.3 Hz, 1H), 6.94 (d, J=1.3 Hz, 1H), 5.53 (q, J=7.0 Hz, 1H), 3.81-3.73 (m, 3H), 1.69 (d, J=7.0 Hz, 3H). Compound 254 (15 mg, 35.4 umol, 33.3% yield) was obtained as white solid. LCMS (ESI): RT=0.871 min, mass calcd for $C_{24}H_{20}F_3N_3O$ 423.43 m/z found 424.0[M+H]$^+$, $^1$H NMR (400 MHz, $CD_3OD$) δ 8.39 (d, J=1.3 Hz, 1H), 7.95 (d, J=8.3 Hz, 1H), 7.80-7.70 (m, 4H), 7.59-7.52 (m, 3H), 7.45 (dd, J=1.1, 7.1 Hz, 1H), 6.93 (d, J=0.9 Hz, 1H), 6.81 (d, J=1.0 Hz, 1H), 5.42-5.37 (m, 1H), 3.68-3.60 (m, 3H), 3.22-3.18 (m, 9H), 1.56 (d, J=7.0 Hz, 3H).

Example 217: N-(3-azidopropyl)-5-(4-(trifluoromethyl)phenyl)-2-naphthamide (Compound 256)

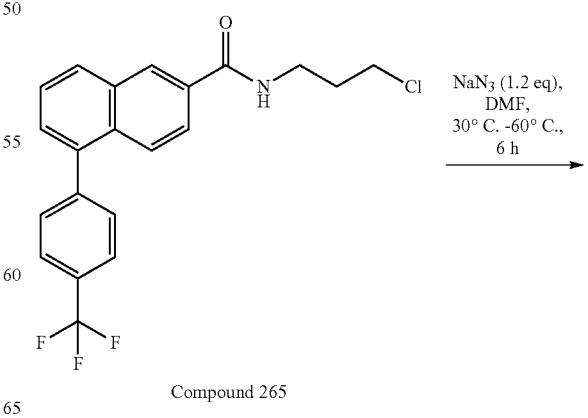

Compound 265

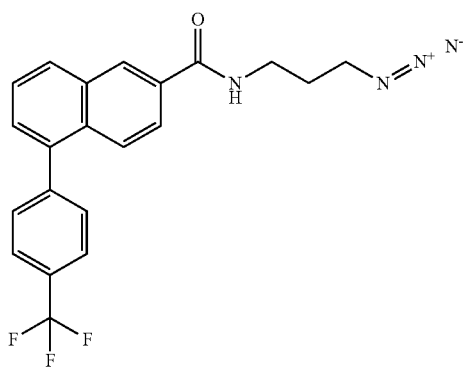

Compound 256

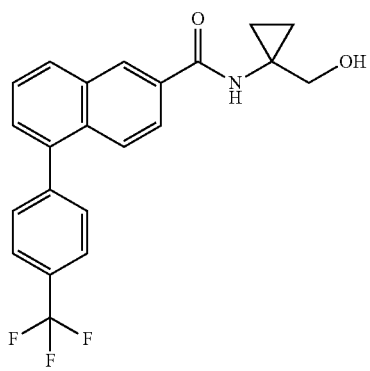

Compound 257

To a solution of Compound 265 (25 mg, 63.8 umol, 1 eq) in DMF (1 mL) at 30° C. was added NaN$_3$ (5.0 mg, 76.6 umol, 1.2 eq). The resulting mixture was stirred at 60° C. for 6 h. The reaction mixture was diluted with water (20 mL) and extracted with EA (20 mL*3). The combined organic layers were washed with brine (20 mL), dried over Na$_2$SO$_4$, filtered and concentrated under reduced pressure to give a residue (containing some DMF). The residue was purified by prep-HPLC (column: Waters Xbridge 150*50 10u; mobile phase: [water (0.05% ammonia hydroxide v/v)-ACN]; B %: 59%-89%, 10 min) to give Compound 256 (15.8 mg, 39.7 umol, 62.3% yield) as a white solid. LCMS (ESI): RT=0.898 min, mass calc. for C$_{21}$H$_{17}$F$_3$N$_4$O 398.14, m/z found 399.0 [M+H]$^+$; $^1$H NMR (400 MHz, CDCl$_3$) δ 8.38 (d, J=1.8 Hz, 1H), 8.00 (d, J=8.3 Hz, 1H), 7.91-7.85 (m, 1H), 7.78 (d, J=7.5 Hz, 3H), 7.65-7.58 (m, 3H), 7.52 (dd, J=1.1, 7.2 Hz, 1H), 6.55 (brs, 1H), 3.64 (q, J=6.5 Hz, 2H), 3.51 (t, J=6.5 Hz, 2H), 1.98 (quin, J=6.5 Hz, 2H).

To a solution 218-1 (25 mg, 79 umol, 1 eq) and HATU (45.1 mg, 0.12 mmol, 1.5 eq) in DMF (1 mL) at 30° C. were added 218-1a (8.3 mg, 95 umol, 1.2 eq) and TEA (24.0 mg, 0.24 mmol, 33 uL, 3 eq). The mixture was stirred at 30° C. for 16 h. The reaction mixture was concentrated under reduced pressure to give a residue, which was purified by prep-HPLC (column: Waters Xbridge 150*25 5u; mobile phase: [water (0.05% ammonia hydroxide v/v)-ACN]; B %: 49%-79%, 9 min) to give the title compound (16 mg, 42 umol, 52.5% yield) as a white solid. LCMS (ESI): RT=0.819 min, mass calc. for C$_{22}$H$_{18}$F$_3$NO$_2$ 385.13, m/z found 386.0 [M+H]$^+$; $^1$H NMR (400 MHz, CDCl$_3$) δ 8.35 (d, J=1.8 Hz, 1H), 7.99 (d, J=8.3 Hz, 1H), 7.87 (d, J=8.8 Hz, 1H), 7.81-7.73 (m, 3H), 7.65-7.59 (m, 3H), 7.53 (dd, J=1.1, 7.2 Hz, 1H), 6.81 (s, 1H), 3.94 (t, J=5.1 Hz, 1H), 3.77 (d, J=5.0 Hz, 2H), 1.10-1.06 (m, 2H), 1.05-1.01 (m, 2H)

Example 219: (R)—N-(1-amino-1-oxopropan-2-yl)-5-(4-(trifluoromethyl)phenyl)-2-naphthamide (Compound 258)

Example 218: N-(1-(hydroxymethyl)cyclopropyl)-5-(4-(trifluoromethyl)phenyl)-2-naphthamide (Compound 257)

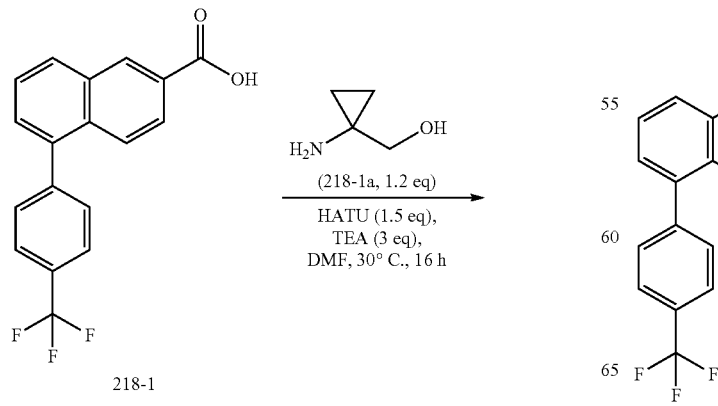

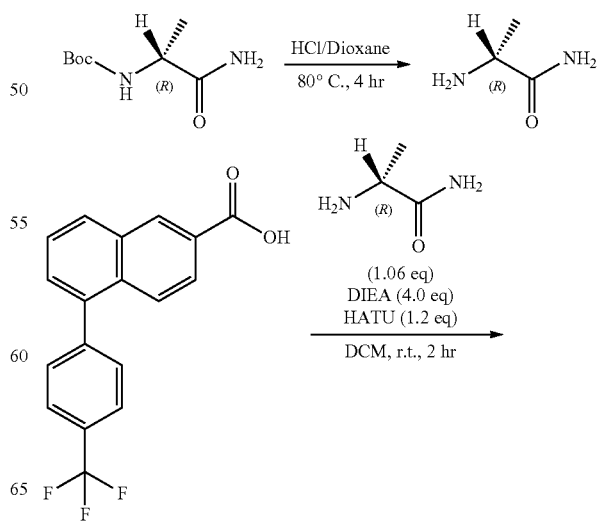

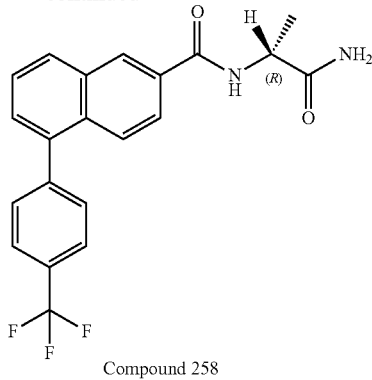

Compound 258

(R)-2-aminopropanamide

To a solution of tert-butyl N-[(1R)-2-amino-1-methyl-2-oxo-ethyl]carbamate (1 g, 5.31 mmol, 1 eq) in HCl/dioxane (4 M, 15 mL, 11.29 eq) was stirred at 80° C. for 4 hr. The reaction mixture was concentrated under reduced pressure. Compound (2R)-2-aminopropanamide (412 mg, 3.31 mmol, 62.2% yield, HCl) was obtained as a white solid. The crude product was used into the next step without further purification.

(R)—N-(1-amino-1-oxopropan-2-yl)-5-(4-(trifluoromethyl)phenyl)-2-naphthamide To a solution of 5-[4-(trifluoromethyl)phenyl]naphthalene-2-carboxylic acid (50 mg, 0.15 mmol, 1 eq) and HATU (72.1 mg, 0.18 mmol, 1.2 eq) in DCM (2 mL) was added DIPEA (81.7 mg, 0.63 mmol, 0.11 mL, 4 eq). After addition, the mixture was stirred at the same temperature (25° C.) for 0.5 hr, and then (2R)-2-aminopropanamide (20.8 mg, 0.16 mmol, 1.06 eq, HCl) was added. The mixture was stirred at 25° C. for 1.5 hr. The reaction mixture was added H$_2$O (20 mL) and extracted with EA (10 mL*3). The combined organic layers were washed with brine (20 mL), dried with anhydrous Na$_2$SO$_4$, filtered and concentrated under reduced pressure to give a residue. The residue was purified by prep-HPLC (column: Waters Xbridge 150*25 5u; mobile phase: [water (0.05% ammonia hydroxide v/v)-ACN]; B %: 50%-80%, 7 min). The title compound (36 mg, 93.1 umol, 58.9% yield) was obtained as a white solid. LCMS (ESI): RT=0.788 min, mass calcd for C$_{21}$H$_{17}$F$_3$N$_2$O$_2$ 386.37 m/z found 409.0 [M+Na]$^+$, NMR (400 MHz, DMSO-d$_6$) δ 8.69-8.58 (m, 2H), 8.14 (d, J=8.3 Hz, 1H), 8.03-7.89 (m, 3H), 7.82 (d, J=8.8 Hz, 1H), 7.78-7.66 (m, 3H), 7.60 (dd, J=1.0, 7.0 Hz, 1H), 7.44 (s, 1H), 7.04 (s, 1H), 4.49 (quin, J=7.2 Hz, 1H), 1.39 (d, J=7.3 Hz, 3H).

Example 220: (S)—N-(1-amino-1-oxopropan-2-yl)-5-(4-(trifluoromethyl)phenyl)-2-naphthamide (Compound 259)

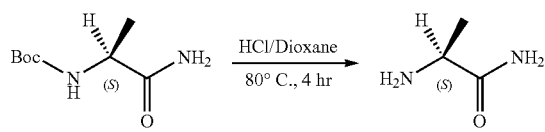

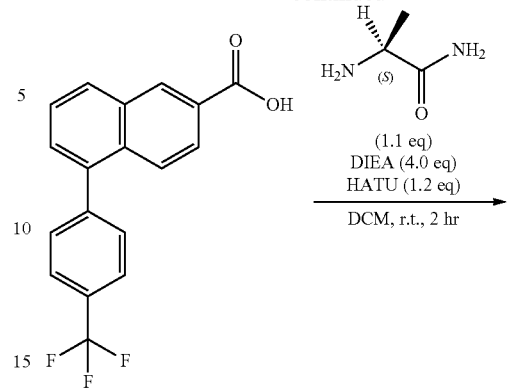

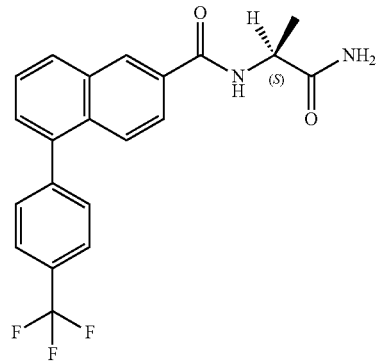

Compound 259

(S)-2-aminopropanamide

To a solution of tert-butyl N-[(1S)-2-amino-1-methyl-2-oxo-ethyl]carbamate (1 g, 5.31 mmol, 1 eq) in HCl/dioxane (4 M, 15 mL, 11.29 eq) was stirred at 80° C. for 4 hr. The reaction mixture was concentrated under reduced pressure. Compound (2S)-2-aminopropanamide (400 mg, 3.21 mmol, 60.44% yield, HCl) was obtained as a white solid. The crude product was used into the next step without further purification.

(S)—N-(1-amino-1-oxopropan-2-yl)-5-(4-(trifluoromethyl)phenyl)-2-naphthamide To a solution of 5-[4-(trifluoromethyl)phenyl]naphthalene-2-carboxylic acid (100 mg, 0.31 mmol, 1 eq) and HATU (144.2 mg, 0.37 mmol, 1.2 eq) in DCM (3 mL) was added DIEA (163.4 mg, 1.26 mmol, 0.22 mL, 4 eq). After addition, the mixture was stirred at 25° C. for 0.5 hr, and then (2S)-2-aminopropanamide (43.3 mg, 0.34 mmol, 1.1 eq, HCl) was added. The resulting mixture was stirred at 25° C. for 1.5 hr. The reaction mixture was added H$_2$O (50 mL) and extracted with EA (30 mL*3). The combined organic layers were washed with brine (20 mL), dried with anhydrous Na$_2$SO$_4$, filtered and concentrated under reduced pressure to give a residue. The residue was purified by prep-HPLC (column: Waters Xbridge 150*25 5u; mobile phase: [water (0.05% ammonia hydroxide v/v)-ACN]; B %: 50%-80%, 7 min). The title compound (80 mg, 0.20 mmol, 65.4% yield) was obtained as a white solid. LCMS (ESI): RT=0.789 min, mass calcd for C$_{21}$H$_{17}$F$_3$N$_2$O$_2$ 386.37 m/z found 409.0 [M+Na]$^+$, $^1$H NMR (400 MHz, DMSO-d$_6$) δ 8.67-8.59 (m, 2H), 8.13 (d, J=8.0 Hz, 1H), 8.00-7.89 (m, 3H), 7.81 (d, J=9.0 Hz, 1H), 7.77-7.67 (m, 3H), 7.60 (d, J=6.3 Hz, 1H), 7.43 (br s, 1H), 7.03 (s, 1H), 4.49 (quin, J=7.2 Hz, 1H), 1.38 (d, J=7.0 Hz, 3H).

Example 221: N-[2-hydroxy-1-(2-pyridyl)ethyl]-8-[4-(trifluoromethyl)phenyl]quinoline-3-carboxamide (Compound 260)

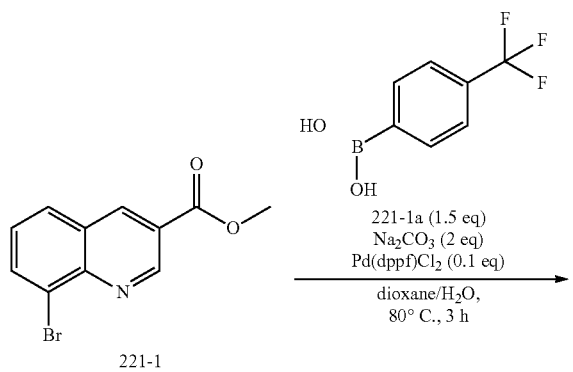

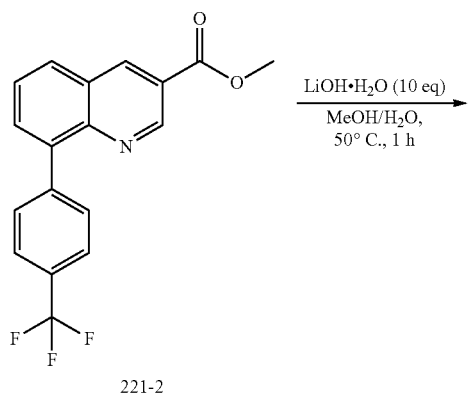

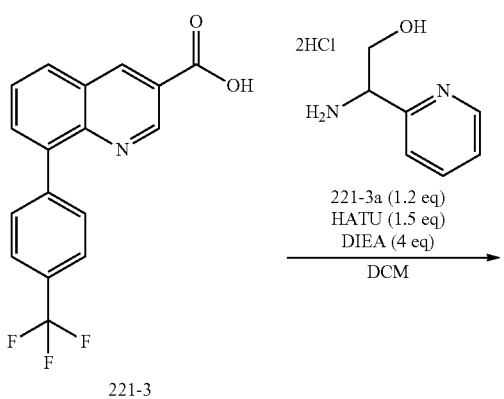

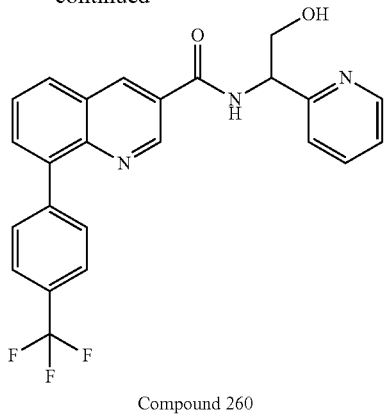

Compound 260

Methyl 8-[4-(trifluoromethyl)phenyl]quinoline-3-carboxylate

To a mixture of 221-1 (100 mg, 0.38 mmol, 1 eq) and 221-1a (107.1 mg, 0.56 mmol, 1.5 eq) in dioxane (3 mL) and $H_2O$ (0.5 mL) were added $Na_2CO_3$ (79.7 mg, 0.75 mmol, 2 eq) and Pd(dppf)Cl$_2$ (27.5 mg, 37.6 umol, 0.1 eq). The mixture was degassed and purged with $N_2$ for 3 times. The mixture was stirred at 80° C. for 3 h. LCMS detected the desired compound. The mixture was cooled to 25° C., diluted with water (10 mL) and extracted with EtOAc (20 mL*3). The combined organic layer was washed with brine (20 mL), dried over $Na_2SO_4$, filtered and concentrated. The residue was purified by column chromatography (SiO$_2$, Ethyl acetate/Petroleum ether=0% to 20%) to give methyl 221-2 (110 mg, 0.32 mmol, 84.8% yield) as white solid. LCMS (ESI): RT=0.912 min, mass calcd. for $C_{18}H_{12}F_3NO_2$ 331.08, m/z found 331.9 [M+H]$^+$.

8-[4-(trifluoromethyl)phenyl]quinoline-3-carboxylic acid

To a mixture of 221-2 (100 mg, 0.30 mmol, 1 eq) in MeOH (4 mL) and $H_2O$ (1 mL) was added LiOH·H$_2$O (126.7 mg, 3.02 mmol, 10 eq). The mixture was stirred at 50° C. for 1 h. The mixture was cooled to 25° C. and concentrated. The residue was diluted with water (15 mL), adjusted to pH=5~6 with HCl (1 M), extracted with EtOAc (20 mL*3). The combined organic layer was washed with brine (20 mL), dried over $Na_2SO_4$, filtered and concentrated to give 221-3 (100 mg, crude) as white solid. LCMS (ESI): RT=0.819 min, mass calcd. for $C_{17}H_{10}F_3NO_2$ 317.07, m/z found 317.9 [M+H]$^+$.

N-[2-hydroxy-1-(2-pyridyl)ethyl]-8-[4-(trifluoromethyl)phenyl]quinoline-3-carboxamide To a mixture of 221-3 (50 mg, 0.16 mmol, 1 eq) and HATU (89.9 mg, 0.24 mmol, 1.5 eq) in DCM (2 mL) was added DIEA (81.5 mg, 0.63 mmol, 0.11 mL, 4 eq). The mixture was stirred at 25° C. for 0.5 h. 221-3a (39.9 mg, 0.19 mmol, 1.2 eq, 2HCl salt) was added into the mixture. The mixture was stirred at 25° C. for 2 h. LCMS detected the desired compound. The mixture concentrated. The residue was purified by prep-HPLC (column: Xtimate C18 150*25 mm*5 um; mobile phase: [water (0.05% ammonia hydroxide v/v)-ACN]; B %: 45%-75%, 7.8 min) to give the title compound (39.6 mg, 90.7 umol, 57.5% yield) as white solid.

LCMS (ESI): RT=0.723 min, mass calcd. for $C_{24}H_{18}F_3N_3O_2$ 437.14, m/z found 438.0 [M+H]$^+$; $^1$H NMR (400 MHz, CDCl$_3$) δ 9.38 (d, J=2.4 Hz, 1H), 8.73 (d, J=2.0 Hz, 1H), 8.56 (d, J=4.0 Hz, 1H), 8.20 (br d, J=6.8 Hz, 1H), 7.99-7.97 (m, 1H), 7.82-7.70 (m, 7H), 7.51 (d, J=8.4 Hz, 1H), 7.31-7.28 (m, 1H), 5.43-5.39 (m, 1H), 4.19-4.15 (m, 1H), 4.09-4.05 (m, 1H).

Example 222: N-(2-azidoethyl)-5-(4-(trifluoromethyl)phenyl)-2-naphthamide (Compound 261)

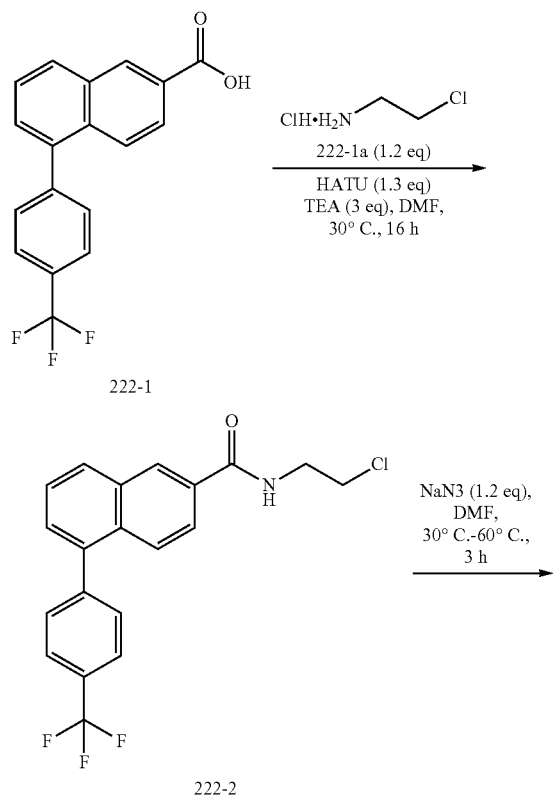

N-(2-chloroethyl)-5-(4-(trifluoromethyl)phenyl)-2-naphthamide

To a solution of 222-1 (50 mg, 0.16 mmol, 1 eq), 222-1a (22.0 mg, 0.19 mmol, 1.2 eq, HCl) and HATU (78.1 mg, 0.21 mmol, 1.3 eq) in DMF (1 mL) at 30° C. was added TEA (48.0 mg, 0.47 mmol, 66 uL, 3 eq). The resulting mixture was stirred at 30° C. for 16 h. The reaction mixture was diluted with water (20 mL) and extracted with EA (20 mL*3). The combined organic layers were washed with brine (20 mL), dried over Na$_2$SO$_4$, filtered and concentrated under reduced pressure to give a residue. The residue was purified by flash silica gel chromatography (ISCO®; 12 g SepaFlash® Silica Flash Column, Eluent of 0-50% Ethylacetate/Petroleum ether gradient @ 30 mL/min) and prep-TLC (PE:EA=3:1, UV) to give 222-2 (40 mg, 89.6 umol, 56.7% yield) as a white solid. LCMS (ESI): RT=0.886 min, mass calc. for $C_{20}H_{15}ClF_3NO$ 377.08, m/z found 377.9 [M+H]$^+$.

N-(2-azidoethyl)-5-(4-(trifluoromethyl)phenyl)-2-naphthamide

To a solution of 222-2 (40 mg, 0.11 mmol, 1 eq) in DMF (1 mL) at 30° C. was added NaN$_3$ (8.3 mg, 0.13 mmol, 1.2 eq). The resulting mixture was stirred at 60° C. for 3 h. The reaction mixture was quenched with water (10 mL) and extracted with EA (10 mL*3). The combined organic layers were washed with brine (10 mL), dried over Na$_2$SO$_4$, filtered and concentrated under reduced pressure to give a residue (containing some DMF). The residue was purified by prep-HPLC (column: Xtimate C18 150*25 mm*5 um; mobile phase: [water (0.05% ammonia hydroxide v/v)-ACN]; B %: 63%-93%, 9.5 min) to give the title compound (6.5 mg, 17.0 umol, 16.0% yield) as a white solid. LCMS (ESI): RT=0.875 min, mass calc. for $C_{20}H_{15}F_3N_4O$ 384.12, m/z found 385.0 [M+H]$^+$; $^1$H NMR (400 MHz, CDCl$_3$) δ 8.39 (d, J=1.5 Hz, 1H), 8.01 (d, J=8.0 Hz, 1H), 7.91-7.87 (m, 1H), 7.82-7.76 (m, 3H), 7.66-7.60 (m, 3H), 7.52 (dd, J=1.1, 7.2 Hz, 1H), 6.60 (brs, 1H), 3.72 (q, J=5.7 Hz, 2H), 3.67-3.60 (m, 2H).

Example 223: N-(2-(pyridin-2-yl) propan-2-yl)-5-(4-(trifluoromethyl)phenyl)-2-naphthamide (Compound 262)

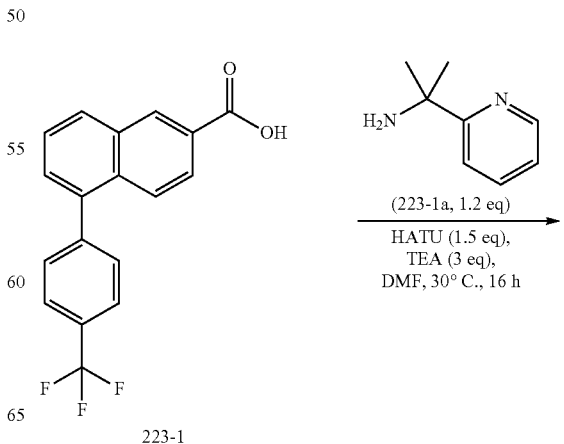

611

-continued

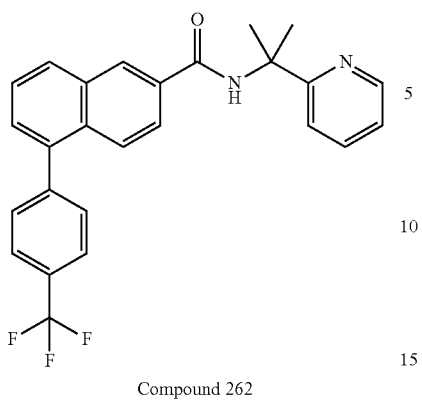

Compound 262

612

-continued

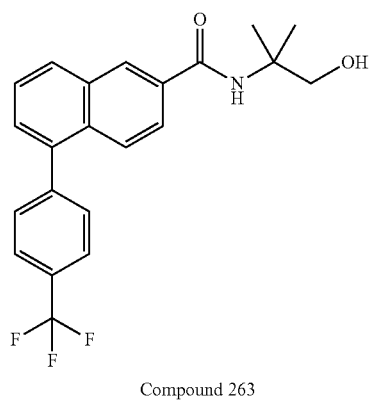

Compound 263

To a solution of 223-1 (25 mg, 79 umol, 1 eq) and HATU (45.1 mg, 0.12 mmol, 1.5 eq) in DMF (1 mL) at 30° C. were added 223-1a (12.9 mg, 95 umol, 1.2 eq) and TEA (24.00 mg, 0.24 mmol, 33 uL, 3 eq). The mixture was stirred at 30° C. for 16 h. The reaction mixture was concentrated under reduced pressure to give the residue which was purified by prep-HPLC (column: Xtimate C18 150*25 mm*5 um; mobile phase: [water (10 mM $NH_4HCO_3$)-ACN]; B %: 68%-78%, 8.5 min) to give the title compound (20 mg, 46 umol, 58.2% yield) as a white solid. LCMS (ESI): RT=0.789 min, mass calc. for $C_{26}H_{21}F_3N_2O$ 434.16 m/z found 435.0 [M+H]$^+$; $^1$H NMR (400 MHz, CDCl$_3$) δ 9.10 (s, 1H), 8.59 (td, J=0.8, 4.1 Hz, 1H), 8.52 (d, J=1.5 Hz, 1H), 8.04 (d, J=8.0 Hz, 1H), 7.97-7.88 (m, 2H), 7.81-7.77 (m, 3H), 7.65-7.60 (m, 3H), 7.53-7.49 (m, 2H), 1.94 (s, 6H).

To a solution of 224-1 (20 mg, 63 umol, 1 eq) and HATU (36.1 mg, 95 umol, 1.5 eq) in DMF (1 mL) at 30° C. were added 224-1a (6.8 mg, 76 umol, 7 uL, 1.2 eq) and TEA (19.2 mg, 0.19 mmol, 26 uL, 3 eq). The mixture was stirred at 30° C. for 16 h. The reaction mixture was concentrated under reduced pressure to give the residue which was purified by prep-HPLC (column: Waters Xbridge 150*25 5u; mobile phase: [water (0.05% ammonia hydroxide v/v)-ACN]; B %: 55%-85%, 7.8 min) to give the title compound (20 mg, 52 umol, 81.6% yield) as a white solid. LCMS (ESI): RT=0.866 min, mass calc. for $C_{22}H_{20}F_3NO_2$ 387.14, m/z found 388.0 [M+H]$^+$; $^1$H NMR (400 MHz, CDCl$_3$) δ 8.33 (d, J=1.4 Hz, 1H), 7.99 (d, J=8.3 Hz, 1H), 7.87 (d, J=8.9 Hz, 1H), 7.80-7.74 (m, 3H), 7.63-7.59 (m, 3H), 7.54-7.51 (m, 1H), 6.34 (brs, 1H), 4.62 (t, J=6.2 Hz, 1H), 3.76 (d, J=6.1 Hz, 2H), 1.48 (s, 6H)

Example 224: N-(1-hydroxy-2-methylpropan-2-yl)-5-(4-(trifluoromethyl)phenyl)-2-naphthamide (Compound 263)

Example 225: N-(tert-butyl)-5-(4-(trifluoromethyl)phenyl)-2-naphthamide (Compound 264)

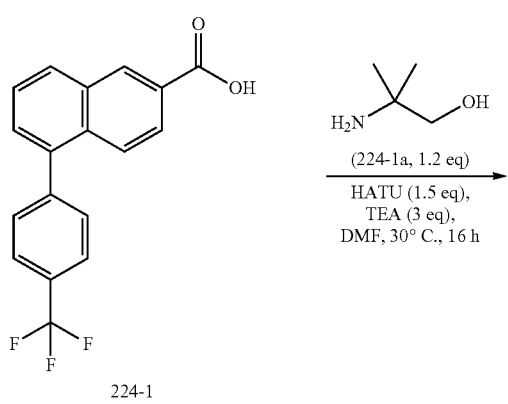

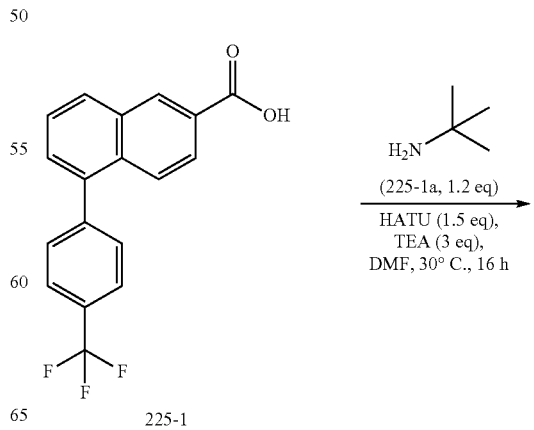

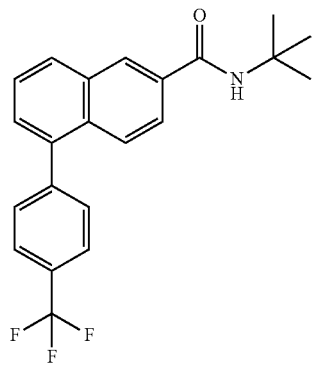

Compound 264

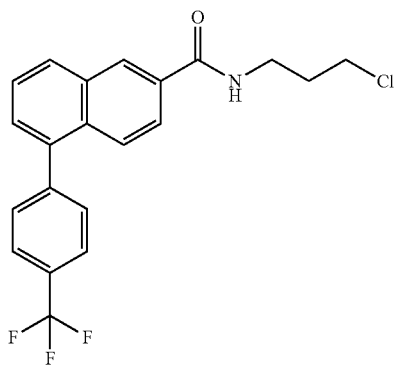

Compound 265

To a solution of 225-1 (25 mg, 79 umol, 1 eq) and HATU (45.1 mg, 0.12 mmol, 1.5 eq) in DMF (1 mL) at 30° C. were added 225-1a (6.9 mg, 95 umol, 10 uL, 1.2 eq) and TEA (24.0 mg, 0.24 mmol, 33 uL, 3 eq). The mixture was stirred at 30° C. for 16 h. The reaction mixture was concentrated under reduced pressure to give a residue which was purified by prep-HPLC (column: Xtimate C18 150*25 mm*5 um; mobile phase: [water (0.05% ammonia hydroxide v/v)-ACN]; B %: 70%-100%, 7 min) to give the title compound (22 mg, 59 umol, 74.9% yield) as a white solid. LCMS (ESI): RT=0.939 min, mass calc. for $C_{22}H_{20}F_3NO$ 371.15, m/z found 372.0 [M+H]$^+$; $^1$H NMR (400 MHz, CDCl$_3$) δ 8.30 (d, J=1.1 Hz, 1H), 7.98 (d, J=8.3 Hz, 1H), 7.87-7.84 (m, 1H), 7.80-7.74 (m, 3H), 7.63-7.58 (m, 3H), 7.49 (d, J=7.0 Hz, 1H), 6.11 (brs, 1H), 1.54 (s, 9H)

To a solution of 226-1 (25 mg, 79 umol, 1 eq) and HATU (45.1 mg, 0.12 mmol, 1.5 eq) in DMF (1 mL) at 30° C. were added 226-1a (12.3 mg, 95 umol, 10 uL, 1.2 eq) and TEA (24.00 mg, 0.24 mmol, 33 uL, 3 eq). The mixture was stirred at 30° C. for 16 h. The reaction mixture was concentrated under reduced pressure to give a residue, which was purified by prep-HPLC (column: Waters Xbridge 150*25 5u; mobile phase: [water (0.05% ammonia hydroxide v/v)-ACN]; B %: 65%-95%, 7 min) to give the title compound (20 mg, 51 umol, 64.6% yield) as a white solid. LCMS (ESI): RT=0.900 min, mass calc. for $C_{21}H_{17}ClF_3NO$ 391.10, m/z found 392.0 [M+H]$^+$; $^1$H NMR (400 MHz, CDCl$_3$) δ 8.38 (d, J=1.8 Hz, 1H), 7.99 (d, J=8.3 Hz, 1H), 7.91-7.84 (m, 1H), 7.82-7.74 (m, 3H), 7.65-7.58 (m, 3H), 7.52 (dd, J=1.0, 7.0 Hz, 1H), 6.54 (brs, 1H), 4.93-4.89 (m, 1H), 3.75-3.66 (m, 4H), 2.19 (quin, J=6.5 Hz, 2H)

Example 227: (S)—N-(1-(pyridin-2-yl)ethyl)-5-(4-(trifluoromethyl)phenyl)quinoxaline-2-carboxamide (Compound 266)

Example 226: N-(3-chloropropyl)-5-(4-(trifluoromethyl) phenyl)-2-naphthamide (Compound 265)

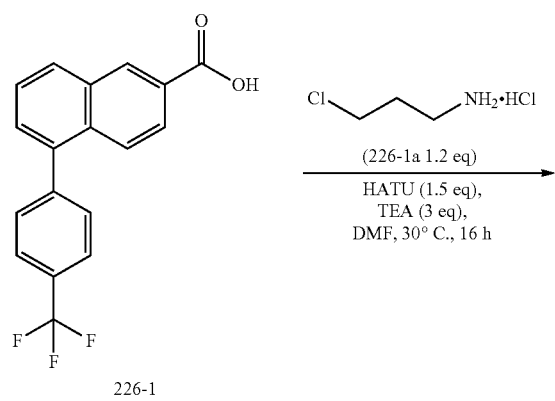

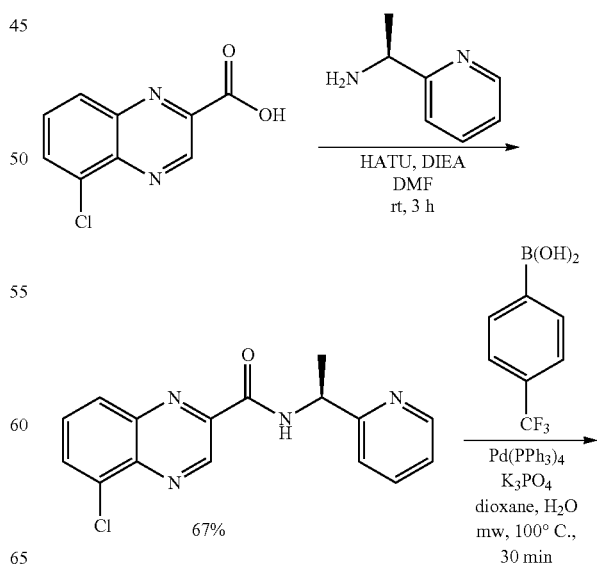

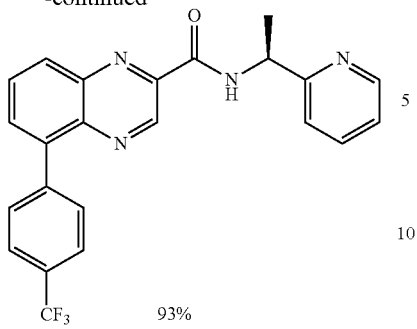

Compound 266

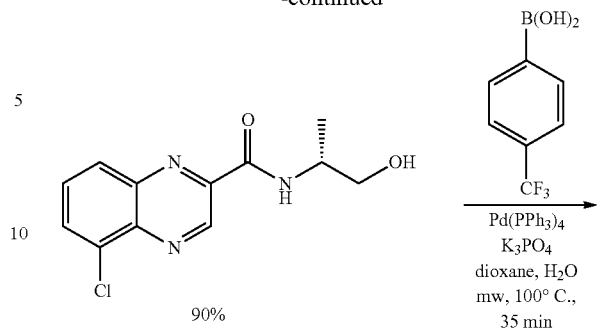

Compound 267

(S)-5-chloro-N-(1-(pyridin-2-yl)ethyl)quinoxaline-2-carboxamide

5-Chloroquinoxaline-2-carboxylic acid (70 mg, 0.33 mmol, 1 equiv.), (S)-1-(pyridin-2-yl)ethan-1-amine (49 mg, 0.4 mmol, 1.2 equiv.), and HATU (255 mg, 0.67 mmol, 2 equiv.) were dissolved in DMF (0.5 mL) at rt. DIEA (0.23 mL, 1.34 mmol, 4 equiv.) was added slowly, and the mixture was stirred at rt until consumption of the acid as determined by LCMS, 3 hr. Upon completion, the reaction mixture was diluted with $H_2O$ and stirred rapidly for 20 min. The resulting solid was filtered, rinsed with $H_2O$, and dried to give the desired amide product as a tan solid, 80 mg, 67%, LCMS $[M+H]^+$=313.

(S)—N-(1-(pyridin-2-yl)ethyl)-5-(4-(trifluoromethyl)phenyl)quinoxaline-2-carboxamide (S)-5-chloro-N-(1-(pyridin-2-yl)ethyl)quinoxaline-2-carboxamide (80 mg, 0.26 mmol, 1 equiv.), (4-(trifluoromethyl)phenyl)boronic acid (58 mg, 0.31 mmol, 1.2 equiv.), $Pd(PPh_3)_4$ (3 mg, 0.026 mmol, 0.1 equiv.), and 4:1 dioxane/4N $K_2CO_3$(aq) (1 mL:0.25 mL) were thoroughly purged with $N_2$ for 10 min. The reaction mixture was sealed in a microwave vessel and irradiated at 100° C. for 30 min. The mixture was cooled to rt, diluted with EtOAc, washed with $H_2O$, brine, dried with $Na_2SO_4$, and concentrated. The residue was purified by FCC 0 to 25% THF in DCM gradient to give the title compound as a yellow solid (100 mg, 93%). LCMS $[M+H]^+$=423. $^1H$ NMR (600 MHz, DMSO-$d_6$) δ ppm 1.64 (d, J=6.91 Hz, 3H) 5.39 (quin, J=7.13 Hz, 1H) 7.48-7.63 (m, 1H) 7.79 (d, J=7.98 Hz, 1H) 7.83-7.92 (m, 4H) 8.02-8.15 (m, 3H) 8.31 (dd, J=7.15, 2.66 Hz, 1H) 8.70 (dd, J=5.23, 0.73 Hz, 1H) 9.43 (s, 1H) 9.58 (d, J=7.70 Hz, 1H).

Example 228: (R)—N-(1-hydroxypropan-2-yl)-5-(4-(trifluoromethyl)phenyl)quinoxaline-2-carboxamide (Compound 267)

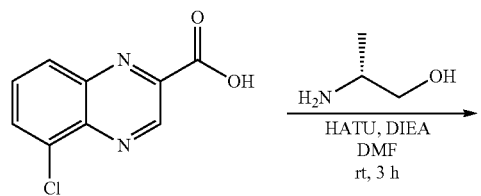

(R)-5-Chloro-N-(1-hydroxypropan-2-yl)quinoxaline-2-carboxamide

5-Chloroquinoxaline-2-carboxylic acid (70 mg, 0.33 mmol, 1 equiv.), (R)-2-aminopropan-1-ol (30 mg, 0.4 mmol, 1.2 equiv.), and HATU (255 mg, 0.67 mmol, 2 equiv.) were dissolved in DMF (0.5 mL) at rt. DIEA (0.23 mL, 1.34 mmol, 4 equiv.) was added slowly, and the mixture was stirred at rt until consumption of the acid as determined by LCMS, 3 hr. Upon completion, the reaction mixture was diluted with $H_2O$ and stirred rapidly for 20 min. The resulting solid was filtered, rinsed with $H_2O$, and dried to give the desired amide product as a tan solid, 80 mg, 90%, LCMS $[M+H]^+$=266.

(R)—N-(1-hydroxypropan-2-yl)-5-(4-(trifluoromethyl)phenyl)quinoxaline-2-carboxamide (R)-5-Chloro-N-(1-hydroxypropan-2-yl)quinoxaline-2-carboxamide (80 mg, 0.3 mmol, 1 equiv.), (4-(trifluoromethyl)phenyl)boronic acid (68 mg, 0.36 mmol, 1.2 equiv.), $Pd(PPh_3)_4$ (35 mg, 0.03 mmol, 0.1 equiv.), and 4:1 dioxane/4N $K_2CO_3$(aq) (1 mL:0.25 mL) were thoroughly purged with $N_2$ for 10 min. The reaction mixture was sealed in a microwave vessel and irradiated at 100° C. for 35 min. The mixture was cooled to rt, diluted with EtOAc, washed with $H_2O$, brine, dried with $Na_2SO_4$, and concentrated. The residue was purified by FCC 0 to 25% THF in DCM gradient to give the title compound as a yellow solid (73 mg, 65%). LCMS $[M+H]^+$=376.

Example 229: N-Isopropyl-5-(4-(trifluoromethyl)phenyl)quinoxaline-2-carboxamide (Compound 268)

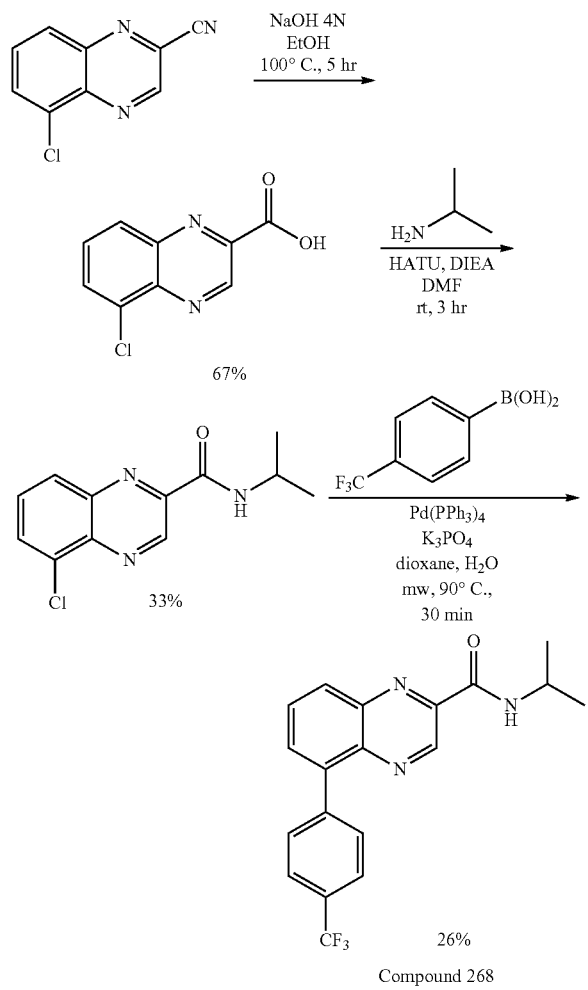

5-Chloroquinoxaline-2-carboxylic Acid

5-Chloroquinoxaline-2-carbonitrile (500 mg, 2.6 mmol, 1 equiv.), 4N NaOH(aq) (6 mL), and H$_2$O (6 mL) were heated to 100° C. in a sealed vessel. The mixture was stirred at 100° C. for 5 hr. After cooling to room temperature, the mixture was diluted with EtOAc and the organic layer separated. The aqueous layer was acidified with 2N HCl and extracted with EtOAc. The organic layer was dried with Na$_2$SO$_4$ and concentrated to give the desired product, a colorless solid, 366 mg, 67%. LCMS [M+H]$^+$=209.

5-Chloro-N-isopropylquinoxaline-2-carboxamide

5-Chloroquinoxaline-2-carboxylic acid (70 mg, 0.33 mmol, 1 equiv.), propane-amine (24 mg, 0.4 mmol, 1.2 equiv.), and HATU (255 mg, 0.67 mmol, 2 equiv.) were dissolved in DMF (0.5 mL) at rt. DIEA (0.23 mL, 1.34 mmol, 4 equiv.) was added slowly, and the mixture was stirred at rt until consumption of the acid as determined by LCMS, 3 hr. Upon completion, the reaction mixture was diluted with H$_2$O and stirred rapidly for 20 min. The resulting solid was filtered, rinsed with H$_2$O, and dried to give the desired amide product as a tan solid, 27 mg, 33%, LCMS [M+H]$^+$=250.

N-Isopropyl-5-(4-(trifluoromethyl)phenyl)quinoxaline-2-carboxamide

5-Chloro-N-isopropylquinoxaline-2-carboxamide (27 mg, 0.11 mmol, 1 equiv.), (4-(trifluoromethyl)phenyl)boronic acid (25 mg, 0.13 mmol, 1.2 equiv.), Pd(PPh$_3$)$_4$ (12 mg, 0.01 mmol, 0.1 equiv.), and 4:1 dioxane/4N K$_2$CO$_3$(aq) (0.8 mL:0.2 mL) were thoroughly purged with N$_2$ for 10 min. The reaction mixture was sealed in a microwave vessel and irradiated at 90° C. for 30 min. The mixture was cooled to rt, diluted with EtOAc, washed with H$_2$O, brine, dried with Na$_2$SO$_4$, and concentrated. The residue was purified by FCC 0 to 25% THF in DCM gradient to give the title compound as a tan solid (10 mg, 26%). LCMS [M+H]$^+$=360.

Example 230: (S)—N-(1-(oxetan-3-yl)ethyl)-5-(4-(trifluoromethyl)phenyl)-2-naphthamide (Compound 269) and (R)—N-(1-(oxetan-3-yl)ethyl)-5-(4-(trifluoromethyl)phenyl)-2-naphthamide (Compound 270)

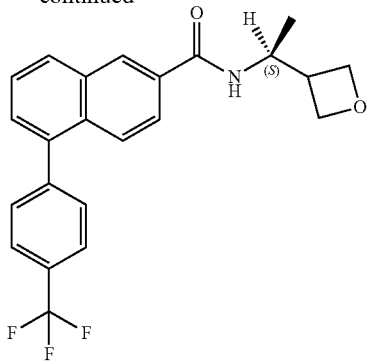

Compound 269

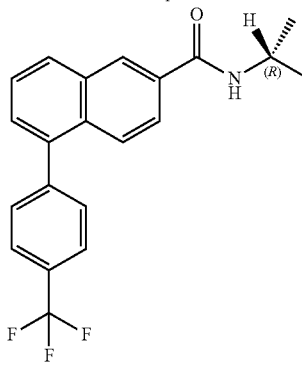

Compound 270

N-(1-(oxetan-3-yl)ethyl)-5-(4-(trifluoromethyl)phenyl)-2-naphthamide

The mixture of 5-[4-(trifluoromethyl)phenyl]naphthalene-2-carboxylic acid (100 mg, 0.31 mmol, 1 eq), HATU (180.3 mg, 0.47 mmol, 1.5 eq) and DIPEA (122.5 mg, 0.94 mmol, 0.16 mL, 3 eq) in DCM (2 mL) was stirred at 25° C. for 1 hr. Then 1-(oxetan-3-yl)ethanamine (35.1 mg, 0.34 mmol, 1.1 eq) was added into the mixture and the mixture was stirred at 25° C. for another 1 hr. The reaction mixture was diluted with $H_2O$ (10 mL) and the mixture was extracted with EA (10 mL*3). The combined organic phase was washed with brine (10 mL*2), dried with anhydrous $Na_2SO_4$, filtered and concentrated in vacuum. The residue was purified by column chromatography ($SiO_2$, Petroleum ether/Ethyl acetate=1:0 to 5:1). Compound N-[1-(oxetan-3-yl)ethyl]-5-[4-(trifluoromethyl)phenyl]naphthalene-2-carboxamide (126 mg, 0.29 mmol, 91.7% yield) was obtained as colorless oil.

(S)—N-(1-(oxetan-3-yl)ethyl)-5-(4-(trifluoromethyl) phenyl)-2-naphthamide (Compound 269) and (R)—N-(1-(oxetan-3-yl)ethyl)-5-(4-(trifluoromethyl)phenyl)-2-naphthamide (Compound 270)

The racemic compound N-[1-(oxetan-3-yl)ethyl]-5-[4-(trifluoromethyl)phenyl]naphthalene-2-carboxamide (99 mg, 0.24 mmol, 1 eq) was purified by SFC (column: REGIS (s,s) WHELK-O1 (250 mm*30 mm, 5 um); mobile phase: [0.1% $NH_3H_2O$ ETOH]; B %: 45%-45%, min). Compound 269 (13.7 mg, 33.7 umol, 13.6% yield) was obtained as a white solid. LCMS (ESI): RT=0.956 min, mass calcd for $C_{23}H_{20}F_3NO_2$ 399.41 m/z found 400.0 $[M+H]^+$, $^1H$ NMR (400 MHz, $CD_3OD$) δ 8.35 (s, 1H), 7.96 (d, J=8.1 Hz, 1H), 7.78-7.71 (m, 4H), 7.60-7.52 (m, 3H), 7.46 (dd, J=1.1, 7.1 Hz, 1H), 4.74-4.66 (m, 2H), 4.53 (t, J=6.3 Hz, 1H), 4.51-4.45 (m, 1H), 4.43 (t, J=6.3 Hz, 1H), 3.17-3.07 (m, 1H), 1.12 (d, J=6.6 Hz, 3H). Compound 270 (18.5 mg, 45.5 umol, 18.3% yield) was obtained as a white solid. LCMS (ESI): RT=0.959 min, mass calcd for $C_{23}H_{20}F_3NO_2$ 399.41 m/z found 400.0 $[M+H]^+$, $^1H$ NMR (400 MHz, $CD_3OD$) δ 8.35 (s, 1H), 7.96 (d, J=8.3 Hz, 1H), 7.78-7.70 (m, 4H), 7.61-7.53 (m, 3H), 7.47 (d, J=7.0 Hz, 1H), 4.73-4.67 (m, 2H), 4.54 (t, J=6.1 Hz, 1H), 4.50-4.46 (m, 1H), 4.43 (t, J=6.3 Hz, 1H), 3.17-3.08 (m, 1H), 1.13 (d, J=6.8 Hz, 3H).

Example 231: (S)—N-(1-methoxypropan-2-yl)-5-(4-(trifluoromethyl)phenyl)quinoxaline-2-carboxamide (Compound 271)

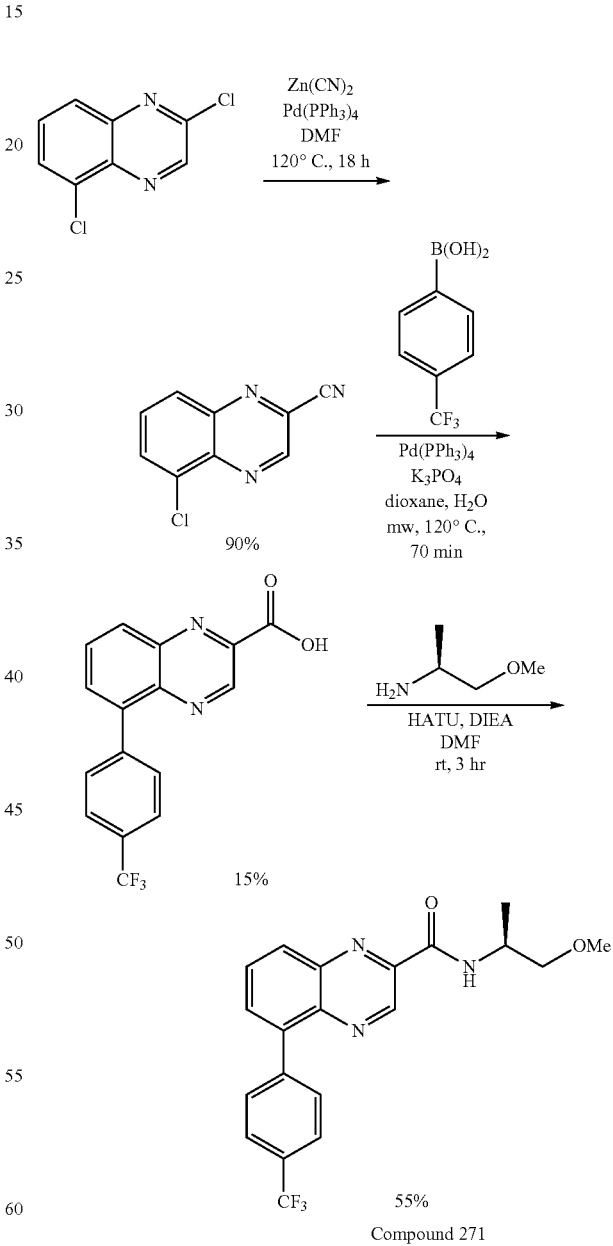

5-Chloroquinoxaline-2-carbonitrile 2,5-Dichloroquinoxaline (1 g, 5 mmol, 1 equiv.), $Zn(CN)_2$ (294 mg, 2.5 mmol, 0.5 equiv.), $Pd(PPh_3)_4$ (578 mg, 0.5 mmol, 0.1 equiv.), and DMF (10 mL, 0.5M) were thoroughly purged with $N_2$ for 10 min. The reaction mixture was heated at 120° C. for 18 hr. The mixture was carefully added to 60 mL rapidly stirring water and the resultant solid was filtered and dried to give 5-chloroquinoxaline-2-carbonitrile (850 mg, 90% yield) as a colorless solid. LCMS [M+H]$^+$= 190.

5-(4-(Trifluoromethyl)phenyl)quinoxaline-2-carboxylic Acid

5-Chloroquinoxaline-2-carbonitrile (100 mg, 0.53 mmol, 1 equiv.), (4-(trifluoromethyl)phenyl)boronic acid (120 mg, 0.63 mmol, 1.2 equiv.), $K_3PO_4$ (281 mg, 1.33 mmol, 2.5 equiv.), Pd(PPh$_3$)$_4$ (61 mg, 0.05 mmol, 0.1 equiv.), and 4:1 dioxane/H$_2$O (2 mL:0.5 mL, 0.2M) were thoroughly purged with $N_2$ for 10 min. The reaction mixture was sealed in a microwave vessel and irradiated at 120° C. for 70 min. The mixture was cooled to rt, diluted with EtOAc, carefully neutralized with 1N HCl(aq), and separated. The organic layer was washed with H$_2$O, brine, dried with Na$_2$SO$_4$, and concentrated. The residue was purified by FCC 0 to 10% MeOH in DCM gradient to give 5-(4-(trifluoromethyl)phenyl)quinoxaline-2-carboxylic acid (25 mg, 0.08 mmol, 15% yield). LCMS [M+H]$^+$=319.

(S)—N-(1-methoxypropan-2-yl)-5-(4-(trifluoromethyl)phenyl)quinoxaline-2-carboxamide 5-(4-(Trifluoromethyl)phenyl)quinoxaline-2-carboxylic acid (1 equiv.), (S)-1-methoxypropan-2-amine (1.2 equiv.), and HATU (1.2 equiv.) were dissolved in DMF (0.2M) at rt. DIEA (2 equiv.) was added slowly, and the mixture was stirred at rt until consumption of the acid as determined by LCMS, 2.5 hr. Upon completion, the reaction mixture was diluted with H$_2$O and stirred rapidly for 20 min. The resulting solid was filtered, rinsed with H$_2$O, and dried to give the desired amide product as a colorless solid, 6 mg, 55%, LCMS [M+H]$^+$=390. $^1$H NMR (500 MHz, DMSO-d$_6$) δ ppm 1.26-1.32 (m, 3H) 3.43-3.47 (m, 3H) 3.51-3.56 (m, 2H) 4.30-4.36 (m, 1H) 8.00-8.07 (m, 3H) 8.37 (dd, J=8.35, 1.50 Hz, 1H) 8.52 (dd, J=7.29, 1.46 Hz, 1H) 8.63 (d, J=8.12 Hz, 2H) 9.79 (s, 1H) 10.02 (d, J=7.65 Hz, 1H).

Example 232: (S)—N-(pent-3-yn-2-yl)-5-(4-(trifluoromethyl)phenyl)-2-naphthamide (Compound 272) and (R)—N-(pent-3-yn-2-yl)-5-(4-(trifluoromethyl)phenyl)-2-naphthamide (Compound 273)

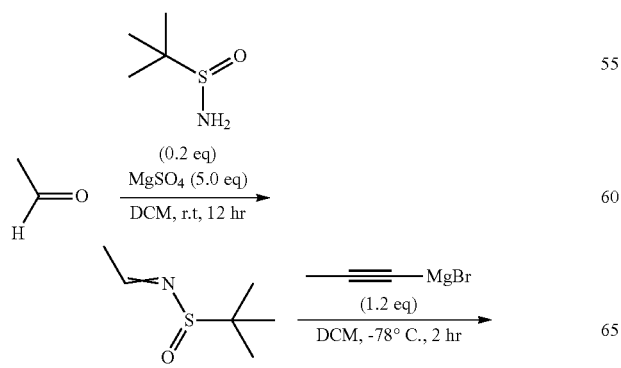

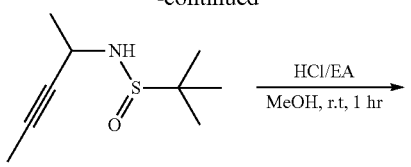

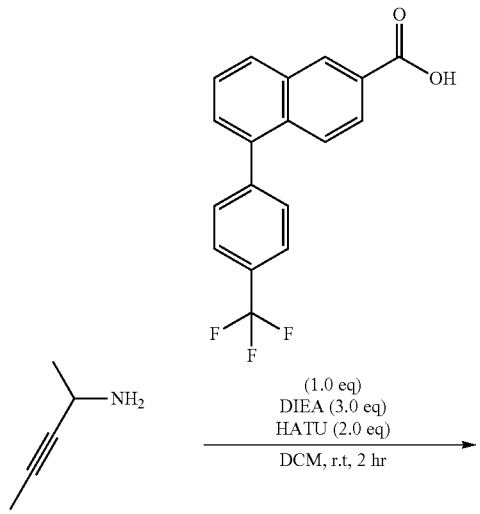

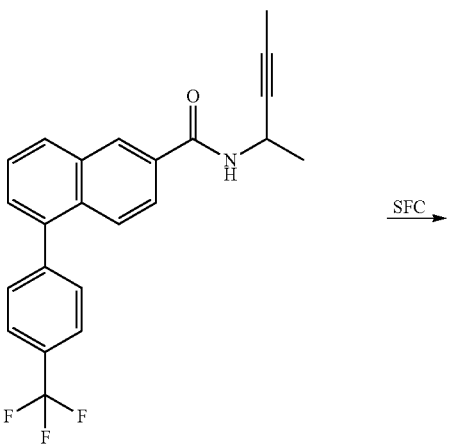

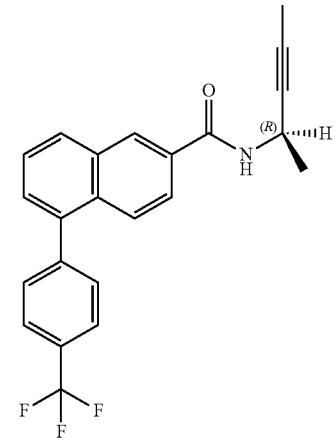

Compound 273

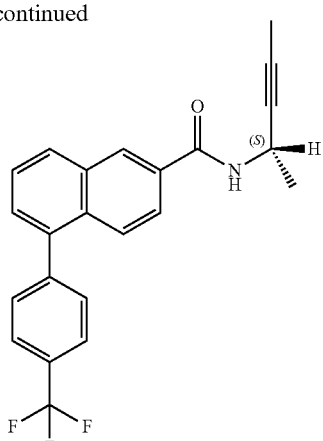

Compound 272

N-ethylidene-2-methylpropane-2-sulfinamide

To a mixture of 2-methylpropane-2-sulfinamide (5 g, 41.25 mmol, 1 eq) in DCM (50 mL) was added acetaldehyde (9.09 g, 206.27 mmol, 11.58 mL, 5 eq) and MgSO$_4$ (24.83 g, 206.27 mmol, 5 eq). The mixture was stirred for 12 hrs at 25° C. The mixture was filtered and the filtered cake was washed with EA (20 mL*3). The mixture was concentrated in vacuum. The residue was purified by column chromatography (SiO$_2$, Petroleum ether/Ethyl acetate=100/1 to 50:1). Compound N-ethylidene-2-methyl-propane-2-sulfinamide (5 g, 33.96 mmol, 82.3% yield) was obtained as a light yellow oil.

2-methyl-N-(pent-3-yn-2-yl)propane-2-sulfinamide

To a mixture of N-ethylidene-2-methyl-propane-2-sulfinamide (1 g, 6.79 mmol, 1 eq) in THF (5 mL) was added bromo(prop-1-ynyl)magnesium (0.5 M, 16.30 mL, 1.2 eq). The mixture was stirred for 2 hrs at −78° C. The mixture was quenched by EA (30 mL), and the mixture was extracted with EA (20 mL*3). The combined organic phase was washed with brine (20 mL*3), dried with anhydrous Na$_2$SO$_4$, filtered and concentrated in vacuum. The residue was used into the next step without further purification. Compound 2-methyl-N-(1-methylbut-2-ynyl)propane-2-sulfinamide (1.5 g, crude) was obtained as a yellow oil.

Pent-3-yn-2-amine

To a mixture of 2-methyl-N-(1-methylbut-2-ynyl)propane-2-sulfinamide (1 g, 5.34 mmol, 1 eq) in MeOH (3 mL) was added HCl/EtOAc (4 M, 19.10 mL, 14.31 eq). The mixture was stirred for 1 hr at 25° C. The mixture was concentrated in vacuum. The residue was used to the next step without further purification. Compound pent-3-yn-2-amine (1 g, crude) was obtained as yellow oil.

N-(pent-3-yn-2-yl)-5-(4-(trifluoromethyl)phenyl)-2-naphthamide

To a mixture of 5-[4-(trifluoromethyl)phenyl]naphthalene-2-carboxylic acid (0.1 g, 0.31 mmol, 1 eq) in DCM (5 mL) was added DIPEA (122.5 mg, 0.94 mmol, 0.16 mL, 3 eq) and HATU (240.4 mg, 0.63 mmol, 2 eq). The mixture was stirred for 1 hr at 25° C. pent-3-yn-2-amine (78.8 mg, 0.94 mmol, 3 eq) was added the mixture. The mixture was stirred for 1 hr at 25° C. The mixture was quenched by H$_2$O (30 mL), and the mixture was filtered and the filtered cake was washed with EA (20 mL*3). The combined organic phase was washed with brine (20 mL*3), dried with anhydrous Na$_2$SO$_4$, filtered and concentrated in vacuum. The residue was purified by pre-HPLC (column: Xtimate C18 150*25 mm*5 um; mobile phase: [water (10 mM NH$_4$HCO$_3$)-ACN]; B %: 56%-86%, 8.5 min). Compound N-(1-methylbut-2-ynyl)-5-[4-(trifluoromethyl)phenyl]naphthalene-2-carboxamide (16 mg, 41.9 umol, 13.2% yield) was obtained as a white solid.

(S)—N-(pent-3-yn-2-yl)-5-(4-(trifluoromethyl)phenyl)-2-naphthamide (Compound 272) and (R)—N-(pent-3-yn-2-yl)-5-(4-(trifluoromethyl)phenyl)-2-naphthamide (Compound 273)

N-(1-methylbut-2-ynyl)-5-[4-(trifluoromethyl)phenyl] naphthalene-2-carboxamide (16 mg, 41.9 umol, 1 eq) was purified by SFC. The racemic compound was purified by pre-SFC (column: DAICEL CHIRALPAK AS-H (250 mm*30 mm, 5 um); mobile phase: [0.1% NH$_3$H$_2$O ETOH]; B %: 20%-20%, min). Compound 273 (3.1 mg, 8.2 mmol) was obtained as a white solid. LCMS (ESI): RT=0.918 min, mass calcd for C$_{23}$H$_{18}$F$_3$NO 381.39 m/z found 382.0 [M+H]$^+$, $^1$H NMR (400 MHz, CD$_3$OD) δ 8.49 (s, 1H), 8.09 (d, J=8.3 Hz, 1H), 7.91-7.84 (m, 4H), 7.72-7.65 (m, 3H), 7.58 (dd, J=1.1, 7.1 Hz, 1H), 4.99-4.91 (m, 1H), 1.84 (d, J=2.3 Hz, 3H), 1.50 (d, J=6.9 Hz, 3H). Compound 272 (2.7 mg, 7.2 umol) was obtained as a white solid. LCMS (ESI): RT=0.910 min, mass calcd for C$_{23}$H$_{18}$F$_3$NO 381.39 m/z found 382.0 [M+H]$^+$, $^1$H NMR (400 MHz, CD$_3$OD) δ 8.49 (s, 1H), 8.09 (d, J=8.3 Hz, 1H), 7.91-7.83 (m, 4H), 7.74-7.65 (m, 3H), 7.59 (d, J=6.8 Hz, 1H), 4.98-4.93 (m, 1H), 1.84 (d, J=2.3 Hz, 3H), 1.50 (d, J=6.9 Hz, 3H).

Example 233: (S)—N-(but-3-yn-2-yl)-5-(4-(trifluoromethyl)phenyl)-2-naphthamide (Compound 274) and (R)—N-(but-3-yn-2-yl)-5-(4-(trifluoromethyl)phenyl)-2-naphthamide (Compound 275)

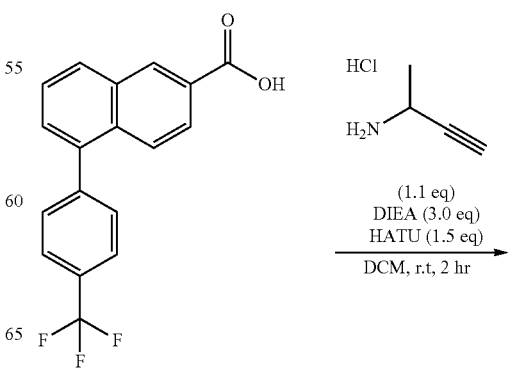

(1.1 eq)
DIEA (3.0 eq)
HATU (1.5 eq)
DCM, r.t, 2 hr

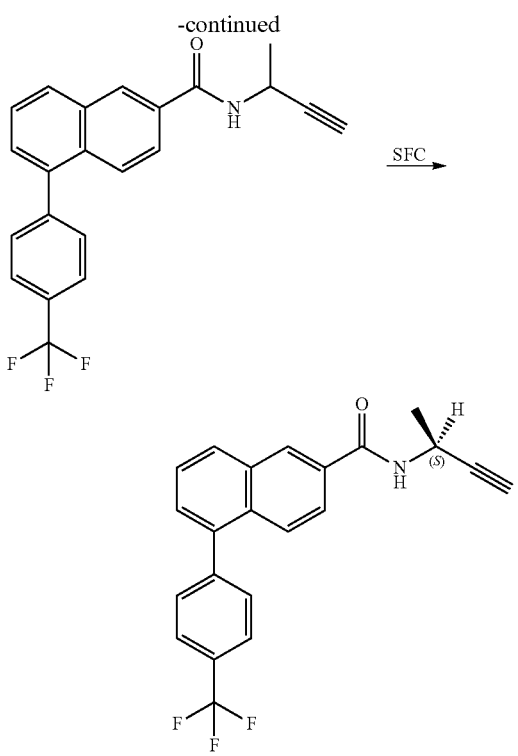

Compound 274

Compound 275

N-(but-3-yn-2-yl)-5-(4-(trifluoromethyl)phenyl)-2-naphthamide

The mixture of 5-[4-(trifluoromethyl)phenyl]naphthalene-2-carboxylic acid (100 mg, 0.31 mmol, 1 eq), HATU (180.3 mg, 0.47 mmol, 1.5 eq) and DIPEA (122.5 mg, 0.94 mmol, 0.16 mL, 3 eq) in DCM (2 mL) was stirred at 25° C. for 1 hr. Then but-3-yn-2-amine (36.7 mg, 0.34 mmol, 1.1 eq, HCl) was added into the mixture and the mixture was stirred at 25° C. for another 1 hr. The reaction mixture was diluted with H$_2$O (10 mL) and the mixture was extracted with EA (10 mL*3). The combined organic phase was washed with brine (10 mL*2), dried with anhydrous Na$_2$SO$_4$, filtered and concentrated in vacuum. The residue was purified by column chromatography (SiO$_2$, Petroleum ether/Ethyl acetate=1/0 to 5:1). Compound N-(1-methylprop-2-ynyl)-5-[4-(trifluoromethyl)phenyl]naphthalene-2-carboxamide (97 mg, 0.26 mmol, 83.2% yield) was obtained as a white solid (S)—N-(but-3-yn-2-yl)-5-(4-(trifluoromethyl)phenyl)-2-naphthamide (Compound 274) and (R)—N-(but-3-yn-2-yl)-5-(4-(trifluoromethyl)phenyl)-2-naphthamide (Compound 275)

N-(1-methylprop-2-ynyl)-5-[4-(trifluoromethyl)phenyl]naphthalene-2-carboxamide (97 mg, 0.26 mmol, 1 eq) was purified by SFC. The racemic compound was separated by SFC (column: DAICEL CHIRALPAK AS-H (250 mm*30 mm, 5 um); mobile phase: [0.1% NH$_3$H$_2$O ETOH]; B %: 30%-30%, min). Compound 274 (18.6 mg, 50.6 umol, 19.1% yield) was obtained as a white solid. LCMS (ESI): RT=1.009 min, mass calcd for C$_{22}$H$_{16}$F$_3$NO 367.36 m/z found 368.0 [M+H]$^+$, $^1$H NMR (400 MHz, DMSO-d$_6$) δ 9.08 (d, J=8.0 Hz, 1H), 8.60 (d, J=1.3 Hz, 1H), 8.14 (d, J=8.3 Hz, 1H), 7.97-7.89 (m, 3H), 7.82 (d, J=9.0 Hz, 1H), 7.77-7.68 (m, 3H), 7.61 (d, J=6.3 Hz, 1H), 4.92 (dt, J=2.3, 7.4 Hz, 1H), 3.23 (d, J=2.3 Hz, 1H), 1.46 (d, J=7.0 Hz, 3H). Compound 275 (25.5 mg, 69.4 umol, 26.2% yield) was obtained as a white solid LCMS (ESI): RT=1.006 min, mass calcd for C$_{22}$H$_{16}$F$_3$NO 367.36 m/z found 368.0 [M+H]$^+$, $^1$H NMR (400 MHz, DMSO-d$_6$) δ 9.08 (d, J=7.8 Hz, 1H), 8.60 (s, 1H), 8.14 (d, J=8.3 Hz, 1H), 7.97-7.91 (m, 3H), 7.82 (d, J=8.8 Hz, 1H), 7.77-7.68 (m, 3H), 7.63-7.59 (m, 1H), 4.96-4.88 (m, 1H), 3.23 (d, J=2.3 Hz, 1H), 1.46 (d, J=7.0 Hz, 3H).

Example 234: (S)—N-(1-(1H-imidazol-4-yl)ethyl)-5-(4-(trifluoromethyl)phenyl)-2-naphthamide (Compound 276) and (R)—N-(1-(1H-imidazol-4-yl)ethyl)-5-(4-(trifluoromethyl)phenyl)-2-naphthamide (Compound 277)

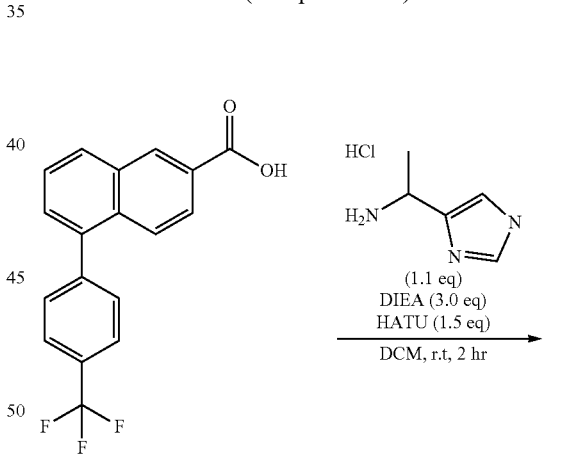

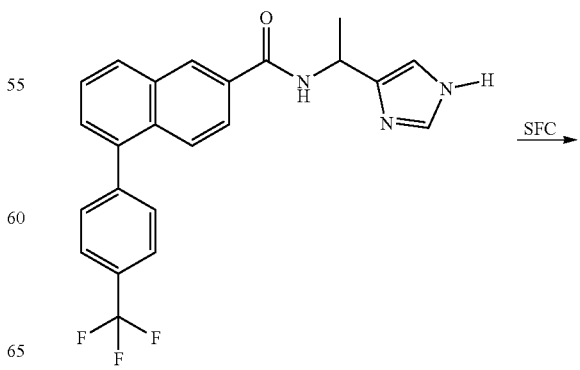

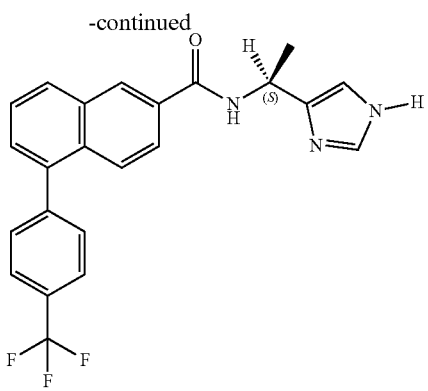

Compound 276

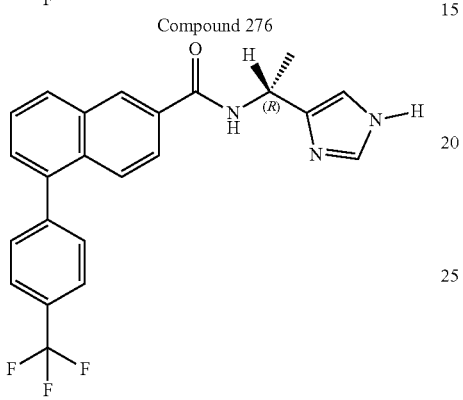

Compound 277

N-(1-(1H-imidazol-4-yl)ethyl)-5-(4-(trifluoromethyl)phenyl)-2-naphthamide

The mixture of 5-[4-(trifluoromethyl)phenyl]naphthalene-2-carboxylic acid (100 mg, 0.31 mmol, 1 eq), HATU (180.3 mg, 0.47 mmol, 1.5 eq) and DIPEA (122.5 mg, 0.94 mmol, 0.16 mL, 3 eq) in DCM (2 mL) was stirred at 25° C. for 1 hr. Then 1-(1H-imidazol-4-yl)ethanamine (64.0 mg, 0.34 mmol, 1.1 eq, 2HCl) was added into the mixture and the mixture was stirred at 25° C. for another 1 hr. The reaction mixture was diluted with H$_2$O (10 mL) and the mixture was extracted with EA (10 mL*3). The combined organic phase was washed with brine (10 mL*2), dried with anhydrous Na$_2$SO$_4$, filtered and concentrated in vacuum. The residue was purified by prep-HPLC (column: Xtimate C18 150*25 mm*5 um; mobile phase: [water (0.05% HCl)-ACN]; B %: 27%-57%, 8.5 min). Compound N-[1-(1H-imidazol-4-yl)ethyl]-5-[4-(trifluoromethyl)phenyl]naphthalene-2-carboxamide (56 mg, 0.13 mmol, 43.2% yield) was obtained as a yellow solid.

(S)—N-(1-(1H-imidazol-4-yl)ethyl)-5-(4-(trifluoromethyl)phenyl)-2-naphthamide (Compound 276) and (R)—N-(1-(1H-imidazol-4-yl)ethyl)-5-(4-(trifluoromethyl)phenyl)-2-naphthamide (Compound 277)

The compound N-[1-(1H-imidazol-4-yl)ethyl]-5-[4-(trifluoromethyl)phenyl]naphthalene-2-carboxamide (56 mg, 0.13 mmol, 1 eq) was purified by SFC. The racemic compound was separated by SFC (column: DAICEL CHIRALPAK AD-H (250 mm*30 mm, 5 um); mobile phase: [0.1% NH3H2O ETOH]; B %: 30%-30%, min). Compound 276 (24 mg, 58.0 umol, 42.4% yield) was obtained as a white solid. LCMS (ESI): RT=0.847 min, mass calcd for C$_{23}$H$_{18}$F$_3$N$_3$O 409.40 m/z found 410.0 [M+H]$^+$, $^1$H NMR (400 MHz, CD$_3$OD) δ 8.54 (s, 1H), 8.09 (br d, J=8.3 Hz, 1H), 7.98-7.80 (m, 4H), 7.77-7.63 (m, 4H), 7.59 (br d, J=7.1 Hz, 1H), 5.63 (br d, J=7.1 Hz, 1H), 4.41-4.34 (m, 3H), 1.75 (d, J=7.1 Hz, 3H). Compound 277 (10 mg, 24.1 umol, 17.6% yield) was obtained as a white solid. LCMS (ESI): RT=0.846 min, mass calcd for C$_{23}$H$_{18}$F$_3$N$_3$O 409.40 m/z found 410.0 [M+H]$^+$, $^1$H NMR (400 MHz, CD$_3$OD) δ 8.50 (s, 1H), 8.05 (br d, J=8.0 Hz, 1H), 7.93-7.87 (m, 1H), 7.83 (br d, J=9.0 Hz, 3H), 7.71-7.59 (m, 4H), 7.59-7.50 (m, 1H), 7.07 (s, 1H), 5.39 (q, J=6.8 Hz, 1H), 1.64 (d, J=7.0 Hz, 3H).

Example 235: (S)—N-(1-(2-methyl-2H-tetrazol-5-yl)ethyl)-5-(4-(trifluoromethyl)phenyl)-2-naphthamide (Compound 278) and (R)—N-(1-(2-methyl-2H-tetrazol-5-yl)ethyl)-5-(4-(trifluoromethyl)phenyl)-2-naphthamide (Compound 279)

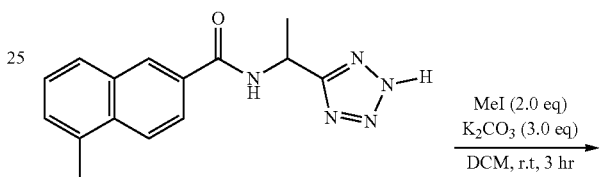

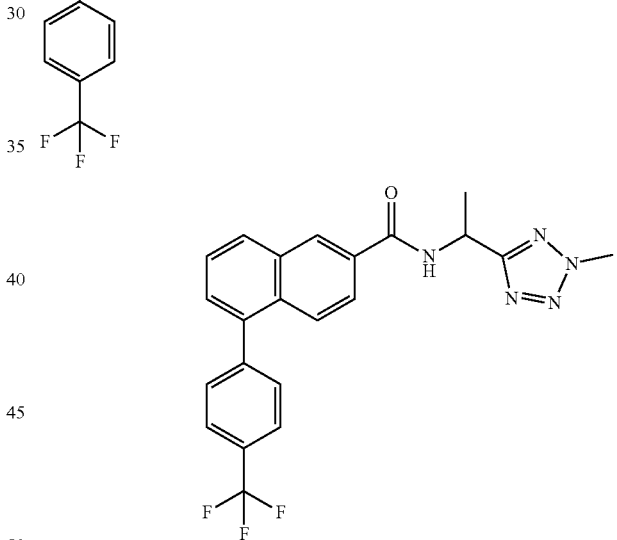

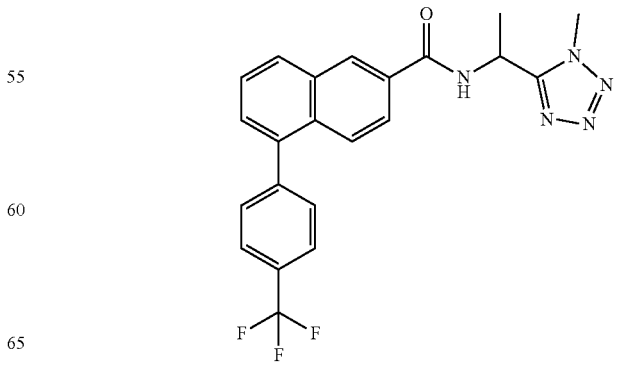

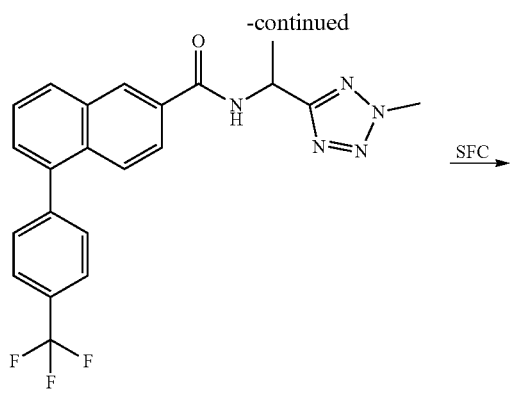

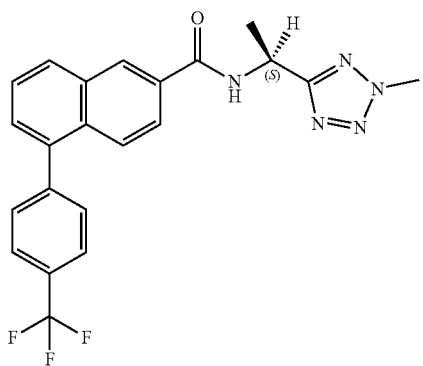

Compound 278

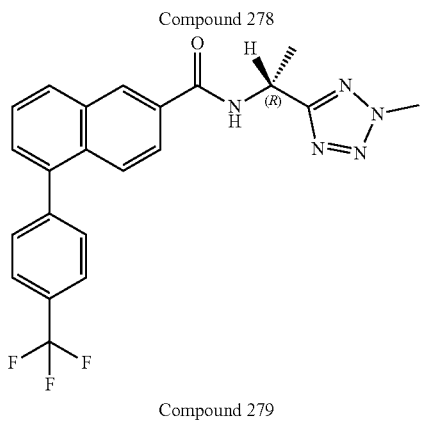

Compound 279

N-(1-(2-methyl-2H-tetrazol-5-yl)ethyl)-5-(4-(trifluoromethyl)phenyl)-2-naphthamide and N-(1-(1-methyl-1H-tetrazol-5-yl)ethyl)-5-(4-(trifluoromethyl)phenyl)-2-naphthamide To the solution of N-[1-(2H-tetrazol-5-yl)ethyl]-5-[4-(trifluoromethyl)phenyl]naphthalene-2-carboxamide (0.3 g, 0.72 mmol, 1 eq) in DMF (3 mL) was added CH$_3$I (207.0 mg, 1.46 mmol, 90.8 uL, 2 eq) and K$_2$CO$_3$ (302.3 mg, 2.19 mmol, 3 eq). The mixture was stirred at 25° C. for 3 hr. The reaction solution was added to H$_2$O (10 mL). The mixture was extracted with ethyl acetate (20 mL*3). The combined organic phase was washed with brine (20 mL*3), dried with anhydrous Na$_2$SO$_4$, filtered and concentrated in vacuum. The residue was purified by pre-HPLC (column: Xtimate C18 150*25 mm*5 um; mobile phase: [water (0.05% HCl)-ACN]; B %: 48%-78%, 8.5 min). Compound N-[1-(1-methyltetrazol-5-yl)ethyl]-5-[4-(trifluoromethyl)phenyl] naphthalene-2-carboxamide (15 mg, 35.2 umol, 4.8% yield) was obtained as a white solid. Compound N-[1-(2-methyltetrazol-5-yl)ethyl]-5-[4-(trifluoromethyl)phenyl]naphthalene-2-carboxamide (21 mg, 49.3 umol, 6.7% yield) was obtained as a white solid.

(S)—N-(1-(2-methyl-2H-tetrazol-5-yl)ethyl)-5-(4-(trifluoromethyl)phenyl)-2-naphthamide (Compound 278) and (R)—N-(1-(2-methyl-2H-tetrazol-5-yl)ethyl)-5-(4-(trifluoromethyl)phenyl)-2-naphthamide (Compound 279)

N-[1-(2-methyltetrazol-5-yl)ethyl]-5-[4-(trifluoromethyl)phenyl]naphthalene-2-carboxamide (21 mg, 49.3 umol, 1 eq) was purified by SFC. The residue was purified by pre-SFC (DAICEL CHIRALPAK AD-H (250 mm*30 mm, 5 um), 0.1% NH$_3$H$_2$O ETOH, 40%, 40%). Compound 278 (2.7 mg, 6.5 umol, 13.2% yield) was obtained as a white solid. LCMS (ESI): RT=0.851 min, mass calcd for C$_{22}$H$_{18}$F$_3$N$_5$O 425.41 m/z found 426.0 [M+H]$^+$, $^1$H NMR (400 MHz, CD$_3$OD) δ 8.54 (s, 1H), 8.09 (br d, J=8.3 Hz, 1H), 7.98-7.80 (m, 4H), 7.77-7.63 (m, 4H), 7.59 (br d, J=7.1 Hz, 1H), 5.63 (br d, J=7.1 Hz, 1H), 4.41-4.34 (m, 3H), 1.75 (d, J=7.1 Hz, 3H). Compound 279 (2.8 mg, 6.6 umol, 13.4% yield) was obtained as a white solid. LCMS (ESI): RT=0.852 min, mass calcd for C$_{22}$H$_{18}$F$_3$N$_5$O 425.41 m/z found 426.0 [M+H]$^+$, $^1$H NMR (400 MHz, CD$_3$OD) δ 8.53 (d, J=1.3 Hz, 1H), 8.10-8.04 (m, 1H), 7.93-7.81 (m, 4H), 7.71-7.64 (m, 3H), 7.59-7.54 (m, 1H), 5.61 (q, J=7.1 Hz, 1H), 4.38-4.32 (m, 3H), 1.77-1.70 (m, 3H).

Example 236: (S)—N-(1-(1-methyl-1H-tetrazol-5-yl)ethyl)-5-(4-(trifluoromethyl)phenyl)-2-naphthamide (Compound 280) and (R)—N-(1-(1-methyl-1H-tetrazol-5-yl)ethyl)-5-(4-(trifluoromethyl)phenyl)-2-naphthamide (Compound 281)

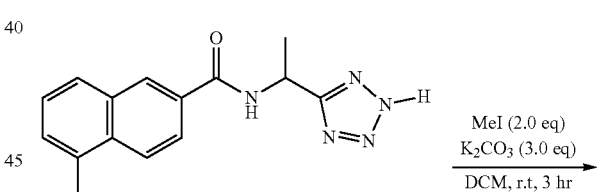

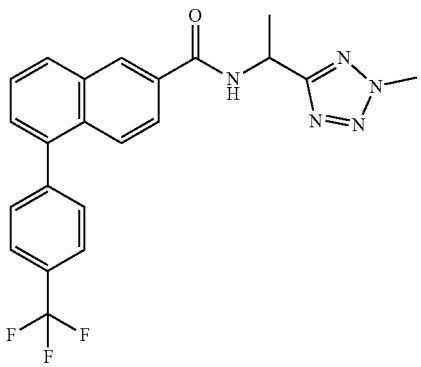

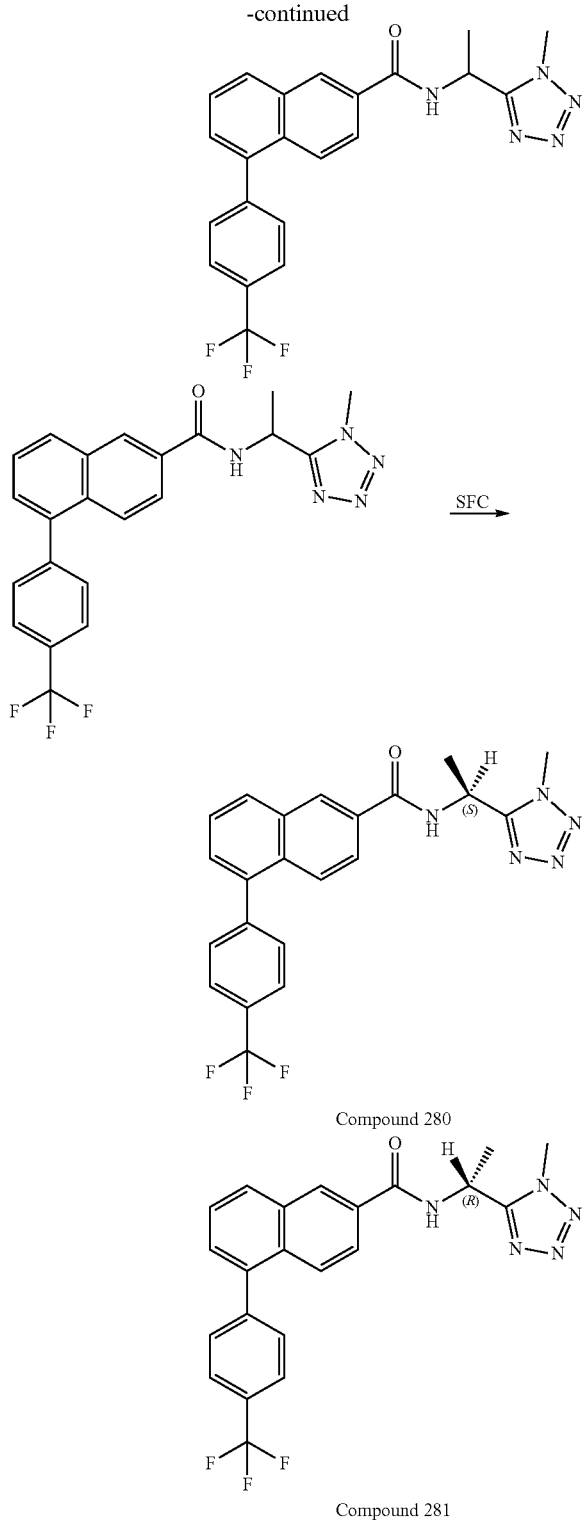

N-(1-(2-methyl-2H-tetrazol-5-yl)ethyl)-5-(4-(trifluoromethyl)phenyl)-2-naphthamide and N-(1-(1-methyl-1H-tetrazol-5-yl)ethyl)-5-(4-(trifluoromethyl)phenyl)-2-naphthamide To the solution of N-[1-(2H-tetrazol-5-yl)ethyl]-5-[4-(trifluoromethyl)phenyl]naphthalene-2-carboxamide (0.3 g, 0.72 mmol, 1 eq) in DMF (3 mL) was added CH$_3$I (207.0 mg, 1.46 mmol, 90.8 uL, 2 eq) and K$_2$CO$_3$ (302.3 mg, 2.19 mmol, 3 eq). The mixture was stirred at 25° C. for 3 hr. The reaction solution was added to H$_2$O (10 mL). The mixture was extracted with ethyl acetate (20 mL*3). The combined organic phase was washed with brine (20 mL*3), dried with anhydrous Na$_2$SO$_4$, filtered and concentrated in vacuum. The residue was purified by pre-HPLC (column: Xtimate C18 150*25 mm*5 um; mobile phase: [water (0.05% HCl)-ACN]; B %: 48%-78%, 8.5 min). Compound N-[1-(1-methyltetrazol-5-yl)ethyl]-5-[4-(trifluoromethyl)phenyl]naphthalene-2-carboxamide (15 mg, 35.2 umol, 4.8% yield) was obtained as a white solid. Compound N-[1-(2-methyltetrazol-5-yl)ethyl]-5-[4-(trifluoromethyl)phenyl]naphthalene-2-carboxamide (21 mg, 49.3 umol, 6.7% yield) was obtained as a white solid.

(S)—N-(1-(1-methyl-1H-tetrazol-5-yl)ethyl)-5-(4-(trifluoromethyl)phenyl)-2-naphthamide (Compound 280) and (R)—N-(1-(1-methyl-1H-tetrazol-5-yl)ethyl)-5-(4-(trifluoromethyl)phenyl)-2-naphthamide (Compound 281)

N-[1-(1-methyltetrazol-5-yl)ethyl]-5-[4-(trifluoromethyl)phenyl]naphthalene-2-carboxamide (15 mg, 35.2 umol, 1 eq) was purified by SFC. The residue was purified by pre-SFC (DAICEL CHIRALPAK AD-H (250 mm*30 mm, 5 um), 0.1% NH$_3$H$_2$O ETOH, 40%, 40%). Compound 280 (2.9 mg, 6.8 umol, 19.4% yield) was obtained as a white solid. LCMS (ESI): RT=0.839 min, mass calcd for C$_{22}$H$_{18}$F$_3$N$_5$O 425.41 m/z found 426.0 [M+H]$^+$, $^1$H NMR (400 MHz, CD$_3$OD) δ 8.41 (s, 1H), 7.96 (d, J=8.3 Hz, 1H), 7.79-7.70 (m, 4H), 7.57 (br d, J=7.1 Hz, 3H), 7.47 (d, J=7.0 Hz, 1H), 5.54 (d, J=7.0 Hz, 1H), 4.50 (s, 2H), 4.09 (s, 3H), 1.69 (d, J=7.0 Hz, 3H). Compound 281 (2.9 mg, 6.8 umol, 19.3% yield) was obtained as a white solid. LCMS (ESI): RT=0.839 min, mass calcd for C$_{22}$H$_{18}$F$_3$N$_5$O 425.41 m/z found 426.0 [M+H]$^+$, $^1$H NMR (400 MHz, CD$_3$OD) δ 8.53 (s, 1H), 8.09 (d, J=8.1 Hz, 1H), 7.92-7.83 (m, 4H), 7.72-7.66 (m, 3H), 7.60 (d, J=6.9 Hz, 1H), 5.66 (d, J=7.0 Hz, 1H), 4.21 (s, 3H), 1.81 (d, J=7.0 Hz, 3H).

Example 237: (S)—N-(1-(pyrazin-2-yl)ethyl)-5-(4-(trifluoromethyl)phenyl)-2-naphthamide (Compound 282) and (R)—N-(1-(pyrazin-2-yl)ethyl)-5-(4-(trifluoromethyl)phenyl)-2-naphthamide (Compound 283)

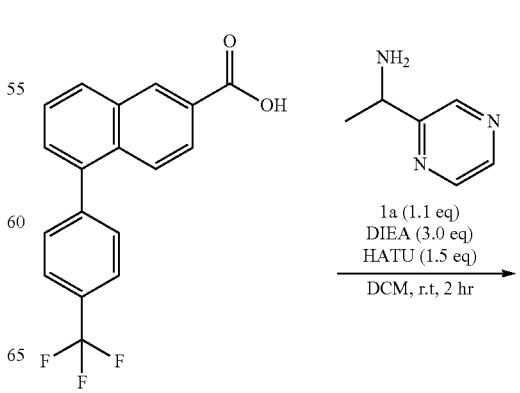

1a (1.1 eq)
DIEA (3.0 eq)
HATU (1.5 eq)
DCM, r.t, 2 hr

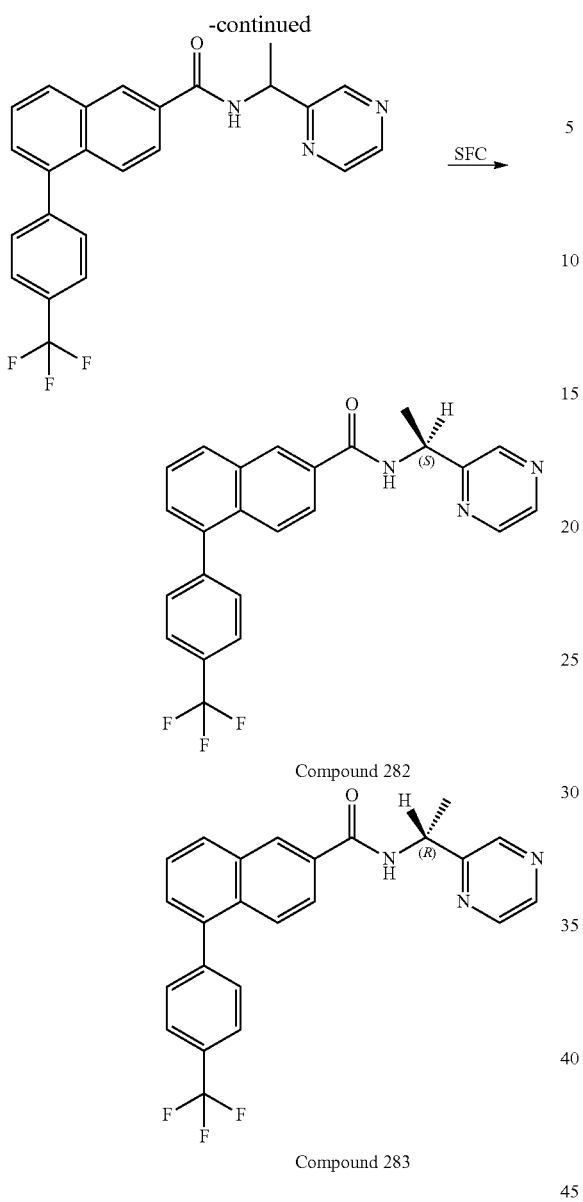

Compound 282

Compound 283

The mixture of 5-[4-(trifluoromethyl)phenyl]naphthalene-2-carboxylic acid (100 mg, 0.31 mmol, 1 eq), HATU (180.3 mg, 0.47 mmol, 1.5 eq) and DIPEA (122.5 mg, 0.94 mmol, 0.16 mL, 3 eq) in DCM (2 mL) was stirred at 25° C. for 1 hr. Then 1-pyrazin-2-ylethanamine (42.8 mg, 0.34 mmol, 1.1 eq) was added into the mixture and the mixture was stirred at 25° C. for another 1 hr. The reaction mixture was diluted with H$_2$O (10 mL) and the mixture was extracted with EA (10 mL*3). The combined organic phase was washed with brine (10 mL*2), dried with anhydrous Na$_2$SO$_4$, filtered and concentrated in vacuum. The residue was purified by prep-HPLC (column: Waters Xbridge 150*25 5u; mobile phase: [water (0.05% ammonia hydroxide v/v)-ACN]; B %: 50%-80%, 7.8 min). The racemic compound (14 mg, 32.5 umol, 10.3% yield) was obtained as a white solid. The racemic compound was separated by SFC (column: REGIS (s,s) WHELK-O1 (250 mm*30 mm, 5 um); mobile phase: [0.1% NH3H2O ETOH]; B %: 50%-50%, min). Compound 282 (4.7 mg, 11.0 umol, 33.2% yield) was obtained as a white solid. LCMS (ESI): RT=0.964 min, mass calcd for C$_{24}$H$_{18}$F$_3$N$_3$O 421.41 m/z found 422.0 [M+H]$^+$, $^1$H NMR (400 MHz, CD$_3$OD) δ 8.74 (d, J=1.3 Hz, 1H), 8.62 (dd, J=1.5, 2.5 Hz, 1H), 8.54 (d, J=1.5 Hz, 1H), 8.51 (d, J=2.8 Hz, 1H), 8.09 (d, J=8.3 Hz, 1H), 7.93-7.89 (m, 1H), 7.88-7.82 (m, 3H), 7.72-7.64 (m, 3H), 7.58 (dd, J=1.3, 7.0 Hz, 1H), 5.41 (q, J=7.0 Hz, 1H), 1.69 (d, J=7.0 Hz, 3H). Compound 283 (6.4 mg, 15.0 umol, 45.2% yield) was obtained as a white solid. LCMS (ESI): RT=0.970 min, mass calcd for C$_{24}$H$_{18}$F$_3$N$_3$O 421.41 m/z found 422.0 [M+H]$^+$, $^1$H NMR (400 MHz, CD$_3$OD) δ 8.72 (d, J=1.4 Hz, 1H), 8.61 (dd, J=1.6, 2.4 Hz, 1H), 8.52 (dd, J=1.9, 12.1 Hz, 2H), 8.08 (d, J=8.3 Hz, 1H), 7.93-7.81 (m, 4H), 7.71-7.64 (m, 3H), 7.57 (dd, J=1.1, 7.0 Hz, 1H), 5.40 (q, J=7.0 Hz, 1H), 1.68 (d, J=7.1 Hz, 3H).

Example 238: (S)—N-(1-(2H-tetrazol-5-yl)ethyl)-5-(4-(trifluoromethyl)phenyl)-2-naphthamide (Compound 284) and (R)—N-(1-(2H-tetrazol-5-yl)ethyl)-5-(4-(trifluoromethyl)phenyl)-2-naphthamide (Compound 285)

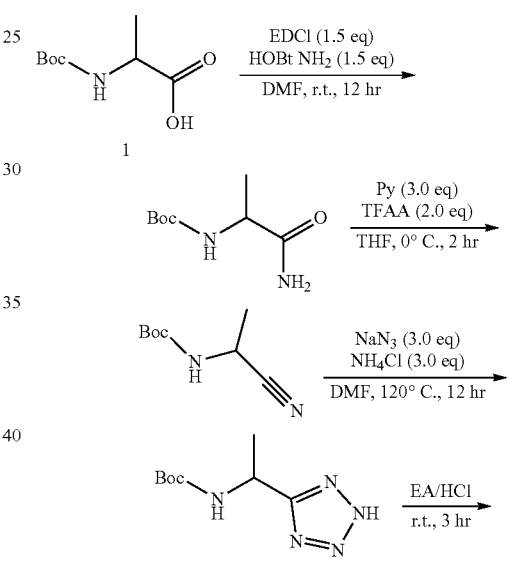

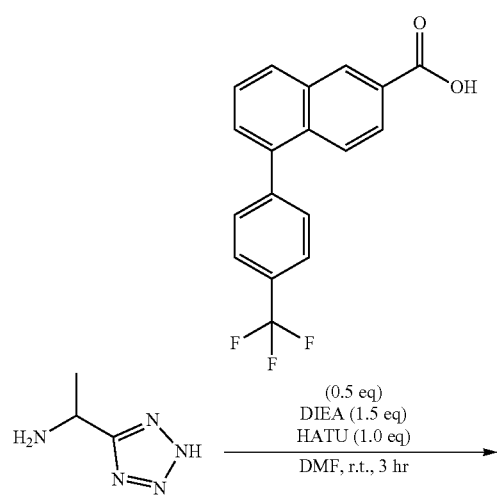

-continued

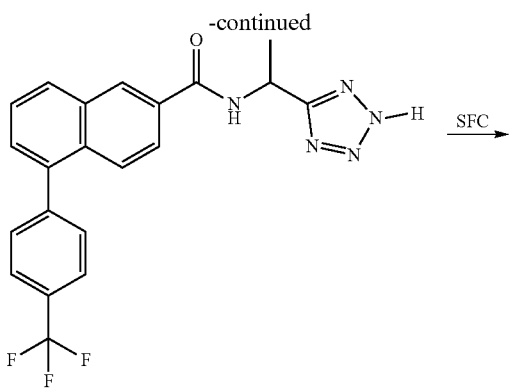

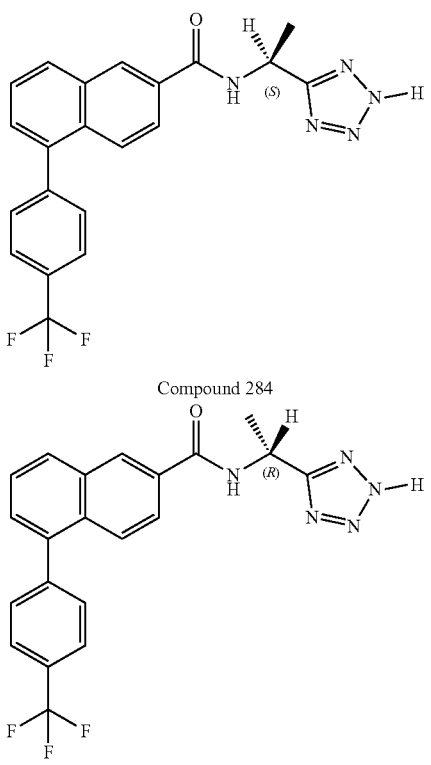

Compound 284

Compound 285

Tert-Butyl (1-amino-1-oxopropan-2-yl)carbamate

To a mixture of 2-(tert-butoxycarbonylamino)propanoic acid (2.5 g, 13.21 mmol, 1 eq) in DMF (10 mL) was added EDCI (3.80 g, 19.82 mmol, 1.5 eq) and ammonium; 1-oxidobenzotriazole (3.02 g, 19.82 mmol, 1.5 eq). The mixture was stirred for 12 hrs at 25° C. The mixture was quenched by H₂O (30 mL), and the mixture was extracted with EA (20 mL*3). The combined organic phase was washed with brine (20 mL*3), dried with anhydrous Na₂SO₄, filtered and concentrated in vacuum. The residue was used to the next step without further purification. Compound tert-butyl N-(2-amino-1-methyl-2-oxo-ethyl)carbamate (2.5 g, crude) was obtained as a white solid.

Tert-Butyl (1-cyanoethyl)carbamate

To a mixture of tert-butyl N-(2-amino-1-methyl-2-oxo-ethyl)carbamate (2 g, 10.63 mmol, 1 eq) in THF (5 mL) was added PYRIDINE (2.52 g, 31.88 mmol, 2.57 mL, 3 eq) and TFAA (4.46 g, 21.25 mmol, 2.96 mL, 2 eq). The mixture was stirred for 2 hrs at 0° C. The mixture was quenched by H₂O (30 mL), and the mixture was extracted with EA (20 mL*3). The combined organic phase was washed with brine (20 mL*3), dried with anhydrous Na₂SO₄, filtered and concentrated in vacuum. The residue was used to the next step without further purification. Compound tert-butyl N-(1-cyanoethyl)carbamate (1.8 g, crude) was obtained as a white solid.

Tert-Butyl (1-(2H-tetrazol-5-yl)ethyl)carbamate

To the solution of tert-butyl N-(1-cyanoethyl)carbamate (1.8 g, 10.58 mmol, 1 eq) in DMF (20 mL) was added NaN₃ (3.19 g, 49.07 mmol, 4.64 eq) and NH₄Cl (1.70 g, 31.73 mmol, 1.11 mL, 3 eq). The mixture was stirred at 120° C. for 12 hr. The reaction solution was added to H₂O (20 mL). The aqueous phase was adjusted to pH=5 and extracted with ethyl acetate (50 mL*3). The combined organic phase was washed with brine (30 mL*5), dried with anhydrous Na₂SO₄, filtered and concentrated in vacuum. The residue was used the next step without purification. Compound tert-butyl N-[1-(1H-tetrazol-5-yl)ethyl]carbamate (1.2 g, crude) was obtained as a yellow oil.

1-(2H-tetrazol-5-yl)ethanamine

To a mixture of tert-butyl N-[1-(1H-tetrazol-5-yl)ethyl]carbamate (0.2 g, 0.93 mmol, 1 eq) was added HCl/EtOAc (4 M, 3.36 mL, 14.31 eq). The mixture was stirred for 3 hrs at 25° C. The mixture was quenched by H₂O (30 mL), and the mixture was adjusted pH to 8 with NaOH (4M). The mixture was extracted with EA (10 mL*3). The combined organic phase was washed with brine (10 mL*3), dried with anhydrous Na₂SO₄, filtered and concentrated in vacuum. The residue was used to the next step without further purification. Compound 1-(1H-tetrazol-5-yl)ethanamine (0.087 g, crude) was obtained as a yellow oil.

(S)—N-(1-(2H-tetrazol-5-yl)ethyl)-5-(4-(trifluoromethyl)phenyl)-2-naphthamide (Compound 284) and (R)—N-(1-(2H-tetrazol-5-yl)ethyl)-5-(4-(trifluoromethyl)phenyl)-2-naphthamide (Compound 285)

To a solution of 5-[4-(trifluoromethyl)phenyl]naphthalene-2-carboxylic acid (0.1 g, 0.31 mmol, 1 eq) in DMF (5 mL) was added HATU (240.4 mg, 0.63 mmol, 2 eq) and Et₃N (95.9 mg, 0.94 mmol, 0.13 mL, 3 eq). The mixture was stirred for 0.5 hrs at 25° C. 1-(1H-tetrazol-5-yl)ethanamine (71.5 mg, 0.63 mmol, 2 eq) was added to the mixture. The mixture was stirred for 2.5 hr at 25° C. The mixture was quenched by H₂O (30 mL), and the mixture was filtered and the filtered cake was washed with EA (20 mL*3). The combined organic phase was washed with brine (20 mL*3), dried with anhydrous Na₂SO₄, filtered and concentrated in vacuum. The residue was purified by (column: Xtimate C18 150*25 mm*5 um; mobile phase: [water (0.05% HCl)-ACN]; B %: 43%-73%, 8.5 min). The racemic compound N-[1-(2H-tetrazol-5-yl)ethyl]-5-[4-(trifluoromethyl)phenyl] naphthalene-2-carboxamide (70 mg, 0.17 mmol, 53.8% yield) was obtained as a white solid. The racemic compound was separated by pre-SFC (DAICEL CHIRALPAK IG (250 mm*50 mm, 10 um), 0.1% NH3H2O ETOH, 30%, 30%). Compound 284 (13.8 mg, 33.6 umol, 23.1% yield) was obtained as a white solid. LCMS (ESI): RT=0.805 min, mass calcd for $C_{21}H_{16}F_3N_5O$ 411.38 m/z found 434.0 [M+Na]⁺, ¹H NMR (400 MHz, CD₃OD) δ 8.50 (d, J=1.0 Hz, 1H), 8.05

(d, J=8.3 Hz, 1H), 7.92-7.80 (m, 4H), 7.70-7.62 (m, 3H), 7.57-7.53 (m, 1H), 7.47 (dd, J=7.4, 8.4 Hz, 1H), 6.62 (d, J=7.3 Hz, 1H), 6.50 (d, J=8.5 Hz, 1H), 5.18 (q, J=6.9 Hz, 1H), 4.58 (br s, 1H), 3.09 (s, 6H), 1.59 (d, J=7.0 Hz, 3H). Compound 285 (14.0 mg, 34.1 umol, 23.4% yield) was obtained as a white solid. LCMS (ESI): RT=0.808 min, mass calcd for $C_{21}H_{16}F_3N_5O$ 411.38 m/z found 434.0 [M+Na]$^+$, $^1$H NMR (400 MHz, CD$_3$OD) δ 8.51 (d, J=1.3 Hz, 1H), 8.06 (d, J=8.3 Hz, 1H), 7.92-7.81 (m, 4H), 7.71-7.63 (m, 3H), 7.56 (dd, J=1.1, 7.2 Hz, 1H), 7.47 (dd, J=7.4, 8.4 Hz, 1H), 6.62 (d, J=7.3 Hz, 1H), 6.51 (d, J=8.5 Hz, 1H), 5.18 (q, J=6.8 Hz, 1H), 3.10 (s, 6H), 1.59 (d, J=7.0 Hz, 3H).

Example 239: (R)—N-(1-(6-(dimethylamino)pyridin-2-yl)ethyl)-5-(4-(trifluoromethyl)phenyl)-2-naphthamide (Compound 286) and (S)—N-(1-(6-(dimethylamino)pyridin-2-yl)ethyl)-5-(4-(trifluoromethyl)phenyl)-2-naphthamide (Compound 287)

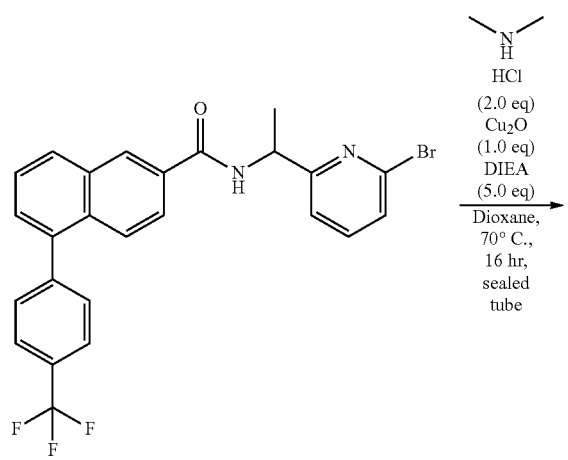

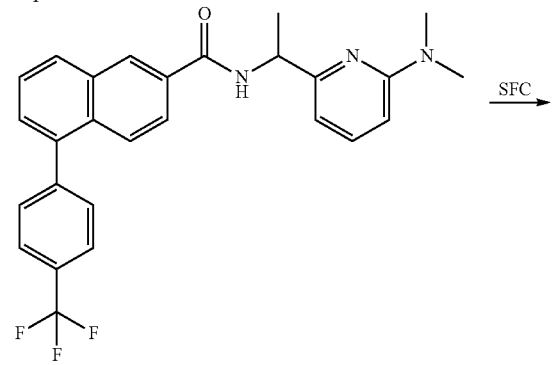

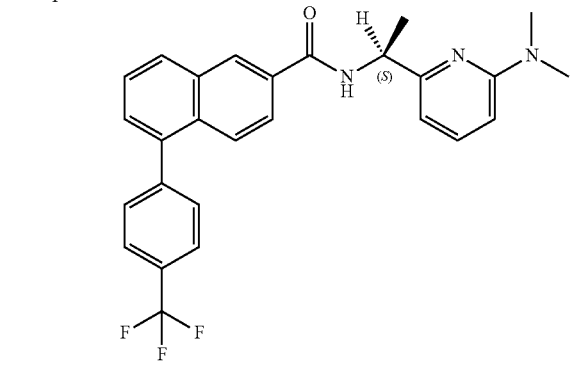

Compound 287

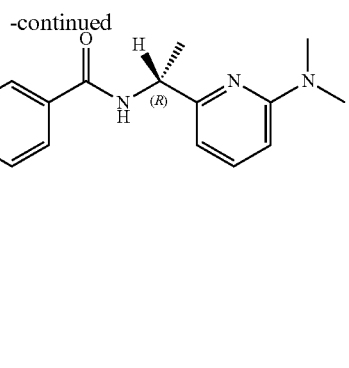

Compound 286

A mixture of N-[1-(6-bromo-2-pyridyl)ethyl]-5-[4-(trifluoromethyl)phenyl]naphthalene-2-carboxamide (200 mg, 0.40 mmol, 1 eq), N-methylmethanamine (65.3 mg, 0.80 mmol, 73.4 uL, 2 eq, HCl), Cu$_2$O (57.3 mg, 0.40 mmol, 40.9 uL, 1 eq), DIPEA (258.8 mg, 2.00 mmol, 348.8 uL, 5 eq) in dioxane (2 mL) were loaded in a sealed reaction tube. The reaction temperature was increased to 70° C. and the reaction mixture was stirred at 70° C. for 16 hr. The residue was poured into H$_2$O (20 mL) and stirred for 5 min. The aqueous phase was extracted with EA (10 mL*3). The combined organic phase was washed with brine (20 mL), dried with anhydrous Na$_2$SO$_4$, filtered and concentrated in vacuum. The residue was purified by flash silica gel chromatography (12 g SepaFlash® Silica Flash Column, EA/PE: 0~70%) to give 103 mg the racemic product. And then the racemic product was separated by chiral SFC (column: DAICEL CHIRALPAK AD (250 mm*30 mm, 10 um); mobile phase: [0.1% NH3H2O IPA]; B %: 30%-30%, min). Compound 286 (21.6 mg, 45.2 umol, 11.2% yield) was obtained as a white solid. LCMS (ESI): RT=0.788 min, mass calcd for $C_{27}H_{24}F_3N_3O$ 463.49 m/z found 464.1 [M+H]$^+$, NMR (400 MHz, CD$_3$OD) δ 8.51 (d, J=1.3 Hz, 1H), 8.06 (d, J=8.3 Hz, 1H), 7.92-7.81 (m, 4H), 7.71-7.63 (m, 3H), 7.56 (dd, J=1.1, 7.2 Hz, 1H), 7.47 (dd, J=7.4, 8.4 Hz, 1H), 6.62 (d, J=7.3 Hz, 1H), 6.51 (d, J=8.5 Hz, 1H), 5.18 (q, J=6.8 Hz, 1H), 3.10 (s, 6H), 1.59 (d, J=7.0 Hz, 3H). Compound 287 (21.3 mg, 43.6 umol, 10.9% yield) was obtained as a white solid. LCMS (ESI): RT=0.803 min, mass calcd for $C_{27}H_{24}F_3N_3O$ 463.49 m/z found 464.2 [M+H]$^+$, $^1$H NMR (400 MHz, CD$_3$OD) δ 8.50 (d, J=1.0 Hz, 1H), 8.05 (d, J=8.3 Hz, 1H), 7.92-7.80 (m, 4H), 7.70-7.62 (m, 3H), 7.57-7.53 (m, 1H), 7.47 (dd, J=7.4, 8.4 Hz, 1H), 6.62 (d, J=7.3 Hz, 1H), 6.50 (d, J=8.5 Hz, 1H), 5.18 (q, J=6.9 Hz, 1H), 4.58 (br s, 1H), 3.09 (s, 6H), 1.59 (d, J=7.0 Hz, 3H).

Example 240: N-(3-phenyloxetan-3-yl)-5-(4-(trifluoromethyl)phenyl)-2-naphthamide (Compound 288)

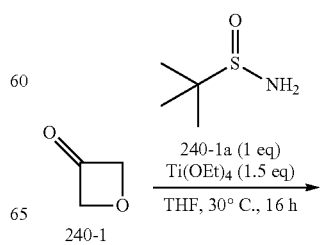

240-1

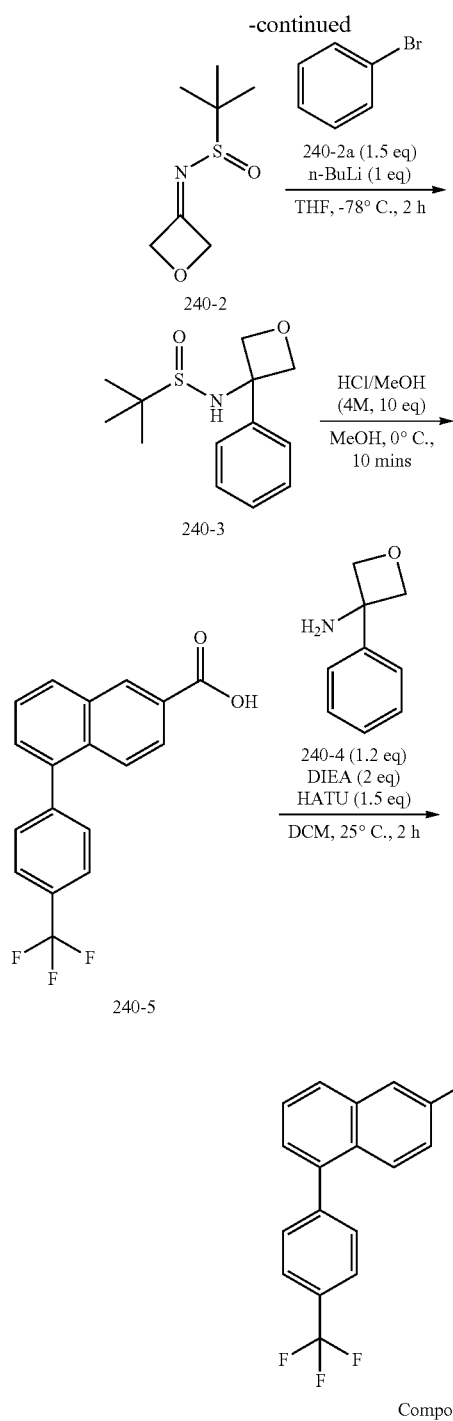

2-methyl-N-(oxetan-3-ylidene)propane-2-sulfinamide

To a solution of compound 240-1 (5.0 g, 69.4 mmol, 1 eq) and compound 240-1a (8.4 g, 69.4 mmol, 1 eq) in THF (100 mL) was added Ti(OEt)$_4$ (23.7 g, 104.1 mmol, 21.58 mL, 1.5 eq). The mixture was stirred at 30° C. for 16 h. 100 mL of water was added into the mixture. Yellow solid was precipitated out. The mixture was diluted with EtOAc (80 mL) and filtered. The filter cake was washed with EtOAc (100 mL*2). The combined organic layer was concentrated. The residue was purified by column chromatography (SiO$_2$, Ethyl acetate/Petroleum ether=0% to 15%) to give compound 240-2 (2.5 g, 14.27 mmol, 20.6% yield) as a yellow liquid.

2-methyl-N-(3-phenyloxetan-3-yl)propane-2-sulfinamide

To a solution of compound 240-2a (1.08 g, 6.85 mmol, 0.72 mL, 1.5 eq) in THF (5 mL) was added n-BuLi (2.5 M, 1.83 mL, 1 eq) at −78° C. The mixture was stirred at −78° C. for 1 hr. compound 2 (800 mg, 4.56 mmol, 1 eq) in THF (1 mL) was added. The mixture was stirred at −78° C. for 1 hr. The mixture was quenched with NH$_4$Cl (10 mL). The mixture was extracted with EA (20 mL*3). The organic layer was dried over Na$_2$SO$_4$, filtered and concentrated. The residue was purified by flash silica gel chromatography (ISCO®; 10 g SepaFlash® Silica Flash Column, Eluent of 0-70% Ethyl acetate/Petroleum ether gradient @18 mL/min) to give compound 240-3 (400 mg, 1.58 mmol, 34.6% yield) as a yellow oil. $^1$H NMR (400 MHz, CDCl$_3$) δ 7.47-7.30 (m, 5H), 5.21 (d, J=6.9 Hz, 1H), 5.09-5.05 (m, 2H), 5.04-5.00 (m, 1H), 4.15-4.11 (m, 1H), 1.21 (s, 9H).

3-phenyloxetan-3-amine

To a solution of compound 240-3 (100 mg, 0.39 mmol, 1 eq) in MeOH (1 mL) was added HCl/MeOH (4 M, 0.99 mL, 10 eq) at 0° C. The mixture was stirred at 0° C. for 10 mins. Sat. NaHCO$_3$ was added to the mixture until pH=6-7. The mixture was concentrated. The residue was dissolved in EA/MeOH (v/v=10/1). The mixture was filtered. The filtrate was concentrated to give compound 240-4 (50.0 mg, 0.34 mmol, 84.9% yield) as a yellow oil. $^1$H NMR (400 MHz, CDCl$_3$) δ 7.56-7.51 (m, 2H), 7.42 (t, J=7.6 Hz, 2H), 7.35-7.30 (m, 1H), 5.01 (d, J=6.5 Hz, 2H), 4.80 (d, J=6.5 Hz, 2H).

N-(3-phenyloxetan-3-yl)-5-(4-(trifluoromethyl)phenyl)-2-naphthamide

To a solution of compound 240-5 (50.0 mg, 0.16 mmol, 1 eq), HATU (90.2 mg, 0.24 mmol, 1.5 eq) and compound 240-4 (23.6 mg, 0.16 mmol, 1 eq) in DCM (1 mL) was added DIEA (40.9 mg, 0.32 mmol, 55 uL, 2 eq). The mixture was stirred at 25° C. for 2 hr. The mixture was diluted with H$_2$O (5 mL). The mixture was extracted with EA (10 mL*3). The organic layer was dried over Na$_2$SO$_4$, filtered and concentrated. The residue was purified by prep-HPLC (column: Waters Xbridge 150*25 5u; mobile phase: [water (0.05% ammonia hydroxide v/v)-ACN]; B %: 65%-95%, 7.8 min) to give the title compound (16.2 mg, 36.3 umol, 23.0% yield) as a white solid. LCMS (ESI): RT=0.903 min, mass calc. for C$_{27}$H$_{20}$F$_3$NO$_2$ 447.14, m/z found 448.0 [M+H]$^+$; $^1$H NMR (400 MHz, CDCl$_3$) δ 8.46 (s, 1H), 8.01 (d, J=8.3 Hz, 1H), 7.93-7.83 (m, 2H), 7.79 (d, J=8.1 Hz, 2H), 7.68-7.59 (m, 5H), 7.54 (d, J=7.1 Hz, 1H), 7.42 (t, J=7.7 Hz, 2H), 7.36-7.30 (m, 1H), 7.06 (br s, 1H), 5.22 (d, J=6.8 Hz, 2H), 5.09 (d, J=6.8 Hz, 2H).

Example 241: (S)—N-(1-cyclopropylethyl)-5-(4-(trifluoromethyl)phenyl)-2-naphthamide (Compound 289) and (R)—N-(1-cyclopropylethyl)-5-(4-(trifluoromethyl)phenyl)-2-naphthamide (Compound 290)

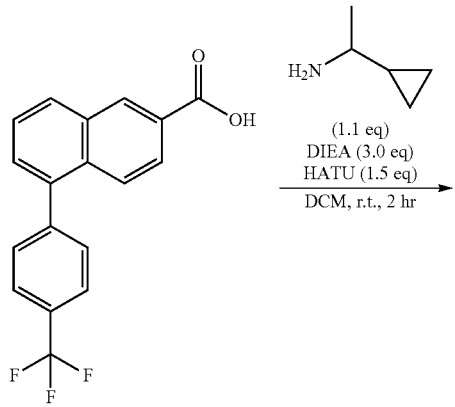

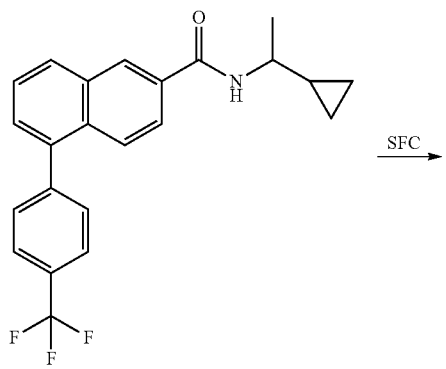

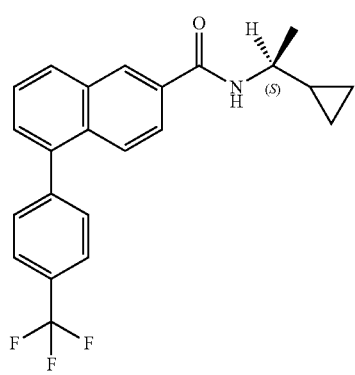

Compound 289

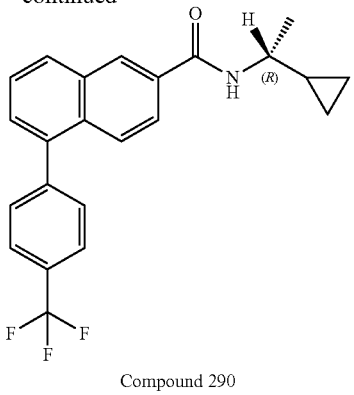

Compound 290

(S)—N-(1-cyclopropylethyl)-5-(4-(trifluoromethyl)phenyl)-2-naphthamide (Compound 289) and (R)—N-(1-cyclopropylethyl)-5-(4-(trifluoromethyl)phenyl)-2-naphthamide (Compound 290)

The mixture of 5-[4-(trifluoromethyl)phenyl]naphthalene-2-carboxylic acid (100 mg, 0.31 mmol, 1 eq), HATU (180.3 mg, 0.47 mmol, 1.5 eq) and DIPEA (122.5 mg, 0.94 mmol, 0.16 mL, 3 eq) in DCM (2 mL) was stirred at 25° C. for 1 hr. Then 1-cyclopropylmethanamine (29.6 mg, 0.34 mmol, 1.1 eq) was added into the mixture and the mixture was stirred at 25° C. for another 1 hr. The reaction mixture was diluted with $H_2O$ (10 mL) and the mixture was extracted with EA (10 mL*3). The combined organic phase was washed with brine (10 mL*2), dried with anhydrous $Na_2SO_4$, filtered and concentrated in vacuum. The residue was purified by prep-HPLC (column: Xtimate C18 150*25 mm*5 um; mobile phase: [water (0.05% HCl)-ACN]; B %: 61%-91%, 8.5 min). The racemic compound N-(1-cyclopropylethyl)-5-[4-(trifluoromethyl)phenyl]naphthalene-2-carboxamide (65 mg, 0.16 mmol, 53% yield) was obtained as a white solid. The racemic compound was separated by SFC (column: DAICEL CHIRALPAK AS-H (250 mm*30 mm, 5 um); mobile phase: [0.1% NH3H2O ETOH]; B %: 25%-25%, min). Compound 289 (20 mg, 51.6 umol, 30.4% yield) was obtained as a white solid. LCMS (ESI): RT=1.038 min, mass calcd for $C_{23}H_{20}F_3NO$ 383.41 m/z found 384.0 $[M+H]^+$, $^1H$ NMR (400 MHz, $CD_3OD$) δ 8.45 (s, 1H), 8.04 (br t, J=7.4 Hz, 1H), 7.90-7.76 (m, 4H), 7.70-7.59 (m, 3H), 7.56-7.48 (m, 1H), 3.63-3.48 (m, 1H), 1.35 (d, J=6.6 Hz, 3H), 1.12-1.02 (m, 1H), 0.62-0.46 (m, 2H), 0.45-0.24 (m, 2H). Compound 290 (30 mg, 77.4 umol, 45.6% yield) was obtained as a white solid. LCMS (ESI): RT=1.036 min, mass calcd for $C_{23}H_{20}F_3NO$ 383.41 m/z found 384.0 $[M+H]^+$, $^1H$ NMR (400 MHz, $CD_3OD$) δ 8.45 (s, 1H), 8.04 (br t, J=7.4 Hz, 1H), 7.90-7.76 (m, 4H), 7.70-7.59 (m, 3H), 7.56-7.48 (m, 1H), 3.63-3.48 (m, 1H), 1.35 (d, J=6.6 Hz, 3H), 1.12-1.02 (m, 1H), 0.62-0.46 (m, 2H), 0.45-0.24 (m, 2H).

General Procedure for Preparation of Compound 291-Compound 297

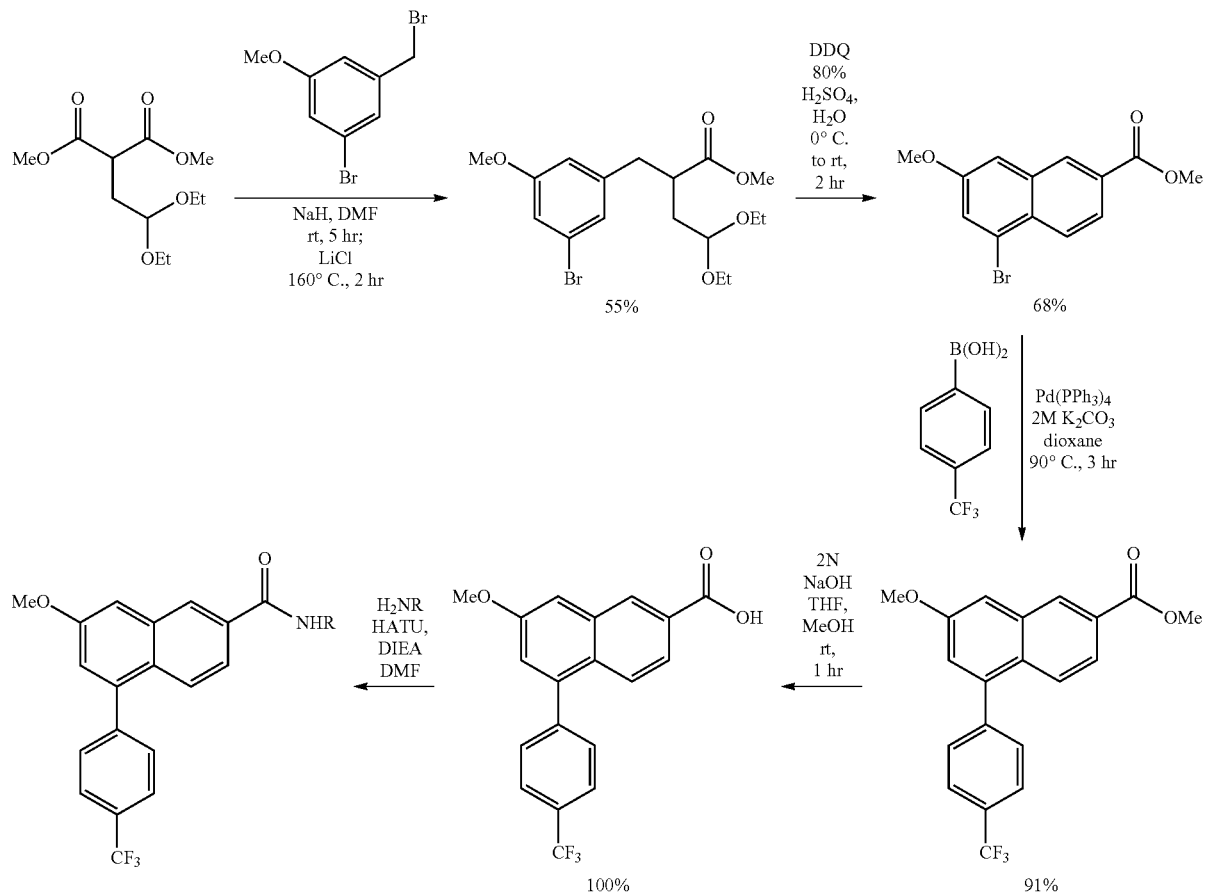

Methyl 2-(3-bromo-5-methoxybenzyl)-4,4-diethoxybutanoate

NaH 60% in mineral oil (1.03 g, 25.7 mmol, 2.7 equiv.) was carefully added to 1-bromo-3-(bromomethyl)-5-methoxybenzene (2.66 g, 9.5 mmol, 1 equiv.) in 20 mL DMF and stirred at rt for 1 hr. Dimethyl 2-(2,2-diethoxyethyl) malonate (3.5 g, 14.3 mmol, 1.5 equiv.) in 12 mL DMF was added dropwise and stirred at rt for 4 hr. LiCl (445 mg, 10.5 mmol, 1.1 equiv.) was carefully added and the mixture was heated to 160° C. for 2 hr. The reaction mixture was cooled to rt, diluted Et$_2$O, and washed with sat. aq. NH$_4$Cl, H$_2$O, and brine. The organic layer was dried with Na$_2$SO$_4$, concentrated, and purified by FCC, 0 to 15% EtOAc in Hexane gradient to give methyl 2-(3-bromo-5-methoxybenzyl)-4,4-diethoxybutanoate (2.037 g, 5.2 mmol, 55% yield) as a yellow oil. LCMS [M+H]$^+$=389.

Methyl 5-bromo-7-methoxy-2-naphthoate

Methyl 2-(3-bromo-5-methoxybenzyl)-4,4-diethoxybutanoate (390 mg, 1 mmol, 1 equiv.) in MeOH (0.5 mL) was carefully added to DDQ (230 mg, 1.01 mmol, 1.01 equiv.) in 2 mL of 80% H$_2$SO$_4$(aq) at 0° C. The mixture was stirred at 0° C. for 1 hr and slowly warmed to rt over 1 hr. The solid was filtered, re-dissolved in EtOAc, and the organic layer was washed with H$_2$O, brine, dried with Na$_2$SO$_4$, and concentrated. The residue was purified by FCC, 0 to 20% EtOAc in Hexane gradient to give methyl 5-bromo-7-methoxy-2-naphthoate (200 mg, 0.68 mmol, 68% yield), colorless solid. LCMS [M+H]$^+$=295.

Methyl 7-methoxy-5-(4-(trifluoromethyl)phenyl)-2-naphthoate

5-Bromo-7-methoxy-2-naphthoate (800 mg, 2.7 mmol, 1 equiv.), (4-(trifluoromethyl)phenyl)boronic acid (618 mg, 3.2 mmol, 1.2 equiv.), Pd(PPh$_3$)$_4$ (61 mg, 0.05 mmol, 0.1 equiv.), and 4:1 dioxane/2M K$_2$CO$_3$(aq) (10.8 mL:2.7 mL, 0.2M) were thoroughly purged with N$_2$ for 10 min. The mixture was heated to 90° C. for 3 hr. The reaction mixture was cooled to rt, diluted EtOAc, and washed with sat. aq. NH$_4$Cl, H$_2$O, and brine. The organic layer was dried with Na$_2$SO$_4$, concentrated, and purified by FCC, 0 to 20% EtOAc in Hexane gradient to give methyl 7-methoxy-5-(4-(trifluoromethyl)phenyl)-2-naphthoate (884 mg, 2.5 mmol, 91% yield), colorless solid. LCMS [M+H]$^+$=361.

7-Methoxy-5-(4-(trifluoromethyl)phenyl)-2-naphthoic Acid

Methyl 7-methoxy-5-(4-(trifluoromethyl)phenyl)-2-naphthoate (724 mg, 2 mmol, 1 equiv.) was stirred in 24 mL of a 1:1:1 mixture of THF:MeOH:2N NaOH(aq) at rt for 2 hr. The mixture was concentrated, and the residue was dissolved in DCM and acidified with 2N HCl(aq). The organic layer was dried with Na₂SO₄ and concentrated to give 7-methoxy-5-(4-(trifluoromethyl)phenyl)-2-naphthoic acid (690 mg, 2 mmol, 100% yield), colorless solid. LCMS [M+H]⁺=347.

Example 242: N-(2-Hydroxy-1-(pyridin-2-yl)ethyl)-7-methoxy-5-(4-(trifluoromethyl)phenyl)-2-naphthamide (Compound 291)

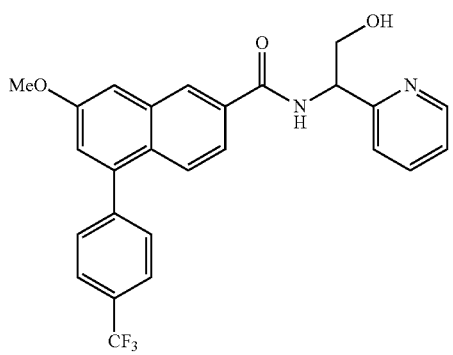 [SMILES: COc1cc(-c2ccc(C(F)(F)F)cc2)c2ccc(C(=O)NC(CO)c3ccccn3)cc2c1]

7-Methoxy-5-(4-(trifluoromethyl)phenyl)-2-naphthoic acid (1 equiv.), 2-amino-2-(pyridin-2-yl)ethan-1-ol dihydrochloride (1.2 equiv.), and HATU (1.2 equiv.) were dissolved in DMF (0.2M) at rt. DIEA (4 equiv.) was added slowly, and the mixture was stirred at rt until consumption of the acid as determined by LCMS, 2.5 hr. Upon completion, the reaction mixture was diluted with H₂O and stirred rapidly for 20 min. The resulting solid was filtered, rinsed with H₂O, and dried to give the desired amide product as a colorless solid, 23 mg, 86%, LCMS [M+H]⁺=467.

Example 243: (S)-7-Methoxy-N-(1-(pyridin-2-yl)ethyl)-5-(4-(trifluoromethyl)phenyl)-2-naphthamide (Compound 292)

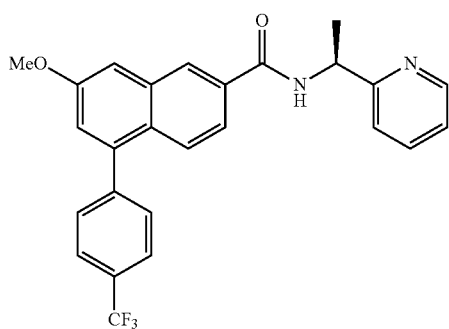 [SMILES: COc1cc(-c2ccc(C(F)(F)F)cc2)c2ccc(C(=O)N[C@@H](C)c3ccccn3)cc2c1]

7-Methoxy-5-(4-(trifluoromethyl)phenyl)-2-naphthoic acid (1 equiv.), (S)-1-(pyridin-2-yl)ethan-1-amine (1.2 equiv.), and HATU (1.2 equiv.) were dissolved in DMF (0.2M) at rt. DIEA (2 equiv.) was added slowly, and the mixture was stirred at rt until consumption of the acid as determined by LCMS, 2.5 hr. Upon completion, the reaction mixture was diluted with H₂O and stirred rapidly for 20 min. The resulting solid was filtered, rinsed with H₂O, and dried to give the desired amide product as a colorless solid, 19 mg, 75%, LCMS [M+H]⁺=451.

Example 244: (R)-7-Methoxy-N-(1-(pyridin-2-yl)ethyl)-5-(4-(trifluoromethyl)phenyl)-2-naphthamide (Compound 293)

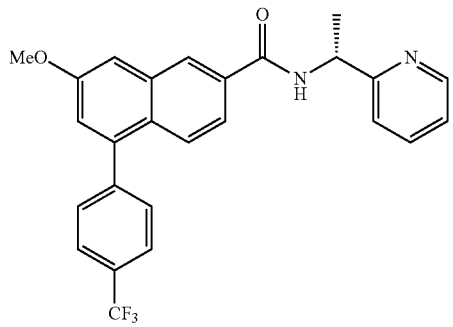 [SMILES: COc1cc(-c2ccc(C(F)(F)F)cc2)c2ccc(C(=O)N[C@H](C)c3ccccn3)cc2c1]

7-Methoxy-5-(4-(trifluoromethyl)phenyl)-2-naphthoic acid (1 equiv.), (R)-1-(pyridin-2-yl)ethan-1-amine (1.2 equiv.), and HATU (1.2 equiv.) were dissolved in DMF (0.2M) at rt. DIEA (2 equiv.) was added slowly, and the mixture was stirred at rt until consumption of the acid as determined by LCMS, 2.5 hr. Upon completion, the reaction mixture was diluted with H₂O and stirred rapidly for 20 min. The resulting solid was filtered, rinsed with H₂O, and dried to give the desired amide product as a colorless solid, 21 mg, 81%, LCMS [M+H]⁺=451.

Example 245: (S)-7-Methoxy-N-(1-methoxypropan-2-yl)-5-(4-(trifluoromethyl)phenyl)-2-naphthamide (Compound 294)

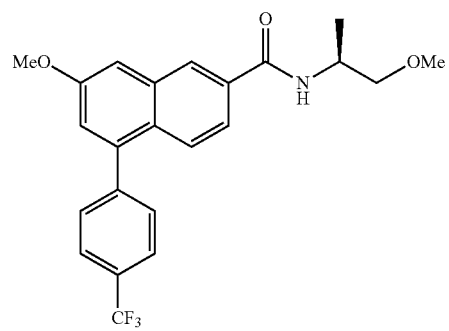

7-Methoxy-5-(4-(trifluoromethyl)phenyl)-2-naphthoic acid (1 equiv.), (S)-1-methoxypropan-2-amine hydrochloride (1.2 equiv.), and HATU (1.2 equiv.) were dissolved in DMF (0.2M) at rt. DIEA (3 equiv.) was added slowly, and the mixture was stirred at rt until consumption of the acid as determined by LCMS, 2.5 hr. Upon completion, the reaction mixture was diluted with H₂O and stirred rapidly for 20 min. The resulting solid was filtered, rinsed with H₂O, and dried to give the desired amide product as a colorless solid, 18 mg, 75%, LCMS [M+H]⁺=418.

Example 246: (R)-7-Methoxy-N-(1-methoxypropan-2-yl)-5-(4-(trifluoromethyl)phenyl)-2-naphthamide (Compound 295)

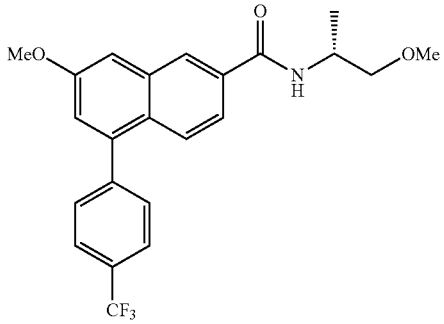 [SMILES: COC[C@@H](C)NC(=O)c1ccc2c(-c3ccc(C(F)(F)F)cc3)cc(OC)cc2c1]

7-Methoxy-5-(4-(trifluoromethyl)phenyl)-2-naphthoic acid (1 equiv.), (R)-1-methoxypropan-2-amine hydrochloride (1.2 equiv.), and HATU (1.2 equiv.) were dissolved in DMF (0.2M) at rt. DIEA (3 equiv.) was added slowly, and the mixture was stirred at rt until consumption of the acid as determined by LCMS, 2.5 hr. Upon completion, the reaction mixture was diluted with $H_2O$ and stirred rapidly for 20 min. The resulting solid was filtered, rinsed with $H_2O$, and dried to give the desired amide product as a colorless solid, 23 mg, 94%, LCMS $[M+H]^+$=418.

Example 247: (S)—N-(1-Hydroxypropan-2-yl)-7-methoxy-5-(4-(trifluoromethyl)phenyl)-2-naphthamide (Compound 296)

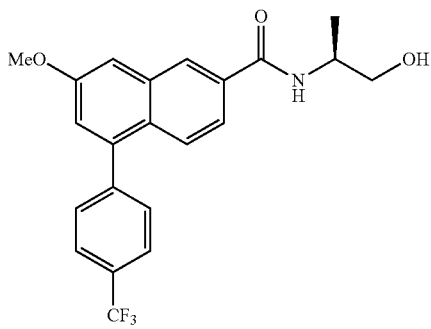 [SMILES: COc1cc(-c2ccc(C(F)(F)F)cc2)c2ccc(C(=O)N[C@@H](C)CO)cc2c1]

7-Methoxy-5-(4-(trifluoromethyl)phenyl)-2-naphthoic acid (1 equiv.), (S)-2-aminopropan-1-ol (1.2 equiv.), and HATU (1.2 equiv.) were dissolved in DMF (0.2M) at rt. DIEA (2 equiv.) was added slowly, and the mixture was stirred at rt until consumption of the acid as determined by LCMS, 2.5 hr. Upon completion, the reaction mixture was diluted with $H_2O$ and stirred rapidly for 20 min. The resulting solid was filtered, rinsed with $H_2O$, and dried to give the desired amide product as a colorless solid, 19 mg, 82%, LCMS $[M+H]^+$=404.

Example 248: (R)—N-(1-Hydroxypropan-2-yl)-7-methoxy-5-(4-(trifluoromethyl)phenyl)-2-naphthamide (Compound 297)

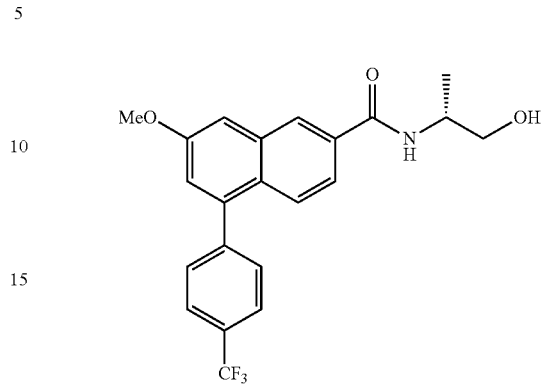

7-Methoxy-5-(4-(trifluoromethyl)phenyl)-2-naphthoic acid (1 equiv.), (R)-2-aminopropan-1-ol (1.2 equiv.), and HATU (1.2 equiv.) were dissolved in DMF (0.2M) at rt. DIEA (2 equiv.) was added slowly, and the mixture was stirred at rt until consumption of the acid as determined by LCMS, 2.5 hr. Upon completion, the reaction mixture was diluted with $H_2O$ and stirred rapidly for 20 min. The resulting solid was filtered, rinsed with $H_2O$, and dried to give the desired amide product as a colorless solid, 15 mg, 65%, LCMS $[M+H]^+$=404.

Example 249: N-Isopropyl-6-(4-(trifluoromethyl)phenyl)-[1,2,4]triazolo[5,1-a]isoquinoline-9-carboxamide (Compound 298)

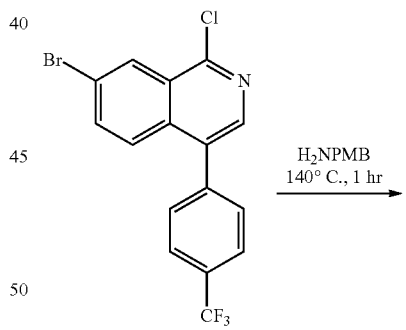

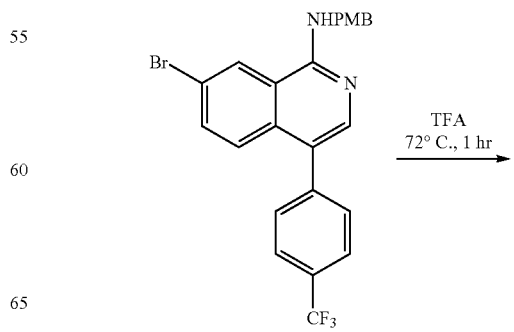

-continued

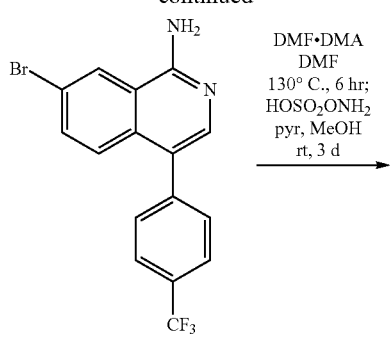

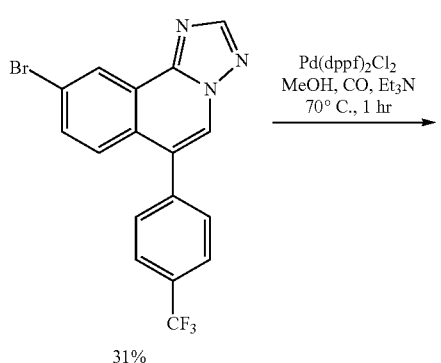
31%

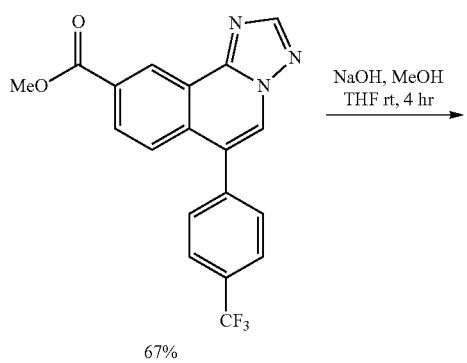
67%

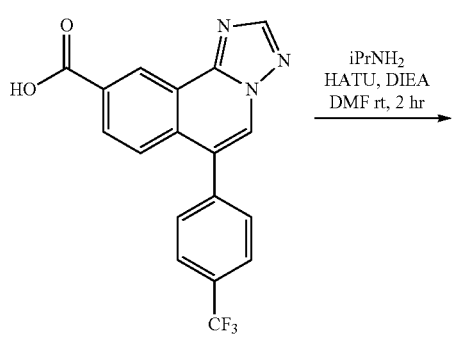

-continued

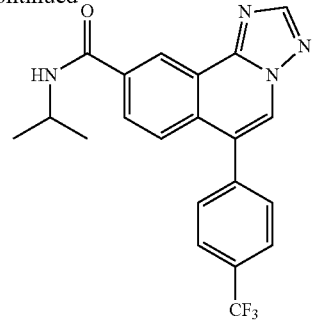
Compound 298

7-Bromo-N-(4-methoxybenzyl)-4-(4-(trifluoromethyl)phenyl)isoquinolin-1-amine

7-Bromo-1-chloro-4-(4-(trifluoromethyl)phenyl)isoquinoline (60 mg, 1 equiv.) and (4-methoxyphenyl)methanamine (0.06 mL, 3 equiv.) were heated to 140° C. for 1 hr. the reaction was cooled to rt, and passed through a silica plug with 25% EtOAc in Hex and concentrated to give the desired product, which was used directly in the next step without further purification. LCMS [M+H]$^+$=487.

7-Bromo-4-(4-(trifluoromethyl)phenyl)isoquinolin-1-amine

7-Bromo-N-(4-methoxybenzyl)-4-(4-(trifluoromethyl)phenyl)isoquinolin-1-amine (1 equiv.) and TFA (0.5 mL) were heated to 72° C. for 1 hr. the reaction mixture was concentrated, diluted with DCM, neutralized with NaHCO$_3$, dried with Na$_2$SO$_4$, concentrated and used directly in the nest step without further purification. LCMS [M+H]$^+$=367.

9-Bromo-6-(4-(trifluoromethyl)phenyl)-[1,2,4]triazolo[5,1-a]isoquinoline

7-Bromo-4-(4-(trifluoromethyl)phenyl)isoquinolin-1-amine (1 equiv.), DMF·DMA (0.1 mL) and DMF (1 mL) were heated at 130° C. for 6 hr. The reaction was cooled and concentrated. The residue was re-suspended in MeOH (1 mL), and pyridine (0.1 mL) and hydroxylamine-O-sulfonic acid (29 mg, 1.01 equiv.) were added at rt. The reaction was stirred at rt for 2 d. The mixture was diluted with EtOAc, washed with sat. aq. NH$_4$Cl, H$_2$O, and brine. The organic layer was dried with Na$_2$SO$_4$, concentrated, and purified by FCC, 0 to 30% EtOAc in Hexane gradient to give the desired product (19 mg, 31%). LCMS [M+H]$^+$=392.

Methyl 6-(4-(trifluoromethyl)phenyl)-[1,2,4]triazolo[5,1-a]isoquinoline-9-carboxylate To a mixture 9-Bromo-6-(4-(trifluoromethyl)phenyl)-[1,2,4]triazolo[5,1-a]isoquinoline (19 mg, 1 equiv.) in MeOH (0.1M) was added Pd(dppf)$_2$Cl$_2$ (0.05 equiv.) and Et$_3$N (2 equiv.). CO(g) was bubbled for 1 h at 70° C. After cooling to rt, the reaction mixture was concentrated and purified directly by FCC (5 to 40% EtOAc in Hex) to give the desired product. (12 mg, 67%). LCMS [M+H]$^+$=372.

6-(4-(Trifluoromethyl)phenyl)-[1,2,4]triazolo[5,1-a]isoquinoline-9-carboxylic Acid Methyl 6-(4-(trifluoromethyl)phenyl)-[1,2,4]triazolo[5,1-a]isoquinoline-9-carboxylate (12 mg, 1 equiv.), was suspended in MeOH/THF (1:1, 0.05M) and treated with 2N NaOH (0.1M) for 4 h. The reaction mixture was filtered and acidified to pH 2 and the resulting solid was filtered to give a colorless solid (11 mg). LCMS [M+H]$^+$=358.

N-Isopropyl-6-(4-(trifluoromethyl)phenyl)-[1,2,4]triazolo[5,1-a]isoquinoline-9-carboxamide 6-(4-(Trifluoromethyl)phenyl)-[1,2,4]triazolo[5,1-a]isoquinoline-9-carboxylic acid (1 equiv.), propan-2-amine (1.2 equiv.), and HATU (1.2 equiv.) were dissolved in DMF (0.2M) at rt. DIEA (2 equiv.) was added slowly, and the mixture was stirred at rt until consumption of the acid as determined by LCMS, 2 hr. Upon completion, the reaction mixture was diluted with H$_2$O and stirred rapidly for 20 min. The resulting solid was filtered, rinsed with H$_2$O, and dried to give the desired amide product as a colorless solid. LCMS [M+H]$^+$=399.

Example 250: N-Isopropyl-6-(4-(trifluoromethyl)phenyl)imidazo[2,1-a]isoquinoline-9-carboxamide (Compound 299)

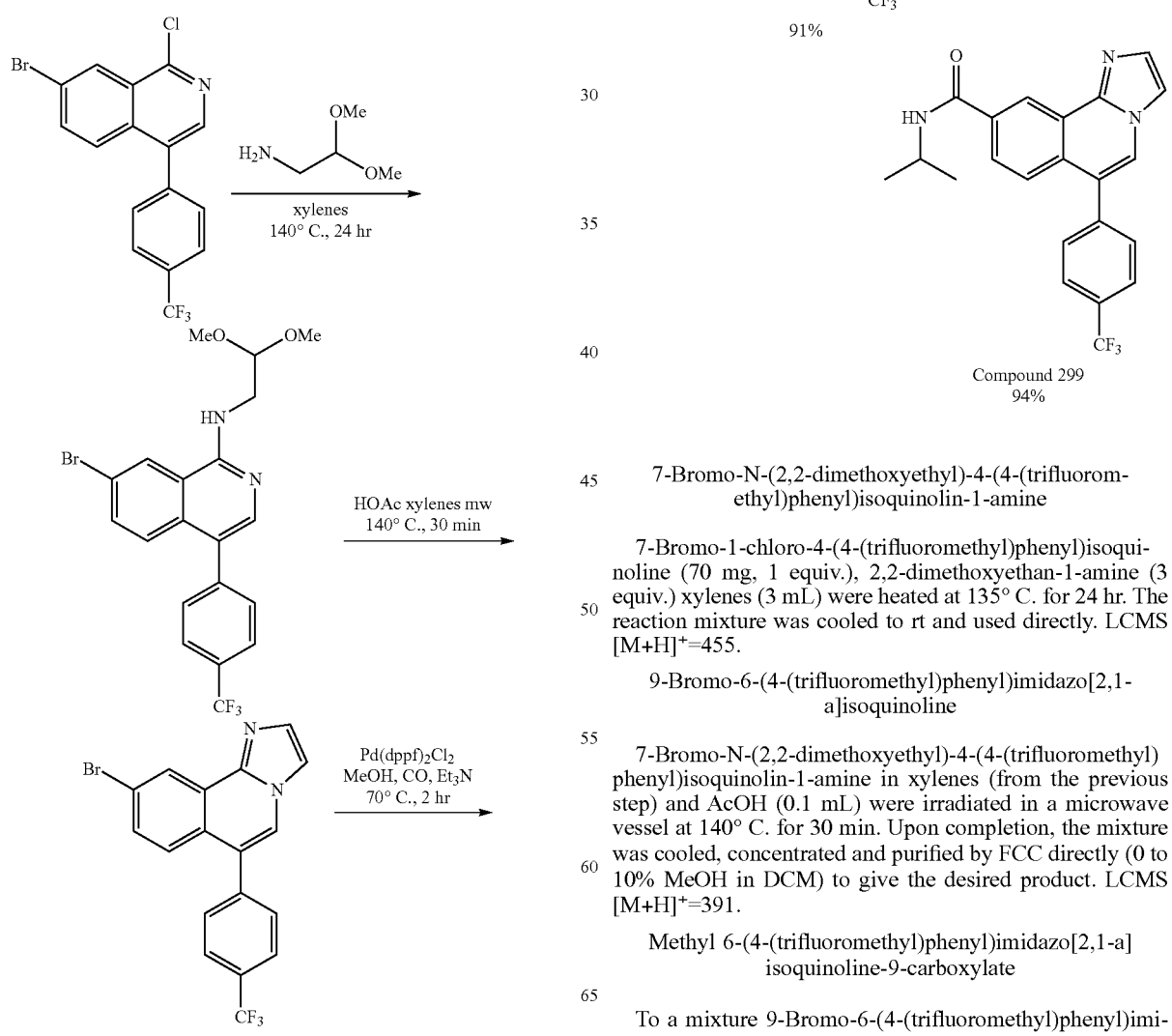

Compound 299
94%

7-Bromo-N-(2,2-dimethoxyethyl)-4-(4-(trifluoromethyl)phenyl)isoquinolin-1-amine

7-Bromo-1-chloro-4-(4-(trifluoromethyl)phenyl)isoquinoline (70 mg, 1 equiv.), 2,2-dimethoxyethan-1-amine (3 equiv.) xylenes (3 mL) were heated at 135° C. for 24 hr. The reaction mixture was cooled to rt and used directly. LCMS [M+H]$^+$=455.

9-Bromo-6-(4-(trifluoromethyl)phenyl)imidazo[2,1-a]isoquinoline

7-Bromo-N-(2,2-dimethoxyethyl)-4-(4-(trifluoromethyl)phenyl)isoquinolin-1-amine in xylenes (from the previous step) and AcOH (0.1 mL) were irradiated in a microwave vessel at 140° C. for 30 min. Upon completion, the mixture was cooled, concentrated and purified by FCC directly (0 to 10% MeOH in DCM) to give the desired product. LCMS [M+H]$^+$=391.

Methyl 6-(4-(trifluoromethyl)phenyl)imidazo[2,1-a]isoquinoline-9-carboxylate

To a mixture 9-Bromo-6-(4-(trifluoromethyl)phenyl)imidazo[2,1-a]isoquinoline (1 equiv.) in MeOH (0.1M) was added Pd(dppf)₂Cl₂ (0.05 equiv.) and Et₃N (2 equiv.). CO(g) was bubbled for 1 h at 70° C. After cooling to rt, the resulting solid was filtered and washed with minimal MeOH to give a red solid, which was used directly in the next step without further purification (25 mg, 38%). LCMS [M+H]⁺=371.

6-(4-(Trifluoromethyl)phenyl)imidazo[2,1-a]isoquinoline-9-carboxylic Acid

Methyl 6-(4-(trifluoromethyl)phenyl)imidazo[2,1-a]isoquinoline-9-carboxylate (25 mg, 1 equiv.), was suspended in MeOH/THF (1:1, 0.05M) and treated with 2N NaOH (0.1M) for 2 h. The reaction mixture was filtered and acidified to pH 2 and the resulting solid was filtered to give a pale yellow solid (22 mg, 91%). LCMS [M+H]⁺=357.

N-Isopropyl-6-(4-(trifluoromethyl)phenyl)imidazo[2,1-a]isoquinoline-9-carboxamide 6-(4-(Trifluoromethyl)phenyl)imidazo[2,1-a]isoquinoline-9-carboxylic acid (22 mg, 1 equiv.), propan-2-amine (1.2 equiv.), and HATU (1.2 equiv.) were dissolved in DMF (0.2M) at rt. DIEA (2 equiv.) was added slowly, and the mixture was stirred at rt until consumption of the acid as determined by LCMS, 2 hr. Upon completion, the reaction mixture was diluted with H₂O and stirred rapidly for 20 min. The resulting solid was filtered, rinsed with H₂O, and dried to give the desired amide product as a colorless solid (24 mg, 94%). LCMS [M+H]⁺=398.

Example 251: N-Isopropyl-5-(4-(trifluoromethyl)phenyl)-[1,2,4]triazolo[1,5-a]quinoline-8-carboxamide (Compound 300)

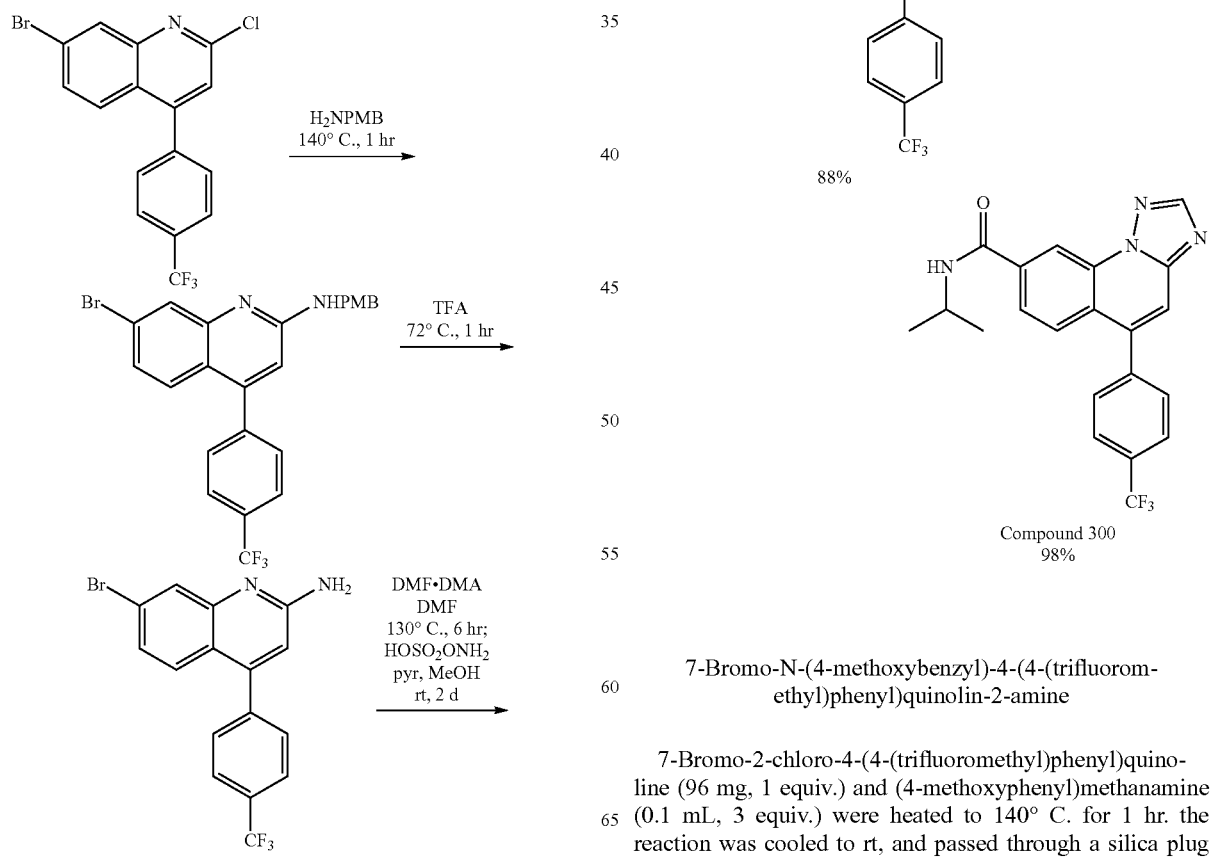

7-Bromo-N-(4-methoxybenzyl)-4-(4-(trifluoromethyl)phenyl)quinolin-2-amine

7-Bromo-2-chloro-4-(4-(trifluoromethyl)phenyl)quinoline (96 mg, 1 equiv.) and (4-methoxyphenyl)methanamine (0.1 mL, 3 equiv.) were heated to 140° C. for 1 hr. the reaction was cooled to rt, and passed through a silica plug with 25% EtOAc in Hex and concentrated to give the desired product, which was used directly in the next step without further purification. LCMS [M+H]$^+$=487.

7-Bromo-4-(4-(trifluoromethyl)phenyl)quinolin-2-amine

7-Bromo-N-(4-methoxybenzyl)-4-(4-(trifluoromethyl) phenyl)quinolin-2-amine (1 equiv.) and TFA (0.3 mL) were heated to 72° C. for 1 hr. the reaction mixture was concentrated, diluted with DCM, neutralized with NaHCO$_3$, dried with Na$_2$SO$_4$, concentrated and used directly in the nest step without further purification. LCMS [M+H]$^+$=367.

8-Bromo-5-(4-(trifluoromethyl)phenyl)-[1,2,4]triazolo[1,5-a]quinoline

7-Bromo-4-(4-(trifluoromethyl)phenyl)quinolin-2-amine (92 mg, 0.25 mmol, 1 equiv.), DMF·DMA (0.1 mL) and DMF (1 mL) were heated at 130° C. for 6 hr. The reaction was cooled and concentrated. The residue was re-suspended in MeOH (1 mL), and pyridine (0.1 mL) and hydroxylamine-O-sulfonic acid (29 mg, 1.01 equiv.) were added at rt. The reaction was stirred at rt for 2 d. The mixture was diluted with EtOAc, washed with sat. aq. NH$_4$Cl, H$_2$O, and brine. The organic layer was dried with Na$_2$SO$_4$, concentrated, and purified by FCC, 0 to 30% EtOAc in Hexane gradient to give the desired product (50 mg, 51%). LCMS [M+H]$^+$=392.

Methyl 5-(4-(trifluoromethyl)phenyl)-[1,2,4]triazolo[1,5-a]quinoline-8-carboxylate To a mixture 8-Bromo-5-(4-(trifluoromethyl)phenyl)-[1, 2,4]triazolo[1,5-a]quinoline (50 mg, 1 equiv.) in MeOH (0.1M) was added Pd(dppf)$_2$Cl$_2$ (7 mg, 0.05 equiv.) and Et$_3$N (0.04 mL, 2 equiv.). CO(g) was bubbled for 1 h at 70° C. After cooling to rt, the reaction mixture was concentrated and purified directly by FCC (5 to 40% EtOAc in Hex) to give the desired product. (24 mg, 50%). LCMS [M+H]$^+$=372.

5-(4-(Trifluoromethyl)phenyl)-[1,2,4]triazolo[1,5-a]quinoline-8-carboxylic Acid Methyl 5-(4-(trifluoromethyl)phenyl)-[1,2,4]triazolo[1,5-a]quinoline-8-carboxylate (24 mg, 1 equiv.), was suspended in MeOH/THF (1:1, 0.05M) and treated with 2N NaOH (0.1M) for 4 h. The reaction mixture was filtered and acidified to pH 2 and the resulting solid was filtered to give a colorless solid (20 mg, 88%). LCMS [M+H]$^+$=358.

N-Isopropyl-5-(4-(trifluoromethyl)phenyl)-[1,2,4]triazolo[1,5-a]quinoline-8-carboxamide 5-(4-(Trifluoromethyl)phenyl)-[1,2,4]triazolo[1,5-a]quinoline-8-carboxylic acid (1 equiv.), propan-2-amine (1.2 equiv.), and HATU (1.2 equiv.) were dissolved in DMF (0.2M) at rt. DIEA (2 equiv.) was added slowly, and the mixture was stirred at rt until consumption of the acid as determined by LCMS, 2 hr. Upon completion, the reaction mixture was diluted with H$_2$O and stirred rapidly for 20 min. The resulting solid was filtered, rinsed with H$_2$O, and dried to give the desired amide product as a colorless solid (11 mg, 98%). LCMS [M+H]$^+$=399.

Example 252: N-Methyl-6-(4-(trifluoromethyl)phenyl)tetrazolo[5,1-a]isoquinoline-9-sulfonamide (Compound 301)

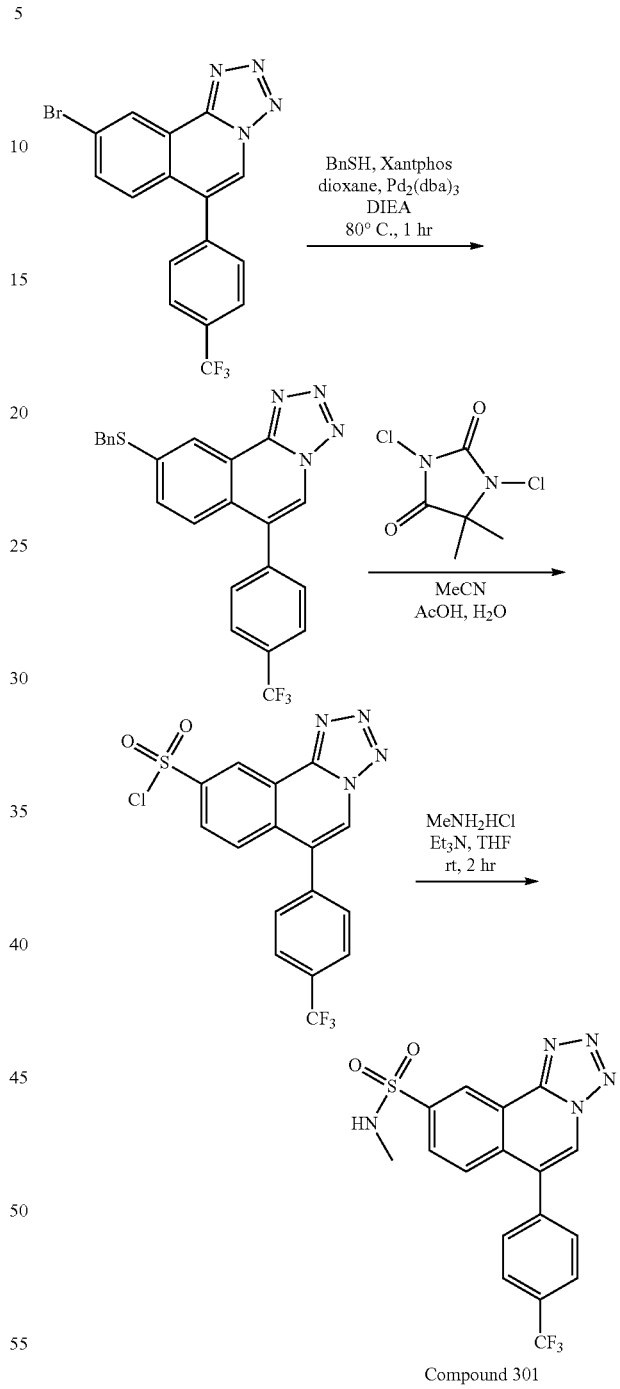

Compound 301

9-(Benzylthio)-6-(4-(trifluoromethyl)phenyl)tetrazolo[5,1-a]isoquinoline

To a mixture of 9-bromo-6-(4-(trifluoromethyl)phenyl) tetrazolo[5,1-a]isoquinoline (1 equiv.), Xantphos (5 mol %), Pd$_2$(dba)$_3$ (2.5 mol %) under N$_2$ was added dioxane (0.1M) and DIEA (2.0 equiv.) and then heated to 80° C. for 10 min before addition of BnSH (1.2 equiv.). Heating continued for 1 hr before being cooled to rt. The mixture was concentrated and purified by FCC (25% EtOAc in Hex) to give 9-(benzylthio)-6-(4-(trifluoromethyl)phenyl)tetrazolo[5,1-a]isoquinoline. LCMS [M+H]⁺=437.

N-Methyl-6-(4-(trifluoromethyl)phenyl)tetrazolo[5,1-a]isoquinoline-9-sulfonamide 9-(Benzylthio)-6-(4-(trifluoromethyl)phenyl)tetrazolo[5,1-a]isoquinoline (1 equiv.) was dissolved in MeCN (0.05M) and cooled to 0° C. and treated with HOAc (1.5 mL/mmol) and water (1 mL/mmol) followed with 1,3-dichloro-5,5-dimethylimidazolidine-2,4-dione (2.0 equiv.). After 2 hr, the reaction mixture was diluted with EtOAc (20 mL) and washed with water, brine, dried and concentrated to give a yellow solid used directly in the next step. A solution of 6-(4-(trifluoromethyl)phenyl)tetrazolo[5,1-a]isoquinoline-9-sulfonyl chloride (1 equiv.) in DCM (0.2M) was added to a mixture of MeNH₂ HCl salt (110 mg) and Et₃N (0.4 mL) in THF (2 mL). The resulting suspension was stirred at rt for 2 hr, diluted with EtOAc, and washed with sat. aq. NH₄Cl, H₂O, and brine. The organic layer was dried with Na₂SO₄, concentrated, and purified by FCC to give the desired product. LCMS [M+H]⁺=408. ¹H NMR (400 MHz, METHANOL-d₄) δ ppm 2.62 (s, 3H) 7.84 (br d, J=7.83 Hz, 2H) 7.89-8.07 (m, 3H) 8.25 (br dd, J=8.61, 1.96 Hz, 1H) 9.00-9.12 (m, 1H) 9.13-9.35 (m, 1H).

Example 253: N-Isopropyl-5-(4-(trifluoromethyl)phenyl)imidazo[1,2-a]quinoline-8-carboxamide (Compound 302)

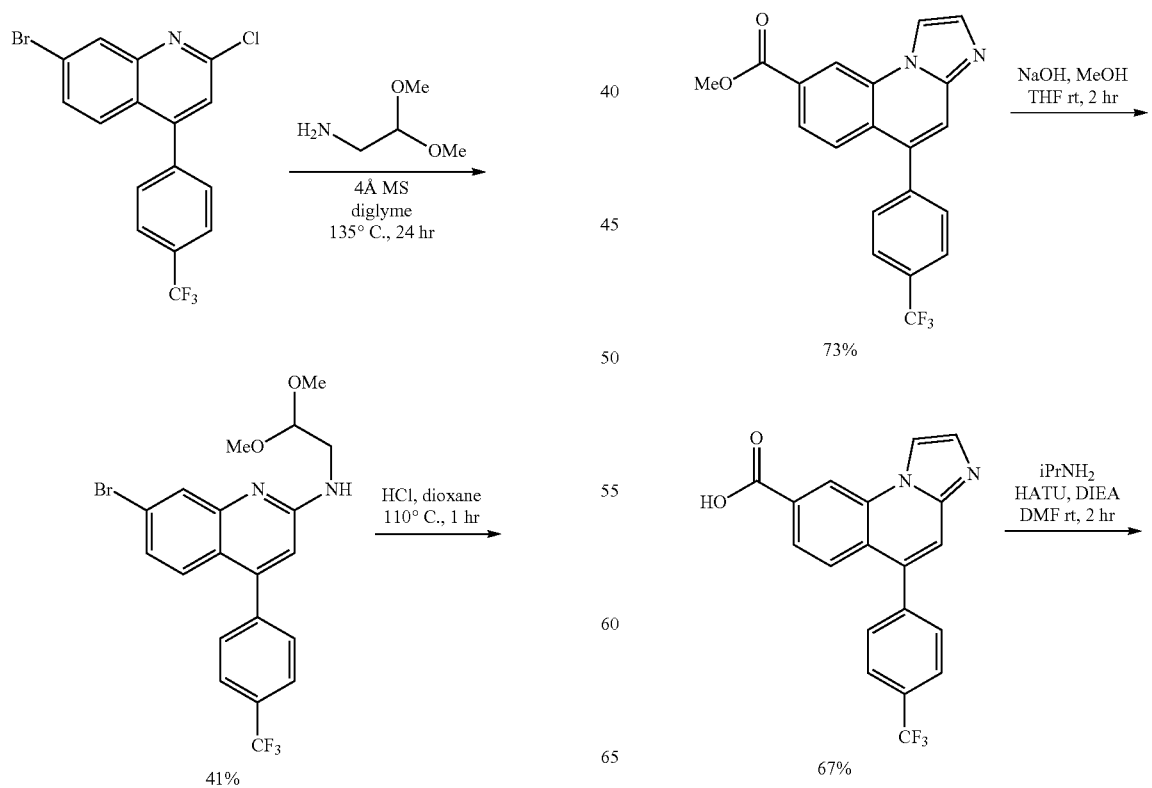

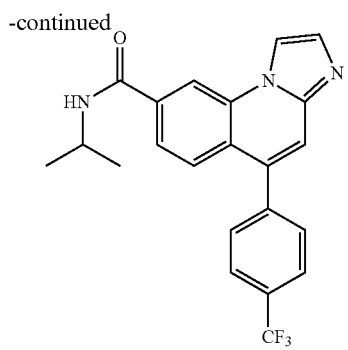

Compound 302
93%

7-Bromo-N-(2,2-dimethoxyethyl)-4-(4-(trifluoromethyl)phenyl)quinolin-2-amine 7-Bromo-2-chloro-4-(4-(trifluoromethyl)phenyl)quinoline (386 mg, 1 mmol, 1 equiv.), 2,2-dimethoxyethan-1-amine (0.33 mL, 3 mmol, 3 equiv.), 4 Å MS (100 mg), and diglyme (3 mL) were heated at 135° C. for 24 hr. The reaction mixture was cooled to rt, diluted with EtOAc, filtered, and concentrated. The residue was purified by FCC (0 to 40% EtOAc in Hex) to give the desired product. (185 mg, 41%). LCMS [M+H]$^+$=455.

2-((7-Bromo-4-(4-(trifluoromethyl)phenyl)quinolin-2-yl)amino)acetaldehyde

7-Bromo-N-(2,2-dimethoxyethyl)-4-(4-(trifluoromethyl)phenyl)quinolin-2-amine (176 mg, 0.4 mmol, 1 equiv.), 6N HCl (1 mL), and dioxane (4 mL) were heated to 110° C. for 1 hr. Upon consumption of the sm by LCMS, the mixture was cooled to rt, diluted with DCM, neutralized with sat. aq. NaHCO$_3$, and extracted with DCM. The combined organic fractions were dried with Na$_2$SO$_4$, concentrated and used directly in the nest step without further purification. LCMS [M+H]$^+$=409.

8-Bromo-5-(4-(trifluoromethyl)phenyl)imidazo[1,2-a]quinoline 2-((7-Bromo-4-(4-(trifluoromethyl)phenyl)quinolin-2-yl)amino)acetaldehyde (from the previous step), AcOH (0.3 mL), and xylenes (3 mL) were sealed in a microwave vessel and irradiated at 140° C. for 30 min. After cooling to rt, the residue was concentrated and directly purified by FCC (0 to 75% EtOAc in Hex) to give the desired product. (25 mg, 16%). LCMS [M+H]$^+$=391.

Methyl 5-(4-(trifluoromethyl)phenyl)imidazo[1,2-a]quinoline-8-carboxylate

To a mixture of 8-bromo-5-(4-(trifluoromethyl)phenyl)imidazo[1,2-a]quinoline (25 mg, 1 equiv.) in MeOH (0.1M) was added Pd(dppf)$_2$Cl$_2$ (3 mg, 0.05 equiv.) and Et$_3$N (0.02 mL, 2 equiv.). CO(g) was bubbled for 1 h at 70° C. After cooling to rt, the reaction mixture was concentrated and purified directly by FCC (5 to 40% EtOAc in Hex) to give the desired product. (17 mg, 73%). LCMS [M+H]$^+$=371.

5-(4-(Trifluoromethyl)phenyl)imidazo[1,2-a]quinoline-8-carboxylic Acid

Methyl 5-(4-(trifluoromethyl)phenyl)imidazo[1,2-a]quinoline-8-carboxylate (17 mg, 1 equiv.), was suspended in MeOH/THF (1:1, 0.05M) and treated with 2N NaOH (0.1M) for 2 h. The reaction mixture was filtered and acidified to pH 2 and the resulting solid was filtered to give a colorless solid (11 mg, 67%). LCMS [M+H]$^+$=357.

N-Isopropyl-5-(4-(trifluoromethyl)phenyl)imidazo[1,2-a]quinoline-8-carboxamide 5-(4-(Trifluoromethyl)phenyl)imidazo[1,2-a]quinoline-8-carboxylic acid (1 equiv.), propan-2-amine (1.2 equiv.), and HATU (1.2 equiv.) were dissolved in DMF (0.2M) at rt. DIEA (2 equiv.) was added slowly, and the mixture was stirred at rt until consumption of the acid as determined by LCMS, 2 hr. Upon completion, the reaction mixture was diluted with H$_2$O and stirred rapidly for 20 min. The resulting solid was filtered, rinsed with H$_2$O, and dried to give the desired amide product as a colorless solid (11 mg, 93%). LCMS [M+H]$^+$=398.

Example 254: N-Methyl-6-(4-(trifluoromethyl)phenyl)-[1,2,4]triazolo[3,4-a]isoquinoline-9-sulfonamide (Compound 303)

-continued

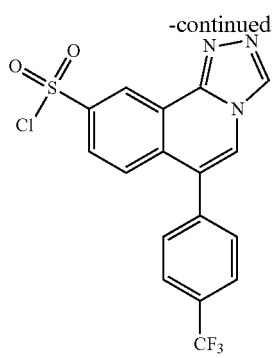

MeNH₂HCl
Et₃N, THF
rt, 2 hr
→

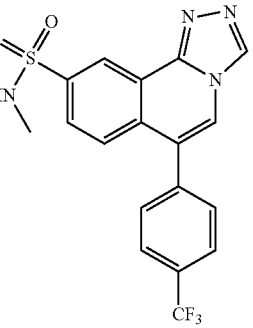

Compound 303

9-(Benzylthio)-6-(4-(trifluoromethyl)phenyl)-[1,2,4]triazolo[3,4-a]isoquinoline To a mixture of 9-bromo-6-(4-(trifluoromethyl)phenyl)-[1,2,4]triazolo[3,4-a]isoquinoline (1 equiv.), Xantphos (5 mol %), Pd₂(dba)₃ (2.5 mol %) under N₂ was added dioxane (0.1M) and DIEA (2.0 equiv.) and then heated to 80° C. for 10 min before addition of BnSH (1.2 equiv.). Heating continued for 1 hr before being cooled to rt. The mixture was concentrated and purified by FCC (25% EtOAc in Hex) to give 9-(benzylthio)-6-(4-(trifluoromethyl)phenyl)-[1,2,4]triazolo[3,4-a]isoquinoline. LCMS [M+H]⁺=436.

N-Methyl-6-(4-(trifluoromethyl)phenyl)-[1,2,4]triazolo[3,4-a]isoquinoline-9-sulfonamide 9-(Benzylthio)-6-(4-(trifluoromethyl)phenyl)-[1,2,4]triazolo[3,4-a]isoquinoline (1 equiv.) was dissolved in MeCN (0.05M) and cooled to 0° C. and treated with HOAc (1.5 mL/mmol) and water (1 mL/mmol) followed with 1,3-dichloro-5,5-dimethylimidazolidine-2,4-dione (2.0 equiv.). After 2 hr, the reaction mixture was diluted with EtOAc (20 mL) and washed with water, brine, dried and concentrated to give a yellow solid used directly in the next step. A solution of 6-(4-(trifluoromethyl)phenyl)-[1,2,4]triazolo[3,4-a]isoquinoline-9-sulfonyl chloride (1 equiv.) in DCM (0.2M) was added to a mixture of MeNH₂ HCl salt (110 mg) and Et₃N (0.4 mL) in THF (2 mL). The resulting suspension was stirred at rt for 2 hr, diluted with EtOAc, and washed with sat. aq. NH₄Cl, H₂O, and brine. The organic layer was dried with Na₂SO₄, concentrated, and purified by FCC to give the desired product. LCMS [M+H]⁺=407. ¹H NMR (400 MHz, DMSO-d₆) δ ppm 3.14 (d, J=8.61 Hz, 3H) 7.74-7.87 (m, 3H) 7.95 (br d, J=8.61 Hz, 1H) 8.00-8.13 (m, 1H) 8.51-8.63 (m, 1H) 8.94-9.06 (m, 1H) 9.24-9.42 (m, 1H).

Example 255: N-Isopropyl-6-(4-(trifluoromethyl)phenyl)-[1,2,4]triazolo[3,4-a]isoquinoline-9-carboxamide (Compound 304)

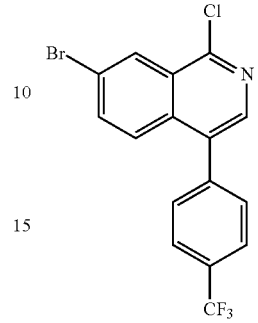

1) H₂NNH₂·H₂O
EtOH, 60° C., 16 hr
2) HC(OEt)₃ 130° C., 1 hr
→

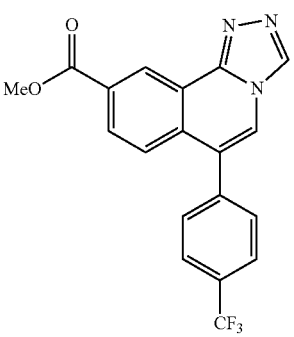

Pd(dppf)₂Cl₂
MeOH, CO, Et₃N
70° C., 2 hr
→

54%

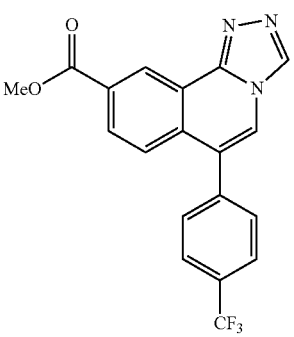

NaOH, MeOH
THF
rt, 2 hr
→

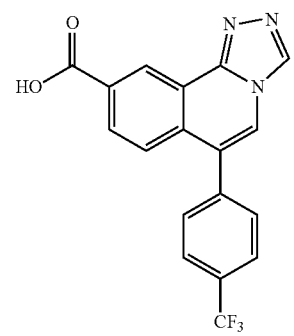

iPrNH₂
HATU,
DIEA DMF
rt, 2 hr
→

38%

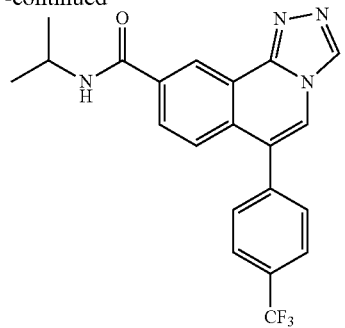

Compound 304

9-Bromo-6-(4-(trifluoromethyl)phenyl)-[1,2,4]triazolo[3,4-a]isoquinoline

7-Bromo-1-chloro-4-(4-(trifluoromethyl)phenyl)isoquinoline (200 mg, 1 equiv.), H₂NNH₂·H₂O (0.13 mL, 5 equiv.) and EtOH (6 mL) were heated to 90° C. for 16 hr. Upon completion, the mixture was added to H₂O, and the resultant solid was filtered, rinsed with H₂O, and dried. The solid and HC(OEt)₃ (10 mL) were heated to 130° C. for 1 hr. The reaction mixture was cooled, added to H₂O, filtered, and rinsed with Et₂O to give the desired product (107 mg, 54%). LCMS [M+H]⁺=391.

Methyl 6-(4-(trifluoromethyl)phenyl)-[1,2,4]triazolo[3,4-a]isoquinoline-9-carboxylate To a mixture 9-bromo-6-(4-(trifluoromethyl)phenyl)-[1,2,4]triazolo[3,4-a]isoquinoline (100 mg, 1 equiv.) in MeOH (0.1M) was added Pd(dppf)₂Cl₂ (0.05 equiv.) and Et₃N (2 equiv.). CO(g) was bubbled for 1 h at 70° C. After cooling to rt, the resulting solid was filtered and washed with minimal MeOH to give a red solid, which was used directly in the next step without further purification. LCMS [M+H]⁺= 372.

6-(4-(Trifluoromethyl)phenyl)-[1,2,4]triazolo[3,4-a]isoquinoline-9-carboxylic Acid Methyl 6-(4-(trifluoromethyl)phenyl)-[1,2,4]triazolo[3,4-a]isoquinoline-9-carboxylate (1 equiv.), was suspended in MeOH/THF (1:1, 0.05M) and treated with 2N NaOH (0.1M) for 2 h. The reaction mixture was filtered and acidified to pH 2 and the resulting solid was filtered to give a pale yellow solid (35 mg, 38%). LCMS [M+H]⁺=358.

N-Isopropyl-6-(4-(trifluoromethyl)phenyl)-[1,2,4]triazolo[3,4-a]isoquinoline-9-carboxamide 6-(4-(Trifluoromethyl)phenyl)-[1,2,4]triazolo[3,4-a]isoquinoline-9-carboxylic acid (1 equiv.), propan-2-amine (1.2 equiv.), and HATU (1.2 equiv.) were dissolved in DMF (0.2M) at rt. DIEA (2 equiv.) was added slowly, and the mixture was stirred at rt until consumption of the acid as determined by LCMS, 2 hr. Upon completion, the reaction mixture was diluted with H₂O and stirred rapidly for 20 min. The resulting solid was filtered, rinsed with H₂O, and dried to give the desired amide product as a colorless solid (6 mg). LCMS [M+H]⁺=399.

Example 256: N-Isopropyl-6-(4-(trifluoromethyl)phenyl)tetrazolo[5,1-a]isoquinoline-9-carboxamide (Compound 305)

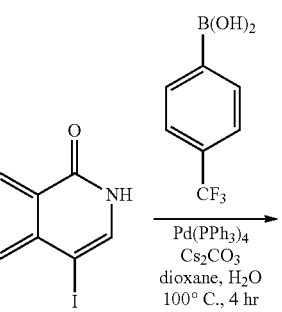

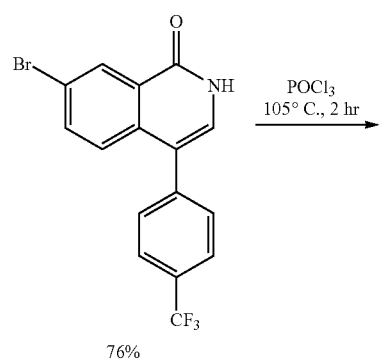

76%

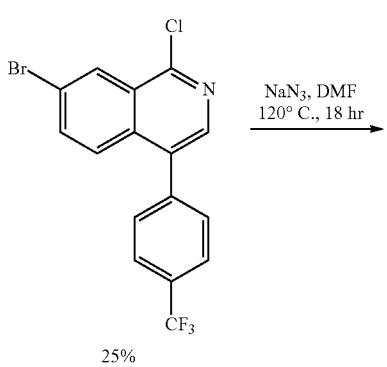

25%

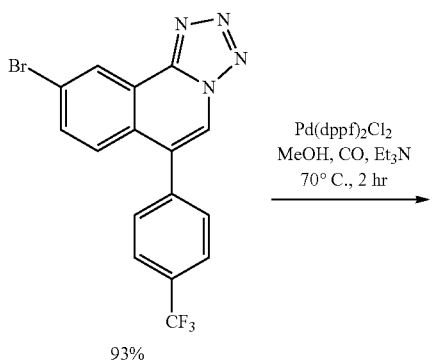

93%

-continued

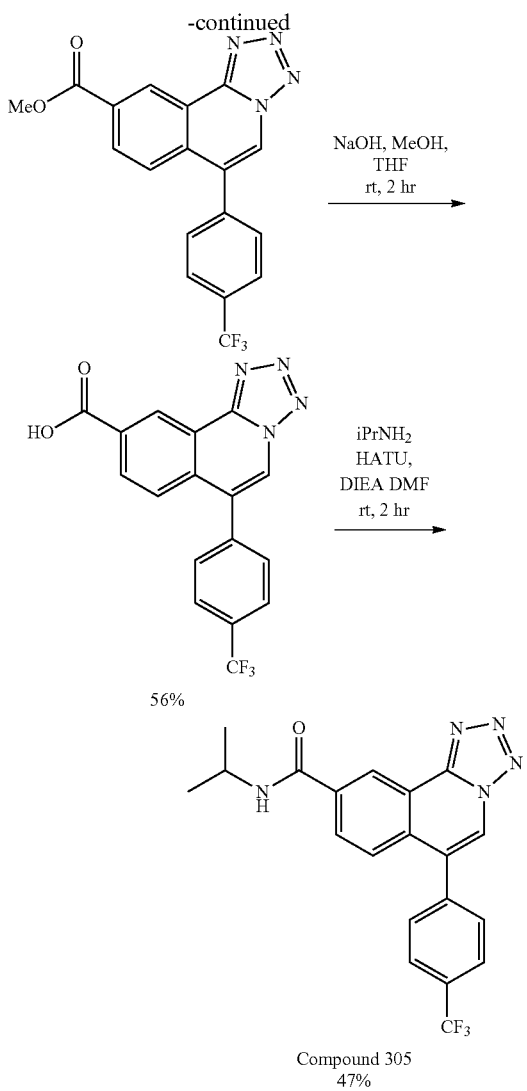

Compound 305
56%
47%

7-Bromo-4-(4-(trifluoromethyl)phenyl)isoquinolin-1 (2H)-one

7-Bromo-4-iodoisoquinolin-1 (2H)-one (2 g, 1 equiv.), Cs$_2$CO$_3$ (1.1 equiv.), (4-(trifluoromethyl)phenyl)boronic acid (1.1 equiv.), dioxane (200 mL), and H$_2$O (60 mL) were combined and thoroughly purged with N$_2$ for 10 min at rt. Pd(PPh$_3$)$_4$ (0.1 equiv.) was added and the mixture was heated at 100° C. for 4 hr. After cooling to rt, the reaction mixture was diluted with EtOAc, washed with sat. aq. NH$_4$Cl, H$_2$O, and brine. The organic layer was dried with Na$_2$SO$_4$, concentrated, and purified by FCC, 0 to 60% EtOAc in Hexane gradient to give the desired product (1.6 g, 76%). LCMS [M+H]$^+$=368.

7-Bromo-1-chloro-4-(4-(trifluoromethyl)phenyl) isoquinoline

7-Bromo-4-(4-(trifluoromethyl)phenyl)isoquinolin-1 (2H)-one (1.6 g, 1 equiv.) and POCl$_3$ (10 mL) were heated to 105° C. for 2 hr. The mixture was added carefully to ice-cold H$_2$O, and the resulting solid was carefully neutralized with NaHCO$_3$ to give the desired product (420 mg, 25%). LCMS [M+H]$^+$=386.

9-Bromo-6-(4-(trifluoromethyl)phenyl)tetrazolo[5,1-a]isoquinoline

7-Bromo-1-chloro-4-(4-(trifluoromethyl)phenyl)isoquinoline (200 mg, 1 equiv.), NaN$_3$ (34 mg, 1 equiv.), and DMF (1.5 mL) were heated to 120° C. for 18 hr. The mixture was added to H$_2$O, filtered, and rinsed with H$_2$O to dive the desired product as a tan solid (189 mg, 93%). LCMS [M+H]$^+$=392.

Methyl 6-(4-(trifluoromethyl)phenyl)tetrazolo[5,1-a] isoquinoline-9-carboxylate To a mixture 9-bromo-6-(4-(trifluoromethyl)phenyl)tetrazolo[5,1-a]isoquinoline (100 mg, 1 equiv.) in MeOH (0.1M) was added Pd(dppf)$_2$Cl$_2$ (0.05 equiv.) and Et$_3$N (2 equiv.). CO(g) was bubbled for 1 h at 70° C. After cooling to rt, the resulting solid was filtered and washed with minimal MeOH to give a red solid, which was used directly in the next step without further purification. LCMS [M+H]$^+$=373.

6-(4-(Trifluoromethyl)phenyl)tetrazolo[5,1-a]isoquinoline-9-carboxylic Acid

Methyl 6-(4-(trifluoromethyl)phenyl)tetrazolo[5,1-a]isoquinoline-9-carboxylate (1 equiv.), was suspended in MeOH/THF (1:1, 0.05M) and treated with 2N NaOH (0.1M) for 2 h. The reaction mixture was filtered and acidified to pH 2 and the resulting solid was filtered to give a pale yellow solid (51 mg, 56%). LCMS [M+H]$^+$=359.

N-Isopropyl-6-(4-(trifluoromethyl)phenyl)tetrazolo [5,1-a]isoquinoline-9-carboxamide 6-(4-(Trifluoromethyl)phenyl)tetrazolo[5,1-a]isoquinoline-9-carboxylic acid (1 equiv.), propan-2-amine (1.2 equiv.), and HATU (1.2 equiv.) were dissolved in DMF (0.2M) at rt. DIEA (2 equiv.) was added slowly, and the mixture was stirred at rt until consumption of the acid as determined by LCMS, 2 hr. Upon completion, the reaction mixture was diluted with H$_2$O and stirred rapidly for 20 min. The resulting solid was filtered, rinsed with H$_2$O, and dried to give the desired amide product as a colorless solid (23 mg, 47%). LCMS [M+H]$^+$=400. $^1$H NMR (400 MHz, DMSO-d$_6$) δ ppm 1.22 (br d, J=5.09 Hz, 6H) 4.08-4.26 (m, 1H) 6.99-7.21 (m, 1H) 7.74-7.92 (m, 2H) 7.99 (br d, J=7.04 Hz, 1H) 8.06 (br d, J=6.26 Hz, 1H) 8.17-8.39 (m, 1H) 8.86 (br dd, J=6.07, 0.98 Hz, 1H) 9.27 (br s, 1H).

Example 257: N-Isopropyl-1-methyl-2-oxo-4-(4-(trifluoromethyl)phenyl)-1,2-dihydroquinoline-7-carboxamide (Compound 306)

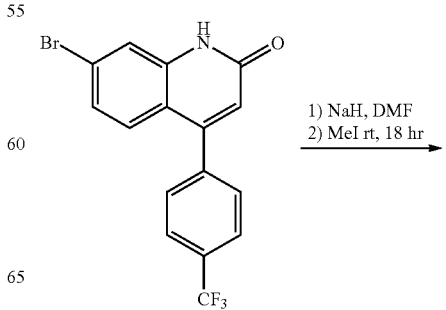

1) NaH, DMF
2) MeI rt, 18 hr

667

-continued

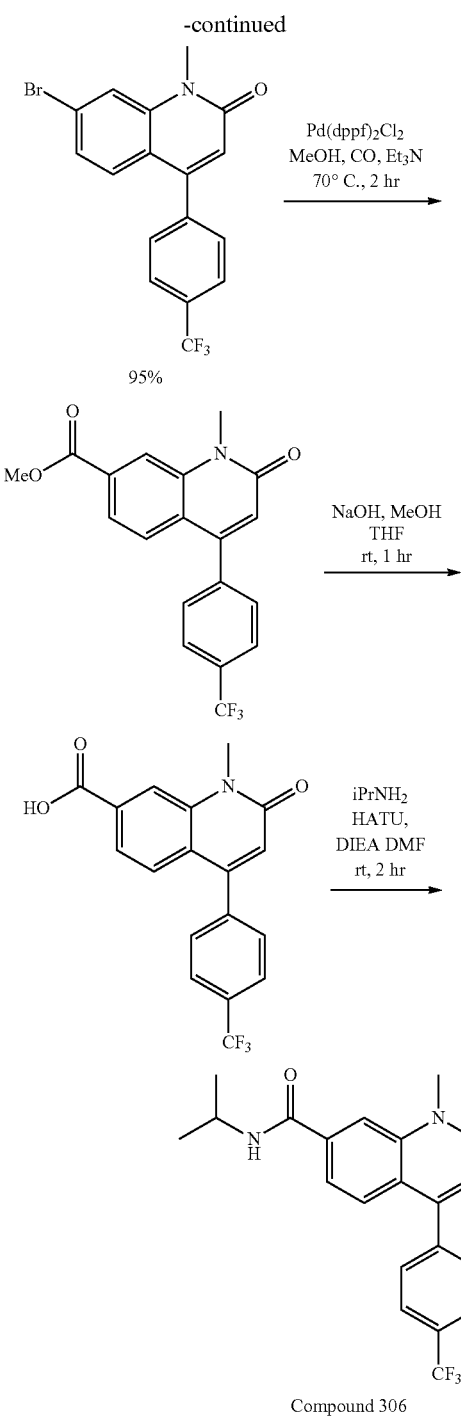

Compound 306

7-Bromo-1-methyl-4-(4-(trifluoromethyl)phenyl)quinolin-2 (1H)-one

7-Bromo-4-(4-(trifluoromethyl)phenyl)quinolin-2 (1H)-one (185 mg, 0.5 mmol) in DMF (3 mL) at rt was treated with NaH (30 mg, 60%, 1.5 eq) for 15 min before addition of MeI (0.076 mL, 2.1 eq) and the reaction mixture was stirred overnight. The reaction mixture was diluted with water (3 mL) and filtered to give a white solid (200 mg, 100%). LCMS [M+H]$^+$=382.

668

Methyl 1-methyl-2-oxo-4-(4-(trifluoromethyl)phenyl)-1,2-dihydroquinoline-7-carboxylate To a mixture of 7-bromo-1-methyl-4-(4-(trifluoromethyl) phenyl)quinolin-2 (1H)-one (1 equiv.) in MeOH (0.1M) was added Pd(dppf)$_2$Cl$_2$ (0.05 equiv.) and Et$_3$N (2 equiv.). CO(g) was bubbled for 1 h at 70° C. After cooling to rt, the resulting solid was filtered and washed with minimal MeOH to give a red solid. LCMS [M+H]$^+$=362.

1-Methyl-2-oxo-4-(4-(trifluoromethyl)phenyl)-1,2-dihydroquinoline-7-carboxylic Acid Methyl 1-methyl-2-oxo-4-(4-(trifluoromethyl)phenyl)-1,2-dihydroquinoline-7-carboxylate (1 equiv.), was suspended in MeOH/THF (1:1, 0.05M) and treated with 2N NaOH (0.1M) for 1 h. The reaction mixture was filtered and acidified to pH 2 and the resulting solid was filtered to give a pale yellow solid. LCMS [M+H]$^+$=348.

N-Isopropyl-1-methyl-2-oxo-4-(4-(trifluoromethyl) phenyl)-1,2-dihydroquinoline-7-carboxamide 1-Methyl-2-oxo-4-(4-(trifluoromethyl)phenyl)-1,2-dihydroquinoline-7-carboxylic acid (1 equiv.), propan-2-amine (1.2 equiv.), and HATU (1.2 equiv.) were dissolved in DMF (0.2M) at rt. DIEA (2 equiv.) was added slowly, and the mixture was stirred at rt until consumption of the acid as determined by LCMS, 2 hr. Upon completion, the reaction mixture was diluted with H$_2$O and stirred rapidly for 20 min. The resulting solid was filtered, rinsed with H$_2$O, and dried to give the desired amide product as a colorless solid. LCMS [M+H]$^+$=389. $^1$H NMR (400 MHz, DMSO-d$_6$) δ ppm 1.02-1.29 (m, 6H) 3.75 (br s, 3H) 4.02-4.20 (m, 1H) 6.52-6.76 (m, 1H) 7.27-7.54 (m, 1H) 7.54-7.80 (m, 3H) 7.82-7.98 (m, 3H) 8.44-8.56 (m, 1H).

Example 258: N-Isopropyl-5-(4-(trifluoromethyl) phenyl)-[1,2,4]triazolo[4,3-a]quinoline-8-carboxamide (Compound 307)

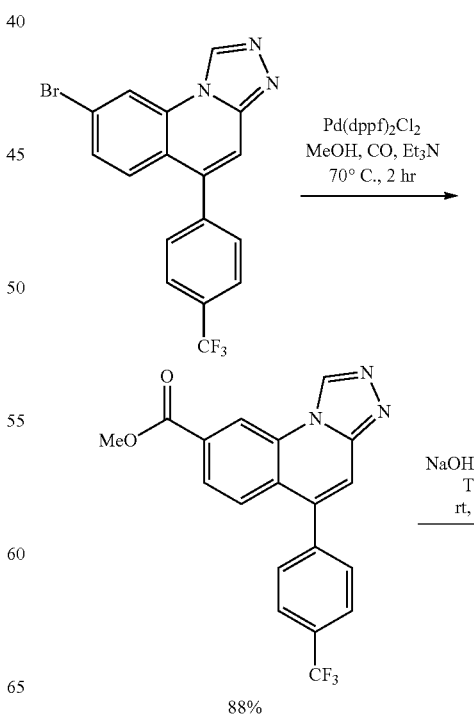

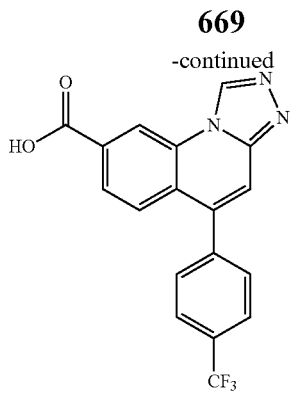

55%

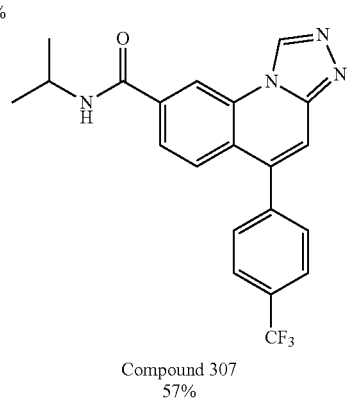

Compound 307
57%

Methyl 5-(4-(trifluoromethyl)phenyl)-[1,2,4]triazolo[4,3-a]quinoline-8-carboxylate To a mixture of 8-bromo-5-(4-(trifluoromethyl)phenyl)-[1,2,4]triazolo[4,3-a]quinoline (1 equiv.) in MeOH (0.1M) was added Pd(dppf)$_2$Cl$_2$ (0.05 equiv.) and Et$_3$N (2 equiv.). CO(g) was bubbled for 1 h at 70° C. After cooling to rt, the resulting solid was filtered and washed with minimal MeOH to give a red solid (85 mg, 88%). LCMS [M+H]$^+$=372.

5-(4-(Trifluoromethyl)phenyl)-[1,2,4]triazolo[4,3-a]quinoline-8-carboxylic Acid

Methyl 5-(4-(trifluoromethyl)phenyl)-[1,2,4]triazolo[4,3-a]quinoline-8-carboxylate (1 equiv.), was suspended in MeOH/THF (1:1, 0.05M) and treated with 2N NaOH (0.1M) for 2 h. The reaction mixture was filtered and acidified to pH 2 and the resulting solid was filtered to give a pale yellow solid (45 mg, 55%). LCMS [M+H]$^+$=358.

N-Isopropyl-5-(4-(trifluoromethyl)phenyl)-[1,2,4]triazolo[4,3-a]quinoline-8-carboxamide 5-(4-(Trifluoromethyl)phenyl)-[1,2,4]triazolo[4,3-a]quinoline-8-carboxylic acid (1 equiv.), propan-2-amine (1.2 equiv.), and HATU (1.2 equiv.) were dissolved in DMF (0.2M) at rt. DIEA (2 equiv.) was added slowly, and the mixture was stirred at rt until consumption of the acid as determined by LCMS, 2 hr. Upon completion, the reaction mixture was diluted with H$_2$O and stirred rapidly for 20 min. The resulting solid was filtered, rinsed with H$_2$O, and dried to give the desired amide product as a colorless solid (10 mg, 57%). LCMS [M+H]$^+$=399. $^1$H NMR (400 MHz, DMSO-d$_6$) δ ppm 1.11-1.30 (m, 6H) 4.06-4.22 (m, 1H) 7.70 (br d, J=7.43 Hz, 1H) 7.75-7.87 (m, 2H) 7.95 (br d, J=7.04 Hz, 3H) 8.38-8.57 (m, 1H) 8.92 (br s, 1H) 10.06 (br s, 1H).

Example 259: N-Isopropyl-5-(4-(trifluoromethyl)phenyl)tetrazolo[1,5-a]quinoline-8-carboxamide (Compound 308)

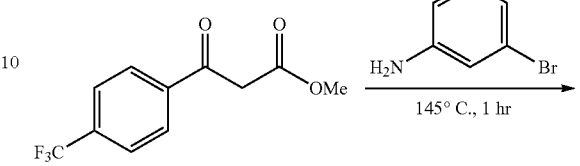

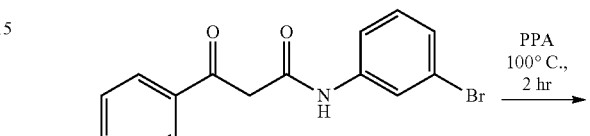

32%

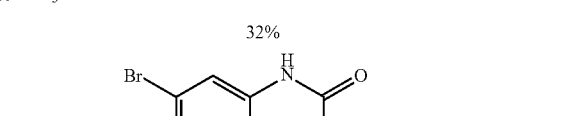

70%

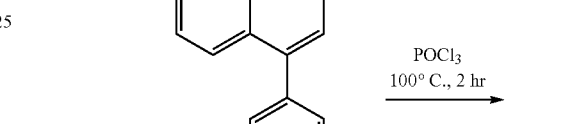

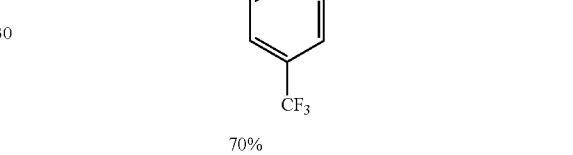

72%

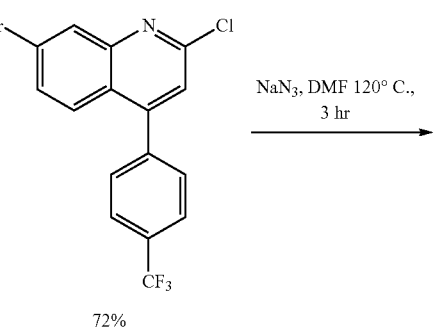

90%

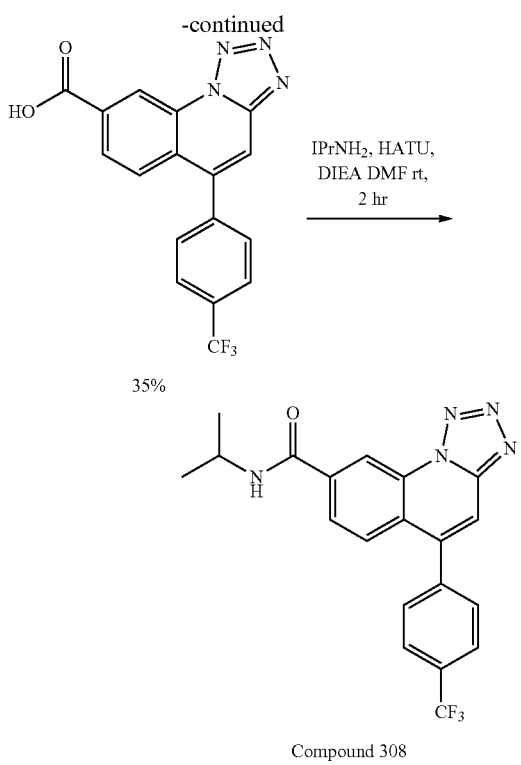

Compound 308

N-(3-Bromophenyl)-3-oxo-3-(4-(trifluoromethyl)phenyl)propanamide

Methyl 3-oxo-3-(4-(trifluoromethyl)phenyl) synthesized according to *J. Org. Chem.* 2018, 83, 303-313, (12.3 g, 50 mmol, 1 equiv.) and 3-bromoaniline (8.6 g, 1 equiv.) were mixed and heated to 145° C. for 1 hr and cooled to rt. DCM/hexane (10/10 mL) were added and filtered to give a solid and then washed with a minimum amount of DCM to give the desired product (6.2 g, 32%). LCMS [M+H]⁺=387.

7-Bromo-4-(4-(trifluoromethyl)phenyl)quinolin-2(1H)-one

N-(3-Bromophenyl)-3-oxo-3-(4-(trifluoromethyl)phenyl) propanamide (3 g, 7.8 mmol) was added to PPA (20 mL) at 50° C., heated to 100° C. for 2 hr and then mixed with ice water. The resulted solid was filtered, dried and recrystallized with EtOH to give a white solid (2 g, 70%). LCMS [M+H]⁺=369.

7-Bromo-2-chloro-4-(4-(trifluoromethyl)phenyl)quinoline

7-Bromo-4-(4-(trifluoromethyl)phenyl)quinolin-2-ol (2 g, 5.4 mmol) was suspended in POCl₃ (15 mL) and heated to 100° C. for 2 hr. Solvent was removed and quenched with ice water. The resulted mixture was neutralized with ammonium hydroxide and extracted with DCM. The organics were washed with water, dried and concentrated to give a yellow solid (1.5 g, 72%). LCMS [M+H]⁺=387.

8-Bromo-5-(4-(trifluoromethyl)phenyl)tetrazolo[1,5-a]quinoline

A mixture of 7-Bromo-2-chloro-4-(4-(trifluoromethyl) phenyl)quinolone (386 mg, 1 equiv.), NaN₃ (65 mg, 1 equiv.) and DMF (2 mL) was heated to 120° C. for 3 h and then cooled to rt. The reaction mixture was diluted with EtOAc, washed with H₂O, brine, dried with Na₂SO₄, and concentrated. The residue was recrystallized in EtOAc to give a white crystal (200 mg, 51%). LCMS [M+H]⁺=393.

5-(4-(Trifluoromethyl)phenyl)tetrazolo[1,5-a]quinoline-8-carboxylic Acid

8-Bromo-5-(4-(trifluoromethyl)phenyl)tetrazolo[1,5-a] quinoline (61 mg, 0.16 mmol) in THF (5 mL) at −78° C. under N₂ was treated with nBuLi (2.5 M, 0.068 mL, 1.1 equiv.) dropwise. After 30 min, CO₂ was bubbled through for 15 min. The reaction mixture was warmed to rt and quenched with water (2 mL), concentrated, extracted with ether, and neutralized to give a white solid as 5-(4-(trifluoromethyl)phenyl)tetrazolo[1,5-a]quinoline-8-carboxylic acid (20 mg, 35%). LCMS [M+H]⁺=359.

N-Isopropyl-5-(4-(trifluoromethyl)phenyl)tetrazolo[1,5-a]quinoline-8-carboxamide 5-(4-(Trifluoromethyl)phenyl)tetrazolo[1,5-a]quinoline-8-carboxylic acid (1 equiv.), propan-2-amine (1.2 equiv.), and HATU (1.2 equiv.) were dissolved in DMF (0.2M) at rt. DIEA (2 equiv.) was added slowly, and the mixture was stirred at rt until consumption of the acid as determined by LCMS, 2 hr. Upon completion, the reaction mixture was diluted with H₂O and stirred rapidly for 20 min. The resulting solid was filtered, rinsed with H₂O, and dried to give the desired amide product as a colorless solid. LCMS [M+H]⁺=400.

Example 260: N-Methyl-5-(4-(trifluoromethyl)phenyl)-[1,2,4]triazolo[4,3-a]quinoline-8-sulfonamide (Compound 309)

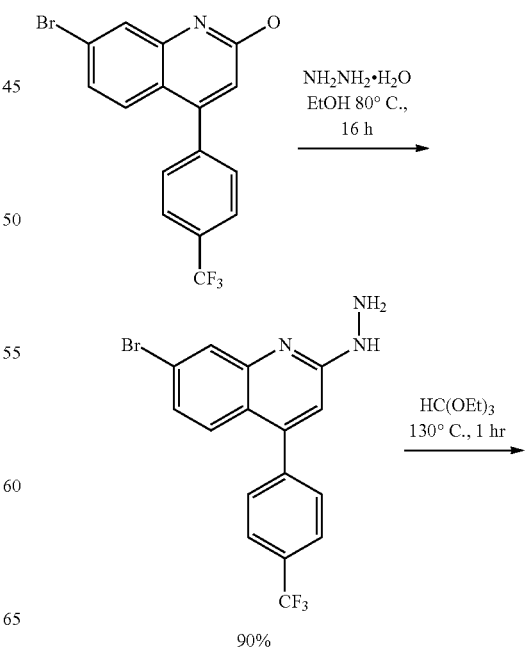

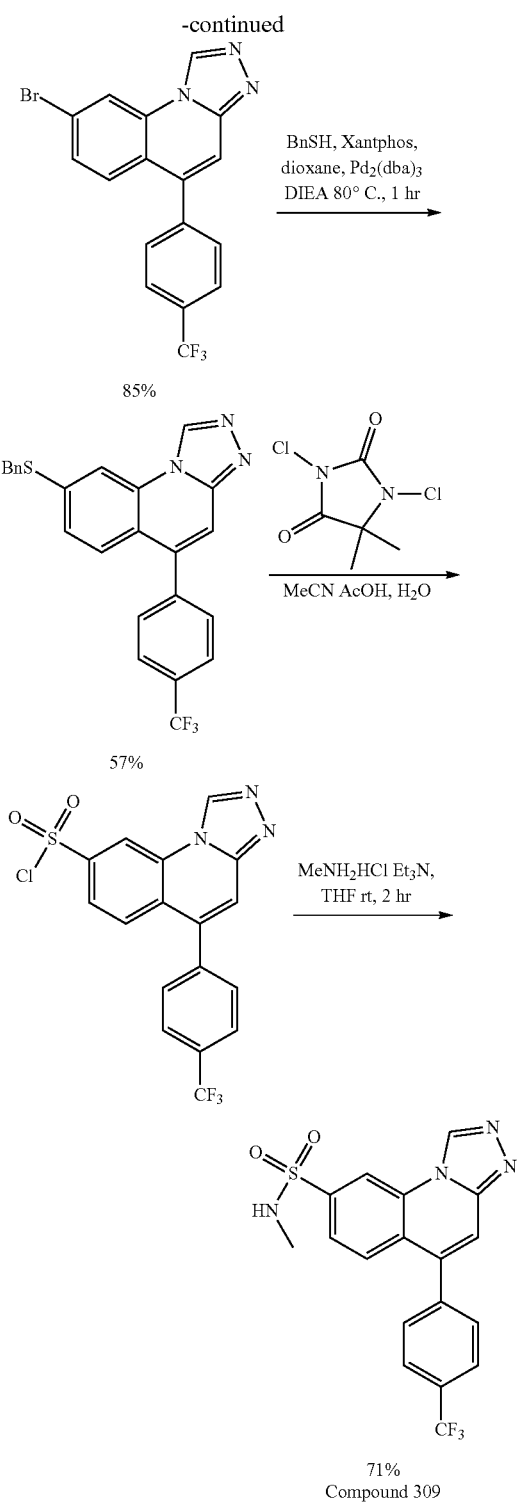

7-Bromo-2-hydrazinyl-4-(4-(trifluoromethyl)phenyl)quinoline

7-Bromo-2-chloro-4-(4-(trifluoromethyl)phenyl)quinoline (386 mg, 1.0 mmol) in EtOH (1 mL) was treated with hydrazine monohydrate (500 mg, 10 equiv.) and heated to 80° C. overnight. After being cooled to rt, the reaction mixture was diluted with water, filtered, washed with H₂O, and dried to give a white solid (360 mg, 90%). LCMS [M+H]⁺=382.

8-Bromo-5-(4-(trifluoromethyl)phenyl)-[1,2,4]triazolo[4,3-a]quinoline

7-Bromo-2-hydrazinyl-4-(4-(trifluoromethyl)phenyl)quinoline (360 mg, 1 equiv.) was dissolved in HC(OEt)₃ (10 mL) and heated to 130° C. for 1 hr. After cooling to rt, the resulting solid was filtered and dried (300 mg, 85%). LCMS [M+H]⁺=393.

8-(Benzylthio)-5-(4-(trifluoromethyl)phenyl)-[1,2,4]triazolo[4,3-a]quinoline

To a mixture of 8-bromo-5-(4-(trifluoromethyl)phenyl)-[1,2,4]triazolo[4,3-a]quinolone (60 mg, 0.15 mmol), Xantphos (4.4 mg, 5%), Pd₂(dba)₃ (3.4 mg, 2.5 mol %) under N₂ was added dioxane (2 mL) and DIEA (0.053 mL, 2.0 equiv.) and then heated to 80° C. for 10 min before addition of BnSH (0.019 mL, 1.2 equiv.). Heating continued for 1 hr before being cooled to rt. The mixture was concentrated and purified by FCC (25% EtOAc in Hex) to give a yellow solid as 8-(benzylthio)-5-(4-(trifluoromethyl)phenyl)-[1,2,4]triazolo[4,3-a]quinolone (38 mg, 58%). LCMS [M+H]⁺=436.

N-Methyl-5-(4-(trifluoromethyl)phenyl)-[1,2,4]triazolo[4,3-a]quinoline-8-sulfonamide 8-(Benzylthio)-5-(4-(trifluoromethyl)phenyl)-[1,2,4]triazolo[4,3-a]quinolone (38 mg, 1 equiv.) was dissolved in MeCN (3 mL) and cooled to 0° C. and treated with HOAc (0.032 mL) and water (0.021 mL) followed with 1,3-dichloro-5,5-dimethylimidazolidine-2,4-dione (35 mg, 2.0 equiv.). After 2 hr, the reaction mixture was diluted with EtOAc (20 mL) and washed with water, brine, dried and concentrated to give a yellow solid used directly in the next step. A solution of 5-(4-(trifluoromethyl)phenyl)tetrazolo[1,5-a]quinoline-8-sulfonyl chloride (38 mg, 0.092 mmol) in DCM (0.5 mL) was added to a mixture of MeNH₂ HCl salt (110 mg) and Et₃N (0.4 mL) in THF (2 mL). The resulting suspension was stirred at rt for 2 hr, diluted with EtOAc, and washed with sat. aq. NH₄Cl, H₂O, and brine. The organic layer was dried with Na₂SO₄, concentrated, and purified by FCC, 0 to 75% EtOAc in Hexane gradient to give white solid (26 mg, 71%). LCMS [M+H]⁺=407. ¹H NMR (400 MHz, DMSO-d₆) δ ppm 3.34 (s, 3H) 7.72-7.99 (m, 7H) 8.91 (br s, 1H) 10.26 (br s, 1H).

Example 261: N-Methyl-5-(4-(trifluoromethyl)phenyl)tetrazolo[1,5-a]quinoline-8-sulfonamide (Compound 310)

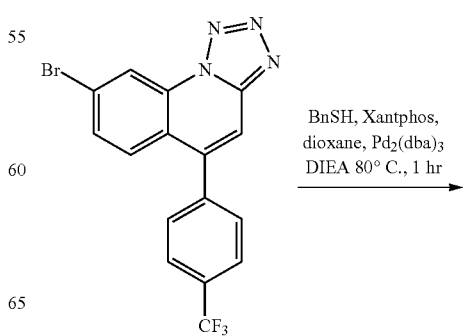

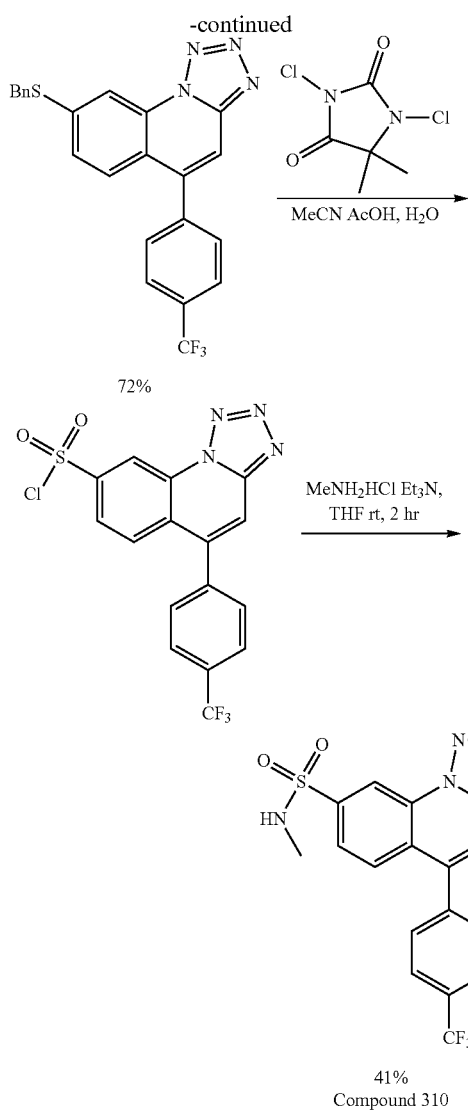

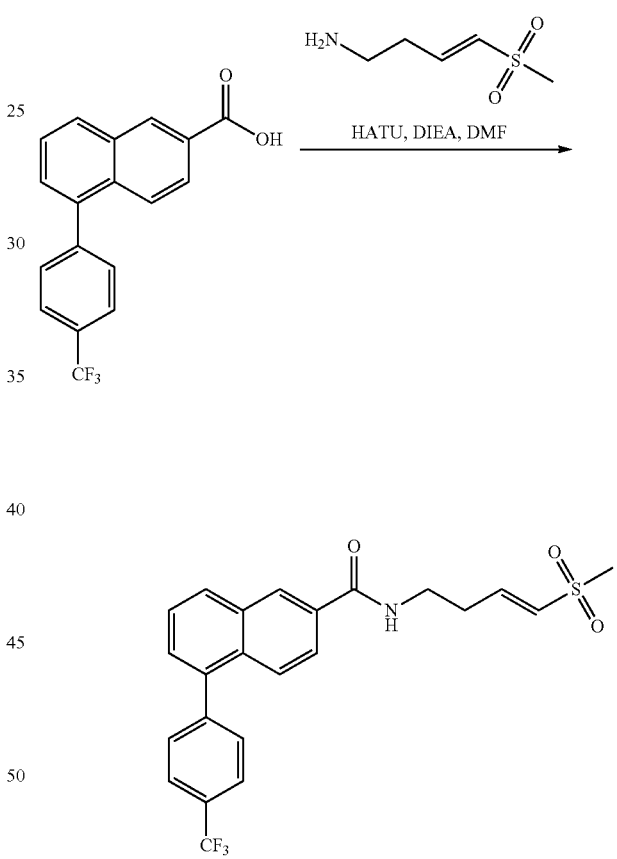

Compound 311

8-(Benzylthio)-5-(4-(trifluoromethyl)phenyl)tetrazolo[1,5-a]quinoline

To a mixture of 8-bromo-5-(4-(trifluoromethyl)phenyl)tetrazolo[1,5-a]quinoline (60 mg, 0.15 mmol), Xantphos (4.4 mg, 5%), Pd$_2$(dba)$_3$ (3.4 mg, 2.5%) under N$_2$ was added dioxane (2 mL) and DIEA (0.053 mL, 2.0 eq) and then heated to 80° C. for 10 min before addition of BnSH (0.019 mL, 1.2 eq). Heating was continued for 1 hr before being cooled to rt. The mixture was purified by FCC (25% EtOAc in Hex) to give 8-(benzylthio)-5-(4-(trifluoromethyl)phenyl) tetrazolo[1,5-a]quinoline (47 mg, 72%) as a yellow solid. LCMS [M+H]$^+$=436.

N-Methyl-5-(4-(trifluoromethyl)phenyl)tetrazolo[1,5-a]quinoline-8-sulfonamide 8-(Benzylthio)-5-(4-(trifluoromethyl)phenyl)tetrazolo[1,5-a]quinoline (47 mg, 1 equiv.) was dissolved in MeCN (6 mL) and cooled to 0° C. and treated with HOAc (0.039 mL), water (0.026 mL), followed with 1,3-dichloro-5,5-dimethylimidazolidine-2,4-dione (43 mg, 2.0 equiv.). After 2 hr, the reaction mixture was diluted with EtOAc (20 mL) and washed with water, brine, dried and concentrated to give a yellow solid (41 mg) used directly in the next step. A solution of 5-(4-(trifluoromethyl)phenyl)tetrazolo[1,5-a]quinoline-8-sulfonyl chloride (41 mg, 0.10 mmol) in DCM (0.5 mL) was added to a mixture of MeNH$_2$ HCl salt (118 mg) and Et$_3$N (0.3 mL) in THF (2 mL). The resulting suspension was stirred at rt for 2 hr, diluted with EtOAc, and washed with sat. aq. NH$_4$Cl, H$_2$O, and brine. The organic layer was dried with Na$_2$SO$_4$, concentrated, and purified by FCC, 0 to 75% EtOAc in Hexane gradient to give a white solid (16 mg, 41%). LCMS [M+H]$^+$=408. $^1$H NMR (400 MHz, DMSO-r&) δ ppm 3.34 (s, 3H) 7.84 (br d, J=7.04 Hz, 2H) 7.93-8.14 (m, 4H) 8.21-8.44 (m, 1H) 9.01 (br s, 1H).

Example 262: (E)-N-(4-(Methylsulfonyl)but-3-en-1-yl)-5-(4-(trifluoromethyl)phenyl)-2-naphthamide (Compound 311)

5-(4-(Trifluoromethyl)phenyl)-2-naphthoic acid (1 equiv.), (E)-4-(methylsulfonyl)but-3-en-1-amine (1.2 equiv.) (synthesized according to JACS, 2010, 132, 12853-12855), and HATU (1.2 equiv.) were dissolved in DMF (0.2M) at rt. DIEA (2 equiv.) was added slowly, and the mixture was stirred at rt until consumption of the acid as determined by LCMS, 2 hr. Upon completion, the reaction mixture was diluted with H$_2$O and stirred rapidly for 20 min. The resulting solid was filtered, rinsed with H$_2$O, and dried to give the desired amide product, tan solid. LCMS [M+H]$^+$= 448.

Example 263: (E)-N-(3-(Methylsulfonyl)allyl)-5-(4-(trifluoromethyl)phenyl)-2-naphthamide (Compound 312)

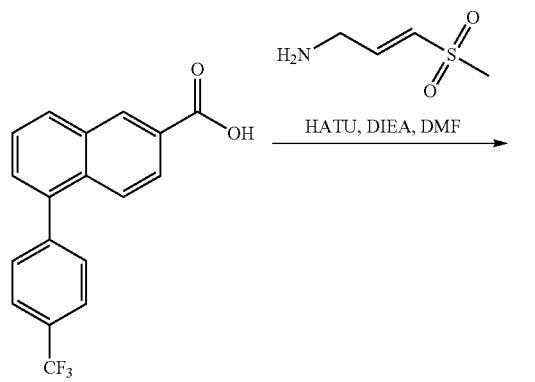

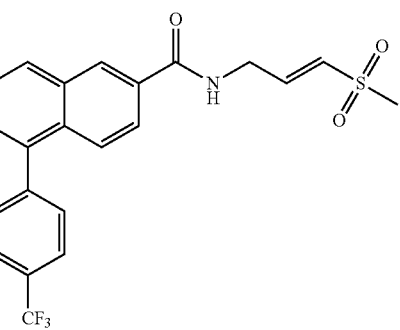

Compound 312

5-(4-(Trifluoromethyl)phenyl)-2-naphthoic acid (1 equiv.), (E)-3-(methylsulfonyl)prop-2-en-1-amine (1.2 equiv.), and HATU (1.2 equiv.) were dissolved in DMF (0.2M) at rt. DIEA (2 equiv.) was added slowly, and the mixture was stirred at rt until consumption of the acid as determined by LCMS, 2 hr. Upon completion, the reaction mixture was diluted with H₂O and stirred rapidly for 20 min. The resulting solid was filtered, rinsed with H₂O, and dried to give the desired amide product, tan solid. LCMS [M+H]⁺ =434.

Example 264: N-[(1R)-3-(dimethylamino)-1-methyl-propyl]-5-[4-(trifluoromethyl)phenyl]naphthalene-2-carboxamide (Compound 313)

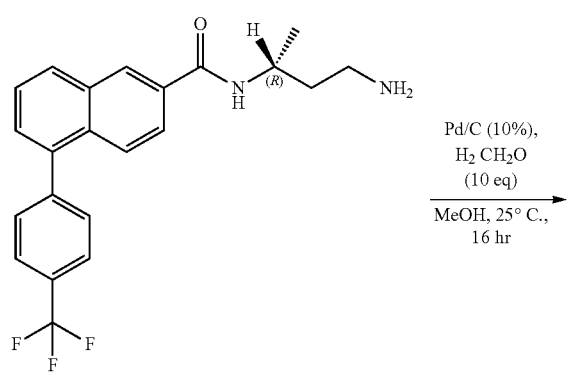

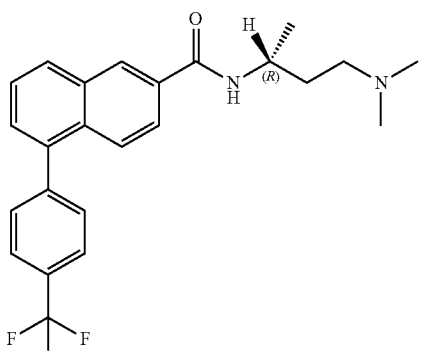

Compound 313

N-[(1R)-3-(dimethylamino)-1-methyl-propyl]-5-[4-(trifluoromethyl)phenyl]naphthalene-2-carboxamide To a solution of N-[(1S)-3-amino-1-methyl-propyl]-5-[4-(trifluoromethyl)phenyl]naphthalene-2-carboxamide (50 mg, 0.12 mmol, 1 eq) and formaldehyde (210.0 mg, 2.59 mmol, 20 eq) in MeOH (2 mL) was added Pd/C (50 mg, 10%) under N₂. The suspension was degassed under vacuum and purged with H₂ several times. The mixture was stirred under H₂ (15 psi) at 25° C. for 16 hours. The reaction mixture was filtered and the filtrate was concentrated under reduce pressure. The residue was purified by prep-HPLC (column: 3_Phenomenex Luna C18 75*30 mm*3 um; mobile phase: [water (0.05% HCl)-ACN]; B %: 30%-60%, 6.5 min) to give N-[(1R)-3-(dimethylamino)-1-methyl-propyl]-5-[4-(trifluoromethyl)phenyl]naphthalene-2-carboxamide (7.38 mg, 12.5% yield, HCl) as a white solid. LCMS (ESI): RT=0.872 min, mass calcd for $C_{24}H_{25}F_3N_2O$ 414.19 m/z, found 415.3 [M+H]⁺, ¹H NMR (400 MHz, DMSO-d₆) δ 10.48 (br s, 1H), 8.70-8.59 (m, 2H), 8.13 (d, J=8.3 Hz, 1H), 7.98 (dd, J=1.6, 8.9 Hz, 1H), 7.93 (d, J=8.0 Hz, 2H), 7.82 (d, J=9.0 Hz, 1H), 7.77-7.68 (m, 3H), 7.60 (d, J=6.3 Hz, 1H), 4.14-4.10 (m, 1H), 4.15-4.08 (m, 2H), 3.18-3.02 (m, 2H), 2.75 (t, J=4.6 Hz, 6H), 2.06-1.88 (m, 2H), 1.26 (d, J=6.5 Hz, 3H).

Example 265: N-[(1S)-1-[1-(2-fluoroethyl)azetidin-3-yl]ethyl]-8-[4-(trifluoromethyl)phenyl]quinoline-3-carboxamide (Compound 314)

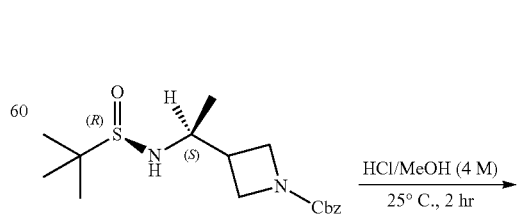

265-1

-continued

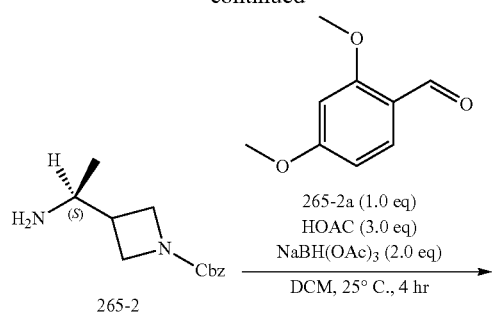

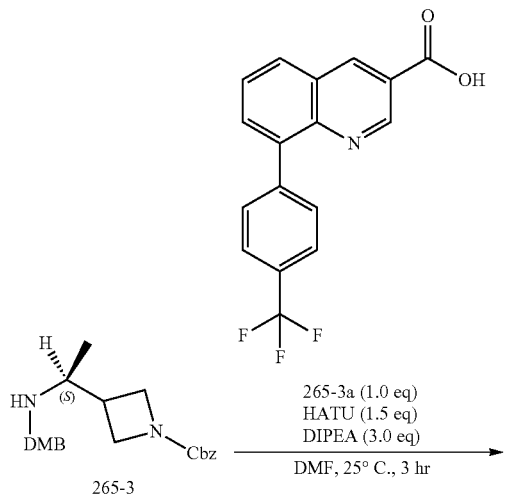

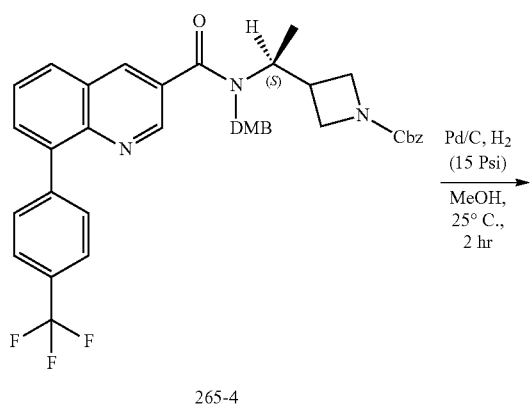

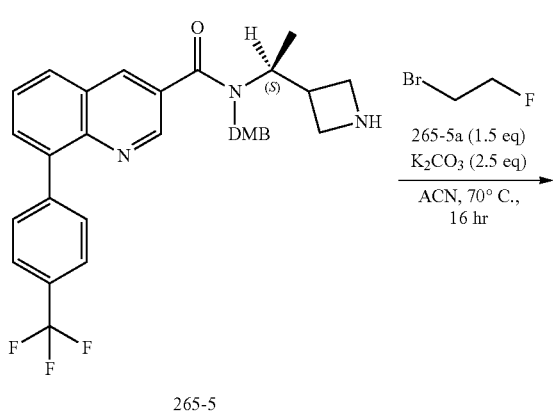

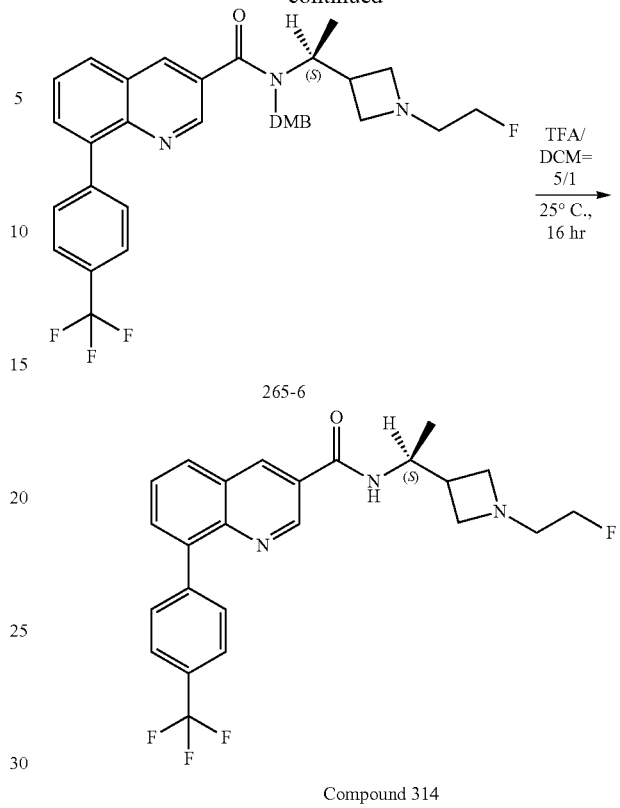

Compound 314

Benzyl 3-[(1S)-1-aminoethyl]azetidine-1-carboxylate

To a solution of 265-1 (3.8 g, 11.23 mmol, 1 eq) in MeOH (30 mL) was added HCl/MeOH (4 M, 5 mL, 1.8 eq). The mixture was stirred at 25° C. for 2 hr. TLC (DCM/MeOH=10/1, UV 254, I$_2$) indicated the starting material was consumed completely and one new spot formed. LCMS indicated the starting material was consumed completely and ~95% of desired compound was detected. The reaction mixture was concentrated under reduced pressure to remove MeOH and HCl/MeOH to give 265-2 (2.61 g, crude) as a colorless. The crude product was used for next step without further purification.

Benzyl 3-[(1S)-1-[(2,4-dimethoxyphenyl)methylamino]ethyl]azetidine-1-carboxylate To a solution of 265-2a (1.6 g, 9.63 mmol, 1 eq) and 265-2 (2.26 g, 9.63 mmol, 1 eq) in DCM (30 mL) was added HOAc (1.73 g, 28.89 mmol, 1.65 mL, 3 eq) and stirred at 25° C. for 2 hr, and then NaBH(OAc)$_3$ (4.08 g, 19.26 mmol, 2 eq) was added. The resulting mixture was stirred at 25° C. for 2 hr. TLC (EA/PE=1/1, UV 254) indicated the starting material was consumed completely and one new spot formed. LCMS indicated the starting material was consumed completely and ~63% of desired compound was detected. Then iced water (30 mL) was added and the mixture was neutralized to pH=9~10 with aq.NaOH (2 M). The aqueous phase was extracted with EA (40 mL*3). The combined organic phase was washed with brine (60 mL), dried with anhydrous Na$_2$SO$_4$, filtered and concentrated in vacuum. The residue was purified by flash silica gel chromatography (20 g SepaFlash® Silica Flash Column, EA/PE: 0~50%) to give 265-3 (2.8 g, 7.28 mmol, 75.6% yield) as a yellow oil.

Benzyl 3-[(1S)-1-[(2,4-dimethoxyphenyl)methyl-[8-[4-(trifluoromethyl)phenyl]quinoline-3-carbonyl]amino]ethyl]azetidine-1-carboxylate A mixture of 265-3a (2.0 g, 6.30 mmol, 1 eq), HATU (3.60 g, 9.46 mmol, 1.5 eq) in DMF (20 mL) was added DIPEA (2.44 g, 18.91 mmol, 3.3 mL, 3 eq) at 25° C. After addition, the mixture was stirred at 25° C. for 1 hr, and then 265-3 (2.67 g, 6.93 mmol, 1.1 eq) in DMF (5 mL) was added. The resulting mixture was stirred at 25° C. for 2 hr. TLC (DCM/MeOH=20/1, UV 254) indicated the starting material was consumed completely and one new main spot formed. LCMS indicated the starting material was consumed completely and ~55% of desired compound was detected. The reaction mixture was diluted with $H_2O$ (50 mL) and stirred for 5 min. The aqueous phase was extracted with EA (15 mL*3). The combined organic phase was washed with brine (20 mL), dried with anhydrous $Na_2SO_4$, filtered and concentrated in vacuum. The residue was purified by flash silica gel chromatography (20 g SepaFlash® Silica Flash Column, EA/PE: 0~40%) to give 265-4 (2.6 g, 3.12 mmol, 49.5% yield) as a yellow oil. It was checked by LCMS.

N-[(1S)-1-(azetidin-3-yl)ethyl]-N-[(2,4-dimethoxyphenyl)methyl]-8-[4-(trifluoromethyl)phenyl]quinoline-3-carboxamide To a solution of 265-4 (2.5 g, 3.66 mmol, 1 eq) in MeOH (35 mL) was added Pd/C (500 mg, 10%) under $N_2$. The suspension was degassed under vacuum and purged with $H_2$ several times. The mixture was stirred under $H_2$ (15 psi) at 25° C. for 2 hrs. LCMS indicated the starting material was consumed completely and ~80% of desired compound was detected. The reaction mixture was filtered and the cake was washed with MeOH (10 mL*2). The filter was concentrated in vacuo to give 265-5 (1.95 g, crude) as a yellow oil. The crude product was used for next step without further purification.

N-[(2,4-dimethoxyphenyl)methyl]-N-[(1S)-1-[1-(2-fluoroethyl)azetidin-3-yl]ethyl]-8-[4-(trifluoromethyl)phenyl]quinoline-3-carboxamide To a solution of 265-5 (200 mg, 0.36 mmol, 1 eq) in MeCN (2 mL) was added $K_2CO_3$ (125.7 mg, 0.91 mmol, 2.5 eq) and 265-5a (69.3 mg, 0.55 mmol, 1.5 eq). The mixture was stirred at 70° C. for 16 hr. LCMS indicated the starting material was consumed completely and ~91% of desired compound was detected. The reaction mixture was diluted with $H_2O$ (30 mL) and stirred for 5 min. The aqueous phase was extracted with EA (15 mL*3). The combined organic phase was washed with brine (20 mL), dried with anhydrous $Na_2SO_4$, filtered and concentrated in vacuum to give 265-6 (188 mg, crude) as a yellow solid. The crude product was used for next step without further purification.

N-[(1S)-1-[1-(2-fluoroethyl)azetidin-3-yl]ethyl]-8-[4-(trifluoromethyl)phenyl]quinoline-3-carboxamide (Compound 314)

To a solution of 265-6 (165 mg, 0.28 mmol, 1 eq) in DCM (0.4 mL) was added TFA (3.1 g, 27.0 mmol, 2 mL, 97.5 eq). The mixture was stirred at 25° C. for 16 hr. LCMS indicated the starting material was consumed completely and ~77% of desired compound was detected. HPLC indicated the starting material was consumed completely and ~85% of desired compound was detected. $K_2CO_3$ (solid) was added to quench the reaction and adjust the pH to 9-10. The reaction mixture was filtered and the cake was washed with MeOH (10 mL*2). The filter was concentrated in vacuo to give product. The crude product was purified by prep-HPLC (column: Waters Xbridge 150*25 mm*5 um; mobile phase: [water (0.05% NH3H2O)-ACN]; B %: 45%-75%, 9.5 min) to afford the title compound (26.3 mg, 59.0 umol, 21.3% yield) as a white solid. LCMS (ESI): RT=0.759 min, mass calcd for $C_{24}H_{23}F_4N_3O$ 445.18, m/z found 446.1 [M+H]$^+$; $^1$H NMR (400 MHz, CDCl$_3$) δ 9.38 (d, J=2.3 Hz, 1H), 8.71 (d, J=2.3 Hz, 1H), 8.16 (d, J=5.8 Hz, 1H), 7.98 (dd, J=1.4, 8.2 Hz, 1H), 7.85-7.80 (m, 3H), 7.79-7.74 (m, 2H), 7.72-7.66 (m, 1H), 4.55 (t, J=4.8 Hz, 1H), 4.43 (t, J=4.8 Hz, 1H), 4.37-4.28 (m, 1H), 3.47-3.39 (m, 3H), 3.25 (dd, J=3.3, 6.5 Hz, 1H), 2.88-2.81 (m, 1H), 2.80-2.73 (m, 1H), 2.58-2.50 (m, 1H), 1.32 (d, J=6.5 Hz, 3H).

Example 266: N-[(1S)-1-[1-(2-hydroxyethyl)azetidin-3-yl]ethyl]-8-[4-(trifluoromethyl)phenyl]quinoline-3-carboxamide (Compound 315)

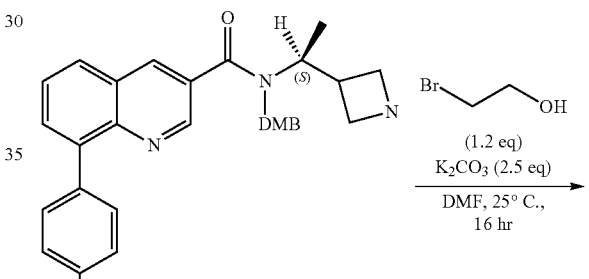

266-1

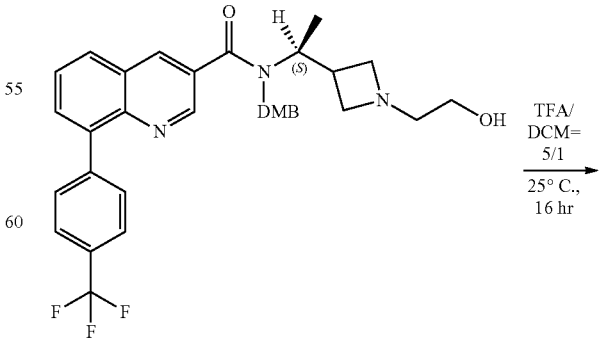

266-2

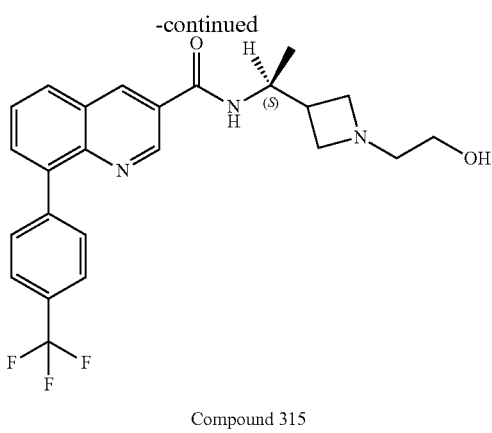

Compound 315

N-[(2,4-dimethoxyphenyl)methyl]-N-[(1S)-1-[1-(2-hydroxyethyl)azetidin-3-yl]ethyl]-8-[4-(trifluoromethyl)phenyl]quinoline-3-carboxamide To a solution of compound 266-1 (200 mg, 0.36 mmol, 1 eq) in DMF (2 mL) was added K2CO3 (125.7 mg, 0.91 mmol, 2.5 eq) and 2-bromoethanol (54.6 mg, 0.44 mmol, 31.0 uL, 1.2 eq). The mixture was stirred at 25° C. for 16 h. LCMS indicated the starting material was consumed completely and ~75% of desired compound was detected. The reaction mixture was diluted with H₂O (30 mL) and stirred for 5 min. The aqueous phase was extracted with EA (15 mL*3). The combined organic phase was washed with brine (20 mL), dried with anhydrous Na₂SO₄, filtered and concentrated in vacuum to give 266-2 (176 mg, crude) as a yellow solid. The crude product was used for next step without further purification.

N-[(1S)-1-[1-(2-hydroxyethyl)azetidin-3-yl]ethyl]-8-[4-(trifluoromethyl)phenyl]quinoline-3-carboxamide (Compound 315)

To a solution of 266-2 (150 mg, 0.25 mmol, 1 eq) in DCM (0.4 mL) was added TFA (3.08 g, 27.01 mmol, 2.00 mL, 106.9 eq). The mixture was stirred at 25° C. for 16 hr. LCMS indicated the starting material was consumed completely and ~63% of desired compound was detected. K₂CO₃ (solid) was added to quench the reaction and adjust the pH to 9-10. The reaction mixture was filtered and the cake was washed with MeOH (10 mL*2). The filter was concentrated in vacuum to give product. The crude product was purified by prep-HPLC (column: Waters Xbridge 150*25 mm*5 um; mobile phase: [water (0.05% NH3H2O)-ACN]; B %: 50%-50%, 9.5 min) to afford the title compound (20.6 mg, 46.5 mmol, 18.4% yield) as a white solid. LCMS (ESI): RT=0.740 min, mass calcd for $C_{24}H_{24}F_3N_3O_2$ 443.18, m/z found 444.1 [M+H]⁺; ¹H NMR (400 MHz, CDCl₃) δ 9.32 (d, J=2.4 Hz, 1H), 8.71 (d, J=2.3 Hz, 1H), 7.99 (dd, J=1.4, 8.1 Hz, 1H), 7.84-7.79 (m, 3H), 7.79-7.74 (m, 2H), 7.70 (dd, J=7.3, 8.1 Hz, 1H), 7.48 (d, J=6.8 Hz, 1H), 4.37 (m, 1H), 3.59 (t, J=5.3 Hz, 2H), 3.44-3.37 (m, 2H), 3.35-3.30 (m, 1H), 3.19-3.13 (m, 1H), 2.65 (dd, J=4.7, 5.8 Hz, 2H), 2.61-2.52 (m, 1H), 1.29 (d, J=6.5 Hz, 3H).

Example 267: N-[(1R)-3-(ethylamino)-1-methyl-propyl]-8-[4-(trifluoromethyl)phenyl]quinoline-3-carboxamide (Compound 316)

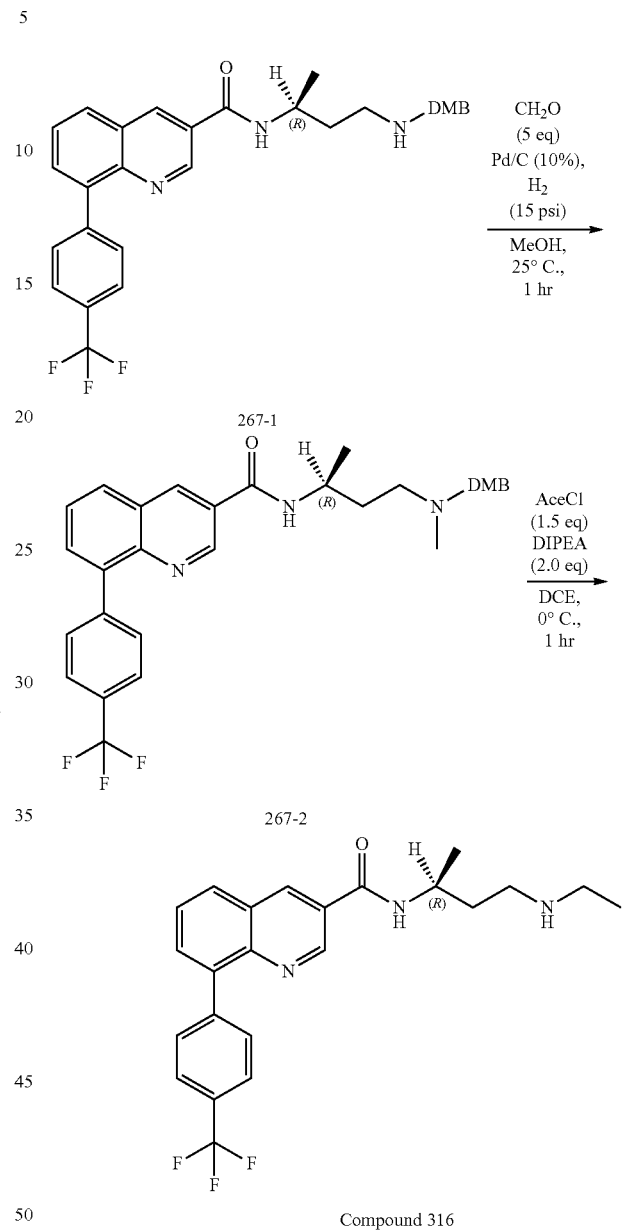

Compound 316

N-[(1R)-3-[(2,4-dimethoxyphenyl)methyl-ethyl-amino]-1-methyl-propyl]-8-[4-(trifluoromethyl)phenyl]quinoline-3-carboxamide To a solution of 267-1 (50 mg, 93.0 umol, 1 eq) in MeOH (3 mL) was added acetaldehyde (20.4 mg, 0.46 mmol, 26.1 uL, 5 eq) and Pd/C (25 mg, 10%). The suspension was degassed under vacuum and purged with H₂ several times. The mixture was stirred under H₂ (15 psi) at 25° C. for 1 hours. The reaction mixture was filtered and concentrated under reduced pressure to give a residue. The crude product was used into the next step without further purification. Compound 267-2 (50 mg, crude) was obtained as a white solid. LCMS (ESI): RT=0.925 min, mass calcd for C$_{32}$H$_{34}$F$_3$N$_3$O$_3$ 565.26 m/z found 566.4 [M+H]$^+$.

N-[(1R)-3-(ethylamino)-1-methyl-propyl]-8-[4-(trifluoromethyl)phenyl]quinoline-3-carboxamide (Compound 316)

To a solution of 267-2 (50 mg, 88.4 umol, 1 eq) in DCE (1.5 mL) were added DIPEA (22.8 mg, 0.17 mmol, 30.7 uL, 2.0 eq) and 1-chloroethyl carbonochloridate (18.9 mg, 0.13 mmol, 1.5 eq) at 0° C. Then the mixture was stirred at 0° C. for 1 hr. The reaction mixture was concentrated under reduced pressure to give a residue. The residue was purified by prep-TLC (SiO$_2$, DCM:MeOH=10:1) to give the desired product (30 mg). The product (30 mg) was purified by prep-HPLC (column: 3_Phenomenex Luna C18 75*30 mm*3 um; mobile phase: [water (0.05% HCl)-ACN]; B %: 25%-55%, 6.5 min) (2.0 mg, 4.5 umol, 5.1% yield, HCl). LCMS (ESI): RT=0.843 min, mass calcd for C$_{23}$H$_{24}$F$_3$N$_3$O 415.19 m/z found 416.3 [M+H]$^+$. $^1$H NMR (400 MHz, CD$_3$OD) δ9.29 (d, J=2.3 Hz, 1H), 9.10 (d, J=2.3 Hz, 1H), 8.23 (dd, J=1.3, 8.3 Hz, 1H), 8.00 (dd, J=1.4, 7.3 Hz, 1H), 7.92-7.86 (m, 1H), 7.84 (s, 4H), 4.41-4.20 (m, 1H), 3.16-3.02 (m, 4H), 2.11-1.89 (m, 2H), 1.41 (d, J=6.6 Hz, 3H), 1.35 (t, J=7.3 Hz, 3H).

Example 268: (R)—N-(1-(1-(2,2-difluoroethyl)azetidin-3-yl)ethyl)-8-(4-(trifluoromethyl)phenyl)quinoline-3-carboxamide (Compound 317)

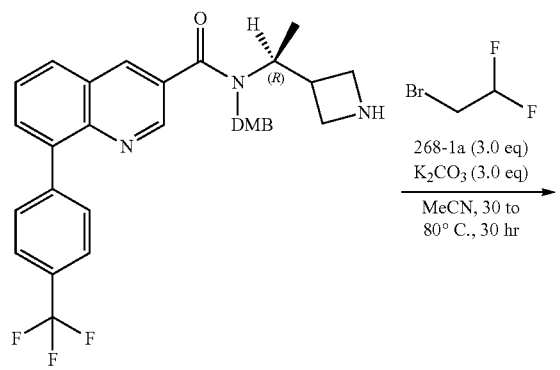

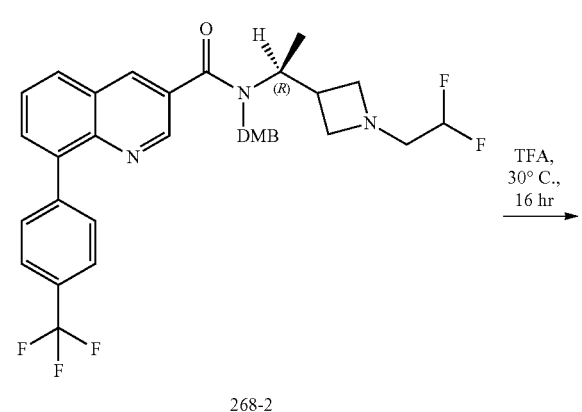

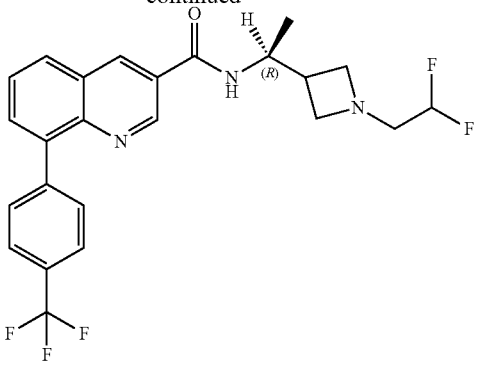

Compound 317

(R)—N-(1-(1-(2,2-difluoroethyl)azetidin-3-yl)ethyl)-N-(2,4-dimethoxybenzyl)-8-(4-(trifluoromethyl)phenyl)quinoline-3-carboxamide To a solution of 268-1 (50 mg, 91.0 umol, 1 eq) and K$_2$CO$_3$ (37.7 mg, 0.27 mmol, 3 eq) in ACN (1 mL) at 30° C. was added 268-1a (39.6 mg, 0.27 mmol, 3 eq), and the resulting mixture was stirred at 80° C. for 30 h. The reaction mixture was diluted with water (20 mL) and extracted with EA (20 mL*3). The combined organic layers were washed with brine (20 mL), dried over anhydrous Na$_2$SO$_4$, filtered and concentrated under reduced pressure to give 268-2 (55 mg, 89.6 umol, 98.5% yield) as colorless oil, which was used directly for next step.

(R)—N-(1-(1-(2,2-difluoroethyl)azetidin-3-yl)ethyl)-8-(4-(trifluoromethyl)phenyl)quinoline-3-carboxamide (Compound 317)

The solution of 268-2 (55 mg, 89.6 umol, 1 eq) in TFA (1 mL) was stirred at 30° C. for 16 h. The reaction mixture was concentrated under reduced pressure to remove TFA. The residue was basified with NH$_3$·H$_2$O (1 mL) and then concentrated to give a residue. The residue was purified by prep-HPLC (column: Waters Xbridge 150*25 mm*5 um; mobile phase: [water (0.05% NH3H2O+10 mM NH4HCO3)-ACN]; B %: 47%-77%, 9.5 min) to give the desired compound (13.1 mg, 28.4 umol, 31.7% yield) as a white solid. LCMS (ESI): RT=0.777 min, mass calc. for C$_{24}$H$_{22}$F$_5$N$_3$O 463.17, m/z found 464.2 [M+H]$^+$; $^1$H NMR (400 MHz, DMSO-d$_6$) δ 9.23 (d, J=2.3 Hz, 1H), 8.87 (d, J=2.3 Hz, 1H), 8.61 (d, J=8.3 Hz, 1H), 8.18 (dd, J=1.3, 8.3 Hz, 1H), 7.93 (dd, J=1.3, 7.2 Hz, 1H), 7.87 (q, J=8.4 Hz, 4H), 7.82-7.77 (m, 1H), 6.10-5.73 (m, 1H), 4.36-4.19 (m, 1H), 3.35-3.33 (m, 2H), 3.08 (t, J=6.8 Hz, 1H), 3.00 (t, J=6.9 Hz, 1H), 2.77 (dt, J=4.2, 16.2 Hz, 2H), 2.63-2.55 (m, 1H), 1.11 (d, J=6.6 Hz, 3H).

Example 269: (R)—N-(1-(1-(2-fluoroethyl)azetidin-3-yl)ethyl)-8-(4-(trifluoromethyl)phenyl)quinoline-3-carboxamide (Compound 318)

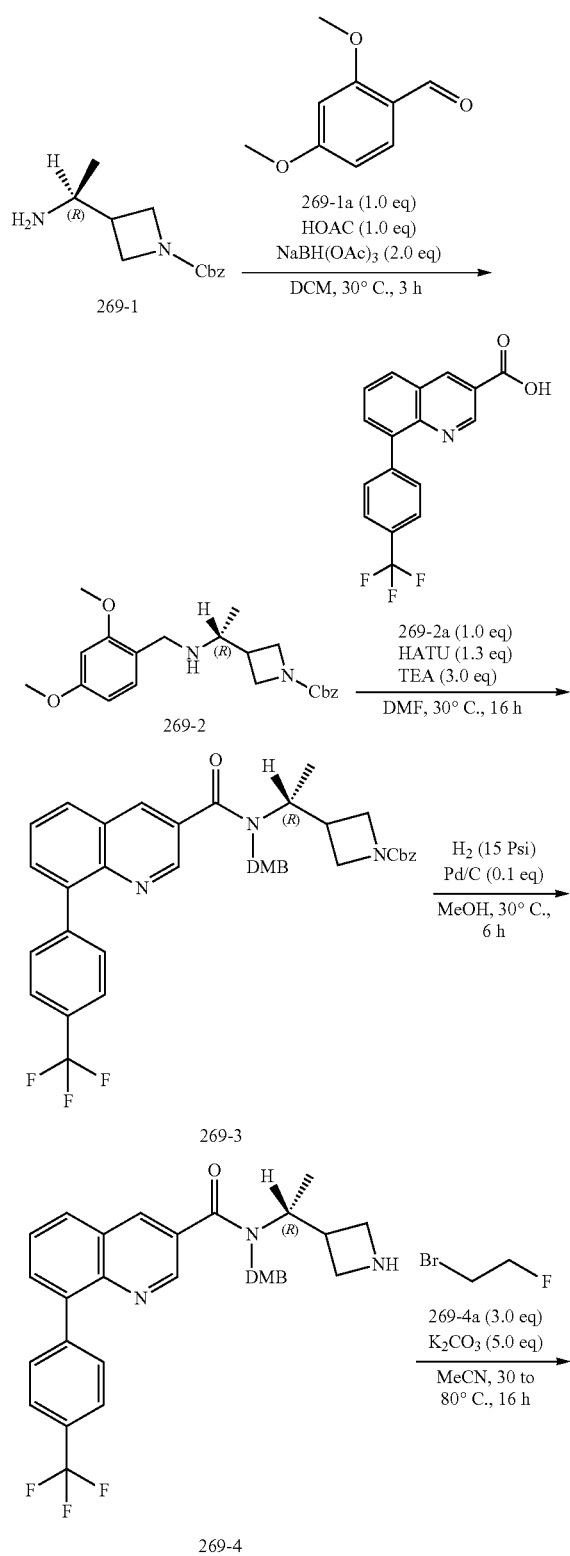

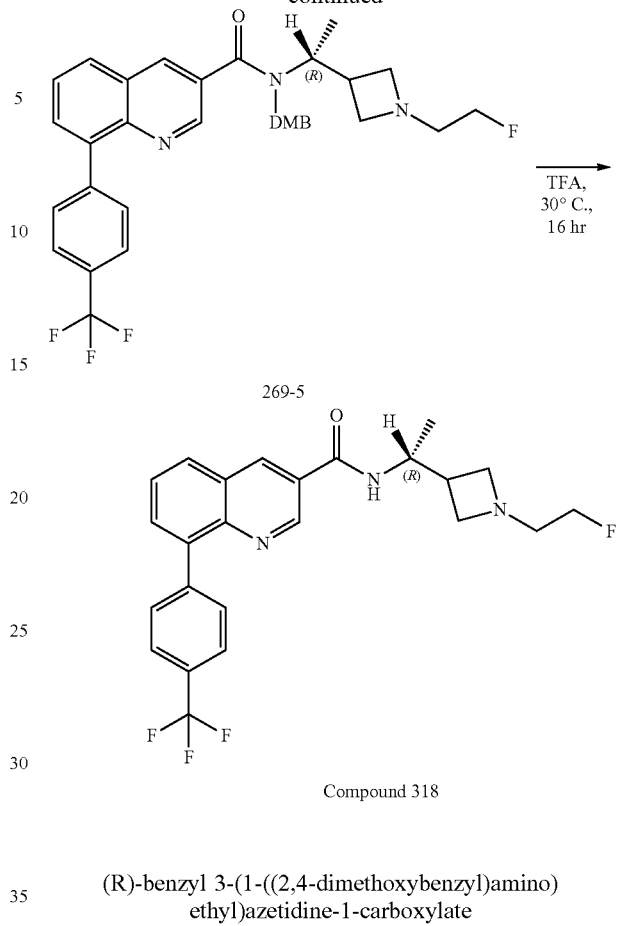

Compound 318

(R)-benzyl 3-(1-((2,4-dimethoxybenzyl)amino)ethyl)azetidine-1-carboxylate

To a solution of 269-1a (500 mg, 3.01 mmol, 1 eq) and 269-1 (775.5 mg, 3.31 mmol, 1.1 eq) in DCM (10 mL) at 30° C. was added HOAc (180.7 mg, 3.01 mmol, 0.17 mL, 1 eq), and the mixture was stirred at 30° C. for 1 h. Then NaBH(OAc)$_3$ (1.28 g, 6.02 mmol, 2 eq) was added into the above mixture at 30° C., and the resulting mixture was stirred at 30° C. for 2 h. The reaction mixture was concentrated under reduced pressure to give a residue. The residue was diluted with saturated Na$_2$CO$_3$ solution (20 mL) and extracted with EA (20 mL*3). The combined organic layers were washed with brine (20 mL), dried over anhydrous Na$_2$SO$_4$, filtered and concentrated under reduced pressure to give 269-2 (1.10 g, 2.86 mmol, 95.1% yield) as colorless oil, which was used directly for next step.

(R)-benzyl 3-(1-(N-(2,4-dimethoxybenzyl)-8-(4-(trifluoromethyl)phenyl)quinoline-3-carboxamido)ethyl)azetidine-1-carboxylate To a solution of 269-2a (650 mg, 2.05 mmol, 1 eq), 269-2 (1.04 g, 2.25 mmol, 1.1 eq) and HATU (1.01 g, 2.66 mmol, 1.3 eq) in DMF (10 mL) at 30° C. was added TEA (621.9 mg, 6.15 mmol, 0.86 mL, 3 eq), and the resulting mixture was stirred at 30° C. for 16 h. The reaction mixture was concentrated under reduced pressure to give a residue. The residue was diluted with water (20 mL) and extracted with EA (20 mL*3). The combined organic layers were washed with brine (20 mL), dried over anhydrous Na$_2$SO$_4$, filtered and concentrated under reduced pressure to give a residue. The residue was purified by flash silica gel chromatography (ISCO®; 20 g SepaFlash® Silica Flash Column, Eluent of 0-50% Ethylacetate/Petroleum ether gradient @35 mL/min) to give 269-3 (1.1 g, 1.51 mmol, 73.8% yield) as a white solid. LCMS (ESI): RT=1.024 min, mass calc. for $C_{39}H_{36}F_3N_3O_5$ 683.26, m/z found 684.2 $[M+H]^+$.

(R)—N-(1-(azetidin-3-yl)ethyl)-N-(2,4-dimethoxybenzyl)-8-(4-(trifluoromethyl)phenyl)quinoline-3-carboxamide To a solution of 269-3 (1.1 g, 1.61 mmol, 1 eq) in MeOH (20 mL) at 30° C. was added Pd/C (171.2 mg, 0.16 mmol, 10%, 0.1 eq), and the resulting mixture was stirred at 30° C. for 6 h. The reaction mixture was filtered to remove the Pd/C and the filtrate was concentrated under reduced pressure to give 269-4 (850 mg, 1.48 mmol, 92.3% yield) as a white solid. LCMS (ESI): RT=0.811 min, mass calc. for $C_{31}H_{30}F_3N_3O_3$ 549.22, m/z found 550.1 $[M+ACN+H]^+$.

(R)—N-(2,4-dimethoxybenzyl)-N-(1-(1-(2-fluoroethyl)azetidin-3-yl)ethyl)-8-(4-(trifluoromethyl)phenyl)quinoline-3-carboxamide To a solution of 269-4 (40 mg, 72.8 umol, 1 eq) and $K_2CO_3$ (50.3 mg, 0.36 mmol, 5 eq) in ACN (1 mL) at 30° C. was added 269-4a (27.7 mg, 0.22 mmol, 3 eq), and the resulting mixture was stirred at 80° C. for 30 h. The reaction mixture was diluted with water (20 mL) and extracted with EA (20 mL*3). The combined organic layers were washed with brine (20 mL), dried over anhydrous $Na_2SO_4$, filtered and concentrated under reduced pressure to give 269-5 (40 mg, 67.2 umol, 92.3% yield) as colorless oil.

WX2798: (R)—N-(1-(1-(2-fluoroethyl)azetidin-3-yl)ethyl)-8-(4-(trifluoromethyl)phenyl)quinoline-3-carboxamide The solution of 269-5 (40 mg, 67.2 umol, 1 eq) in TFA (1 mL) was stirred at 30° C. for 16 h. The reaction mixture was concentrated under reduced pressure to remove TFA. The residue was basified with $NH_3 \cdot H_2O$ (1 mL) and then concentrated under reduced pressure to give a residue. The residue was purified by prep-HPLC (column: Waters Xbridge 150*25 mm*5 um; mobile phase: [water (0.05% $NH_3H_2O$)-ACN]; B %: 49%-69%, 9.5 min) to give the title compound (8.3 mg, 18.5 umol, 27.5% yield) as a yellow solid. LCMS (ESI): RT=0.752 min, mass calc. for $C_{24}H_{23}F_4N_3O$ 445.18, m/z found 446.1 $[M+H]^+$; $^1H$ NMR (400 MHz, DMSO-$d_6$) δ 9.24 (d, J=2.3 Hz, 1H), 8.87 (d, J=2.3 Hz, 1H), 8.60 (d, J=8.3 Hz, 1H), 8.23-8.14 (m, 1H), 7.93 (dd, J=1.3, 7.0 Hz, 1H), 7.91-7.83 (m, 4H), 7.82-7.77 (m, 1H), 4.42 (t, J=4.9 Hz, 1H), 4.33-4.29 (m, 1H), 4.29-4.20 (m, 1H), 3.31 (s, 2H), 3.00 (t, J=6.7 Hz, 1H), 2.91 (t, J=6.7 Hz, 1H), 2.67 (t, J=4.8 Hz, 1H), 2.61-2.54 (m, 2H), 1.12 (d, J=6.5 Hz, 3H).

Example 270: N-[(1R)-3-(Dimethylamino)-1-methyl-propyl]-8-[4-(trifluoromethyl)phenyl]quinoline-3-carboxamide (Compound 319)

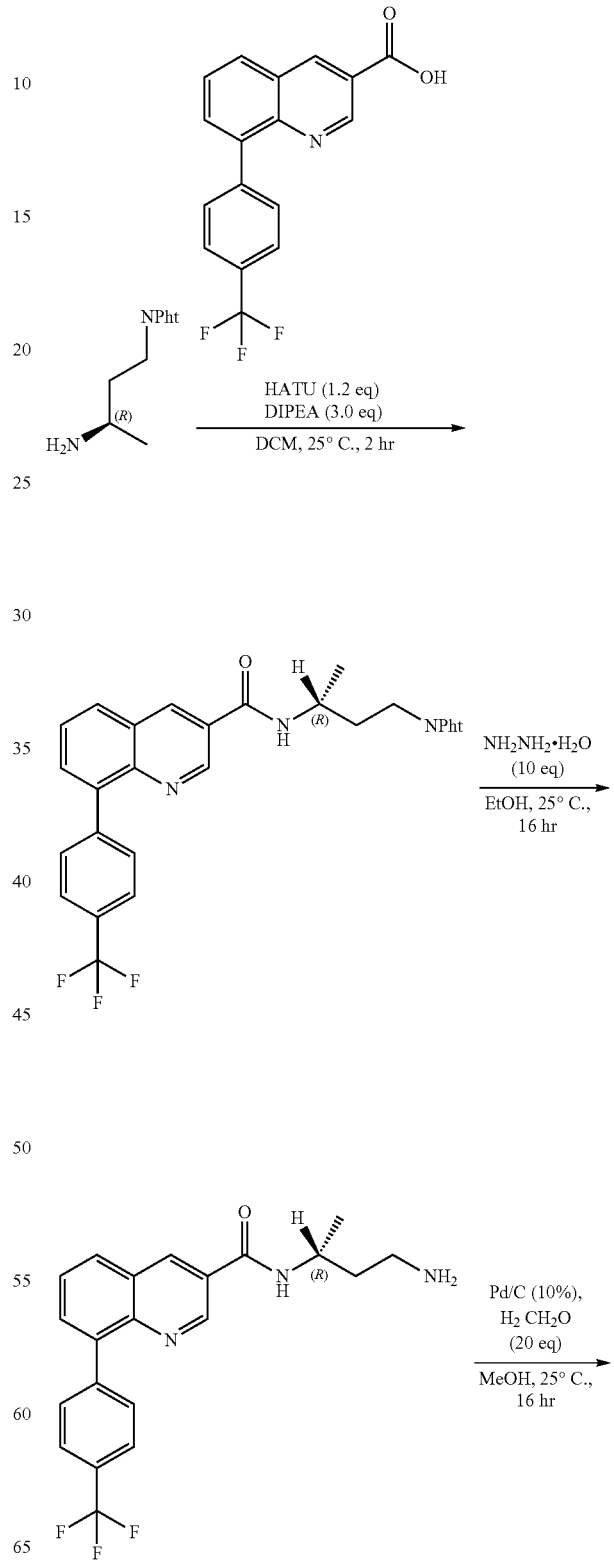

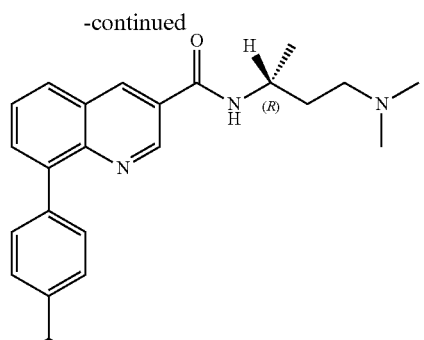

Compound 319

N-[(1R)-3-(1,3-Dioxoisoindolin-2-yl)-1-methyl-propyl]-8-[4-(trifluoromethyl)phenyl]quinoline-3-carboxamide To a solution of 2-[(3R)-3-aminobutyl]isoindoline-1,3-dione (500 mg, 1.96 mmol, 1 eq, HCl) and 8-[4-(trifluoromethyl)phenyl]quinoline-3-carboxylic acid (622.7 mg, 1.96 mmol, 1 eq) in DCM (5 mL) were added HATU (895.6 mg, 2.36 mmol, 1.2 eq) and DIPEA (761.1 mg, 5.89 mmol, 3 eq). The mixture was stirred at 25° C. for 2 hr. The mixture was diluted with water (10 mL) and the resultant mixture was extracted with EA (20 mL*3). The combined organic layers were dried over $Na_2SO_4$, filtered and concentrated to dryness under reduced pressure. The residue was purified by flash silica gel chromatography (ISCO®; 12 g SepaFlash® Silica Flash Column, Eluent of 0~90% Petroleum ether/Ethyl acetate ether gradient @30 mL/min) to give N-[(17)-3-(1,3-dioxoisoindolin-2-yl)-1-methyl-propyl]-8-[4-(trifluoromethyl)phenyl]quinoline-3-carboxamide (767 mg, 1.48 mmol, 75.50% yield) was obtained as a white solid.

N-[(1R)-3-Amino-1-methyl-propyl]-8-[4-(trifluoromethyl)phenyl]quinoline-3-carboxamide To a solution of N-[(1R)-3-(1,3-dioxoisoindolin-2-yl)-1-methyl-propyl]-8-[4-(trifluoromethyl)phenyl]quinoline-3-carboxamide (650 mg, 1.26 mmol, 1 eq) in EtOH (7 mL) was added $NH_2NH_2 \cdot H_2O$ (739.7 mg, 12.56 mmol, 85%, 10 eq), and then the reaction mixture was stirred at 25° C. for 16 hours. The reaction suspension was filtered and the organic layer was concentrated under reduce pressure. The residue was diluted with water (30 mL) and the resultant mixture was extracted with DCM (50 mL*3). The combined organic layers were dried over $Na_2SO_4$, filtered and concentrated to dryness under reduced pressure to give N-[(1R)-3-amino-1-methyl-propyl]-8-[4-(trifluoromethyl)phenyl]quinoline-3-carboxamide (403 mg, 72.8% yield) was obtained as a light yellow solid

N-[(1R)-3-(Dimethylamino)-1-methyl-propyl]-8-[4-(trifluoromethyl)phenyl]quinoline-3-carboxamide To a solution of N-[(1R)-3-amino-1-methyl-propyl]-8-[4-(trifluoromethyl)phenyl]quinoline-3-carboxamide (50 mg, 0.12 mmol, 1 eq) and formaldehyde (209.4 mg, 2.58 mmol, 20 eq) in MeOH (2 mL) was added Pd/C (50 mg, 10%) under $N_2$. The suspension was degassed under vacuum and purged with $H_2$ several times. The mixture was stirred under $H_2$ (15 psi) at 25° C. for 16 hours. The reaction mixture was filtered and the filtrate was concentrated under reduce pressure. The residue was purified by prep-HPLC (column: 3_Phenomenex Luna C18 75*30 mm*3 um; mobile phase: [water (0.05% HCl)-ACN]; B %: 15%-45%, 6.5 min) to give N-[(1R)-3-(dimethylamino)-1-methyl-propyl]-8-[4-(trifluoromethyl)phenyl]quinoline-3-carboxamide (10.12 mg, 22.17 umol, 17.18% yield, HCl) as a white solid. LCMS (ESI): RT=0.756 min, mass calcd for $C_{23}H_{24}F_3N_3O$ 415.19 m/z, found 416.3 $[M+H]^+$, $^1H$ NMR (400 MHz, DMSO-$d_6$) δ 10.64 (br s, 1H), 9.31 (d, J=2.3 Hz, 1H), 9.02 (d, J=2.0 Hz, 1H), 8.90 (d, J=8.3 Hz, 1H), 8.21-8.16 (m, 1H), 7.95 (dd, J=1.3, 7.0 Hz, 1H), 7.91-7.85 (m, 4H), 7.84-7.79 (m, 1H), 4.23-4.08 (m, 1H), 3.19-3.05 (m, 2H), 2.74 (t, J=4.3 Hz, 6H), 2.10-1.86 (m, 2H), 1.27 (d, J=6.5 Hz, 3H).

Example 271: (R)—N-(1-(1-cyclopropylazetidin-3-yl)ethyl)-5-(4-(trifluoromethyl)phenyl)-2-naphthamide (Compound 320)

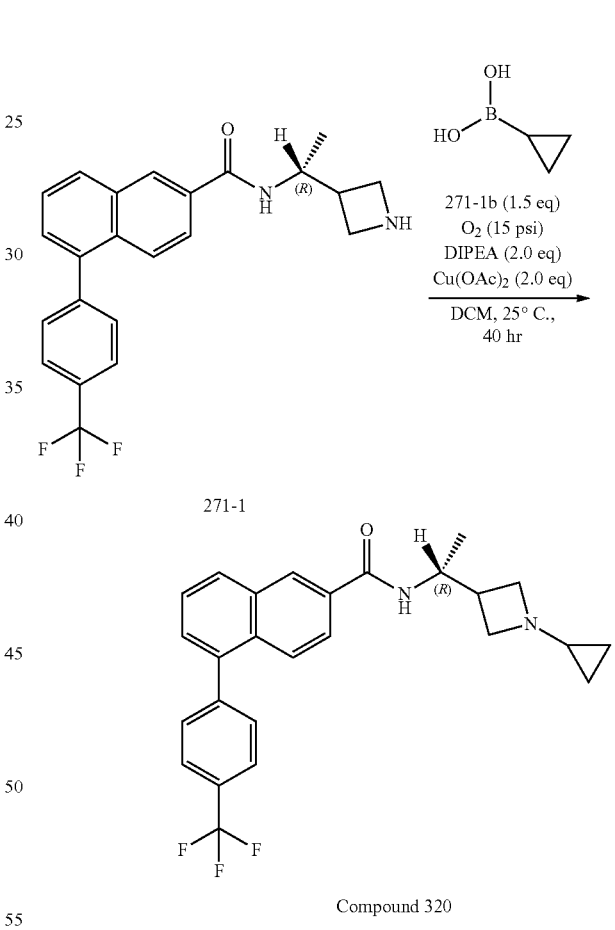

Compound 320

(R)—N-(1-(1-cyclopropylazetidin-3-yl)ethyl)-5-(4-(trifluoromethyl)phenyl)-2-naphthamide To a mixture of 271-1 (60.0 mg, 0.15 mmol, 1.0 eq) and 271-1a (19.4 mg, 0.23 mmol, 1.5 eq) in DCM (5 mL) were added $Cu(OAc)_2$ (54.7 mg, 0.30 mmol, 2.0 eq) and DIPEA (38.9 mg, 0.30 mmol, 52 uL, 2.0 eq) in one portion at 30° C. The suspension was degassed under vacuum and purged with $O_2$ several times. The mixture was stirred under $O_2$ (15 psi) at 30° C. for 40 hours. The reaction mixture was concentrated under reduced pressure to give a residue, which was purified by prep-HPLC: (column: Welch Xtimate C18 150*25 mm*5 um; mobile phase: [water (0.05% NH3H2O)-ACN]; B %: 57%-87%, 9.5 min) to give the desired compound (6.85 mg, 16 umol, 10.3% yield) as a yellow solid. LCMS (ESI): RT=0.878 min, mass calc. for $C_{26}H_{25}F_3N_2O$ 438.19, m/z found 439.3 [M+H]$^+$; $^1$H NMR (400 MHz, DMSO-d$_6$) δ 8.52 (s, 1H), 8.43 (brd, J=7.8 Hz, 1H), 8.12 (brd, J=8.5 Hz, 1H), 7.92 (brd, J=8.0 Hz, 3H), 7.80 (brd, J=8.6 Hz, 1H), 7.74 (brd, J=7.6 Hz, 2H), 7.70-7.66 (m, 1H), 7.59 (brd, J=6.8 Hz, 1H), 4.24 (brd, J=6.8 Hz, 1H), 3.29 (brs, 3H), 3.09-2.95 (m, 2H), 1.83 (brs, 1H), 1.10 (brd, J=6.4 Hz, 3H), 0.35-0.17 (m, 4H).

Example 272: 8-(2-fluoro-4-(trifluoromethyl)phenyl)-6-methoxyquinoline-3-carboxylic Acid (Compound 321)

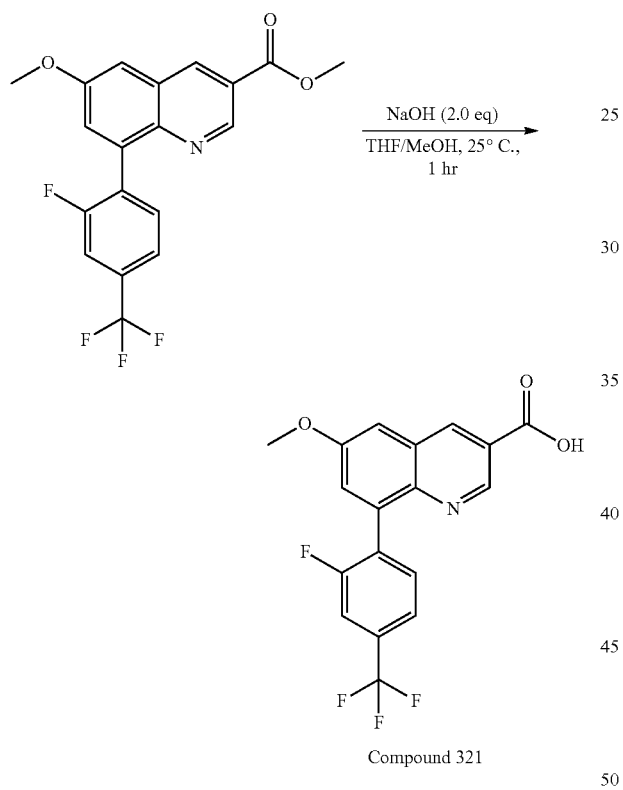

Compound 321

To a solution of compound methyl 8-(2-fluoro-4-(trifluoromethyl)phenyl)-6-methoxyquinoline-3-carboxylate (30.0 mg, 79.0 umol, 1.0 eq) in THF (0.6 mL) and MeOH (0.2 mL) was added NaOH (1 M, 0.16 mL, 2.0 eq). The reaction mixture was stirred at 25° C. for 1 hour. LC-MS showed starting material was consumed completely and one main peak with desired MS was detected. The reaction mixture was adjusted with HCl (1M) to pH=5, and then the suspension was extracted with EA (20 mL*3). The combined organic layers were dried over Na$_2$SO$_4$, filtered and concentrated to dryness under reduced pressure to give the title compound (14.48 mg, 49.6% yield) as a white solid. LCMS (ESI): RT=0.931 min, mass calcd. for $C_{18}H_{11}F_4NO_3$ 365.07, m/z found 366.0 [M+H]$^+$; $^1$H NMR (400 MHz, DMSO-d$_6$) δ 9.09 (s, 1H), 8.94 (s, 1H), 7.82 (d, J=9.5 Hz, 1H), 7.79-7.70 (m, 3H), 7.62 (d, J=2.1 Hz, 1H), 3.97 (s, 3H).

Example 273: 7-methoxy-5-(4-(trifluoromethyl)phenyl)-2-naphthoic Acid (Compound 322)

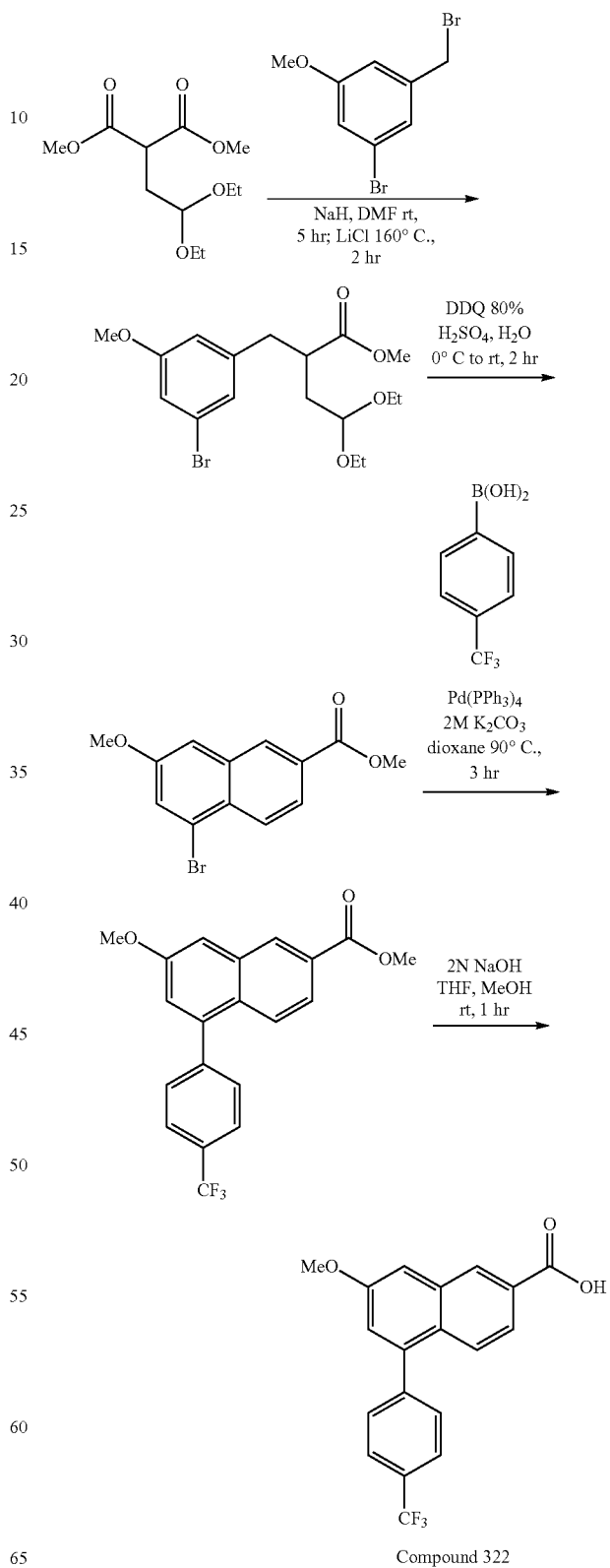

Compound 322

Step 1: methyl 2-(3-bromo-5-methoxybenzyl)-4,4-diethoxybutanoate

NaH 60% in mineral oil (1.03 g, 25.7 mmol, 2.7 equiv.) was carefully added to 1-bromo-3-(bromomethyl)-5-methoxybenzene (2.66 g, 9.5 mmol, 1 equiv.) in 20 mL DMF and stirred at rt for 1 hr. Dimethyl 2-(2,2-diethoxyethyl) malonate (3.5 g, 14.3 mmol, 1.5 equiv.) in 12 mL DMF was added dropwise and stirred at rt until LCMS showed complete consumption of the SM, 4 hr. LiCl (445 mg, 10.5 mmol, 1.1 equiv.) was carefully added and the mixture was heated to 160° C. for 2 hr. The reaction mixture was cooled to rt, diluted Et$_2$O, and washed with sat. aq. NH$_4$Cl, H$_2$O, and brine. The organic layer was dried with Na$_2$SO$_4$, concentrated, and purified by FCC, 0 to 15% EtOAc in Hexane gradient to give methyl 2-(3-bromo-5-methoxybenzyl)-4,4-diethoxybutanoate (2.037 g, 5.2 mmol, 55% yield) as a yellow oil. LCMS calcd: 389 ([M+H]$^+$), m/z found: 389.

Step 2: methyl 5-bromo-7-methoxy-2-naphthoate

Methyl 2-(3-bromo-5-methoxybenzyl)-4,4-diethoxybutanoate (390 mg, 1 mmol, 1 equiv.) in MeOH (0.5 mL) was carefully added to DDQ (230 mg, 1.01 mmol, 1.01 equiv.) in 2 mL of 80% H$_2$SO$_4$(aq) at 0° C. The mixture was stirred at 0° C. for 1 hr and slowly warmed to rt over 1 hr. The solid was filtered, re-dissolved in EtOAc, and the organic layer was washed with H$_2$O, brine, dried with Na$_2$SO$_4$, and concentrated. The residue was purified by FCC, 0 to 20% EtOAc in Hexane gradient to give methyl 5-bromo-7-methoxy-2-naphthoate (200 mg, 0.68 mmol, 68% yield), colorless solid. LCMS calcd: 295 ([M+H]$^+$), m/z found: 295.

Step 3: methyl 7-methoxy-5-(4-(trifluoromethyl)phenyl)-2-naphthoate

5-Bromo-7-methoxy-2-naphthoate (800 mg, 2.7 mmol, 1 equiv.), (4-(trifluoromethyl)phenyl)boronic acid (618 mg, 3.2 mmol, 1.2 equiv.), Pd(PPh$_3$)$_4$ (61 mg, 0.05 mmol, 0.1 equiv.), and 4:1 dioxane/2M K$_2$CO$_3$(aq) (10.8 mL:2.7 mL, 0.2M) were thoroughly purged with N$_2$ for 10 min. The mixture was heated to 90° C. for 3 hr, whereupon LCMS indicated complete consumption of SM. The reaction mixture was cooled to rt, diluted EtOAc, and washed with sat. aq. NH$_4$Cl, H$_2$O, and brine. The organic layer was dried with Na$_2$SO$_4$, concentrated, and purified by FCC, 0 to 20% EtOAc in Hexane gradient to give methyl 7-methoxy-5-(4-(trifluoromethyl)phenyl)-2-naphthoate (884 mg, 2.5 mmol, 91% yield), colorless solid. LCMS calcd: 361 ([M+H]$^+$), m/z found: 361.

Step 4: 7-methoxy-5-(4-(trifluoromethyl)phenyl)-2-naphthoic Acid

Methyl 7-methoxy-5-(4-(trifluoromethyl)phenyl)-2-naphthoate (724 mg, 2 mmol, 1 equiv.) was stirred in 24 mL of a 1:1:1 mixture of THF:MeOH:2N NaOH(aq) at rt for 2 hr. The reaction was concentrated, and the residue was dissolved in DCM and acidified with 2N HCl(aq). The organic layer was dried with Na$_2$SO$_4$ and concentrated to give 7-methoxy-5-(4-(trifluoromethyl)phenyl)-2-naphthoic acid (690 mg, 2 mmol, 100% yield), colorless solid. LCMS calcd: 347 ([M+H]$^+$), m/z found: 347.

Example 274: 6-cyclopropoxy-8-(4-(trifluoromethyl)phenyl)quinoline-3-carboxylic acid (Compound 323)

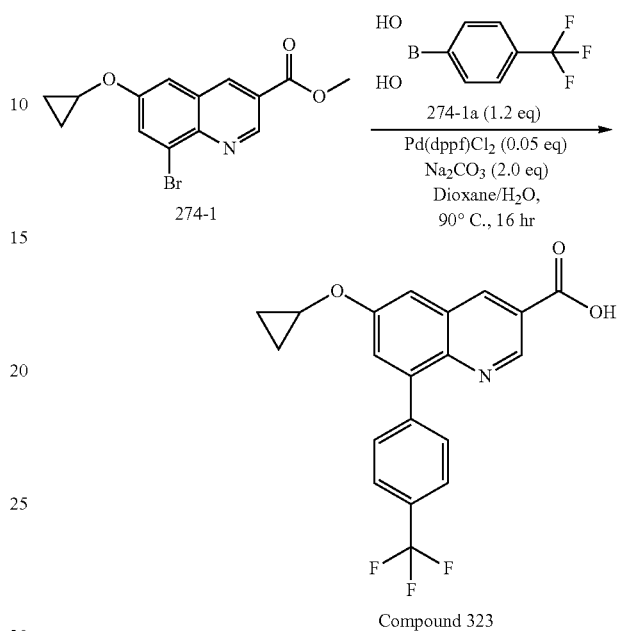

Compound 323

To a solution of compound 274-1 (30 mg, 93 umol, 1.0 eq), compound 274-1a (21.2 mg, 0.11 mmol, 1.2 eq) and Na$_2$CO$_3$ (29.6 mg, 0.28 mmol, 3.0 eq) in Dioxane (2 mL) and H$_2$O (0.4 mL) was added Pd(dppf)Cl$_2$ (3.4 mg, 4.6 umol, 0.05 eq) under N$_2$. The reaction mixture was stirred at 90° C. for 16 hours. LC-MS showed starting material was consumed completely and one main peak with desired MS was detected. The reaction mixture was adjusted with HCl (1M) to pH=6, and then the suspension was extracted with EA (10 mL*2). The combined organic layers were dried over Na$_2$SO$_4$, filtered and concentrated to dryness under reduced pressure. The residue was purified by prep-HPLC to give the title compound (14.63 mg, 37% yield, HCl) as a white solid. LCMS (ESI): RT=1.002 min, mass calcd. for C$_{20}$H$_{14}$F$_3$NO$_3$ 373.09, m/z found 373.9 [M+H]$^+$; $^1$H NMR (400 MHz, DMSO-d$_6$) δ 9.14 (d, J=2.3 Hz, 1H), 8.97 (d, J=2.3 Hz, 1H), 7.93 (d, J=2.8 Hz, 1H), 7.90-7.82 (m, 4H), 7.60 (d, J=2.8 Hz, 1H), 4.10-4.03 (m, 1H), 0.96-0.89 (m, 2H), 0.82-0.76 (m, 2H).

Example 275: 6-(trifluoromethoxy)-8-[4-(trifluoromethyl) phenyl]quinoline-3-carboxylic Acid (Compound 324)

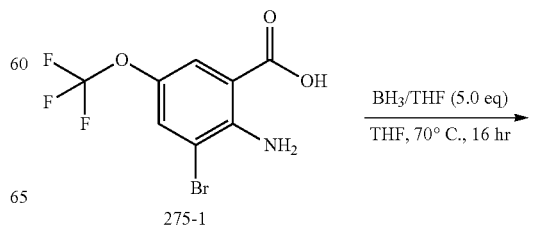

275-1

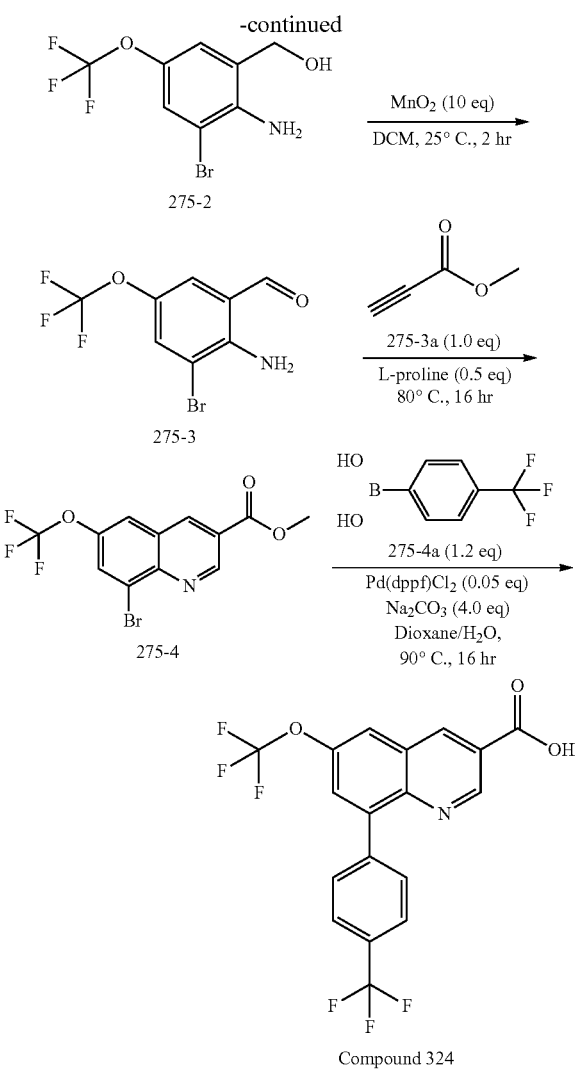

Step 1: [2-amino-3-bromo-5-(trifluoromethoxy)phenyl]methanol

To a mixture of compound 275-1 (400 mg, 1.3 mmol, 1.0 eq) in THF (1 mL) was added BH₃·THF (1 M, 6.7 mL, 5.0 eq) at 0° C. under N₂ atmosphere. The mixture was stirred at 70° C. for 4 hr. LCMS showed desired product. TLC (PE:EA=1:1, UV) showed new spots formed. The mixture was quenched by MeOH (3 mL) at 0° C. The mixture was diluted with H₂O (5 mL) and extracted with EA (10 mL*3). The organic phases were combined, dried over Na₂SO₄, filtered and concentrated under reduced pressure to give a residue. The residue was purified by flash silica gel chromatography. Compound 275-2 (380 mg, 1.33 mmol, 99.64% yield) was obtained as a white solid. LCMS (ESI): RT=0.741 min, mass calc. for $C_8H_7BrF_3NO_2$ 284.96, m/z found 285.8 [M+H]⁺; ¹H NMR (400 MHz, CDCl₃) δ 7.33-7.32 (m, 1H), 6.96 (s, 1H), 4.68-4.65 (m, 2H).

Step 2: 2-amino-3-bromo-5-(trifluoromethoxy)benzaldehyde

To a mixture of compound 275-2 (470 mg, 1.6 mmol, 1.0 eq) in DCM (5 mL) was added MnO₂ (1.4 g, 16.4 mmol, 10.0 eq). The mixture was stirred at 25° C. for 3 hr. LCMS showed desired product. TLC (PE:EA=3:1, UV) showed new spot formed. The mixture was filtered. The filtrate was concentrated under reduced pressure to give a residue. Compound 275-3 (442 mg, 1.5 mmol, 89% yield) was obtained as a yellow solid. LCMS (ESI): RT=0.813 min, mass calc. for $C_8H_5BrF_3NO_2$ 282.95, m/z found 283.7.

Step 3: methyl 8-bromo-6-(trifluoromethoxy)quinoline-3-carboxylate

To a mixture of compound 275-3 (440 mg, 1.5 mmol, 1.0 eq) and compound 275-3a (156.3 mg, 1.9 mmol, 1.2 eq) in EtOH (5 mL) was added L-proline (89.2 mg, 0.774 mmol, 0.5 eq). The mixture was stirred at 80° C. for 16 hr. LCMS showed desired product. TLC (PE:EA=5:1, UV) showed new sport formed. The mixture was diluted with H₂O (10 mL) and extracted with EA (20 mL*3). The organic phases were combined, dried over Na₂SO₄, filtered and concentrated under reduced pressure to give a residue. The residue was purified by flash silica gel chromatography. Compound 275-4 (445 mg, 1.3 mmol, 82% yield) was obtained as a white solid. LCMS (ESI): RT=0.847 min, mass calc. for $C_{12}H_7BrF_3NO_3$ 348.96, m/z found 351.7 [M+H]⁺; ¹H NMR (400 MHz, CDCl₃) δ 9.57-9.56 (m, 1H), 8.87-8.86 (m, 1H), 8.06-8.05 (m, 1H), 7.77 (s, 1H), 4.05 (s, 3H).

Step 4: 6-(trifluoromethoxy)-8-[4-(trifluoromethyl)phenyl]quinoline-3-carboxylic Acid To a mixture of compound 275-4 (50 mg, 0.143 mmol, 1.0 eq), compound 275-4a (32.5 mg, 0.171 mmol, 1.2 eq), H₂O (0.5 mL) and Na₂CO₃ (45.4 mg, 0.428 mmol, 3.0 eq) in dioxane (2 mL) was added Pd(dppf)Cl₂ (5.2 mg, 7.1 umol, 0.05 eq). The mixture was degassed and purged with N₂ for 3 times. The mixture was stirred at 90° C. for 16 hr under N₂ atmosphere. LCMS showed desired product. The mixture pH was adjusted to pH=6 by sat.citric acid. The mixture was diluted with H₂O (10 mL) and extracted with EA (20 mL*3). The organic phases were combined, dried over Na₂SO₄, filtered and concentrated under reduced pressure to give a residue. The residue was purified by prep-HPLC. The title compound (17.86 mg, 44.51 umol, 31.16% yield) was obtained. LCMS (ESI): RT=0.896 min, mass calc. for $C_{18}H_9F_6NO_3$ 401.5, m/z found 401.8 [M+H]⁺; ¹H NMR (400 MHz, CDCl₃) δ 9.52-9.51 (m, 1H), 8.97-8.96 (m, 1H), 7.84-7.79 (m, 5H), 7.74 (s, 1H).

Example 276: 6-methoxy-8-(4-(trifluoromethyl)phenyl)quinoline-3-carboxylic acid (Compound 325)

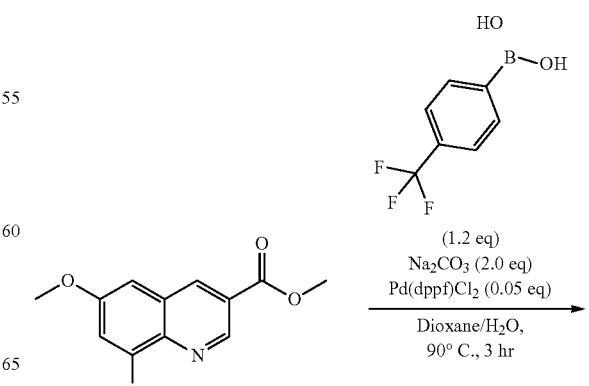

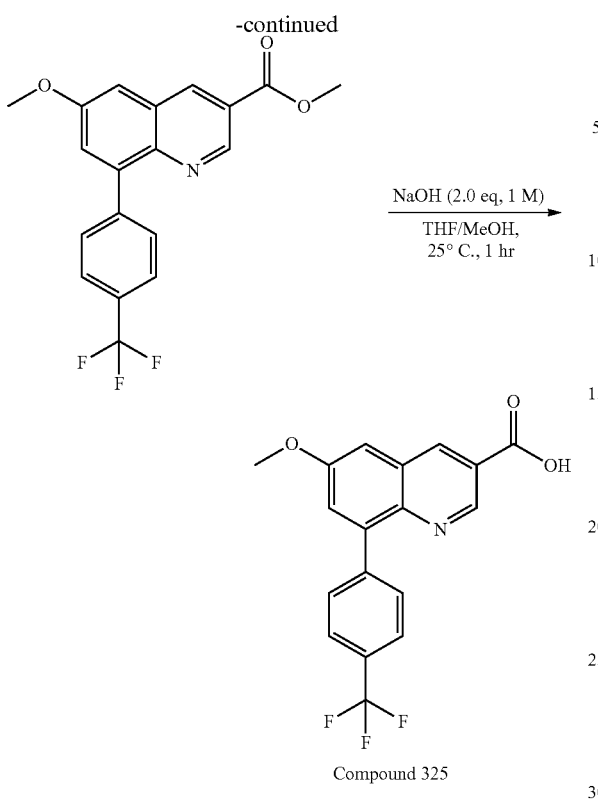

Compound 325

Step 1: methyl 6-methoxy-8-(4-(trifluoromethyl)phenyl)quinoline-3-carboxylate To a solution of methyl 8-bromo-6-methoxy-quinoline-3-carboxylate (300 mg, 1.01 mmol, 1 eq), [4-(trifluoromethyl)phenyl]boronic acid (230.9 mg, 1.22 mmol, 1.2 eq) and Na$_2$CO$_3$ (214.7 mg, 2.03 mmol, 2 eq) in Dioxane (5 mL) and H$_2$O (1 mL) was added Pd(dppf)Cl$_2$ (37.0 mg, 50 umol, 0.05 eq). The reaction mixture was stirred at 90° C. for 3 hrs. LC-MS showed starting material was consumed completely and one main peak with desired MS was detected. The reaction mixture was concentrated under reduced pressure. The mixture was diluted with water (10 mL) and the resultant mixture was extracted with EA (20 mL*3). The combined organic layers were dried over Na$_2$SO$_4$, filtered and concentrated to dryness under reduced pressure. The residue was purified by column chromatography over silica gel to afford methyl 6-methoxy-8-(4-(trifluoromethyl)phenyl)quinoline-3-carboxylate (350 mg, 95.6% yield) as a white solid.

Step 2: 6-methoxy-8-(4-(trifluoromethyl)phenyl)quinoline-3-carboxylic Acid

To a solution of methyl 6-methoxy-8-[4-(trifluoromethyl)phenyl]quinoline-3-carboxylate (350 mg, 0.96 mmol, 1 eq) in THF (6 mL) and MeOH (2 mL) was added NaOH (1 M, 1.94 mL, 2 eq). The reaction mixture was stirred at 25° C. for 1 hr. TLC (Petroleum ether:Ethyl acetate=2:1, UV) showed the starting material was consumed. The reaction mixture was concentrated under reduced pressure, and then the residue was diluted with water (10 mL). The mixture was adjusted with HCl (1M) to pH=5, and then the suspension was filtered to obtain 6-methoxy-8-(4-(trifluoromethyl)phenyl)quinoline-3-carboxylic acid (306.07 mg, 89% yield) as a white solid. LCMS (ESI): RT=0.942 min, mass calcd for C$_{18}$H$_{12}$F$_3$NO$_3$ 347.08 m/z, found 348.0 [M+H]$^+$; $^1$H NMR (400 MHz, DMSO-d$_6$) δ 9.13 (d, J=2.3 Hz, 1H), 8.93 (d, J=2.0 Hz, 1H), 7.91-7.81 (m, 4H), 7.71 (d, J=2.9 Hz, 1H), 7.60 (d, J=2.9 Hz, 1H), 3.97 (s, 3H).

Example 277: 5,6-dichloro-8-(4-(trifluoromethyl)phenyl)quinoline-3-carboxylic Acid (Compound 326)

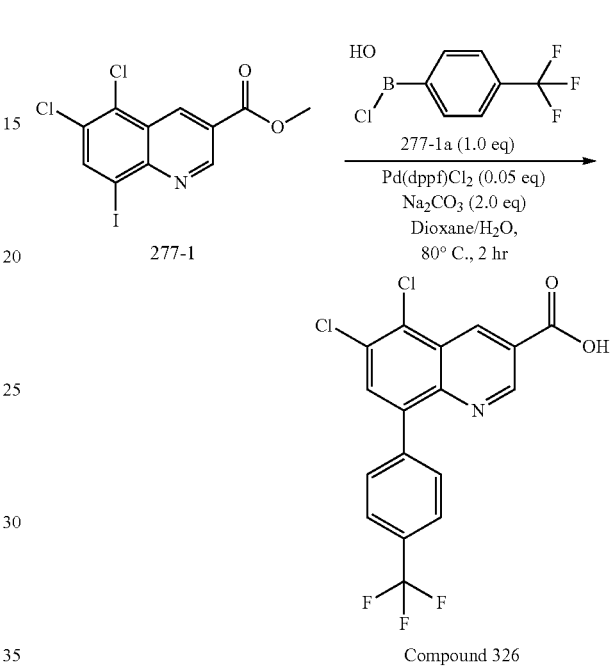

Compound 326

To a solution of compound 277-1 (20 mg, 52 umol, 1.0 eq), compound 277-1a (9.9 mg, 52 umol, 1.0 eq) and Na$_2$CO$_3$ (11 mg, 0.10 mmol, 2 eq) in Dioxane (1.5 mL) and H$_2$O (0.3 mL) was added Pd(dppf)Cl$_2$ (1.9 mg, 2.6 umol, 0.05 eq). The reaction mixture was stirred at 80° C. for 16 hours under N$_2$. LC-MS showed starting material was consumed completely and one main peak with desired MS was detected. The reaction mixture was adjusted with HCl (1M) to pH=5. The mixture was diluted with water (5 mL) and the resultant mixture was extracted with EA (20 mL*3). The combined organic layers were dried over Na$_2$SO$_4$, filtered and concentrated to dryness under reduced pressure. The residue was purified by prep-HPLC to give the title compound (3.56 mg, 16% yield) as a white solid. LCMS (ESI): RT=1.031 min, mass calcd. for C$_{17}$H$_8$Cl$_2$F$_3$NO$_2$ 384.99, m/z found 385.9 [M+H]$^+$; $^1$H NMR (400 MHz, DMSO-d$_6$) δ 9.37 (s, 1H), 9.13 (s, 1H), 8.23 (s, 1H), 7.93-7.86 (m, 4H).

Example 278: 6-ethoxy-8-(4-(trifluoromethyl)phenyl)quinoline-3-carboxylic Acid (Compound 327)

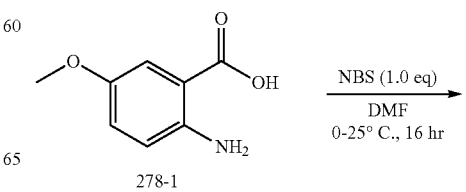

278-1

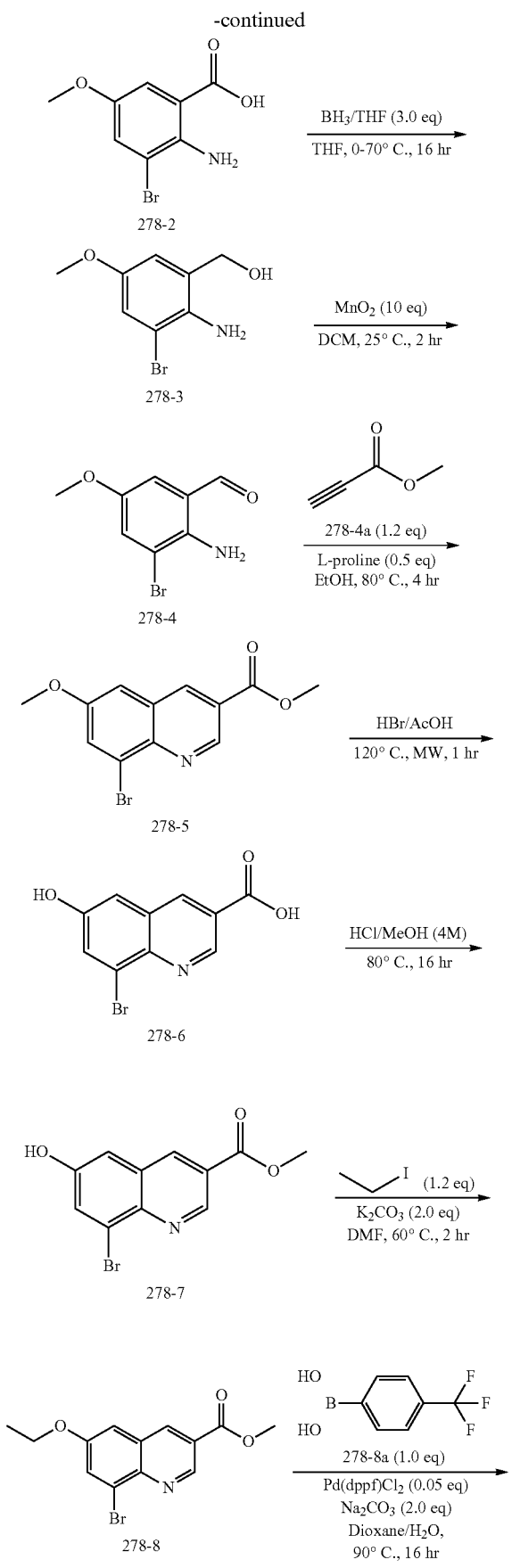

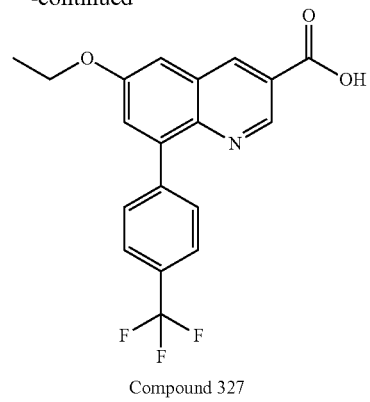

Compound 327

Step 1: 2-amino-3-bromo-5-methoxybenzoic Acid

A solution of compound 278-1 (10.0 g, 59.8 mmol, 1.0 eq) in DMF (200 mL) was added NBS (10.7 g, 59.8 mmol, 1.0 eq) at 0° C. The reaction mixture was stirred at 25° C. for 16 hours. LC-MS showed starting material was consumed completely and one main peak with desired MS was detected. The reaction mixture was concentrated under reduced pressure. The residue was poured into water and the suspension was filtered to give 278-2 (8.7 g, crude) as a deep purple solid. $^1$H NMR (400 MHz, DMSO-$d_6$) δ 7.39-7.36 (m, 1H), 7.34 (d, J=3.0 Hz, 1H), 3.69 (s, 3H).

Step 2: (2-amino-3-bromo-5-methoxyphenyl)methanol

To a solution of compound 278-2 (1.0 g, 4.1 mmol, 1.0 eq) in THF (2 mL) was added BH$_3$·THF (1 M, 12.2 mL, 3.0 eq) at 0° C. The reaction was stirred at 70° C. for 16 hours. TLC (Petroleum ether:Ethyl acetate=2:1) showed the starting material was consumed and one main spot was formed. After the reaction was cooled to 0° C., and then the reaction was quenched with MeOH (10 mL). The suspension was concentrated under reduced pressure. The mixture was diluted with water (30 mL) and the resultant mixture was extracted with EA (50 mL*3). The combined organic layers were dried over Na$_2$SO$_4$, filtered and concentrated to dryness under reduced pressure. The residue was purified by column chromatography over silica gel to give 278-3 (700 mg, 74% yield) as a brown solid.

Step 3: 2-amino-3-bromo-5-methoxybenzaldehyde

To a solution of compound 278-3 (2.2 g, 9.5 mmol, 1 eq) in DCM (40 mL) was added MnO$_2$ (8.2 g, 95 mmol, 10 eq). The reaction mixture was stirred at 25° C. for 2 hours. The reaction mixture was filtered and the filtrate was concentrated under reduced pressure. The residue was purified by column chromatography over silica gel to give 278-4 (1.7 g, 78% yield) as a yellow solid.

Step 4: methyl 8-bromo-6-methoxyquinoline-3-carboxylate

To a solution of compound 278-4 (5.3 g, 23 mmol, 1.0 eq) and compound 278-4a (2.3 g, 28 mmol, 2.30 mL, 1.2 eq) in EtOH (60 mL) was added L-proline (1.33 g, 11.5 mmol, 0.5 eq). The reaction mixture was stirred at 80° C. for 16 hours. The reaction was cooled to 25° C., and then water (30 mL)

was added. The suspension was vigorous stirred for 20 min and filtered to obtain the cake. The solid was collected and concentrated under high vacuum to give 278-5 (5.5 g, 80% yield) as a light yellow solid. $^1$H NMR (400 MHz, CDCl$_3$) δ 9.38 (d, J=1.8 Hz, 1H), 8.74 (d, J=1.8 Hz, 1H), 7.85 (d, J=2.6 Hz, 1H), 7.16 (d, J=2.6 Hz, 1H), 4.02 (s, 3H), 3.95 (s, 3H).

Step 5: 8-bromo-6-hydroxyquinoline-3-carboxylic Acid

Compound 278-5 (500 mg, 1.69 mmol, 1.0 eq) was taken up into a microwave tube in HBr/AcOH (4 mL). The sealed tube was heated at 120° C. for 1 hour under microwave. The reaction mixture was poured into ice-water (15 g). The resultant mixture was extracted with EA (30 mL*3). The combined organic layers were dried over Na$_2$SO$_4$, filtered and concentrated to dryness under reduced pressure to give 278-6 (450 mg, 76% yield) as a yellow solid.

Step 6: methyl 8-bromo-6-hydroxyquinoline-3-carboxylate

A mixture of compound 278-6 (450 mg, 1.68 mmol, 1.0 eq) in HCl/MeOH (10 mL) was stirred at 80° C. for 16 hours. The reaction mixture was concentrated under reduced pressure. The mixture was diluted with Sat. NaHCO$_3$ (30 mL) and the resultant mixture was extracted with EA (50 mL*3). The combined organic layers were dried over Na$_2$SO$_4$, filtered and concentrated to dryness under reduced pressure. The residue was purified by column chromatography over silica gel to give 278-7 (320 mg, 67% yield) as a light yellow solid. $^1$H NMR (400 MHz, DMSO-d$_6$) δ 10.63 (s, 1H), 9.16 (d, J=2.0 Hz, 1H), 8.88 (d, J=2.0 Hz, 1H), 7.84 (d, J=2.5 Hz, 1H), 7.44 (d, J=2.5 Hz, 1H), 3.95 (s, 3H).

Step 7: methyl 8-bromo-6-hydroxyquinoline-3-carboxylate

To a solution of compound 278-7 (50 mg, 0.18 mol, 1 eq) and K$_2$CO$_3$ (37 mg, 0.27 mol, 1.5 eq) in DMF (1 mL) was added EtI (33 mg, 0.21 mol, 17 uL, 1.2 eq). The reaction mixture was stirred at 60° C. for 2 hours. The reaction mixture was concentrated under reduced pressure. The mixture was diluted with water (10 mL) and the resultant mixture was extracted with EA (30 mL*3). The combined organic layers were dried over Na$_2$SO$_4$, filtered and concentrated to dryness under reduced pressure to give 278-8 (50 mg, crude) as a white solid.

Step 8: 6-ethoxy-8-(4-(trifluoromethyl)phenyl)quinoline-3-carboxylic acid

To a solution of compound 278-8 (50 mg, 0.16 mmol, 1.0 eq), compound 278-8a (37 mg, 0.19 mmol, 1.2 eq) and Na$_2$CO$_3$ (34 mg, 0.32 mmol, 2.0 eq) in Dioxane (2 mL) and H$_2$O (0.4 mL) was added Pd(dppf)Cl$_2$ (5.9 mg, 8.1 umol, 0.05 eq). The reaction mixture was stirred at 90° C. for 16 hours. The reaction mixture was concentrated under reduced pressure. The mixture was diluted with water (10 mL) and the resultant mixture was extracted with EA (20 mL*3). The combined organic layers were dried over Na$_2$SO$_4$, filtered and concentrated to dryness under reduced pressure. The residue was purified by prep-HPLC to give the title compound (26.61 mg, 41.5% yield, HCl) as a gray solid. LCMS (ESI): RT=0.863 min, mass calcd. for C$_{19}$H$_{14}$F$_3$NO$_3$ 361.09, m/z found 361.9 [M+H]$^+$; $^1$H NMR (500 MHz, DMSO-d$_6$) δ 9.12 (d, J=2.0 Hz, 1H), 8.92 (d, J=2.0 Hz, 1H), 7.91-7.82 (m, 4H), 7.70 (d, J=2.8 Hz, 1H), 7.58 (d, J=2.8 Hz, 1H), 4.28-4.22 (m, 2H), 1.44 (t, J=6.9 Hz, 3H).

Example 279: 5,6-difluoro-8-(4-(trifluoromethyl) phenyl)quinoline-3-carboxylic Acid (Compound 328)

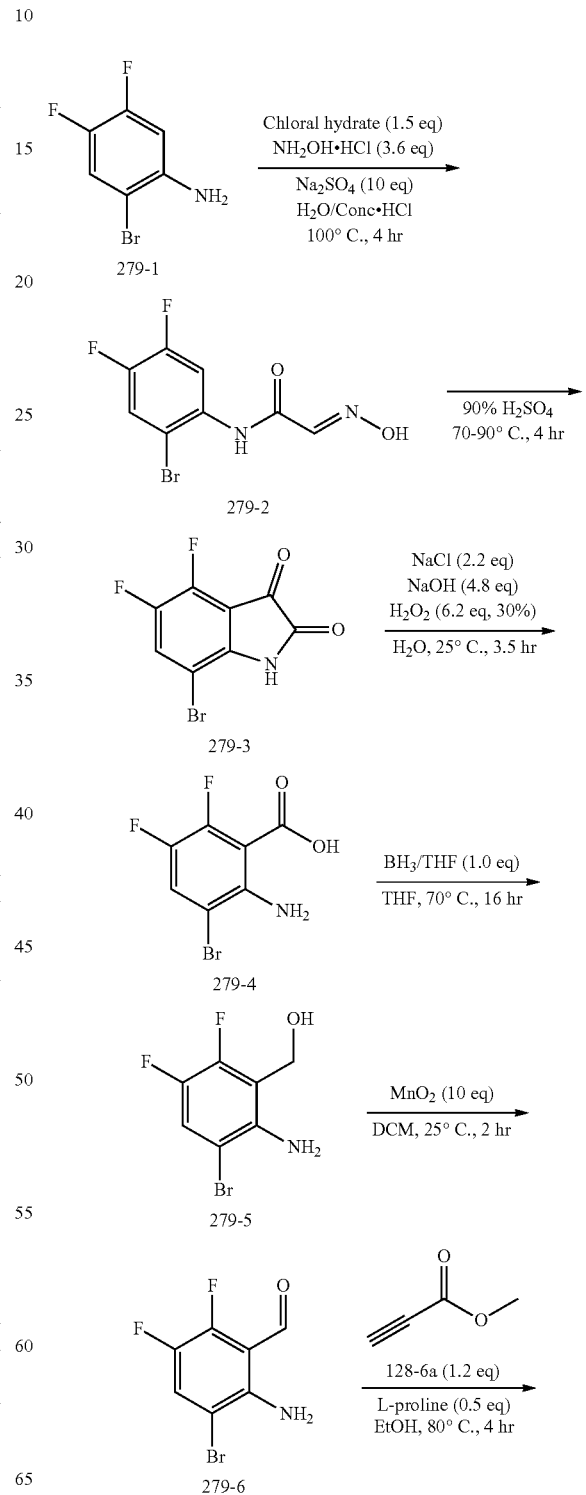

-continued

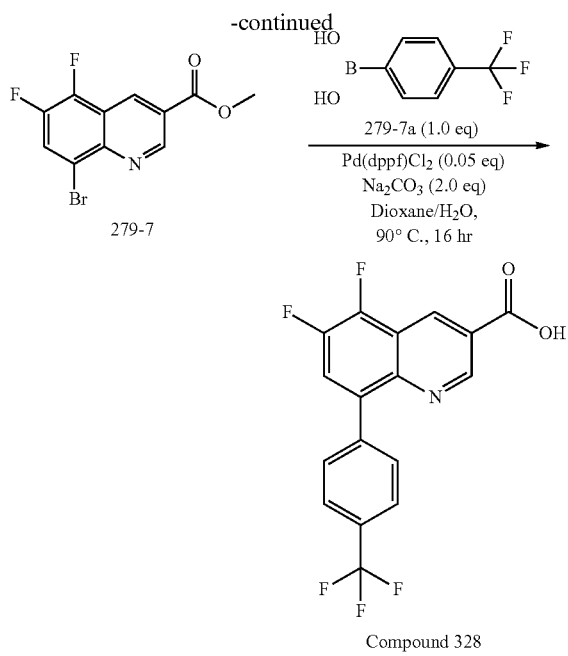

Compound 328

Step 1: N-(2-bromo-4,5-difluorophenyl)-2-(hydroxyimino)acetamide

To a solution of compound 279-1 (1.0 g, 4.8 mmol, 1.0 eq) in H$_2$O (21 mL) were added conc.HCl (0.16 mL), Na$_2$SO$_4$ (6.83 g, 48.1 mmol, 10 eq), chloral hydrate (1.19 g, 7.21 mmol, 1.5 eq) and hydroxylamine hydrochloride (1.2 g, 17.3 mmol, 3.6 eq). The reaction mixture was stirred at 100° C. for 4 hours. The reaction mixture was extracted with EA (50 mL*3). The combined organic layers were dried over Na$_2$SO$_4$, filtered and concentrated to dryness under reduced pressure. The residue was purified by column chromatography over silica gel to give 279-2 (700 mg, 52% yield) as a white solid. $^1$H NMR (400 MHz, CDCl$_3$) δ 8.88 (s, 1H), 8.45 (dd, J=7.9, 12.4 Hz, 1H), 8.18 (s, 1H), 7.61 (s, 1H), 7.43 (dd, J=7.9, 9.2 Hz, 1H).

Step 2: 7-bromo-4,5-difluoroindoline-2,3-dione

Compound 279-2 (700 mg, 2.51 mmol, 1.0 eq) was added to 90% aqueous H$_2$SO$_4$ (7 mL) by portion at 70° C. The mixture was stirred at 90° C. for 4 hours. The mixture was diluted with water (30 mL) and the resultant mixture was extracted with EA (50 mL*3). The combined organic layers were dried over Na$_2$SO$_4$, filtered and concentrated to dryness under reduced pressure. The residue was purified by column chromatography over silica gel to give 279-3 (220 mg, 33% yield) as a brown solid. $^1$H NMR (400 MHz, DMSO-d$_6$) δ 11.52 (s, 1H), 8.11 (dd, J=7.5, 10.6 Hz, 1H).

Step 3: 2-amino-3-bromo-5,6-difluorobenzoic Acid

A solution of compound 279-3 (220 mg, 0.840 mmol, 1.0 eq), NaCl (108 mg, 1.85 mmol, 2.2 eq) and NaOH (80 mg, 2.0 mmol, 2.4 eq) in H$_2$O (10 mL) was stirred at 25° C. for 0.5 hour. H$_2$O$_2$ (0.5 mL, 5.20 mmol, 30% solution, 6.2 eq) was added slowly, followed by an aqueous NaOH solution (80 mg NaOH in 10 mL of H$_2$O). The reaction mixture was stirred at 25° C. for 3 hours. The suspension was adjusted with HCl (1M) to pH=3, and extracted with EA (30 mL*3). The combined organic layers were dried over Na$_2$SO$_4$, filtered and concentrated to dryness under reduced pressure to give 279-4 (130 mg, 57% yield) as a brown solid. $^1$H NMR (400 MHz, DMSO-d$_6$) δ 7.90 (dd, J=8.2, 9.9 Hz, 1H).

Step 4: (2-amino-3-bromo-5,6-difluorophenyl)methanol

To a solution of compound 279-4 (100 mg, 0.39 mmol, 1.0 eq) in THF (3 mL) was added BH$_3$·THF (1 M, 0.40 uL, 1.0 eq) at 25° C. The reaction mixture was stirred 70° C. for 16 hours. The reaction mixture was cooled to 0° C., and then MeOH (5 mL) was added. The mixture was stirred for 10 min, and then the reaction mixture was concentrated under reduced pressure. The residue was purified by column chromatography over silica gel to give 279-5 (50 mg, 53% yield) as a yellow solid. $^1$H NMR (40.0 MHz, CDCl$_3$) δ 7.21-7.16 (m, 1H), 4.74 (d, J=2.1 Hz, 2H).

Step 5: 2-amino-3-bromo-5,6-difluorobenzaldehyde

A mixture of compound 279-5 (50 mg, 0.21 mmol, 1.0 eq) and MnO$_2$ (183 mg, 2.10 mmol, 10.0 eq) in DCM (1 mL) was stirred at 25° C. for 2 hours. The reaction mixture was filtered, and then the filtrate was concentrated under reduce pressure to give 279-6 (35 mg, 70% yield) as a yellow solid. $^1$H NMR (400 MHz, CDCl$_3$) δ 10.19 (s, 1H), 7.47 (dd, J=8.3, 9.3 Hz, 1H), 6.64 (br s, 2H)

Step 6: methyl 8-bromo-5,6-difluoroquinoline-3-carboxylate

A mixture of compound 279-6 (35 mg, 0.15 mmol, 1.0 eq), compound 279-6a (15 mg, 0.18 mmol, 1.2 eq) and L-proline (8.5 mg, 74 umol, 0.5 eq) in EtOH (2 mL) was stirred at 80° C. for 4 hours. The reaction mixture was concentrated under reduced pressure. The residue was purified by column chromatography over silica gel to give 279-7 (32 mg, 71% yield) as a yellow solid. $^1$H NMR (400 MHz, CDCl$_3$) δ 9.56 (d, J=1.8 Hz, 1H), 9.14 (d, J=2.0 Hz, 1H), 8.09 (dd, J=7.8, 9.8 Hz, 1H), 4.07 (s, 3H).

Step 7: 5,6-difluoro-8-(4-(trifluoromethyl)phenyl)quinoline-3-carboxylic acid To a solution of compound 279-7 (30 mg, 99 umol, 1.0 eq), compound 279-7a (19 mg, 99 umol, 1.0 eq) and Na$_2$CO$_3$ (21 mg, 0.20 mmol, 2.0 eq) in Dioxane (2 mL) and H$_2$O (0.4 mL) was added Pd(dppf)Cl$_2$ (3.6 mg, 5.0 umol, 0.05 eq). The reaction mixture was stirred at 90° C. for 16 hours. LC-MS showed starting material was remained and one peak with desired MS was detected. The reaction mixture was concentrated under reduced pressure. The residue was adjusted with HCl (1M) to pH=6 and extracted with EA (20 mL*3). The combined organic layers were dried over Na$_2$SO$_4$, filtered and concentrated under vacuum. The residue was purified by prep-HPLC to give the title compound (4.50 mg, 11% yield) as a light yellow solid. LCMS (ESI): RT=0.974 min, mass calcd. for C$_{17}$H$_8$F$_5$NO$_2$ 353.05, m/z found 354.0 [M+H]$^+$; $^1$H NMR (400 MHz, DMSO-d$_6$) δ 13.90 (br s, 1H), 9.33 (d, J=1.8 Hz, 1H), 9.02 (d, J=2.0 Hz, 1H), 8.22 (dd, J=8.5, 11.3 Hz, 1H), 7.89 (s, 4H).

Example 280: 5-[4-(pentafluoro-sulfanyl)phenyl]naphthalene-2-carboxylic Acid (Compound 329)

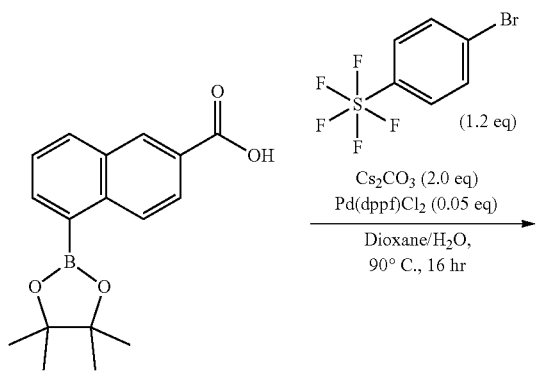

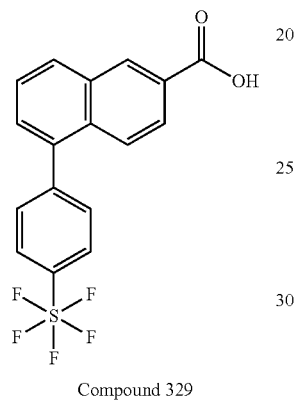

Compound 329

To a mixture of 5-(4,4,5,5-tetramethyl-1,3,2-dioxaborolan-2-yl)naphthalene-2-carboxylic acid (43.94 mg, 0.14 mmol, 1 eq) and (4-bromophenyl)-pentafluoro-sulfane (50.06 mg, 0.17 mmol, 1.2 eq) in dioxane (3 mL) was added Pd(dppf)Cl$_2$ (5.39 mg, 7.3 umol, 0.05 eq), KOAc (43.40 mg, 0.44 mmol, 3 eq) under N$_2$. The mixture was stirred for 10 hrs at 100° C. LCMS showed the reaction was complete. The mixture was quenched by H$_2$O (30 mL), and the mixture was extracted with EA (20 mL*3). The combined organic phase was washed with brine (20 mL*3), dried with anhydrous Na$_2$SO$_4$, filtered and concentrated in vacuum. The residue was purified by pre-HPLC. Compound 5-[4-(pentafluoro-sulfanyl)phenyl]naphthalene-2-carboxylic acid (11.48 mg, 29.1 umol, 19.7% yield) was obtained as a white solid. LCMS (ESI): RT=0.882 min, mass calc. for: C$_{17}$H$_{11}$F$_5$O$_2$S 374.33, m/z found 318.1; $^1$H NMR (400 MHz, DMSO-d6) δ 13.67-12.55 (m, 1H), 8.72 (s, 1H), 8.25 (d, J=8.0 Hz, 1H), 8.09 (d, J=8.5 Hz, 2H), 8.00 (dd, J=1.4, 8.9 Hz, 1H), 7.85 (d, J=9.0 Hz, 1H), 7.79-7.64 (m, 4H).

Example 281: 5-[4-(trifluoromethyl)phenyl]naphthalene-2-carboxylic Acid (Compound 330)

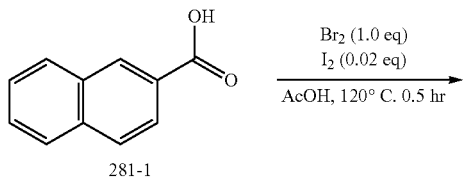

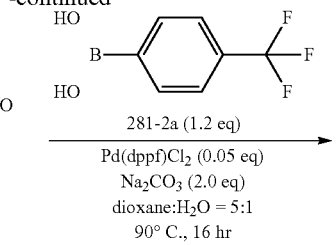

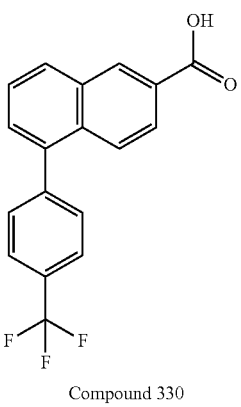

Compound 330

Step 1: 5-bromonaphthalene-2-carboxylic Acid

To a solution of compound 281-1 (2.0 g, 11.6 mmol, 1.0 eq) in AcOH (10 mL) was added Br$_2$ (1.9 g, 11.6 mmol, 1.0 eq) and I$_2$ (59 mg, 0.23 mmol, 0.02 eq). The mixture was stirred at 120° C. for 0.5 hr. The reaction mixture was cooled to room temperature to give a white solid. The mixture was isolated by filtration, washed with acetic acid (40 mL*3) and then H$_2$O (30 mL*3) to obtain compound 281-2 (2.5 g, crude) as a white solid. $^1$H NMR (400 MHz, DMSO-d$_6$) δ 8.66 (d, J=1.25 Hz, 1H), 8.20 (m, 2H), 8.13 (dd, J=8.78, 1.76 Hz, 1H), 8.01 (m, 1H), 7.53 (m, 1H).

Step 2: 5-[4-(trifluoromethyl)phenyl]naphthalene-2-carboxylic Acid

To a solution of compound 281-2 (200 mg, 0.80 mmol, 1.0 eq) compound 281-2a (182 mg, 0.96 mmol, 1.2 eq) and Na$_2$CO$_3$ (253 mg, 2.39 mmol, 3.0 eq) in dioxane (3 mL) and H$_2$O (0.6 mL) was added Pd(dppf)Cl$_2$ (29 mg, 40 umol, 0.05 eq). The mixture was stirred at 90° C. for 16 hr. The mixture was diluted with water (15 mL) and the resultant mixture was extracted with EA (40 mL*3). The combined organic layers were dried over Na$_2$SO$_4$, filtered and concentrated to dryness under reduced pressure. The residue was purified by prep-HPLC to obtain the title compound (11.08 mg, 4.4% yield) as a white solid. $^1$H NMR (400 MHz, DMSO-d$_6$) δ 8.63 (s, 1H), 8.17 (d, J=8.28 Hz, 1H), 8.06 (m, 1H), 8.00 (dd, J=8.78, 1.51 Hz, 1H), 7.92 (d, J=8.28 Hz, 2H), 7.76 (m, 3H), 7.67 (t, J=7.53 Hz, 1H), 7.58 (d, J=6.78 Hz, 1H).

Example 282: 5-(6-(trifluoromethyl)pyridin-3-yl)-2-naphthoic Acid (Compound 331)

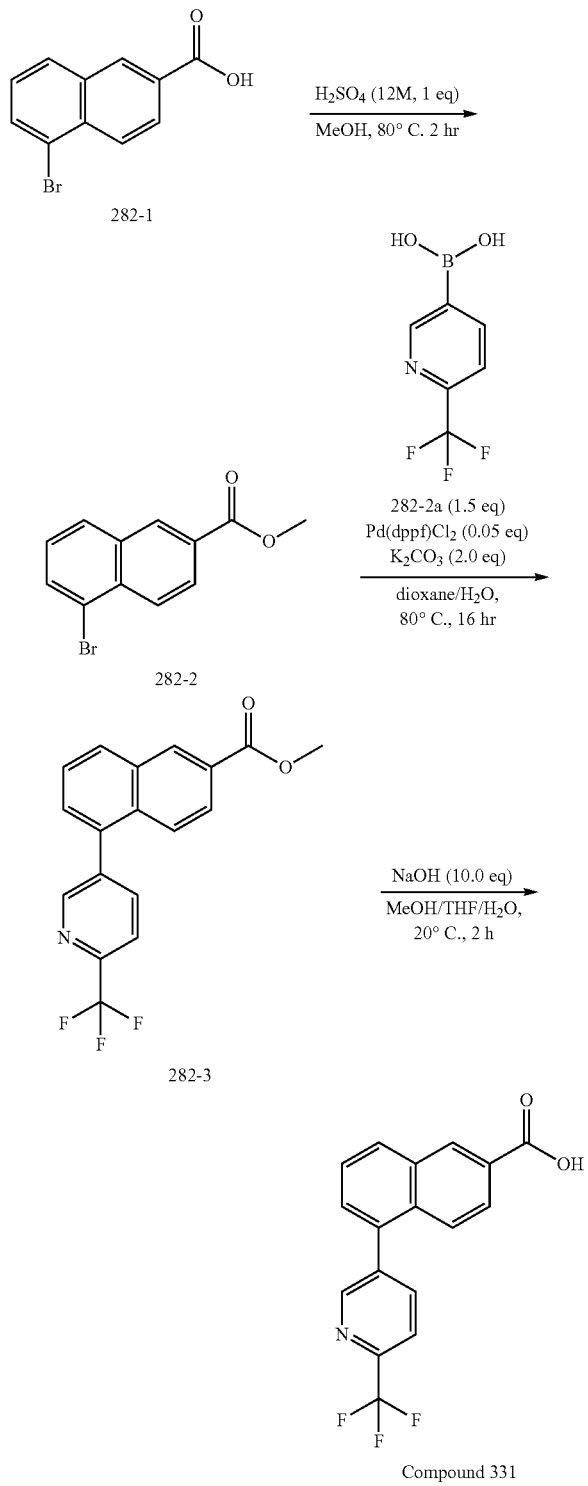

Compound 331

Step 1: Methyl 5-bromo-2-naphthoate

To a solution of compound 282-1 (1.8 g, 7.17 mmol, 1 eq) in MeOH (10 mL) was added $H_2SO_4$ (12 M, 0.3 mL, 0.5 eq). The mixture was stirred at 80° C. for 2 hr. TLC (PE/EA=5/1) indicated the starting material was consumed completely. The mixture was concentrated. The residue was diluted with $H_2O$ (20 mL). The mixture was extracted with EA (30 mL*3). The organic layer was dried over $Na_2SO_4$, filtered and concentrated to give compound 282-2 (1.8 g, crude) as a white solid.

Step 2: Methyl 5-(6-(trifluoromethyl)pyridin-3-yl)-2-naphthoate

To a solution of compound 282-2 (300.0 mg, 1.13 mmol, 1 eq), compound 282-2a (324.1 mg, 1.70 mmol, 1.5 eq) and $K_2CO_3$ (312.8 mg, 2.26 mmol, 2 eq) in dioxane (4 mL) and $H_2O$ (1 mL) was added Pd(dppf)$Cl_2$ (41.4 mg, 56.6 umol, 0.05 eq). The mixture was degassed and purged with $N_2$ for 3 times, then the mixture was stirred at 80° C. for 16 hr under $N_2$. TLC (PE/EA=10/1) showed new spot formed. The mixture was diluted with $H_2O$ (10 mL). The mixture was extracted with EA (20 mL*3). The organic layer was dried over $Na_2SO_4$, filtered and concentrated. The residue was purified by flash silica gel chromatography to give compound 282-3 (290.0 mg, 0.86 mmol, 75.8% yield) as a white solid.

Step 3: 5-(6-(trifluoromethyl)pyridin-3-yl)-2-naphthoic Acid

To a solution of compound 282-3 (290.0 mg, 0.86 mmol, 1 eq) in MeOH (3 mL) and THF (1.5 mL) was added NaOH (350.1 mg, 8.75 mmol, 10 eq) in H2O (1.5 mL). The mixture was stirred at 20° C. for 1 hr. LCMS showed desired product formed. TLC (PE/EA=10/1) indicated the starting material was consumed completely. The mixture was concentrated. 1N HCl was added to the residue until pH=6-7. The mixture was extracted with EA (15 mL*3). The organic layer was dried over $Na_2SO_4$, filtered and concentrated to give the title compound (250.0 mg, 0.79 Mmol, 90.0% yield) as a white solid. LCMS (ESI): RT=0.814 min, mass calc. for $C_{17}H_{10}F_3NO_2$ 317.07, m/z found 317.9 [M+H]$^+$; $^1$H NMR (400 MHz, DMSO-d$_6$) δ 8.93 (d, J=1.8 Hz, 1H), 8.74 (d, J=1.5 Hz, 1H), 8.32-8.25 (m, 2H), 8.10 (d, J=8.0 Hz, 1H), 8.02 (dd, J=1.8, 8.8 Hz, 1H), 7.83 (d, J=8.8 Hz, 1H), 7.78-7.70 (m, 2H).

Example 283: 5-[5-(trifluoromethyl)-2-thienyl]naphthalene-2-carboxylic acid (Compound 332)

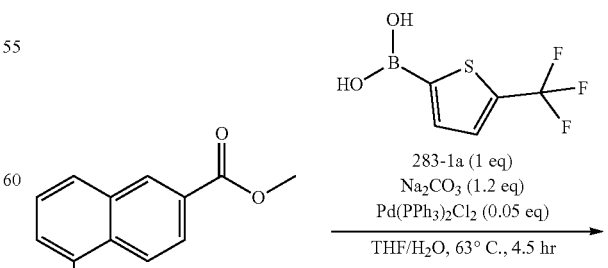

-continued

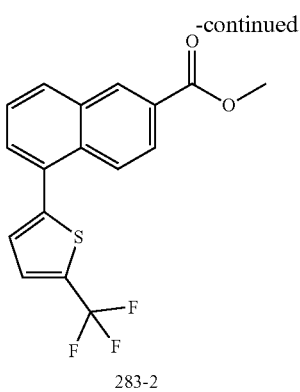

283-2

NaOH (10 eq)
MeOH/THF/H₂O,
20° C., 1 h

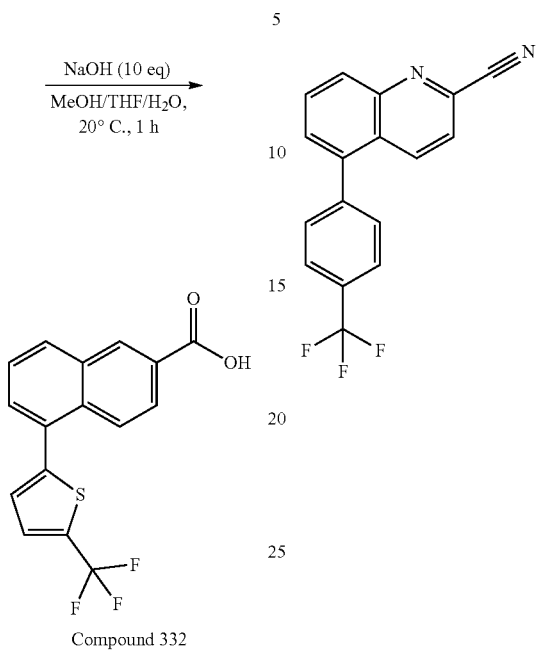

Compound 332

Example 284: 5-(4-(trifluoromethyl)phenyl)quinoline-2-carboxylic Acid (Compound 333)

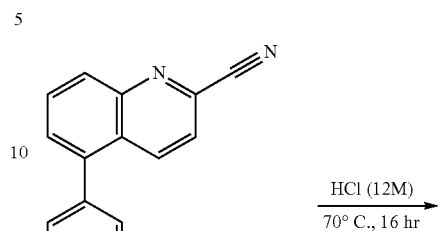

HCl (12M)
70° C., 16 hr

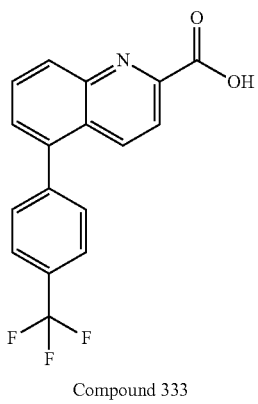

Compound 333

Step 1: methyl 5-[5-(trifluoromethyl)-2-thienyl]naphthalene-2-carboxylate

To a solution of 283-1 (100.0 mg, 0.38 mmol, 1 eq) and 283-1a (73.9 mg, 0.38 mmol, 1 eq) in THF (2 mL) and H₂O (0.5 mL) were added Na₂CO₃ (48.0 mg, 0.45 mmol, 1.2 eq) and Pd(PPh₃)₂Cl₂ (13.2 mg, 18.9 umol, 0.05 eq). The mixture was degassed under vacuum and purged with N₂ 3 times. The mixture was stirred at 63° C. for 4.5 hours. LCMS did not detect desired compound. TLC (PE/EA=10/1, UV) showed new spots formed. The mixture was diluted with H₂O (10 mL), extracted with EA (20 mL*3). The combined organic layer was washed with brine (10 mL), dried over Na₂SO₄, filtered and concentrated. The residue was purified by flash silica gel chromatography to give 283-2 (100.0 mg, 0.28 mmol, 74.9% yield) as a white solid.

Step 2: 5-[5-(trifluoromethyl)-2-thienyl]naphthalene-2-carboxylic Acid

To a mixture of 283-2 (100.0 mg, 0.30 mmol, 1 eq) in MeOH (2 mL), THF (0.7 mL) and H₂O (0.7 mL) was added NaOH (118.9 mg, 2.97 mmol, 10 eq). The mixture was stirred at 20° C. for 1 h. TLC (PE/EA=5/1, UV) showed starting material was consumed completely. The mixture was concentrated. The residue was diluted with H₂O (10 mL) and adjusted PH=6-7 with 1N HCl. The mixture was extracted with EA (20 mL*3). The combined organic layers were washed with brine (15 mL), dried over Na₂SO₄, filtered and concentrated under reduced pressure to give the title compound (90 mg, crude) was obtained as white solid. LCMS (ESI): RT=2.788-2.921 min, mass calc. for $C_{16}H_9F_3O_2S$ 322.03, m/z found 321.02 [M−H]⁻; ¹H NMR (400 MHz, CDCl₃) δ 8.78 (d, J=1.3 Hz, 1H), 8.24-8.13 (m, 2H), 8.07 (d, J=8.0 Hz, 1H), 7.71 (dd, J=1.1, 7.2 Hz, 1H), 7.66-7.58 (m, 1H), 7.56-7.52 (m, 1H), 7.24-7.18 (m, 1H).

A mixture of compound 5-(4-(trifluoromethyl)phenyl)quinoline-2-carbonitrile (30.0 mg, 0.10 mmol, 1.0 eq) in conc. HCl (1 mL, 12M) was stirred at 70° C. for 16 hours. LC-MS showed starting material was consumed completely and one main peak with desired MS was detected. The reaction mixture was cooled to 25° C., and then the suspension was filtered to give a residue as a white solid. The residue was purified by prep-HPLC to give the title compound (11.43 mg, 31.8% yield) as a yellow solid. LCMS (ESI): RT=0.887 min, mass calcd. for $C_{17}H_{10}F_3NO_2$ 417.26, m/z found 418.0 [M+H]⁺; ¹H NMR (400 MHz, DMSO-d₆) δ 8.35 (d, J=8.8 Hz, 1H), 8.26 (d, J=8.5 Hz, 1H), 8.12 (d, J=8.8 Hz, 1H), 8.03-7.90 (m, 3H), 7.85-7.72 (m, 3H).

Example 285: 5-(4-(trifluoromethyl)phenyl)quinoxaline-2-carboxylic Acid (Compound 334)

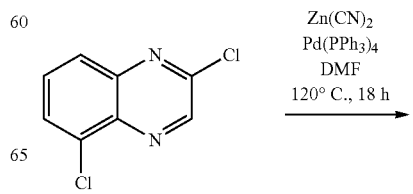

Zn(CN)₂
Pd(PPh₃)₄
DMF
120° C., 18 h

713

-continued

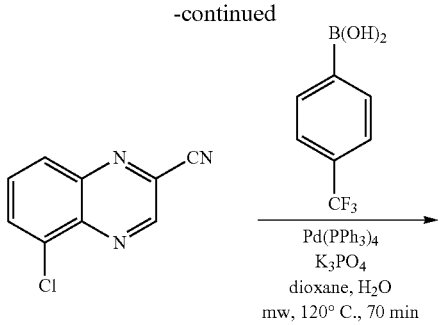

Step 1: 5-chloroquinoxaline-2-carbonitrile 2,5-Dichloroquinoxaline (1 g, 5 mmol, 1 equiv.), $Zn(CN)_2$ (294 mg, 2.5 mmol, 0.5 equiv.), $Pd(PPh_3)_4$ (578 mg, 0.5 mmol, 0.1 equiv.), and DMF (10 mL, 0.5M) were thoroughly purged with $N_2$ for 10 min. The reaction mixture was heated at 120° C. for 18 hr, until complete consumption of the starting material by LCMS. The mixture was carefully added to 60 mL rapidly stirring water and the resultant solid was filtered and dried to give 5-chloroquinoxaline-2-carbonitrile (850 mg, 90% yield) as a colorless solid. LCMS calcd: 190 ($[M+H]^+$), m/z found: 190.

Step 2: 5-(4-(trifluoromethyl)phenyl)quinoxaline-2-carboxylic Acid

5-Chloroquinoxaline-2-carbonitrile (100 mg, 0.53 mmol, 1 equiv.), (4-(trifluoromethyl)phenyl)boronic acid (120 mg, 0.63 mmol, 1.2 equiv.), $K_3PO_4$ (281 mg, 1.33 mmol, 2.5 equiv.), $Pd(PPh_3)_4$ (61 mg, 0.05 mmol, 0.1 equiv.), and 4:1 dioxane/$H_2O$ (2 mL:0.5 mL, 0.2M) were thoroughly purged with $N_2$ for 10 min. The reaction mixture was sealed in a microwave vessel and irradiated at 120° C. for 70 min. The mixture was cooled to rt, diluted with EtOAc, carefully neutralized with 1N HCl(aq), and separated. The organic layer was washed with $H_2O$, brine, dried with $Na_2SO_4$, and concentrated. The residue was purified by FCC 0 to 10% MeOH in DCM gradient to give 5-(4-(trifluoromethyl)phenyl)quinoxaline-2-carboxylic acid (25 mg, 0.08 mmol, 15% yield). LCMS calcd: 319 ($[M+H]^+$), m/z found: 319.

714

Example 286: 1-hydroxy-5-(4-(trifluoromethyl)phenyl)-2-naphthoic Acid (Compound 335)

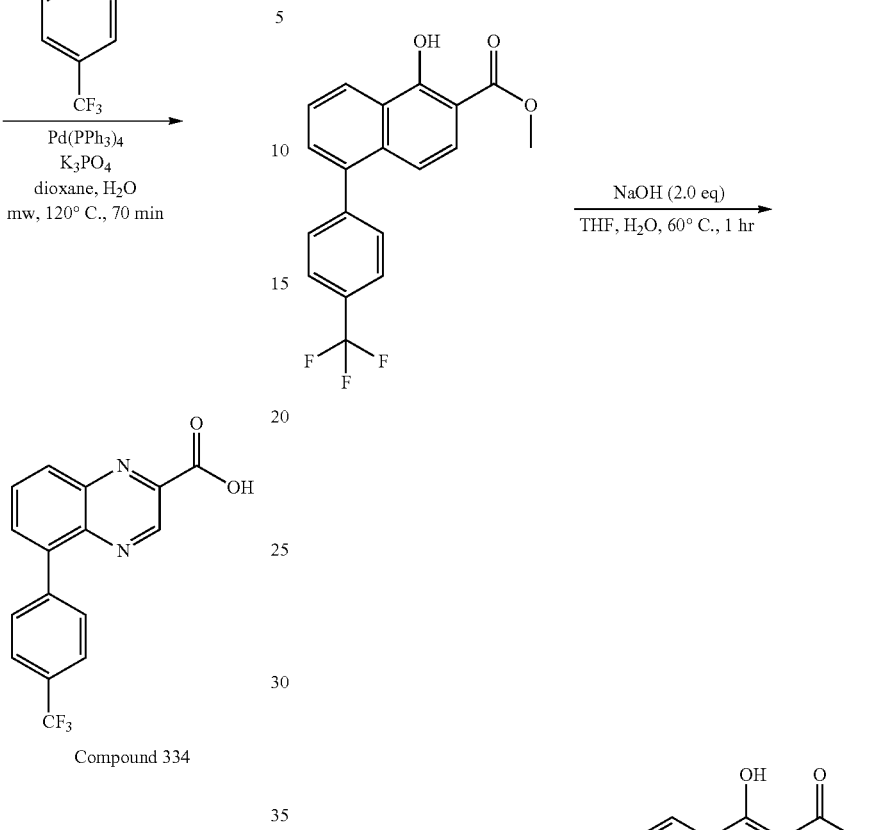

To a solution of methyl 1-hydroxy-5-[4-(trifluoromethyl)phenyl]naphthalene-2-carboxylate (30 mg, 86.6 umol, 1 eq) in THF (1 mL) and $H_2O$ (0.2 mL) was added NaOH (6.9 mg, 0.17 mmol, 2 eq). The mixture was stirred at 60° C. for 1 hr. LCMS showed the starting material was consumed. TLC (PE:EA=5:1) indicated the starting material was consumed and one new spot was detected. The HCl (1 M, 3 mL) was added to the solution to make the PH=5. The mixture was extracted with ethyl acetate (5 mL*3). The combined organic layers were washed with brine (8 mL*2), dried over anhydrous $Na_2SO_4$, filtered and concentrated in vacuum. The residue was purified by prep-HPLC. Compound 1-hydroxy-5-[4-(trifluoromethyl)phenyl]naphthalene-2-carboxylic acid (14.1 mg, 42.2 umol, 48.8% yield) was obtained as a white solid. $^1$H NMR (400 MHz, DMSO-$d_6$) δ=8.33 (d, J=8.0 Hz, 1H), 7.87 (d, J=8.0 Hz, 2H), 7.71 (dd, J=8.4, 15.7 Hz, 3H), 7.53-7.40 (m, 2H), 6.87 (d, J=8.8 Hz, 1H).

Example 287: 4-[4-(trifluoromethyl)phenyl]isoquinoline-7-carboxylic Acid (Compound 336)

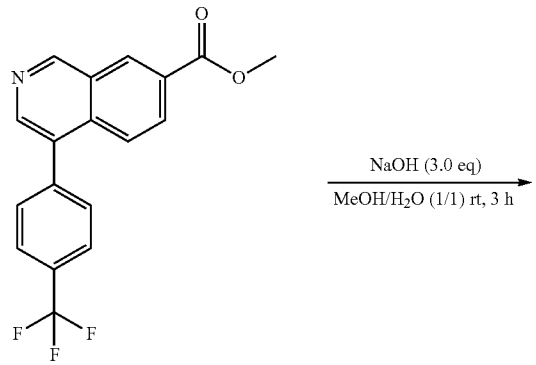

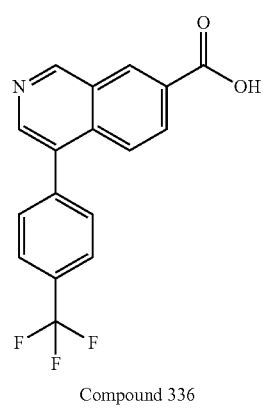

Compound 336

To a solution of methyl 4-(4-(trifluoromethyl)phenyl)isoquinoline-7-carboxylate (80 mg, 0.24 mmol, 1 eq) in MeOH (2 mL), THF (2 mL) and H$_2$O (2 mL) was added NaOH (28.9 mg, 0.72 mmol, 3 eq). The reaction was stirred at 25° C. for 2 hr. MeOH and THF was removed. The aqueous layer was adjusted pH to 5-6 with 1N aq.HCl and extracted with EA (2*15 mL). The organic layer was dried over Na$_2$SO$_4$ and concentrated. The residue was triturated with MeOH (15 mL), filtered and dried under reduced pressure to give the title compound LCMS (ESI): RT=0.710 min, mass calcd for C$_{17}$H$_{10}$F$_3$NO$_2$ 317.07, m/z found 317.9 [M+H]$^+$, $^1$H NMR (400 MHz, DMSO-d$_6$) δ 13.43 (s, 1H), 9.60 (s, 1H), 8.92 (s, 1H), 8.62 (s, 1H), 8.26 (dd, J=8.82, 1.56 Hz, 1H), 7.96 (d, J=8.13 Hz, 2H), 7.91 (d, J=8.76 Hz, 1H), 7.83 (d, J=8.00 Hz, 2H).

Example 288: 2-methyl-1-oxo-4-[4-(trifluoromethyl)phenyl]isoquinoline-7-carboxylic Acid (Compound 337)

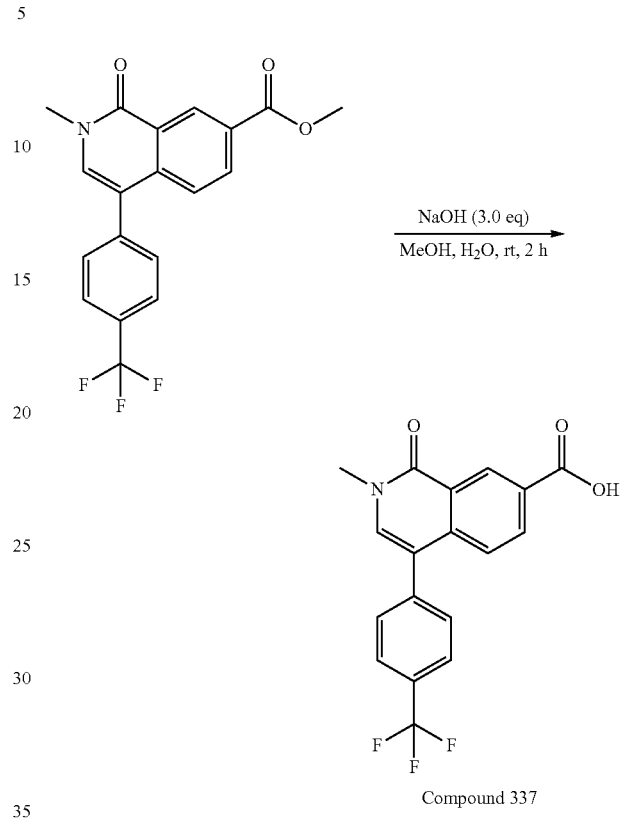

Compound 337

To a solution of methyl 2-methyl-1-oxo-4-(4-(trifluoromethyl)phenyl)-1,2-dihydroisoquinoline-7-carboxylate (20 mg, 55.3 umol, 1 eq) in MeOH (1.5 mL), THF (1.5 mL) and H$_2$O (2 mL) was added NaOH (6.6 mg, 0.16 mmol, 3 eq). The reaction was stirred at 25° C. for 1.5 hr. LCMS showed that 88% of desired product was detected. The reaction was removed the MeOH and THF. The residue was adjusted pH to 5 with 1N aq. HCl and extracted with EA (2*10 mL). The organic layer was dried over Na$_2$SO$_4$ and concentrated. The title compound was obtained. LCMS (ESI): RT=0.908 min, mass calc. for C$_{18}$H$_{12}$F$_3$NO$_3$ 347.08, m/z found 348.4 [M+1]$^+$. $^1$H NMR (400 MHz, CHLOROFORM-d) δ 9.12-9.28 (m, 1H), 8.19 (d, J=8.38 Hz, 1H), 7.69 (d, J=8.13 Hz, 2H), 747 (d, J=8.00 Hz, 3H), 7.12 (s, 1H), 3.62 (s, 3H).

II. Biological Evaluation

Example A1: YAP Reporter Assay

HEK293T cells stably transfected with 8XTBD luciferase reporter and pRLTK in 384-well plates were treated with the test compounds, starting from 3 μM (final concentration in assay plate), 1:3 dilution, and 10 points in quadruplicates. Post 24-hr incubation with compounds at 37° C. and 5% CO2, cells were lysed and 8XTBD-driven firefly luciferase and control TK-driven renilla luciferase activities were measured using Promega Dual-Luciferase Reporter Assay System.

Reagents: The reagents used for this study are: DMEM: Invitrogen #11960077, Dual-Glo Luciferase Assay System: Promega-E2980, Puromycin Dihydrochloride: Invitrogen-A1113803, 384-well plate: PerkinElmer-6007480, L-GLU- TAMINE: Invitrogen-25030164, Hygromycin B: Invitrogen-10687010, and Penicillin-Streptomycin: Merk-TMS-AB2-C Media: The media used for this assay were: Culture Medium: DMEM+1 ug/mL puromycin+200 ug/mL hygromycin (with 10% FBS+1 mM L-glutamine); and Assay Medium: DMEM (with 10% FBS+1 mM L-glutamine+1× P/S).

Cell Plating: The appropriate media was warmed at 37° C. by water bath: Culture Medium, Assay Medium, 1*D-PBS, 0.05% trypsin-EDTA. The cells were trypsinized after removing all media, then washed with 1*sterile D-PBS and then with 2 ml 0.05% trypsin-EDTA. The cells were then incubated at RT for one minute. Then 10 ml/75 cm2 flask Assay Medium was added to each flask. Using a 10 ml pipette, the cells were then gently resuspended in the media, until the clumps completely disappeared. The cells were then transferred into 50 ml centrifuge tubes and were centrifuged at 800 rpm for 5 mins. The medium was removed and the cells were resuspended with Assay Medium. An aliquot of cells was used to count the cell density (cells/ml). The cell suspension was then diluted with Assay Medium to a concentration of 6×104 cells/ml. 50 ul cells suspension was then plated to 384-well plate (PerkinElmer-6007480), 3×103 cells/well and the cells were incubated in an incubator at 37° C. 5% CO2.

Compound Treatment: In the afternoon (incubation of the plate with 3-4 hrs), the test compounds were added by Echo, starting from 3 uM (final concentration in the assay plate), 1:3 dilution, 10 points, quadruplicates. The plate was placed at 37° C. 5% CO2 incubator for 24 hrs.

Detection: The Dual-Glo Luciferase Reagent was prepared by transferring the contents of one bottle of Dual-Glo Luciferase Buffer to one bottle of Dual-Glo Luciferase Substrate to create the Dual-Glo Luciferase Reagent. Mixing was performed by inversion until the substrate was thoroughly dissolved. After mixing, the reagent was aliquoted into 15 ml tubes. In the afternoon (24 hrs post compound treatment), the DMEM+ medium in the 384 well plates were aspirated by Microplate Washer.

Measuring firefly luciferase activity: 20 ul Dual-Glo Luciferase Reagent was added to the 384-well plates. The plates were protected from light to prevent interference with the assay. The plates were shaken for 1 min followed centrifuging plates at 1000 rpm for 30 seconds. After waiting at least 10 minutes, the firefly luminescence was measured by Envision.

Measuring renilla luciferase activity: 20 ul Stop-Glo Reagent was added to the 384-well plates. The plates were shaken for 1 min and then centrifuged at 1000 rpm for 30 seconds. After waiting at least 10 minutes, the renilla luminescence was measured by Envision.

Compound $IC_{50}$ and maximum inhibition on the firefly luciferase and renilla luciferase activities were reported separately. $IC_{50}$ for firefly luciferase activity are shown in the Table 4 below.

TABLE 4

| Compound No. | Name | Firefly Luciferase $IC_{50}$ (μM) |
|---|---|---|
| 1 | N-isopropyl-5-(4-(trifluoromethyl)phenyl)-2-naphthamide | A |
| 2 | N-(methylsulfonyl)-5-(4-(trifluoromethyl)phenyl)-2-naphthamide | A |
| 3 | N-methyl-5-(4-(trifluoromethyl)phenyl)naphthalene-2-sulfonamide | A |
| 4 | N-isopropyl-8-(4-(trifluoromethyl)phenyl)quinoline-3-carboxamide | A |
| 5 | N-ethyl-5-(4-(trifluoromethyl)phenyl)naphthalene-2-sulfonamide | A |
| 6 | N-isopropyl-5-(4-(trifluoromethyl)phenyl)naphthalene-2-sulfonamide | B |
| 7 | N-isopropyl-4-[4-(trifluoromethyl)phenyl]quinoline-7-carboxamide | B |
| 8 | 8-bromo-N-isopropyl-5-(4-(trifluoromethyl)phenyl)-2-naphthamide | A |
| 9 | methyl 1-[4-(trifluoromethyl)phenyl]isoquinoline-6-carboxylate | B |
| 10 | methyl 1-chloro-4-[4-(trifluoromethyl)phenyl]isoquinoline-7-carboxylate | C |
| 11 | N-isopropyl-1-[4-(trifluoromethyl)phenyl]isoquinoline-6-carboxamide | A |
| 12 | tert-butyl (7-(isopropylcarbamoyl)-4-(4-(trifluoromethyl)phenyl)naphthalen-1-yl)carbamate | B |
| 13 | 8-chloro-N-isopropyl-5-(4-(trifluoromethyl)phenyl)-2-naphthamide | A |
| 14 | methyl 1-oxo-4-[4-(trifluoromethyl)phenyl]-2H-isoquinoline-7-carboxylate | A |
| 15 | methyl 2-methyl-1-oxo-4-[4-(trifluoromethyl)phenyl]isoquinoline-7-carboxylate | B |
| 16 | 8-amino-N-isopropyl-5-(4-(trifluoromethyl)phenyl)-2-naphthamide | A |
| 17 | 8-acetamido-N-isopropyl-5-(4-(trifluoromethyl)phenyl)-2-naphthamide | A |
| 18 | N-isopropyl-8-methylsulfanyl-5-[4-(trifluoromethyl)phenyl]naphthalene-2-carboxamide | A |
| 19 | N-isopropyl-8-methyl-5-[4-(trifluoromethyl)phenyl]naphthalene-2-carboxamide | A |
| 20 | 8-ethynyl-N-isopropyl-5-[4-(trifluoromethyl)phenyl]naphthalene-2-carboxamide | A |
| 21 | 8-ethyl-N-isopropyl-5-[4-(trifluoromethyl)phenyl]naphthalene-2-carboxamide | A |
| 22 | 8-cyclopropyl-N-isopropyl-5-(4-(trifluoromethyl)phenyl)-2-naphthamide | A |
| 23 | N-isopropyl-8-(methylsulfonamido)-5-(4-(trifluoromethyl)phenyl)-2-naphthamide | A |
| 24 | methyl 4-[4-(trifluoromethyl)phenyl]isoquinoline-7-carboxylate | A |
| 25 | N-isopropyl-4-[4-(trifluoromethyl)phenyl]isoquinoline-7-carboxamide | B |

TABLE 4-continued

| Compound No. | Name | Firefly Luciferase IC$_{50}$ (µM) |
|---|---|---|
| 26 | N-isopropyl-2-methyl-1-oxo-4-(4-(trifluoromethyl)phenyl)-1,2-dihydroisoquinoline-7-carboxamide | A |
| 27 | N-isopropyl-8-methylsulfinyl-5-[4-(trifluoromethyl)phenyl]naphthalene-2-carboxamide | B |
| 28 | N-isopropyl-8-methylsulfonyl-5-[4-(trifluoromethyl)phenyl]naphthalene-2-carboxamide | C |
| 29 | N-sulfamoyl-5-(4-(trifluoromethyl)phenyl)-2-naphthamide | B |
| 30 | N-isopropyl-8-(N-methylacetamido)-5-(4-(trifluoromethyl)phenyl)-2-naphthamide | B |
| 31 | 8-amino-7-bromo-N-isopropyl-5-(4-(trifluoromethyl)phenyl)-2-naphthamide | A |
| 32 | 7-bromo-N-isopropyl-5-[4-(trifluoromethyl)phenyl]naphthalene-2-carboxamide | A |
| 33 | 8-amino-7-chloro-N-isopropyl-5-(4-(trifluoromethyl)phenyl)-2-naphthamide | A |
| 34 | N-isopropyl-8-(N-methylmethylsulfonamido)-5-(4-(trifluoromethyl)phenyl)-2-naphthamide | C |
| 35 | N-isopropyl-5-[4-(trifluoromethyl)phenyl]benzo[e][1,2,3]benzoxadiazole-8-carboxamide | B |
| 36 | 7-chloro-N-isopropyl-5-(4-(trifluoromethyl)phenyl)-2-naphthamide | A |
| 37 | N-isopropyl-8-methoxy-5-[4-(trifluoromethyl)phenyl]naphthalene-2-carboxamide | A |
| 38 | 7-ethynyl-N-isopropyl-5-(4-(trifluoromethyl)phenyl)-2-naphthamide | A |
| 39 | N-isopropyl-7-methoxy-5-[4-(trifluoromethyl)phenyl]naphthalene-2-carboxamide | A |
| 40 | N-(2-(2-(2-acetamidoethoxy)ethoxy)ethyl)-5-(4-(trifluoromethyl)phenyl)-2-naphthamide | A |
| 41 | N-isopropyl-7-methyl-5-(4-(trifluoromethyl)phenyl)-2-naphthamide | A |
| 42 | N-isopropyl-7-(methylthio)-5-(4-(trifluoromethyl)phenyl)-2-naphthamide | A |
| 43 | 7-cyclopropyl-N-isopropyl-5-[4-(trifluoromethyl)phenyl]naphthalene-2-carboxamide | A |
| 44 | 7-amino-N-isopropyl-5-[4-(trifluoromethyl)phenyl]naphthalene-2-carboxamide | A |
| 45 | N-isopropyl-7-methylsulfinyl-5-[4-(trifluoromethyl)phenyl]naphthalene-2-carboxamide | B |
| 46 | N-isopropyl-7-methylsulfonyl-5-[4-(trifluoromethyl)phenyl]naphthalene-2-carboxamide | A |
| 47 | 7-ethyl-N-isopropyl-5-(4-(trifluoromethyl)phenyl)-2-naphthamide | A |
| 48 | 7-acetamido-N-isopropyl-5-(4-(trifluoromethyl)phenyl)-2-naphthamide | B |
| 49 | tert-butyl (2-(2-(2-(5-(4-(trifluoromethyl)phenyl)-2-naphthamido)ethoxy)ethoxy)ethyl)carbamate | B |
| 50 | N-(2-(2-(2-aminoethoxy)ethoxy)ethyl)-5-(4-(trifluoromethyl)phenyl)-2-naphthamide | B |
| 51 | N-isopropyl-7-(N-methylacetamido)-5-(4-(trifluoromethyl)phenyl)-2-naphthamide | B |
| 52 | N-isopropyl-7-(methylsulfonamido)-5-(4-(trifluoromethyl)phenyl)-2-naphthamide | A |
| 53 | N-isopropyl-7-(N-methylmethylsulfonamido)-5-(4-(trifluoromethyl)phenyl)-2-naphthamide | B |
| 54 | N-(2,2,2-trifluoroethyl)-5-(4-(trifluoromethyl)phenyl)-2-naphthamide | A |
| 55 | N-cyclopropyl-5-(4-(trifluoromethyl)phenyl)-2-naphthamide | A |
| 56 | N-(1,3-dihydroxypropan-2-yl)-5-(4-(trifluoromethyl)phenyl)-2-naphthamide | A |
| 57 | N-(2-(2-methoxyethoxy)ethyl)-5-(4-(trifluoromethyl)phenyl)-2-naphthamide | B |
| 58 | N-(2-methoxyethyl)-5-(4-(trifluoromethyl)phenyl)-2-naphthamide | A |
| 59 | (S)-N-(1-aminopropan-2-yl)-5-(4-(trifluoromethyl)phenyl)-2-naphthamide | B |
| 60 | (R)-N-(1-aminopropan-2-yl)-5-(4-(trifluoromethyl)phenyl)-2-naphthamide | A |
| 62 | N-(1,3-difluoropropan-2-yl)-5-(4-(trifluoromethyl)phenyl)-2-naphthamide | B |
| 63 | 2-amino-N-isopropyl-5-(4-(trifluoromethyl)phenyl)naphtho[1,2-d]thiazole-8-carboxamide | A |
| 64 | (S)-N-(1-(dimethylamino)propan-2-yl)-5-(4-(trifluoromethyl)phenyl)-2-naphthamide | C |
| 65 | (R)-N-(1-(dimethylamino)propan-2-yl)-5-(4-(trifluoromethyl)phenyl)-2-naphthamide | C |
| 66 | (S)-N-(1-(pyrrolidin-1-yl)propan-2-yl)-5-(4-(trifluoromethyl)phenyl)-2-naphthamide | B |

TABLE 4-continued

| Compound No. | Name | Firefly Luciferase IC$_{50}$ (μM) |
|---|---|---|
| 67 | (R)-N-(1-(pyrrolidin-1-yl)propan-2-yl)-5-(4-(trifluoromethyl)phenyl)-2-naphthamide | B |
| 68 | N-isopropyl-5-(4-(trifluoromethyl)phenyl)naphtho[1,2-d]thiazole-8-carboxamide | A |
| 70 | (R)-N-(1-morpholinopropan-2-yl)-5-(4-(trifluoromethyl)phenyl)-2-naphthamide | C |
| 71 | N-isopropyl-5-(4-(trifluoromethyl)phenyl)naphtho[1,2-d]oxazole-8-carboxamide | A |
| 72 | 5,6-Difluoro-N-isopropyl-8-(4-(trifluoromethyl)phenyl)quinoline-3-carboxamide | A |
| 73 | 5,6-Difluoro-N-(methylsulfonyl)-8-(4-(trifluoromethyl)phenyl)quinoline-3-carboxamide | B |
| 76 | N-(4-oxo-2,8,11-trioxa-5-azatridecan-13-yl)-5-(4-(trifluoromethyl)phenyl)-2-naphthamide | B |
| 77 | N-(5-oxo-2,9,12-trioxa-6-azatetradecan-14-yl)-5-(4-(trifluoromethyl)phenyl)-2-naphthamide | B |
| 78 | N-(ethylsulfonyl)-5-(4-(trifluoromethyl)phenyl)-2-naphthamide | B |
| 80 | 6-ethoxy-N-isopropyl-8-(4-(trifluoromethyl)phenyl)quinoline-3-carboxamide | A |
| 81 | 6-ethoxy-N-(methylsulfonyl)-8-(4-(trifluoromethyl)phenyl)quinoline-3-carboxamide | B |
| 84 | (S)-N-(1-hydroxypropan-2-yl)-5-(4-(trifluoromethyl)phenyl)-2-naphthamide | A |
| 85 | (R)-N-(1-hydroxypropan-2-yl)-5-(4-(trifluoromethyl)phenyl)-2-naphthamide | A |
| 86 | N-(2-hydroxyethyl)-5-(4-(trifluoromethyl)phenyl)-2-naphthamide | A |
| 87 | N-isopropyl-8-(trifluoromethyl)-5-(4-(trifluoromethyl)phenyl)-2-naphthamide | B |
| 88 | 8-iodo-N-isopropyl-5-(4-(trifluoromethyl)phenyl)-2-naphthamide | B |
| 89 | (S)-N-(1-methoxypropan-2-yl)-5-(4-(trifluoromethyl)phenyl)-2-naphthamide | A |
| 90 | (S)-N-(1-(pyridin-2-yl)ethyl)-5-(4-(trifluoromethyl)phenyl)-2-naphthamide | A |
| 91 | (R)-N-(1-(pyridin-2-yl)ethyl)-5-(4-(trifluoromethyl)phenyl)-2-naphthamide | B |
| 92 | N-(1-(methylamino)propan-2-yl)-5-(4-(trifluoromethyl)phenyl)-2-naphthamide | B |
| 93 | (R)-N-(1-methoxypropan-2-yl)-5-(4-(trifluoromethyl)phenyl)-2-naphthamide | A |
| 94 | 5,6-Dichloro-N-isopropyl-8-(4-(trifluoromethyl)phenyl)quinoline-3-carboxamide | A |
| 95 | 7-amino-8-hydroxy-N-isopropyl-5-(4-(trifluoromethyl)phenyl)-2-naphthamide | B |
| 96 | 5,6-dichloro-N-(methylsulfonyl)-8-(4-(trifluoromethyl)phenyl)quinoline-3-carboxamide | B |
| 97 | N-isopropyl-6-methoxy-8-[4-(trifluoromethyl)phenyl]quinoline-3-carboxamide | A |
| 98 | N-[(1R)-2-hydroxy-1-methyl-ethyl]-6-methoxy-8-[4-(trifluoromethyl)phenyl]quinoline-3-carboxamide | A |
| 99 | (R)-N-(1-hydroxypropan-2-yl)-8-(4-(trifluoromethyl)phenyl)quinoline-3-carboxamide | A |
| 100 | (R)-N-(1-methoxypropan-2-yl)-8-(4-(trifluoromethyl)phenyl)quinoline-3-carboxamide | B |
| 101 | (R)-N-(1-(pyridin-2-yl)ethyl)-8-(4-(trifluoromethyl)phenyl)quinoline-3-carboxamide | B |
| 102 | (S)-N-(1-methoxypropan-2-yl)-8-(4-(trifluoromethyl)phenyl)quinoline-3-carboxamide | A |
| 103 | (S)-N-(1-(pyridin-2-yl)ethyl)-8-(4-(trifluoromethyl)phenyl)quinoline-3-carboxamide | A |
| 104 | N-isopropyl-6-(trifluoromethoxy)-8-[4-(trifluoromethyl)phenyl]quinoline-3-carboxamide | A |
| 105 | N-[2-hydroxy-1-(2-pyridyl)ethyl]-6-methoxy-8-[4-(trifluoromethyl)phenyl]quinoline-3-carboxamide | A |
| 106 | 6-methoxy-N-[(1R)-1-(2-pyridyl)ethyl]-8-[4-(trifluoromethyl)phenyl]quinoline-3-carboxamide | B |
| 107 | 6-methoxy-N-[(1R)-2-methoxy-1-methyl-ethyl]-8-[4-(trifluoromethyl)phenyl]quinoline-3-carboxamide | A |
| 108 | 6-methoxy-N-[(1S)-1-(2-pyridyl)ethyl]-8-[4-(trifluoromethyl)phenyl]quinoline-3-carboxamide | A |
| 109 | 6-methoxy-N-[(1S)-2-methoxy-1-methyl-ethyl]-8-[4-(trifluoromethyl)phenyl]quinoline-3-carboxamide | A |
| 110 | N-(2-hydroxy-1-(pyridin-2-yl)ethyl)-5-(4-(trifluoromethyl)phenyl)-2-naphthamide | A |
| 111 | N-(prop-2-yn-1-yl)-5-(4-(trifluoromethyl)phenyl)-2-naphthamide | A |
| 112 | N-(but-3-yn-1-yl)-5-(4-(trifluoromethyl)phenyl)-2-naphthamide | A |
| 113 | N-(cyanomethyl)-5-(4-(trifluoromethyl)phenyl)-2-naphthamide | A |

TABLE 4-continued

| Compound No. | Name | Firefly Luciferase IC$_{50}$ (μM) |
|---|---|---|
| 114 | N-(2-cyanoethyl)-5-(4-(trifluoromethyl)phenyl)-2-naphthamide | A |
| 115 | N,N'-(disulfanediylbis(ethane-2,1-diyl))bis(5-(4-(trifluoromethyl)phenyl)-2-naphthamide) | C |
| 116 | 6-cyclopropoxy-N-isopropyl-8-(4-(trifluoromethyl)phenyl)quinoline-3-carboxamide | A |
| 121 | N-(1-phenylcyclopropyl)-5-[4-(trifluoromethyl)phenyl]naphthalene-2-carboxamide | A |
| 122 | 6-cyclopropoxy-N-(methylsulfonyl)-8-(4-(trifluoromethyl)phenyl)quinoline-3-carboxamide | B |
| 123 | N-(methylsulfonyl)-6-(trifluoromethoxy)-8-(4-(trifluoromethyl)phenyl)quinoline-3-carboxamide | C |
| 124 | N-(2-(methylamino)ethyl)-5-(4-(trifluoromethyl)phenyl)-2-naphthamide | B |
| 125 | N-(2-(N-methylcyanamido)ethyl)-5-(4-(trifluoromethyl)phenyl)-2-naphthamide | A |
| 126 | N-(3-(methylamino)propyl)-5-(4-(trifluoromethyl)phenyl)-2-naphthamide | B |
| 127 | N-(3-(N-methylcyanamido)propyl)-5-(4-(trifluoromethyl)phenyl)-2-naphthamide | B |
| 128 | (S)-N-(1-(6-aminopyridin-2-yl)ethyl)-5-(4-(trifluoromethyl)phenyl)-2-naphthamide | B |
| 129 | (R)-N-(1-(6-aminopyridin-2-yl)ethyl)-5-(4-(trifluoromethyl)phenyl)-2-naphthamide | A |
| 130 | N-[(1S)-1-(azetidin-3-yl)-2-hydroxy-ethyl]-5-[4-(trifluoromethyl)phenyl]naphthalene-2-carboxamide | C |
| 133 | (R)-N-(1-(1-(2-hydroxyethyl)azetidin-3-yl)ethyl)-5-(4-(trifluoromethyl)phenyl)-2-naphthamide | B |
| 137 | (R)-N-(1-(1-(2,2-difluoroethyl)azetidin-3-yl)ethyl)-5-(4-(trifluoromethyl)phenyl)-2-naphthamide | B |
| 140 | N-[(1S)-1-[1-(2-hydroxyethyl)azetidin-3-yl]ethyl]-5-[4-(trifluoromethyl)phenyl]naphthalene-2-carboxamide | B |
| 141 | (R)-N-(1-(3-hydroxyazetidin-3-yl)ethyl)-8-(4-(trifluoromethyl)phenyl)quinoline-3-carboxamide | C |
| 143 | N-[(1S)-1-(1-Isopropylazetidin-3-yl)ethyl]-5-[4-(trifluoromethyl)phenyl]naphthalene-2-carboxamide | C |
| 144 | (R)-N-(1-(1-(2-fluoroethyl)azetidin-3-yl)ethyl)-5-(4-(trifluoromethyl)phenyl)-2-naphthamide | B |
| 148 | N-[(1R)-1-(1-Ethylazetidin-3-yl)ethyl]-5-[4-(trifluoromethyl)phenyl]naphthalene-2-carboxamide | B |
| 149 | N-[(1S)-1-(1-Ethylazetidin-3-yl)ethyl]-5-[4-(trifluoromethyl)phenyl]naphthalene-2-carboxamide | B |
| 150 | N-[(1R)-1-(1-Ethylazetidin-3-yl)ethyl]-8-[4-(trifluoromethyl)phenyl]quinoline-3-carboxamide | C |
| 153 | N-[(1R)-1-(1-methylazetidin-3-yl)ethyl]-5-[4-(trifluoromethyl)phenyl]naphthalene-2-carboxamide | B |
| 155 | (S)-N-(1-(3-hydroxyazetidin-3-yl)ethyl)-5-(4-(trifluoromethyl)phenyl)-2-naphthamide | B |
| 156 | N-[(1R)-1-(1-methylazetidin-3-yl)ethyl]-8-[4-(trifluoromethyl)phenyl]quinoline-3-carboxamide | B |
| 158 | N-[(1R)-1-(Azetidin-3-yl)ethyl]-8-[4-(trifluoromethyl)phenyl]quinoline-3-carboxamide | B |
| 160 | N-(1,5-dihydroxypentan-3-yl)-8-(4-(trifluoromethyl)phenyl)quinoline-3-carboxamide | C |
| 161 | N-(1,5-dihydroxypentan-3-yl)-5-(4-(trifluoromethyl)phenyl)-2-naphthamide | B |
| 162 | N-[(1S)-2-hydroxy-1-(2-pyridyl)ethyl]-5-[4-(trifluoromethyl)phenyl]naphthalene-2-carboxamide | C |
| 163 | N-[(1R)-2-hydroxy-1-(2-pyridyl)ethyl]-5-[4-(trifluoromethyl)phenyl]naphthalene-2-carboxamide | A |
| 164 | (S)-N-(3-hydroxy-1-(pyridin-2-yl)propyl)-5-(4-(trifluoromethyl)phenyl)-2-naphthamide | A |
| 165 | (R)-N-(3-hydroxy-1-(pyridin-2-yl)propyl)-5-(4-(trifluoromethyl)phenyl)-2-naphthamide | C |
| 166 | N-[(1S)-3-hydroxy-1-methyl-propyl]-5-[4-(trifluoromethyl)phenyl]naphthalene-2-carboxamide | A |
| 167 | N-[(1R)-3-hydroxy-1-methyl-propyl]-5-[4-(trifluoromethyl)phenyl]naphthalene-2-carboxamide | A |
| 168 | (S)-N-(4-aminobutan-2-yl)-5-(4-(trifluoromethyl)phenyl)-2-naphthamide | A |
| 169 | (R)-N-(4-aminobutan-2-yl)-5-(4-(trifluoromethyl)phenyl)-2-naphthamide | B |
| 170 | N-((2-(fluoromethyl)pyrimidin-4-yl)methyl)-5-(4-(trifluoromethyl)phenyl)-2-naphthamide | A |
| 171 | N-((2-((Isoxazol-3-yloxy)methyl)pyrimidin-4-yl)methyl)-5-(4-(trifluoromethyl)phenyl)-2-naphthamide | B |

TABLE 4-continued

| Compound No. | Name | Firefly Luciferase IC$_{50}$ (μM) |
|---|---|---|
| 172 | N-((2-((2,6-difluorophenoxy)methyl)pyrimidin-4-yl)methyl)-5-(4-(trifluoromethyl)phenyl)-2-naphthamide | C |
| 173 | N-[(1R)-1-(3H-benzimidazol-4-yl)ethyl]-5-[4-(trifluoromethyl)phenyl]naphthalene-2-carboxamide | B |
| 174 | N-[(1S)-1-(3H-benzimidazol-4-yl)ethyl]-5-[4-(trifluoromethyl)phenyl]naphthalene-2-carboxamide | A |
| 176 | N-[(1R)-1-(benzothiophen-7-yl)ethyl]-5-[4-(trifluoromethyl)phenyl]naphthalene-2-carboxamide | B |
| 177 | N-[(1R)-1-(2-oxo-1H-quinolin-8-yl)ethyl]-5-[4-(trifluoromethyl)phenyl]naphthalene-2-carboxamide | A |
| 178 | N-[(1S)-1-(2-oxo-1H-quinolin-8-yl)ethyl]-5-[4-(trifluoromethyl)phenyl]naphthalene-2-carboxamide | C |
| 179 | N-((2-cyanopyrimidin-4-yl)methyl)-5-(4-(trifluoromethyl)phenyl)-2-naphthamide | A |
| 180 | N-((2-chloropyrimidin-4-yl)methyl)-5-(4-(trifluoromethyl)phenyl)-2-naphthamide | B |
| 181 | N-((2-chloropyrimidin-4-yl)methyl)-5-(4-(trifliioromethyl)phenyl)-2-naphthamide | A |
| 182 | N-[(1R)-1-(1H-indazol-7-yl)ethyl]-5-[4-(trifluoromethyl)phenyl]naphthalene-2-carboxamide | A |
| 183 | N-[(1S)-1-(1H-indazol-7-yl)ethyl]-5-[4-(trifluoromethyl)phenyl]naphthalene-2-carboxamide | C |
| 184 | 3-((5-(4-(Trifluoromethyl)phenyl)-2-naphthamido)methyl)-1,2,4-thiadiazole-5-carboxamide | A |
| 185 | N-(pyrimidin-4-ylmethyl)-5-(4-(trifluoromethyl)phenyl)-2-naphthamide | A |
| 186 | N-((2-cyanopyridin-4-yl)methyl)-5-(4-(trifluoromethyl)phenyl)-2-naphthamide | A |
| 187 | N-((6-((2,6-difluorophenoxy)methyl)pyridin-2-yl)methyl)-5-(4-(trifluoromethyl)phenyl)-2-naphthamide | B |
| 188 | N-[3-hydroxy-1-(2-pyridyl)propyl]-5-[4-(trifluoromethyl)phenyl]naphthalene-2-carboxamide | A |
| 190 | N-((6-fluoropyridin-2-yl)methyl)-5-(4-(trifluoromethyl)phenyl)-2-naphthamide | B |
| 191 | N-((6-cyanopyridin-2-yl)methyl)-5-(4-(trifluoromethyl)phenyl)-2-naphthamide | B |
| 192 | N-(3-((isoxazol-3-yloxy)methyl)benzyl)-5-(4-(trifluoromethyl)phenyl)-2-naphthamide | B |
| 193 | N-((1,2,4-thiadiazol-3-yl)methyl)-5-(4-(trifluoromethyl)phenyl)-2-naphthamide | A |
| 195 | (S)-N-(1-(1-methyl-1H-imidazol-4-yl)ethyl)-5-(4-(trifluoromethyl)phenyl)-2-naphthamide | A |
| 196 | (R)-N-(1-(1-methyl-1H-imidazol-4-yl)ethyl)-5-(4-(trifluoromethyl)phenyl)-2-naphthamide | B |
| 197 | N-(1-hydroxy-3-(pyridin-2-yl)propan-2-yl)-5-(4-(trifluoromethyl)phenyl)-2-naphthamide | B |
| 198 | N-[(E)-6-isoxazol-3-yloxyhex-4-enyl]-5-[4-(trifluoromethyl)phenyl]naphthalene-2-carboxamide | A |
| 199 | (R)-N-(1-(1-acetylazetidin-3-yl)ethyl)-5-(4-(trifluoromethyl)phenyl)-2-naphthamide | B |
| 200 | (S)-N-(1-(1-acetylazetidin-3-yl)ethyl)-5-(4-(trifluoromethyl)phenyl)-2-naphthamide | B |
| 201 | 3-(1-(5-(4-(Trifluoromethyl)phenyl)-2-naphthamido)ethyl)-1,2,4-thiadiazole-5-carboxamide | A |
| 202 | N-[(E)-6-amino-6-oxo-hex-4-enyl]-5-[4-(trifluoromethyl)phenyl]naphthalene-2-carboxamide | B |
| 203 | (R)-N-(1-(azetidin-3-yl)ethyl)-5-(4-(trifluoromethyl)phenyl)-2-naphthamide | A |
| 204 | (S)-N-(1-(azetidin-3-yl)ethyl)-5-(4-(trifluoromethyl)phenyl)-2-naphthamide | B |
| 206 | (R)-N-(1-(2-chlorophenyl)ethyl)-5-(4-(trifluoromethyl)phenyl)-2-naphthamide | A |
| 208 | N-(3-(2-methoxyethoxy)benzyl)-5-(4-(trifluoromethyl)phenyl)-2-naphthamide | A |
| 209 | (E)-5-[[5-[4-(trifluoromethyl)phenyl]naphthalene-2-carbonyl]amino]pent-2-enoic acid | C |
| 210 | N-((2-methoxypyridin-4-yl)methyl)-5-(4-(trifluoromethyl)phenyl)-2-naphthamide | B |
| 211 | N-((2-fluoropyridin-4-yl)methyl)-5-(4-(trifluoromethyl)phenyl)-2-naphthamide | A |
| 212 | N-(1-methoxy-2-methylpropan-2-yl)-5-(4-(trifluoromethyl)phenyl)-2-naphthamide | A |
| 213 | (R)-N-(1-(4-aminopyridin-2-yl)ethyl)-5-(4-(trifluoromethyl)phenyl)-2-naphthamide | B |
| 214 | (S)-N-(1-(4-aminopyridin-2-yl)ethyl)-5-(4-(trifluoromethyl)phenyl)-2-naphthamide | C |

TABLE 4-continued

| Compound No. | Name | Firefly Luciferase IC$_{50}$ (µM) |
|---|---|---|
| 215 | N-(3-cyanobenzyl)-5-(4-(trifluoromethyl)phenyl)-2-naphthamide | A |
| 216 | N-[(Z)-4-cyanobut-3-enyl]-5-[4-(trifluoromethyl)phenyl]naphthalene-2-carboxamide | B |
| 217 | N-[(E)-4-cyanobut-3-enyl]-5-[4-(trifluoromethyl)phenyl]naphthalene-2-carboxamide | A |
| 218 | (R)-N-[1-(2-amino-3-pyridyl)ethyl]-5-[4-(trifluoromethyl)phenyl]naphthalene-2-carboxamide | A |
| 220 | N-((1,2,4-thiadiazol-5-yl)methyl)-5-(4-(trifluoromethyl)phenyl)-2-naphthamide | A |
| 221 | N-((3-methyl-1,2,4-thiadiazol-5-yl)methyl)-5-(4-(trifluoromethyl)phenyl)-2-naphthamide | A |
| 222 | N-[(E)-5-amino-5-oxo-pent-3-enyl]-5-[4-(trifluoromethyl)phenyl]naphthalene-2-carboxamide | A |
| 223 | (R)-N-(1-(4-(dimethylamino)pyridin-2-yl)ethyl)-5-(4-(trifluoromethyl)phenyl)-2-naphthamide | B |
| 224 | (S)-N-(1-(4-(dimethylamino)pyridin-2-yl)ethyl)-5-(4-(trifluoromethyl)phenyl)-2-naphthamide | C |
| 225 | N-(1-(4-bromopyridin-2-yl)ethyl)-5-(4-(trifluoromethyl)phenyl)-2-naphthamide | A |
| 227 | N-[(E)-5-cyanopent-4-enyl]-5-[4-(trifluoromethyl)phenyl]naphthalene-2-carboxamide | A |
| 228 | N-[(Z)-5-cyanopent-4-enyl]-5-[4-(trifluoromethyl)phenyl]naphthalene-2-carboxamide | A |
| 229 | N-(pyridin-4-ylmethyl)-5-(4-(trifluoromethyl)phenyl)-2-naphthamide | A |
| 230 | methyl (E)-5-[[5-[4-(trifluoromethyl)phenyl]naphthalene-2-carbonyl]amino]pent-2-enoate | B |
| 231 | N-(5-cyano-5-hydroxy-pentyl)-5-[4-(trifluoromethyl)phenyl]naphthalene-2-carboxamide | B |
| 232 | (S)-8-(2-Fluoro-4-(trifluoromethyl)phenyl)-6-methoxy-N-(1-(pyridin-2-yl)ethyl)quinoline-3-carboxamide | A |
| 233 | (R)-8-(2-Fluoro-4-(trifluoromethyl)phenyl)-N-(1-hydroxypropan-2-yl)-6-methoxyquinoline-3-carboxamide | A |
| 234 | N-(3-(3-methoxypropanamido)benzyl)-5-(4-(trifluoromethyl)phenyl)-2-naphthamide | A |
| 235 | N-(3-aminobenzyl)-5-(4-(trifluoromethyl)phenyl)-2-naphthamide | A |
| 236 | tert-butyl(3-((5-(4-(trifluoromethyl)phenyl)-2-naphthamido)methyl)phenyl)carbamate | B |
| 237 | N-(3-acetamidobenzyl)-5-(4-(trifluoromethyl)phenyl)-2-naphthamide | A |
| 238 | N-(5-hydroxypentyl)-5-[4-(trifluoromethyl)phenyl]naphthalene-2-carboxamide | B |
| 239 | N-(pyridin-2-ylmethyl)-5-(4-(trifluoromethyl)phenyl)-2-naphthamide | A |
| 240 | N-(3-methoxybenzyl)-5-(4-(trifluoromethyl)phenyl)-2-naphthamide | B |
| 241 | N-benzyl-5-(4-(trifluoromethyl)phenyl)-2-naphthamide | A |
| 242 | (R)-N-(1-(1H-imidazol-2-yl)ethyl)-5-(4-(trifluoromethyl)phenyl)-2-naphthamide | B |
| 243 | (S)-N-(1-(1H-imidazol-2-yl)ethyl)-5-(4-(trifluoromethyl)phenyl)-2-naphthamide | B |
| 244 | (S)-N-(1-(Pyridin-2-yl)ethyl)-5-(4-(trifluoromethyl)phenyl)quinoline-2-carboxamide | A |
| 245 | N-[(E)-5-hydroxypent-3-enyl]-5-[4-(trifluoromethyl)phenyl]naphthalene-2-carboxamide | B |
| 246 | (S)-N-(1-Methoxypropan-2-yl)-5-(4-(trifluoromethyl)phenyl)quinoline-2-carboxamide | B |
| 247 | (R)-N-(1-Hydroxypropan-2-yl)-5-(4-(trifluoromethyl)phenyl)quinoline-2-carboxamide | B |
| 248 | N-isopropyl-5-(4-(trifluoromethyl)phenyl)quinoline-2-carboxamide | B |
| 249 | N-(4-chlorobutyl)-5-(4-(trifluoromethyl)phenyl)-2-naphthamide | B |
| 250 | N-(1-(pyridin-2-yl)cyclopropyl)-5-(4-(trifluoromethyl)phenyl)-2-naphthamide | B |
| 251 | (S)-N-(1-cyclobutylethyl)-5-(4-(trifluoromethyl)phenyl)-2-naphthamide | B |
| 252 | (S)-N-(1-cyclobutylethyl)-5-(4-(trifluoromethyl)phenyl)-2-naphthamide | B |
| 253 | (S)-N-(1-(1-methyl-1H-imidazol-2-yl)ethyl)-5-(4-(trifluoromethyl)phenyl)-2-naphthamide | C |
| 254 | (R)-N-(1-(1-methyl-1H-imidazol-2-yl)ethyl)-5-(4-(trifluoromethyl)phenyl)-2-naphthamide | B |
| 255 | N-(4-hydroxybutyl)-5-(4-(trifluoromethyl)phenyl)-2-naphthamide | B |
| 256 | N-(3-azidopropyl)-5-(4-(trifluoromethyl)phenyl)-2-naphthamide | B |
| 257 | N-(1-(hydroxymethyl)cyclopropyl)-5-(4-(trifluoromethyl)phenyl)-2-naphthamide | A |
| 258 | (R)-N-(1-amino-1-oxopropan-2-yl)-5-(4-(trifluoromethyl)phenyl)-2-naphthamide | B |

TABLE 4-continued

| Compound No. | Name | Firefly Luciferase IC$_{50}$ (μM) |
|---|---|---|
| 259 | (S)-N-(1-amino-1-oxopropan-2-yl)-5-(4-(trifluoromethyl)phenyl)-2-naphthamide | B |
| 260 | N-[2-hydroxy-1-(2-pyridyl)ethyl]-8-[4-(trifluoromethyl)phenyl]quinoline-3-carboxamide | A |
| 261 | N-(2-azidoethyl)-5-(4-(trifluoromethyl)phenyl)-2-naphthamide | A |
| 262 | N-(2-(pyridin-2-yl)propan-2-yl)-5-(4-(trifluoromethyl)phenyl)-2-naphthamide | B |
| 263 | N-(1-hydroxy-2-methylpropan-2-yl)-5-(4-(trifluoromethyl)phenyl)-2-naphthamide | B |
| 264 | N-(tert-butyl)-5-(4-(trifluoromethyl)phenyl)-2-naphthamide | B |
| 265 | N-(3-chloropropyl)-5-(4-(trifluoromethyl)phenyl)-2-naphthamide | B |
| 266 | (S)-N-(1-(pyridin-2-yl)ethyl)-5-(4-(trifluoromethyl)phenyl)quinoxaline-2-carboxamide | B |
| 267 | (R)-N-(1-hydroxypropan-2-yl)-5-(4-(trifluoromethyl)phenyl)quinoxaline-2-carboxamide | B |
| 268 | N-Isopropyl-5-(4-(trifluoromethyl)phenyl)quinoxaline-2-carboxamide | B |
| 269 | (S)-N-(1-(oxetan-3-yl)ethyl)-5-(4-(trifluoromethyl)phenyl)-2-naphthamide | A |
| 270 | (R)-N-(1-(oxetan-3-yl)ethyl)-5-(4-(trifluoromethyl)phenyl)-2-naphthamide | B |
| 272 | (S)-N-(pent-3-yn-2-yl)-5-(4-(trifluoromethyl)phenyl)-2-naphthamide | A |
| 273 | (R)-N-(pent-3-yn-2-yl)-5-(4-(trifluoromethyl)phenyl)-2-naphthamide | A |
| 274 | (S)-N-(but-3-yn-2-yl)-5-(4-(trifluoromethyl)phenyl)-2-naphthamide | A |
| 275 | (R)-N-(but-3-yn-2-yl)-5-(4-(trifluoromethyl)phenyl)-2-naphthamide | A |
| 276 | (S)-N-(1-(1H-imidazol-4-yl)ethyl)-5-(4-(trifluoromethyl)phenyl)-2-naphthamide | B |
| 277 | (R)-N-(1-(1H-imidazol-4-yl)ethyl)-5-(4-(trifluoromethyl)phenyl)-2-naphthamide | B |
| 278 | (S)-N-(1-(2-methyl-2H-tetrazol-5-yl)ethyl)-5-(4-(trifluoromethyl)phenyl)-2-naphthamide | B |
| 279 | (R)-N-(1-(2-methyl-2H-tetrazol-5-yl)ethyl)-5-(4-(trifluoromethyl)phenyl)-2-naphthamide | A |
| 280 | (S)-N-(1-(1-methyl-1H-tetrazol-5-yl)ethyl)-5-(4-(trifluoromethyl)phenyl)-2-naphthamide | C |
| 281 | (R)-N-(1-(1-methyl-1H-tetrazol-5-yl)ethyl)-5-(4-(trifluoromethyl)phenyl)-2-naphthamide | B |
| 282 | (S)-N-(1-(pyrazin-2-yl)ethyl)-5-(4-(trifluoromethyl)phenyl)-2-naphthamide | B |
| 283 | (R)-N-(1-(pyrazin-2-yl)ethyl)-5-(4-(trifluoromethyl)phenyl)-2-naphthamide | A |
| 286 | (R)-N-(1-(6-(dimethylamino)pyridin-2-yl)ethyl)-5-(4-(trifluoromethyl)phenyl)-2-naphthamide | A |
| 287 | (S)-N-(1-(6-(dimethylamino)pyridin-2-yl)ethyl)-5-(4-(trifluoromethyl)phenyl)-2-naphthamide | B |
| 288 | N-(3-phenyloxetan-3-yl)-5-(4-(trifluoromethyl)phenyl)-2-naphthamide | A |
| 289 | (S)-N-(1-cyclopropylethyl)-5-(4-(trifluoromethyl)phenyl)-2-naphthamide | A |
| 290 | (R)-N-(1-cyclopropylethyl)-5-(4-(trifluoromethyl)phenyl)-2-naphthamide | A |
| 291 | N-(2-Hydroxy-1-(pyridin-2-yl)ethyl)-7-methoxy-5-(4-(trifluoromethyl)phenyl)-2-naphthamide | A |
| 292 | (S)-7-Methoxy-N-(1-(pyridin-2-yl)ethyl)-5-(4-(trifluoromethyl)phenyl)-2-naphthamide | A |
| 293 | (R)-7-Methoxy-N-(1-(pyridin-2-yl)ethyl)-5-(4-(trifluoromethyl)phenyl)-2-naphthamide | A |
| 294 | (S)-7-Methoxy-N-(1-methoxypropan-2-yl)-5-(4-(trifluoromethyl)phenyl)-2-naphthamide | A |
| 295 | (R)-7-Methoxy-N-(1-methoxypropan-2-yl)-5-(4-(trifluoromethyl)phenyl)-2-naphthamide | A |
| 296 | (S)-N-(1-Hydroxypropan-2-yl)-7-methoxy-5-(4-(trifluoromethyl)phenyl)-2-naphthamide | A |
| 297 | (R)-N-(1-Hydroxypropan-2-yl)-7-methoxy-5-(4-(trifluoromethyl)phenyl)-2-naphthamide | A |
| 298 | N-Isopropyl-6-(4-(trifluoromethyl)phenyl)-[1,2,4]triazolo[5,1-a]isoquinoline-9-carboxamide | B |
| 299 | N-Isopropyl-6-(4-(trifluoromethyl)phenyl)imidazo[2,1-a]isoquinoline-9-carboxamide | B |
| 300 | N-Isopropyl-5-(4-(trifluoromethyl)phenyl)-[1,2,4]triazolo[1,5-a]quinoline-8-carboxamide | B |
| 306 | N-Isopropyl-1-methyl-2-oxo-4-(4-(trifluoromethyl)phenyl)-1,2-dihydroquinoline-7-carboxamide | B |

TABLE 4-continued

| Compound No. | Name | Firefly Luciferase IC$_{50}$ (μM) |
|---|---|---|
| 307 | N-Isopropyl-5-(4-(trifluoromethyl)phenyl)-[1,2,4]triazolo[4,3-a]quinoline-8-carboxamide | B |
| 311 | (E)-N-(4-(Methylsulfonyl)but-3-en-1-yl)-5-(4-(trifluoromethyl)phenyl)-2-naphthamide | A |
| 313 | N-[(1R)-3-(dimethylamino)-1-methyl-propyl]-5-[4-(trifluoromethyl)phenyl]naphthalene-2-carboxamide | B |
| 316 | N-[(1R)-3-(ethylamino)-1-methyl-propyl]-8-[4-(trifluoromethyl)phenyl]quinoline-3-carboxamide | B |
| 317 | (R)-N-(1-(1-(2,2-difluoroethyl)azetidin-3-yl)ethyl)-8-(4-(trifluoromethyl)phenyl)quinoline-3-carboxamide | B |
| 318 | (R)-N-(1-(1-(2-fluoroethyl)azetidin-3-yl)ethyl)-8-(4-(trifluoromethyl)phenyl)quinoline-3-carboxamide | B |
| 319 | N-[(1R)-3-(Dimethylamino)-1-methyl-propyl]-8-[4-(trifluoromethyl)phenyl]quinoline-3-carboxamide | B |
| 320 | (R)-N-(1-(1-cyclopropylazetidin-3-yl)ethyl)-5-(4-(trifluoromethyl)phenyl)-2-naphthamide | B |
| 321 | 8-(2-Fluoro-4-(trifluoromethyl)phenyl)-6-methoxyquinoline-3-carboxylic acid | A |
| 322 | 7-Methoxy-5-(4-(trifluoromethyl)phenyl)-2-naphthoic acid | A |
| 323 | 6-Cyclopropoxy-8-(4-(trifluoromethyl)phenyl)quinoline-3-carboxylic acid | A |
| 324 | 6-(Trifluoromethoxy)-8-[4-(trifluoromethyl)phenyl]quinoline-3-carboxylic acid | A |
| 325 | 6-Methoxy-8-(4-(trifluoromethyl)phenyl)quinoline-3-carboxylic acid | A |
| 326 | 5,6-Dichloro-8-(4-(trifluoromethyl)phenyl)quinoline-3-carboxylic acid | A |
| 327 | 6-Ethoxy-8-(4-(trifluoromethyl)phenyl)quinoline-3-carboxylic acid | A |
| 328 | 5,6-Difluoro-8-(4-(trifluoromethyl)phenyl)quinoline-3-carboxylic acid | A |
| 329 | 5-[4-(pentafluoro-sulfanyl)phenyl]naphthalene-2-carboxylic acid | A |
| 330 | 5-[4-(Trifluoromethyl)phenyl]naphthalene-2-carboxylic acid | A |
| 331 | 5-(6-(trifluoromethyl)pyridin-3-yl)-2-naphthoic acid | B |
| 332 | 5-[5-(trifluoromethyl)-2-thienyl]naphthalene-2-carboxylic acid | A |
| 333 | 5-(4-(trifluoromethyl)phenyl)quinoline-2-carboxylic acid | B |
| 334 | 5-(4-(trifluoromethyl)phenyl)quinoxaline-2-carboxylic acid | B |
| 335 | 1-hydroxy-5-(4-(trifluoromethyl)phenyl)-2-naphthoic acid | A |
| 336 | 4-[4-(trifluoromethyl)phenyl]isoquinoline-7-carboxylic acid | B |
| 337 | 2-methyl-1-oxo-4-(4-(trifluoromethyl)phenyl)-1,2-dihydroisoquinoline-7-carboxylic acid | B |

Note:
Biochemical assay IC$_{50}$ data are designated within the following ranges:
A: ≤0.100 μM
B: >0.100 μM to ≤1.000 μM
C: >1.000 μM to ≤3.000 μM
D: >3.000 μM Example A2: Tumor Suppression Assay The procedures described herein for the tumor suppression assay is as described in PCT/US2013/043752 (WO 2013/188138). Mouse procedures are performed according to the guidelines of approved animal protocol and based on the methods. After the cells are grown to 90%>confluence, these cells are harvested by trypsinization, washed in phosphate-buffered saline (PBS), and resuspended in PBS supplemented with 50% Matrigel (BD Biosciences). An appropriate number of cells is prepared for administration, such as 200 μL per injection site. Immuno-compromised mice are injected on the dorsolateral sites subcutaneously. Any one of the compounds described herein is formulated accordingly and is then administered at a suitable dose. Control mice received vehicle alone. The average tumor diameter (two perpendicular axes of the tumor are measured) are recorded. The data are expressed in tumor volume estimated by ([width]2×length/2). Paired, two-tailed Student's t-test is performed to access the statistical significance.

Example A3: Cell Proliferation Assay

Cancer cell lines are plated in 384-well plates 24 h before drug treatment. Post incubation for various time periods with the test compounds, starting from 3 μM (final concentration in assay plate), 1:3 dilution, and 10 points in duplicates, the number of viable cells and proliferative cells are determined using CellTiter-Glo® Luminescent Cell Viability Assay Kit (Promega) and Click-iT EdU HCS Assay Kit (Invitrogen) according to the manufacturers' protocols. The IC$_{50}$ values and maximum % inhibition of the test compounds are calculated using the dose response curves.

The examples and embodiments described herein are for illustrative purposes only and various modifications or changes suggested to persons skilled in the art are to be included within the spirit and purview of this application and scope of the appended claims.

What is claimed is:

1. A compound of Formula (IVa) or Formula (IVb), or a pharmaceutically acceptable salt or a pharmaceutically acceptable solvate thereof:

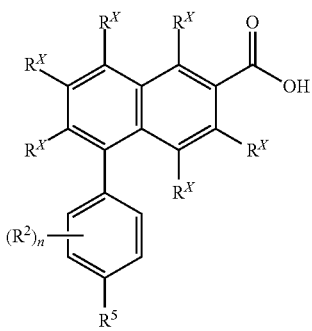

Formula (IVa)

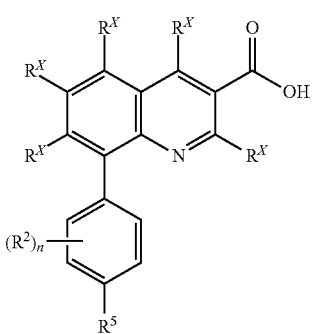

Formula (IVb)

wherein,
R$^X$ is independently hydrogen, halogen, nitro, oxo, thioxo, imino, oximo, —OR$^3$, —SR$^3$, —CN, —C(=O)R$^2$, —S(=O)R$^3$, —S(=O)$_2$R$^3$, —N(R$^3$)$_2$, —NR$^3$S(=O)$_2$R$^3$, —NR$^3$C(=O)R$^3$, —NR$^3$C(=O)OR$^3$, substituted or unsubstituted C$_1$-C$_6$ alkyl, substituted or unsubstituted C$_1$-C$_6$haloalkyl, substituted or unsubstituted C$_2$-C$_4$alkenyl, substituted or unsubstituted C$_2$-C$_4$alkynyl, substituted or unsubstituted C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted aralkyl, substituted or unsubstituted aryl, or substituted or unsubstituted heteroaryl;
each R$^2$ is independently —CN, —OR$^3$, —SR$^3$, —S(=O)$_2$R$^3$, —N(R$^3$)$_2$, —C(=O)OR$^3$, —N$_3$, F, substituted or unsubstituted C$_1$-C$_6$alkyl, substituted or unsubstituted C$_1$-C$_6$haloalkyl, substituted or unsubstituted C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted aralkyl, substituted or unsubstituted aryl, or substituted or unsubstituted heteroaryl;
each R$^3$ is independently hydrogen, substituted or unsubstituted C$_1$-C$_6$alkyl, substituted or unsubstituted C$_1$-C$_6$haloalkyl, substituted or unsubstituted C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted aralkyl, substituted or unsubstituted aryl, or substituted or unsubstituted heteroaryl;
R$^5$ is F, —SF$_5$, substituted C$_1$-C$_6$alkyl, substituted or unsubstituted C$_1$-C$_6$haloalkyl, substituted C$_1$-C$_6$alkyloxy, or substituted C$_1$-C$_6$alkylthio; and
n is 0, 1, 2, 3, or 4.

2. The compound of claim 1, or a pharmaceutically acceptable salt or a pharmaceutically acceptable solvate thereof, wherein the compound has a structure of Formula (IVa):

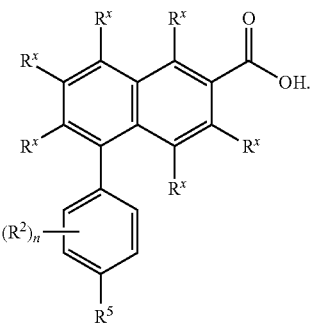

Formula (IVa)

3. The compound of claim 1, or a pharmaceutically acceptable salt or a pharmaceutically acceptable solvate thereof, wherein the compound has a structure of Formula (IVb):

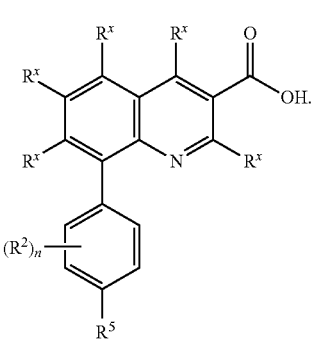

Formula (IVb)

4. The compound of claim 1, or a pharmaceutically acceptable salt or a pharmaceutically acceptable solvate thereof, wherein:
each R$^X$ is independently hydrogen, halogen, —OR$^3$, —SR$^3$, —CN, —S(=O$_3$)R$^3$, —S(=O)$_2$R$^3$, —N(R$^3$)$_2$, —NR$^3$S(=O)$_2$R$^3$, —NR$^3$C(=O)R$^3$, substituted or unsubstituted C$_1$-C$_6$alkyl, substituted or unsubstituted C$_1$-C$_6$haloalkyl, substituted or unsubstituted C$_2$-C$_4$alkenyl, substituted or unsubstituted C$_2$-C$_4$alkynyl, or substituted or unsubstituted C$_1$-C$_6$heteroalkyl; and
each R$^3$ is independently hydrogen, substituted or unsubstituted C$_1$-C$_6$alkyl, substituted or unsubstituted C$_1$-C$_6$haloalkyl, substituted or unsubstituted C$_1$-C$_6$heteroalkyl, substituted or unsubstituted C$_3$-C$_{10}$cycloalkyl, or substituted or unsubstituted C$_2$-C$_{10}$heterocycloalkyl.

5. The compound of claim 1, or a pharmaceutically acceptable salt or a pharmaceutically acceptable solvate thereof, wherein:
each R$^X$ is independently hydrogen, —OCH$_3$, —OCH$_2$CH$_3$, —OCH$_2$CH$_2$CH$_3$, or —OCH(CH$_3$)$_2$, —OCF$_3$, —OCH$_2$CF$_3$, cyclopropyloxy, or cyclobutyloxy.

6. The compound of claim 1, or a pharmaceutically acceptable salt or a pharmaceutically acceptable solvate thereof, wherein:
R$^5$ is substituted or unsubstituted C$_1$-C$_6$haloalkyl, substituted C$_1$-C$_6$alkyloxy, or substituted C$_1$-C$_6$alkylthio.

7. The compound of claim 1, or a pharmaceutically acceptable salt or a pharmaceutically acceptable solvate thereof, wherein:

R⁵ is —CH₂F, —CHF₂, —CF₃, —CH₂CH₂F, —CH₂CHF₂, —CF₂CH₃, —CH₂CF₃, —OCH₂F, —OCHF₂, —OCF₃, —OCH₂CH₂F, —OCH₂CHF₂, —OCF₂CH₃, —OCH₂CF₃, —SCH₂F, —SCHF₂, —SCF₃, —SCH₂CH₂F, —SCH₂CHF₂, —SCF₂CH₃, or —SCH₂CF₃.

8. The compound of claim 1, or a pharmaceutically acceptable salt or a pharmaceutically acceptable solvate thereof, wherein:

each $R^2$ is independently —CN, —OR³, —SR³, —S(=O)₂R³, —N(R³)₂, —C(=O)OR³, —N₃, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, or substituted or unsubstituted $C_2$-$C_{10}$heterocycloalkyl; and each $R^3$ is independently hydrogen, substituted or unsubstituted $C_1$-$C_6$alkyl, substituted or unsubstituted $C_1$-$C_6$haloalkyl, substituted or unsubstituted $C_1$-$C_6$heteroalkyl, substituted or unsubstituted $C_3$-$C_{10}$cycloalkyl, or substituted or unsubstituted $C_2$-$C_{10}$heterocycloalkyl.

9. A method for treating a cancer in a subject in need thereof comprising administering to the subject a therapeutically effective amount of a compound of claim 1, or a pharmaceutically acceptable salt or pharmaceutically acceptable solvate thereof, wherein the cancer is mediated by activation of transcriptional coactivator with PDZ binding motif/Yes-associated protein transcription coactivator (TAZ/YAP) and the treatment is for therapeutic benefit.

10. The compound of claim 1, or a pharmaceutically acceptable salt or a pharmaceutically acceptable solvate thereof, wherein n is 0.

11. A compound, or a pharmaceutically acceptable salt or a pharmaceutically acceptable solvate thereof, wherein the compound is selected from the group consisting of:

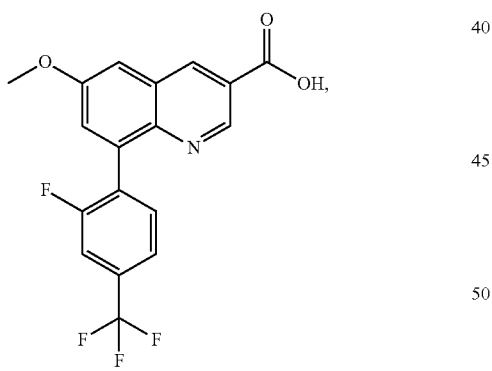

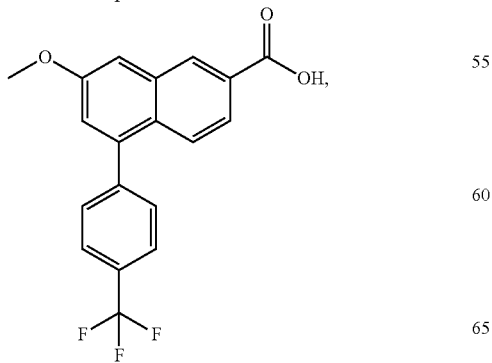

-continued

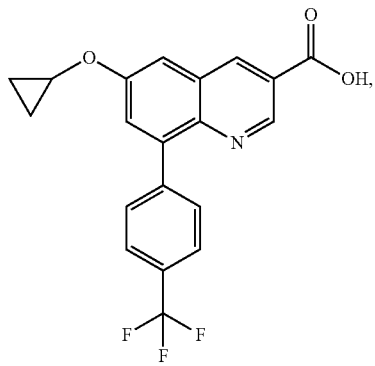

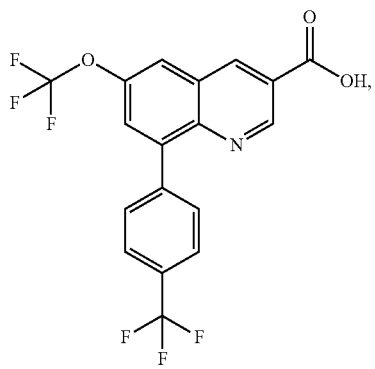

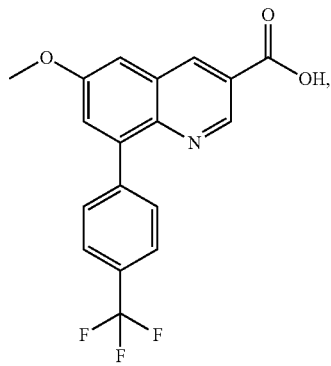

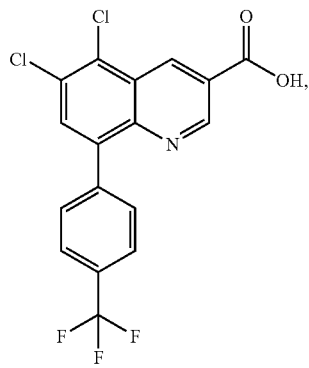

737
-continued
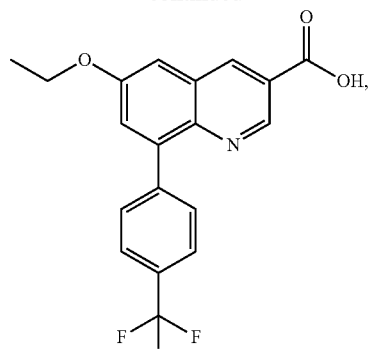
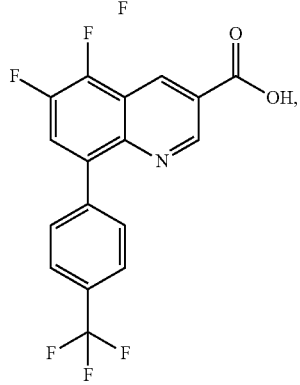
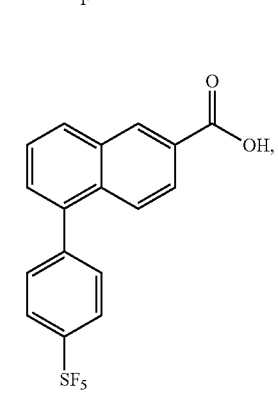
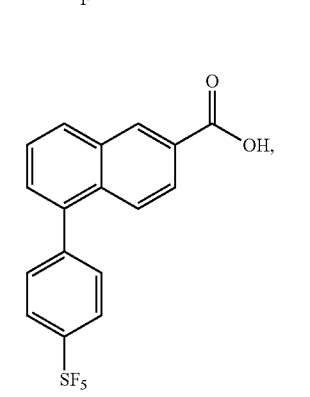
738
-continued
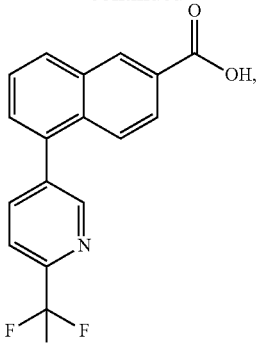
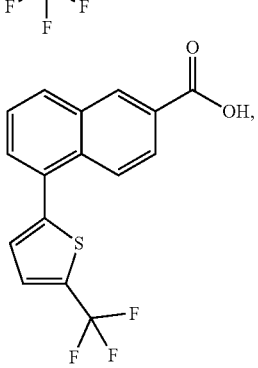
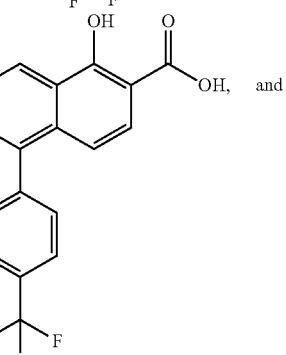
and
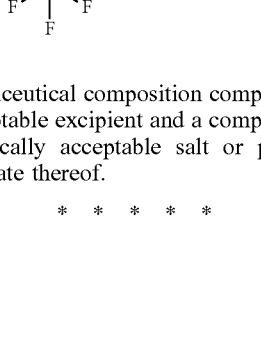
12. A pharmaceutical composition comprising a pharmaceutically acceptable excipient and a compound of claim 1, or pharmaceutically acceptable salt or pharmaceutically acceptable solvate thereof.
* * * * *